US011384063B2

(12) United States Patent
Crew et al.

(10) Patent No.: US 11,384,063 B2
(45) Date of Patent: Jul. 12, 2022

(54) MODULATORS OF ESTROGEN RECEPTOR PROTEOLYSIS AND ASSOCIATED METHODS OF USE

(71) Applicant: Arvinas Operations, Inc., New Haven, CT (US)

(72) Inventors: Andrew P. Crew, Guilford, CT (US); Hanqing Dong, Madison, CT (US); Jing Wang, Milford, CT (US); Yimin Qian, Plainsboro, NJ (US)

(73) Assignee: ARVINAS OPERATIONS, INC., New Haven, CT (US)

( * ) Notice: Subject to any disclaimer, the term of this patent is extended or adjusted under 35 U.S.C. 154(b) by 0 days.

(21) Appl. No.: 16/810,764

(22) Filed: Mar. 5, 2020

(65) Prior Publication Data

US 2020/0199107 A1    Jun. 25, 2020

Related U.S. Application Data

(62) Division of application No. 15/881,318, filed on Jan. 26, 2018, now Pat. No. 10,604,506.

(60) Provisional application No. 62/587,378, filed on Nov. 16, 2017, provisional application No. 62/450,740, filed on Jan. 26, 2017.

(51) Int. Cl.
| | |
|---|---|
| *C07D 401/14* | (2006.01) |
| *C07D 471/04* | (2006.01) |
| *C07D 409/12* | (2006.01) |
| *C07D 403/06* | (2006.01) |
| *A61P 35/00* | (2006.01) |
| *C07D 405/14* | (2006.01) |
| *C07D 413/14* | (2006.01) |
| *C07D 417/12* | (2006.01) |
| *C07D 417/14* | (2006.01) |
| *C07D 403/14* | (2006.01) |

(52) U.S. Cl.
CPC ............ *C07D 401/14* (2013.01); *A61P 35/00* (2018.01); *C07D 403/06* (2013.01); *C07D 403/14* (2013.01); *C07D 405/14* (2013.01); *C07D 409/12* (2013.01); *C07D 413/14* (2013.01); *C07D 417/12* (2013.01); *C07D 417/14* (2013.01); *C07D 471/04* (2013.01)

(58) Field of Classification Search
CPC .. C07D 413/14; C07D 405/14; C07D 403/06; C07D 409/12; C07D 471/04; A61P 35/00
USPC ......................................................... 514/443
See application file for complete search history.

(56) References Cited

U.S. PATENT DOCUMENTS

| | | | |
|---|---|---|---|
| 5,492,922 A | 2/1996 | Palkowitz et al. | |
| 5,681,835 A | 10/1997 | Willson | |
| 5,877,219 A | 3/1999 | Willson | |
| 6,207,716 B1 | 3/2001 | Willson | |
| 6,306,663 B1 | 10/2001 | Kenten et al. | |
| 6,670,348 B1 | 12/2003 | Rosen et al. | |
| 7,030,141 B2 | 4/2006 | Bigge et al. | |
| 7,041,298 B2 | 5/2006 | Deshaies et al. | |
| 7,208,157 B2 | 4/2007 | Sakamoto et al. | |
| 7,244,851 B2 | 7/2007 | Cohen et al. | |
| 7,345,081 B2 | 3/2008 | Cohen et al. | |
| 7,419,975 B2 | 9/2008 | Palermo et al. | |
| 7,517,906 B2 | 4/2009 | Condon et al. | |
| 7,915,293 B2 | 3/2011 | Ramesh | |
| 9,500,653 B2 | 11/2016 | Crews et al. | |
| 9,632,089 B2 | 4/2017 | Crews et al. | |
| 9,988,376 B2 * | 6/2018 | Campos | .................. A61P 43/00 |
| 2006/0128632 A1 | 6/2006 | Sharma et al. | |
| 2008/0051432 A1 | 2/2008 | Zhang | |
| 2008/0214501 A1 | 9/2008 | Pan et al. | |
| 2008/0269140 A1 | 10/2008 | Wang et al. | |
| 2010/0203012 A1 | 8/2010 | Laurent et al. | |
| 2011/0195043 A1 | 8/2011 | Sun et al. | |
| 2012/0270800 A1 | 10/2012 | Verdine et al. | |

(Continued)

FOREIGN PATENT DOCUMENTS

| | | |
|---|---|---|
| CN | 1844118 A | 10/2006 |
| CN | 102477033 | 5/2012 |

(Continued)

OTHER PUBLICATIONS

Ahn, et al., "HIF-1alpha peptide derivatives with modifications at the hydroxyproline residue as activators of HIF-1alpha", Bioorg Med Chem Lett. 19(15), 2009, 4403-4405 (Aug. 1, 2009).

(Continued)

*Primary Examiner* — Kahsay Habte
(74) *Attorney, Agent, or Firm* — Bryan D. Zerhusen, Esq.; Nicholas R. Herrel, Esq.; Cantor Colburn LLP

(57) ABSTRACT

The present disclosure relates to bifunctional compounds, which find utility as modulators of estrogen receptor (target protein). In particular, the present disclosure is directed to bifunctional compounds, which contain on one end a cereblon, Von Hippel-Lindau ligase-binding moiety, Inhibitors of Apotosis Proteins, or mouse double-minute homolog 2 ligand, which binds to the respective E3 ubiquitin ligase, and on the other end a moiety which binds the target protein, such that the target protein is placed in proximity to the ubiquitin ligase to effect degradation (and inhibition) of target protein. The present disclosure exhibits a broad range of pharmacological activities associated with degradation/inhibition of target protein. Diseases or disorders that result from aggregation or accumulation of the target protein are treated or prevented with compounds and compositions of the present disclosure.

8 Claims, 3 Drawing Sheets

(56) References Cited

U.S. PATENT DOCUMENTS

| | | |
|---|---|---|
| 2014/0235629 A1 | 8/2014 | Bartberger et al. |
| 2014/0243372 A1 | 8/2014 | Rew |
| 2014/0302523 A1 | 10/2014 | Crews et al. |
| 2014/0356322 A1 | 12/2014 | Crews et al. |
| 2015/0119435 A1 | 4/2015 | Crews et al. |
| 2015/0291562 A1 | 10/2015 | Crew et al. |
| 2015/0344473 A1 | 10/2015 | Du et al. |
| 2016/0022642 A1 | 1/2016 | Crews et al. |
| 2016/0045607 A1 | 2/2016 | Crew et al. |
| 2016/0058872 A1 | 3/2016 | Crew et al. |
| 2016/0136230 A1 | 5/2016 | Campos et al. |
| 2016/0214972 A1 | 7/2016 | Jin et al. |
| 2016/0243247 A1 | 8/2016 | Bradner et al. |
| 2016/0272639 A1 | 9/2016 | Crew et al. |
| 2016/0368911 A1 | 12/2016 | Campos et al. |
| 2017/0008904 A1 | 1/2017 | Crew et al. |
| 2017/0037004 A1 | 2/2017 | Crew et al. |
| 2017/0065719 A1 | 3/2017 | Qian et al. |
| 2017/0121321 A1 | 5/2017 | Crews et al. |
| 2017/0281784 A1 | 10/2017 | Wang et al. |
| 2017/0307614 A1 | 10/2017 | Crews et al. |
| 2017/0327469 A1 | 11/2017 | Crew et al. |
| 2018/0015087 A1 | 1/2018 | Liu et al. |
| 2018/0072711 A1 | 3/2018 | Crew et al. |
| 2018/0099940 A1 | 4/2018 | Crew et al. |
| 2018/0125821 A1 | 5/2018 | Crew et al. |
| 2018/0147202 A1 | 5/2018 | Crew et al. |
| 2018/0155322 A1 | 6/2018 | Crew et al. |
| 2018/0177750 A1 | 6/2018 | Crew et al. |
| 2018/0179183 A1 | 6/2018 | Crew et al. |
| 2018/0193470 A1 | 7/2018 | Crew et al. |
| 2018/0215731 A1 | 8/2018 | Crew et al. |
| 2018/0228907 A1 | 8/2018 | Crew et al. |
| 2018/0237418 A1 | 8/2018 | Crew et al. |
| 2018/0256586 A1 | 9/2018 | Crew et al. |
| 2021/0238193 A1 | 8/2021 | Mainolfi et al. |

FOREIGN PATENT DOCUMENTS

| | | |
|---|---|---|
| CN | 103688176 A | 3/2014 |
| EP | 2985285 | 2/2016 |
| JP | A-2004-525889 | 8/2004 |
| JP | A-2010-502627 | 1/2010 |
| RU | 2008112221 A | 10/2009 |
| RU | 2448101 C2 | 4/2012 |
| RU | 2011121567 A | 10/2012 |
| RU | 2012138709 A | 3/2014 |
| WO | WO 1998/003502 | 1/1998 |
| WO | WO 1998/045287 | 10/1998 |
| WO | WO 1999/015521 | 4/1999 |
| WO | WO 2000/066119 | 11/2000 |
| WO | WO 2002/066512 | 8/2002 |
| WO | WO 2002/100845 | 12/2002 |
| WO | WO 2005/097791 | 10/2005 |
| WO | WO 2006/069063 | 6/2006 |
| WO | WO 2006/113942 | 10/2006 |
| WO | WO 2007/101347 | 9/2007 |
| WO | WO 2007/106670 | 9/2007 |
| WO | WO 2007/130626 | 11/2007 |
| WO | WO 2008/011392 | 1/2008 |
| WO | WO 2008/014236 | 1/2008 |
| WO | WO 2008/109057 | 9/2008 |
| WO | WO 2008/128121 | 10/2008 |
| WO | WO 2008/128171 | 10/2008 |
| WO | WO 2008/134679 | 11/2008 |
| WO | WO 2009/015254 | 1/2009 |
| WO | WO 2009/060292 | 5/2009 |
| WO | WO 2010/107485 | 9/2010 |
| WO | WO 2010/141805 | 12/2010 |
| WO | WO 2011/008260 | 1/2011 |
| WO | WO 2012/003281 | 1/2012 |
| WO | WO 2012/040527 | 3/2012 |
| WO | WO 2012/078559 | 6/2012 |
| WO | WO 2012/090104 | 7/2012 |
| WO | WO 2013/071035 | 5/2013 |
| WO | WO 2013/071039 | 5/2013 |
| WO | WO 2013/106643 | 7/2013 |
| WO | WO 2013/106646 | 7/2013 |
| WO | WO 2013/170147 | 11/2013 |
| WO | WO 2013/175417 | 11/2013 |
| WO | WO 2013/178570 | 12/2013 |
| WO | WO 2014/011712 | 1/2014 |
| WO | WO 2014/020502 | 2/2014 |
| WO | WO 2014/025759 | 2/2014 |
| WO | WO 2014/038606 | 3/2014 |
| WO | WO 2014/047024 | 3/2014 |
| WO | WO 2014/055461 | 4/2014 |
| WO | WO 2014/074658 | 5/2014 |
| WO | WO 2014/100065 | 6/2014 |
| WO | WO 2014/100071 | 6/2014 |
| WO | WO 2014/107713 | 7/2014 |
| WO | WO 2014/108452 | 7/2014 |
| WO | WO 2014/123418 | 8/2014 |
| WO | WO 2014/134201 | 9/2014 |
| WO | WO 2014/151863 | 9/2014 |
| WO | WO 2015/000867 | 1/2015 |
| WO | WO 2015/000868 | 1/2015 |
| WO | WO 2015/006524 | 1/2015 |
| WO | WO 2015/160845 | 10/2015 |
| WO | WO 2016/105518 | 6/2016 |
| WO | WO 2016/118666 | 7/2016 |
| WO | WO 2016/146985 | 9/2016 |
| WO | WO 2016/169989 | 10/2016 |
| WO | WO 2016/172134 | 10/2016 |
| WO | WO 2016/197114 | 12/2016 |
| WO | WO 2017/011590 | 1/2017 |
| WO | WO 2017/024318 A1 | 2/2017 |
| WO | WO 2017/024319 A1 | 2/2017 |
| WO | WO 2017/030814 | 2/2017 |
| WO | WO 2017/046036 | 3/2017 |
| WO | WO 2017/079267 | 5/2017 |
| WO | WO 2017/161119 | 9/2017 |
| WO | WO 2017/185036 | 10/2017 |
| WO | WO 2017/197051 | 11/2017 |
| WO | WO 2018/148440 | 8/2018 |

OTHER PUBLICATIONS

Ali, S. et al. Molecular mechanisms and mode of tamoxifen resistance in breast cancer. Bioinformation 12, 135-139 (Jun. 15, 2016).

Ardecky, RJ, et al., "Design, synthesis and evaluation of inhibitor of apoptosis protein (IAP) antagonists that are highly selective for the BIR2 domain of XIAP", Bioorg. Med. Chem., 23(14): 4253-4257 (Jul. 15, 2013).

Asano M, et al., "Design, sterioselective synthesis, and biological evaluation of novel tri-cyclic compounds as inhibitor of apoptosis proteins (IAP) antagonists", Bioorg. Med. Chem., 21(18): 5725-5737 (Jul. 18, 2013).

Bargagna-Mohan, et al., "Use of PROTACS as molecular probes of angiogenesis", Bioorg Med Chem Left. 15(11) 2005, 2724-2727 (Jun. 2, 2005).

Battista, M. J. & Schmidt, M. Fulvestrant for the treatment of endometrial cancer. Expert Opin Investig Drugs 25, 475-483 (Mar. 8, 2016).

Begam, J.A., et al., Estrogen receptor agonists/antagonists in breast cancer therapy: A Critical Review, Bioorganic Chemistry 71, 257-274 (Feb. 23, 2017).

Bhatnagar, A. S. The discovery and mechanism of action of letrozole. Breast Cancer Res Treat 105, 7-17 (Oct. 2007).

Bondeson DP, et al. "Lessons in PROTAC Design from Selective Degradation with a Promiscuous Warhead." *Cell Chem Biol* 25(1):78-87 e75 (Jan. 18, 2018).

Bondeson, et al., (2017) "Targeted Protein Degradation by Small Molecules." *Annu Rev Pharmacol Toxicol* 57:107-123 (Jan. 2017).

Bondeson, et al., "Catalytic in vivo protein knockdown by small-molecule PROTACS", National Chem Biol. 11(8), 611-617 (Aug. 2015).

Brunton, L.L., et al., eds., 11th ed, (2008) Chemotherapy of Neoplastic Diseases in, Goodman & Gilman's: The Pharmacological Basis of Therapeutics, pp. 853-908.

(56) References Cited

OTHER PUBLICATIONS

Buckley, et al., "HaloPROTACS: use of small molecule PROTACS to induce degradation of HaloTag fusion proteins", ACS Chem Biol. 10(8), 2015, 1831-1837 (Aug. 21, 2015).
Buckley, et al., "Small-molecule inhibitors of the interaction between the E3 ligase VHL and HIF1a", Angew Chem Int Ed Engl.51(46), Nov. 12, 2012, 11463-11467 (Nov. 12, 2012).
Buckley, et al., "Targeting the von Hippel-Lindau E3 ubiquitin ligase using small molecules to disrupt the VHL/HIF-1α interaction", Journal of the American Chemical Society , 134(10): 4465-4468 (Feb. 27, 2012).
Burke, et al., "Design, Synthesis and Biological Evaluation of Doxorubicin-Formaldehyde Conjugates Targeted to Breast Cancer Cells", Journal of Medicinal Chemistry, , vol. 47, No. 5, pp. 1193-1206 (Jan. 24, 2004).
Burslem GM, et al. (2018) "The Advantages of Targeted Protein Degradation Over Inhibition: An RTK Case Study." *Cell Chem Biol* 25(1):67-77 e63 (Jan. 18, 2018).
Burslem, et al., (2017) "Small-Molecule Modulation of Protein Homeostasis." *Chem Rev* 117(17):11269-11301 (Sep. 13, 2017).
Capitosti, S., et al., "Thalidomide analogues demonstrate dual inhibition of both angiogenesis and prostate cancer", Bioorganic & Medicinal Chemistry 12, (2004) 327-336 (Dec. 31, 2003).
Carmony, KC, et al., "PROTAC-Induced Proteolytic Targeting", Methods Mol. Biol., 2012, vol. 832, pp. 627-638. (Dec. 31, 2011).
CAS Registry No. 1004933-70-3, which entered STN on Feb. 21, 2008.
CAS Registry No. 871986-52-6 entered STN Jan. 16, 2006.
Chan, et al., (2018) "Impact of Target Warhead and Linkage Vector on Inducing Protein Degradation: Comparison of Bromodomain and Extra-Terminal (BET) Degraders Derived from Triazolodiazepine (JQ1) and Tetrahydroquinoline (I-BET726) BET Inhibitor Scaffolds." *J Med Chem* 61(2):504-513 (Jun. 8, 2017).
Chene, P., et al., "Inhibiting the p53-MDM2 interaction: an important target for cancer therapy" Nat. Rev. Cancer (2003), 3, 102-109 (Feb. 2003).
Cheng-Gen, Feng, et al., "Progress in Antiestrogens for the Treatment of Breast Cancer", Chinese Journal of New Drugs, vol. 15., No. 13, pp. 1051-1057, (Dec. 31, 2006) (With Abstract).
Choo, E. F. et al. Preclinical Disposition of GDC-0973 and Prospective and Retrospective Analysis of Human Dose and Efficacy Predictions. Drug Metab Dispos 40, 919-927 (May 2012).
Churcher I., "Protac-Induced Protein Degradation in Drug Discovery: Breaking the Rules or Just Making New Ones?" *J Med Chem* 61(2):444-452 (Jan. 25, 2018).
Cohen, F, et al., "Orally bioavailable antagonists of inhibitor of apoptosis proteins based on an azabicyclooctane scaffold", J. Med. Chem., 52(6), 1723-1734 (Mar. 26, 2009).
Cohen, F. et al., "Antagonists of inhibitors of apoptosis proteins based on thiazole amide isosteres", Bioorg. Med. Chem. Lett., 20(7), 2229-2233 (Feb. 7, 2010).
Connor, C.E., et al., "Circumventing tamoxifen resistance in breast cancers using antiestrogens that induce unique conformational changes in the estrogen receptor", Cancer Res. 61: 2917-2922 (Apr. 1, 2001).
Contino-Pepin, Christiane, et al., "Preliminary biological evaluations of new thalidomide analogues for multiple sclerosis application", Bioorganic & Medicinal Chemistry Letter 19 (2009), 878-881 (Dec. 6, 2008).
Corson, et al., "Design and applications of bifunctional small molecules: why two heads are better than one", ACS Chemical Biology vol. 3 No. 11, pp. 677-692; (Nov. 21, 2008).
Crew AP, et al. (2018) "Identification and Characterization of Von Hippel-Lindau-Recruiting Proteolysis Targeting Chimeras (PROTACs) of TANK-Binding Kinase 1." *J Med Chem* 61(2):583-598 (Jul. 10, 2017).
Crews, C. M., "Targeting the undruggable proteome: the small molecules of my dreams", *Chem Biol* 17, 551-555, doi:S1074-5521(10)00196-1 [pii] 10.1016/j.chembiol.2010.05.011 (Jun. 25, 2010).

Cromm, et al., (2017) "Targeted Protein Degradation: from Chemical Biology to Drug Discovery." Cell Chem Biol 24(9):1181-1190 (Jun. 22, 2017).
Cyrus, et al., "Jostling for position: optimizing linker location in the design of estrogen receptor-targeting PROTACs", Chem Med Chem. 5(7), Jul. 5, 2010, 979-985 (Jul. 5, 2010).
Cyrus, K. et al., "Impact of Linker Length on the Activity of PROTACs," Mol. Biosyst., 2011, vol. 7, No. 2, pp. 359-364 (Feb. 2011).
Cyrus, K. et al., "Two-Headed PROTAC: An Effective New Tool for Targeted Protein Degradation," Chembiochem., 2010, vol. 11, pp. 1531-1534 (Jul. 26, 2010).
Deroo, B.J., et al., "Estrogen receptors and human disease", Journal of Clinical Investigation, (2006), vol. 116(3), pp. 561-570 (Mar. 2006).
Di, J et al. "Reactivation of p53 by inhibiting Mdm2 E3 Ligase: a novel antitumor approach", Current Cancer Drug Targets (2011), 11(8), 987-994 (Oct. 2011).
Ding, Q, et al., "Discovery of RG7388, a potent and selective p53-MDM2 inhibitor in clinical development", J Med Chem. Jul. 25, 2013; 56(14):5979-83. doi: 10.1021/jm400487c. Epub Jul. 16, 2013. PubMed PMID: 23808545 (J. Med. Chem. (2013) 56, 5979-5983 Ding, et al.). (Jul. 25, 2013).
Dixon, S. J. et al., "Identifying druggable disease-modifying gene products",. *Curr Opin Chem Biol* 13, 549-555, doi:S1367-5931(09)00107-0 [pii] 10.1016/j.cbpa.2009.08.003 (Dec. 2009).
Fischer, et al., "Structure of the DDB1-DRBN E3 Ubiquitin ligase in complex with thalidomide", Nature, vol. 512, pp. 49-53 (Jul. 16, 2014).
Flygare, J.A., et al. "Small-molecule pan-IAP antagonists: a patent review", Expert Opin. Ther. Pat., 20 (2), 251-267 (Feb. 2010).
Gadd, M.S., et al., "Structural basis of PROTAC cooperative recognition for selective protein degradation", Nat Chem Biol 13, 514-521 (May 2017).
Galdeano, et al., "Structure-guided design and optimization of small molecules targeting the protein-protein interaction between the von hippel-lindau (VHL) E3 ubiquitin ligase and the Hypoxia inducible factor (HIH) alpha subunit with in vitro nanomolar affinities", Journal Med Chem, Aug. 2014, vol. 57, pp. 8657-8663 (Aug. 28, 2014).
Garner, F., Shomali, M., Paquin, D., Lyttle, C. R. & Hattersley, G. RAD1901: a novel, orally bioavailable selective estrogen receptor degrader that demonstrates antitumor activity in breast cancer xenograft models. Anticancer Drugs 26, 948-956 (Oct. 2015).
Golub, et al., "Molecular classification of cancer: class discovery and class prediction by gene expression monitoring", Science 286, 531-537 (1991) (Nov. 1999).
Gosink, M et al., "Redirecting the specificity of ubiquitination by modifying ubiquitin-conjugating enzymes", Pro. Natl. Acad Sci, vol. 92, pp. 9117-9121, (Sep. 26, 1995).
Haupt, Y. et al., "Mdm2 promotes the rapid degradation of p53", Nature 387, 296-299 (May 15, 1997).
Heldring, et al., "Estrogen Receptors: How Do They Signal and What are Their Targets", Physiological Reviews (2007), vol. 87, pp. 905-931 (Jul. 2007).
Hennessy, EJ, et al., "Discovery of aminopiperidine-based Smac mimetics as IAP antagonists", Bioorg. Med. Chem. Lett., 22(4), 1690-1694 (Feb. 15, 2012).
Hines, J., et al., "Posttranslational protein knockdown coupled to receptor tyrosine kinase activation with phosphoPROTACs", Proc Natl Acad Sci USA 110, 8942-8947 (May 28, 2013).
Hird, AW, et al., "Structure-based design and synthesis of tricyclic IAP (Inhibitors of Apoptosis Proteins) inhibitors", Bioorg. Med. Chem. Lett., 24(7): 1820-1824 (Apr. 1, 2014).
Hoffmann, J. et al. Characterization of New Estrogen Receptor Destabilizing Compounds: Effects on Estrogen-Sensitive and Tamoxifen-Resistant Breast Cancer. JNCI Journal of the National Cancer Institute 96, 210-218 (Feb. 4, 2004).
Hon, et al., "Structural basis for the recognition of hydroxyproline in Hlf-1 alpha by pVHL", Nature 417, 975-978 (Jun. 27, 2002).
Hu, Jiantao, et al., Discovery of ERD-308 as a Highly Potent Proteolysis Targeting Chimera (PROTAC) Degrader of Estrogen Receptor (ER), DOI: 10.1021/acs.jmedchem.8b01572, Journal of

(56) References Cited

OTHER PUBLICATIONS

Medicinal Chemistry, vol. 62, pp. 1420-1442, (Jan. 18, 2019), http://dx.doi.org/10.1021/acs.jmedchem.8b01572.
Huang HT, et al. (2018) "A Chemoproteomic Approach to Query the Degradable Kinome Using a Multi-kinase Degrader." *Cell Chem Biol* 25(1):88-99 e86 (Jan. 18, 2018).
Huang, et al., (2016) "Drugging the undruggables: exploring the ubiquitin system for drug development." *Cell Res* 26(4):484-498 (Apr. 2016).
Hughes, et al., (2017) "Molecular recognition of ternary complexes: a new dimension in the structure-guided design of chemical degraders." *Essays Biochem* 61 (5):505-516 (Nov. 8, 2017).
Ivan, M., et al., "HIFa Targeted for VHL-Mediated Destruction by Proline Hydroxylation: Implications for O2 Sensing", Science, vol. 292, No. 5516, pp. 464-468, (Apr. 20, 2001).
Jang, E.R. et al., "Targeted Degradation of Proteins by PROTACs," Curr. Protoc. Chem. Biol., 2010, vol. 2, No. 2, pp. 71-87 (Jun. 1, 2010).
Jiang, et al., "Synthesis of 7alpha-substituted derivatives of 17beta-estradiol", Steroids 71(5), May 2006, 334-342 (Abstract) (May 7, 2006).
Jordan, V.C. et al., "A monohydroxylated metabolite of tamoxifen with potent antioestrogenic activity", Endocrinol 75: 305-316 (Nov. 1977).
Jordan, V.C., et al., Selective Estrogen-Receptor Modulators and Antihormonal Resistance in Breast Cancer, Journal of Clinical Oncology, vol. 25, No. 36, (Dec. 20, 2007).
Jordan, V.C., et al., The evolution of nonsteroidal antiestrogens to become selective estrogen receptor modulators, 90 Steroids, 3-12 (2014) (Jun. 17, 2014).
Kim, K. B. & Crews, C. M. From epoxomicin to carfilzomib: chemistry, biology, and medical outcomes. Nat Prod Rep 30, 600-604 (May 2013).
Kim, K.S., "Discovery of tetrahydroisoquinoline-based bivalent heterodimeric IAP antagonists", Bioorg. Med. Chem. Lett. 24(21), 5022-5029 (Sep. 15, 2014).
Knott, Edward (1955). "Compounds containing sulphur chromophores. Part I. The action of bases on heterocyclic sulphide quarternary salts", Journal of The Chemical Society (resumed). 10.1039/jr9550000916. 949-954 (1955).
Kronke, et al., "Lenalidomide Causes Selective Degradation of IKZF1 and IKZF3 in Multiple Myeloma Cells", Science 343, 301-305 (Jan. 17, 2014).
Lai, A. et al. Identification of GDC-0810 (ARN-810), an Orally Bioavailable Selective Estrogen Receptor Degrader (SERD) that Demonstrates Robust Activity in Tamoxifen-Resistant Breast Cancer Xenografts. J. Med. Chem. 58, 4888 4904 (May 22, 2015).
Lai, A.C., et al., "Modular PROTAC Design for the Degradation of Oncogenic BCR-ABL", Angew Chem Int Ed Engl 55, 807-810 (Jan. 11, 2016).
Lai, et al., (2017) "Induced protein degradation: an emerging drug discovery paradigm." *Nat Rev Drug Discov* 16(2): 101-114 (Feb. 2017).
Lala, et al., "Role of nitric oxide in tumor progression: Lessons from experimental tumors", Cancer and Metastasis Reviews 17:91-106 (Mar. 1998).
Lebraud, H., et al., "Protein Degradation by In-Cell Self-Assembly of Proteolysis Targeting Chimeras", ACS Central Science, 2, 927-934 (Dec. 5, 2016).
Lee, et al., "Targeted Degradation of the Aryl Hydrocarbon Receptor by the PROTAC Approach: A Useful Chemical Genetic Tool", ChemBioChem vol. 8, Issue 17, pp. 2058-2062, (Nov. 23, 2007).
Levine, et al., Targeting the androgen receptor with steroid conjugates, J. Med. Chem., vol. 57., No. 20. pp. 8224-8237, (Jun. 17, 2014).
Li, Yan, et al., "Single polymer-drug conjugate carrying two drugs for fixed-dose co-delivery", Medicinal Chemistry, 2014, vol. 4(10): 676-683 (Jan. 2014).

Liu, Hong, et al., "Bioactivation of the selective estrogen receptor modulator desmethylated arzoxifene to quinoids: 4'-fluoro substitution prevents quinoid formation", Chem. Res. Toxicol. 2005, 18, 162-173 (Feb. 18, 2005).
Liu, K., et al., "Design and biological characterization of hybrid compounds of curcumin and thalidomide for multiple myeloma", Org. Biomol. Chem. 2013, 11, 4757-4763 (Mar. 25, 2013).
Lopez-Girona, A. et al., Cereblon is a direct protein target for immunomodulatory and antiproliferative activities of lenalidomide and pomalidomide, Leukemia 26: 2326-2335, (Nov. 2012).
Lu, et al., "Hijacking the E3 ubiquitin ligase cereblon to efficiently target BRD4", Chem Biol 22(6), (Jun. 4, 2015), 755-763.
Lu, et al., "The myeloma drug lenalidomide promotes the cereblon-dependent destruction of ikaros proteins", Science 343, 305-309 (Jan. 17, 2014).
Ma, C. X., Reinert, T., Chmielewska, I. & Ellis, M. J. Mechanisms of aromatase inhibitor resistance. Nature Reviews Cancer 15, 261-275 (May 2015).
Mahalingam, D., et al., "Targeting HSP90 for cancer therapy", Br J Cancer 100, 1523-1529 (May 19, 2009).
Maniaci C, et al. (2017) "Homo-PROTACs: bivalent small-molecule dimerizers of the VHL E3 ubiquitin ligase to induce self-degradation." *Nat Commun* 8(1):830 1-13 (Oct. 10, 2017).
Mannhold, R., et al., "IAP antagonists: promising candidates for cancer therapy", Drug Discov. Today, 15 (5-6), 210-219 (Mar. 15, 2010).
McGuire, et al., "Taxol: A unique antineoplastic agent with significant activity in advanced ovarian epithelial neoplasms", Ann. Intern, Med., 111:273, (Aug. 15, 1989).
Medline Plus Trusted Health Information for You, www.nlm.nih.gov/medlineplus/cancer.html pp. 1-10, (2007).
Min, Jung-hyun, et al., "Structure of an HIV-1-alpha—pVHL complex: hydroxyproline recognition in signaling", (Jun. 7, 2002, 296: 1886-1889.
Miyazaki, M., et al., "Discovery of DS-5272 as a promising candidate: a potent and orally active p53-MDM2 interaction inhibitor", Bioorg. Med. Chem. Lett. (Mar. 31, 2015) 23, 2360-2367.
Muller, G., et al., "Amino-Substituted Thalodomide Analogs: Potent Inhibitors of TNF-α Production", Bioorganic & Medicinal Chemistry Letters 9 (Jun. 7, 1999) 1625-1630.
Nathan, M. R. & Schmid, P. A Review of Fulvestrant in Breast Cancer. Oncol Ther 5, 17-29 (May 8, 2017).
Ndubaku, C, et al., "Antagonism of c-IAP and XIAP proteins is required for efficient induction of cell death by small-molecule IAP antagonists", ACS Chem Biol. 4(7):557-566 (Jul. 17, 2009).
Nektesa, T.K., et al., "Chemical biology: Greasy tags for protein removal", Nature 487, 308-309 (Jul. 18, 2012).
Nekiesa, Targeted protein degradation by PROTACs. Pharmacology & Therapeutics 174, 138-144 (Feb. 14, 2017).
Nikolovska-Coleska, et al., "Interaction of a cyclic, Bivalent Smac Mimetic with the X-linked inhibitor of apoptosis protein", Biochemistry, 2008, 47(37), pp. 9811-9824 (Aug. 22, 2008).
Ohoka, N. et al. SNIPER(TACC3) induces cytoplasmic vacuolization and sensitizes cancer cells to Bortezomib. Cancer Sci. 108, 1032-1041 (Apr. 26, 2017).
Oost, T.K et al., "Discovery of potent antagonists of the antiapoptotic protein XIAP for the treatment of cancer", Journal of Medicinal Chemistry 2004, 47, 4417-4426 (Jul. 31, 2004).
Ottis P, et al. (2017) "Assessing Different E3 Ligases for Small Molecule Induced Protein Ubiquitination and Degradation." *ACS Chem Biol* 12(10):2570-2578.
Ottis, et al., (2017) "Proteolysis-Targeting Chimeras: Induced Protein Degradation as a Therapeutic Strategy." *ACS Chem Biol* 12(4):892-898 (Aug. 2, 2017).
Perez, HL," Discovery of potent heterodimeric antagonists of inhibitor of apoptosis proteins (IAPs) with sustained antitumor activity", J. Med. Chem. 58(3), 1556-1562 (Jan. 13, 2015).
Poutiainen, PK, et al., "Design, synthesis, and biological evaluation of nonsteroidal cycloalkane[d]isoxazole-containing androgen receptor modulators", J. Med. Chem. 55, 6316-6327 (Jul. 2, 2012).
Powell, C. E. et al. Chemically Induced Degradation of Anaplastic Lymphoma Kinase (ALK). J. Med. Chem. 61, 4249-4255 (Apr. 24, 2018).

(56) References Cited

OTHER PUBLICATIONS

Puppala, D. et al., "Development of an Aryl Hydrocarbon Receptor Antagonist Using the Proteolysis-Targeting chimeric Molecules Approach: A Potential Tool for Chemoprevention," Mol. Pharmacol., 2008, vol. 73, No. 4, pp. 1064-1071.
Qin, Zhihui, et al., "Benzothiophene selective estrogen receptor modulators with modulated oxidative activity and receptor affinity", J. Med Chem 2007, 50, 2682-2692 (Jan. 4, 2008).
Raina, et al., (2017) "Targeted protein knockdown using small molecule degraders." Curr Opin Chern Biol 39:46-53 (Aug. 2017).
Raina, K., et al., "PROTAC-induced BET protein degradation as a therapy for castration-resistant prostate cancer", Proc Natl Acad Sci USA 113, 7124-7129 (Jun. 6, 2016).
Remillard D, et al. (2017) "Degradation of the BAF Complex Factor BRD9 by Heterobifunctional Ligands." *Angew Chem Int Ed Engl* 56(21):5738-5743 (Apr. 8, 2017).
Rew, Y, et al., "Discovery of AM-7209, a potent and selective 4-amidobenzoic acid inhibitor of the MDM2-p53 interaction", J Med Chem. Dec. 26, 2014;57(24):10499-10511. doi: 10.1021/jm501550p. Epub Dec. 4, 2014. PubMed PMID: 25384157. (J. Med. Chem. (2014) 57, 10499-10511 Rew, et al.) (Dec. 26, 2014).
Robertson, J. F. R. Fulvestrant (Faslodex)—how to make a good drug better. Oncologist 12, 774-784 (Jul. 2007).
Rodriguez-Gonzalez, et al., "Targeting steroid hormone receptors for ubiquitination and degradation in breast and prostate cancer", Oncogene. 27(57), 7201-7211 (Dec. 4, 2008).
Rotili, D., et al., "Photoactivable peptides for identifying enzyme-substrate and protein-protein interactions", Chem Commun (Carob) 47(5), 1488-1490 (Feb. 2011).
Ruchelman, A., et al., "Isosteric analogs of lenalidominde and pomalidomide: Synthesis and biological activity", Bioorganic & Medicinal Chemistry Letters 23 (2013) 360-365 (Oct. 27, 2012).
Sakamoto, et al., "Development of Protacs to target cancer-promoting proteins for ubiquitination and degradation", Mol Cell Proteomics. 2(12), 1350-1358 (Dec. 2003).
Sakamoto, et al., "Protacs: chimeric molecules that target proteins to the Skp 1-Cullin-F box complex for ubiquitination and degradation", Proc Natl Acad Sci U S A.98(15), 8554-8559 (Jul. 17, 2001).
Salami, J. & Crews, C. M. Waste disposal—An attractive strategy for cancer therapy. Science 355, 1163-1167 (Mar. 17, 2017).
Schiedel, M., et al., "Chemically Induced Degradation of Sirtuin 2 (Sirt2) by a Proteolysis Targeting Chimera (PROTAC) Based on Sirtuin Rearranging Ligands (SirReals)", J Med Chem. (Apr. 5, 2017), 61:482-491.
Schneekloth, et al., Chemical Genetic Control of Protein Levels: Selective in Vivo Targeted Degradation, J Am Chem Soc. 126(12), 3748-3754 (Mar. 31, 2004).
Schneekloth, et al., Targeted intracellular protein degradation induced by a small molecule: En route to chemical proteomics, Bioorg. Med. Chem. Lett. 18 (2008) 5904-5908 (Nov. 15, 2008).
Smith, et al., "Targeted Intracellular Protein Degradation Induced by a Small Molecule: En Route to Chemical Proteomics", Bioorg Med Chem Lett. 18(22), 5904-5908 (Nov. 15, 2008).
Stanton, et al., (2018) "Chemically induced proximity in biology and medicine." *Science* 359(6380) (Mar. 9, 2018).
Stewart, Scott G., et al., "Efforts toward elucidating Thalidomide's molecular target: An Expedient Synthesis of the first Thalidomide Biotin Analogue" Org. Biomol., Chem., 2010, 8, 4059-4062 (Jul. 13, 2010).
STN transcript excerpt Nov. 24, 2017 "Compounds containing sulfur Chromophores v. Complex cyanines" (Nov. 24, 2017).
Stoppler, Melissa Conrad., Endometriosis [online], "Endometriosis Definition and Facts" URL http://www.medicinenet.com/endometriosis/article.htm, retrieved on (Apr. 5, 2017).
Stoppler, Melissa Conrad., Endometriosis [online], "What about surgery for Endometriosis?" URL http://www.medicinenet.com/endometriosis/article.htm, retrieved on (Apr. 5, 2017).
Suh, N. et al. Arzoxifene, a new selective estrogen receptor modulator for chemoprevention of experimental breast cancer. Cancer Res. 61, 8412-8415 (Dec. 2001).
Sun, B. et al. BET protein proteolysis targeting chimera (PROTAC) exerts potent lethal activity against mantle cell lymphoma cells. Leukemia 32, 343-352 (Feb. 2018).
Sun, D, et al., "Discovery of AMG 232, a potent, selective, and orally bioavailable MDM2-p53 inhibitor in clinical development", J Med Chem.;57(4):1454-72. doi: 10.1021/jm401753e. Epub Feb. 5, 2014. PubMed PMID: 24456472. (Feb. 27, 2014).
Sun, et al., "Potent bivalent Smac mimetics: effect of the linker on binding to inhibitor apoptosis proteins (IAPs) and anticancer activity", J. Med. Chem. 53, 3306-3318 (Apr. 13, 2011).
Toure, et al., (2016) "Small-Molecule PROTACS: New Approaches to Protein Degradation." *Angew Chem Int Ed Engl* 55(6):1966-1973 (Feb. 5, 2016).
Trewartha D, Carter K. "Advances in prostate cancer treatment", Nat Rev Drug Discov;12(11):823-824. doi: 10.1038/nrd4068. PubMed PMID: 24172327 (Nov. 2013).
Turk, B. E., "Binding of thalidomide to alphal-acid glycoprotein may be involved in its inhibition of tumor necrosis factor alpha production", Proc. Natl. Acad. Sci. U.S.A. 1996, 93, 7552-7556 (Jul. 23, 1996).
Vamos M., et al., "Expedient synthesis of highly potent antagonists of inhibitor of apoptosis proteins (IAPs) with unique selectivity for ML-IAP", ACS Chem. Biol., 8(4), 725-732 (Jan. 16, 2013).
Van Molle, et al., "Dissecting fragment-based lead discovery at the von Hippel-Lindau protein:hypoxia inducible factor 1a protein-protein interface", Chem Biol. 19(10), 1300-1312 (Oct. 26, 2012).
Vassilev, et al., "In vivo activation of the p53 pathway by small-molecule antagonists of MDM2", Science 303, 844-848 (Feb. 6, 2004).
Vazquez, A. et al., "The genetics of the p53 pathway, apoptosis and cancer therapy", Nat. Rev. Drug. Dis., 7, 979-982 (Dec. 2008).
Vu, B. et al. "Discovery of RG7112: a small-molecule MDM2 inhibitor in clinical development", ACS Med. Chem. Lett. (2013) 4, 466-469 (Apr. 2, 2013).
Wang J, et al., "Discovery of novel second mitochondrial-derived activator of caspase mimetics as selective inhibitor or apoptosis protein inhibitors", J. Pharmacol. Exp. Ther., 349(2): 319-29 (May 2014).
Wang, C. et al. Estrogen induces c-myc gene expression via an upstream enhancer activated by the estrogen receptor and the AP-1 transcription factor. Mol. Endocrinol. 25, 1527-1538 (Aug. 11, 2011).
Wang, S., et al. "Small-molecule inhibitors of the MDM2-p53 protein-protein interaction (MDM2 inhibitors) in clinical trials for cancer treatment", J. Med. Chem. (2015) 58, 1038-1052 (Nov. 14, 2014).
Wang, S., et al. "Temporal activation of p53 by a specific MDM2 inhibitor is selectively toxic to tumors and leads to complete tumor growth inhabitation", PNAS USA (2008) 105, 3933-3938 (Mar. 3, 2008).
Weir, H. M. et al. AZD9496: An Oral Estrogen Receptor Inhibitor That Blocks the Growth of ER-Positive and ESR1-Mutant Breast Tumors in Preclinical Models. Cancer Res. 76, 3307-3318 (Jun. 1, 2016).
Willson, T.M. et al., "3-[4-(1,2-Diphenylbut-1-Enyl)Phenyl] Acrylic Acid: A non-steroidal estrogen with functional selectivity for bone over uterus in rats", Journal of Medicinal Chemistry, American Chemical Society, US May 25, 1994, vol. 37 No. 11, pp. 1550-1552 (May 1, 1994).
Winter, et al., "Phthalimide Conjugation as a strategy for in vivo target protein degradation", Science, 2015 vol. 348 (6241), pp. 1376-1381 [Pub online: May 21, 2015].
Yu, F. & Bender, W. The mechanism of tamoxifen in breast cancer prevention. Breast Cancer Research 3, A74 (May 31, 2001).
Zengerle, et al., "Selective Small Molecule Induced Degradation of the BET Bromodomain Protein BRD4" ACS Chemical Biology, vol. 10, pp. 1770-1777 (Jun. 2, 2015).
Zhang B et al., "Small-molecule MDM2-p5 3 inhibitors: recent advances", Future Med. Chem. (Apr. 29, 2015) 7, 631-645.
Zhang, D. et al., "Targeted Degradation of Proteins by Small Molecules: A Novel Tool for Functional Proteomics," comb Chem. High Throughput Screen., 2004, vol. 7, No. 7, pp. 689-697 (Nov. 2004).

(56) References Cited

OTHER PUBLICATIONS

Zhong, H. et al., "Modulation of Hypoxia-inducible Factor 1α Expression by the Epidermal Growth Factor/Phosphatidylinositol 3-Kinase/PTEN/AKT/FRAP Pathway in Human Prostate Cancer Cells: Implications for Tumor Angiogenesis and Therapeutics", Cancer res, (2000) 60(6), 1541-1545 (Mar. 15, 2000).

Zhou, B., et al. "Discovery of a Small-Molecule Degrader of Bromodomain and Extra-Terminal (BET) Proteins with Picomolar Cellular Potencies and Capable of Achieving Tumor Regression", J Med Chem. 61(2), 462-481 (2018) (DOI:10.1021/acs.jmedchem. 6b01816) (Mar. 24, 2017).

U.S. Appl. No. 15/881,318, filed Jan. 26, 2018, US 2018-0237418 A1.

\* cited by examiner

MODULATORS OF ESTROGEN RECEPTOR PROTEOLYSIS AND ASSOCIATED METHODS OF USE

MODULATORS OF ESTROGEN RECEPTOR PROTEOLYSIS AND ASSOCIATED METHODS OF USE

CROSS-REFERENCE TO RELATED APPLICATIONS

The present application is a divisional application of Ser. No. 15/881,318, filed 31 Mar. 2020, published as U.S. patent Ser. No. 10,604,506, and titled MODULATORS OF ESTROGEN RECEPTOR PROTEOLYSIS AND ASSOCIATED METHODS OF USE, which claims priority to and the benefit of U.S. Provisional Patent Application No. 62/450,740, filed 26 Jan. 2017, and U.S. Provisional Patent Application No. 62/587,378, filed 16 Nov. 2017, each of which is incorporated by reference herein in its entirety for all purposes.

INCORPORATION BY REFERENCE

U.S. patent application Ser. No. 15/230,354, filed on Aug. 5, 2016; and U.S. patent application Ser. No. 15/206,497 filed 11 Jul. 2016; and U.S. patent application Ser. No. 15/209,648 filed 13 Jul. 2016; and U.S. patent application Ser. No. 14/730,728, filed on Oct. 11, 2017; and U.S. patent application Ser. No. 14/686,640, filed on Apr. 14, 2015, published as U.S. Patent Application Publication No. 2015/0291562; and U.S. patent application Ser. No. 14/792,414, filed on Jul. 6, 2015, published as U.S. Patent Application Publication No. 2016/0058872; and U.S. patent application Ser. No. 14/371,956, filed on Jul. 11, 2014, published as U.S. Patent Application Publication No. 2014/0356322; and U.S. patent application Ser. No. 15/074,820, filed on Mar. 18, 2016, published as U.S. Patent Application Publication No. 2016/0272639; and U.S. Patent Application Ser. No. 62/452,972, filed Jan. 31, 2017; and U.S. patent application Ser. No. 15/706,064, filed on Sep. 15, 2017, entitled "INDOLE DERIVATIVES AS ESTROGEN RECEPTOR DEGRADES", filed Jan. 31, 2017; and International Patent Application No. PCT/US2016/023258, filed Mar. 18, 2016, published as International Patent Application Publication No. W2016/149668, are incorporated herein by reference in their entirety. Furthermore, all references cited herein are incorporated by reference herein in their entirety.

FIELD OF THE INVENTION

The description provides bifunctional compounds comprising a target protein binding moiety and an E3 ubiquitin ligase binding moiety, and associated methods of use. The bifunctional compounds are useful as modulators of targeted ubiquitination, especially with respect to estrogen receptor (ER), which are degraded and/or otherwise inhibited by bifunctional compounds according to the present disclosure, and the treatment of disease and conditions mediated by the ER, e.g. the treatment of breast cancer.

BACKGROUND

The estrogen receptor (ER) is a member of the nuclear hormone receptor family and functions as a ligand-activated transcription factor involved with the up and down regulation of gene expression. The natural hormone for the estrogen receptor is 17-beta-estradiol (E2) and closely related metabolites. Binding of estradiol to the estrogen receptor causes a dimerization of the receptor and the dimer in turn binds to estrogen response elements (ERE's) on DNA. The ER-DNA complex recruits other transcription factors responsible for the transcription of DNA downstream from the ERE into mRNA, which is eventually translated into protein. Alternatively, the interaction of ER with DNA may be indirect through the intermediacy of other transcription factors, most notably fos and jun. Since the expression of a large number of genes is regulated by the estrogen receptor and since the estrogen receptor is expressed in many cell types, modulation of the estrogen receptor through binding of either natural hormones or synthetic ER ligands can have profound effects on the physiology and pathophysiology of the organism.

A variety of diseases have their etiology and/or pathology mediated by the ER. Collectively these diseases are called estrogen-dependent diseases. Estrogens are critical for sexual development in females. In addition, estrogens play an important role in maintaining bone density, regulation of blood lipid levels, and appear to have neuroprotective effects. Consequently, decreased estrogen production in post-menopausal women is associated with a number of diseases such as osteoporosis, atherosclerosis, depression and cognitive disorders. Conversely, certain types of proliferative diseases such as breast and uterine cancer and endometriosis are stimulated by estrogens and therefore antiestrogens (i.e. estrogen antagonists) have utility in the prevention and treatment of these types of disorders.

There are two different forms of the estrogen receptor, usually referred to as $\alpha$ and $\beta$, each encoded by a separate gene (ESR1 and ESR2, respectively). Both ERs are widely expressed in different tissue types, but there are some notable differences in their expression patterns. The ER$\alpha$ is found in endometrium, breast cancer cells, ovarian stroma cells, and the hypothalamus. In males, ER$\alpha$ protein is found in the epithelium of the efferent ducts. The expression of the ER$\beta$ protein has been documented in kidney, brain, bone, heart, lungs, intestinal mucosa, prostate, and endothelial cells. Development therefore of selective ligands may therefore preserve the beneficial aspects of estrogen.

Breast cancer is the most common malignancy to affect women and worldwide, the incidence of the disease is increasing. Estrogens, in particular, act as endocrine growth factors for at least one-third of breast cancers, and depriving the tumor of this stimulus is a recognized therapy for advanced disease in premenopausal women, this is achieved by the ablation of ovarian function through surgical, radio therapeutics, or medical means and, in postmenopausal women, by the use of aromatase inhibitors.

An alternative approach to estrogen withdrawal is to antagonize estrogen with antiestrogens. These are drugs that bind to and compete for estrogen receptors (ER) present in estrogen-responsive tissue. Conventional nonsteroidal antiestrogens, such as tamoxifen, compete efficiently for ER binding but their effectiveness is often limited by the partial agonism they display, which results in an incomplete blockade of estrogen-mediated activity. A specific or "pure" antiestrogen with high affinity for ER and without any agonist effect may have advantages over conventional nonsteroidal anti-estrogens in the treatment of estrogen-dependent disease. Fulvestrant is the first of a new class of potent pure anti-estrogens and is completely free of the partial agonist, estrogen-like activity, associated with currently available antiestrogens like tamoxifen.

As such, there is a need for other approaches to antagonize the ER receptor. One approach would be to develop selective ER down regulators or degraders that reduce ER expression at either the transcript or protein level.

Several methods are available for the manipulation of protein levels, including proteolysis targeting chimeric molecules (PROTACs), which contain a ligand that recognizes the target protein linked to a ligand that binds to a specific E3 ubiquitin ligase. It would be desirable to have a small molecule which can simultaneously bind ER and an E3 ubiquitin ligase and which promotes ubiquitination of ER and leads to degradation of ER by the proteasome.

Most small molecule drugs bind enzymes or receptors in tight and well-defined pockets. On the other hand, protein-protein interactions are notoriously difficult to target using small molecules due to their large contact surfaces and the shallow grooves or flat interfaces involved. E3 ubiquitin ligases (of which hundreds are known in humans) confer substrate specificity for ubiquitination, and therefore, are more attractive therapeutic targets than general proteasome inhibitors due to their specificity for certain protein substrates. The development of ligands of E3 ligases has proven challenging, in part due to the fact that they must disrupt protein-protein interactions. However, recent developments have provided specific ligands which bind to these ligases. For example, since the discovery of nutlins, the first small molecule E3 ligase inhibitors, additional compounds have been reported that target E3 ligases but the field remains underdeveloped. For example, since the discovery of Nutlins, the first small molecule E3 ligase mouse double minute 2 homolog (MDM2) inhibitors, additional compounds have been reported that target MDM2 (i.e., human double minute 2 or HDM2) E3 ligases (J. Di, et al. *Current Cancer Drug Targets* (2011), 11(8), 987-994).

Tumor suppressor gene p53 plays an important role in cell growth arrest and apoptosis in response to DNA damage or stress (A. Vazquez, et al. *Nat. Rev. Drug. Dis.* (2008), 7, 979-982), and inactivation of p53 has been suggested as one of the major pathway for tumor cell survival (A. J. Levine, et al. *Nature* (2000), 408, 307-310). In cancer patients, about 50% were found with p53 mutation (M. Hollstein, et al. *Science* (1991), 233, 49-53), while patients with wild type p53 were often found p53 down regulation by MDM2 through the protein-protein interaction of p53 and MDM2 (P. Chene, et al. *Nat. Rev. Cancer* (2003), 3, 102-109). Under normal cell condition without oncogenic stress signal, MDM2 keeps p53 at low concentration. In response to DNA damage or cellular stress, p53 level increases, and that also causes increase in MDM2 due to the feedback loop from p53/MDM2 auto regulatory system. In other words, p53 regulates MDM2 at the transcription level, and MDM2 regulates p53 at its activity level (A. J. Levine, et al. *Genes Dev.* (1993) 7, 1126-1132).

Several mechanisms can explain p53 down regulation by MDM2. First, MDM2 binds to N-terminal domain of p53 and blocks expression of p53-responsive genes (J. Momand, et al. *Cell* (1992), 69, 1237-1245). Second, MDM2 shuttles p53 from nucleus to cytoplasm to facilitate proteolytic degradation (J. Roth, et al. *EMBO J.* (1998), 17, 554-564). Lastly, MDM2 carries intrinsic E3 ligase activity of conjugating ubiquitin to p53 for degradation through ubiquitin-dependent 26s proteasome system (UPS) (Y. Haupt, et al. *Nature* (1997) 387, 296-299). As such, because MDM2 functions as E3 ligase, recruiting MDM2 to a disease causing protein and effectuating its ubiquitination and degradation is an approach of high interest for drug discovery.

One E3 ligase with exciting therapeutic potential is the von Hippel-Lindau (VHL) tumor suppressor, the substrate recognition subunit of the E3 ligase complex VCB, which also consists of elongins B and C, Cul2 and Rbx1. The primary substrate of VHL is Hypoxia Inducible Factor 1α (HIF-1α), a transcription factor that upregulates genes such as the pro-angiogenic growth factor VEGF and the red blood cell inducing cytokine erythropoietin in response to low oxygen levels. The first small molecule ligands of Von Hippel Lindau (VHL) to the substrate recognition subunit of the E3 ligase were generated, and crystal structures were obtained confirming that the compound mimics the binding mode of the transcription factor HIF-1a, the major substrate of VHL.

Cereblon is a protein that in humans is encoded by the CRBN gene. CRBN orthologs are highly conserved from plants to humans, which underscores its physiological importance. Cereblon forms an E3 ubiquitin ligase complex with damaged DNA binding protein 1 (DDB1), Cullin-4A (CUL4A), and regulator of cullins 1 (ROC 1). This complex ubiquitinates a number of other proteins. Through a mechanism which has not been completely elucidated, cereblon ubquitination of target proteins results in increased levels of fibroblast growth factor 8 (FGF8) and fibroblast growth factor 10 (FGF10). FGF8 in turn regulates a number of developmental processes, such as limb and auditory vesicle formation. The net result is that this ubiquitin ligase complex is important for limb outgrowth in embryos. In the absence of cereblon, DDB1 forms a complex with DDB2 that functions as a DNA damage-binding protein.

Thalidomide, which has been approved for the treatment of a number of immunological indications, has also been approved for the treatment of certain neoplastic diseases, including multiple myeloma. In addition to multiple myeloma, thalidomide and several of its analogs are also currently under investigation for use in treating a variety of other types of cancer. While the precise mechanism of thalidomide's anti-tumor activity is still emerging, it is known to inhibit angiogenesis. Recent literature discussing the biology of the imides includes Lu et al. *Science* 343, 305 (2014) and Krnke et al. *Science* 343, 301 (2014).

Significantly, thalidomide and its analogs e.g. pomolinamiode and lenalinomide, are known to bind cereblon. These agents bind to cereblon, altering the specificity of the complex to induce the ubiquitination and degradation of Ikaros (IKZF1) and Aiolos (IKZF3), transcription factors essential for multiple myeloma growth. Indeed, higher expression of cereblon has been linked to an increase in efficacy of imide drugs in the treatment of multiple myeloma.

Inhibitors of Apoptosis Proteins (IAPs) are a protein family involved in suppressing apoptosis, i.e. cell death. The human IAP family includes 8 members, and numerous other organisms contain IAP homologs. IAPs contain an E3 ligase specific domain and baculoviral IAP repeat (BIR) domains that recognize substrates, and promote their ubiquitination. IAPs promote ubiquitination and can directly bind and inhibit caspases. Caspases are proteases (e.g. caspase-3, caspase-7 and caspace-9) that implement apoptosis. As such, through the binding of caspases, IAPs inhibit cell death. However, pro-apoptotic stimuli can result in the release of mitochondrial proteins DIABLO (also known as second mitochondria-derived activator of caspases or SMAC) and HTRA2 (also known as Omi). Binding of DIABLO and HTRA2 appears to block IAP activity.

SMAC interacts with essentially all known IAPs including XIAP, c-IAP1, c-IAP2, NIL-IAP, Bruce, and survivin.

The first four amino acids (AVPI) of mature SMAC bind to a portion of IAPs, which is believed to be essential for blocking the anti-apoptotic effects of IAPs.

Bifunctional compounds such as those that are described in U.S. patent Application Publications 2015-0291562 and 2014-0356322 (incorporated herein by reference), function to recruit endogenous proteins to an E3 ubiquiuin ligase for degradation. In particular, the publications describe bifunctional or proteolysis targeting chimeric (PROTAC) compounds, which find utility as modulators of targeted ubiquitination of a variety of polypeptides and other proteins (such as estrogen receptor), which are then degraded and/or otherwise inhibited by the bifunctional compounds.

An ongoing need exists in the art for effective treatments for disease associated with overexpression or aggregation of ER. However, non-specific effects, and the inability to target and modulate ER, remain as obstacles to the development of effective treatments. As such, small-molecule therapeutic agents that target ER and that leverage or potentiate cereblon's, MDM2's, and IAPs' substrate specificity would be very useful.

SUMMARY

The present disclosure describes bifunctional compounds which function to recruit endogenous proteins to an E3 ubiquitin ligase for degradation, and methods of using the same. In particular, the present disclosure provides bifunctional or proteolysis targeting chimeric (PROTAC) compounds, which find utility as modulators of targeted ubiquitination of a variety of polypeptides and other proteins, such as estrogen receptor, which are then degraded and/or otherwise inhibited by the bifunctional compounds as described herein. An advantage of the compounds provided herein is that a broad range of pharmacological activities is possible, consistent with the degradation/inhibition of targeted polypeptides from virtually any protein class or family. In addition, the description provides methods of using an effective amount of the compounds as described herein for the treatment or amelioration of a disease condition, such as cancer, e.g., breast cancer.

As such, in one aspect the disclosure provides bifunctional or PROTAC compounds, which comprise an E3 ubiquitin ligase binding moiety (i.e., a ligand for an E3 ubqutin ligase or "ULM" group), and a moiety that binds a target protein (i.e., a protein/polypeptide targeting ligand or "PTM" group) such that the target protein/polypeptide is placed in proximity to the ubiquitin ligase to effect degradation (and inhibition) of that protein. In a preferred embodiment, the ULM (ubiquitination ligase modulator) can be Von Hippel-Lindau E3 ubiquitin ligase (VHL) binding moiety (VLM), or a cereblon E3 ubiquitin ligase binding moiety (CLM), or a mouse double miniute 2 homolog (MDM2) E3 ubiquitin ligase binding moiety (MLM), or an IAP E3 ubiquitin ligase binding moiety (i.e., a "ILM"). For example, the structure of the bifunctional compound can be depicted as:

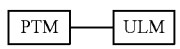

The respective positions of the PTM and ULM moieties (e.g., VLM, CLM, MLM or ILM) as well as their number as illustrated herein is provided by way of example only and is not intended to limit the compounds in any way. As would be understood by the skilled artisan, the bifunctional compounds as described herein can be synthesized such that the number and position of the respective functional moieties can be varied as desired.

In certain embodiments, the bifunctional compound further comprises a chemical linker ("L"). In this example, the structure of the bifunctional compound can be depicted as:

where PTM is a protein/polypeptide targeting moiety, L is a linker, e.g., a bond or a chemical group coupling PTM to ULM, and ULM is a IAP E3 ubiquitin ligase binding moiety, or a Von Hippel-Lindau E3 ubiquitin ligase (VHL) binding moiety (VLM), or a cereblon E3 ubiquitin ligase binding moiety (CLM), or a mouse double minute 2 homolog (MDM2) E3 ubiquitin ligase binding moiety (MLM).

For example, the structure of the bifunctional compound can be depicted as:

wherein: PTM is a protein/polypeptide targeting moiety; "L" is a linker (e.g. a bond or a chemical linker group) coupling the PTM and at least one of VLM, CLM, MLM, ILM, or a combination thereof; VLM is Von Hippel-Lindau E3 ubiquitin ligase binding moiety that binds to VHL E3 ligase; CLM is cereblon E3 ubiquitin ligase binding moiety that binds to cereblon; MLM is an MDM2 E3 ubiquitin ligase binding moiety; and ILM is a IAP binding moiety which binds to IAP.

In certain preferred embodiments, the ILM is an AVPI tetrapeptide fragment. As such, in certain additional embodiments, the ILM of the bifunctional compound comprises the amino acids alanine (A), valine (V), proline (P), and isoleucine (I) or their unnatural mimetics, respectively. In additional embodiments, the amino acids of the AVPI tetrapeptide fragment are connected to each other through amide bonds (i.e., —C(O)NH— or —NHC(O)—).

In certain embodiments, the compounds as described herein comprise multiple independently selected ULMs, multiple PTMs, multiple chemical linkers or a combination thereof.

In certain embodiments, ILM comprises chemical moieties such as those described herein.

In additional embodiments, VLM can be hydroxyproline or a derivative thereof. Furthermore, other contemplated VLMs are included in U.S. Patent Application Publication No. 2014/03022523, which as discussed above, is incorporated herein in its entirety.

In an embodiment, the CLM comprises a chemical group derived from an imide, a thioimide, an amide, or a thioamide. In a particular embodiment, the chemical group is a phthalimido group, or an analog or derivative thereof. In a certain embodiment, the CLM is thalidomide, lenalidomide, pomalidomide, analogs thereof, isosteres thereof, or derivatives thereof. Other contemplated CLMs are described in U.S. Patent Application Publication No. 2015/0291562, which is incorporated herein in its entirety.

In certain embodiments, MLM can be nutlin or a derivative thereof. Furthermore, other contemplated MLMs are included in U.S. patent application Ser. No. 15/206,497 filed 11 Jul. 2016, which as discussed above, is incorporated herein in its entirety. In certain additional embodiments, the MLM of the bifunctional compound comprises chemical moieties such as substituted imidazolines, substituted spiroindolinones, substituted pyrrolidines, substituted piperidinones, substituted morpholinones, substituted pyrrolopyrimidines, substituted imidazolopyridines, substituted thiazoloimidazoline, substituted pyrrolopyrrolidinones, and substituted isoquinolinones.

In additional embodiments, the MLM comprises the core structures mentioned above with adjacent bis-aryl substitutions positioned as cis- or trans-configurations.

In certain embodiments, "L" is a bond. In additional embodiments, the linker "L" is a connector with a linear non-hydrogen atom number in the range of 1 to 20. The connector "L" can contain, but not limited to the functional groups such as ether, amide, alkane, alkene, alkyne, ketone, hydroxyl, carboxylic acid, thioether, sulfoxide, and sulfone. The linker can contain aromatic, heteroaromatic, cyclic, bicyclic and tricyclic moieties. Substitution with halogen, such as Cl, F, Br and I can be included in the linker. In the case of fluorine substitution, single or multiple fluorines can be included.

In certain embodiments, VLM is a derivative of trans-3-hydroxyproline, where both nitrogen and carboxylic acid in trans-3-hydroxyproline are functionalized as amides.

In certain embodiments, CLM is a derivative of piperidine-2,6-dione, where piperidine-2,6-dione can be substituted at the 3-position, and the 3-substitution can be bicyclic hetero-aromatics with the linkage as C—N bond or C—C bond. Examples of CLM can be, but not limited to, pomalidomide, lenalidomide and thalidomide and their derivatives.

In an additional aspect, the description provides therapeutic compositions comprising an effective amount of a compound as described herein or salt form thereof, and a pharmaceutically acceptable carrier. The therapeutic compositions modulate protein degradation and/or inhibition in a patient or subject, for example, an animal such as a human, and can be used for treating or ameliorating disease states or conditions which are modulated through the degraded/inhibited protein. In certain embodiments, the therapeutic compositions as described herein may be used to effectuate the degradation of proteins of interest for the treatment or amelioration of a disease, e.g., cancer. In yet another aspect, the present disclosure provides a method of ubiquitinating/degrading a target protein in a cell. In certain embodiments, the method comprises administering a bifunctional compound as described herein comprising an ILM and a PTM, a PTM and a VLM, or a PTM and a CLM, or a PTM and a MLM, preferably linked through a linker moiety, as otherwise described herein, wherein the VLM/ILM/CLM/MLM is coupled to the PTM through a linker to target protein that binds to PTM for degradation. Similarly, the PTM can be coupled to VLM or CLM or MLM or ILM through a linker to target a protein or polypeptide for degradation. Degradation of the target protein will occur when the target protein is placed in proximity to the E3 ubiquitin ligase, thus resulting in degradation/inhibition of the effects of the target protein and the control of protein levels. The control of protein levels afforded by the present disclosure provides treatment of a disease state or condition, which is modulated through the target protein by lowering the level of that protein in the cells of a patient.

In still another aspect, the description provides methods for treating or ameliorating a disease, disorder or symptom thereof in a subject or a patient, e.g., an animal such as a human, comprising administering to a subject in need thereof a composition comprising an effective amount, e.g., a therapeutically effective amount, of a compound as described herein or salt form thereof, and a pharmaceutically acceptable carrier, wherein the composition is effective for treating or ameliorating the disease or disorder or symptom thereof in the subject.

In another aspect, the description provides methods for identifying the effects of the degradation of proteins of interest in a biological system using compounds according to the present disclosure.

The preceding general areas of utility are given by way of example only and are not intended to be limiting on the scope of the present disclosure and appended claims. Additional objects and advantages associated with the compositions, methods, and processes of the present disclosure will be appreciated by one of ordinary skill in the art in light of the instant claims, description, and examples. For example, the various aspects and embodiments of the disclosure may be utilized in numerous combinations, all of which are expressly contemplated by the present description. These additional aspects and embodiments are expressly included within the scope of the present disclosure. The publications and other materials used herein to illuminate the background of the disclosure, and in particular cases, to provide additional details respecting the practice, are incorporated by reference.

BRIEF DESCRIPTION OF THE DRAWINGS

The accompanying drawings, which are incorporated into and form a part of the specification, illustrate several embodiments of the present disclosure and, together with the description, serve to explain the principles of the disclosure. The drawings are only for the purpose of illustrating an embodiment of the disclosure and are not to be construed as limiting the disclosure. Further objects, features and advantages of the disclosure will become apparent from the following detailed description taken in conjunction with the accompanying figures showing illustrative embodiments of the disclosure, in which:

(FIG. 1A) Exemplary PROTACs comprise a protein targeting moiety (PTM; darkly shaded rectangle), a ubiquitin ligase binding moiety (ULM; lightly shaded triangle), and optionally a linker moiety (L; black line) coupling or tethering the PTM to the ULM. (FIG. 1B) Illustrates the functional use of the PROTACs as described herein. Briefly, the ULM recognizes and binds to a specific E3 ubiquitin ligase, and the PTM binds and recruits a target protein bringing it into close proximity to the E3 ubiquitin ligase. Typically, the E3 ubiquitin ligase is complexed with an E2 ubiquitin-conjugating protein, and either alone or via the E2 protein catalyzes attachment of ubiquitin (dark circles) to a lysine on the target protein via an isopeptide bond. The poly-ubiquitinated protein (far right) is then targeted for degradation by the proteosomal machinery of the cell.

DETAILED DESCRIPTION

The following is a detailed description provided to aid those skilled in the art in practicing the present disclosure. Those of ordinary skill in the art may make modifications and variations in the embodiments described herein without departing from the spirit or scope of the present disclosure. All publications, patent applications, patents, figures and other references mentioned herein are expressly incorporated by reference in their entirety.

Figure 1A:
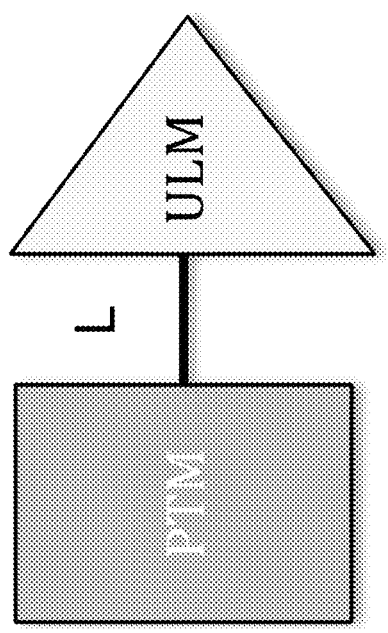
FIGS. 1A and 1B. Illustration of general principle for PROTAC function.
Figure 1B:
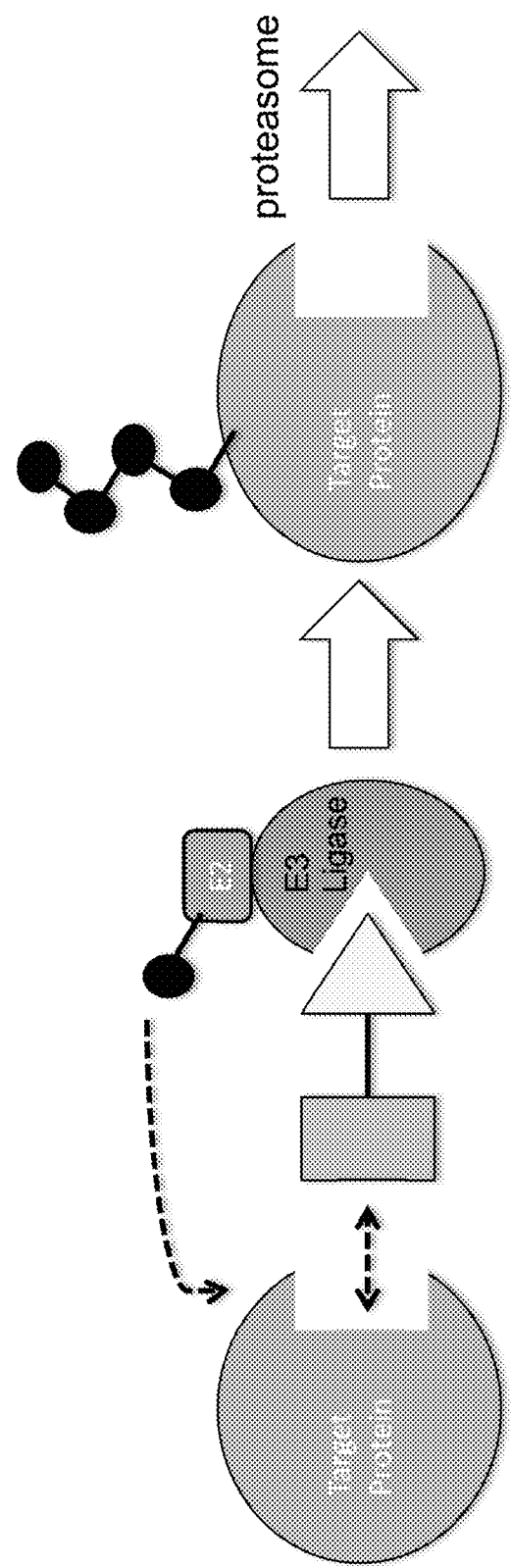

Presently described are compositions and methods that relate to the surprising and unexpected discovery that an E3 ubiquitin ligase protein (e.g., inhibitors of apoptosis proteins (IAP), a Von Hippel-Lindau E3 ubiquitin ligase (VHL), a cereblon E3 ubiquitin ligase, or a mouse double minute 2 homolog (MDM2) E3 ubiquitin ligase) ubiquitinates a target protein once it and the target protein are placed in proximity by a bifunctional or chimeric construct that binds the E3 ubiquitin ligase protein and the target protein. Accordingly the present disclosure provides such compounds and compositions comprising an E3 ubiquintin ligase binding moiety ("ULM") coupled to a protein target binding moiety ("PTM"), which result in the ubiquitination of a chosen target protein (such as estrogen receptor [ER]), which leads to degradation of the target protein by the proteasome (see FIGS. 1A and 1B). The present disclosure also provides a library of compositions and the use thereof.

In certain aspects, the present disclosure provides compounds which comprise a ligand, e.g., a small molecule ligand (i.e., having a molecular weight of below 2,000, 1,000, 500, or 200 Daltons), which is capable of binding to a ubiquitin ligase, such as IAP, VHL, MDM2, or cereblon. The compounds also comprise a moiety that is capable of binding to target protein, in such a way that the target protein is placed in proximity to the ubiquitin ligase to effect degradation (and/or inhibition) of that protein. Small molecule can mean, in addition to the above, that the molecule is non-peptidyl, that is, it is not generally considered a peptide, e.g., comprises fewer than 4, 3, or 2 amino acids. In accordance with the present description, the PTM, ULM or PROTAC molecule can be a small molecule.

Unless otherwise defined, all technical and scientific terms used herein have the same meaning as commonly understood by one of ordinary skill in the art to which this disclosure belongs. The terminology used in the description is for describing particular embodiments only and is not intended to be limiting of the disclosure.

Where a range of values is provided, it is understood that each intervening value, to the tenth of the unit of the lower limit unless the context clearly dictates otherwise (such as in the case of a group containing a number of carbon atoms in which case each carbon atom number falling within the range is provided), between the upper and lower limit of that range and any other stated or intervening value in that stated range is encompassed within the disclosure. The upper and lower limits of these smaller ranges may independently be included in the smaller ranges is also encompassed within the disclosure, subject to any specifically excluded limit in the stated range. Where the stated range includes one or both of the limits, ranges excluding either both of those included limits are also included in the disclosure.

The following terms are used to describe the present disclosure. In instances where a term is not specifically defined herein, that term is given an art-recognized meaning by those of ordinary skill applying that term in context to its use in describing the present disclosure.

The articles "a" and "an" as used herein and in the appended claims are used herein to refer to one or to more than one (i.e., to at least one) of the grammatical object of the article unless the context clearly indicates otherwise. By way of example, "an element" means one element or more than one element.

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e., "one or the other but not both") when preceded by terms of exclusivity, such as "either," "one of," "only one of," or "exactly one of."

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

As used herein in the specification and in the claims, the phrase "at least one," in reference to a list of one or more elements, should be understood to mean at least one element selected from anyone or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a nonlimiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

It should also be understood that, in certain methods described herein that include more than one step or act, the order of the steps or acts of the method is not necessarily limited to the order in which the steps or acts of the method are recited unless the context indicates otherwise.

The terms "co-administration" and "co-administering" or "combination therapy" refer to both concurrent administration (administration of two or more therapeutic agents at the same time) and time varied administration (administration of one or more therapeutic agents at a time different from that of the administration of an additional therapeutic agent or agents), as long as the therapeutic agents are present in the patient to some extent, preferably at effective amounts, at the same time. In certain preferred aspects, one or more of the present compounds described herein, are coadministered in combination with at least one additional bioactive agent, especially including an anticancer agent. In particularly preferred aspects, the co-administration of compounds results in synergistic activity and/or therapy, including anti-cancer activity.

The term "compound", as used herein, unless otherwise indicated, refers to any specific chemical compound disclosed herein and includes tautomers, regioisomers, geometric isomers, and where applicable, stereoisomers, including optical isomers (enantiomers) and other stereoisomers (diastereomers) thereof, as well as pharmaceutically acceptable salts and derivatives, including prodrug and/or deuterated forms thereof where applicable, in context. Deuterated small molecules contemplated are those in which one or more of the hydrogen atoms contained in the drug molecule have been replaced by deuterium.

Within its use in context, the term compound generally refers to a single compound, but also may include other compounds such as stereoisomers, regioisomers and/or optical isomers (including racemic mixtures) as well as specific enantiomers or enantiomerically enriched mixtures of disclosed compounds. The term also refers, in context to prodrug forms of compounds which have been modified to facilitate the administration and delivery of compounds to a site of activity. It is noted that in describing the present compounds, numerous substituents and variables associated with same, among others, are described. It is understood by those of ordinary skill that molecules which are described herein are stable compounds as generally described hereunder. When the bond is shown, both a double bond and single bond are represented or understood within the context of the compound shown and well-known rules for valence interactions.

The term "ubiquitin ligase" refers to a family of proteins that facilitate the transfer of ubiquitin to a specific substrate protein, targeting the substrate protein for degradation. For example, IAP an E3 ubiquitin ligase protein that alone or in combination with an E2 ubiquitin-conjugating enzyme causes the attachment of ubiquitin to a lysine on a target protein, and subsequently targets the specific protein substrates for degradation by the proteasome. Thus, E3 ubiquitin ligase alone or in complex with an E2 ubiquitin conjugating enzyme is responsible for the transfer of ubiquitin to targeted proteins. In general, the ubiquitin ligase is involved in polyubiquitination such that a second ubiquitin is attached to the first; a third is attached to the second, and so forth. Polyubiquitination marks proteins for degradation by the proteasome. However, there are some ubiquitination events that are limited to mono-ubiquitination, in which only a single ubiquitin is added by the ubiquitin ligase to a substrate molecule. Mono-ubiquitinated proteins are not targeted to the proteasome for degradation, but may instead be altered in their cellular location or function, for example, via binding other proteins that have domains capable of binding ubiquitin. Further complicating matters, different lysines on ubiquitin can be targeted by an E3 to make chains. The most common lysine is Lys48 on the ubiquitin chain. This is the lysine used to make polyubiquitin, which is recognized by the proteasome.

The term "patient" or "subject" is used throughout the specification to describe an animal, preferably a human or a domesticated animal, to whom treatment, including prophylactic treatment, with the compositions according to the present disclosure is provided. For treatment of those infections, conditions or disease states which are specific for a specific animal such as a human patient, the term patient refers to that specific animal, including a domesticated animal such as a dog or cat or a farm animal such as a horse, cow, sheep, etc. In general, in the present disclosure, the term patient refers to a human patient unless otherwise stated or implied from the context of the use of the term.

The term "effective" is used to describe an amount of a compound, composition or component which, when used within the context of its intended use, effects an intended result. The term effective subsumes all other effective amount or effective concentration terms, which are otherwise described or used in the present application.

Compounds and Compositions

In one aspect, the description provides compounds comprising an E3 ubiquitin ligase binding moiety ("ULM") that is an IAP E3 ubiquitin ligase binding moiety (an "ILM"), a cereblon E3 ubiquitin ligase binding moiety (a "CLM"), a Von Hippel-Lindae E3 ubiquitin ligase (VHL) binding moiety (VLM), and/or a mouse double minute 2 homologue (MDM2) E3 ubiquitin ligase binding moiety (MLM). In an exemplary embodiment, the ULM is coupled to a target protein binding moiety (PTM) via a chemical linker (L) according to the structure:

PTM-L-ULM (A)

wherein L is a bond or a chemical linker group, ULM is a E3 ubiquitin ligase binding moiety, and PTM is a target protein binding moiety. The number and/or relative positions of the moieties in the compounds illustrated herein is provided by way of example only. As would be understood by the skilled artisan, compounds described herein can be synthesized with any desired number and/or relative position of the respective functional moieties.

The terms ULM, ILM, VLM, MLM, and CLM are used in their inclusive sense unless the context indicates otherwise. For example, the term ULM is inclusive of all ULMs, including those that bind IAP (i.e., ILMs), MDM2 (i.e., MLM), cereblon (i.e., CLM), and VHL (i.e., VLM). Further, the term ILM is inclusive of all possible IAP E3 ubiquitin ligase binding moieties, the term MLM is inclusive of all possible MDM2 E3 ubiquitin ligase binding moieties, the term VLM is inclusive of all possible VHL binding moieties, and the term CLM is inclusive of all cereblon binding moieties.

In another aspect, the present disclosure provides bifunctional or multifunctional compounds (e.g., PROTACs) useful for regulating protein activity by inducing the degradation of a target protein. In certain embodiments, the compound comprises an ILM or a VLM or a CLM or a MLM coupled, e.g., linked covalently, directly or indirectly, to a moiety that binds a target protein (i.e., a protein targeting moiety or a "PTM"). In certain embodiments, the ILM/VLM/CLM/MLM and PTM are joined or coupled via a chemical linker (L). The ILM binds the IAP E3 ubiquitin ligase, the VLM binds VHL, CLM binds the cereblon E3 ubiquitin ligase, and MLM binds the MDM2 E3 ubiquitin ligase, and the PTM recognizes a target protein and the interaction of the respective moieties with their targets facilitates the degradation of the target protein by placing the target protein in proximity to the ubiquitin ligase protein. An exemplary bifunctional compound can be depicted as:

PTM-ILM (B)

PTM-CLM (C)

PTM-VLM (D)

PTM-MLM (E)

In certain embodiments, the bifunctional compound further comprises a chemical linker ("L"). For example, the bifunctional compound can be depicted as:

PTM-L-ILM (F)

PTM-L-CLM (G)

PTM-L-VLM (H)

PTM-L-MLM (I)

wherein the PTM is a protein/polypeptide targeting moiety, the L is a chemical linker, the ILM is a IAP E3 ubiquitin ligase binding moiety, the CLM is a cereblon E3 ubiquitin ligase binding moiety, the VLM is a VHL binding moiety, and the MLM is a MDM2 E3 ubiquitin ligase binding moiety.

In certain embodiments, the ULM (e.g., a ILM, a CLM, a VLM, or a MLM) shows activity or binds to the E3 ubiquitin ligase (e.g., IAP E3 ubiquitin ligase, cereblon E3 ubiquitin ligase, VHL, or MDM2 E3 ubiquitin ligase) with an $IC_{50}$ of less than about 200 PM. The $IC_{50}$ can be determined according to any method known in the art, e.g., a fluorescent polarization assay.

In certain additional embodiments, the bifunctional compounds described herein demonstrate an activity with an $IC_{50}$ of less than about 100, 50, 10, 1, 0.5, 0.1, 0.05, 0.01, 0.005, 0.001 mM, or less than about 100, 50, 10, 1, 0.5, 0.1, 0.05, 0.01, 0.005, 0.001 µM, or less than about 100, 50, 10, 1, 0.5, 0.1, 0.05, 0.01, 0.005, 0.001 nM, or less than about 100, 50, 10, 1, 0.5, 0.1, 0.05, 0.01, 0.005, 0.001 pM.

In certain embodiments, the compounds as described herein comprise multiple PTMs (targeting the same or different protein targets), multiple ULMs, one or more ULMs (i.e., moieties that bind specifically to multiple/different E3 ubiquitin ligase, e.g., VHL, IAP, cereblon, and/or MDM2) or a combination thereof. In any of the aspects or embodiments described herein, the PTMs and ULMs (e.g., ILM, VLM, CLM, and/or MLM) can be coupled directly or via one or more chemical linkers or a combination thereof. In additional embodiments, where a compound has multiple ULMs, the ULMs can be for the same E3 ubiquitin ligase or each respective ULM can bind specifically to a different E3 ubiquitin ligase. In still further embodiments, where a compound has multiple PTMs, the PTMs can bind the same target protein or each respective PTM can bind specifically to a different target protein.

In certain embodiments, where the compound comprises multiple ULMs, the ULMs are identical. In additional embodiments, the compound comprising a plurality of ULMs (e.g., ULM, ULM', etc.), at least one PTM coupled to a ULM directly or via a chemical linker (L) or both. In certain additional embodiments, the compound comprising a plurality of ULMs further comprises multiple PTMs. In still additional embodiments, the PTMs are the same or, optionally, different. In still further embodiments, wherein the PTMs are different, the respective PTMs may bind the same protein target or bind specifically to a different protein target.

In certain embodiments, the compound may comprise a plurality of ULMs and/or a plurality of ULM's. In further embodiments, the compound comprising at least two different ULMs, a plurality of ULMs, and/or a plurality of ULM's further comprises at least one PTM coupled to a ULM or a ULM' directly or via a chemical linker or both. In any of the embodiments described herein, a compound comprising at least two different ULMs can further comprise multiple PTMs. In still additional embodiments, the PTMs are the same or, optionally, different. In still further embodiments, wherein the PTMs are different the respective PTMs may bind the same protein target or bind specifically to a different protein target. In still further embodiments, the PTM itself is a ULM (or ULM'), such as an ILM, a VLM, a CLM, a MLM, an ILM', a VLM', a CLM', and/or a MLM'.

In additional embodiments, the description provides the compounds as described herein including their enantiomers, diastereomers, solvates and polymorphs, including pharmaceutically acceptable salt forms thereof, e.g., acid and base salt forms.

The term "independently" is used herein to indicate that the variable, which is independently applied, varies independently from application to application.

The term "alkyl" shall mean within its context a linear, branch-chained or cyclic fully saturated hydrocarbon radical or alkyl group, preferably a $C_1$-$C_{10}$, more preferably a $C_1$-$C_6$, alternatively a $C_1$-$C_3$ alkyl group, which may be optionally substituted. Examples of alkyl groups are methyl, ethyl, n-butyl, sec-butyl, n-hexyl, n-heptyl, n-octyl, n-nonyl, n-decyl, isopropyl, 2-methylpropyl, cyclopropyl, cyclopropylmethyl, cyclobutyl, cyclopentyl, cyclopen-tylethyl, cyclohexylethyl and cyclohexyl, among others. In certain embodiments, the alkyl group is end-capped with a halogen group (At, Br, Cl, F, or I). In certain preferred embodiments, compounds according to the present disclosure which may be used to covalently bind to dehalogenase enzymes. These compounds generally contain a side chain (often linked through a polyethylene glycol group) which terminates in an alkyl group which has a halogen substituent (often chlorine or bromine) on its distal end which results in covalent binding of the compound containing such a moiety to the protein.

The term "Alkenyl" refers to linear, branch-chained or cyclic $C_2$-$C_{10}$ (preferably $C_2$-$C_6$) hydrocarbon radicals containing at least one C=C bond.

The term "Alkynyl" refers to linear, branch-chained or cyclic $C_2$-$C_{10}$ (preferably $C_2$-$C_6$) hydrocarbon radicals containing at least one C≡C bond.

The term "alkylene" when used, refers to a —$(CH_2)_n$— group (n is an integer generally from 0-6), which may be optionally substituted. When substituted, the alkylene group preferably is substituted on one or more of the methylene groups with a $C_1$-$C_6$ alkyl group (including a cyclopropyl group or a t-butyl group), but may also be substituted with one or more halo groups, preferably from 1 to 3 halo groups or one or two hydroxyl groups, O—($C_1$-$C_6$ alkyl) groups or amino acid sidechains as otherwise disclosed herein. In certain embodiments, an alkylene group may be substituted with a urethane or alkoxy group (or other group) which is further substituted with a polyethylene glycol chain (of from 1 to 10, preferably 1 to 6, often 1 to 4 ethylene glycol units) to which is substituted (preferably, but not exclusively on the distal end of the polyethylene glycol chain) an alkyl chain substituted with a single halogen group, preferably a chlorine group. In still other embodiments, the alkylene (often, a methylene) group, may be substituted with an amino acid sidechain group such as a sidechain group of a natural or unnatural amino acid, for example, alanine, β-alanine, arginine, asparagine, aspartic acid, cysteine, cystine, glutamic acid, glutamine, glycine, phenylalanine, histidine, isoleucine, lysine, leucine, methionine, proline, serine, threonine, valine, tryptophan or tyrosine.

The term "unsubstituted" shall mean substituted only with hydrogen atoms. A range of carbon atoms which includes $C_0$ means that carbon is absent and is replaced with H. Thus, a range of carbon atoms which is $C_0$-$C_6$ includes carbons atoms of 1, 2, 3, 4, 5 and 6 and for $C_0$, H stands in place of carbon.

The term "substituted" or "optionally substituted" shall mean independently (i.e., where more than substituent occurs, each substituent is independent of another substituent) one or more substituents (independently up to five substitutents, preferably up to three substituents, often 1 or 2 substituents on a moiety in a compound according to the present disclosure and may include substituents which themselves may be further substituted) at a carbon (or nitrogen) position anywhere on a molecule within context, and includes as substituents hydroxyl, thiol, carboxyl, cyano (C≡N), nitro ($NO_2$), halogen (preferably, 1, 2 or 3 halogens, especially on an alkyl, especially a methyl group such as a trifluoromethyl), an alkyl group (preferably, $C_1$-$C_{10}$, more preferably, $C_1$-$C_6$), aryl (especially phenyl and substituted phenyl for example benzyl or benzoyl), alkoxy group (preferably, $C_1$-$C_6$ alkyl or aryl, including phenyl and substituted phenyl), thioether ($C_1$-$C_6$ alkyl or aryl), acyl (preferably, $C_1$-$C_6$ acyl), ester or thioester (preferably, $C_1$-$C_6$ alkyl or aryl) including alkylene ester (such that attachment is on the alkylene group, rather than at the ester function which is preferably substituted with a $C_1$-$C_6$ alkyl or aryl group), preferably, $C_1$-$C_6$ alkyl or aryl, halogen (preferably, F or Cl), amine (including a five- or six-membered cyclic alkylene amine, further including a $C_1$-$C_6$ alkyl amine or a $C_1$-$C_6$ dialkyl amine which alkyl groups may be substituted with one or two hydroxyl groups) or an optionally substituted —N($C_0$-$C_6$ alkyl)C(O)(O—$C_1$-$C_6$ alkyl) group (which may be optionally substituted with a polyethylene glycol chain to which is further bound an alkyl group containing a single halogen, preferably chlorine substituent), hydrazine, amido, which is preferably substituted with one or two $C_1$-$C_6$ alkyl groups (including a carboxamide which is optionally substituted with one or two $C_1$-$C_6$ alkyl groups), alkanol (preferably, $C_1$-$C_6$ alkyl or aryl), or alkanoic acid (preferably, $C_1$-$C_6$ alkyl or aryl). Substituents according to the present disclosure may include, for example —$SiR_1R_2R_3$ groups where each of $R_1$ and $R_2$ is as otherwise described herein and $R_3$ is H or a $C_1$-$C_6$ alkyl group, preferably $R_1$, $R_2$, $R_3$ in this context is a $C_1$-$C_3$ alkyl group (including an isopropyl or t-butyl group). Each of the above-described groups may be linked directly to the substituted moiety or alternatively, the substituent may be linked to the substituted moiety (preferably in the case of an aryl or heteraryl moiety) through an optionally substituted —$(CH_2)_m$— or alternatively an optionally substituted —$(OCH_2)_m$—, —$(OCH_2CH_2)_m$— or —$(CH_2CH_2O)_m$— group, which may be substituted with any one or more of the above-described substituents. Alkylene groups —$(CH_2)_m$— or —$(CH_2)_n$— groups or other chains such as ethylene glycol chains, as identified above, may be substituted anywhere on the chain. Preferred substitutents on alkylene groups include halogen or $C_1$-$C_6$ (preferably $C_1$-$C_3$) alkyl groups, which may be optionally substituted with one or two hydroxyl groups, one or two ether groups (O—$C_1$-$C_6$ groups), up to three halo groups (preferably F), or a sideshain of an amino acid as otherwise described herein and optionally substituted amide (preferably carboxamide substituted as described above) or urethane groups (often with one or two $C_0$-$C_6$ alkyl substitutents, which group(s) may be further substituted). In certain embodiments, the alkylene group (often a single methylene group) is substituted with one or two optionally substituted $C_1$-$C_6$ alkyl groups, preferably $C_1$-$C_4$ alkyl group, most often methyl or O-methyl groups or a sidechain of an amino acid as otherwise described herein. In the present disclosure, a moiety in a molecule may be optionally substituted with up to five substituents, preferably up to three substituents. Most often, in the present disclosure moieties which are substituted are substituted with one or two substituents.

The term "substituted" (each substituent being independent of any other substituent) shall also mean within its context of use $C_1$-$C_6$ alkyl, $C_1$-$C_6$ alkoxy, halogen, amido, carboxamido, sulfone, including sulfonamide, keto, carboxy, $C_1$-$C_6$ ester (oxyester or carbonylester), $C_1$-$C_6$ keto, urethane —O—C(O)—$NR_1R_2$ or —N($R_1$)—C(O)—O—$R_1$, nitro, cyano and amine (especially including a $C_1$-$C_6$ alkylene-$NR_1R_2$, a mono- or di-$C_1$-$C_6$ alkyl substituted amines which may be optionally substituted with one or two hydroxyl groups). Each of these groups contain unless otherwise indicated, within context, between 1 and 6 carbon atoms. In certain embodiments, preferred substituents will include for example, —NH—, —NHC(O)—, —O—, =O, —$(CH_2)_m$— (here, m and n are in context, 1, 2, 3, 4, 5 or 6), —S—, —S(O)—, $SO_2$— or —NH—C(O)—NH—, —$(CH_2)_n$OH, —$(CH_2)_n$SH, —$(CH_2)_n$COOH, $C_1$-$C_6$ alkyl, —$(CH_2)_n$O—($C_1$-$C_6$ alkyl), —$(CH_2)_n$C(O)—($C_1$-$C_6$ alkyl), —$(CH_2)_n$OC(O)—($C_1$-$C_6$ alkyl), —$(CH_2)_n$C(O)O—($C_1$-$C_6$ alkyl), —$(CH_2)_n$NHC(O)—$R_1$, —$(CH_2)_n$C(O)—$NR_1R_2$, —$(OCH_2)_n$OH, —$(CH_2O)_n$COOH, $C_1$-$C_6$ alkyl, —$(OCH_2)_n$O—($C_1$-$C_6$ alkyl), —$(CH_2O)_n$C(O)—($C_1$-$C_6$ alkyl), —$(OCH_2)_n$NHC(O)—$R_1$, —$(CH_2O)_n$C(O)—$NR_1R_2$, —$S(O)_2$—$R_S$, —S(O)—$R_S$ ($R_S$ is $C_1$-$C_6$ alkyl or a —$(CH_2)_m$—$NR_1R_2$ group), $NO_2$, CN or halogen (F, Cl, Br, I, preferably F or Cl), depending on the context of the use of the substituent. $R_1$ and $R_2$ are each, within context, H or a $C_1$-$C_6$ alkyl group (which may be optionally substituted with one or two hydroxyl groups or up to three halogen groups, preferably fluorine). The term "substituted" shall also mean, within the chemical context of the compound defined and substituent used, an optionally substituted aryl or heteroaryl group or an optionally substituted heterocyclic group as otherwise described herein. Alkylene groups may also be substituted as otherwise disclosed herein, preferably with optionally substituted $C_1$-$C_6$ alkyl groups (methyl, ethyl or hydroxymethyl or hydroxyethyl is preferred, thus providing a chiral center), a sidechain of an amino acid group as otherwise described herein, an amido group as described hereinabove, or a urethane group O—C(O)—$NR_1R_2$ group where $R_1$ and $R_2$ are as otherwise described herein, although numerous other groups may also be used as substituents.

Various optionally substituted moieties may be substituted with 3 or more substituents, preferably no more than 3 substituents and preferably with 1 or 2 substituents. It is noted that in instances where, in a compound at a particular position of the molecule substitution is required (principally, because of valency), but no substitution is indicated, then that substituent is construed or understood to be H, unless the context of the substitution suggests otherwise.

The term "aryl" or "aromatic", in context, refers to a substituted (as otherwise described herein) or unsubstituted monovalent aromatic radical having a single ring (e.g., benzene, phenyl, benzyl) or condensed rings (e.g., naphthyl, anthracenyl, phenanthrenyl, etc.) and can be bound to the compound according to the present disclosure at any available stable position on the ring(s) or as otherwise indicated in the chemical structure presented. Other examples of aryl groups, in context, may include heterocyclic aromatic ring systems, "heteroaryl" groups having one or more nitrogen, oxygen, or sulfur atoms in the ring (moncyclic) such as imidazole, furyl, pyrrole, furanyl, thiene, thiazole, pyridine, pyrimidine, pyrazine, triazole, oxazole or fused ring systems such as indole, quinoline, indolizine, azaindolizine, benzofurazan, etc., among others, which may be optionally substituted as described above. Among the heteroaryl groups which may be mentioned include nitrogen-containing heteroaryl groups such as pyrrole, pyridine, pyridone, pyridazine, pyrimidine, pyrazine, pyrazole, imidazole, triazole, triazine, tetrazole, indole, isoindole, indolizine, azaindolizine, purine, indazole, quinoline, dihydroquinoline, tetrahydroquinoline, isoquinoline, dihydroisoquinoline, tetrahydroisoquinoline, quinolizine, phthalazine, naphthyridine, quinoxaline, quinazoline, cinnoline, pteridine, imidazopyridine, imidazotriazine, pyrazinopyridazine, acridine, phenanthridine, carbazole, carbazoline, pyrimidine, phenanthroline, phenacene, oxadiazole, benzimidazole, pyrrolopyridine, pyrrolopyrimidine and pyridopyrimidine; sulfur-containing aromatic heterocycles such as thiophene and benzothiophene; oxygen-containing aromatic heterocycles such as furan, pyran, cyclopentapyran, benzofuran and isobenzofuran; and aromatic heterocycles comprising 2 or more hetero atoms selected from among nitrogen, sulfur and oxygen, such as thiazole, thiadizole, isothiazole, benzoxazole, benzothiazole, benzothiadiazole, phenothiazine, isoxazole, furazan, phenoxazine, pyrazoloxazole, imidazothiazole, thienofuran, furopyrrole, pyridoxazine, furopyridine, furopyrimidine, thienopyrimidine and oxazole, among others, all of which may be optionally substituted.

The term "substituted aryl" refers to an aromatic carbocyclic group comprised of at least one aromatic ring or of multiple condensed rings at least one of which being aromatic, wherein the ring(s) are substituted with one or more substituents. For example, an aryl group can comprise a substituent(s) selected from: —(CH$_2$)$_n$OH, —(CH$_2$)$_n$—O—(C$_1$-C$_6$)alkyl, —(CH$_2$)$_n$—O—(CH$_2$)$_n$—(C$_1$-C$_6$)alkyl, —(CH$_2$)$_n$—C(O)(C$_0$-C$_6$) alkyl, —(CH$_2$)$_n$—C(O)O(C$_0$-C$_6$) alkyl, —(CH$_2$)$_n$—OC(O)(C$_0$-C$_6$)alkyl, amine, mono- or di-(C$_1$-C$_6$ alkyl) amine wherein the alkyl group on the amine is optionally substituted with 1 or 2 hydroxyl groups or up to three halo (preferably F, Cl) groups, OH, COOH, C$_1$-C$_6$ alkyl, preferably CH$_3$, CF$_3$, OMe, OCF$_3$, NO$_2$, or CN group (each of which may be substituted in ortho-, meta- and/or para-positions of the phenyl ring, preferably para-), an optionally substituted phenyl group (the phenyl group itself is preferably connected to a PTM group, including a ULM group, via a linker group), and/or at least one of F, Cl, OH, COOH, CH$_3$, CF$_3$, OMe, OCF$_3$, NO$_2$, or CN group (in ortho-, meta- and/or para-positions of the phenyl ring, preferably para-), a naphthyl group, which may be optionally substituted, an optionally substituted heteroaryl, preferably an optionally substituted isoxazole including a methylsubstituted isoxazole, an optionally substituted oxazole including a methylsubstituted oxazole, an optionally substituted thiazole including a methyl substituted thiazole, an optionally substituted isothiazole including a methyl substituted isothiazole, an optionally substituted pyrrole including a methylsubstituted pyrrole, an optionally substituted imidazole including a methylimidazole, an optionally substituted benzimidazole or methoxybenzylimidazole, an optionally substituted oximidazole or methyloximidazole, an optionally substituted diazole group, including a methyldiazole group, an optionally substituted triazole group, including a methylsubstituted triazole group, an optionally substituted pyridine group, including a halo-(preferably, F) or methylsubstitutedpyridine group or an oxapyridine group (where the pyridine group is linked to the phenyl group by an oxygen), an optionally substituted furan, an optionally substituted benzofuran, an optionally substituted dihydrobenzofuran, an optionally substituted indole, indolizine or azaindolizine (2, 3, or 4-azaindolizine), an optionally substituted quinoline, and combinations thereof.

"Carboxyl" denotes the group —C(O)OR, where R is hydrogen, alkyl, substituted alkyl, aryl, substituted aryl, heteroaryl or substituted heteroaryl, whereas these generic substituents have meanings which are identical with definitions of the corresponding groups defined herein.

The term "heteroaryl" or "hetaryl" can mean but is in no way limited to an optionally substituted quinoline (which may be attached to the pharmacophore or substituted on any carbon atom within the quinoline ring), an optionally substituted indole (including dihydroindole), an optionally substituted indolizine, an optionally substituted azaindolizine (2, 3 or 4-azaindolizine) an optionally substituted benzimidazole, benzodiazole, benzoxofuran, an optionally substituted imidazole, an optionally substituted isoxazole, an optionally substituted oxazole (preferably methyl substituted), an optionally substituted diazole, an optionally substituted triazole, a tetrazole, an optionally substituted benzofuran, an optionally substituted thiophene, an optionally substituted thiazole (preferably methyl and/or thiol substituted), an optionally substituted isothiazole, an optionally substituted triazole (preferably a 1,2,3-triazole substituted with a methyl group, a triisopropylsilyl group, an optionally substituted —(CH$_2$)$_m$—O—C$_1$-C$_6$ alkyl group or an optionally substituted —(CH$_2$)$_m$—C(O)—O—C$_1$-C$_6$ alkyl group), an optionally substituted pyridine (2-, 3, or 4-pyridine) or a group according to the chemical structure:

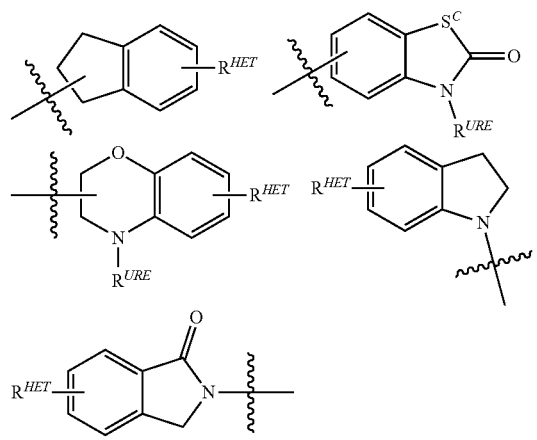

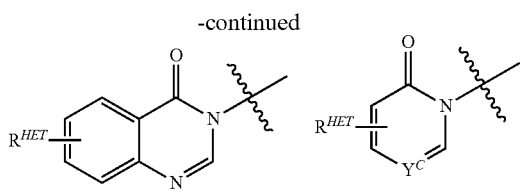

wherein:
- $S^c$ is $CHR^{SS}$, $NR^{URE}$, or O;
- $R^{HET}$ is H, CN, $NO_2$, halo (preferably Cl or F), optionally substituted $C_1$-$C_6$ alkyl (preferably substituted with one or two hydroxyl groups or up to three halo groups (e.g. $CF_3$), optionally substituted $O(C_1$-$C_6$ alkyl) (preferably substituted with one or two hydroxyl groups or up to three halo groups) or an optionally substituted acetylenic group —C≡C—$R_a$ where $R_a$ is H or a $C_1$-$C_6$ alkyl group (preferably $C_1$-$C_3$ alkyl);
- $R^{SS}$ is H, CN, $NO_2$, halo (preferably F or Cl), optionally substituted $C_1$-$C_6$ alkyl (preferably substituted with one or two hydroxyl groups or up to three halo groups), optionally substituted O—($C_1$-$C_6$ alkyl) (preferably substituted with one or two hydroxyl groups or up to three halo groups) or an optionally substituted —C(O)($C_1$-$C_6$ alkyl) (preferably substituted with one or two hydroxyl groups or up to three halo groups);
- $R^{URE}$ is H, a $C_1$-$C_6$ alkyl (preferably H or $C_1$-$C_3$ alkyl) or a —C(O)($C_1$-$C_6$ alkyl), each of which groups is optionally substituted with one or two hydroxyl groups or up to three halogen, preferably fluorine groups, or an optionally substituted heterocycle, for example piperidine, morpholine, pyrrolidine, tetrahydrofuran, tetrahydrothiophene, piperidine, piperazine, each of which is optionally substituted, and
- $Y^C$ is N or C—$R^{YC}$, where $R^{YC}$ is H, OH, CN, $NO_2$, halo (preferably Cl or F), optionally substituted $C_1$-$C_6$ alkyl (preferably substituted with one or two hydroxyl groups or up to three halo groups (e.g. $CF_3$), optionally substituted $O(C_1$-$C_6$ alkyl) (preferably substituted with one or two hydroxyl groups or up to three halo groups) or an optionally substituted acetylenic group —C≡C—$R_a$ where $R_a$ is H or a $C_1$-$C_6$ alkyl group (preferably $C_1$-$C_3$ alkyl).

The terms "aralkyl" and "heteroarylalkyl" refer to groups that comprise both aryl or, respectively, heteroaryl as well as alkyl and/or heteroalkyl and/or carbocyclic and/or heterocycloalkyl ring systems according to the above definitions.

The term "arylalkyl" as used herein refers to an aryl group as defined above appended to an alkyl group defined above. The arylalkyl group is attached to the parent moiety through an alkyl group wherein the alkyl group is one to six carbon atoms. The aryl group in the arylalkyl group may be substituted as defined above.

The term "Heterocycle" refers to a cyclic group which contains at least one heteroatom, e.g., N, O or S, and may be aromatic (heteroaryl) or non-aromatic. Thus, the heteroaryl moieties are subsumed under the definition of heterocycle, depending on the context of its use. Exemplary heteroaryl groups are described hereinabove.

Exemplary heterocyclics include: azetidinyl, benzimidazolyl, 1,4-benzodioxanyl, 1,3-benzodioxolyl, benzoxazolyl, benzothiazolyl, benzothienyl, dihydroimidazolyl, dihydropyranyl dihydrofuranyl, dioxanyl, dioxolanyl, ethyleneurea, 1,3-dioxolane, 1,3-dioxane, 1,4-dioxane, furyl, homopiperidinyl, imidazolyl, imidazolinyl, imidazolidinyl, indolinyl, indolyl, isoquinolinyl, isothiazolidinyl, isothiazolyl, isoxazolidinyl, isoxazolyl, morpholinyl, naphthyridinyl, oxazolidinyl, oxazolyl, pyridone, 2-pyrrolidone, pyridine, piperazinyl, N-methylpiperazinyl, piperidinyl, phthalimide, succinimide, pyrazinyl, pyrazolinyl, pyridyl, pyrimidinyl, pyrrolidinyl, pyrrolinyl, pyrrolyl, quinolinyl, tetrahydrofuranyl, tetrahydropyranyl, tetrahydroquinoline, thiazolidinyl, thiazolyl, thienyl, tetrahydrothiophene, oxane, oxetanyl, oxathiolanyl, thiane among others.

Heterocyclic groups can be optionally substituted with a member selected from the group consisting of alkoxy, substituted alkoxy, cycloalkyl, substituted cycloalkyl, cycloalkenyl, substituted cycloalkenyl, acyl, acylamino, acyloxy, amino, substituted amino, aminoacyl, aminoacyloxy, oxyaminoacyl, azido, cyano, halogen, hydroxyl, keto, thioketo, carboxy, carboxyalkyl, thioaryloxy, thioheteroaryloxy, thioheterocyclooxy, thiol, thioalkoxy, substituted thioalkoxy, aryl, aryloxy, heteroaryl, heteroaryloxy, heterocyclic, heterocyclooxy, hydroxyamino, alkoxyamino, nitro, —SO-alkyl, —SO-substituted alkyl, —SOaryl, —SO-heteroaryl, —SO$_2$-alkyl, —SO$_2$-substituted alkyl, —SO$_2$-aryl, oxo (=O), and —SO2-heteroaryl. Such heterocyclic groups can have a single ring or multiple condensed rings. Examples of nitrogen heterocycles and heteroaryls include, but are not limited to, pyrrole, imidazole, pyrazole, pyridine, pyrazine, pyrimidine, pyridazine, indolizine, isoindole, indole, indazole, purine, quinolizine, isoquinoline, quinoline, phthalazine, naphthylpyridine, quinoxaline, quinazoline, cinnoline, pteridine, carbazole, carboline, phenanthridine, acridine, phenanthroline, isothiazole, phenazine, isoxazole, phenoxazine, phenothiazine, imidazolidine, imidazoline, piperidine, piperazine, indoline, morpholino, piperidinyl, tetrahydrofuranyl, and the like as well as N-alkoxynitrogen containing heterocycles. The term "heterocyclic" also includes bicyclic groups in which any of the heterocyclic rings is fused to a benzene ring or a cyclohexane ring or another heterocyclic ring (for example, indolyl, quinolyl, isoquinolyl, tetrahydroquinolyl, and the like).

The term "cycloalkyl" can mean but is in no way limited to univalent groups derived from monocyclic or polycyclic alkyl groups or cycloalkanes, as defined herein, e.g., saturated monocyclic hydrocarbon groups having from three to twenty carbon atoms in the ring, including, but not limited to, cyclopropyl, cyclobutyl, cyclopentyl, cyclohexyl, cycloheptyl and the like. The term "substituted cycloalkyl" can mean but is in no way limited to a monocyclic or polycyclic alkyl group and being substituted by one or more substituents, for example, amino, halogen, alkyl, substituted alkyl, carbyloxy, carbylmercapto, aryl, nitro, mercapto or sulfo, whereas these generic substituent groups have meanings which are identical with definitions of the corresponding groups as defined in this legend.

"Heterocycloalkyl" refers to a monocyclic or polycyclic alkyl group in which at least one ring carbon atom of its cyclic structure being replaced with a heteroatom selected from the group consisting of N, O, S or P. "Substituted heterocycloalkyl" refers to a monocyclic or polycyclic alkyl group in which at least one ring carbon atom of its cyclic structure being replaced with a heteroatom selected from the group consisting of N, O, S or P and the group is containing one or more substituents selected from the group consisting of halogen, alkyl, substituted alkyl, carbyloxy, carbylmercapto, aryl, nitro, mercapto or sulfo, whereas these generic substituent group have meanings which are identical with definitions of the corresponding groups as defined in this legend.

The term "hydrocarbyl" shall mean a compound which contains carbon and hydrogen and which may be fully saturated, partially unsaturated or aromatic and includes aryl groups, alkyl groups, alkenyl groups and alkynyl groups.

The term "independently" is used herein to indicate that the variable, which is independently applied, varies independently from application to application.

The term "lower alkyl" refers to methyl, ethyl or propyl

The term "lower alkoxy" refers to methoxy, ethoxy or propoxy.

In any of the embodiments described herein, the W, X, Y, Z, G, G', R, R', R", Q1-Q4, A, and Rn can independently be covalently coupled to a linker and/or a linker to which is attached one or more PTM, ULM, ILM or ILM' groups.

Exemplary CLMs

Neo-Imide Compounds

In one aspect the description provides compounds useful for binding and/or inhibiting cereblon. In certain embodiments, the compound is selected from the group consisting of chemical structures:

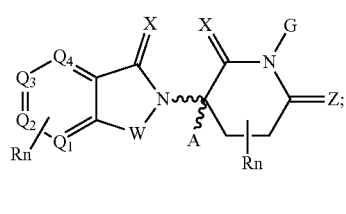
(a)

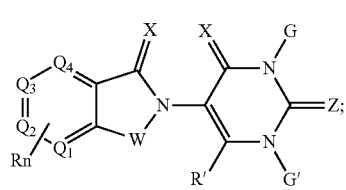
(b)

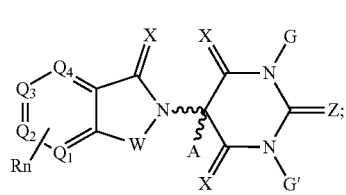
(c)

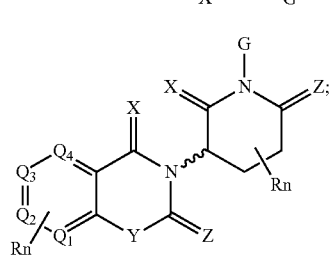
(d)

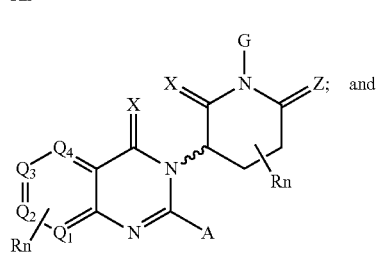
(e) and

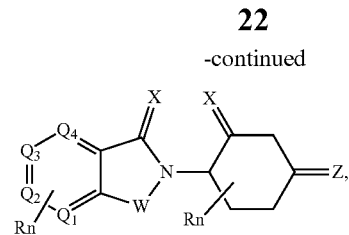
(f)

wherein:
W of Formulas (a) through (f) is independently selected from the group $CH_2$, CHR, C=O, $SO_2$, NH, and N-alkyl;
X of Formulas (a) through (f) is independently selected from the group O, S and $H_2$;
Y of Formulas (a) through (f) is independently selected from the group $CH_2$, —C=CR', NH, N-alkyl, N-aryl, N-hetaryl, N-cycloalkyl, N-heterocyclyl, O, and S;
Z of Formulas (a) through (f) is independently selected from the group O, and S or $H_2$ except that both X and Z cannot be $H_2$;
G and G' of Formulas (a) through (f) are independently selected from the group H, alkyl (linear, branched, optionally substituted), OH, R'OCOOR, R'OCONRR", $CH_2$-heterocyclyl optionally substituted with R', and benzyl optionally substituted with R';
Q1-Q4 of Formulas (a) through (f) represent a carbon C substituted with a group independently selected from R', N or N-oxide;
A of Formulas (a) through (f) is independently selected from the group H, alkyl (linear, branched, optionally substituted), cycloalkyl, Cl and F;
R of Formulas (a) through (f) comprises, but is not limited to: —CONR'R", —OR', —NR'R", —SR', —$SO_2$R', —$SO_2$NR'R", —CR'R"—, —CR'NR'R"—, (—CR'O)$_n$ R", -aryl, -hetaryl, -alkyl (linear, branched, optionally substituted), -cycloalkyl, -heterocyclyl, —P(O)(OR') R", —P(O)R'R", —OP(O)(OR')R", —OP(O)R'R", —Cl, —F, —Br, —I, —$CF_3$, —CN, —NR'$SO_2$NR'R", —NR'CONR'R", —CONR'COR", —NR'C(=N—CN) NR'R", —C(=N—CN)NR'R", —NR'C(=N—CN)R", —NR'C(=C—$NO_2$)NR'R", —$SO_2$NR'COR", —$NO_2$, —$CO_2$R', —C(C=N—OR')R", —CR'=CR'R", —CCR', —S(C=O)(C=N—R')R", —$SF_5$ and —$OCF_3$
R' and R" of Formulas (a) through (f) are independently selected from a bond, H, alkyl, cycloalkyl, aryl, heteroaryl, heterocyclic, —C(=O)R, heterocyclyl, each of which is optionally substituted;
n of Formulas (a) through (f) is an integer from 1-10 (e.g., 1-4, 1, 2, 3, 4, 5, 6, 7, 8, 9, or 10); ⌇ of Formulas (a) through (f) represents a bond that may be stereospecific ((R) or (S)) or non-stereospecific; and R$_n$ of Formulas (a) through (f) comprises 1-4 independent functional groups or atoms.

Exemplary CLMs

In any of the compounds described herein, the CLM comprises a chemical structure selected from the group:

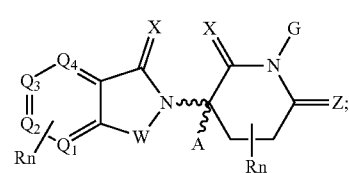
(a)

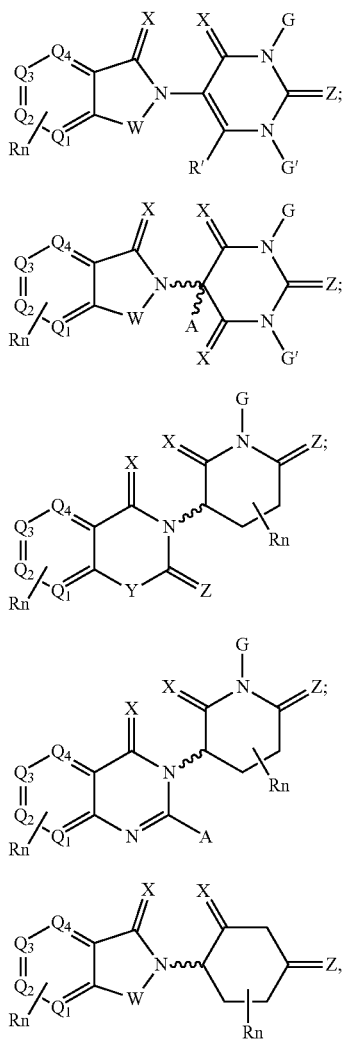

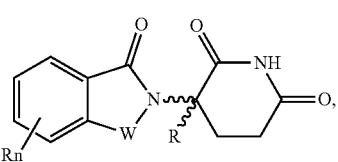

—SO2NR'R", —CR'R"—, —CR'NR'R"—, -aryl, -hetaryl, -alkyl, -cycloalkyl, -heterocyclyl, —P(O)(OR')R", —P(O)R'R", —OP(O)(OR')R", —OP(O)R'R", —Cl, —F, —Br, —I, —CF3, —CN, —NR'SO2NR'R", —NR'CONR'R", —CONR'COR", —NR'C(=N—CN)NR'R", —C(=N—CN)NR'R", —NR'C(=N—CN)R", —NR'C(=C—NO2)NR'R", —SO2NR'COR", —NO2, —CO2R', —C(C=N—OR')R", —CR'=CR'R", —CCR', —S(C=O)(C=N—R')R", —SF5 and —OCF3;

R' and R" of Formulas (a) through (f) are independently selected from a bond, H, alkyl, cycloalkyl, aryl, heteroaryl, heterocyclic, —C(=O)R, heterocyclyl, each of which is optionally substituted;

n of Formulas (a) through (f) is an integer from 1-10 (e.g., 1-4, 1, 2, 3, 4, 5, 6, 7, 8, 9, or 10); ∿∿∿ of Formulas (a) through (f) represents a bond that may be stereospecific ((R) or (S)) or non-stereospecific; and Rn of Formulas (a) through (f) comprises 1-4 independent functional groups or atoms, and optionally, one of which is modified to be covalently joined to a PTM, a chemical linker group (L), a ULM, CLM (or CLM') or combination thereof.

In certain embodiments described herein, the CLM or ULM comprises a chemical structure selected from the group:

Formula (g)

wherein:

W of Formula (g) is independently selected from the group CH$_2$, C=O, NH, and N-alkyl;

R of Formula (g) is independently selected from a H, methyl, or optionally substituted linear, branched, optionally substituted alkyl [e.g., optionally substituted $C_1$-$C_6$ alkyl (linear, branched, optionally substituted)];

∿∿∿ of Formula (g) represents a bond that may be stereospecific ((R) or (S)) or non-stereospecific; and Rn of Formula (g) comprises 1-4 independently selected functional groups or atoms, and optionally, one of which is modified to be covalently joined to a PTM, a chemical linker group (L), a ULM, CLM (or CLM') or combination thereof.

In any of the embodiments described herein, the W, X, Y, Z, G, G', R, R', R", Q1-Q4, A, and Rn of Formulas (a) through (g) can independently be covalently coupled to a linker and/or a linker to which is attached one or more PTM, ULM, CLM or CLM' groups.

In any of the aspects or embodiments described herein, Rn comprises from 1 to 4 functional groups or atoms, for example, O, OH, N, C1-C6 alkyl, $C_1$-$C_6$ alkoxy, amine, amide, or carboxy, and optionally, one of which is modified to be covalently joined to a PTM, a chemical linker group (L), a ULM, CLM (or CLM') or combination thereof.

More specifically, non-limiting examples of CLMs include those shown below as well as those "hybrid" molecules that arise from the combination of 1 or more of the different features shown in the molecules below.

wherein:

W of Formulas (a) through (f) is independently selected from the group CH$_2$, CHR, C=O, SO$_2$, NH, and N-alkyl;

X of Formulas (a) through (f) is independently selected from the group O, S and H2;

Y of Formulas (a) through (f) is independently selected from the group CH$_2$, —C=CR', NH, N-alkyl, N-aryl, N-hetaryl, N-cycloalkyl, N-heterocyclyl, O, and S;

Z of Formulas (a) through (f) is independently selected from the group O, and S or H2 except that both X and Z cannot be H2;

G and G' of Formulas (a) through (f) are independently selected from the group H, alkyl (linear, branched, optionally substituted), OH, R'OCOOR, R'OCONRR", CH$_2$-heterocyclyl optionally substituted with R', and benzyl optionally substituted with R';

Q1-Q4 of Formulas (a) through (f) represent a carbon C substituted with a group independently selected from R', N or N-oxide;

A of Formulas (a) through (f) is independently selected from the group H, alkyl (linear, branched, optionally substituted), cycloalkyl, Cl and F;

R of Formulas (a) through (f) comprises, but is not limited to: —CONR'R", —OR', —NR'R", —SR', —SO2R',

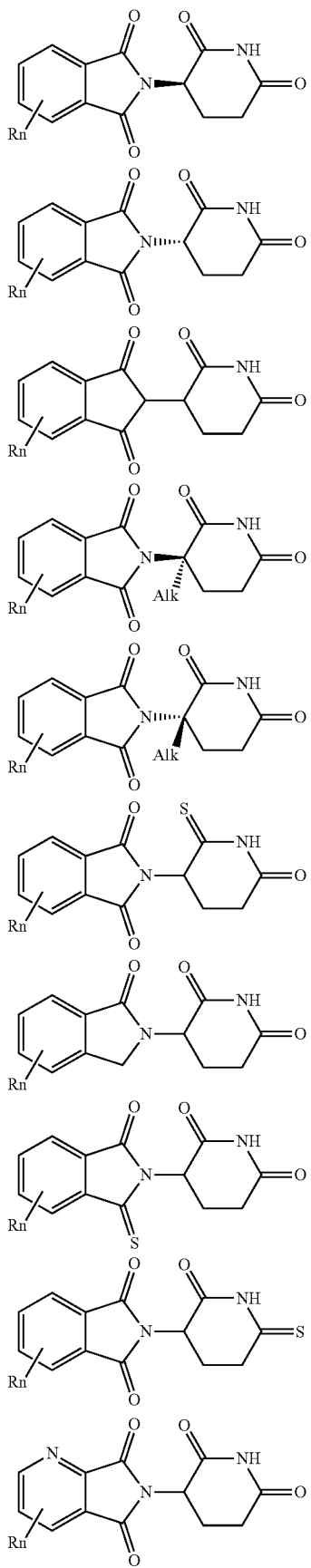
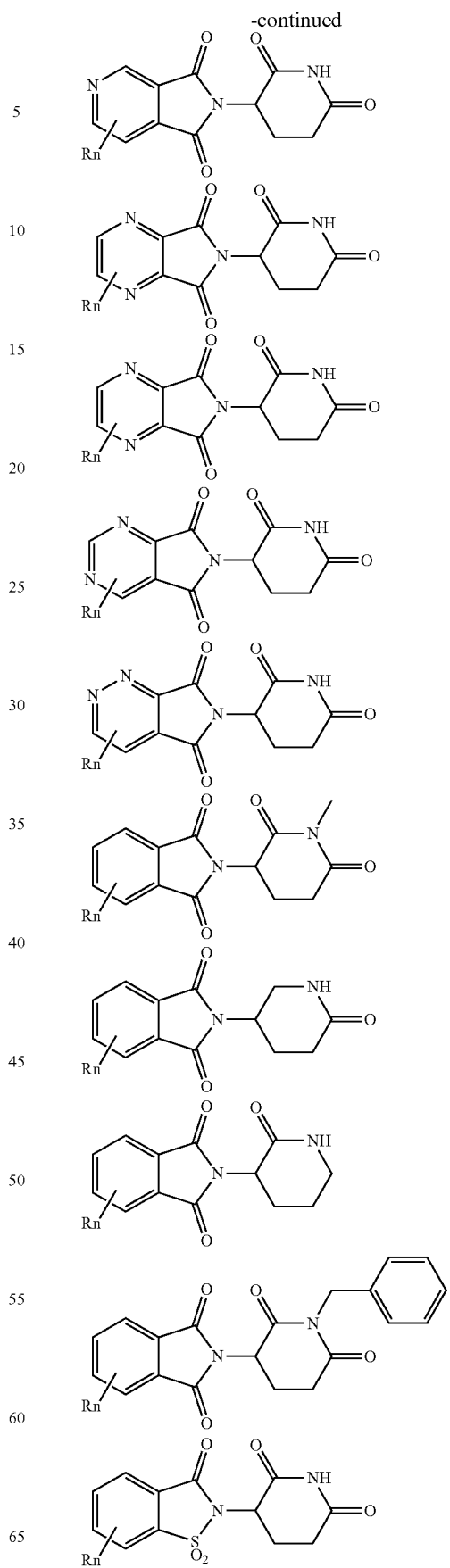

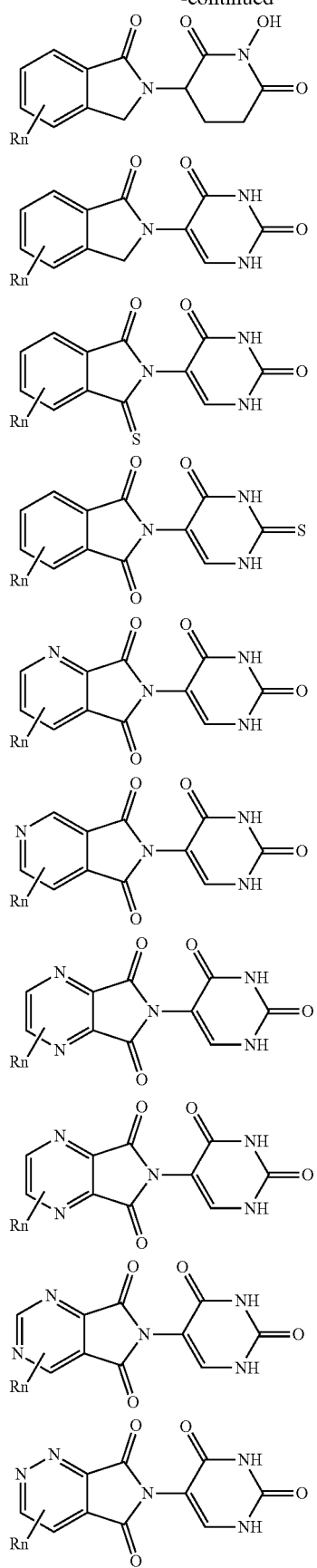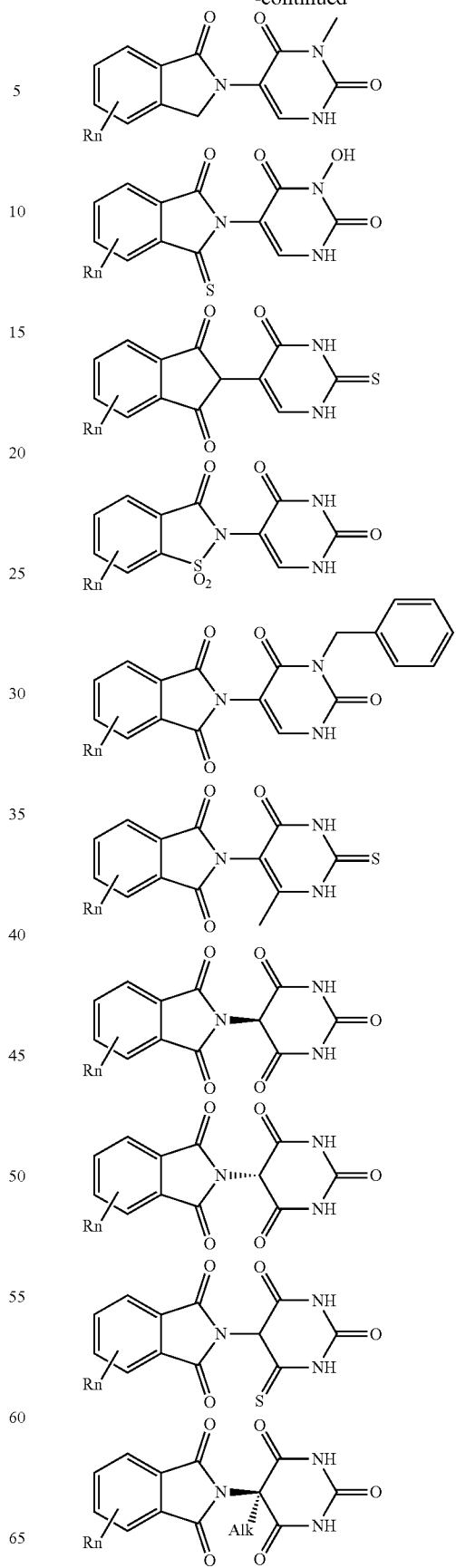

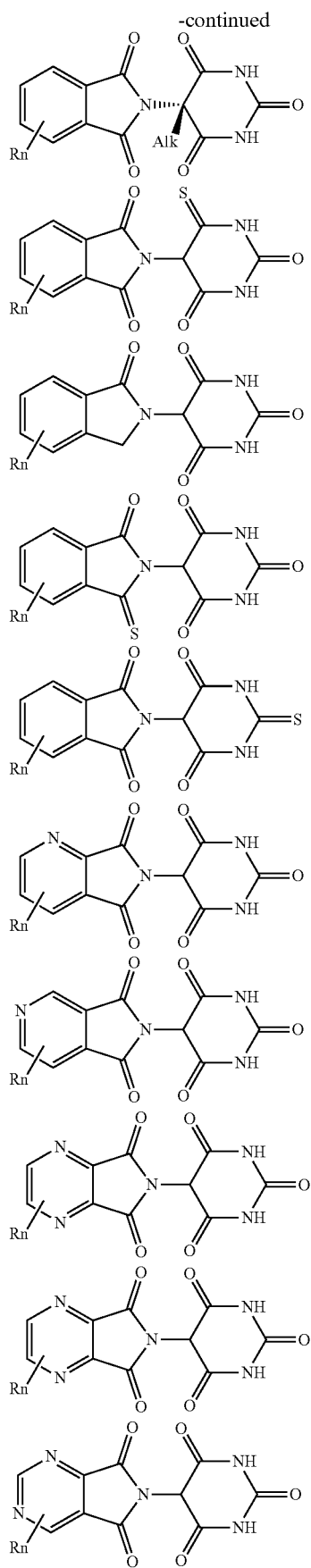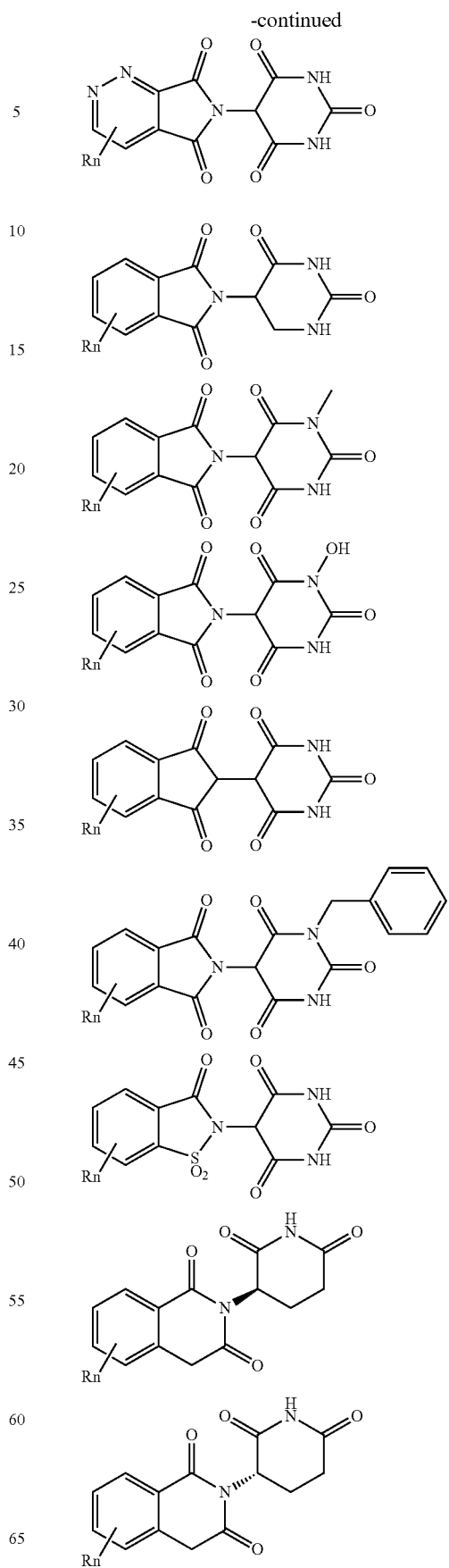

31
-continued
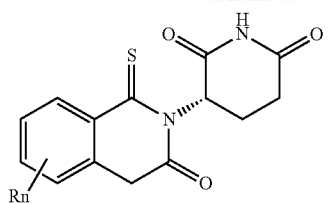
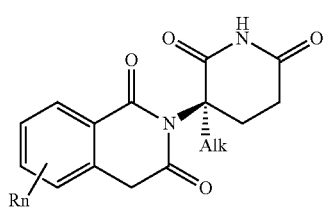
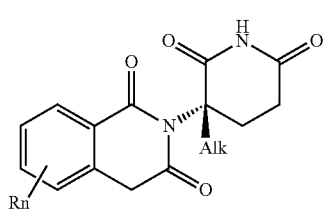
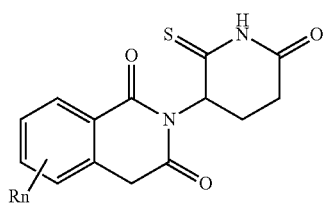
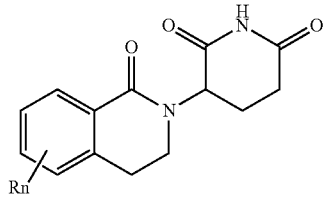
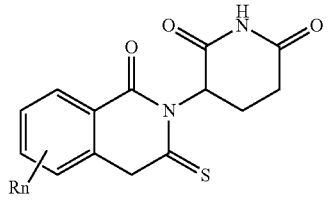
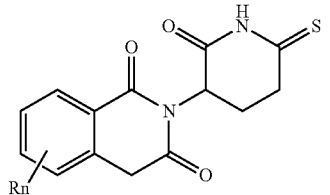
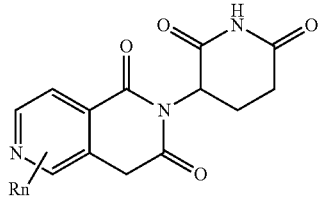
32
-continued
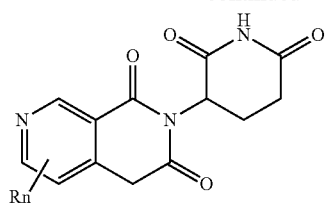
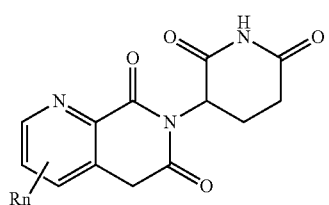
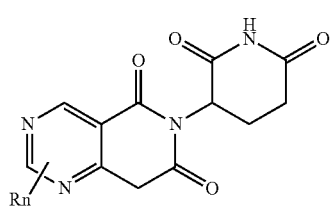
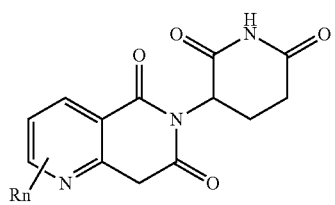
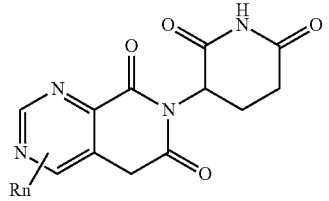
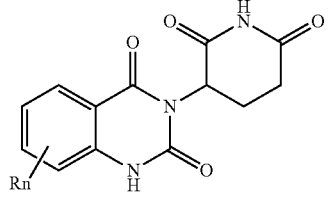
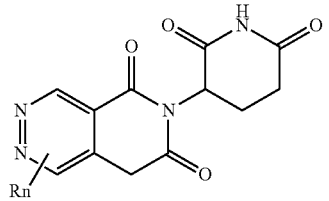
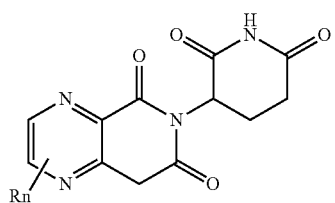

-continued
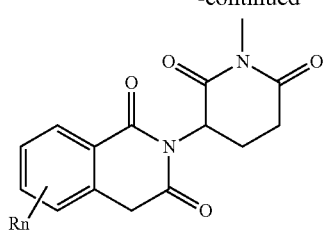
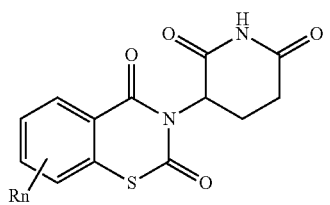
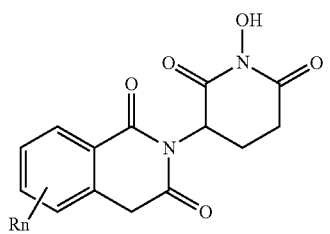
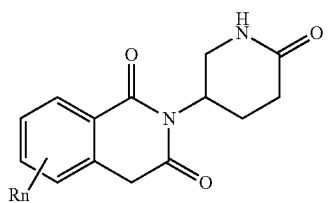
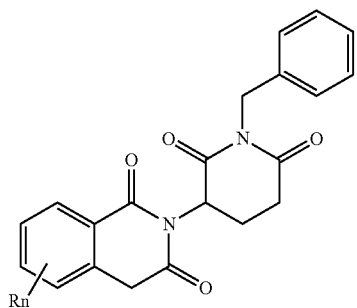
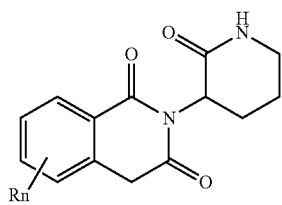
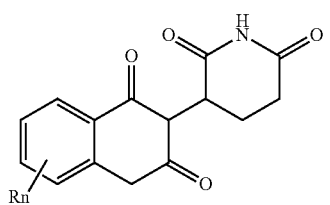
-continued
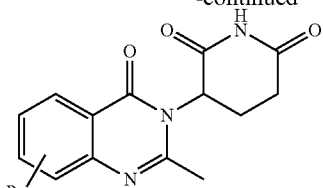
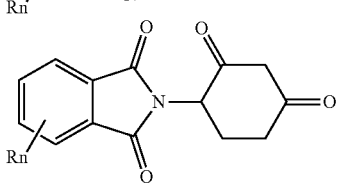
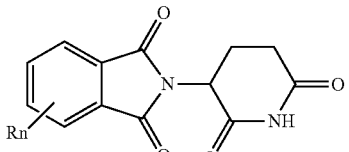
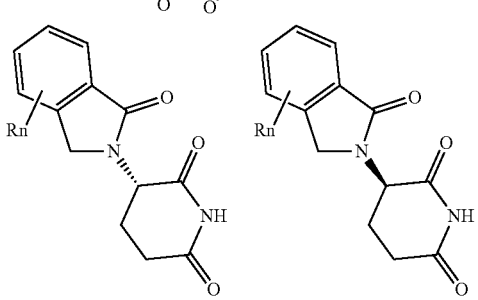
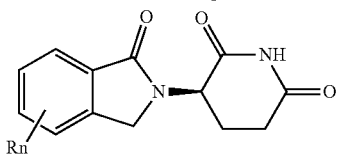
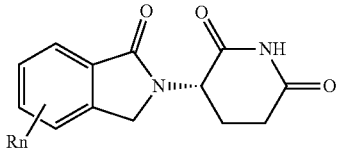
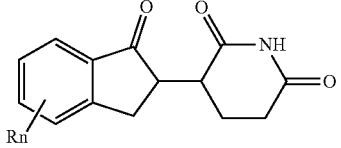
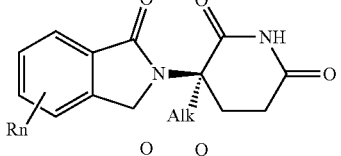
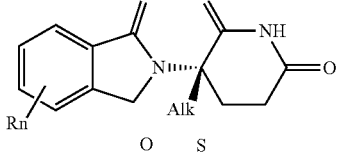
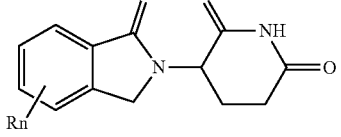

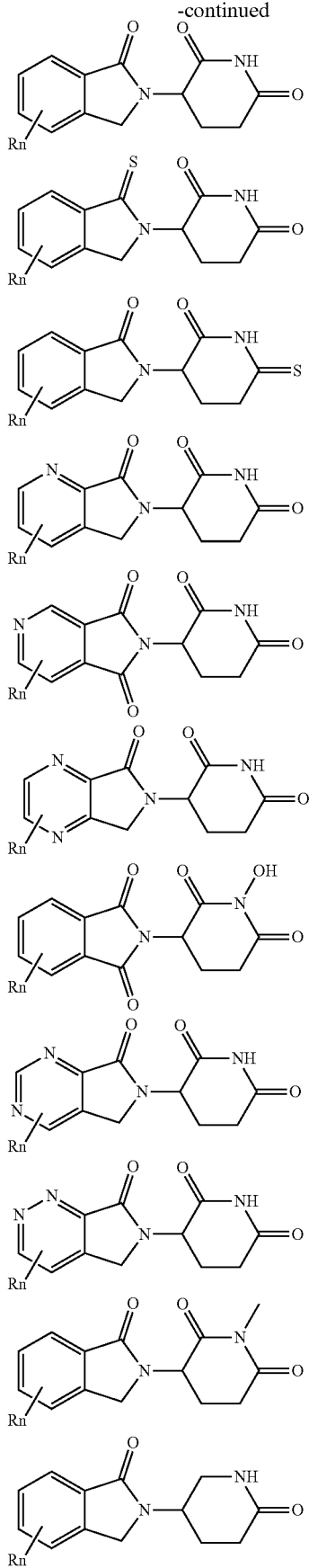
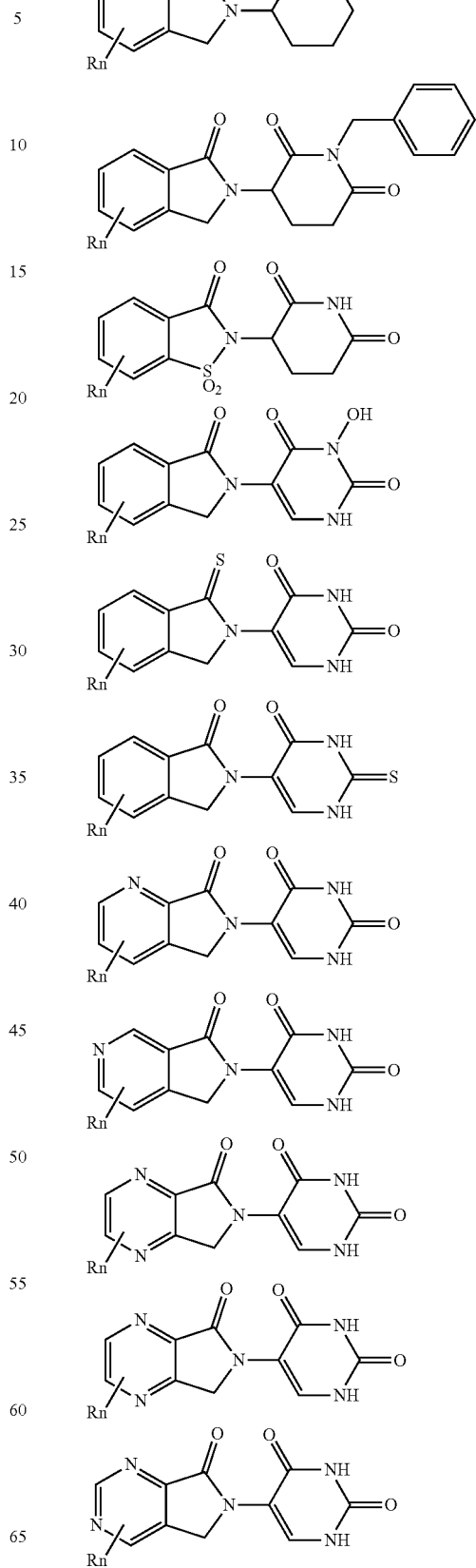

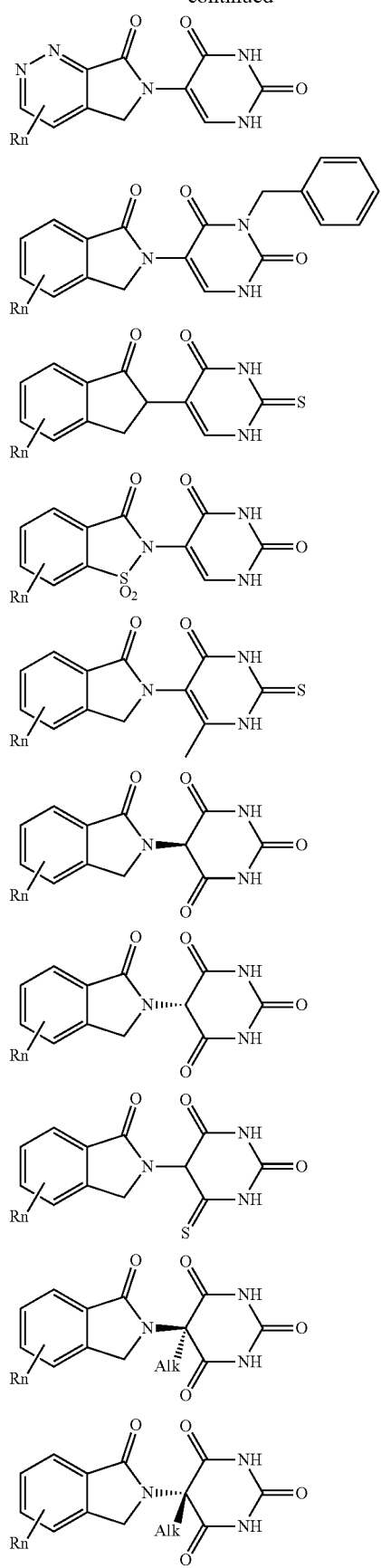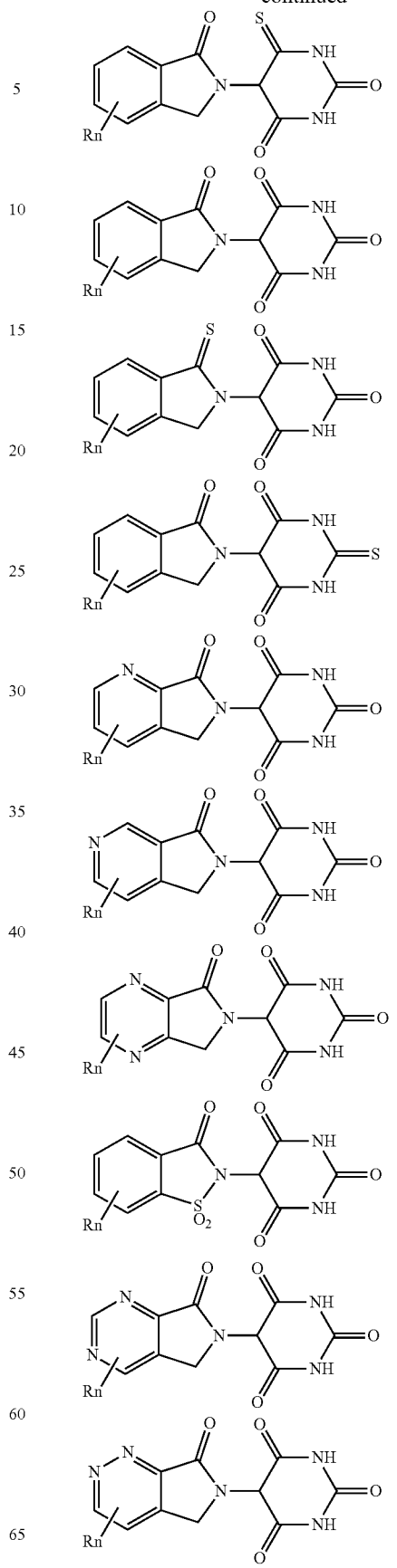

-continued
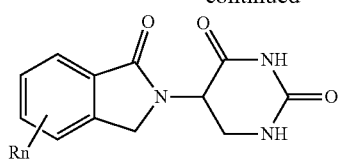
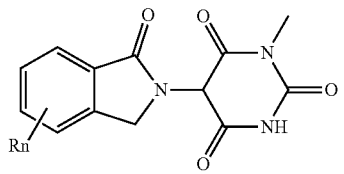
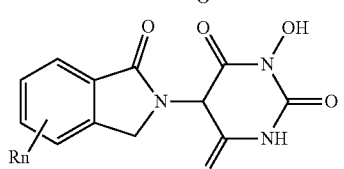
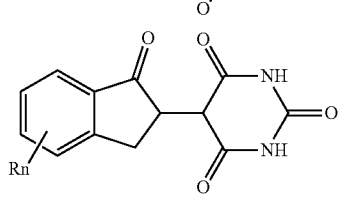
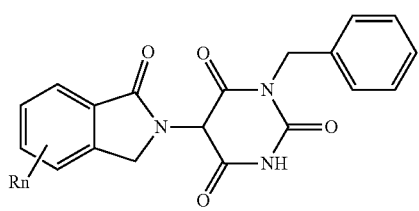
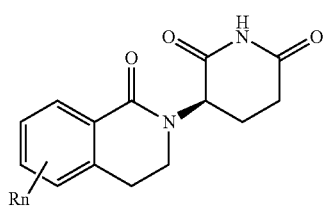
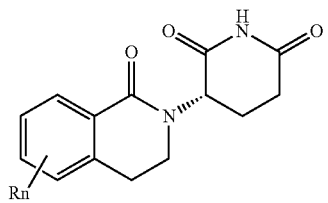
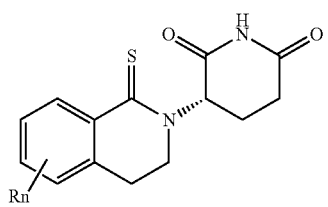
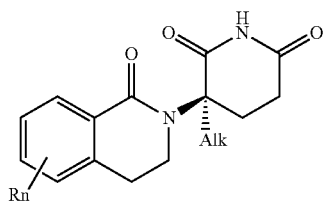
-continued
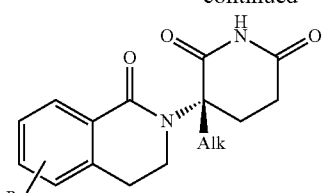
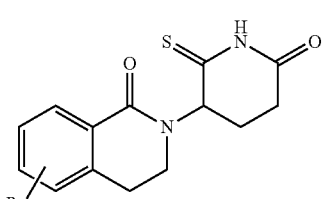
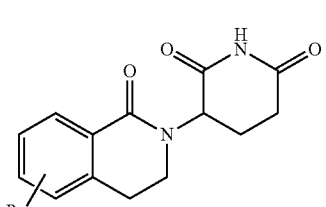
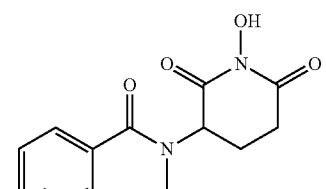
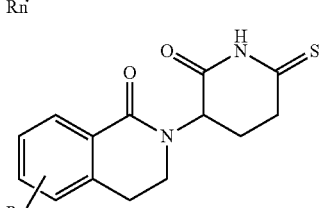
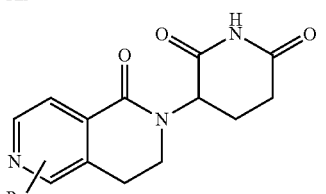
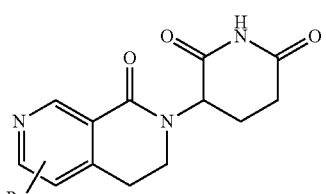
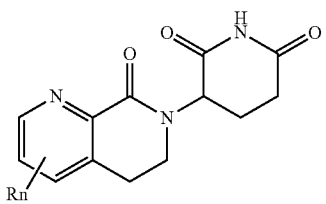

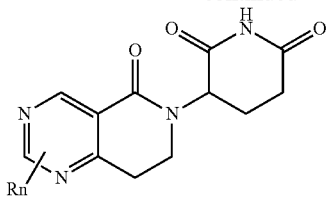
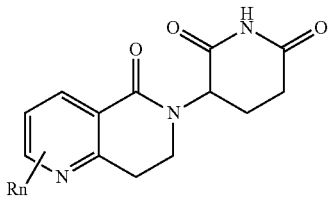
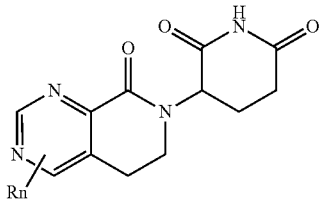
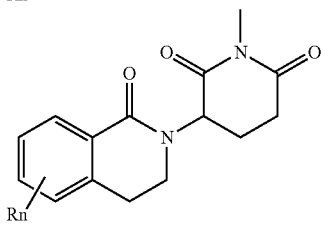
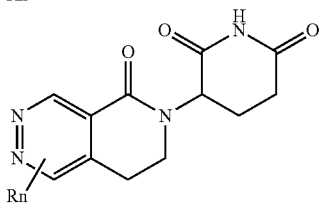
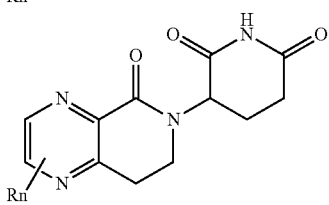
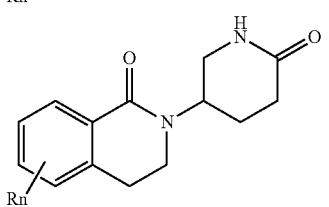
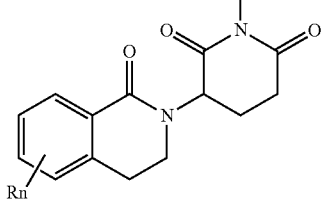
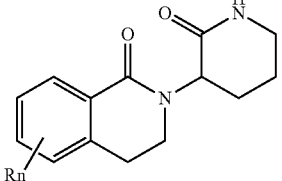
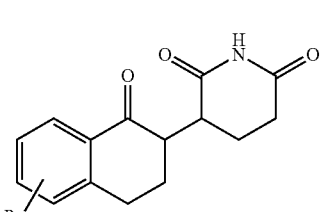
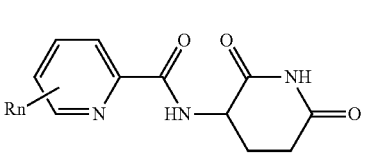
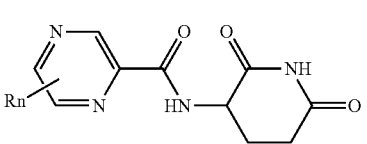
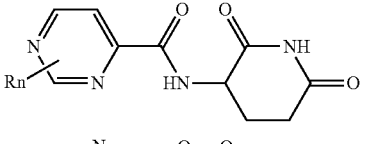
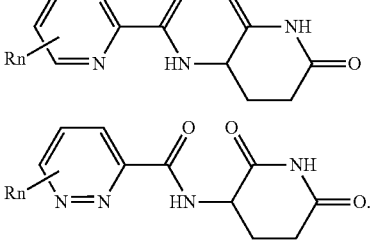
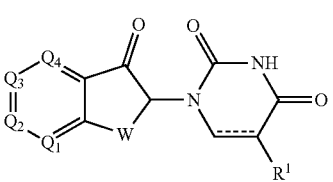
In any of the compounds described herein, the CLM comprises a chemical structure selected from the group:
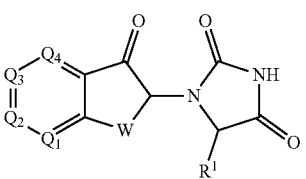

(j) 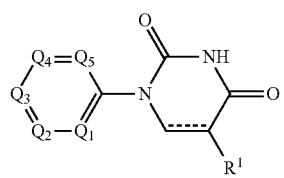
(k) 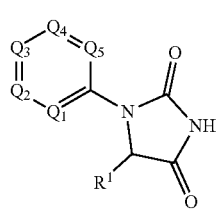
(l) 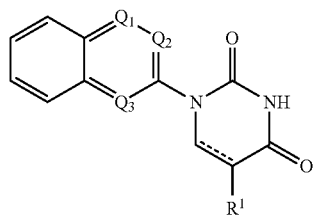
(m) 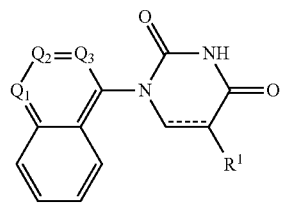
(n) 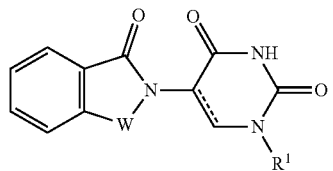
(o) 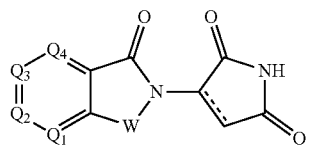
(p) 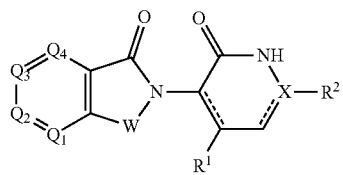
(q) 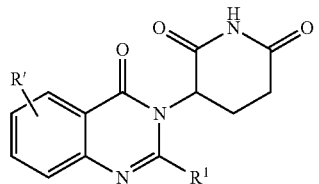
(r) 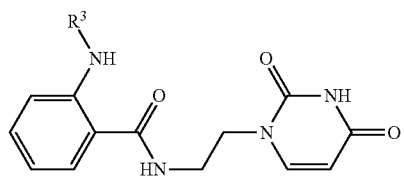
(s) 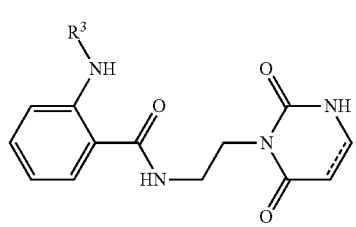
(t) 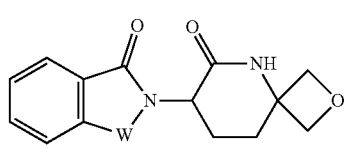
(u) 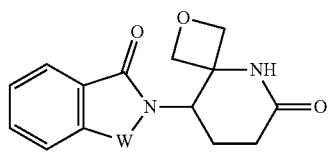
(v) 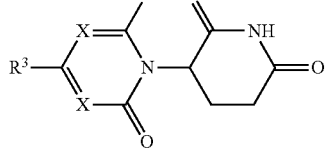
(w) 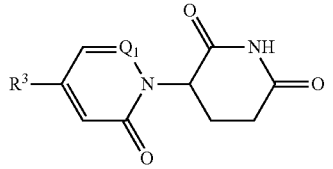
(x) 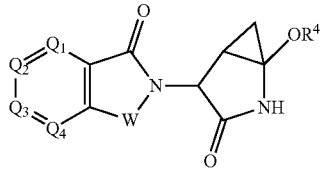
(y) 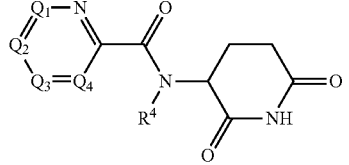

-continued

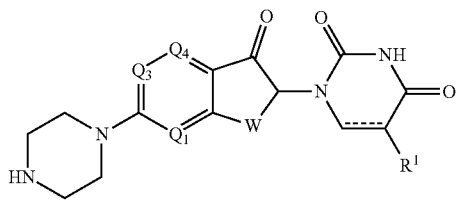
(z)

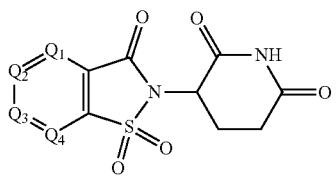
(aa)

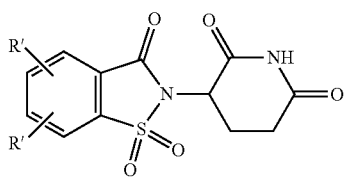
(ab)

wherein:
- W of Formulas (h) through (ab) is independently selected from $CH_2$, CHR, C=O, $SO_2$, NH, and N-alkyl;
- $Q_1$, $Q_2$, $Q_3$, $Q_4$, $Q_5$ of Formulas (h) through (ab) are independently represent a carbon C substituted with a group independently selected from R', N or N-oxide;
- $R^1$ of Formulas (h) through (ab) is selected from H, CN, C1-C3 alkyl;
- $R^2$ of Formulas (h) through (ab) is selected from the group H, CN, C1-C3 alkyl, $CHF_2$, $CF_3$, CHO;
- $R^3$ of Formulas (h) through (ab) is selected from H, alkyl, substituted alkyl, alkoxy, substituted alkoxy;
- $R^4$ of Formulas (h) through (ab) is selected from H, alkyl, substituted alkyl;
- $R^5$ of Formulas (h) through (ab) is H or lower alkyl;
- X of Formulas (h) through (ab) is C, CH or N;
- R' of Formulas (h) through (ab) is selected from H, halogen, alkyl, substituted alkyl, alkoxy, substituted alkoxy;
- R of Formulas (h) through (ab) is H, OH, lower alkyl, lower alkoxy, cyano, halogenated lower alkoxy, or halogenated lower alkyl
- ⫽ of Formulas (h) through (ab) is a single or double bond; and
- the CLM is covalently joined to a PTM, a chemical linker group (L), a ULM, CLM (or CLM') or combination thereof.

In any aspect or embodiment described herein, the CLM or CLM' is covalently joined to a PTM, a chemical linker group (L), a ULM, a CLM, a CLM', or a combination thereof via an R group (such as, R, $R^1$, $R^2$, $R^3$, $R^4$ or R'), W, X, or a Q group (such as, $Q_1$, $Q_2$, $Q_3$, $Q_4$, or $Q_5$) of Formulas (h) through (ab).

In any of the embodiments described herein, the CLM or CLM' is covalently joined to a PTM, a chemical linker group (L), a ULM, a CLM, a CLM', or a combination thereof via W, X, R, $R^1$, $R^2$, $R^3$, $R^4$, $R^5$, R', $Q_1$, $Q_2$, $Q_3$, $Q_4$, and $Q_5$ of Formulas (h) through (ab).

In any of the embodiments described herein, the W, X, $R^1$, $R^2$, $R^3$, $R^4$, R', $Q_1$, $Q_2$, $Q_3$, $Q_4$, and $Q_5$ of Formulas (h) through (ab) can independently be covalently coupled to a linker and/or a linker to which is attached to one or more PTM, ULM, ULM', CLM or CLM' groups.

More specifically, non-limiting examples of CLMs include those shown below as well as "hybrid" molecules or compounds that arise from combining 1 or more features of the following compounds:

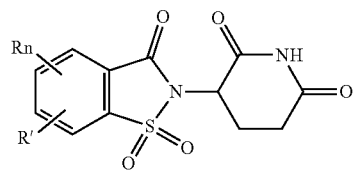
(ac)

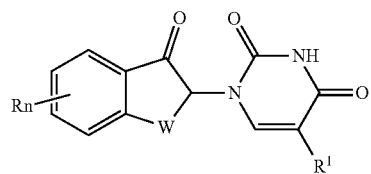
(ad)

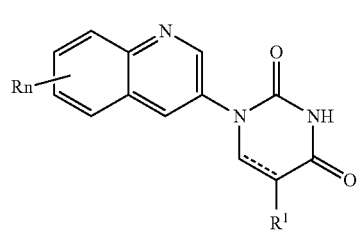
(ae)

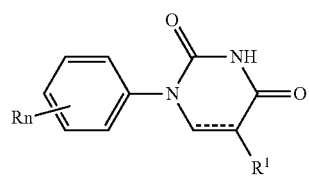
(af)

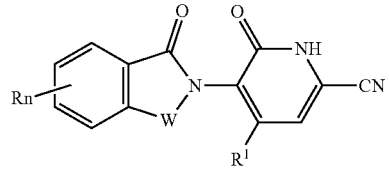
(ag)

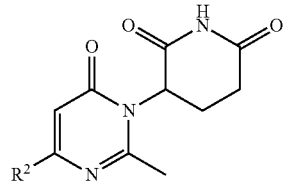
(ah)

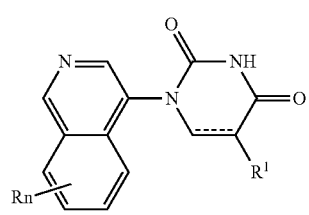
(ai)

-continued

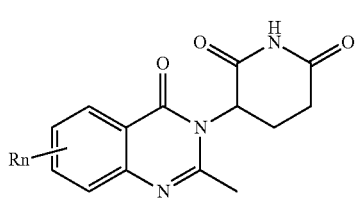
(aj)

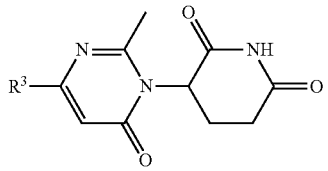
(ak)

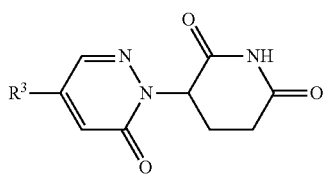
(al)

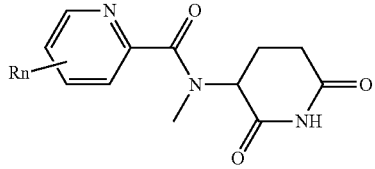
(am)

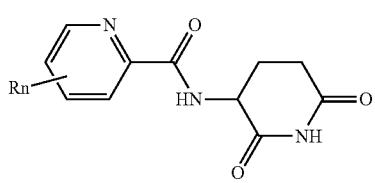
(an)

wherein:
W of Formulas (ac) through (an) is independently selected from the group $CH_2$, CHR, C=O, $SO_2$, NH, and N-alkyl;
$R^1$ of Formulas (ac) through (an) is selected from the group H, CN, C1-C3 alkyl;
$R^3$ of Formulas (ac) through (an) is selected from H, alkyl, substituted alkyl, alkoxy, substituted alkoxy;
R of Formulas (ac) through (an) is H;

⫽ is a single or double bond; and
Rn of Formulas (ac) through (an) comprises a functional group or an atom.

In any of the embodiments described herein, the W, $R^1$, $R^2$, $Q_1$, $Q_2$, $Q_3$, $Q_4$, and Rn of Formulas (ac) through (an) can independently be covalently coupled to a linker and/or a linker to which is attached one or more PTM, ULM, ULM', CLM or CLM' groups.

In any of the embodiments described herein, the $R^1$, $R^2$, $Q_1$, $Q_2$, $Q_3$, $Q_4$, and Rn of Formulas (ac) through (an) can independently be covalently coupled to a linker and/or a linker to which is attached one or more PTM, ULM, ULM', CLM or CLM' groups.

In any of the embodiments described herein, the $Q_1$, $Q_2$, $Q_3$, $Q_4$, and Rn of Formulas (ac) through (an) can independently be covalently coupled to a linker and/or a linker to which is attached one or more PTM, ULM, ULM', CLM or CLM' groups.

In any aspect or embodiment described herein, $R_n$ of Formulas (ac) through (an) is modified to be covalently joined to the linker group (L), a PTM, a ULM, a second CLM having the same chemical structure as the CLM, a CLM', a second linker, or any multiple or combination thereof.

In any aspect or embodiment described herein, the CLM is selected from:

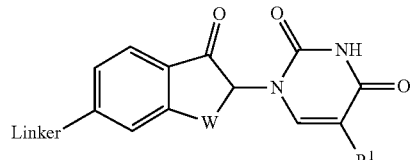

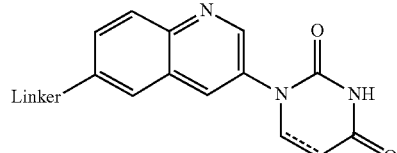

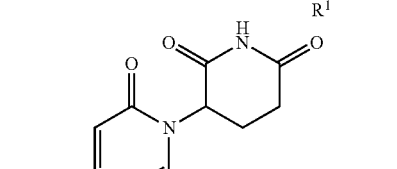

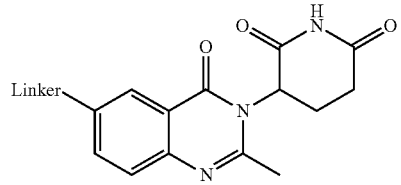

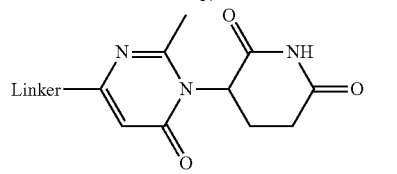

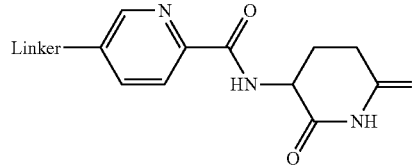

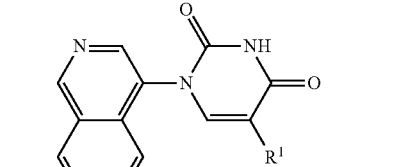

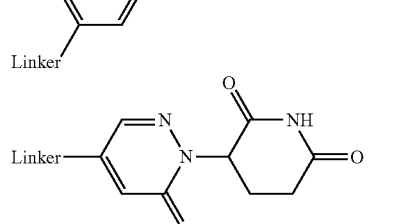

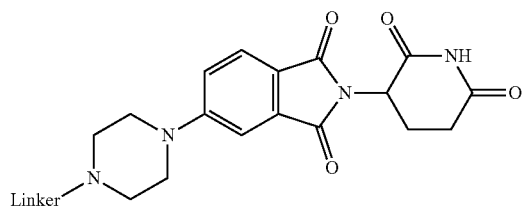
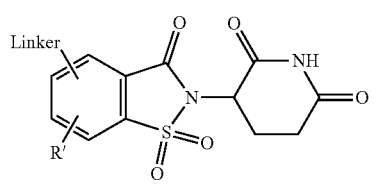
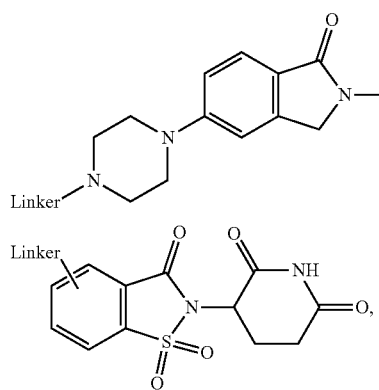

wherein R' is a halogen and R¹ is as described above with regard to Formulas (h) through (ab) or (ac) through (an).

In certain cases, the CLM can be imides that bind to cereblon E3 ligase. These imides and linker attachment point can be but not limited to the following structures:

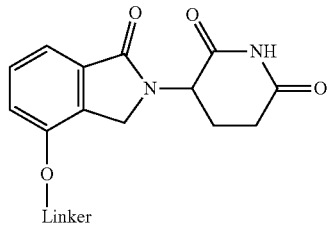
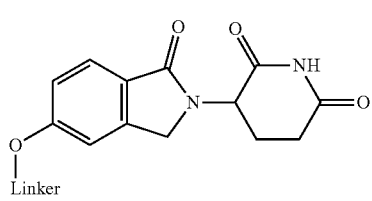
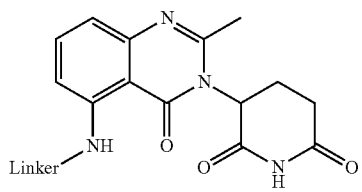
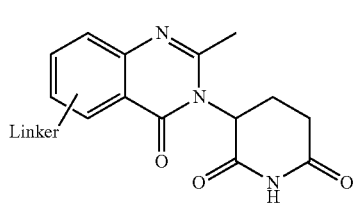
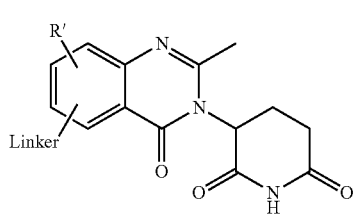
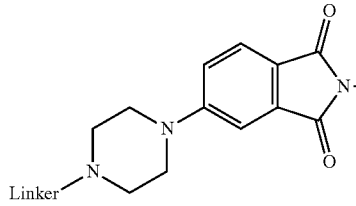
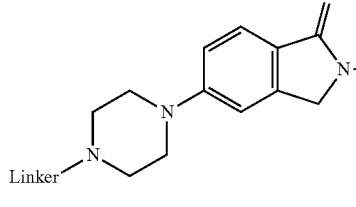

wherein R' is a halogen.

Exemplary VLMs

In certain embodiments of the compounds as described herein, ULM is VLM and comprises a chemical structure selected from the group ULM-a:

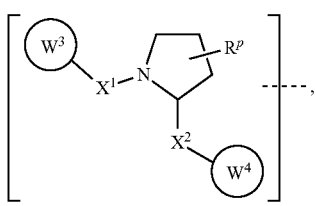

ULM-a wherein:
- a dashed line indicates the attachment of at least one PTM, another ULM or VLM or MLM or ILM or CLM (i.e., ULM' or VLM' or CLM' or ILM' or MLM'), or a chemical linker moiety coupling at least one PTM, a ULM' or a VLM' or a CLM' or a ILM' or a MLM' to the other end of the linker;
- $X^1$, $X^2$ of Formula ULM-a are each independently selected from the group of a bond, O, $NR^{Y3}$, $CR^{Y3}R^{Y4}$, C=O, C=S, SO, and $SO_2$;
- $R^{Y3}$, $R^{Y4}$ of Formula ULM-a are each independently selected from the group of H, linear or branched $C_{1-6}$ alkyl, optionally substituted by 1 or more halo, optionally substituted $C_{1-6}$ alkoxyl (e.g., optionally substituted by 0-3 $R^P$ groups);
- $R^P$ of Formula ULM-a is 0, 1, 2, or 3 groups, each independently selected from the group H, halo, —OH, $C_{1-3}$ alkyl, C=O;
- $W^3$ of Formula ULM-a is selected from the group of an optionally substituted -T-N($R^{1a}R^{1b}$)$X^3$, optionally substituted -T-N($R^{1a}R^{1b}$), optionally substituted -T-Aryl, an optionally substituted -T-Heteroaryl, an optionally substituted T-biheteroaryl, an optionally substituted -T-Heterocycle, an optionally substituted -T-biheterocycle, an optionally substituted —$NR^1$-T-Aryl, an optionally substituted —$NR^1$-T-Heteroaryl or an optionally substituted —$NR^1$-T-Heterocycle;
- $X^3$ of Formula ULM-a is C=O, $R^1$, $R^{1a}$, $R^{1b}$;
- each of $R^1$, $R^{1a}$, $R^{1b}$ is independently selected from the group consisting of H, linear or branched $C_1$-$C_6$ alkyl group optionally substituted by 1 or more halo or —OH groups, $R^{Y3}$C=O, $R^{Y3}$C=S, $R^{Y3}$SO, $R^{Y3}SO_2$, N($R^{Y3}R^{Y4}$)C=O, N($R^{Y3}R^{Y4}$)C=S, N($R^{Y3}R^{Y4}$)SO, and N($R^{Y3}R^{Y4}$)$SO_2$;
- T of Formula ULM-a is covalently bonded to $X^1$ and is selected from the group of an optionally substituted alkyl, —$(CH_2)_n$— group, wherein each one of the methylene groups is optionally substituted with one or two substituents selected from the group of halogen, methyl, a linear or branched $C_1$-$C_6$ alkyl group optionally substituted by 1 or more halogen or —OH groups or an amino acid side chain optionally substituted;
- $W^4$ of Formula ULM-a is an optionally substituted —$NR_1$-T-Aryl, an optionally substituted —$NR_1$-T-Heteroaryl group or an optionally substituted —$NR_1$-T-Heterocycle, where —$NR_1$ is covalently bonded to $X^2$ and R1 is H or $CH_3$, preferably H.

In any of the embodiments described herein, T is selected from the group of an optionally substituted alkyl, —$(CH_2)_n$— group, wherein each one of the methylene groups is optionally substituted with one or two substituents selected from the group of halogen, methyl, a linear or branched $C_1$-$C_6$ alkyl group optionally substituted by 1 or more halogen or —OH groups or an amino acid side chain optionally substituted; and n is 0 to 6, often 0, 1, 2, or 3, preferably 0 or 1.

In certain embodiments, $W^4$ of Formula ULM-a is

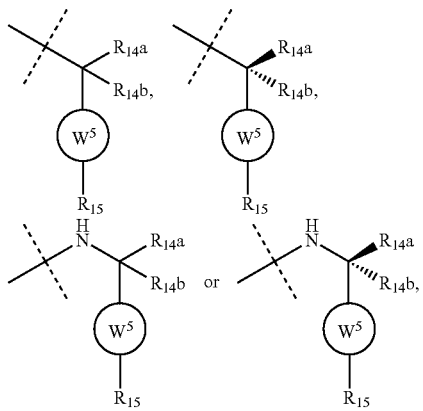

wherein $R_{14a}$, $R_{14b}$, are each independently selected from the group of H, haloalkyl, or optionally substituted alkyl.

In any of the embodiments, $W^5$ of Formula ULM-a is selected from the group of a phenyl or a 5-10 membered heteroaryl, $R_{15}$ of Formula ULM-a is selected from the group of H, halogen, CN, OH, $NO_2$, N $R_{14a}R_{14b}$, $OR_{14a}$, $CONR_{14a}R_{14b}$, $NR_{14a}COR_{14b}$, $SO_2NR_{14a}R_{14b}$, $NR_{14a}SO_2R_{14b}$, optionally substituted alkyl, optionally substituted haloalkyl, optionally substituted haloalkoxy; aryl, heteroaryl, cycloalkyl, or cycloheteroalkyl (each optionally substituted);

In additional embodiments, $W^4$ substituents for use in the present disclosure also include specifically (and without limitation to the specific compound disclosed) the $W^4$ substituents which are found in the identified compounds disclosed herein. Each of these $W^4$ substituents may be used in conjunction with any number of $W^3$ substituents which are also disclosed herein.

In certain additional embodiments, ULM-a, is optionally substituted by 0-3 $R^P$ groups in the pyrrolidine moiety. Each $R^P$ is independently H, halo, —OH, $C_{1-3}$alkyl, C=O.

In any of the embodiments described herein, the $W^3$, $W^4$ of Formula ULM-a can independently be covalently coupled to a linker which is attached one or more PTM groups.

and wherein the dashed line indicates the site of attachment of at least one PTM, another ULM (ULM') or a chemical linker moiety coupling at least one PTM or a ULM' or both to ULM.

In certain embodiments, ULM is VHL and is represented by the structure:

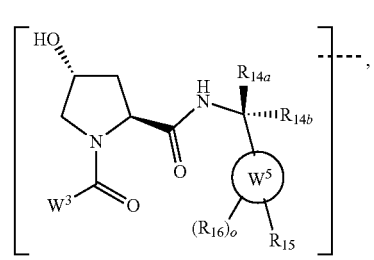

ULM-b wherein:
$W^3$ of Formula ULM-b is selected from the group of an optionally substituted aryl, optionally substituted heteroaryl, or

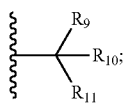

R₉ and R₁₀ of Formula ULM-b are independently hydrogen, optionally substituted alkyl, optionally substituted cycloalkyl, optionally substituted hydroxyalkyl, optionally substituted heteroaryl, or haloalkyl, or R₉, R₁₀, and the carbon atom to which they are attached form an optionally substituted cycloalkyl;

R₁₁ of Formula ULM-b is selected from the group of an optionally substituted heterocyclic, optionally substituted alkoxy, optionally substituted heteroaryl, optionally substituted aryl,

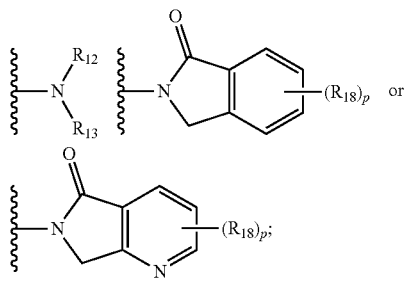

R₁₂ of Formula ULM-b is selected from the group of H or optionally substituted alkyl;

R₁₃ of Formula ULM-b is selected from the group of H, optionally substituted alkyl, optionally substituted alkylcarbonyl, optionally substituted (cycloalkyl)alkylcarbonyl, optionally substituted aralkylcarbonyl, optionally substituted arylcarbonyl, optionally substituted (heterocyclyl)carbonyl, or optionally substituted aralkyl;

R₁₄ₐ, R₁₄ᵦ of Formula ULM-b, are each independently selected from the group of H, haloalkyl, or optionally substituted alkyl;

W⁵ of Formula ULM-b is selected from the group of a phenyl or a 5-10 membered heteroaryl, R₁₅ of Formula ULM-b is selected from the group of H, halogen, CN, OH, NO₂, NR₁₄ₐR₁₄ᵦ, OR₁₄ₐ, CONR₁₄ₐR₁₄ᵦ, NR₁₄ₐCOR₁₄ᵦ, SO₂NR₁₄ₐR₁₄ᵦ, NR₁₄ₐSO₂R₁₄ᵦ, optionally substituted alkyl, optionally substituted haloalkyl, optionally substituted haloalkoxy; aryl, heteroaryl, cycloalkyl, or cycloheteroalkyl (each optionally substituted);

R₁₆ of Formula ULM-b is independently selected from the group of H, halo, optionally substituted alkyl, optionally substituted haloalkyl, hydroxy, or optionally substituted haloalkoxy;

o of Formula ULM-b is 0, 1, 2, 3, or 4;

R₁₈ of Formula ULM-b is independently selected from the group of H, halo, optionally substituted alkoxy, cyano, optionally substituted alkyl, haloalkyl, haloalkoxy or a linker; and p of Formula ULM-b is 0, 1, 2, 3, or 4, and wherein the dashed line indicates the site of attachment of at least one PTM, another ULM (ULM') or a chemical linker moiety coupling at least one PTM or a ULM' or both to ULM.

In certain embodiments, R₁₅ of Formula ULM-b is

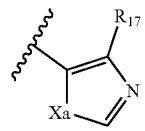

wherein R₁₇ is H, halo, optionally substituted C₃₋₆cycloalkyl, optionally substituted C₁₋₆alkyl, optionally substituted C₁₋₆alkenyl, and C₁₋₆haloalkyl; and Xa is S or O.

In certain embodiments, R₁₇ of Formula ULM-b is selected from the group methyl, ethyl, isopropyl, and cyclopropyl.

In certain additional embodiments, R₁₅ of Formula ULM-b is selected from the group consisting of:

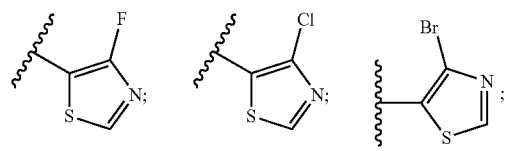

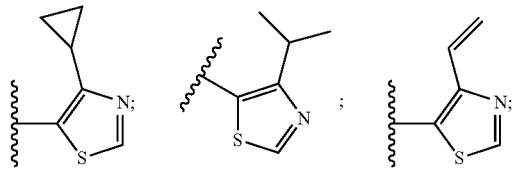

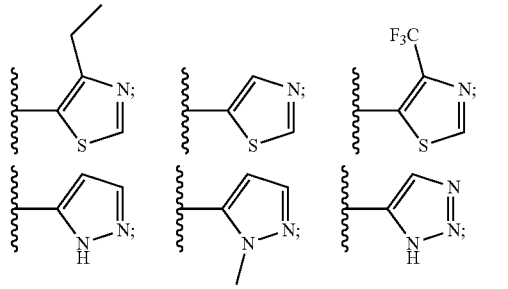

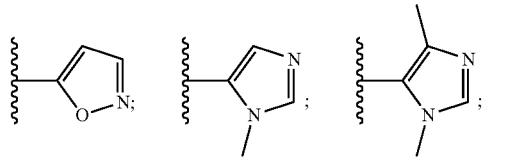

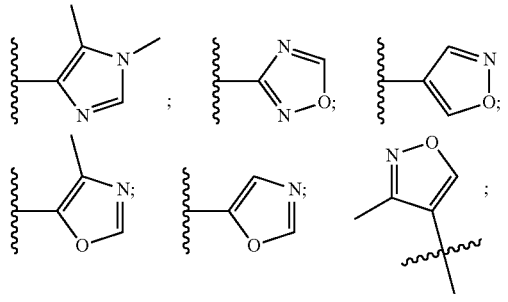

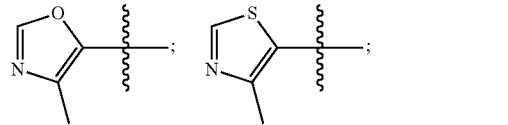

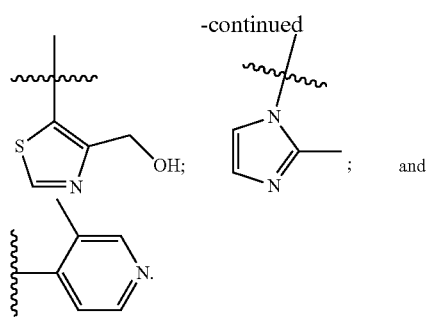
In certain embodiments, $R_{11}$ of Formula ULM-b is selected from the group consisting of:
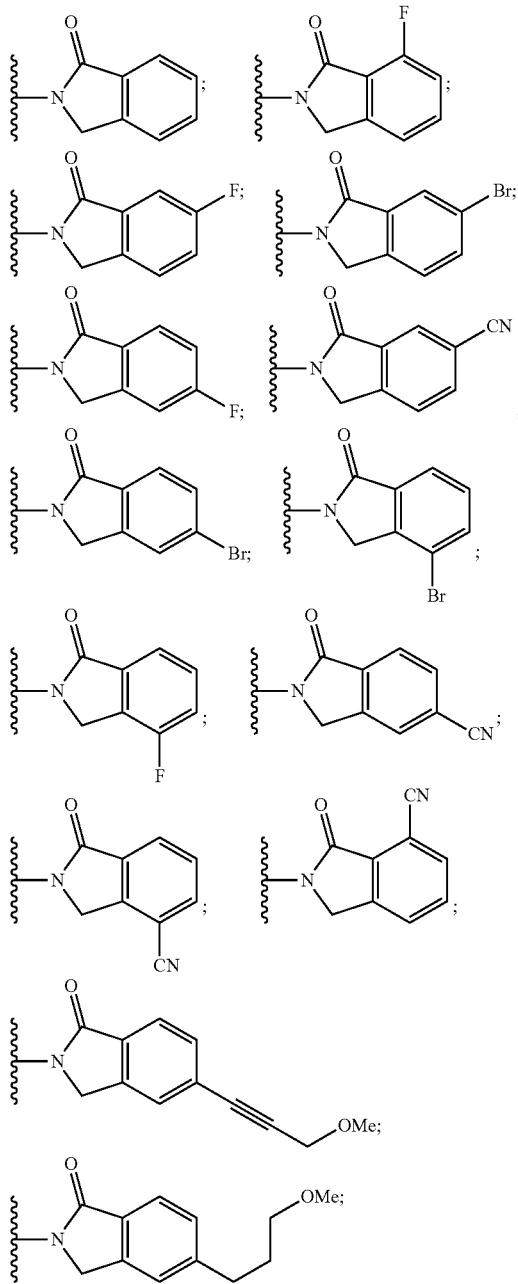
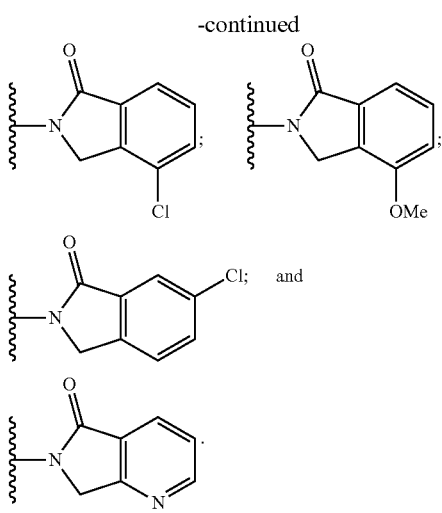
In certain embodiments, ULM has a chemical structure selected from the group of:
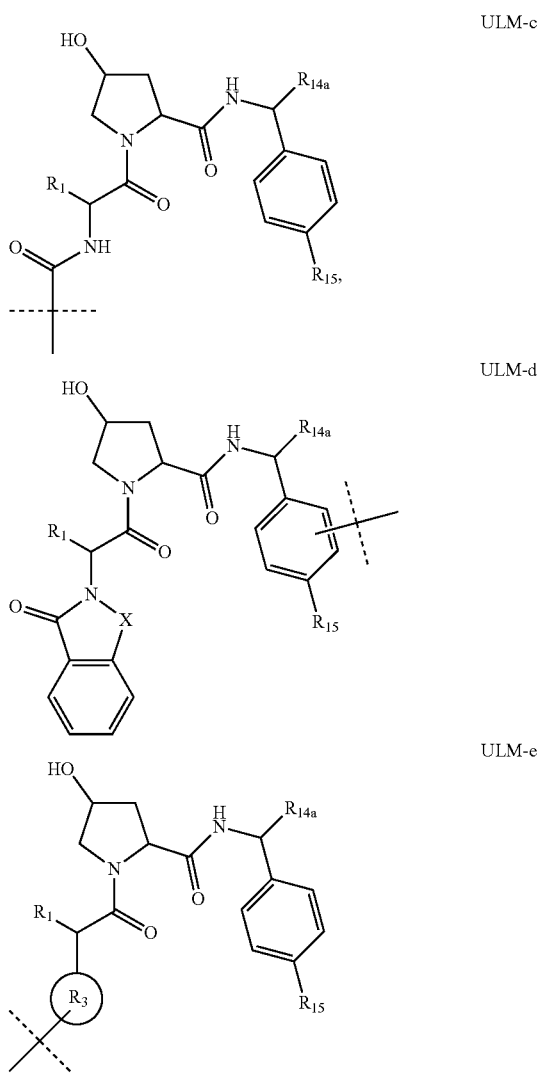

wherein:
- $R_1$ of Formulas ULM-c, ULM-d, and ULM-e is H, ethyl, isopropyl, tert-butyl, sec-butyl, cyclopropyl, cyclobutyl, cyclopentyl, or cyclohexyl; optionally substituted alkyl, optionally substituted hydroxyalkyl, optionally substituted heteroaryl, or haloalkyl;
- $R_{14a}$ of Formulas ULM-c, ULM-d, and ULM-e is H, haloalkyl, optionally substituted alkyl, methyl, fluoromethyl, hydroxymethyl, ethyl, isopropyl, or cyclopropyl;
- $R_{15}$ of Formulas ULM-c, ULM-d, and ULM-e is selected from the group consisting of H, halogen, CN, OH, $NO_2$, optionally substituted heteroaryl, optionally substituted aryl; optionally substituted alkyl, optionally substituted haloalkyl, optionally substituted haloalkoxy, cycloalkyl, or cycloheteroalkyl (each optionally substituted);
- X of Formulas ULM-c, ULM-d, and ULM-e is C, $CH_2$, or C=O
- $R_3$ of Formulas ULM-c, ULM-d, and ULM-e is absent or an optionally substituted 5 or 6 membered heteroaryl; and
- wherein the dashed line indicates the site of attachment of at least one PTM, another ULM (ULM') or a chemical linker moiety coupling at least one PTM or a ULM' or both to ULM.

In certain embodiments, ULM comprises a group according to the chemical structure:

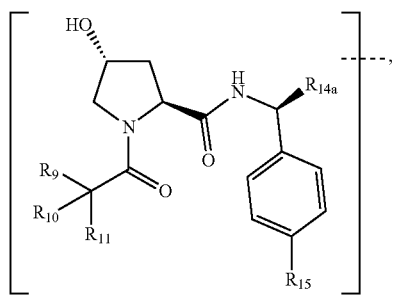

ULM-f wherein:
- $R_{14a}$ of Formula ULM-f is H, haloalkyl, optionally substituted alkyl, methyl, fluoromethyl, hydroxymethyl, ethyl, isopropyl, or cyclopropyl;
- $R_9$ of Formula ULM-f is H;
- $R_{10}$ of Formula ULM-f is H, ethyl, isopropyl, tert-butyl, sec-butyl, cyclopropyl, cyclobutyl, cyclopentyl, or cyclohexyl;
- $R_{11}$ of Formula ULM-f is

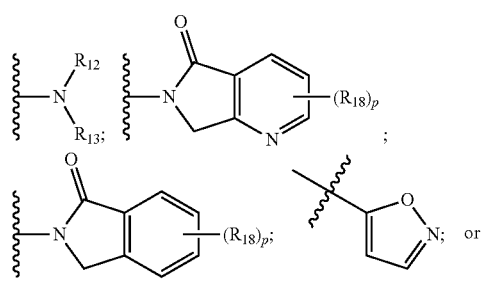

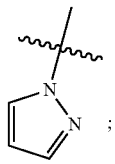

or optionally substituted heteroaryl;
- p of Formula ULM-f is 0, 1, 2, 3, or 4;
- each $R_{18}$ of Formula ULM-f is independently halo, optionally substituted alkoxy, cyano, optionally substituted alkyl, haloalkyl, haloalkoxy or a linker;
- $R_{12}$ of Formula ULM-f is H, C=O;
- $R_{13}$ of Formula ULM-f is H, optionally substituted alkyl, optionally substituted alkylcarbonyl, optionally substituted (cycloalkyl)alkylcarbonyl, optionally substituted aralkylcarbonyl, optionally substituted arylcarbonyl, optionally substituted (heterocyclyl)carbonyl, or optionally substituted aralkyl,
- $R_{15}$ of Formula ULM-f is selected from the group consisting of H, halogen, Cl, CN, OH, $NO_2$, optionally substituted heteroaryl, optionally substituted aryl;

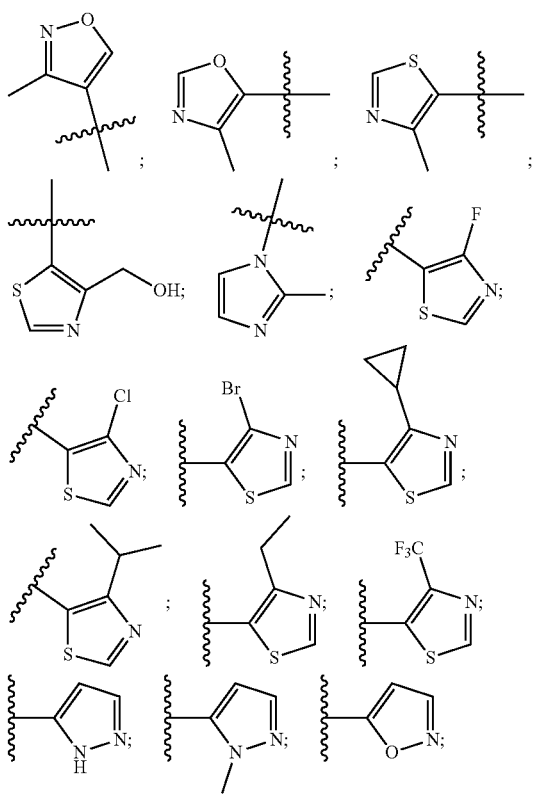

and
wherein the dashed line of Formula ULM-f indicates the site of attachment of at least one PTM, another ULM (ULM') or a chemical linker moiety coupling at least one PTM or a ULM' or both to ULM.
In certain embodiments, the ULM is selected from the following structures:
ULM-a1
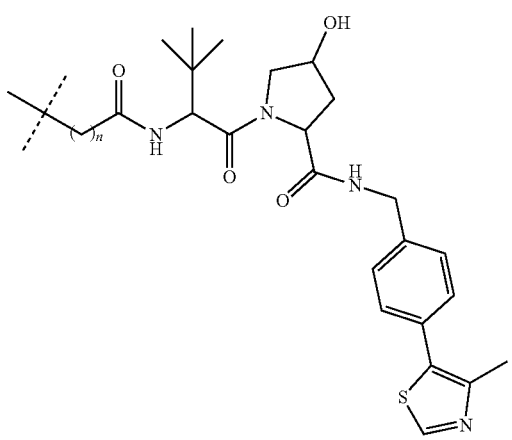
ULM-a2
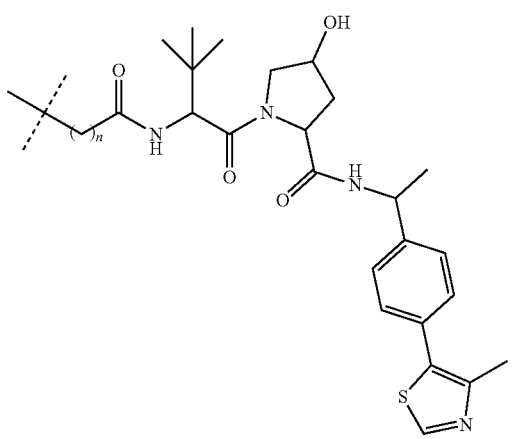
ULM-a3
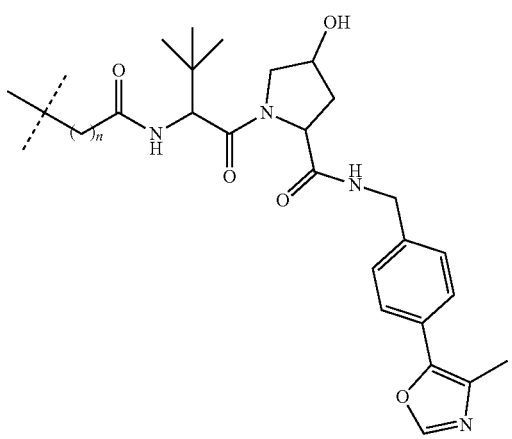
ULM-a4
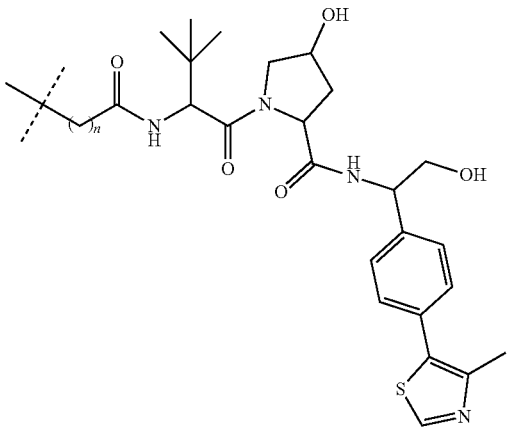
ULM-a5
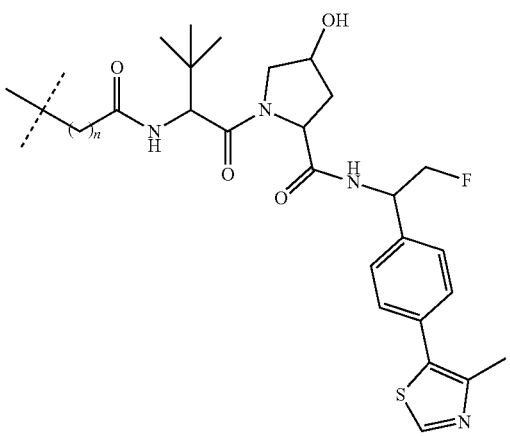
ULM-a6
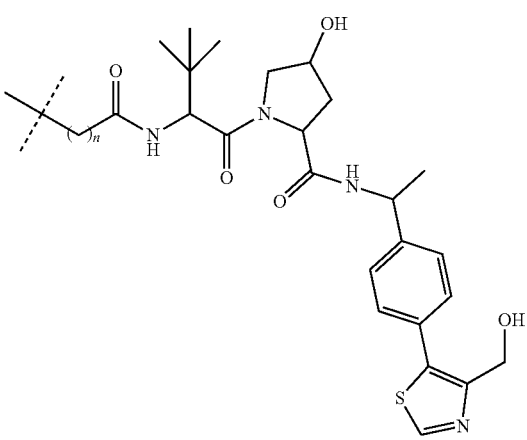

-continued
ULM-a7
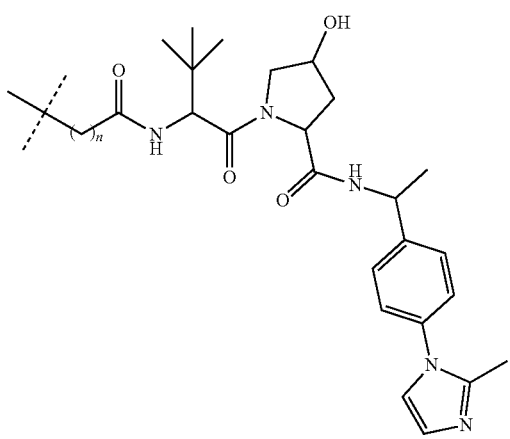
ULM-a10
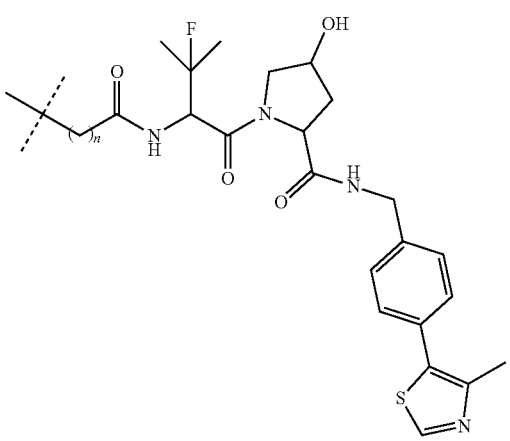
ULM-a8
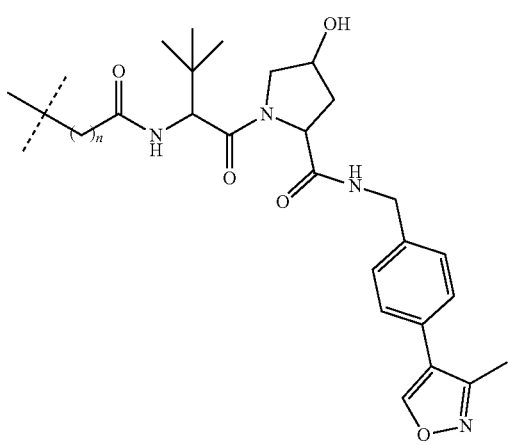
ULM-a11
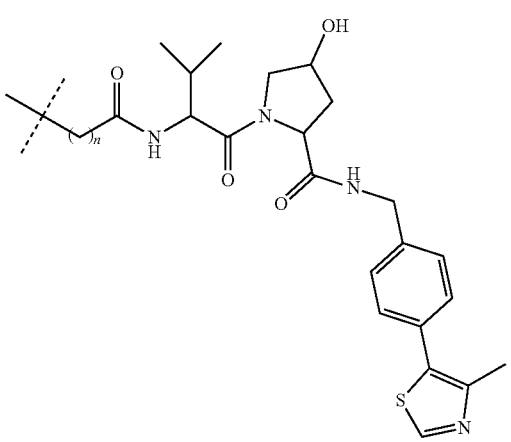
ULM-a9
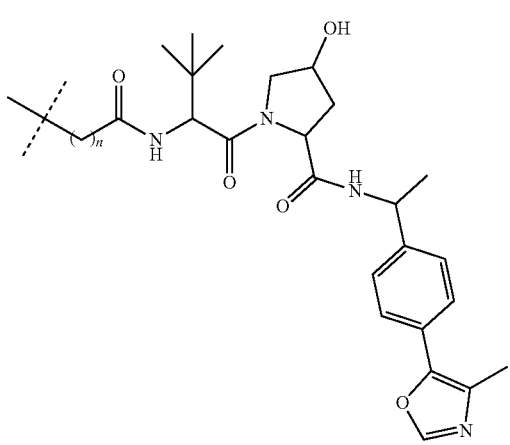
ULM-a12

ULM-a13
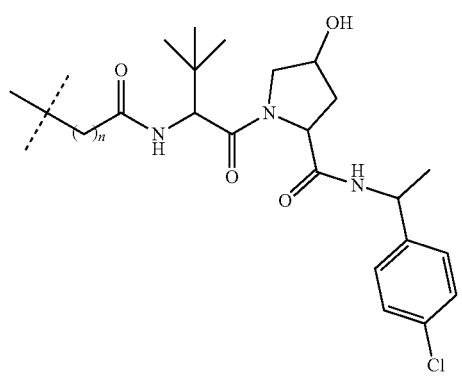
ULM-b1
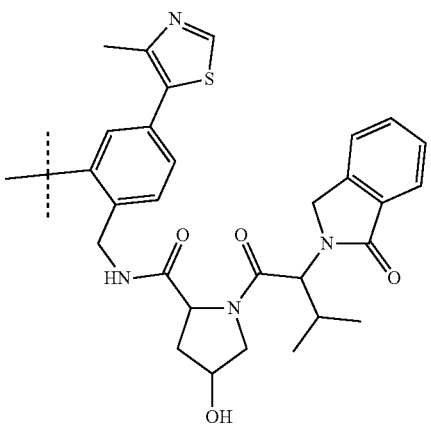
ULM-a14
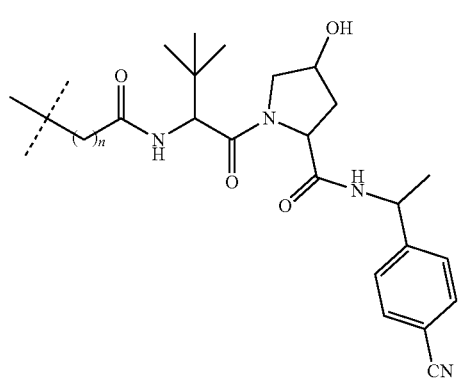
ULM-b2
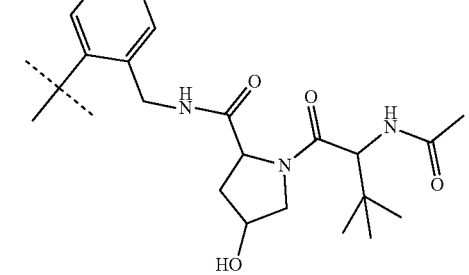
ULM-a15
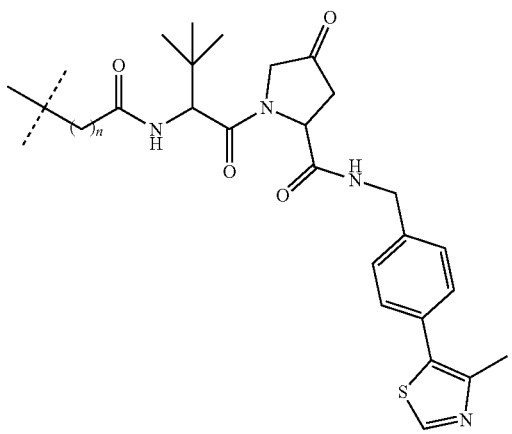
ULM-b3
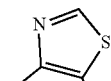
wherein n is 0 or 1.
In certain embodiments, the ULM is selected from the following structures:

ULM-b4
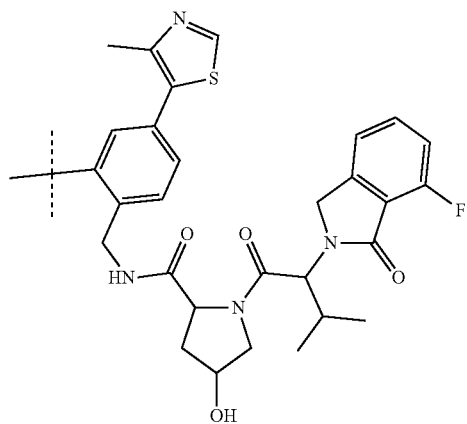
ULM-b5
ULM-b6
ULM-b7
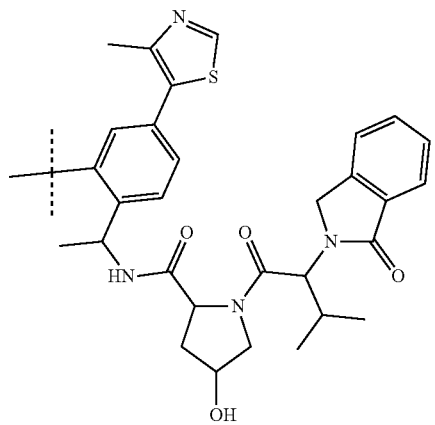
ULM-b8
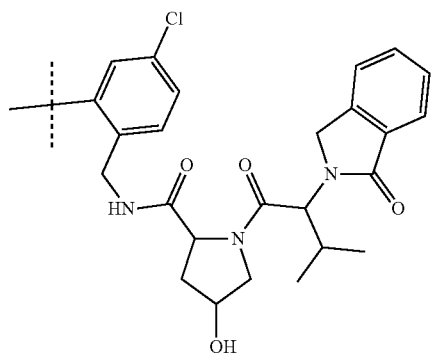
ULM-b9
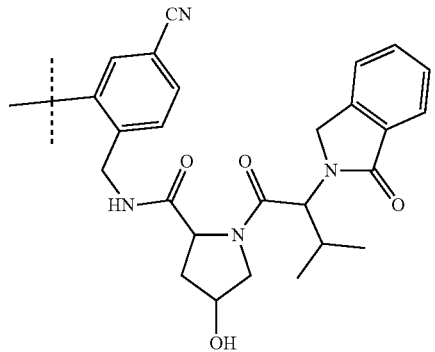
ULM-b10
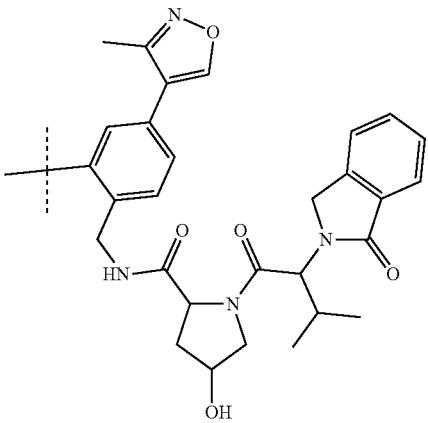

-continued
ULM-b11
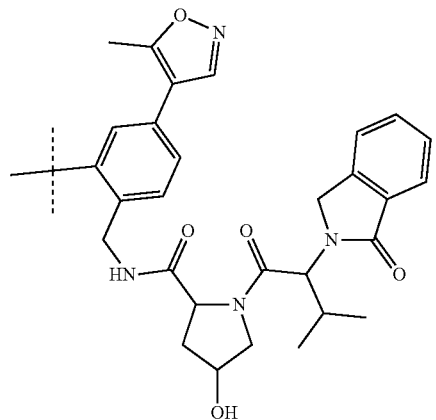
ULM-b12
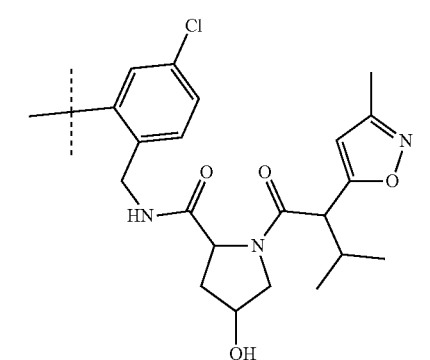
ULM-c1
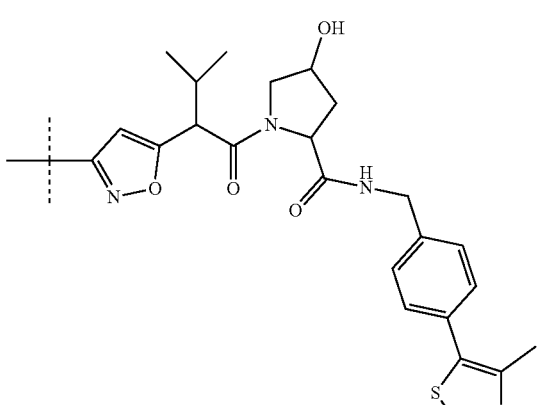
ULM-c2
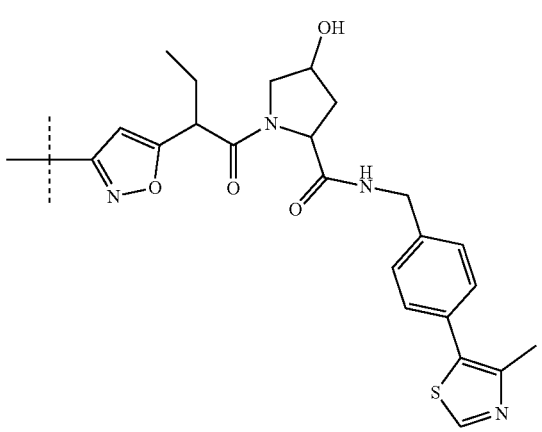
ULM-c3
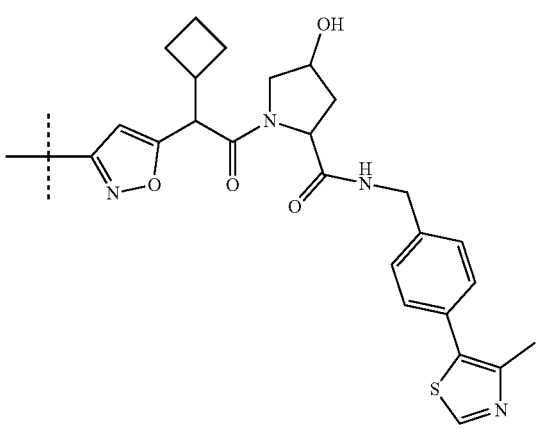
ULM-c4
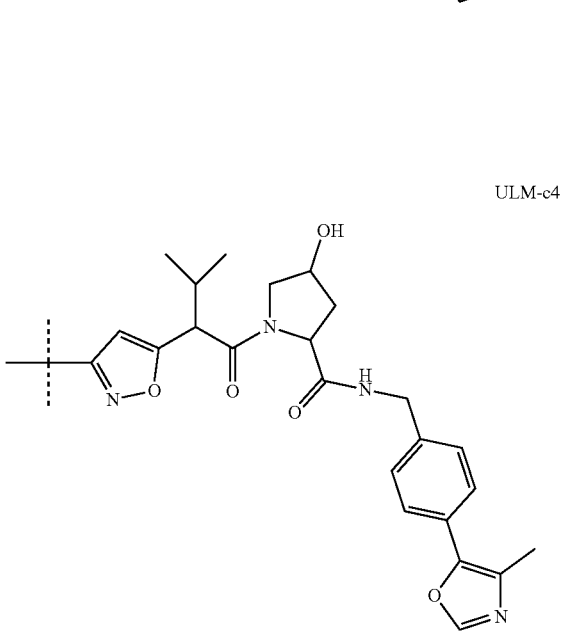
ULM-c5
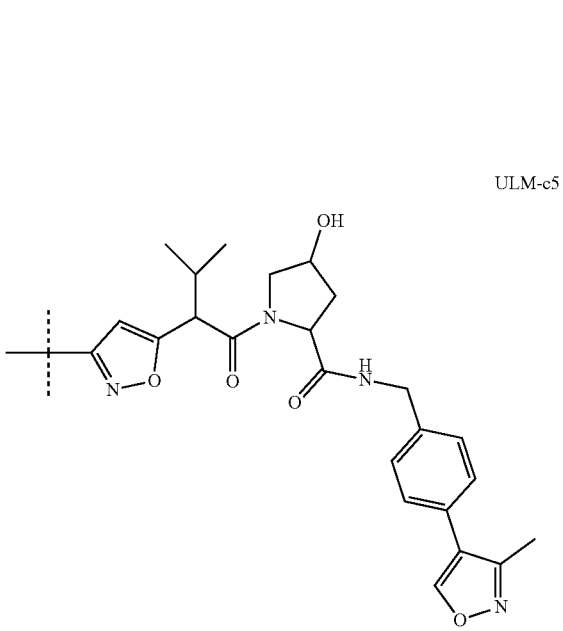

-continued
ULM-c6
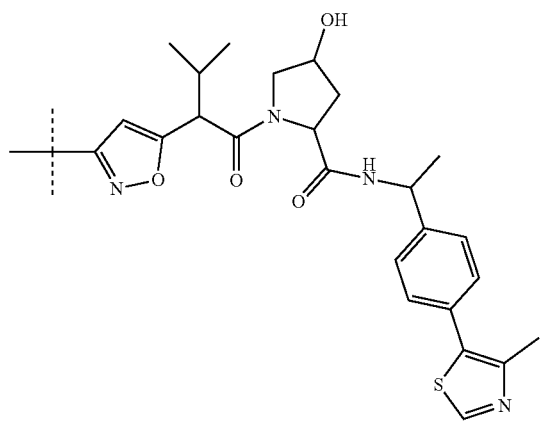
ULM-c9
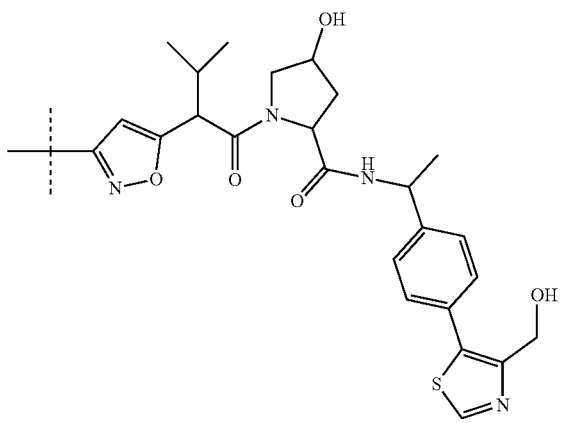
ULM-c7
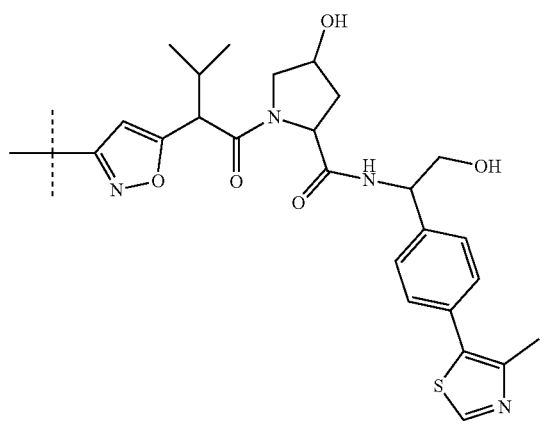
ULM-c10
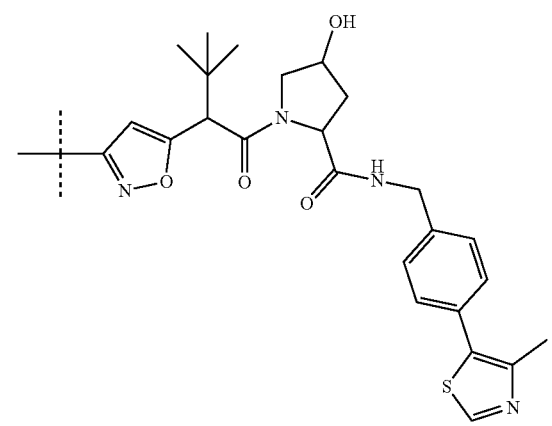
ULM-c8
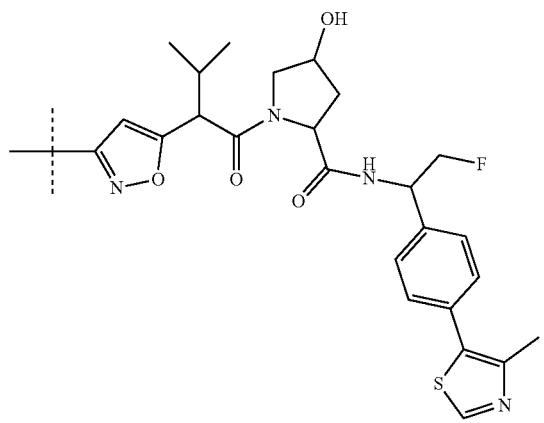
ULM-c11
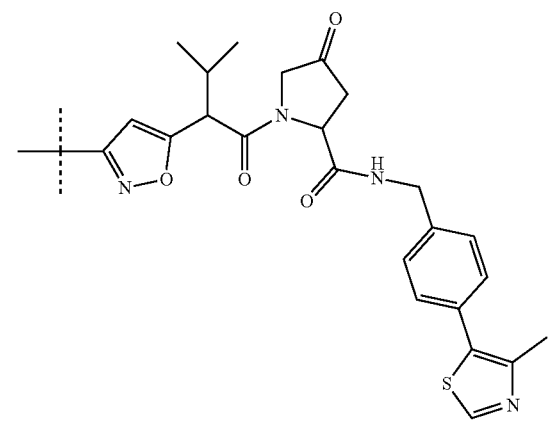

ULM-c12
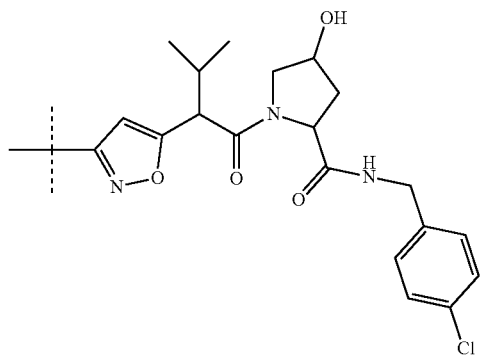
ULM-c13
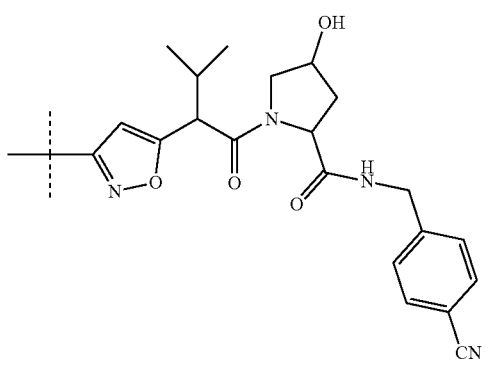
ULM-c14
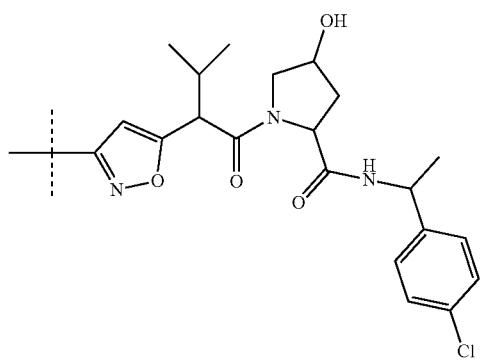
ULM-c15
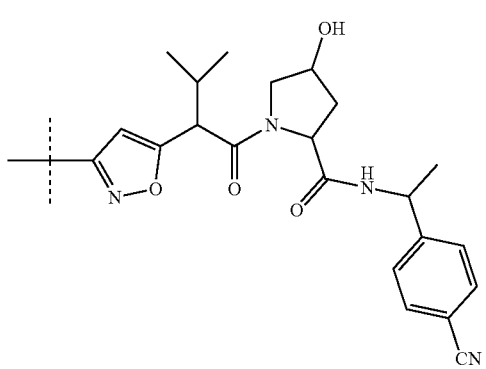
ULM-d1
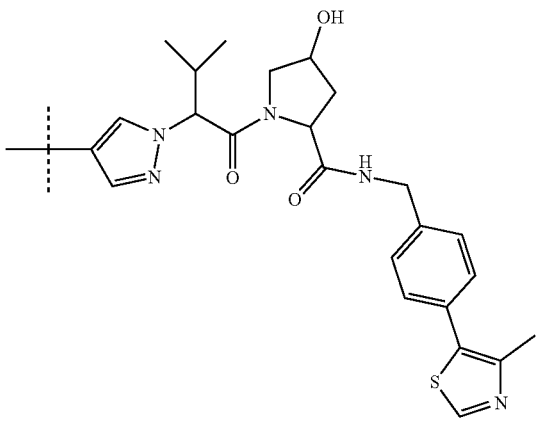
ULM-d2
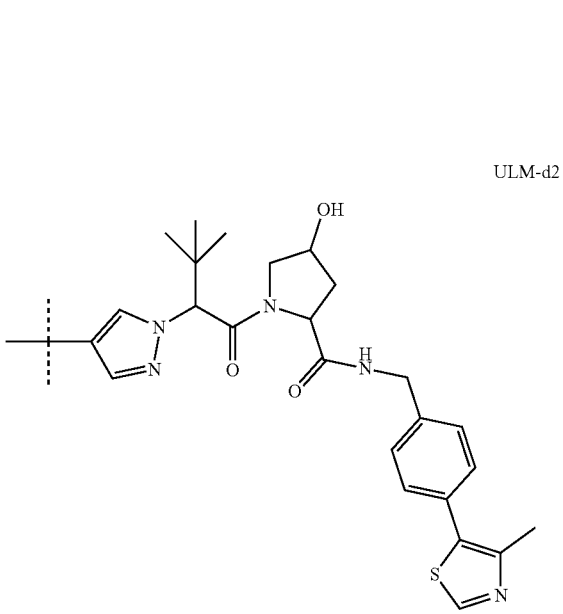
ULM-d3
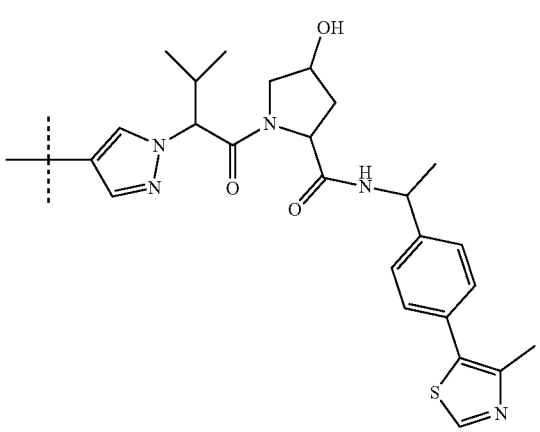

ULM-d4

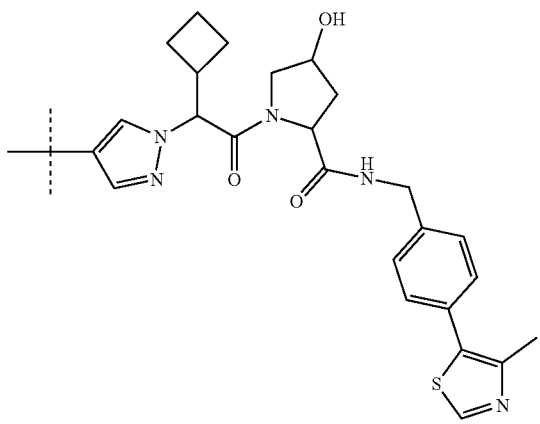

ULM-d5

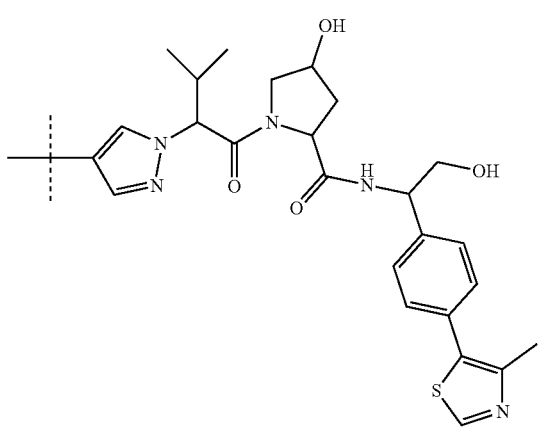

ULM-d6

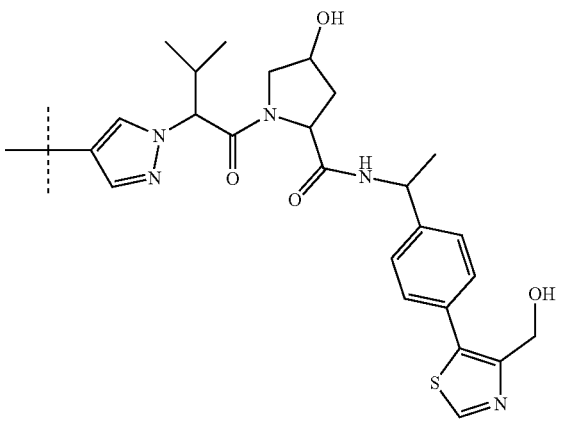

ULM-d7

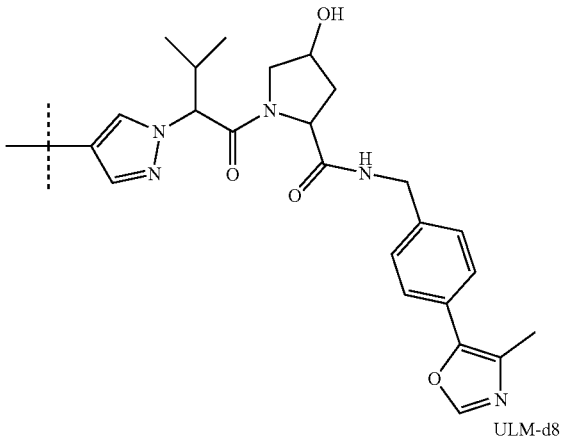

ULM-d8

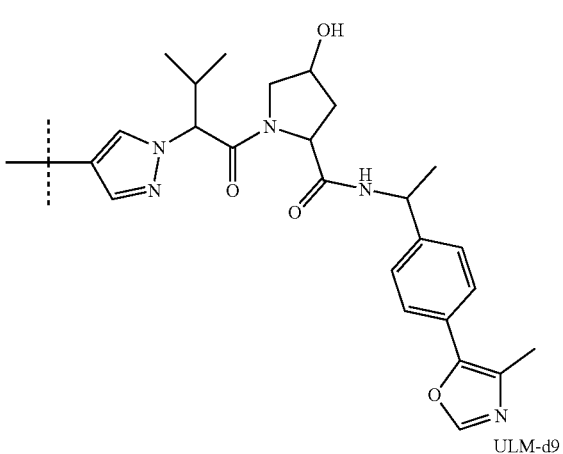

ULM-d9

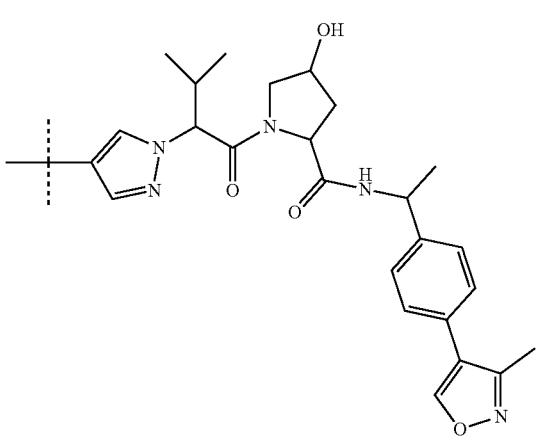

wherein, the phenyl ring in ULM-a1 through ULM-a15, ULM-b1 through ULM-b 12, ULM-c1 through ULM-c15 and ULM-d1 through ULM-d9 is optionally substituted with fluorine, lower alkyl and alkoxy groups, and wherein the dashed line indicates the site of attachment of at least one PTM, another ULM (ULM') or a chemical linker moiety coupling at least one PTM or a ULM' or both to ULM-a.

In one embodiment, the phenyl ring in ULM-a1 through ULM-a15, ULM-b1 through ULM-b12, ULM-c1 through ULM-c15 and ULM-d1 through ULM-d9 can be functionalized as the ester to make it a part of the prodrug.

In certain embodiments, the hydroxyl group on the pyrrolidine ring of ULM-a1 through ULM-a15, ULM-b1 through ULM-b12, ULM-c1 through ULM-c15 and ULM-d1 through ULM-d9, respectively, comprises an ester-linked prodrug moiety.

In any of the aspects or embodiments described herein, the ULM and where present, ULM', are each independently a group according to the chemical structure:

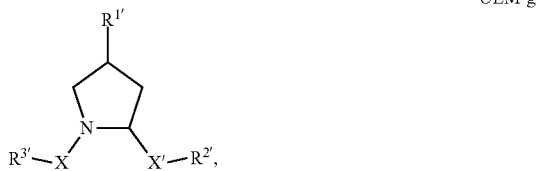

ULM-g wherein:

$R^{1'}$ of ULM-g is an optionally substituted $C_1$-$C_6$ alkyl group, an optionally substituted $-(CH_2)_nOH$, an optionally substituted $-(CH_2)_nSH$, an optionally substituted $(CH_2)_n-O-(C_1-C_6)$alkyl group, an optionally substituted $(CH_2)_n$—WCOCW—$(C_0-C_6)$alkyl group containing an epoxide moiety WCOCW where each W is independently H or a $C_1$-$C_3$ alkyl group, an optionally substituted $-(CH_2)_nCOOH$, an optionally substituted $-(CH_2)_nC(O)-(C_1-C_6$ alkyl), an optionally substituted $-(CH_2)_nNHC(O)-R_1$, an optionally substituted $-(CH_2)_nC(O)-NR_1R_2$, an optionally substituted $-(CH_2)_nOC(O)-NR_1R_2$, $-(CH_2O)_nH$, an optionally substituted $-(CH_2)_nOC(O)-(C_1-C_6$ alkyl), an optionally substituted $-(CH_2)_nC(O)-O-(C_1-C_6$ alkyl), an optionally substituted $-(CH_2O)_nCOOH$, an optionally substituted $-(OCH_2)_nO-(C_1-C_6$ alkyl), an optionally substituted $-(CH_2O)_nC(O)-(C_1-C_6$ alkyl), an optionally substituted $-(OCH_2)_nNHC(O)-R_1$, an optionally substituted $-(CH_2O)_nC(O)-NR_1R_2$, $-(CH_2CH_2O)_nH$, an optionally substituted $-(CH_2CH_2O)_nCOOH$, an optionally substituted $-(OCH_2CH_2)_nO-(C_1-C_6$ alkyl), an optionally substituted $-(CH_2CH_2O)_nC(O)-(C_1-C_6$ alkyl), an optionally substituted $-(OCH_2CH_2)_nNHC(O)-R_1$, an optionally substituted $-(CH_2CH_2O)_nC(O)-NR_1R_2$, an optionally substituted $-SO_2R_S$, an optionally substituted $S(O)R_S$, $NO_2$, CN or halogen (F, Cl, Br, I, preferably F or Cl);

$R_1$ and $R_2$ of ULM-g are each independently H or a $C_1$-$C_6$ alkyl group which may be optionally substituted with one or two hydroxyl groups or up to three halogen groups (preferably fluorine);

$R_S$ of ULM-g is a $C_1$-$C_6$ alkyl group, an optionally substituted aryl, heteroaryl or heterocycle group or a $-(CH_2)_mNR_1R_2$ group;

X and X' of ULM-g are each independently C=O, C=S, —S(O), $S(O)_2$, (preferably X and X' are both C=O);

$R^{2'}$ of ULM-g is an optionally substituted $-(CH_2)_n-(C=O)_u(NR_1)_v(SO_2)_w$alkyl group, an optionally substituted $-(CH_2)_n-(C=O)_u(NR_1)_v(SO_2)_wNR_{1N}R_{2N}$ group, an optionally substituted $-(CH_2)_n-(C=O)_u(NR_1)_v(SO_2)_w$-Aryl, an optionally substituted $-(CH_2)_n-(C=O)_u(NR_1)_v(SO_2)_w$-Heteroaryl, an optionally substituted $-(CH_2)_n-(C=O)_vNR_1(SO_2)_w$-Heterocycle, an optionally substituted $-NR^1-(CH_2)_n-C(O)_u(NR_1)_v(SO_2)_w$-alkyl, an optionally substituted $-NR^1-(CH_2)_n-C(O)_u(NR_1)_v(SO_2)_w-NR_{1N}R_{2N}$, an optionally substituted $-NR^1-(CH_2)_n-C(O)_u(NR_1)_v(SO_2)_w-NR_1C(O)R_{1N}$, an optionally substituted $-NR^1-(CH_2)_n-(C=O)_u(NR_1)_v(SO_2)_w$-Aryl, an optionally substituted $-NR^1-(CH_2)_n-(C=O)_u(NR_1)_v(SO_2)_w$-Heteroaryl or an optionally substituted $-NR^1-(CH_2)_n-(C=O)_uNR_1(SO_2)_w$-Heterocycle, an optionally substituted $-X^{R2'}$-alkyl group; an optionally substituted $-X^{R2'}$- Aryl group; an optionally substituted $-X^{R2'}$- Heteroaryl group; an optionally substituted $-X^{R2'}$- Heterocycle group; an optionally substituted;

$R^{3'}$ of ULM-g is an optionally substituted alkyl, an optionally substituted $-(CH_2)_n-(O)_u(NR_1)_v(SO_2)_w$-alkyl, an optionally substituted $-(CH_2)_n-C(O)_u(NR_1)_v(SO_2)_w-NR_{1N}R_{2N}$, an optionally substituted $-(CH_2)_n-C(O)_u(NR_1)_v(SO_2)_w-NR_1C(O)R_{1N}$, an optionally substituted $-(CH_2)_n-C(O)_u(NR_1)_v(SO_2)_w-C(O)NR_1R_2$, an optionally substituted $-(CH_2)_n-C(O)_u(NR_1)_v(SO_2)_w$-Aryl, an optionally substituted $-(CH_2)-C(O)_u(NR_1)_v(SO_2)_w$-Heteroaryl, an optionally substituted $-(CH_2)-C(O)_u(NR_1)_v(SO_2)_w$-Heterocycle, an optionally substituted $-NR^1-(CH_2)-C(O)_u(NR_1)_v(SO_2)_w$-alkyl, an optionally substituted $-NR^1-(CH_2)_n-C(O)_u(NR_1)_v(SO_2)_w-NR_{1N}R_{2N}$, an optionally substituted $-NR^1-(CH_2)_n-C(O)_u(NR_1)_v(SO_2)_w-NR_1C(O)R_{1N}$, an optionally substituted $-NR^1-(CH_2)_n-C(O)_u(NR_1)_v(SO_2)_w$-Aryl, an optionally substituted $-NR^1-(CH_2)_n-C(O)_u(NR_1)_v(SO_2)_w$-Heteroaryl, an optionally substituted $-NR^1-(CH_2)-C(O)_u(NR_1)_v(SO_2)_w$-Heterocycle, an optionally substituted $-O-(CH_2)_n-(C=O)_u(NR_1)_v(SO_2)_w$-alkyl, an optionally substituted $-O-(CH_2)_n-(C=O)_u(NR_1)_v(SO_2)_w-NR_{1N}R_{2N}$, an optionally substituted $-O-(CH_2)_n-(C=O)_u(NR_1)_v(SO_2)_w-NR_1C(O)R_{1N}$, an optionally substituted $-O-(CH_2)_n-(C=O)_u(NR_1)_v(SO_2)_w$-Aryl, an optionally substituted $-O-(CH_2)-(C=O)_u(NR_1)_v(SO_2)_w$-Heteroaryl or an optionally substituted $-O-(CH_2)_n-(C=O)_u(NR_1)_v(SO_2)_w$-Heterocycle; $-(CH_2)_n-(V)_{n'}-(CH_2)_n-(V)_{n'}$-alkyl group, an optionally substituted $-(CH_2)_n-(V)_{n'}-(CH_2)_n-(V)_{n'}$-Aryl group, an optionally substituted $-(CH_2)_n-(V)_{n'}-(CH_2)_n-(V)_{n'}$-Heteroaryl group, an optionally substituted $-(CH_2)_n-(V)_{n'}-(CH_2)_n-(V)_{n'}$-Heterocycle group, an optionally substituted $-(CH_2)_n-N(R_{1'})(C=O)_{m'}-(V)_{n'}$-alkyl group, an optionally substituted $-(CH_2)_n-N(R_{1'})(C=O)_{m'}-(V)_{n'}$-Aryl group, an optionally substituted $-(CH_2)_n-N(R_{1'})(C=O)_{m'}-(V)_{n'}$-Heteroaryl group, an optionally substituted $-(CH_2)_n-N(R_{1'})(C=O)_{m'}-(V)_{n'}$-Heterocycle group, an optionally substituted $-X^{R3'}$- alkyl group; an optionally substituted $-X^{R3'}$- Aryl group; an optionally substituted $-X^{R3'}$- Heteroaryl group; an optionally substituted $-X^{R3'}$- Heterocycle group; an optionally substituted;

$R_{1N}$ and $R_{2N}$ of ULM-g are each independently H, $C_1$-$C_6$ alkyl which is optionally substituted with one or two hydroxyl groups and up to three halogen groups or an optionally substituted $-(CH_2)_n$-Aryl, $-(CH_2)_n$-Heteroaryl or $-(CH_2)_n$-Heterocycle group;

V of ULM-g is O, S or $NR_1$;

$R_1$ of ULM-g is the same as above;

$R^1$ and $R_{1'}$ of ULM-g are each independently H or a $C_1$-$C_3$ alkyl group;

$X^{R2'}$ and $X^{R3'}$ of ULM-g are each independently an optionally substituted $-CH_2)_n-$, $-CH_2)_n-CH(X_v)=CH(X_v)-$ (cis or trans), $-CH_2)_n-CH=CH-$, —(CH$_2$CH$_2$O)$_n$— or a C$_3$-C$_6$ cycloalkyl group, where X$_v$ is H, a halo or a C$_1$-C$_3$ alkyl group which is optionally substituted;

each m of ULM-g is independently 0, 1, 2, 3, 4, 5, 6;
each m' of ULM-g is independently 0 or 1;
each n of ULM-g is independently 0, 1, 2, 3, 4, 5, 6;
each n' of ULM-g is independently 0 or 1;
each u of ULM-g is independently 0 or 1;
each v of ULM-g is independently 0 or 1;
each w of ULM-g is independently 0 or 1; and
any one or more of R$^{1'}$, R$^{2'}$, R$^{3'}$, X and X' of ULM-g is optionally modified to be covalently bonded to the PTM group through a linker group when PTM is not ULM', or when PTM is ULM', any one or more of R$^{1'}$, R$^{2'}$, R$^{3'}$, X and X' of each of ULM and ULM' are optionally modified to be covalently bonded to each other directly or through a linker group, or a pharmaceutically acceptable salt, stereoisomer, solvate or polymorph thereof.

In any of the aspects or embodiments described herein, the ULM and when present, ULM', are each independently a group according to the chemical structure:

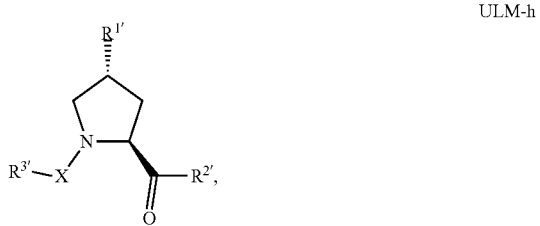

ULM-h wherein:
each of R$^{1'}$, R$^{2'}$ and R$^{3'}$ of ULM-h are the same as above and X is C=O, C=S, —S(O) group or a S(O)$_2$ group, more preferably a C=O group, and
any one or more of R$^{1'}$, R$^{2'}$ and R$^{3'}$ of ULM-h are optionally modified to bind a linker group to which is further covalently bonded to the PTM group when PTM is not ULM', or when PTM is ULM', any one or more of R$^{1'}$, R$^{2'}$, R$^{3'}$ of each of ULM and ULM' are optionally modified to be covalently bonded to each other directly or through a linker group, or
a pharmaceutically acceptable salt, enantiomer, diastereomer, solvate or polymorph thereof.

In any of the aspects or embodiments described herein, the ULM, and when present, ULM', are each independently according to the chemical structure:

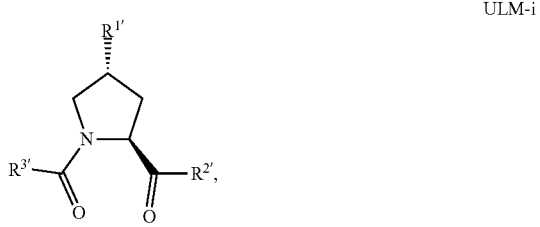

ULM-i wherein:
any one or more of R$^{1'}$, R$^{2'}$ and R$^{3'}$ of ULM-I are optionally modified to bind a linker group to which is further covalently bonded to the PTM group when PTM is not ULM', or when PTM is ULM', any one or more of R$^{1'}$, R$^{2'}$, R$^{3'}$ of each of ULM and ULM' are optionally modified to be covalently bonded to each other directly or through a linker group, or
a pharmaceutically acceptable salt, enantiomer, diastereomer, solvate or polymorph thereof.

In further preferred aspects of the disclosure, R$^{1'}$ of ULM-g through ULM-i is preferably a hydroxyl group or a group which may be metabolized to a hydroxyl or carboxylic group, such that the compound represents a prodrug form of an active compound. Exemplary preferred R$^{1'}$ groups include, for example, —(CH$_2$)$_n$OH, (CH$_2$)$_n$—O—(C$_1$-C$_6$)alkyl group, —(CH$_2$)$_n$COOH, —(CH$_2$O)$_n$H, an optionally substituted —(CH$_2$)$_n$OC(O)—(C$_1$-C$_6$ alkyl), or an optionally substituted —(CH$_2$)$_n$C(O)—O—(C$_1$-C$_6$ alkyl), wherein n is 0 or 1. Where R' is or contains a carboxylic acid group, a hydroxyl group or an amine group, the hydroxyl group, carboxylic acid group or amine (each of which may be optionally substituted), may be further chemically modified to provide a covalent link to a linker group to which the PTM group (including a ULM' group) is bonded;

X and X', where present, of ULM-g and ULM-h are preferably a C=O, C=S, —S(O) group or a S(O)$_2$ group, more preferably a C=O group;

R$^{2'}$ of ULM-g through ULM-i is preferably an optionally substituted —NR$^1$-T-Aryl, an optionally substituted —NR$^1$-T-Heteroaryl group or an optionally substituted —NR$^1$-T-Heterocycle, where R$^1$ is H or CH$_3$, preferably H and T is an optionally substituted —(CH$_2$)$_n$— group, wherein each one of the methylene groups may be optionally substituted with one or two substituents, preferably selected from halogen, an amino acid sidechain as otherwise described herein or a C$_1$-C$_3$ alkyl group, preferably one or two methyl groups, which may be optionally substituted; and n is 0 to 6, often 0, 1, 2 or 3, preferably 0 or 1. Alternatively, T may also be a —(CH$_2$O)$_n$— group, a —(OCH$_2$)$_n$— group, a —(CH$_2$CH$_2$O)$_n$— group, a —(OCH$_2$CH$_2$)$_n$— group, all of which groups are optionally substituted.

Preferred Aryl groups for R$^{2'}$ of ULM-g through ULM-i include optionally substituted phenyl or naphthyl groups, preferably phenyl groups, wherein the phenyl or naphthyl group is optionally connected to a PTM group (including a ULM' group) via a linker group and/or optionally substituted with a halogen (preferably F or Cl), an amine, monoalkyl- or dialkyl amine (preferably, dimethylamine), F, Cl, OH, COOH, C$_1$-C$_6$ alkyl, preferably CH$_3$, CF$_3$, OMe, OCF$_3$, NO$_2$, or CN group (each of which may be substituted in ortho-, meta- and/or para-positions of the phenyl ring, preferably para-), an optionally substituted phenyl group (the phenyl group itself is optionally connected to a PTM group, including a ULM' group, via a linker group), and/or optionally substituted with at least one of F, Cl, OH, COOH, CH$_3$, CF$_3$, OMe, OCF$_3$, NO$_2$, or CN group (in ortho-, meta- and/or para-positions of the phenyl ring, preferably para-), a naphthyl group, which may be optionally substituted, an optionally substituted heteroaryl, preferably an optionally substituted isoxazole including a methylsubstituted isoxazole, an optionally substituted oxazole including a methyl-substituted oxazole, an optionally substituted thiazole including a methyl substituted thiazole, an optionally substituted isothiazole including a methyl substituted isothiazole, an optionally substituted pyrrole including a methyl-substituted pyrrole, an optionally substituted imidazole including a methylimidazole, an optionally substituted benzimidazole or methoxybenzylimidazole, an optionally substituted oximidazole or methyloximidazole, an optionally substituted diazole group, including a methyldiazole group, an optionally substituted triazole group, including a methylsubstituted triazole group, an optionally substituted pyridine group, including a halo-(preferably, F) or methylsubstitutedpyridine group or an oxapyridine group (where the pyridine group is linked to the phenyl group by an oxygen), an optionally substituted furan, an optionally substituted benzofuran, an optionally substituted dihydrobenzofuran, an optionally substituted indole, indolizine or azaindolizine (2, 3, or 4-azaindolizine), an optionally substituted quinoline, an optionally substituted group according to the chemical structure:

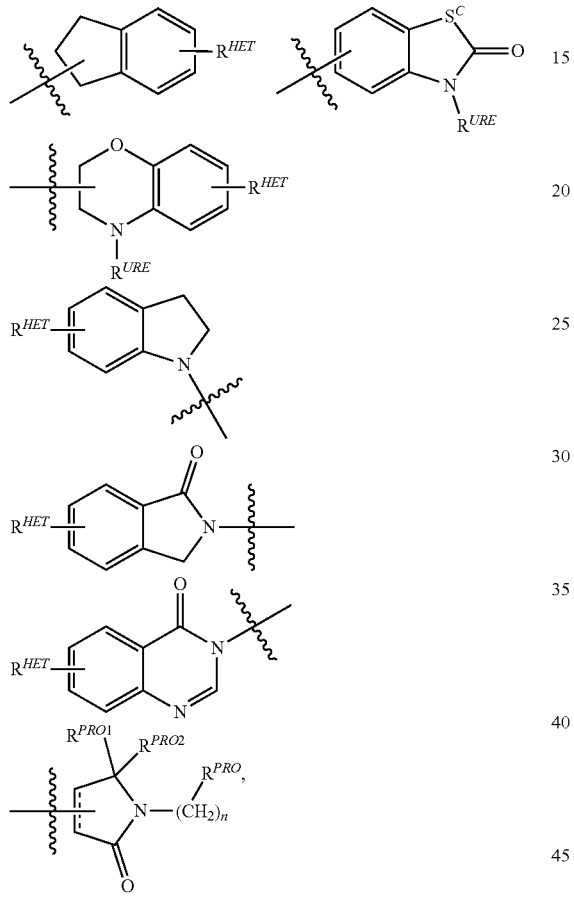

wherein:
  $S^c$ of ULM-g through ULM-i is $CHR^{SS}$, $NR^{URE}$, or O;
  $R^{HET}$ of ULM-g through ULM-i is H, CN, $NO_2$, halo (preferably Cl or F), optionally substituted $C_1$-$C_6$ alkyl (preferably substituted with one or two hydroxyl groups or up to three halo groups (e.g. $CF_3$), optionally substituted $O(C_1$-$C_6$ alkyl) (preferably substituted with one or two hydroxyl groups or up to three halo groups) or an optionally substituted acetylenic group —C≡C—$R_a$ where $R_a$ is H or a $C_1$-$C_6$ alkyl group (preferably $C_1$-$C_3$ alkyl);
  $R^{SS}$ of ULM-g through ULM-i is H, CN, $NO_2$, halo (preferably F or Cl), optionally substituted $C_1$-$C_6$ alkyl (preferably substituted with one or two hydroxyl groups or up to three halo groups), optionally substituted O—($C_1$-$C_6$ alkyl) (preferably substituted with one or two hydroxyl groups or up to three halo groups) or an optionally substituted —C(O)($C_1$-$C_6$ alkyl) (preferably substituted with one or two hydroxyl groups or up to three halo groups);
  $R^{URE}$ of ULM-g through ULM-i is H, a $C_1$-$C_6$ alkyl (preferably H or $C_1$-$C_3$ alkyl) or a —C(O)($C_1$-$C_6$ alkyl) each of which groups is optionally substituted with one or two hydroxyl groups or up to three halogen, preferably fluorine groups, or an optionally substituted phenyl group, an optionally substituted heteroaryl, or an optionally substituted heterocycle, preferably for example piperidine, morpholine, pyrrolidine, tetrahydrofuran);
  $R^{PRO}$ of ULM-g through ULM-i is H, optionally substituted $C_1$-$C_6$ alkyl or an optionally substituted aryl (phenyl or napthyl), heteroaryl or heterocyclic group selected from the group consisting of oxazole, isoxazole, thiazole, isothiazole, imidazole, diazole, oximidazole, pyrrole, pyrollidine, furan, dihydrofuran, tetrahydrofuran, thiene, dihydrothiene, tetrahydrothiene, pyridine, piperidine, piperazine, morpholine, quinoline, (each preferably substituted with a $C_1$-$C_3$ alkyl group, preferably methyl or a halo group, preferably F or Cl), benzofuran, indole, indolizine, azaindolizine;
  $R^{PRO1}$ and $R^{PRO2}$ of ULM-g through ULM-i are each independently H, an optionally substituted $C_1$-$C_3$ alkyl group or together form a keto group; and
  each n of ULM-g through ULM-i is independently 0, 1, 2, 3, 4, 5, or 6 (preferably 0 or 1), or an optionally substituted heterocycle, preferably tetrahydrofuran, tetrahydrothiene, piperidine, piperazine or morpholine (each of which groups when substituted, are preferably substituted with a methyl or halo (F, Br, Cl), each of which groups may be optionally connected to a PTM group (including a ULM' group) via a linker group.

In certain preferred aspects,

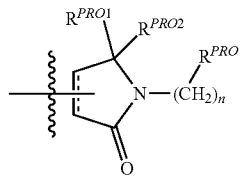

of ULM-g through ULM-i is a

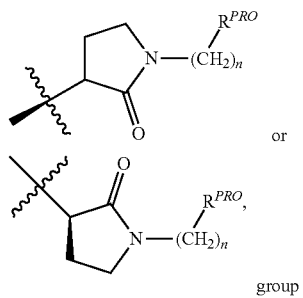

group where $R^{PRO}$ and n of ULM-g through ULM-i are the same as above.

Preferred heteroaryl groups for $R^{2'}$ of ULM-g through ULM-i include an optionally substituted quinoline (which may be attached to the pharmacophore or substituted on any carbon atom within the quinoline ring), an optionally substituted indole, an optionally substituted indolizine, an optionally substituted azaindolizine, an optionally substituted benzofuran, including an optionally substituted benzofuran, an optionally substituted isoxazole, an optionally substituted thiazole, an optionally substituted isothiazole, an optionally substituted thiophene, an optionally substituted pyridine (2-, 3-, or 4-pyridine), an optionally substituted imidazole, an optionally substituted pyrrole, an optionally substituted diazole, an optionally substituted triazole, a tetrazole, an optionally substituted oximidazole, or a group according to the chemical structure:

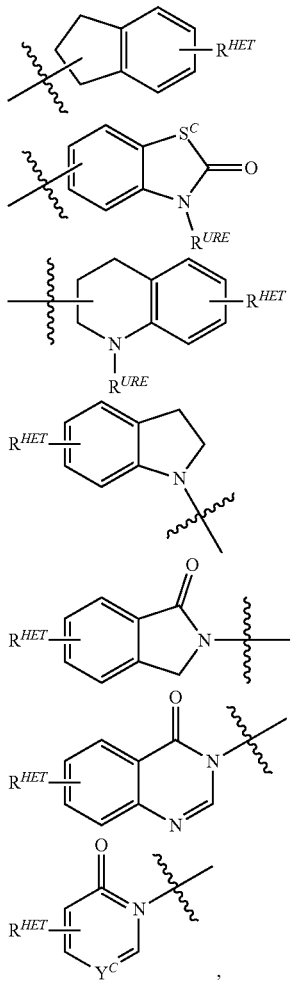

wherein:
$S^c$ of ULM-g through ULM-i is $CHR^{SS}$, $NR^{URE}$, or O;
$R^{HET}$ of ULM-g through ULM-i is H, CN, $NO_2$, halo (preferably Cl or F), optionally substituted $C_1$-$C_6$ alkyl (preferably substituted with one or two hydroxyl groups or up to three halo groups (e.g. $CF_3$), optionally substituted O($C_1$-$C_6$ alkyl) (preferably substituted with one or two hydroxyl groups or up to three halo groups) or an optionally substituted acetylenic group —C≡C—$R_a$ where $R_a$ of ULM-g through ULM-i is H or a $C_1$-$C_6$ alkyl group (preferably $C_1$-$C_3$ alkyl);
$R^{SS}$ of ULM-g through ULM-i is H, CN, $NO_2$, halo (preferably F or Cl), optionally substituted $C_1$-$C_6$ alkyl (preferably substituted with one or two hydroxyl groups or up to three halo groups), optionally substituted O—($C_1$-$C_6$ alkyl) (preferably substituted with one or two hydroxyl groups or up to three halo groups) or an optionally substituted —C(O)($C_1$-$C_6$alkyl) (preferably substituted with one or two hydroxyl groups or up to three halo groups);
$R^{URE}$ of ULM-g through ULM-i is H, a $C_1$-$C_6$ alkyl (preferably H or $C_1$-$C_3$ alkyl) or a —C(O)($C_1$-$C_6$ alkyl), each of which groups is optionally substituted with one or two hydroxyl groups or up to three halogen, preferably fluorine groups, or an optionally substituted heterocycle, for example piperidine, morpholine, pyrrolidine, tetrahydrofuran, tetrahydrothiophene, piperidine, piperazine, each of which is optionally substituted, and
$Y^C$ of ULM-g through ULM-i is N or C—$R^{YC}$, where $R^{YC}$ is H, OH, CN, $NO_2$, halo (preferably Cl or F), optionally substituted $C_1$-$C_6$ alkyl (preferably substituted with one or two hydroxyl groups or up to three halo groups (e.g. $CF_3$), optionally substituted O($C_1$-$C_6$ alkyl) (preferably substituted with one or two hydroxyl groups or up to three halo groups) or an optionally substituted acetylenic group —C≡C—$R_a$ where $R_a$ is H or a $C_1$-$C_6$ alkyl group (preferably $C_1$-$C_3$ alkyl), each of which groups may be optionally connected to a PTM group (including a ULM' group) via a linker group.

Preferred heterocycle groups for $R^{2'}$ of ULM-g through ULM-i include tetrahydrofuran, tetrahydrothiene, tetrahydroquinoline, piperidine, piperazine, pyrrollidine, morpholine, oxane or thiane, each of which groups may be optionally substituted, or a group according to the chemical structure:

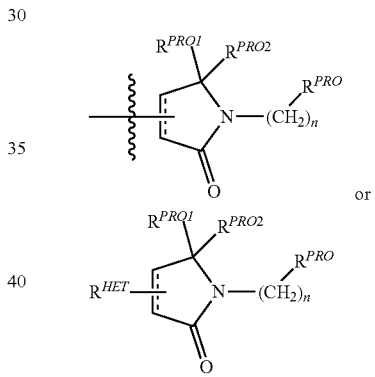

preferably, a

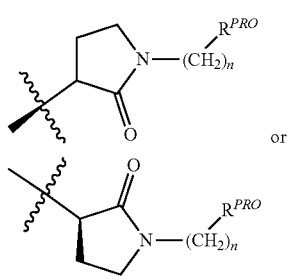

group,
wherein:
$R^{PRO}$ of ULM-g through ULM-i is H, optionally substituted $C_1$-$C_6$ alkyl or an optionally substituted aryl, heteroaryl or heterocyclic group;
$R^{PRO1}$ and $R^{PRO2}$ of ULM-g through ULM-i are each independently H, an optionally substituted $C_1$-$C_3$ alkyl group or together form a keto group and each n of ULM-g through ULM-i is independently 0, 1, 2, 3, 4, 5, or 6 (often 0 or 1), each of which groups may be optionally connected to a PTM group (including a ULM' group) via a linker group.

Preferred $R^{2'}$ substituents of ULM-g through ULM-i also include specifically (and without limitation to the specific compound disclosed) the $R^{2'}$ substituents which are found in the identified compounds disclosed herein (which includes the specific compounds which are disclosed in the present specification, and the figures which are attached hereto). Each of these $R^{2'}$ substituents may be used in conjunction with any number of $R^{3'}$ substituents which are also disclosed herein.

$R^{3'}$ of ULM-g through ULM-i is preferably an optionally substituted -T-Aryl, an optionally substituted-T-Heteroaryl, an optionally substituted -T-Heterocycle, an optionally substituted-$NR^1$-T-Aryl, an optionally substituted —$NR^1$-T-Heteroaryl or an optionally substituted-$NR^1$-T-Heterocycle, where $R^1$ is H or a $C_1$-$C_3$ alkyl group, preferably H or $CH_3$, T is an optionally substituted —$(CH_2)_n$— group, wherein each one of the methylene groups may be optionally substituted with one or two substituents, preferably selected from halogen, a $C_1$-$C_3$ alkyl group or the sidechain of an amino acid as otherwise described herein, preferably methyl, which may be optionally substituted; and n is 0 to 6, often 0, 1, 2, or 3 preferably 0 or 1. Alternatively, T may also be a —$(CH_2O)_n$— group, a —$(OCH_2)_n$— group, a —$(CH_2CH_2O)_n$— group, a —$(OCH_2CH_2)_n$— group, each of which groups is optionally substituted.

Preferred aryl groups for $R^{3'}$ of ULM-g through ULM-i include optionally substituted phenyl or naphthyl groups, preferably phenyl groups, wherein the phenyl or naphthyl group is optionally connected to a PTM group (including a ULM' group) via a linker group and/or optionally substituted with at least one of a halogen (preferably F or Cl), an amine, monoalkyl- or dialkyl amine (preferably, dimethylamine), an amido group (preferably a —$(CH_2)_m$—$NR_1C(O)R_2$ group where m, $R_1$ and $R_2$ are the same as above), a halo (often F or Cl), OH, $CH_3$, $CF_3$, OMe, $OCF_3$, $NO_2$, CN or a $S(O)_2R_S$ group ($R_S$ is a a $C_1$-$C_6$ alkyl group, an optionally substituted aryl, heteroaryl or heterocycle group or a —$(CH_2)_mNR_1R_2$ group), each of which may be substituted in ortho-, meta- and/or para-positions of the phenyl ring, preferably para-), or an Aryl (preferably phenyl), Heteroaryl or Heterocycle. Preferably said substituent phenyl group is an optionally substituted phenyl group (i.e., the substituent phenyl group itself is preferably substituted with at least one of F, Cl, OH, SH, COOH, $CH_3$, $CF_3$, OMe, $OCF_3$, $NO_2$, CN or a linker group to which is attached to a PTM group (including a ULM' group), wherein the substitution occurs in ortho-, meta- and/or para-positions of the phenyl ring, preferably para-), a naphthyl group, which may be optionally substituted including as described above, an optionally substituted heteroaryl (preferably an optionally substituted isoxazole including a methylsubstituted isoxazole, an optionally substituted oxazole including a methylsubstituted oxazole, an optionally substituted thiazole including a methyl substituted thiazole, an optionally substituted pyrrole including a methylsubstituted pyrrole, an optionally substituted imidazole including a methylimidazole, a benzylimidazole or methoxybenzylimidazole, an oximidazole or methyloximidazole, an optionally substituted diazole group, including a methyldiazole group, an optionally substituted triazole group, including a methylsubstituted triazole group, a pyridine group, including a halo-(preferably, F) or methylsubstitutedpyridine group or an oxapyridine group (where the pyridine group is linked to the phenyl group by an oxygen) or an optionally substituted heterocycle (tetrahydrofuran, tetrahydrothiophene, pyrrolidine, piperidine, morpholine, piperazine, tetrahydroquinoline, oxane or thiane. Each of the aryl, heteroaryl or heterocyclic groups may be optionally connected to a PTM group (including a ULM' group) via a linker group.

Preferred Heteroaryl groups for $R^{3'}$ of ULM-g through ULM-i include an optionally substituted quinoline (which may be attached to the pharmacophore or substituted on any carbon atom within the quinoline ring), an optionally substituted indole (including dihydroindole), an optionally substituted indolizine, an optionally substituted azaindolizine (2, 3 or 4-azaindolizine) an optionally substituted benzimidazole, benzodiazole, benzoxofuran, an optionally substituted imidazole, an optionally substituted isoxazole, an optionally substituted oxazole (preferably methyl substituted), an optionally substituted diazole, an optionally substituted triazole, a tetrazole, an optionally substituted benzofuran, an optionally substituted thiophene, an optionally substituted thiazole (preferably methyl and/or thiol substituted), an optionally substituted isothiazole, an optionally substituted triazole (preferably a 1,2,3-triazole substituted with a methyl group, a triisopropylsilyl group, an optionally substituted —$(CH_2)_m$—O—$C_1$-$C_6$ alkyl group or an optionally substituted —$(CH_2)_m$—C(O)—O—$C_1$-$C_6$ alkyl group), an optionally substituted pyridine (2-, 3, or 4-pyridine) or a group according to the chemical structure:

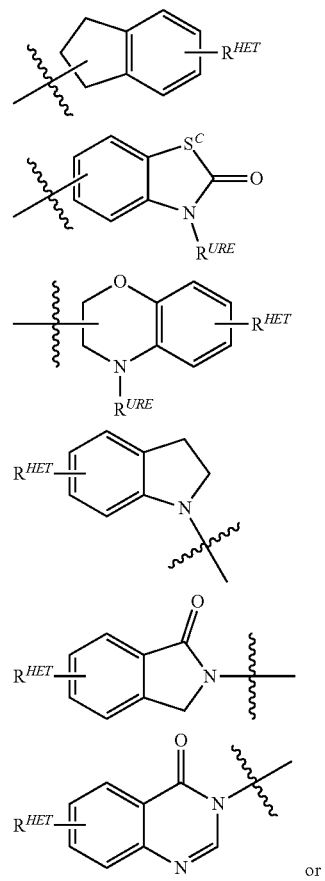

or

-continued

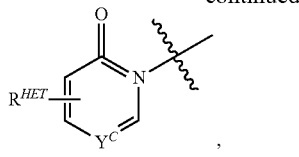

wherein:
- $S^c$ of ULM-g through ULM-i is $CHR^{SS}$, $NR^{URE}$, or O;
- $R^{HET}$ of ULM-g through ULM-i is H, CN, $NO_2$, halo (preferably Cl or F), optionally substituted $C_1$-$C_6$ alkyl (preferably substituted with one or two hydroxyl groups or up to three halo groups (e.g. $CF_3$), optionally substituted $O(C_1$-$C_6$ alkyl) (preferably substituted with one or two hydroxyl groups or up to three halo groups) or an optionally substituted acetylenic group —C≡C—$R_a$ where $R_a$ is H or a $C_1$-$C_6$ alkyl group (preferably $C_1$-$C_3$ alkyl);
- $R^{SS}$ of ULM-g through ULM-i is H, CN, $NO_2$, halo (preferably F or Cl), optionally substituted $C_1$-$C_6$ alkyl (preferably substituted with one or two hydroxyl groups or up to three halo groups), optionally substituted O—($C_1$-$C_6$ alkyl) (preferably substituted with one or two hydroxyl groups or up to three halo groups) or an optionally substituted —C(O)($C_1$-$C_6$alkyl) (preferably substituted with one or two hydroxyl groups or up to three halo groups);
- $R^{URE}$ of ULM-g through ULM-i is H, a $C_1$-$C_6$ alkyl (preferably H or $C_1$-$C_3$ alkyl) or a —C(O)($C_1$-$C_6$ alkyl), each of which groups is optionally substituted with one or two hydroxyl groups or up to three halogen, preferably fluorine groups, or an optionally substituted heterocycle, for example piperidine, morpholine, pyrrolidine, tetrahydrofuran, tetrahydrothiophene, piperidine, piperazine, each of which is optionally substituted, and
- $Y^C$ of ULM-g through ULM-i is N or C—$R^{YC}$, where $R^{YC}$ is H, OH, CN, $NO_2$, halo (preferably Cl or F), optionally substituted $C_1$-$C_6$ alkyl (preferably substituted with one or two hydroxyl groups or up to three halo groups (e.g. $CF_3$), optionally substituted $O(C_1$-$C_6$ alkyl) (preferably substituted with one or two hydroxyl groups or up to three halo groups) or an optionally substituted acetylenic group —C≡C—$R_a$ where $R_a$ is H or a $C_1$-$C_6$ alkyl group (preferably $C_1$-$C_3$ alkyl). Each of said heteroaryl groups may be optionally connected to a PTM group (including a ULM' group) via a linker group.

Preferred heterocycle groups for $R^{3'}$ of ULM-g through ULM-i include tetrahydroquinoline, piperidine, piperazine, pyrrollidine, morpholine, tetrahydrofuran, tetrahydrothiophene, oxane and thiane, each of which groups may be optionally substituted or a group according to the chemical structure:

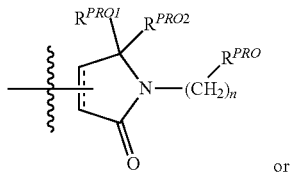

preferably, a


group,
wherein:
- $R^{PRO}$ of ULM-g through ULM-i is H, optionally substituted $C_1$-$C_6$ alkyl or an optionally substituted aryl (phenyl or napthyl), heteroaryl or heterocyclic group selected from the group consisting of oxazole, isoxazole, thiazole, isothiazole, imidazole, diazole, oximidazole, pyrrole, pyrollidine, furan, dihydrofuran, tetrahydrofuran, thiene, dihydrothiene, tetrahydrothiene, pyridine, piperidine, piperazine, morpholine, quinoline, (each preferably substituted with a $C_1$-$C_3$ alkyl group, preferably methyl or a halo group, preferably F or Cl), benzofuran, indole, indolizine, azaindolizine;
- $R^{PRO1}$ and $R^{PRO2}$ of ULM-g through ULM-i are each independently H, an optionally substituted $C_1$-$C_3$ alkyl group or together form a keto group, and
- each n of ULM-g through ULM-i is 0, 1, 2, 3, 4, 5, or 6 (preferably 0 or 1), wherein each of said Heteocycle groups may be optionally connected to a PTM group (including a ULM' group) via a linker group.

Preferred $R^{3'}$ substituents of ULM-g through ULM-i also include specifically (and without limitation to the specific compound disclosed) the $R^{3'}$ substituents which are found in the identified compounds disclosed herein (which includes the specific compounds which are disclosed in the present specification, and the figures which are attached hereto). Each of these $R^{3'}$ substituents may be used in conjunction with any number of $R^{2'}$ substituents, which are also disclosed herein.

In certain alternative preferred embodiments, $R^{2'}$ of ULM-g through ULM-i is an optionally substituted —$NR_1$—$X^{R2'}$-alkyl group, —$NR_1$—$X^{R2'}$-Aryl group; an optionally substituted —$NR_1$—$X^{R2'}$-HET, an optionally substituted —$NR_1$—$X^{R2'}$-Aryl-HET or an optionally substituted —$NR_1$—$X^{R2'}$-HET-Aryl,
wherein:
- $R_1$ of ULM-g through ULM-i is H or a $C_1$-$C_3$ alkyl group (preferably H);
- $X^{R2'}$ of ULM-g through ULM-i is an optionally substituted —$(CH_2)_n$—, —$(CH_2)_n$—$CH(X_v)$=$CH(X_v)$— (cis or trans), —$(CH_2)_n$—CH=CH—, —$(CH_2CH_2O)_n$— or a $C_3$-$C_6$ cycloalkyl group; and $X_v$ of ULM-g through ULM-i is H, a halo or a $C_1$-$C_3$ alkyl group which is optionally substituted with one or two hydroxyl groups or up to three halogen groups;

Alkyl of ULM-g through ULM-i is an optionally substituted $C_1$-$C_{10}$ alkyl (preferably a $C_1$-$C_6$ alkyl) group (in certain preferred embodiments, the alkyl group is end-capped with a halo group, often a Cl or Br);

Aryl of ULM-g through ULM-i is an optionally substituted phenyl or naphthyl group (preferably, a phenyl group); and HET of ULM-g through ULM-i is an optionally substituted oxazole, isoxazole, thiazole, isothiazole, imidazole, diazole, oximidazole, pyrrole, pyrollidine, furan, dihydrofuran, tetrahydrofuran, thiene, dihydrothiene, tetrahydrothiene, pyridine, piperidine, piperazine, morpholine, benzofuran, indole, indolizine, azaindolizine, quinoline (when substituted, each preferably substituted with a $C_1$-$C_3$ alkyl group, preferably methyl or a halo group, preferably F or Cl) or a group according to the chemical structure:

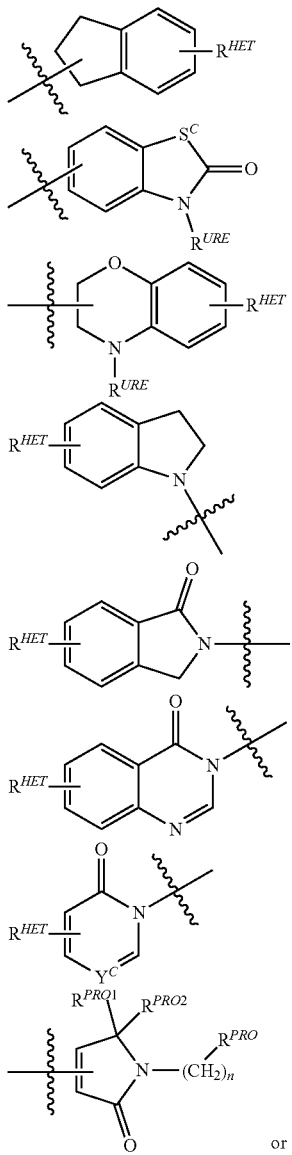

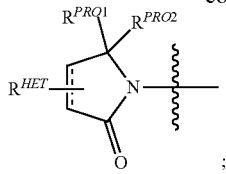

$S^c$ of ULM-g through ULM-i is $CHR^{SS}$, $NR^{URE}$, or O;

$R^{HET}$ of ULM-g through ULM-i is H, CN, $NO_2$, halo (preferably Cl or F), optionally substituted $C_1$-$C_6$ alkyl (preferably substituted with one or two hydroxyl groups or up to three halo groups (e.g. $CF_3$), optionally substituted $O(C_1$-$C_6$ alkyl) (preferably substituted with one or two hydroxyl groups or up to three halo groups) or an optionally substituted acetylenic group —C≡C—$R_a$ where $R_a$ is H or a $C_1$-$C_6$ alkyl group (preferably $C_1$-$C_3$ alkyl);

$R^{SS}$ of ULM-g through ULM-i is H, CN, $NO_2$, halo (preferably F or Cl), optionally substituted $C_1$-$C_6$ alkyl (preferably substituted with one or two hydroxyl groups or up to three halo groups), optionally substituted O—($C_1$-$C_6$ alkyl) (preferably substituted with one or two hydroxyl groups or up to three halo groups) or an optionally substituted —C(O)($C_1$-$C_6$alkyl) (preferably substituted with one or two hydroxyl groups or up to three halo groups);

$R^{URE}$ of ULM-g through ULM-i is H, a $C_1$-$C_6$ alkyl (preferably H or $C_1$-$C_3$ alkyl) or a —C(O)($C_1$-$C_6$ alkyl), each of which groups is optionally substituted with one or two hydroxyl groups or up to three halogen, preferably fluorine groups, or an optionally substituted heterocycle, for example piperidine, morpholine, pyrrolidine, tetrahydrofuran, tetrahydrothiophene, piperidine, piperazine, each of which is optionally substituted;

$Y^C$ of ULM-g through ULM-i is N or C—$R^{YC}$, where $R^{YC}$ is H, OH, CN, $NO_2$, halo (preferably Cl or F), optionally substituted $C_1$-$C_6$ alkyl (preferably substituted with one or two hydroxyl groups or up to three halo groups (e.g. $CF_3$), optionally substituted $O(C_1$-$C_6$ alkyl) (preferably substituted with one or two hydroxyl groups or up to three halo groups) or an optionally substituted acetylenic group —C≡C—$R_a$ where $R_a$ is H or a $C_1$-$C_6$ alkyl group (preferably $C_1$-$C_3$ alkyl);

$R^{PRO}$ of ULM-g through ULM-i is H, optionally substituted $C_1$-$C_6$ alkyl or an optionally substituted aryl (phenyl or napthyl), heteroaryl or heterocyclic group selected from the group consisting of oxazole, isoxazole, thiazole, isothiazole, imidazole, diazole, oximidazole, pyrrole, pyrollidine, furan, dihydrofuran, tetrahydrofuran, thiene, dihydrothiene, tetrahydrothiene, pyridine, piperidine, piperazine, morpholine, quinoline, (each preferably substituted with a $C_1$-$C_3$ alkyl group, preferably methyl or a halo group, preferably F or Cl), benzofuran, indole, indolizine, azaindolizine;

$R^{PRO1}$ and $R^{PRO2}$ of ULM-g through ULM-i are each independently H, an optionally substituted $C_1$-$C_3$ alkyl group or together form a keto group, and each n of ULM-g through ULM-i is independently 0, 1, 2, 3, 4, 5, or 6 (preferably 0 or 1).

Each of said groups may be optionally connected to a PTM group (including a ULM' group) via a linker group.

In certain alternative preferred embodiments of the present disclosure, $R^{3'}$ of ULM-g through ULM-i is an optionally substituted —$(CH_2)_n$—$(V)_{n'}$—$(CH_2)_n$—$(V)_{n'}$—$R^{S3'}$ group, an optionally substituted-$(CH_2)_n$—$N(R_{1'})(C=O)_m$—$(V)_{m'}$—$R^{S3'}$ group, an optionally substituted —$X^{R3'}$— alkyl group, an optionally substituted —$X^{R3'}$-Aryl group; an optionally substituted —$XR^{3'}$-HET group, an optionally substituted —$X^{R3'}$-Aryl-HET group or an optionally substituted —$XR^{3'}$-HET-Aryl group, wherein:
- $R^{S3'}$ is an optionally substituted alkyl group ($C_1$-$C_{10}$, preferably $C_1$-$C_6$ alkyl), an optionally substituted Aryl group or a HET group;
- $R_{1'}$ is H or a $C_1$-$C_3$ alkyl group (preferably H);
- V is O, S or $NR_{1'}$;
- $X^{R3'}$ is —$(CH_2)_n$—, —$(CH_2CH_2O)_n$—, —$CH_2)_n$—CH$(X_v)$=CH$(X_v)$— (cis or trans), —$CH_2)_n$—CH=CH—, or a $C_3$-$C_6$ cycloalkyl group, all optionally substituted;
- $X_v$ is H, a halo or a $C_1$-$C_3$ alkyl group which is optionally substituted with one or two hydroxyl groups or up to three halogen groups;
- Alkyl is an optionally substituted $C_1$-$C_{10}$ alkyl (preferably a $C_1$-$C_6$ alkyl) group (in certain preferred embodiments, the alkyl group is end-capped with a halo group, often a Cl or Br);
- Aryl is an optionally substituted phenyl or napthyl group (preferably, a phenyl group); and
- HET is an optionally substituted oxazole, isoxazole, thiazole, isothiazole, imidazole, diazole, oximidazole, pyrrole, pyrollidine, furan, dihydrofuran, tetrahydrofuran, thiene, dihydrothiene, tetrahydrothiene, pyridine, piperidine, piperazine, morpholine, benzofuran, indole, indolizine, azaindolizine, quinoline (when substituted, each preferably substituted with a $C_1$-$C_3$ alkyl group, preferably methyl or a halo group, preferably F or Cl), or a group according to the chemical structure:

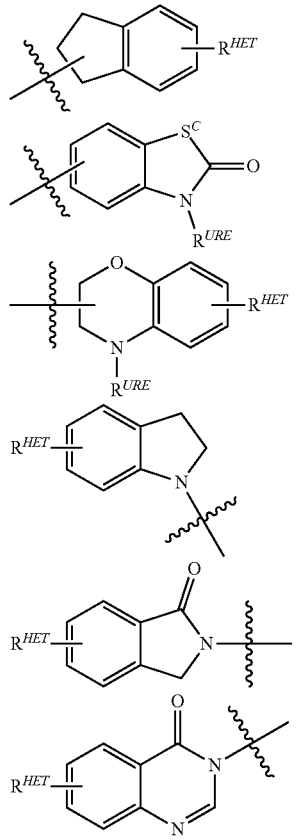

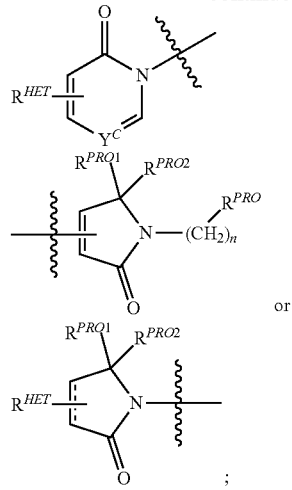

- $S^c$ of ULM-g through ULM-i is $CHR^{SS}$, $NR^{URE}$, or O;
- $R^{HET}$ of ULM-g through ULM-i is H, CN, $NO_2$, halo (preferably Cl or F), optionally substituted $C_1$-$C_6$ alkyl (preferably substituted with one or two hydroxyl groups or up to three halo groups (e.g. $CF_3$), optionally substituted $O(C_1$-$C_6$ alkyl) (preferably substituted with one or two hydroxyl groups or up to three halo groups) or an optionally substituted acetylenic group —C≡C—$R_a$ where $R_a$ is H or a $C_1$-$C_6$ alkyl group (preferably $C_1$-$C_3$ alkyl);
- $R^{SS}$ of ULM-g through ULM-i is H, CN, $NO_2$, halo (preferably F or Cl), optionally substituted $C_1$-$C_6$ alkyl (preferably substituted with one or two hydroxyl groups or up to three halo groups), optionally substituted O—($C_1$-$C_6$ alkyl) (preferably substituted with one or two hydroxyl groups or up to three halo groups) or an optionally substituted —C(O)($C_1$-$C_6$alkyl) (preferably substituted with one or two hydroxyl groups or up to three halo groups);
- $R^{URE}$ of ULM-g through ULM-i is H, a $C_1$-$C_6$ alkyl (preferably H or $C_1$-$C_3$ alkyl) or a —C(O)($C_0$-$C_6$ alkyl), each of which groups is optionally substituted with one or two hydroxyl groups or up to three halogen, preferably fluorine groups, or an optionally substituted heterocycle, for example piperidine, morpholine, pyrrolidine, tetrahydrofuran, tetrahydrothiophene, piperidine, piperazine, each of which is optionally substituted;
- $Y^C$ of ULM-g through ULM-i is N or C—$R^{YC}$, where $R^{YC}$ is H, OH, CN, $NO_2$, halo (preferably Cl or F), optionally substituted $C_1$-$C_6$ alkyl (preferably substituted with one or two hydroxyl groups or up to three halo groups (e.g. $CF_3$), optionally substituted $O(C_1$-$C_6$ alkyl) (preferably substituted with one or two hydroxyl groups or up to three halo groups) or an optionally substituted acetylenic group —C≡C—$R_a$ where $R_a$ is H or a $C_1$-$C_6$ alkyl group (preferably $C_1$-$C_3$ alkyl);
- $R^{PRO}$ of ULM-g through ULM-i is H, optionally substituted $C_1$-$C_6$ alkyl or an optionally substituted aryl (phenyl or napthyl), heteroaryl or heterocyclic group selected from the group consisting of oxazole, isoxazole, thiazole, isothiazole, imidazole, diazole, oximidazole, pyrrole, pyrollidine, furan, dihydrofuran, tetrahydrofuran, thiene, dihydrothiene, tetrahydrothiene, pyridine, piperidine, piperazine, morpholine, quinoline, (each preferably substituted with a $C_1$-$C_3$ alkyl group, preferably methyl or a halo group, preferably F or Cl), benzofuran, indole, indolizine, azaindolizine;

$R^{PRO1}$ and $R^{PRO2}$ of ULM-g through ULM-i are each independently H, an optionally substituted $C_1$-$C_3$ alkyl group or together form a keto group;

each n of ULM-g through ULM-i is independently 0, 1, 2, 3, 4, 5, or 6 (preferably 0 or 1);

each m' of ULM-g through ULM-i is 0 or 1; and each n' of ULM-g through ULM-i is 0 or 1;

wherein each of said compounds, preferably on the alkyl, Aryl or Het groups, is optionally connected to a PTM group (including a ULM' group) via a linker group.

In alternative embodiments, $R^{3'}$ of ULM-g through ULM-i is —$(CH_2)_n$-Aryl, —$(CH_2CH_2O)_n$-Aryl, —$(CH_2)_n$-HET or —$(CH_2CH_2O)_n$-HET, wherein:

said Aryl of ULM-g through ULM-i is phenyl which is optionally substituted with one or two substitutents, wherein said substituent(s) is preferably selected from —$(CH_2)_n$OH, $C_1$-$C_6$ alkyl which itself is further optionally substituted with CN, halo (up to three halo groups), OH, —$(CH_2)_n$O($C_1$-$C_6$)alkyl, amine, mono- or di-($C_1$-$C_6$ alkyl) amine wherein the alkyl group on the amine is optionally substituted with 1 or 2 hydroxyl groups or up to three halo (preferably F, Cl) groups, or said Aryl group of ULM-g through ULM-i is substituted with —$(CH_2)_n$OH, —$(CH_2)_n$—O—($C_1$-$C_6$)alkyl, —$(CH_2)_n$—O—$(CH_2)_n$—($C_1$-$C_6$)alkyl, —$(CH_2)_n$—C(O)($C_0$-$C_6$) alkyl, —$(CH_2)_n$—C(O)O($C_0$-$C_6$)alkyl, —$(CH_2)_n$—OC(O)($C_0$-$C_6$)alkyl, amine, mono- or di-($C_1$-$C_6$ alkyl) amine wherein the alkyl group on the amine is optionally substituted with 1 or 2 hydroxyl groups or up to three halo (preferably F, Cl) groups, CN, $NO_2$, an optionally substituted —$(CH_2)_n$—$(V)_m$—$CH_2)_n$—$(V)_m$—($C_1$-$C_6$)alkyl group, a —$(V)_m$—$(CH_2CH_2O)_n$—$R^{PEG}$ group where V is O, S or $NR_1$, $R_1$ is H or a $C_1$-$C_3$ alkyl group (preferably H) and $R^{PEG}$ is H or a $C_1$-$C_6$ alkyl group which is optionally substituted (including being optionally substituted with a carboxyl group), or said Aryl group of ULM-g through ULM-i is optionally substituted with a heterocycle, including a heteroaryl, selected from the group consisting of oxazole, isoxazole, thiazole, isothiazole, imidazole, diazole, oximidazole, pyrrole, pyrollidine, furan, dihydrofuran, tetrahydrofuran, thiene, dihydrothiene, tetrahydrothiene, pyridine, piperidine, piperazine, morpholine, quinoline, benzofuran, indole, indolizine, azaindolizine, (when substituted each preferably substituted with a $C_1$-$C_3$ alkyl group, preferably methyl or a halo group, preferably F or Cl), or a group according to the chemical structure:

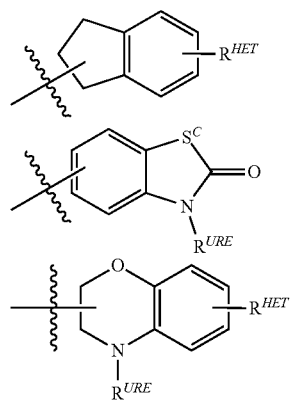

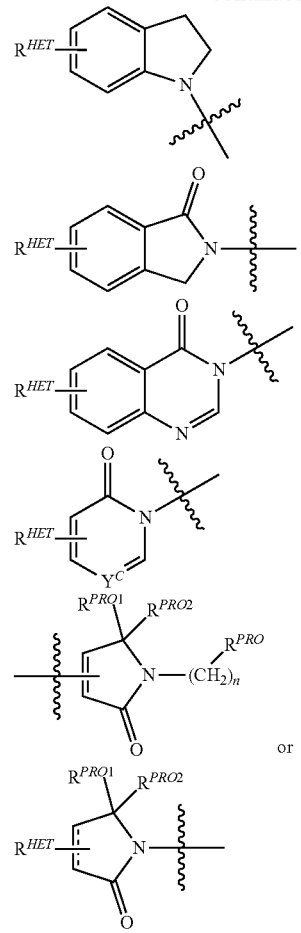

$S^c$ of ULM-g through ULM-i is $CHR^{SS}$, $NR^{URE}$, or O;

$R^{HET}$ of ULM-g through ULM-i is H, CN, $NO_2$, halo (preferably Cl or F), optionally substituted $C_1$-$C_6$ alkyl (preferably substituted with one or two hydroxyl groups or up to three halo groups (e.g. $CF_3$), optionally substituted O($C_1$-$C_6$ alkyl) (preferably substituted with one or two hydroxyl groups or up to three halo groups) or an optionally substituted acetylenic group —C≡C—$R_a$ where $R_a$ is H or a $C_1$-$C_6$ alkyl group (preferably $C_1$-$C_3$ alkyl);

$R^{SS}$ of ULM-g through ULM-i is H, CN, $NO_2$, halo (preferably F or Cl), optionally substituted $C_1$-$C_6$ alkyl (preferably substituted with one or two hydroxyl groups or up to three halo groups), optionally substituted O—($C_1$-$C_6$ alkyl) (preferably substituted with one or two hydroxyl groups or up to three halo groups) or an optionally substituted —C(O)($C_1$-$C_6$alkyl) (preferably substituted with one or two hydroxyl groups or up to three halo groups);

$R^{URE}$ of ULM-g through ULM-i is H, a $C_1$-$C_6$ alkyl (preferably H or $C_1$-$C_3$ alkyl) or a —C(O)($C_0$-$C_6$ alkyl), each of which groups is optionally substituted with one or two hydroxyl groups or up to three halogen, preferably fluorine groups, or an optionally substituted heterocycle, for example piperidine, morpholine, pyrrolidine, tetrahydrofuran, tetrahydrothiophene, piperidine, piperazine, each of which is optionally substituted;

$Y^C$ of ULM-g through ULM-i is N or C—$R^{YC}$, where $R^{YC}$ is H, OH, CN, NO$_2$, halo (preferably Cl or F), optionally substituted $C_1$-$C_6$ alkyl (preferably substituted with one or two hydroxyl groups or up to three halo groups (e.g. CF$_3$), optionally substituted O($C_1$-$C_6$ alkyl) (preferably substituted with one or two hydroxyl groups or up to three halo groups) or an optionally substituted acetylenic group —C≡C—$R_a$ where $R_a$ is H or a $C_1$-$C_6$ alkyl group (preferably $C_1$-$C_3$ alkyl);

$R^{PRO}$ of ULM-g through ULM-i is H, optionally substituted $C_1$-$C_6$ alkyl or an optionally substituted aryl (phenyl or napthyl), heteroaryl or heterocyclic group selected from the group consisting of oxazole, isoxazole, thiazole, isothiazole, imidazole, diazole, oximidazole, pyrrole, pyrollidine, furan, dihydrofuran, tetrahydrofuran, thiene, dihydrothiene, tetrahydrothiene, pyridine, piperidine, piperazine, morpholine, quinoline, (each preferably substituted with a $C_1$-$C_3$ alkyl group, preferably methyl or a halo group, preferably F or Cl), benzofuran, indole, indolizine, azaindolizine;

$R^{PRO1}$ and $R^{PRO2}$ of ULM-g through ULM-i are each independently H, an optionally substituted $C_1$-$C_3$ alkyl group or together form a keto group; HET of ULM-g through ULM-i is preferably oxazole, isoxazole, thiazole, isothiazole, imidazole, diazole, oximidazole, pyrrole, pyrollidine, furan, dihydrofuran, tetrahydrofuran, thiene, dihydrothiene, tetrahydrothiene, pyridine, piperidine, piperazine, morpholine, quinoline, (each preferably substituted with a $C_1$-$C_3$ alkyl group, preferably methyl or a halo group, preferably F or Cl), benzofuran, indole, indolizine, azaindolizine, or a group according to the chemical structure:

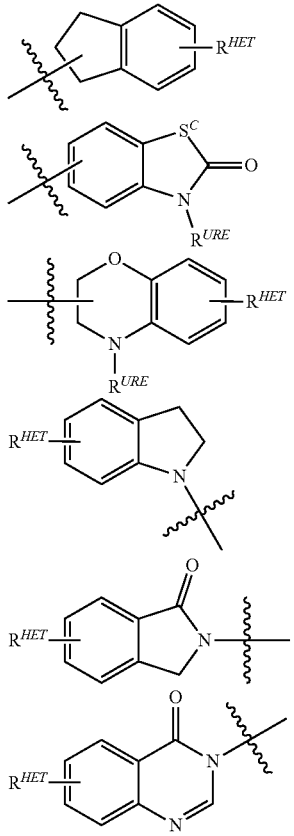

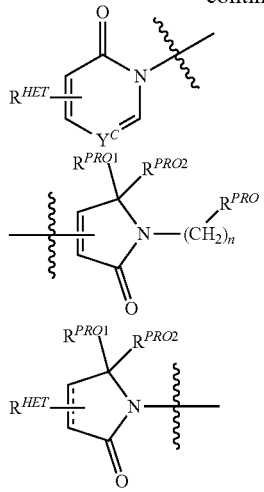

$S^c$ of ULM-g through ULM-i is $CHR^{SS}$, $NR^{URE}$, or O;

$R^{HET}$ of ULM-g through ULM-i is H, CN, NO$_2$, halo (preferably Cl or F), optionally substituted $C_1$-$C_6$ alkyl (preferably substituted with one or two hydroxyl groups or up to three halo groups (e.g. CF$_3$), optionally substituted O($C_1$-$C_6$ alkyl) (preferably substituted with one or two hydroxyl groups or up to three halo groups) or an optionally substituted acetylenic group —C≡C—$R_a$ where $R_a$ is H or a $C_1$-$C_6$ alkyl group (preferably $C_1$-$C_3$ alkyl);

$R^{SS}$ of ULM-g through ULM-i is H, CN, NO$_2$, halo (preferably F or Cl), optionally substituted $C_1$-$C_6$ alkyl (preferably substituted with one or two hydroxyl groups or up to three halo groups), optionally substituted O—($C_1$-$C_6$ alkyl) (preferably substituted with one or two hydroxyl groups or up to three halo groups) or an optionally substituted —C(O)($C_1$-$C_6$alkyl) (preferably substituted with one or two hydroxyl groups or up to three halo groups);

$R^{URE}$ of ULM-g through ULM-i is H, a $C_1$-$C_6$ alkyl (preferably H or $C_1$-$C_3$ alkyl) or a —C(O)($C_0$-$C_6$ alkyl), each of which groups is optionally substituted with one or two hydroxyl groups or up to three halogen, preferably fluorine groups, or an optionally substituted heterocycle, for example piperidine, morpholine, pyrrolidine, tetrahydrofuran, tetrahydrothiophene, piperidine, piperazine, each of which is optionally substituted;

$Y^C$ of ULM-g through ULM-i is N or C—$R^{YC}$, where $R^{YC}$ is H, OH, CN, NO$_2$, halo (preferably Cl or F), optionally substituted $C_1$-$C_6$ alkyl (preferably substituted with one or two hydroxyl groups or up to three halo groups (e.g. CF$_3$), optionally substituted O($C_1$-$C_6$ alkyl) (preferably substituted with one or two hydroxyl groups or up to three halo groups) or an optionally substituted acetylenic group —C≡C—$R_a$ where $R_a$ is H or a $C_1$-$C_6$ alkyl group (preferably $C_1$-$C_3$ alkyl);

$R^{PRO}$ of ULM-g through ULM-i is H, optionally substituted $C_1$-$C_6$ alkyl or an optionally substituted aryl, heteroaryl or heterocyclic group;

$R^{PRO1}$ and $R^{PRO2}$ of ULM-g through ULM-i are each independently H, an optionally substituted $C_1$-$C_3$ alkyl group or together form a keto group;

each m' of ULM-g through ULM-i is independently 0 or 1; and each n of ULM-g through ULM-i is independently 0, 1, 2, 3, 4, 5, or 6 (preferably 0 or 1),
wherein each of said compounds, preferably on said Aryl or HET groups, is optionally connected to a PTM group (including a ULM' group) via a linker group.

In still additional embodiments, preferred compounds include those according to the chemical structure:

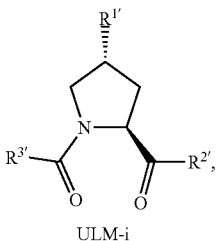

ULM-i wherein:
  $R^{1'}$ of ULM-i is OH or a group which is metabolized in a patient or subject to OH;
  $R^{2'}$ of ULM-i is a —NH—CH$_2$-Aryl-HET (preferably, a phenyl linked directly to a methyl substituted thiazole);
  $R^{3'}$ of ULM-i is a —CHR$^{CR3'}$—NH—C(O)—R$^{3P1}$ group or a —CHR$^{CR3'}$—R$^{3P2}$ group;
  $R^{CR3'}$ of ULM-i is a C$_1$-C$_4$ alkyl group, preferably methyl, isopropyl or tert-butyl;
  $R^{3P1}$ of ULM-i is C$_1$-C$_3$ alkyl (preferably methyl), an optionally substituted oxetane group (preferably methyl substituted, a —(CH$_2$)$_n$OCH$_3$ group where n is 1 or 2 (preferably 2), or a

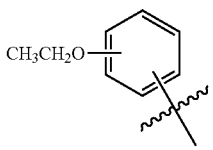

group (the ethyl ether group is preferably meta-substituted on the phenyl moiety), a morpholino group (linked to the carbonyl at the 2- or 3-position;
  $R^{3P2}$ of ULM-i is a

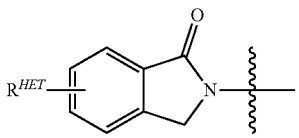

group;
  Aryl of ULM-i is phenyl;
  HET of ULM-i is an optionally substituted thiazole or isothiazole; and
  $R^{HET}$ of ULM-i is H or a halo group (preferably H);
  or a pharmaceutically acceptable salt, stereoisomer, solvate or polymorph thereof, wherein each of said compounds is optionally connected to a PTM group (including a ULM' group) via a linker group.

In certain aspects, bifunctional compounds comprising a ubiquitin E3 ligase binding moiety (ULM), wherein ULM is a group according to the chemical structure:

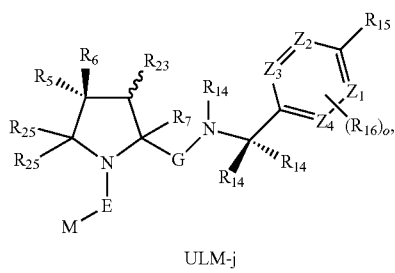

ULM-j wherein:
  each $R_5$ and $R_6$ of ULM-j is independently OH, SH, or optionally substituted alkyl or $R_5$, $R_6$, and the carbon atom to which they are attached form a carbonyl;
  $R_7$ of ULM-j is H or optionally substituted alkyl;
  E of ULM-j is a bond, C=O, or C=S;
  G of ULM-j is a bond, optionally substituted alkyl, —COOH or C=J;
  J of ULM-j is O or N—R$_8$;
  $R_8$ of ULM-j is H, CN, optionally substituted alkyl or optionally substituted alkoxy;
  M of ULM-j is optionally substituted aryl, optionally substituted heteroaryl, optionally substituted heterocyclic or

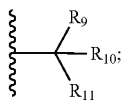

each $R_9$ and $R_{10}$ of ULM-j is independently H; optionally substituted alkyl, optionally substituted cycloalkyl, optionally substituted hydroxyalkyl, optionally substituted thioalkyl, a disulphide linked ULM, optionally substituted heteroaryl, or haloalkyl; or $R_9$, $R_{10}$, and the carbon atom to which they are attached form an optionally substituted cycloalkyl;
  $R_{11}$ of ULM-j is optionally substituted heterocyclic, optionally substituted alkoxy, optionally substituted heteroaryl, optionally substituted aryl, or

$R_{12}$ of ULM-j is H or optionally substituted alkyl;
  $R_{13}$ of ULM-j is H, optionally substituted alkyl, optionally substituted alkylcarbonyl, optionally substituted (cycloalkyl)alkylcarbonyl, optionally substituted aralkylcarbonyl, optionally substituted arylcarbonyl, optionally substituted (heterocyclyl)carbonyl, or optionally substituted aralkyl; optionally substituted (oxoalkyl)carbamate,
  each $R_{14}$ of ULM-j is independently H, haloalkyl, optionally substituted cycloalkyl, optionally substituted alkyl or optionally substituted heterocycloalkyl;
  $R_{15}$ of ULM-j is H, optionally substituted heteroaryl, haloalkyl, optionally substituted aryl, optionally substituted alkoxy, or optionally substituted heterocyclyl;
  each $R_{16}$ of ULM-j is independently halo, optionally substituted alkyl, optionally substituted haloalkyl, CN, or optionally substituted haloalkoxy;

each $R_{25}$ of ULM-j is independently H or optionally substituted alkyl; or both $R_{25}$ groups can be taken together to form an oxo or optionally substituted cycloalkyl group;
$R_{23}$ of ULM-j is H or OH;
$Z_1$, $Z_2$, $Z_3$, and $Z_4$ of ULM-j are independently C or N; and
o of ULM-j is 0, 1, 2, 3, or 4, or a pharmaceutically acceptable salt, stereoisomer, solvate or polymorph thereof.

In certain embodiments, wherein G of ULM-j is C=J, J is O, $R_7$ is H, each $R_{14}$ is H, and o is 0.

In certain embodiments, wherein G of ULM-j is C=J, J is O, $R_7$ is H, each $R_{14}$ is H, $R_{15}$ is optionally substituted heteroaryl, and o is 0. In other instances, E is C=O and M is

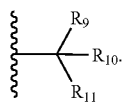

In certain embodiments, wherein E of ULM-j is C=O, $R_{11}$ is optionally substituted heterocyclic or

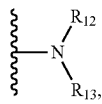

and M is

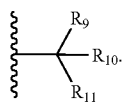

In certain embodiments, wherein E of ULM-j is C=O, M is

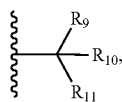

and $R_{11}$ is

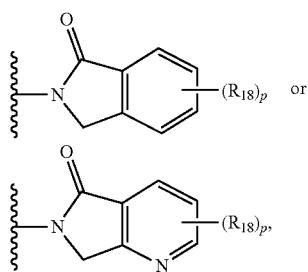

each $R_{18}$ is independently halo, optionally substituted alkoxy, cyano, optionally substituted alkyl, haloalkyl, or haloalkoxy; and p is 0, 1, 2, 3, or 4.

In certain embodiments, ULM and where present, ULM', are each independently a group according to the chemical structure:

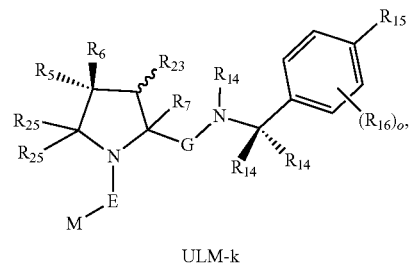

wherein:
G of ULM-k is C=J, J is O;
$R_7$ of ULM-k is H;
each $R_{14}$ of ULM-k is H;
o of ULM-k is 0;
$R_{15}$ of ULM-k is

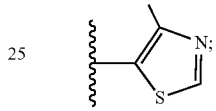

and
$R_{17}$ of ULM-k is H, halo, optionally substituted cycloalkyl, optionally substituted alkyl, optionally substituted alkenyl, and haloalkyl.

In other instances, $R_{17}$ of ULM-k is alkyl (e.g., methyl) or cycloalkyl (e.g., cyclopropyl).

In other embodiments, ULM and where present, ULM', are each independently a group according to the chemical structure:

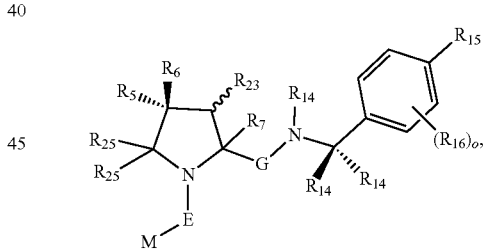

wherein:
G of ULM-k is C=J, J is O;
$R_7$ of ULM-k is H;
each $R_{14}$ of ULM-k is H;
o of ULM-k is 0; and
$R_{15}$ of ULM-k is selected from the group consisting of:

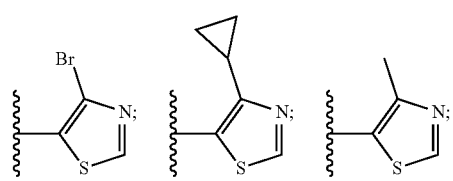

-continued
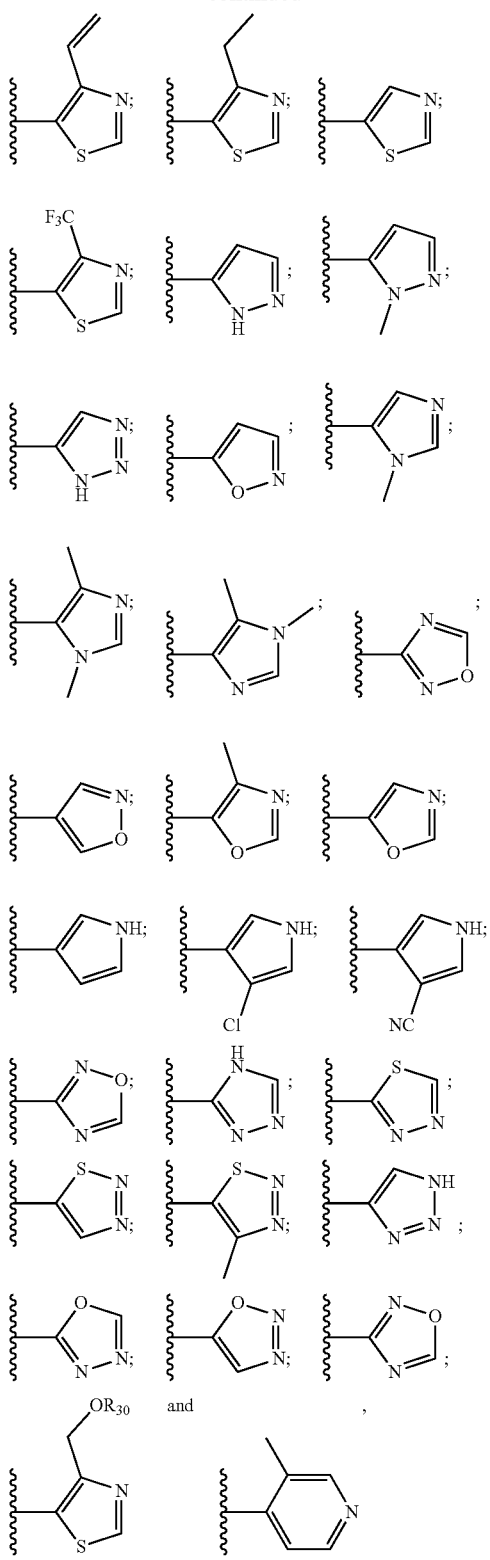
wherein $R_{30}$ of ULM-k is H or an optionally substituted alkyl.
In other embodiments, ULM and where present, ULM', are each independently a group according to the chemical structure:
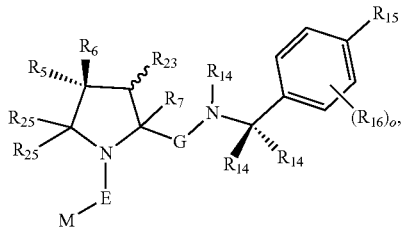
ULM-k
wherein:
E of ULM-k is C=O;
M of ULM-k is
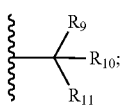
and
$R_{11}$ of ULM-k is selected from the group consisting of:
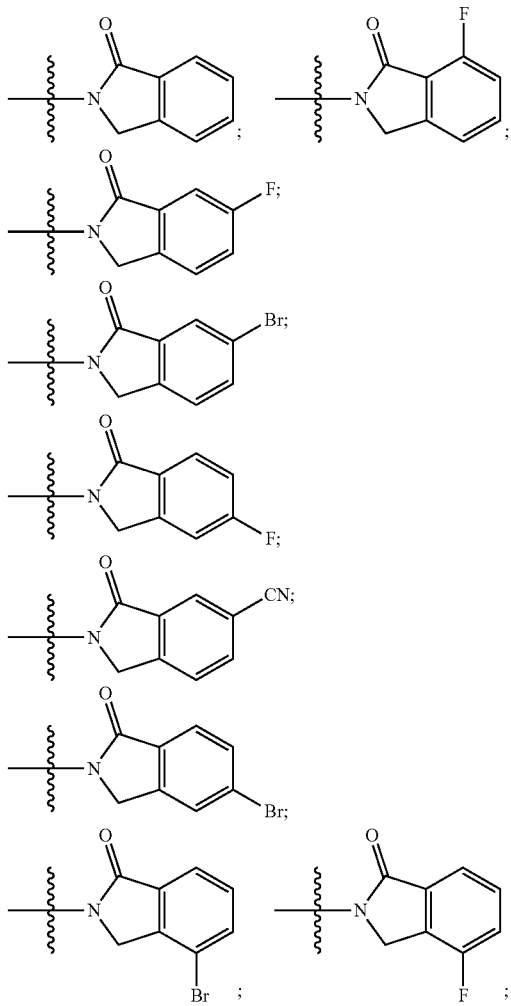

101

-continued

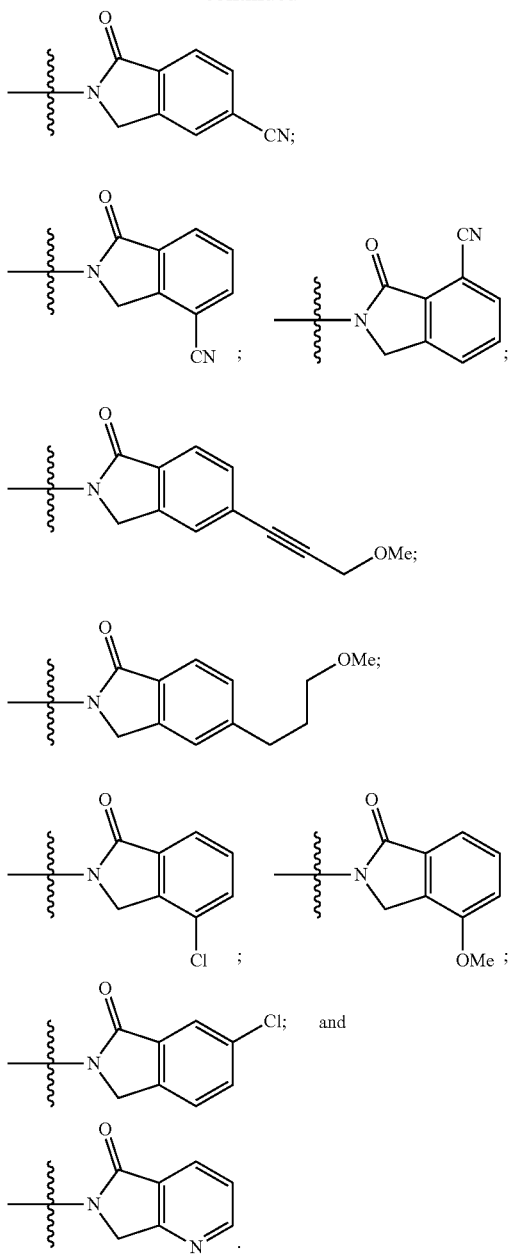

In still other embodiments, a compound of the chemical structure,

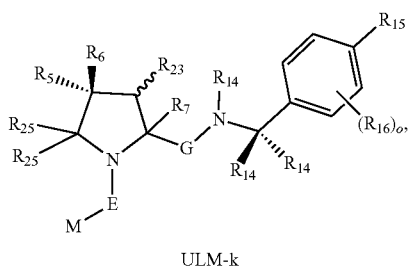

ULM-k wherein E of ULM-k is C=O;

102

$R_{11}$ of ULM-k is

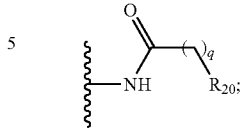

and

M of ULM-k is

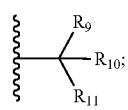

q of ULM-k is 1 or 2;

$R_{20}$ of ULM-k is H, optionally substituted alkyl, optionally substituted cycloalkyl, optionally substituted aryl, or

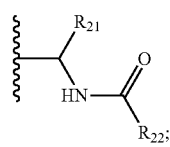

$R_{21}$ of ULM-k is H or optionally substituted alkyl; and $R_{22}$ of ULM-k is H, optionally substituted alkyl, optionally substituted alkoxy, or haloalkyl.

In any embodiment described herein, $R_{11}$ of ULM-j or ULM-k is selected from the group consisting of:

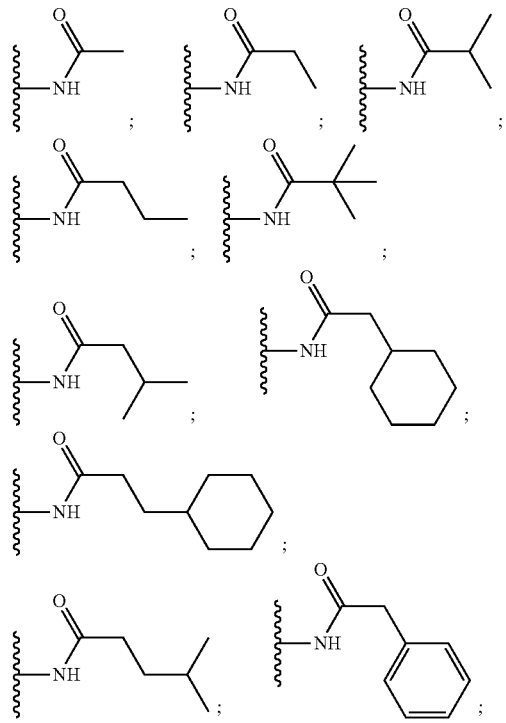

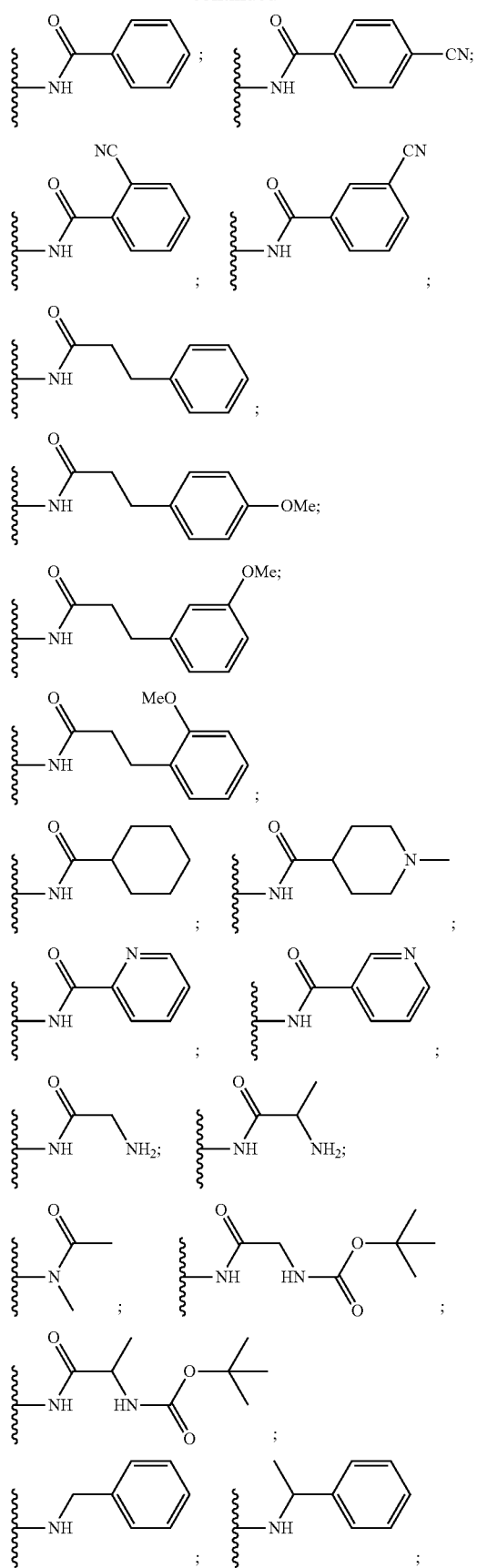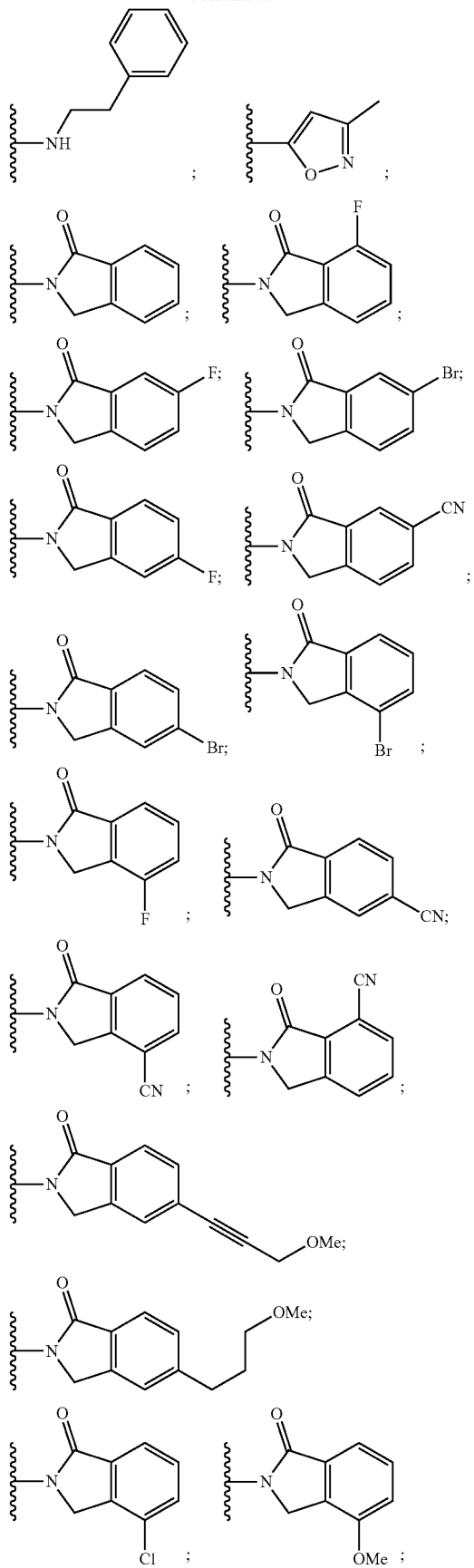

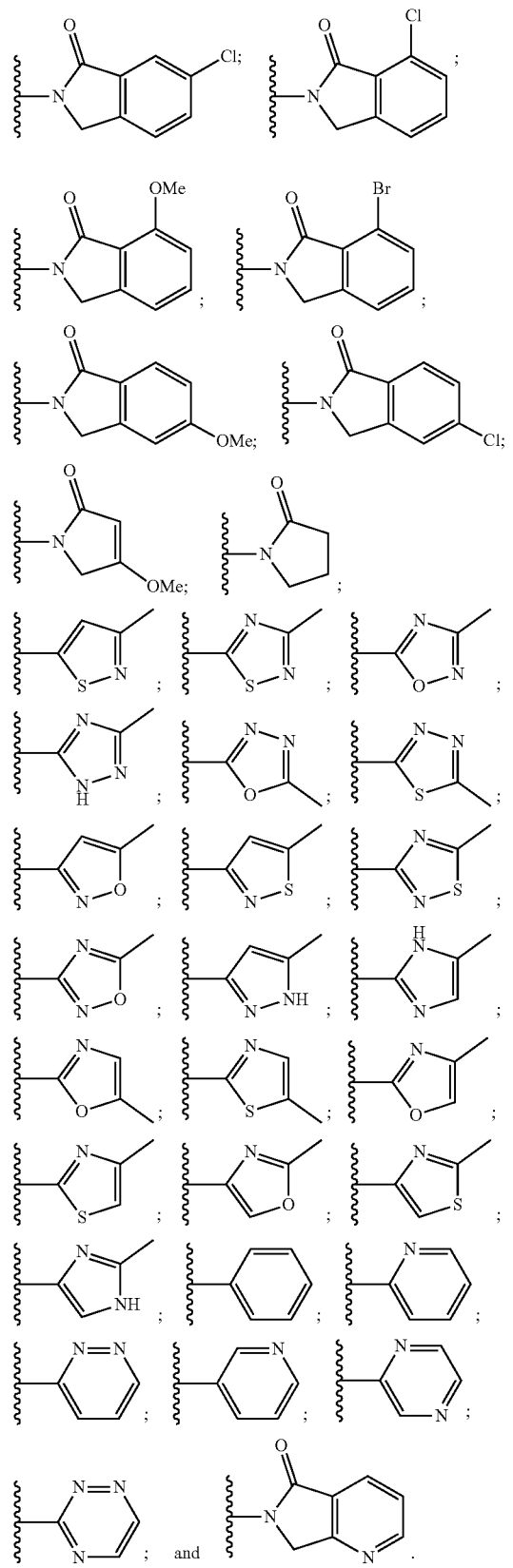
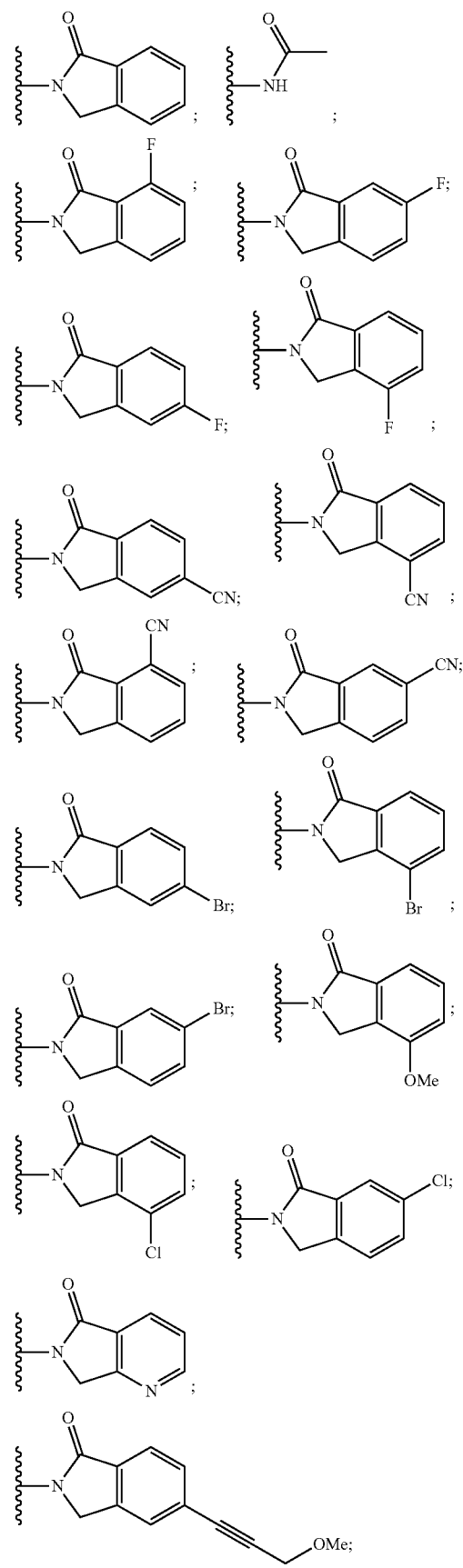
In certain embodiments, $R_{11}$ of ULM-j or ULM-k is selected from the group consisting of:

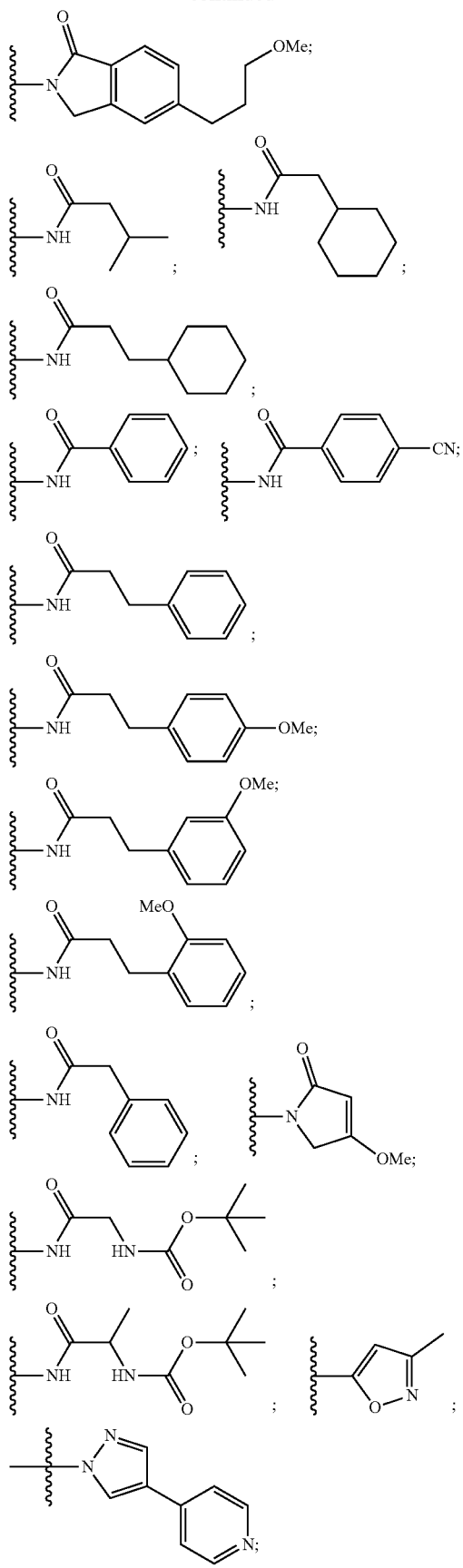

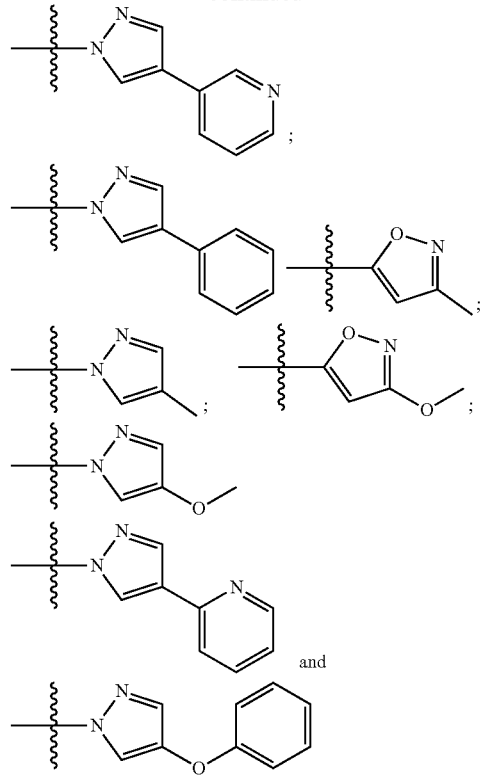

In certain embodiments, ULM (or when present ULM') is a group according to the chemical structure:

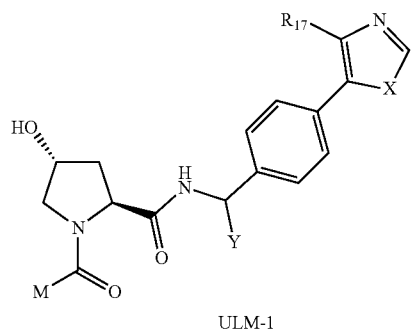

ULM-1 wherein:
X of ULM-1 is O or S;
Y of ULM-1 is H, methyl or ethyl;
$R_{17}$ of ULM-1 is H, methyl, ethyl, hydoxymethyl or cyclopropyl;
M of ULM-1 is is optionally substituted aryl, optionally substituted heteroaryl, or

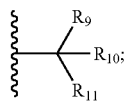

$R_9$ of ULM-1 is H;
$R_{10}$ of ULM-1 is H, optionally substituted alkyl, optionally substituted haloalkyl, optionally substituted heteroaryl, optionally substituted aryl, optionally substituted hydroxyalkyl, optionally substituted thioalkyl or cycloalkyl;

$R_{11}$ of ULM-1 is optionally substituted heteroaromatic, optionally substituted heterocyclic, optionally substituted aryl or

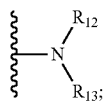

$R_{12}$ of ULM-1 is H or optionally substituted alkyl; and
$R_{13}$ of ULM-1 is H, optionally substituted alkyl, optionally substituted alkylcarbonyl, optionally substituted (cycloalkyl)alkylcarbonyl, optionally substituted aralkylcarbonyl, optionally substituted arylcarbonyl, optionally substituted (heterocyclyl)carbonyl, or optionally substituted aralkyl; optionally substituted (oxoalkyl)carbamate.

In some embodiments, ULM and where present, ULM', are each independently a group according to the chemical structure:

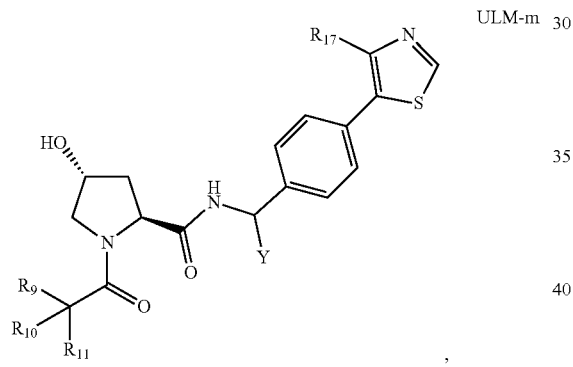

wherein:
Y of ULM-m is H, methyol or ethyl
$R_9$ of ULM-m is H;
$R_{10}$ is isopropyl, tert-butyl, sec-butyl, cyclopentyl, or cyclohexyl;

$R_{11}$ of ULM-m is optionally substituted amide, optionally substituted isoindolinone, optionally substituted isooxazole, optionally substituted heterocycles.

In other preffered embodiments of the disclosure, ULM and where present, ULM', are each independently a group according to the chemical structure:

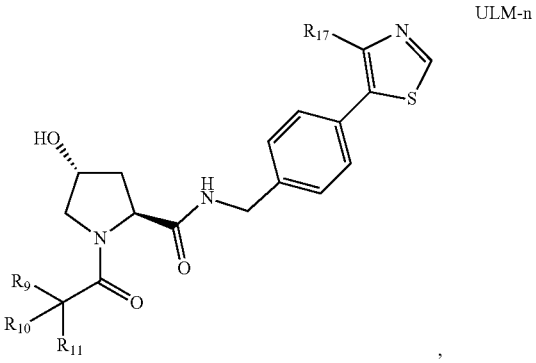

wherein:
$R_{17}$ of ULM-n is methyl, ethyl, or cyclopropyl; and
$R_9$, $R_{10}$, and $R_{11}$ of ULM-n are as defined above. In other instances, $R_9$ is H; and
$R_{10}$ of ULM-n is H, alkyl, or or cycloalkyl (preferably, isopropyl, tert-butyl, sec-butyl, cyclopentyl, or cyclohexyl).

In any of the aspects or embodiments described herein, the ULM (or when present, ULM') as described herein may be a pharmaceutically acceptable salt, enantiomer, diastereomer, solvate or polymorph thereof. In addition, in any of the aspects or embodiments described herein, the ULM (or when present, ULM') as described herein may be coupled to a PTM directly via a bond or by a chemical linker.

In certain aspects of the disclosure, the ULM moiety is selected from the group consisting of:

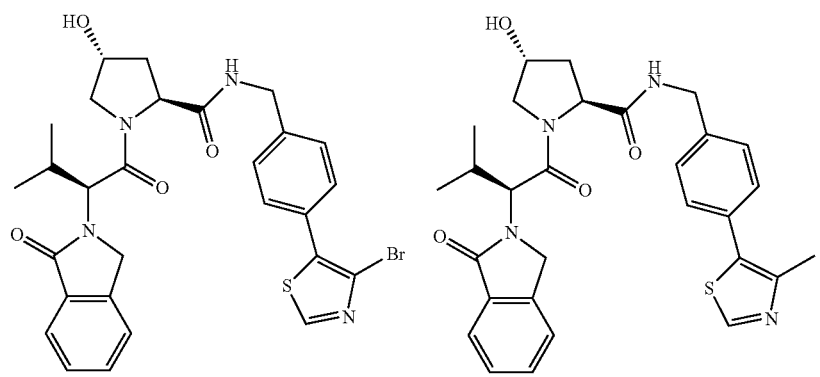

-continued
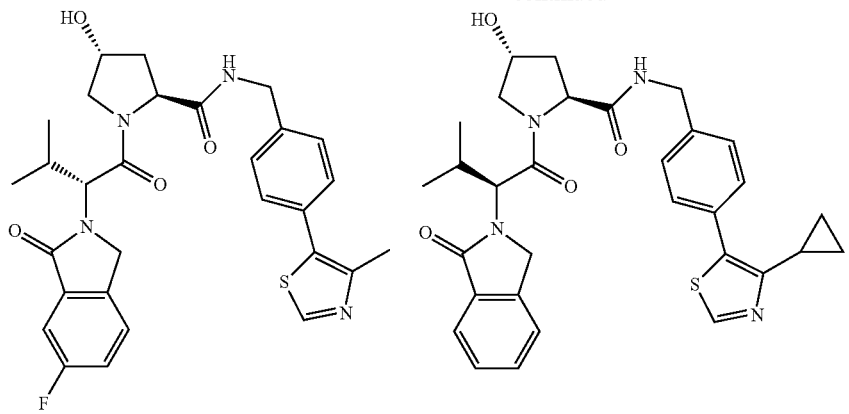
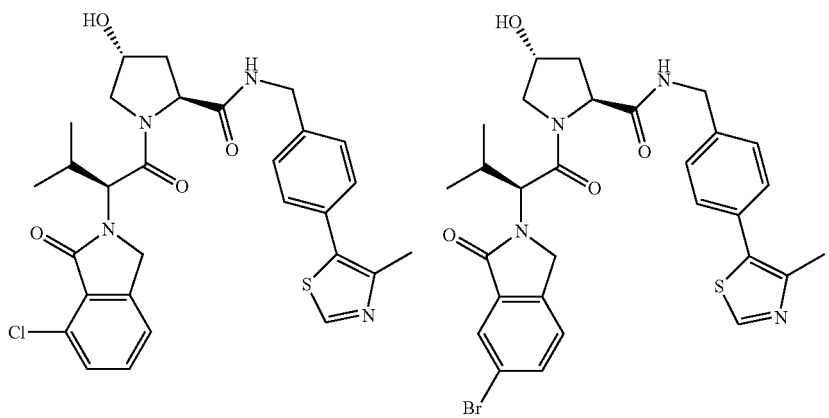
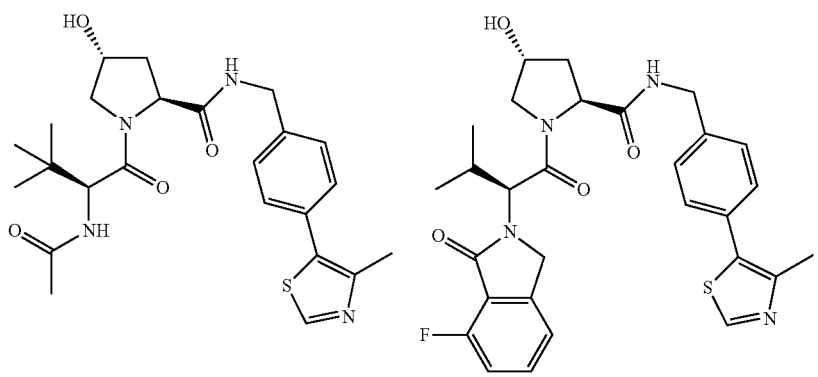
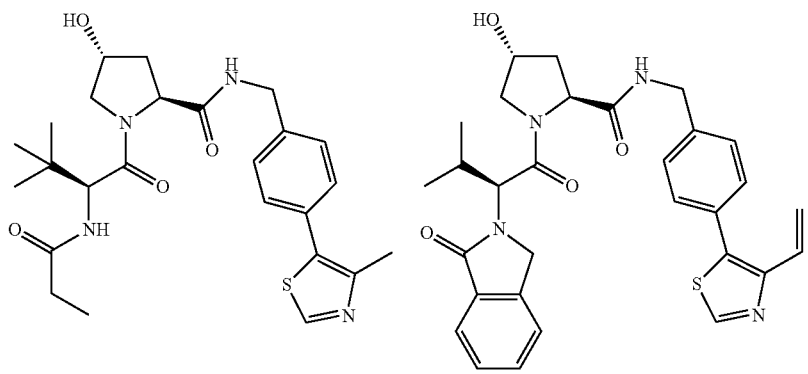

-continued
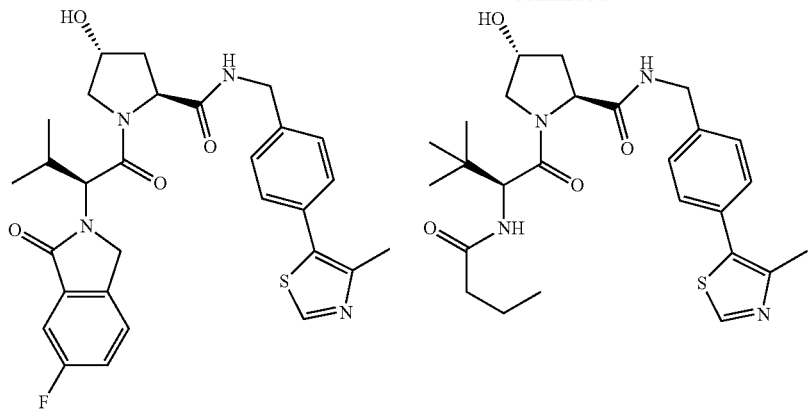
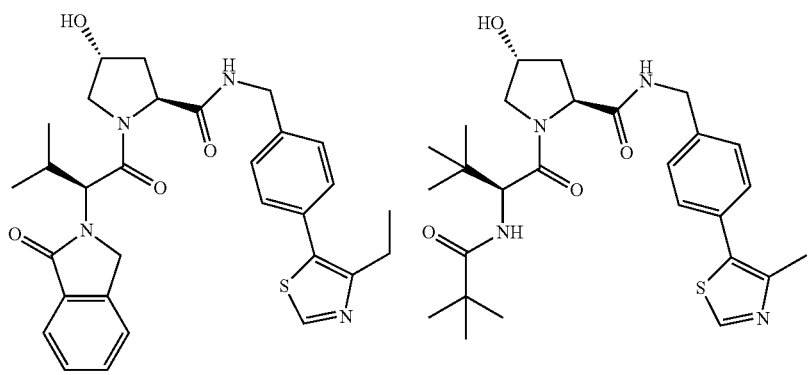
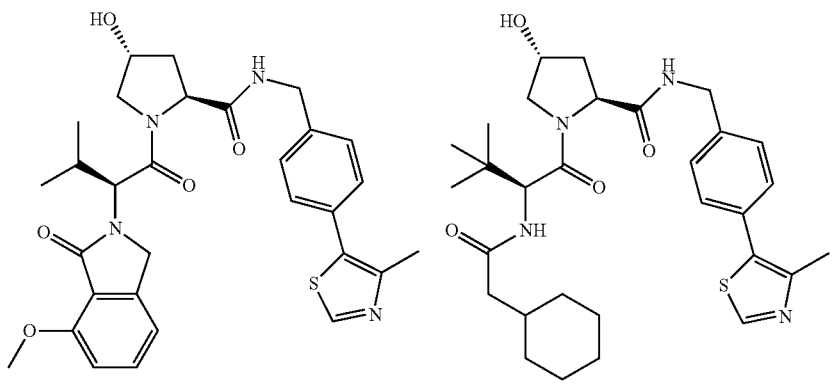
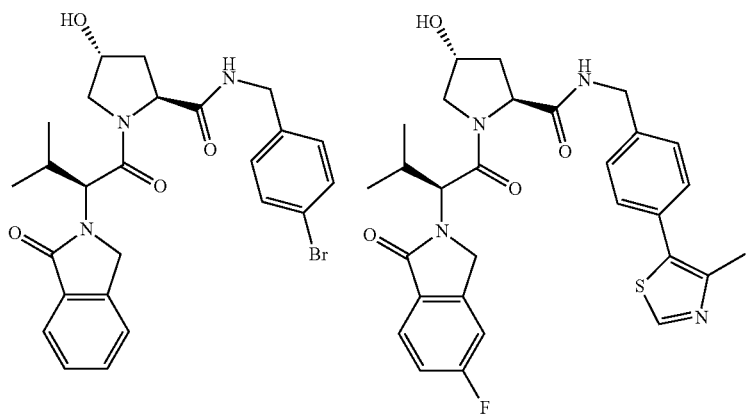

-continued
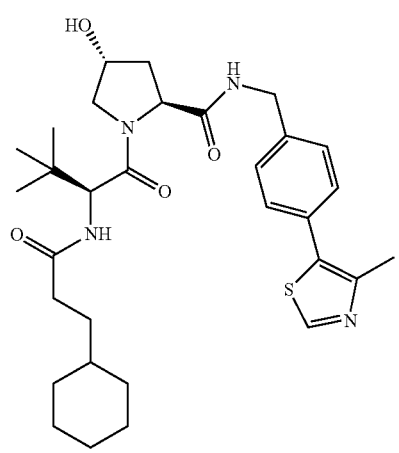
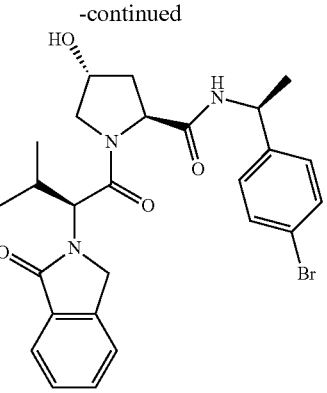
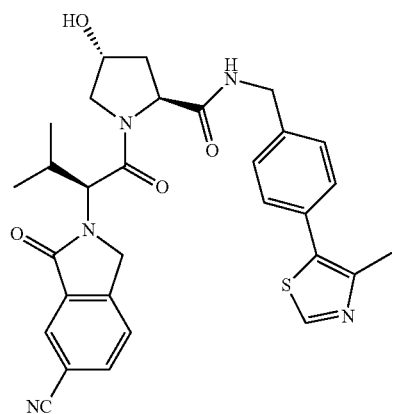
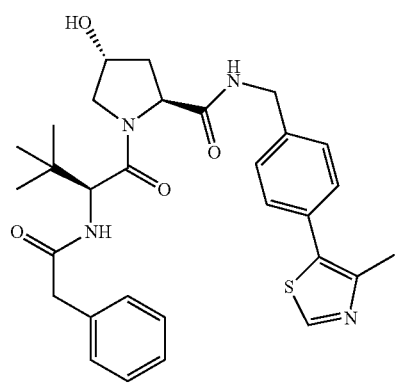
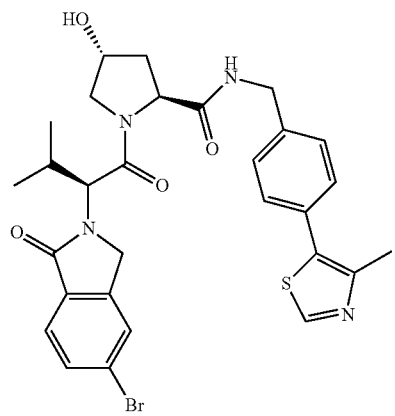
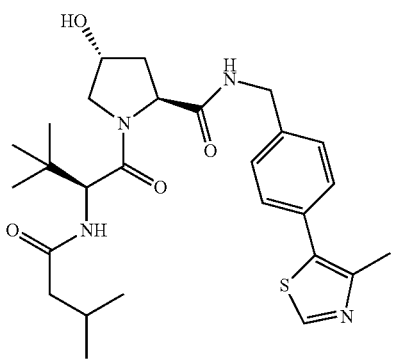
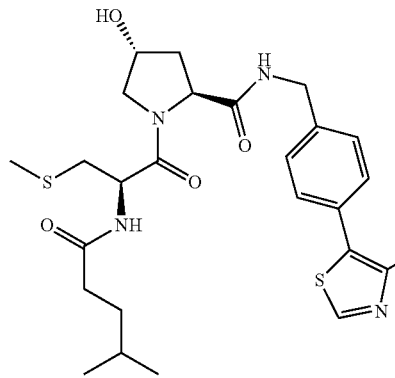
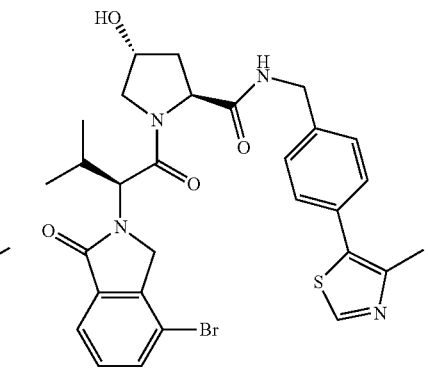

-continued
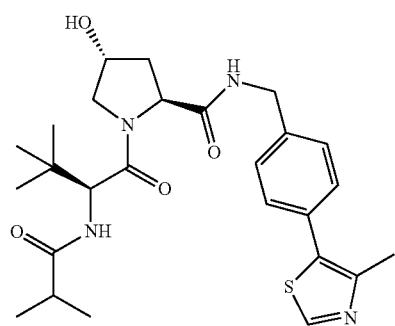 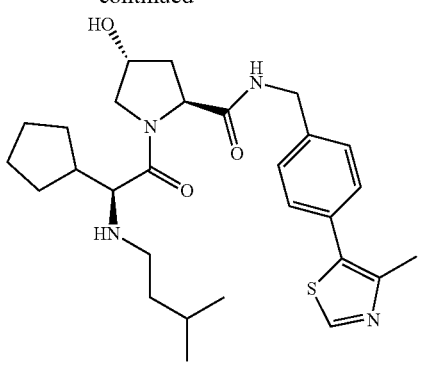
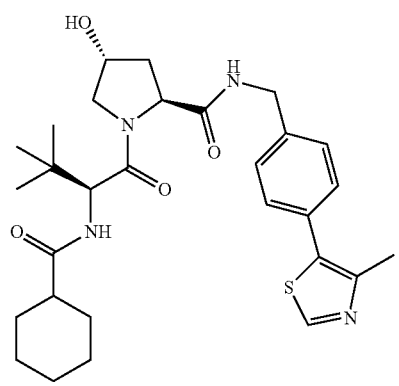 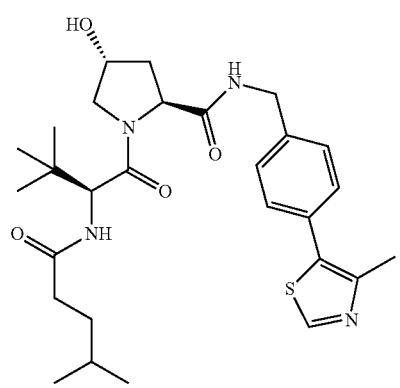
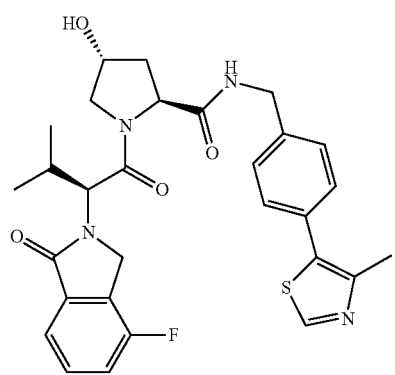 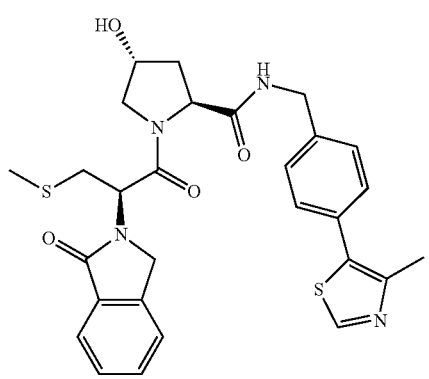
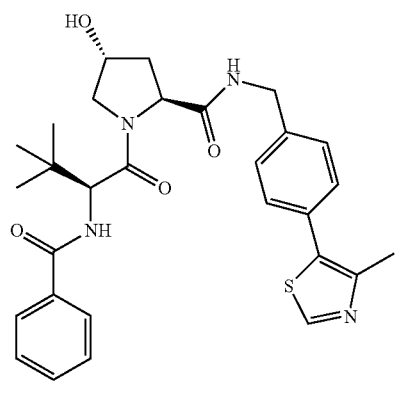 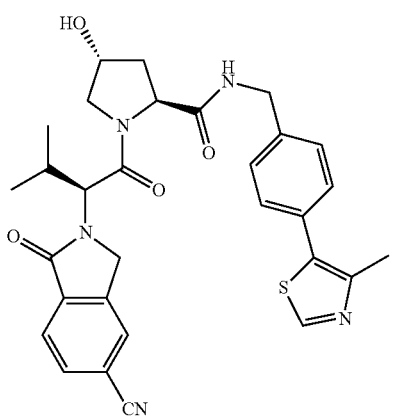

-continued
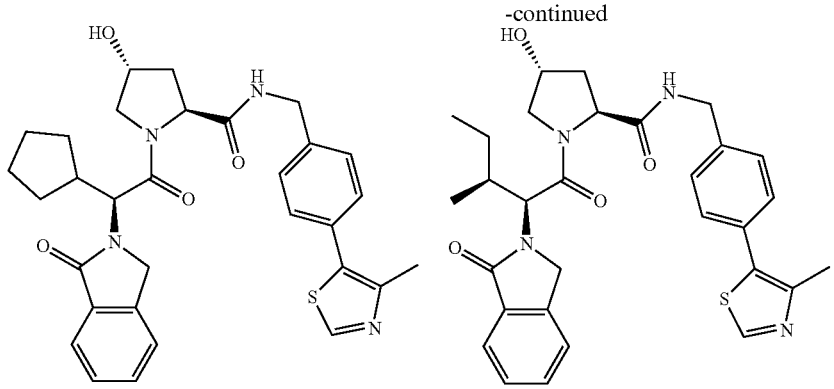
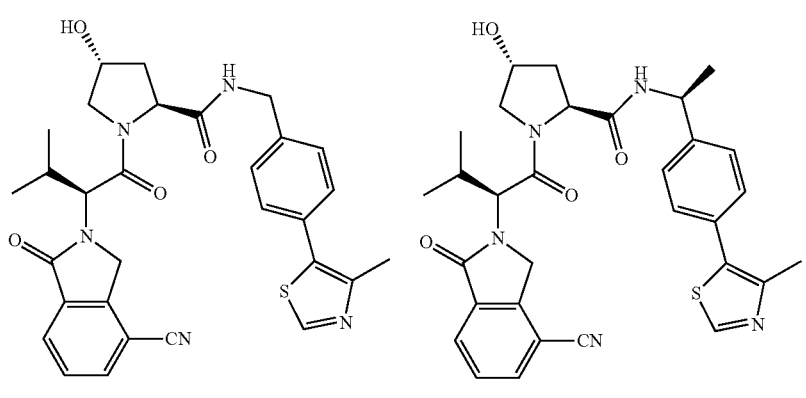
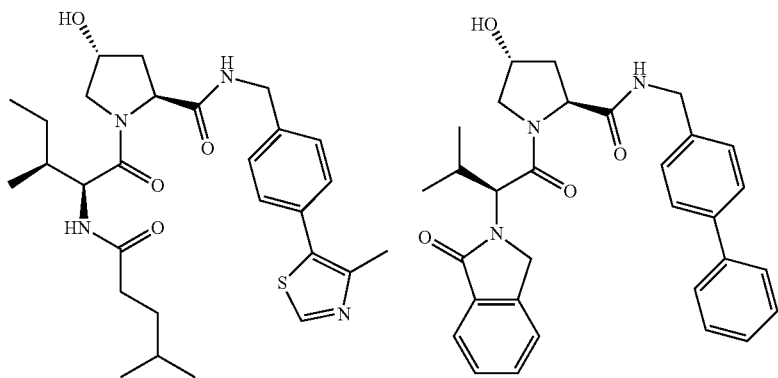
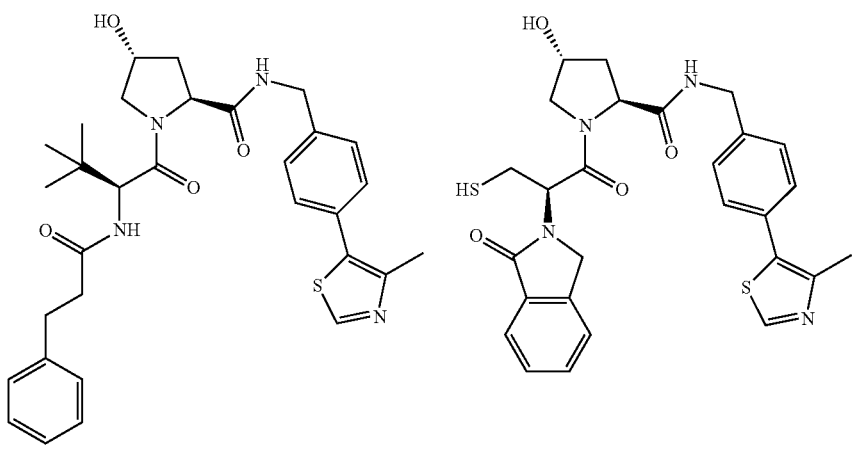

-continued
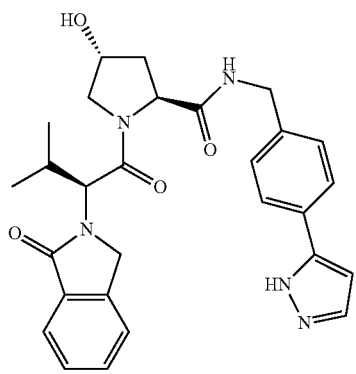
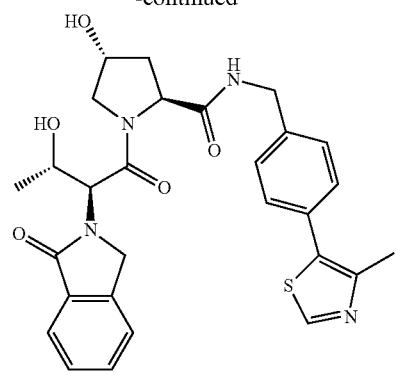
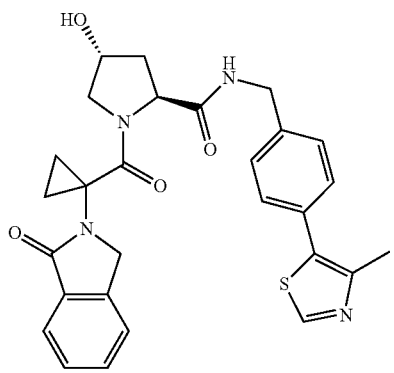
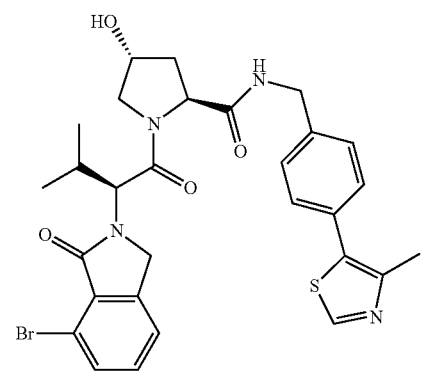
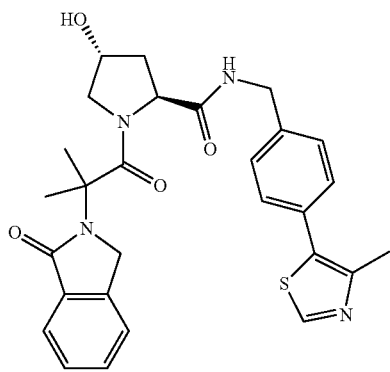
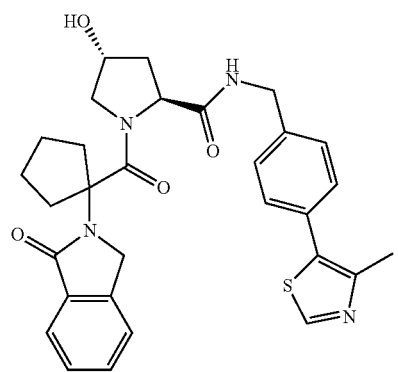
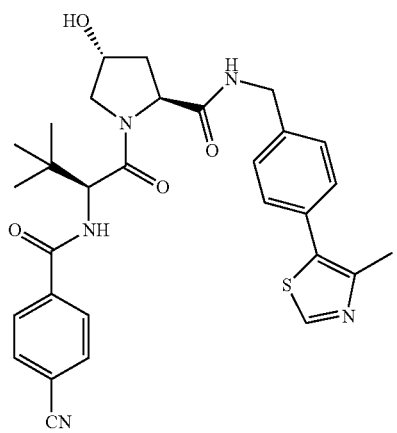
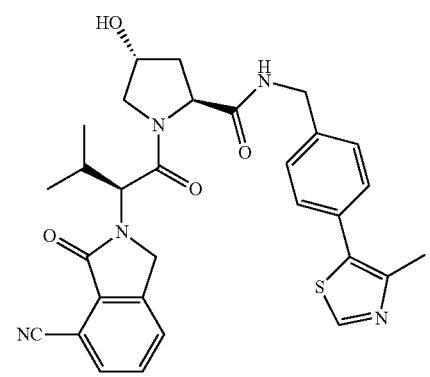

-continued
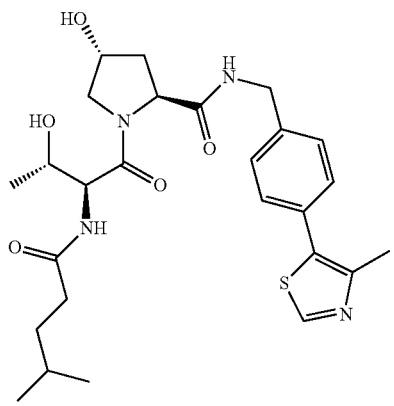
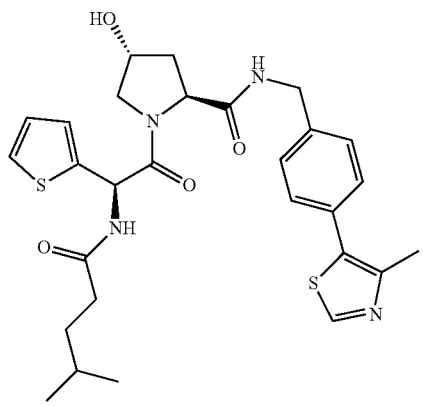
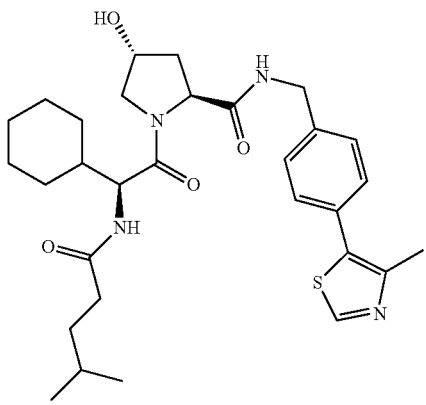
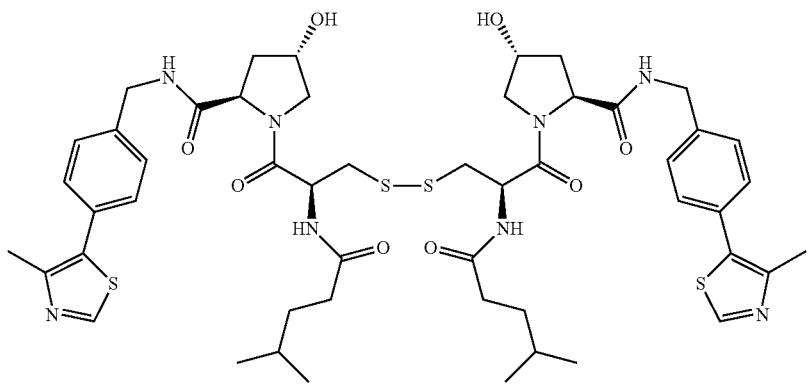
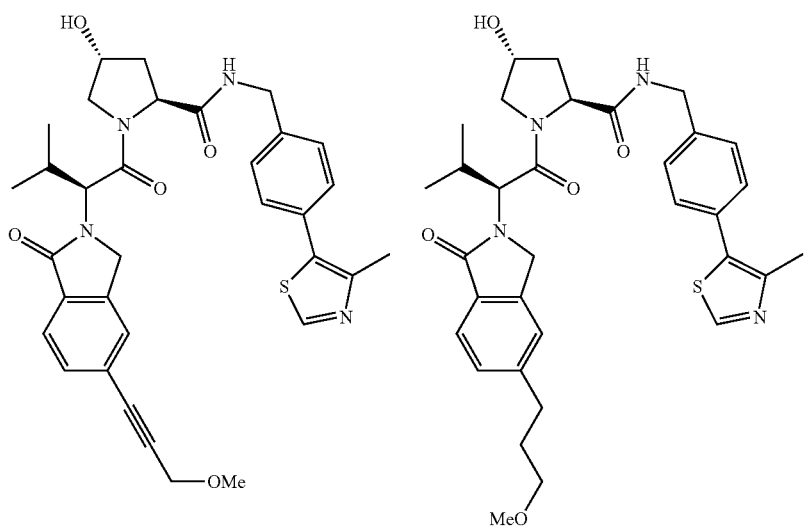

-continued
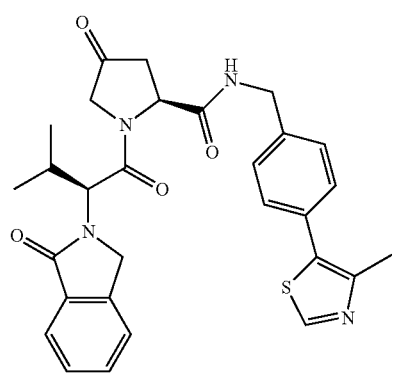
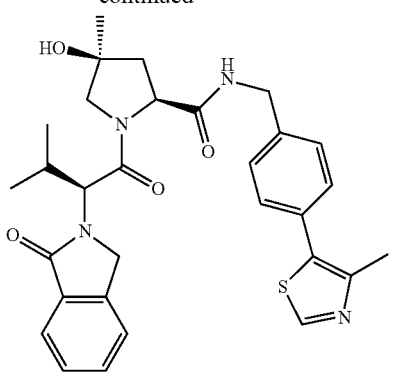
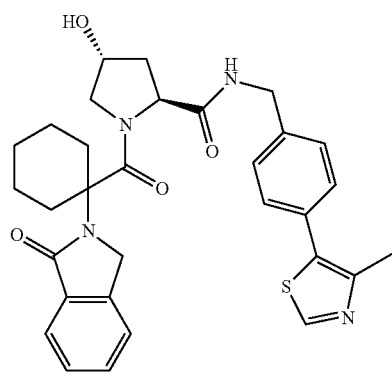
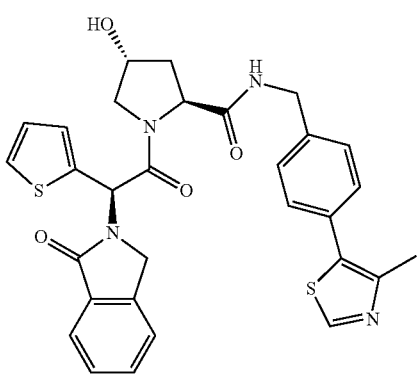
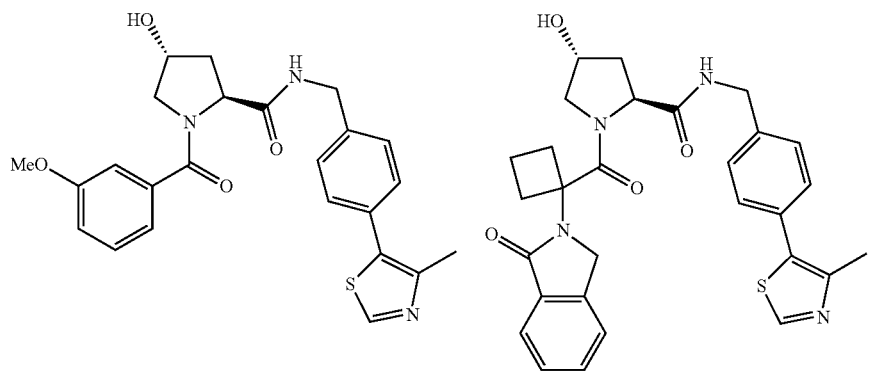
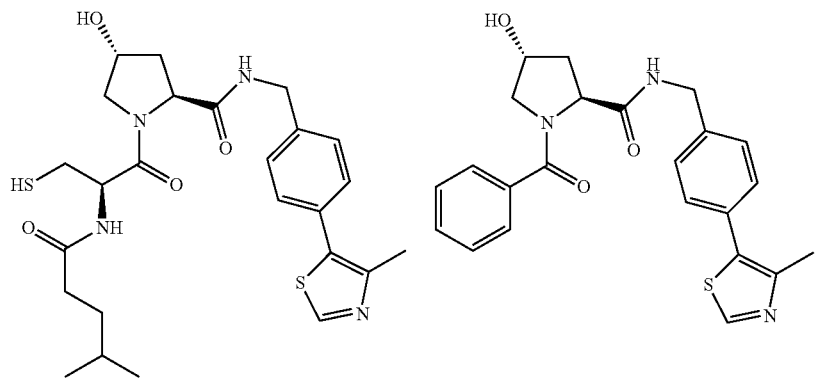

-continued
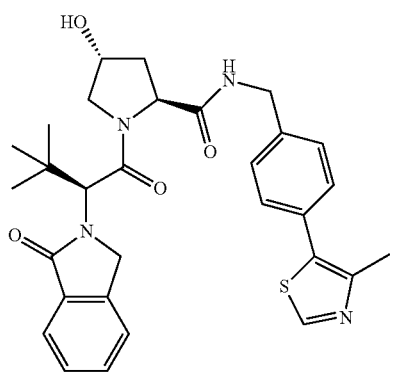
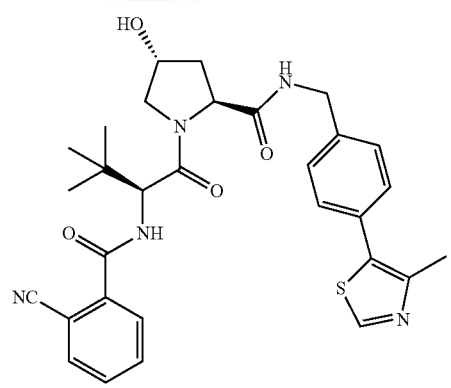
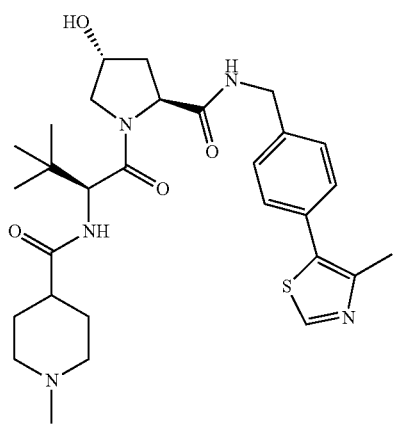
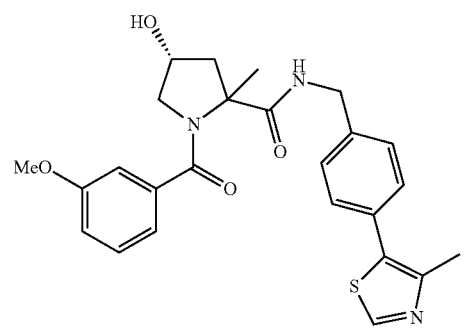
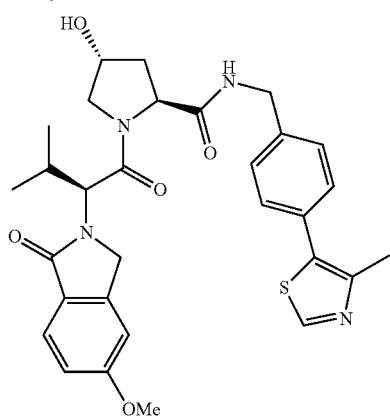
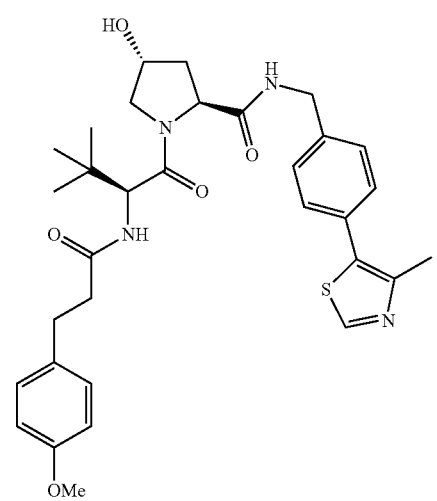
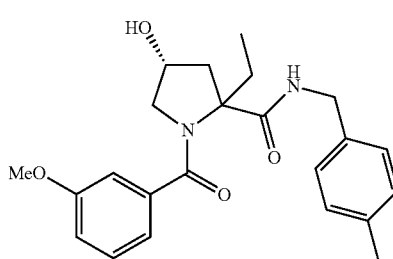
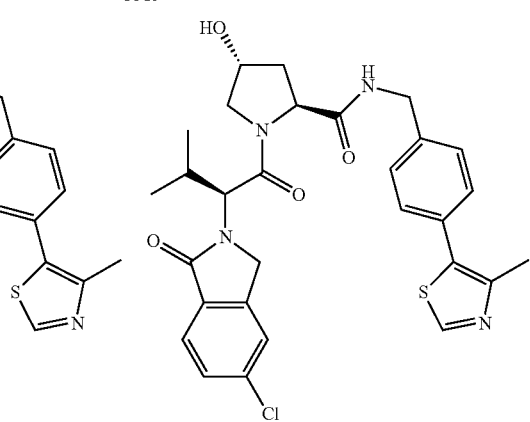

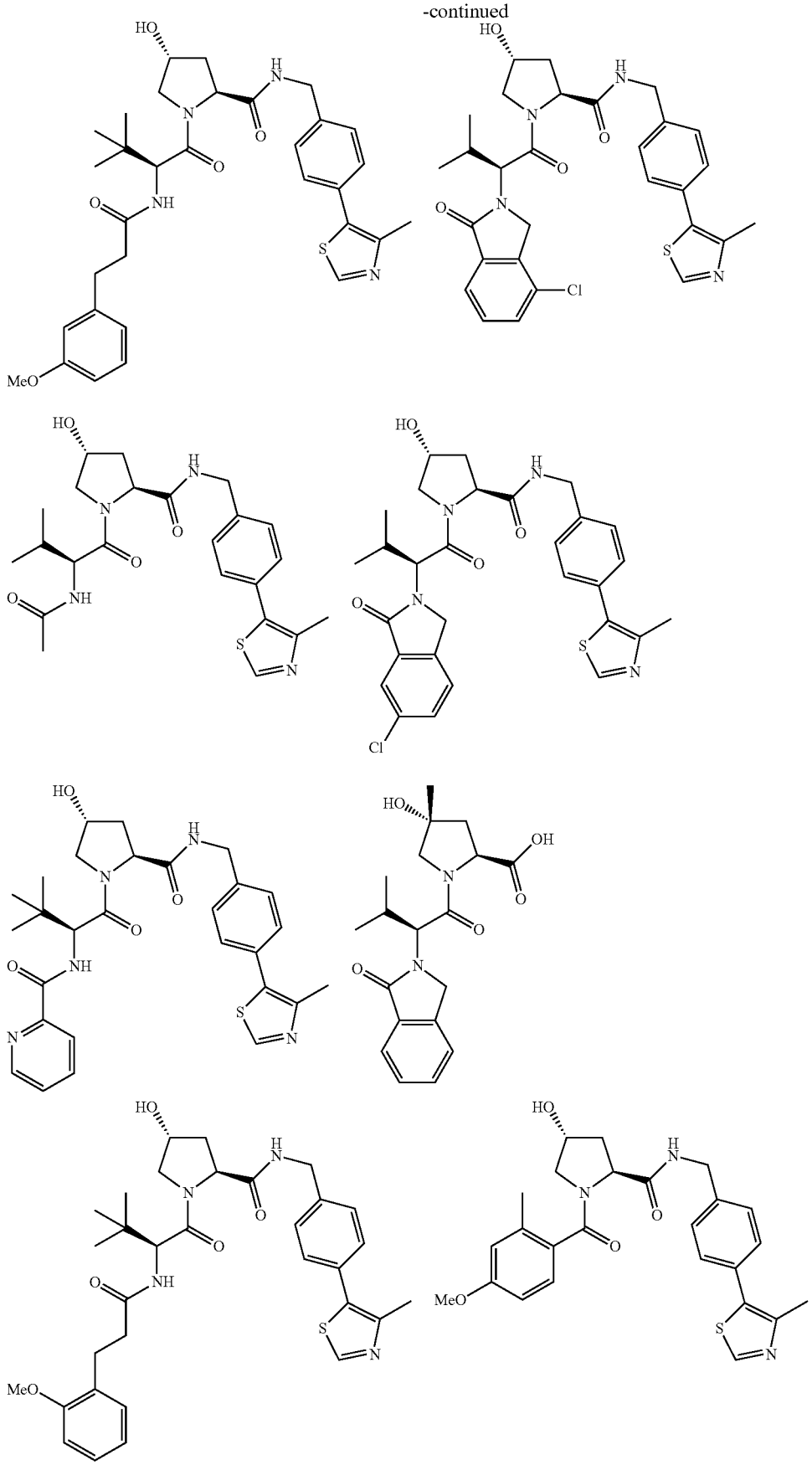

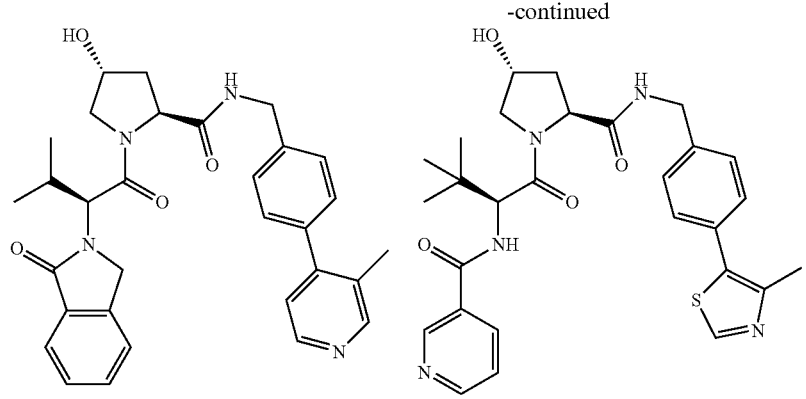
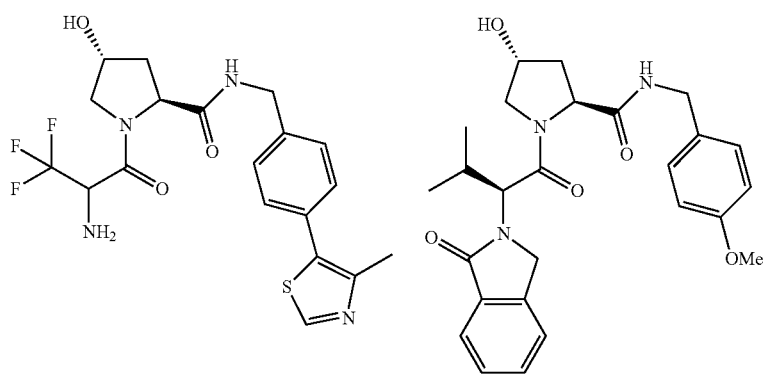
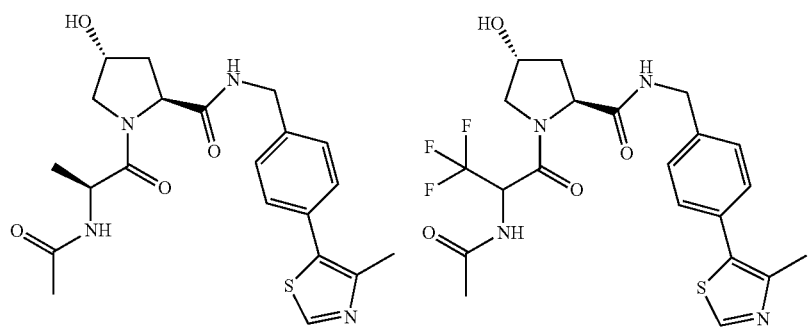
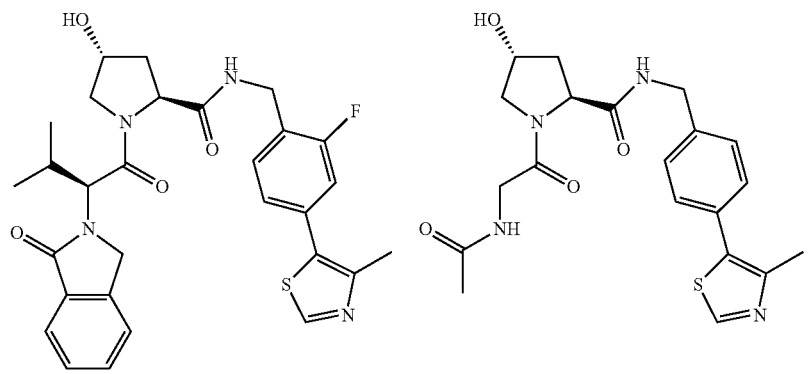

133
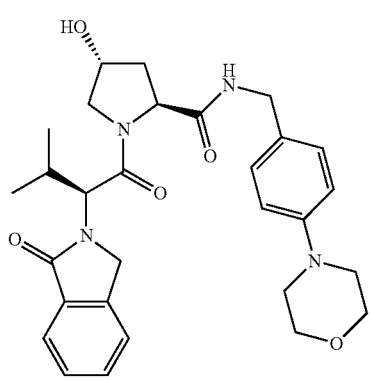
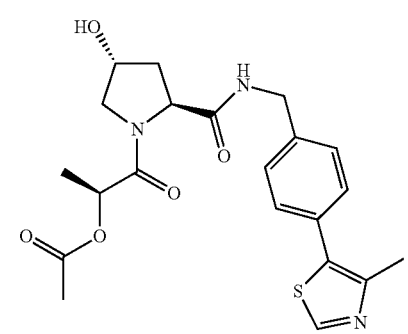
134
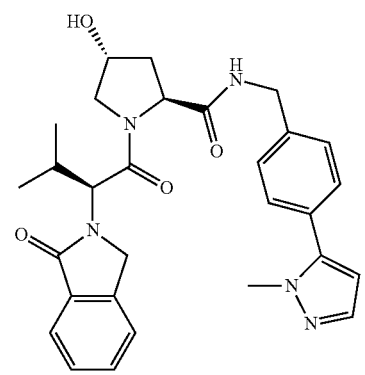
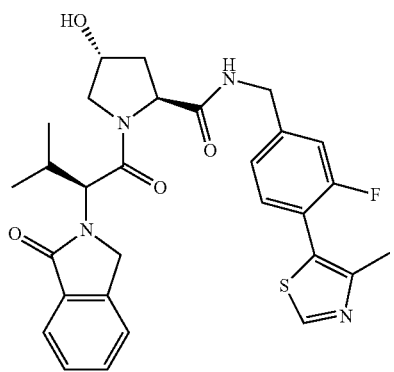
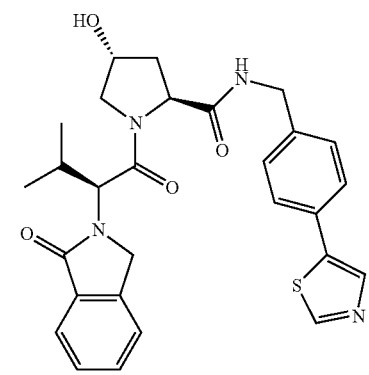
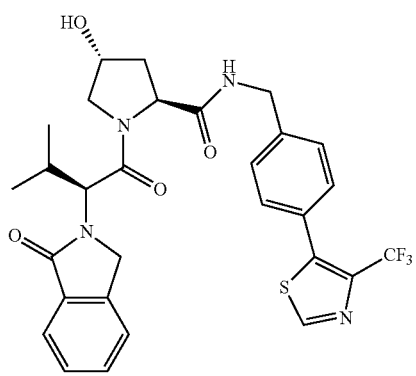
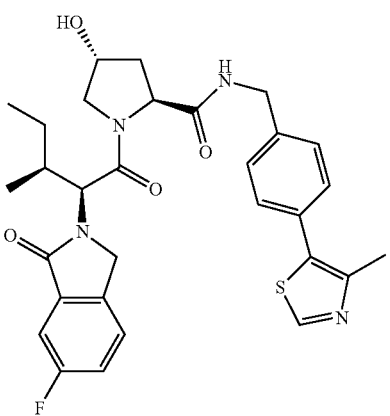
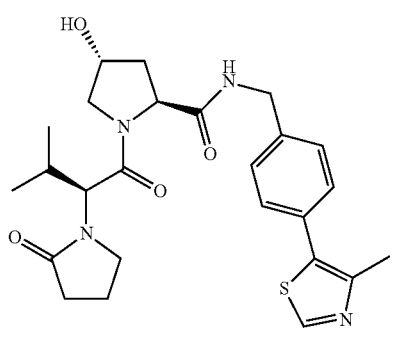
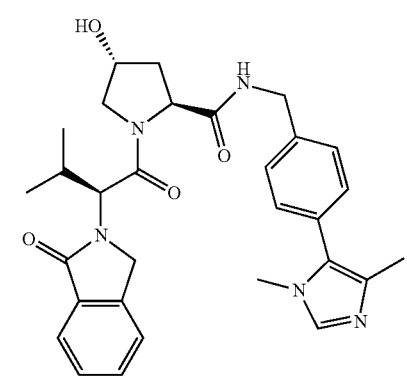

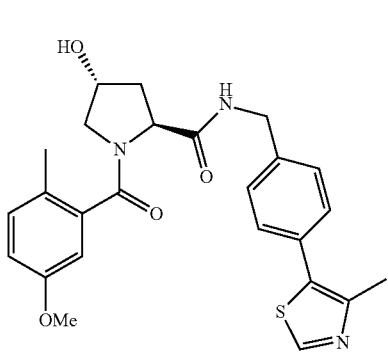
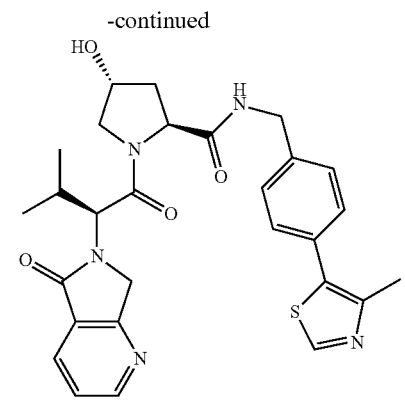
-continued
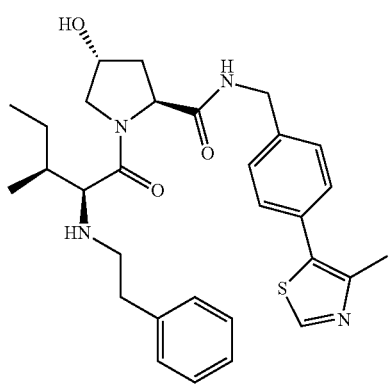
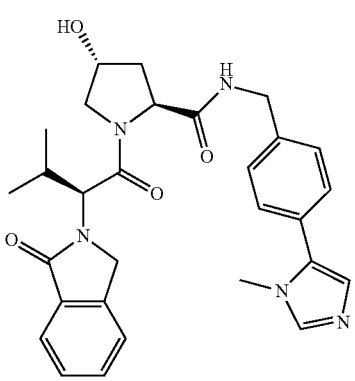
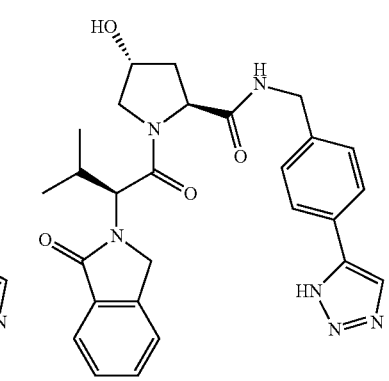
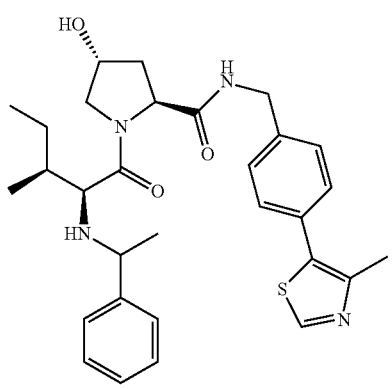
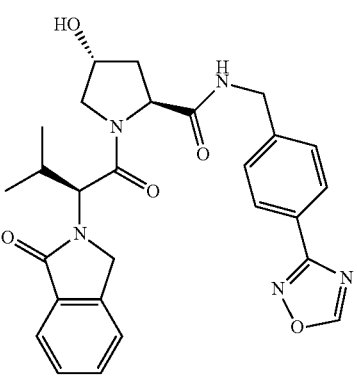
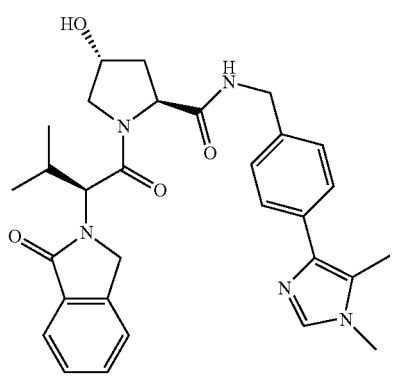
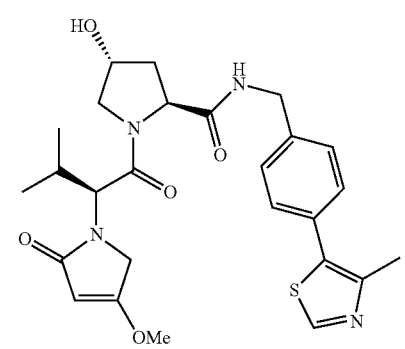

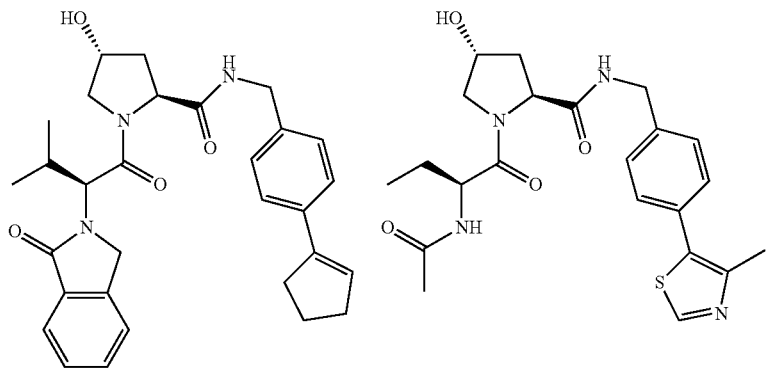
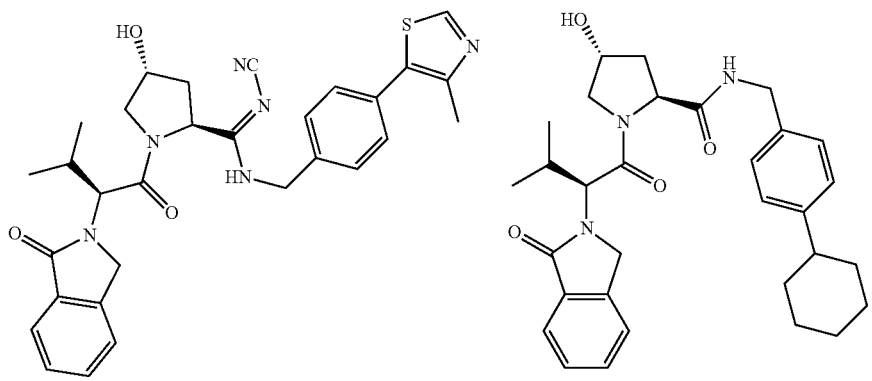
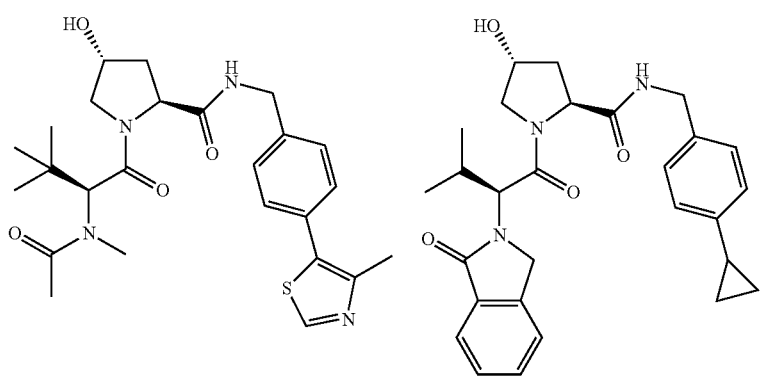
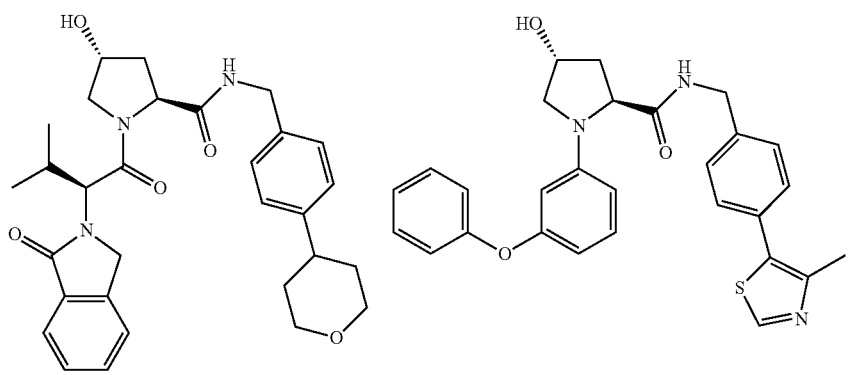

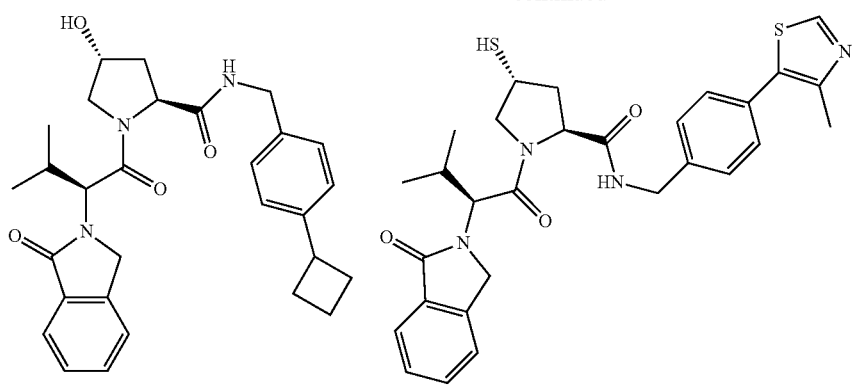
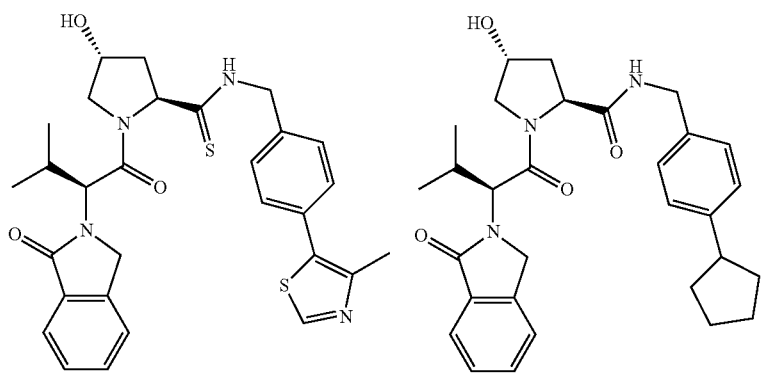
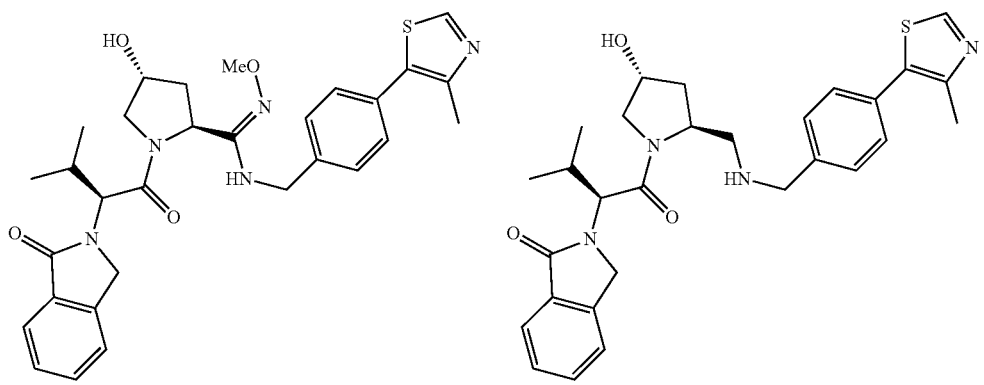
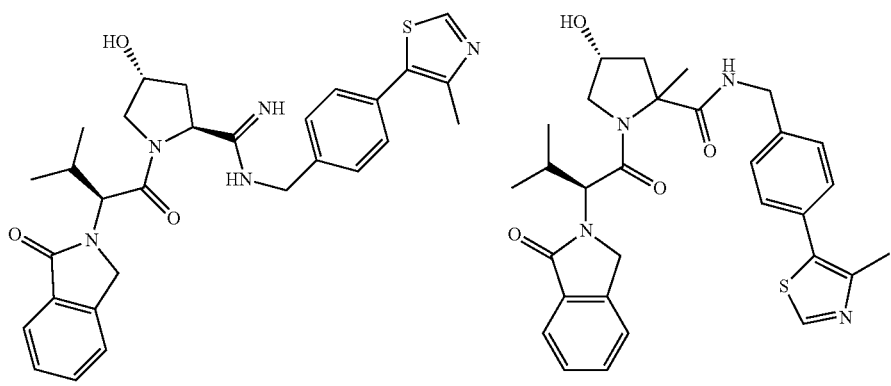

-continued
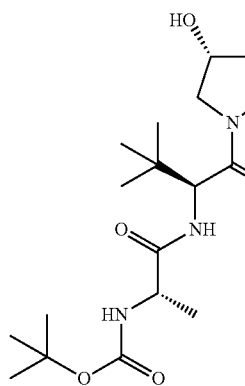 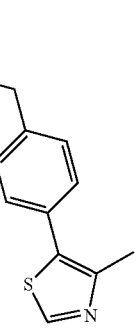 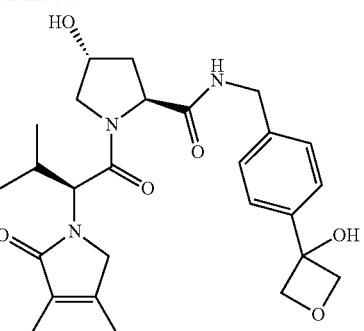
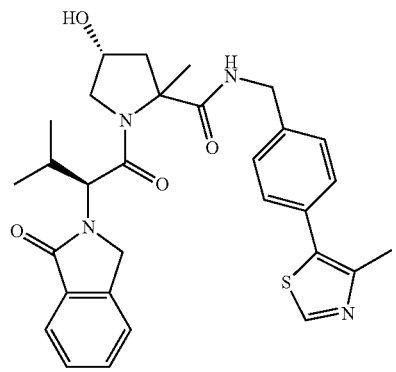 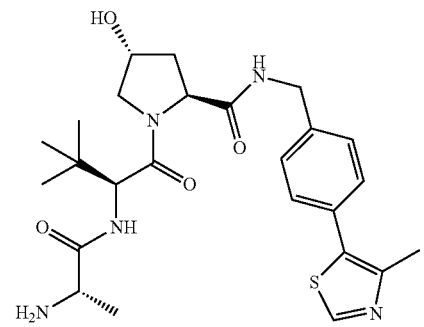
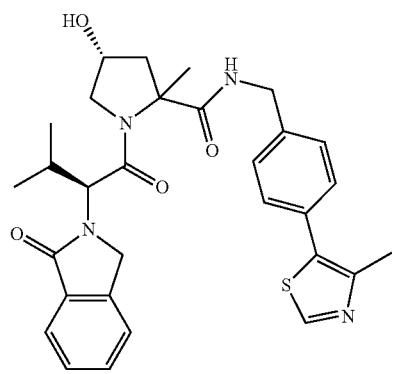 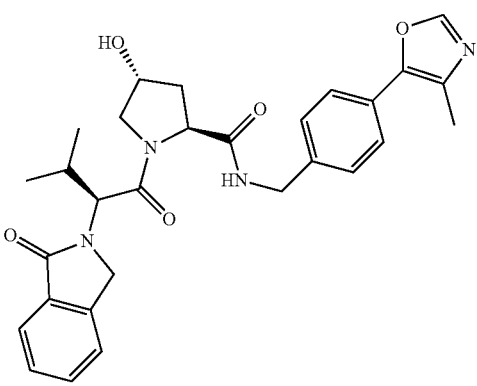
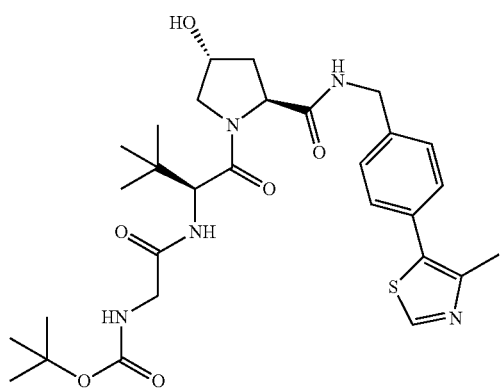 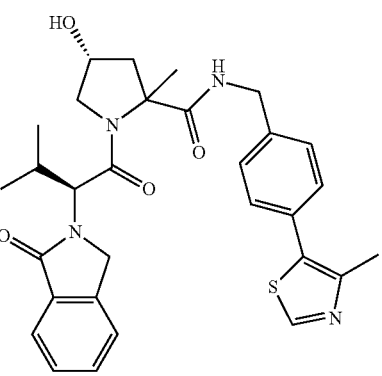

-continued
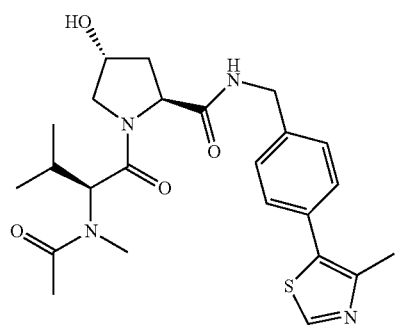
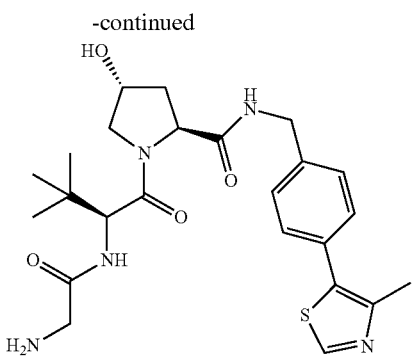
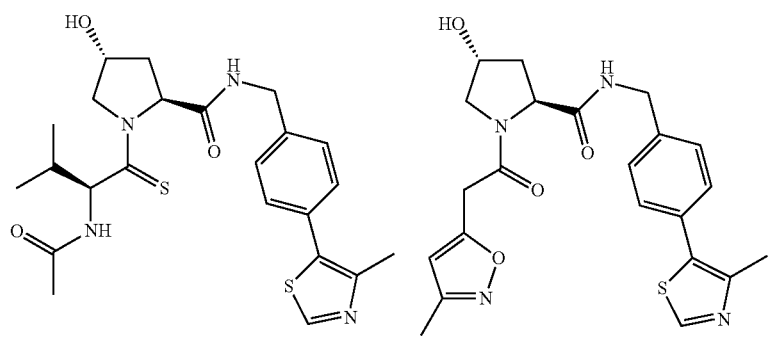
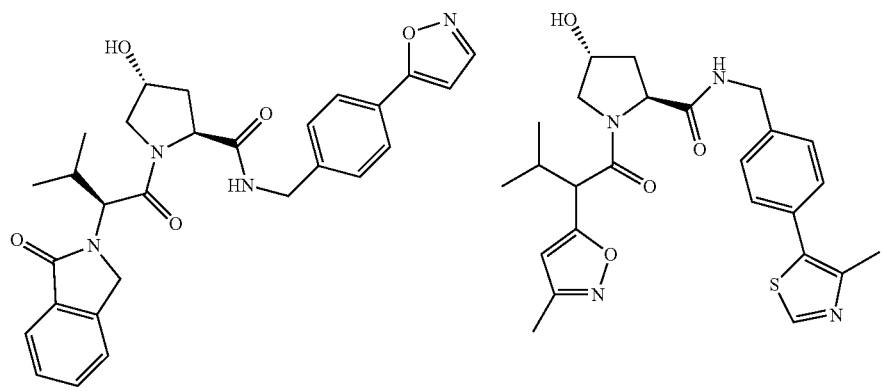
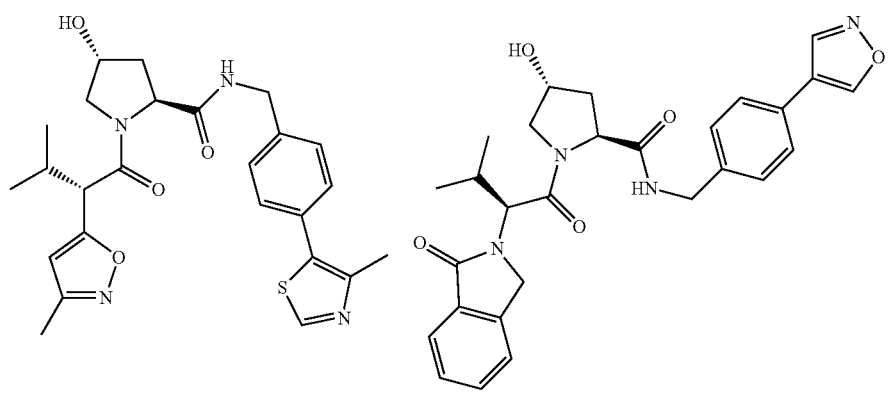

-continued
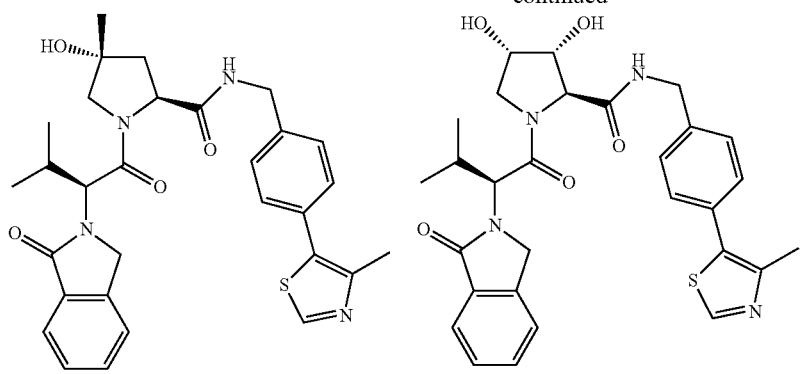
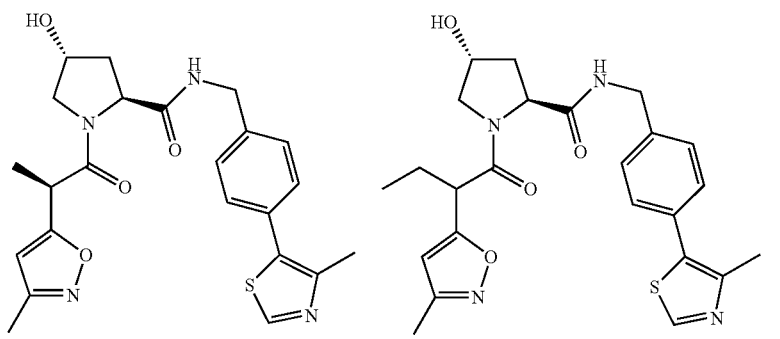
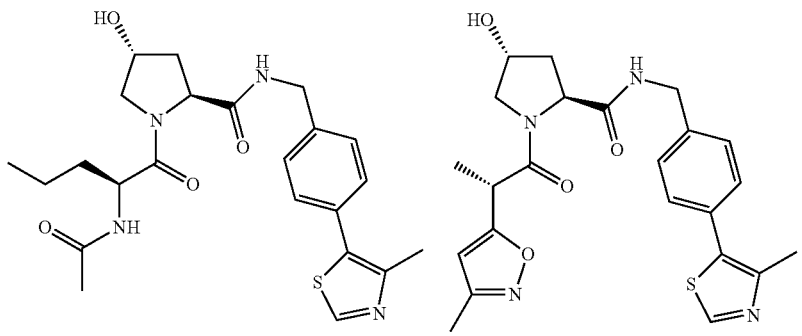
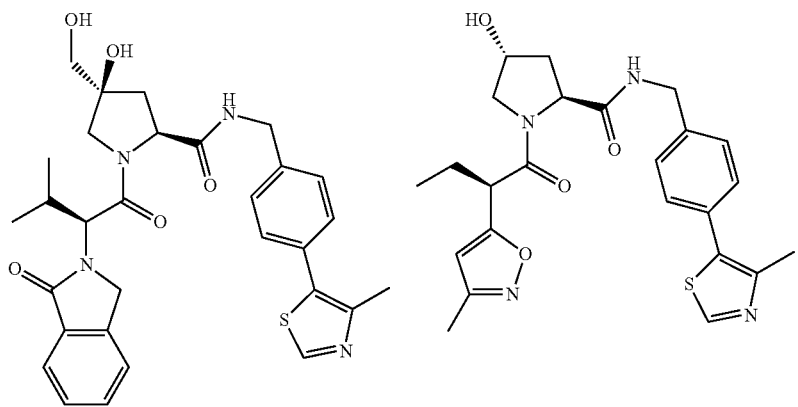

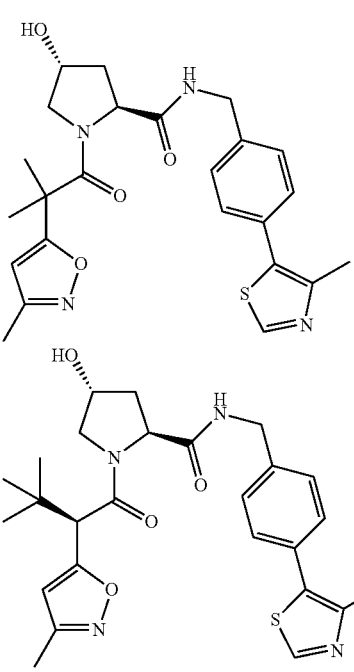
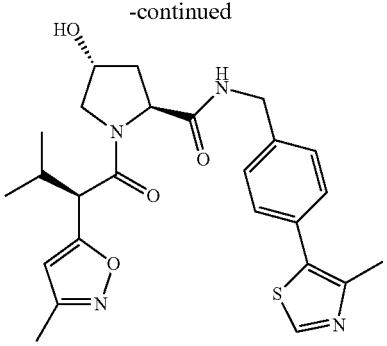
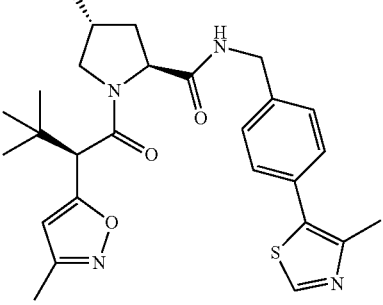
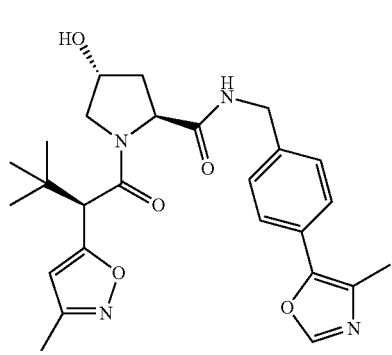
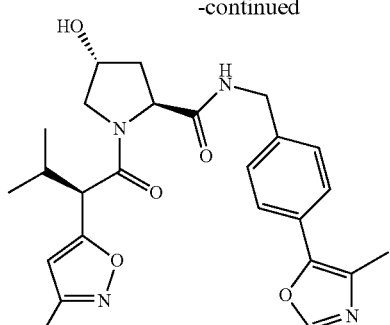
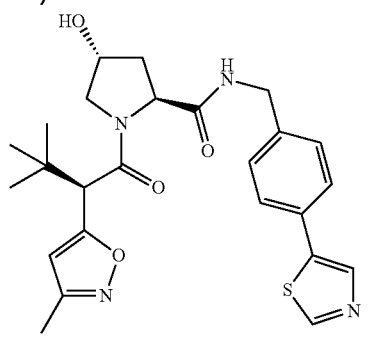
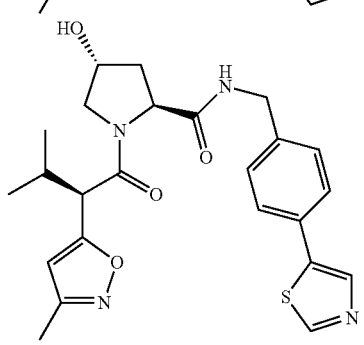
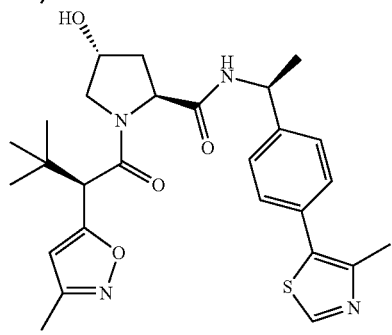
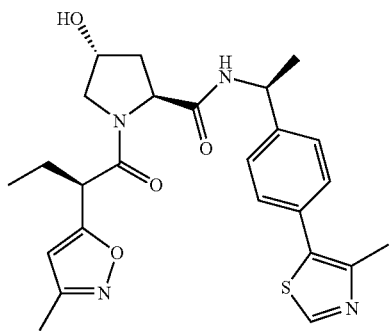

149
-continued
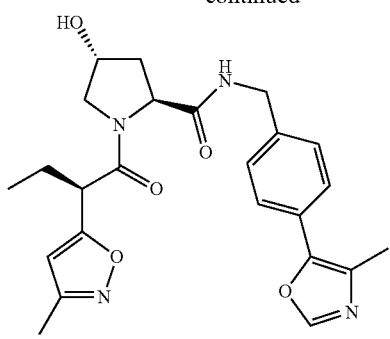
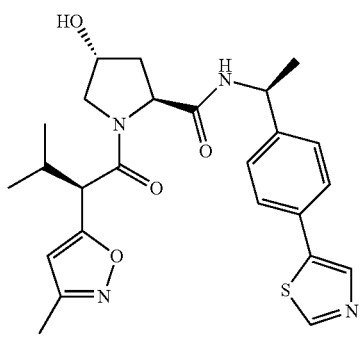
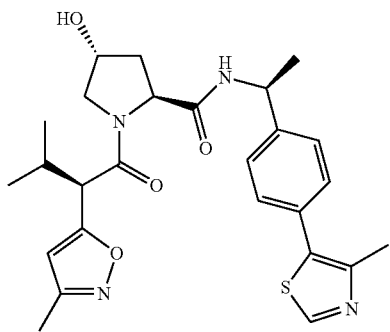
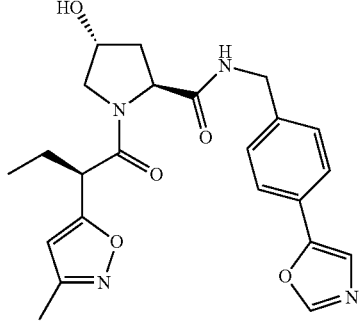
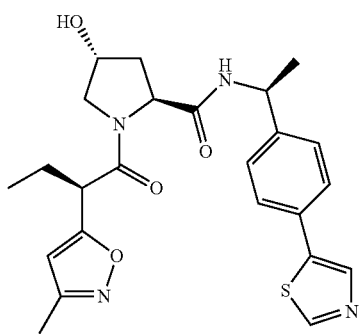
150
-continued
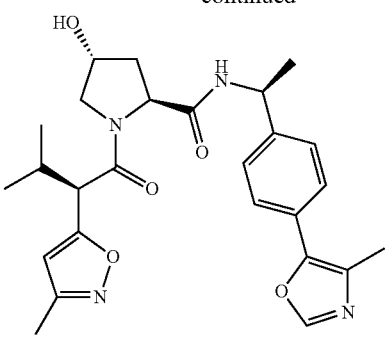
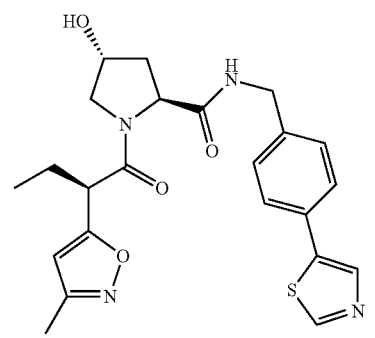
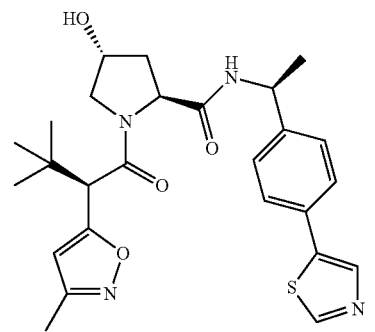
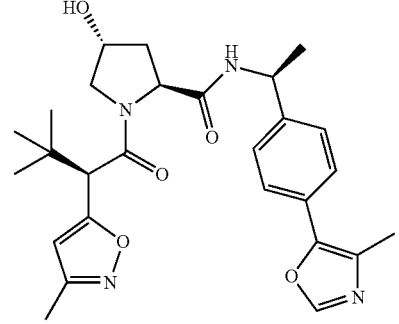
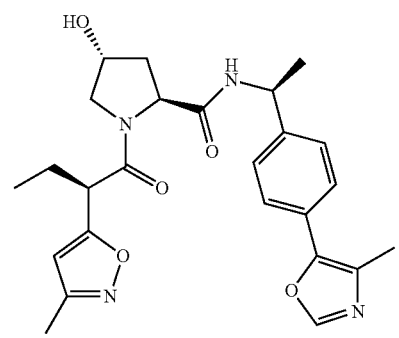

151
-continued
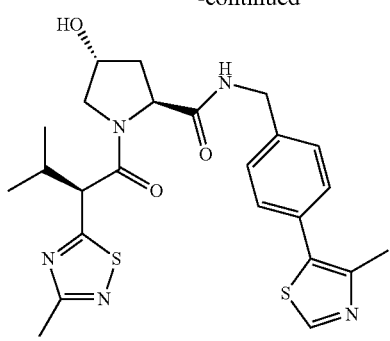
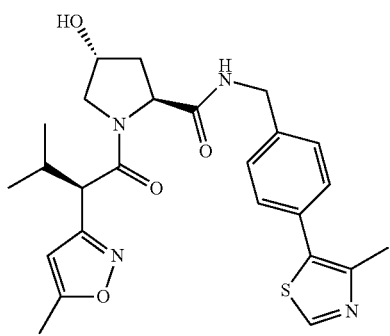
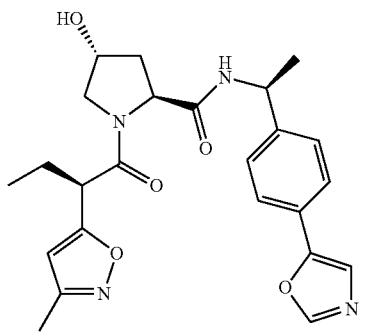
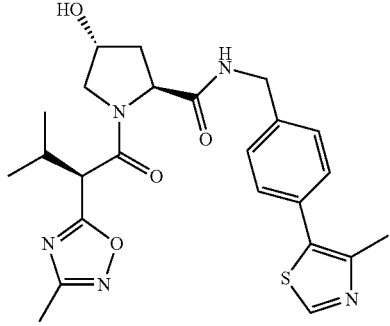
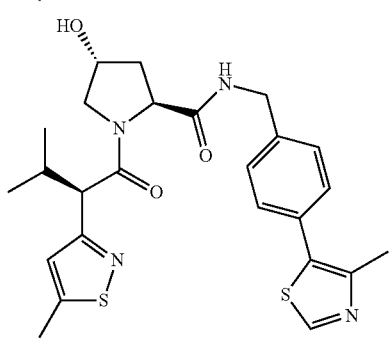
152
-continued
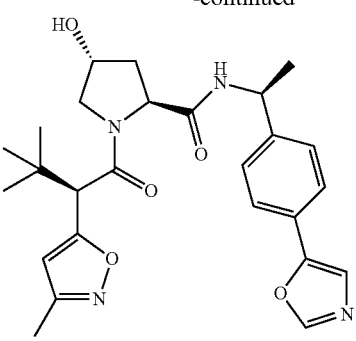
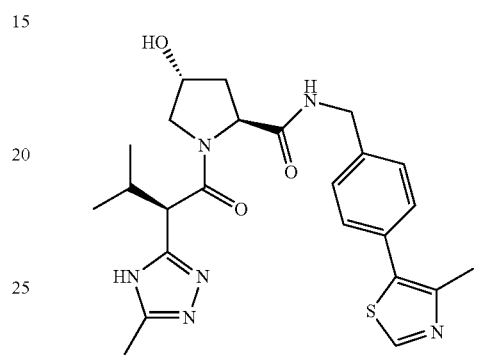
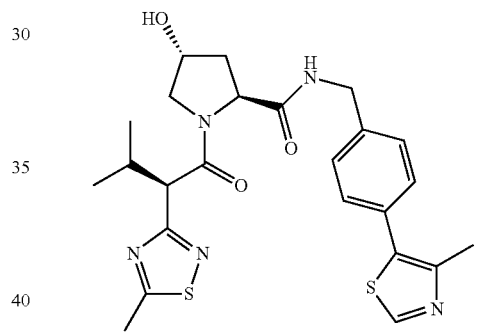
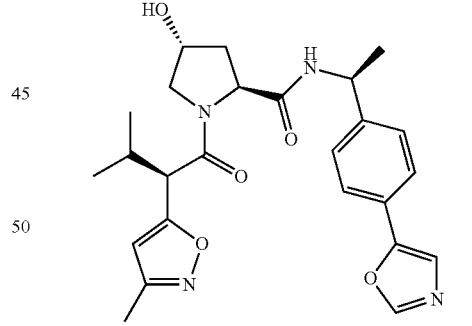
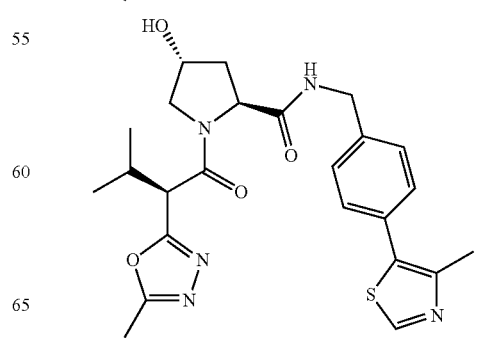

153
-continued
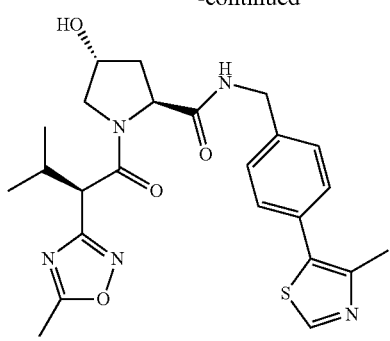
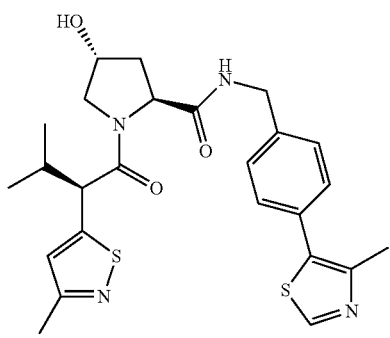
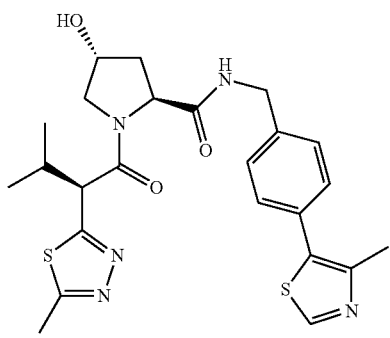
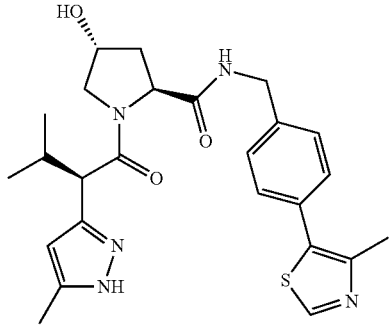
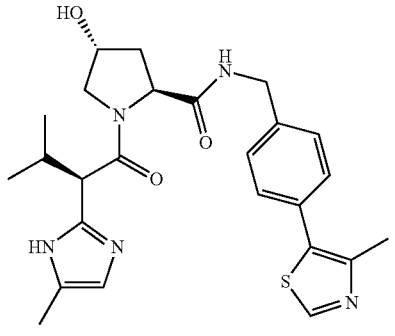
154
-continued
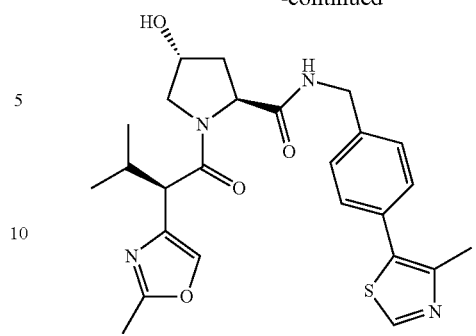
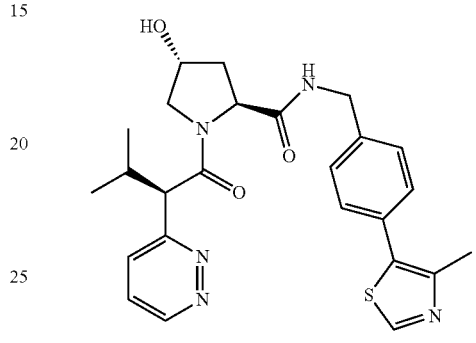
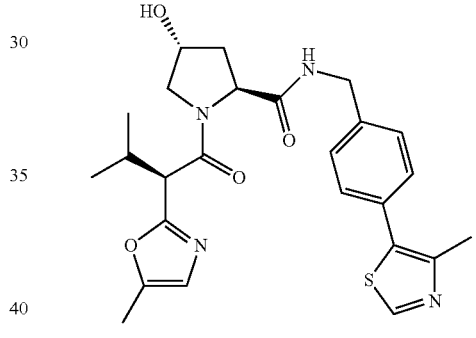
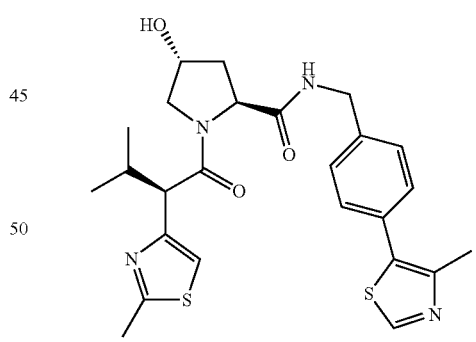
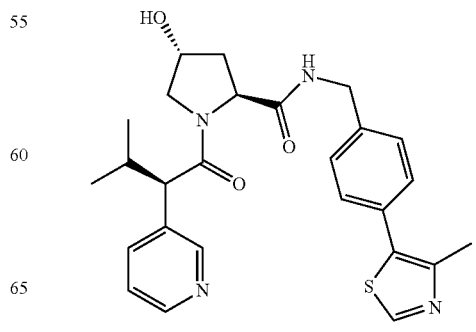

155
-continued
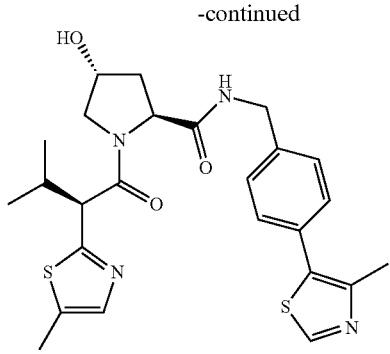
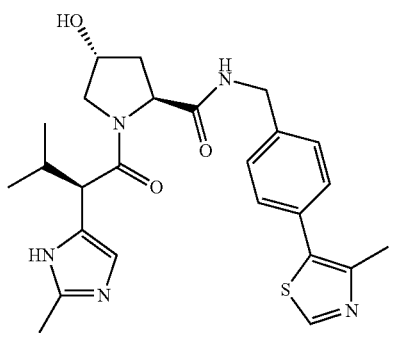
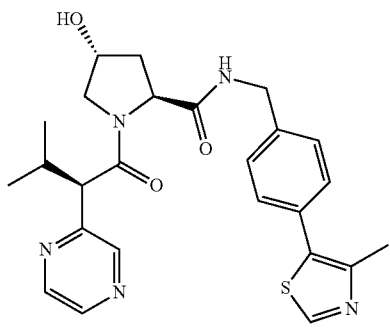
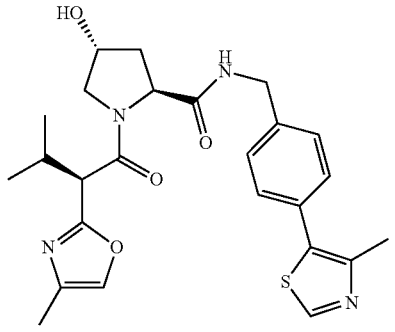
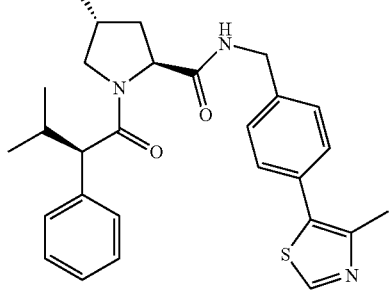
156
-continued
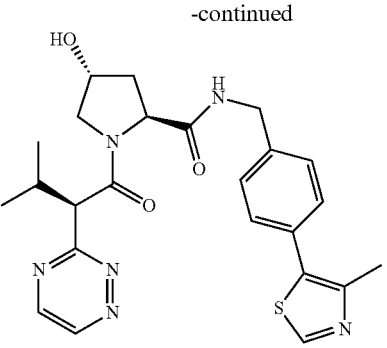
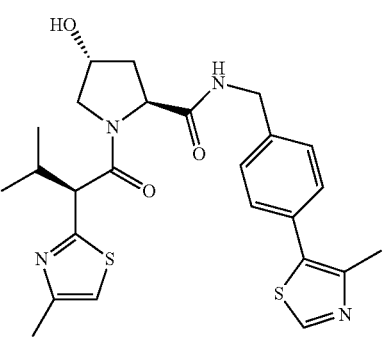
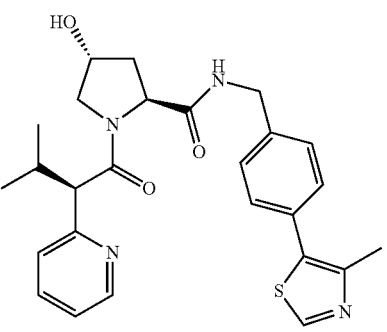
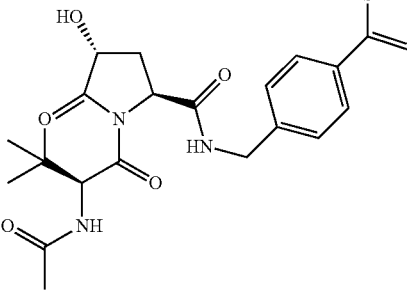
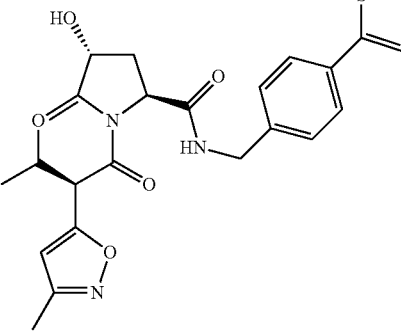

157
-continued
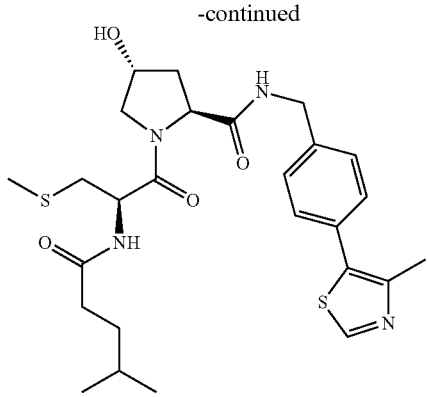
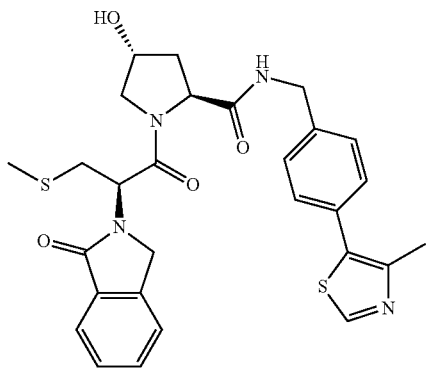
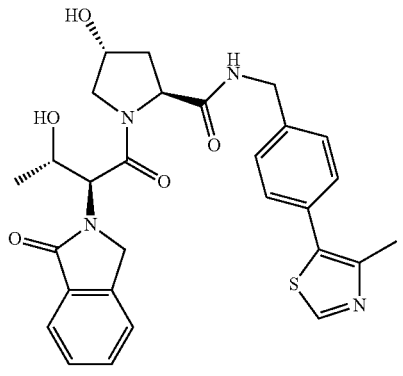
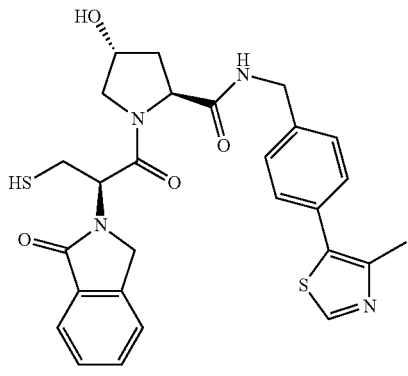
158
-continued
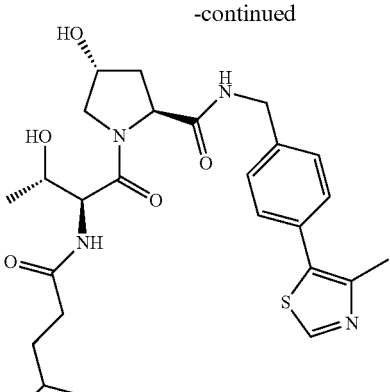
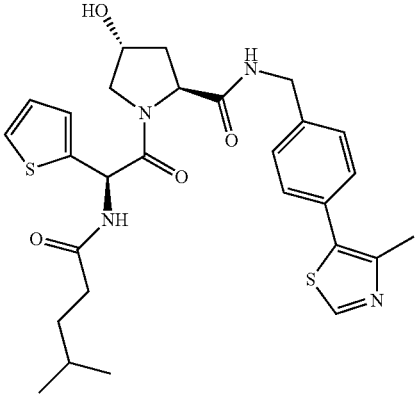
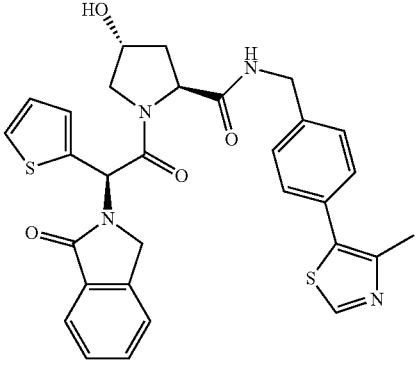
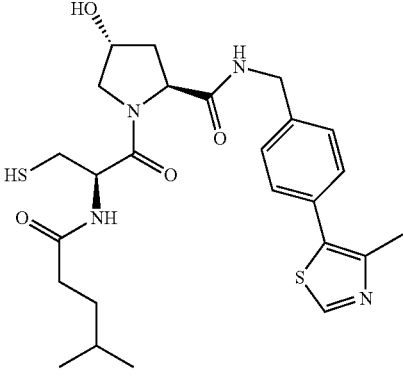

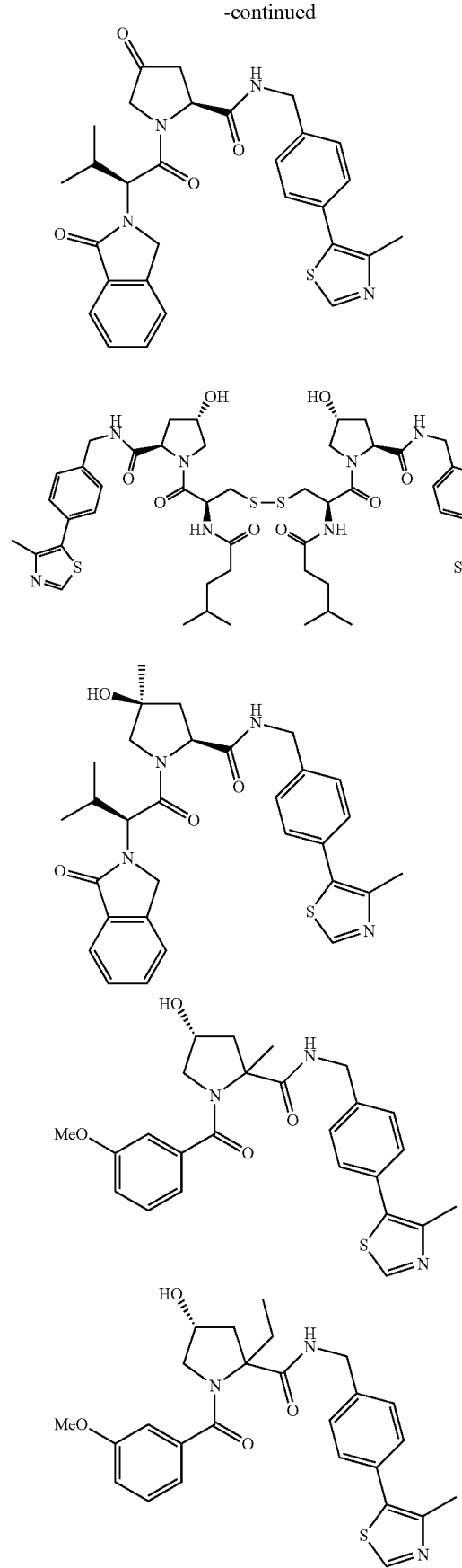

161
-continued
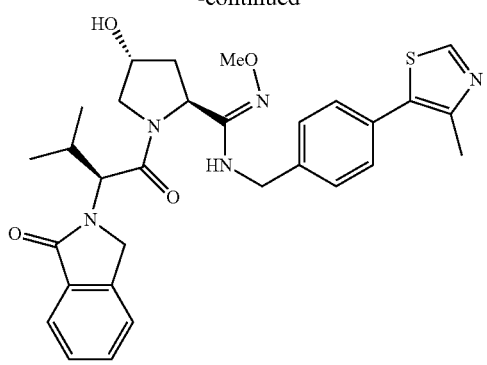
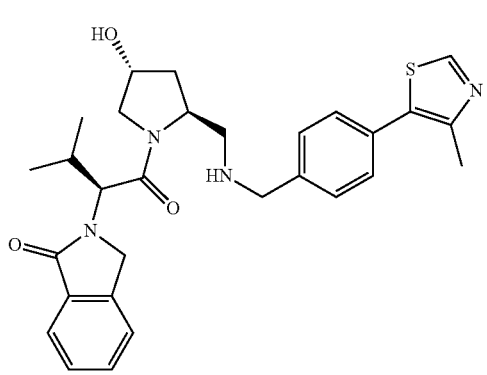
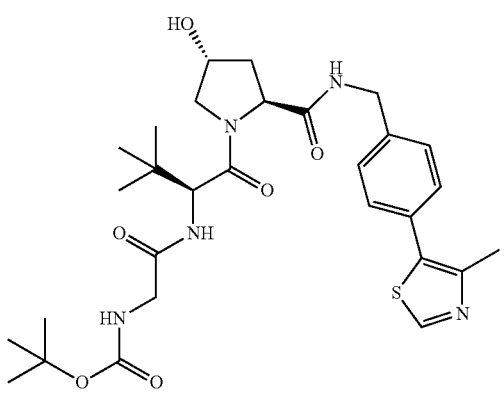
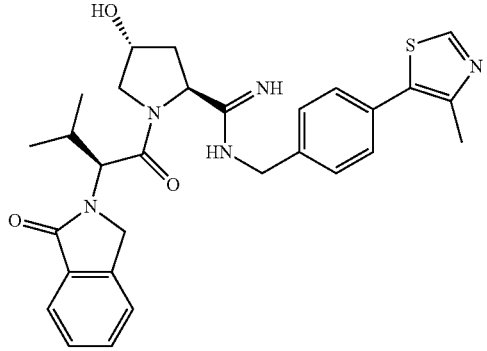
162
-continued
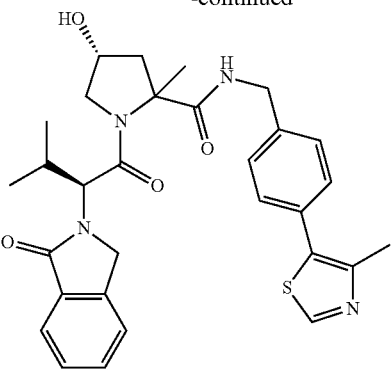
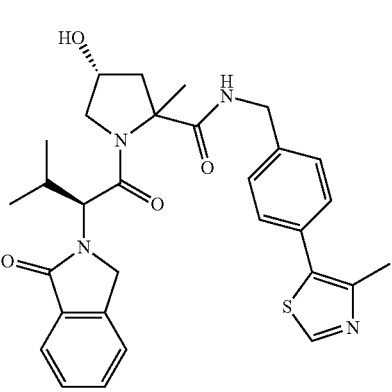
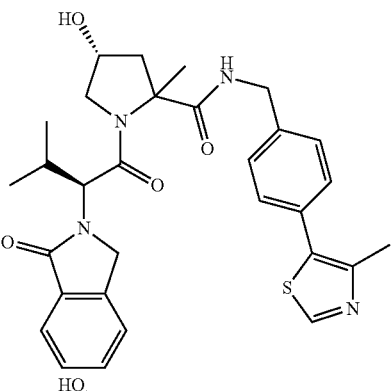
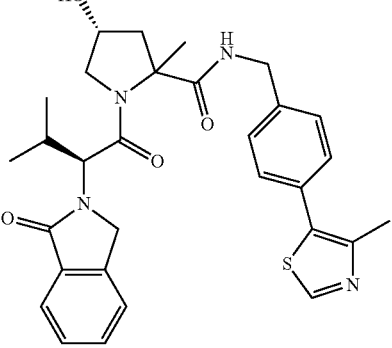

163
-continued
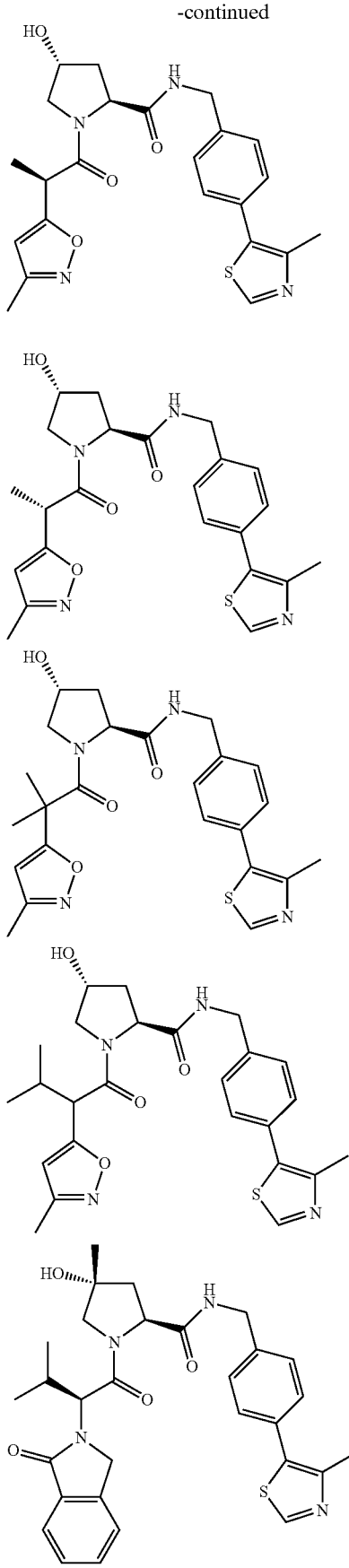
164
-continued
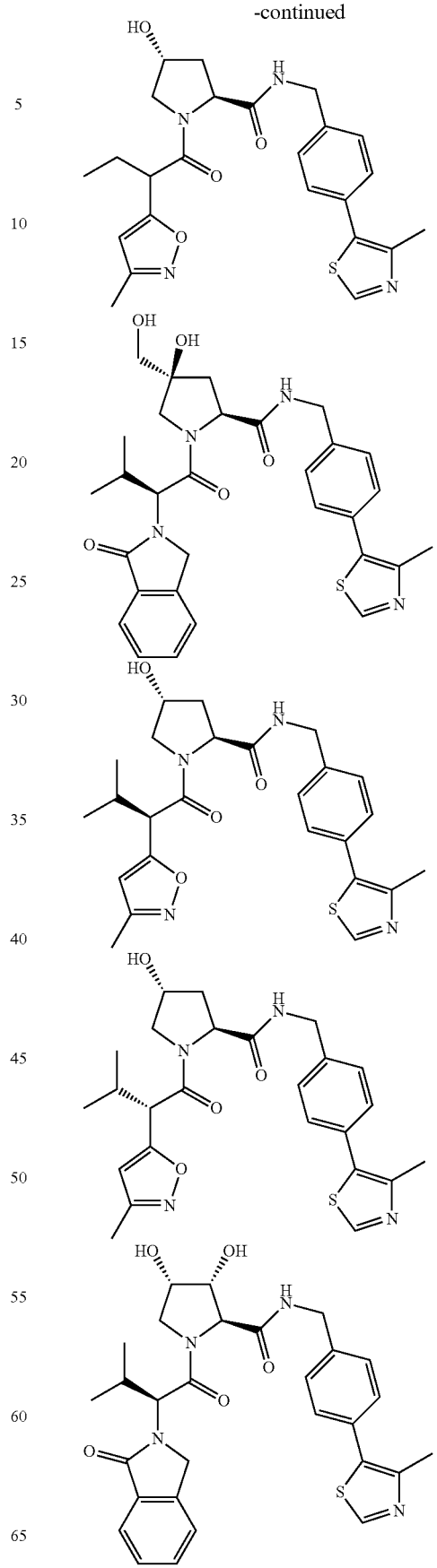

165
-continued
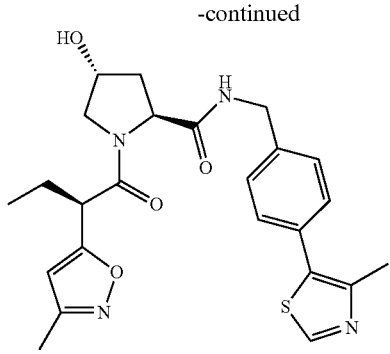
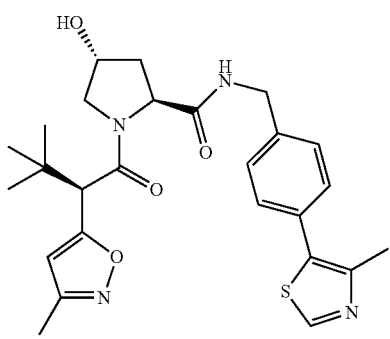
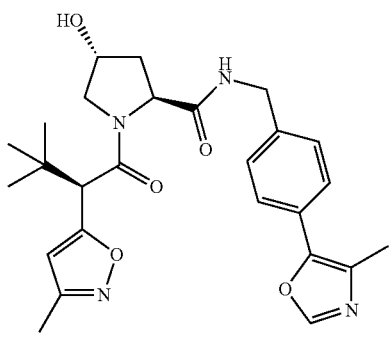
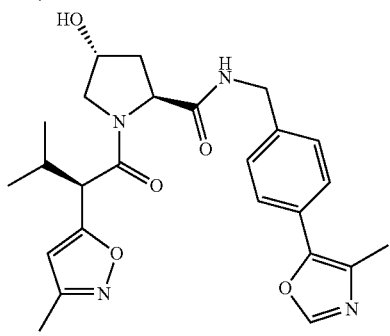
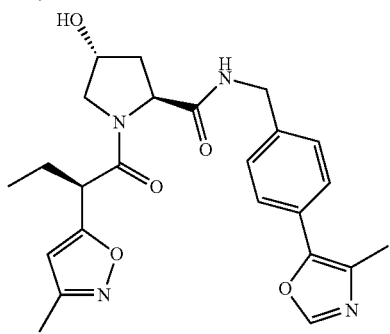
166
-continued
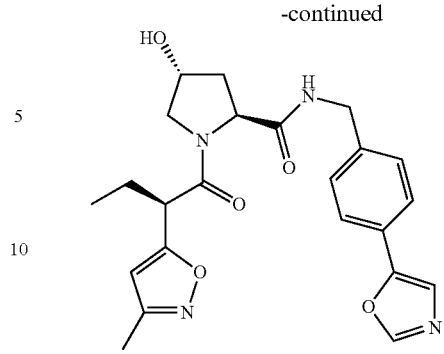
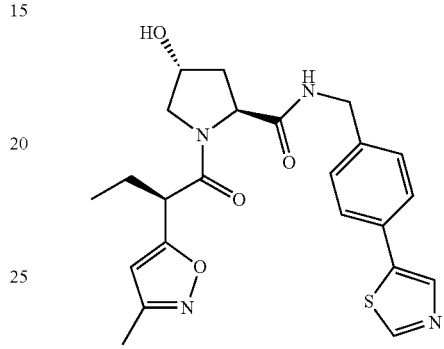
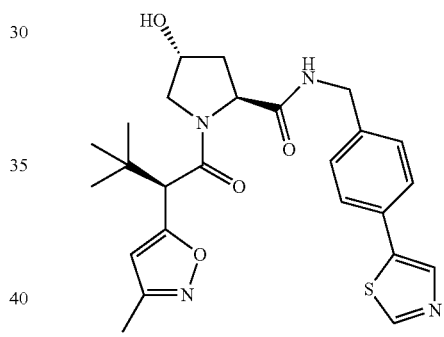
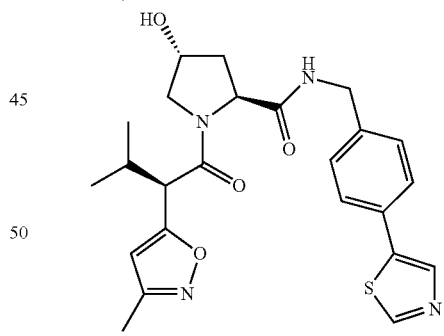
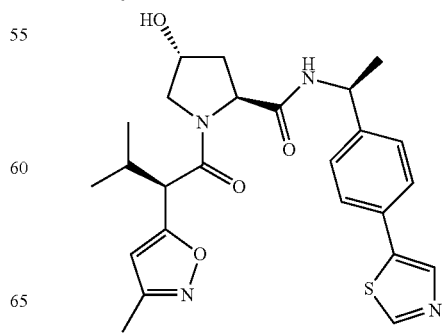

167
-continued
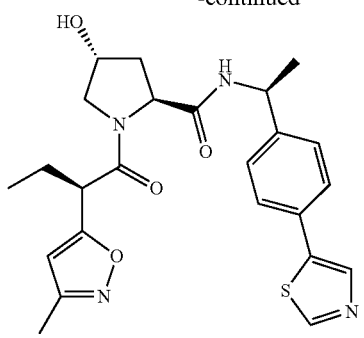
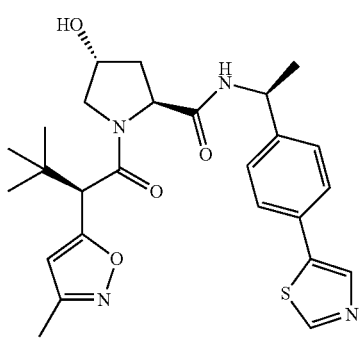
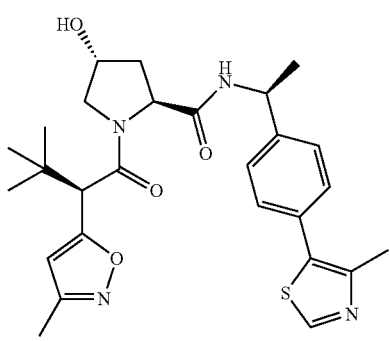
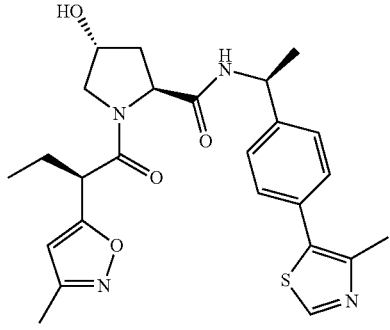
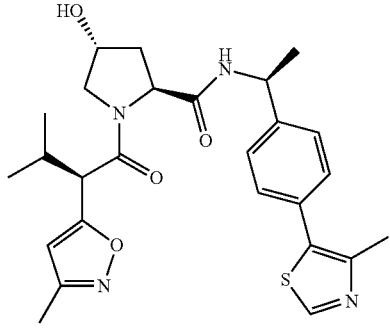
168
-continued
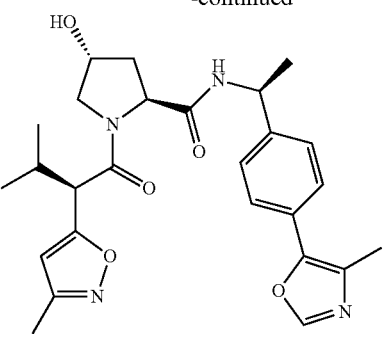
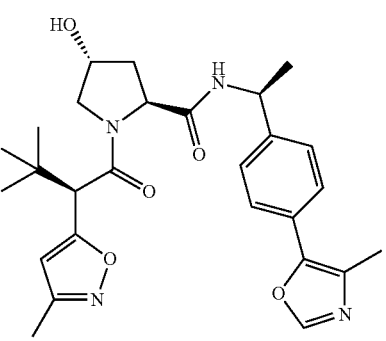
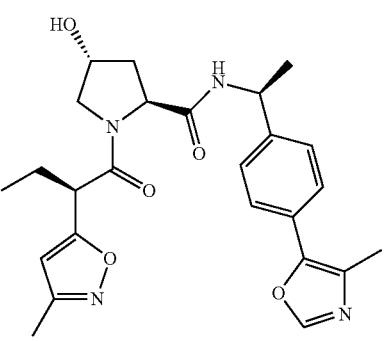
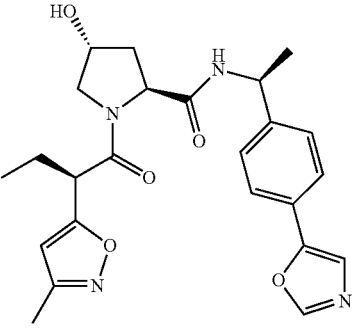
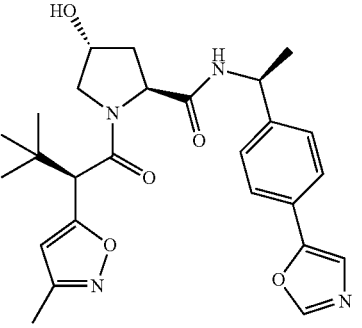

169
-continued
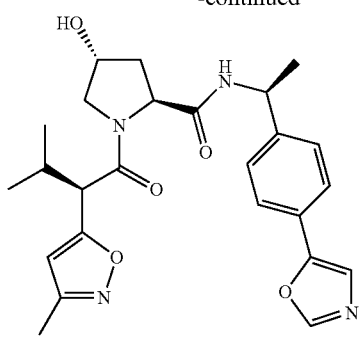
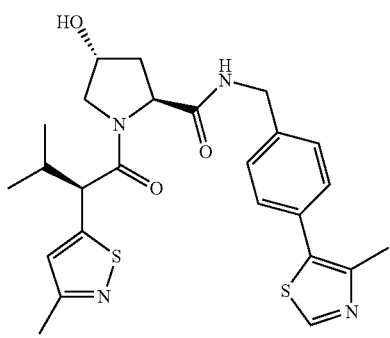
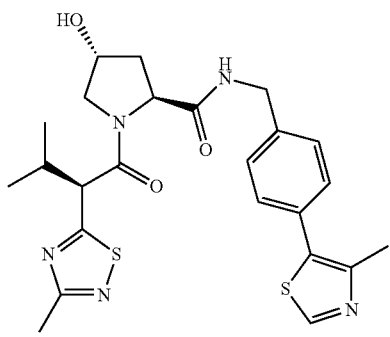
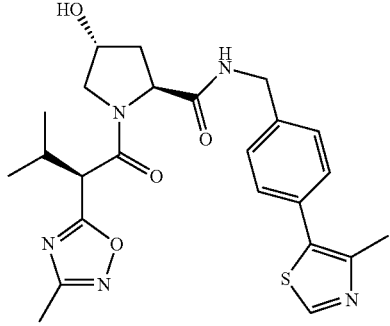
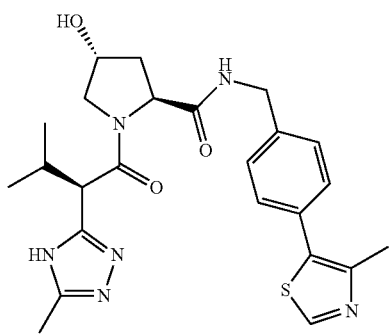
170
-continued
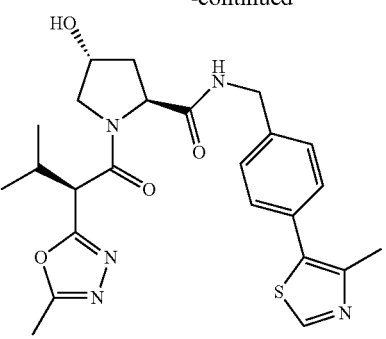
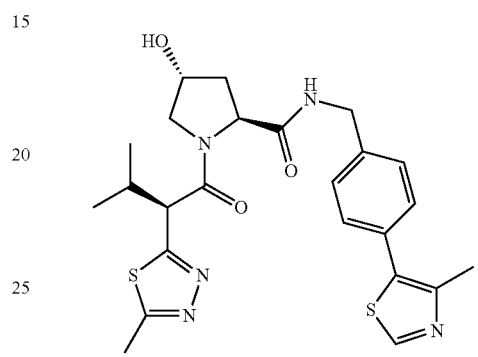
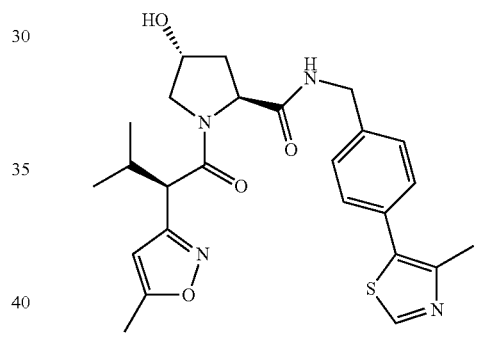
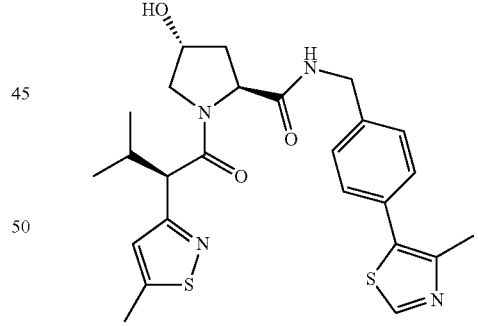
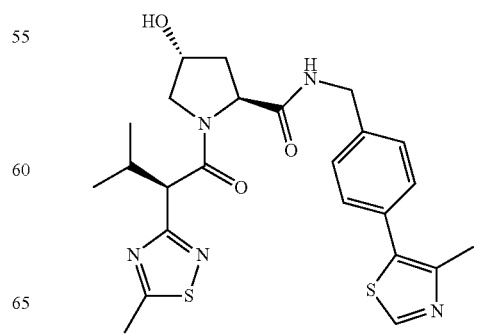

171
-continued
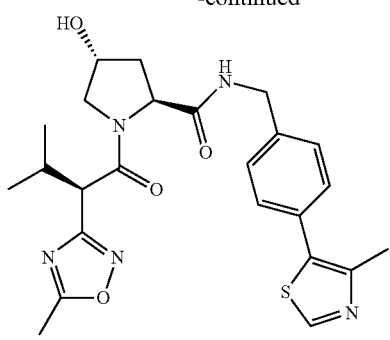
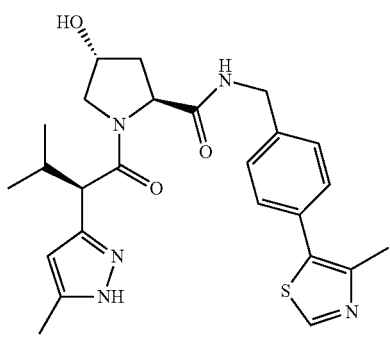
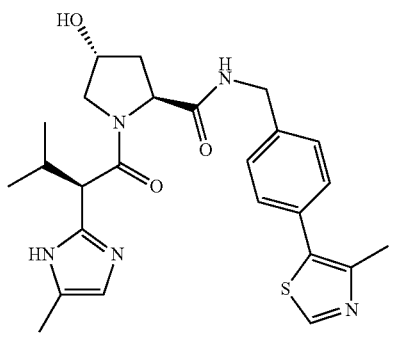
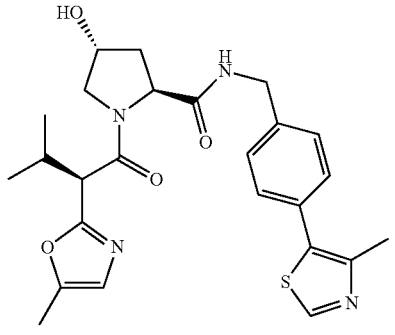
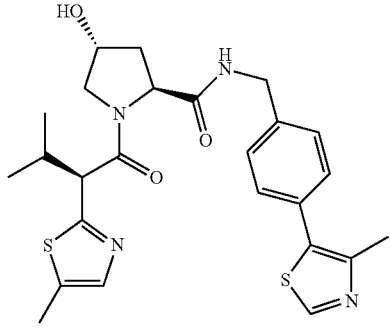
172
-continued
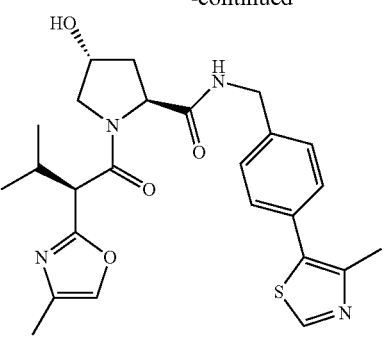
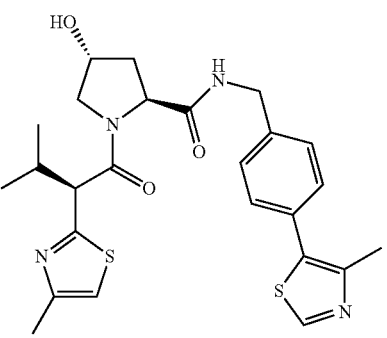
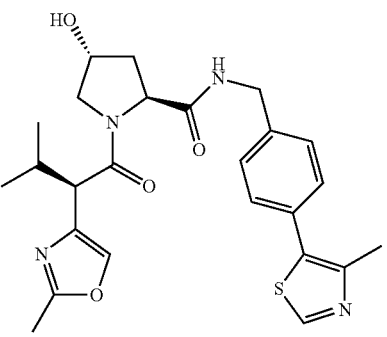
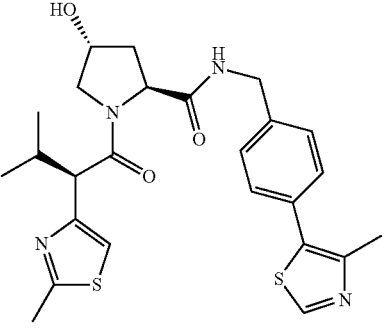
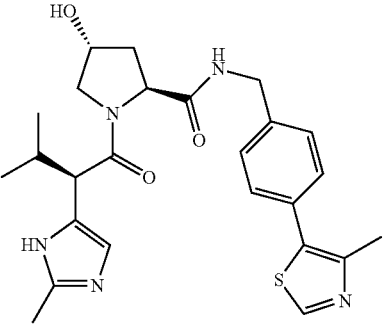

-continued
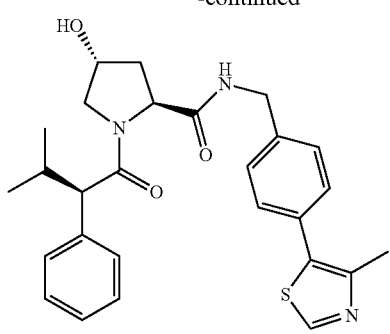
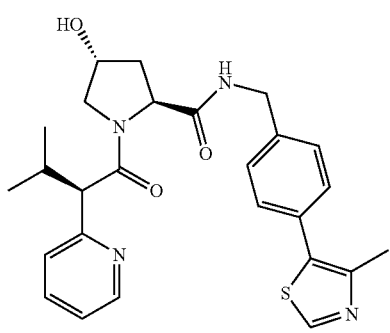
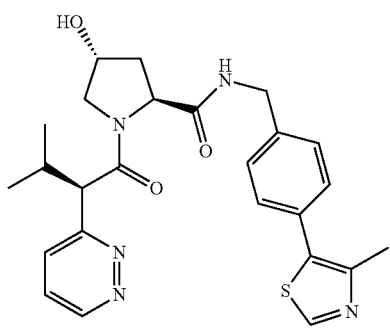
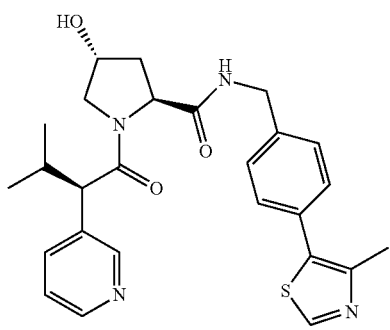
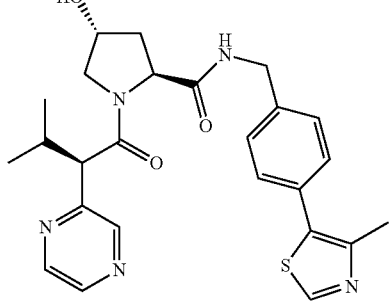
-continued
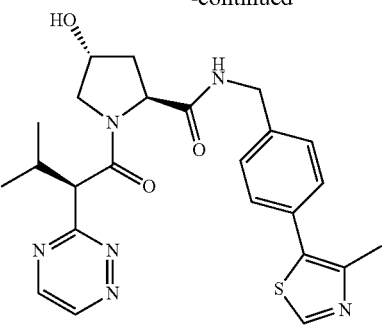
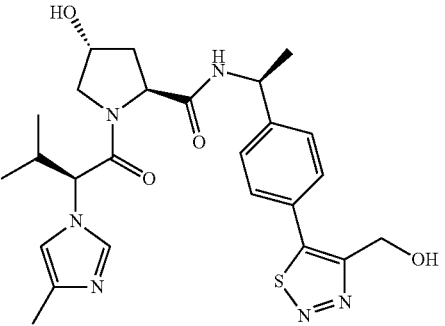
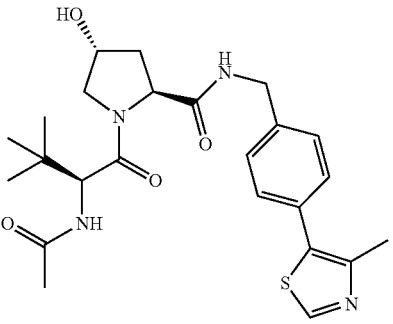
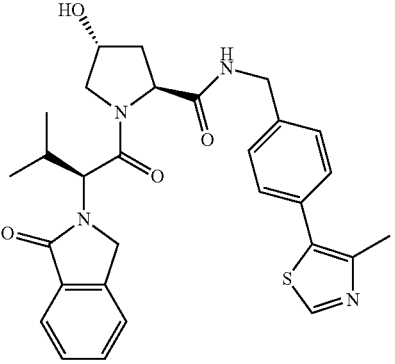
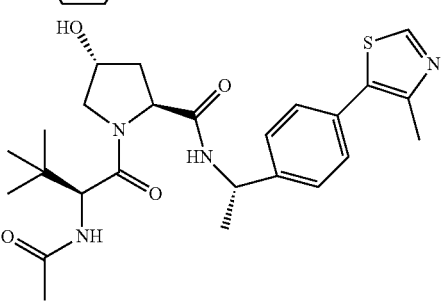

175
-continued
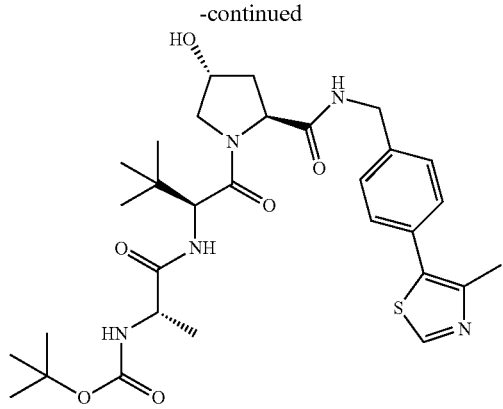
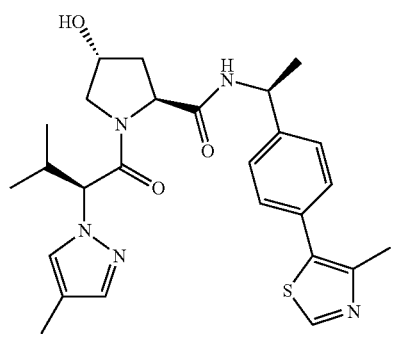
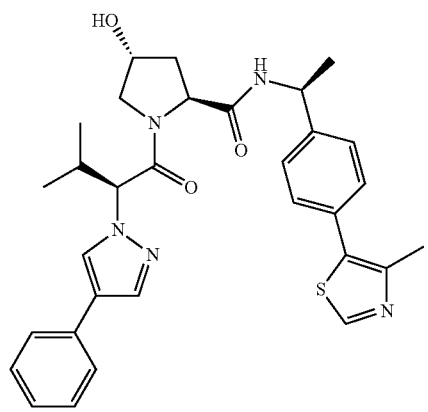
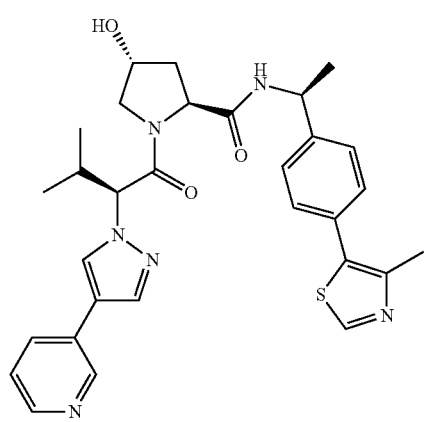
176
-continued
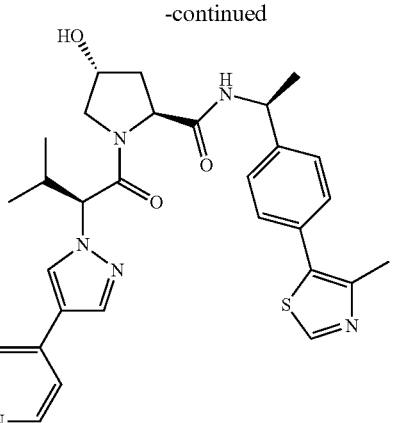
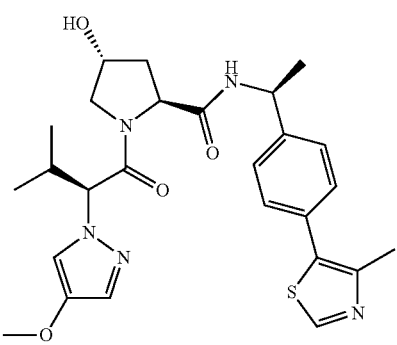
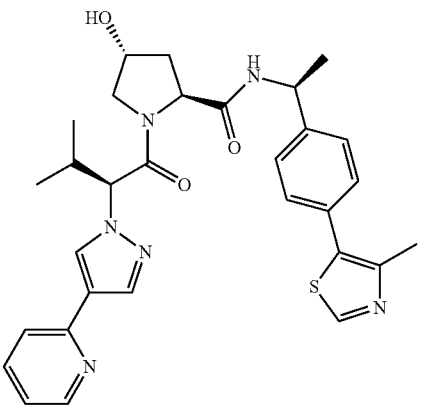
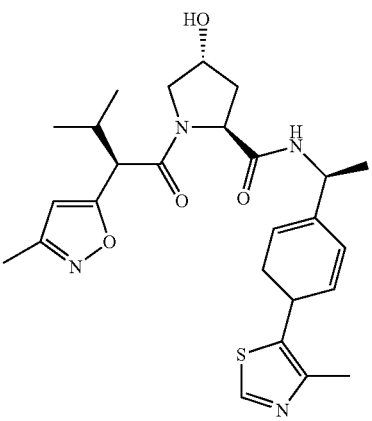

-continued

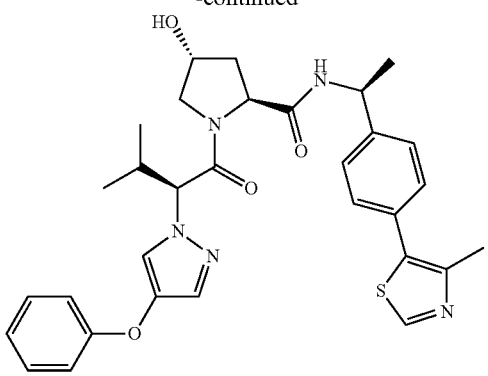

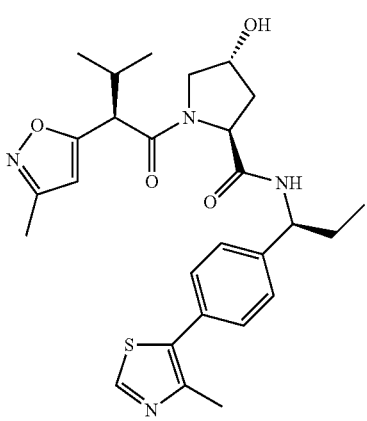

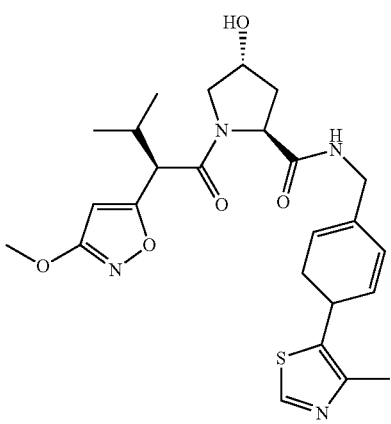

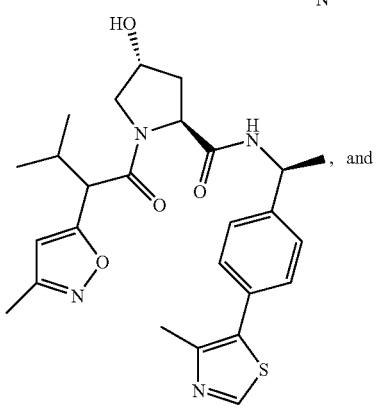, and

-continued

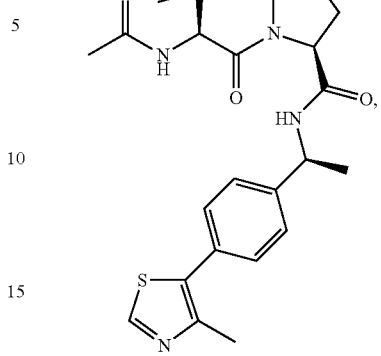

wherein the VLM may be connected to a PTM via a linker, as described herein, at any appropriate location, including, e.g., an aryl, heteroary, phenyl, or phenyl of an indole group, optionally via any appropriate functional group, such as an amine, ester, ether, alkyl, or alkoxy.

Exemplary Linkers

In certain embodiments, the compounds as described herein include one or more PTMs chemically linked or coupled to one or more ULMs (e.g., at least one of CLM, VLM, MLM, ILM, or a combination thereof) via a chemical linker (L). In certain embodiments, the linker group L is a group comprising one or more covalently connected structural units (e.g., -$A^L_1$ ... $(A^L)_q$- or -$(A^L)_q$-), wherein $A^L_1$ is a group coupled to PTM, and $(A^L)_q$ is a group coupled to ULM.

In certain embodiments, the linker group L is -$(A^L)_q$-:
$(A^L)_q$ is a group which is connected to at least one of a ULM (such as a VLM, VLM', CLM, CLM', ILM, ILM', MLM, and/or MLM'), a PTM (such as a PTM and PTM'), or a combination thereof; and q of the linker is an integer greater than or equal to 1;
each $A^L$ is independently selected from the group consisting of, a bond, $CR^{L1}R^{L2}$, O, S, SO, $SO_2$, $NR^{L3}$, $SO_2NR^{L3}$, $SONR^{L3}$, $CONR^{L3}$, $NR^{L3}CONR^{L4}$, $NR^{L3}SO_2NR^{L4}$, CO, $CR^{L1}$=$CR^{L2}$, C≡C, $SiR^{L1}R^{L2}$, $P(O)R^{L1}$, $P(O)OR^{L1}$, $NR^{L3}C$(=NCN)$NR^{L4}$, $NR^{L3}C$(=NCN), $NR^{L3}C$(=$CNO_2$)$NR^{L4}$, $C_{3-11}$cycloalkyl optionally substituted with 0-6 $R^{L1}$ and/or $R^{L2}$ groups, $C_{5-13}$ spirocycloalkyl optionally substituted with 0-9 $R^{L1}$ and/or $R^{L2}$ groups, $C_{3-11}$heterocyclyl optionally substituted with 0-6 $R^{L1}$ and/or $R^{L2}$ groups, $C_{5-13}$ spiroheterocycloalkyl optionally substituted with 0-8 $R^{L1}$ and/or $R^{L2}$ groups, aryl optionally substituted with 0-6 $R^{L1}$ and/or $R^{L2}$ groups, heteroaryl optionally substituted with 0-6 $R^{L1}$ and/or $R^{L2}$ groups, where $R^{L1}$ or $R^{L2}$, each independently are optionally linked to other groups to form cycloalkyl and/or heterocyclyl moiety, optionally substituted with 0-4 $R^{L5}$ groups; and $R^{L1}$, $R^{L2}$, $R^{L3}$, $R^{L4}$ and $R^{L5}$ are, each independently, H, halo, $C_{1-8}$alkyl, $OC_{1-8}$alkyl, $SC_{1-8}$alkyl, $NHC_{1-8}$alkyl, $N(C_{1-8}alkyl)_2$, $C_{3-11}$cycloalkyl, aryl, heteroaryl, $C_{3-11}$heterocyclyl, $OC_{1-8}$cycloalkyl, $SC_{1-8}$cycloalkyl, $NHC_{1-8}$cycloalkyl, $N(C_{1-8}cycloalkyl)_2$, $N(C_{1-8}cycloalkyl)(C_{1-8}alkyl)$, OH, $NH_2$, SH, $SO_2C_{1-8}$alkyl, $P(O)(OC_{1-8}alkyl)(C_{1-8}alkyl)$, $P(O)(OC_{1-8}alkyl)_2$, CC—$C_{1-8}$alkyl, CCH, CH=CH($C_{1-8}$alkyl), C($C_{1-8}$alkyl)=CH($C_{1-8}$alkyl), C($C_{1-8}$alkyl)=C($C_{1-8}$alkyl)$_2$, $Si(OH)_3$, $Si(C_{1-8}alkyl)_3$, $Si(OH)(C_{1-8}alkyl)_2$, $COC_{1-8}$alkyl, CO₂H, halogen, CN, CF₃, CHF₂, CH₂F, NO₂, SF₅, SO₂NHC$_{1-8}$alkyl, SO₂N(C$_{1-8}$alkyl)₂, SONHC$_{1-8}$alkyl, SON(C$_{1-8}$alkyl)₂, CONHC$_{1-8}$alkyl, CON(C$_{1-8}$alkyl)₂, N(C$_{1-8}$alkyl)CONH(C$_{1-8}$alkyl), N(C$_{1-8}$alkyl)CON(C$_{1-8}$alkyl)₂, NHCONH(C$_{1-8}$alkyl), NHCON(C$_{1-8}$alkyl)₂, NHCONH₂, N(C$_{1-8}$alkyl)SO₂NH(C$_{1-8}$alkyl), N(C$_{1-8}$alkyl) SO₂N(C$_{1-8}$alkyl)₂, NH SO₂NH(C$_{1-8}$alkyl), NH SO₂N(C$_{1-8}$alkyl)₂, NH SO₂NH₂.

In certain embodiments, q of the linker is an integer greater than or equal to 0. In certain embodiments, q is an integer greater than or equal to 1.

In certain embodiments, e.g., where q of the linker is greater than 2, $(A^L)_q$ is a group which is connected to ULM, and $A^L{}_1$ and $(A^L)_q$ are connected via structural units of the linker (L).

In certain embodiments, e.g., where q of the linker is 2, $(A^L)_q$ is a group which is connected to $A^L{}_1$ and to a ULM.

In certain embodiments, e.g., where q of the linker is 1, the structure of the linker group L is -$A^L{}_1$-, and $A^L{}_1$ is a group which is connected to a ULM moiety and a PTM moiety.

In certain embodiments, the linker (L) comprises a group represented by a general structure selected from the group consisting of:
—NR(CH₂)$_n$-(lower alkyl)-, —NR(CH₂)$_n$-(lower alkoxyl)-, —NR(CH₂)$_n$-(lower alkoxyl)-OCH₂—, —NR(CH₂)$_n$-(lower alkoxyl)-(lower alkyl)-OCH₂—, —NR(CH₂)$_n$-(cycloalkyl)-(lower alkyl)-OCH₂—, —NR(CH₂)$_n$-(hetero cycloalkyl)-, —NR(CH₂CH₂O)$_n$-(lower alkyl)-O—CH₂—, —NR(CH₂CH₂O)$_n$-(hetero cycloalkyl)-O—CH₂—, —NR(CH₂CH₂O)$_n$-Aryl-O—CH₂—, NR(CH₂CH₂O)$_n$-(hetero aryl)-O—CH₂—, —NR(CH₂CH₂O)$_n$-(cyclo alkyl)-O-(hetero aryl)-O—CH₂—, —NR(CH₂CH₂O)$_n$-(cyclo alkyl)-O-Aryl-O—CH₂—, —NR(CH₂CH₂O)$_n$-(lower alkyl)-NH-Aryl-O—CH₂—, —NR(CH₂CH₂O)$_n$-(lower alkyl)-O-Aryl-CH₂, —NR(CH₂CH₂O)$_n$— cycloalkyl-O-Aryl-, —NR(CH₂CH₂O)$_n$-cycloalkyl-O-(heteroaryl)1-, —NR(CH₂CH₂)$_n$— (cycloalkyl)-O-(heterocycle)-CH₂, —NR(CH₂CH₂)$_n$-(heterocycle)-(heterocycle)-CH₂, —N(R1R2)-(heterocycle)-CH₂; where
n of the linker can be 0 to 10;
R of the linker can be H, lower alkyl;
R1 and R2 of the linker can form a ring with the connecting N.

In certain embodiments, the linker (L) comprises a group represented by a general structure selected from the group consisting of:
—N(R)—(CH2)$_m$-O(CH2)$_n$-O(CH2)$_o$-O(CH2)$_p$-O(CH2)$_q$-O(CH2)$_r$-OCH2-,
—O—(CH2)$_m$-O(CH2)$_n$-O(CH2)$_o$-O(CH2)$_p$-O(CH2)$_q$-O(CH2)$_r$-OCH2-,
—O—(CH2)$_m$-O(CH2)$_n$-O(CH2)$_o$-O(CH2)$_p$-O(CH2)$_q$-O(CH2)$_r$-O—;
—N(R)—(CH2)$_m$-O(CH2)$_n$-O(CH2)$_o$-O(CH2)$_p$-O(CH2)$_q$-O(CH2)$_r$-O—;
—(CH2)$_m$-O(CH2)$_n$-O(CH2)$_o$-O(CH2)$_p$-O(CH2)$_q$-O(CH2)$_r$-O—;
—(CH2)$_m$-O(CH2)$_n$-O(CH2)$_o$-O(CH2)$_p$-O(CH2)$_q$-O(CH2)$_r$-OCH2-;

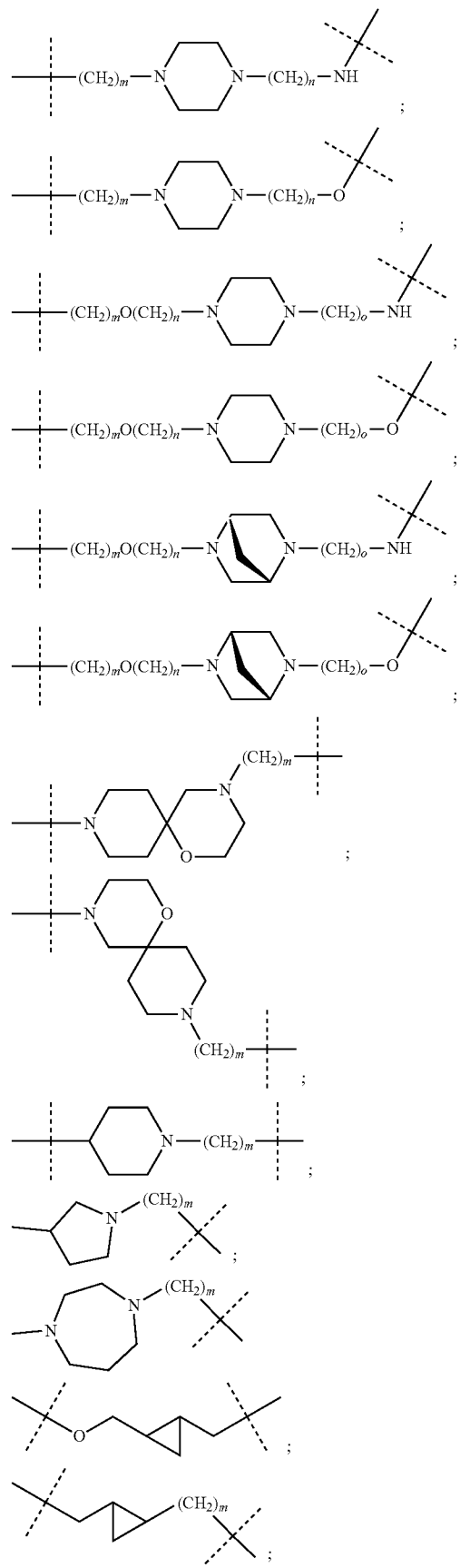

-continued
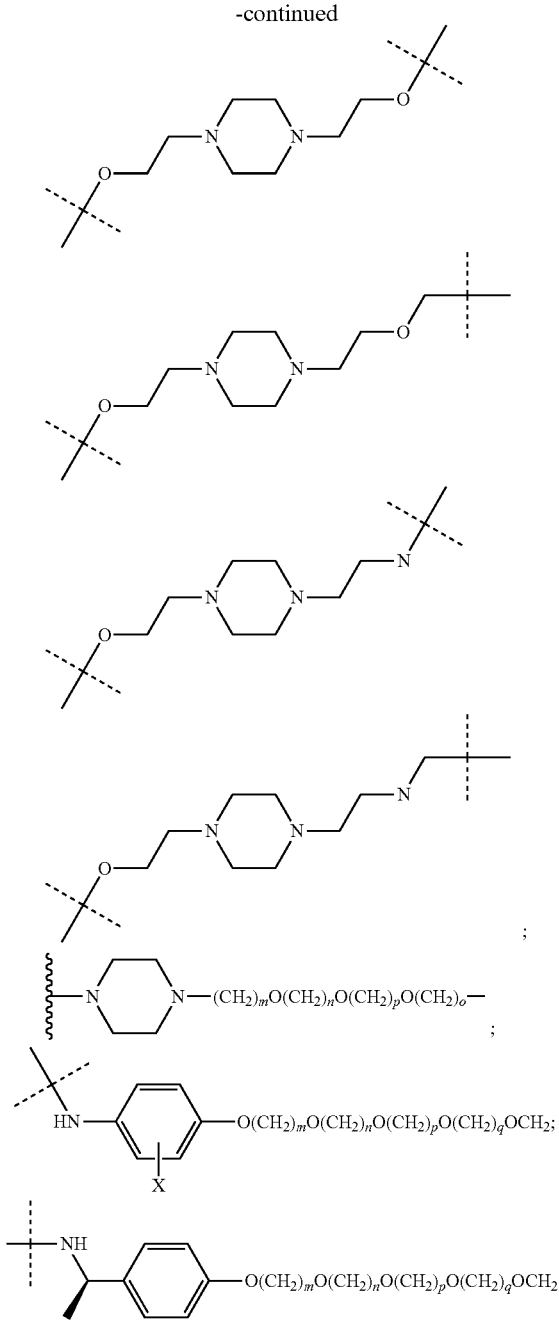
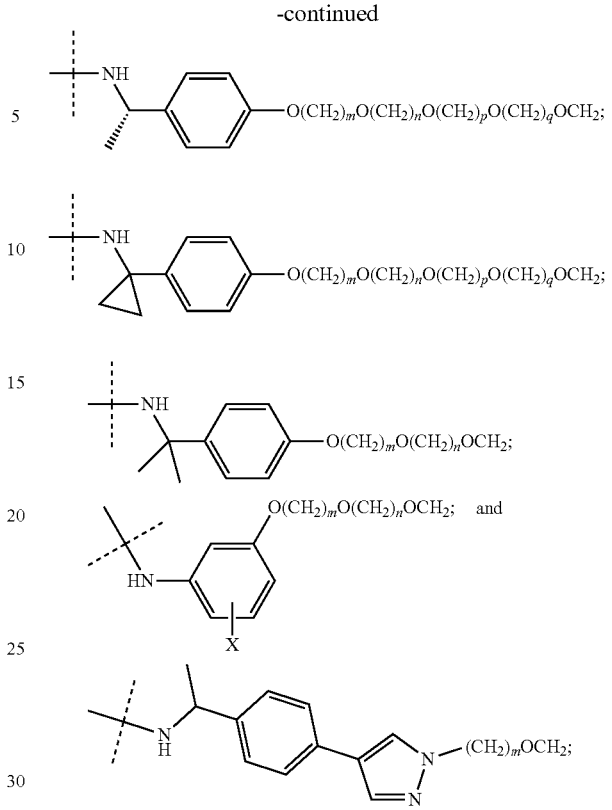
wherein
m, n, o, p, q, and r of the linker are independently 0, 1, 2, 3, 4, 5, 6, 7, 8, 9, 10, 11, 12, 13, 14, 15, 16, 17, 18, 19, or 20;
when the number is zero, there is no N—O or O—O bond
R of the linker is H, methyl and ethyl;
X of the linker is H and F
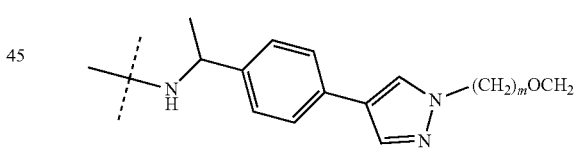
where m of the linker can be 2, 3, 4, 5
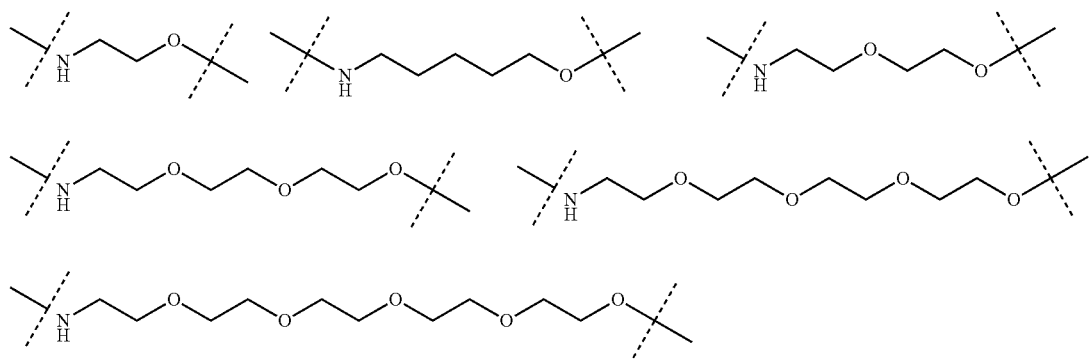

-continued
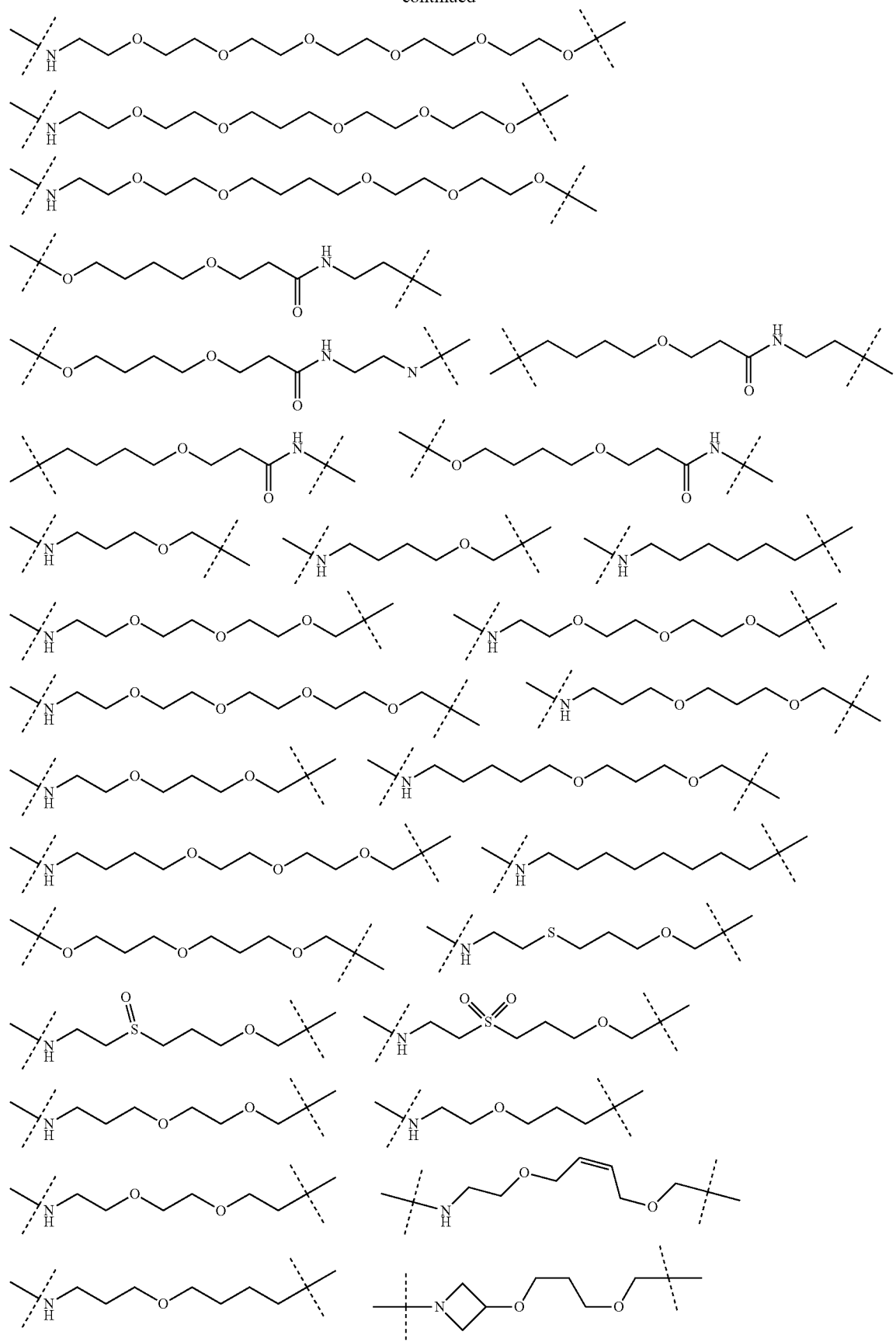

-continued
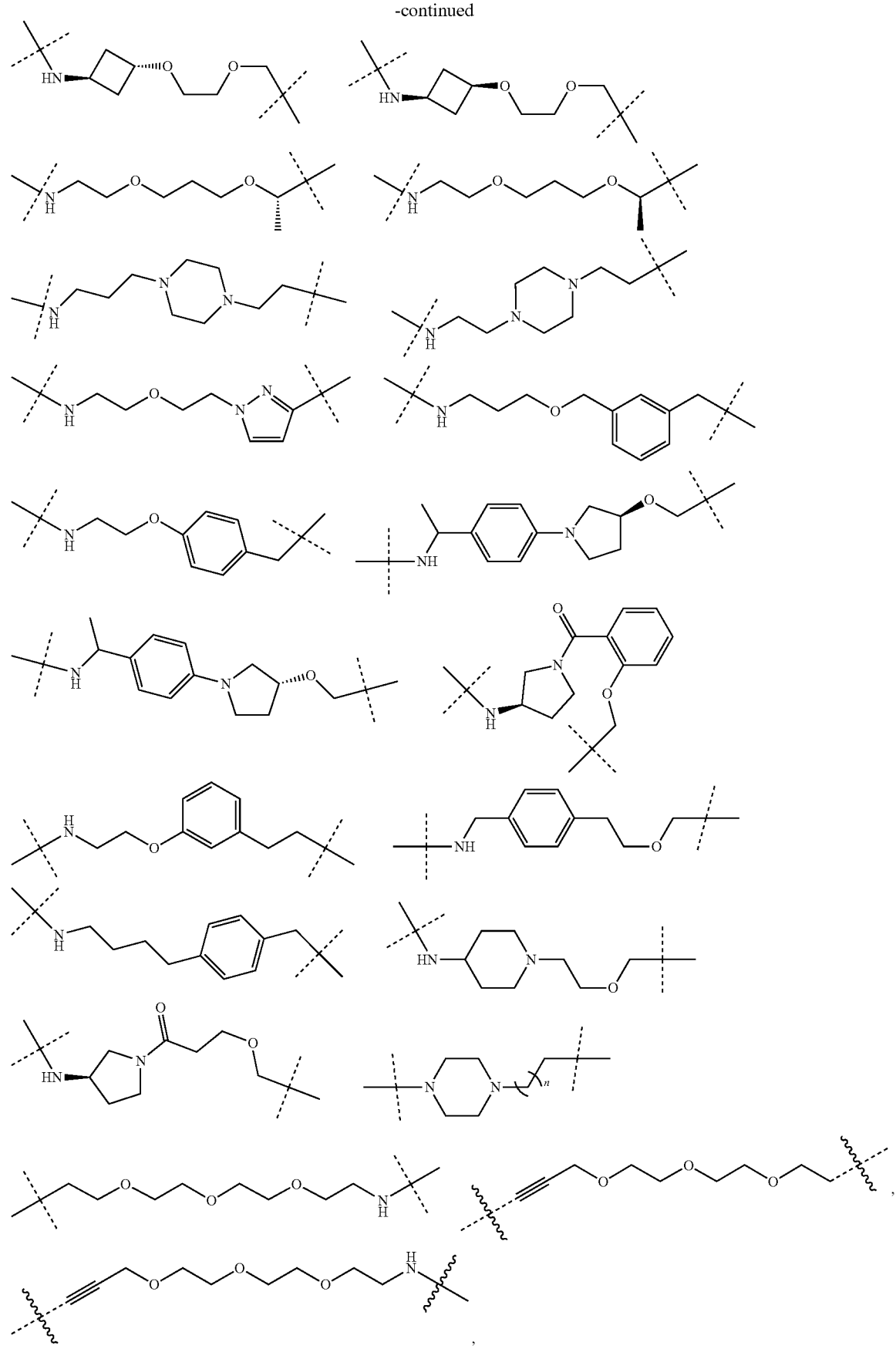

187 188
-continued
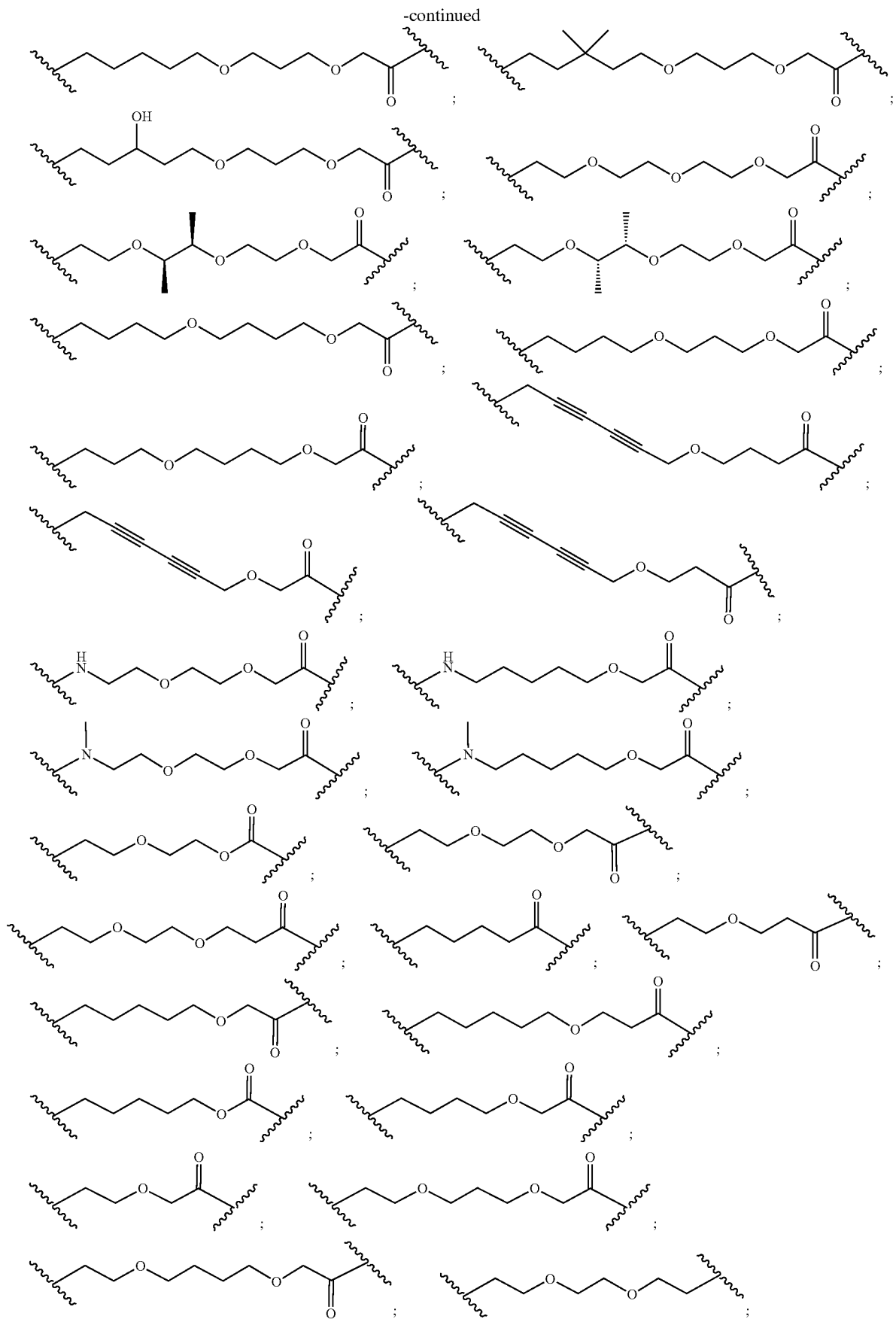

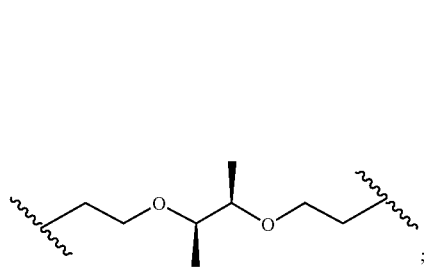;
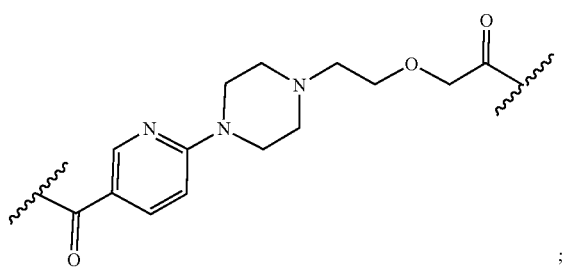;
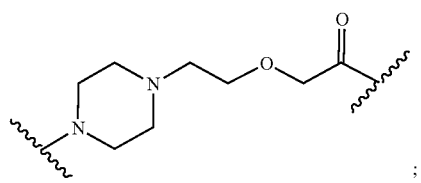;
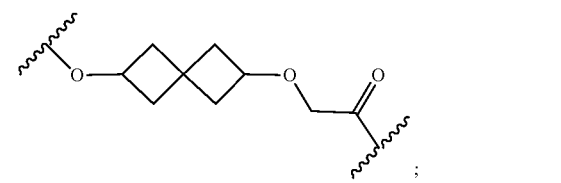;
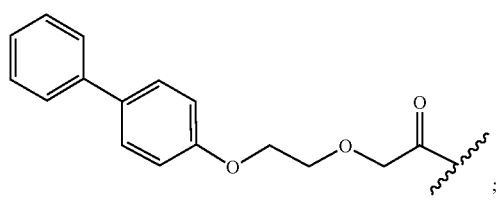;
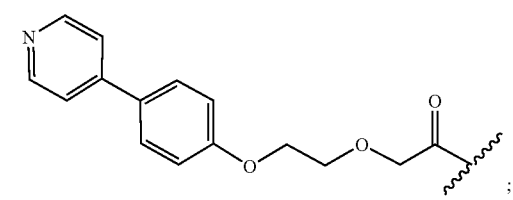;
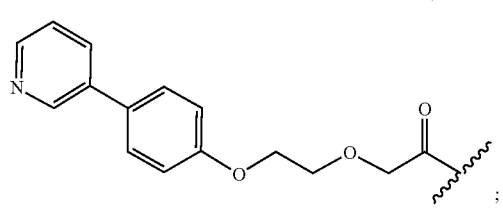;
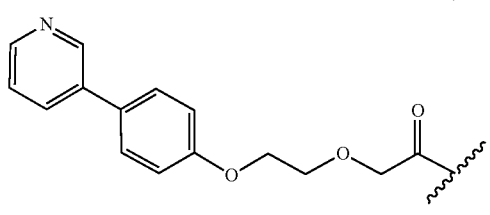;
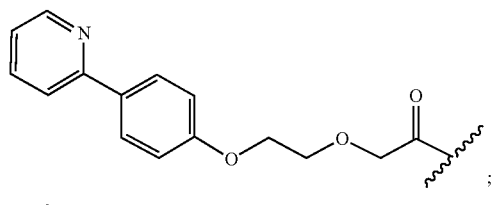;
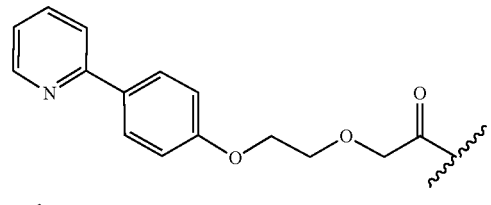;
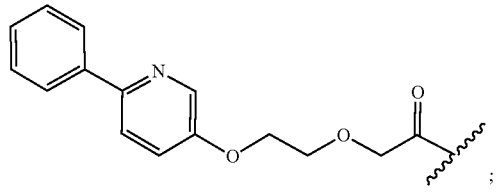;
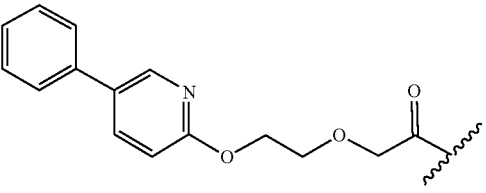;
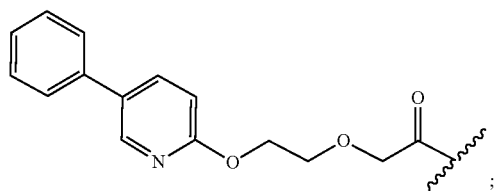;
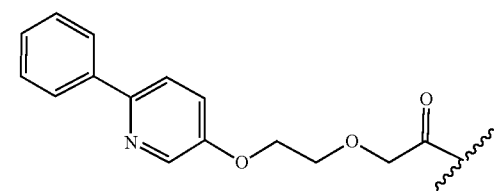;
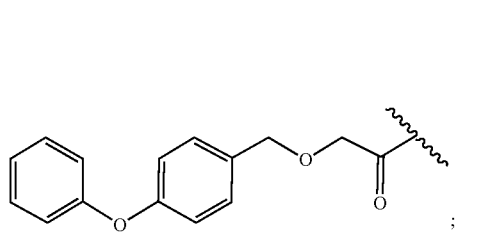;
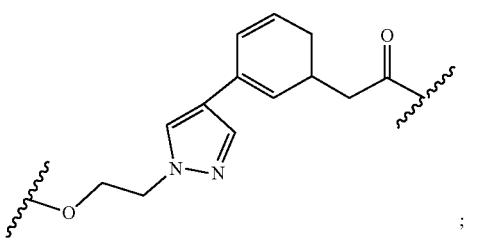;

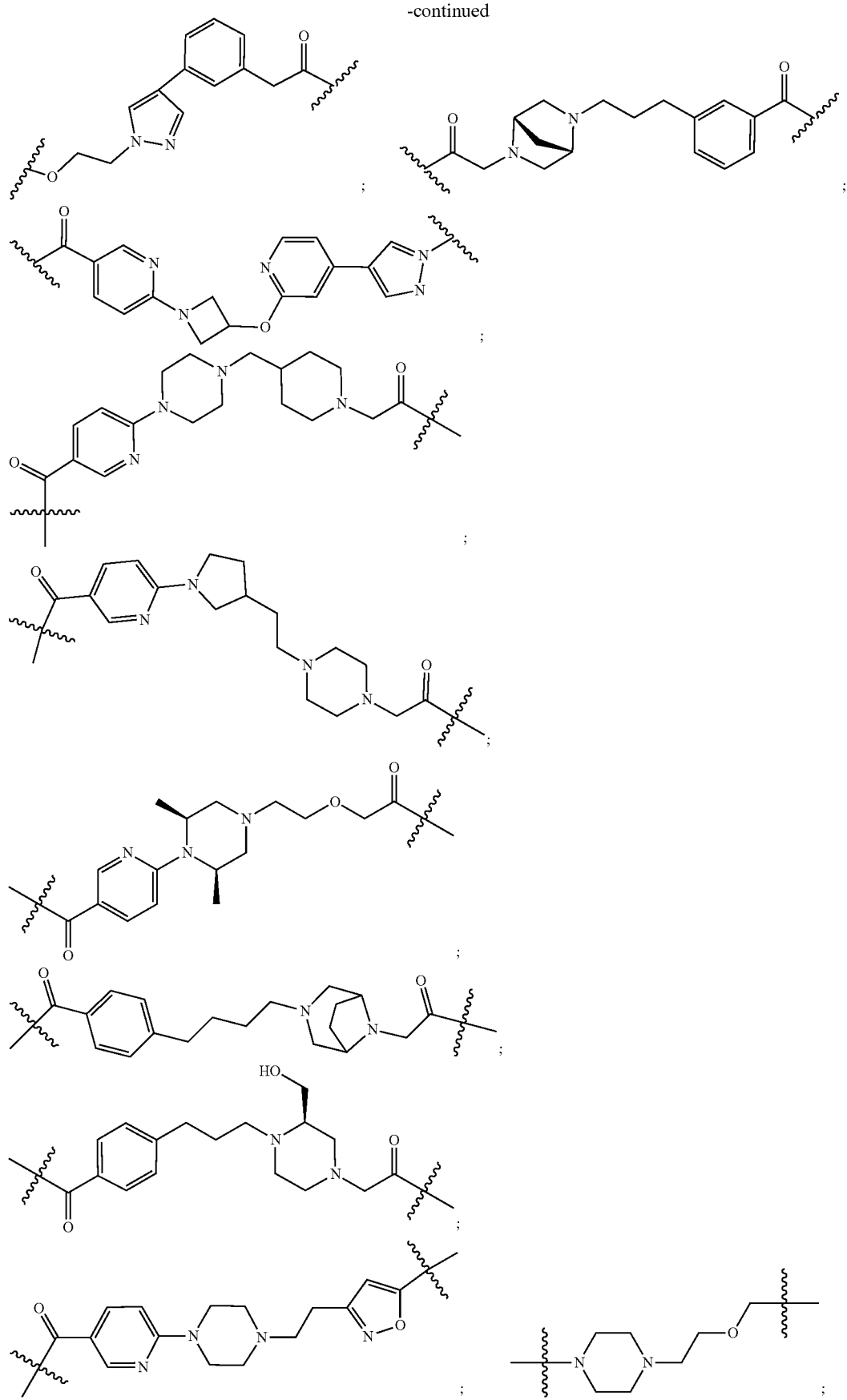

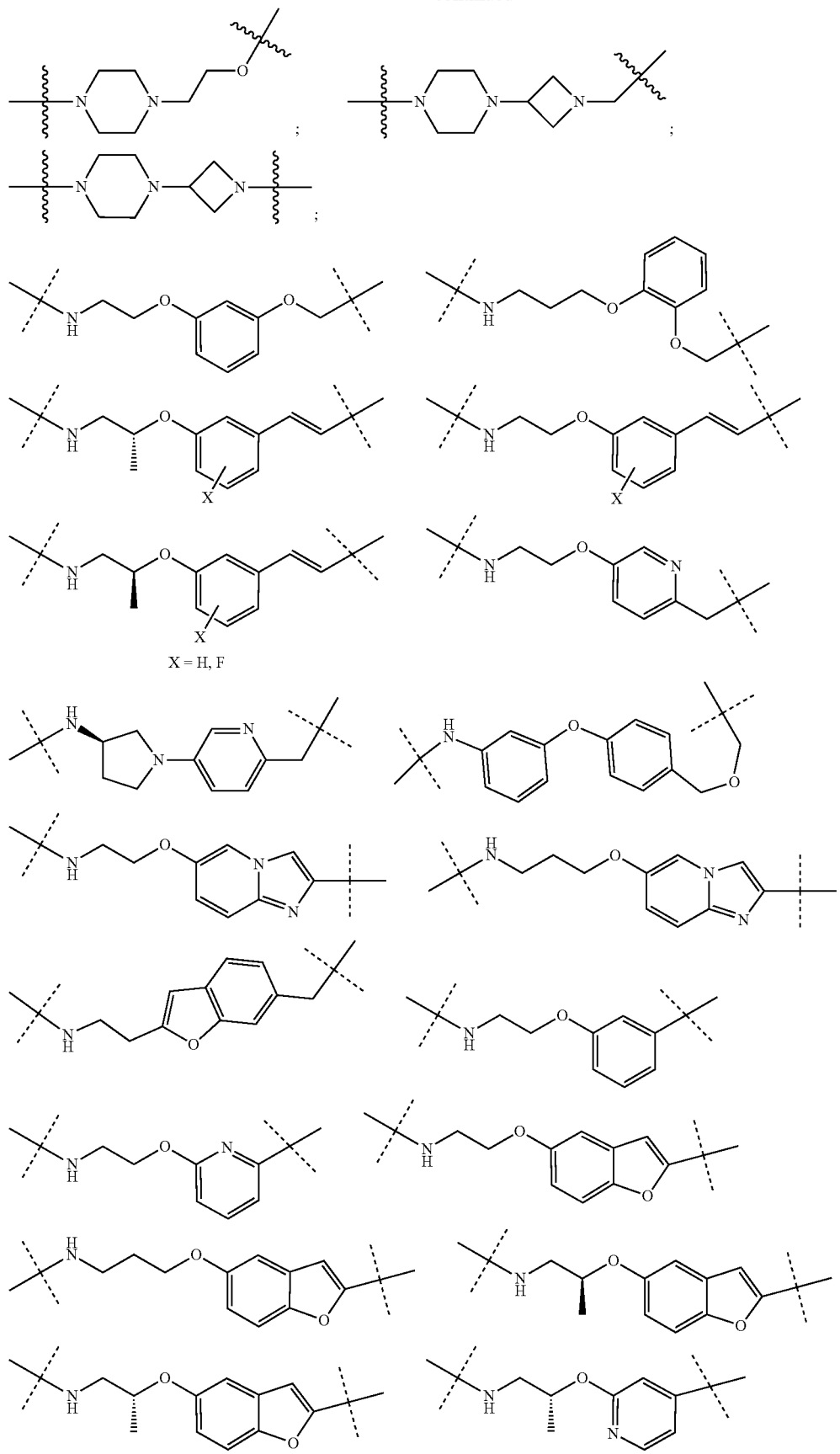

195
196
-continued
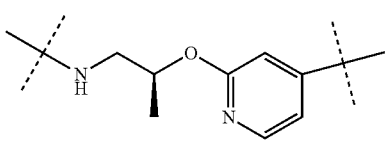
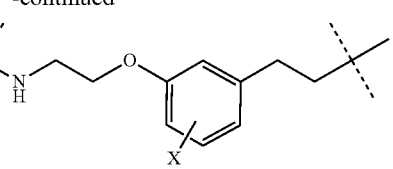
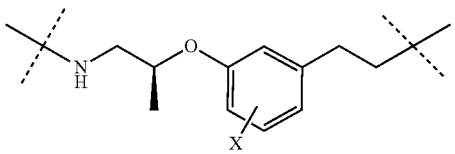
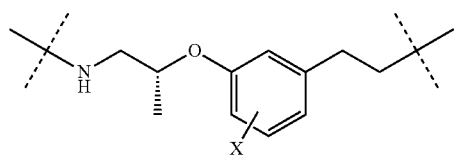
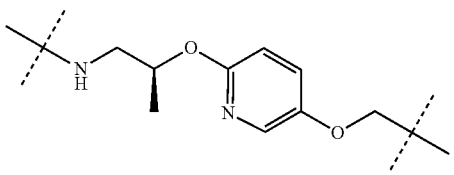
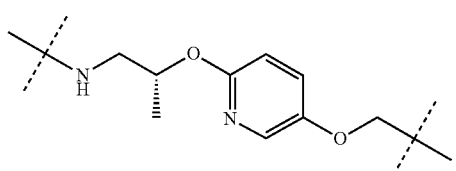
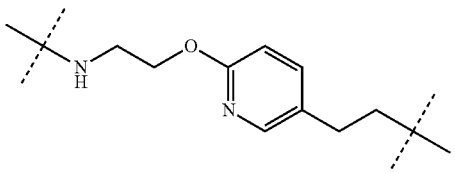
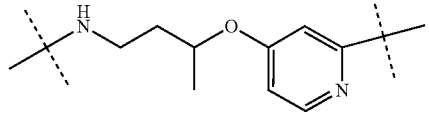
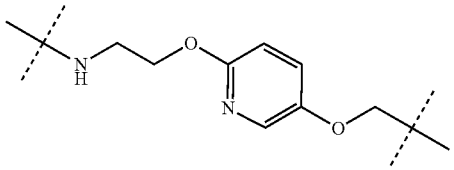
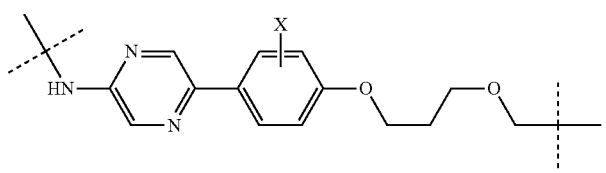
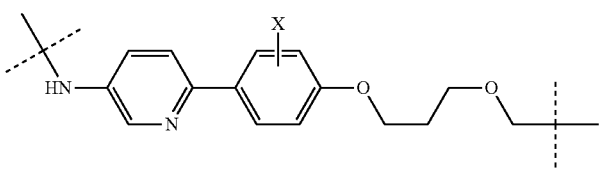
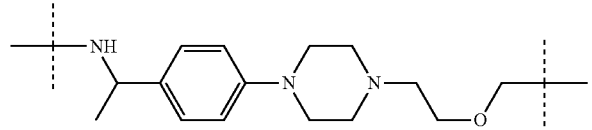
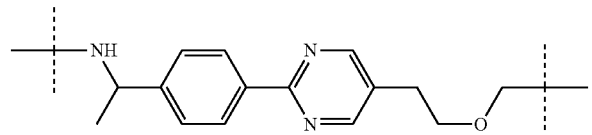
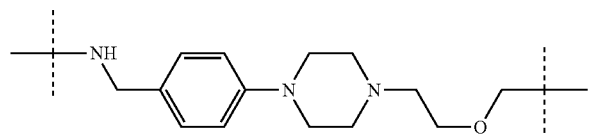
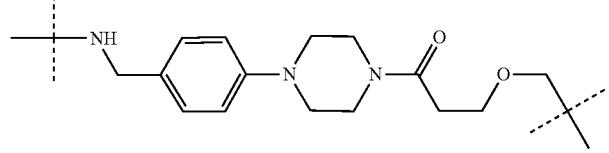
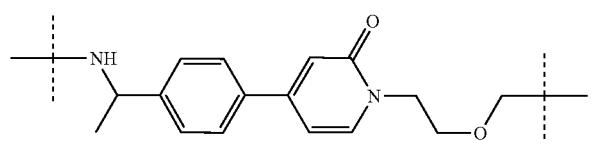
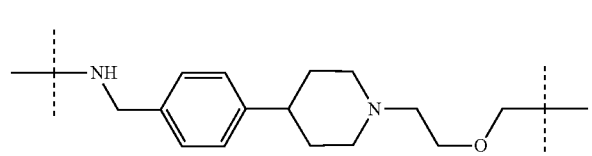
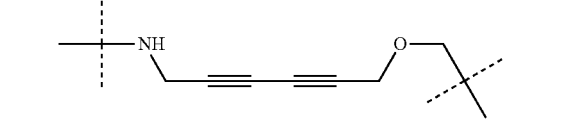
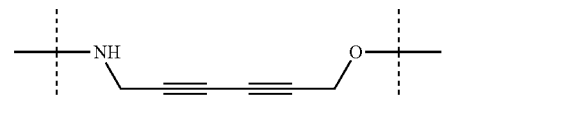

197 198
-continued
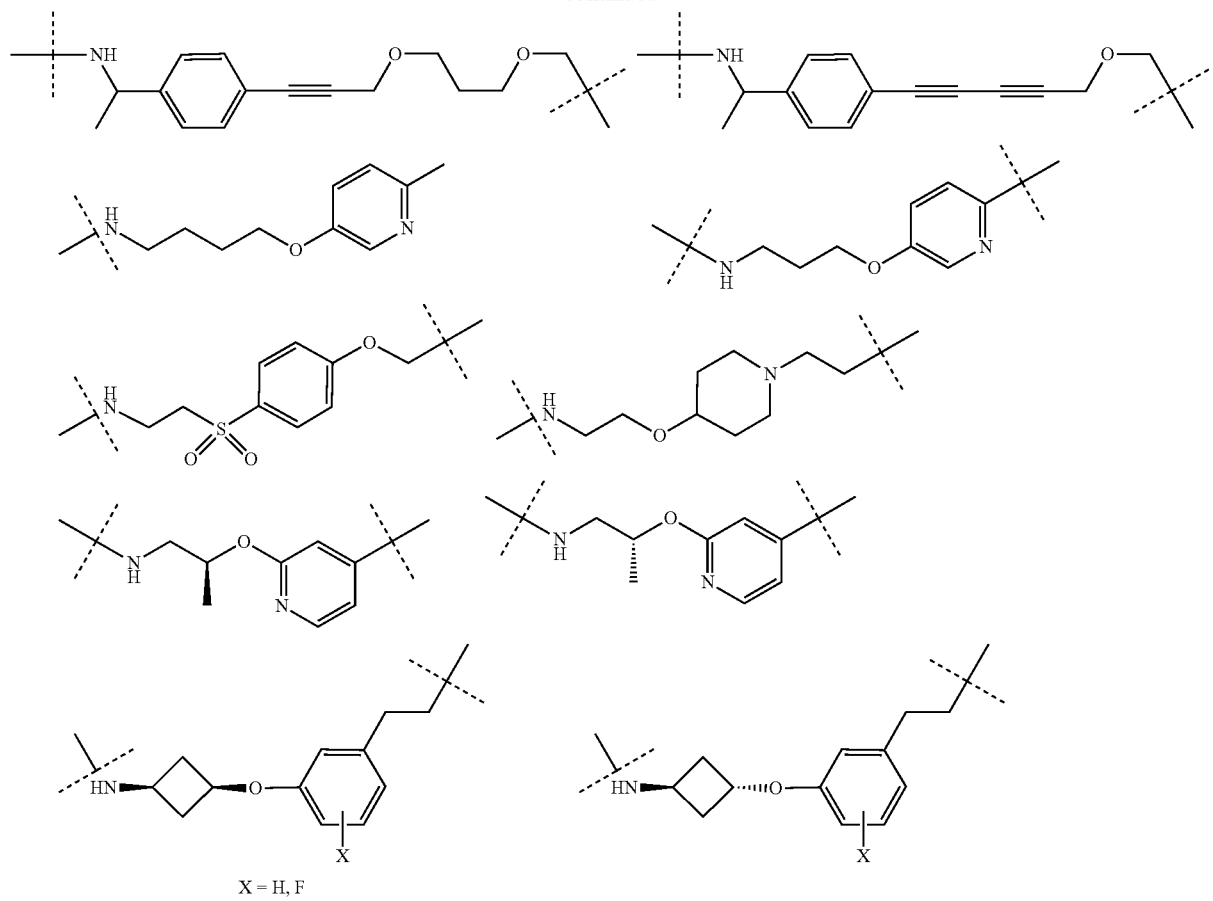
X = H, F
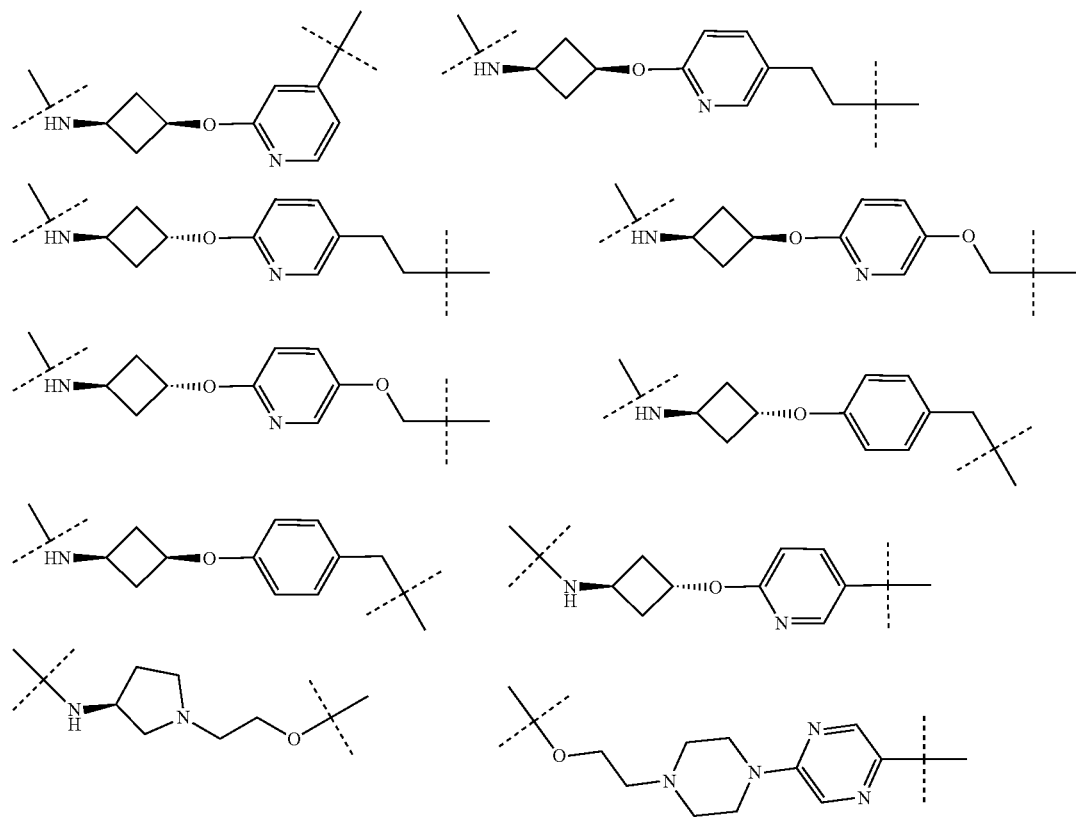

199
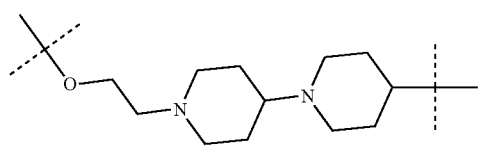
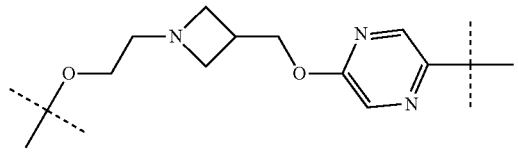
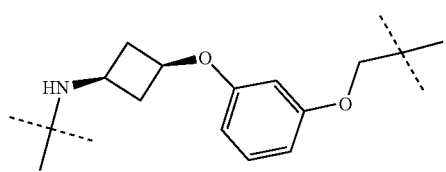
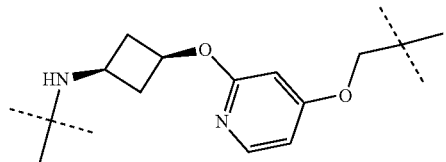
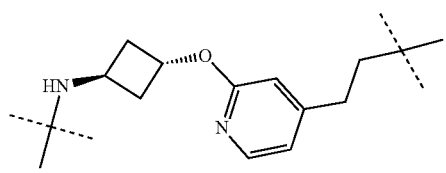
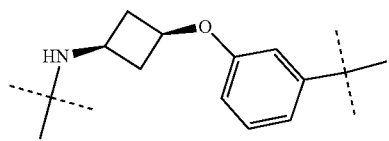
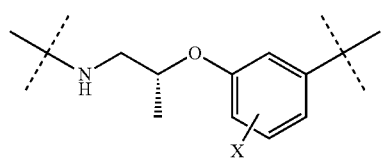
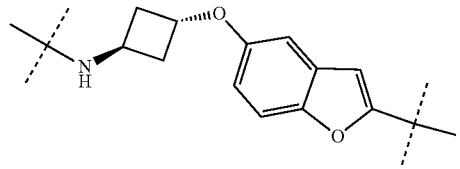
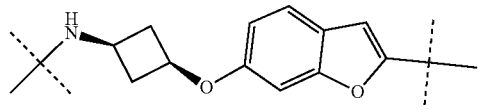
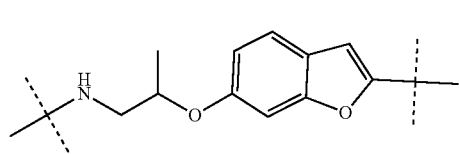
200
-continued
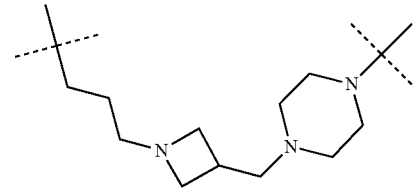
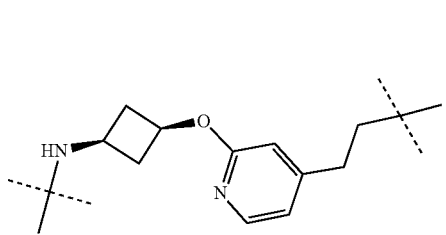
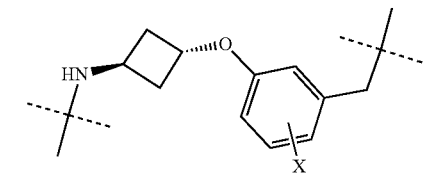
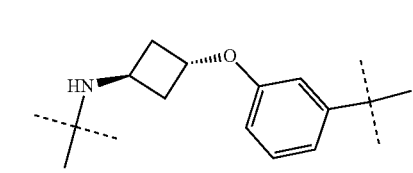
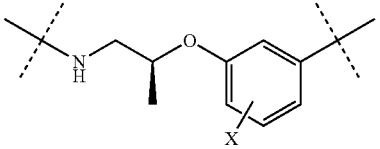
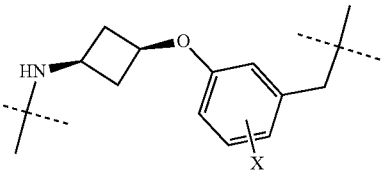
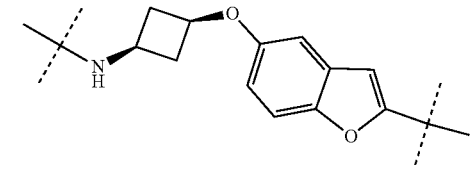
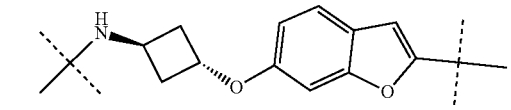
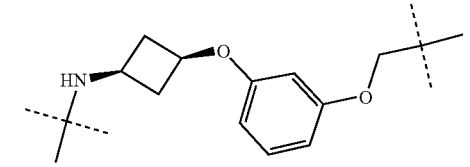

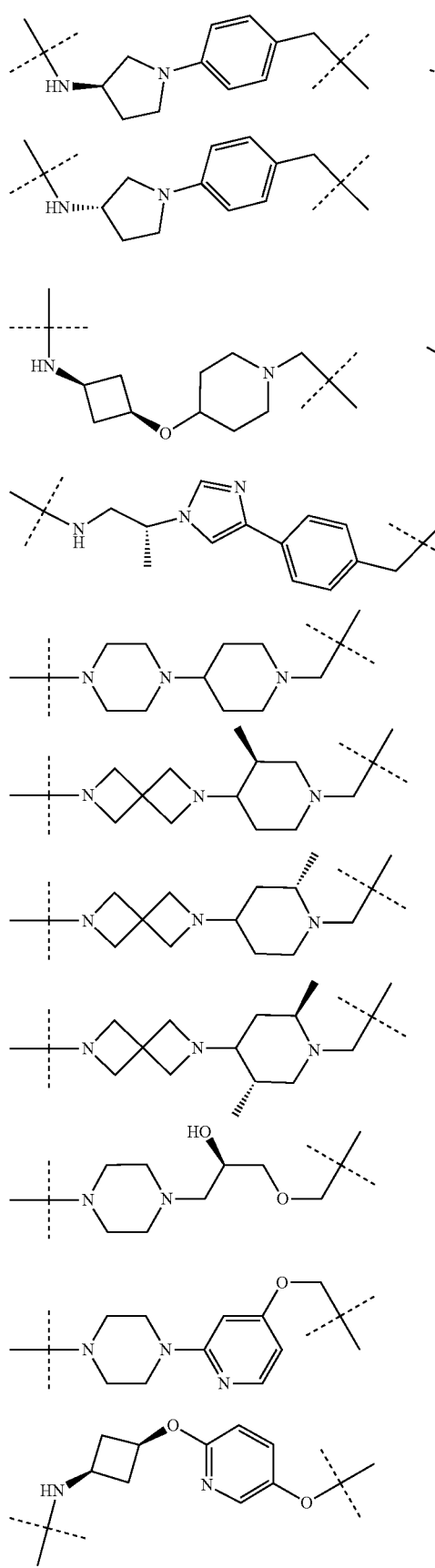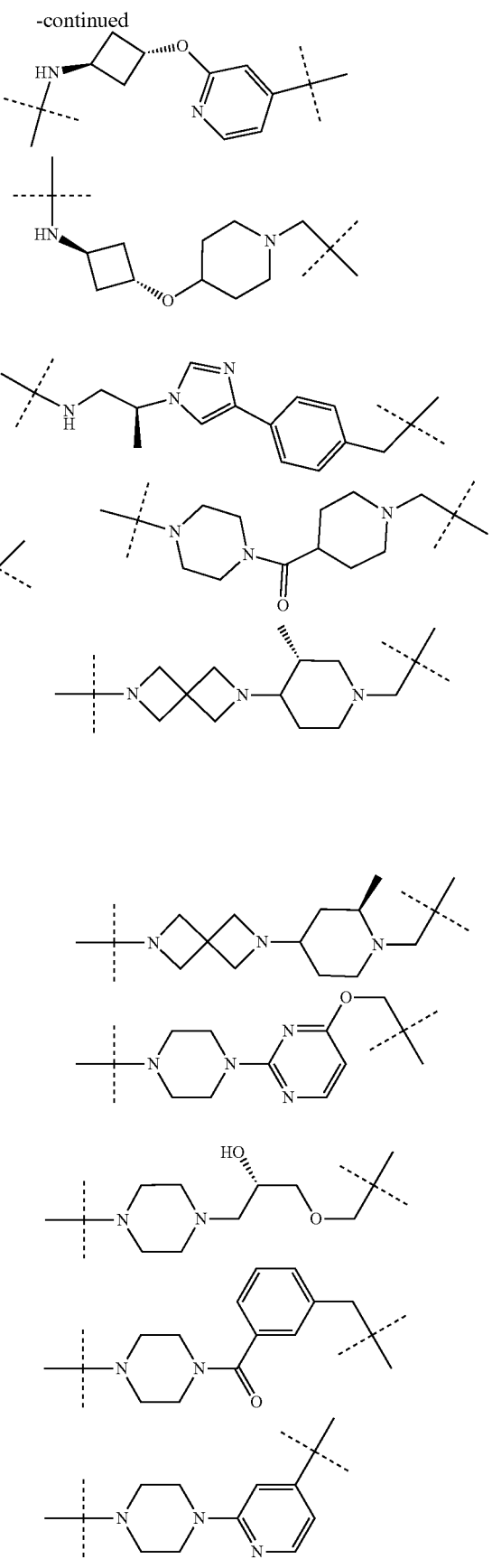

-continued
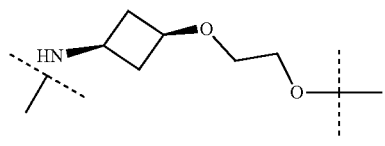
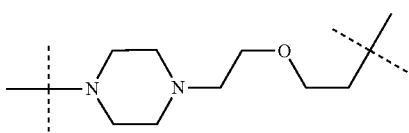
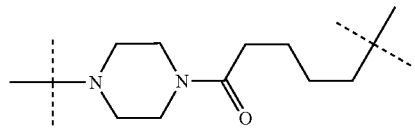
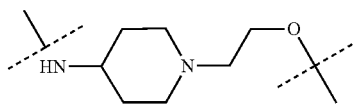
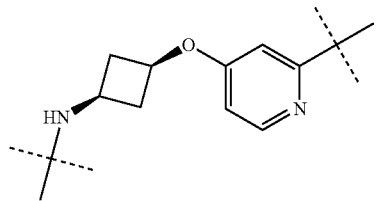
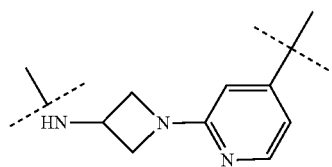
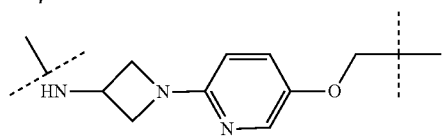
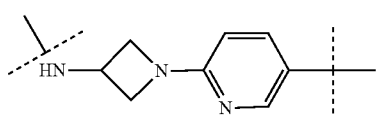
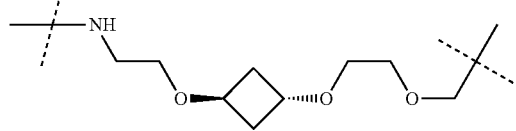
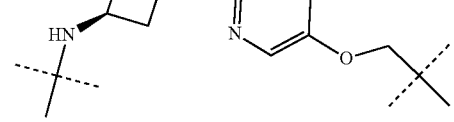
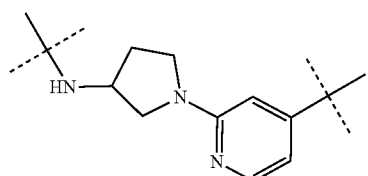
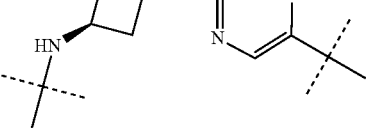
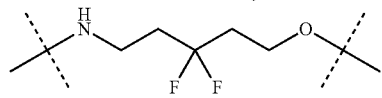
wherein each n and m of the linker can independently be 0, 1, 2, 3, 4, 5, 6, 7, 8, 9, 10, 11, 12, 13, 14, 15, 16, 17, 18, 19, or 20.
In any aspect or embodiment described herein, the linker (L) is selected from the group consisting of:
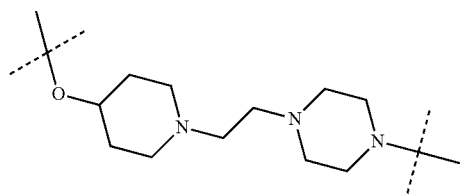
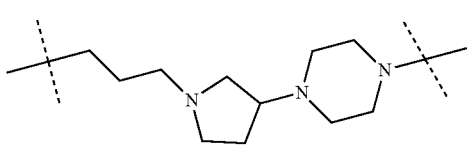
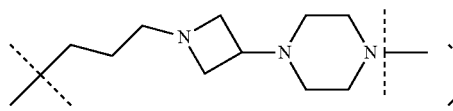
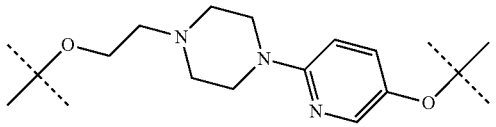

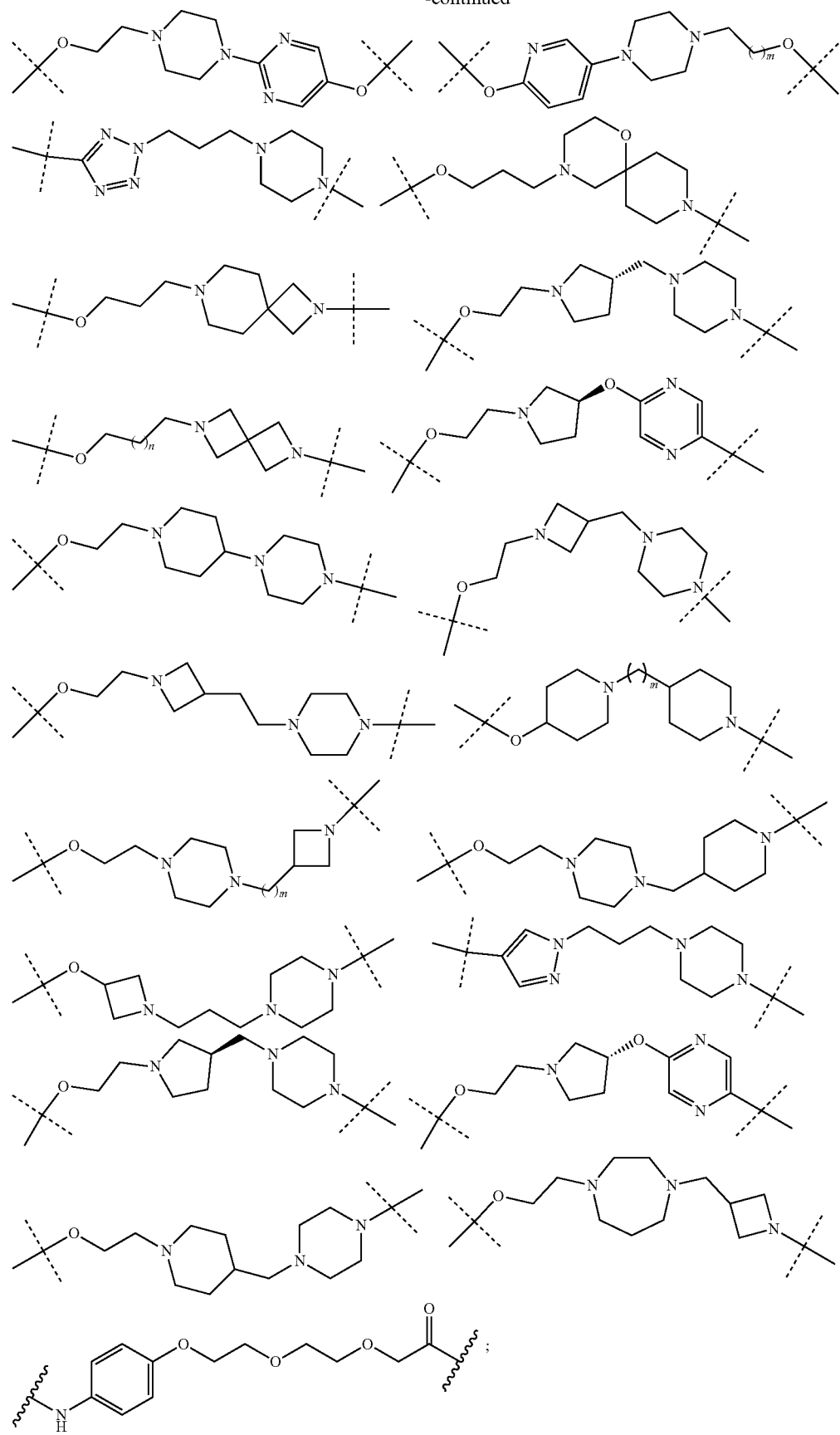

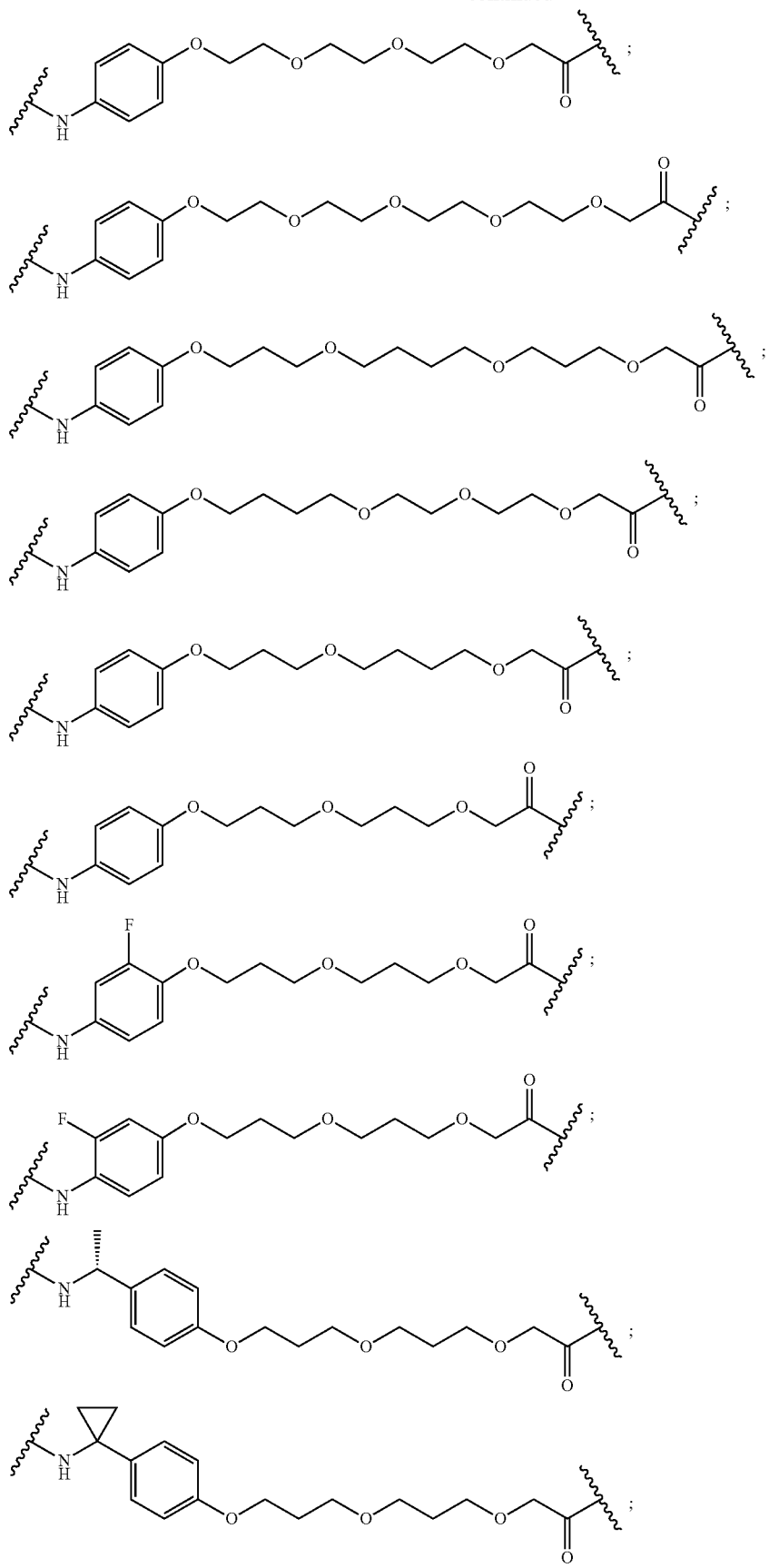

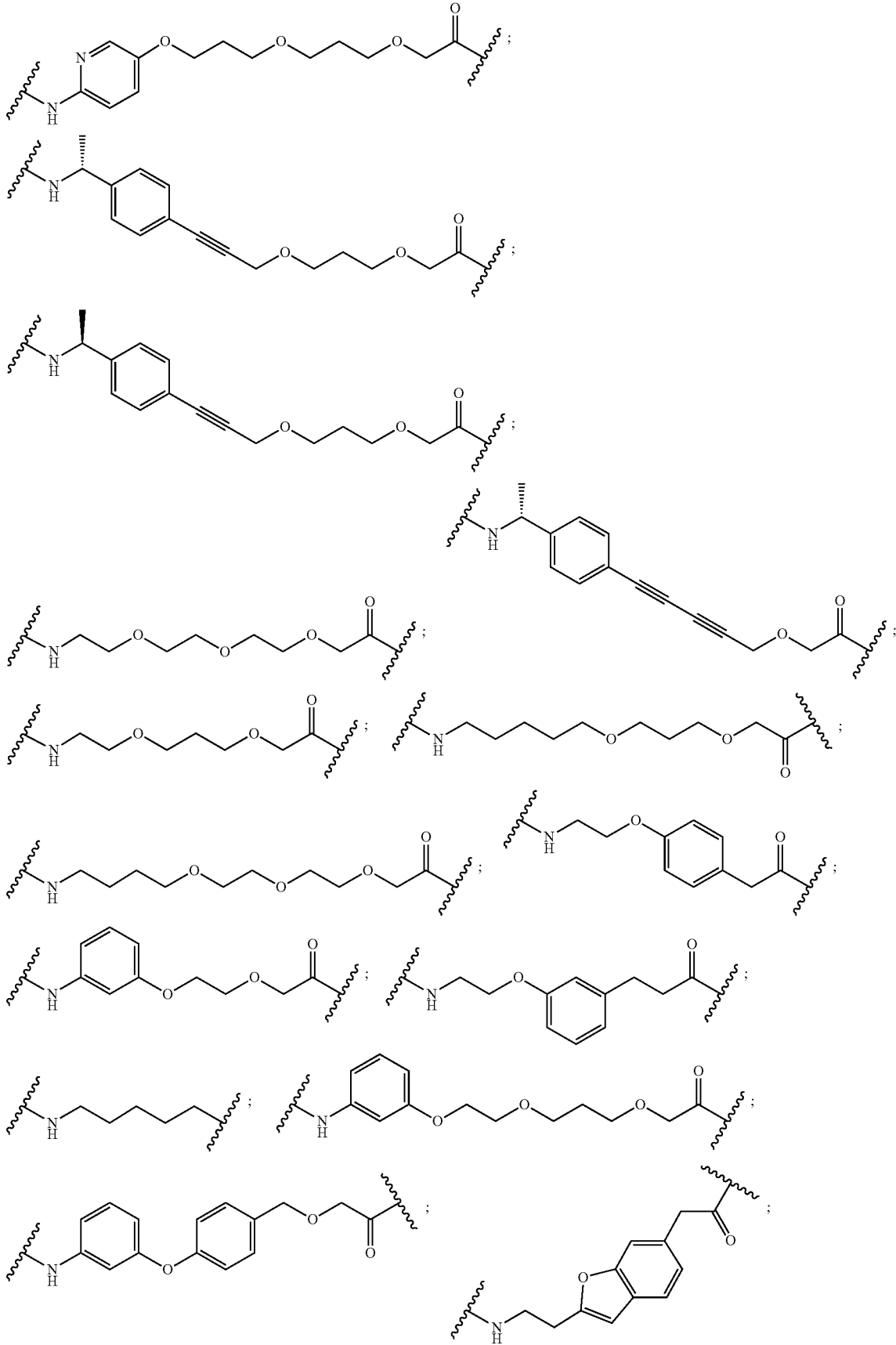

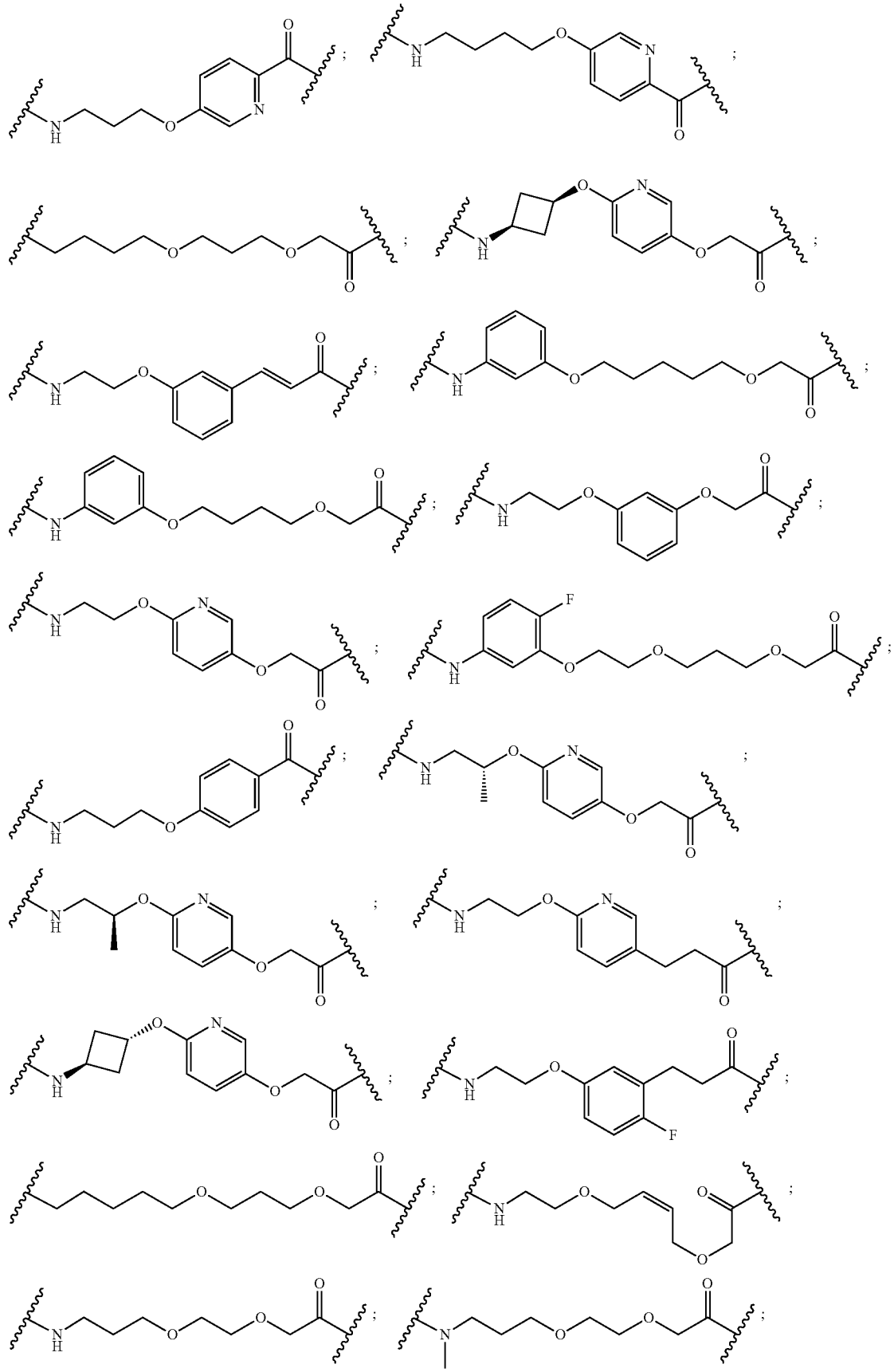

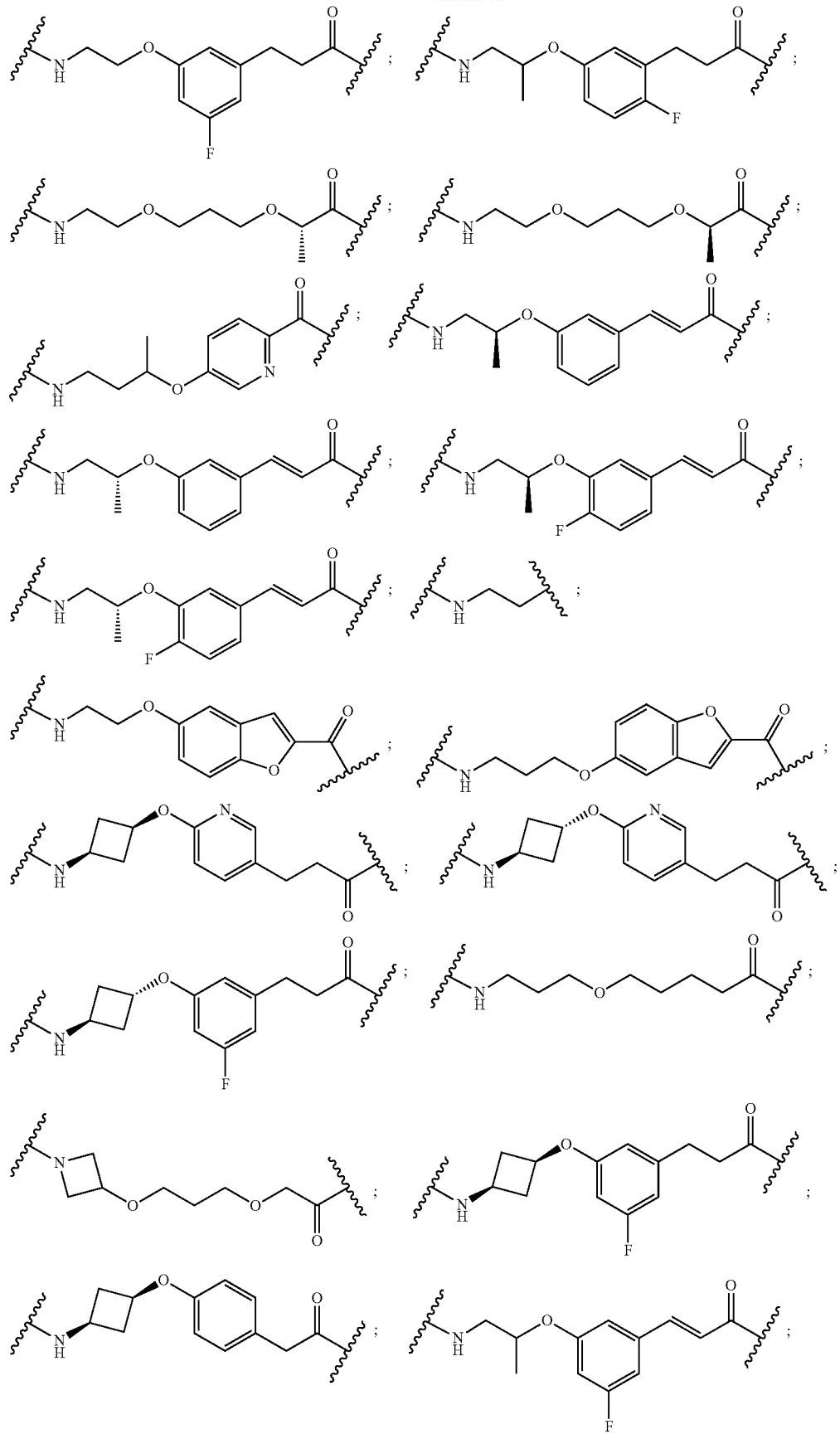

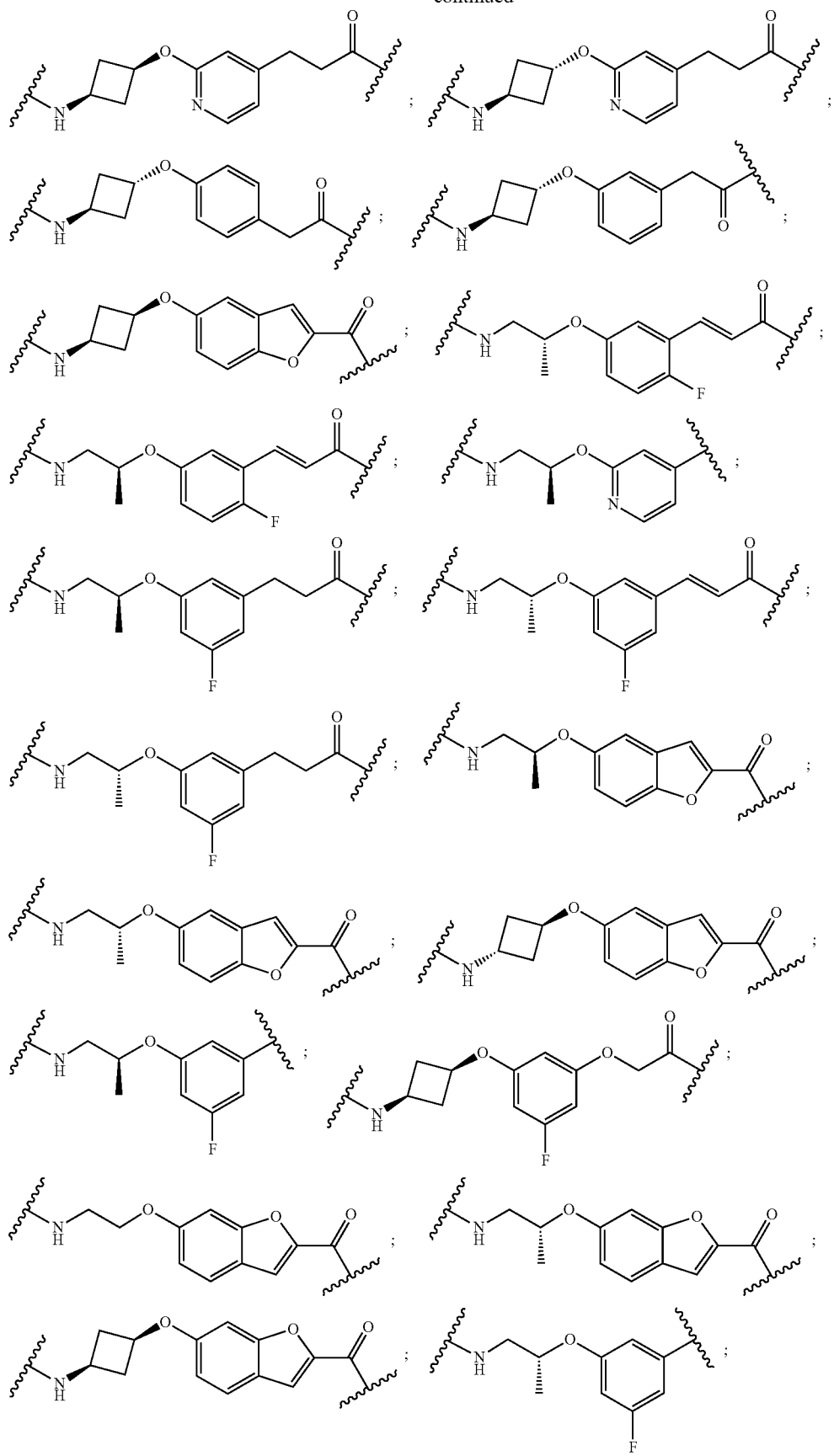

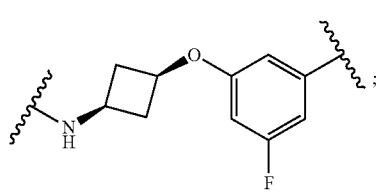
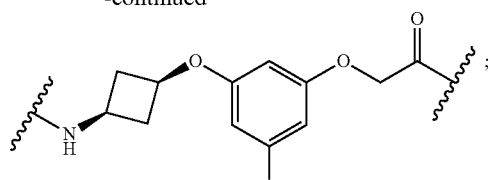
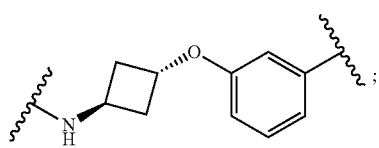
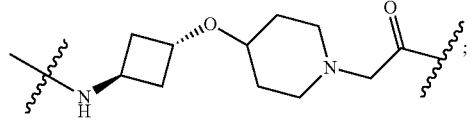
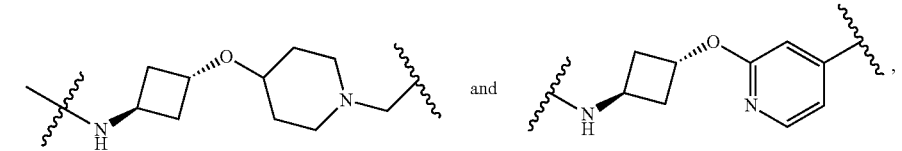
wherein each m and n is independently selected from 0, 1, 2, 3, 4, 5, 6, 7, 8, 9, 10, 11, 12, 13, 14, 15, 16, 17, 18, 19, or 20.
In any aspect or embodiment described herein, the linker (L) is selected from the group consisting of:
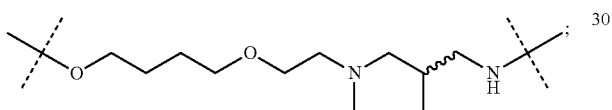
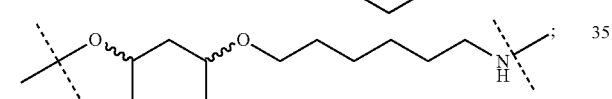
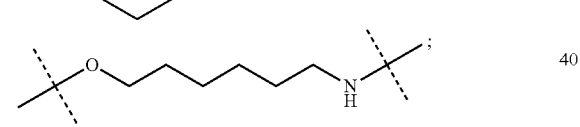
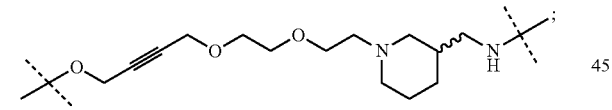
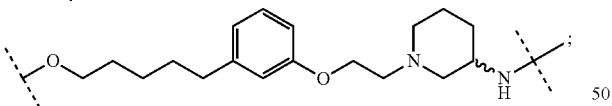
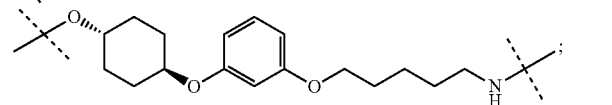
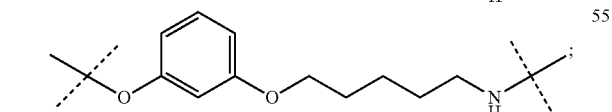
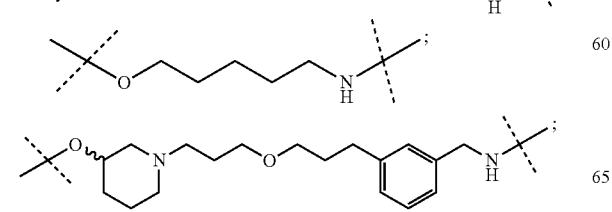
-continued
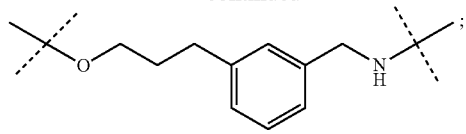
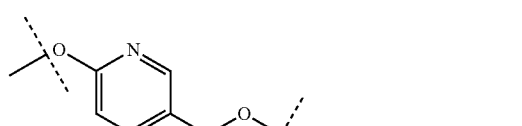
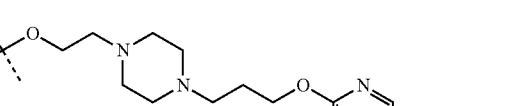
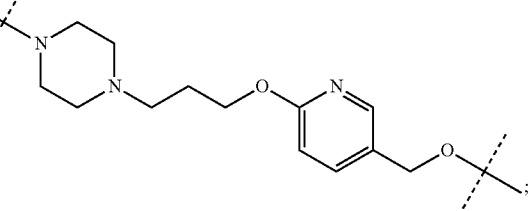

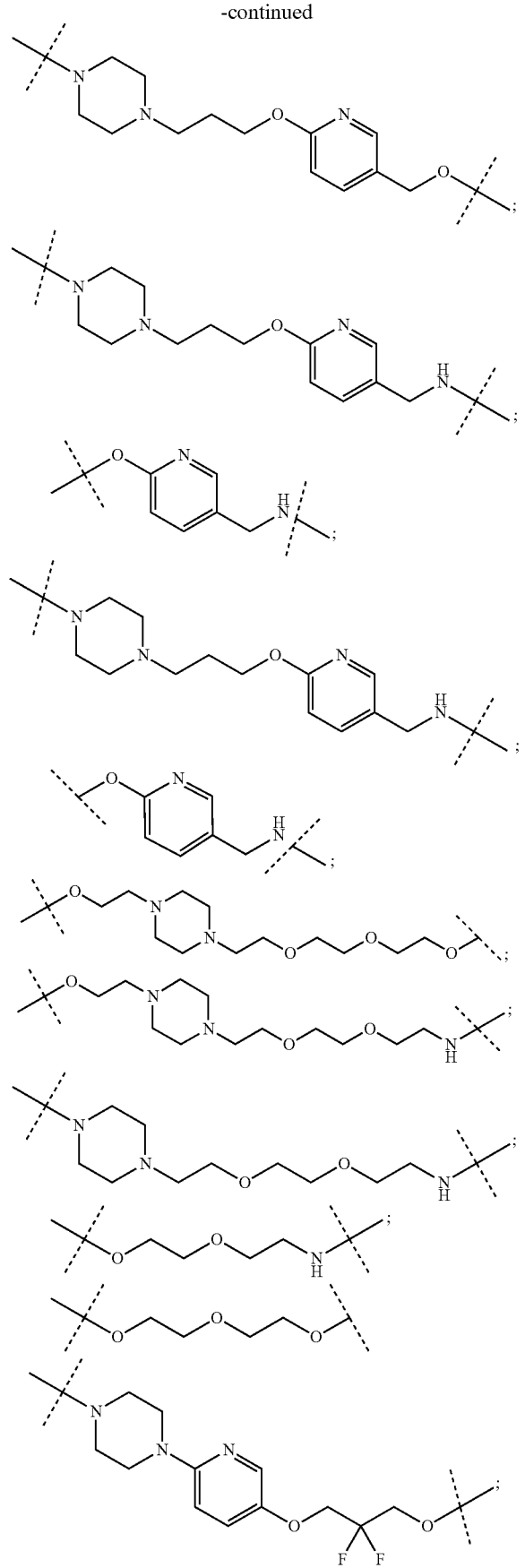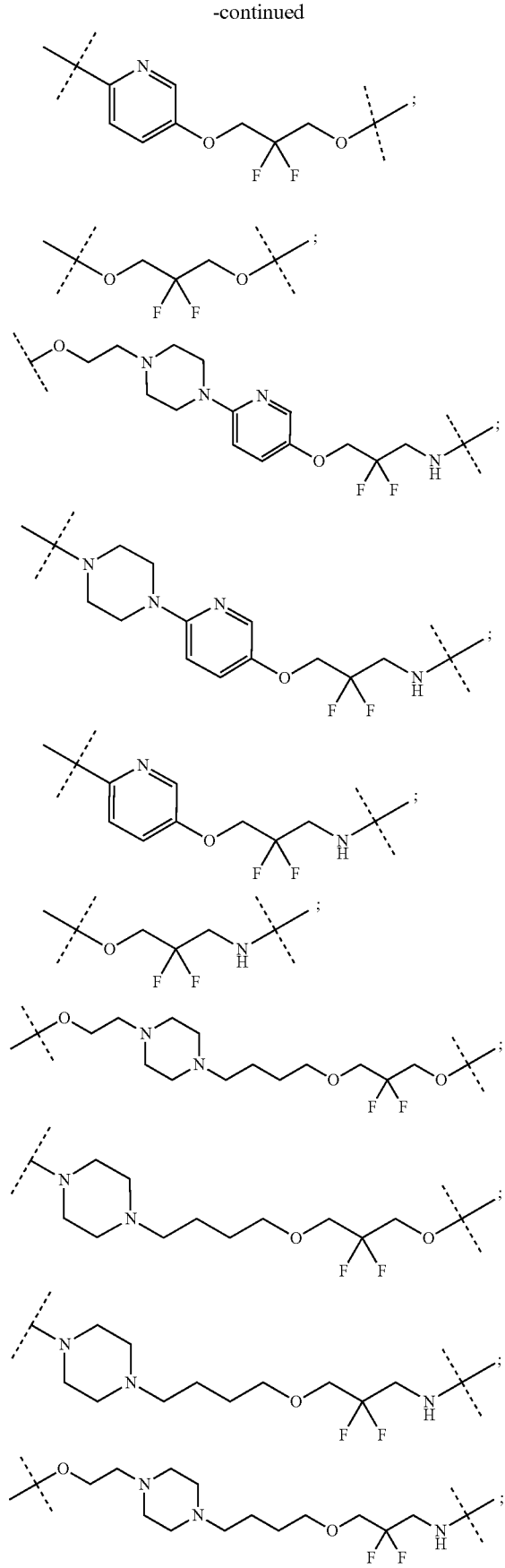

221
-continued
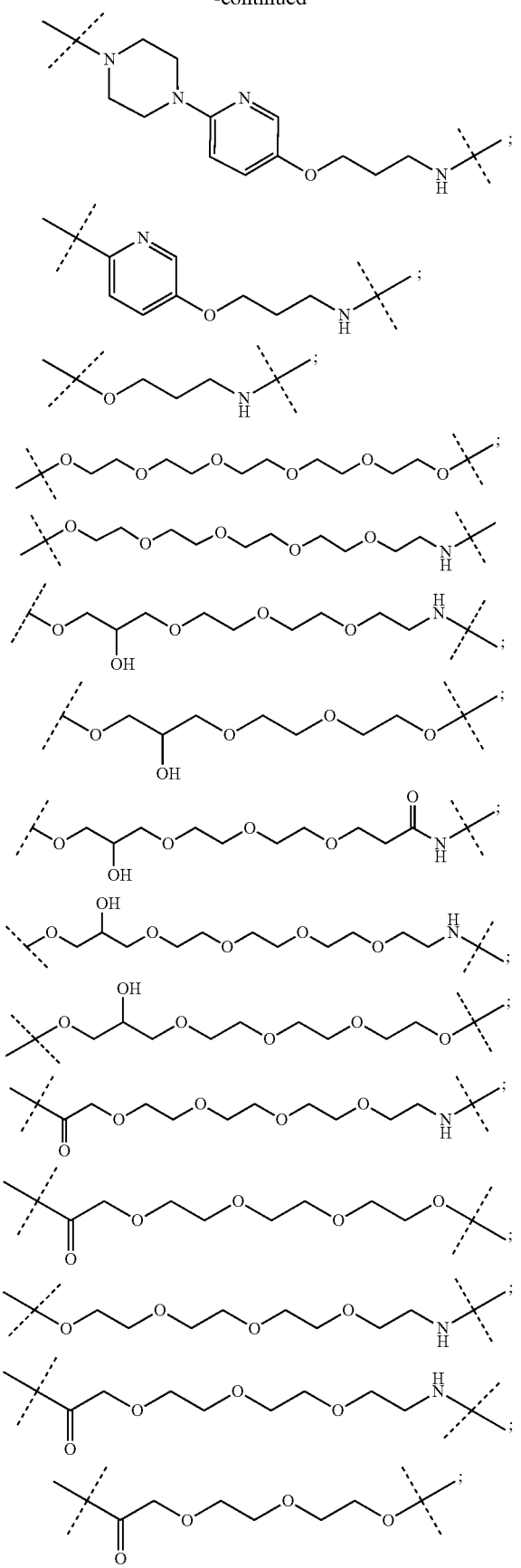
222
-continued
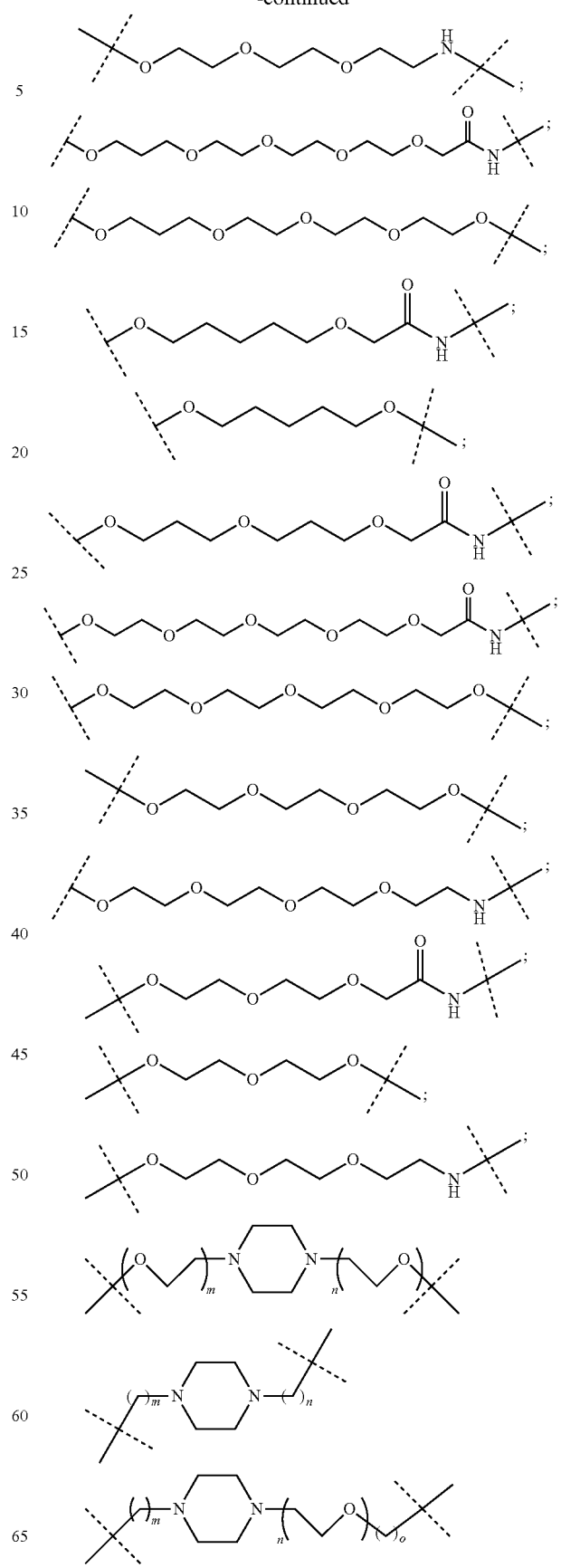

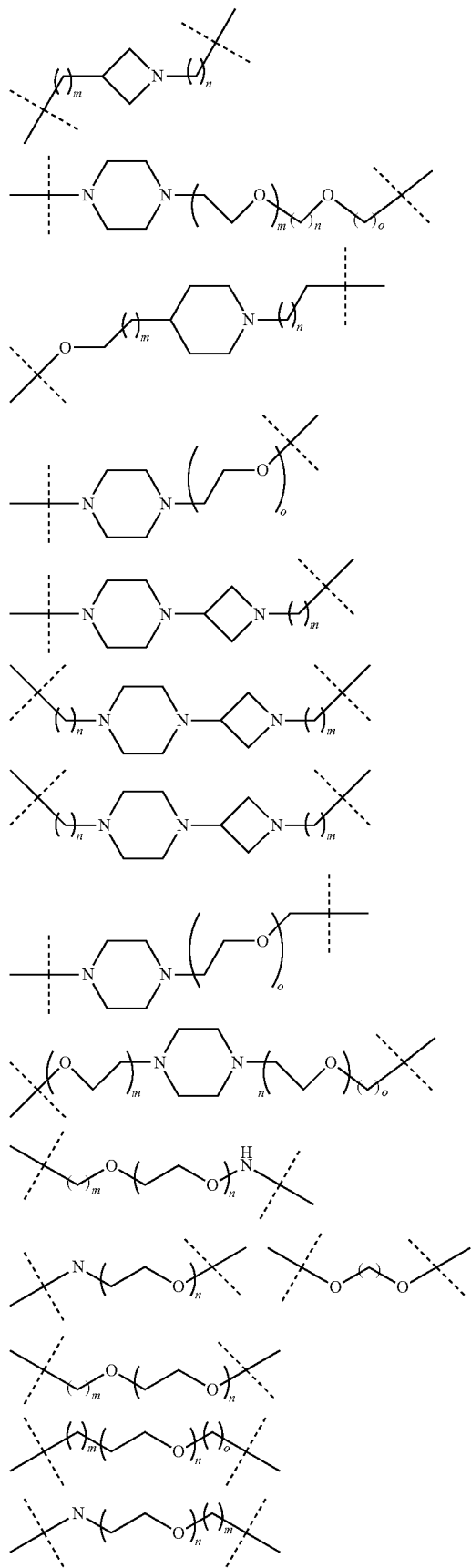
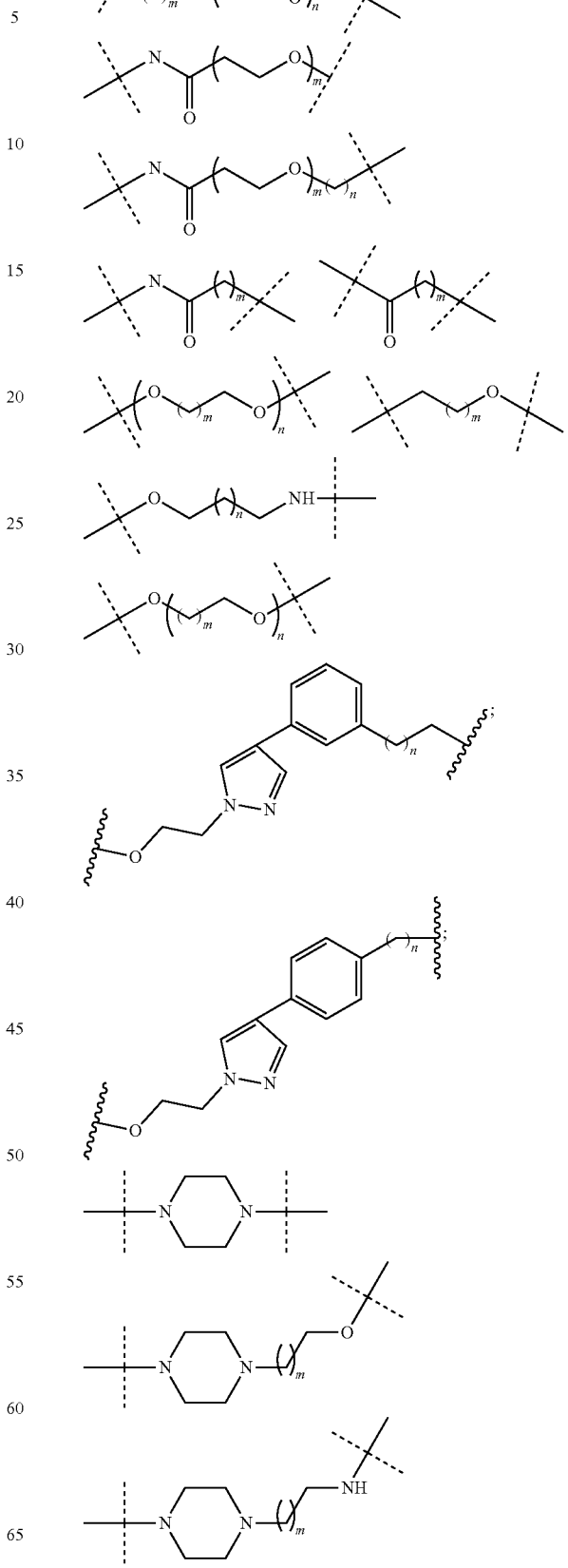

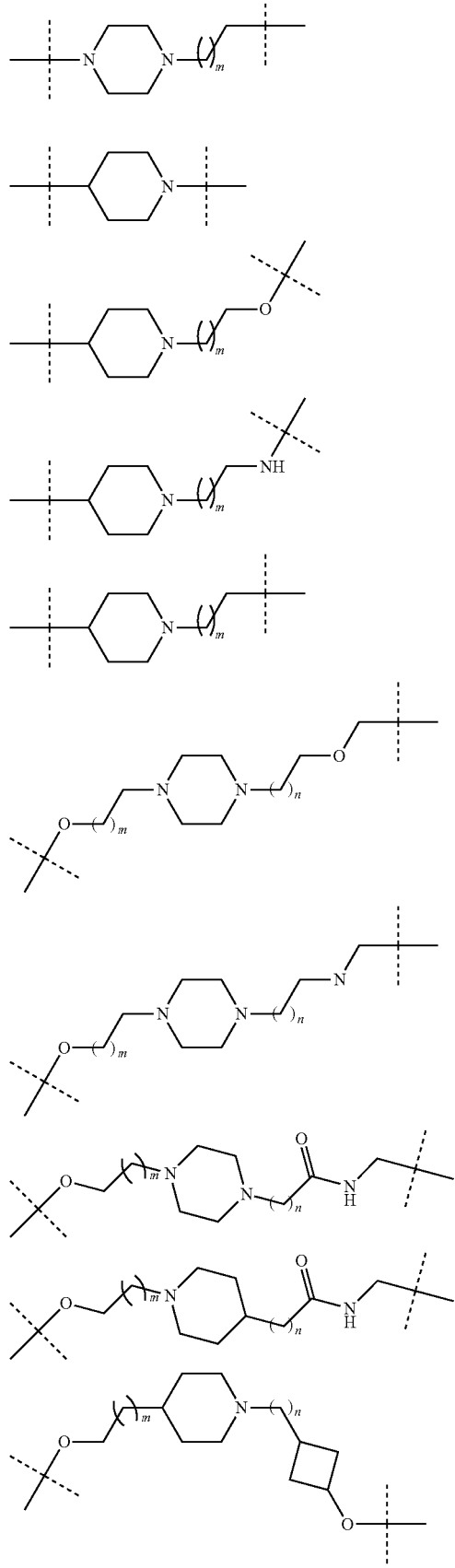
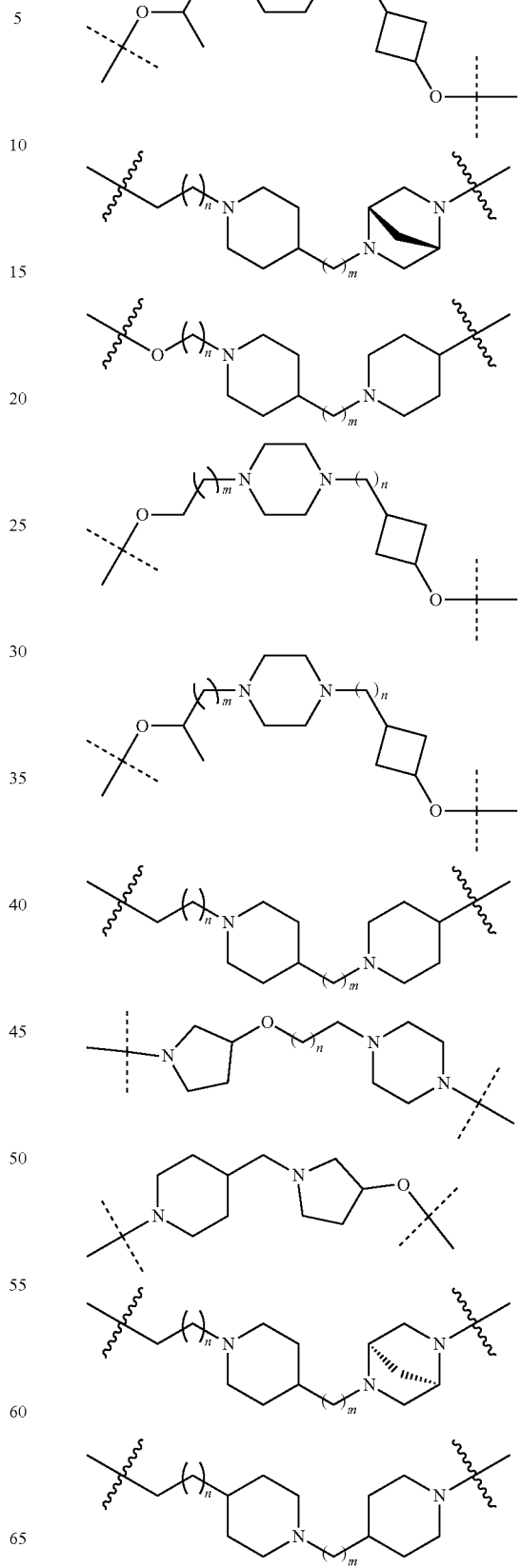

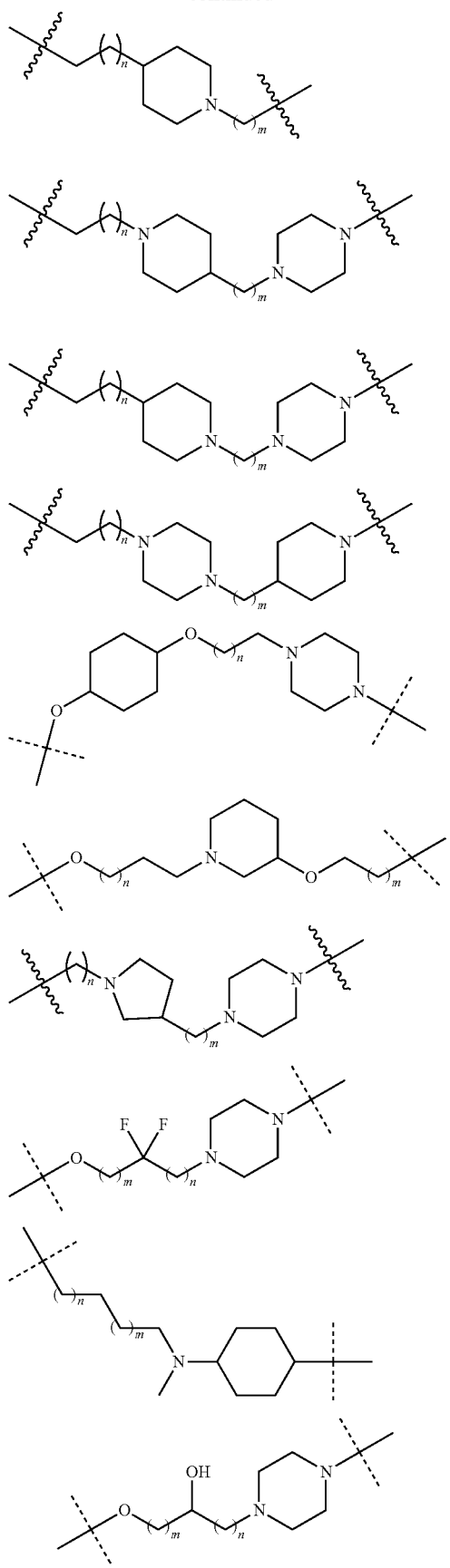
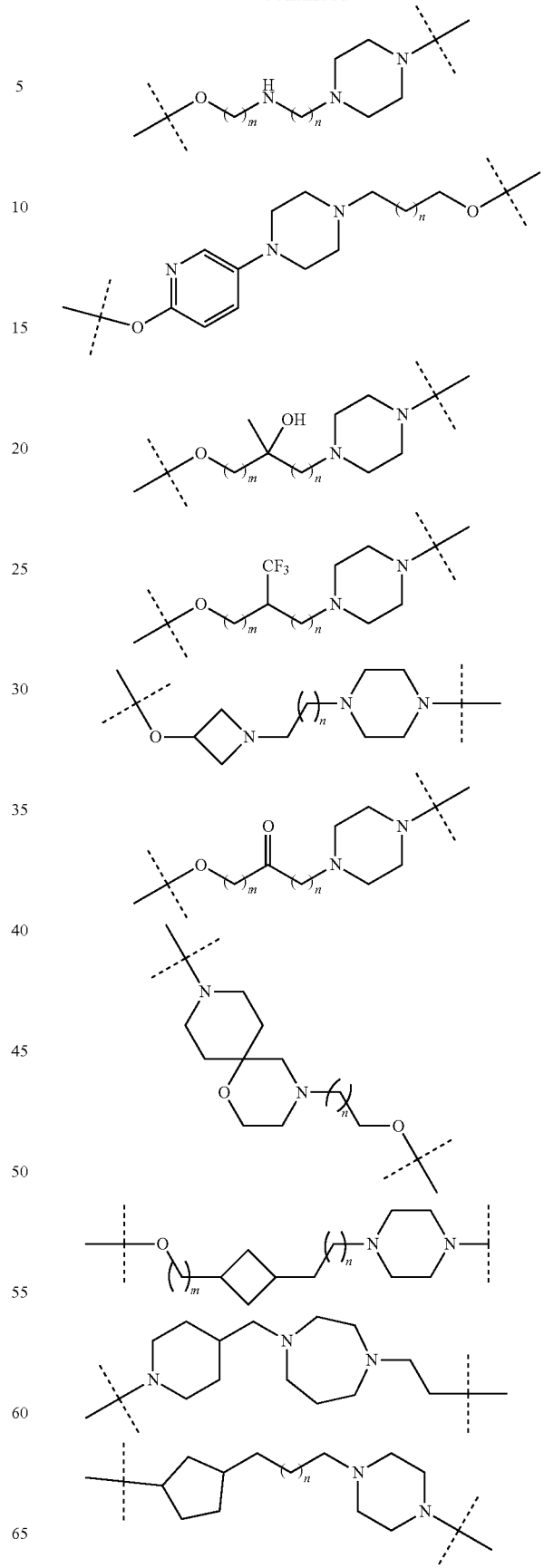

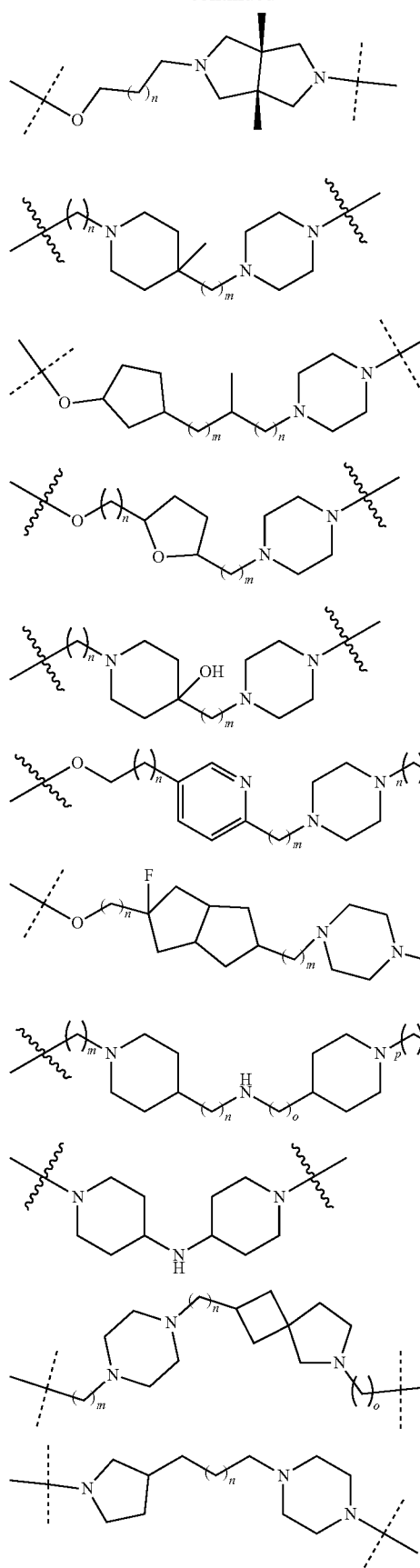
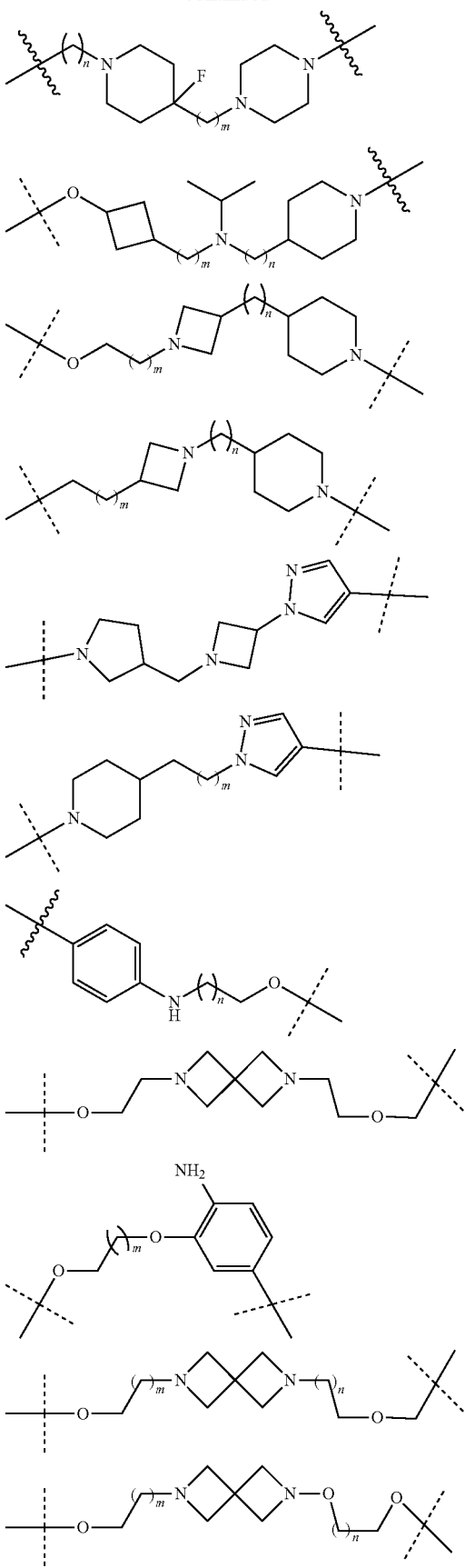

-continued
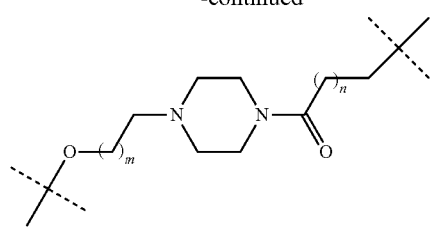
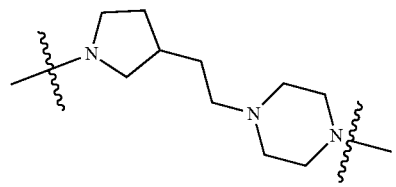
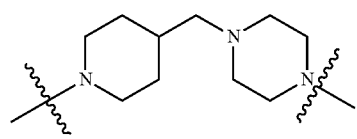
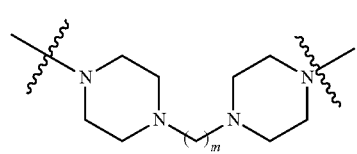
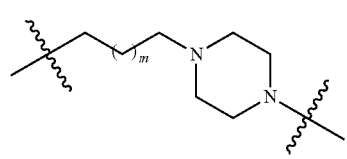
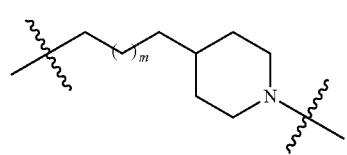
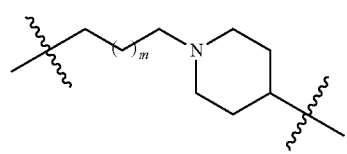
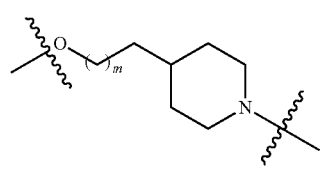
-continued
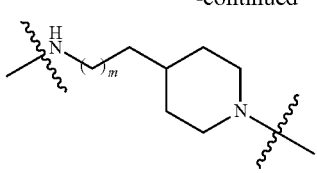
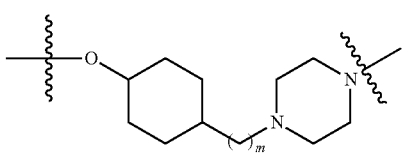
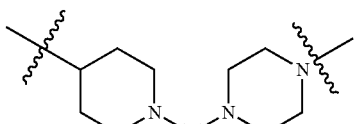
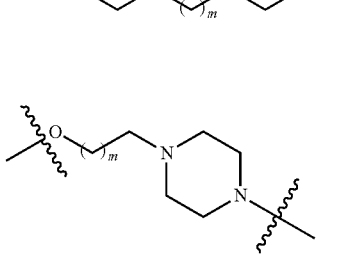
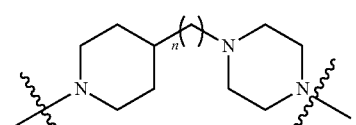
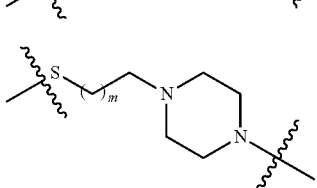
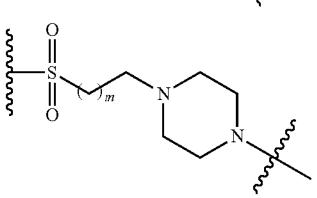
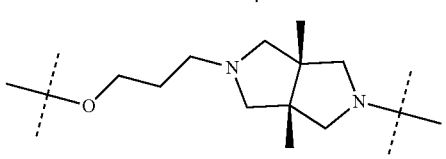
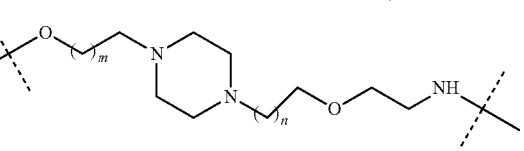

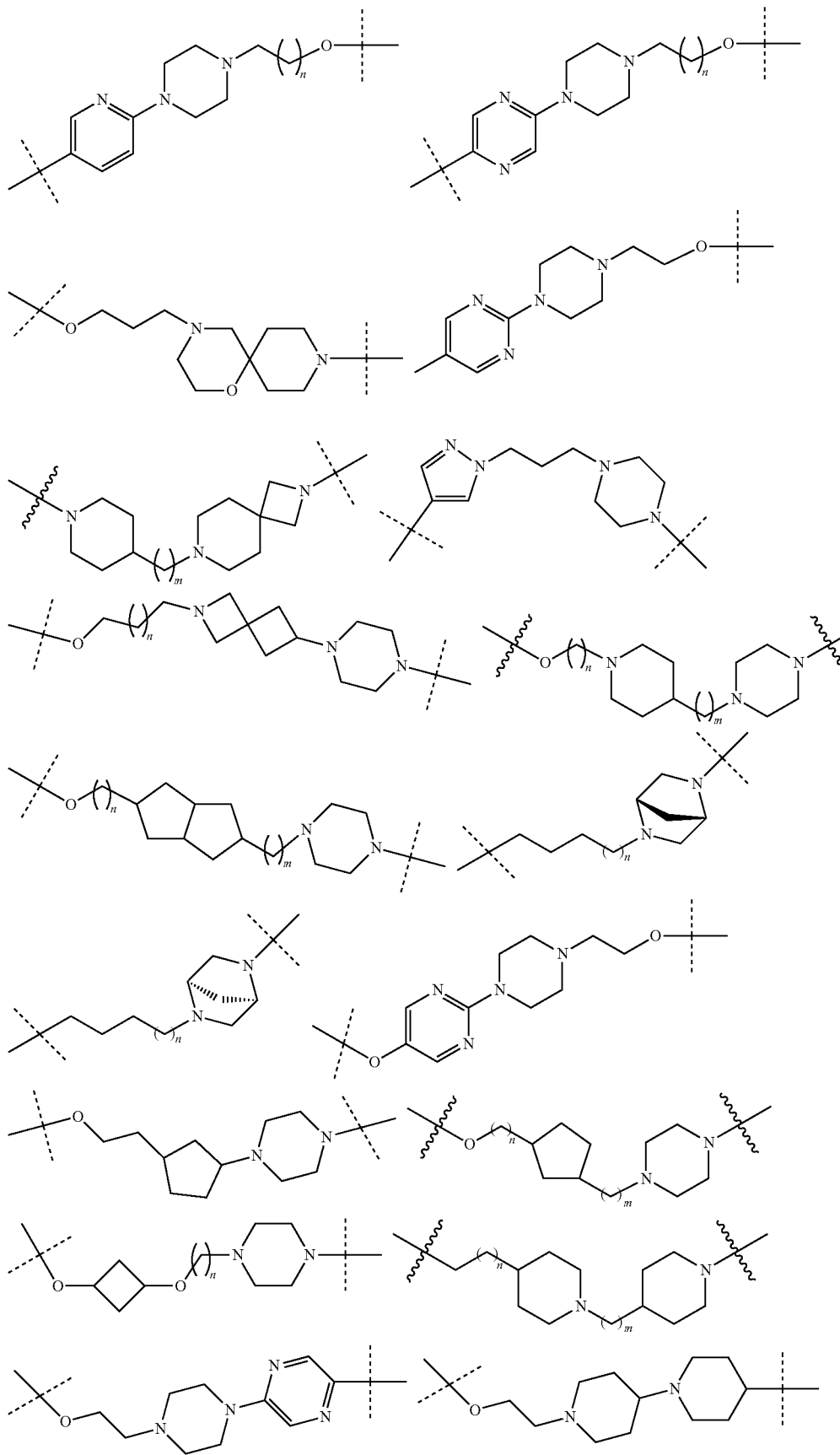

-continued
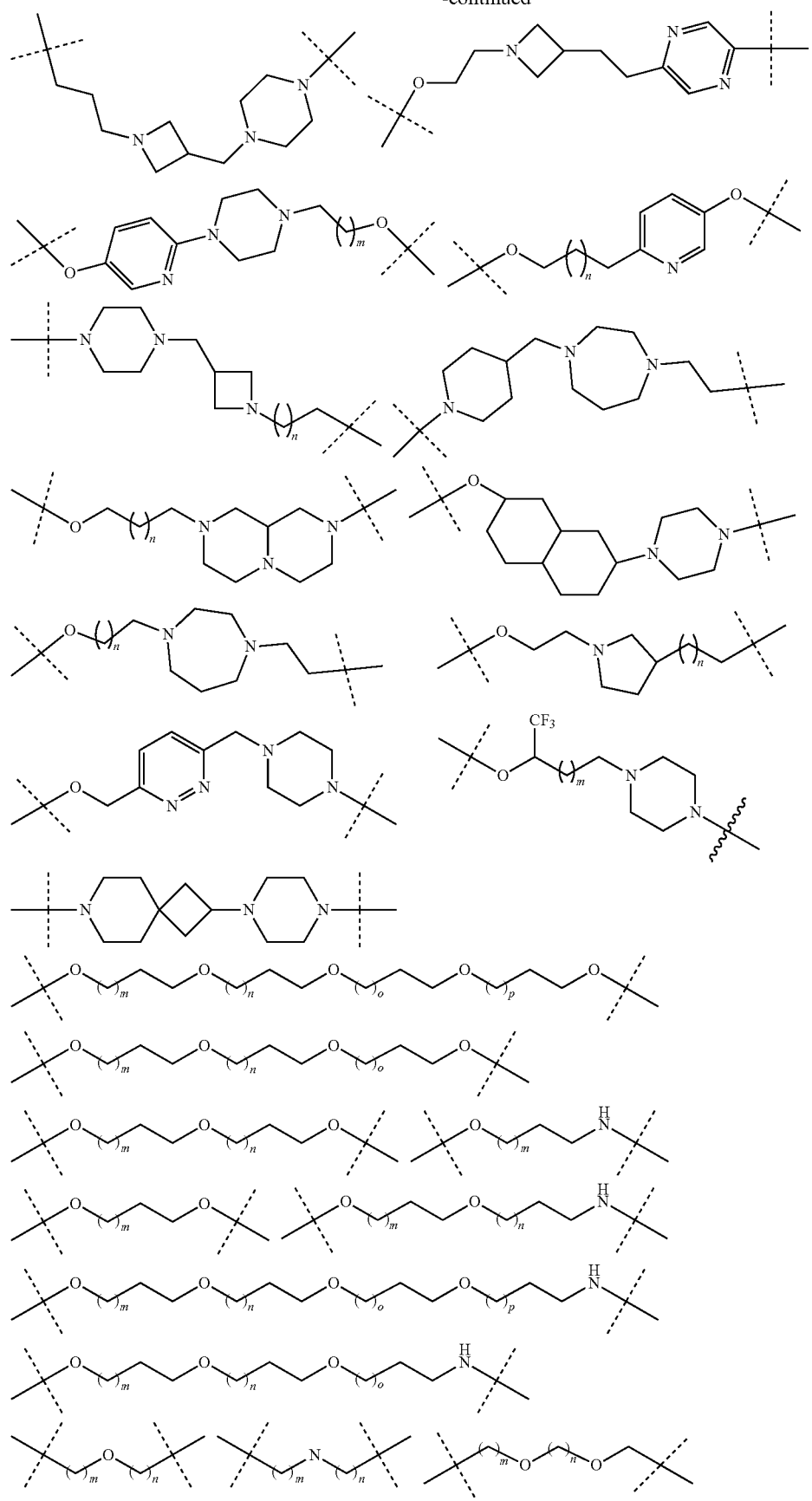

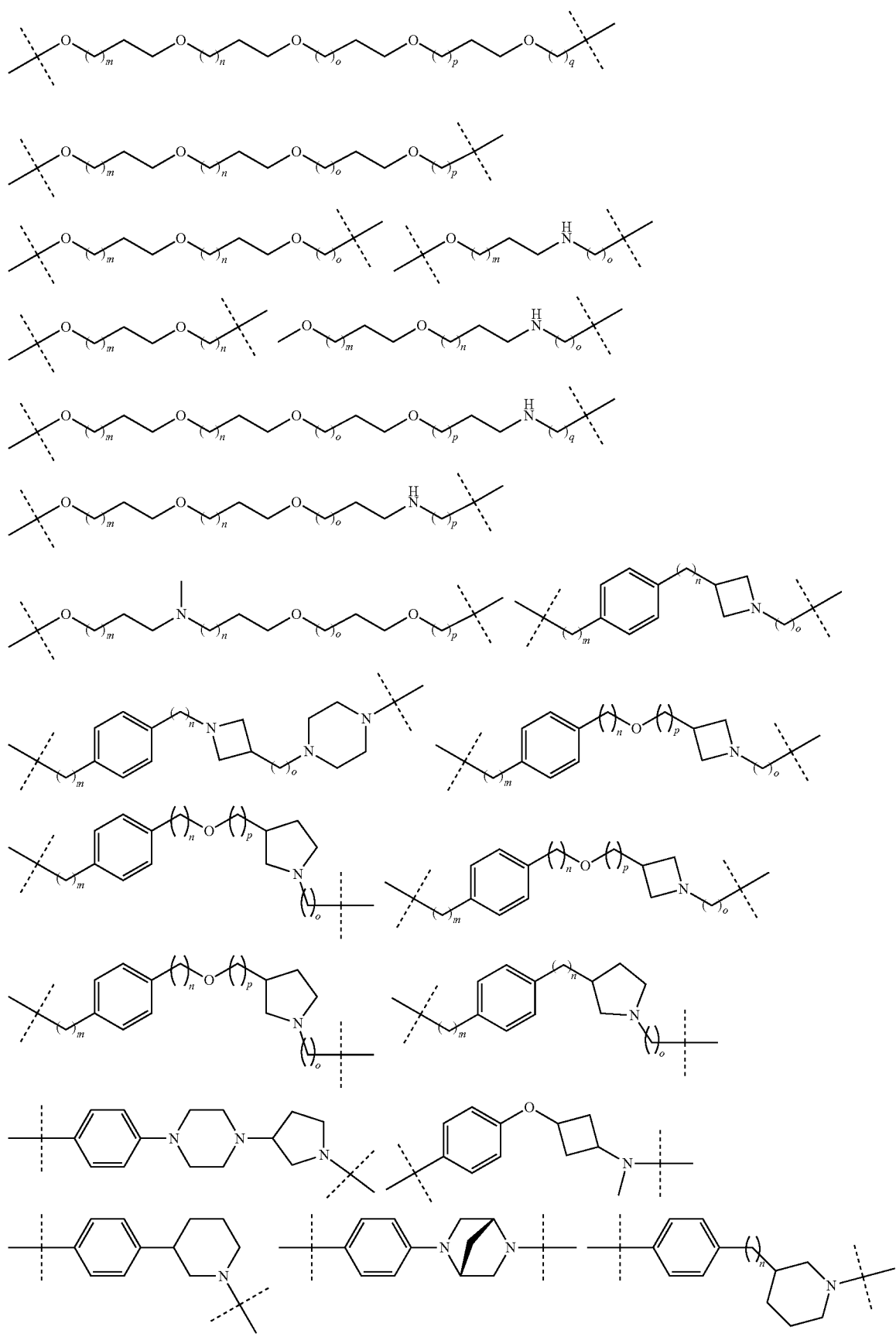

-continued
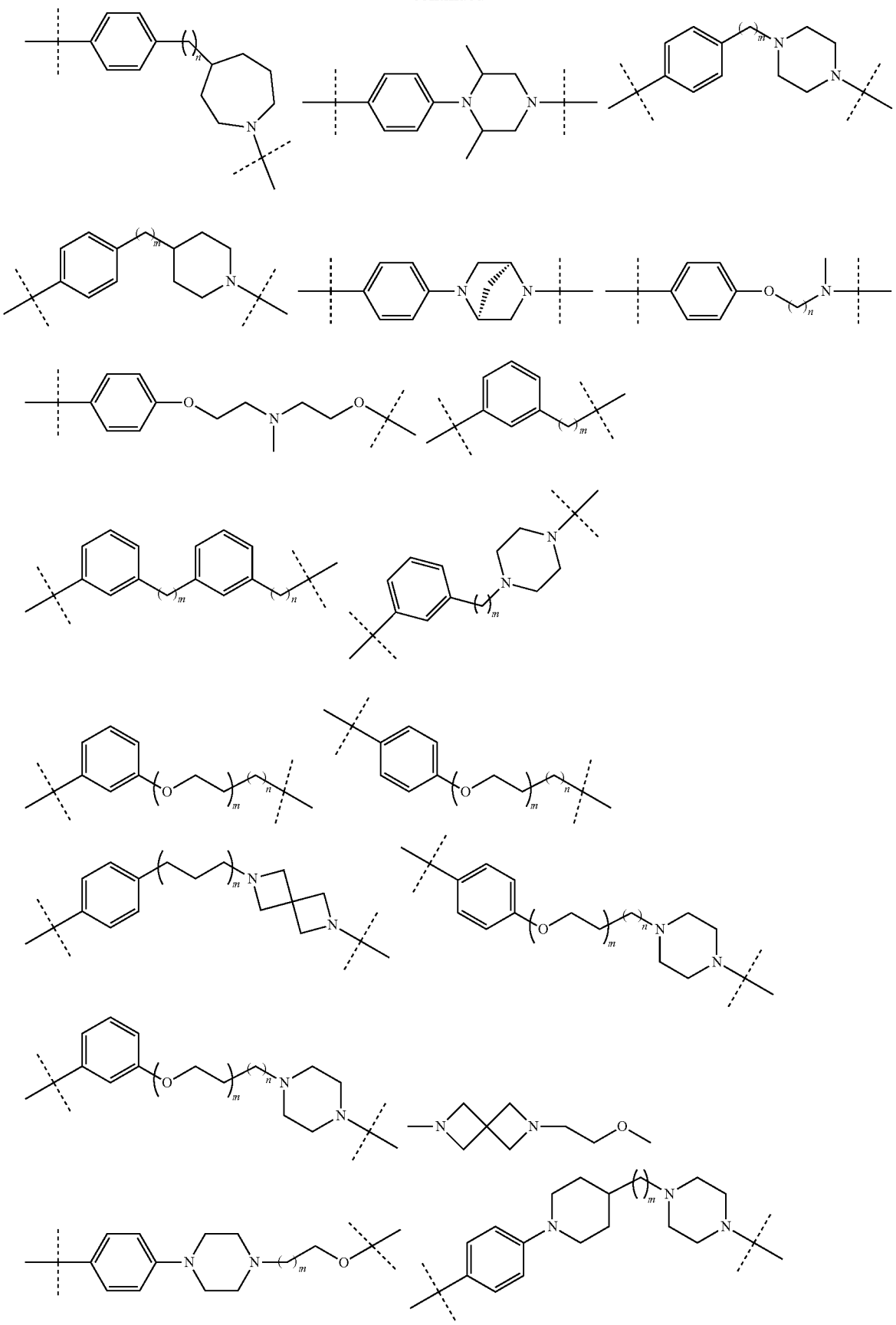

-continued
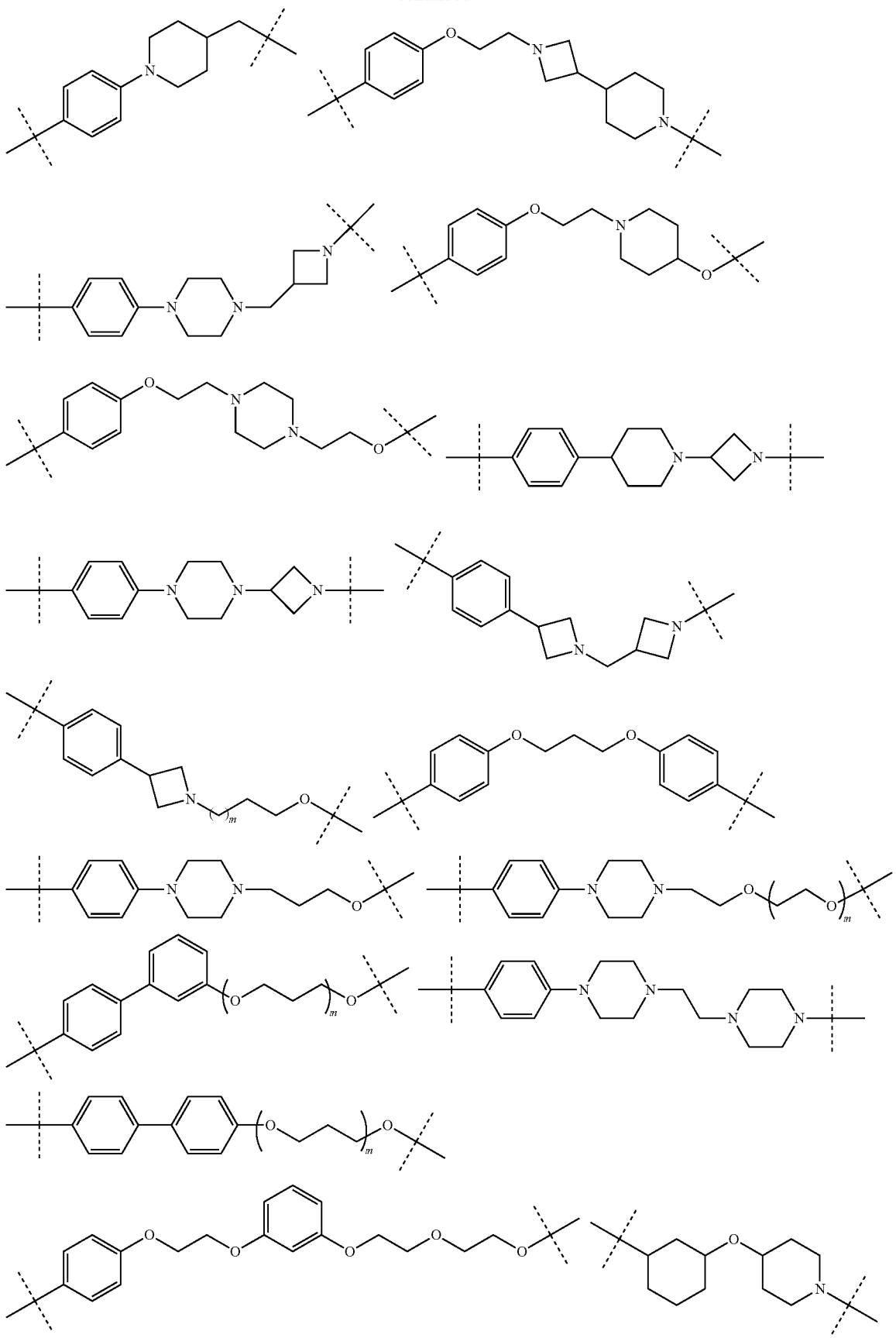

-continued
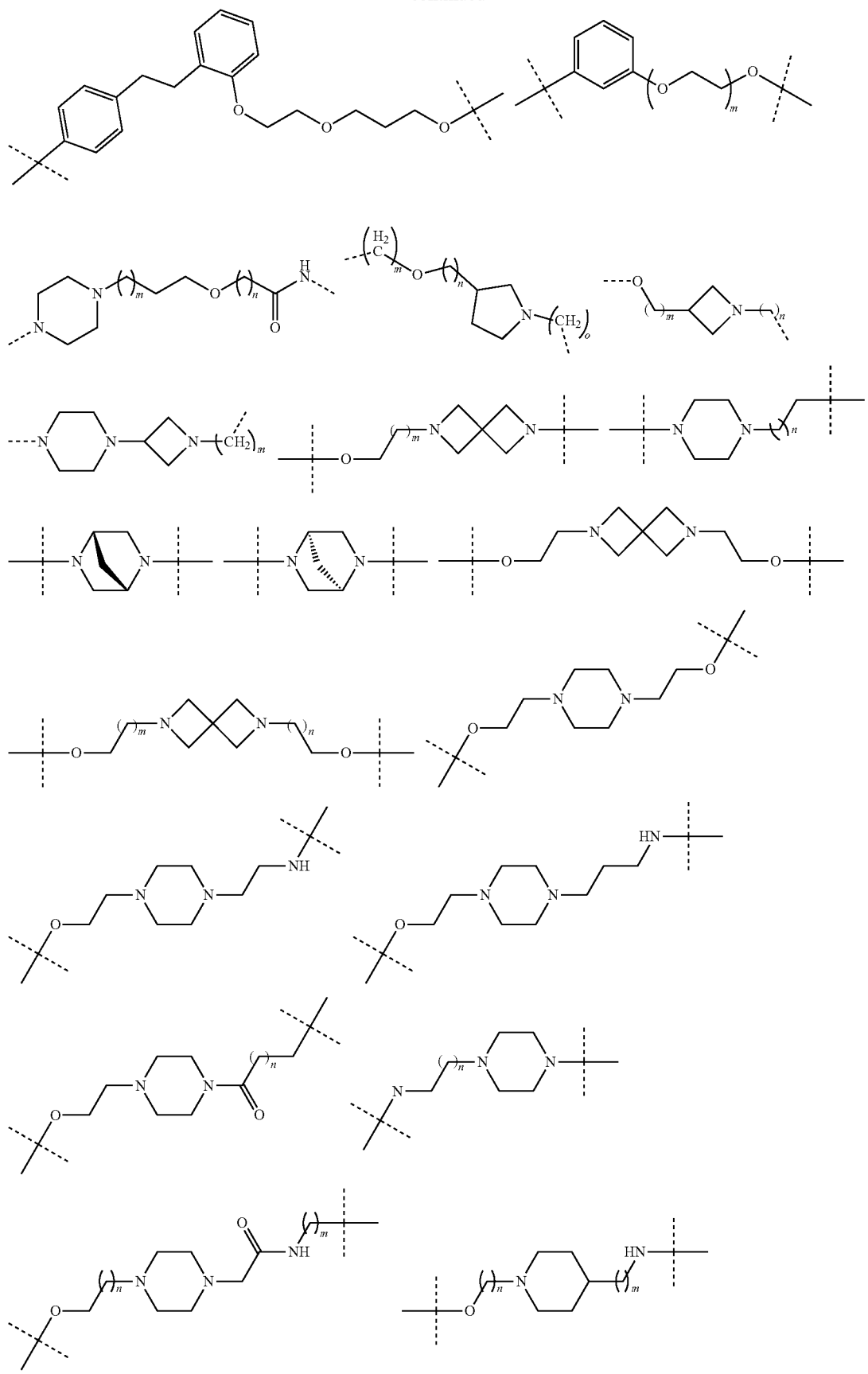

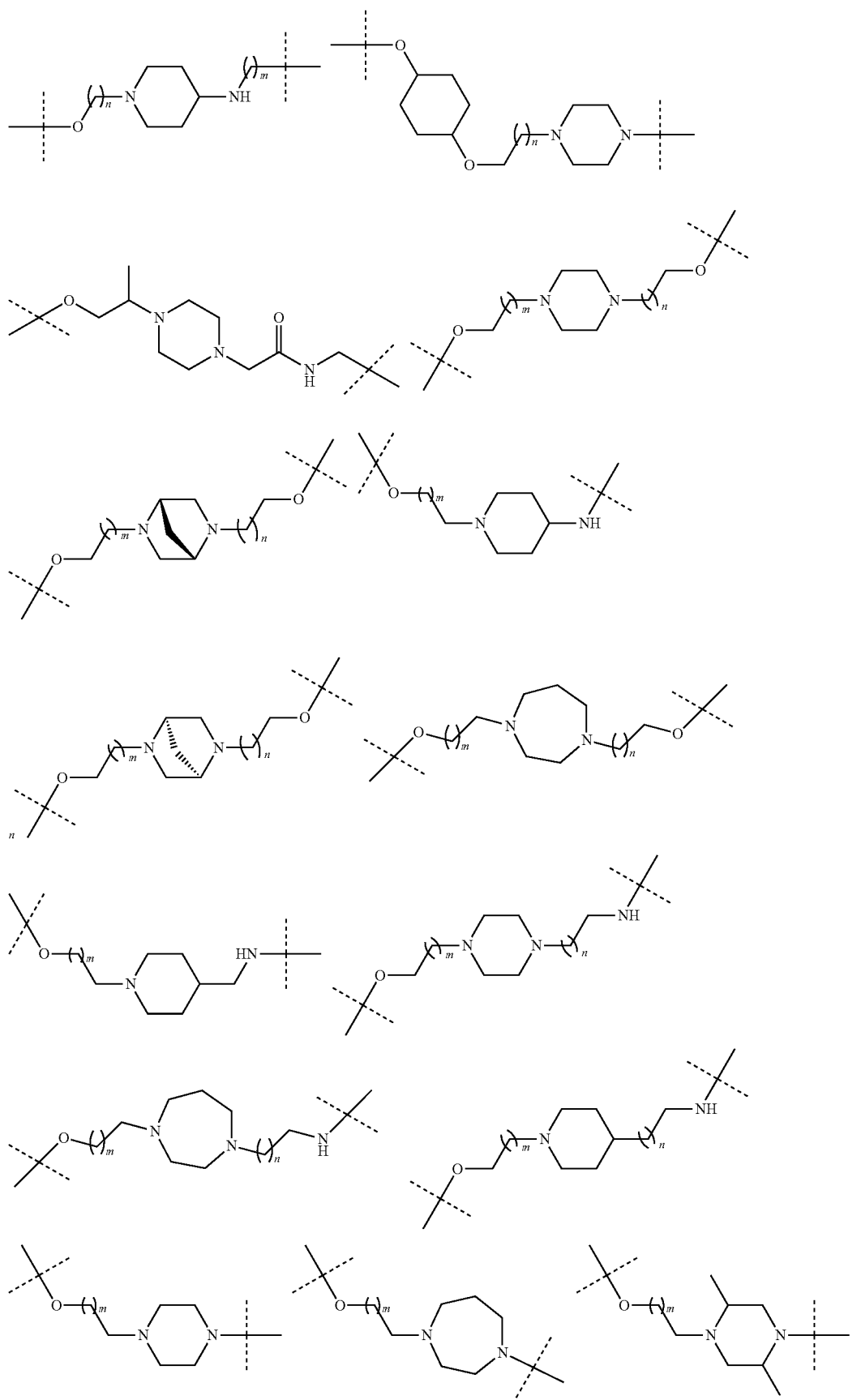

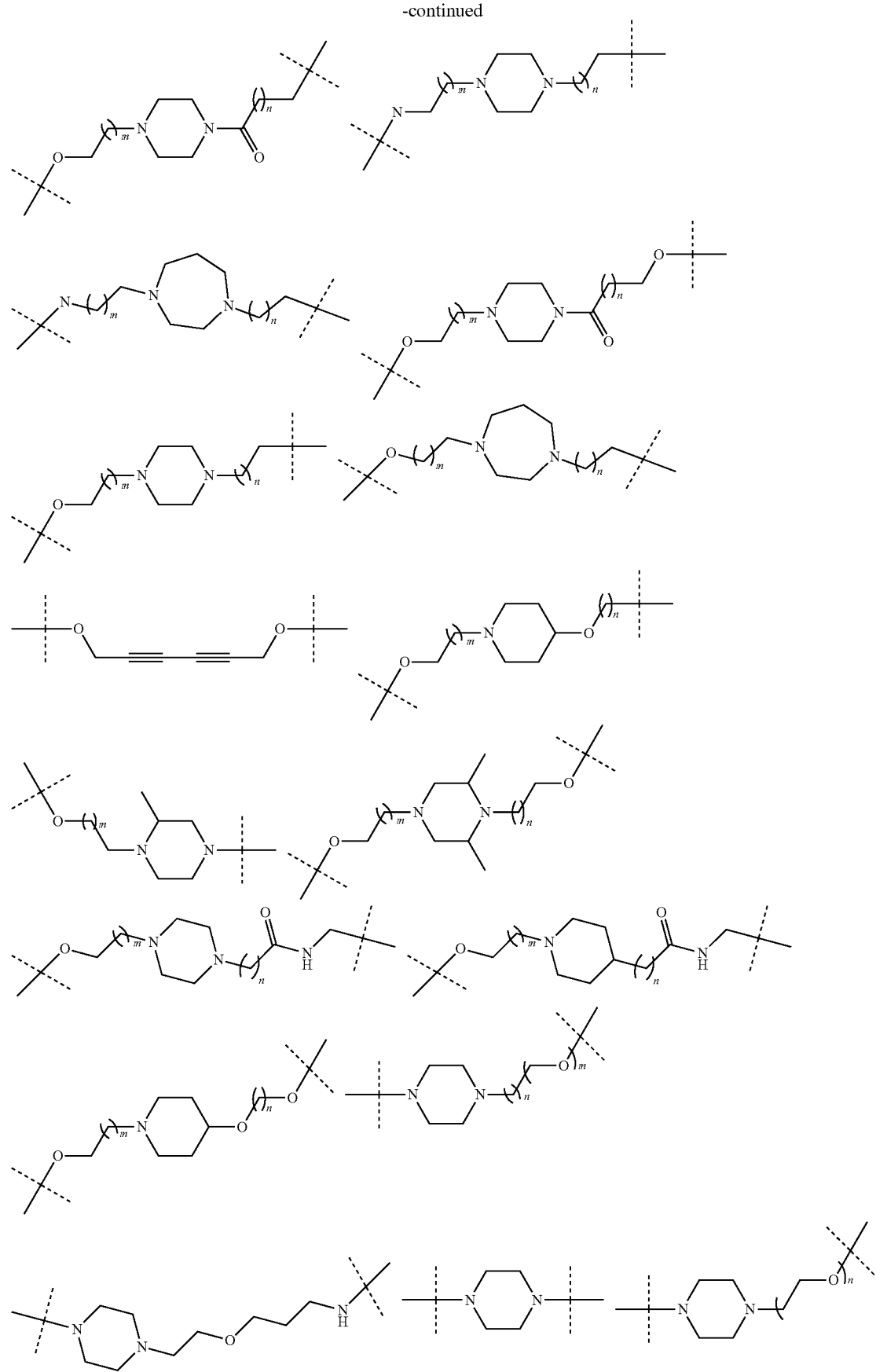

-continued
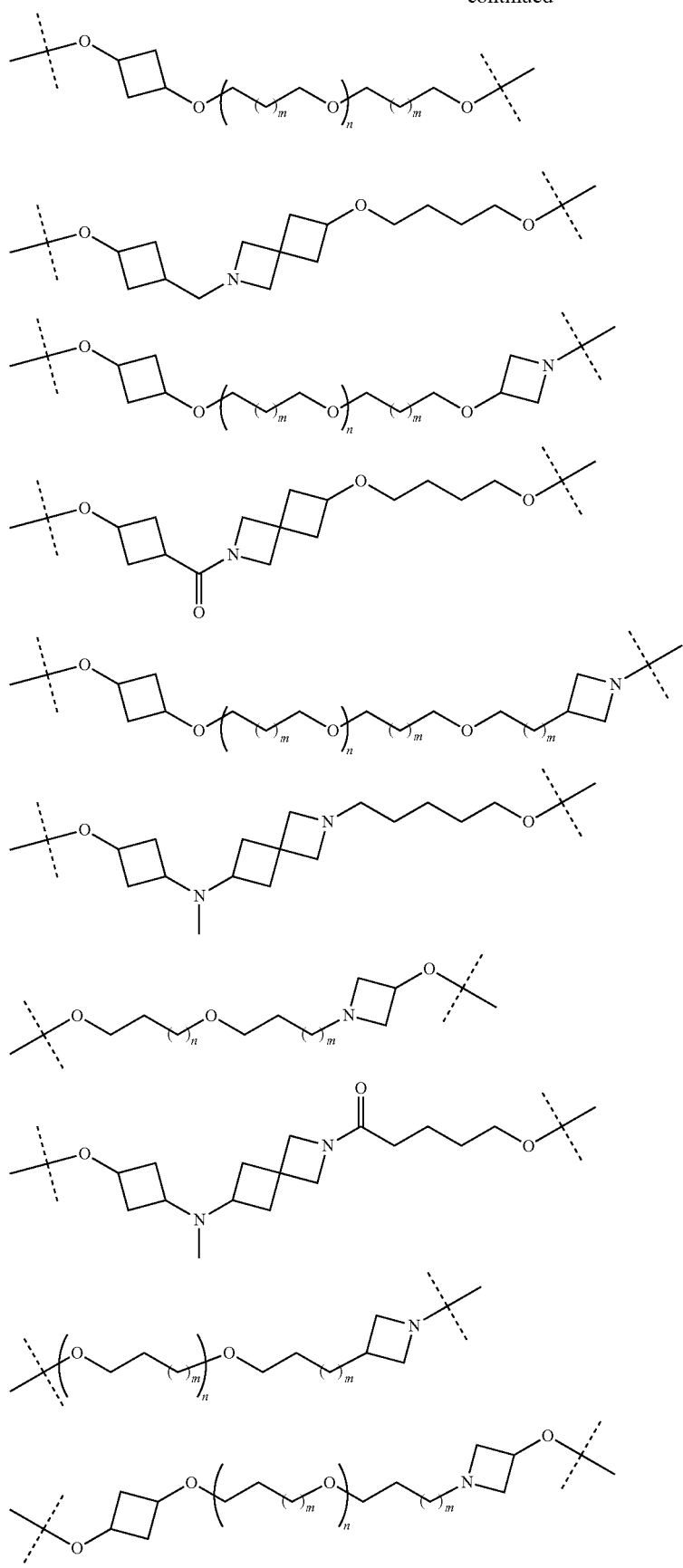

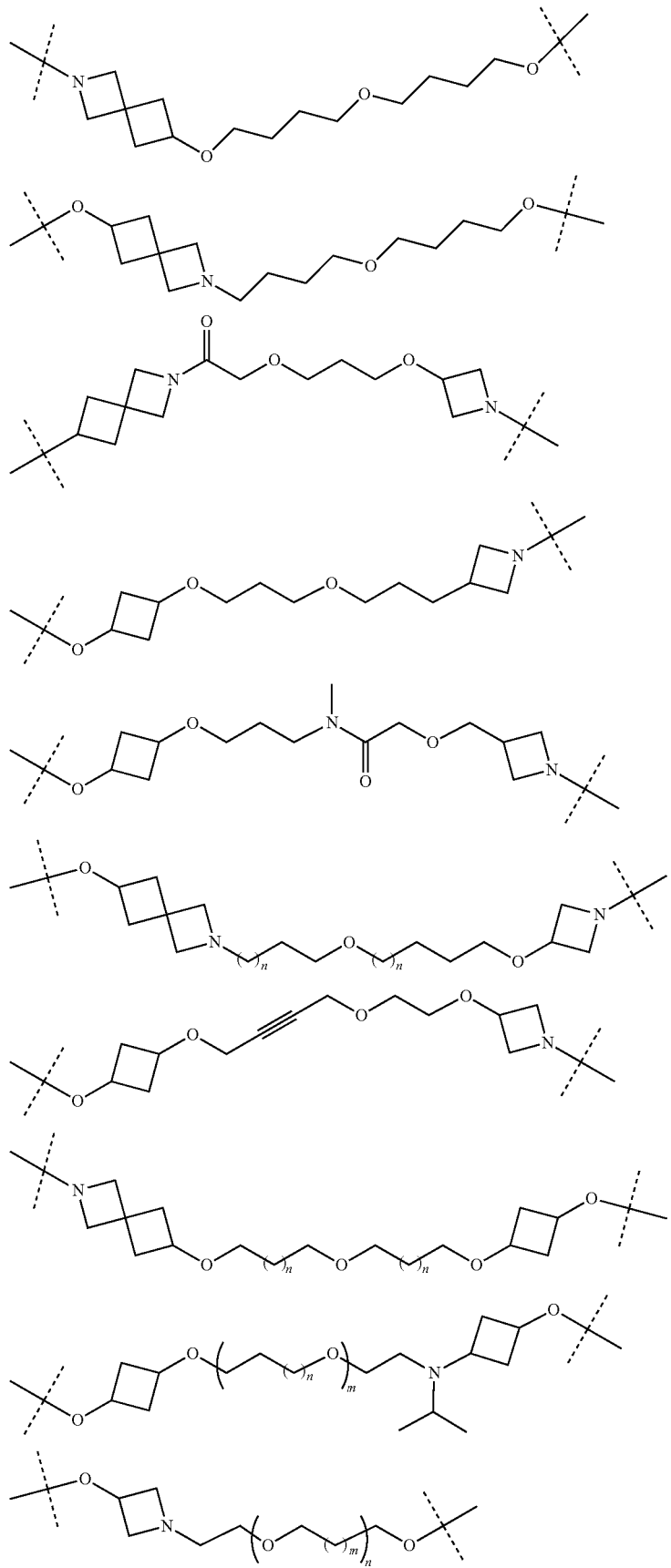

-continued
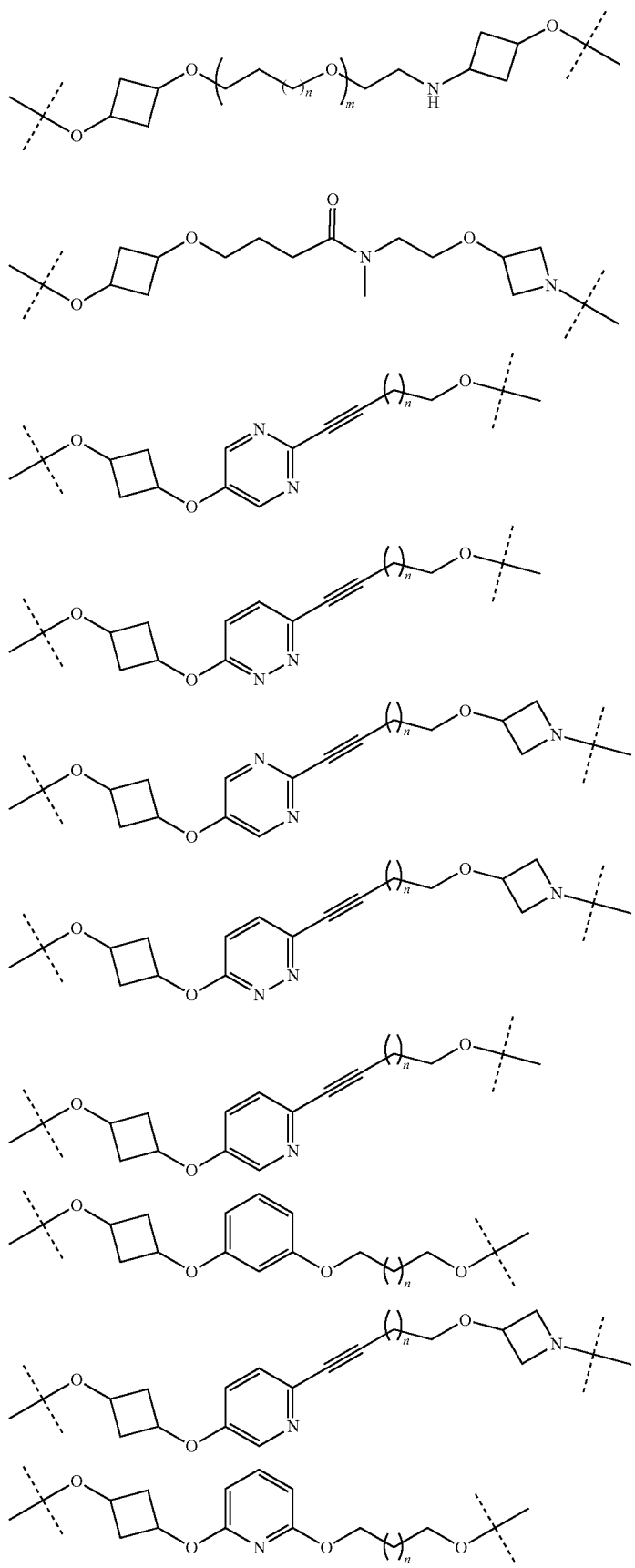

-continued
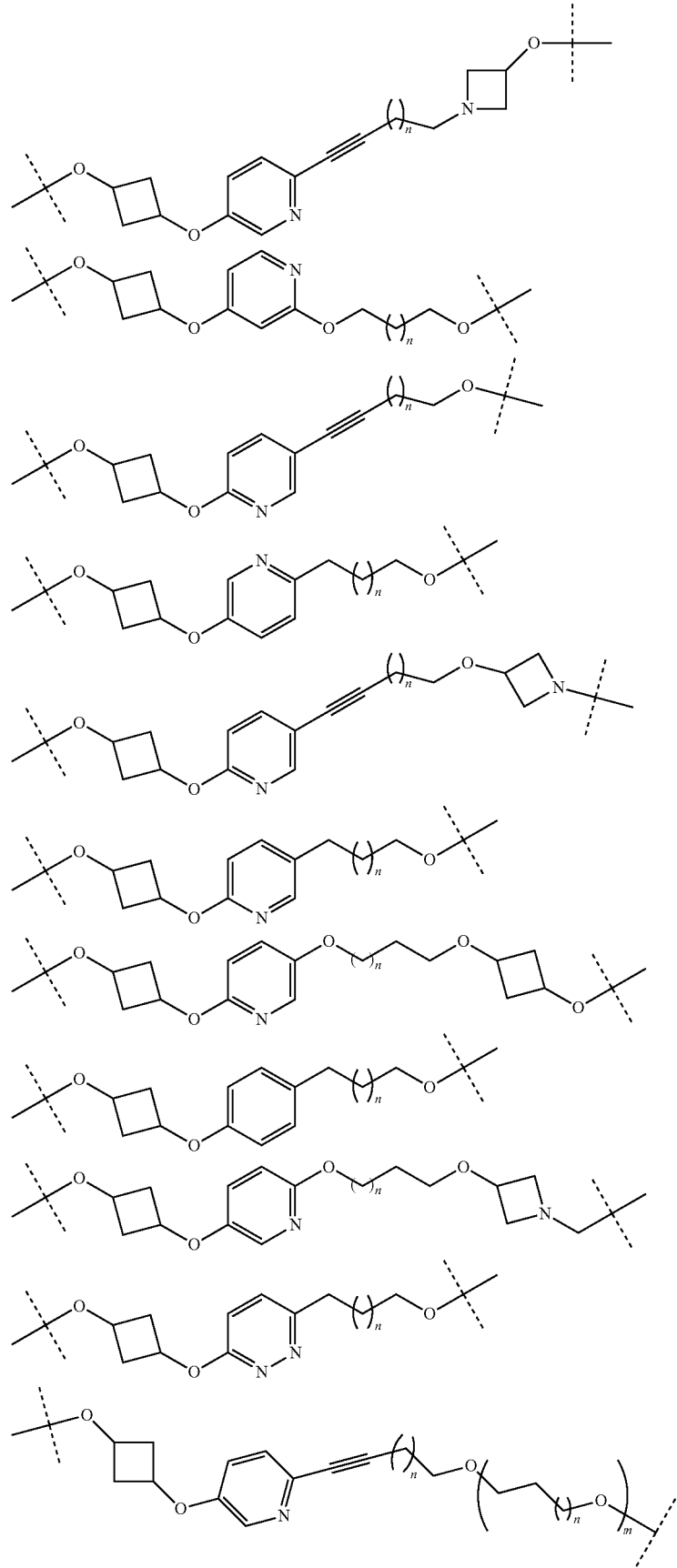

-continued
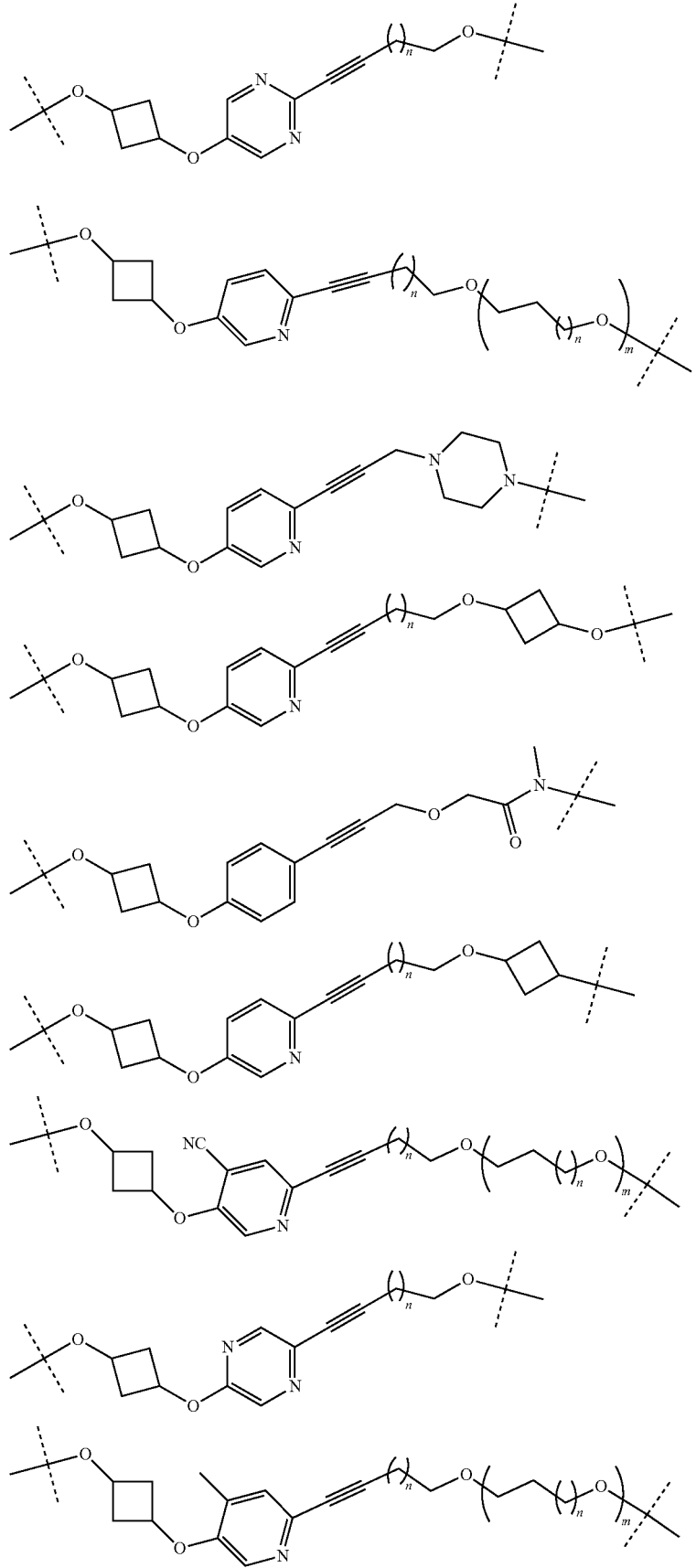

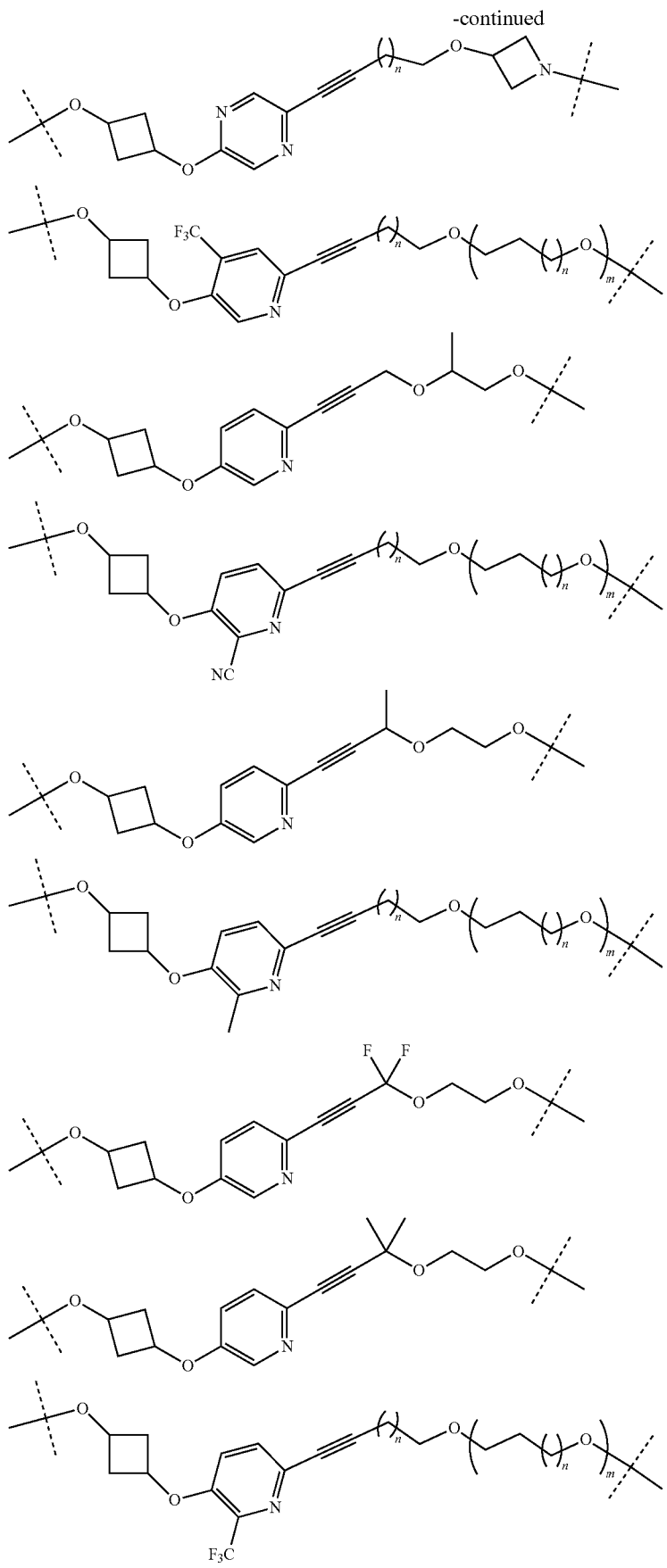

-continued
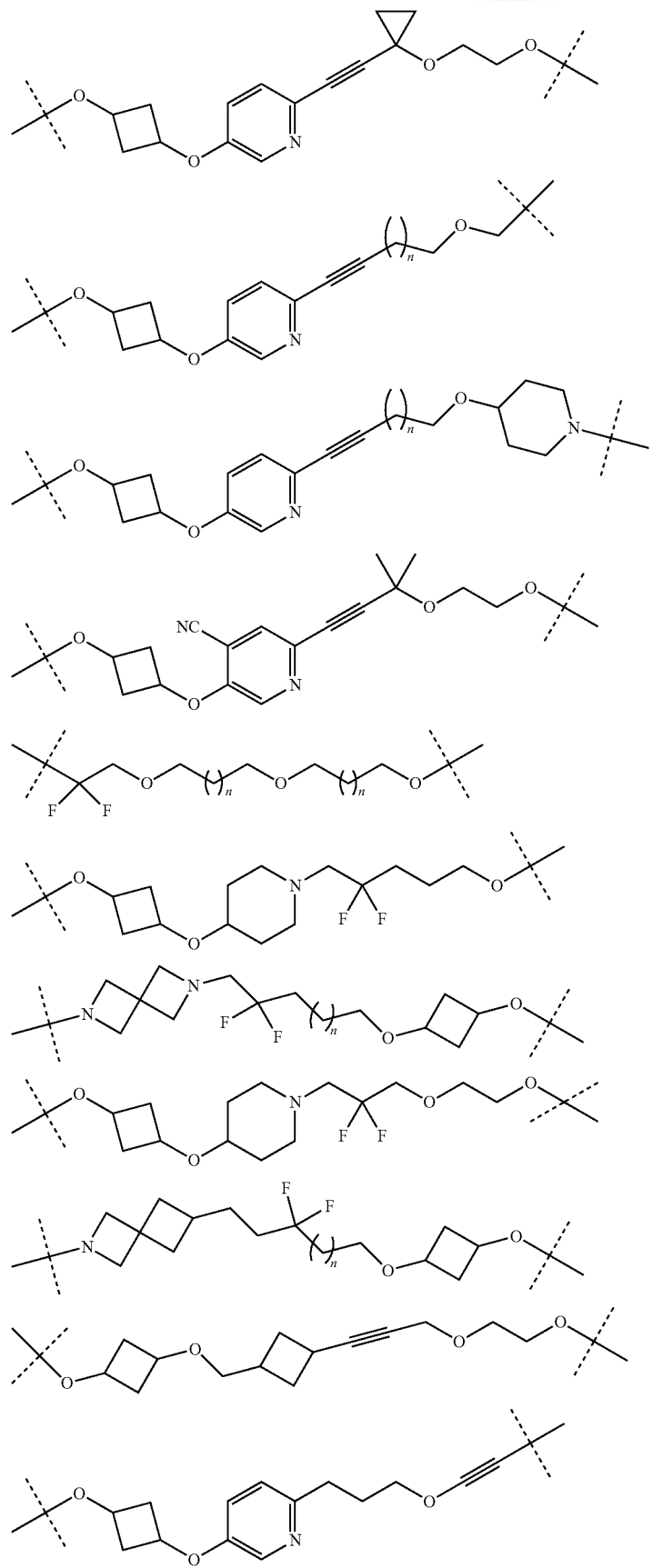

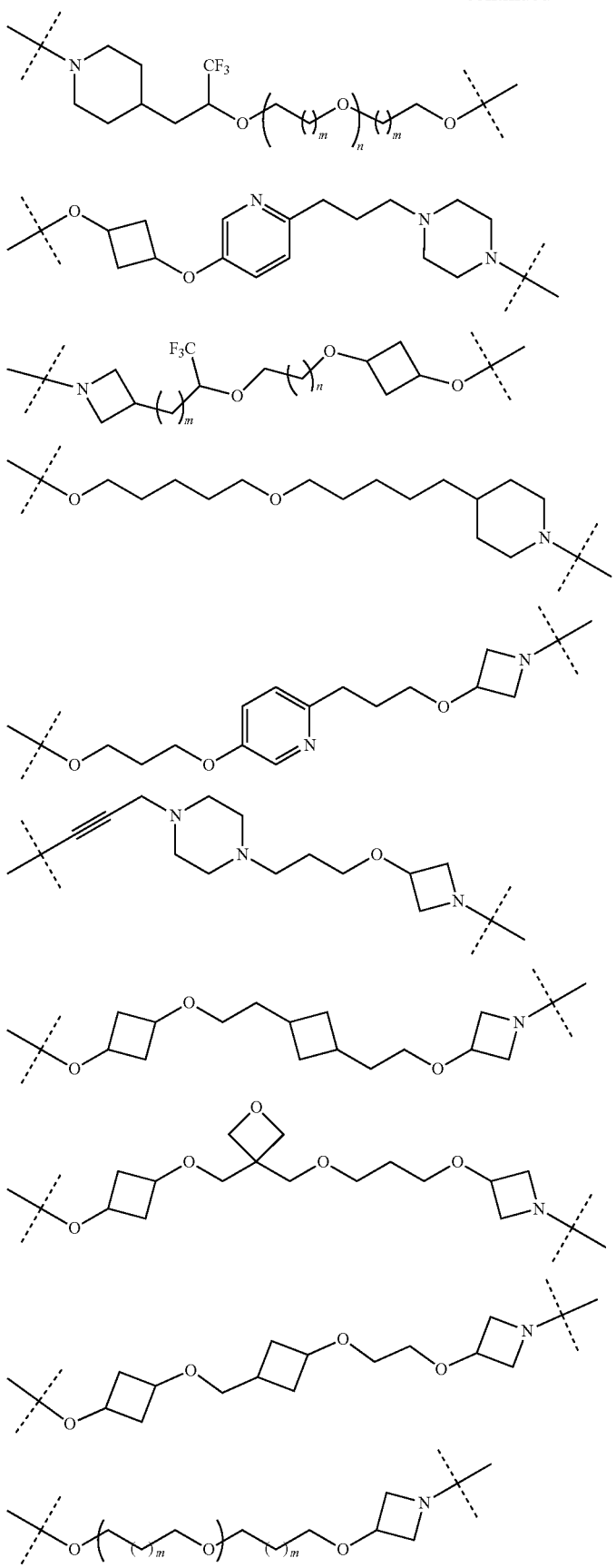

-continued

-continued
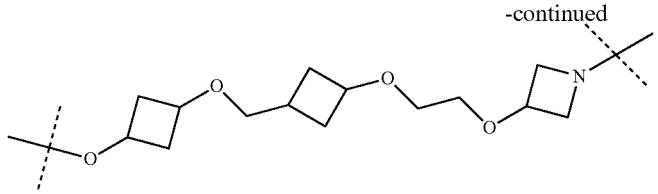
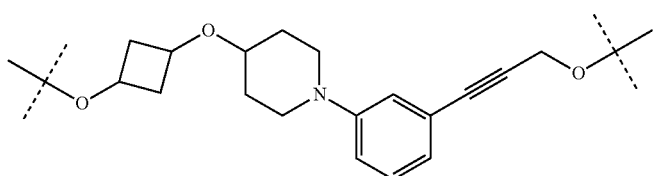
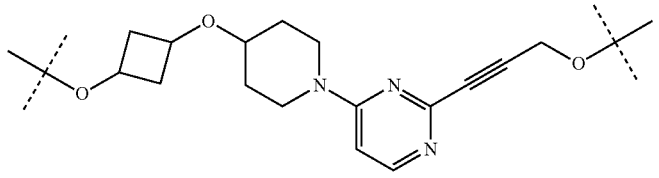
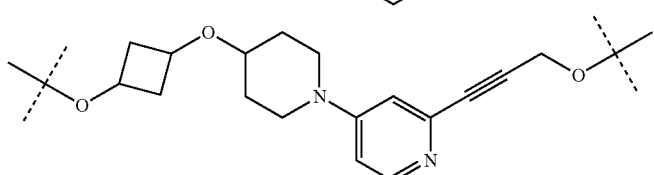
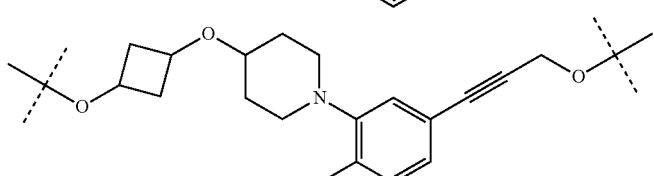
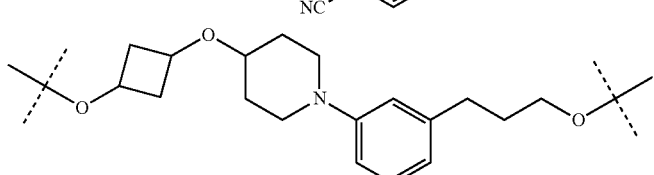
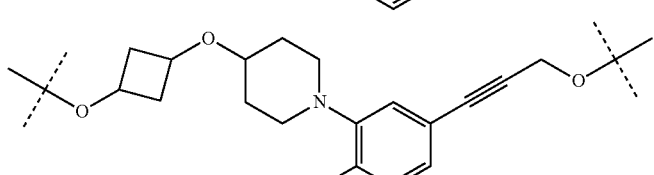
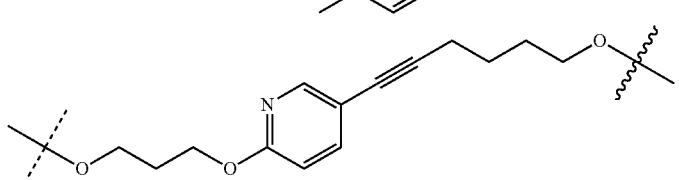
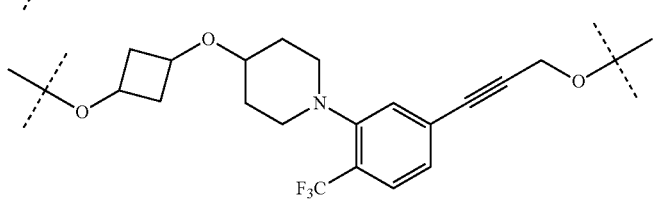

-continued
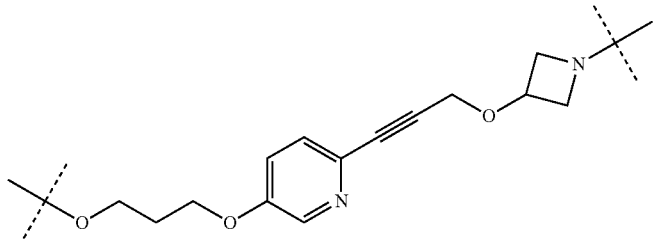
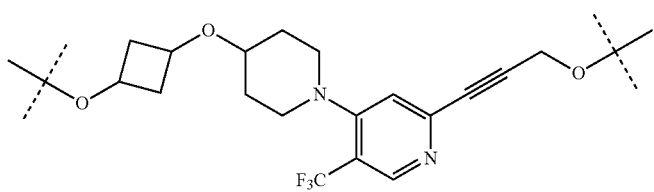
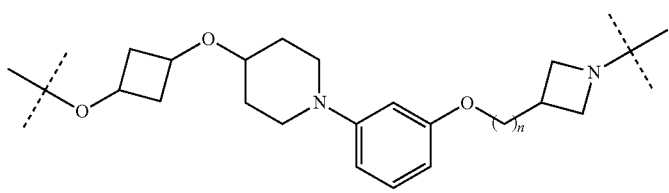
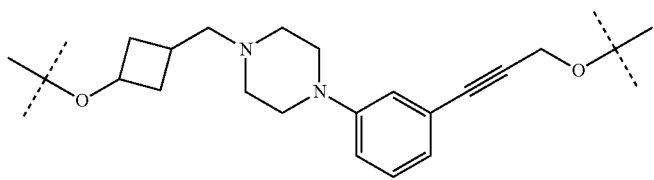
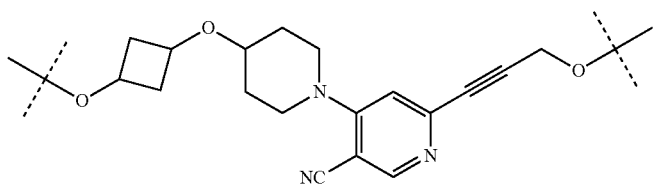
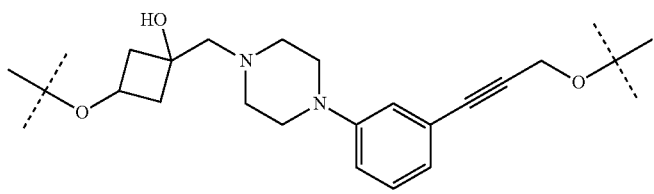
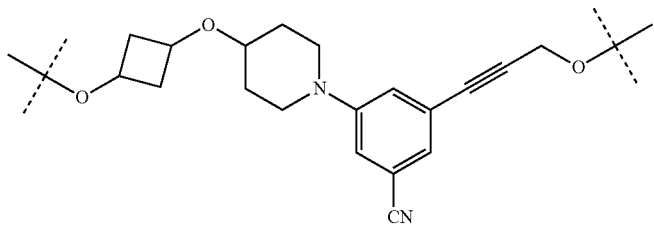
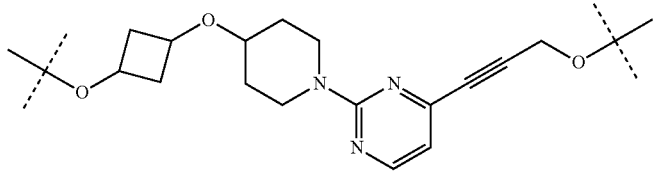

-continued
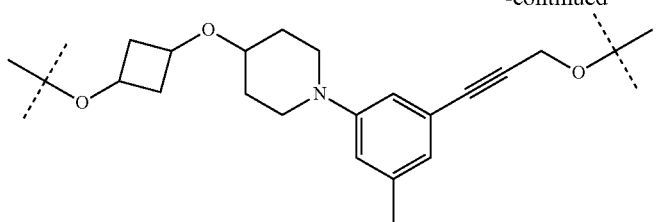
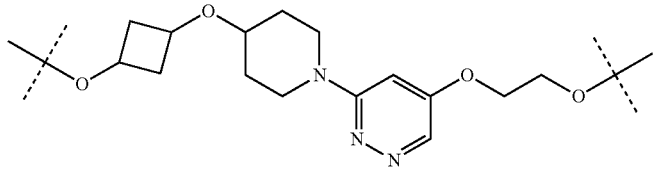
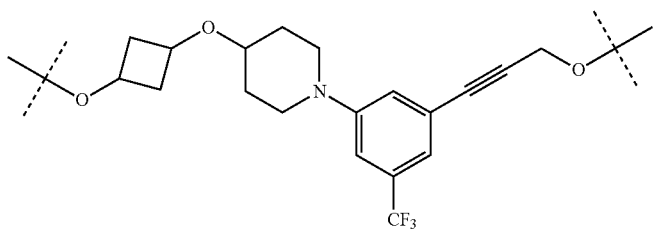
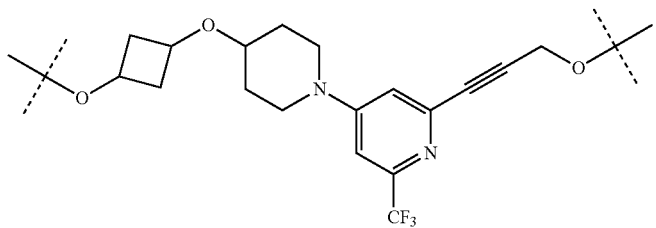
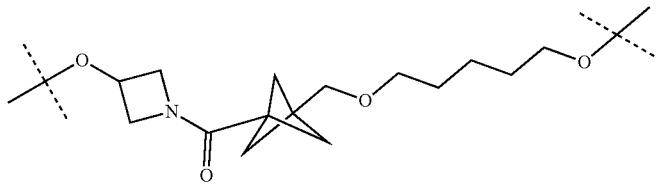
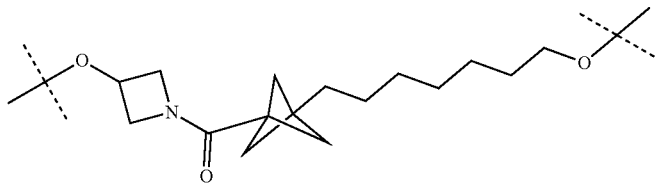
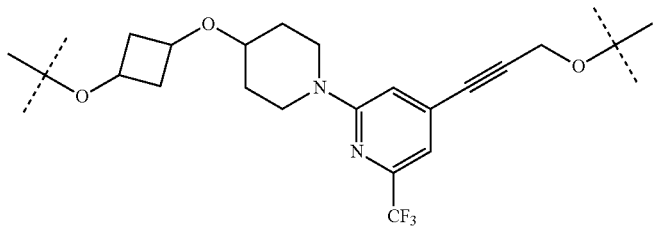
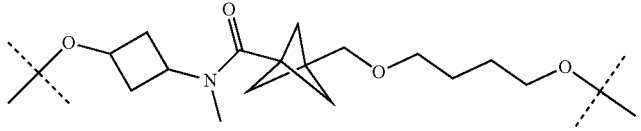

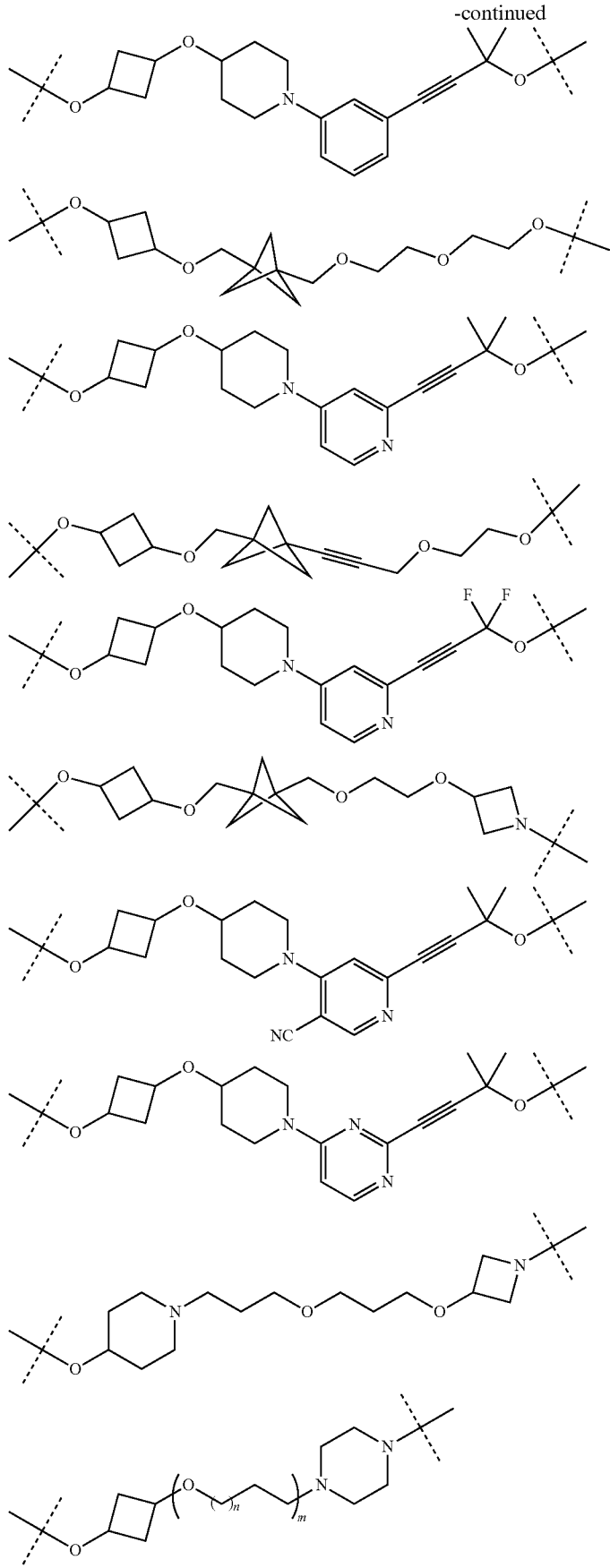

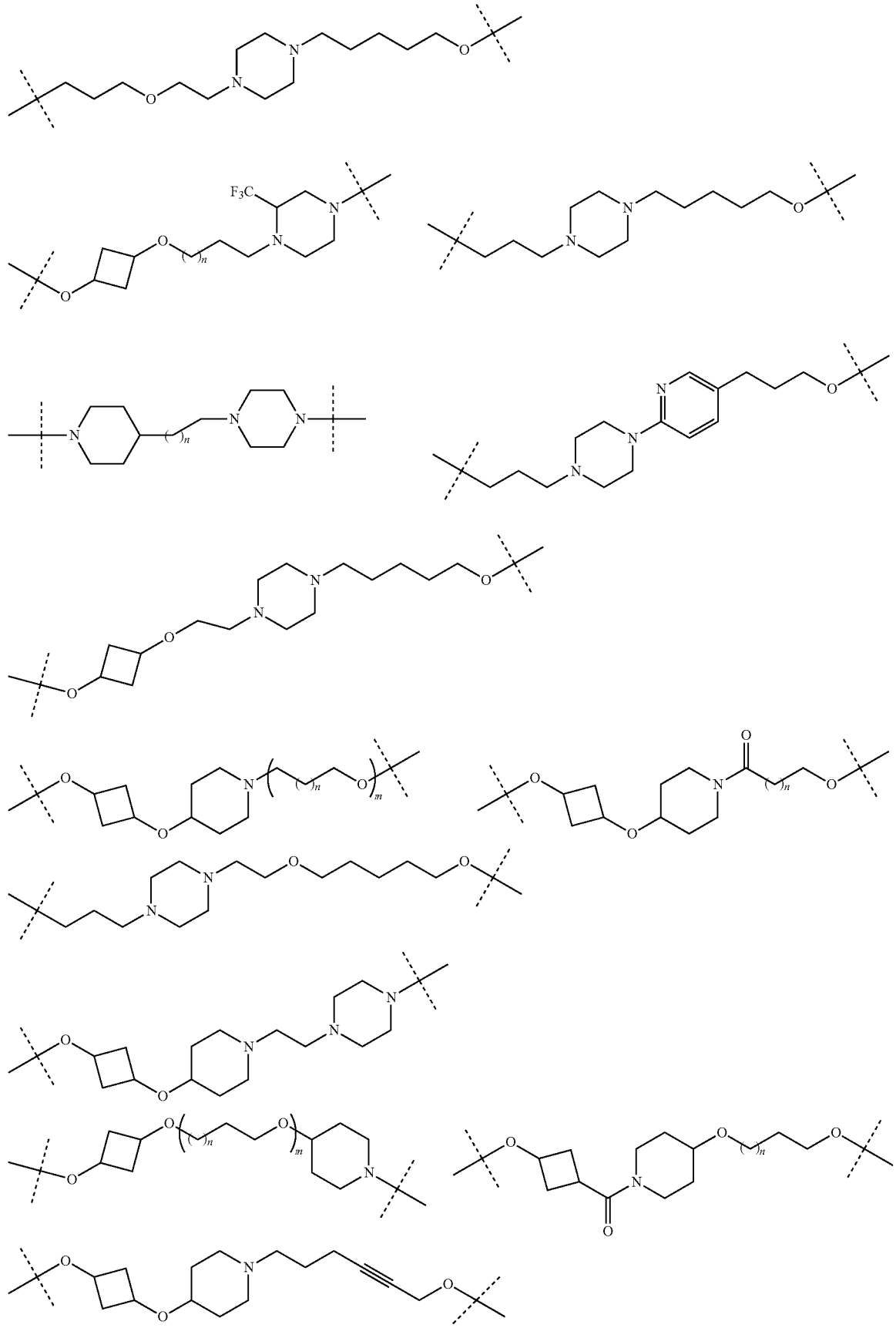

-continued
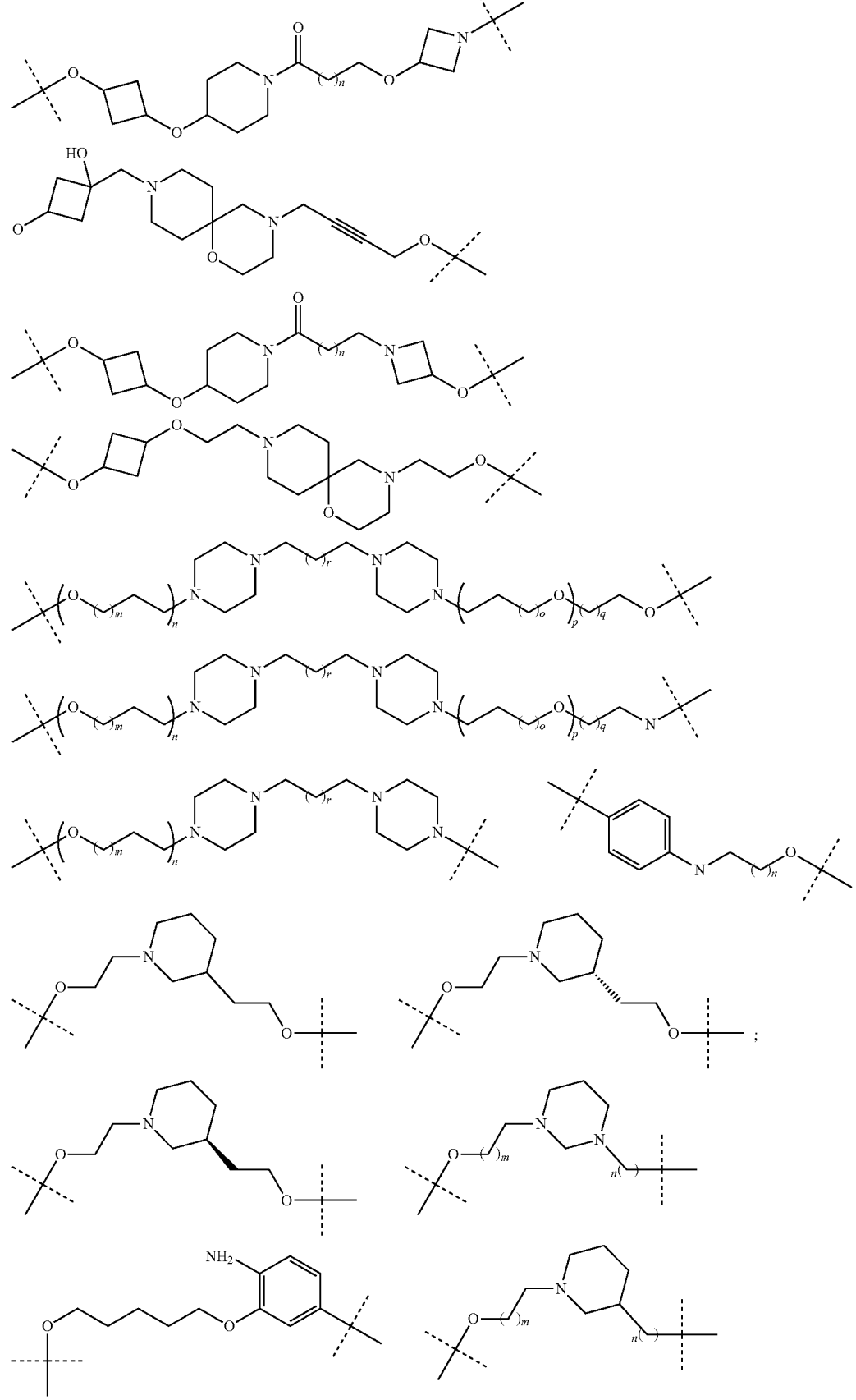

-continued
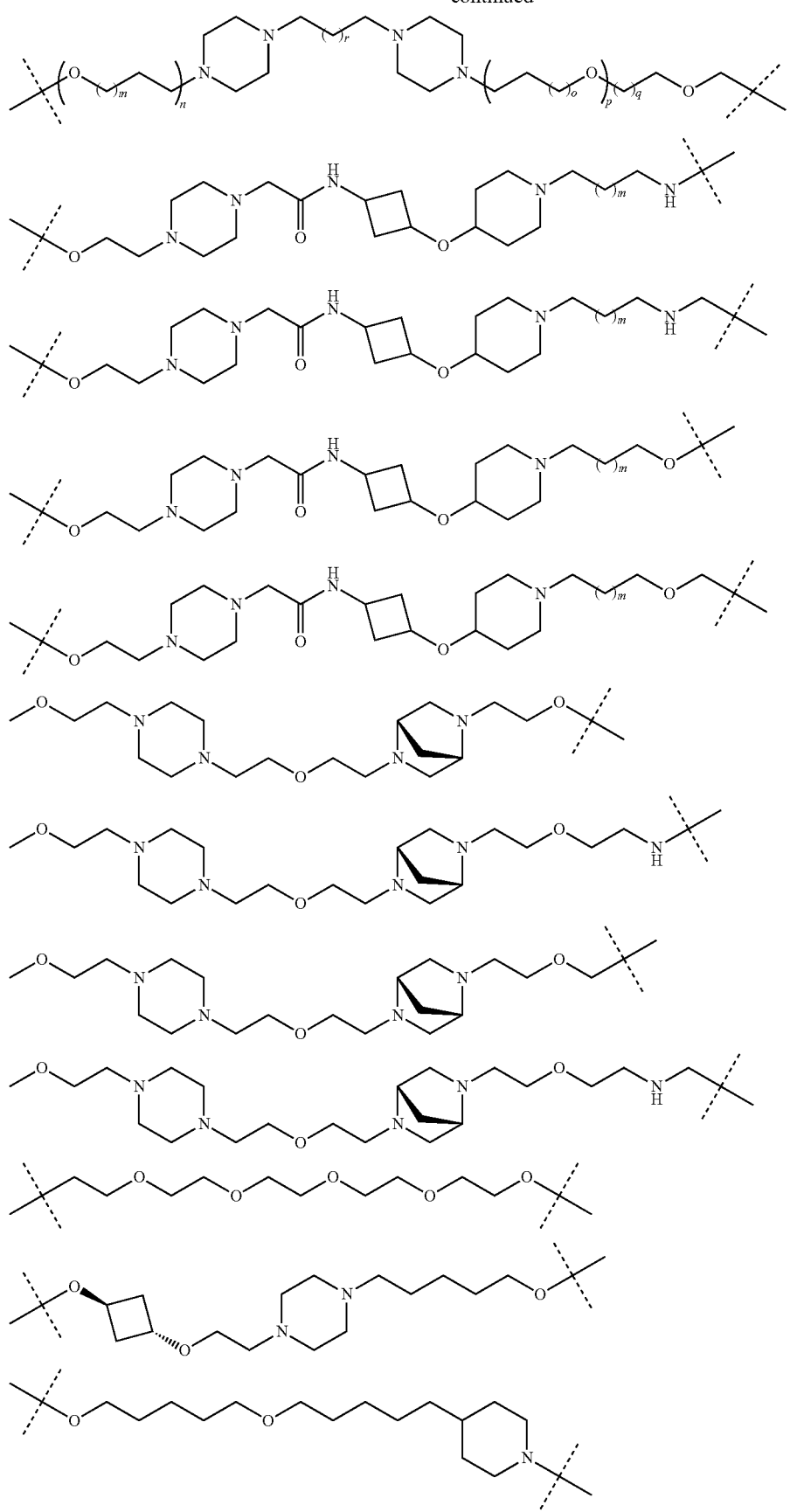

-continued
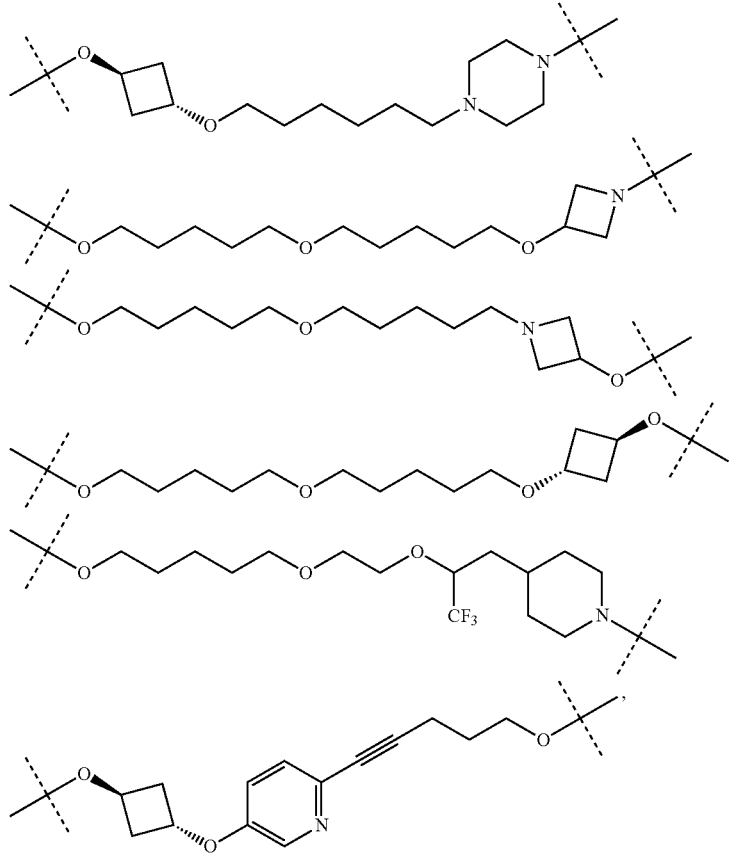
wherein each m, n, o, p, q, or r is independently 0, 1, 2, 3, 4, 5, 6, 7, 8, 9, 10, 11, 12, 13, 14, 15, 16, 17, 18, 19, or 20.
In any aspect or embodiment described herein, L is selected from the group consisting of:
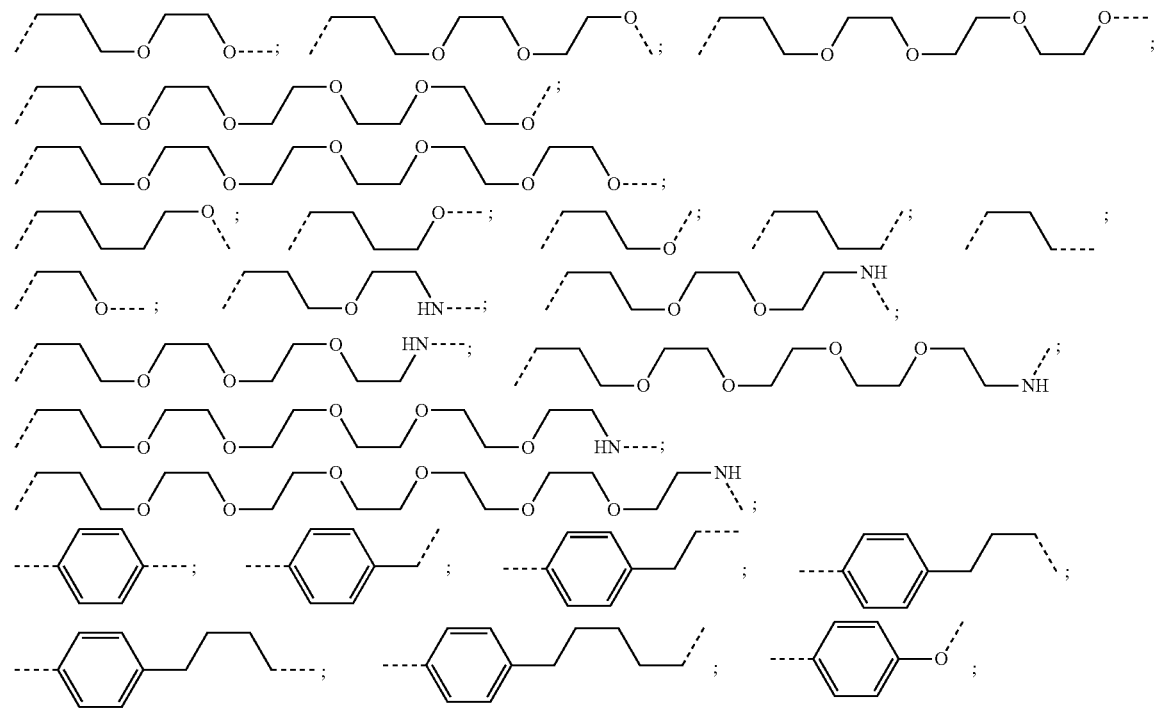

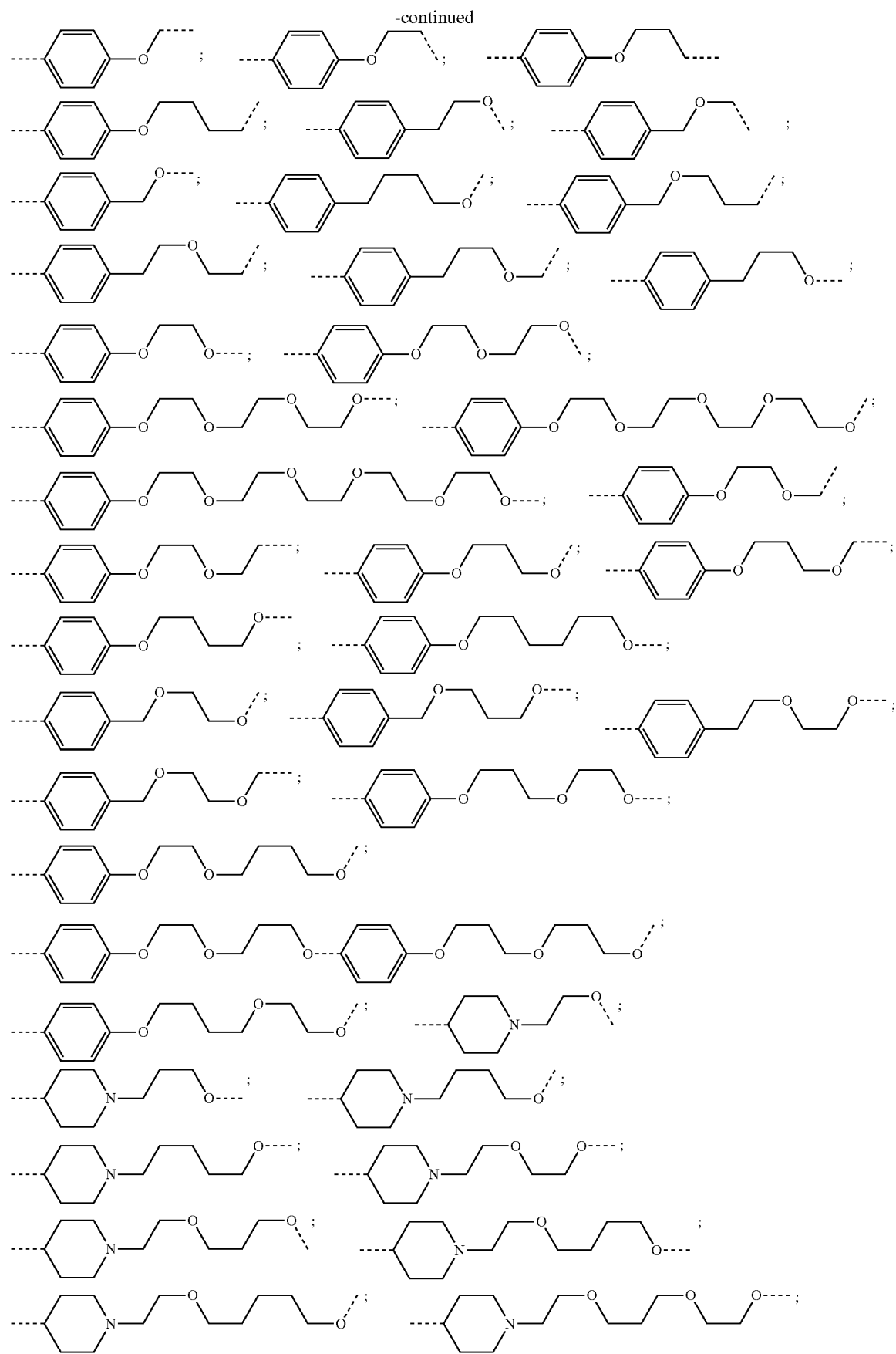
-continued

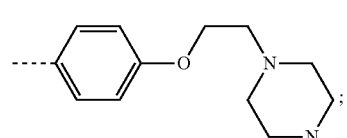
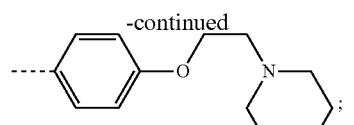
-continued
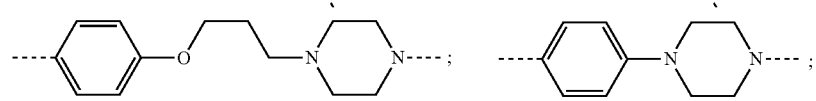
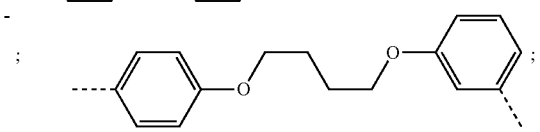
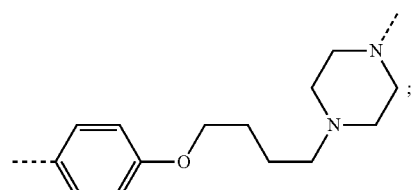
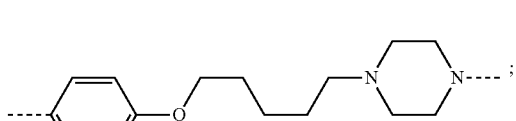
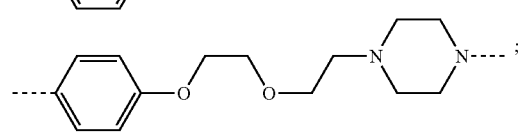
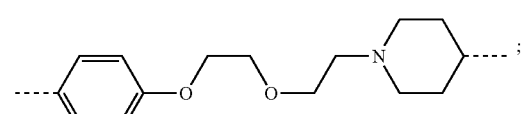
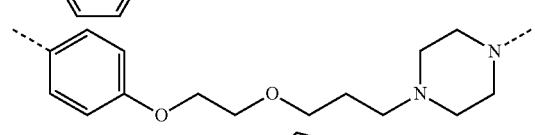
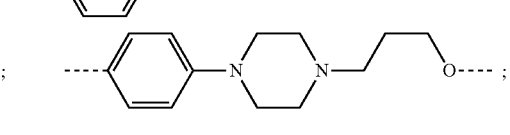
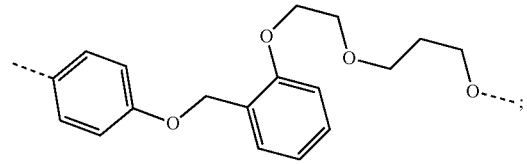
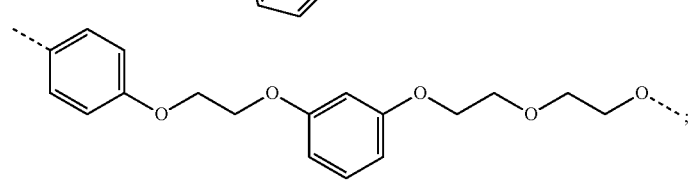
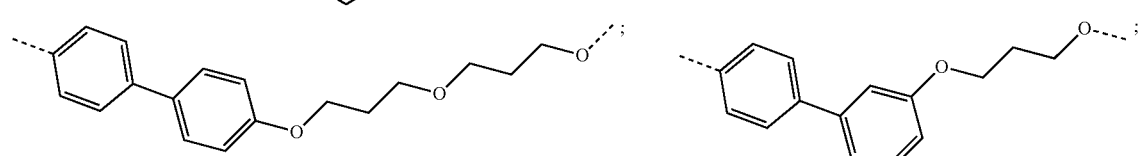
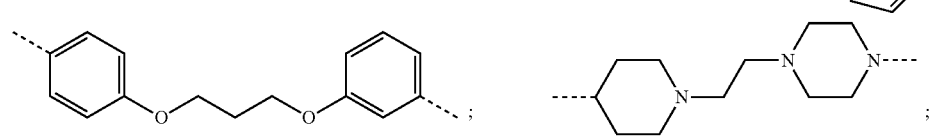
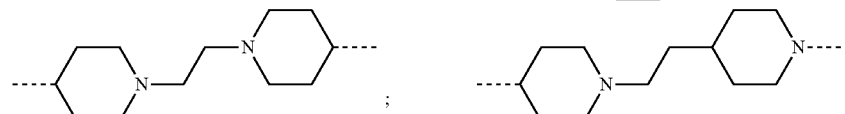
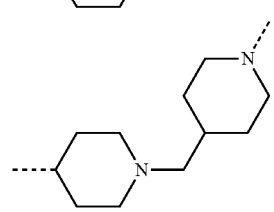
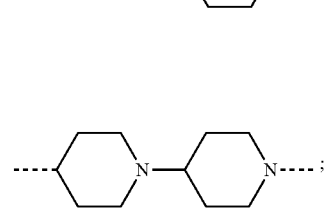
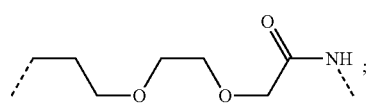

287 288
-continued
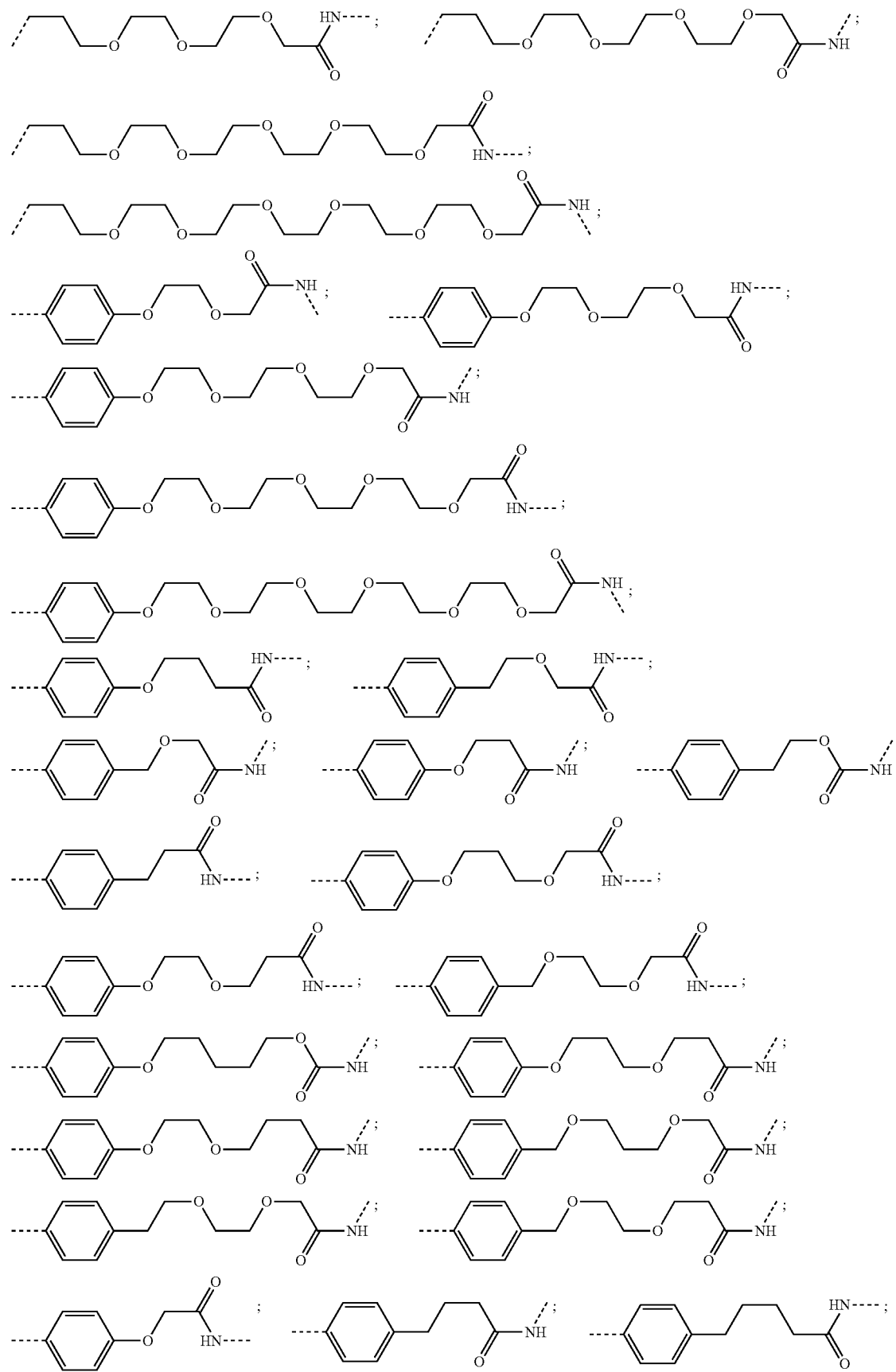

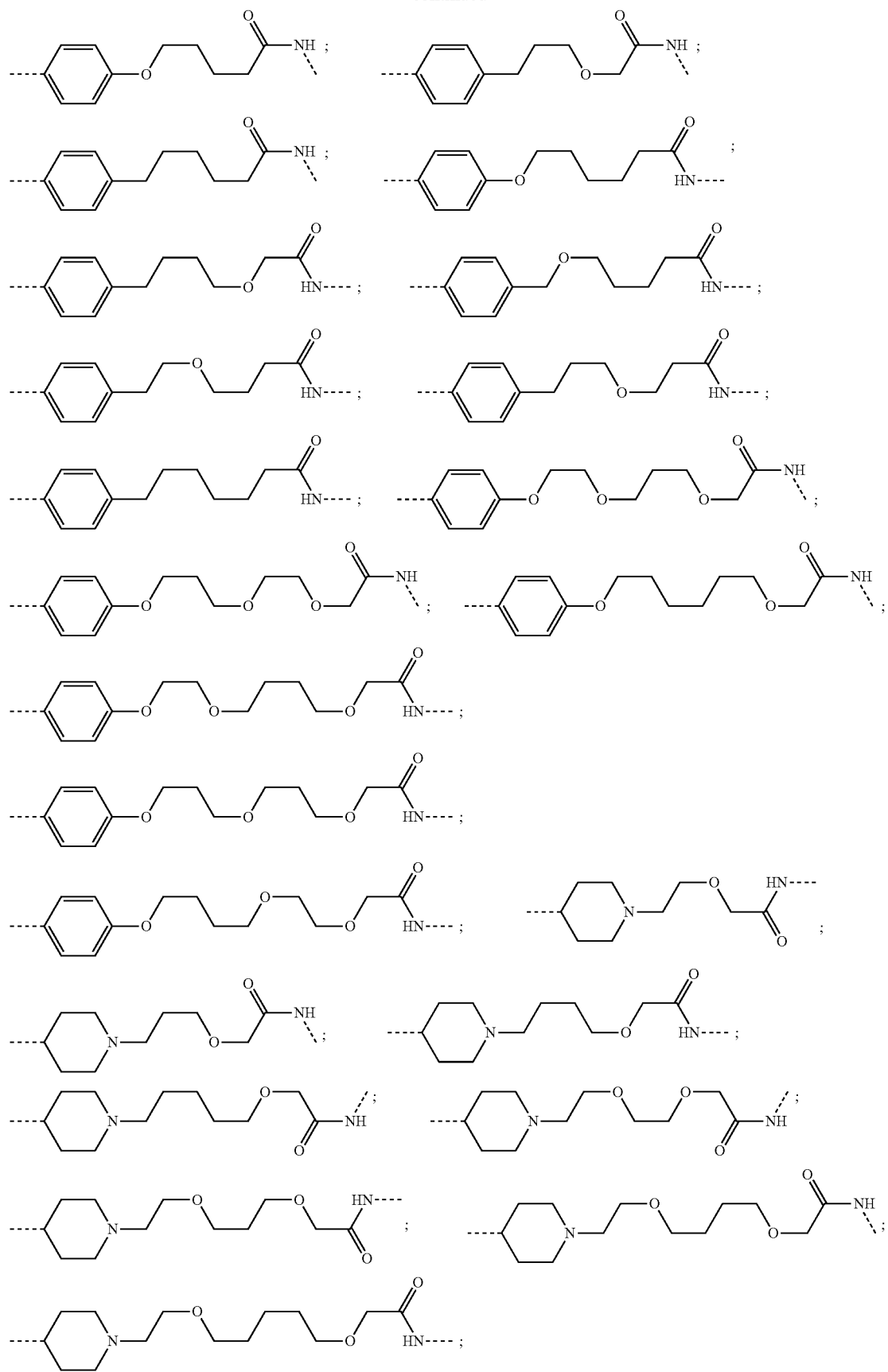

291 292
-continued
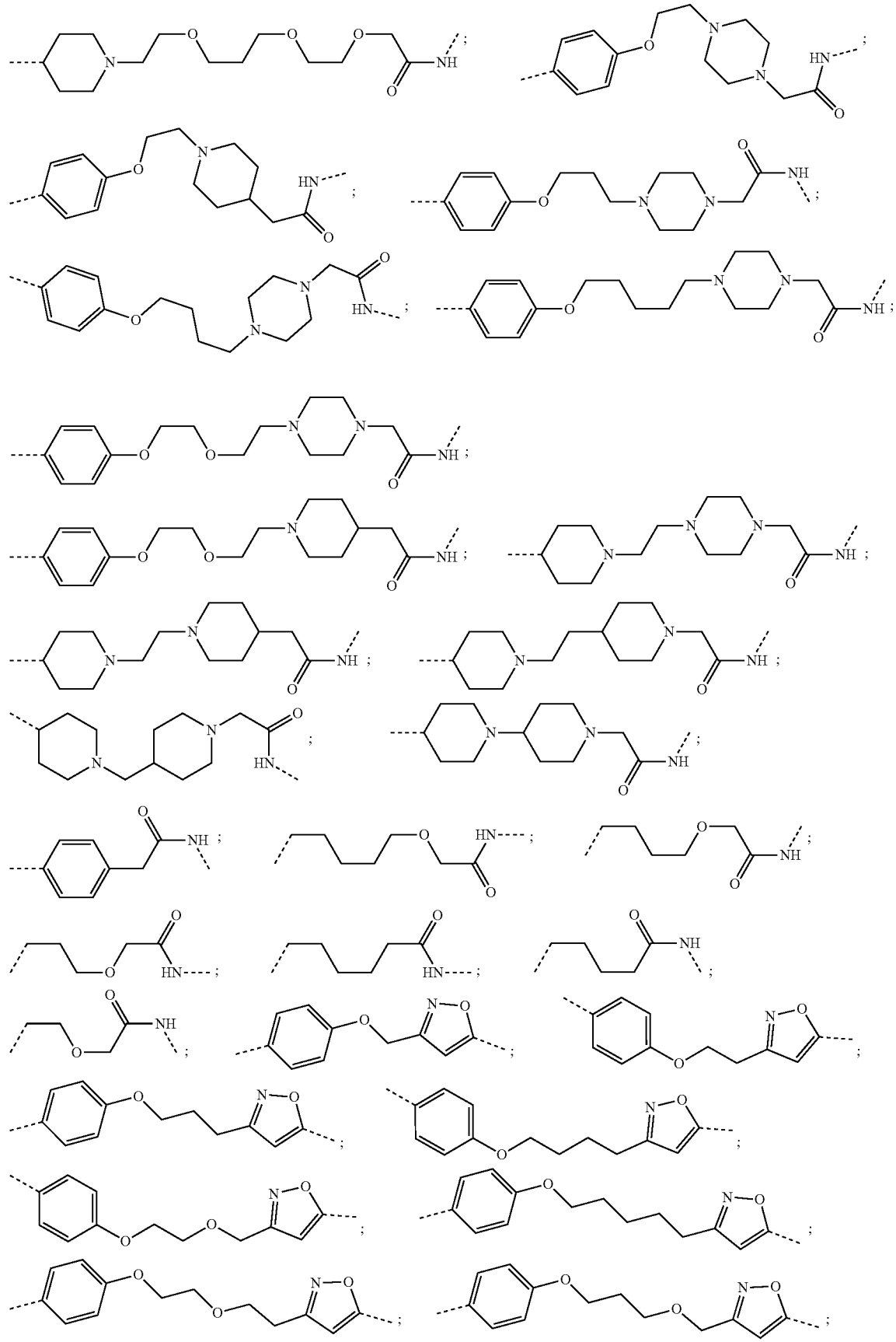

293
-continued
294
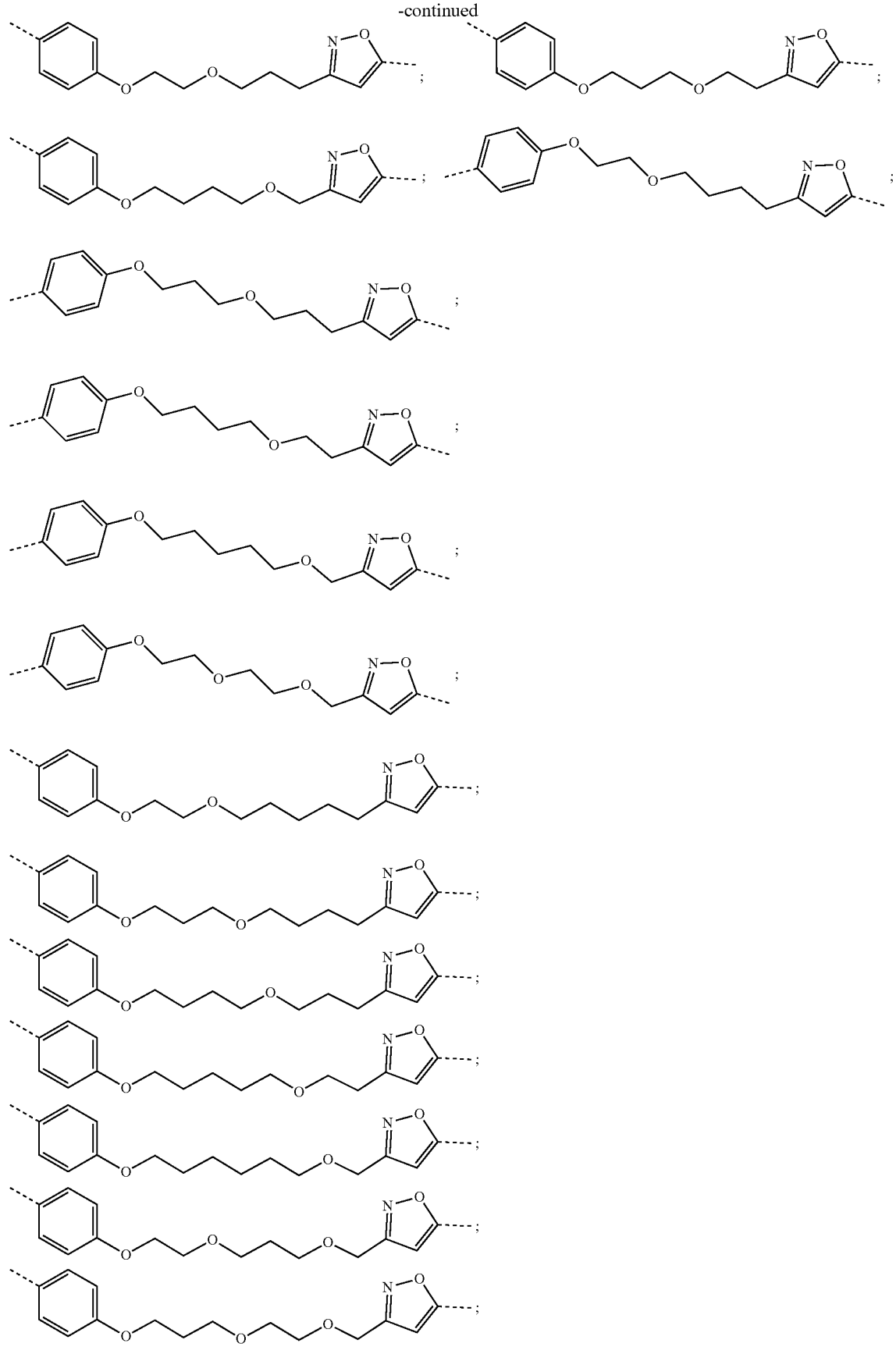

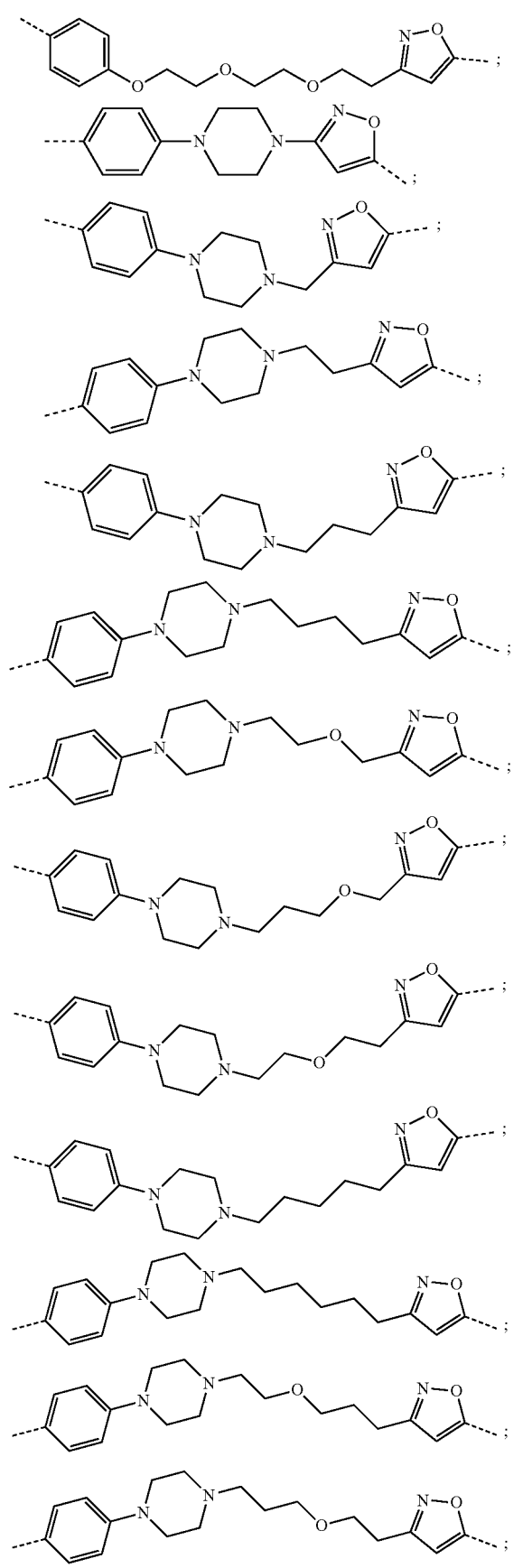
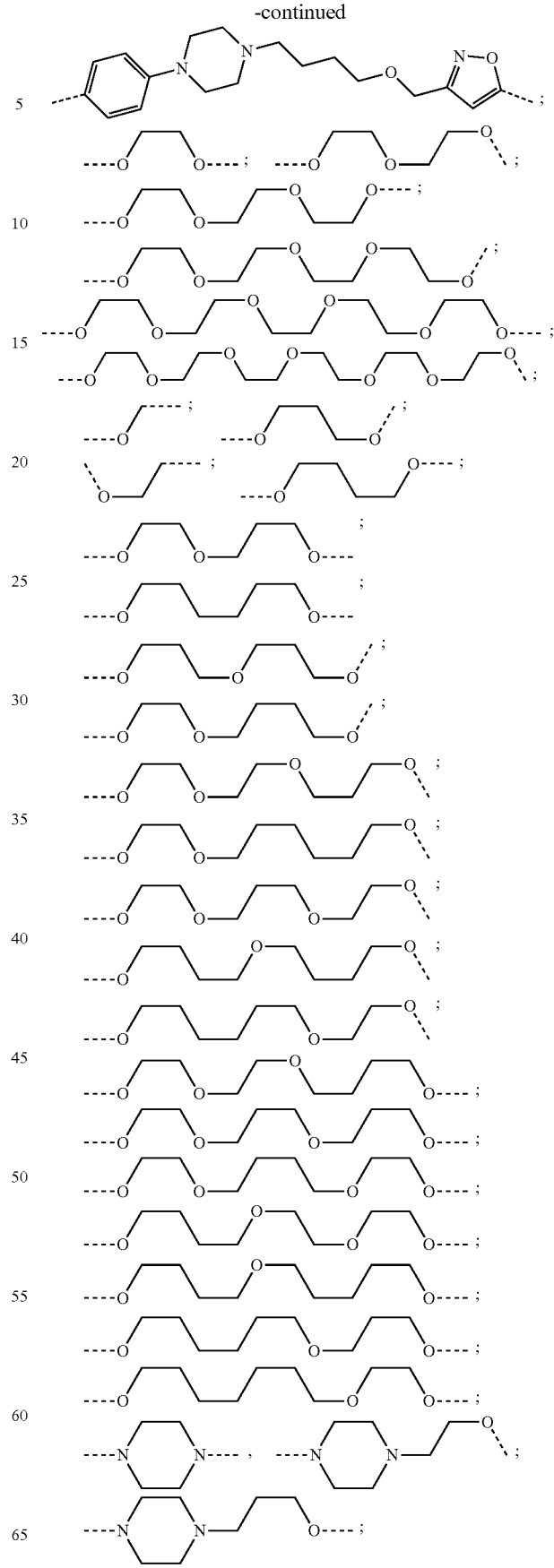

-continued

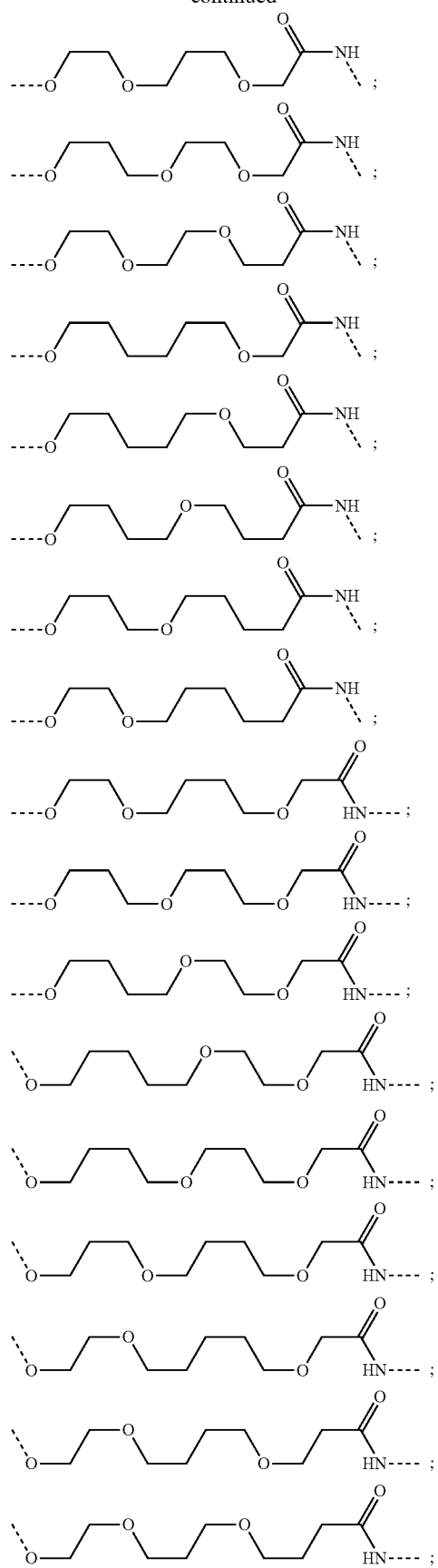
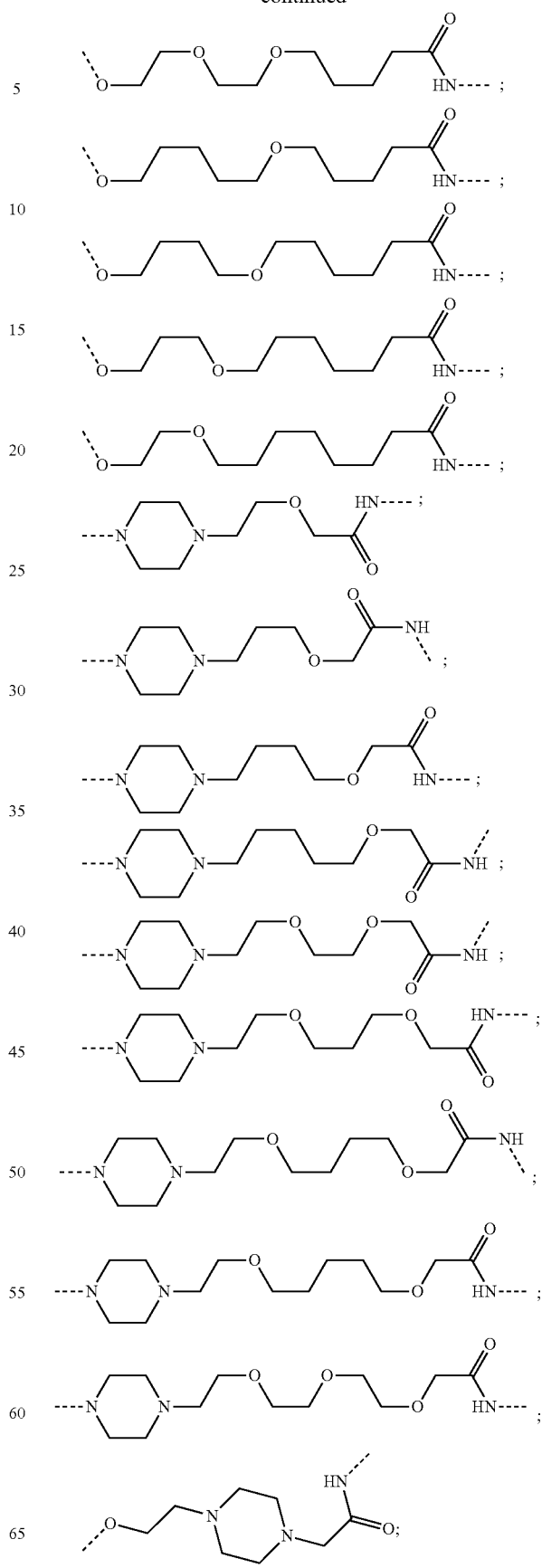

301
-continued
302
-continued
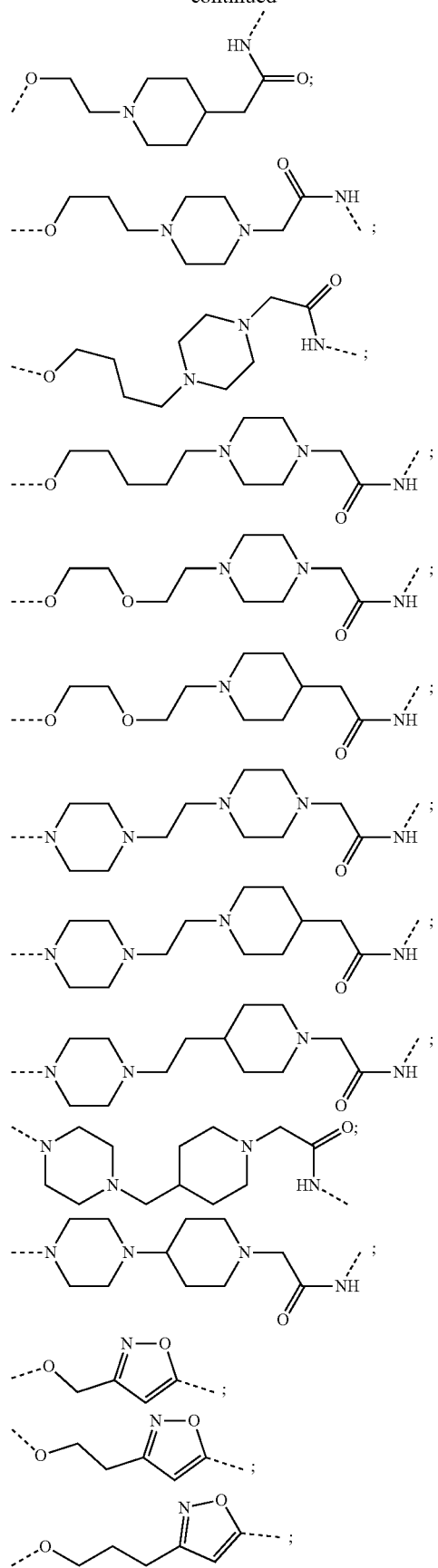
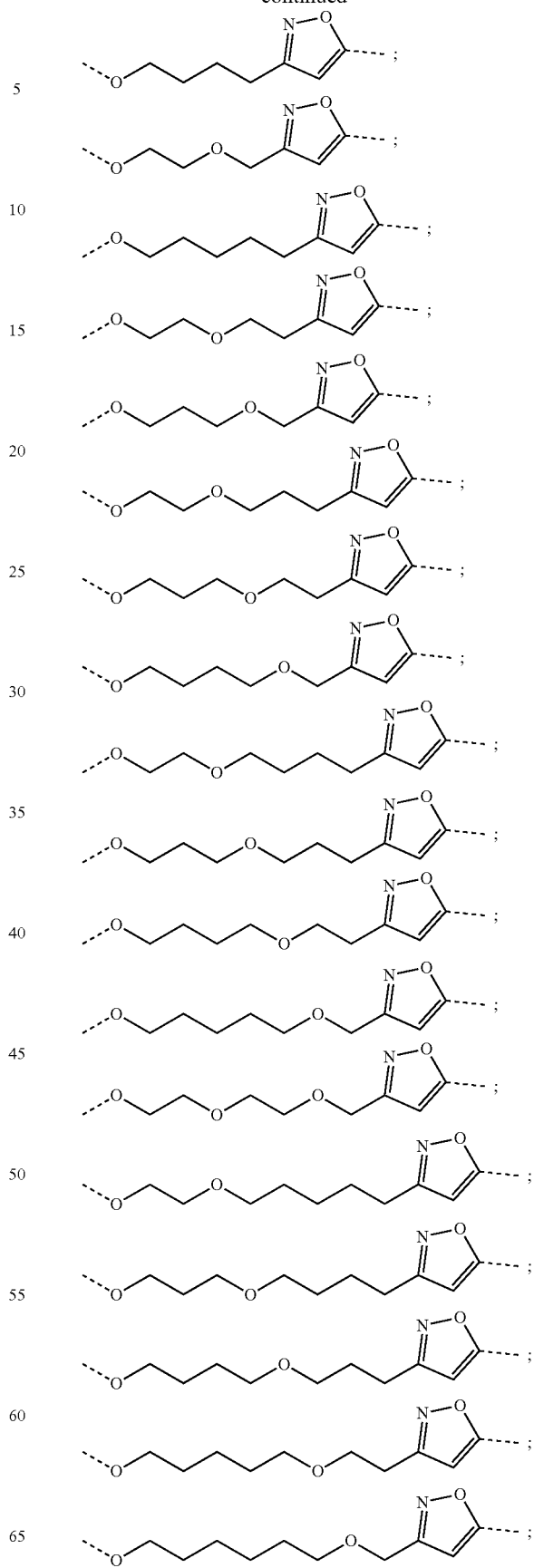

-continued

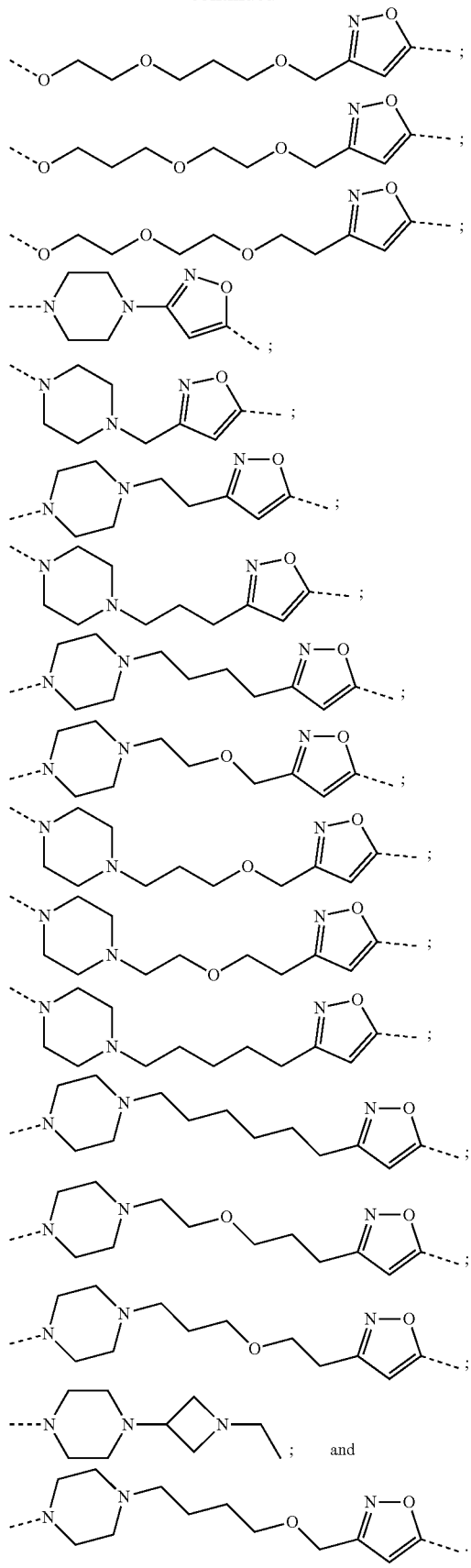

In additional embodiments, the linker (L) comprises a structure selected from, but not limited to the structure shown below, where a dashed line indicates the attachment point to the PTM or ULM moieties.

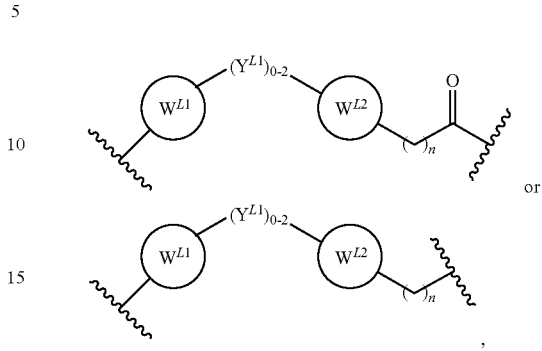

wherein:
$W^{L1}$ and $W^{L2}$ are each independently a 4-8 membered ring with 0-4 heteroatoms, optionally substituted with $R^Q$, each $R^Q$ is independently a H, halo, OH, CN, CF$_3$, C$_1$-C$_6$ alkyl (linear, branched, optionally substituted), C$_1$-C$_6$ alkoxy (linear, branched, optionally substituted), or 2 $R^Q$ groups taken together with the atom they are attached to, form a 4-8 membered ring system containing 0-4 heteroatoms;
$Y^{L1}$ is each independently a bond, C$_1$-C$_6$ alkyl (linear, branched, optionally substituted) and optionally one or more C atoms are replaced with O; or C$_1$-C$_6$ alkoxy (linear, branched, optionally substituted); and
n is 0-10; and
a dashed line indicates the attachment point to the PTM or ULM moieties.

In additional embodiments, the linker (L) comprises a structure selected from, but not limited to the structure shown below, where a dashed line indicates the attachment point to the PTM or ULM moieties.

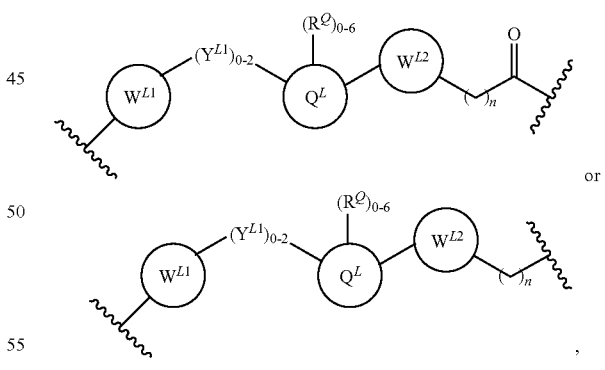

wherein:
$W^{L1}$ and $W^{L2}$ are each independently aryl, heteroaryl, cyclic, heterocyclic, C$_{1-6}$ alkyl, bicyclic, biaryl, biheteroaryl, or biheterocyclic, each optionally substituted with $R^Q$, each $R^Q$ is independently a H, halo, OH, CN, CF$_3$, hydroxyl, nitro, C≡CH, C$_{2-6}$ alkenyl, C$_{2-6}$ alkynyl, C$_1$-C$_6$ alkyl (linear, branched, optionally substituted), C$_1$-C$_6$ alkoxy (linear, branched, optionally substituted), OC$_{1-3}$alkyl (optionally substituted by 1 or more —F), OH, NH$_2$, NR$^{Y1}$R$^{Y2}$, CN, or 2 $R^Q$ groups taken together with the atom they are attached to, form a 4-8 membered ring system containing 0-4 heteroatoms;

$Y^{L1}$ is each independently a bond, $NR^{YL1}$, O, S, $NR^{YL2}$, $CR^{YL1}R^{YL2}$, C=O, C=S, SO, $SO_2$, $C_1$-$C_6$alkyl (linear, branched, optionally substituted) and optionally one or more C atoms are replaced with O; $C_1$-$C_6$ alkoxy (linear, branched, optionally substituted);

$Q^L$ is a 3-6 membered alicyclic or aromatic ring with 0-4 heteroatoms, optionally bridged, optionally substituted with 0-6 $R^Q$, each $R^Q$ is independently H, $C_{1-6}$ alkyl (linear, branched, optionally substituted by 1 or more halo, $C_{1-6}$ alkoxyl), or 2 $R^Q$ groups taken together with the atom they are attached to, form a 3-8 membered ring system containing 0-2 heteroatoms);

$R^{YL1}$, $R^{YL2}$ are each independently H, OH, $C_{1-6}$ alkyl (linear, branched, optionally substituted by 1 or more halo, $C_{1-6}$ alkoxyl), or $R^1$, $R^2$ together with the atom they are attached to, form a 3-8 membered ring system containing 0-2 heteroatoms);

n is 0-10; and a dashed line indicates the attachment point to the PTM or ULM moieties.

In additional embodiments, the linker group is optionally substituted (poly)ethyleneglycol having between 1 and about 100 ethylene glycol units, between about 1 and about 50 ethylene glycol units, between 1 and about 25 ethylene glycol units, between about 1 and 10 ethylene glycol units, between 1 and about 8 ethylene glycol units and 1 and 6 ethylene glycol units, between 2 and 4 ethylene glycol units, or optionally substituted alkyl groups interdispersed with optionally substituted, O, N, S, P or Si atoms. In certain embodiments, the linker is substituted with an aryl, phenyl, benzyl, alkyl, alkylene, or heterocycle group. In certain embodiments, the linker may be asymmetric or symmetrical.

In any of the embodiments of the compounds described herein, the linker group may be any suitable moiety as described herein. In one embodiment, the linker is a substituted or unsubstituted polyethylene glycol group ranging in size from about 1 to about 12 ethylene glycol units, between 1 and about 10 ethylene glycol units, about 2 about 6 ethylene glycol units, between about 2 and 5 ethylene glycol units, between about 2 and 4 ethylene glycol units.

In another embodiment, the present disclosure is directed to a compound which comprises a PTM group as described above, which binds to a target protein or polypeptide (e.g., Estrogen Receptor), which is ubiquitinated by an ubiquitin ligase and is chemically linked directly to the ULM group or through a linker moiety L, or PTM is alternatively a ULM' group which is also a ubiquitin ligase binding moiety, which may be the same or different than the ULM group as described above and is linked directly to the ULM group directly or through the linker moiety; and L is a linker moiety as described above which may be present or absent and which chemically (covalently) links ULM to PTM, or a pharmaceutically acceptable salt, enantiomer, stereoisomer, solvate or polymorph thereof.

In certain embodiments, the linker group L is a group comprising one or more covalently connected structural units independently selected from the group consisting of:

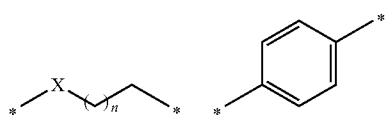

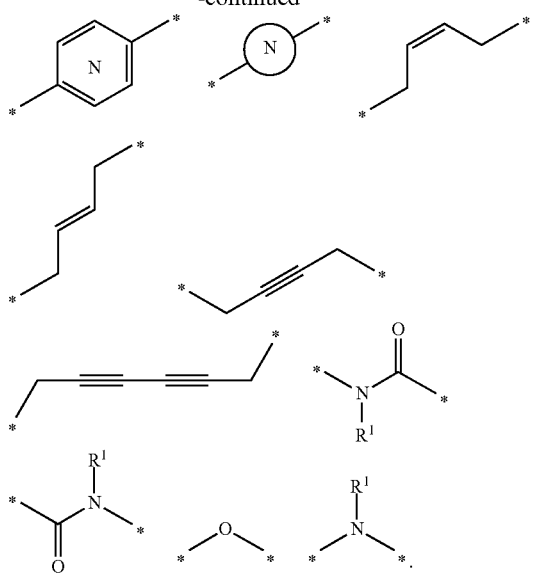

The X is selected from the group consisting of O, N, S, S(O) and $SO_2$; n is integer from 1 to 5; $R^{L1}$ is hydrogen or alkyl,

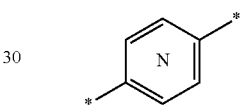

is a mono- or bicyclic aryl or heteroaryl optionally substituted with 1-3 substituents selected from alkyl, halogen, haloalkyl, hydroxy, alkoxy or cyano;

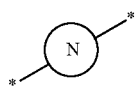

is a mono- or bicyclic cycloalkyl or a heterocycloalkyl optionally substituted with 1-3 substituents selected from alkyl, halogen, haloalkyl, hydroxy, alkoxy or cyano; and the phenyl ring fragment can be optionally substituted with 1, 2 or 3 substituents selected from the group consisting of alkyl, halogen, haloalkyl, hydroxy, alkoxy and cyano. In an embodiment, the linker group L comprises up to 10 covalently connected structural units, as described above.

Although the ULM group and PTM group may be covalently linked to the linker group through any group which is appropriate and stable to the chemistry of the linker, in preferred aspects of the present disclosure, the linker is independently covalently bonded to the ULM group and the PTM group preferably through an amide, ester, thioester, keto group, carbamate (urethane), carbon or ether, each of which groups may be inserted anywhere on the ULM group and PTM group to provide maximum binding of the ULM group on the ubiquitin ligase and the PTM group on the target protein to be degraded. (It is noted that in certain aspects where the PTM group is a ULM group, the target protein for degradation may be the ubiquitin ligase itself). In certain preferred aspects, the linker may be linked to an optionally substituted alkyl, alkylene, alkene or alkyne group, an aryl group or a heterocyclic group on the ULM and/or PTM groups.

Exemplary PTMs

In preferred aspects of the disclosure, the PTM group is a group, which binds to target proteins. Targets of the PTM group are numerous in kind and are selected from proteins that are expressed in a cell such that at least a portion of the sequences is found in the cell and may bind to a PTM group. The term "protein" includes oligopeptides and polypeptide sequences of sufficient length that they can bind to a PTM group according to the present disclosure. Any protein in a eukaryotic system or a microbial system, including a virus, bacteria or fungus, as otherwise described herein, are targets for ubiquitination mediated by the compounds according to the present disclosure. Preferably, the target protein is a eukaryotic protein.

PTM groups according to the present disclosure include, for example, any moiety which binds to a protein specifically (binds to a target protein) and includes the following non-limiting examples of small molecule target protein moieties: Hsp90 inhibitors, selective estrogen receptor modulators, kinase inhibitors, HDM2 & MDM2 inhibitors, compounds targeting Human BET Bromodomain-containing proteins, HDAC inhibitors, human lysine methyltransferase inhibitors, angiogenesis inhibitors, nuclear hormone receptor compounds, immunosuppressive compounds, and compounds targeting the aryl hydrocarbon receptor (AHR), among numerous others. The compositions described below exemplify some of the members of small molecule target protein binding moieties. Such small molecule target protein binding moieties also include pharmaceutically acceptable salts, enantiomers, solvates and polymorphs of these compositions, as well as other small molecules that may target a protein of interest. These binding moieties are linked to the ubiquitin ligase binding moiety preferably through a linker in order to present a target protein (to which the protein target moiety is bound) in proximity to the ubiquitin ligase for ubiquitination and degradation.

Any protein, which can bind to a protein target moiety or PTM group and acted on or degraded by an ubiquitin ligase is a target protein according to the present disclosure. In general, target proteins may include, for example, structural proteins, receptors, enzymes, cell surface proteins, proteins pertinent to the integrated function of a cell, including proteins involved in catalytic activity, aromatase activity, motor activity, helicase activity, metabolic processes (anabolism and catabolism), antioxidant activity, proteolysis, biosynthesis, proteins with kinase activity, oxidoreductase activity, transferase activity, hydrolase activity, lyase activity, isomerase activity, ligase activity, enzyme regulator activity, signal transducer activity, structural molecule activity, binding activity (protein, lipid carbohydrate), receptor activity, cell motility, membrane fusion, cell communication, regulation of biological processes, development, cell differentiation, response to stimulus, behavioral proteins, cell adhesion proteins, proteins involved in cell death, proteins involved in transport (including protein transporter activity, nuclear transport, ion transporter activity, channel transporter activity, carrier activity, permease activity, secretion activity, electron transporter activity, pathogenesis, chaperone regulator activity, nucleic acid binding activity, transcription regulator activity, extracellular organization and biogenesis activity, translation regulator activity. Proteins of interest can include proteins from eukaryotes and prokaryotes including humans as targets for drug therapy, other animals, including domesticated animals, microbials for the determination of targets for antibiotics and other antimicrobials and plants, and even viruses, among numerous others.

The present disclosure may be used to treat a number of disease states and/or conditions, including any disease state and/or condition in which proteins are dysregulated and where a patient would benefit from the degradation and/or inhibition of proteins.

In an additional aspect, the description provides therapeutic compositions comprising an effective amount of a compound as described herein or salt form thereof, and a pharmaceutically acceptable carrier, additive or excipient, and optionally an additional bioactive agent. The therapeutic compositions modulate protein degradation and/or inhibition in a patient or subject, for example, an animal such as a human, and can be used for treating or ameliorating disease states or conditions which are modulated through the degraded/inhibited protein. In certain embodiments, the therapeutic compositions as described herein may be used to effectuate the degradation of proteins of interest for the treatment or amelioration of a disease, e.g., cancer. In certain additional embodiments, the disease is at least one of breast cancer, uterine cancer, ovarian cancer, prostate cancer, endometrial cancer, endometriosis, or a combination thereof.

In alternative aspects, the present disclosure relates to a method for treating a disease state or ameliorating the symptoms of a disease or condition in a subject in need thereof by degrading a protein or polypeptide through which a disease state or condition is modulated comprising administering to said patient or subject an effective amount, e.g., a therapeutically effective amount, of at least one compound as described hereinabove, optionally in combination with a pharmaceutically acceptable carrier, additive or excipient, and optionally an additional bioactive agent, wherein the composition is effective for treating or ameliorating the disease or disorder or symptom thereof in the subject. The method according to the present disclosure may be used to treat a large number of disease states or conditions including cancer, by virtue of the administration of effective amounts of at least one compound described herein. The disease state or condition may be a disease caused by a microbial agent or other exogenous agent such as a virus, bacteria, fungus, protozoa or other microbe or may be a disease state, which is caused by overexpression of a protein, which leads to a disease state and/or condition.

In another aspect, the description provides methods for identifying the effects of the degradation of proteins of interest in a biological system using compounds according to the present disclosure.

The term "target protein" is used to describe a protein or polypeptide, which is a target for binding to a compound according to the present disclosure and degradation by ubiquitin ligase hereunder. Such small molecule target protein binding moieties also include pharmaceutically acceptable salts, enantiomers, solvates and polymorphs of these compositions, as well as other small molecules that may target a protein of interest. These binding moieties are linked to at least one ULM group (e.g. VHL, CLM, ILM, and/or MLM) through at least one linker group L.

Target proteins, which may be bound to the protein target moiety and degraded by the ligase to which the ubiquitin ligase binding moiety is bound, include any protein or peptide, including fragments thereof, analogues thereof, and/or homologues thereof. Target proteins include proteins and peptides having any biological function or activity including structural, regulatory, hormonal, enzymatic, genetic, immunological, contractile, storage, transportation, and signal transduction. More specifically, a number of drug targets for human therapeutics represent protein targets to which protein target moiety may be bound and incorporated into compounds according to the present disclosure. These include proteins which may be used to restore function in numerous polygenic diseases, including for example B7.1 and B7, TINFR1m, TNFR2, NADPH oxidase, BclIBax and other partners in the apotosis pathway, C5a receptor, HMG-CoA reductase, PDE V phosphodiesterase type, PDE IV phosphodiesterase type 4, PDE I, PDEII, PDEIII, squalene cyclase inhibitor, CXCR1, CXCR2, nitric oxide (NO) synthase, cyclo-oxygenase 1, cyclo-oxygenase 2, 5HT receptors, dopamine receptors, G Proteins, i.e., Gq, histamine receptors, 5-lipoxygenase, tryptase serine protease, thymidylate synthase, purine nucleoside phosphorylase, GAPDH trypanosomal, glycogen phosphorylase, Carbonic anhydrase, chemokine receptors, JAW STAT, RXR and similar, HIV 1 protease, HIV 1 integrase, influenza, neuramimidase, hepatitis B reverse transcriptase, sodium channel, multi drug resistance (MDR), protein P-glycoprotein (and MRP), tyrosine kinases, CD23, CD124, tyrosine kinase p56 lck, CD4, CD5, IL-2 receptor, IL-1 receptor, TNF-alphaR, ICAM1, Cat+ channels, VCAM, VLA-4 integrin, selectins, CD40/CD40L, newokinins and receptors, inosine monophosphate dehydrogenase, p38 MAP Kinase, Ras1Raf1MEWERK pathway, interleukin-1 converting enzyme, caspase, HCV, NS3 protease, HCV NS3 RNA helicase, glycinamide ribonucleotide formyl transferase, rhinovirus 3C protease, herpes simplex virus-1 (HSV-I), protease, cytomegalovirus (CMV) protease, poly (ADP-ribose) polymerase, cyclin dependent kinases, vascular endothelial growth factor, oxytocin receptor, microsomal transfer protein inhibitor, bile acid transport inhibitor, 5 alpha reductase inhibitors, angiotensin 11, glycine receptor, noradrenaline reuptake receptor, endothelin receptors, neuropeptide Y and receptor, estrogen receptor (ER), androgen receptors, adenosine receptors, adenosine kinase and AMP deaminase, purinergic receptors (P2Y1, P2Y2, P2Y4, P2Y6, P2X1-7), farnesyltransferases, geranylgeranyl transferase, TrkA a receptor for NGF, beta-amyloid, tyrosine kinase Flk-IIKDR, vitronectin receptor, integrin receptor, Her-21 neu, telomerase inhibition, cytosolic phospholipaseA2 and EGF receptor tyrosine kinase. Additional protein targets include, for example, ecdysone 20-monooxygenase, ER, ion channel of the GABA gated chloride channel, acetylcholinesterase, voltage-sensitive sodium channel protein, calcium release channel, and chloride channels. Still further target proteins include Acetyl-CoA carboxylase, adenylosuccinate synthetase, protoporphyrinogen oxidase, and enolpyruvylshikimate-phosphate synthase.

These various protein targets may be used in screens that identify compound moieties which bind to the protein and by incorporation of the moiety into compounds according to the present disclosure, the level of activity of the protein may be altered for therapeutic end result.

The term "protein target moiety" or PTM is used to describe a small molecule which binds to a target protein or other protein or polypeptide of interest and places/presents that protein or polypeptide in proximity to a ubiquitin ligase, such that degradation of the protein or polypeptide by ubiquitin ligase may occur. Non-limiting examples of small molecule target protein binding moieties include selective estrogen receptor modulators, Hsp90 inhibitors, kinase inhibitors, MDM2 inhibitors, compounds targeting Human BET Bromodomain-containing proteins, HDAC inhibitors, human lysine methyltransferase inhibitors, angiogenesis inhibitors, immunosuppressive compounds, and compounds targeting the aryl hydrocarbon receptor (AHR), among numerous others. The compositions described below exemplify some of the members of the small molecule target proteins.

Exemplary protein target moieties according to the present disclosure include, haloalkane halogenase inhibitors, selective estrogen receptor modulators, Hsp90 inhibitors, kinase inhibitors, MDM2 inhibitors, compounds targeting Human BET Bromodomain-containing proteins, HDAC inhibitors, human lysine methyltransferase inhibitors, angiogenesis inhibitors, immunosuppressive compounds, and compounds targeting the aryl hydrocarbon receptor (AHR).

The compositions described herein exemplify some of the members of these types of small molecule target protein binding moieties. Such small molecule target protein binding moieties also include pharmaceutically acceptable salts, enantiomers, solvates and polymorphs of these compositions, as well as other small molecules that may target a protein of interest. References which are cited herein below are incorporated by reference herein in their entirety.

In any embodiment or aspect described herein, the PTM may be represented by the Formula PTM-I:

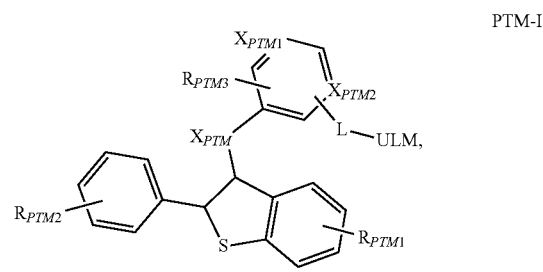

PTM-I wherein:
$X_{PTM}$ is 0 or C=O;
each of $X_{PTM1}$ and $X_{PTM2}$ is independently selected from N or CH;
$R_{PTM1}$ is independently selected from OH, O(CO)$R_{PTM}$, O-lower alkyl, wherein $R_{PTM}$ is an alkyl or aryl group in the ester;
at least one $R_{PTM2}$, each independently selected from H, OH, halogen, CN, CF$_3$, SO$_2$-alkyl, O-lower alkyl;
at least one $R_{PTM3}$, each independently selected from H, halogen;
ULM is an E3 ligase binding moiety as described herein; and
L is a bond or a linker moiety as described herein.

In any embodiment or aspect described herein, the PTM may be represented by the Formula PTM-I:

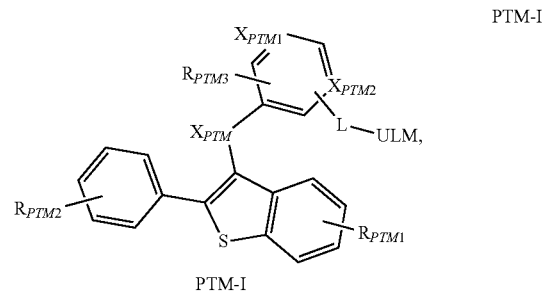

PTM-I wherein:
$X_{PTM}$ is O or C=O;
each of $X_{PTM1}$ and $X_{PTM2}$ is independently selected from N or CH;
$R_{PTM1}$ is independently selected from OH, O(CO)$R_{PTM}$, O-lower alkyl, wherein $R_{PTM}$ is an alkyl or aryl group in the ester;
each $R_{PTM2}$ is independently selected from H, OH, halogen, CN, $CF_3$, $SO_2$-alkyl, O-lower alkyl;
each $R_{PTM3}$ is independently selected from H, halogen;
ULM is an E3 ligase binding moiety as described herein;
L is a bond or a linker moiety as described herein;
the PTM-I comprises as least one of $R_{PTM2}$, at least one $R_{PTM3}$, or a combination thereof on the respective rings.

In any embodiment or aspect described herein, PTM-I has at least one of: two $R_{PTM2}$, two $R_{PTM3}$, or a combination thereof.

In any embodiment or aspect described herein, the PTM may be represented by the Formula PTM-II:

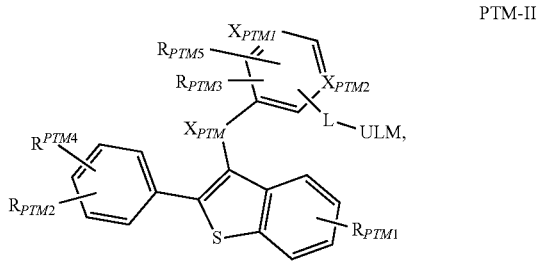

PTM-II wherein:
$X_{PTM}$ is O or C=O;
each of $X_{PTM1}$ and $X_{PTM2}$ is independently selected from N or CH;
$R_{PTM1}$ is independently selected from OH, O(CO)$R_{PTM}$, O-lower alkyl, wherein $R_{PTM}$ is an alkyl or aryl group in the ester;
$R_{PTM2}$ and $R_{PTM4}$ are independently selected from H, OH, halogen, CN, $CF_3$, $SO_2$-alkyl, O-lower alkyl;
$R_{PTM3}$ and $R_{PTM5}$ are independently selected from H, halogen;
ULM is an E3 ligase binding moiety as described herein; and
L is a bond or a linker moiety as described herein.

In certain embodiments, O(CO)$R_{PTM}$ functions as a prodrug of the corresponding phenol in Formula PTM-I or PTM-II.

In any embodiment or aspect described herein, the O-lower alkyl of PTM-I or PTM-II an alkyl chain with carbon number 1 to 3.

Therapeutic Compositions

Pharmaceutical compositions comprising combinations of an effective amount of at least one bifunctional compound as described herein, and one or more of the compounds otherwise described herein, all in effective amounts, in combination with a pharmaceutically effective amount of a carrier, additive or excipient, represents a further aspect of the present disclosure.

The present disclosure includes, where applicable, the compositions comprising the pharmaceutically acceptable salts, in particular, acid or base addition salts of compounds as described herein. The acids which are used to prepare the pharmaceutically acceptable acid addition salts of the aforementioned base compounds useful according to this aspect are those which form non-toxic acid addition salts, i.e., salts containing pharmacologically acceptable anions, such as the hydrochloride, hydrobromide, hydroiodide, nitrate, sulfate, bisulfate, phosphate, acid phosphate, acetate, lactate, citrate, acid citrate, tartrate, bitartrate, succinate, maleate, fumarate, gluconate, saccharate, benzoate, methanesulfonate, ethanesulfonate, benzenesulfonate, p-toluenesulfonate and pamoate [i.e., 1,1'-methylene-bis-(2-hydroxy-3 naphthoate)]salts, among numerous others.

Pharmaceutically acceptable base addition salts may also be used to produce pharmaceutically acceptable salt forms of the compounds or derivatives according to the present disclosure. The chemical bases that may be used as reagents to prepare pharmaceutically acceptable base salts of the present compounds that are acidic in nature are those that form non-toxic base salts with such compounds. Such non-toxic base salts include, but are not limited to those derived from such pharmacologically acceptable cations such as alkali metal cations (e.g., potassium and sodium) and alkaline earth metal cations (e.g., calcium, zinc and magnesium), ammonium or water-soluble amine addition salts such as N-methylglucamine-(meglumine), and the lower alkanolammonium and other base salts of pharmaceutically acceptable organic amines, among others.

The compounds as described herein may, in accordance with the disclosure, be administered in single or divided doses by the oral, parenteral or topical routes. Administration of the active compound may range from continuous (intravenous drip) to several oral administrations per day (for example, Q.I.D.) and may include oral, topical, parenteral, intramuscular, intravenous, sub-cutaneous, transdermal (which may include a penetration enhancement agent), buccal, sublingual and suppository administration, among other routes of administration. Enteric coated oral tablets may also be used to enhance bioavailability of the compounds from an oral route of administration. The most effective dosage form will depend upon the pharmacokinetics of the particular agent chosen as well as the severity of disease in the patient. Administration of compounds according to the present disclosure as sprays, mists, or aerosols for intra-nasal, intra-tracheal or pulmonary administration may also be used. The present disclosure therefore also is directed to pharmaceutical compositions comprising an effective amount of compound as described herein, optionally in combination with a pharmaceutically acceptable carrier, additive or excipient. Compounds according to the present disclosure may be administered in immediate release, intermediate release or sustained or controlled release forms. Sustained or controlled release forms are preferably administered orally, but also in suppository and transdermal or other topical forms. Intramuscular injections in liposomal form may also be used to control or sustain the release of compound at an injection site.

The compositions as described herein may be formulated in a conventional manner using one or more pharmaceutically acceptable carriers and may also be administered in controlled-release formulations. Pharmaceutically acceptable carriers that may be used in these pharmaceutical compositions include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as prolamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

The compositions as described herein may be administered orally, parenterally, by inhalation spray, topically, rectally, nasally, buccally, vaginally or via an implanted reservoir. The term "parenteral" as used herein includes subcutaneous, intravenous, intramuscular, intra-articular, intra-synovial, intrasternal, intrathecal, intrahepatic, intralesional and intracranial injection or infusion techniques. Preferably, the compositions are administered orally, intraperitoneally or intravenously.

Sterile injectable forms of the compositions as described herein may be aqueous or oleaginous suspension. These suspensions may be formulated according to techniques known in the art using suitable dispersing or wetting agents and suspending agents. The sterile injectable preparation may also be a sterile injectable solution or suspension in a non-toxic parenterally-acceptable diluent or solvent, for example as a solution in 1, 3-butanediol. Among the acceptable vehicles and solvents that may be employed are water, Ringer's solution and isotonic sodium chloride solution. In addition, sterile, fixed oils are conventionally employed as a solvent or suspending medium. For this purpose, any bland fixed oil may be employed including synthetic mono- or di-glycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as Ph. Helv or similar alcohol.

The pharmaceutical compositions as described herein may be orally administered in any orally acceptable dosage form including, but not limited to, capsules, tablets, aqueous suspensions or solutions. In the case of tablets for oral use, carriers which are commonly used include lactose and corn starch. Lubricating agents, such as magnesium stearate, are also typically added. For oral administration in a capsule form, useful diluents include lactose and dried corn starch. When aqueous suspensions are required for oral use, the active ingredient is combined with emulsifying and suspending agents. If desired, certain sweetening, flavoring or coloring agents may also be added.

Alternatively, the pharmaceutical compositions as described herein may be administered in the form of suppositories for rectal administration. These can be prepared by mixing the agent with a suitable non-irritating excipient, which is solid at room temperature but liquid at rectal temperature and therefore will melt in the rectum to release the drug. Such materials include cocoa butter, beeswax and polyethylene glycols.

The pharmaceutical compositions as described herein may also be administered topically. Suitable topical formulations are readily prepared for each of these areas or organs. Topical application for the lower intestinal tract can be effected in a rectal suppository formulation (see above) or in a suitable enema formulation. Topically-acceptable transdermal patches may also be used.

For topical applications, the pharmaceutical compositions may be formulated in a suitable ointment containing the active component suspended or dissolved in one or more carriers. Carriers for topical administration of the compounds of this disclosure include, but are not limited to, mineral oil, liquid petrolatum, white petrolatum, propylene glycol, polyoxyethylene, polyoxypropylene compound, emulsifying wax and water. In certain preferred aspects of the disclosure, the compounds may be coated onto a stent which is to be surgically implanted into a patient in order to inhibit or reduce the likelihood of occlusion occurring in the stent in the patient.

Alternatively, the pharmaceutical compositions can be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2-octyldodecanol, benzyl alcohol and water.

For ophthalmic use, the pharmaceutical compositions may be formulated as micronized suspensions in isotonic, pH adjusted sterile saline, or, preferably, as solutions in isotonic, pH adjusted sterile saline, either with our without a preservative such as benzylalkonium chloride. Alternatively, for ophthalmic uses, the pharmaceutical compositions may be formulated in an ointment such as petrolatum.

The pharmaceutical compositions as described herein may also be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents.

The amount of compound in a pharmaceutical composition as described herein that may be combined with the carrier materials to produce a single dosage form will vary depending upon the host and disease treated, the particular mode of administration. Preferably, the compositions should be formulated to contain between about 0.05 milligram to about 750 milligrams or more, more preferably about 1 milligram to about 600 milligrams, and even more preferably about 10 milligrams to about 500 milligrams of active ingredient, alone or in combination with at least one other compound according to the present disclosure.

It should also be understood that a specific dosage and treatment regimen for any particular patient will depend upon a variety of factors, including the activity of the specific compound employed, the age, body weight, general health, sex, diet, time of administration, rate of excretion, drug combination, and the judgment of the treating physician and the severity of the particular disease or condition being treated.

A patient or subject in need of therapy using compounds according to the methods described herein can be treated by administering to the patient (subject) an effective amount of the compound according to the present disclosure including pharmaceutically acceptable salts, solvates or polymorphs, thereof optionally in a pharmaceutically acceptable carrier or diluent, either alone, or in combination with other known therapeutic agents as otherwise identified herein.

These compounds can be administered by any appropriate route, for example, orally, parenterally, intravenously, intradermally, subcutaneously, or topically, including transdermally, in liquid, cream, gel, or solid form, or by aerosol form.

The active compound is included in the pharmaceutically acceptable carrier or diluent in an amount sufficient to deliver to a patient a therapeutically effective amount for the desired indication, without causing serious toxic effects in the patient treated. A preferred dose of the active compound for all of the herein-mentioned conditions is in the range from about 10 ng/kg to 300 mg/kg, preferably 0.1 to 100 mg/kg per day, more generally 0.5 to about 25 mg per kilogram body weight of the recipient/patient per day. A typical topical dosage will range from 0.01-5% wt/wt in a suitable carrier.

The compound is conveniently administered in any suitable unit dosage form, including but not limited to one containing less than 1 mg, 1 mg to 3000 mg, preferably 5 to 500 mg of active ingredient per unit dosage form. An oral dosage of about 25-250 mg is often convenient.

The active ingredient is preferably administered to achieve peak plasma concentrations of the active compound of about 0.00001-30 mM, preferably about 0.1-30 µM. This may be achieved, for example, by the intravenous injection of a solution or formulation of the active ingredient, optionally in saline, or an aqueous medium or administered as a bolus of the active ingredient. Oral administration is also appropriate to generate effective plasma concentrations of active agent.

The concentration of active compound in the drug composition will depend on absorption, distribution, inactivation, and excretion rates of the drug as well as other factors known to those of skill in the art. It is to be noted that dosage values will also vary with the severity of the condition to be alleviated. It is to be further understood that for any particular subject, specific dosage regimens should be adjusted over time according to the individual need and the professional judgment of the person administering or supervising the administration of the compositions, and that the concentration ranges set forth herein are exemplary only and are not intended to limit the scope or practice of the claimed composition. The active ingredient may be administered at once, or may be divided into a number of smaller doses to be administered at varying intervals of time.

Oral compositions will generally include an inert diluent or an edible carrier. They may be enclosed in gelatin capsules or compressed into tablets. For the purpose of oral therapeutic administration, the active compound or its prodrug derivative can be incorporated with excipients and used in the form of tablets, troches, or capsules. Pharmaceutically compatible binding agents, and/or adjuvant materials can be included as part of the composition.

The tablets, pills, capsules, troches and the like can contain any of the following ingredients, or compounds of a similar nature: a binder such as microcrystalline cellulose, gum tragacanth or gelatin; an excipient such as starch or lactose, a dispersing agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring. When the dosage unit form is a capsule, it can contain, in addition to material of the above type, a liquid carrier such as a fatty oil. In addition, dosage unit forms can contain various other materials which modify the physical form of the dosage unit, for example, coatings of sugar, shellac, or enteric agents.

The active compound or pharmaceutically acceptable salt thereof can be administered as a component of an elixir, suspension, syrup, wafer, chewing gum or the like. A syrup may contain, in addition to the active compounds, sucrose as a sweetening agent and certain preservatives, dyes and colorings and flavors.

The active compound or pharmaceutically acceptable salts thereof can also be mixed with other active materials that do not impair the desired action, or with materials that supplement the desired action, such as anti-cancer agents, among others. In certain preferred aspects of the disclosure, one or more compounds according to the present disclosure are coadministered with another bioactive agent, such as an anti-cancer agent or a would healing agent, including an antibiotic, as otherwise described herein.

Solutions or suspensions used for parenteral, intradermal, subcutaneous, or topical application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The parental preparation can be enclosed in ampoules, disposable syringes or multiple dose vials made of glass or plastic.

If administered intravenously, preferred carriers are physiological saline or phosphate buffered saline (PBS).

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art.

Liposomal suspensions may also be pharmaceutically acceptable carriers. These may be prepared according to methods known to those skilled in the art, for example, as described in U.S. Pat. No. 4,522,811 (which is incorporated herein by reference in its entirety). For example, liposome formulations may be prepared by dissolving appropriate lipid(s) (such as stearoyl phosphatidyl ethanolamine, stearoyl phosphatidyl choline, arachadoyl phosphatidyl choline, and cholesterol) in an inorganic solvent that is then evaporated, leaving behind a thin film of dried lipid on the surface of the container. An aqueous solution of the active compound are then introduced into the container. The container is then swirled by hand to free lipid material from the sides of the container and to disperse lipid aggregates, thereby forming the liposomal suspension.

Therapeutic Methods

In an additional aspect, the description provides therapeutic compositions comprising an effective amount of a compound as described herein or salt form thereof, and a pharmaceutically acceptable carrier. The therapeutic compositions modulate protein degradation in a patient or subject, for example, an animal such as a human, and can be used for treating or ameliorating disease states or conditions which are modulated through the degraded protein.

The terms "treat", "treating", and "treatment", etc., as used herein, refer to any action providing a benefit to a patient for which the present compounds may be administered, including the treatment of any disease state or condition which is modulated through the protein to which the present compounds bind. Disease states or conditions, including cancer, which may be treated using compounds according to the present disclosure are set forth hereinabove.

The description provides therapeutic compositions as described herein for effectuating the degradation of proteins of interest for the treatment or amelioration of a disease, e.g., cancer. In certain additional embodiments, the disease is breast cancer, uterine cancer, ovarian cancer, prostate cancer, endometrial cancer, endometriosis, or a combination thereof. As such, in another aspect, the description provides a method of ubiquitinating/degrading a target protein in a cell. In certain embodiments, the method comprises administering a bifunctional compound as described herein comprising, e.g., a ULM and a PTM, preferably linked through a linker moiety, as otherwise described herein, wherein the ULM is coupled to the PTM and wherein the ULM recognizes a ubiquitin pathway protein (e.g., an ubiquitin ligase, such as an E3 ubiquitin ligase including cereblon, VHL, IAP, and/or MDM2) and the PTM recognizes the target protein such that degradation of the target protein will occur when the target protein is placed in proximity to the ubiquitin ligase, thus resulting in degradation/inhibition of the effects of the target protein and the control of protein levels. The control of protein levels afforded by the present disclosure provides treatment of a disease state or condition, which is modulated through the target protein by lowering the level of that protein in the cell, e.g., cell of a patient. In certain embodiments, the method comprises administering an effective amount of a compound as described herein, optionally including a pharmaceutically acceptable excipient, carrier, adjuvant, another bioactive agent or combination thereof.

In additional embodiments, the description provides methods for treating or ameliorating a disease, disorder or symptom thereof in a subject or a patient, e.g., an animal such as a human, comprising administering to a subject in need thereof a composition comprising an effective amount, e.g., a therapeutically effective amount, of a compound as described herein or salt form thereof, and a pharmaceutically acceptable excipient, carrier, adjuvant, another bioactive agent or combination thereof, wherein the composition is effective for treating or ameliorating the disease or disorder or symptom thereof in the subject.

In another aspect, the description provides methods for identifying the effects of the degradation of proteins of interest in a biological system using compounds according to the present disclosure.

In another embodiment, the present disclosure is directed to a method of treating a human patient in need for a disease state or condition modulated through a protein where the degradation of that protein will produce a therapeutic effect in the patient, the method comprising administering to a patient in need an effective amount of a compound according to the present disclosure, optionally in combination with another bioactive agent. The disease state or condition may be a disease caused by a microbial agent or other exogenous agent such as a virus, bacteria, fungus, protozoa or other microbe or may be a disease state, which is caused by overexpression of a protein, which leads to a disease state and/or condition The term "disease state or condition" is used to describe any disease state or condition wherein protein dysregulation (i.e., the amount of protein expressed in a patient is elevated) occurs and where degradation of one or more proteins in a patient may provide beneficial therapy or relief of symptoms to a patient in need thereof. In certain instances, the disease state or condition may be cured.

Disease states or conditions which may be treated using compounds according to the present disclosure include, for example, asthma, autoimmune diseases such as multiple sclerosis, various cancers, ciliopathies, cleft palate, diabetes, heart disease, hypertension, inflammatory bowel disease, mental retardation, mood disorder, obesity, refractive error, infertility, Angelman syndrome, Canavan disease, Coeliac disease, Charcot-Marie-Tooth disease, Cystic fibrosis, Duchenne muscular dystrophy, Haemochromatosis, Haemophilia, Klinefelter's syndrome, Neurofibromatosis, Phenylketonuria, Polycystic kidney disease, (PKD1) or 4 (PKD2) Prader-Willi syndrome, Sickle-cell disease, Tay-Sachs disease, Turner syndrome.

The term "neoplasia" or "cancer" is used throughout the specification to refer to the pathological process that results in the formation and growth of a cancerous or malignant neoplasm, i.e., abnormal tissue that grows by cellular proliferation, often more rapidly than normal and continues to grow after the stimuli that initiated the new growth cease. Malignant neoplasms show partial or complete lack of structural organization and functional coordination with the normal tissue and most invade surrounding tissues, metastasize to several sites, and are likely to recur after attempted removal and to cause the death of the patient unless adequately treated. As used herein, the term neoplasia is used to describe all cancerous disease states and embraces or encompasses the pathological process associated with malignant hematogenous, ascitic and solid tumors. Exemplary cancers which may be treated by the present compounds either alone or in combination with at least one additional anti-cancer agent include squamous-cell carcinoma, basal cell carcinoma, adenocarcinoma, hepatocellular carcinomas, and renal cell carcinomas, cancer of the bladder, bowel, breast, cervix, colon, esophagus, head, kidney, liver, lung, neck, ovary, pancreas, prostate, and stomach; leukemias; benign and malignant lymphomas, particularly Burkitt's lymphoma and Non-Hodgkin's lymphoma; benign and malignant melanomas; myeloproliferative diseases; sarcomas, including Ewing's sarcoma, hemangiosarcoma, Kaposi's sarcoma, liposarcoma, myosarcomas, peripheral neuroepithelioma, synovial sarcoma, gliomas, astrocytomas, oligodendrogliomas, ependymomas, gliobastomas, neuroblastomas, ganglioneuromas, gangliogliomas, medulloblastomas, pineal cell tumors, meningiomas, meningeal sarcomas, neurofibromas, and Schwannomas; bowel cancer, breast cancer, prostate cancer, cervical cancer, uterine cancer, lung cancer, ovarian cancer, testicular cancer, thyroid cancer, astrocytoma, esophageal cancer, pancreatic cancer, stomach cancer, liver cancer, colon cancer, melanoma; carcinosarcoma, Hodgkin's disease, Wilms' tumor and teratocarcinomas. Additional cancers which may be treated using compounds according to the present disclosure include, for example, T-lineage Acute lymphoblastic Leukemia (T-ALL), T-lineage lymphoblastic Lymphoma (T-LL), Peripheral T-cell lymphoma, Adult T-cell Leukemia, Pre-B ALL, Pre-B Lymphomas, Large B-cell Lymphoma, Burkitts Lymphoma, B-cell ALL, Philadelphia chromosome positive ALL and Philadelphia chromosome positive CML.

The term "bioactive agent" is used to describe an agent, other than a compound according to the present disclosure, which is used in combination with the present compounds as an agent with biological activity to assist in effecting an intended therapy, inhibition and/or prevention/prophylaxis for which the present compounds are used. Preferred bioactive agents for use herein include those agents which have pharmacological activity similar to that for which the present compounds are used or administered and include for example, anti-cancer agents, antiviral agents, especially including anti-HIV agents and anti-HCV agents, antimicrobial agents, antifungal agents, etc.

The term "additional anti-cancer agent" is used to describe an anti-cancer agent, which may be combined with compounds according to the present disclosure to treat cancer. These agents include, for example, everolimus, trabectedin, abraxane, TLK 286, AV-299, DN-101, pazopanib, GSK690693, RTA 744, ON 0910.Na, AZD 6244 (ARRY-142886), AMN-107, TKI-258, GSK461364, AZD 1152, enzastaurin, vandetanib, ARQ-197, MK-0457, MLN8054, PHA-739358, R-763, AT-9263, a FLT-3 inhibitor, a VEGFR inhibitor, an EGFR TK inhibitor, an aurora kinase inhibitor, a PIK-1 modulator, a Bcl-2 inhibitor, an HDAC inhbitor, a c-MET inhibitor, a PARP inhibitor, a Cdk inhibitor, an EGFR TK inhibitor, an IGFR-TK inhibitor, an anti-HGF antibody, a PI3 kinase inhibitor, an AKT inhibitor, an mTORC1/2 inhibitor, a JAK/STAT inhibitor, a checkpoint-1 or 2 inhibitor, a focal adhesion kinase inhibitor, a Map kinase kinase (mek) inhibitor, a VEGF trap antibody, pemetrexed, erlotinib, dasatanib, nilotinib, decatanib, panitumumab, amrubicin, oregovomab, Lep-etu, nolatrexed, azd2171, batabulin, ofatumumab, zanolimumab, edotecarin, tetrandrine, rubitecan, tesmilifene, oblimersen, ticilimumab, ipilimumab, gossypol, Bio 111, 131-I-TM-601, ALT-110, BIO 140, CC 8490, cilengitide, gimatecan, IL13-PE38QQR, INO 1001, IPdR$_1$ KRX-0402, lucanthone, LY317615, neuradiab, vitespan, Rta 744, Sdx 102, talampanel, atrasentan, Xr 311, romidepsin, ADS-100380, sunitinib, 5-fluorouracil, vorinostat, etoposide, gemcitabine, doxorubicin, liposomal doxorubicin, 5'-deoxy-5-fluorouridine, vincristine, temozolomide, ZK-304709, seliciclib; PD0325901, AZD-6244, capecitabine, L-Glutamic acid, N-[4-[2-(2-amino-4,7-dihydro-4-oxo-1H-pyrrolo[2,3-d]pyrimidin-5-yl)ethyl]benzoyl]-, disodium salt, heptahydrate, camptothecin, PEG-labeled irinotecan, tamoxifen, toremifene citrate, anastrazole, exemestane, letrozole, DES (diethylstilbestrol), estradiol, estrogen, conjugated estrogen, bevacizumab, IMC-1C11, CHIR-258); 3-[5-(methylsulfonylpiperadinemethyl)-indolyl-quinolone, vatalanib, AG-013736, AVE-0005, goserelin acetate, leuprolide acetate, triptorelin pamoate, medroxyprogesterone acetate, hydroxyprogesterone caproate, megestrol acetate, raloxifene, bicalutamide, flutamide, nilutamide, megestrol acetate, CP-724714; TAK-165, HKI-272, erlotinib, lapatanib, canertinib, ABX-EGF antibody, erbitux, EKB-569, PKI-166, GW-572016, lonafarnib, BMS-214662, tipifarnib; amifostine, NVP-LAQ824, suberoyl analide hydroxamic acid, valproic acid, trichostatin A, FK-228, SU11248, sorafenib, KRN951, aminoglutethimide, arnsacrine, anagrelide, L-asparaginase, *Bacillus* Calmette-Guerin (BCG) vaccine, adriamycin, bleomycin, buserelin, busulfan, carboplatin, carmustine, chlorambucil, cisplatin, cladribine, clodronate, cyproterone, cytarabine, dacarbazine, dactinomycin, daunorubicin, diethylstilbestrol, epirubicin, fludarabine, fludrocortisone, fluoxymesterone, flutamide, gleevec, gemcitabine, hydroxyurea, idarubicin, ifosfamide, imatinib, leuprolide, levamisole, lomustine, mechlorethamine, melphalan, 6-mercaptopurine, mesna, methotrexate, mitomycin, mitotane, mitoxantrone, nilutamide, octreotide, oxaliplatin, pamidronate, pentostatin, plicamycin, porfimer, procarbazine, raltitrexed, rituximab, streptozocin, teniposide, testosterone, thalidomide, thioguanine, thiotepa, tretinoin, vindesine, 13-cis-retinoic acid, phenylalanine mustard, uracil mustard, estramustine, altretamine, floxuridine, 5-deooxyuridine, cytosine arabinoside, 6-mecaptopurine, deoxycoformycin, calcitriol, valrubicin, mithramycin, vinblastine, vinorelbine, topotecan, razoxin, marimastat, COL-3, neovastat, BMS-275291, squalamine, endostatin, SU5416, SU6668, EMD121974, interleukin-12, IM862, angiostatin, vitaxin, droloxifene, idoxyfene, spironolactone, finasteride, cimitidine, trastuzumab, denileukin diftitox, gefitinib, bortezimib, paclitaxel, cremophor-free paclitaxel, docetaxel, epithilone B, BMS-247550, BMS-310705, droloxifene, 4-hydroxytamoxifen, pipendoxifene, ERA-923, arzoxifene, fulvestrant, acolbifene, lasofoxifene, idoxifene, TSE-424, HMR-3339, ZK186619, topotecan, PTK787/ZK 222584, VX-745, PD 184352, rapamycin, 40-O-(2-hydroxyethyl)-rapamycin, temsirolimus, AP-23573, RAD001, ABT-578, BC-210, LY294002, LY292223, LY292696, LY293684, LY293646, wortmannin, ZM336372, L-779, 450, PEG-filgrastim, darbepoetin, erythropoietin, granulocyte colony-stimulating factor, zolendronate, prednisone, cetuximab, granulocyte macrophage colony-stimulating factor, histrelin, pegylated interferon alfa-2a, interferon alfa-2a, pegylated interferon alfa-2b, interferon alfa-2b, azacitidine, PEG-L-asparaginase, lenalidomide, gemtuzumab, hydrocortisone, interleukin-11, dexrazoxane, alemtuzumab, all-transretinoic acid, ketoconazole, interleukin-2, megestrol, immune globulin, nitrogen mustard, methylprednisolone, ibritgumomab tiuxetan, androgens, decitabine, hexamethylmelamine, bexarotene, tositumomab, arsenic trioxide, cortisone, editronate, mitotane, cyclosporine, liposomal daunorubicin, Edwina-asparaginase, strontium 89, casopitant, netupitant, an NK-1 receptor antagonist, palonosetron, aprepitant, diphenhydramine, hydroxyzine, metoclopramide, lorazepam, alprazolam, haloperidol, droperidol, dronabinol, dexamethasone, methylprednisolone, prochlorperazine, granisetron, ondansetron, dolasetron, tropisetron, pegfilgrastim, erythropoietin, epoetin alfa, darbepoetin alfa and mixtures thereof.

The term "anti-HIV agent" or "additional anti-HIV agent" includes, for example, nucleoside reverse transcriptase inhibitors (NRTI), other non-nucloeoside reverse transcriptase inhibitors (i.e., those which are not representative of the present disclosure), protease inhibitors, fusion inhibitors, among others, exemplary compounds of which may include, for example, 3TC (Lamivudine), AZT (Zidovudine), (−)-FTC, ddI (Didanosine), ddC (zalcitabine), abacavir (ABC), tenofovir (PMPA), D-D4FC (Reverset), D4T (Stavudine), Racivir, L-FddC, L-FD4C, NVP (Nevirapine), DLV (Delavirdine), EFV (Efavirenz), SQVM (Saquinavir mesylate), RTV (Ritonavir), IDV (Indinavir), SQV (Saquinavir), NFV (Nelfinavir), APV (Amprenavir), LPV (Lopinavir), fusion inhibitors such as T20, among others, fuseon and mixtures thereof, including anti-HIV compounds presently in clinical trials or in development.

Other anti-HIV agents which may be used in coadministration with compounds according to the present disclosure include, for example, other NNRTI's (i.e., other than the NNRTI's according to the present disclosure) may be selected from the group consisting of nevirapine (BI-R6-587), delavirdine (U-90152S/T), efavirenz (DMP-266), UC-781 (N-[4-chloro-3-(3-methyl-2-butenyloxy)phenyl]-2methyl3-furancarbothiamide), etravirine (TMC125), Trovirdine (Ly300046.HCl), MKC-442 (emivirine, coactinon), HI-236, HI-240, HI-280, HI-281, rilpivirine (TMC-278), MSC-127, HBY 097, DMP266, Baicalin (TJN-151) ADAM-II (Methyl 3',3'-dichloro-4',4"-dimethoxy-5',5"-bis(methoxycarbonyl)-6,6-diphenylhexenoate), Methyl 3-Bromo-5-(1-5-bromo-4-methoxy-3-(methoxycarbonyl) phenyl)hept-1-enyl)-2-methoxybenzoate (Alkenyldiarylmethane analog, Adam analog), (5-chloro-3-(phenylsulfinyl)-2'-indolecarboxamide), AAP-BHAP (U-104489 or PNU-104489), Capravirine (AG-1549, S-1153), atevirdine (U-87201E), aurin tricarboxylic acid (SD-095345), 1-[(6-cyano-2-indolyl)carbonyl]-4-[3-(isopropylamino)-2-pyridinyl]piperazine, 1-[5-[[N-(methyl)methylsulfonylamino]-2-indolylcarbonyl-4-[3-(isopropylamino)-2-pyridinyl] piperazine, 1-[3-(Ethylamino)-2-[pyridinyl]-4-[(5-hydroxy-2-indolyl)carbonyl]piperazine, 1-[(6-Formyl-2-indolyl) carbonyl]-4-[3-(isopropylamino)-2-pyridinyl]piperazine, 1-[[5-(Methylsulfonyloxy)-2-indoyly)carbonyl]-4-[3-(isopropylamino)-2-pyridinyl]piperazine, U88204E, Bis(2-nitrophenyl)sulfone (NSC 633001), Calanolide A (NSC675451), Calanolide B, 6-Benzyl-5-methyl-2-(cyclohexyloxy)pyrimidin-4-one (DABO-546), DPC 961, E-EBU, E-EBU-dm, E-EPSeU, E-EPU, Foscarnet (Foscavir), HEPT (1-[(2-Hydroxyethoxy)methyl]-6-(phenylthio)thymine), HEPT-M (1-[(2-Hydroxyethoxy)methyl]-6-(3-methylphenyl)thio)thymine), HEPT-S(1-[(2-Hydroxyethoxy)methyl]-6-(phenylthio)-2-thiothymine), Inophyllum P, L-737,126, Michellamine A (NSC650898), Michellamine B (NSC649324), Michellamine F, 6-(3,5-Dimethylbenzyl)-1-[(2-hydroxyethoxy)methyl]-5-isopropyluracil, 6-(3,5-Dimethylbenzyl)-1-(ethyoxymethyl)-5-isopropyluracil, NPPS, E-BPTU (NSC 648400), Oltipraz (4-Methyl-5-(pyrazinyl)-3H-1,2-dithiole-3-thione), N-{2-(2-Chloro-6-fluorophenethyl]-N'-(2-thiazolyl)thiourea (PETT Cl, F derivative), N-{2-(2,6-Difluorophenethyl]-N'-[2-(5-bromopyridyl)]thiourea {PETT derivative), N-{2-(2,6-Difluorophenethyl]-N'-[2-(5-methylpyridyl)]thiourea {PETT Pyridyl derivative), N-[2-(3-Fluorofuranyl)ethyl]-N'-[2-(5-chloropyridyl)]thiourea, N-[2-(2-Fluoro-6-ethoxyphenethyl)]-N'-[2-(5-bromopyridyl)]thiourea, N-(2-Phenethyl)-N'-(2-thiazolyl)thiourea (LY-73497), L-697,639, L-697,593, L-697,661, 3-[2-(4,7-Difluorobenzoxazol-2-yl)ethyl}-5-ethyl-6-methyl (pypridin-2(1H)-thione (2-Pyridinone Derivative), 3-[[(2-Methoxy-5,6-dimethyl-3-pyridyl)methyl]amine]-5-ethyl-6-methyl(pypridin-2(1H)-thione, R82150, R82913, R87232, R88703, R89439 (Loviride), R90385, S-2720, Suramin Sodium, TBZ (Thiazolobenzimidazole, NSC 625487), Thiazoloisoindol-5-one, (+)(R)-9b-(3,5-Dimethylphenyl-2,3-dihydrothiazolo[2,3-a]isoindol-5(9bH)-one, Tivirapine (R86183), UC-38 and UC-84, among others.

The term "pharmaceutically acceptable salt" is used throughout the specification to describe, where applicable, a salt form of one or more of the compounds described herein which are presented to increase the solubility of the compound in the gastic juices of the patient's gastrointestinal tract in order to promote dissolution and the bioavailability of the compounds. Pharmaceutically acceptable salts include those derived from pharmaceutically acceptable inorganic or organic bases and acids, where applicable. Suitable salts include those derived from alkali metals such as potassium and sodium, alkaline earth metals such as calcium, magnesium and ammonium salts, among numerous other acids and bases well known in the pharmaceutical art. Sodium and potassium salts are particularly preferred as neutralization salts of the phosphates according to the present disclosure.

The term "pharmaceutically acceptable derivative" is used throughout the specification to describe any pharmaceutically acceptable prodrug form (such as an ester, amide other prodrug group), which, upon administration to a patient, provides directly or indirectly the present compound or an active metabolite of the present compound.

General Synthetic Approach

The synthetic realization and optimization of the bifunctional molecules as described herein may be approached in a step-wise or modular fashion. For example, identification of compounds that bind to the target molecules can involve high or medium throughput screening campaigns if no suitable ligands are immediately available. It is not unusual for initial ligands to require iterative design and optimization cycles to improve suboptimal aspects as identified by data from suitable in vitro and pharmacological and/or ADMET assays. Part of the optimization/SAR campaign would be to probe positions of the ligand that are tolerant of substitution and that might be suitable places on which to attach the linker chemistry previously referred to herein. Where crystallographic or NMR structural data are available, these can be used to focus such a synthetic effort.

In a very analogous way one can identify and optimize ligands for an E3 Ligase, i.e. ULMs/ILMs/VLMs/CLMs/ILMs.

With PTMs and ULMs (e.g. ILMs, VLMs, CLMs, and/or ILMs) in hand, one skilled in the art can use known synthetic methods for their combination with or without a linker moiety. Linker moieties can be synthesized with a range of compositions, lengths and flexibility and functionalized such that the PTM and ULM groups can be attached sequentially to distal ends of the linker. Thus a library of bifunctional molecules can be realized and profiled in in vitro and in vivo pharmacological and ADMET/PK studies. As with the PTM and ULM groups, the final bifunctional molecules can be subject to iterative design and optimization cycles in order to identify molecules with desirable properties.

In some instances, protecting group strategies and/or functional group interconversions (FGIs) may be required to facilitate the preparation of the desired materials. Such chemical processes are well known to the synthetic organic chemist and many of these may be found in texts such as "Greene's Protective Groups in Organic Synthesis" Peter G. M. Wuts and Theodora W. Greene (Wiley), and "Organic Synthesis: The Disconnection Approach" Stuart Warren and Paul Wyatt (Wiley).

Protein Level Control

This description also provides methods for the control of protein levels with a cell. This is based on the use of compounds as described herein, which are known to interact with a specific target protein such that degradation of a target protein in vivo will result in the control of the amount of protein in a biological system, preferably to a particular therapeutic benefit.

The following examples are used to assist in describing the present disclosure, but should not be seen as limiting the present disclosure in any way.

General Synthetic Approach

The synthetic realization and optimization of the bifunctional molecules as described herein may be approached in a step-wise or modular fashion. For example, identification of compounds that bind to the target molecules can involve high or medium throughput screening campaigns if no suitable ligands are immediately available. It is not unusual for initial ligands to require iterative design and optimization cycles to improve suboptimal aspects as identified by data from suitable in vitro and pharmacological and/or ADMET assays. Part of the optimization/SAR campaign would be to probe positions of the ligand that are tolerant of substitution and that might be suitable places on which to attach the linker chemistry previously referred to herein. Where crystallographic or NMR structural data are available, these can be used to focus such a synthetic effort.

In a very analogous way one can identify and optimize ligands for an E3 Ligase, i.e. ULMs/VLMs/CLMs/ILMs/MLMs.

With PTMs and ULMs (e.g. VLMs, CLMs, ILMs, and/or MLMs) in hand, one skilled in the art can use known synthetic methods for their combination with or without a linker moiety. Linker moieties can be synthesized with a range of compositions, lengths and flexibility and functionalized such that the PTM and ULM groups can be attached sequentially to distal ends of the linker. Thus, a library of bifunctional molecules can be realized and profiled in vitro and in vivo pharmacological and ADMET/PK studies. As with the PTM and ULM groups, the final bifunctional molecules can be subject to iterative design and optimization cycles in order to identify molecules with desirable properties.

Compounds of the present disclosure [e.g., the general Formula PTM-I or PTM-II] may be prepared by methods known in the art of organic synthesis as set forth in the specific Examples described herein. In all of the methods, it is well understood that protecting groups for sensitive or reactive groups may be employed where necessary in accordance with general principles of chemistry. Protecting groups are manipulated according to standard methods of organic synthesis (T. W. Green and P. G. M. Wuts (1999) Protective Groups in Organic Synthesis, 3$^{rd}$ edition, John Wiley & Sons). These groups are removed at a convenient stage of the compound synthesis using methods that are readily apparent to those skilled in the art. The selection of processes as well as the reaction conditions and order of their execution shall be consistent with the preparation of compounds of the present disclosure, including compounds of Formula (I). Schemes described below illustrate the general methods of preparing compounds with the structure featured as Formula (I) and Formula (II).

ABBREVIATIONS

ACN: acetonitrile
ADDP: 1,1'-(azodicarbonyl)dipiperidine
BOP: (Benzotriazole-1-yloxy)tris(dimethylamino)phosphonium hexafluorophosphate
DCE: 1,2-dichloroethane
DCM: dichloromethane
DEAD: diethyl azodicarboxylate
DIEA or DIPEA: N,N-diisopropylethylamine
DMA: N,N-dimethylacetamide
DME: Dimethoxyethane
DMF: N,N-dimethylformamide
DMP: Dess-Martin periodinane
ES$^+$: electron spary with positive charge
h: hour.
HATU: 2-(7-aza-1H-benzotriazole-1-yl)-1,1,3,3-tetramethyluronium hexafluorophosphate.
HPLC: high-performance liquid chromatography
LC-MS: liquid chromatography-mass spectrometry
Min: minutes.
NBS: N-bromosuccinimide
NMP: N-methylpyrrolidone
NMR: Nuclear magnetic resonance
RT or t$_R$: retention time
SFC: supercritical fluid chromatography
TBAC: tetrabutylammonium chloride
TCCA: Trichloroisocyanuric acid
TFA: trifluoroacetic acid.
THF: tetrahydrofuran.
TEMPO: 2,2,6,6-tetramethylpiperidine-N-oxide
XPhos: 2-dicyclohexylphosphino-2' 4'6'-triisopropylbiphenyl General Conditions and Analytical Methods All solvents used were commercially acquired and were used without further purification. Reactions were typically run using anhydrous solvents under an inert atmosphere of nitrogen. Flash column chromatography was generally carried out using Silica gel 60 (0.035-0.070 mm particle size).

The synthesis of the claimed compounds can be carried out according to the following schemes. Synthetic routes in these schemes are described as the representative methods. Other methods can also be used for those skilled in the art of synthesis.

General Synthetic Scheme 1 to Prepare Intermediates

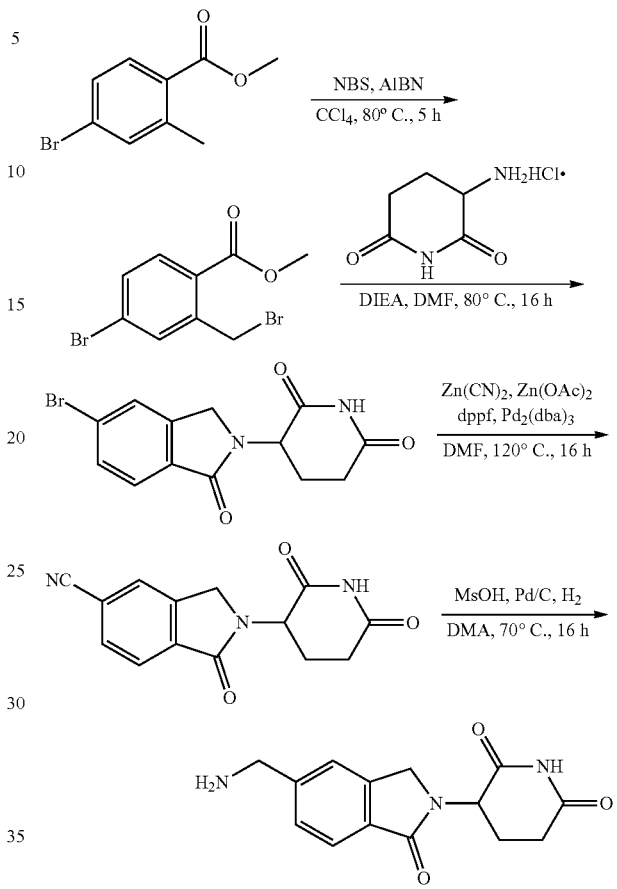

General Synthetic Scheme 2 to Prepare Intermediates

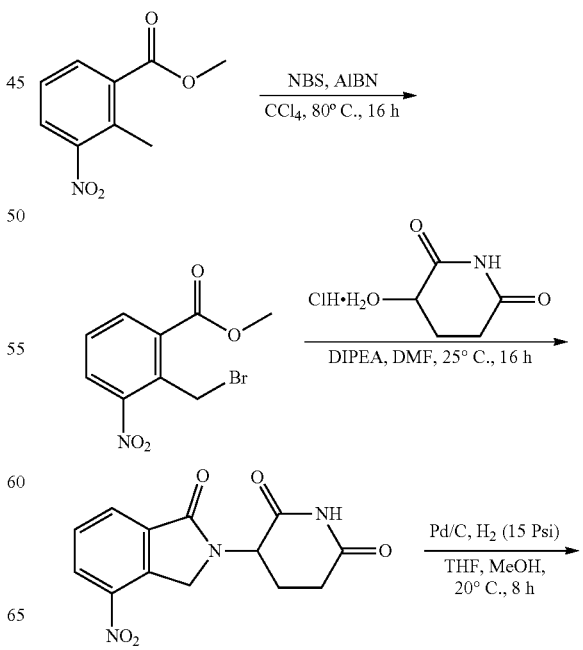

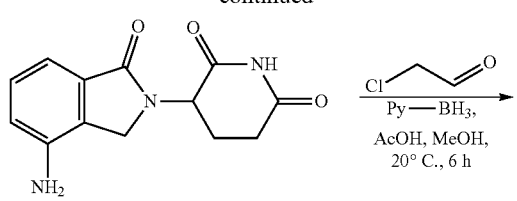
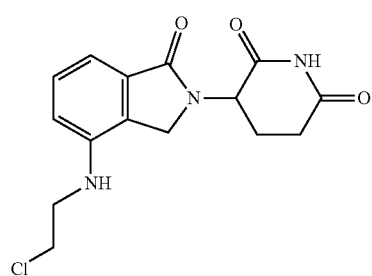
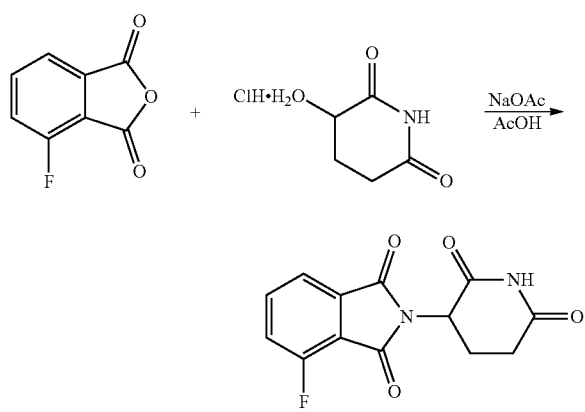
General Synthetic Scheme 3 to Prepare Intermediates
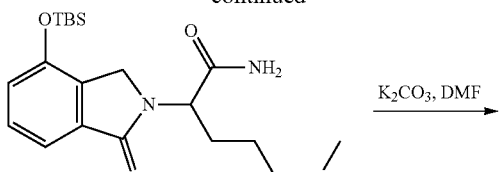
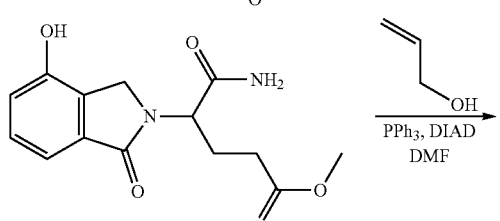
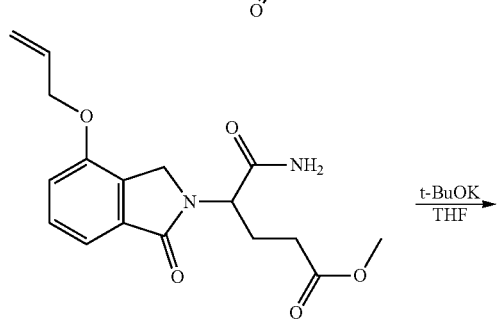
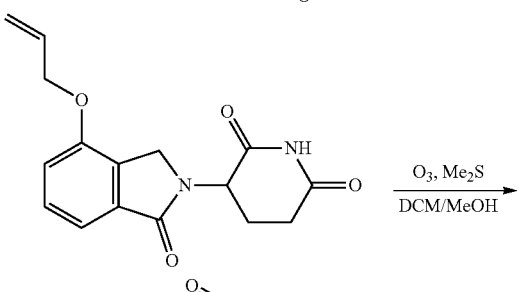
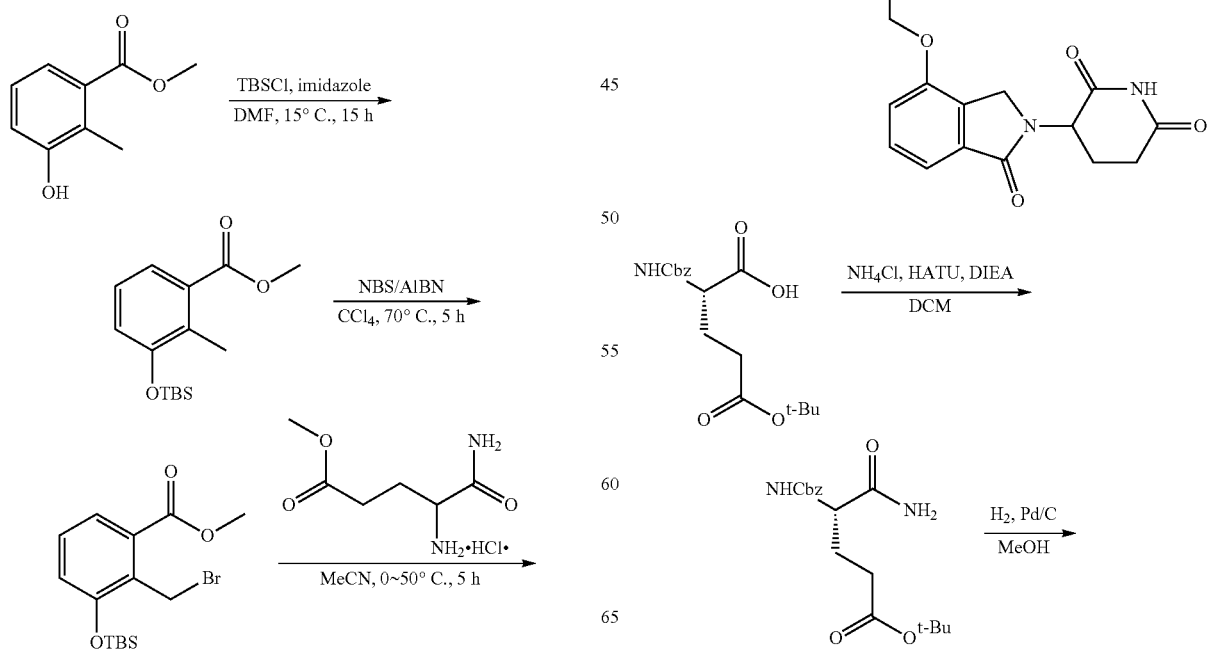

327
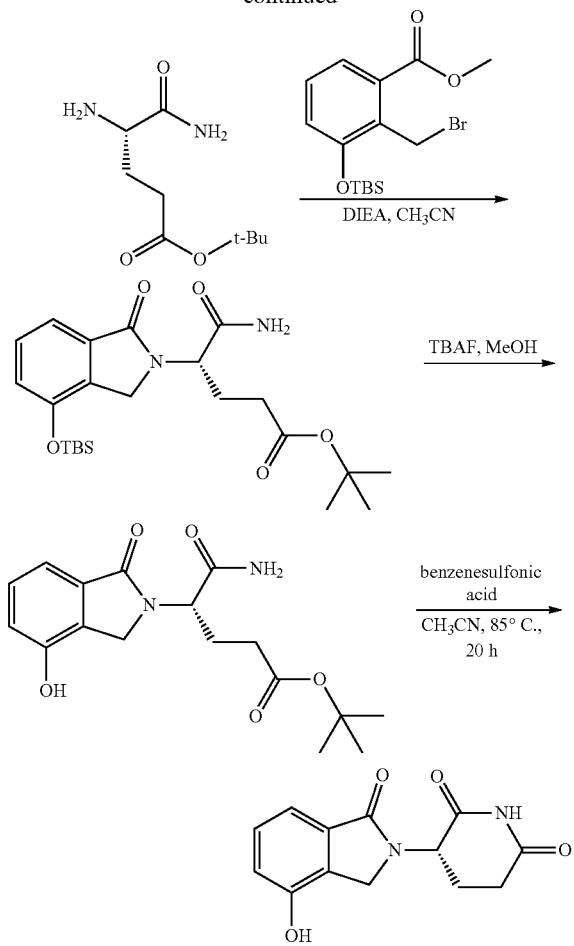
General Synthetic Scheme 4 to Prepare Intermediates
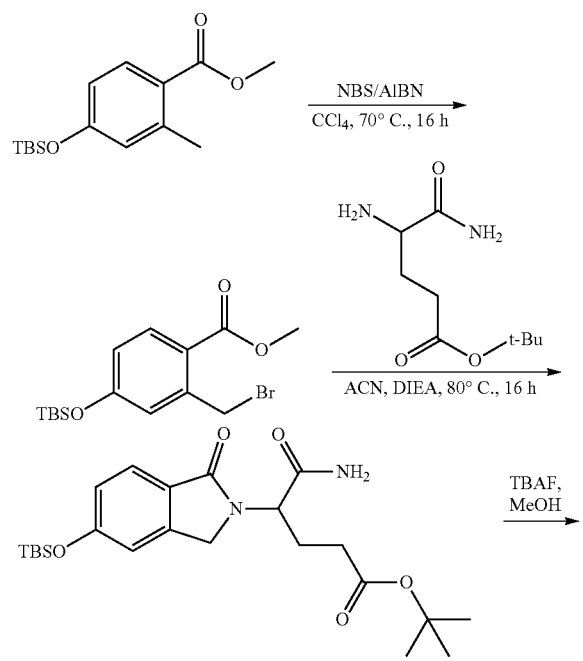
328
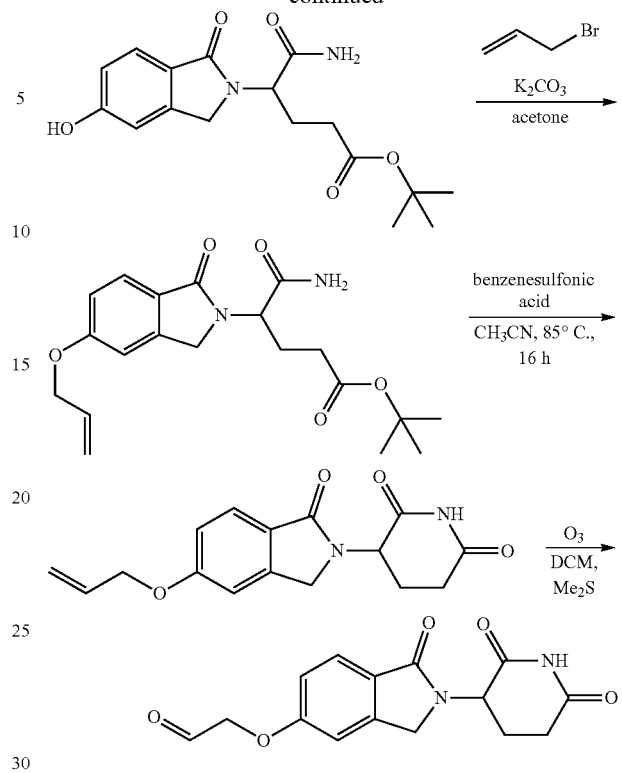
General Synthetic Scheme 5 to Prepare Intermediates
General Synthetic Scheme 6 to Prepare Intermediates
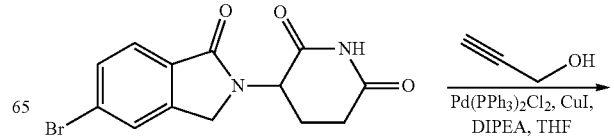

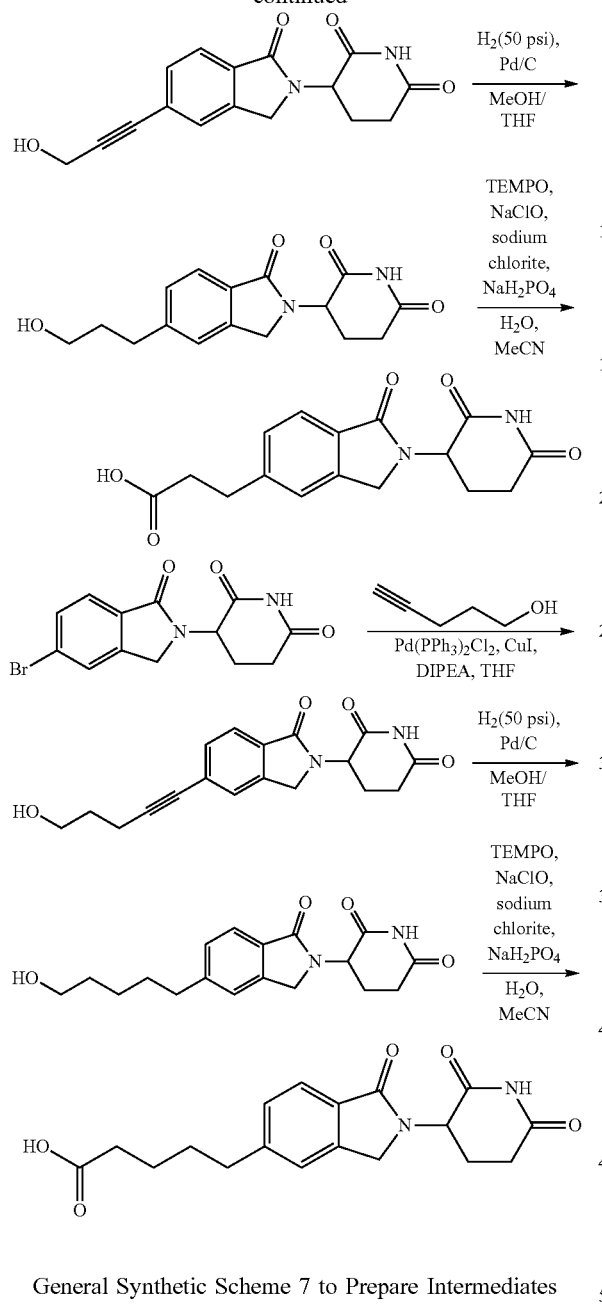
General Synthetic Scheme 7 to Prepare Intermediates
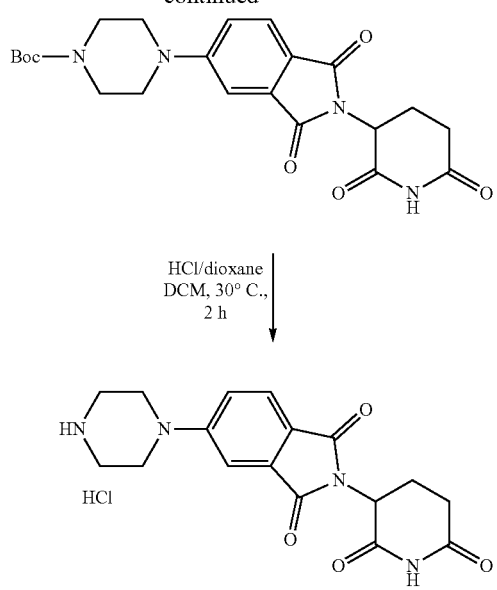
General Synthetic Scheme 8 to Prepare Intermediates 331
-continued
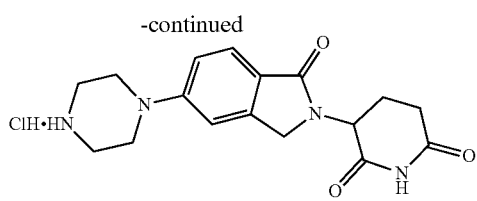
General Synthetic Scheme 9 to Prepare Intermediates
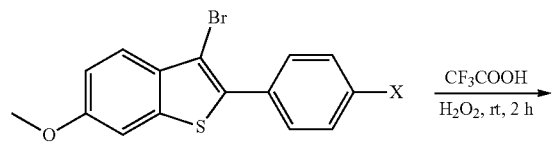
332
-continued
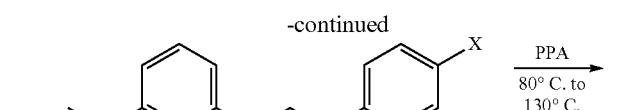
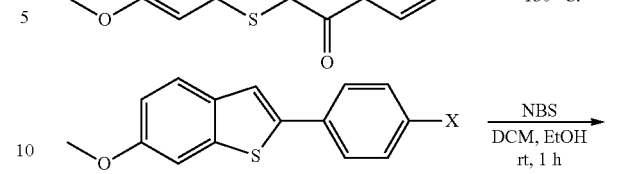
X = H, F, Cl, Br, OCH₃
General Synthetic Scheme 10 to Prepare Intermediates
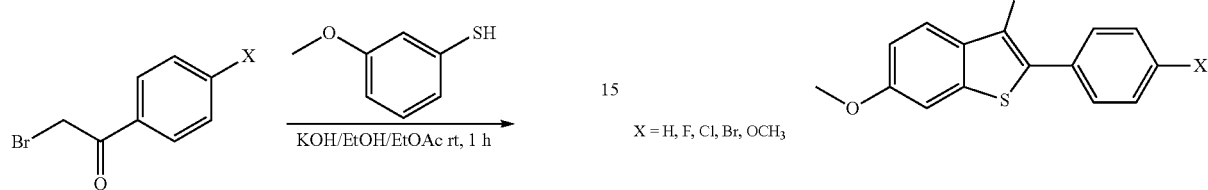
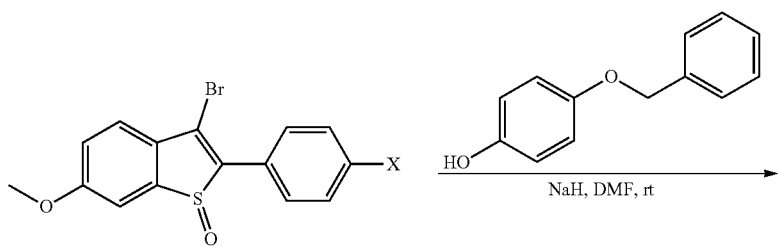
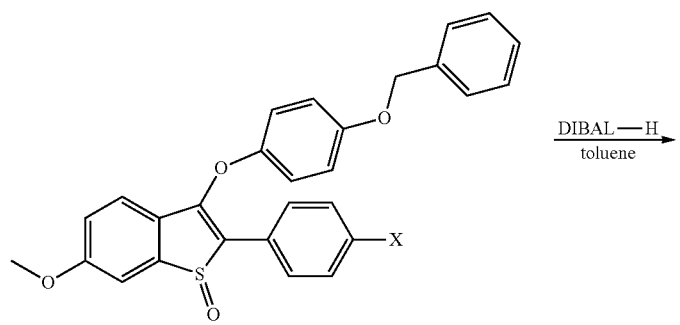
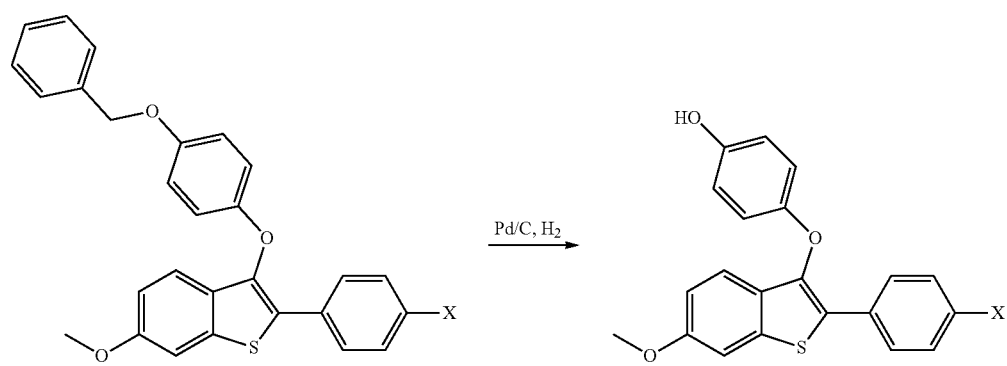
X = H, F, O-alkyl, CF₃

General Synthetic Scheme 11 to Prepare Intermediates
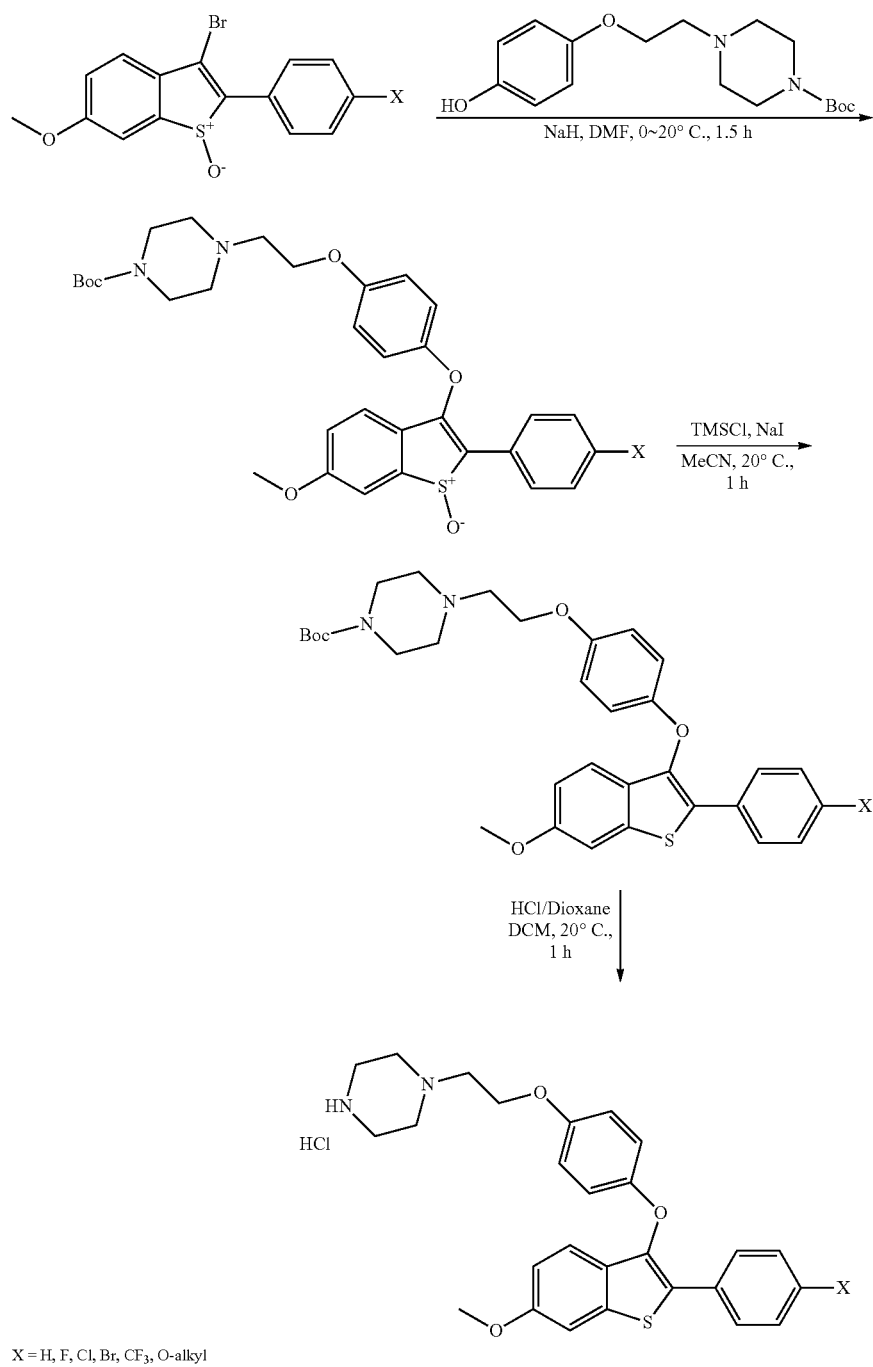
X = H, F, Cl, Br, CF$_3$, O-alkyl
General Synthetic Scheme 12 to Prepare Intermediates
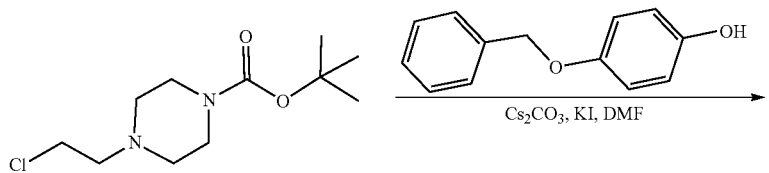

-continued
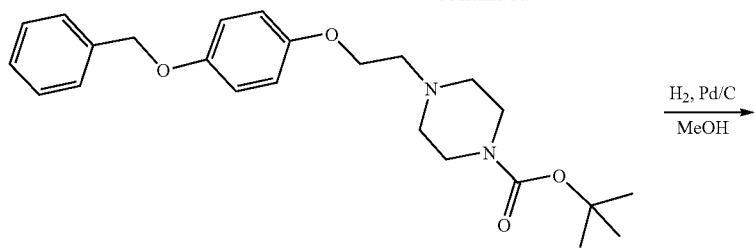
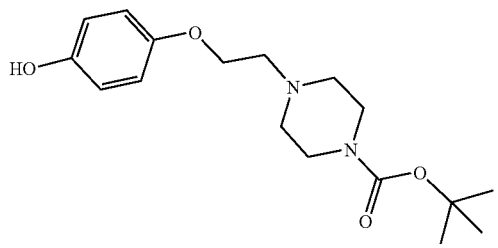
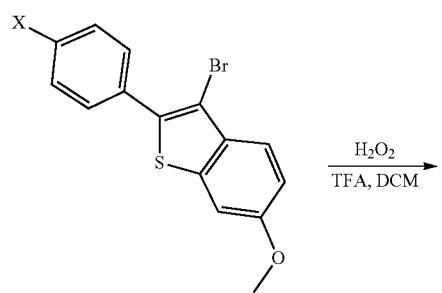
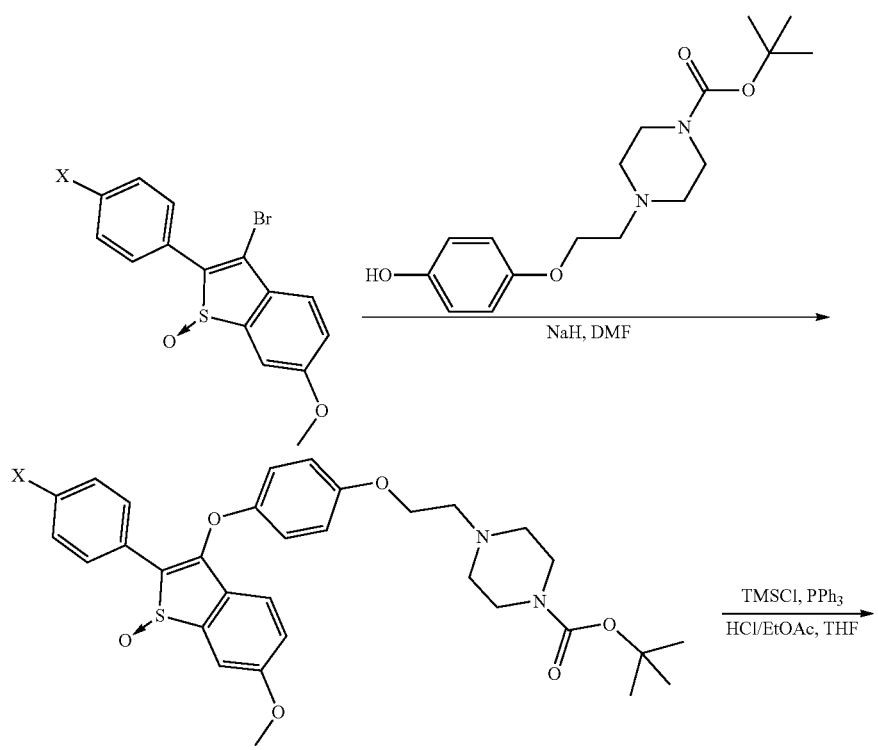

-continued
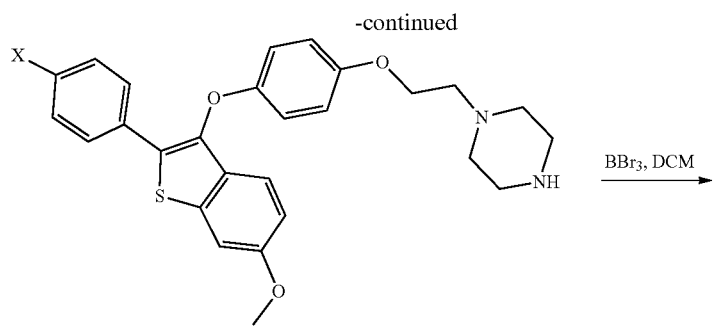
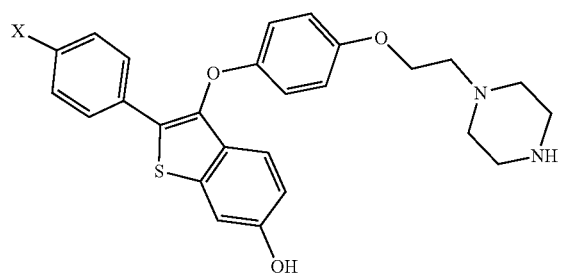
X = H, F, Cl, Br, CF₃, O-alkyl
X = H, F, Cl, Br, CF₃, O-alkyl
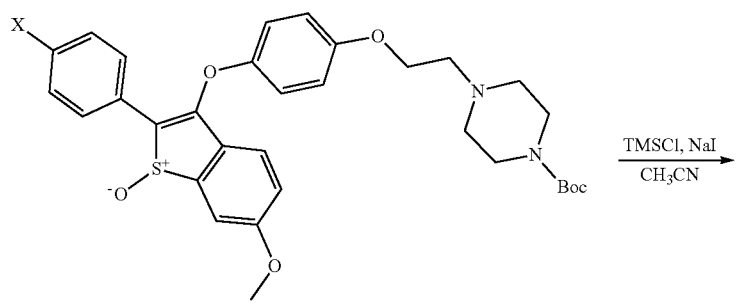
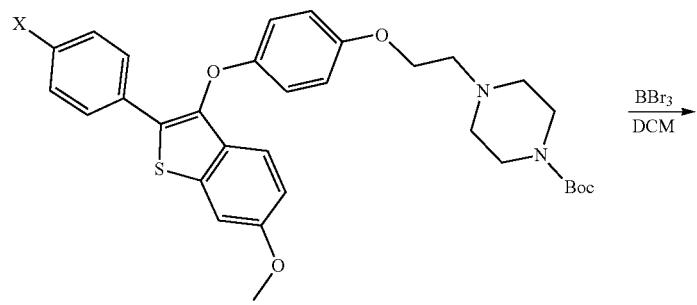
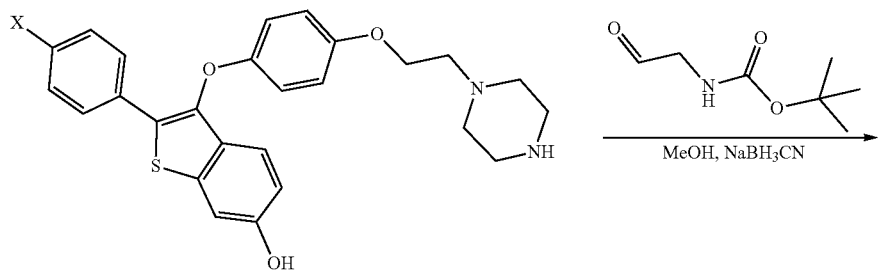

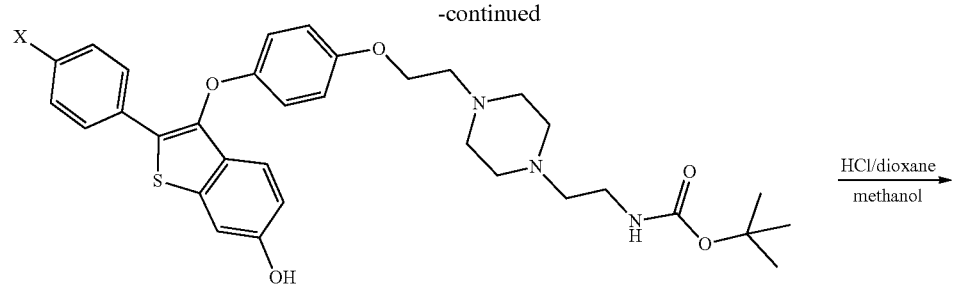
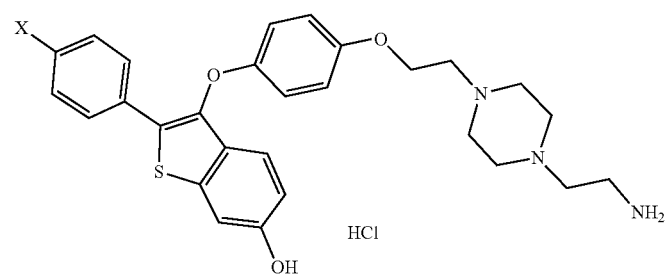
General Synthetic Scheme 13 to Prepare Intermediates.
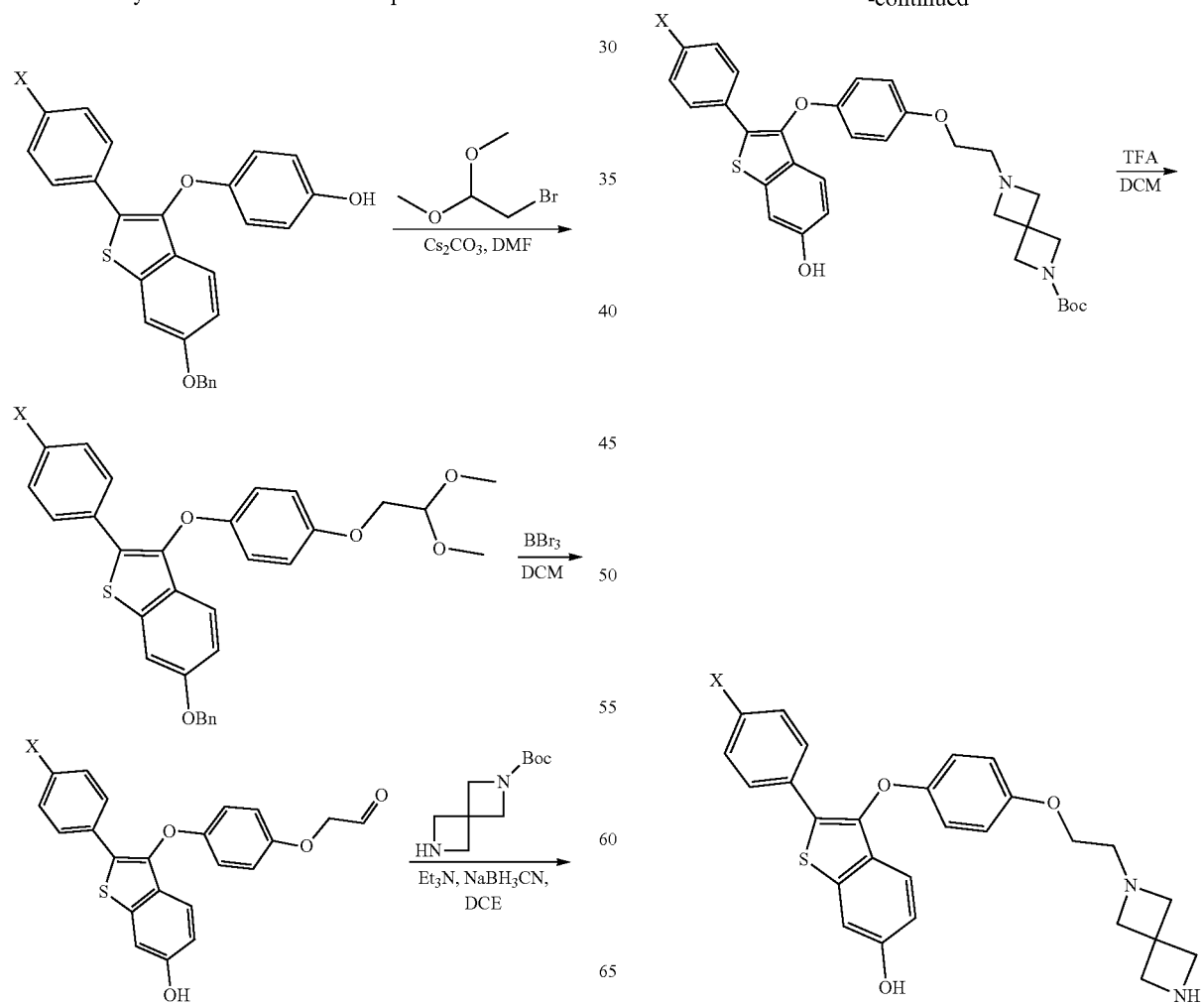

341
-continued
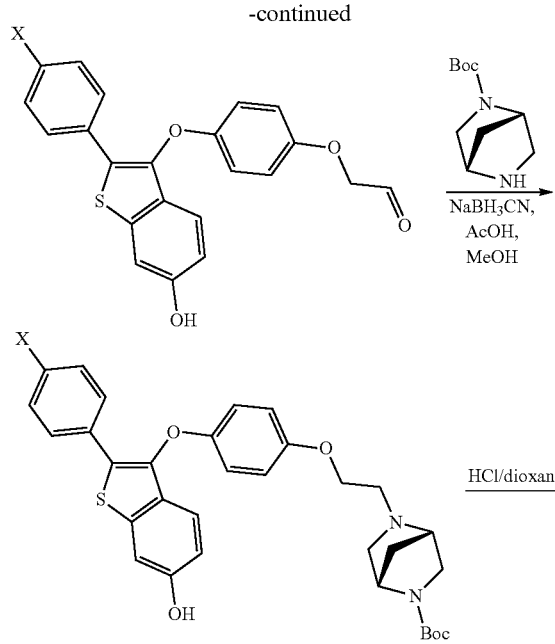
342
-continued
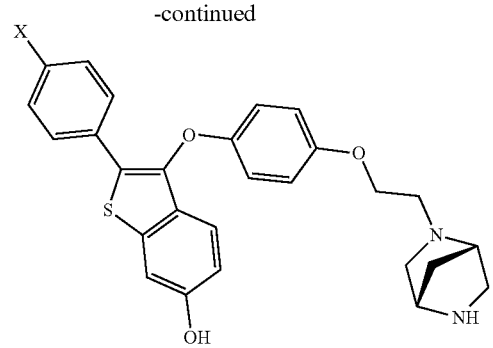
General Synthetic Scheme 14.
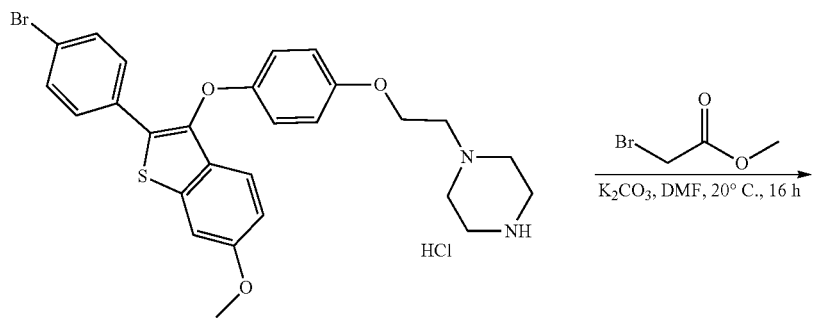
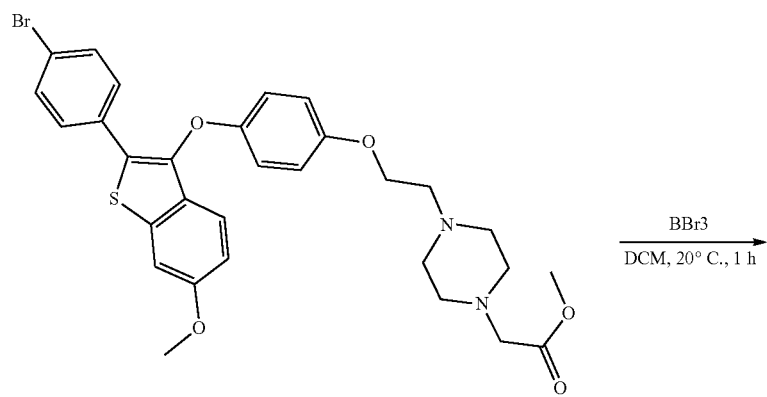

-continued
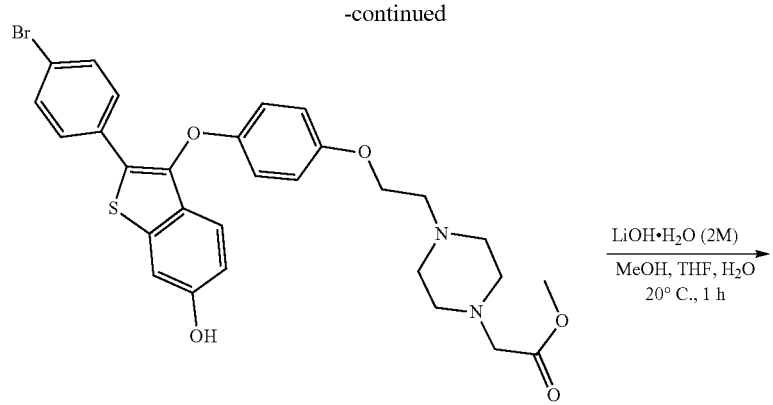
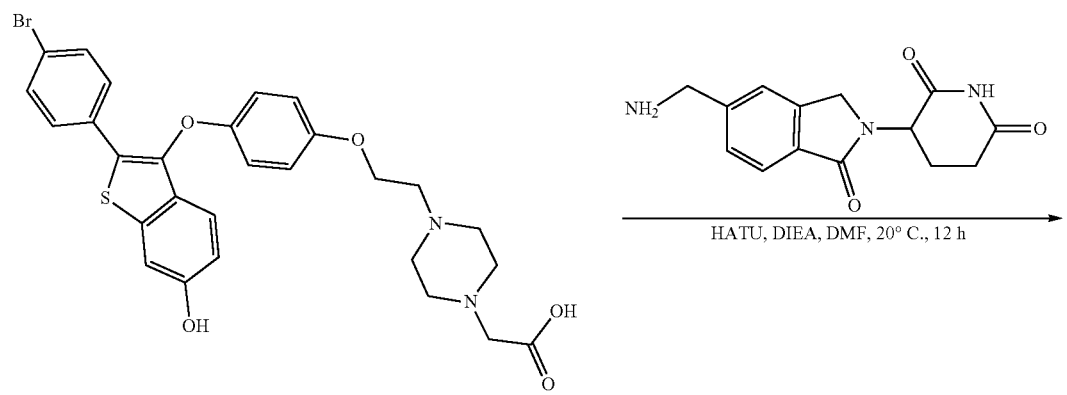
Example 1
General Synthetic Scheme 15.
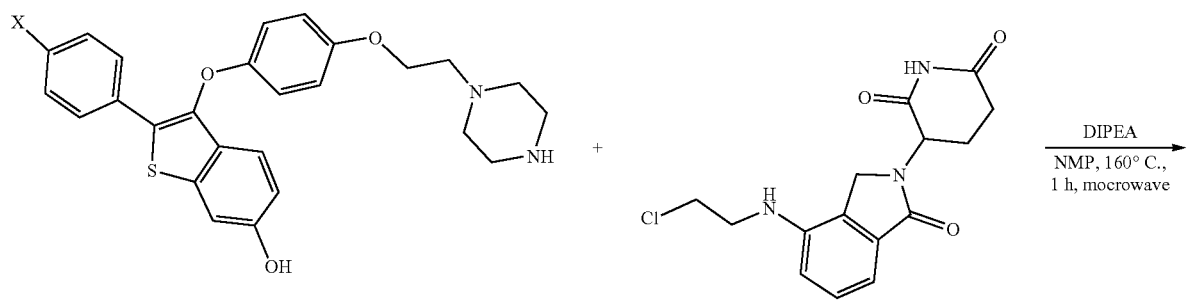

-continued
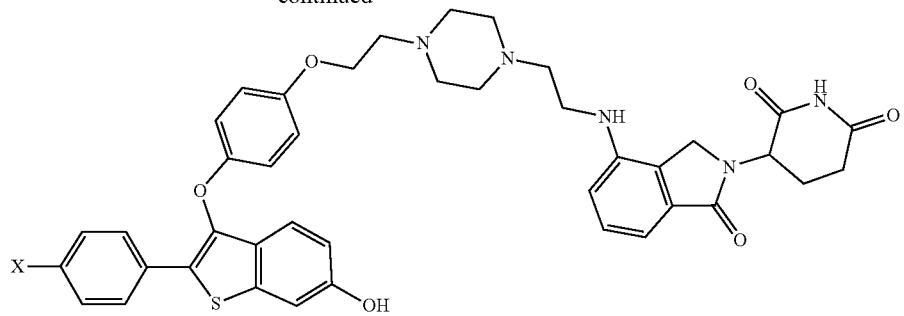
X = H, Example 2
X = OH, Example 4
X = Br, Example 5
General Synthetic Scheme 16.
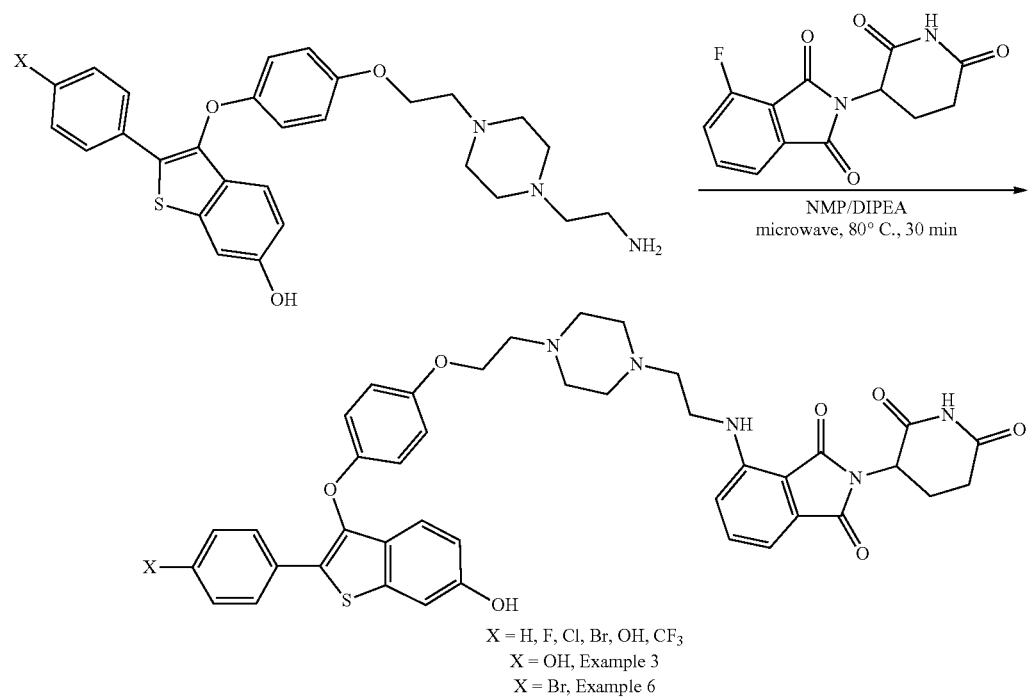
X = H, F, Cl, Br, OH, CF₃
X = OH, Example 3
X = Br, Example 6
General Synthetic Scheme 17.
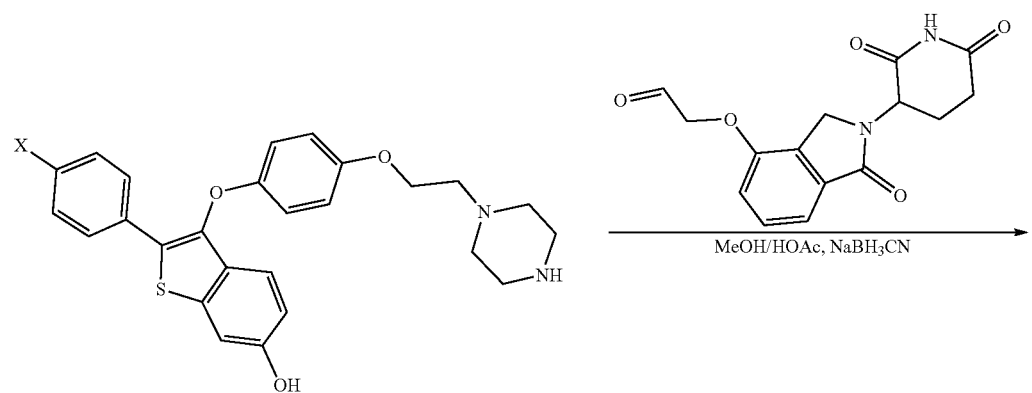

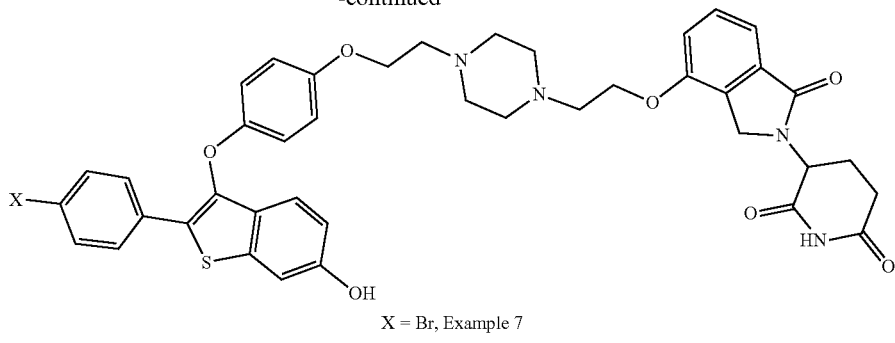
X = Br, Example 7
General Synthetic Scheme 18.
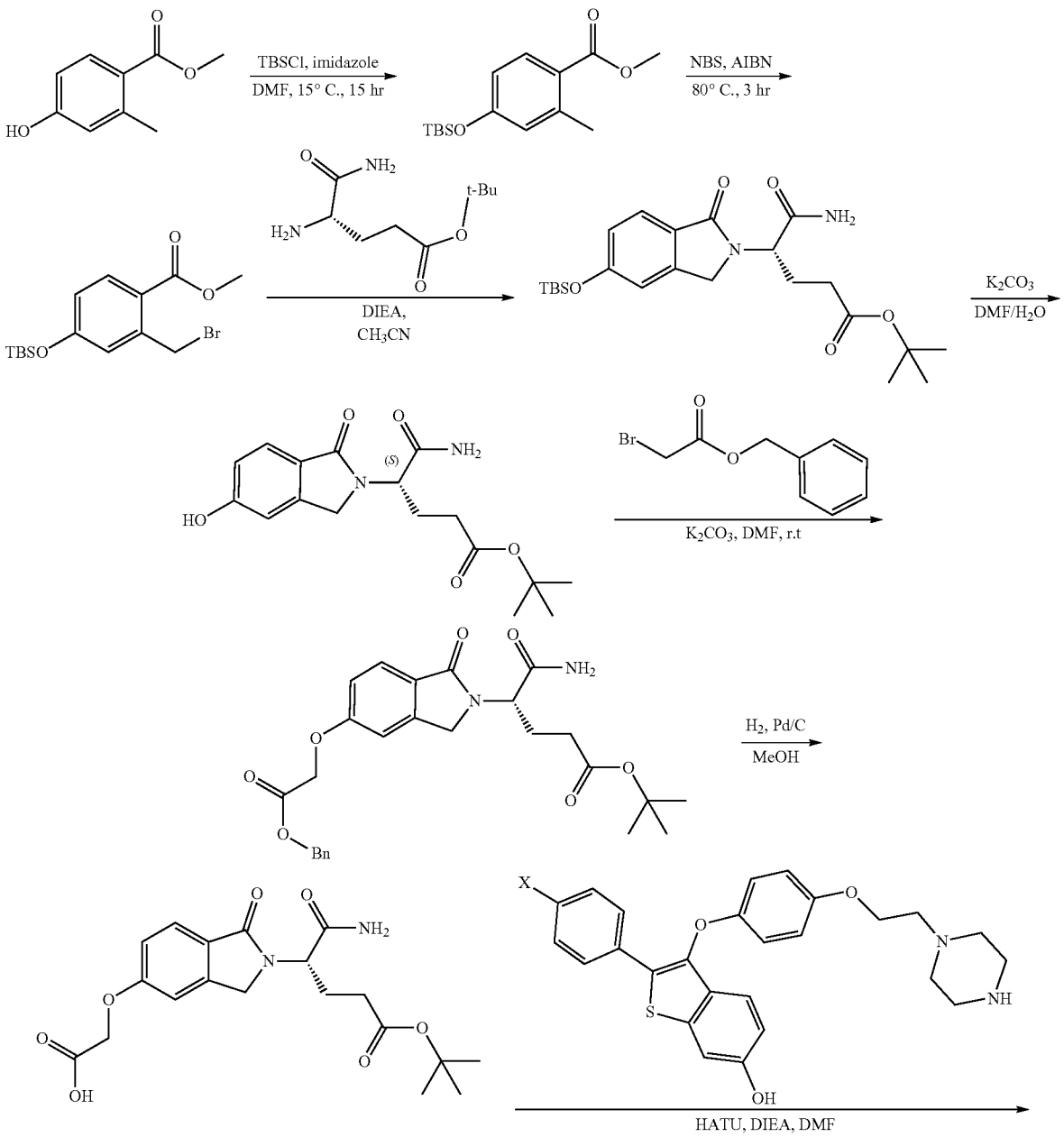

349 350
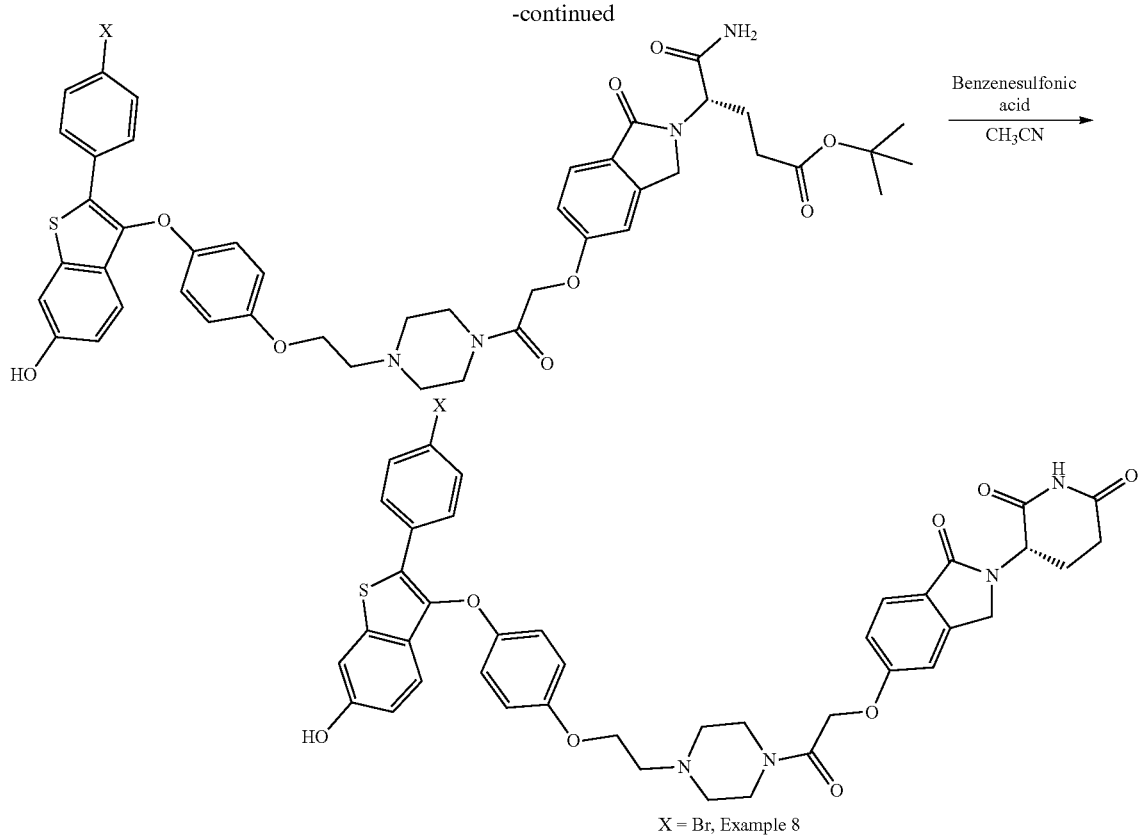
-continued
X = Br, Example 8
General Synthetic Scheme 19.
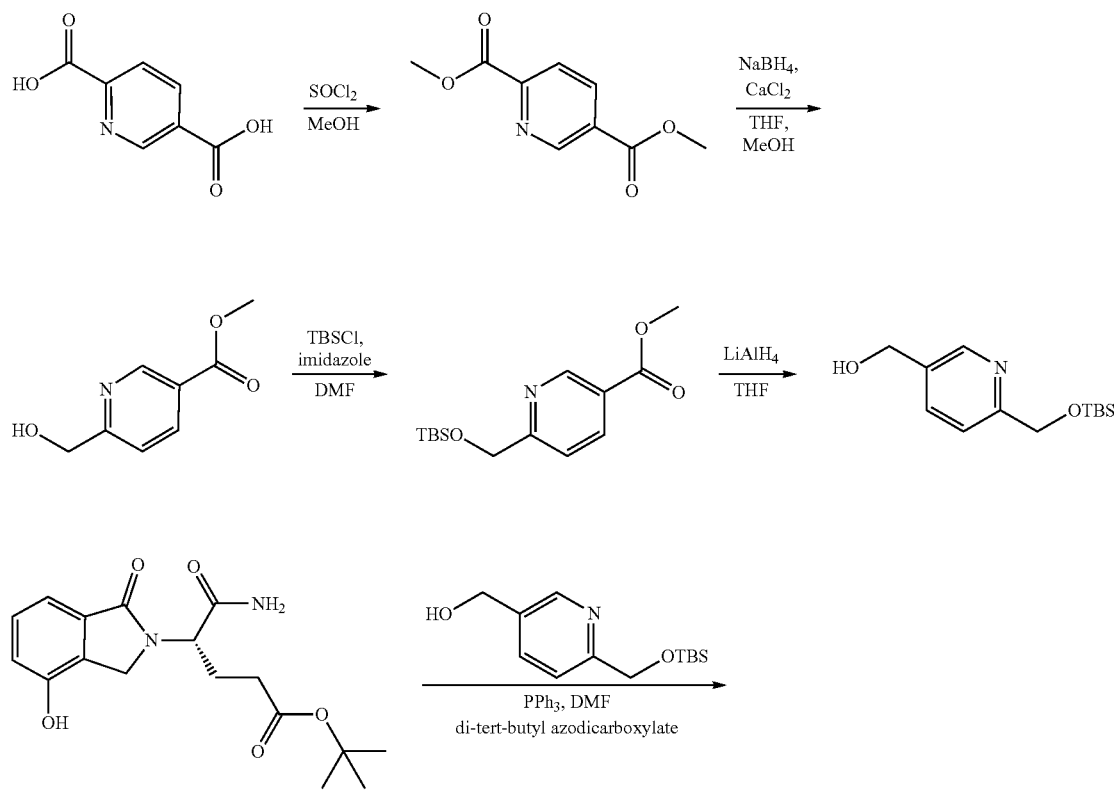

351
-continued
352
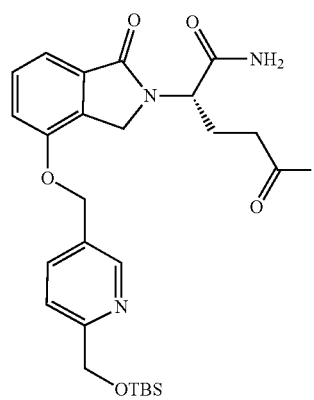
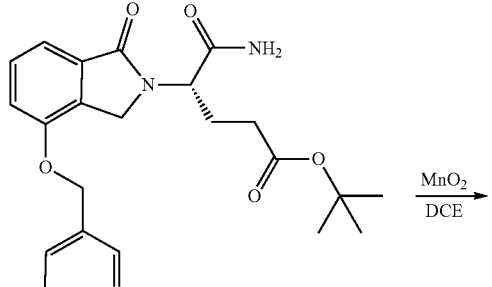
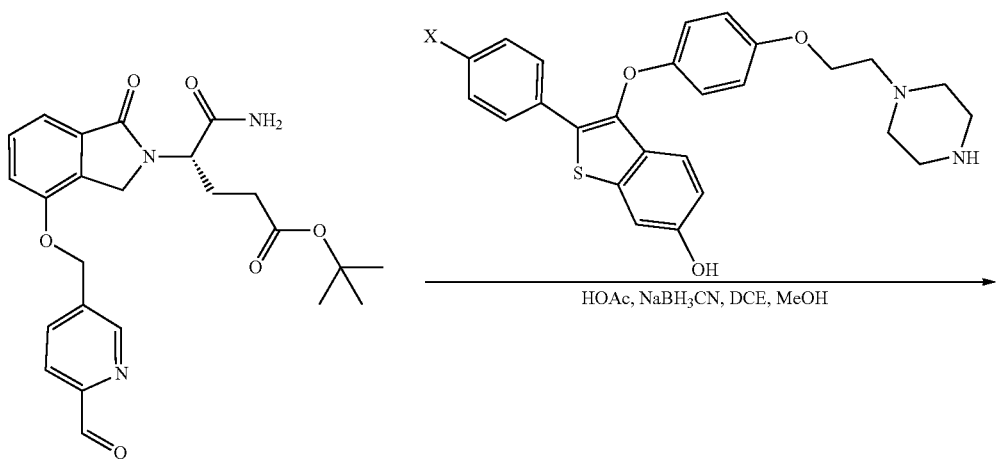
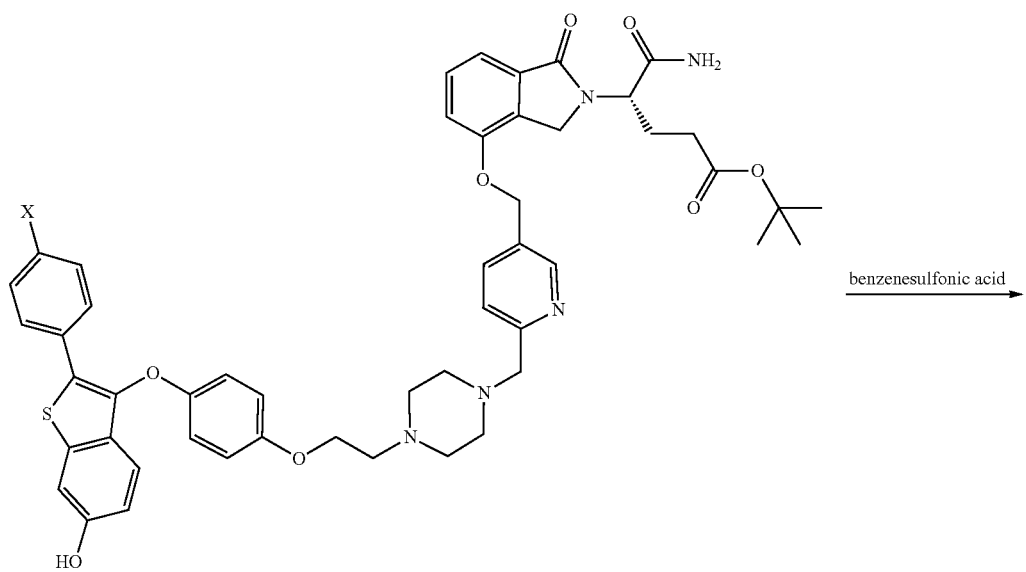

-continued
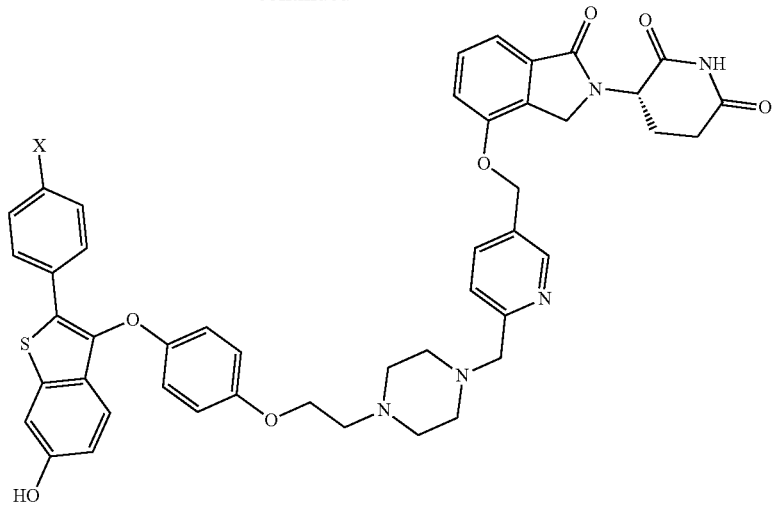
X = Br, Example 9
General Synthetic Scheme 20.
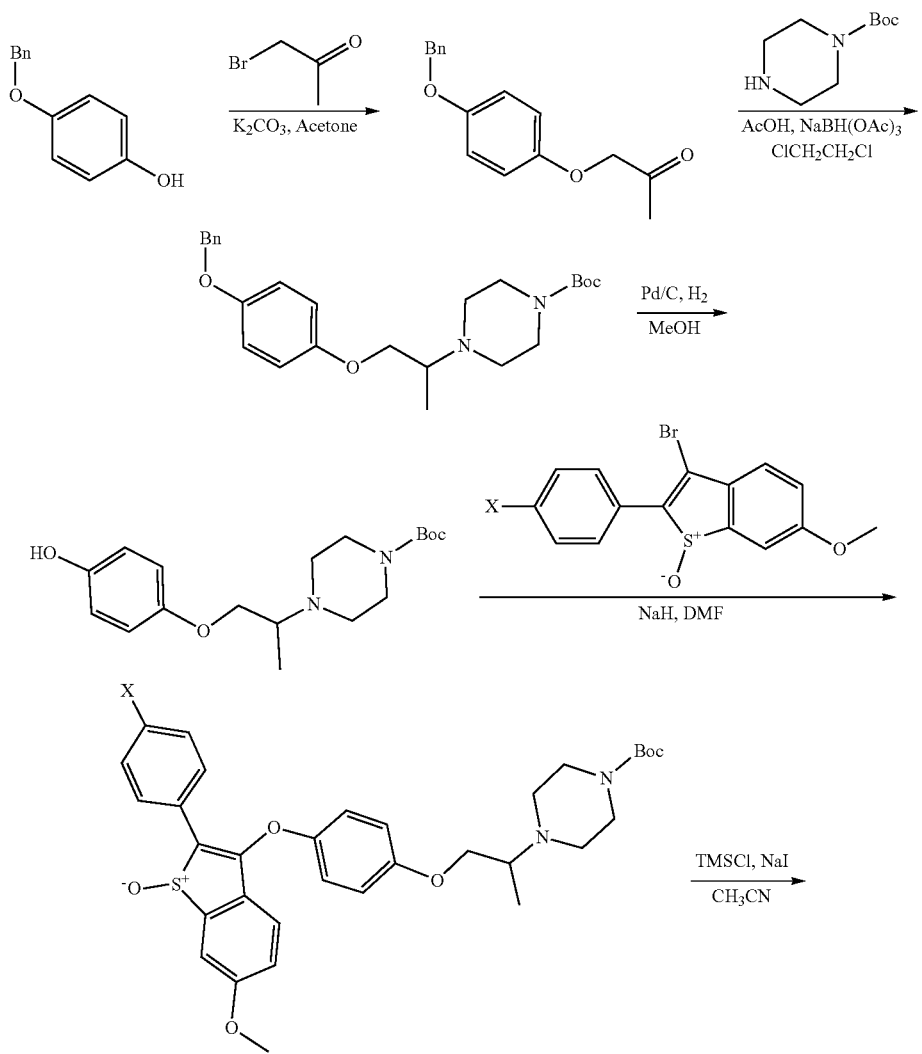

-continued
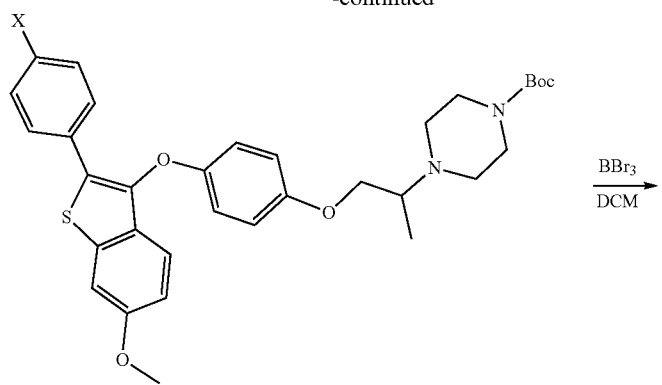
BBr₃
―――→
DCM
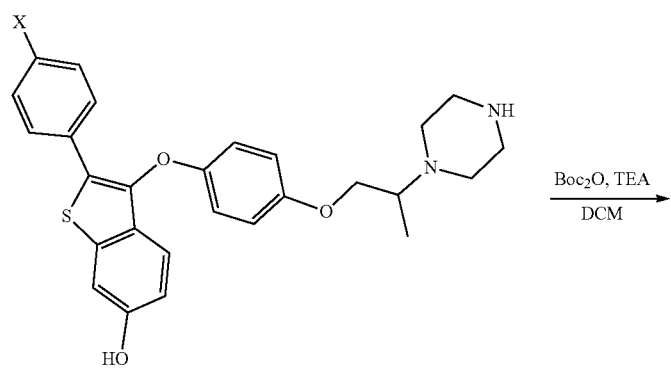
Boc₂O, TEA
―――――→
DCM
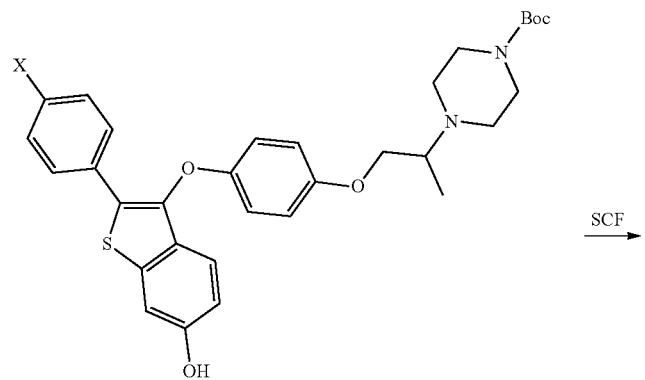
SCF
―――→
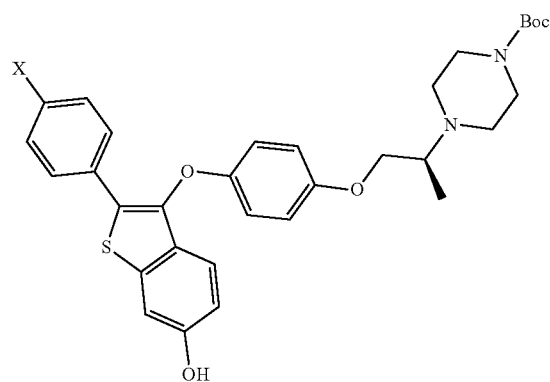
+

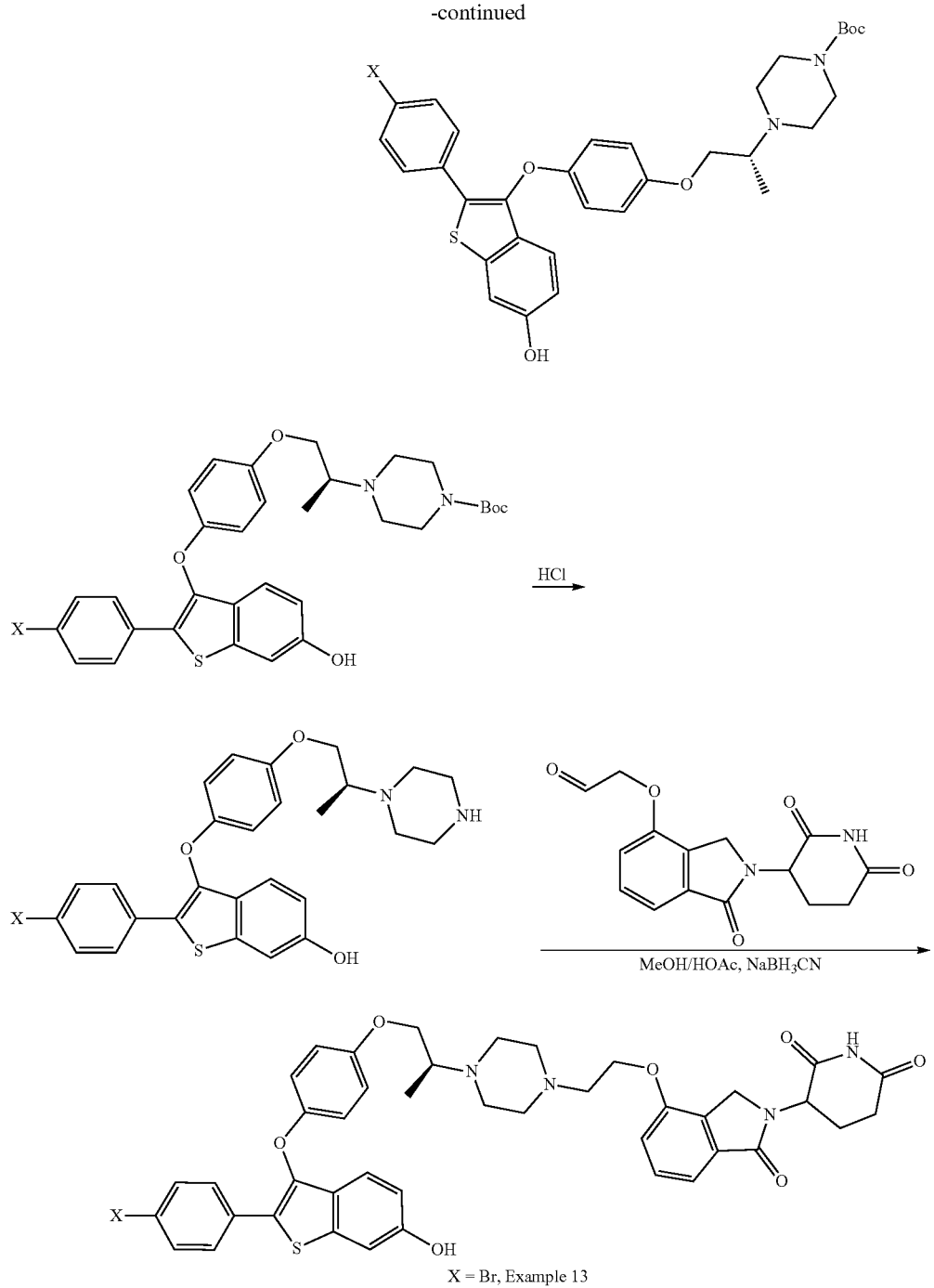
General Synthetic Scheme 21.
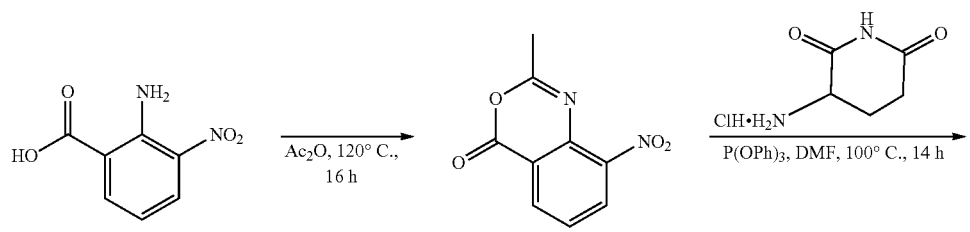

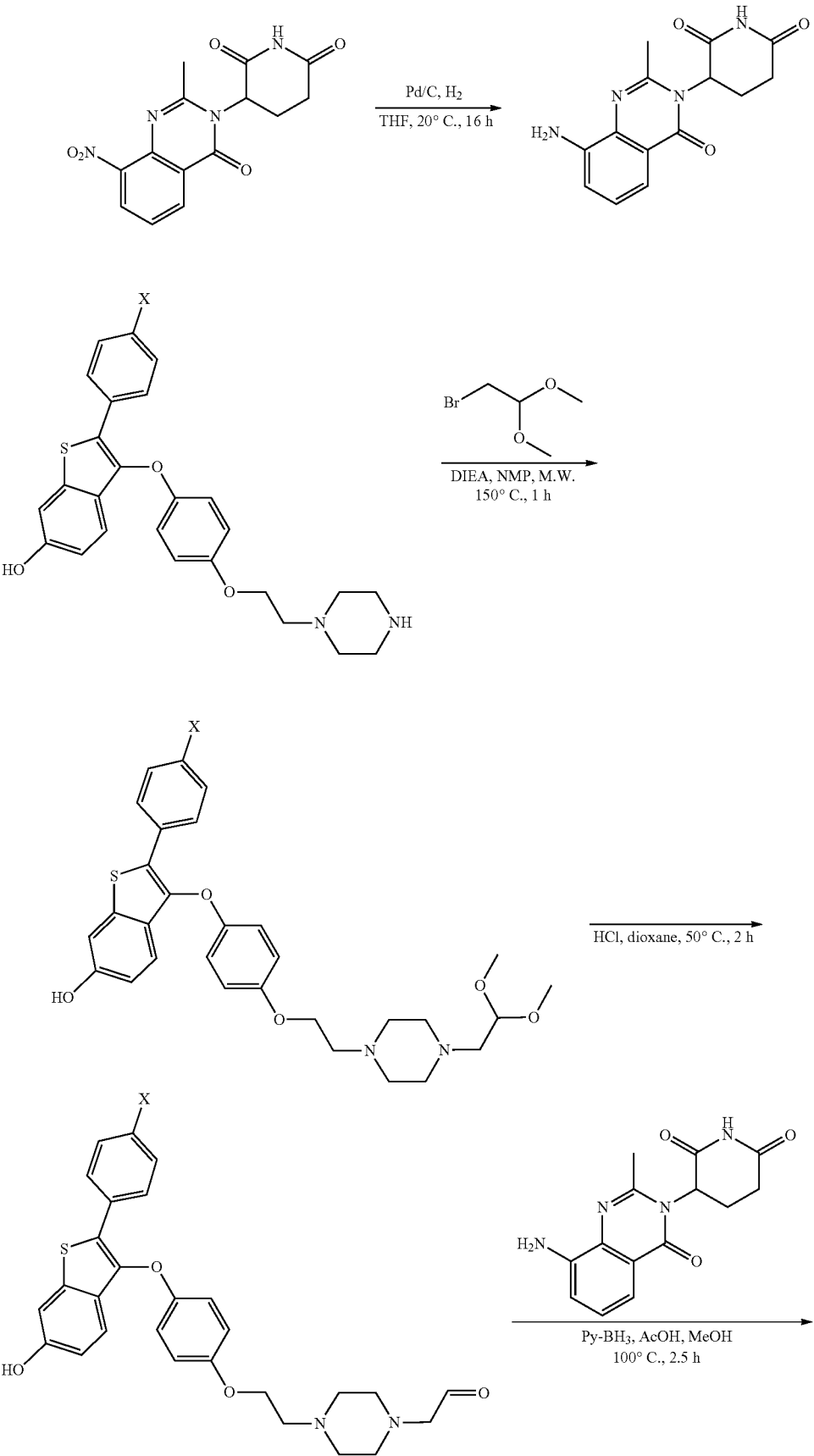

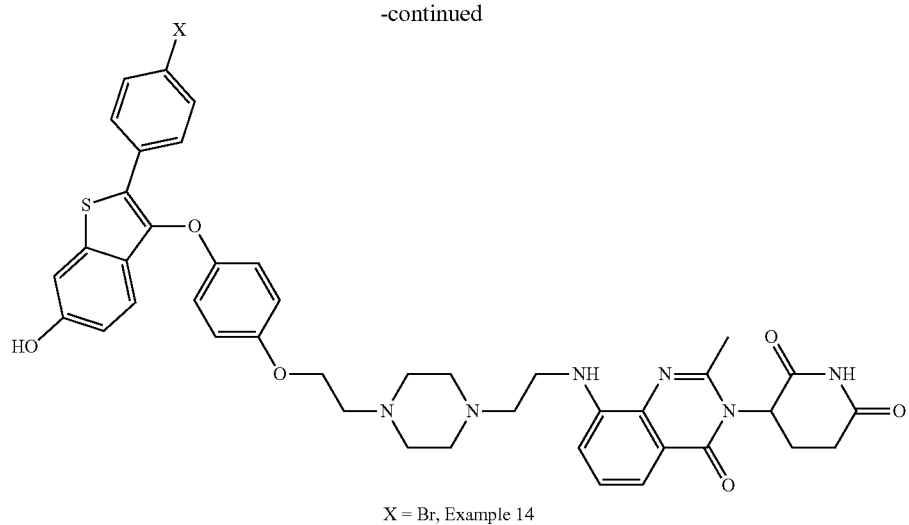
X = Br, Example 14
General Synthetic Scheme 22.
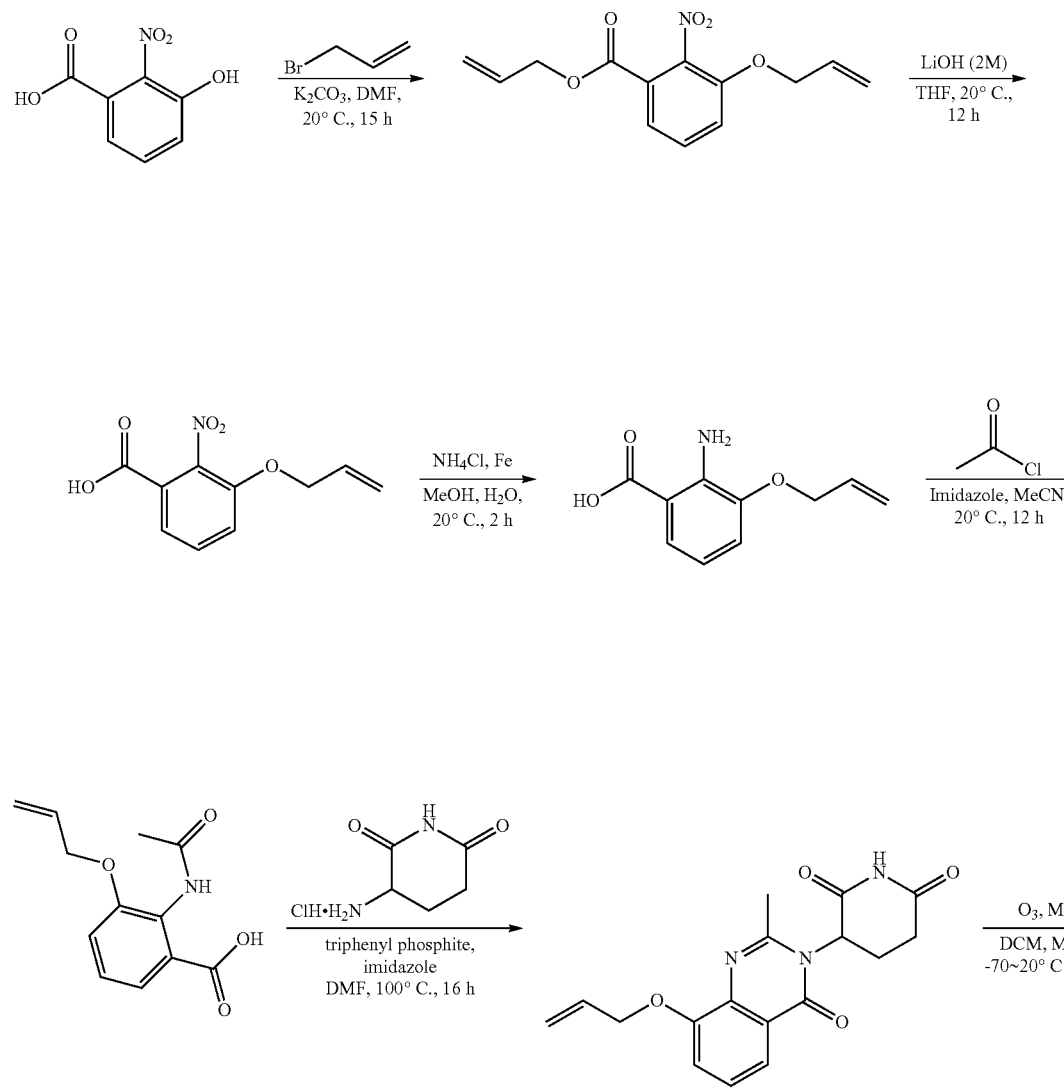

-continued
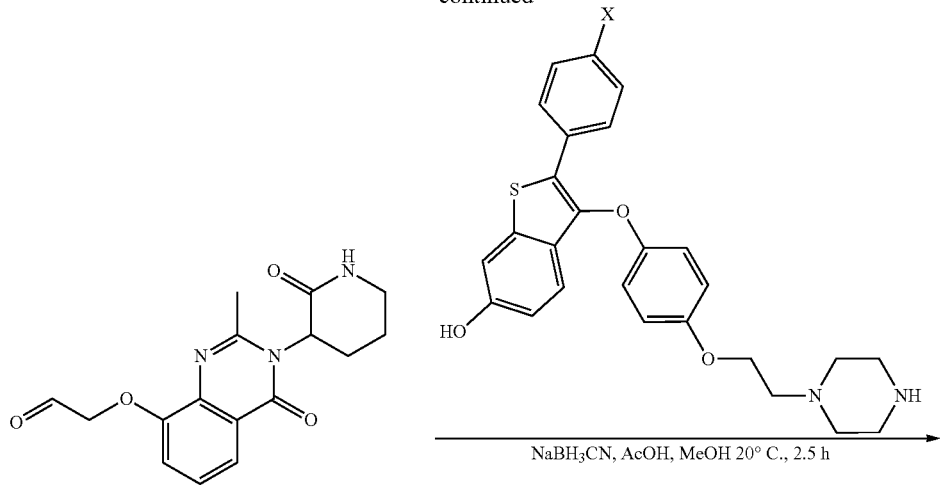
X = Br, Example 16
General Synthetic Scheme 23.
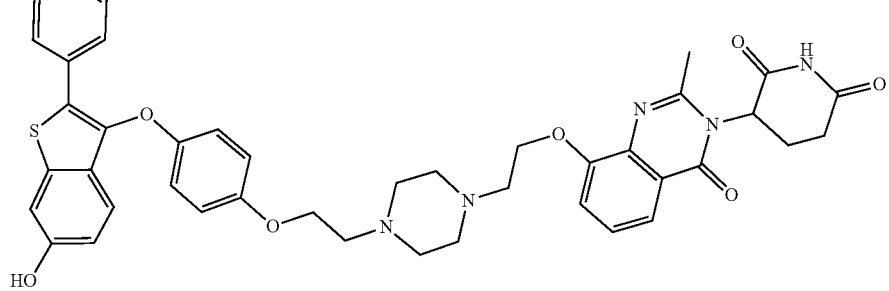
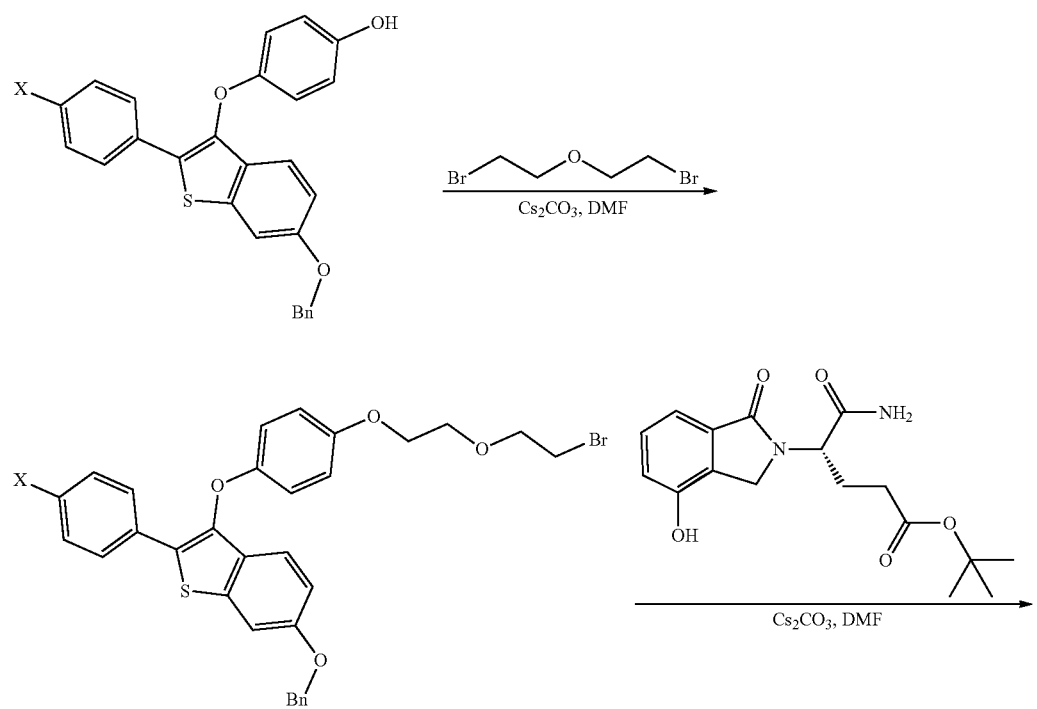

-continued
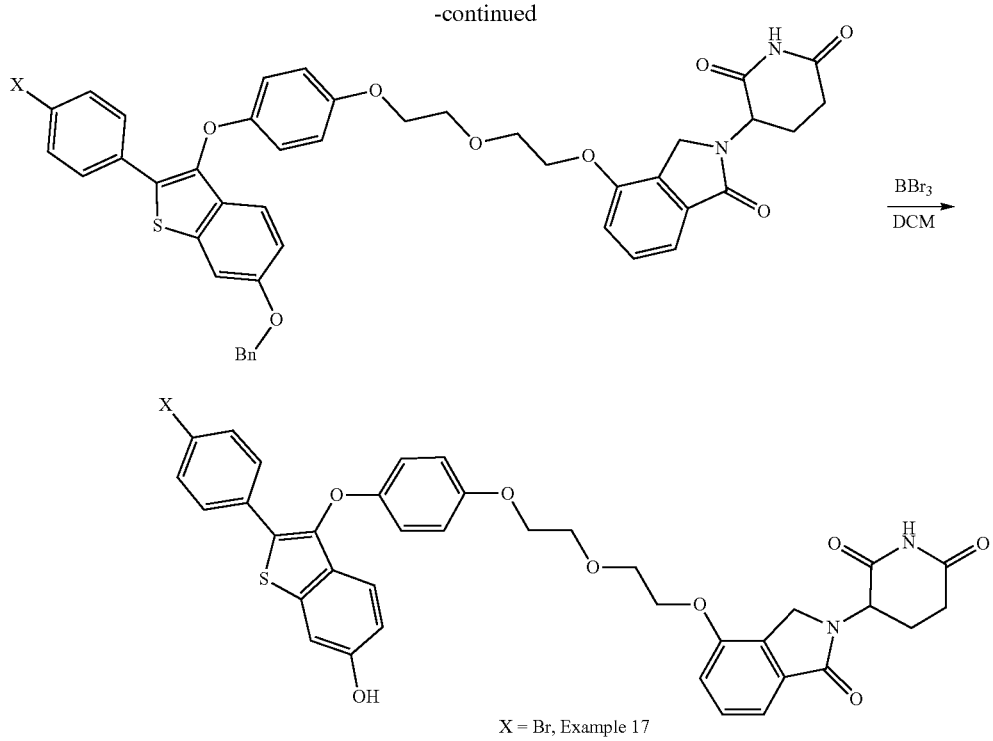
X = Br, Example 17
General Synthetic Scheme 24.
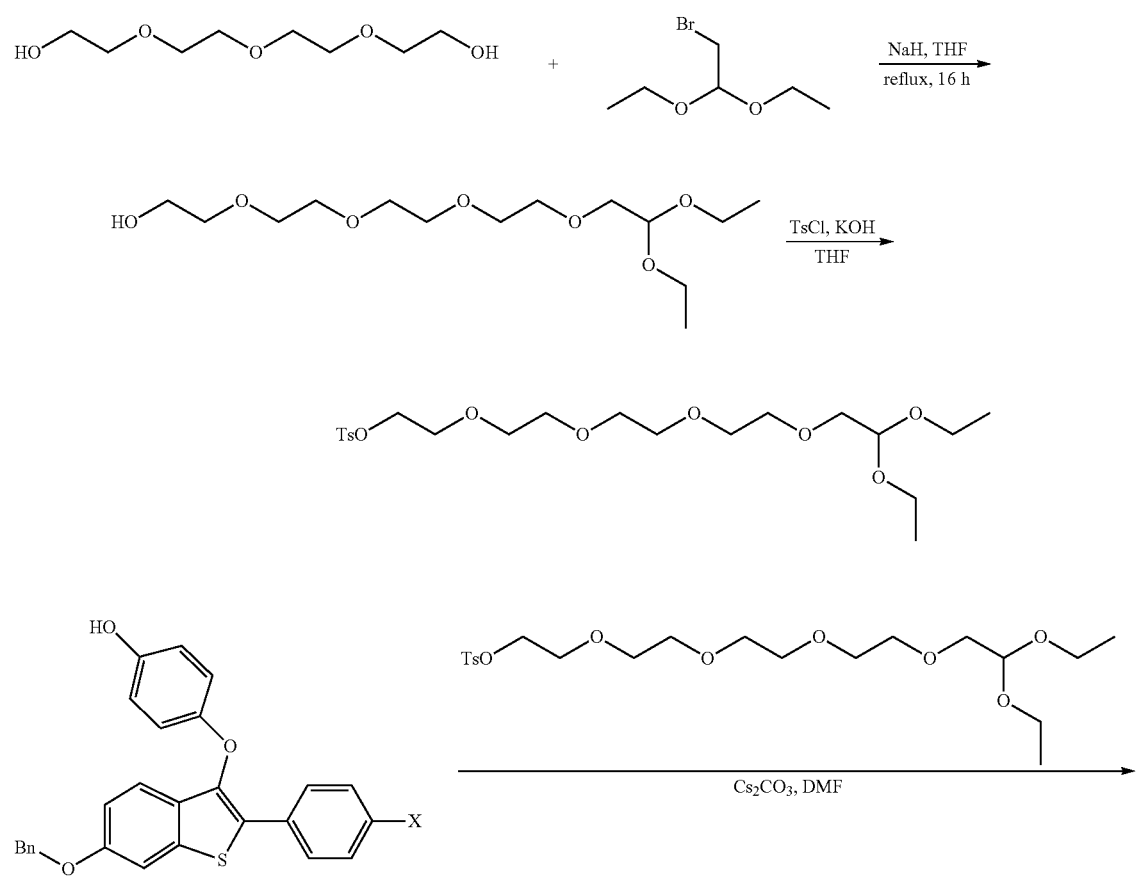

-continued
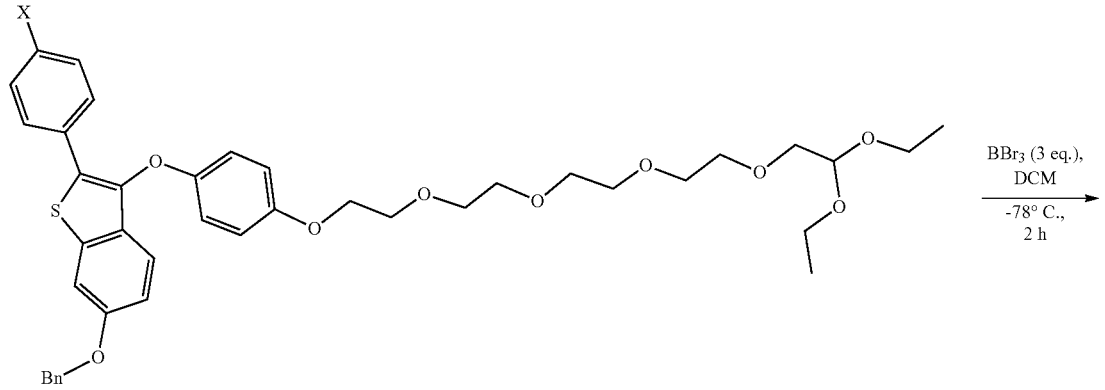
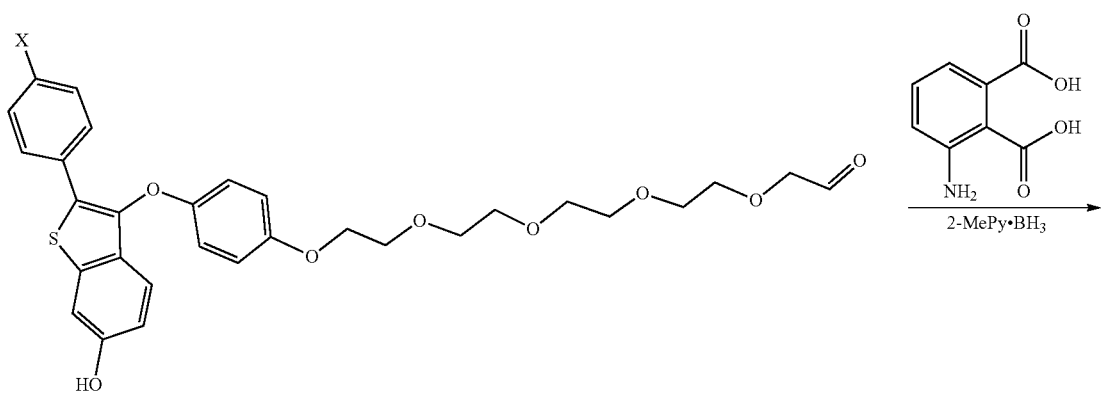
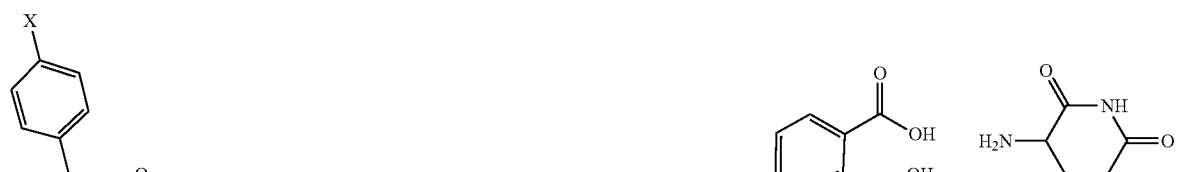
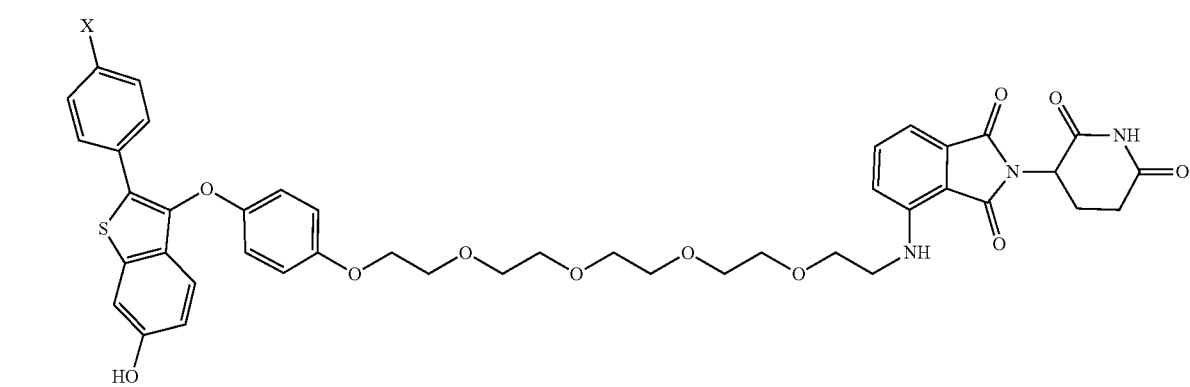
X = Br, Example 20

General Synthetic Scheme 25.
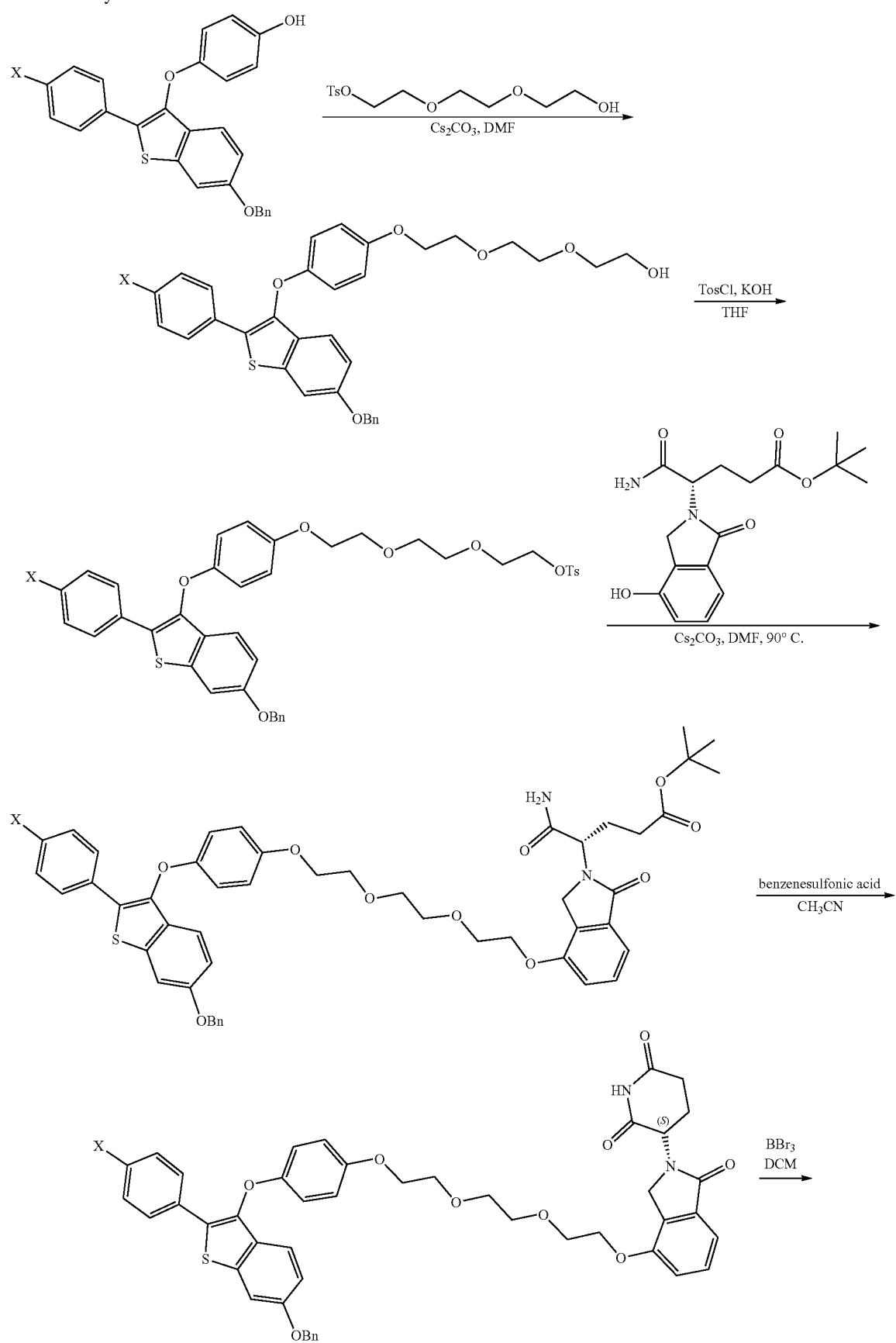

-continued
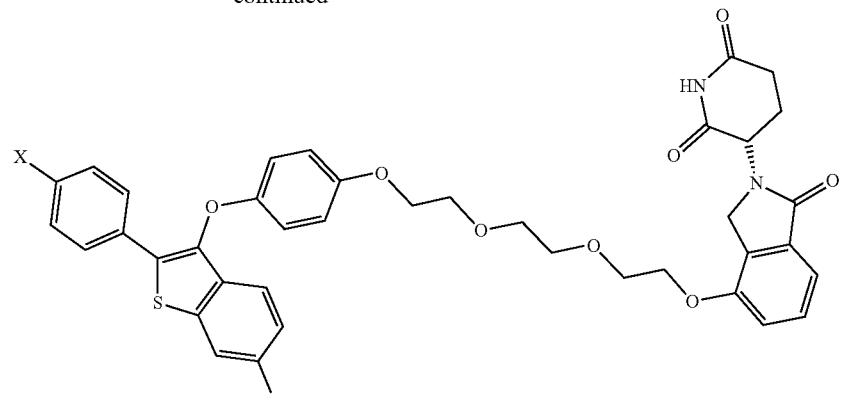
X = Br, Example 19
General Synthetic Scheme 26.
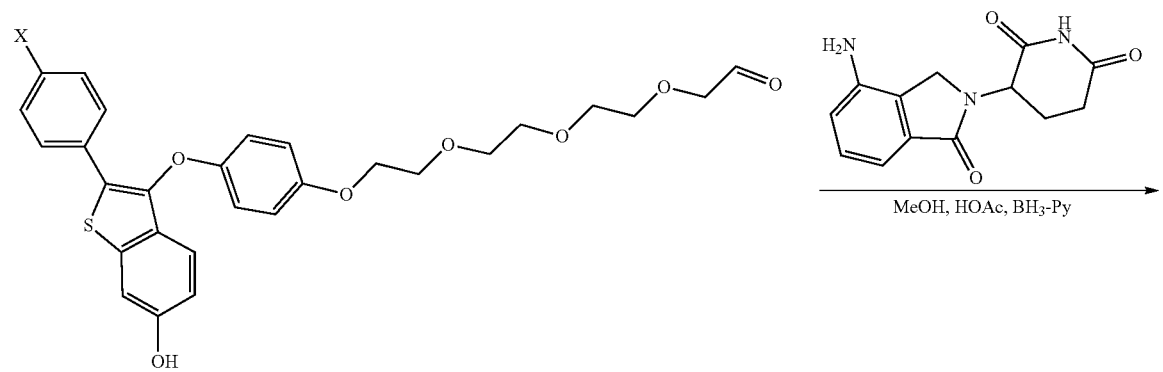
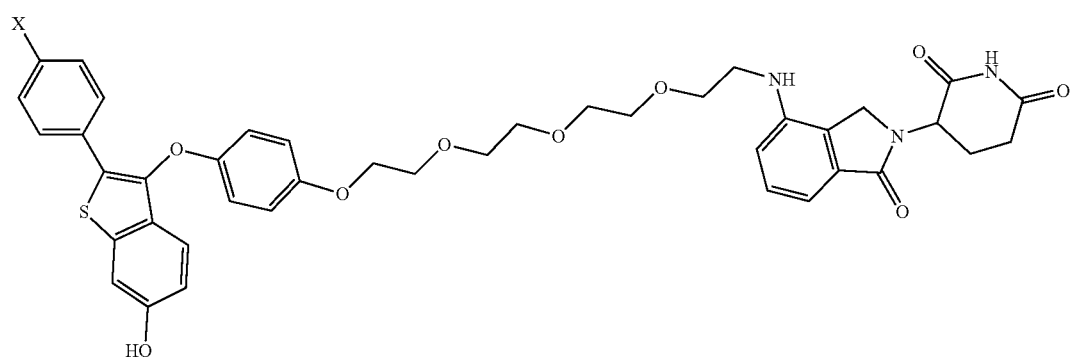
X = Br, Example 22

General Synthetic Scheme 27.
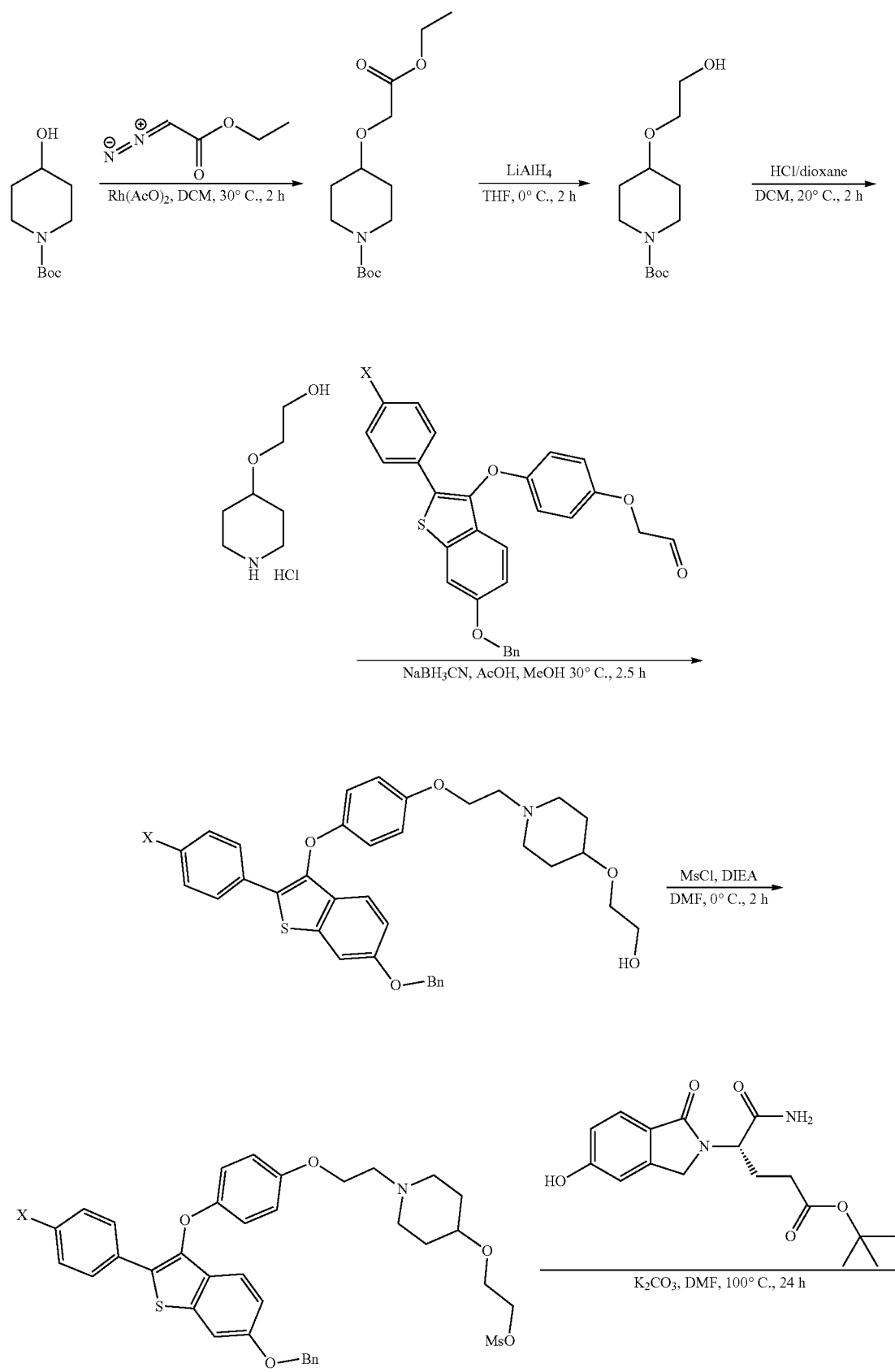

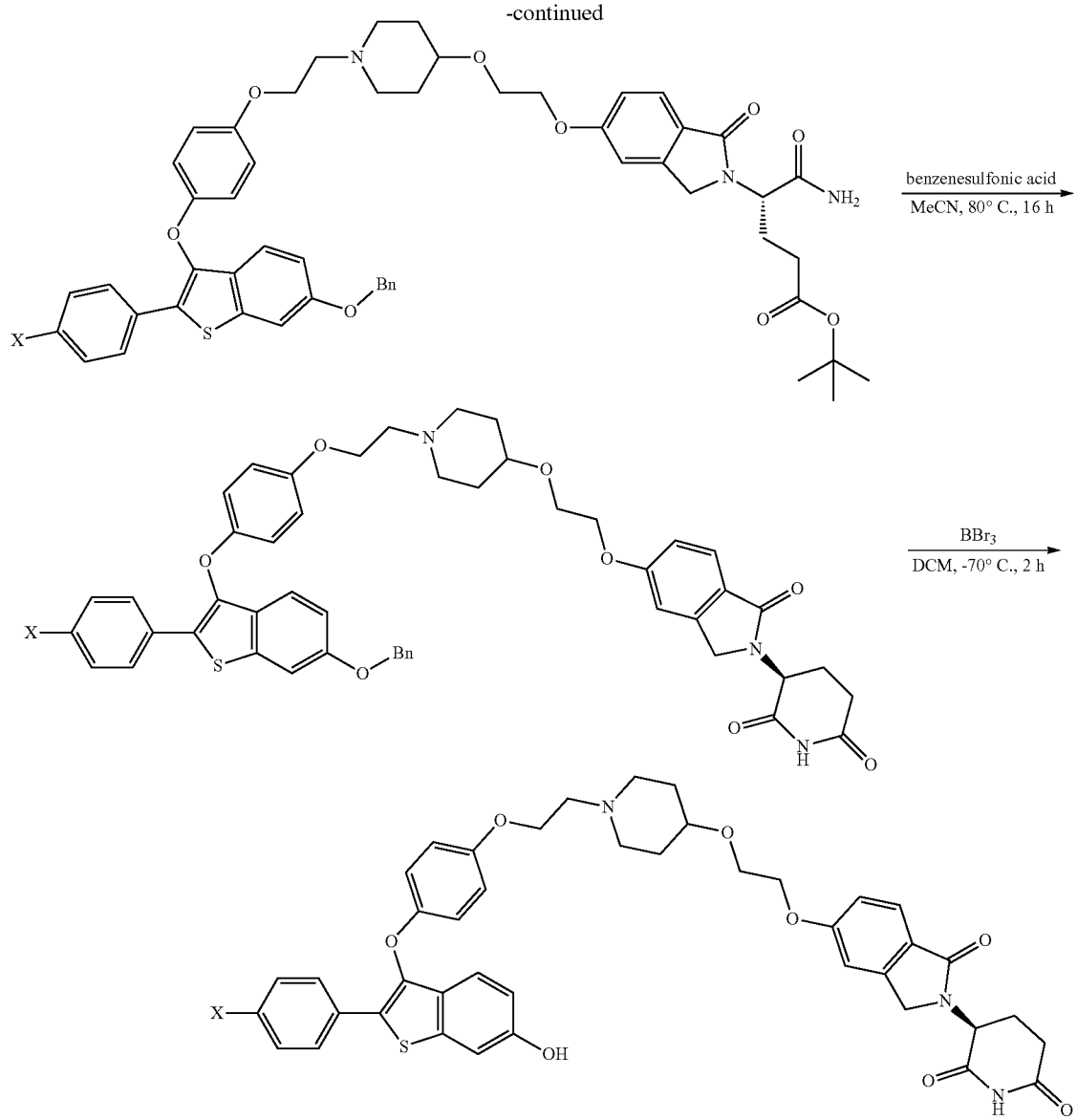
X = Br, Example 44
General Synthetic Scheme 28.
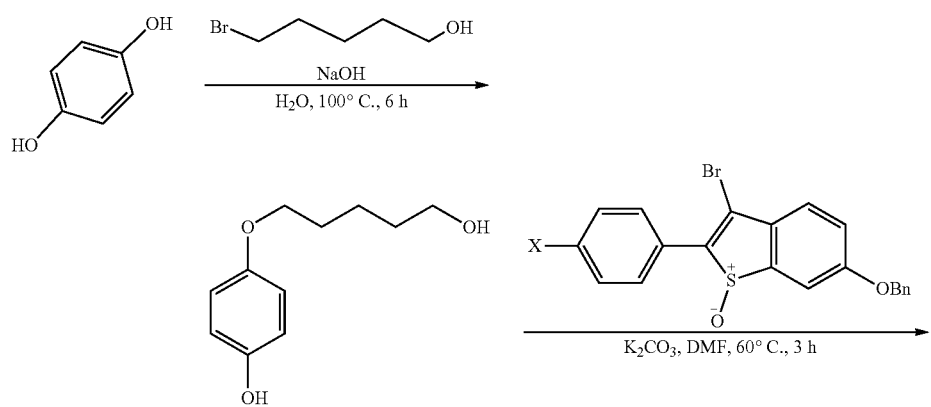

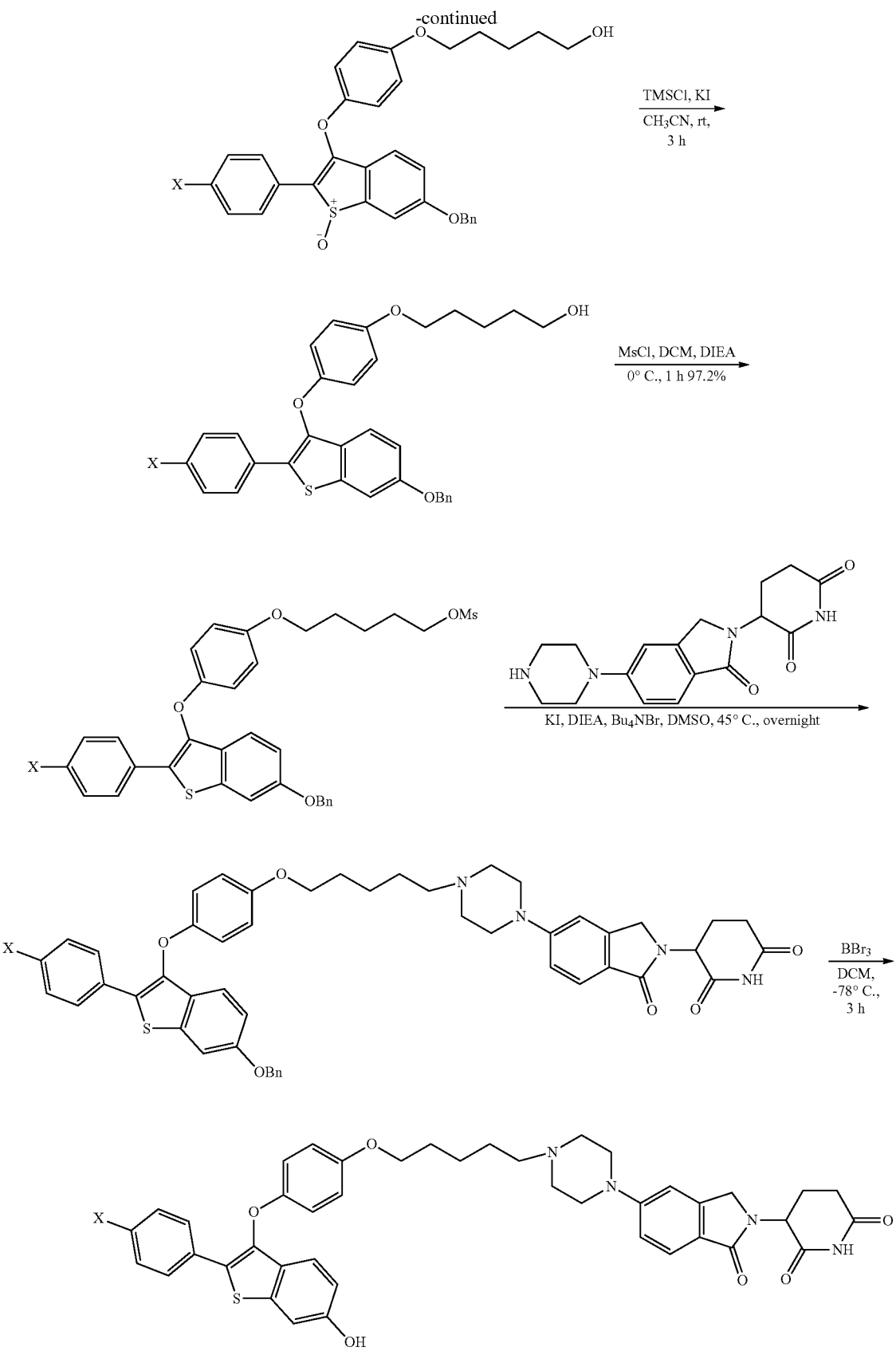
X = Br, Example 52

General Synthetic Scheme 28.
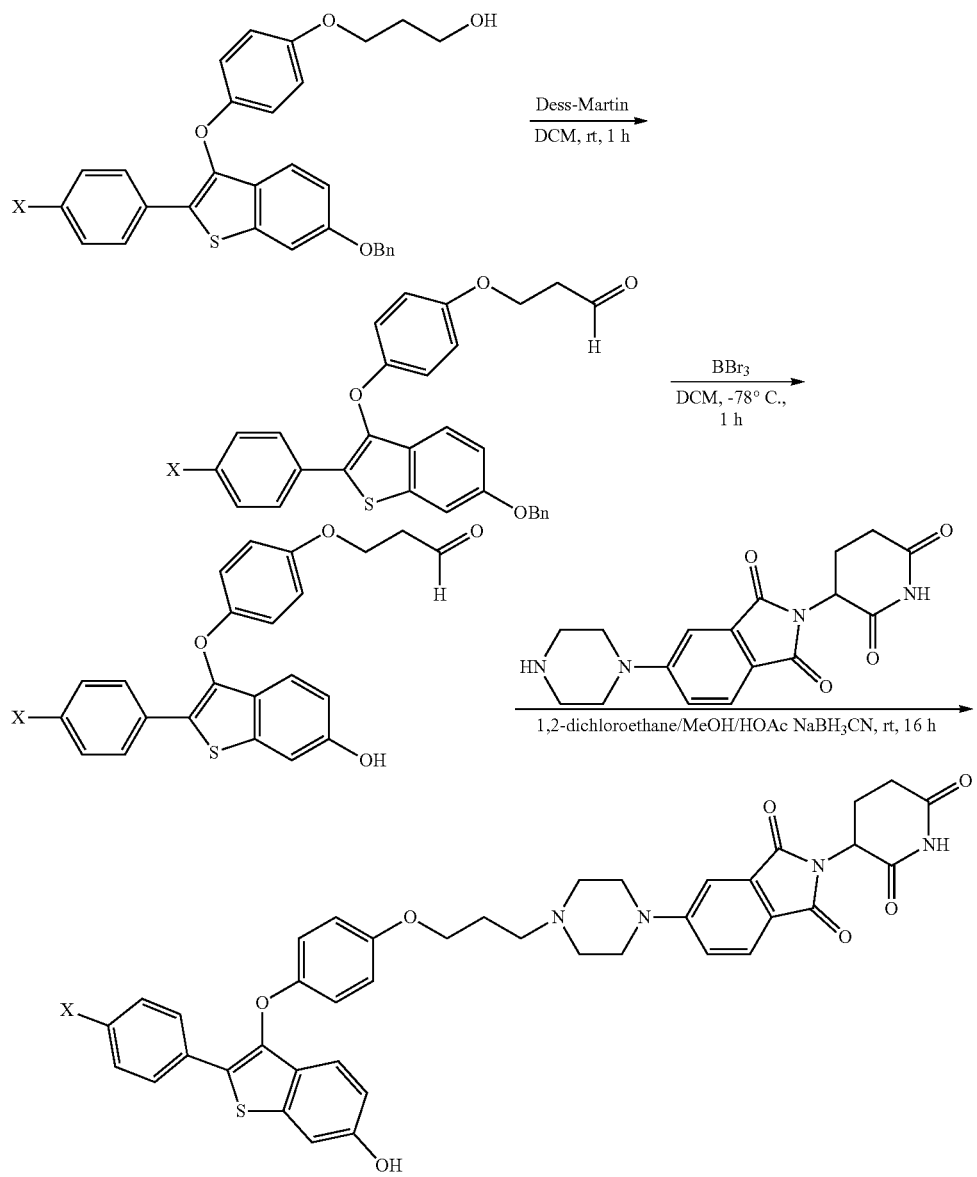
X = Br, Example 49
General Synthetic Scheme 30.
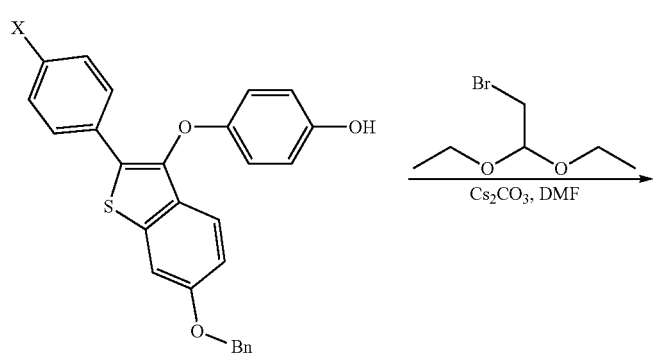

-continued
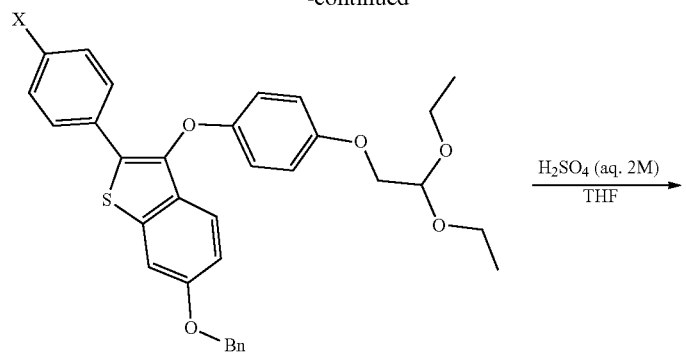
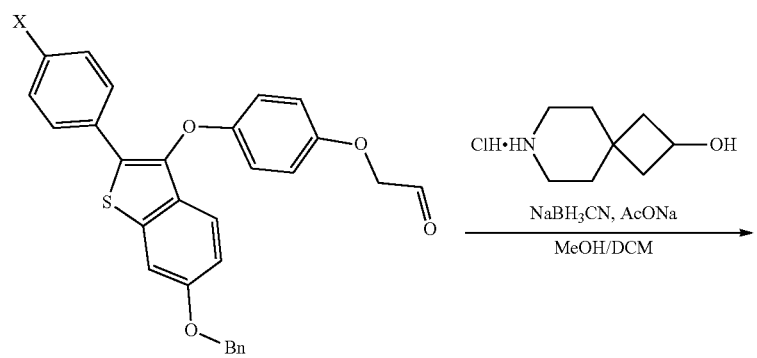
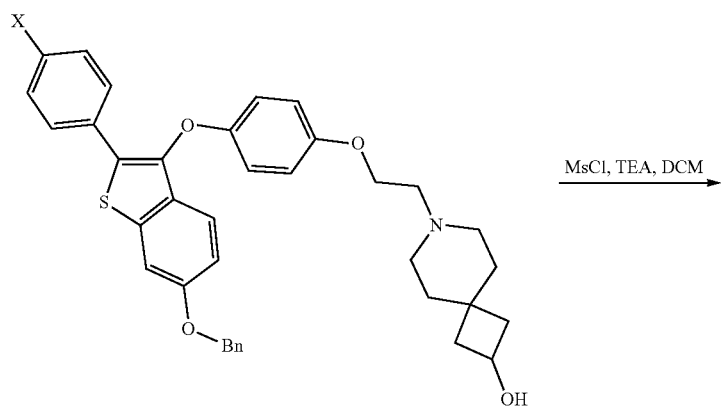
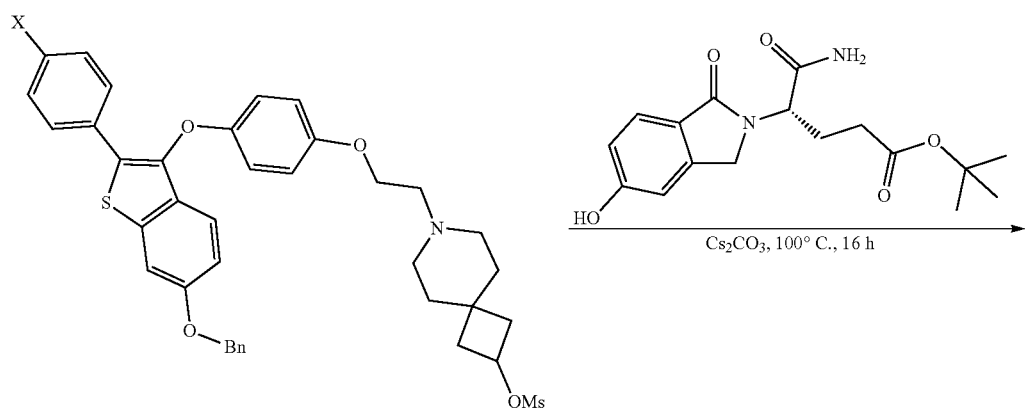

383 384
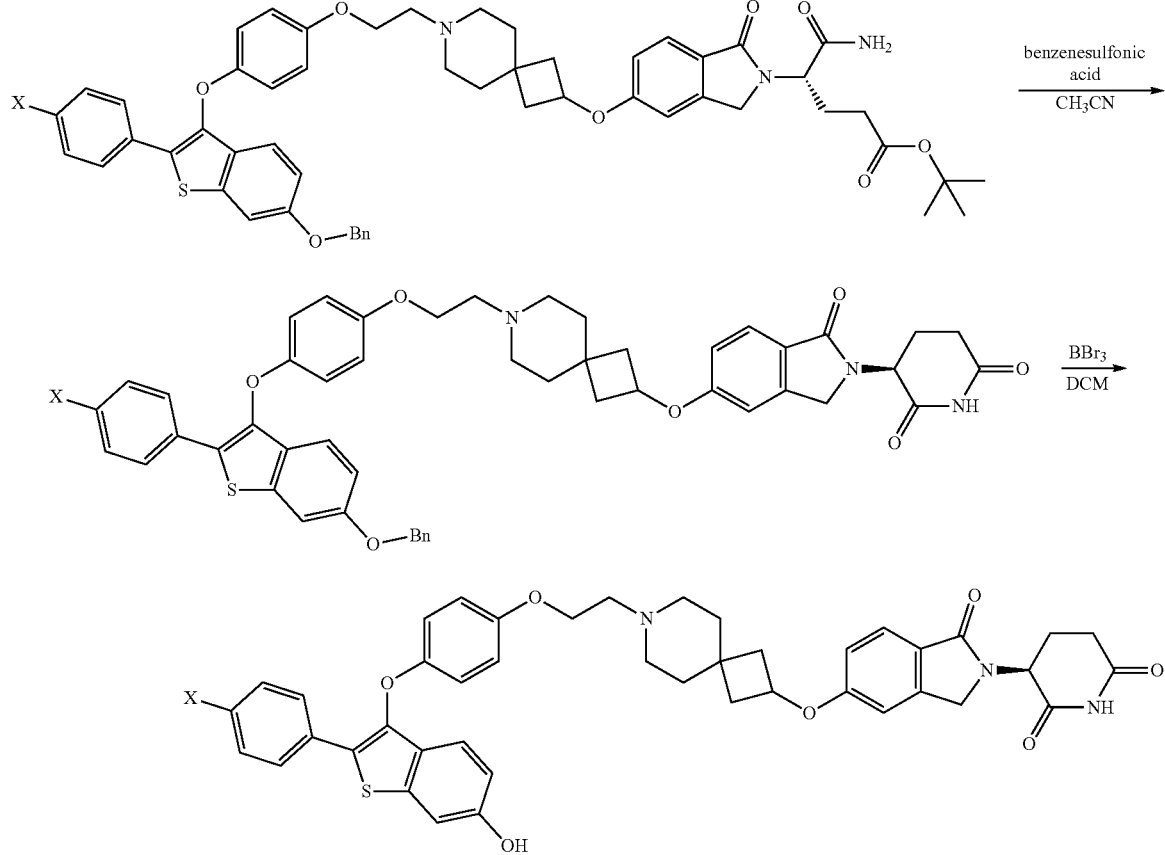
X = Br, Example 50
General Synthetic Scheme 31.
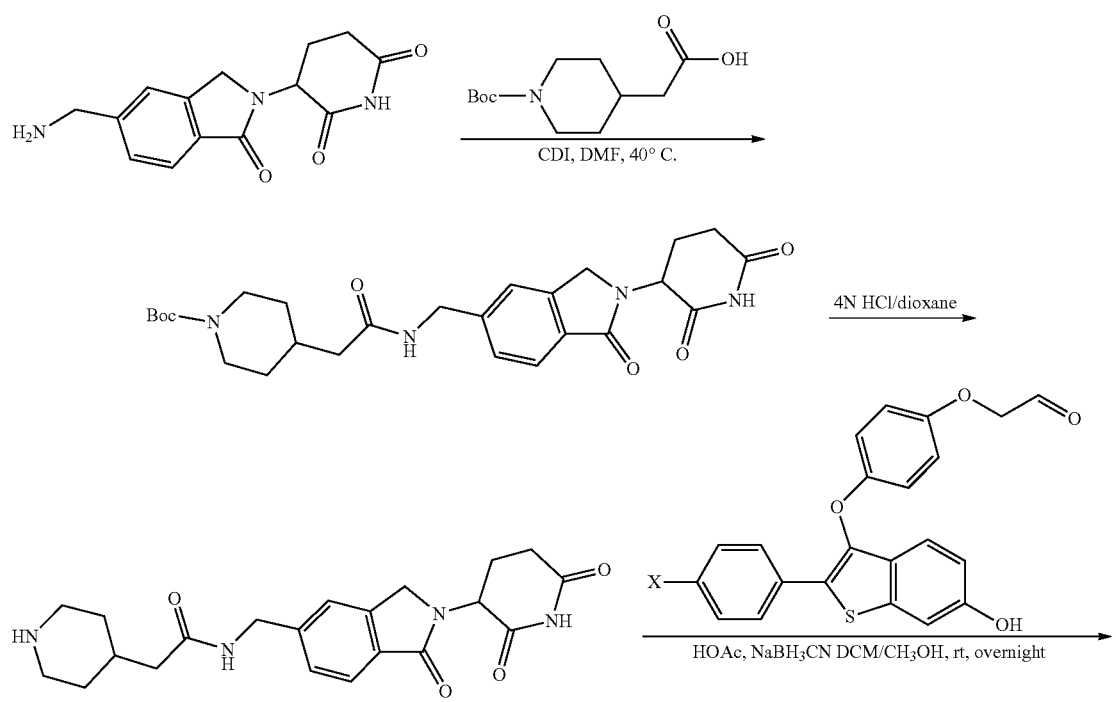

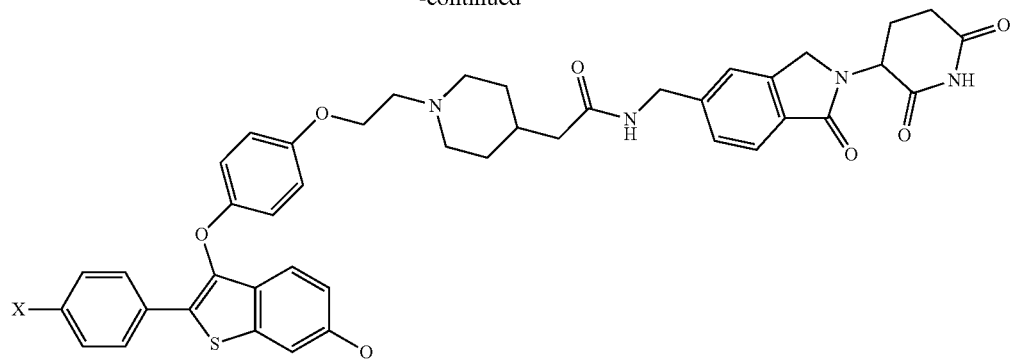
X = Br, Example 63
General Synthetic Scheme 32.
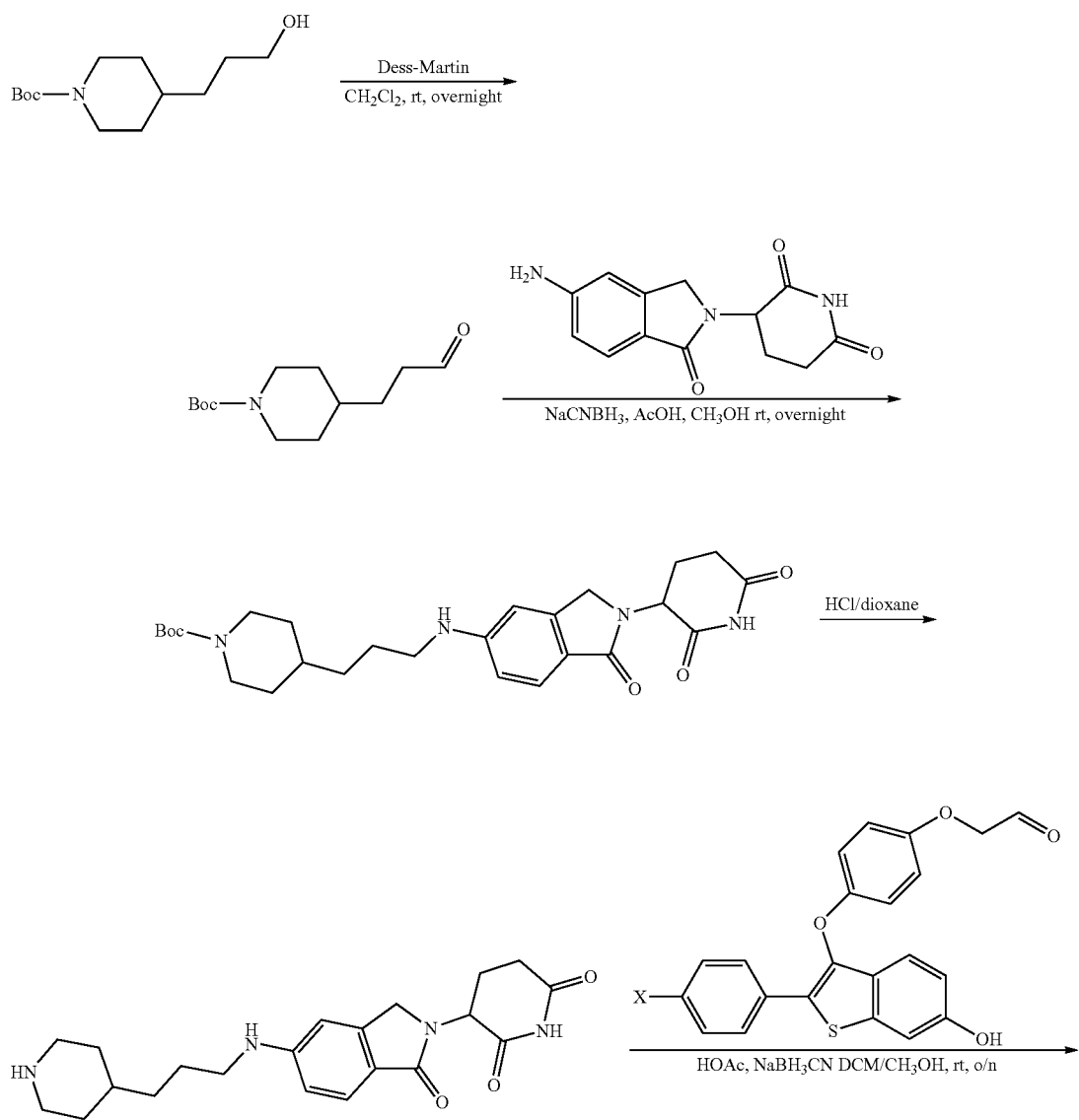

387 388
-continued
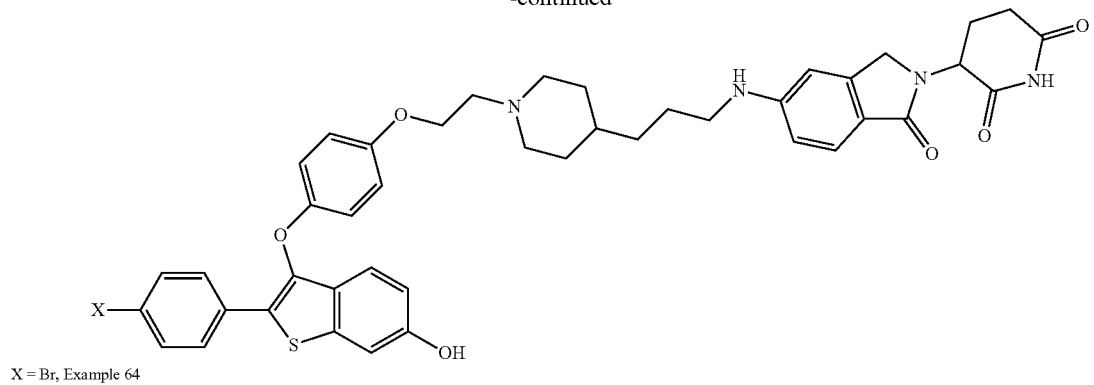
X = Br, Example 64
General Synthetic Scheme 33.
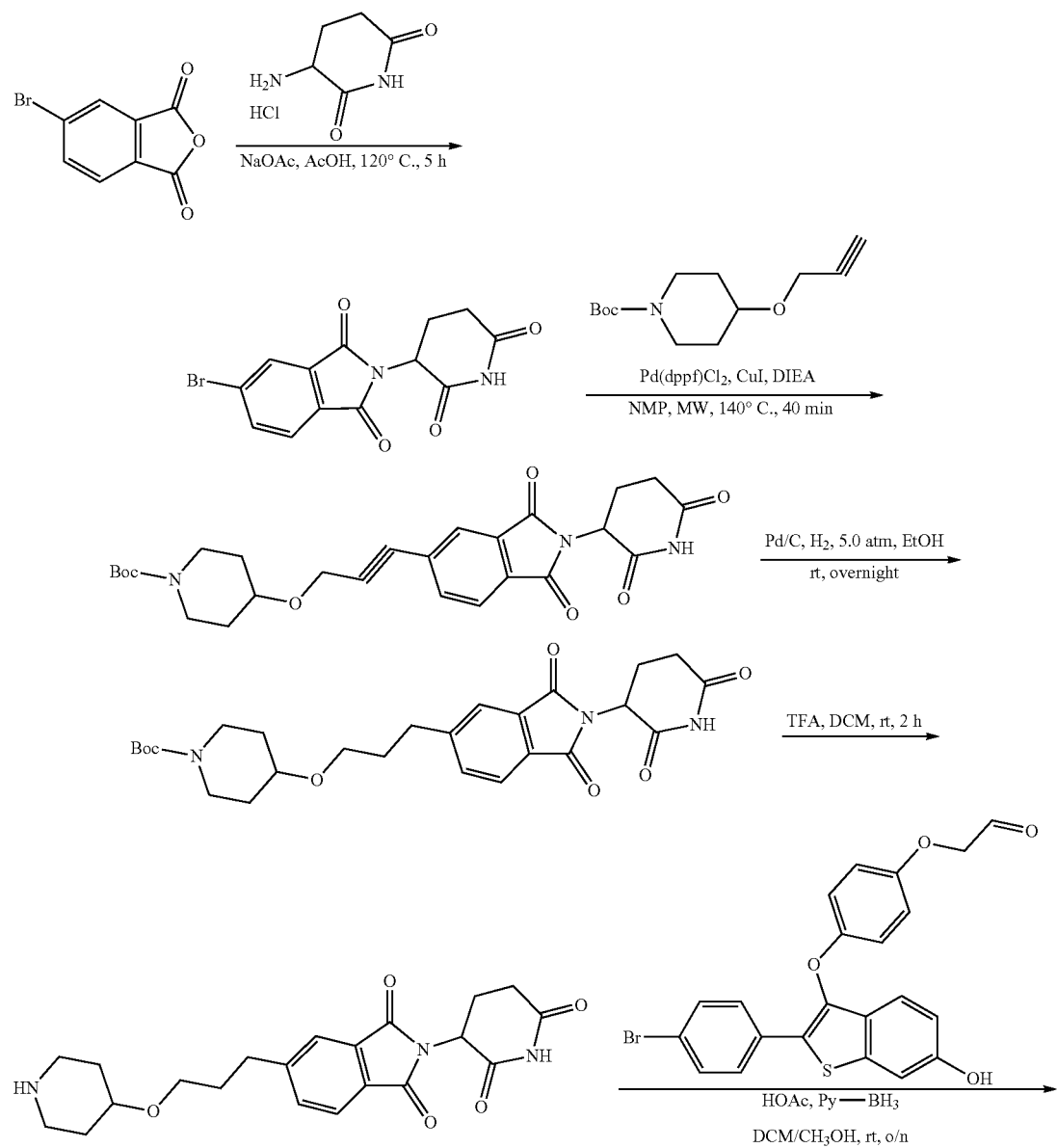

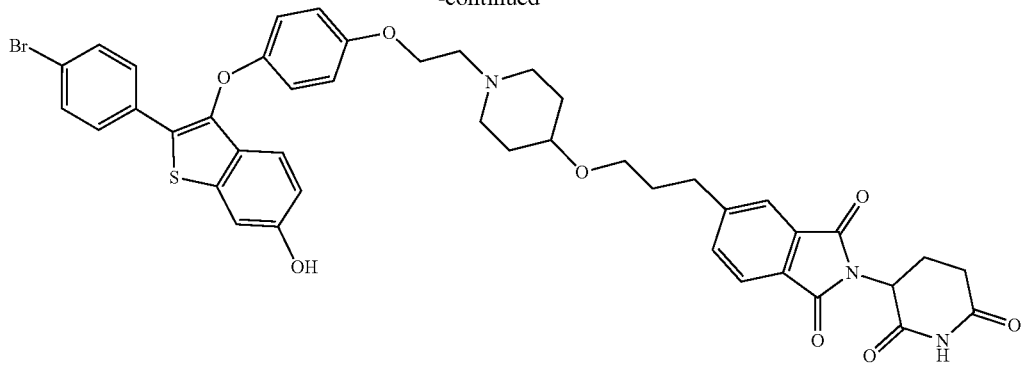
Example 70
General Scheme 1A to Prepare Intermediates
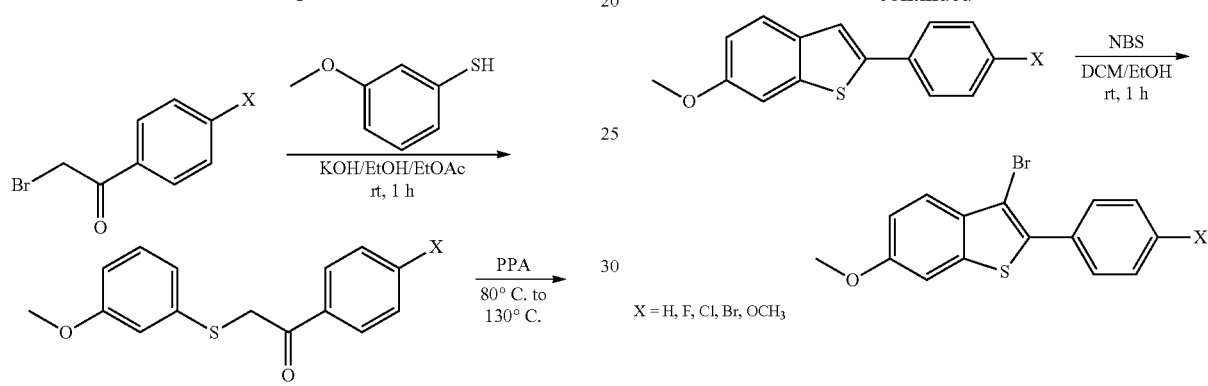
X = H, F, Cl, Br, OCH₃
General Scheme 2A to Prepare Intermediates
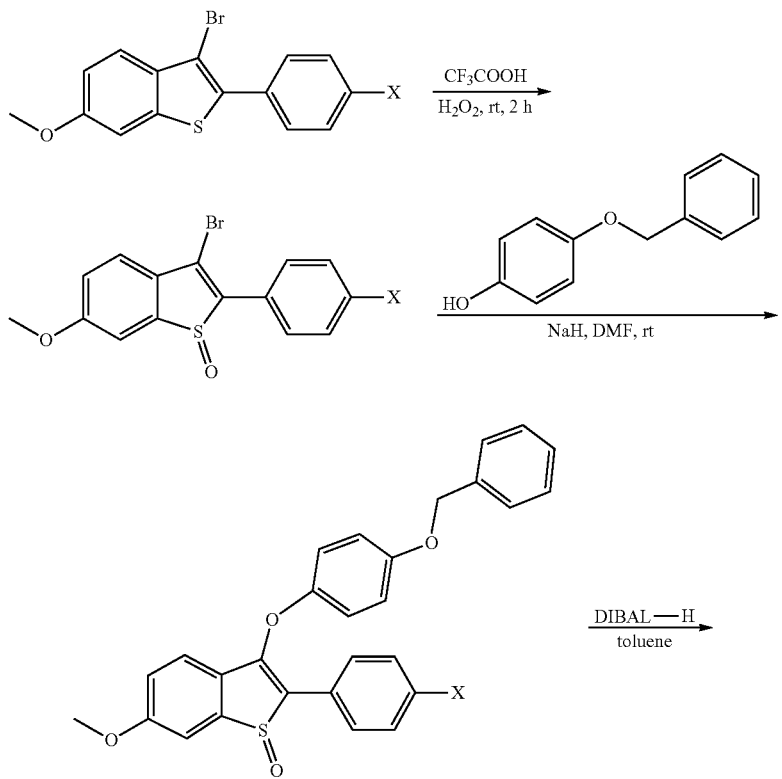

-continued
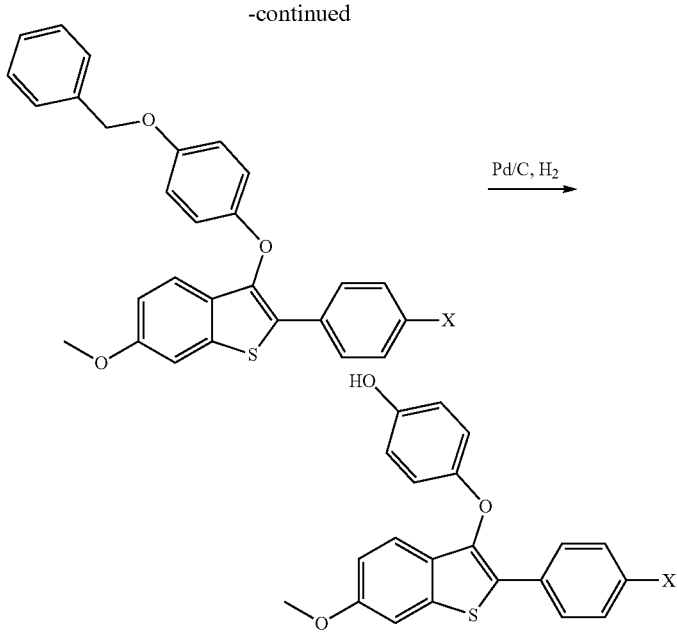
X = H, F, alkoxy
General Scheme 3A to Prepare Intermediates
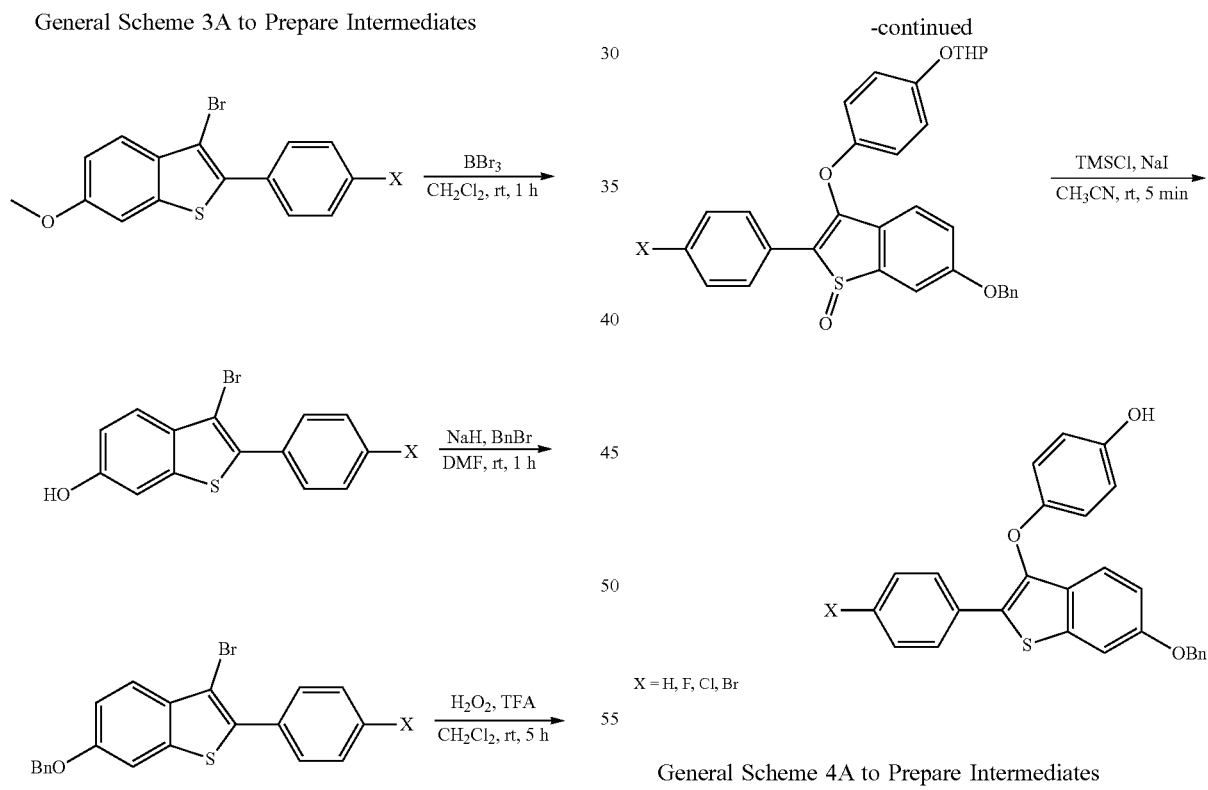
X = H, F, Cl, Br
General Scheme 4A to Prepare Intermediates
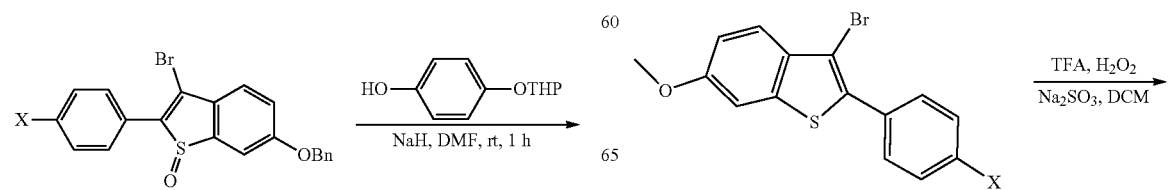

393
-continued
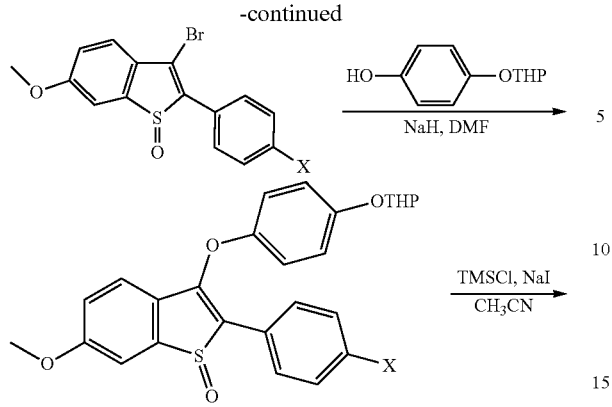
394
-continued
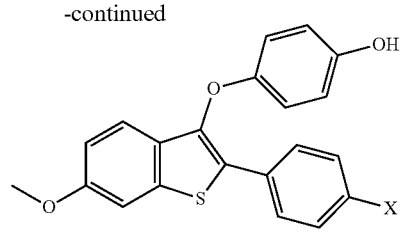
X = H, F, Cl, Br, alkoxy
General Scheme 5A to Prepare Intermediates
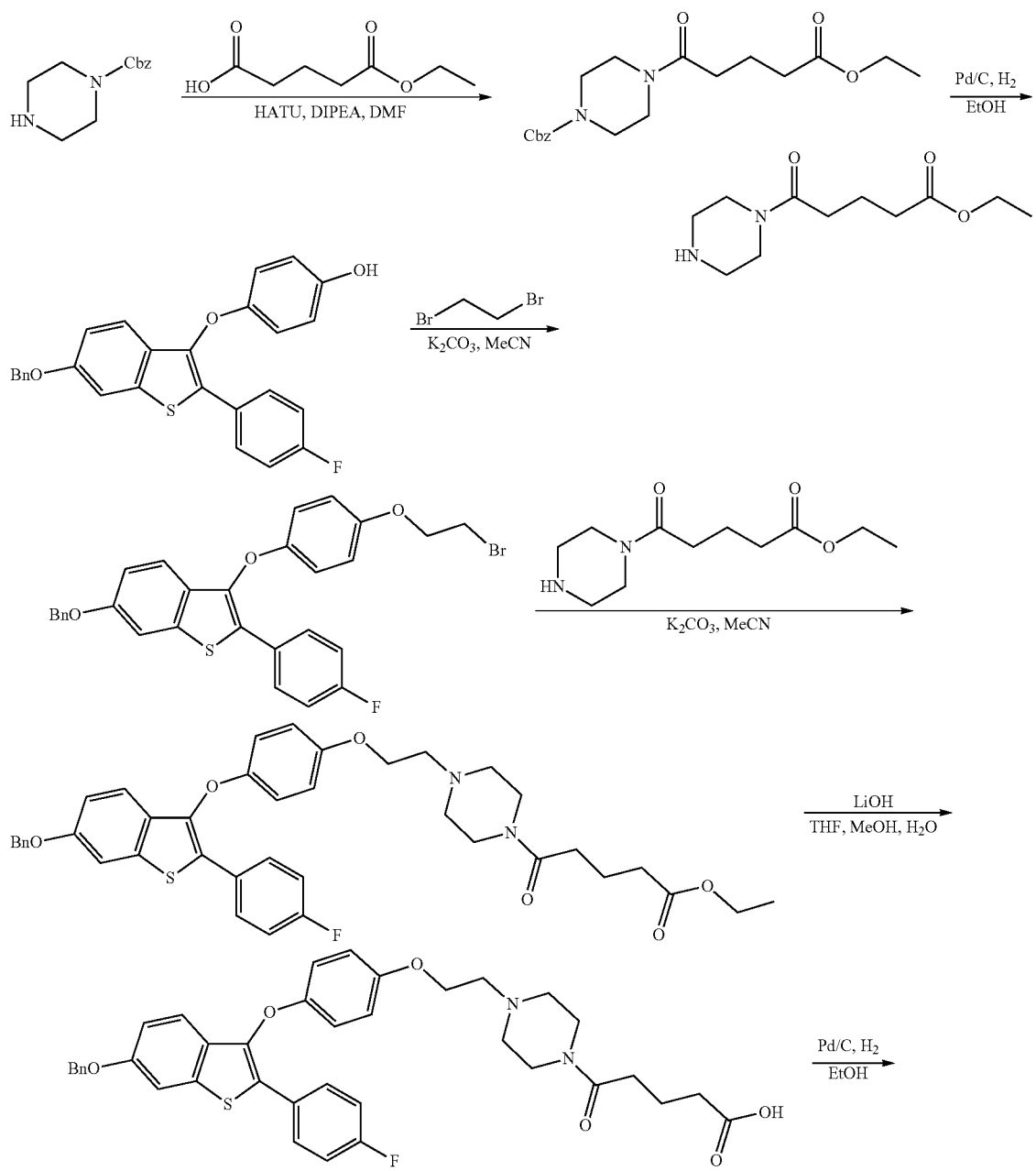

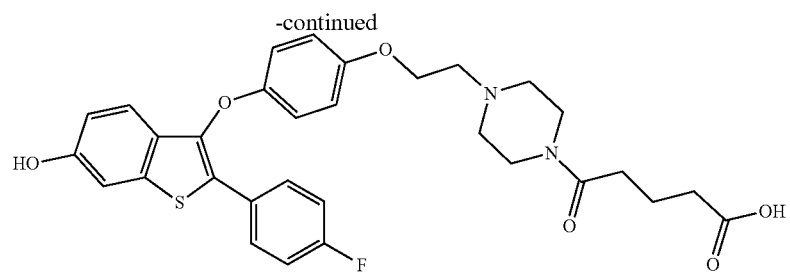
intermediate for Example 114
General Scheme 6A to Prepare Intermediates
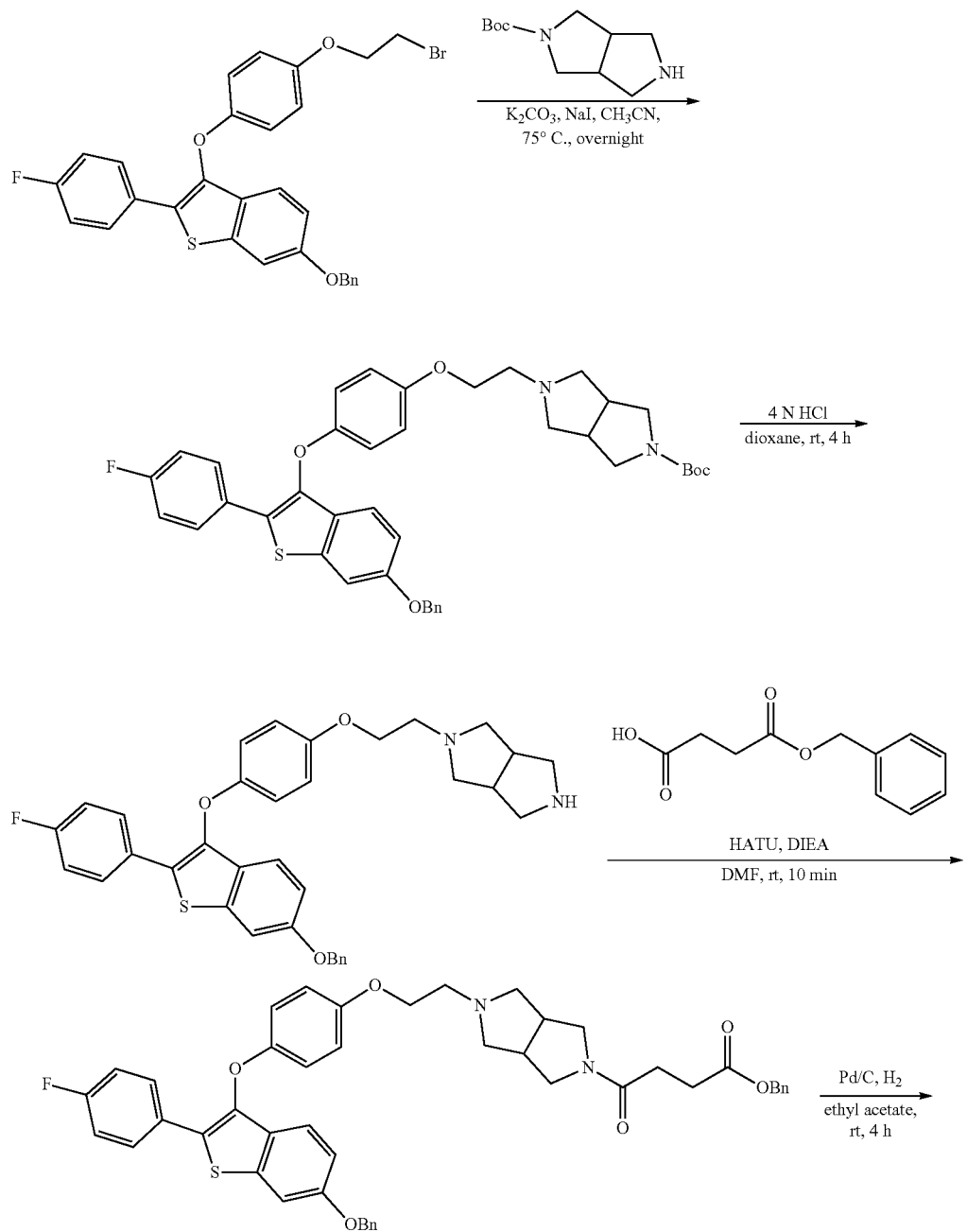

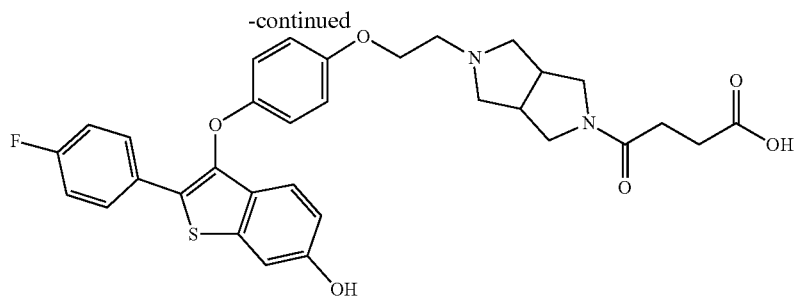
intermediate for Example 115
General Scheme 7A to Prepare Intermediates
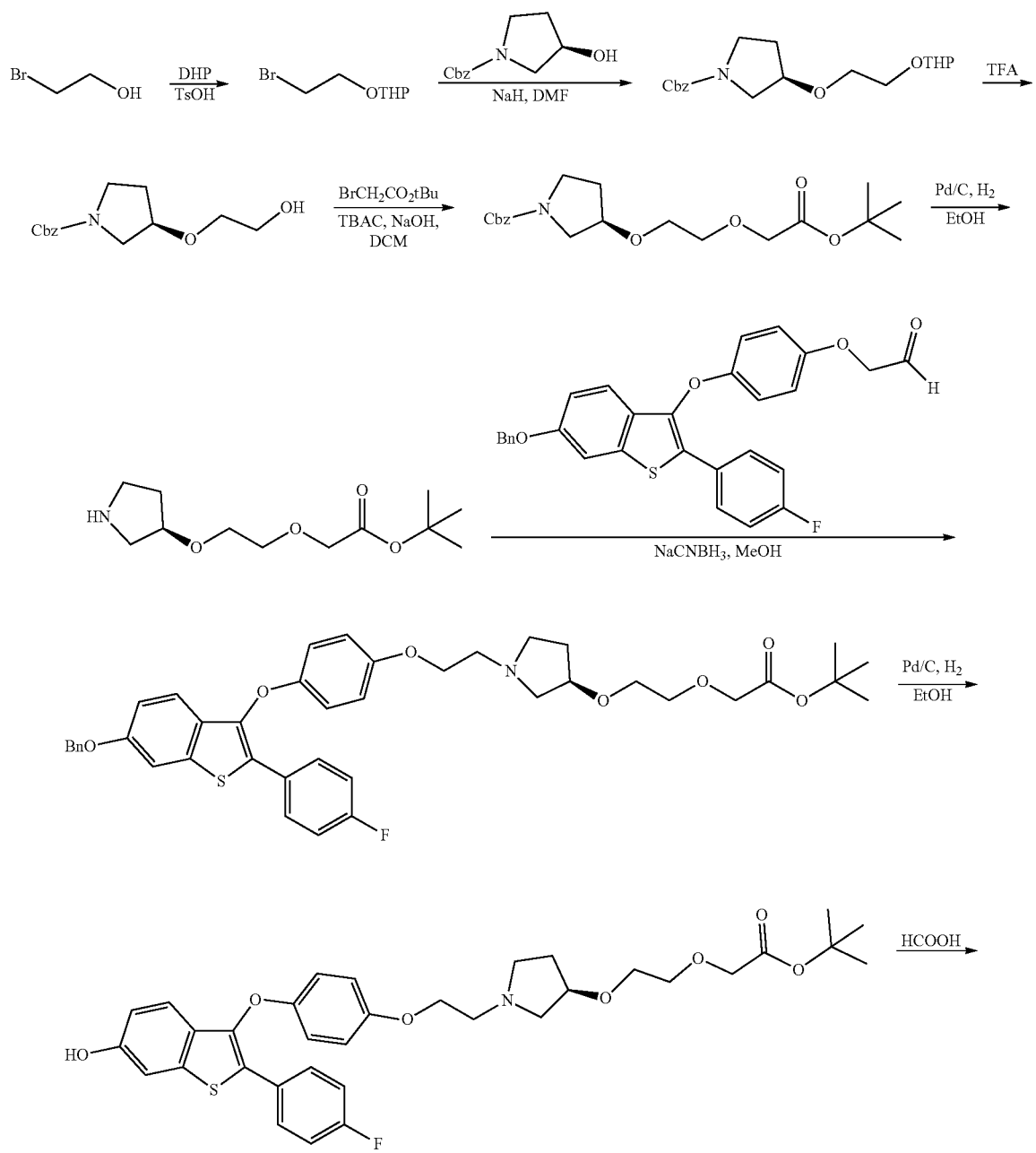

-continued
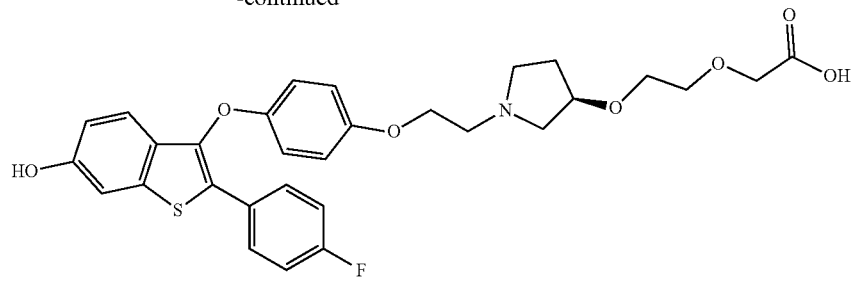
intermediate for Example 116
General Scheme 8A to Prepare Intermediates
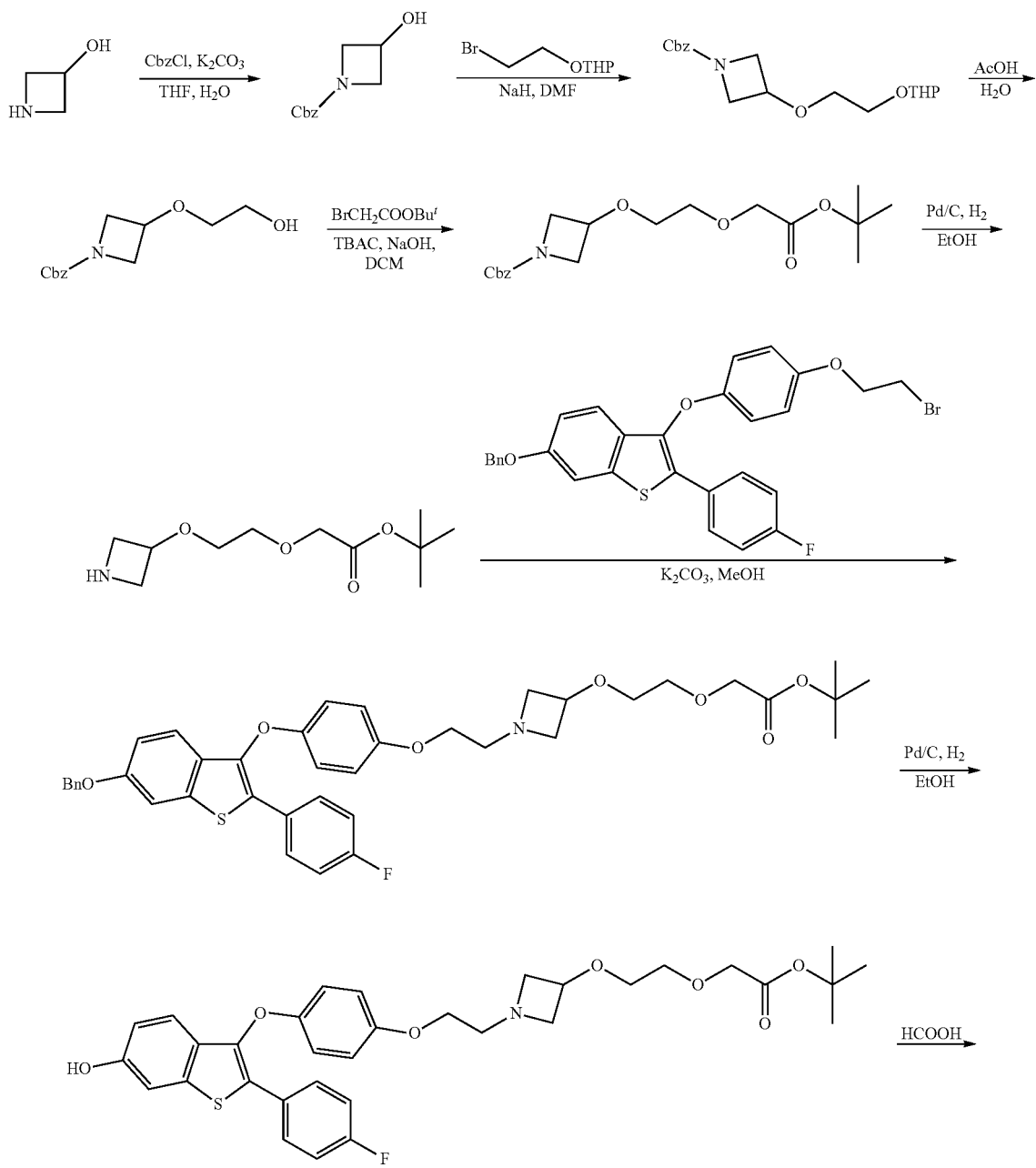

401                                                                                               402
-continued
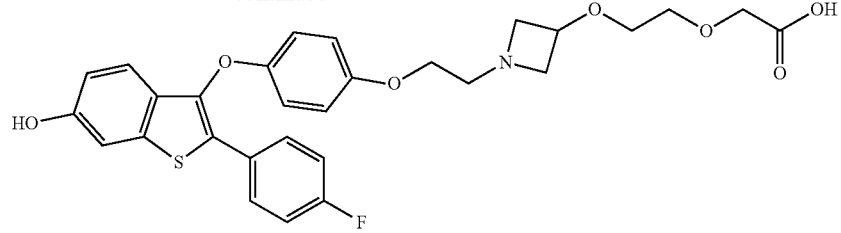
intermediate for Example 117
General Scheme 9A to Prepare Intermediates
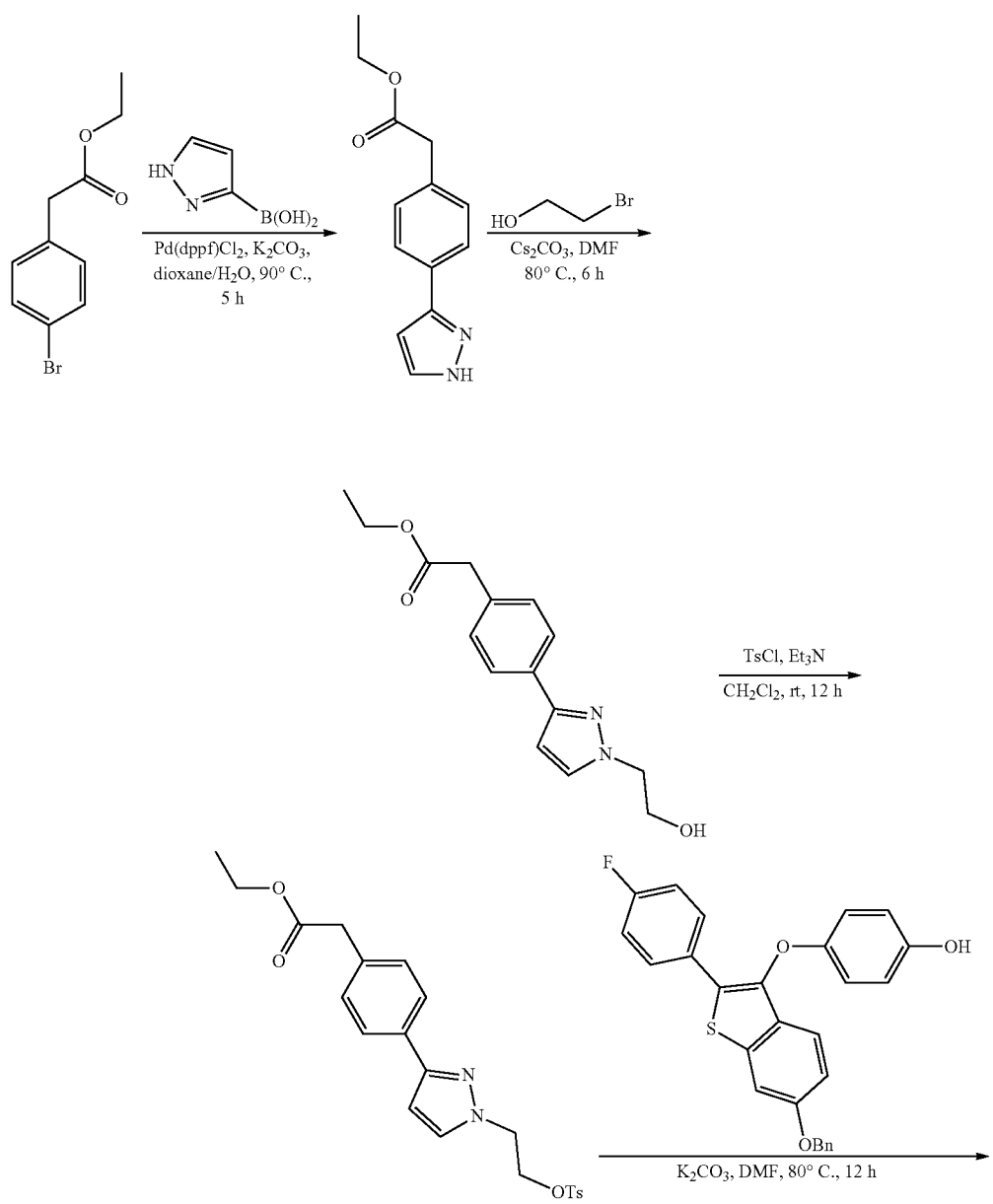

403 404
-continued
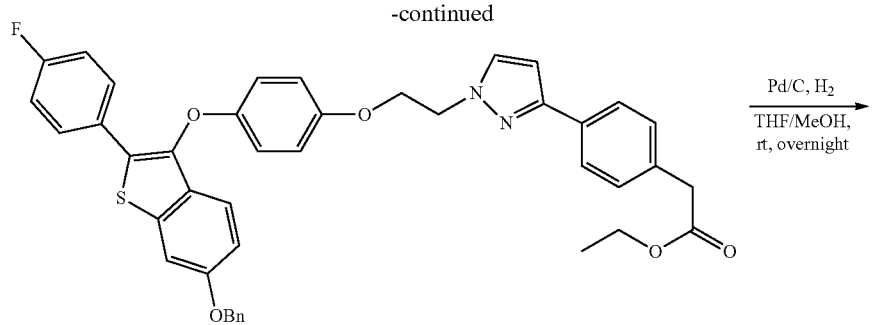
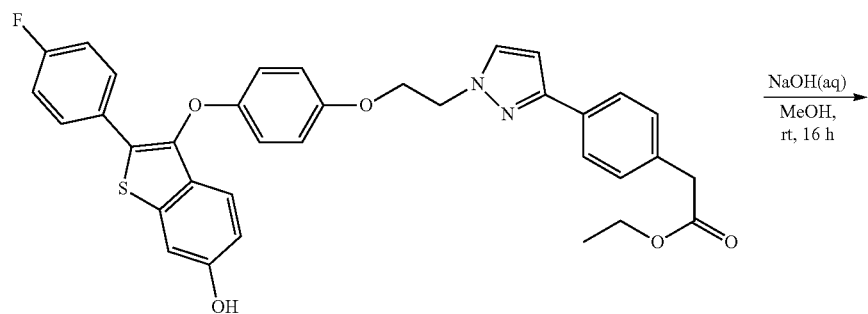
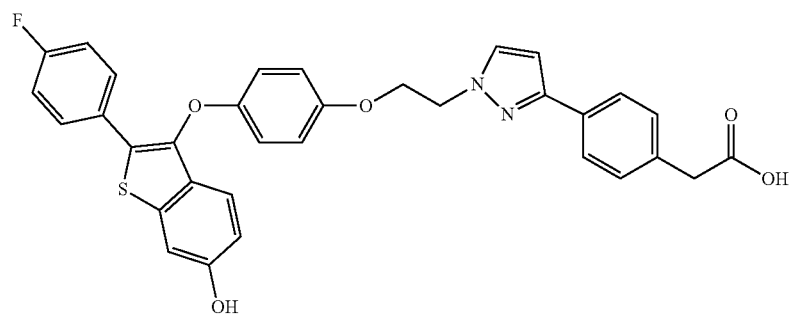
intermediate for Example 121
General Scheme 10A to Prepare Intermediates
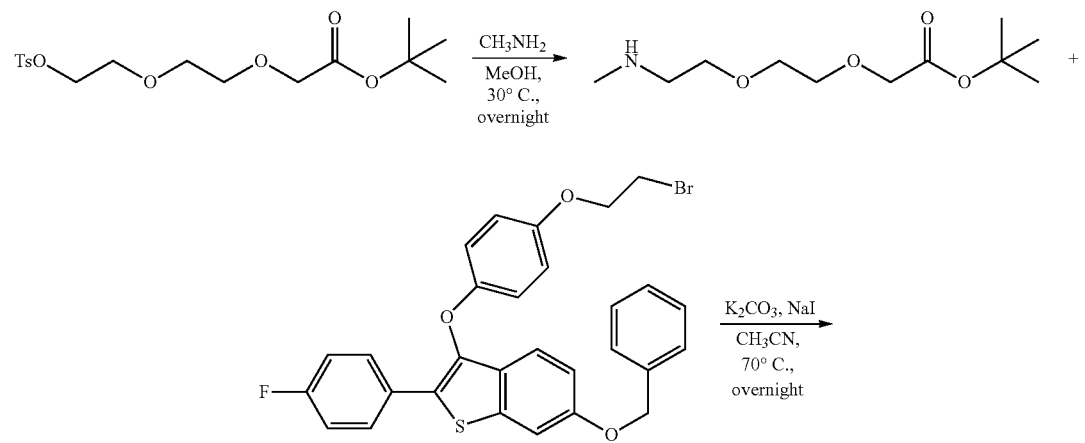

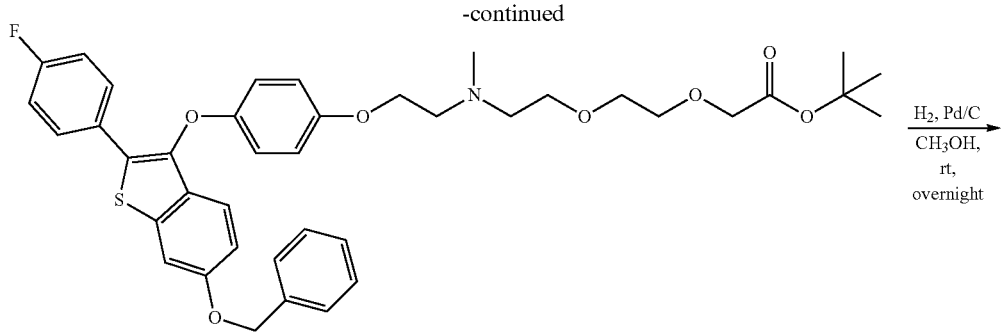
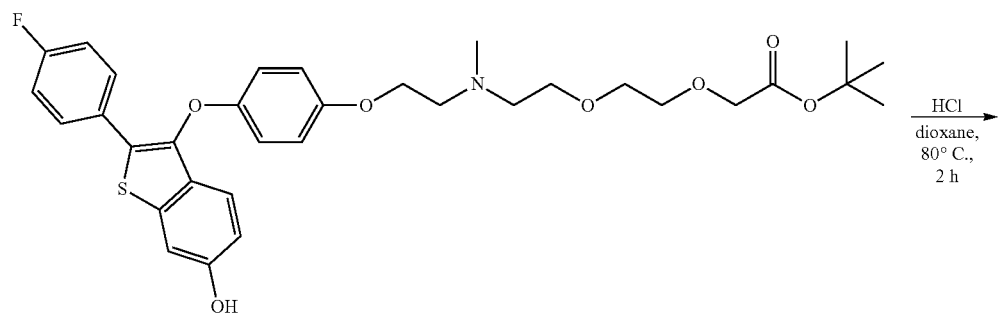
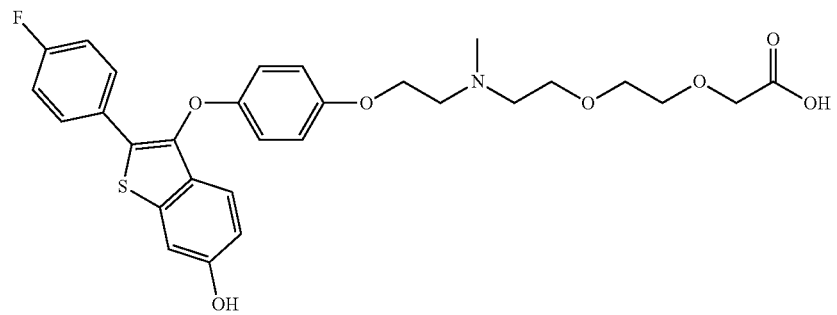
intermediate for Example 128
General Scheme 11A to Prepare Intermediates
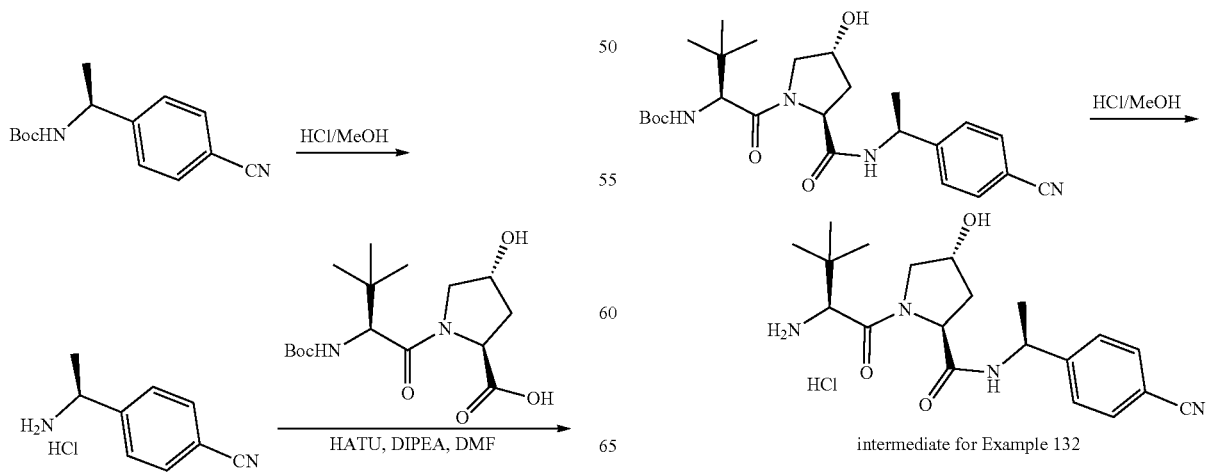

General Scheme 12A to Prepare Intermediates
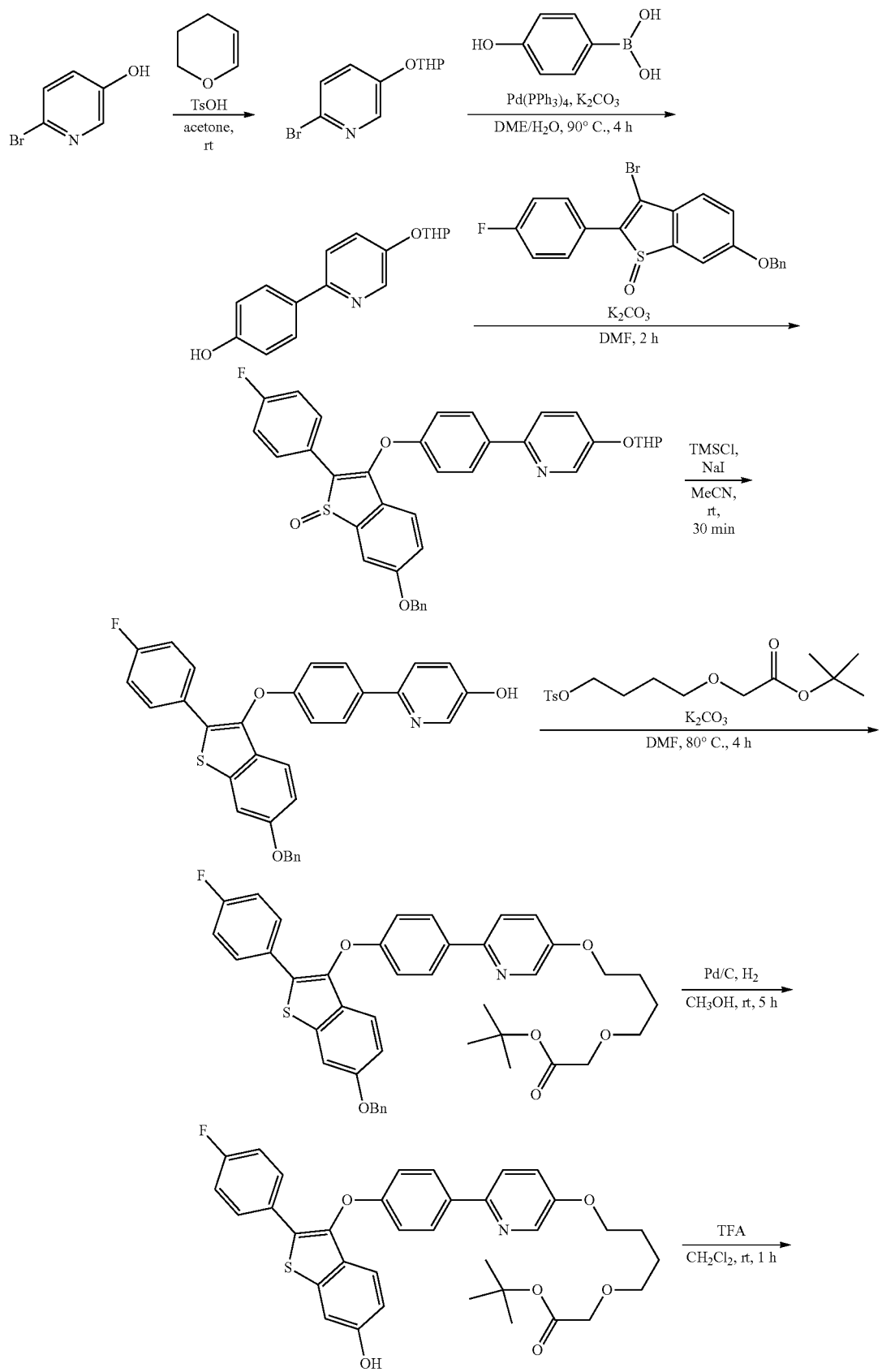

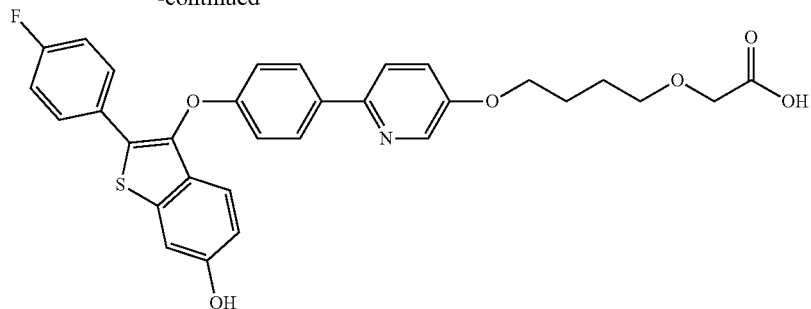
intermediate for Example 133
General Scheme 13A to Prepare Intermediates
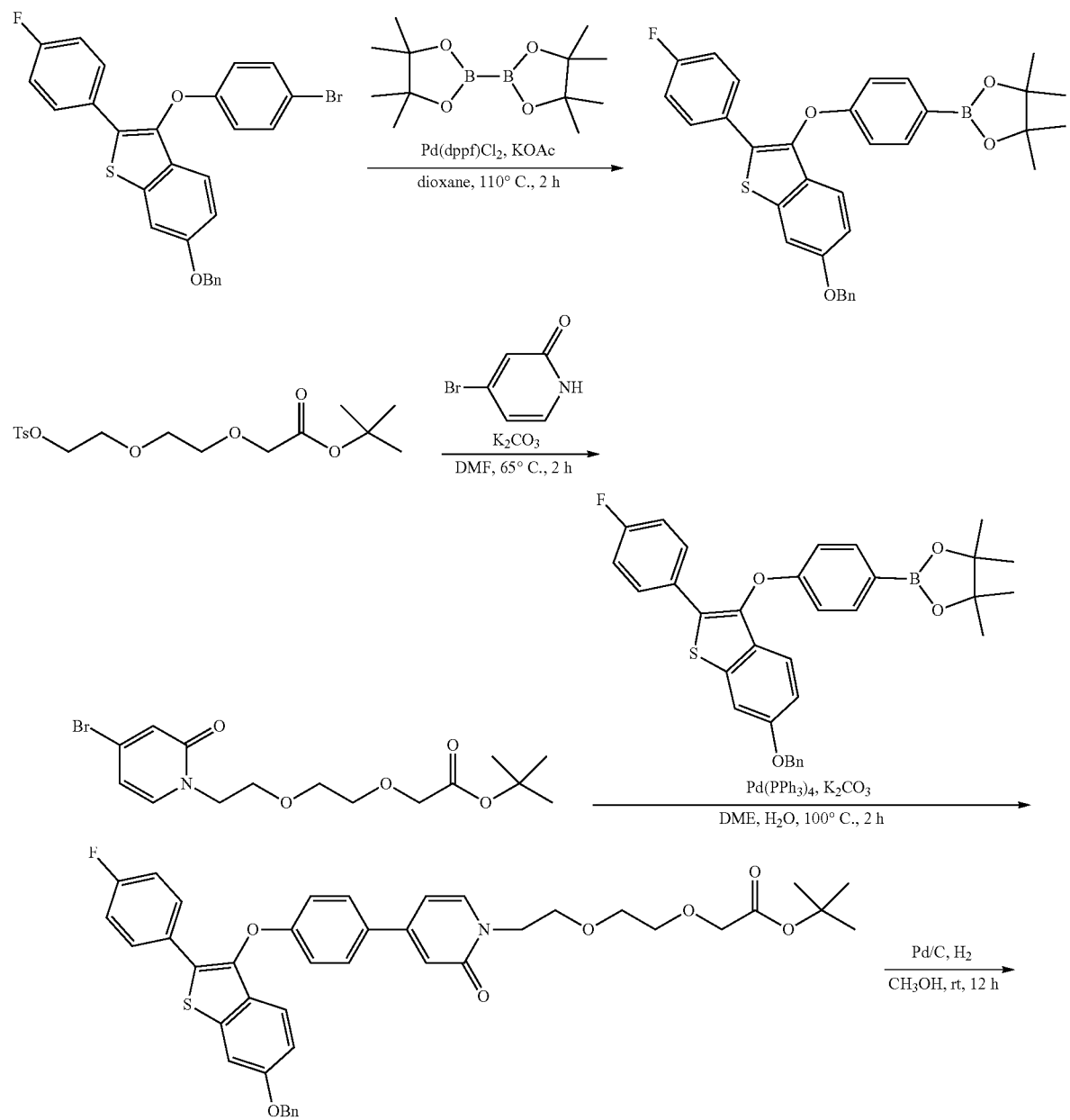

411
-continued
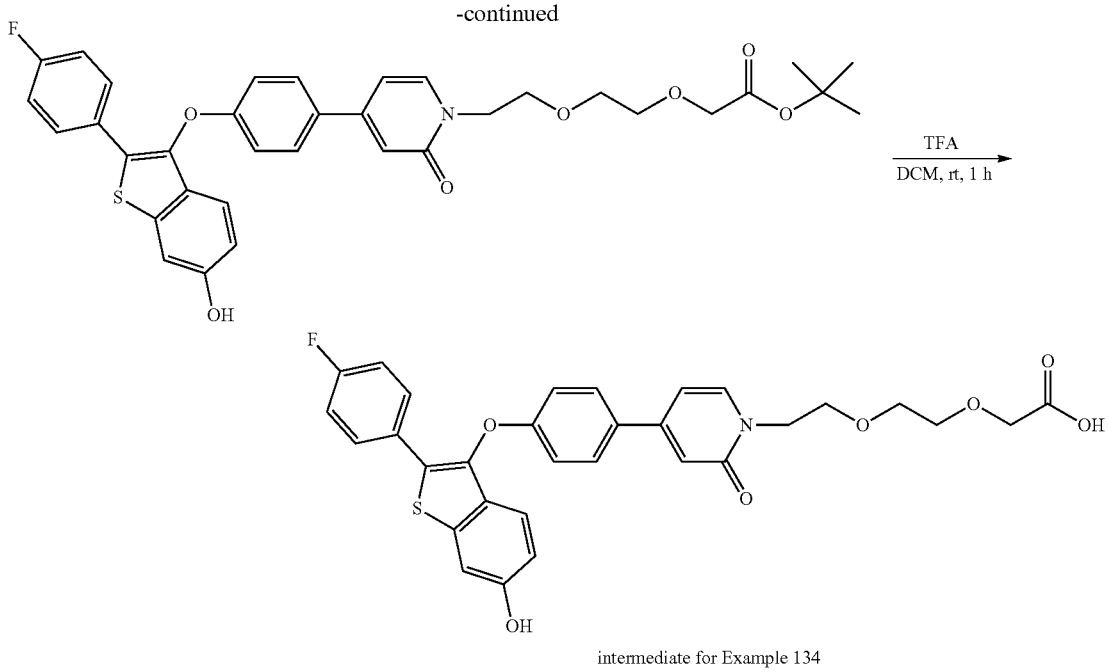
intermediate for Example 134
General Scheme 14A to Prepare Intermediates
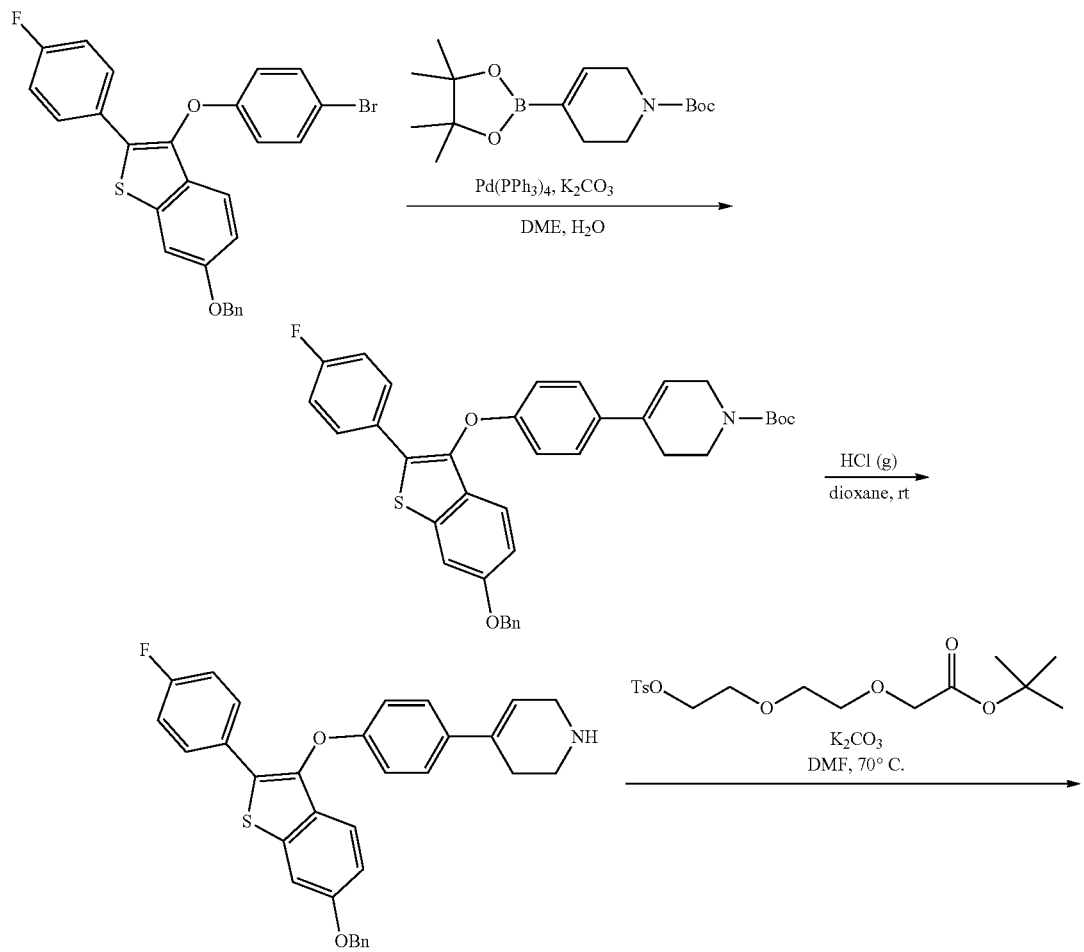

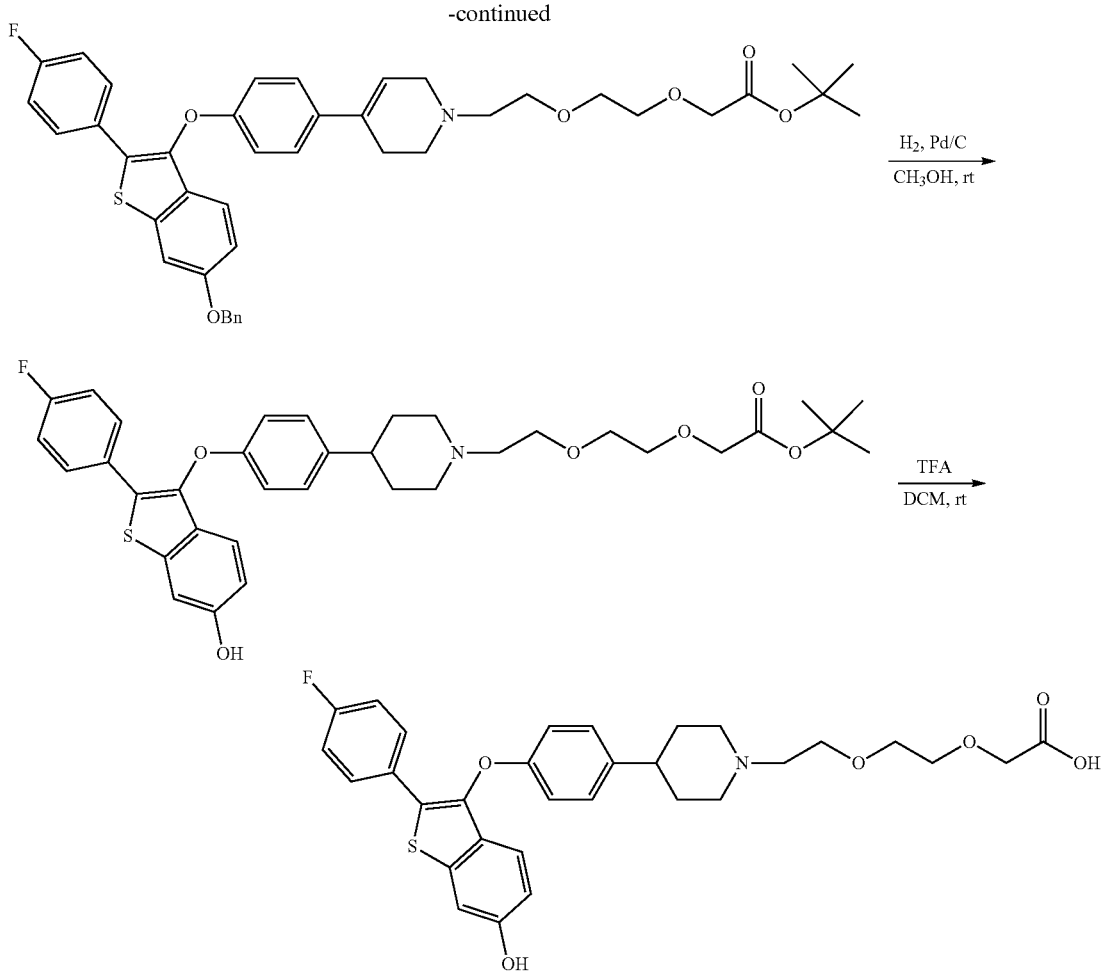
intermediate for Example 135
General Scheme 15A to Prepare Intermediates
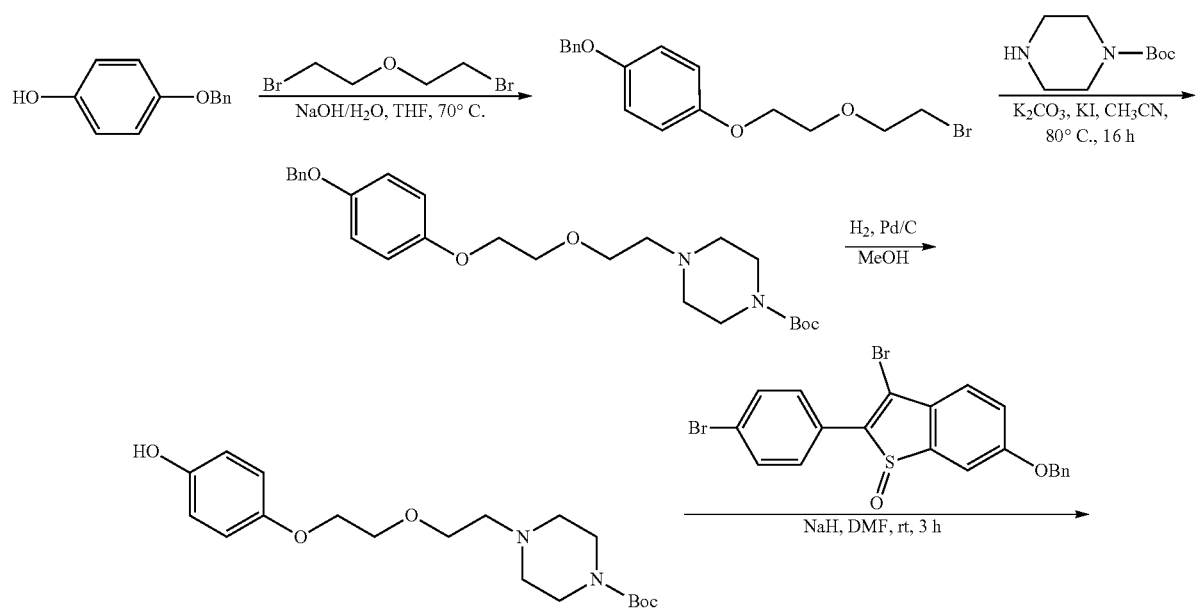

-continued
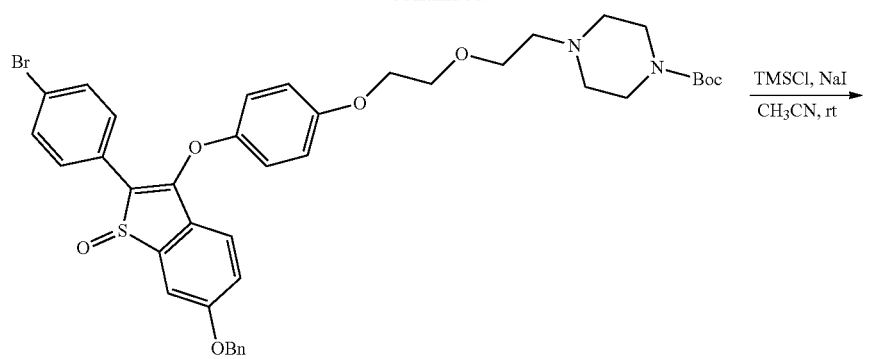
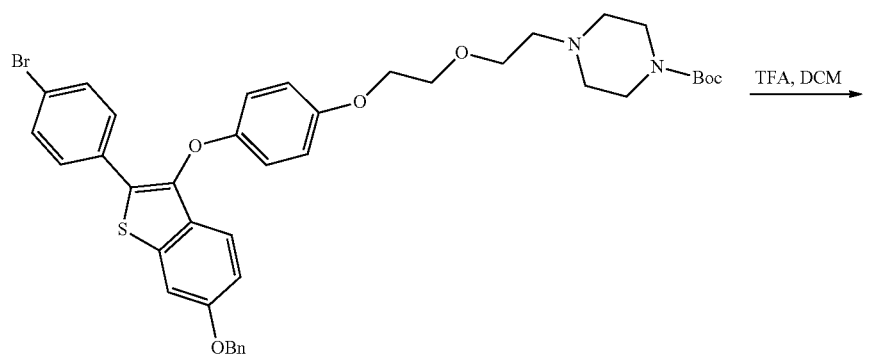
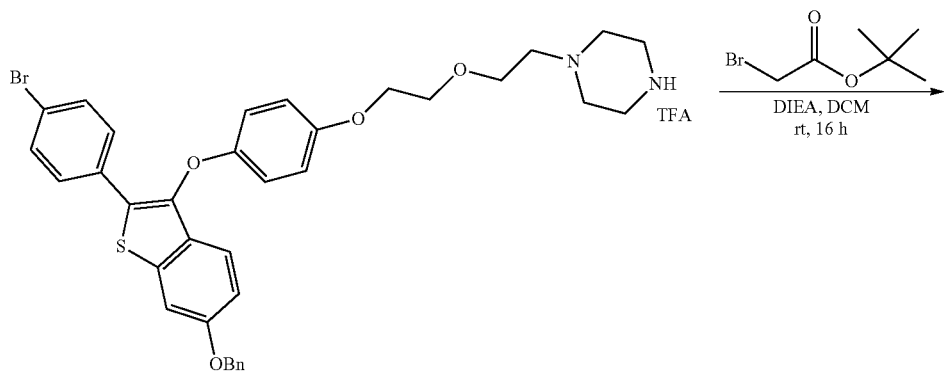
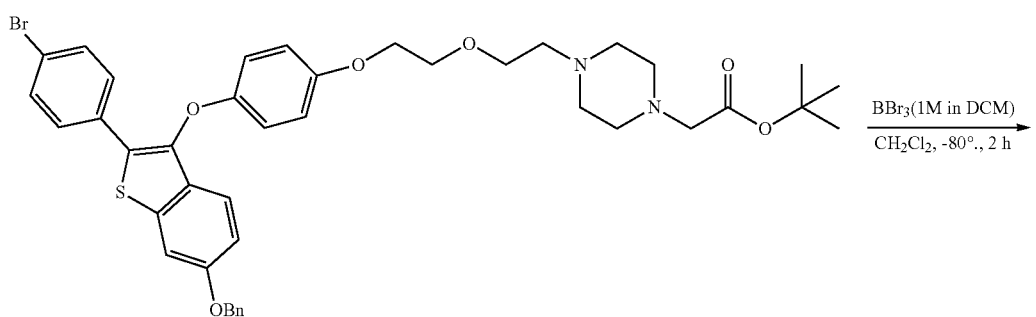

-continued
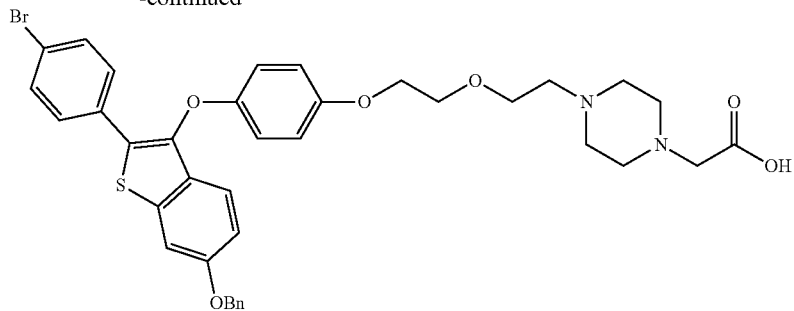
intermediate for Example 159
General Scheme 16A to Prepare Intermediates
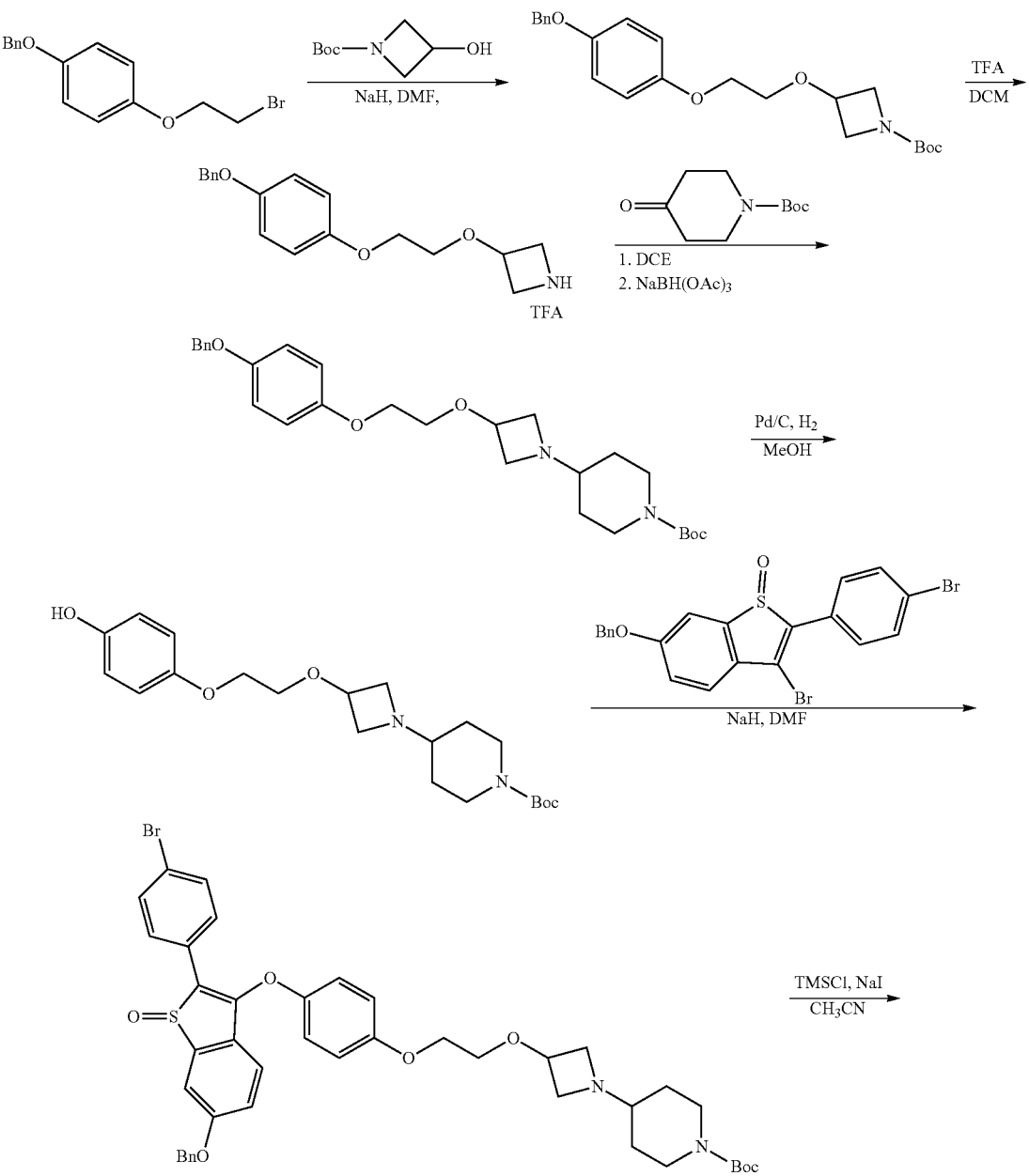

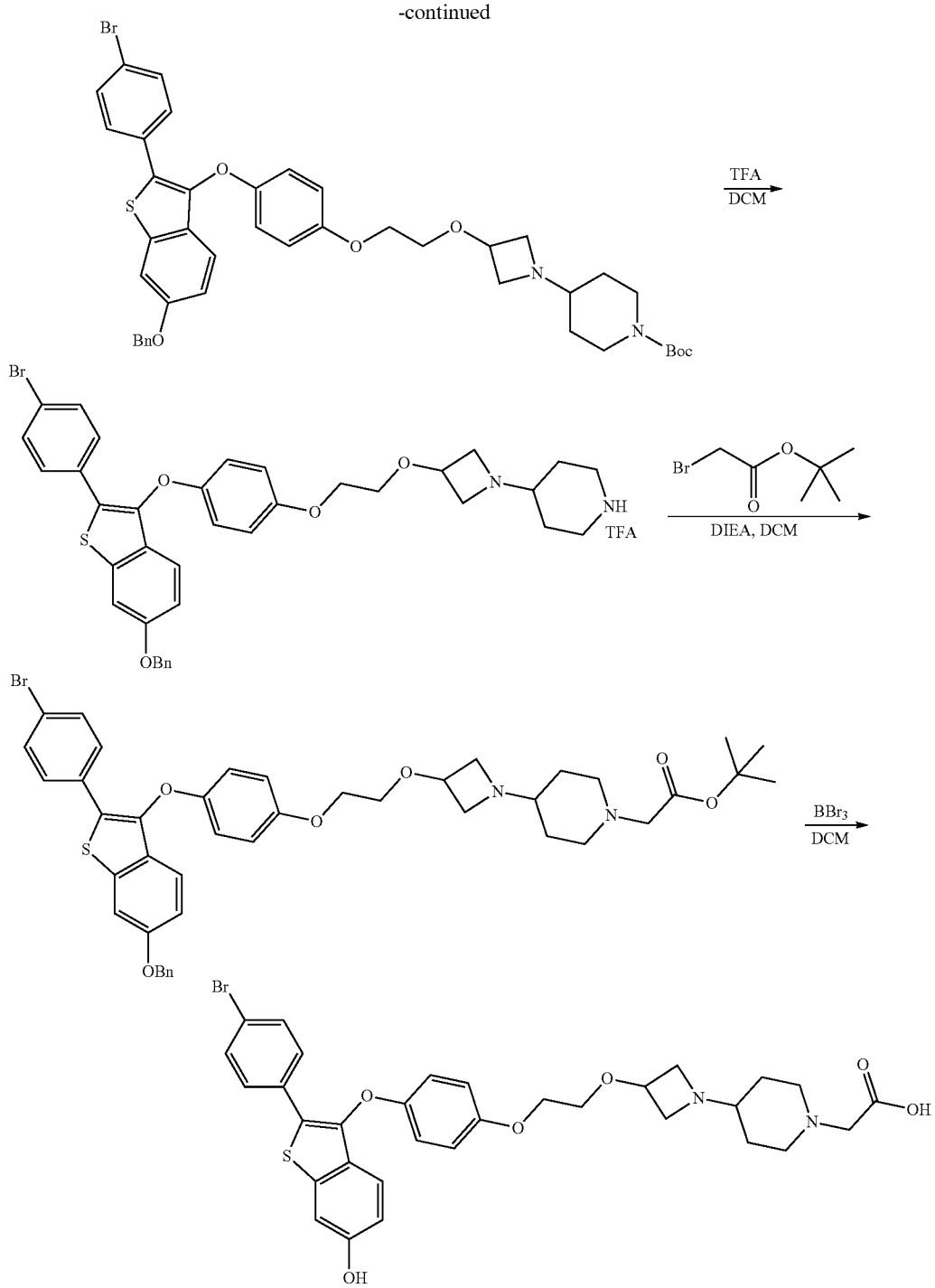
intermediate for Example 161
General Scheme 17A to Prepare Intermediates
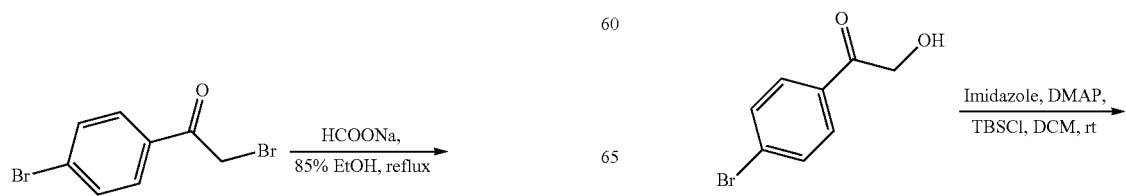

421
-continued
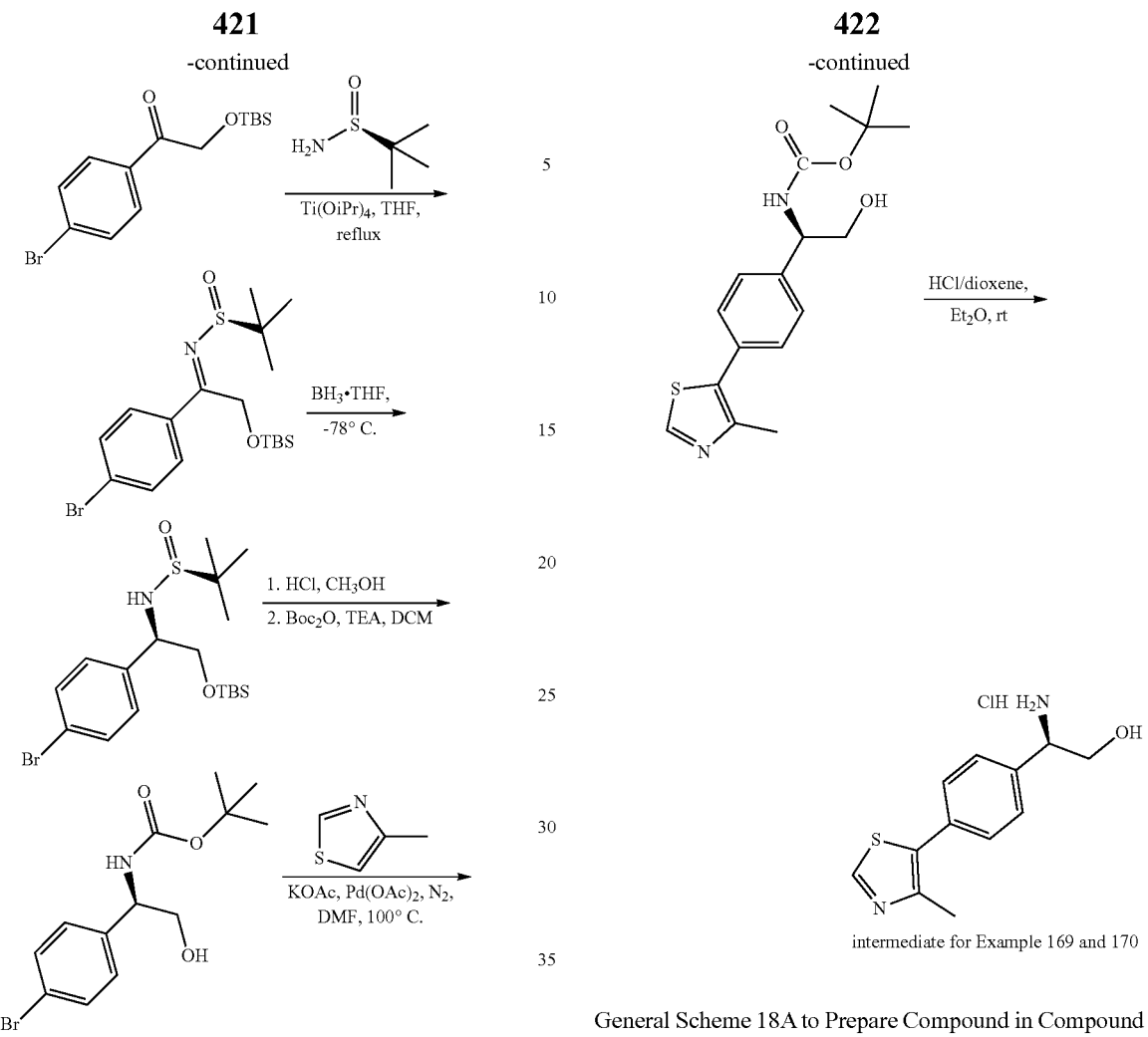
422
-continued
General Scheme 18A to Prepare Compound in Compound 111.
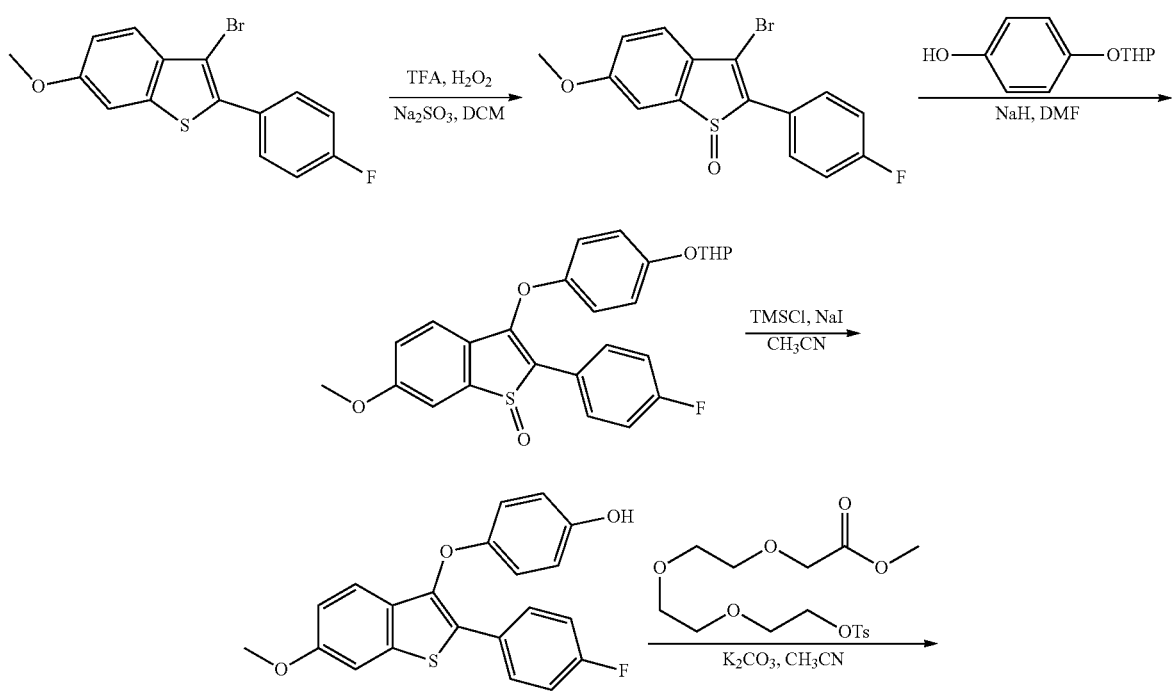

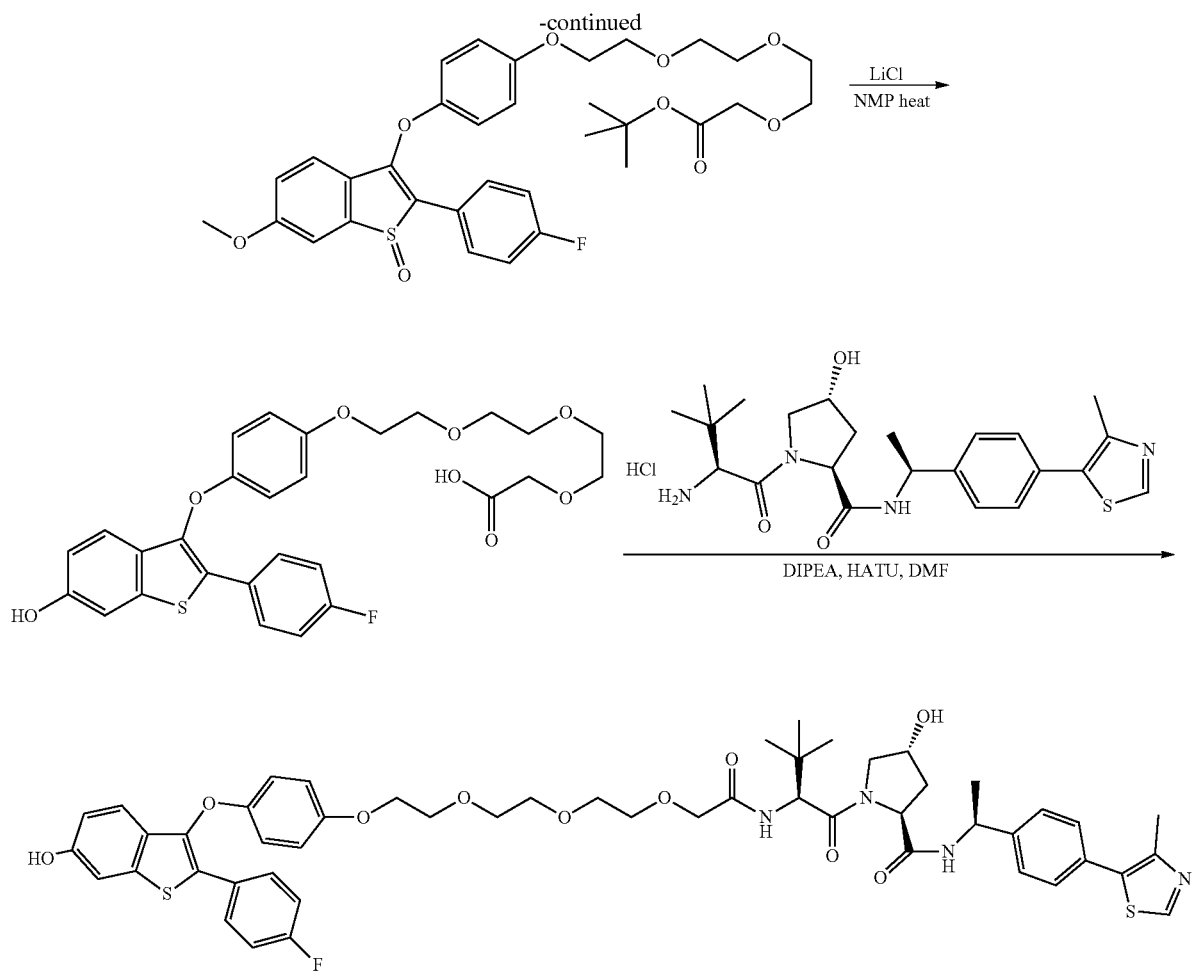
Example 111
General Scheme 19A to Prepare Compound in Compound 140.
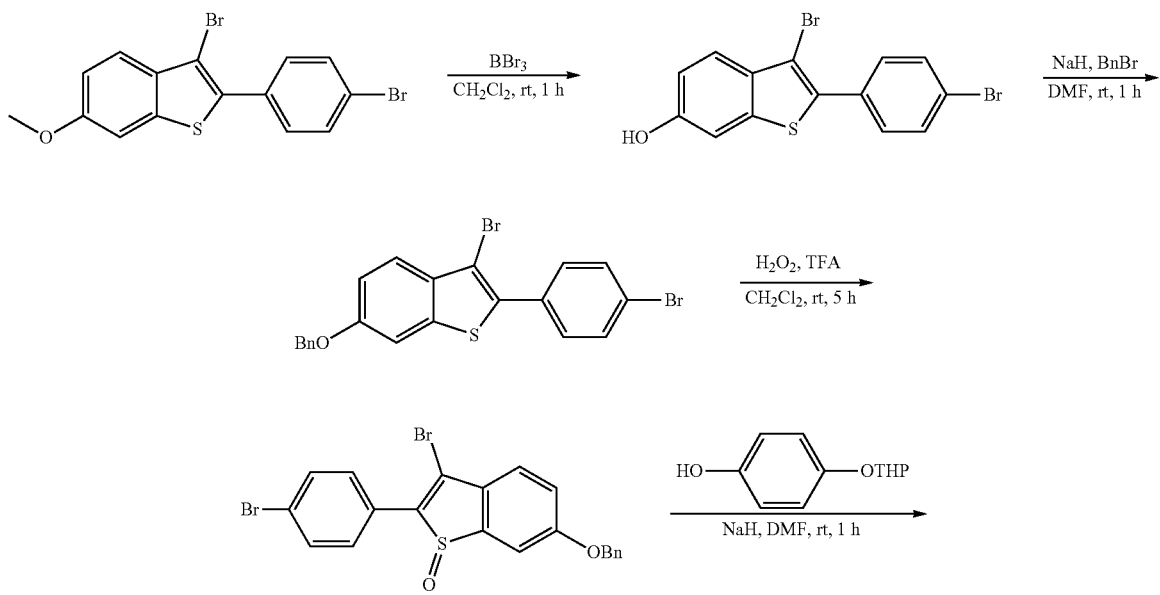

425 426
-continued
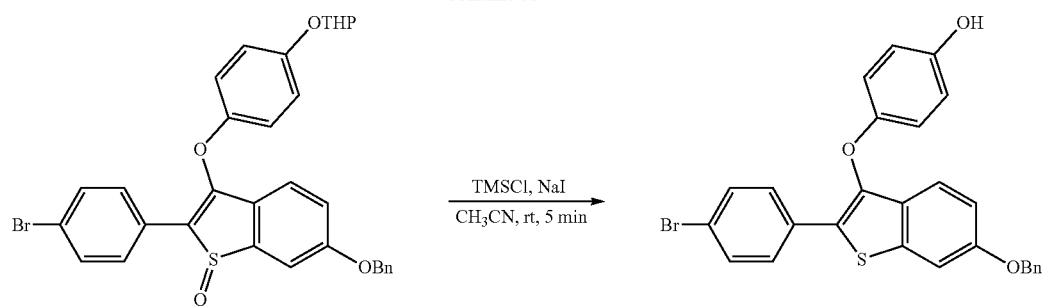
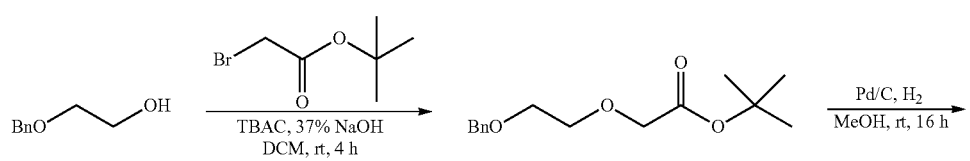
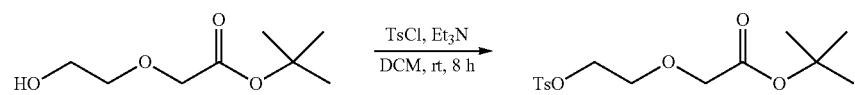
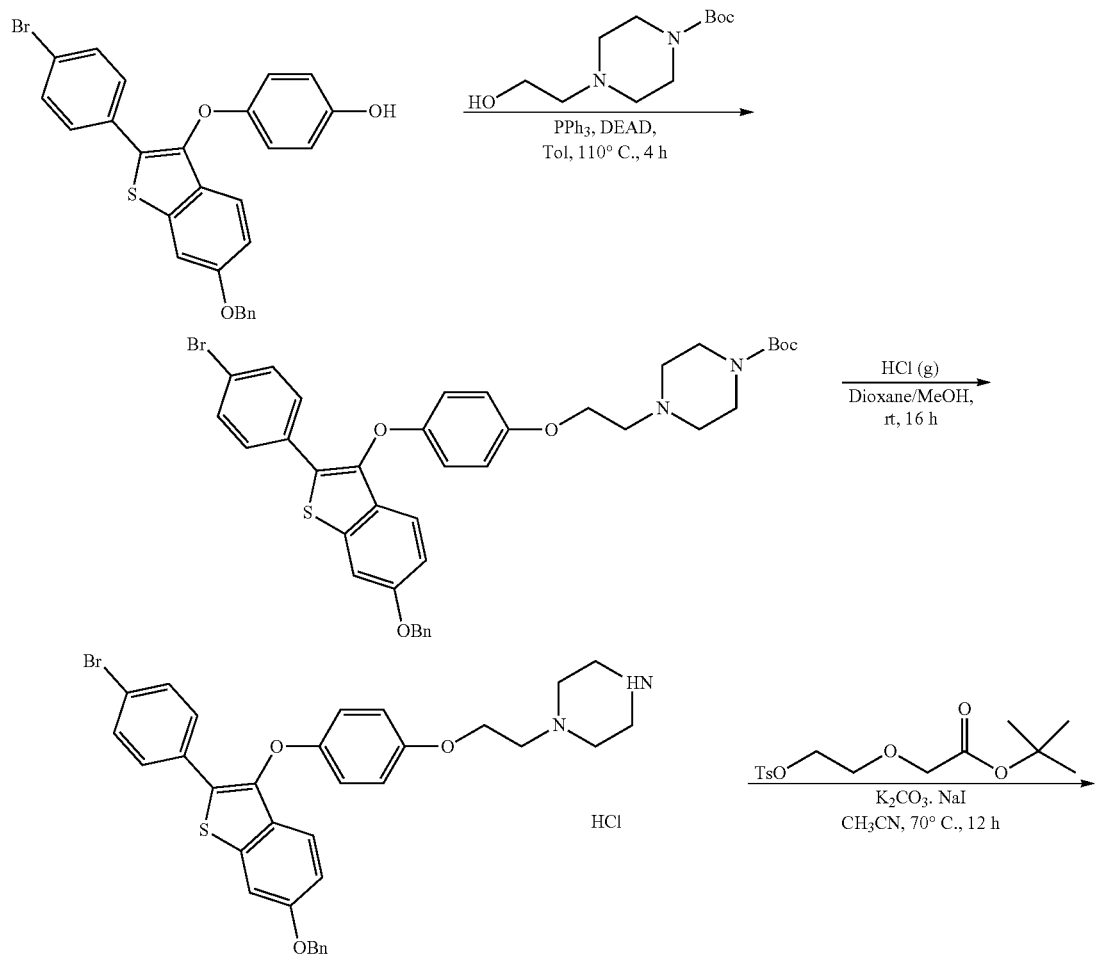

-continued
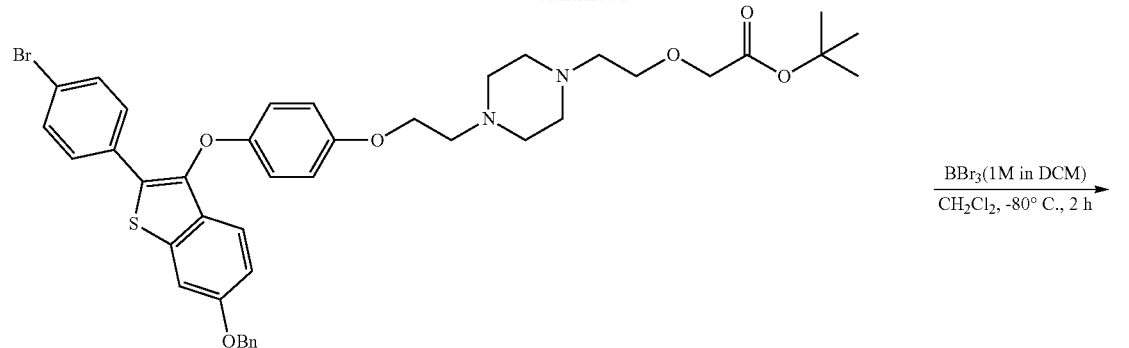
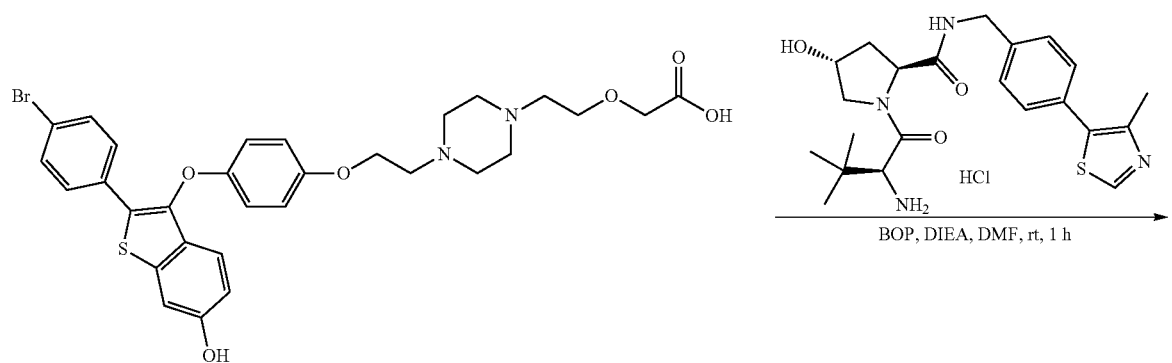
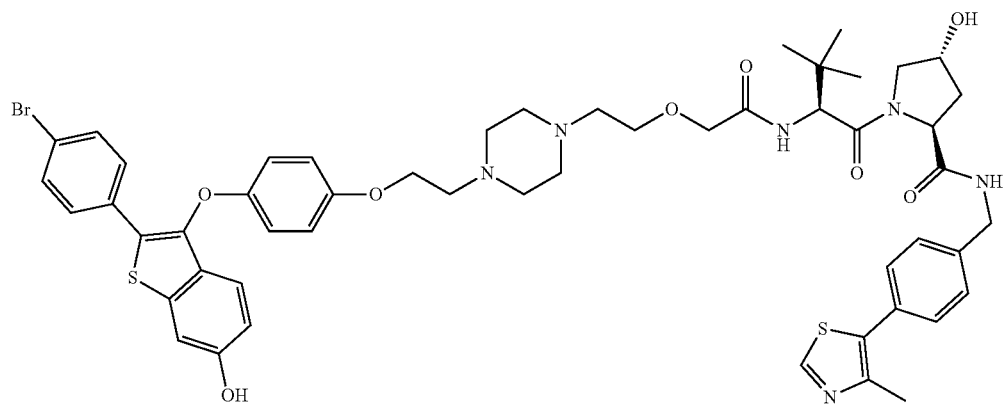
Example 140
General Scheme 20A to Prepare Compound in Example 161, 162, 163, 164, 165 and 166.
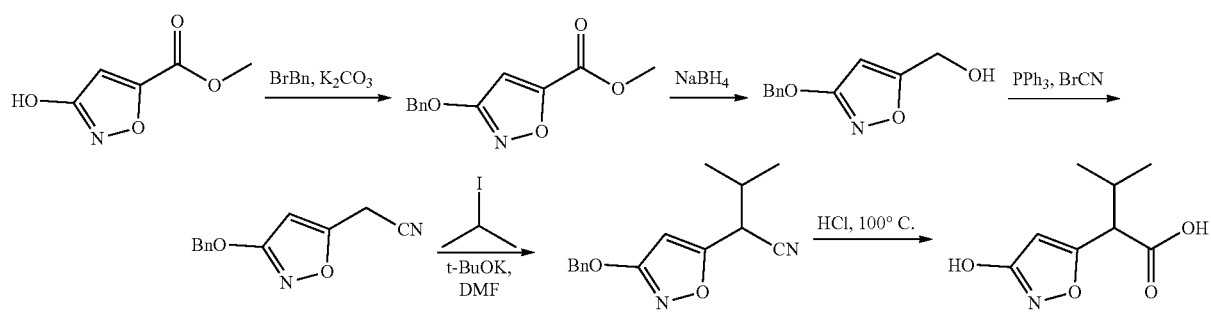

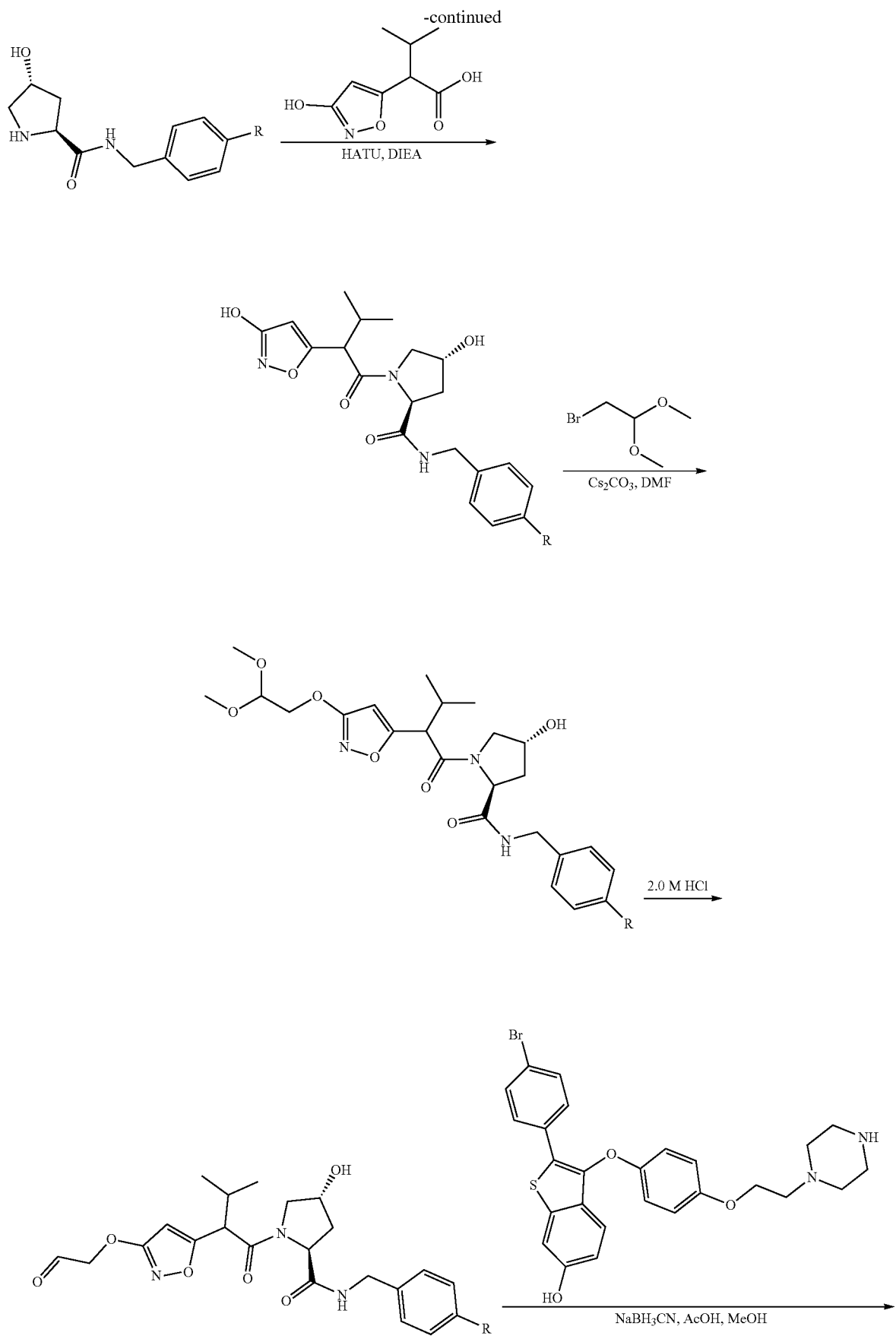

431 432
-continued
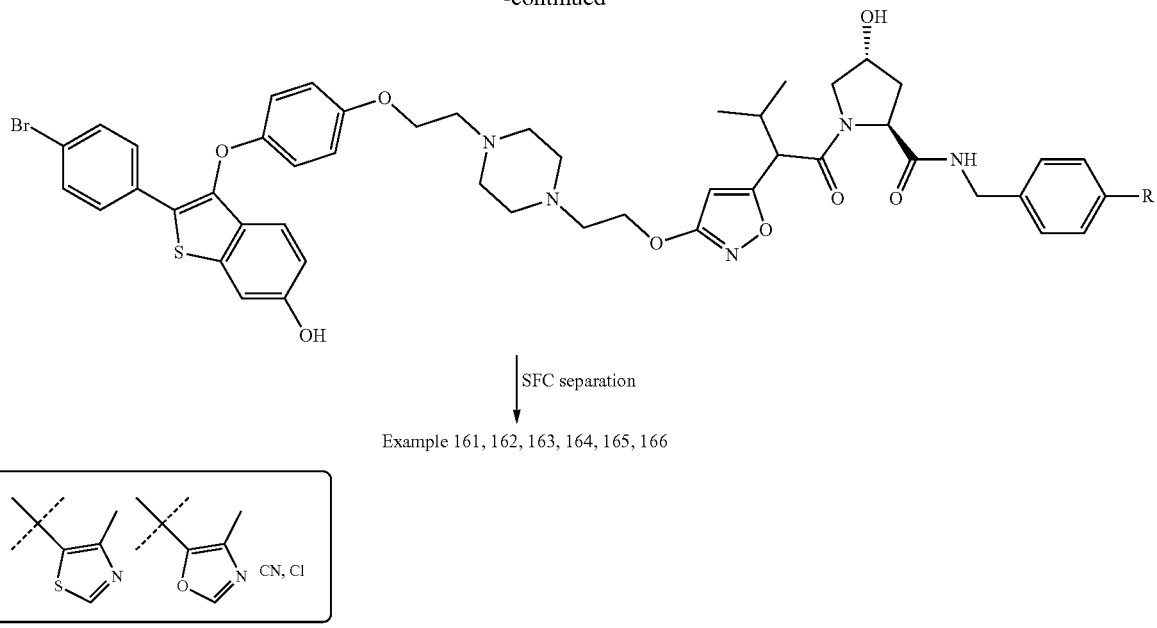
General Scheme 1B to Prepare Compound 170.
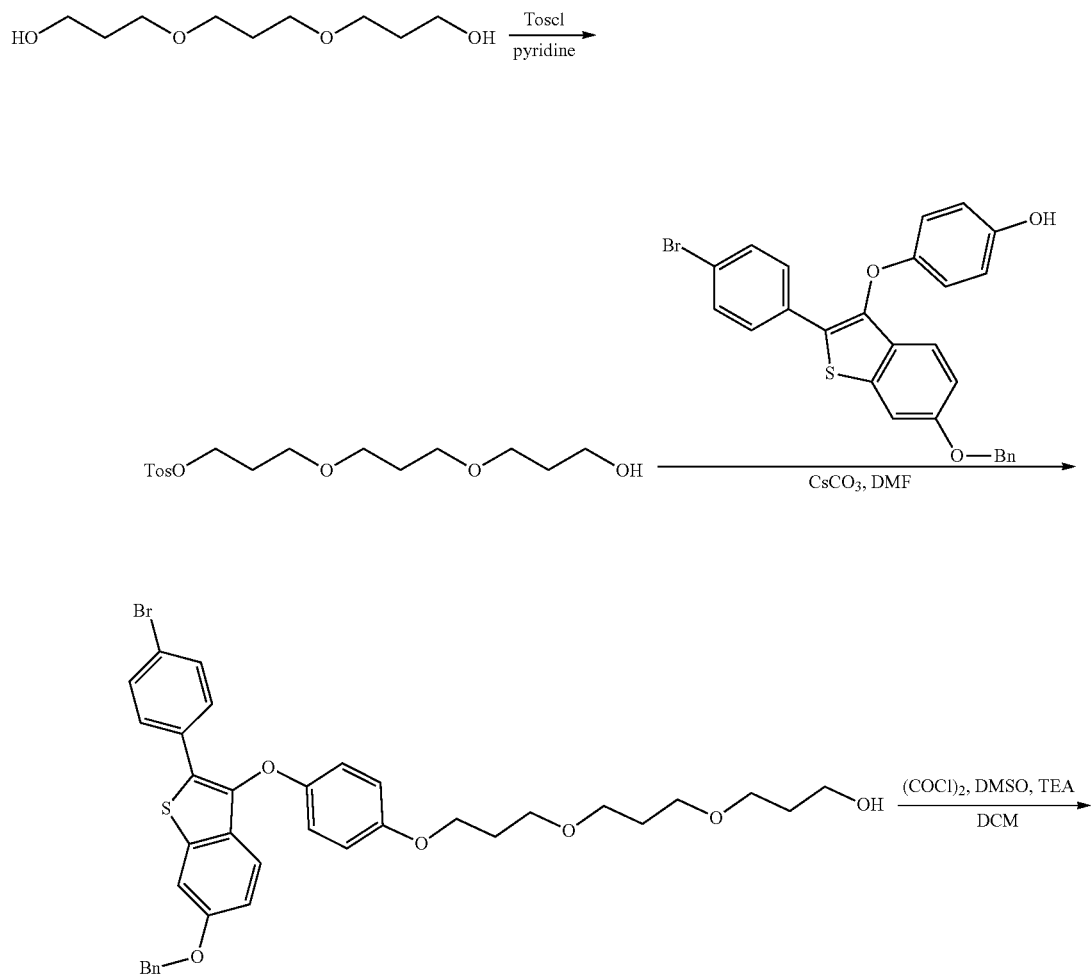

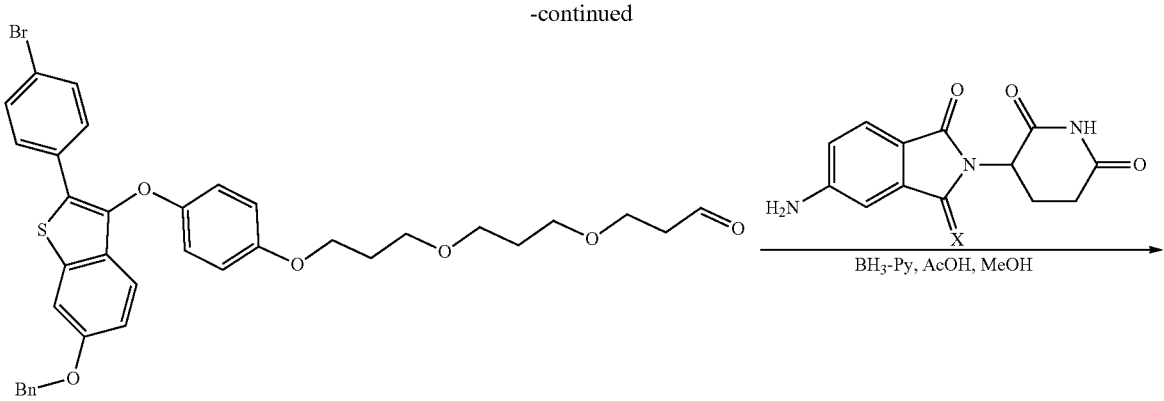
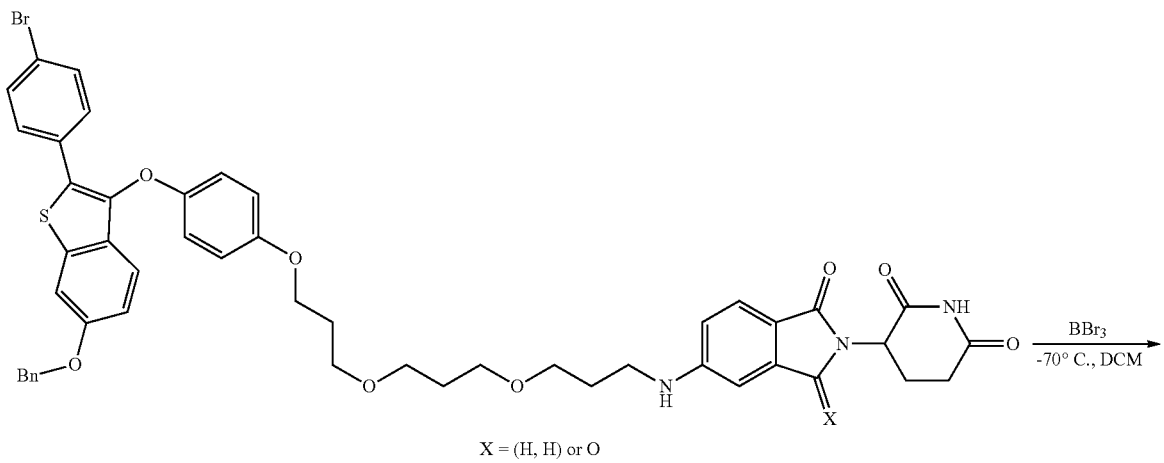
X = (H, H) or O
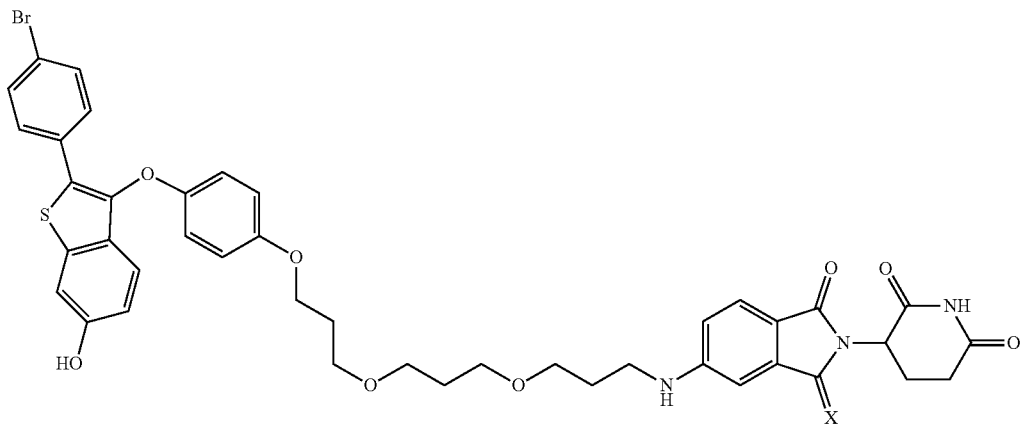
Compound 170 (X = H, H)
General Scheme 2B to Prepare Compound 174.
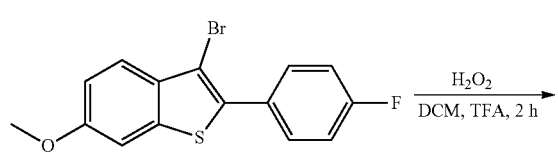

-continued
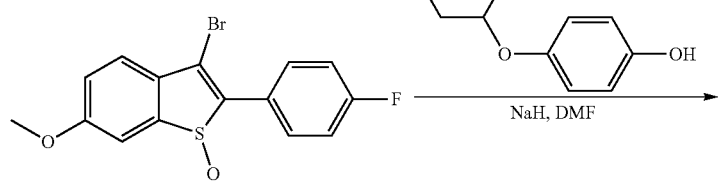
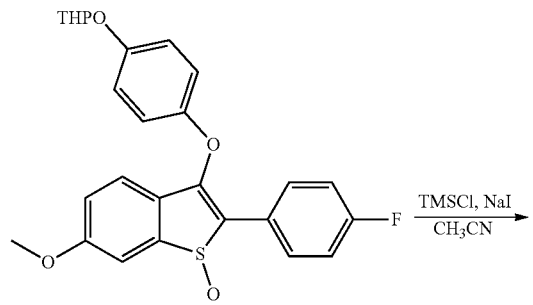
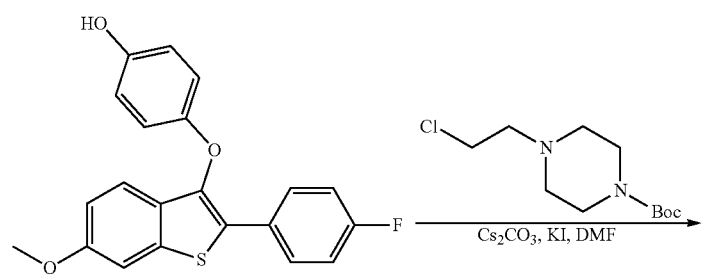
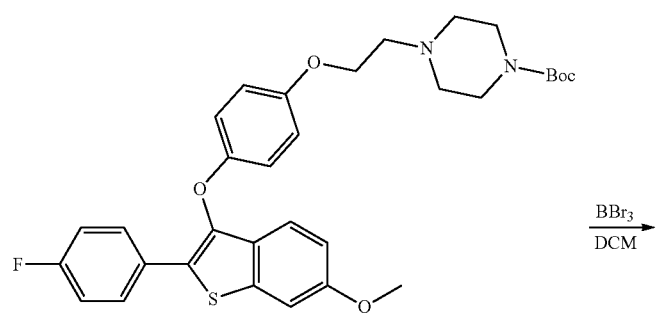
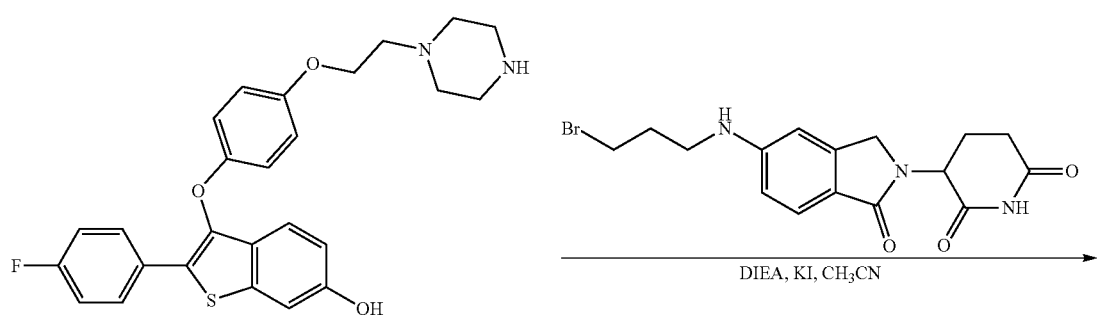

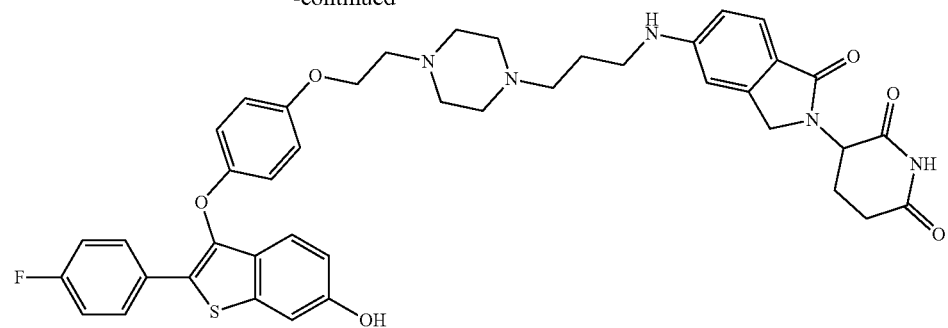
Compound 174
General Scheme 3B to Prepare Compound 175.
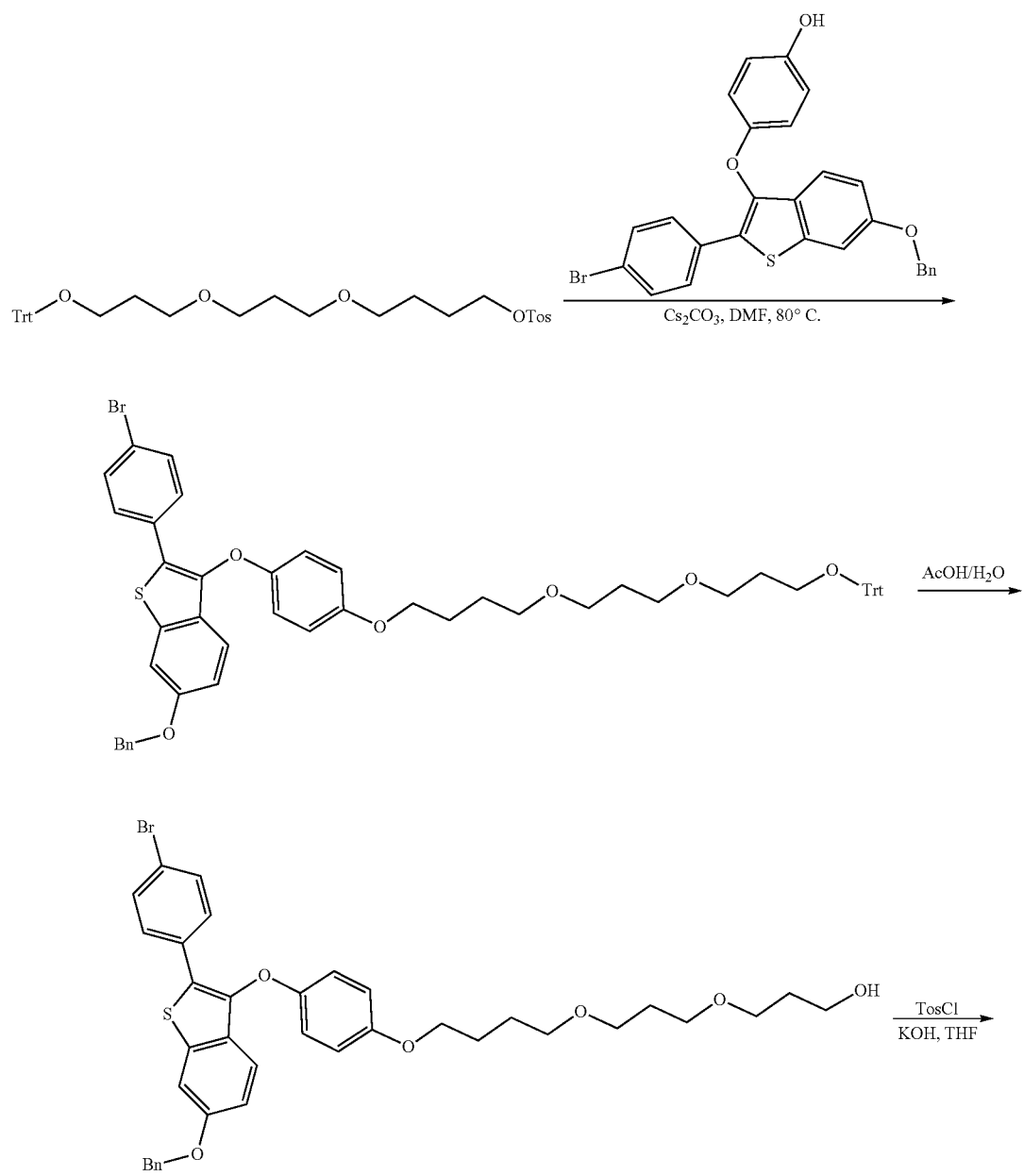

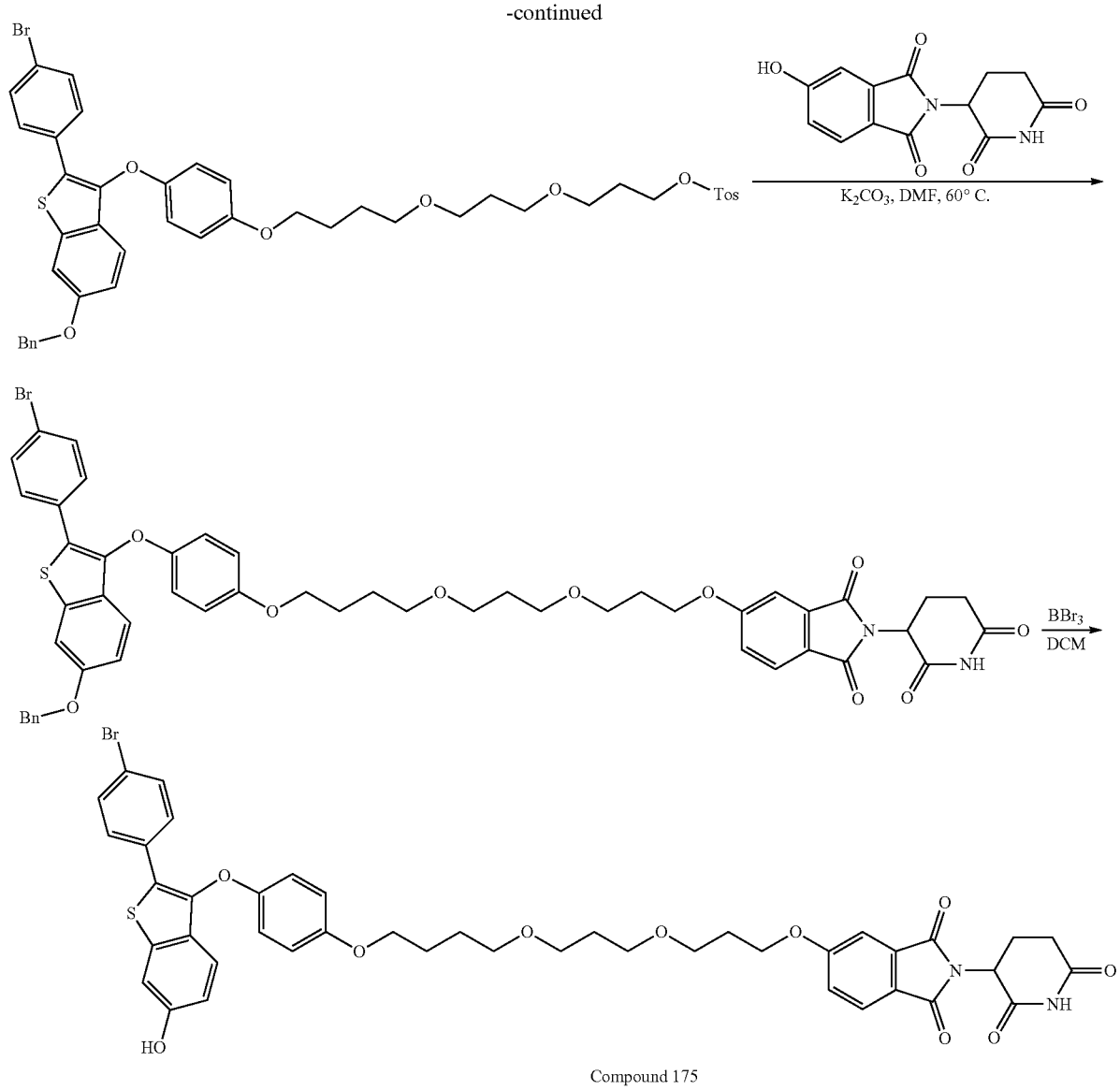
General Scheme 4B to Prepare Compound 177.
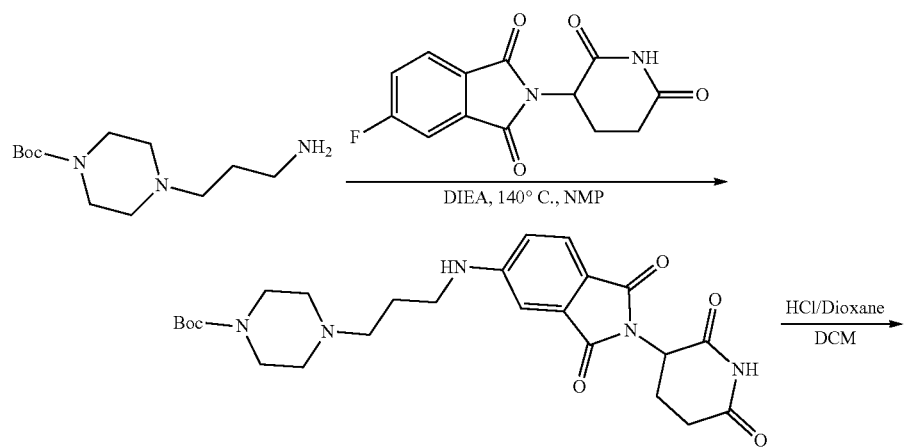

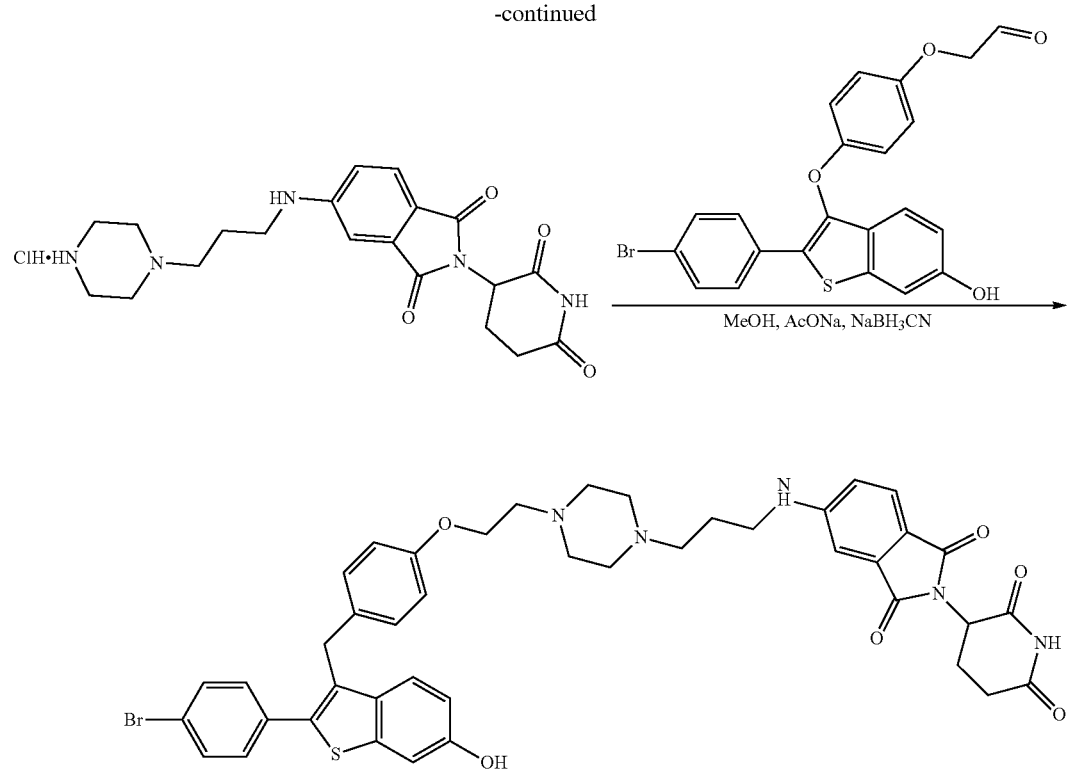
Compound 177
General Scheme 5B to Prepare Compound 178.
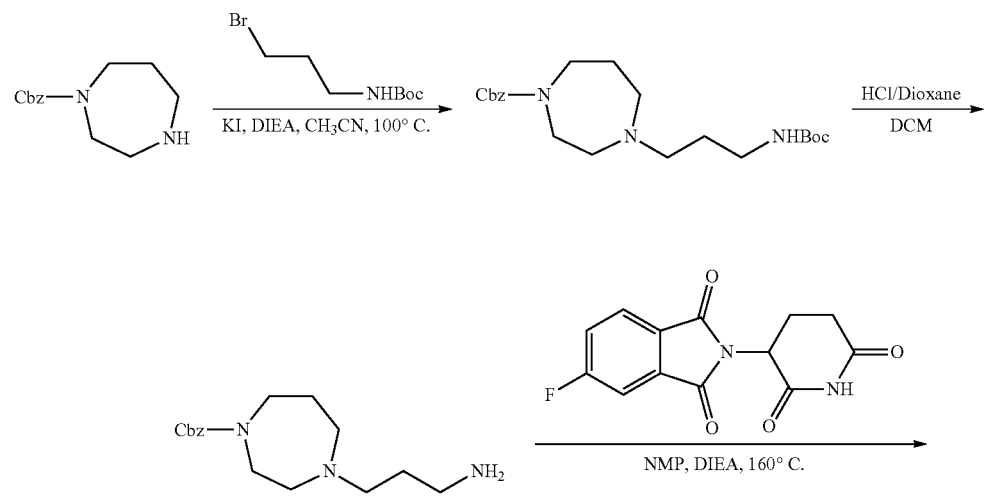

443 444
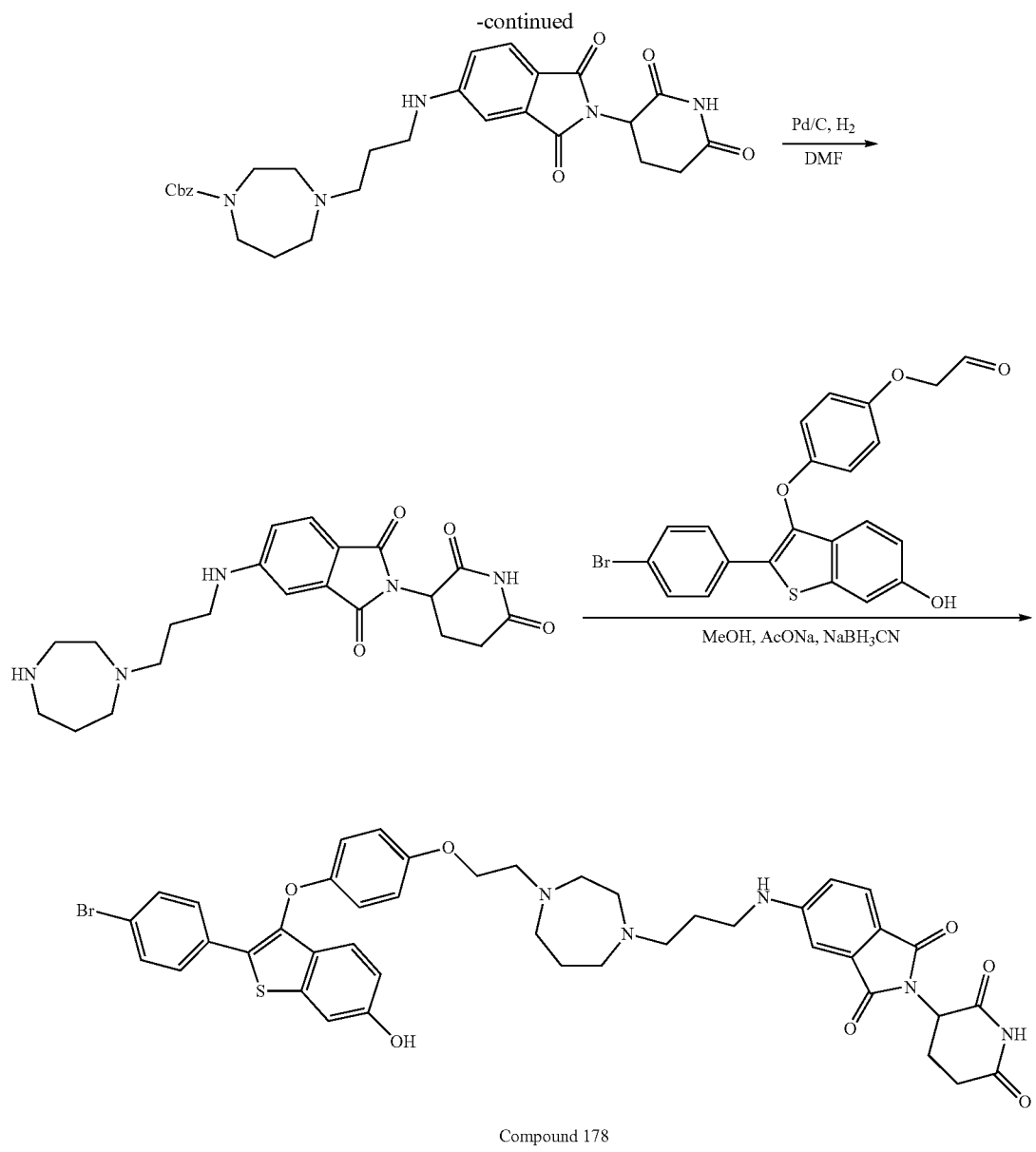
Compound 178
General Scheme 6B to Prepare Compound 180.
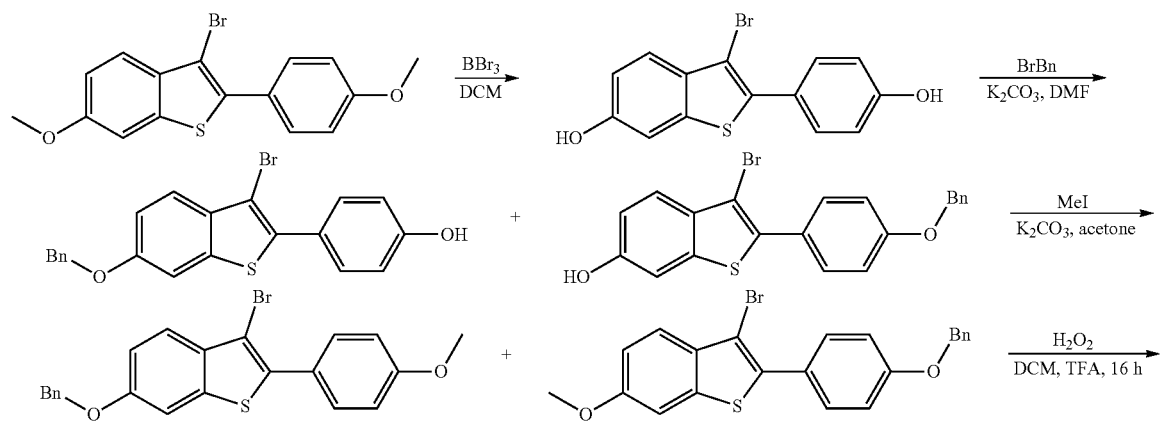

445 -continued 446
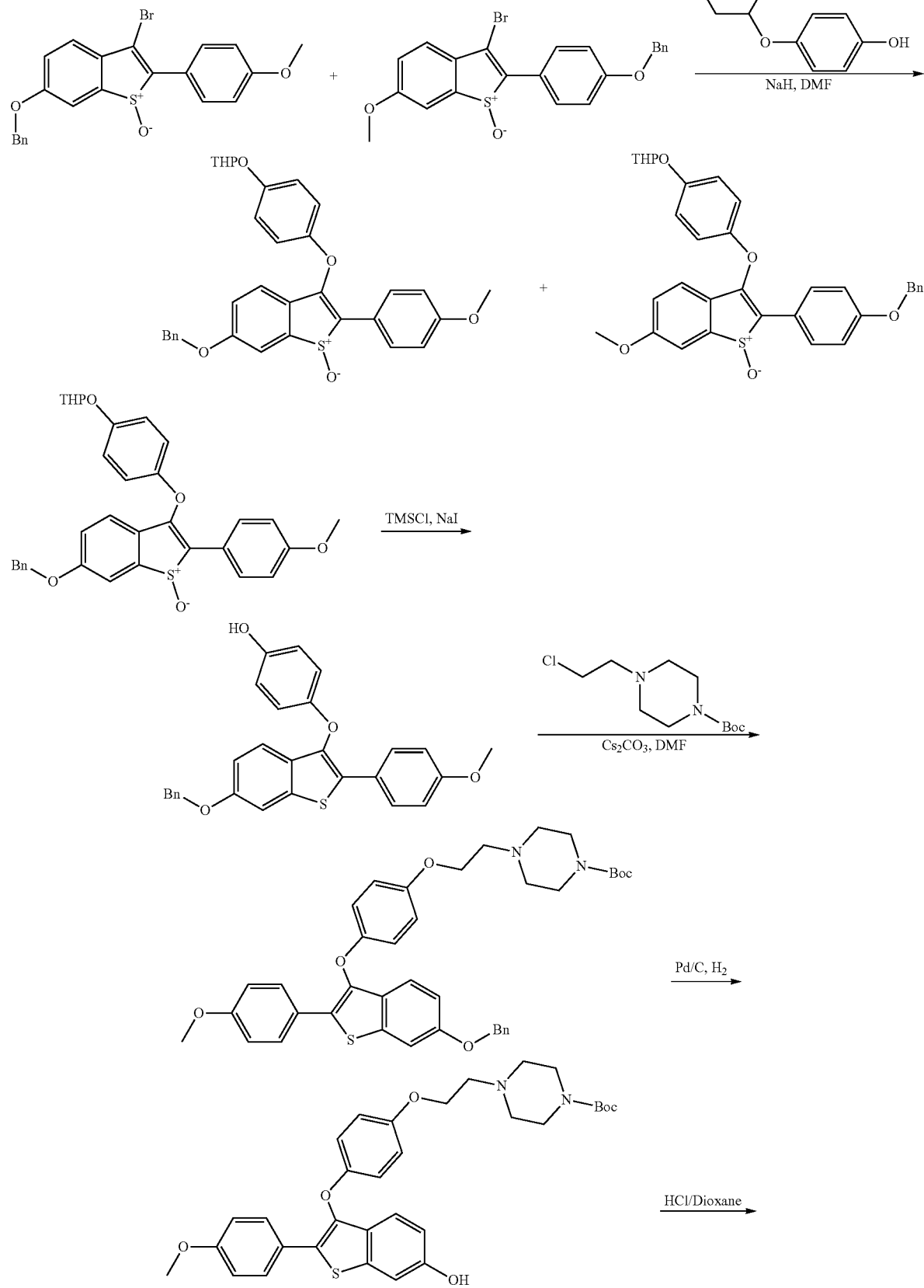

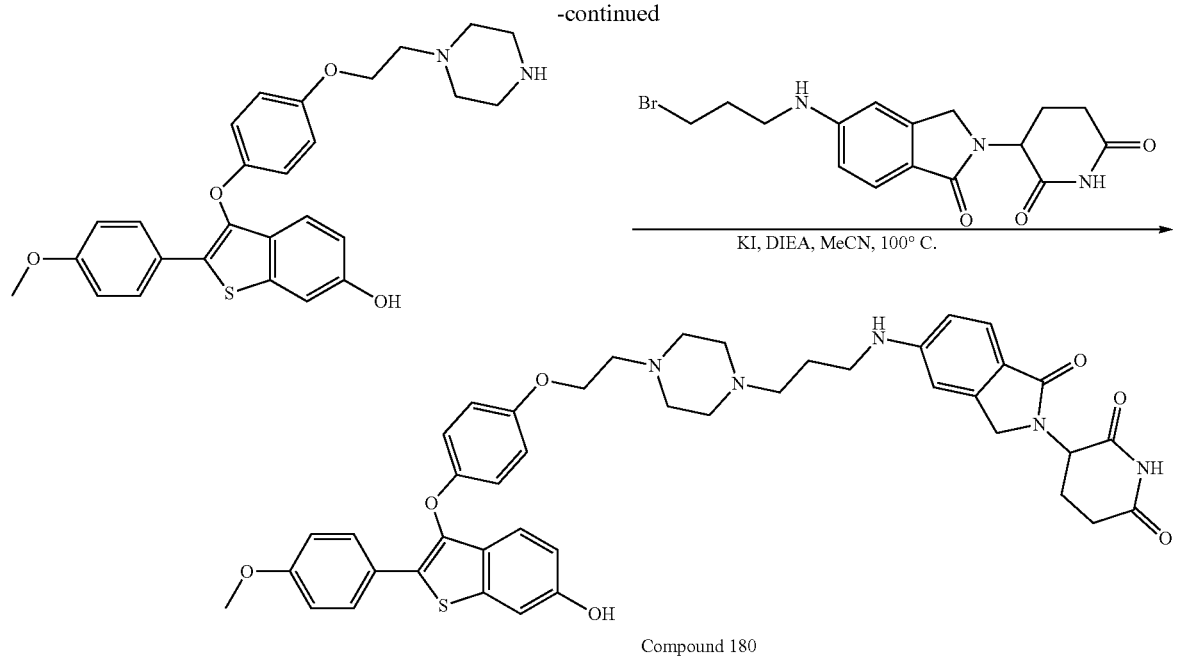
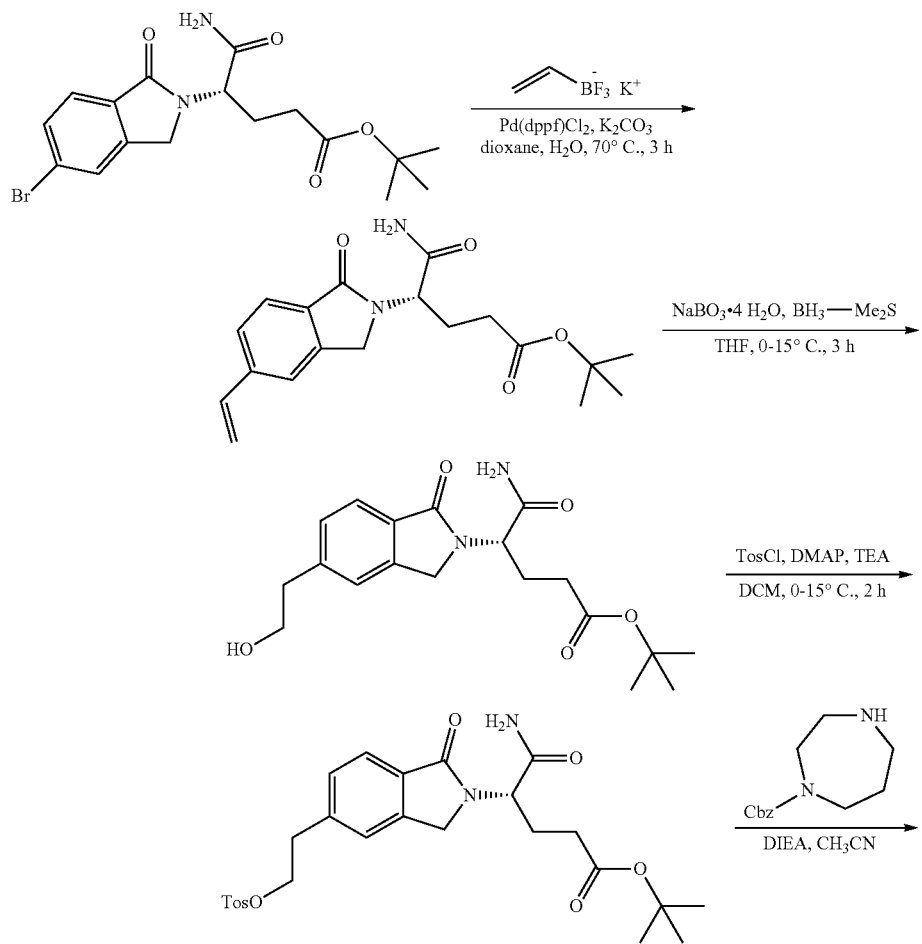
General Scheme 7B to Prepare Compound 182.

449 450
-continued
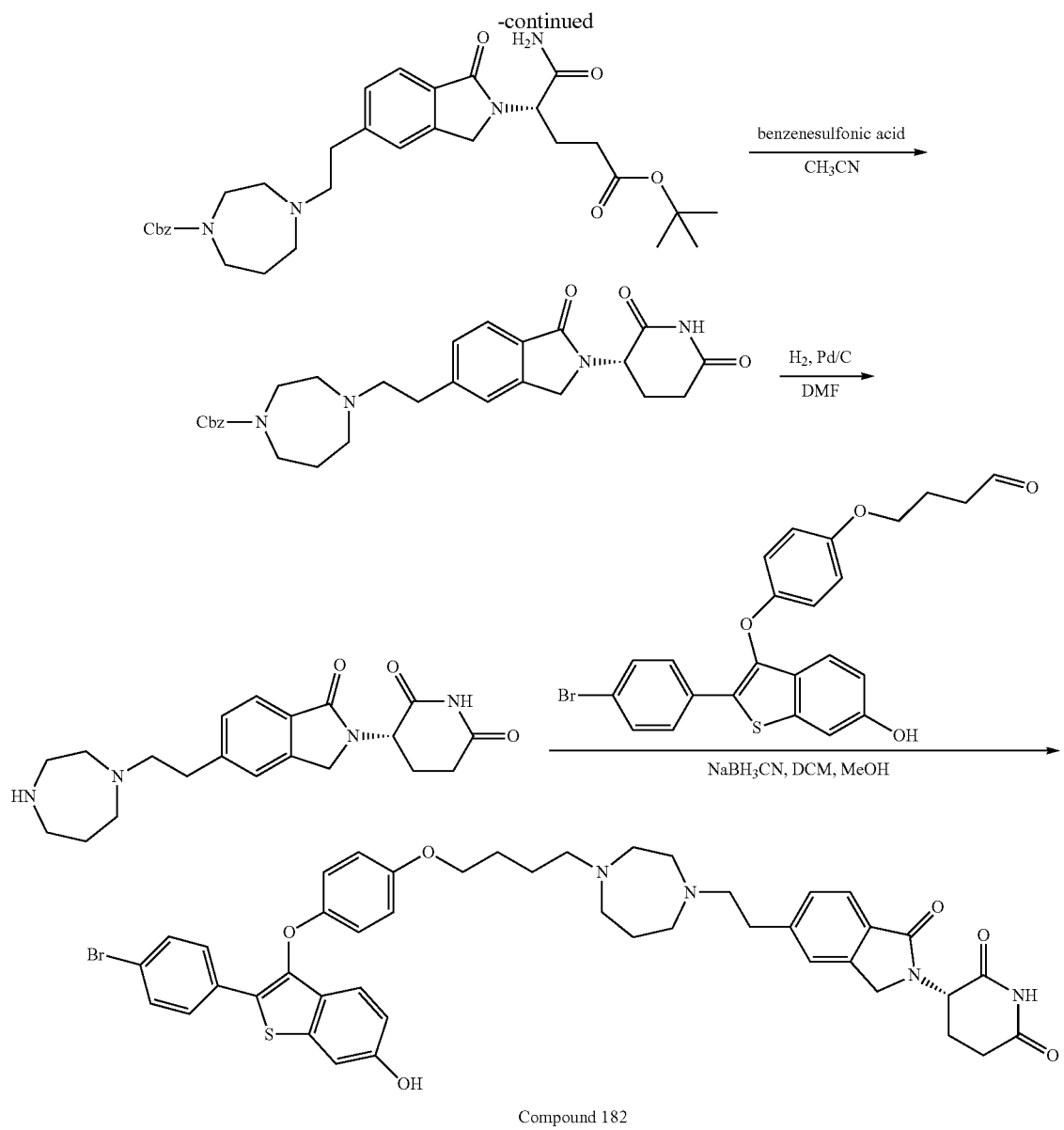
Compound 182
General Scheme 8B to Prepare Compound 183.
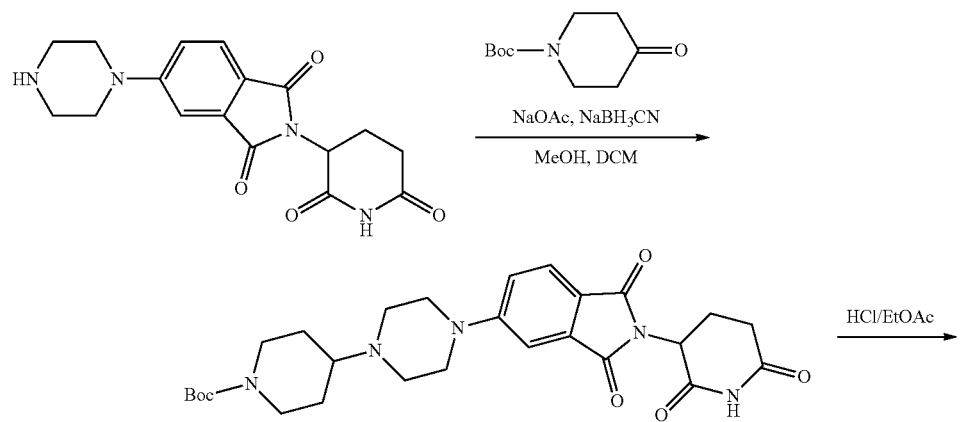

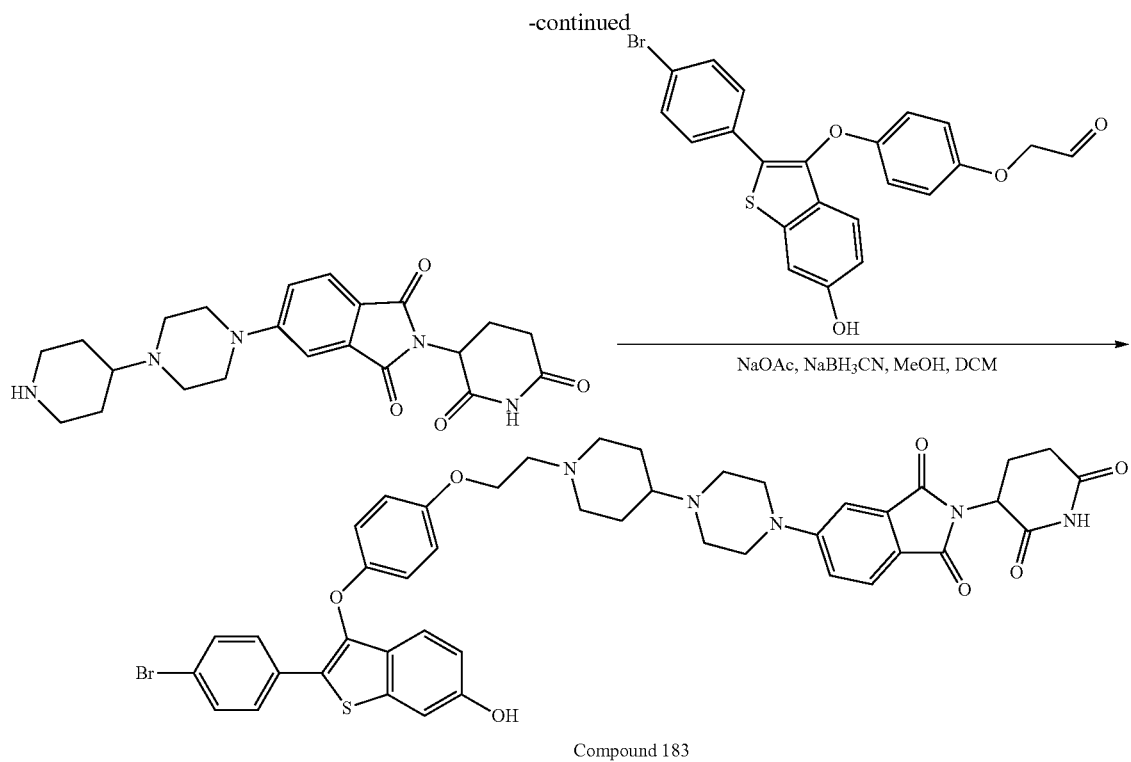
Compound 183
General Scheme 9B to Prepare Compound 184.
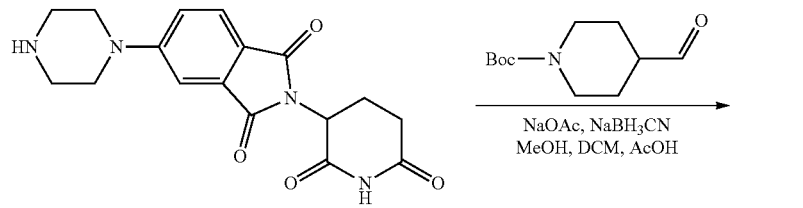
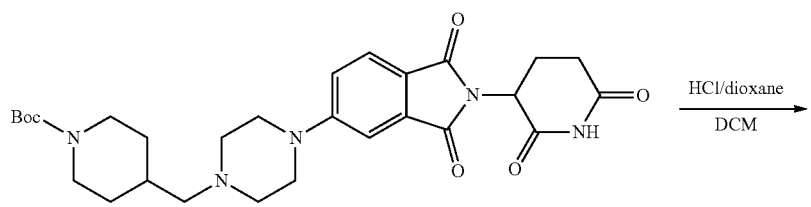
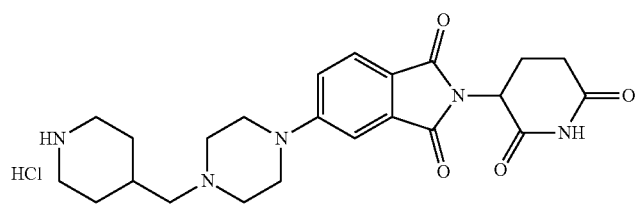

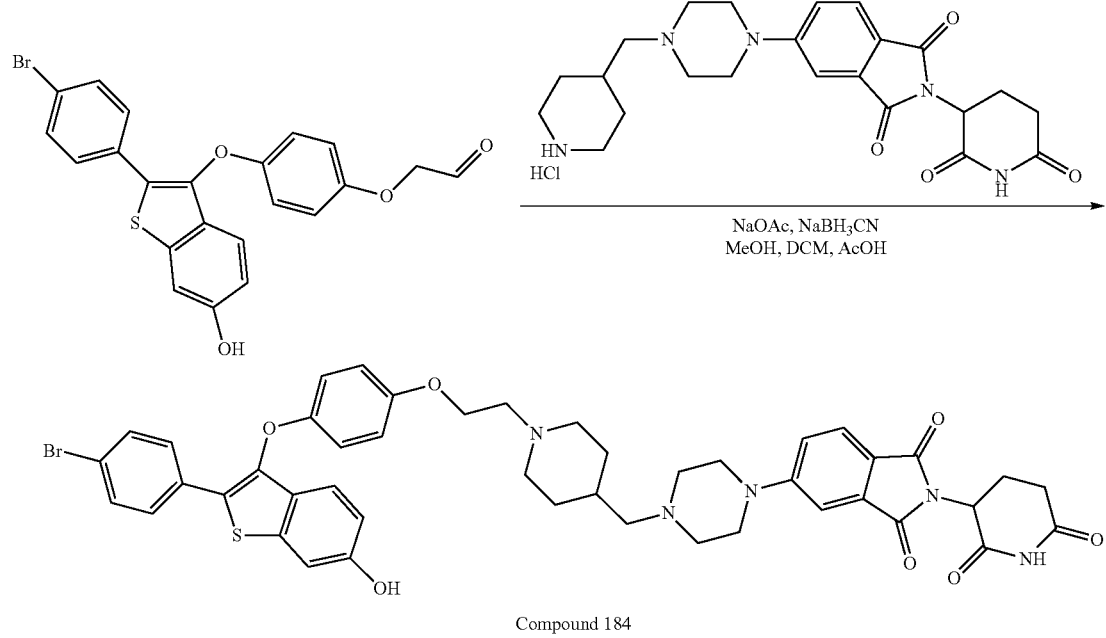
Compound 184
General Scheme 10B to Prepare Compound 185.
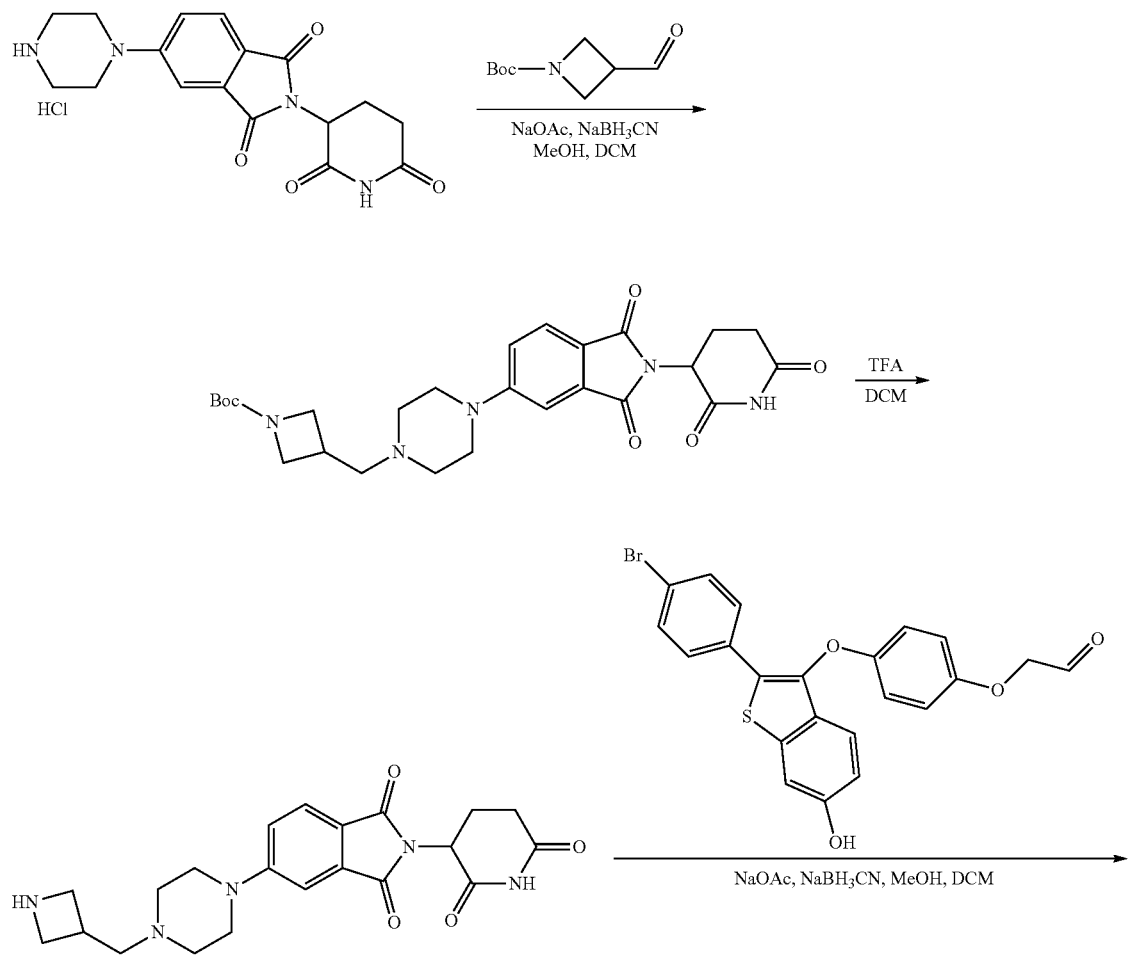

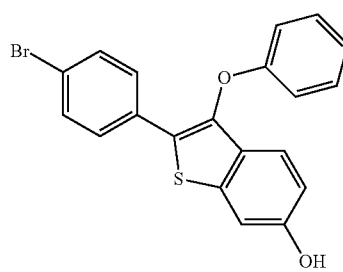
Compound 185
General Scheme 11B to Prepare Intermediate for Compound 186.
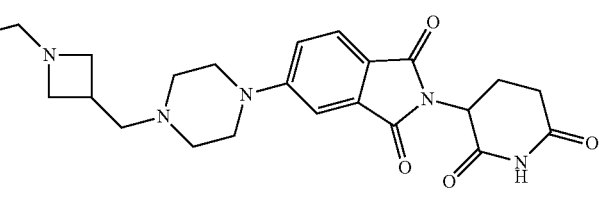
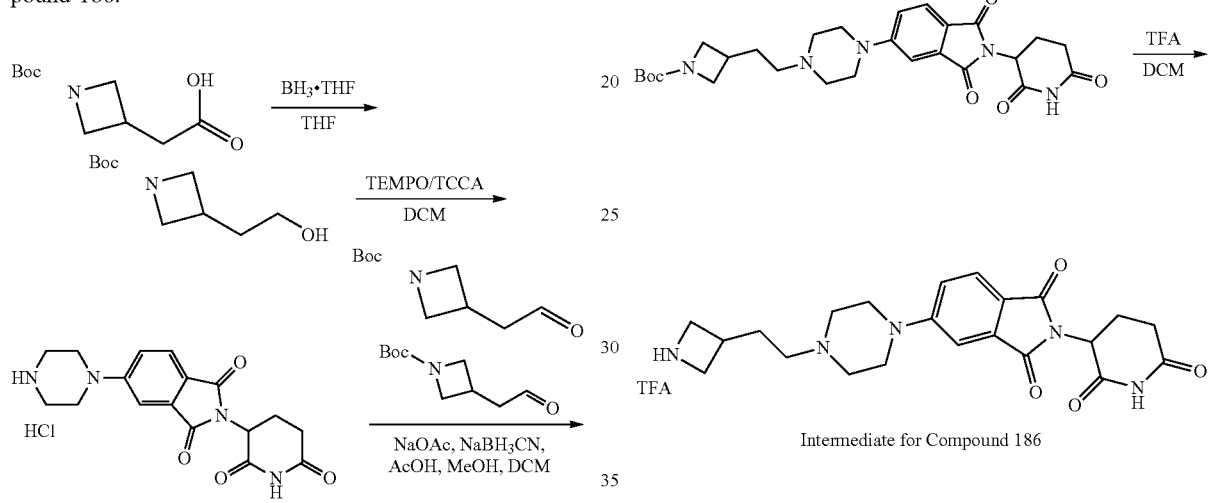
Intermediate for Compound 186
General Scheme 12B to Prepare Compound 187.
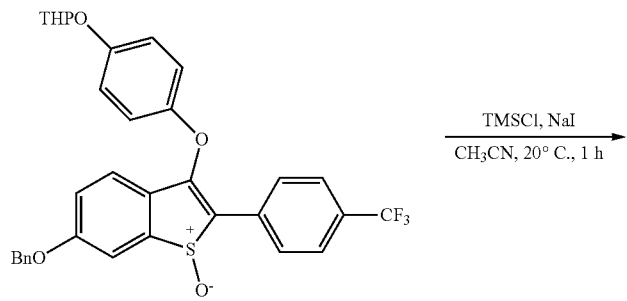
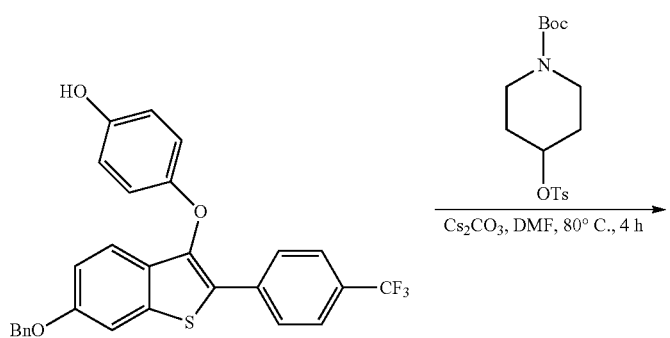

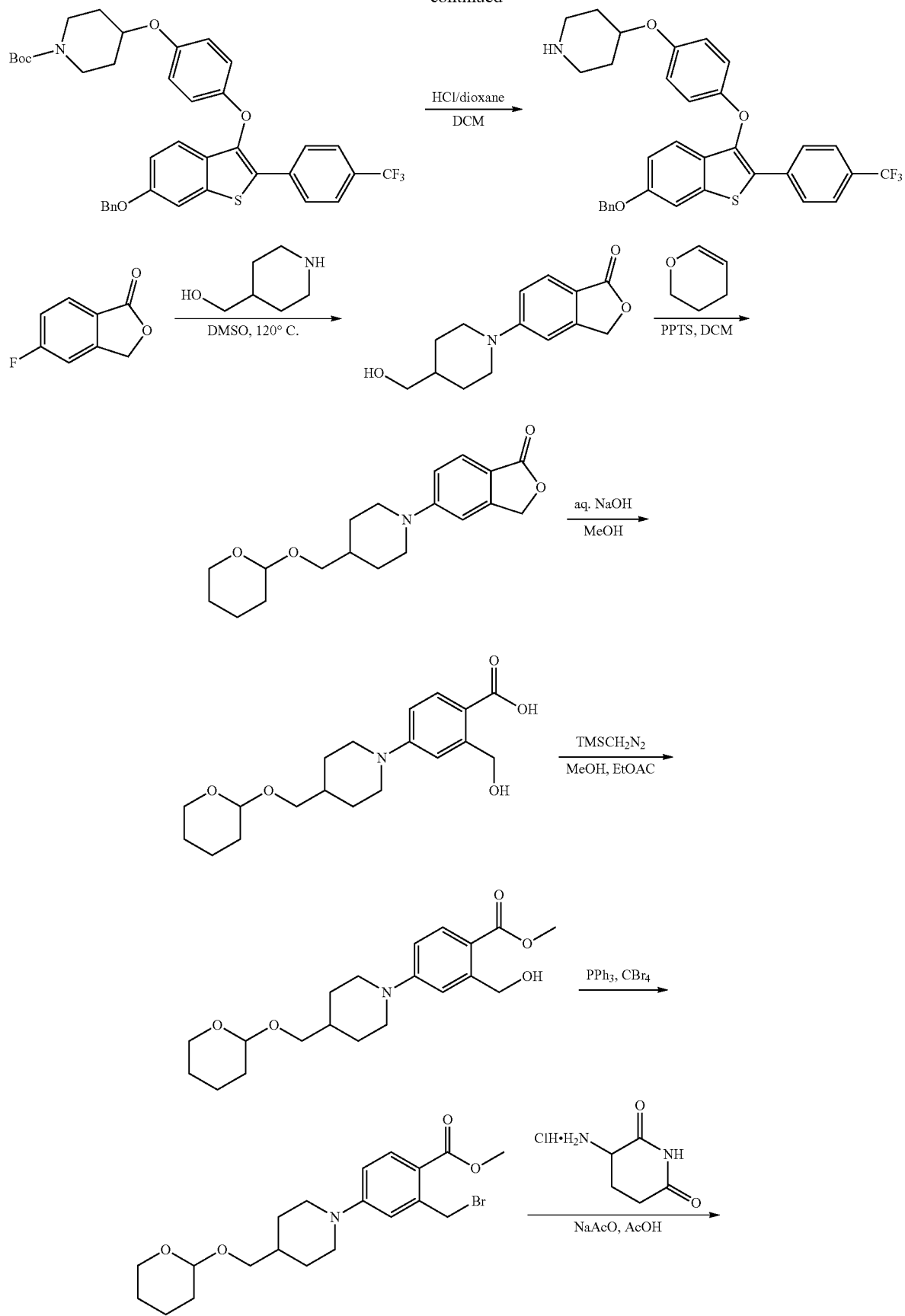

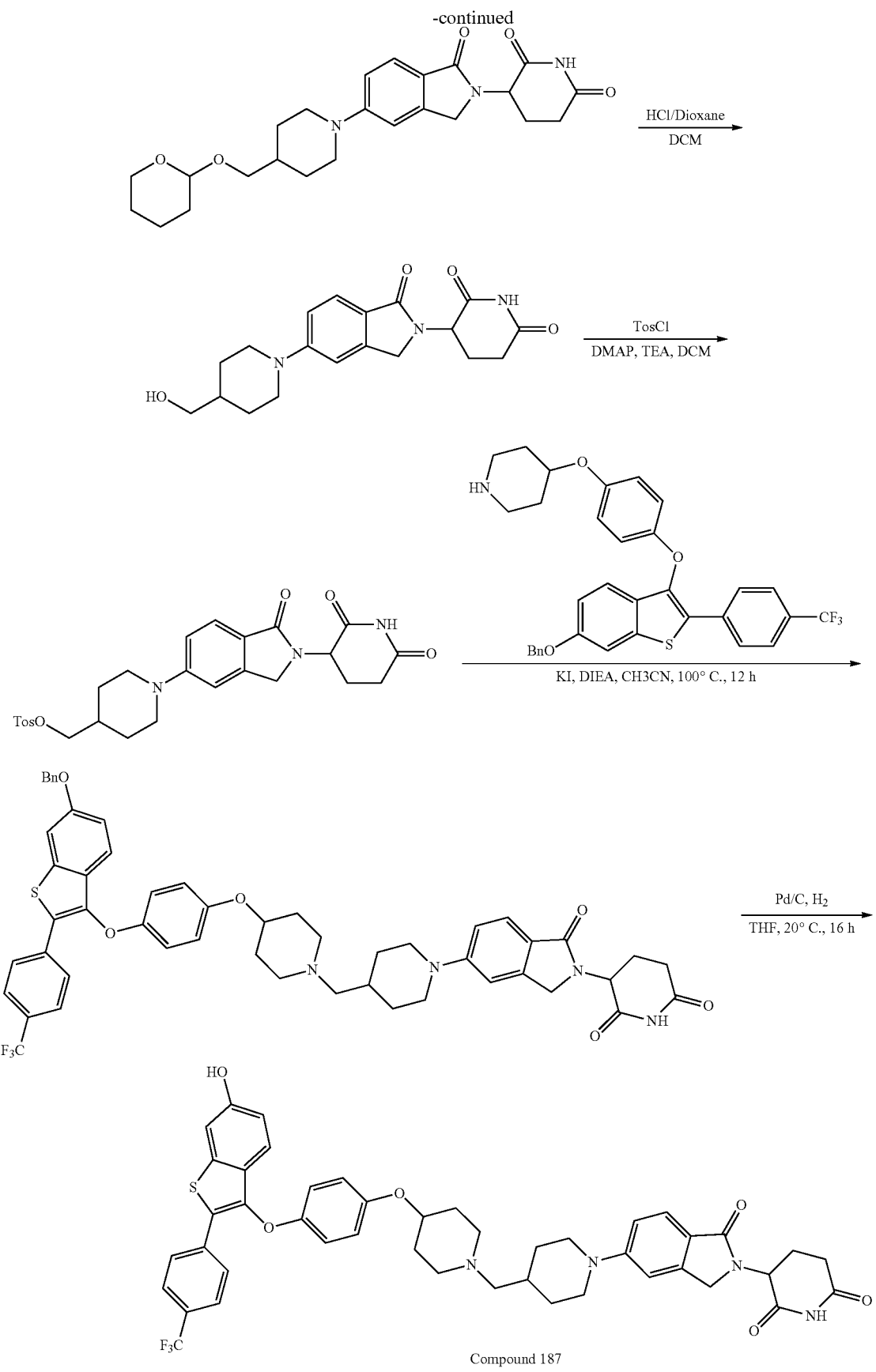
Compound 187

General Scheme 13B to Prepare Intermediate for Compound 188.
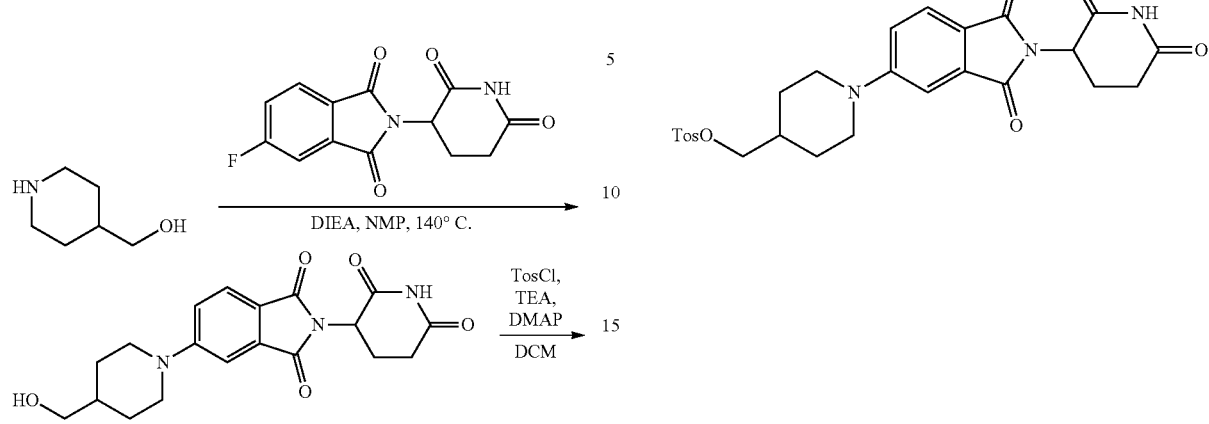
General Scheme 14B to Prepare Compound 189.
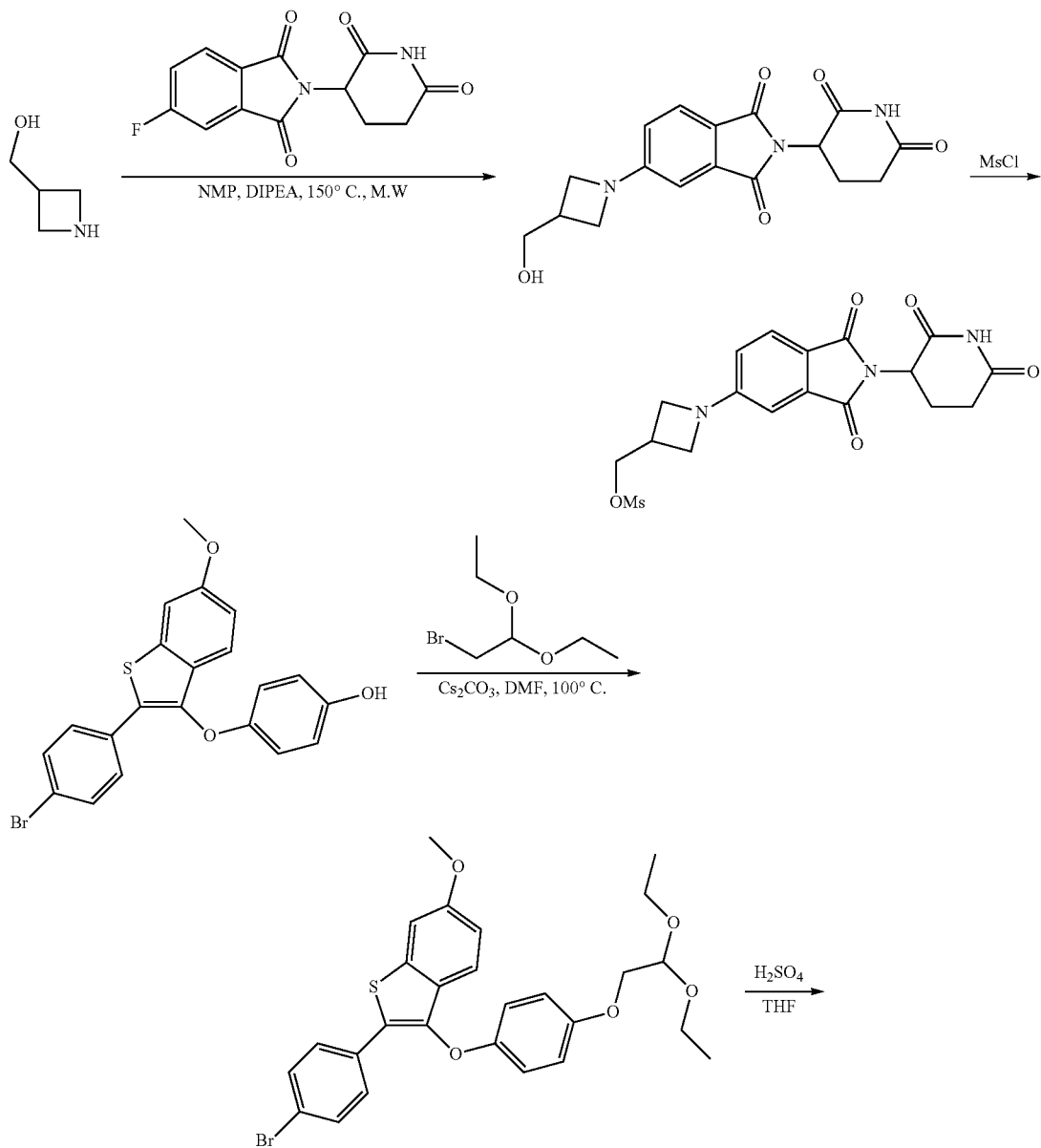

-continued
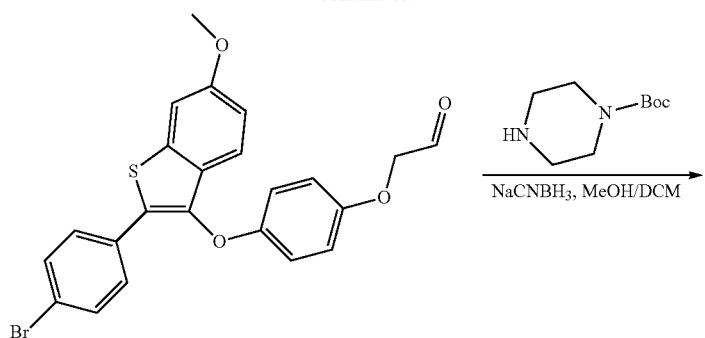
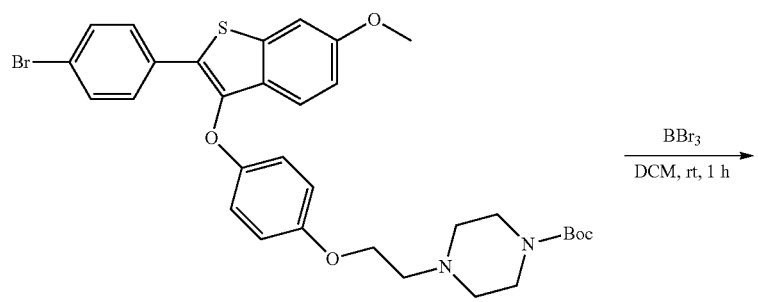
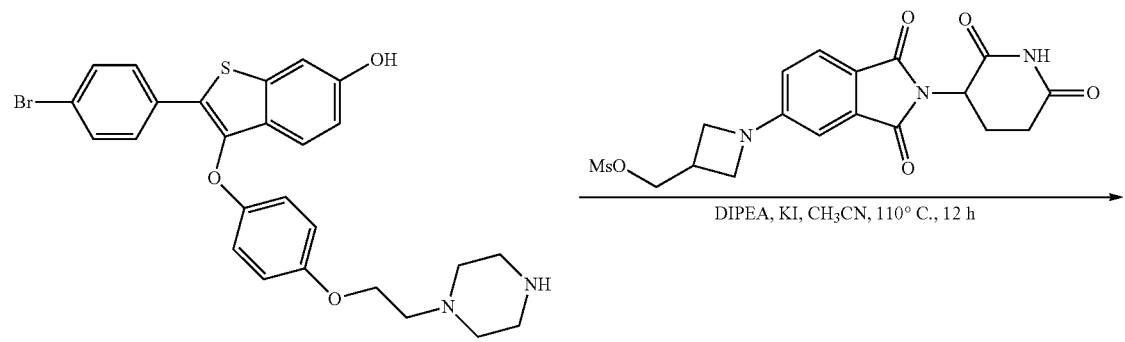
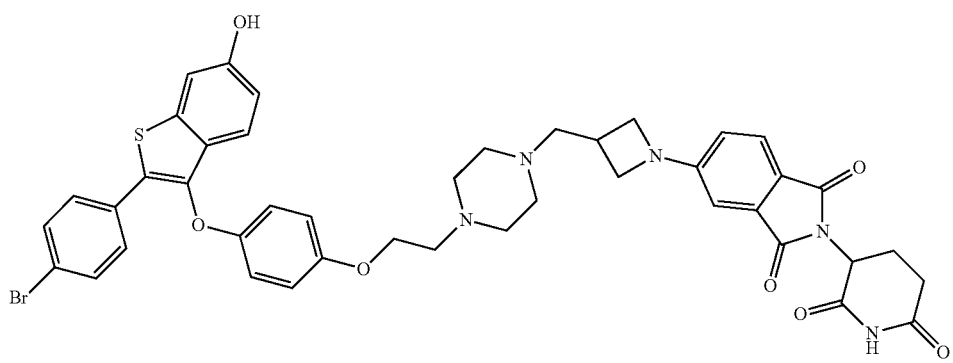
Compound 189

General Scheme 15B to Prepare Intermediate for Compound 190.
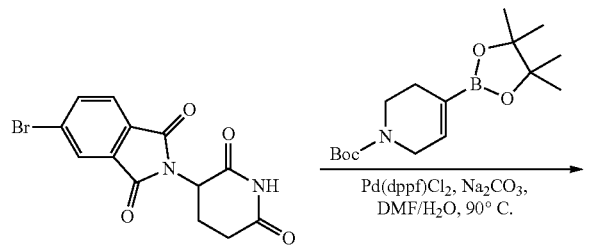
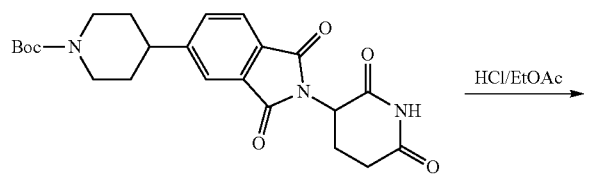
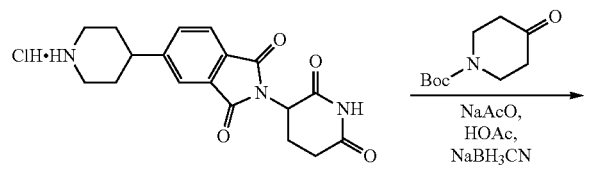
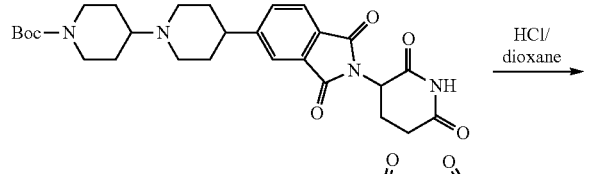
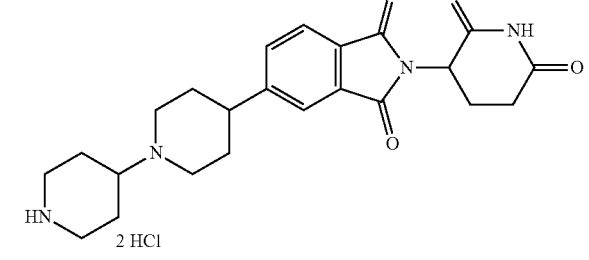
intermediate of compound 190
General Scheme 16B to Prepare Intermediate for Compound 192.
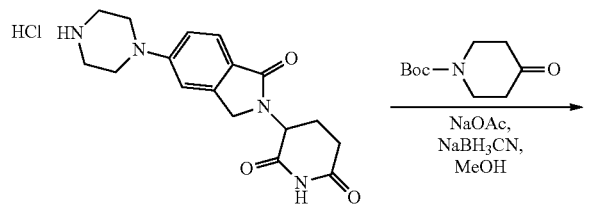
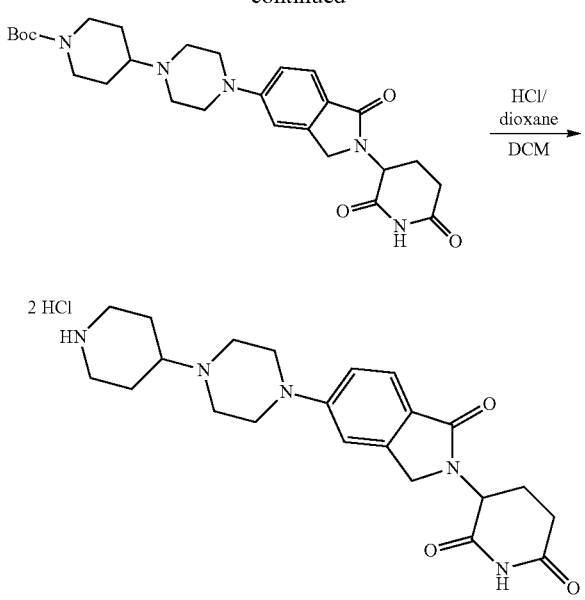
Intermediate for compound 192
General Scheme 17B to Prepare Intermediate for Compound 193.
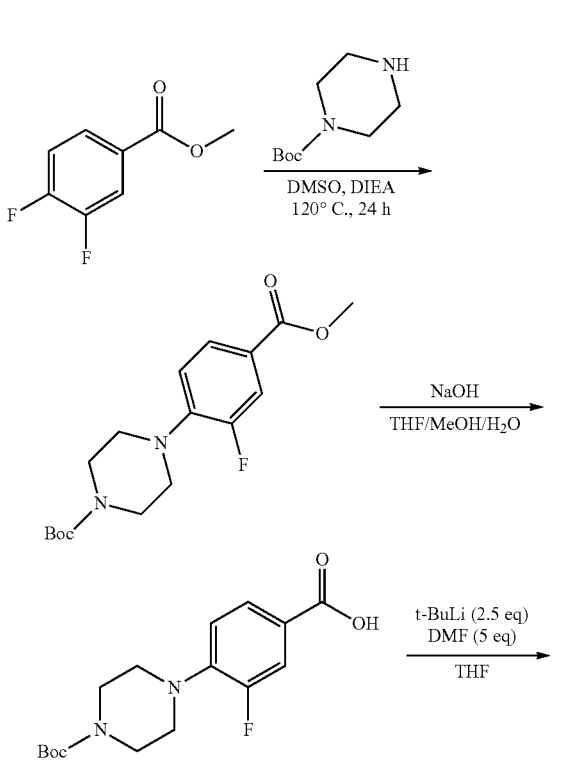
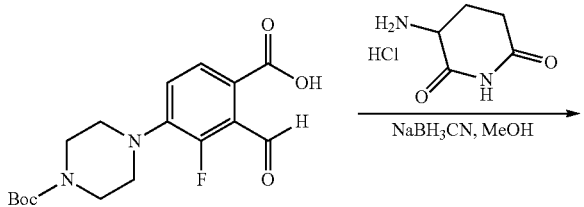

467
-continued
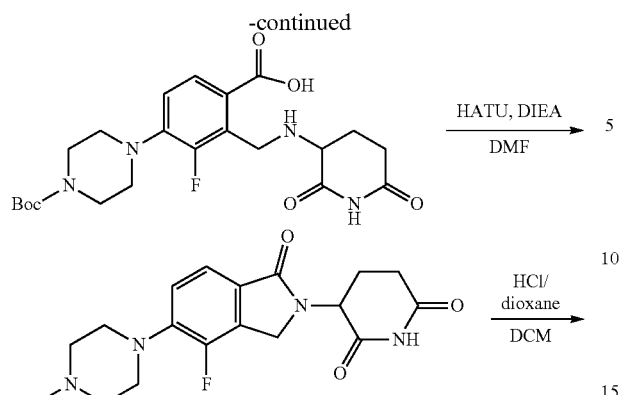
468
-continued
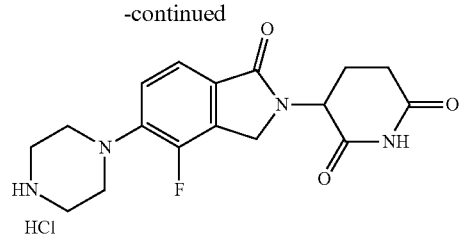
General Scheme 18B to Prepare Intermediate for Compound 197.
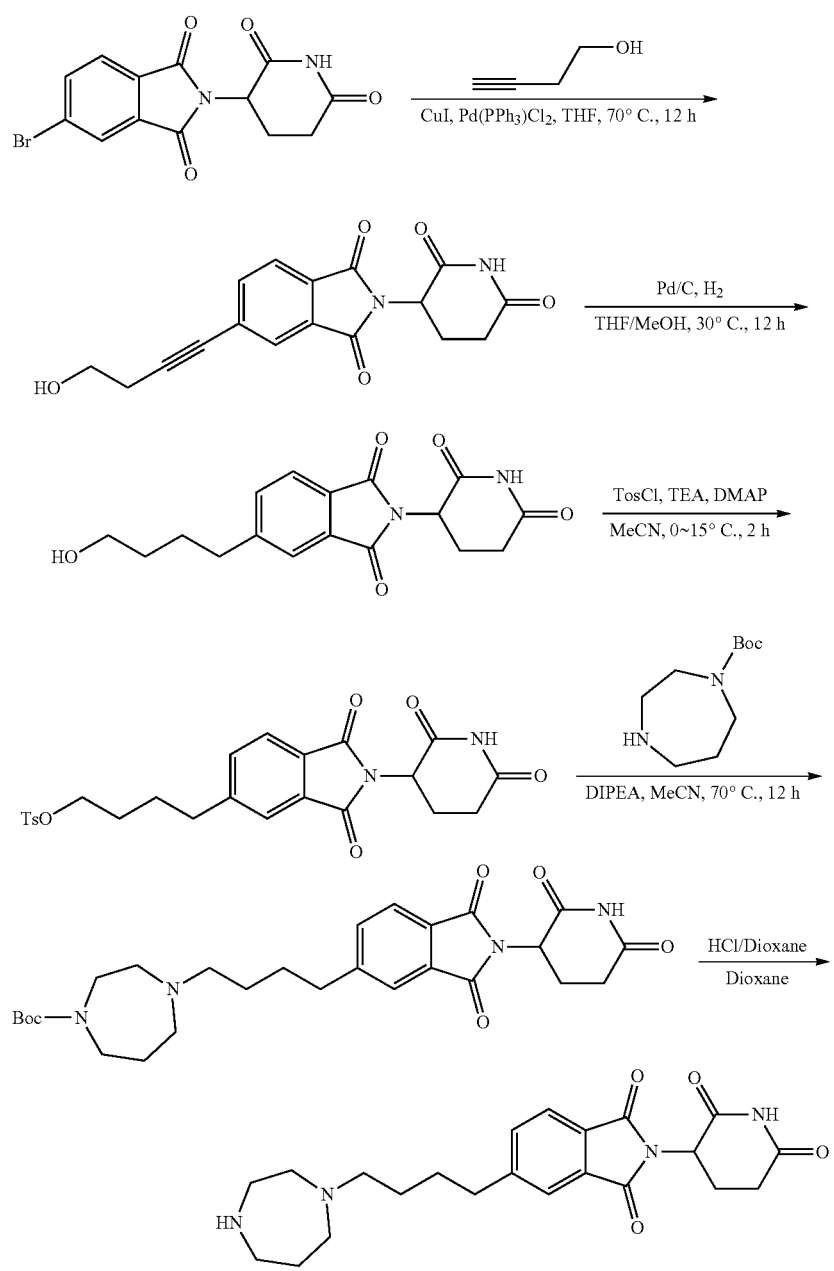

General Scheme 19B to Prepare Intermediate for Compound 198.
General Scheme 20B to Prepare Intermediate for Compound 206.
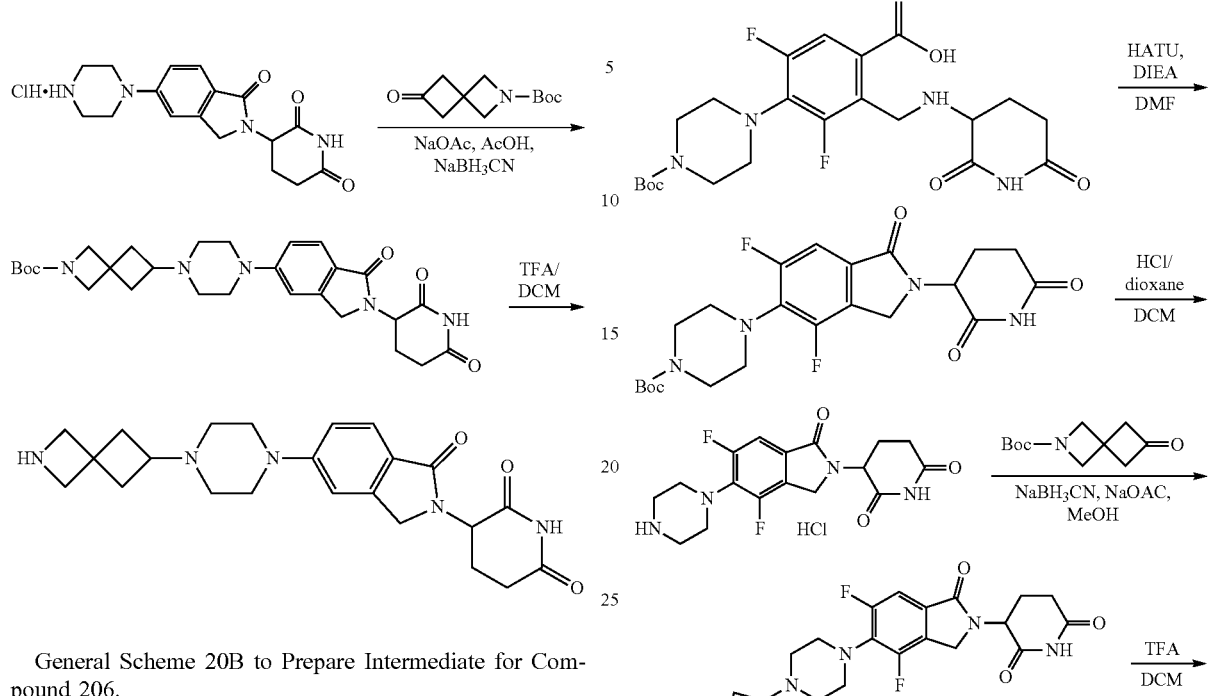
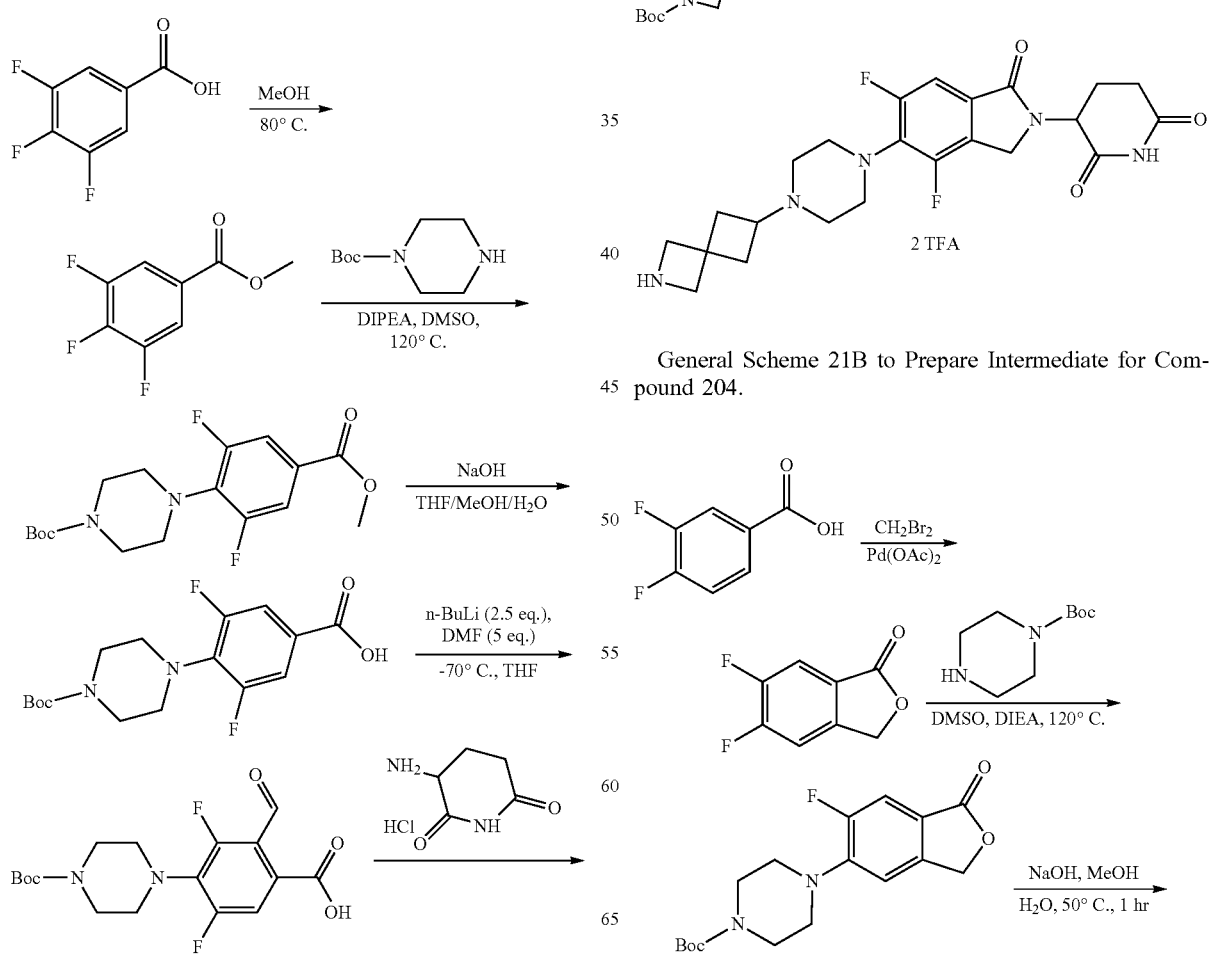
General Scheme 21B to Prepare Intermediate for Compound 204.

471
-continued
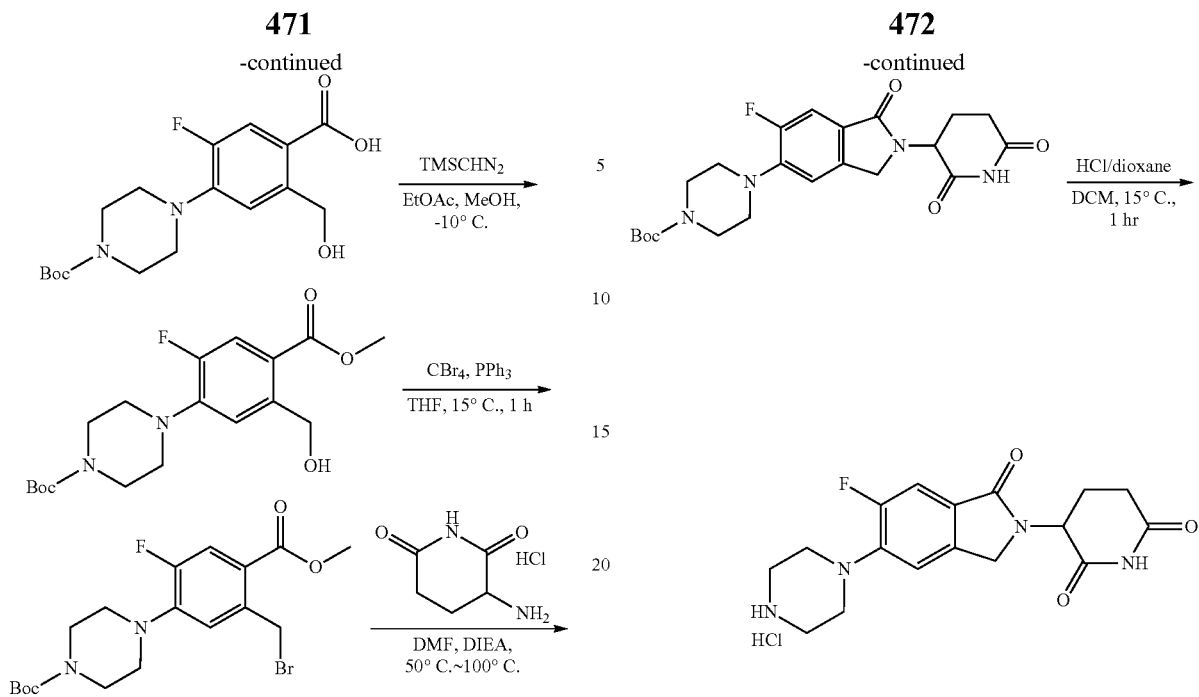
472
-continued
General Scheme 22B to Prepare Compound 207.
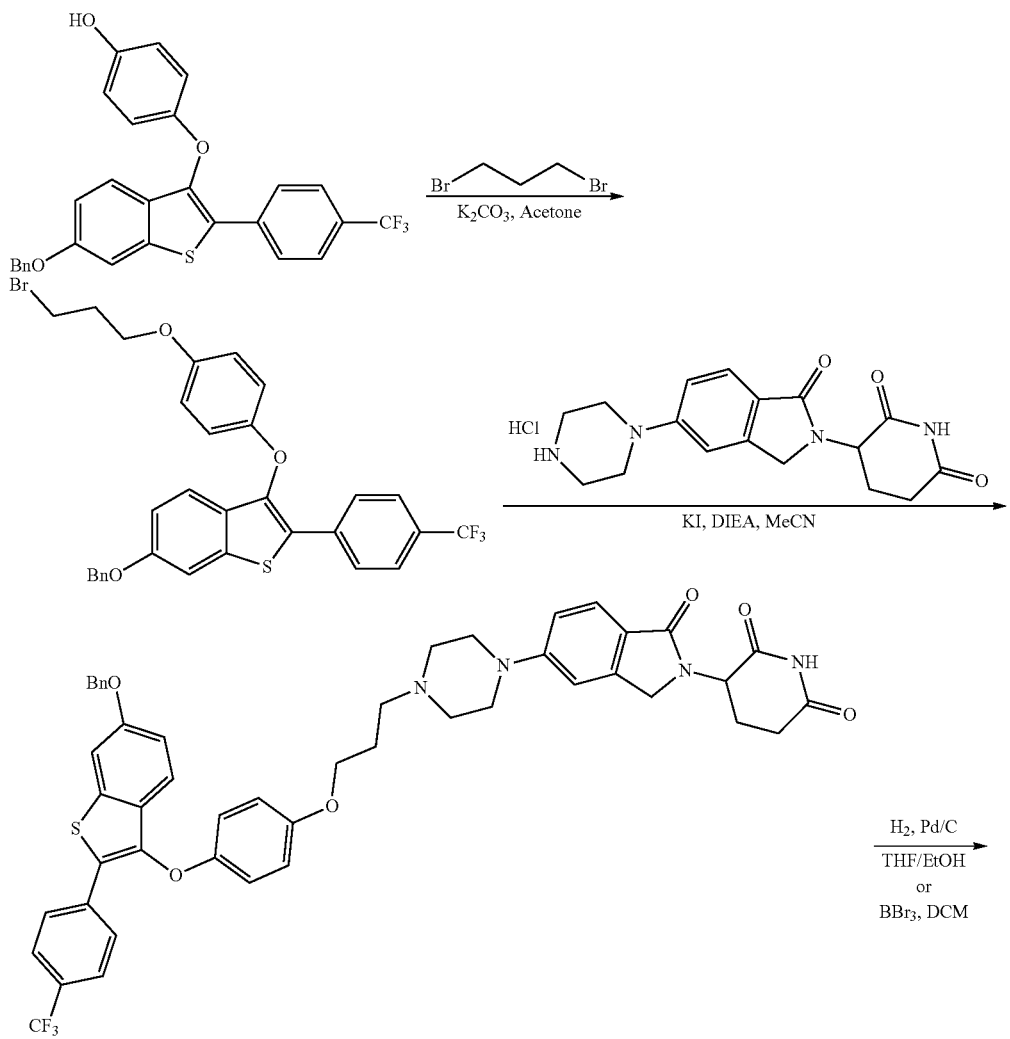

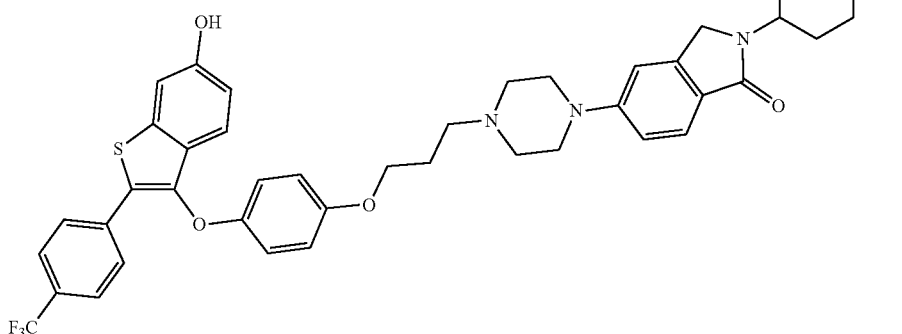
Compound 207
General Scheme 23B to Prepare Compound 209.
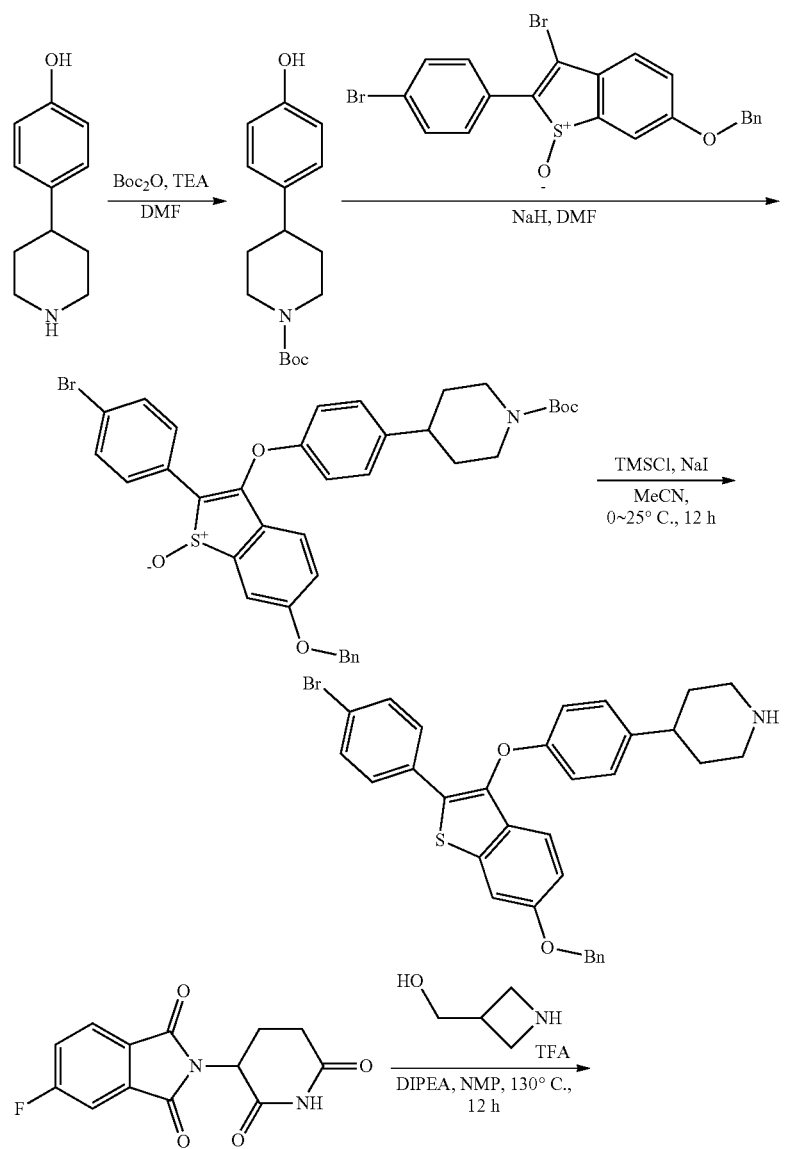

475 476
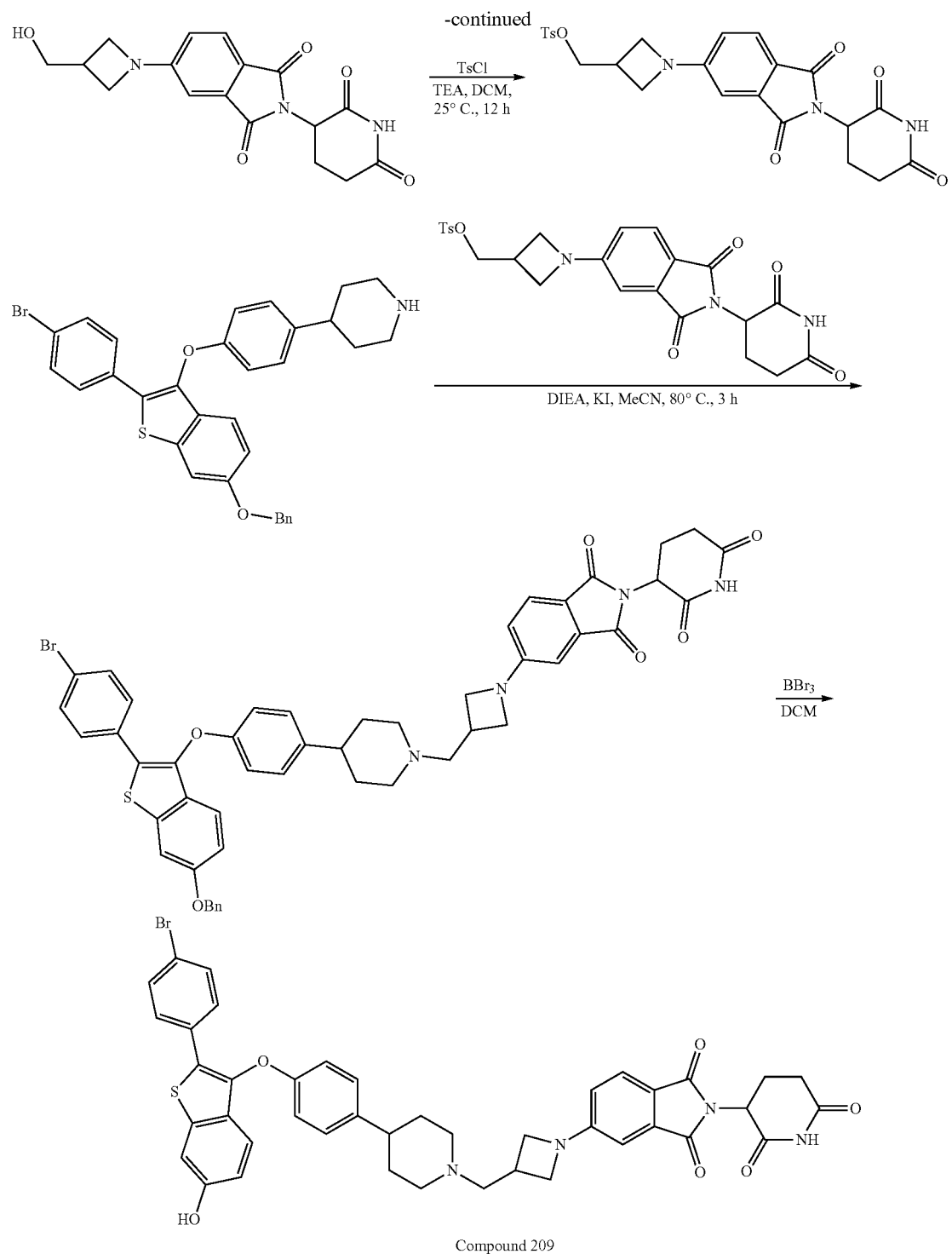
Compound 209
General Scheme 24B to Prepare Compound 211.
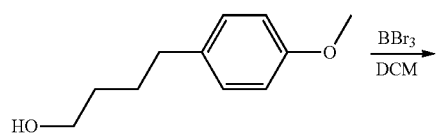

-continued
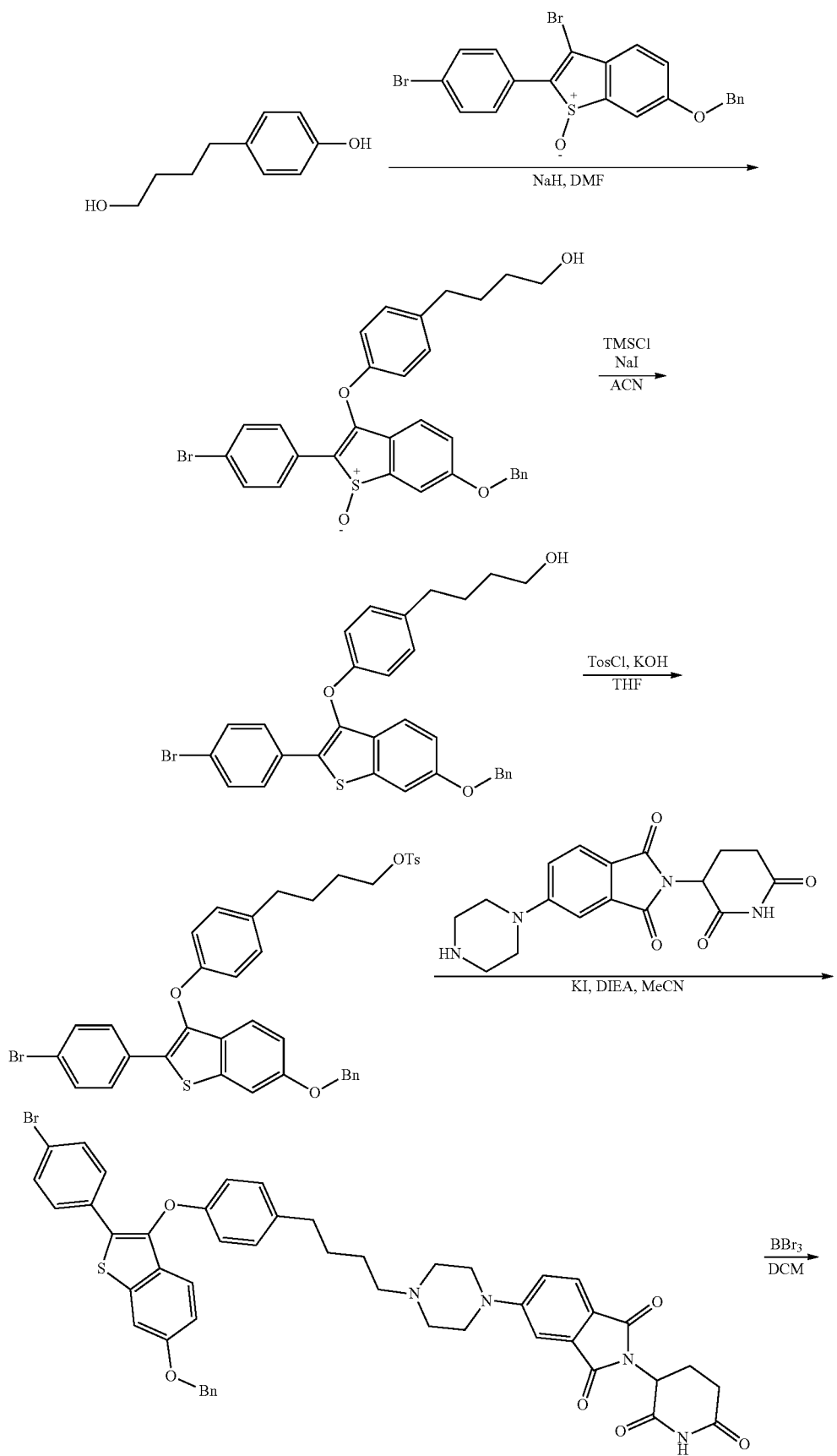

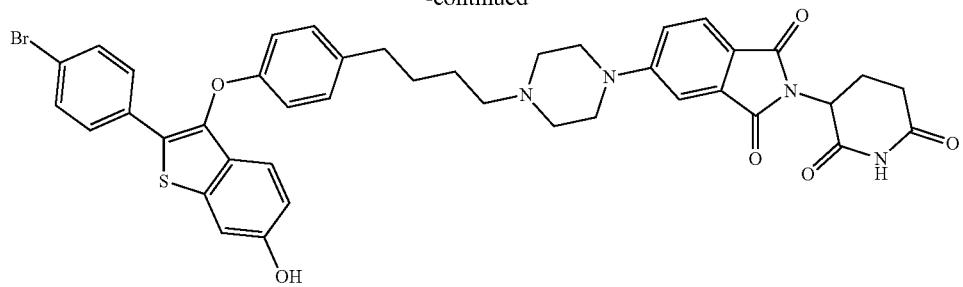
Compound 211
General Scheme 25B to Prepare Compound 212.
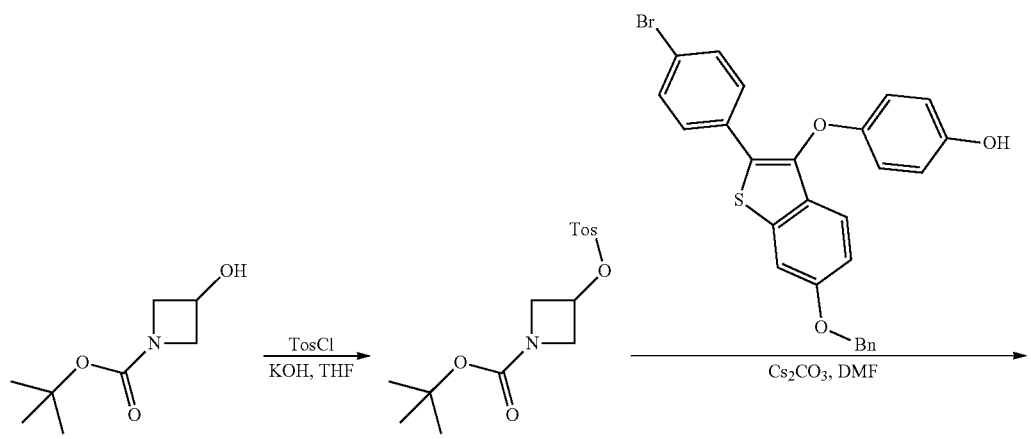
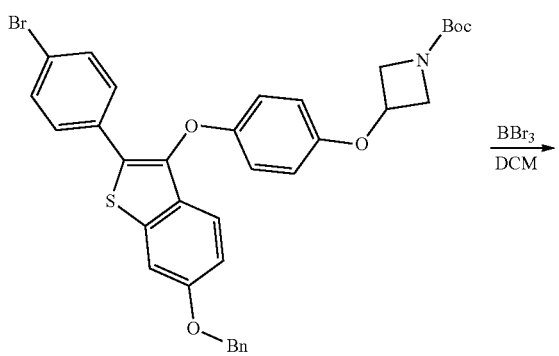
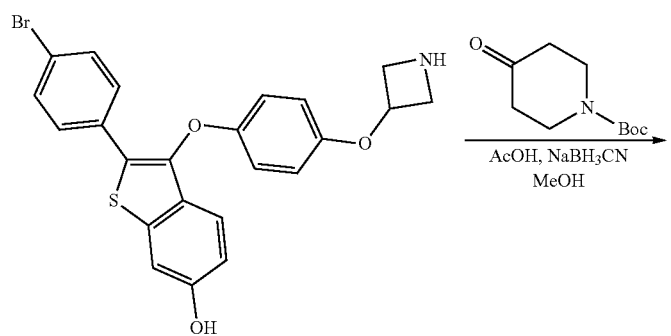

-continued
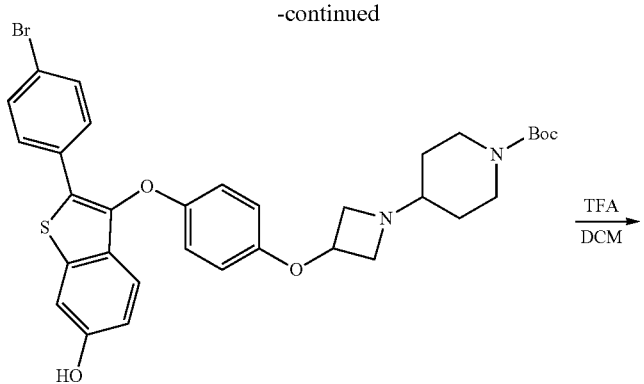
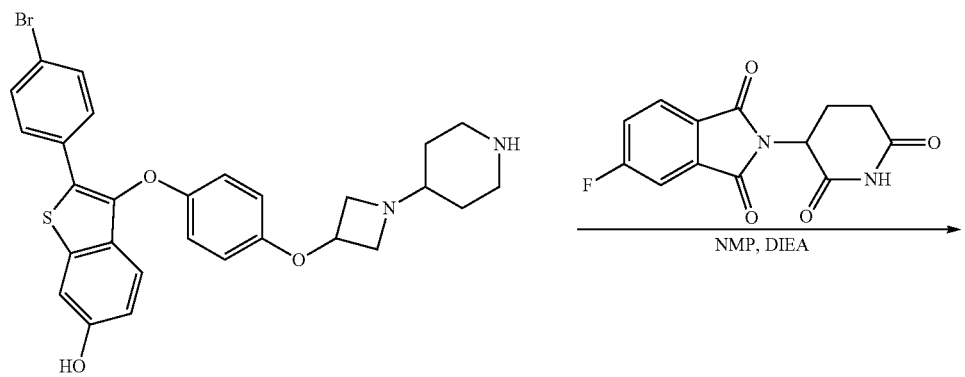
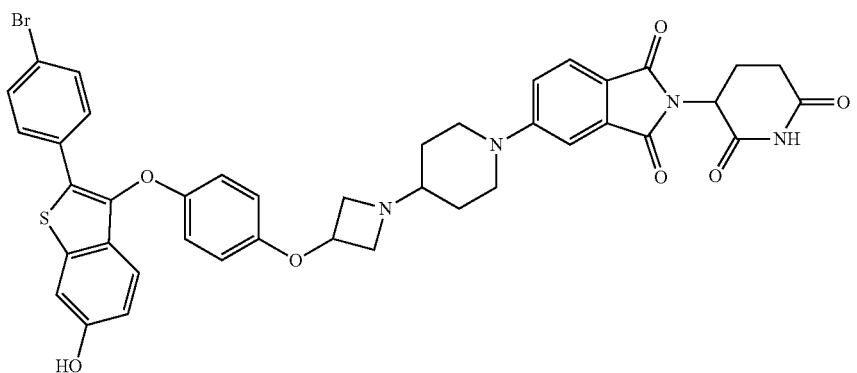
Compound 212
General Scheme 26B to Prepare Compound 213.
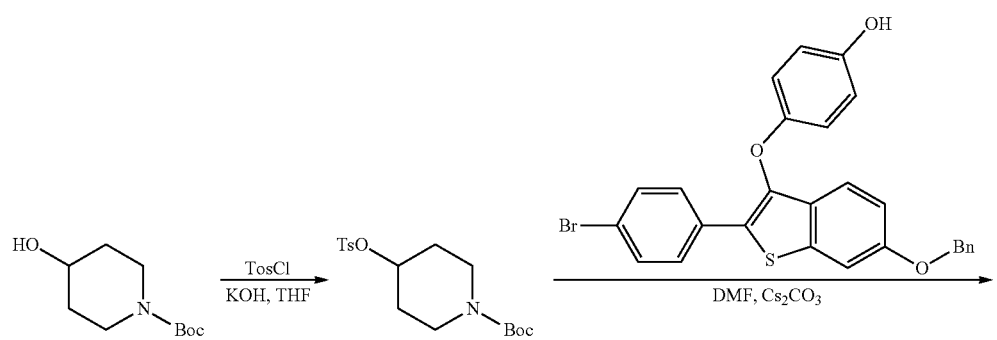

-continued
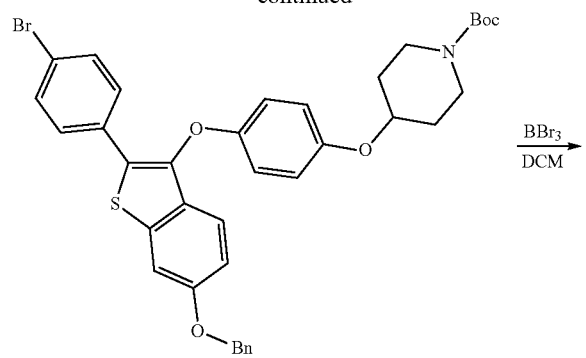
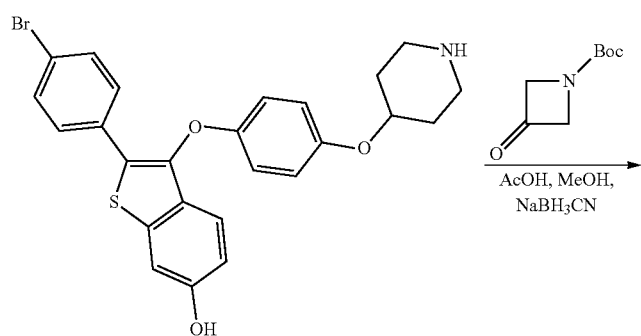
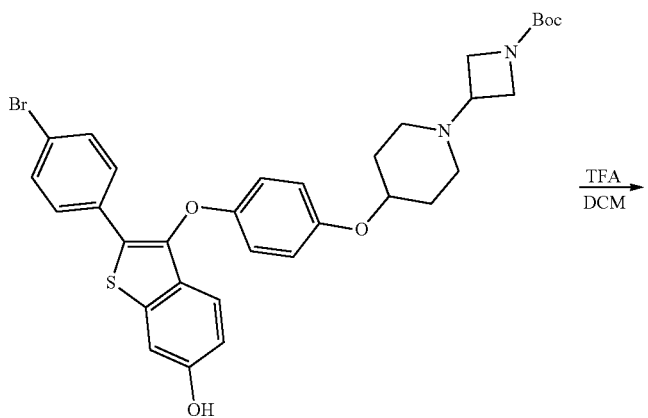
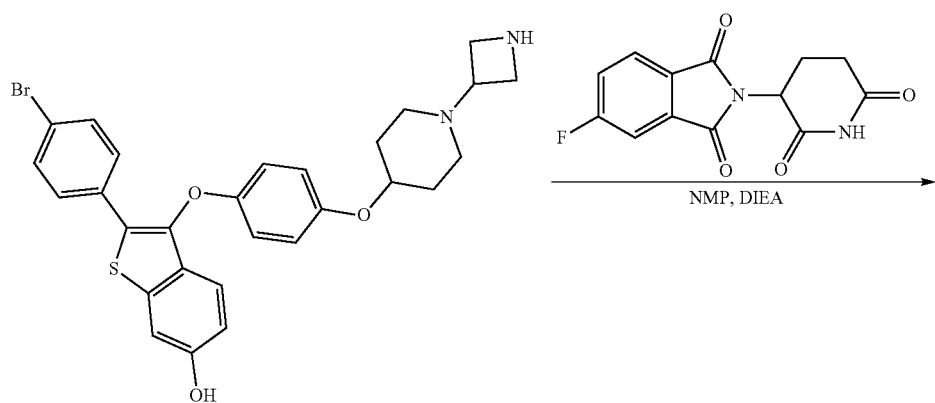

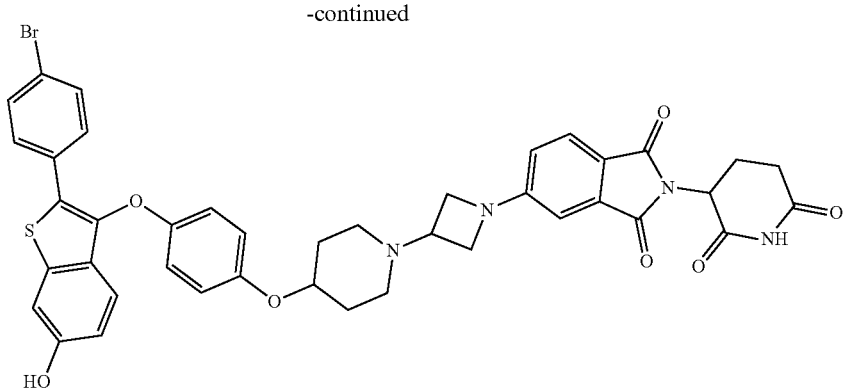
Compound 213
General Scheme 27B to prepare compounds 214 and 216.
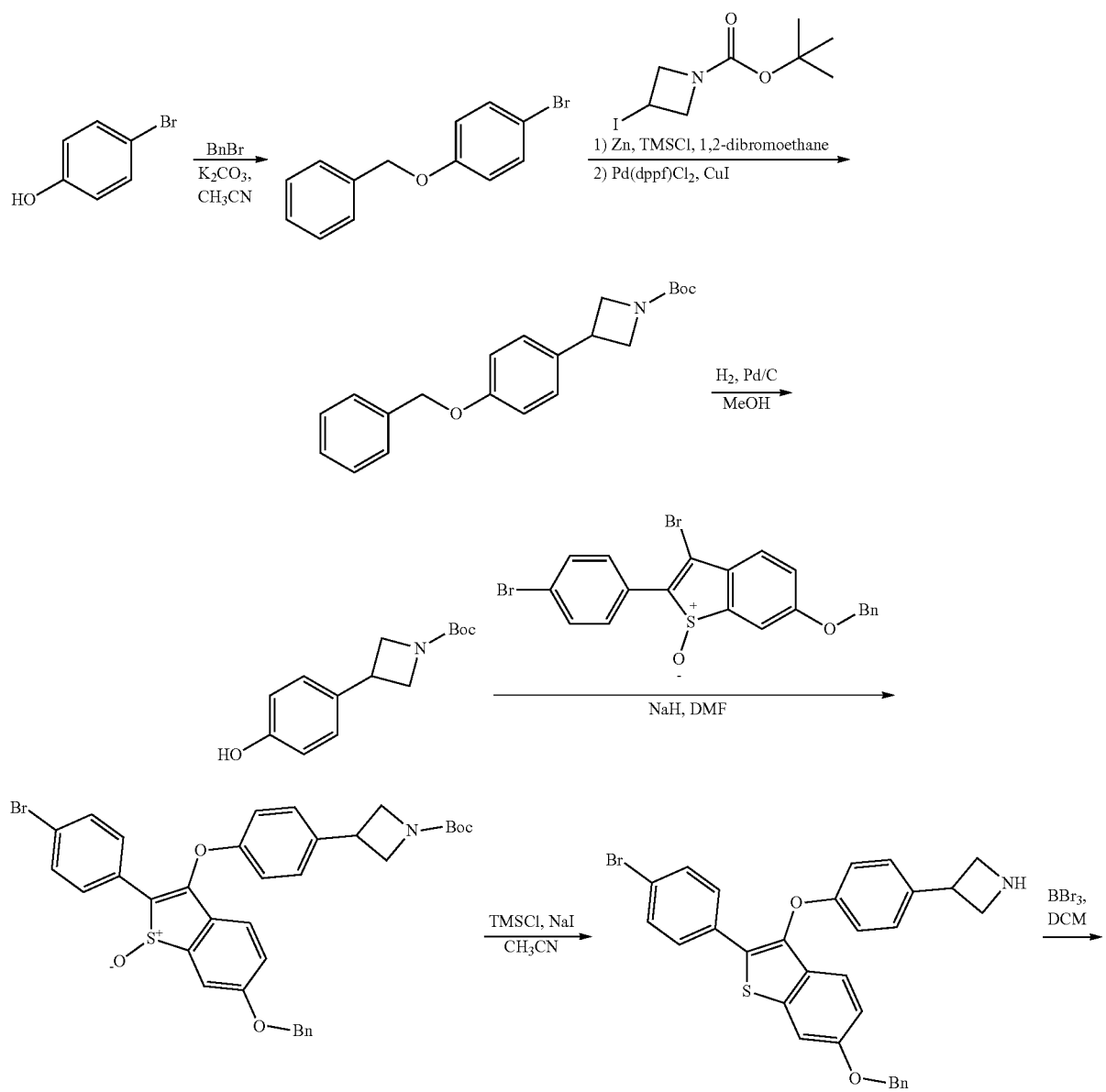

487 488
-continued
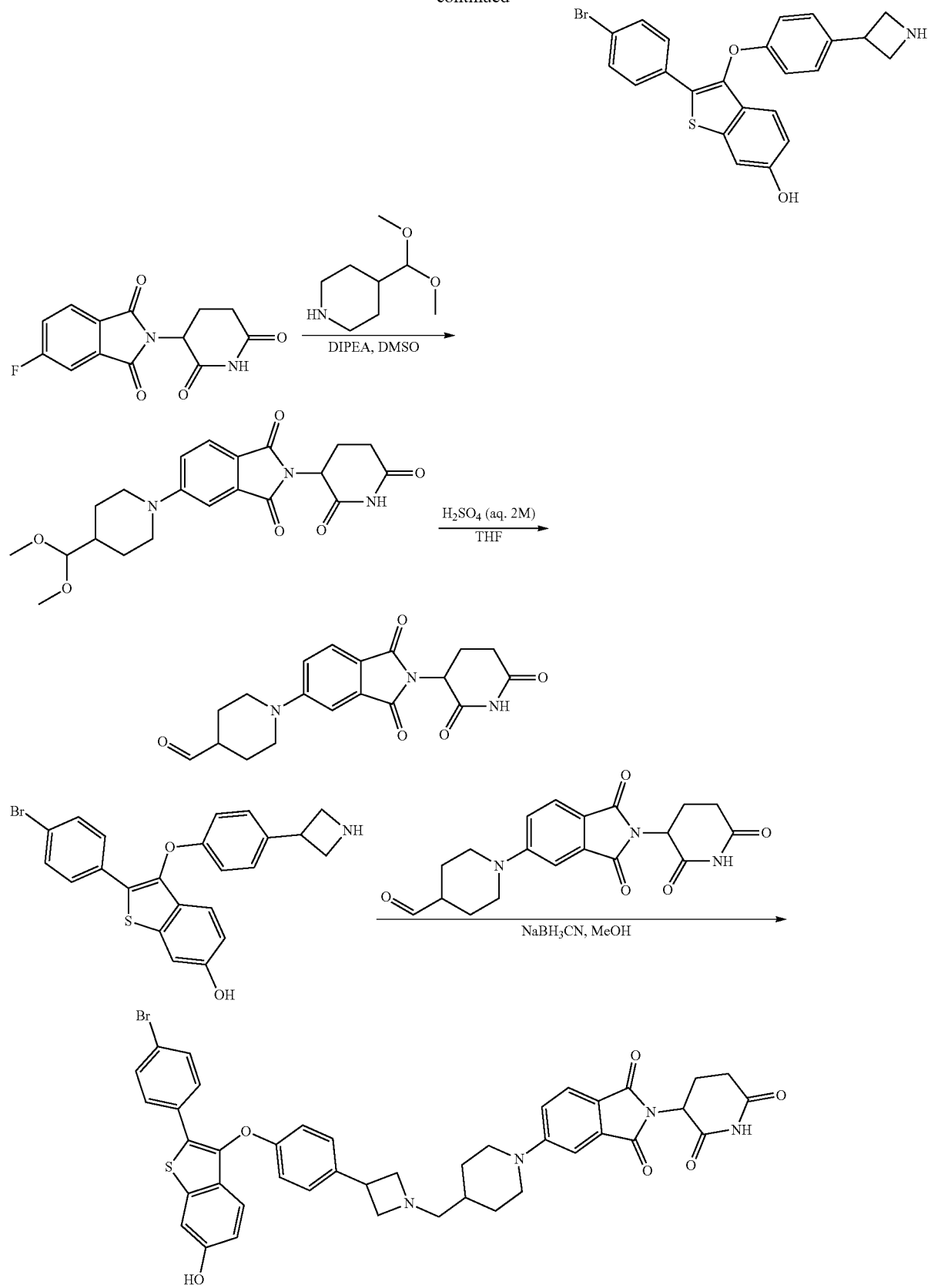
Compound 214

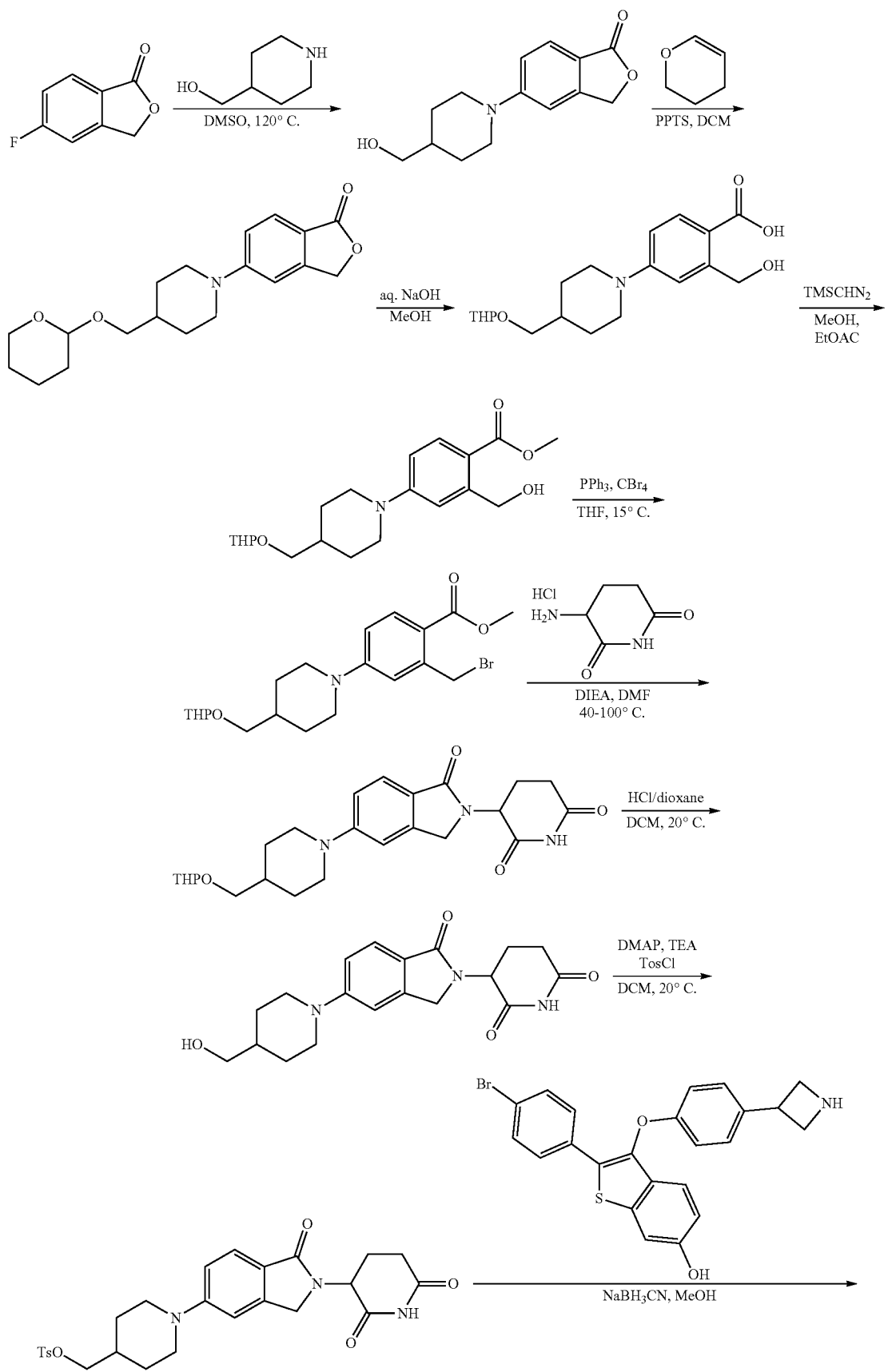

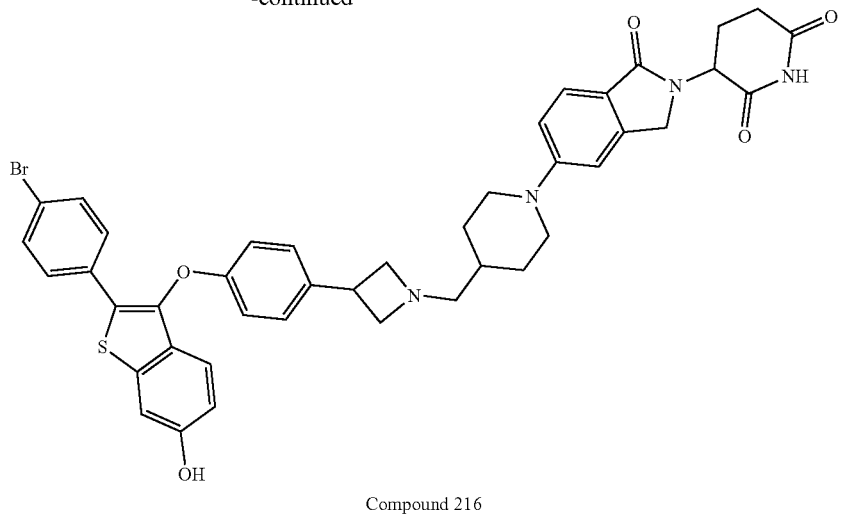
Compound 216
General Scheme 28B to Prepare Intermediate for Compound 218.
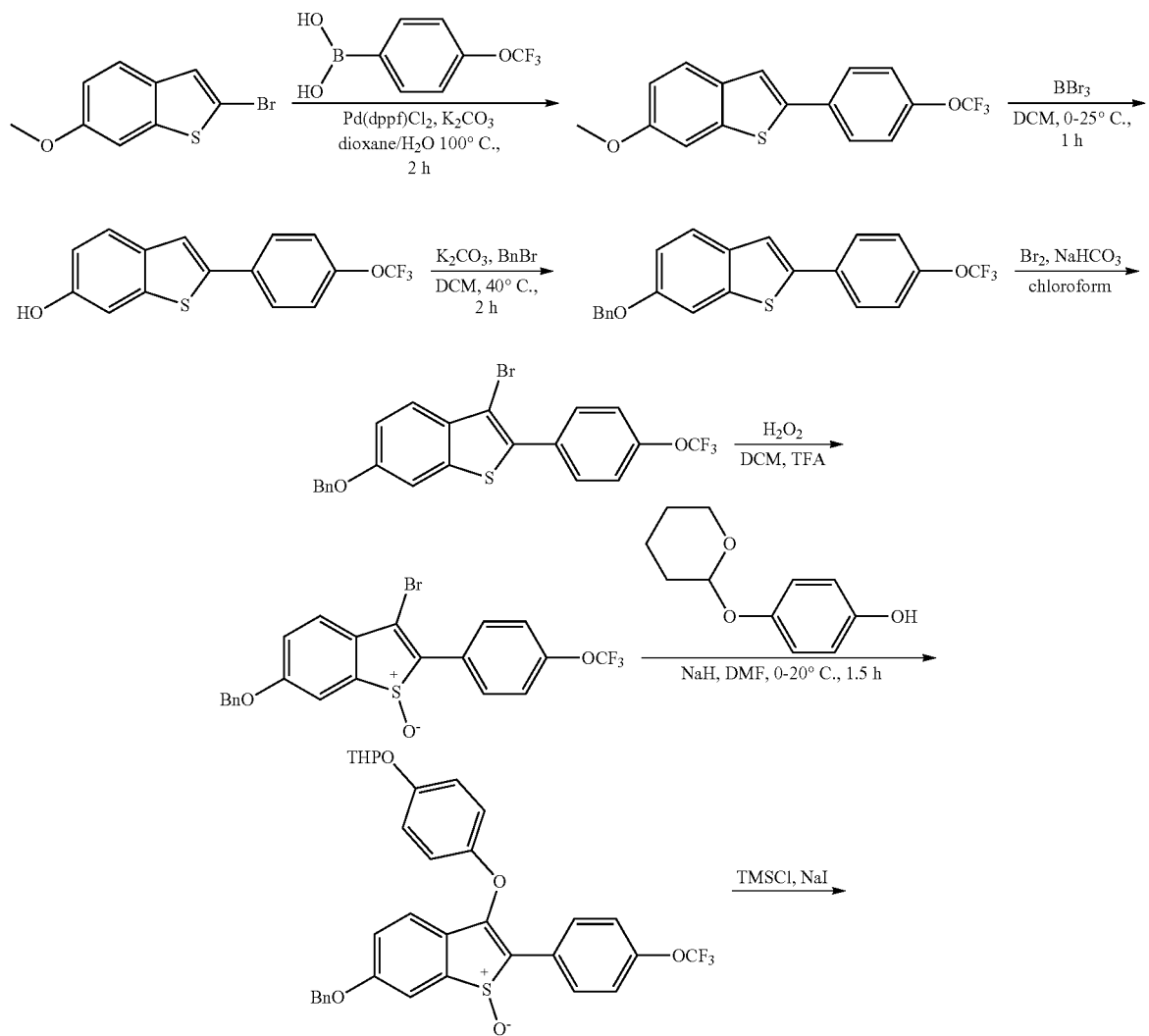

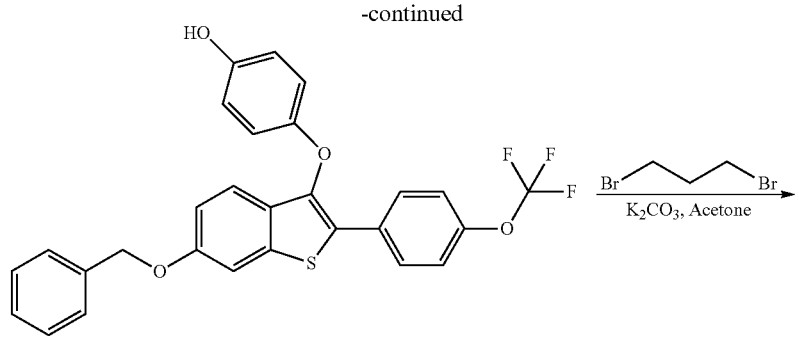
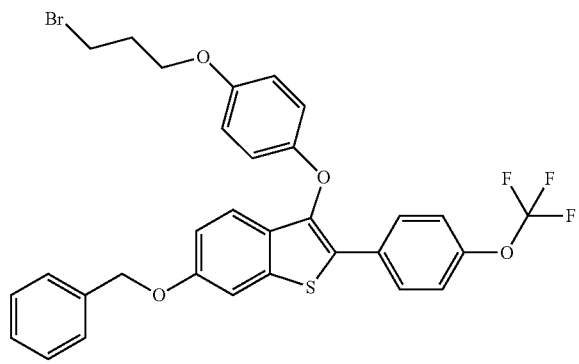
General Scheme 29B to Prepare Intermediate for Compound 222.
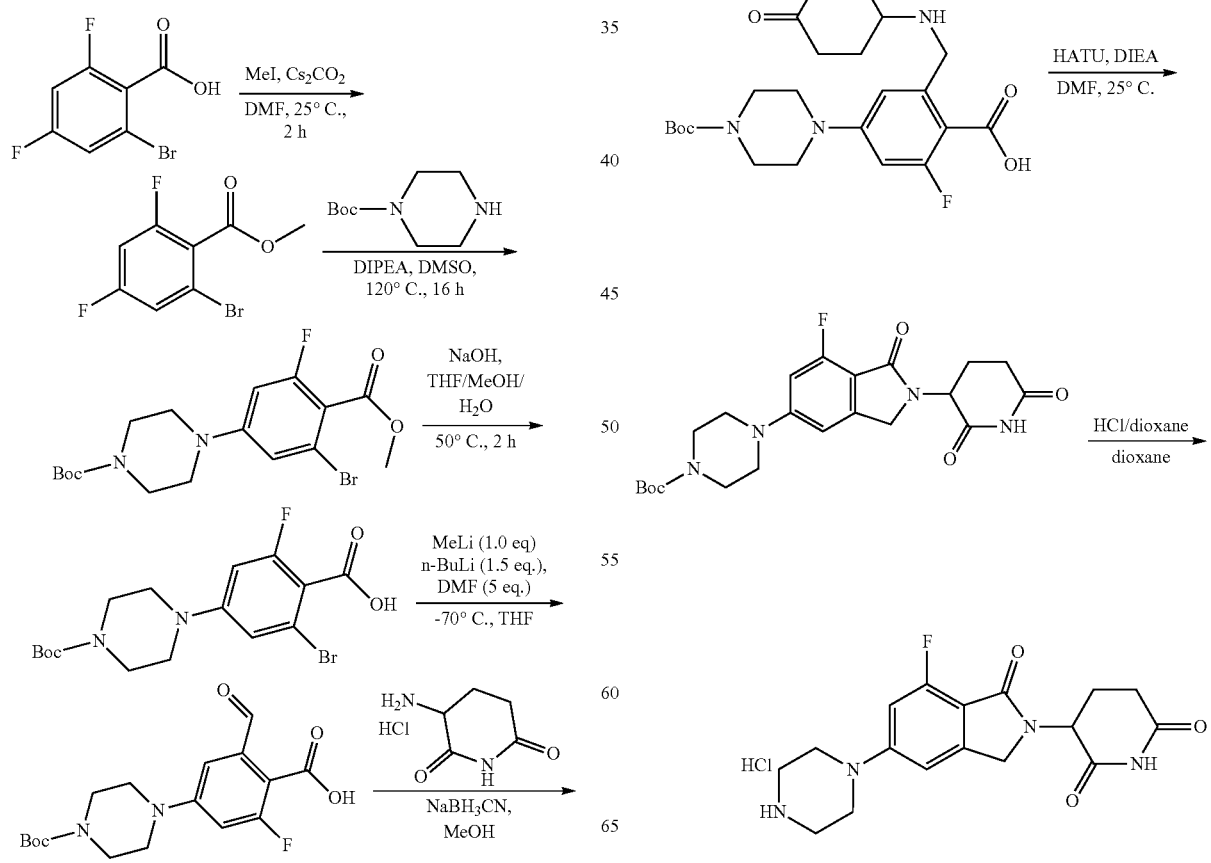

General Scheme 30B to Prepare Compound 223.
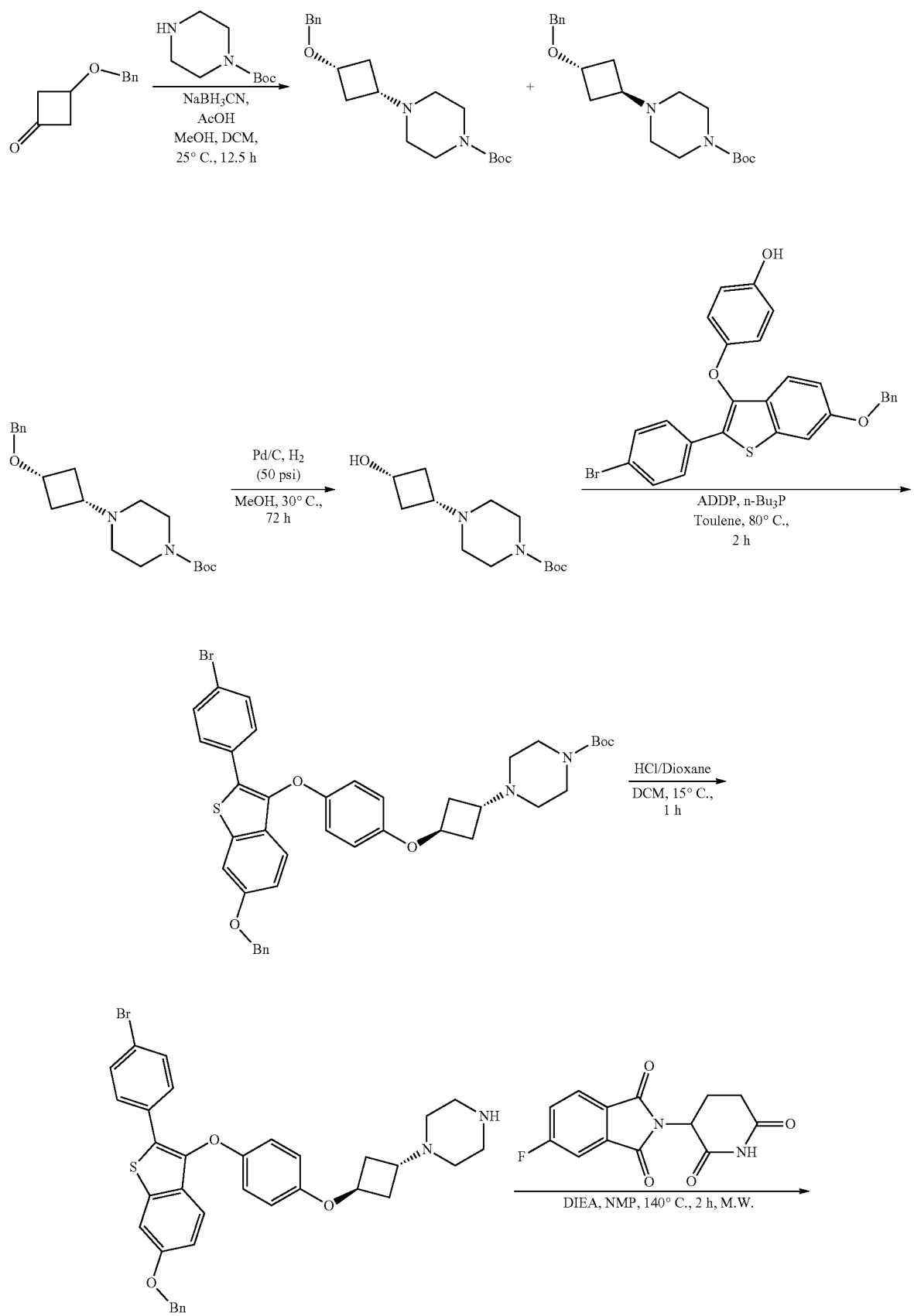

497 498
-continued
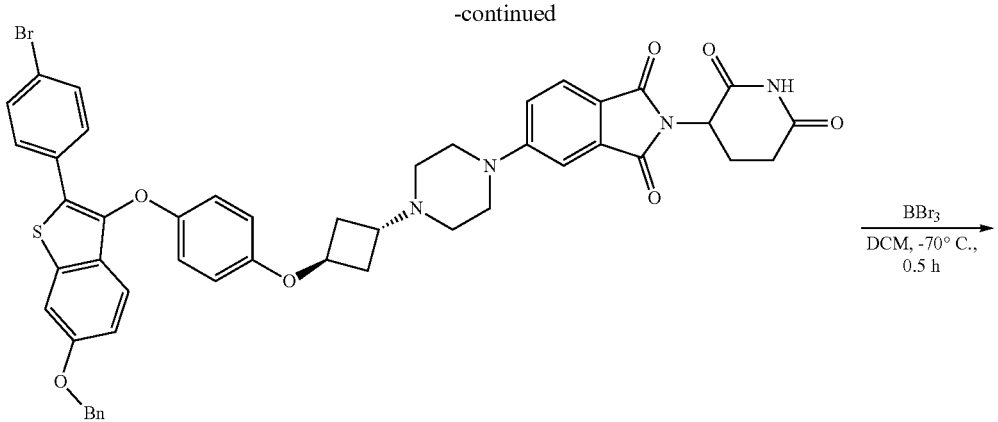
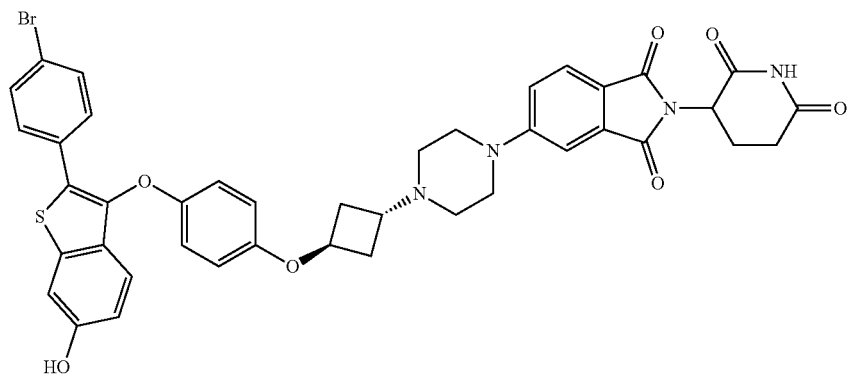
Compound 223
General Scheme 31B to Prepare Compound 224.
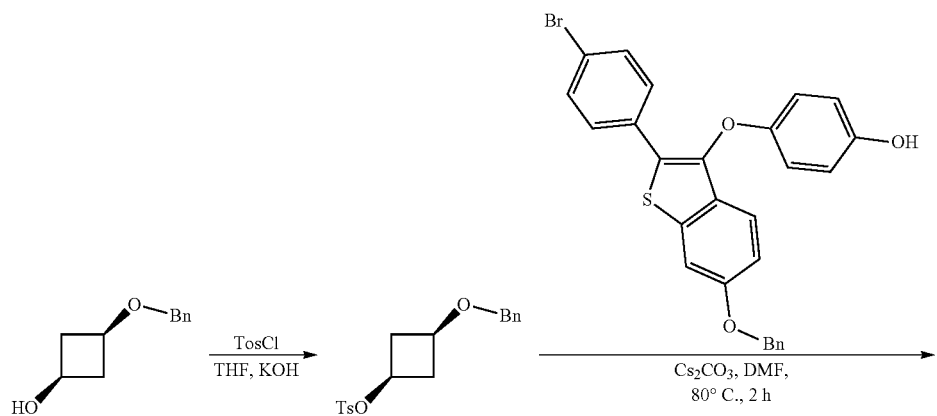

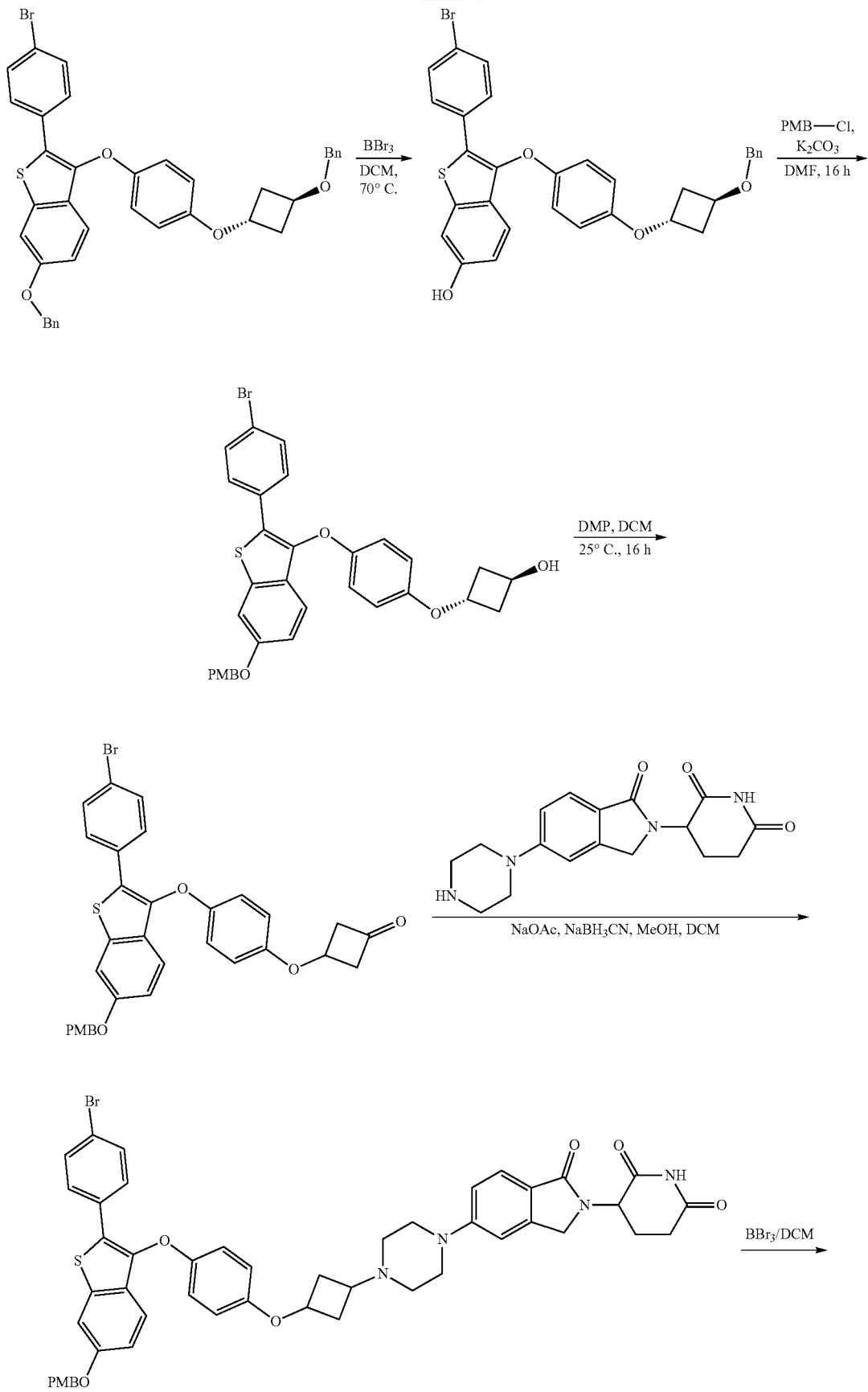

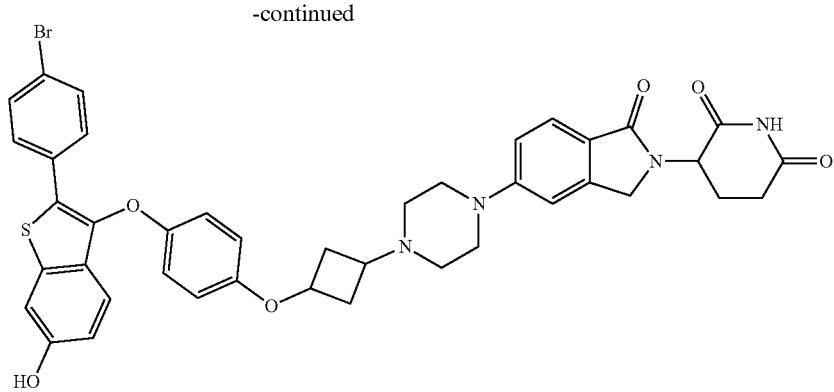
Compound 224
General Scheme 32B to Prepare Intermediate for Compound 225.
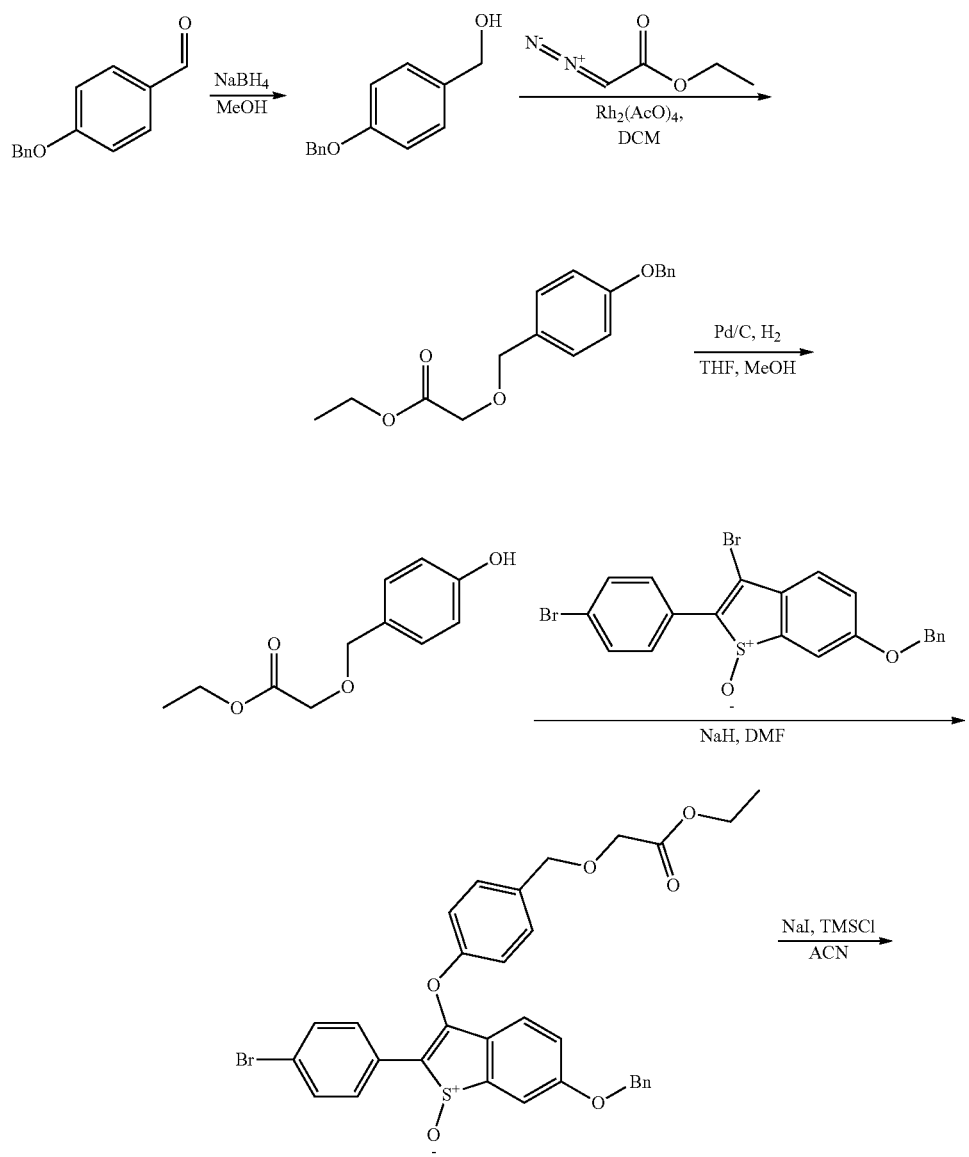

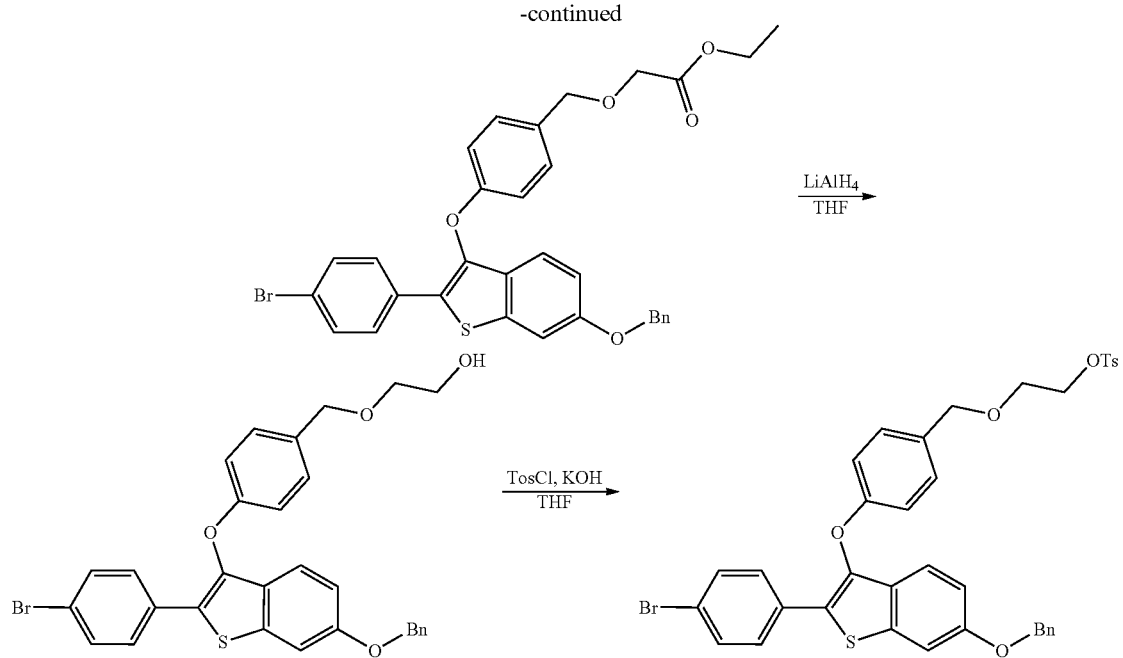
General Scheme 33B to Prepare Compound 226.
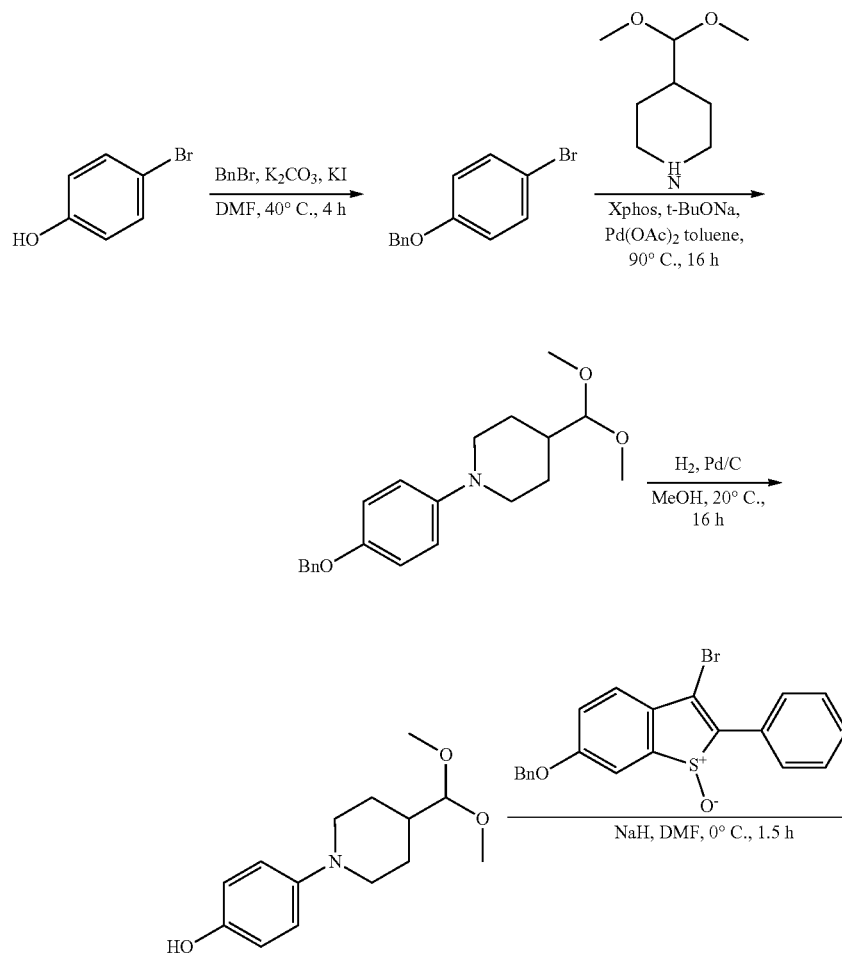

-continued
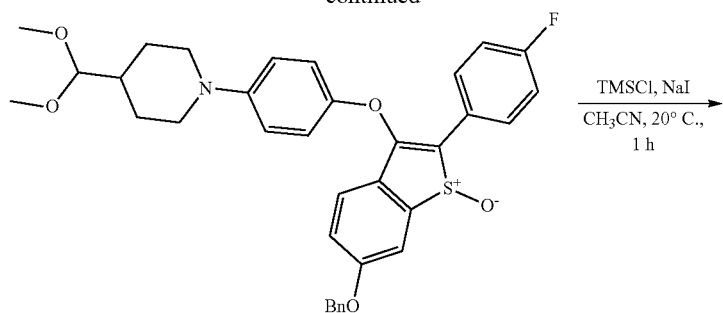
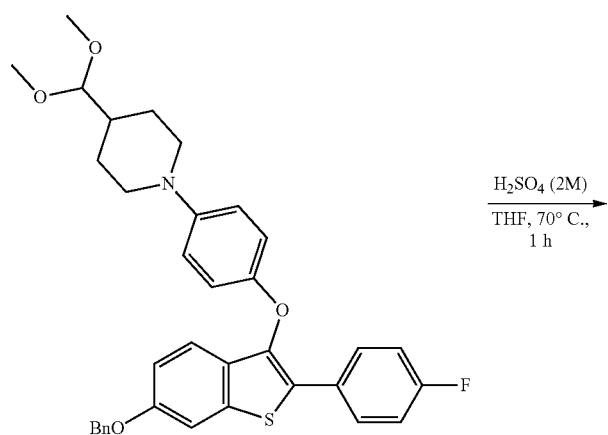
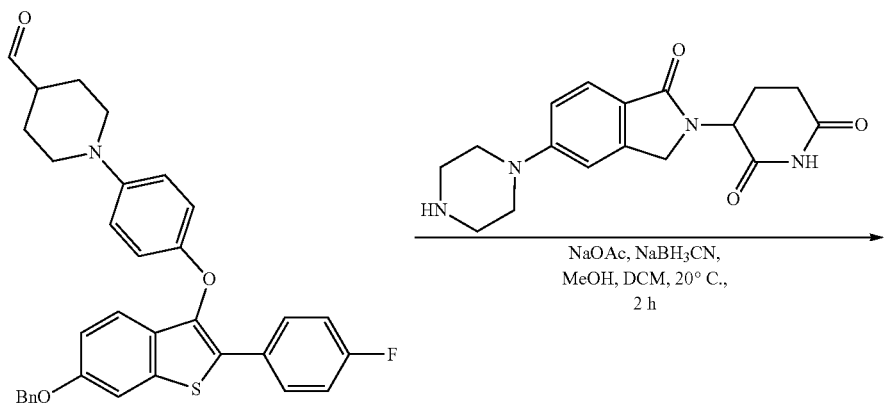

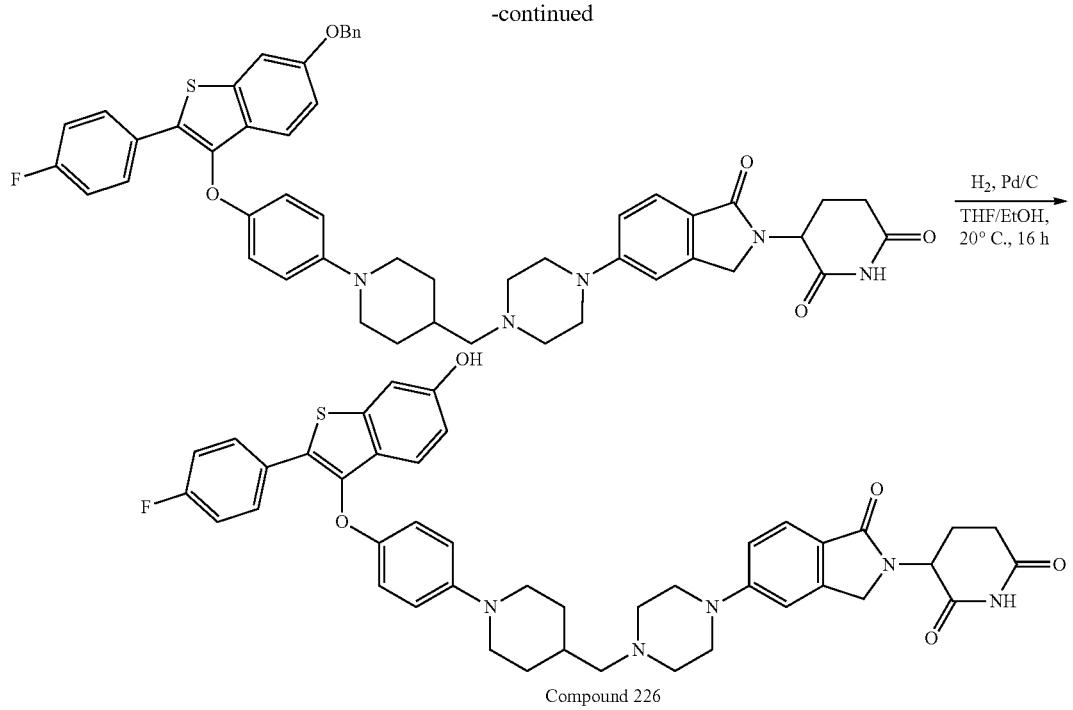
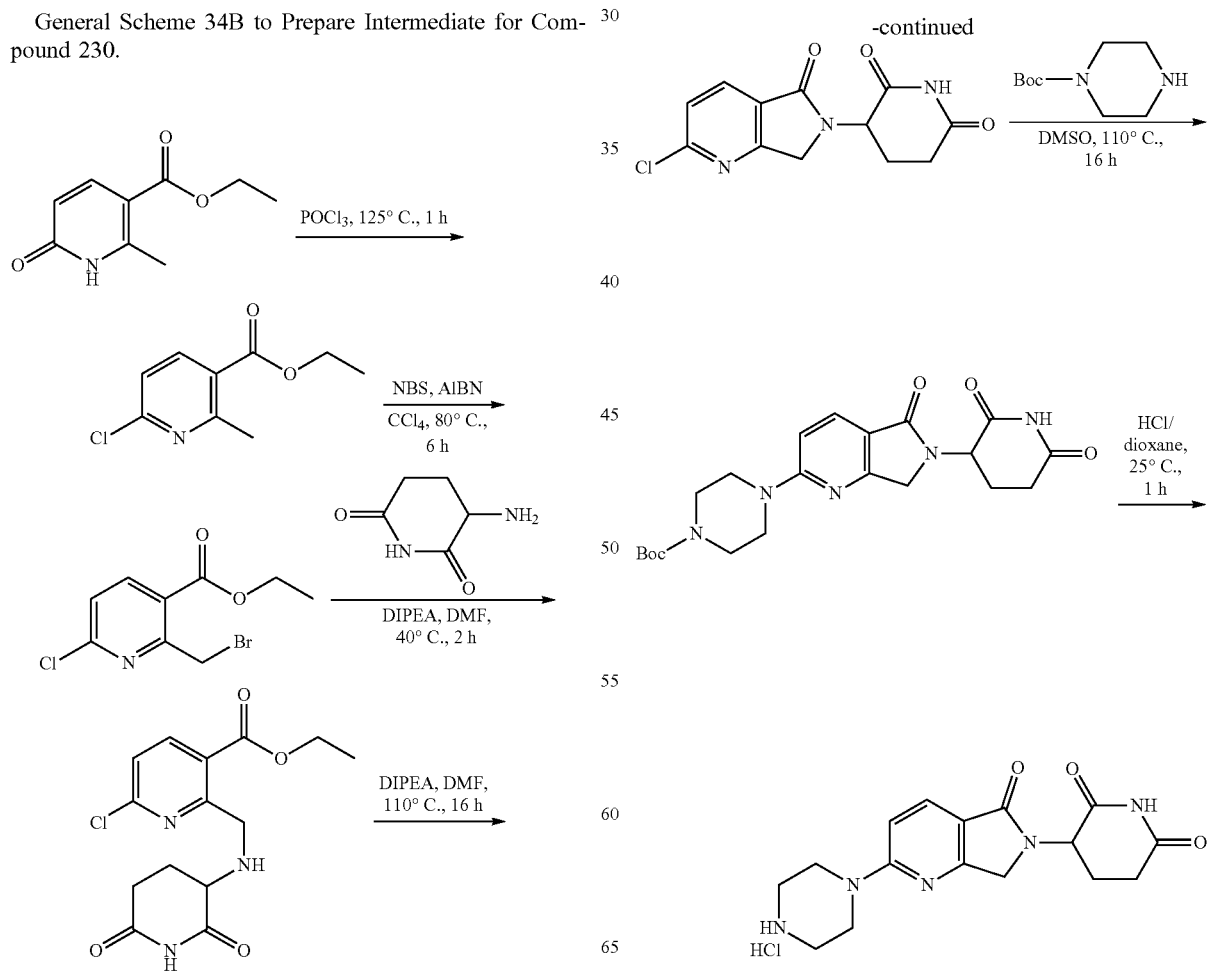
General Scheme 34B to Prepare Intermediate for Compound 230.

General Scheme 35B to Prepare Compound 231.
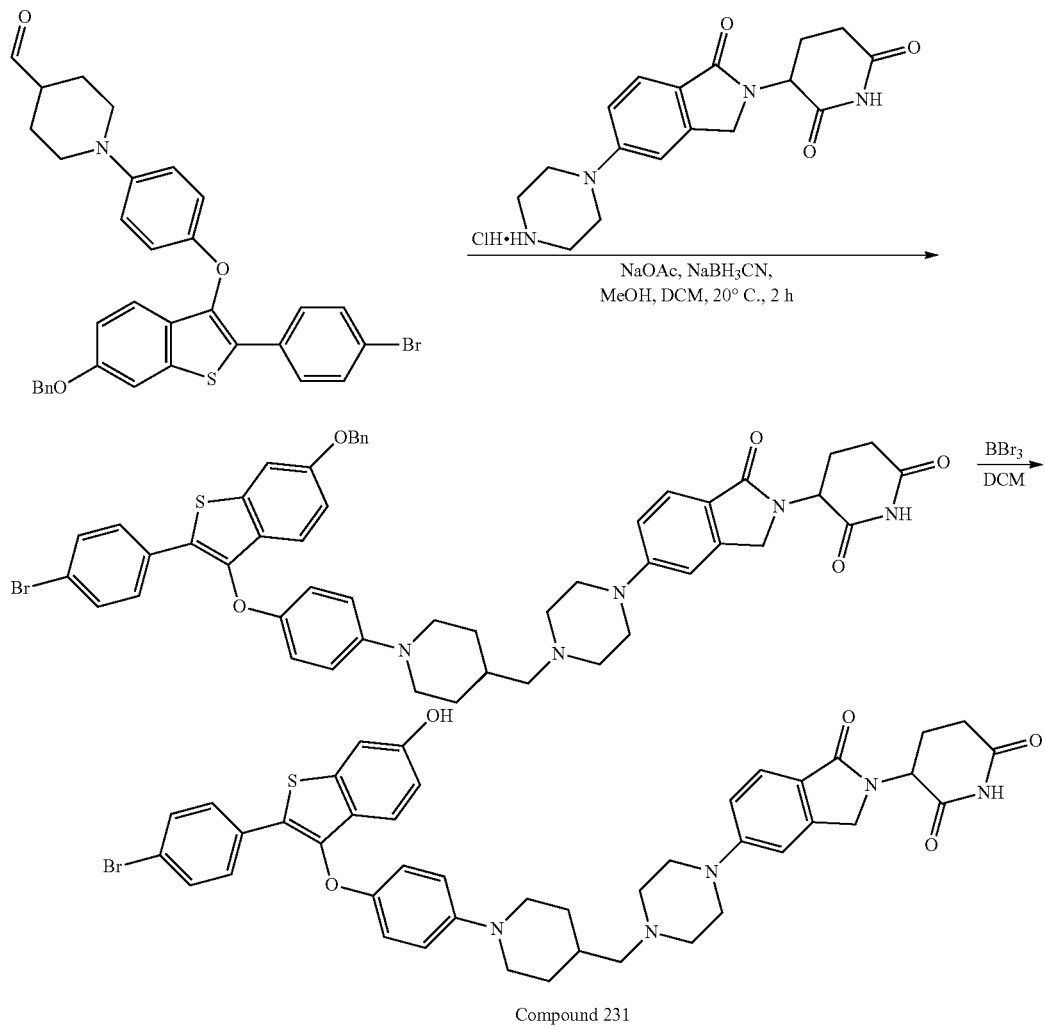
Compound 231
General Scheme 36B to Prepare Intermediate for Compound 232.
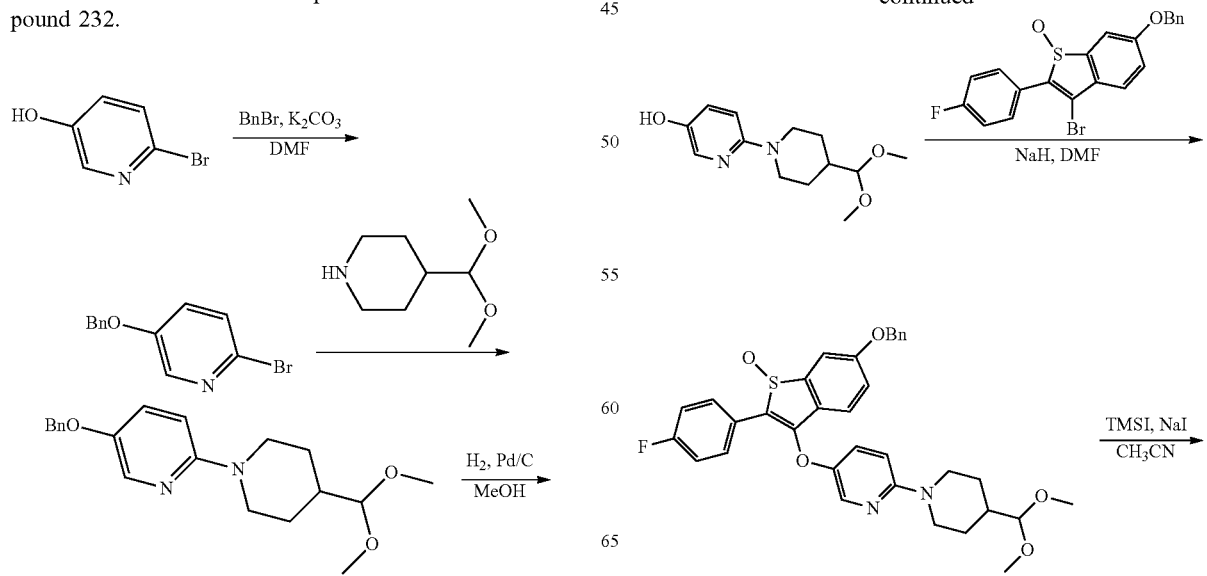

511
-continued
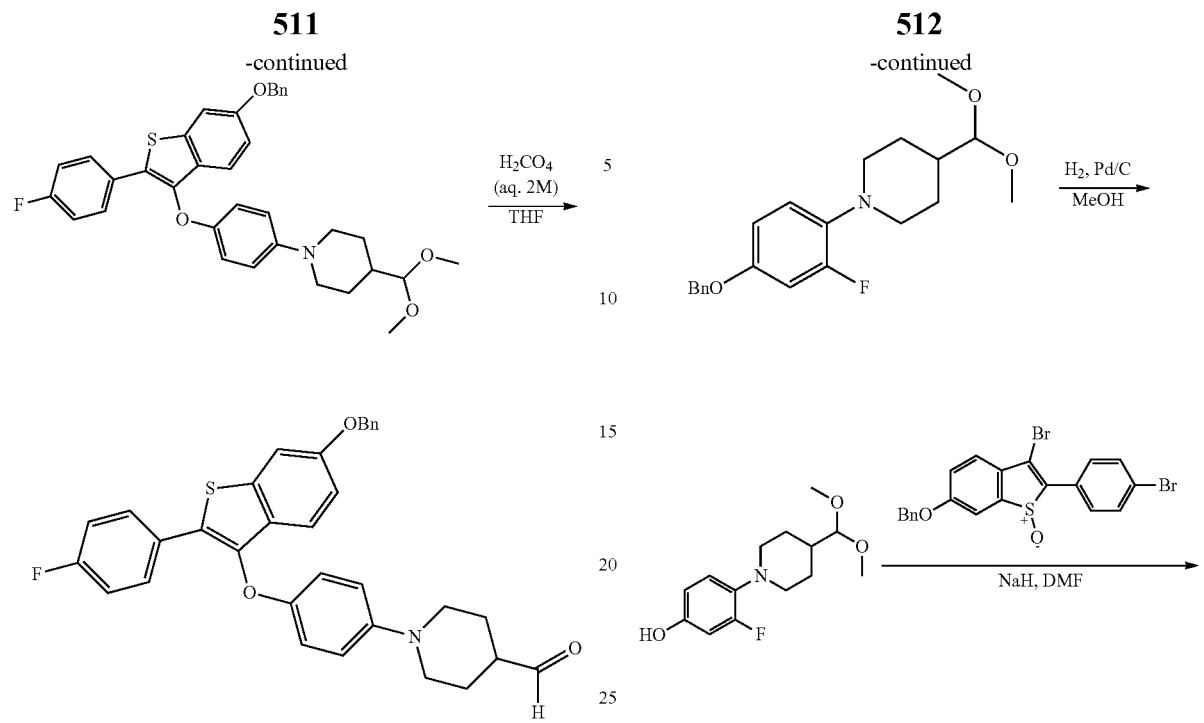
512
-continued
General Scheme 37B to Prepare Intermediate for Compound 238.
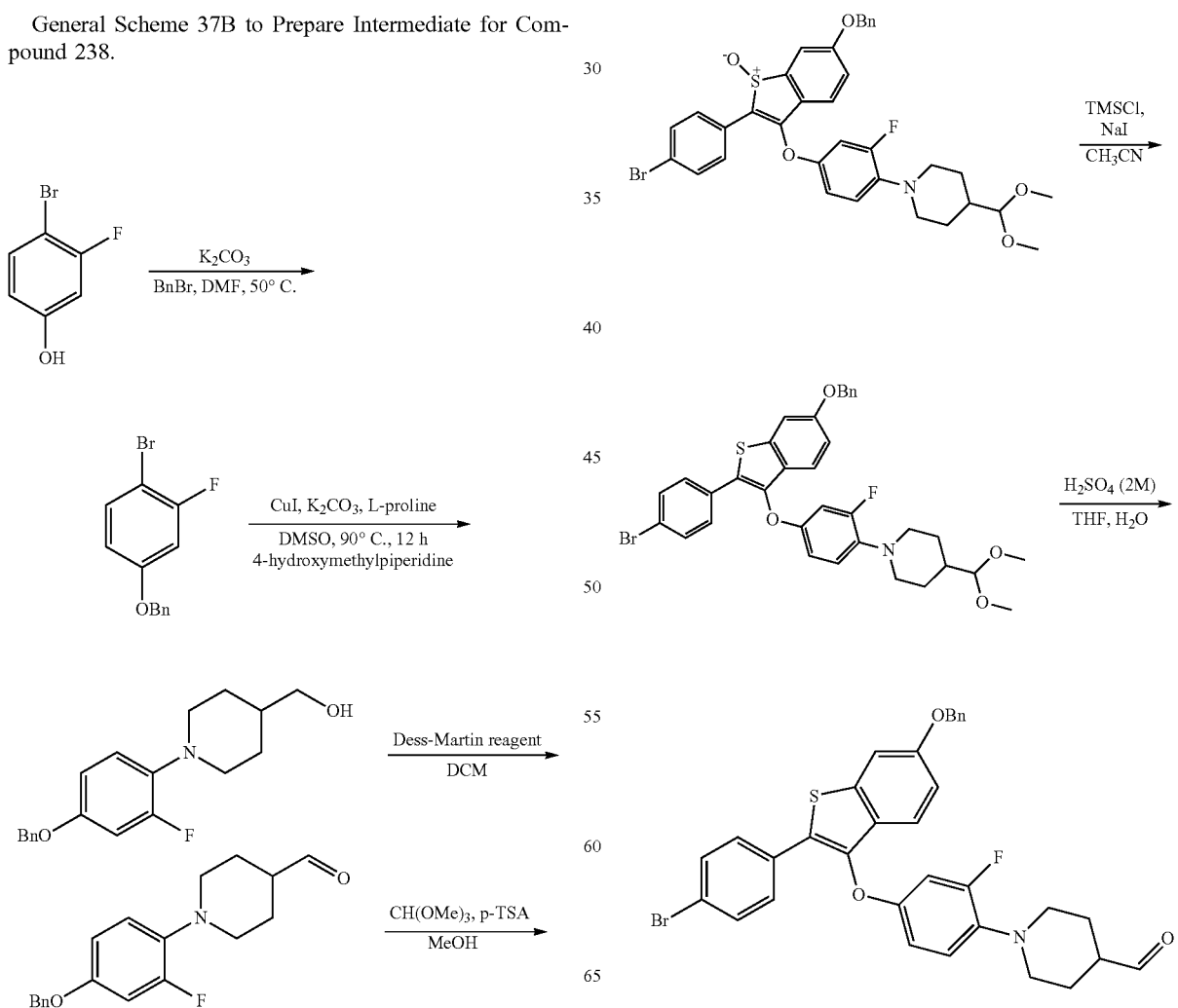

General Scheme 38B to Prepare Compound 240.
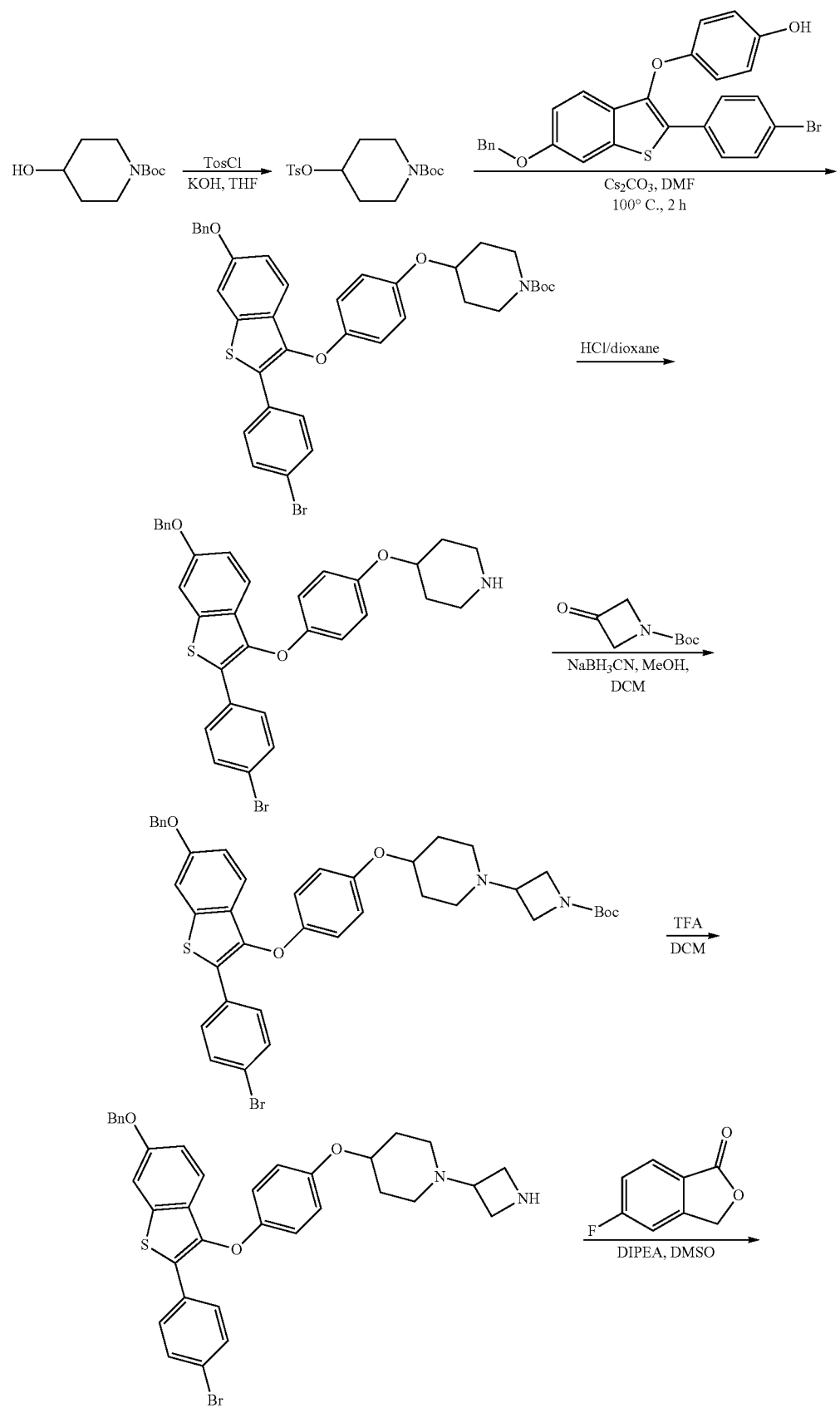

-continued
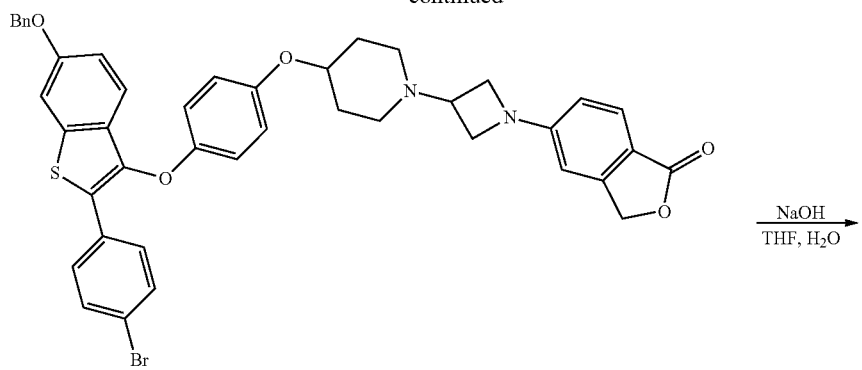
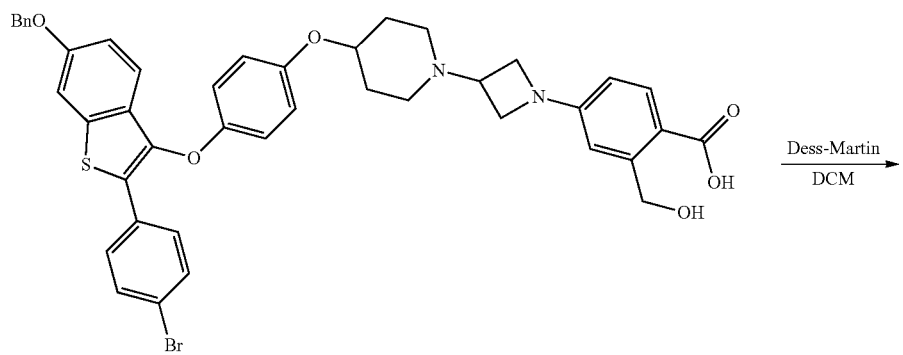
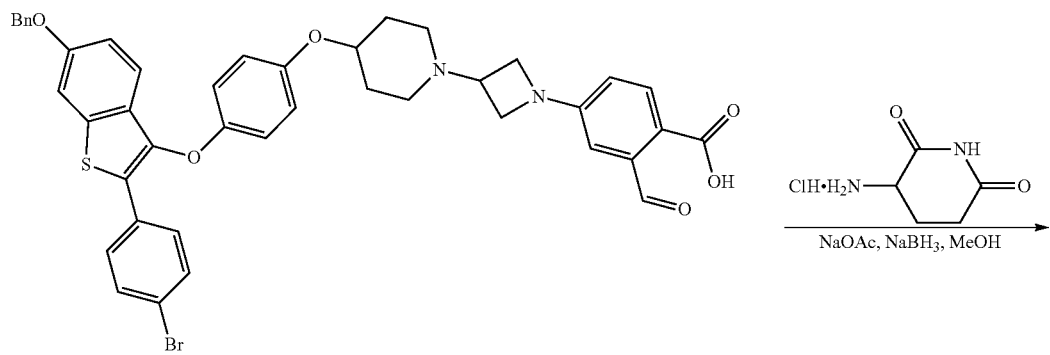
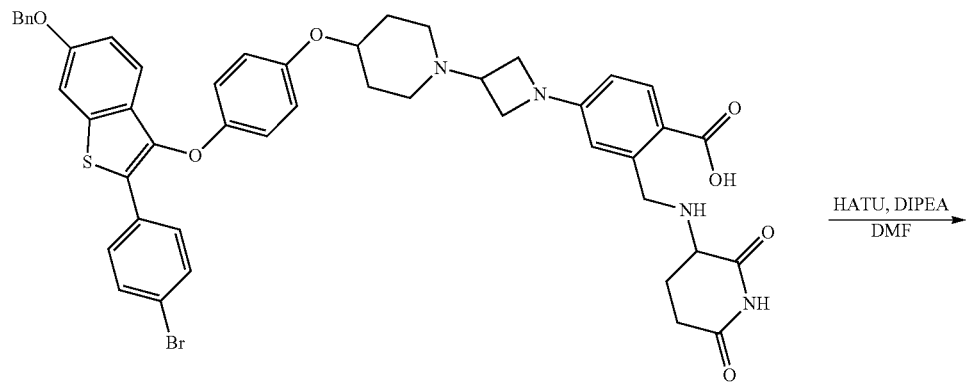

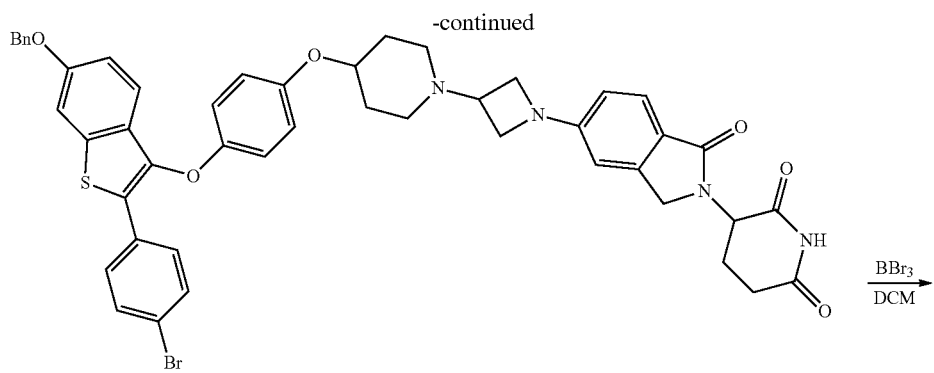
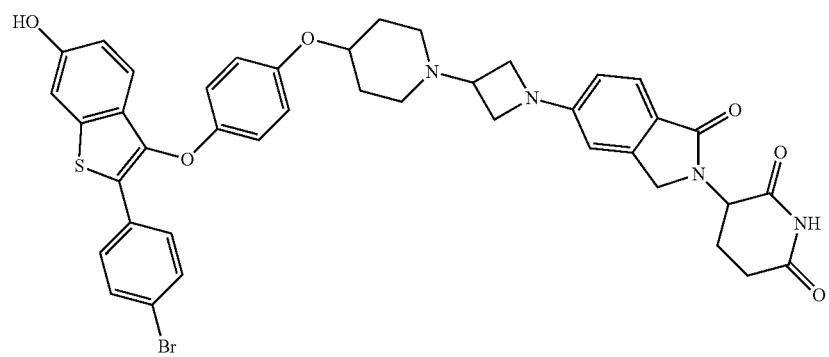
Compound 240
General Scheme 39B to Prepare Intermediate for Compound 241.
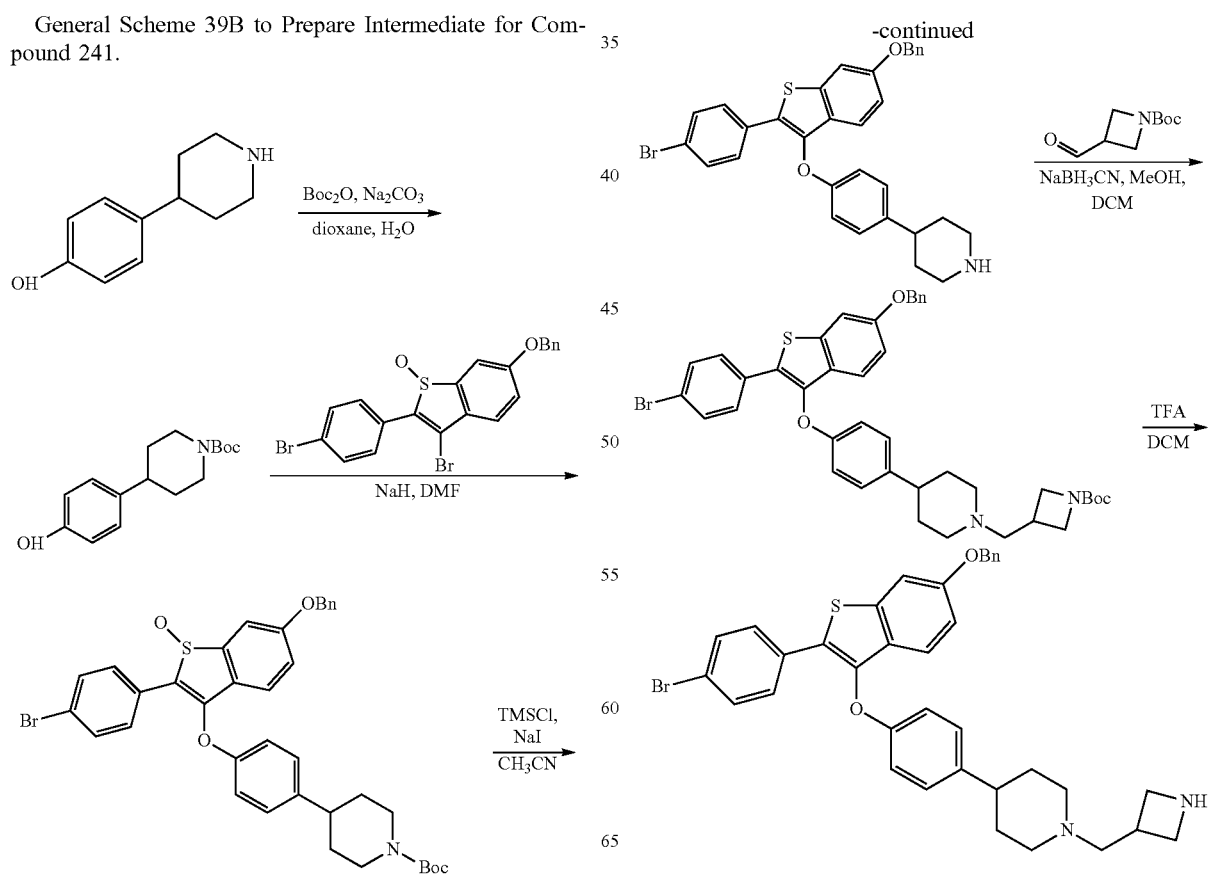

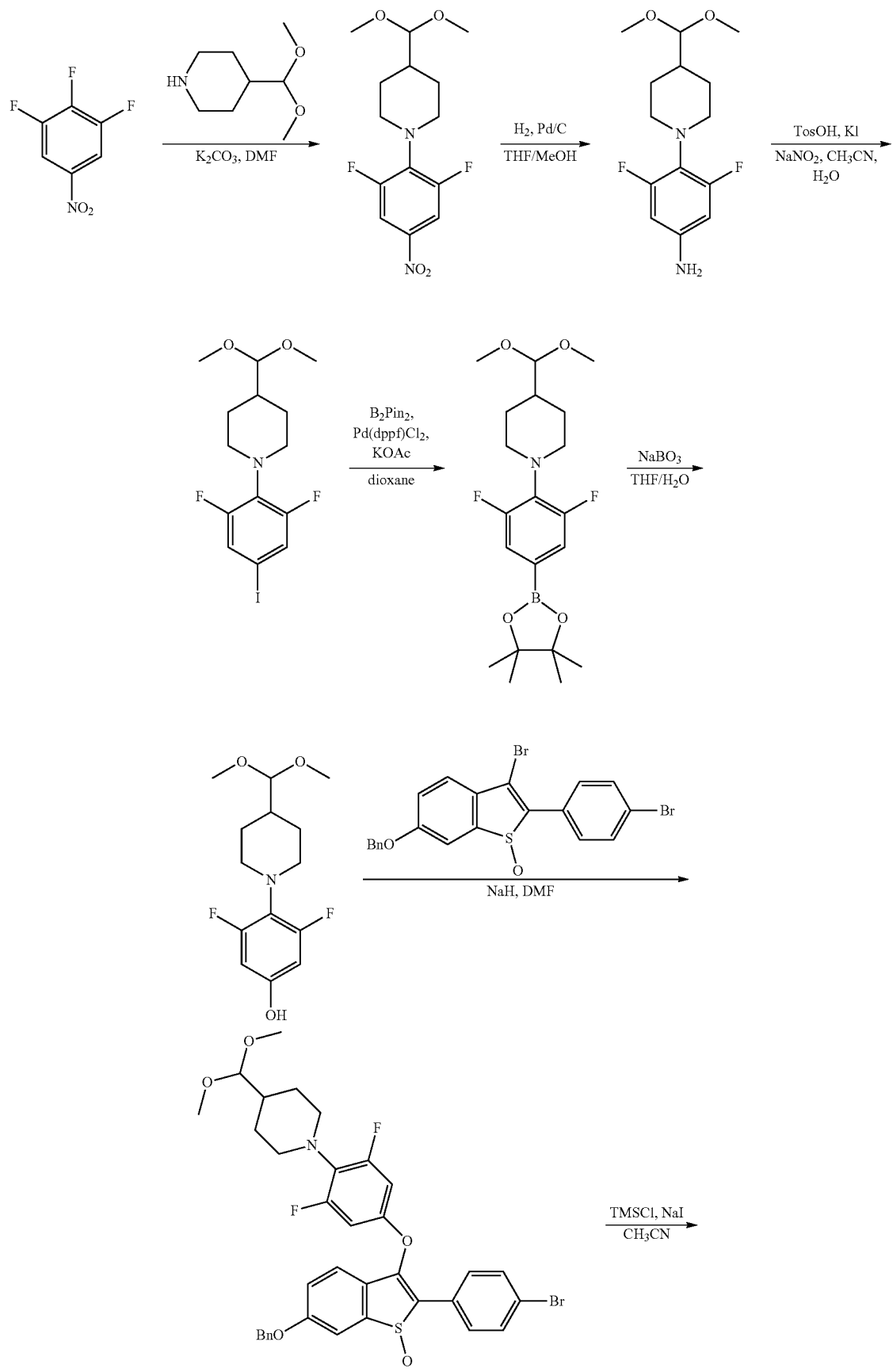

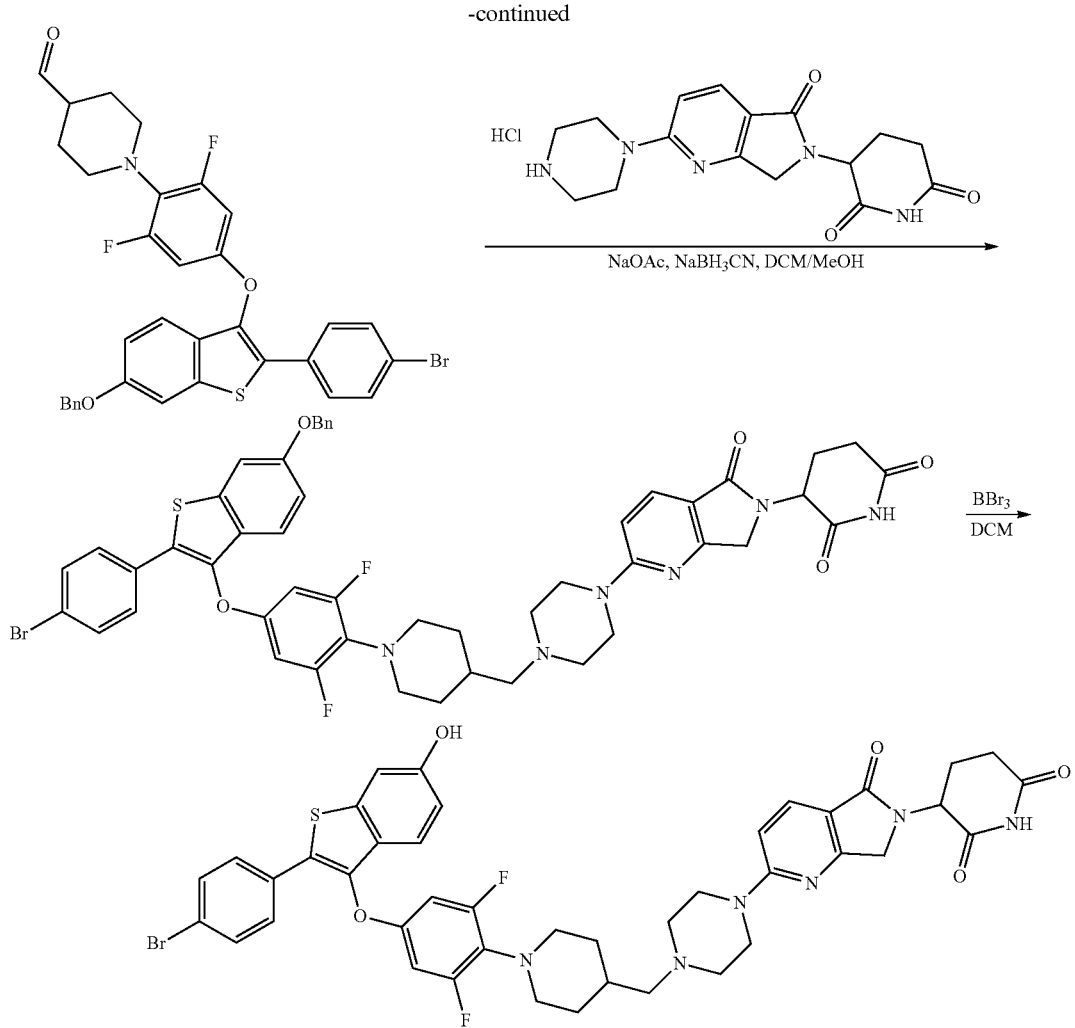
General Scheme 41B to Prepare Compounds 243, 244 and 245.

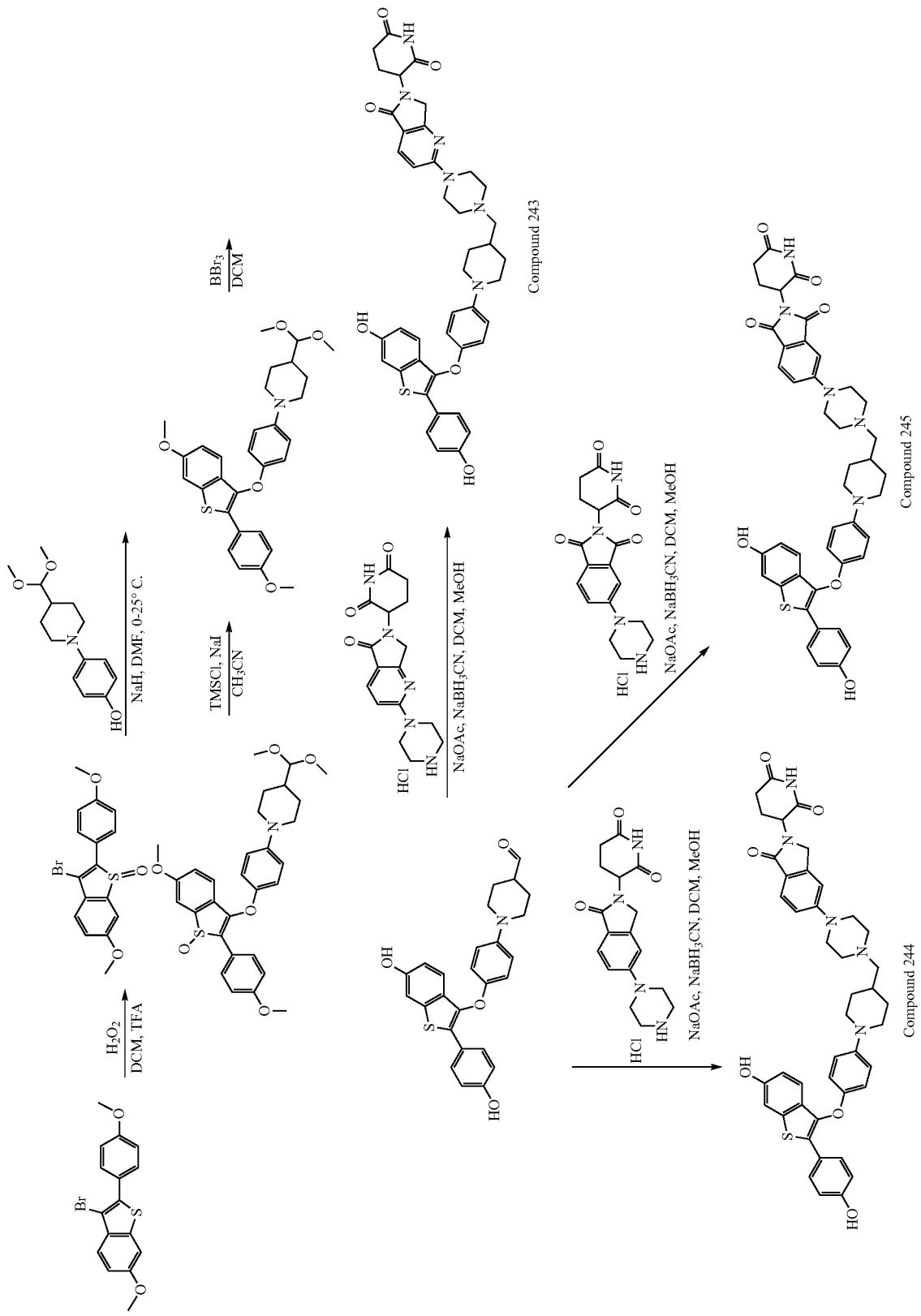

Experiment Procedures of Synthesizing ER PROTACs.
Preparation of 2-{4-[(2R)-1-(4-{[2-(4-bromophenyl)-6-hydroxy-1-benzothiophen-3-yl]oxy}phenoxy)propan-2-yl]piperazin-1-yl}-N-{[2-(2,6-dioxopiperidin-3-yl)-1-oxo-2,3-dihydro-1H-isoindol-5-yl]methyl}acetamide (Compound 11)
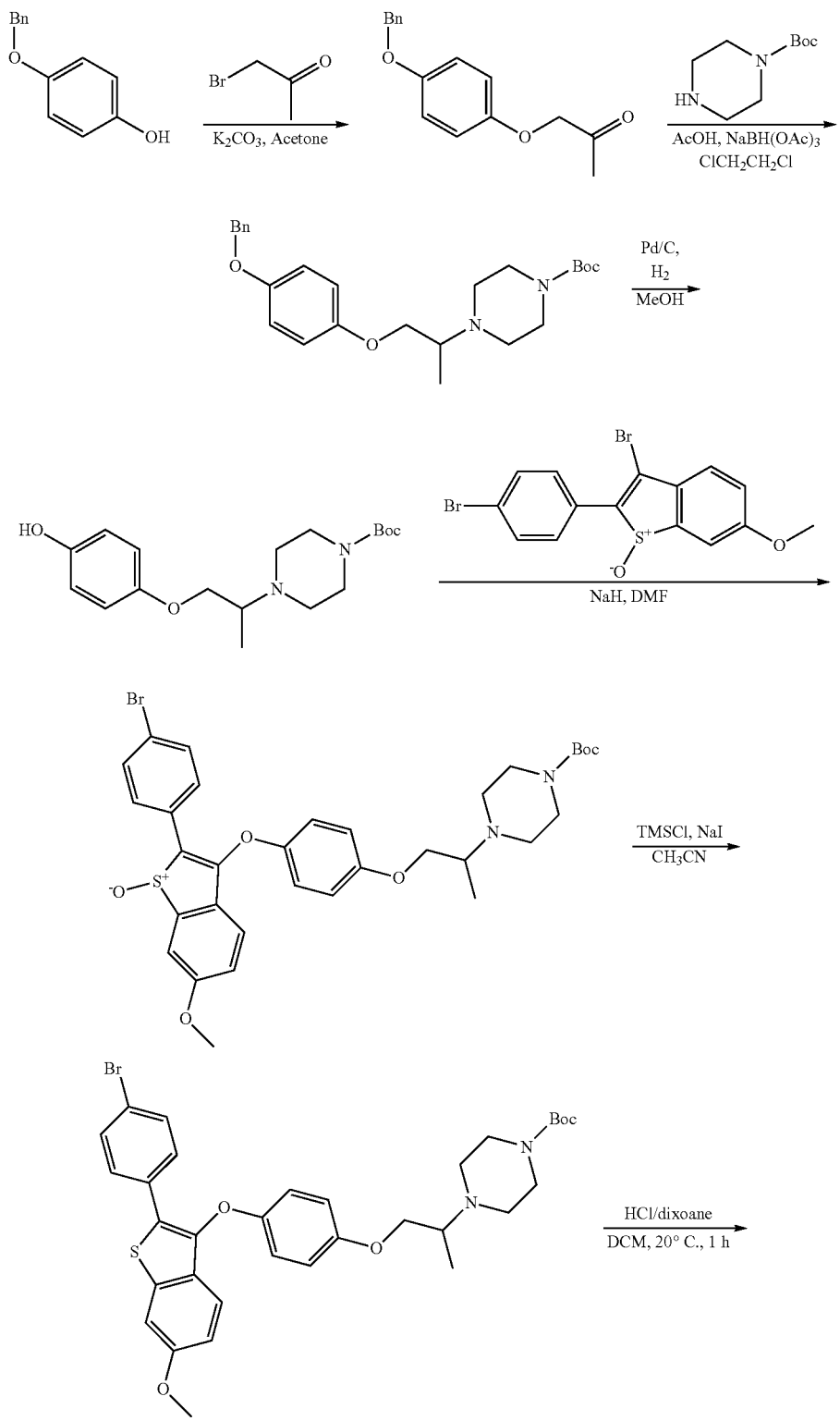

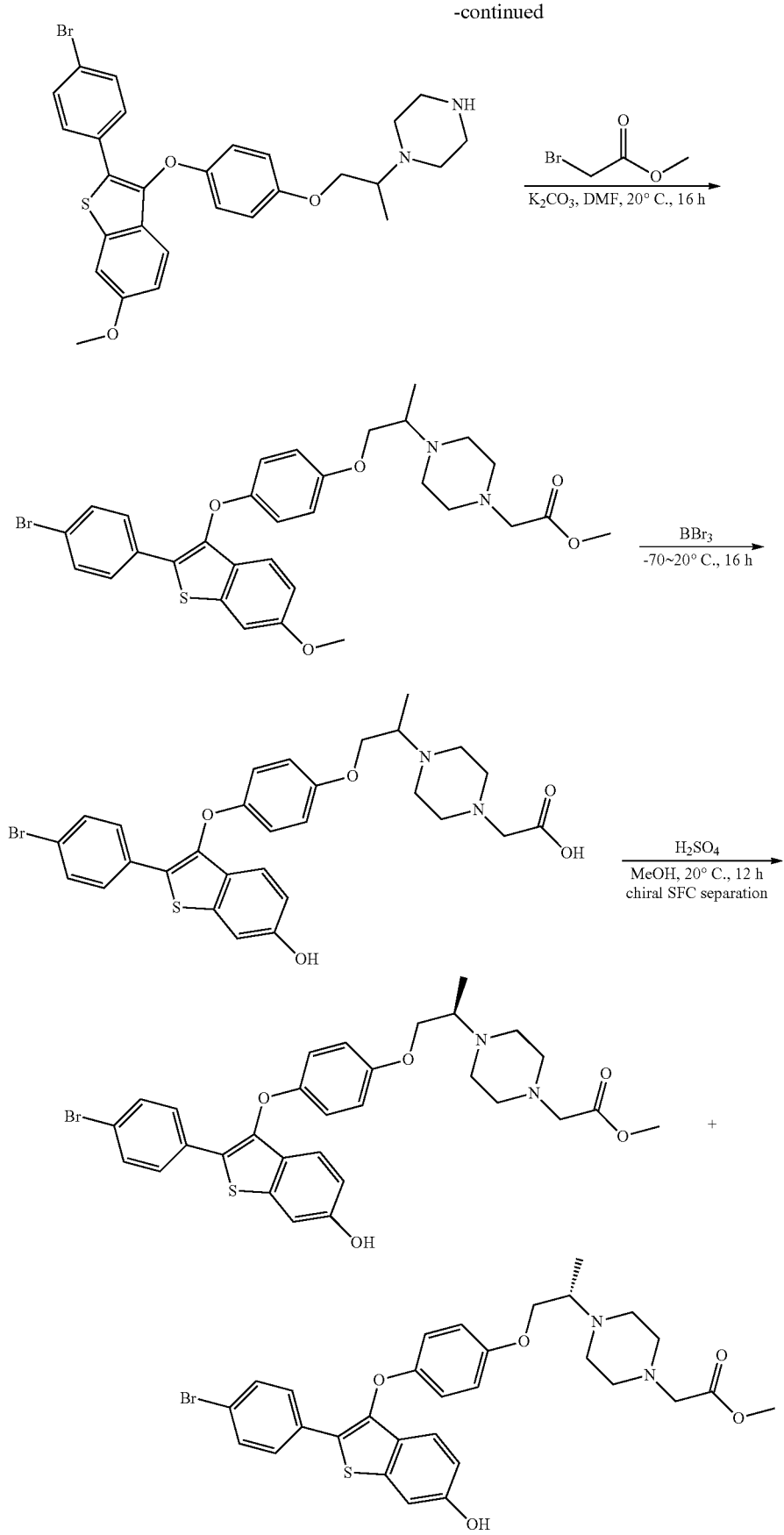

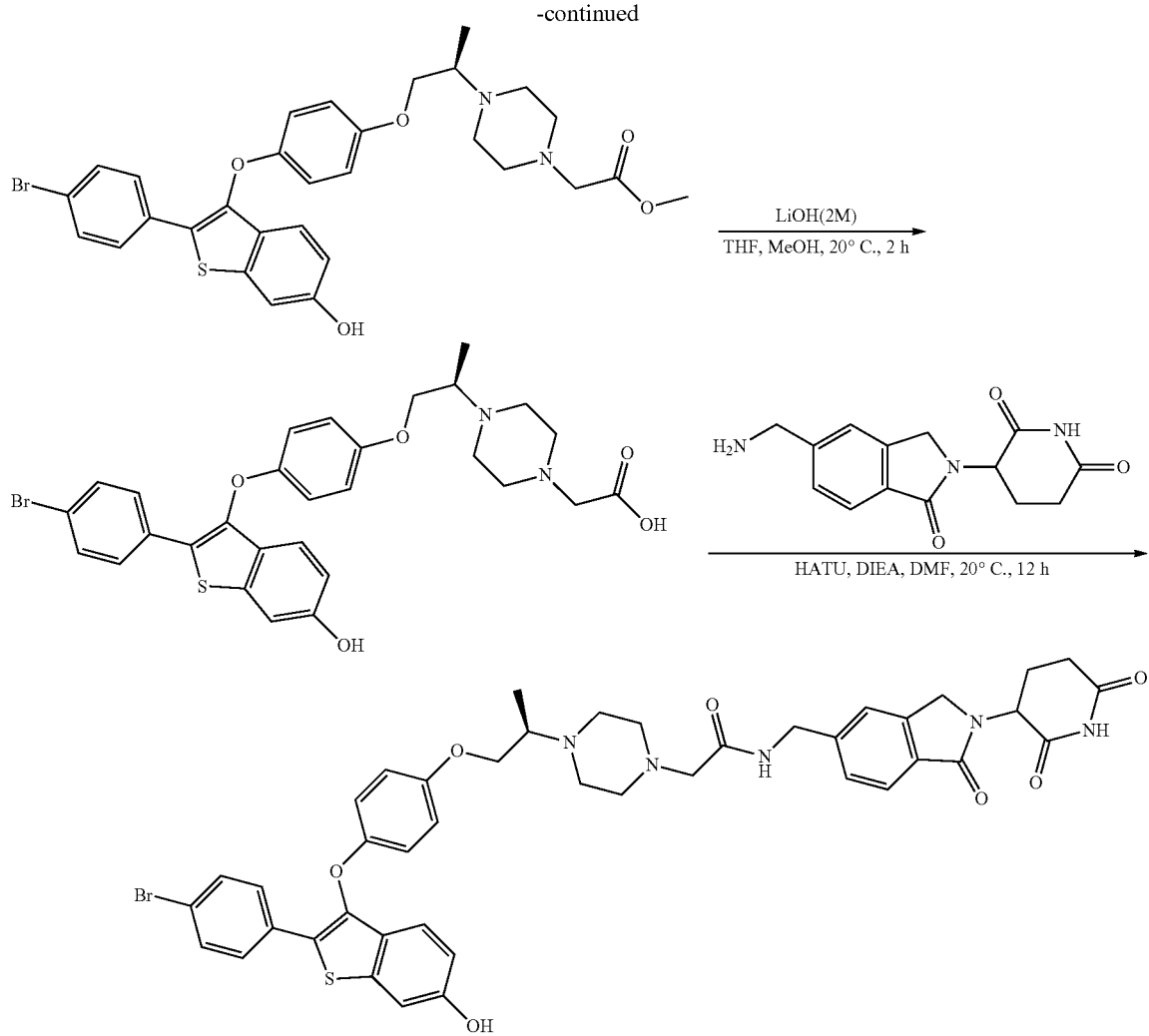

Step 1: Preparation of 1-(4-benzyloxyphenoxy)propan-2-one

To a solution of 4-benzyloxyphenol (3 g, 14.98 mmol, 1.00 eq) in acetone (30 mL) was added potassium carbonate (2.48 g, 17.98 mmol, 1.20 eq) and 1-bromopropan-2-one (2.46 g, 17.98 mmol, 1.20 eq) under nitrogen atmosphere. The reaction mixture was stirred at 60° C. for 5 h. LC/MS showed most of the starting material was consumed. Water (150 mL) was added to the mixture, the resulting mixture was extracted with petroleum ether (50 mL×3). The combined organic phase was washed with brine (80 mL), dried over sodium sulfate, filtered and concentrated in vacuum. The residue was purified by silica gel chromatography (Petroleum ether:Ethyl acetate=30/1 to 3/1) to give 1-(4-benzyloxyphenoxy)propan-2-one (3.3 g, crude) as a white solid.

LC/MS: MS (ESI) m/z: 257.0 [M+1]$^+$; $^1$H NMR: (400 MHz, CDCl$_3$)

δ: 7.44-7.33 (m, 5H), 6.94-6.90 (m, 2H), 6.84-6.82 (m, 2H), 5.03 (s, 2H), 4.50 (s, 2H), 2.28 (s, 3H).

Step 2: Preparation of tert-butyl 4-[2-(4-benzyloxyphenoxy)-1-methyl-ethyl] piperazine-1-carboxylate To a solution of 1-(4-benzyloxyphenoxy) propan-2-one (1.8 g, 7.02 mmol, 1.00 eq) in 1,2-dichloroethane (30 mL) was added tert-butyl piperazine-1-carboxylate (1.05 g, 5.62 mmol, 0.80 eq) and acetic acid (421 mg, 7.02 mmol, 0.41 mL, 1.00 eq). The mixture was stirred at 20° C. for 1 h. Then sodium triacetoxyborohydride (2.23 g, 10.53 mmol, 1.50 eq) was added to the mixture, the reaction was stirred at 20° C. for 5 h. LC/MS showed most of the starting material was consumed. Water (150 mL) and dichloromethane (80 mL) was added to the mixture, and layers were separated. The organic layer was washed with brine (50 mL), dried over sodium sulfate, filtered and concentrated in vacuum. The residue was purification by silica gel chromatography (Petroleum ether/Ethyl acetate=30/1 to 1/1) to give tert-butyl 4-[2-(4-benzyloxyphenoxy)-1-methyl-ethyl]piperazine-1-carboxylate (1.4 g, 3.28 mmol, 47% yield) as a light yellow oil.

LCMS: MS (ESI) m/z: 427.1 [M+1]$^+$; $^1$H NMR: (400 MHz, CDCl$_3$) δ: 7.44-7.30 (m, 5H), 6.94-6.90 (m, 2H), 6.85-6.82 (m, 2H), 5.02 (s, 2H), 4.02-3.98 (m, 1H), 3.85-3.81 (m, 1H), 3.43 (t, J=4.8 Hz, 4H), 3.05-2.97 (m, 1H), 2.65-2.55 (m, 4H), 1.46 (s, 9H), 1.16 (d, J=6.8 Hz, 3H).

Step 3: Preparation of tert-butyl 4-[2-(4-hydroxy-phenoxy)-1-methyl-ethyl]piperazine-1-carboxylate To a solution of tert-butyl 4-[2-(4-benzyloxyphenoxy)-1-methyl-ethyl]piperazine-1-carboxylate (1.4 g, 3.28 mmol, 1.00 eq) in methanol (40 mL) was added Pd/C (200 mg, 10%) under nitrogen atmosphere. The suspension was degassed under vacuum and purged with hydrogen several times. The reaction mixture was stirred at 20° C. for 16 h under hydrogen (50 psi). TLC (Petroleum ether/Ethyl acetate=1/1) showed most of the starting material was consumed. The mixture was filtered and the filtrate was concentrated in vacuum to give tert-butyl 4-[2-(4-hydroxyphenoxy)-1-methyl-ethyl]piperazine-1-carboxylate (1 g, 2.97 mmol, 91% yield) as a yellow oil.

$^1$H NMR: (400 MHz, CDCl$_3$) δ: 8.78-8.73 (m, 4H), 4.00-3.96 (m, 1H), 3.84-3.80 (m, 1H), 3.44 (t, J=4.8 Hz, 4H), 3.03-2.99 (m, 1H), 2.64-2.58 (m, 4H), 1.46 (s, 9H), 1.17 (d, J=6.8 Hz, 3H).

Step 4: Preparation of tert-butyl 4-[2-[4-[2-(4-bromophenyl)-6-methoxy-1-oxido-benzothiophen-1-ium-3-yl]oxyphenoxy]-1-methyl-ethyl]piperazine-1-carboxylate

Step 4-1: Preparation of 3-Bromo-2-(4-bromophenyl)-6-methoxybenzo[b]thiophene To a solution of KOH (25 g 10 eq) in ethanol (1 L) at 15-25° C. was added 3-methoxybenzenethiol (54 g, 1.1 eq) and the mixture was stirred at 15-25° C. for 30 min. Then the mixture was cooled to 0° C. and ethyl acetate (700 mL) and 2-bromo-1-(4-bromophenyl)ethanone (80 g, 1.0 eq) were added subsequently at 0° C. The mixture was stirred at 0° C. for 30 min. The reaction mixture was warmed to rt and stirred for 4 h. Then the solvent was removed under reduced pressure. The residue was extracted with ethyl acetate (500 mL×2), washed with brine (300 mL), and dried over anhydrous Na$_2$SO$_4$. The solvent was removed under reduced pressure. The residue was recrystallized from CH$_3$OH (500 mL) to afford 1-(4-bromophenyl)-2-(3-methoxyphenylthio)ethanone as a yellow solid (100 g, 87%). $^1$HNMR (400 MHz, CDCl$_3$) δ: 7.80 (d, J=8.8 Hz, 2H), 7.61 (d, J=8.8 Hz, 2H), 7.20 (t, J=8.0 Hz, 1H), 6.95 (d, J=8.0 Hz, 1H), 6.91 (t, J=2.0 Hz, 1H), 6.77 (dd, J=8.0, 1.6 Hz, 1H), 4.23 (s, 2H), 3.78 (s, 3H).

To a stirring solution of PPA (1 L) at 80° C. (keep stirring as fast as possible) was added 1-(4-bromophenyl)-2-(3-methoxyphenylthio)ethanone (100 g, 1.0 eq) in portions within 40 min (control the temperature below 95° C.). Then the reaction was heated to 90° C. and stirred for 2 h. The solution was stirred at 130-135° C., for another 16 h. The mixture was cooled to 50-70° C. The reaction mixture was poured into ice water (1.5 L) and stirred for 1 h. The crude product was collected by filtration and the solid was washed with water, and recrystallized with EA to afford 2-(4-bromophenyl)-6-methoxybenzo[b]thiophene as a pale solid 51 g (yield: 52.6%). $^1$HNMR (400 MHz, DMSO) δ: 7.86 (s, 1H), 7.57-7.82 (m, 6H), 7.01-7.03 (m, 1H), 3.84 (s, 3H).

To a suspended mixture of 2-(4-bromophenyl)-6-methoxybenzo[b]thiophene (46 g, 1.0 eq) in dried DCM (1 L) was added N-bromosuccinimide (26 g, 1.02 eq) at 20° C. The reaction mixture was stirred at room temperature for 5h and then quenched by addition of water (500 mL). The mixture was extracted with DCM and the combined organic layers were dried over anhydrous sodium sulfate and the solution was concentrated under vacuum. The residue was recrystallized with EA to afford 3-bromo-2-(4-bromophenyl)-6-methoxybenzo[b]thiophene as a light purple solid (50.0 g, 88%). $^1$HNMR (400 MHz, DMSO) δ: 7.67-7.77 (m, 6H), 77.18 (d, J=7.2 Hz, 1H), 3.87 (s, 3H).

Step 4-2: Preparation of tert-butyl 4-[2-[4-[2-(4-bromophenyl)-6-methoxy-1-oxido-benzothiophen-1-ium-3-yl]oxyphenoxy]-1-methyl-ethyl]piperazine-1-carboxylate To a solution of 3-bromo-2-(4-bromophenyl)-6-methoxybenzothiophene (1.80 g, 4.52 mmol, 1.00 eq) in dichloromethane (18 mL) was drop-wise added trifluoroacetic acid (15 mL). Hydrogen peroxide (769 mg, 6.78 mmol, 0.65 mL, 30% aq. solution, 1.50 eq) was added. The mixture was stirred at 18° C. for 2 h. TLC (petroleum ether:ethyl acetate=3:1, R$_f$=0.24) showed the reaction was completed and a new spot formed. The reaction mixture was quenched by adding saturated sodium sulfite (5 mL) and the mixture was stirred at 18° C. for 10 min, then the mixture was adjusted to pH=(7~8) with saturated sodium bicarbonate (150 mL). The solution was extracted with dichloromethane (50 mL×3). The combined organic phase was washed with saturated brine (50 mL×2), dried with anhydrous sodium sulfate, filtered and concentrated in vacuum. The residue was purified by silica gel column chromatography (petroleum ether:ethyl acetate=10:1 to 1:1) to afford 3-bromo-2-(4-bromophenyl)-6-methoxy-1-oxido-benzothiophen-1-ium (1.10 g, 2.66 mmol, 59% yield) as a yellow solid. $^1$H NMR (400 MHz, CDCl$_3$) δ: 7.73-7.63 (m, 4H), 7.59 (d, J=8.4 Hz, 1H), 7.50 (d, J=2.4 Hz, 1H), 7.16 (dd, J=2.4, 8.4 Hz, 1H), 3.94 (s, 3H).

To a solution of tert-butyl 4-[2-(4-hydroxyphenoxy)-1-methyl-ethyl]piperazine-1-carboxylate (1.0 g, 2.97 mmol, 1.00 eq) in N,N-dimethylformamide (10 mL) was added sodium hydride (143 mg, 3.57 mmol, 60% in mineral oil, 1.20 eq) at 0° C. The mixture was stirred at 20° C. for 0.5 h. Then 3-bromo-2-(4-bromophenyl)-6-methoxy-1-oxido-benzothiophen-1-ium (1.23 g, 2.97 mmol, 1.00 eq) was added, the reaction mixture was stirred at 20° C. for 1 h. TLC (dichloromethane/methanol=20/1) showed most of the starting material was consumed. Saturated ammonium chloride (100 mL) was added to the mixture, the resulting mixture was extracted with ethyl acetate (50 mL×3). The combined organic phase was washed with brine (100 mL), dried over sodium sulfate, filtered and concentrated in vacuum to give tert-butyl 4-[2-[4-[2-(4-bromophenyl)-6-methoxy-1-oxido-benzothiophen-1-ium-3-yl]oxyphenoxy]-1-methyl-ethyl]piperazine-1-carboxylate (2 g, crude) as a yellow oil. LC/MS: MS (ESI) m/z: 668.8, 670.8 [M, M+2]$^+$.

Step 5: Preparation of tert-butyl 4-[2-[4-[2-(4-bromophenyl)-6-methoxy-benzothiophen-3-yl]oxyphenoxy]-1-methyl-ethyl]piperazine-1-carboxylate To a solution of tert-butyl 4-[2-[4-[2-(4-bromophenyl)-6-methoxy-1-oxido-benzothiophen-1-ium-3-yl]oxyphenoxy]-1-methyl-ethyl]piperazine-1-carboxylate (2 g, 2.54 mmol, 1.00 eq) in acetonitrile (20 mL) was added sodium iodide (1.14 g, 7.62 mmol, 3.00 eq) and trimethyl chlorosilane (552 mg, 5.08 mmol, 2.00 eq). The reaction mixture was stirred at 20° C. for 3 h. LC/MS showed most of the starting material was consumed. The reaction was quenched with saturated sodium thiosulfate (50 mL), the resulting mixture was extracted with ethyl acetate (30 mL×3). The combined organic phase was washed with brine (40 mL), dried over sodium sulfate, filtered and concentrated in vacuum. The residue was purified by silica gel chromatography (Petroleum ether/Ethyl acetate=30/1 to 0/1) to give tert-butyl 4-[2-[4-[2-(4-bromophenyl)-6-methoxy-benzothiophen-3-yl]oxyphenoxy]-1-methyl-ethyl]piperazine-1-carboxylate (1.5 g, 2.29 mmol, 90% yield) as a yellow solid. LC/MS: MS (ESI) m/z: 653.1, 655.1 [M, M+2]⁺. ¹H NMR: (400 MHz, CD₃Cl₃) δ: 7.64-7.61 (m, 2H), 7.30-7.26 (m, 3H), 6.90-6.88 (m, 3H), 6.80-6.78 (m, 2H), 3.99-3.95 (m, 1H), 3.88 (d, J=1.6 Hz, 3H), 3.82-3.79 (m, 1H), 3.42 (t, J=4.0 Hz, 4H), 3.02-2.97 (m, 1H), 2.63-2.58 (m, 4H), 1.46 (d, J=8.0 Hz, 9H), 1.15 (d, J=5.6 Hz, 3H).

Step 6: Preparation of 1-[2-[4-[2-(4-bromophenyl)-6-methoxy-benzothiophen-3-yl]oxyphenoxy]-1-methyl-ethyl]piperazine To a solution of tert-butyl 4-[2-[4-[2-(4-bromophenyl)-6-methoxy-benzothiophen-3-yl]oxyphenoxy]-1-methyl-ethyl]piperazine-1-carboxylate (800 mg, 1.22 mmol, 1.00 eq) in dichloromethane (5 mL) was added hydrochloric acid/dioxane (4M, 3 mL, 9.51 eq). The mixture was stirred at 20° C. for 1 hour. The reaction mixture was concentrated under reduced pressure to remove dichloromethane and dioxane to give 1-[2-[4-[2-(4-bromophenyl)-6-methoxy-benzothiophen-3-yl]oxyphenoxy]-1-methyl-ethyl]piperazine (700 mg, 1.19 mmol, 97% yield, hydrochloride) as a white solid. LCMS: MS (ESI) m/z: 555.0 [M+1]⁺.

Step 7: Preparation of methyl 2-(4-(1-(4-((2-(4-bromophenyl)-6-methoxybenzo[b]thiophen-3-yl)oxy)phenoxy)propan-2-yl)piperazin-1-yl)acetate To a solution of 1-[2-[4-[2-(4-bromophenyl)-6-methoxy-benzothiophen-3-yl]oxyphenoxy]-1-methyl-ethyl]piperazine (720 mg, 1.22 mmol, 1.00 eq, hydrochloride) in N,N-dimethylformamide (10 mL) was added potassium carbonate (506 mg, 3.66 mmol, 3.00 eq) and methyl 2-bromoacetate (224 mg, 1.46 mmol, 0.14 mL, 1.20 eq). The mixture was stirred at 20° C. for 16 hours. LC/MS showed the reaction was completed and the desired MS was detected. The reaction mixture was diluted with water (40 mL) and extracted with ethyl acetate (30 mL×3). The combined organic phase was washed with saturated brine (40 mL×2), dried with anhydrous sodium sulfate, filtered and concentrated in vacuum. The residue was purified by silica gel column chromatography (petroleum ether:ethyl acetate=6:1 to 1:1) to give methyl 2-{4-[1-(4-{[2-(4-bromophenyl)-6-methoxy-1-benzothiophen-3-yl]oxy}phenoxy)propan-2-yl]piperazin-1-yl}acetate (500 mg, 0.8 mmol, 66% yield) as a yellow oil. LCMS: MS (ESI) m/z: 627.1 [M+1]⁺;
¹H NMR (400 MHz, DMSO-d₆) δ: 7.65-7.58 (m, 2H), 7.49-7.45 (m, 2H), 7.30-7.23 (m, 2H), 6.91-6.83 (m, 3H), 6.81-6.74 (m, 2H), 4.03-3.94 (m, 1H), 3.87 (s, 3H), 3.85-3.76 (m, 1H), 3.74-3.71 (m, 3H), 3.22 (s, 2H), 3.05-2.98 (m, 1H), 2.82-2.59 (m, 8H), 2.05 (s, 1H), 1.21-1.16 (m, 3H).

Step 8: Preparation of 2-(4-(1-(4-((2-(4-bromophenyl)-6-hydroxybenzo[b]thiophen-3-yl)oxy)phenoxy)propan-2-yl)piperazin-1-yl)acetic acid To a solution of methyl 2-{4-[1-(4-{[2-(4-bromophenyl)-6-methoxy-1-benzothiophen-3-yl]oxy}phenoxy)propan-2-yl]piperazin-1-yl}acetate (500 mg, 0.8 mmol, 1.00 eq) in dichloromethane (10 mL) was added boron tribromide (600 mg, 2.40 mmol, 0.23 mL, 3.00 eq) at −70° C. The mixture was stirred at 20° C. for 16 hours. LC/MS showed the reaction was completed and the desired product was formed. The reaction mixture was quenched with methanol (10 mL) at 0° C. and concentrated under reduced pressure to remove methanol and dichloromethane to give 2-(4-(1-(4-((2-(4-bromophenyl)-6-hydroxybenzo[b]thiophen-3-yl)oxy)phenoxy)propan-2-yl)piperazin-1-yl)acetic acid (380 mg, crude) as a yellow oil, which was directly used for next step without further purification. LCMS: MS (ESI) m/z: 599.0 [M+1]⁺.

Step 9: Preparation of methyl 2-{4-[(2R)-1-(4-{[2-(4-bromophenyl)-6-hydroxy-1-benzothiophen-3-yl]oxy}phenoxy)propan-2-yl]piperazin-1-yl}acetate To a solution of 2-{4-[1-(4-{[2-(4-bromophenyl)-6-methoxy-1-benzothiophen-3-yl]oxy}phenoxy)propan-2-yl]piperazin-1-yl}acetic acid (380 mg, 0.64 mmol, 1.00 eq) in methanol (10 mL) was added sulfuric acid (184 mg, 1.88 mmol, 0.1 mL, 2.95 eq). The mixture was stirred at 70° C. for 12 hours. LC/MS showed the reaction was completed and the desired product was formed. The reaction mixture was adjusted to pH=(8-9) with sodium bicarbonate (2M, 4 mL), and diluted with water (30 mL) and extracted with ethyl acetate (20 mL×2). The combined organic phase was washed with saturated brine (20 mL×2), dried with anhydrous sodium sulfate, filtered and concentrated in vacuum. The residue was purified by prep-TLC (Dichloromethane: Methanol=10:1) to give desired compound (200 mg, yiled 51%, purity 92%) as a white solid, which was further separated by chiral SFC (AD column, 250 mm×30 mm, 10 jpm, 0.1% NH₃.H₂O in IPA) to give methyl 2-{4-[(2R)-1-(4-{[2-(4-bromophenyl)-6-hydroxy-1-benzothiophen-3-yl]oxy}phenoxy)propan-2-yl]piperazin-1-yl}acetate (90 mg, 0.15 mmol, 23% yield) as a yellow oil and methyl 2-{4-[(2S)-1-(4-{[2-(4-bromophenyl)-6-hydroxy-1-benzothiophen-3-yl]oxy}phenoxy)propan-2-yl]piperazin-1-yl}acetate (90 mg, 0.15 mmol, 23% yield) as a yellow oil. LCMS: MS (ESI) m/z: 613.0 [M+1]⁺.

Step 10: Preparation of 2-{4-[(2R)-1-(4-{[2-(4-bromophenyl)-6-hydroxy-1-benzothiophen-3-yl]oxy}phenoxy)propan-2-yl]piperazin-1-yl acetic acid To a solution of methyl 2-{4-[(2R)-1-(4-{[2-(4-bromophenyl)-6-hydroxy-1-benzothiophen-3-yl]oxy}phenoxy)propan-2-yl]piperazin-1-yl}acetate (90 mg, 0.15 mmol, 1.00 eq) in tetrahydrofuran (1 mL) and methanol (2 mL) was added lithium hydroxide monohydrate (2M, 0.5 mL, 6.79 eq). The mixture was stirred at 20° C. for 2 hours. The reaction mixture was quenched with hydrochloric acid (2M, 0.6 mL). The mixture was concentrated under reduced pressure to remove methanol, tetrahydrofuran and water to give 2-{4-[(2R)-1-(4-{[2-(4-bromophenyl)-6-hydroxy-1-benzothiophen-3-yl]oxy}phenoxy)propan-2-yl]piperazin-1-yl}acetic acid (95 mg, crude) as a white solid, which was directly used for next step without further purification. LCMS: MS (ESI) m/z: 598.9 [M+1]⁺.

Step 11: Preparation of 2-{4-[(2R)-1-(4-{[2-(4-bromophenyl)-6-hydroxy-1-benzothiophen-3-yl]oxy}phenoxy)propan-2-yl]piperazin-1-yl}-N-{[2-(2,6-dioxopiperidin-3-yl)-1-oxo-2,3-dihydro-1H-isoindol-5-yl]methyl}acetamide To a solution of 2-{4-[(2R)-1-(4-{[2-(4-bromophenyl)-6-hydroxy-1-benzothiophen-3-yl]oxy}phenoxy)propan-2-yl]piperazin-1-yl}acetic acid (85 mg, 0.14 mmol, 1.00 eq) and 3-[5-(aminomethyl)-1-oxo-isoindolin-2-yl]piperidine-2,6-dione (64 mg, 0.14 mmol, 1.00 eq) in N,N-dimethylformamide (3 mL) was added O-(7-azabenzotriazol-1-yl)-N,N,N',N'-tetramethyluronium hexafluorophosphate (65 mg, 0.17 mmol, 1.20 eq) and diisopropylethylamine (92 mg, 0.7 mmol, 0.1 mL, 5.00 eq). The mixture was stirred at 20° C. for 12 h. LC/MS showed the reaction was completed and the desired product was formed. The reaction mixture was purified by prep-HPLC (column: Boston Green ODS 150 mm×30 mm, 5 μm; mobile phase: water with 0.225% TFA as solvent A and acetonitrile as solvent B; gradient: 27% B-57% B in 10 min). Then the collected fraction was concentrated to remove most of acetonitrile and hydrochloric acid (1M, 2 mL) was added. The solution was lyophilized to give 2-{4-[(2R)-1-(4-{[2-(4-bromophenyl)-6-hydroxy-1-benzothiophen-3-yl]oxy}phenoxy)propan-2-yl]piperazin-1-yl}-N-{[2-(2,6-dioxopiperidin-3-yl)-1-oxo-2,3-dihydro-1H-isoindol-5-yl]methyl}acetamide (54 mg, 0.06 mmol, 43% yield, 98% purity, hydrochloride) as a yellow solid. LCMS: MS (ESI) m/z: 852.2 and 854.2 [M+1]$^+$; $^1$H NMR (400 MHz, DMSO-d$_6$) δ: 10.99 (s, 1H), 9.98 (s, 1H), 9.14-8.78 (m, 1H), 7.69 (d, J=8.0 Hz, 1H), 7.61 (s, 4H), 7.51 (s, 1H), 7.43 (d, J=8.0 Hz, 1H), 7.33 (d, J=2.0 Hz, 1H), 7.14 (d, J=8.8 Hz, 1H), 6.99-6.89 (m, 4H), 6.84 (dd, J=2.0, 8.8 Hz, 1H), 5.11 (dd, J=5.2, 13.2 Hz, 1H), 4.56-4.11 (m, 7H), 4.02-3.53 (m, 10H), 2.96-2.87 (m, 1H), 2.65-2.55 (m, 1H), 2.43-2.35 (m, 1H), 2.05-1.95 (m, 1H), 1.53 (br d, J=6.4 Hz, 1H), 1.38 (s, 2H).

Preparation of 5-{4-[5-(4-{[2-(4-bromophenyl)-6-hydroxy-1-benzothiophen-3-yl]oxy}phenoxy)pentyl]piperazin-1-yl}-2-(2,6-dioxopiperidin-3-yl)-2,3-dihydro-1H-isoindole-1,3-dione (Compound 61)

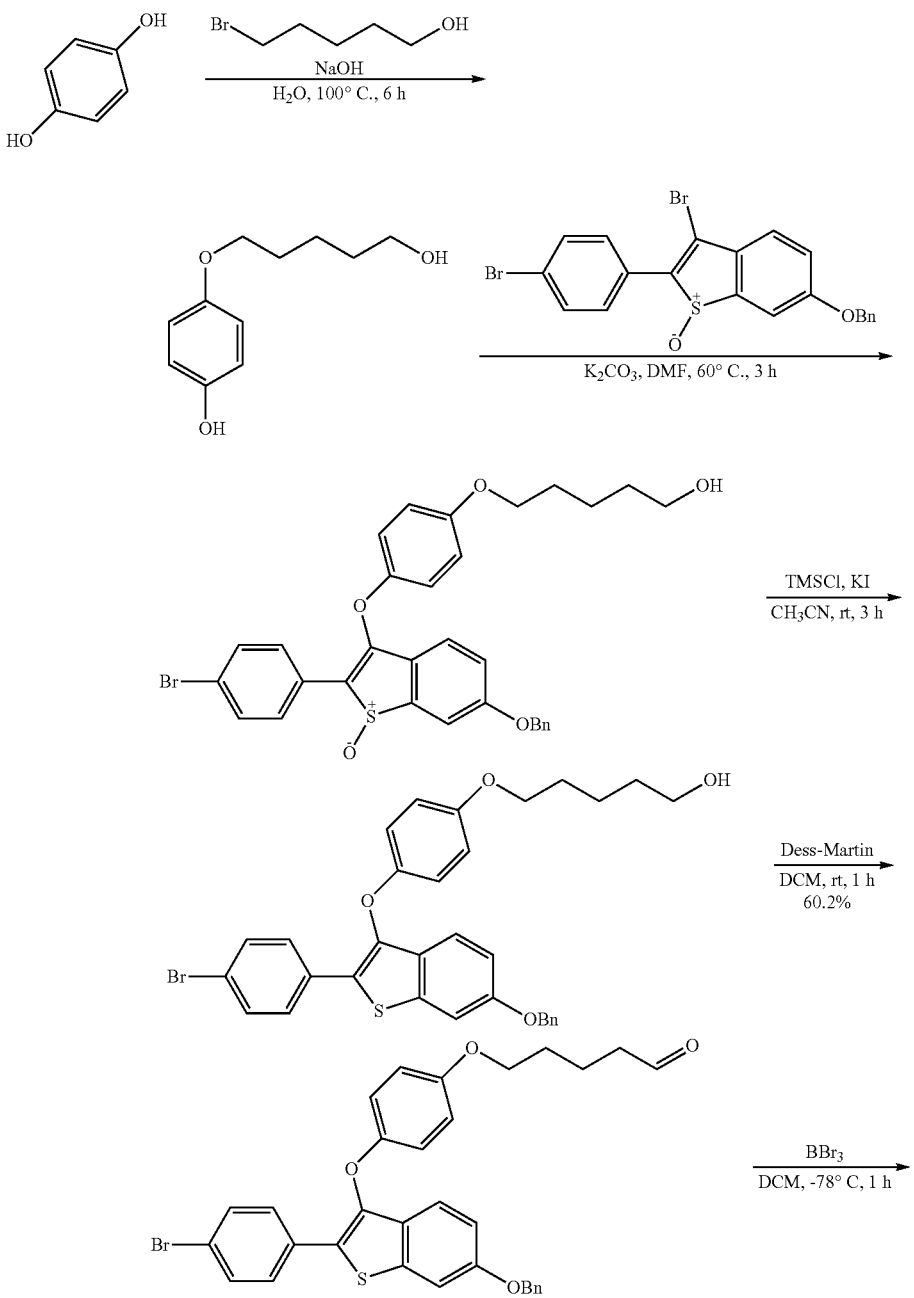

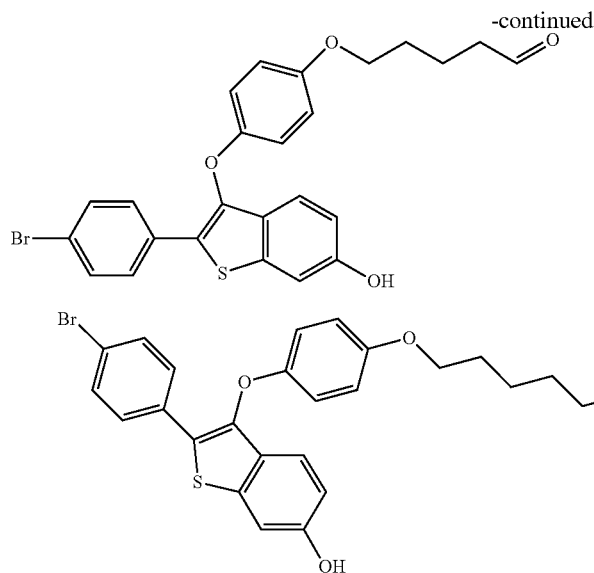

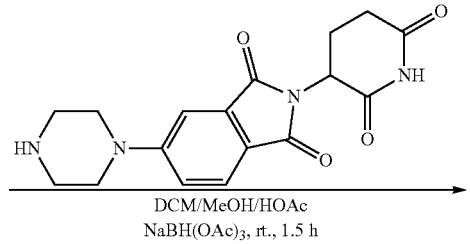

Step 1: Preparation of 4-(5-hydroxypentyloxy)phenol

To a solution of 4-hydroxyphenol (3.0 g, 27.3 mmol) in water (30 mL) was added sodium hydroxide (1.45 g, 36.4 mmol) and 5-bromopentan-1-ol (4.5 g, 27.3 mmol). The mixture was heated to 100° C. for 6 h under $N_2$ gas. After cooling to rt, hydrochloric acid (1.0M) was added to adjust pH to 1.0. The mixture was extracted with ethyl acetate (50 mL×3). The organic layer was washed with brine (50 mL). The combined organic phases were dried over anhydrous sodium sulfate, filtered, and concentrated in vacuo and purified by silica gel (petroether/ethyl acetate=3:1) to provide 4-(5-hydroxypentyloxy)phenol (1.5 g, 48.7%) as a white solid.

$^1$H NMR (400 MHz, CDCl$_3$) δ 1.51-1.54 (2H, m), 1.61-1.66 (2H, m), 1.76-1.83 (2H, m), 3.68 (2H, t, J=6.6 Hz), 3.91 (2H, t, J=6.4 Hz), 4.61 (1H, s), 6.73-6.79 (4H, m).

Step 2: Preparation of 6-(benzyloxy)-2-(4-bromophenyl)-3-{4-[(5-hydroxypentyl)oxy]phenoxy}-1H-1-benzothiophen-1-ium-1-olate To a solution of 4-(5-hydroxypentyloxy)phenol (100 mg, 0.5 mmol) in DMF (5 mL) was added 6-(benzyloxy)-3-bromo-2-(4-bromophenyl)-1H-1-benzothiophen-1-ium-1-olate (400 mg, 0.82 mmol) and potassium carbonate (170 mg, 1.23 mmol). The mixture was heated to 60° C. for 3 h under $N_2$ gas. After cooling to rt, the reaction mixture was diluted with water (10 mL), and the mixture was extracted with ethyl acetate (10 mL×3). The organic layer was washed with brine (10 mL×3). The combined organic phases were dried over anhydrous sodium sulfate, filtered, and concentrated in vacuo to give 6-(benzyloxy)-2-(4-bromophenyl)-3-{4-[(5-hydroxypentyl)oxy]phenoxy}-1H-1-benzothiophen-1-ium-1-olate (200 mg, 64.9%) as yellow oil, which was used to next step without further purification.

Step 3: Preparation of 5-(4-{[6-(benzyloxy)-2-(4-bromophenyl)-1-benzothiophen-3-yl]oxy}phenoxy)pentan-1-ol To a solution of 6-(benzyloxy)-2-(4-bromophenyl)-3-{4-[(5-hydroxypentyl)oxy]phenoxy}-1H-1-benzothiophen-1-ium-1-olate (200 mg, 0.33 mmol) in acetonitrile (10 mL) was added chlorotrimethylsilane (30 mg, 0.3 mmol) and potassium iodide (50 mg, 0.3 mmol). The reaction mixture was stirred at room temperature for 2 h. The mixture was treated with water (10.0 mL) and then extracted with dichloromethane (10.0 mL×2). The combined organic layer was washed with brine (20 mL), dried over anhydrous sodium sulfate, filtered and concentrated in vacuo and purified by preparative TLC to give 5-(4-(6-(benzyloxy)-2-(4-bromophenyl)benzo[b]thiophen-3-yloxy)phenoxy)pentan-1-ol (140 mg, 71.8%) as a yellow solid.

Step 4: Preparation of 5-(4-(6-(benzyloxy)-2-(4-bromophenyl)benzo[b]thiophen-3-yloxy)phenoxy)pentanal To a solution of 5-(4-(6-(benzyloxy)-2-(4-bromophenyl)benzo[b]thiophen-3-yloxy)phenoxy)pentan-1-ol (200 mg, 0.34 mmol) in dichloromethane (20 mL) was added Dess-Martin periodinane (0.44 g, 1.02 mmol). The mixture was stirred at room temperature for 1 h. The mixture was diluted with water (20.0 mL) and extracted with dichloromethane (20.0 mL×2). The combined organic layer was washed with brine (20 mL), dried over anhydrous sodium sulfate, filtered and concentrated in vacuo and purified by pre parative TLC to give 5-(4-(6-(benzyloxy)-2-(4-bromophenyl)benzo[b]thiophen-3-yloxy)phenoxy)pentanal (120 mg, 60.2%) as a yellow solid.

Step 5: Preparation of 5-(4-(2-(4-bromophenyl)-6-hydroxybenzo[b]thiophen-3-yloxy)phenoxy)pentanal To a solution of 5-(4-(6-(benzyloxy)-2-(4-bromophenyl)benzo[b]thiophen-3-yloxy)phenoxy)pentanal (150 mg, 0.2 mmol) in dichloromethane (20 mL) was added boron tribromide (0.30 mL, 1.0M) at −78° C. and stirred for 30 min at this temperature. The reaction mixture was diluted with water (10 mL) and sodium bicarbonate (5 mL), and then extracted with EtOAc (10 mL×3). The organic layer was washed with brine (20 mL). The combined organic phases were dried over anhydrous sodium sulfate, filtered, and concentrated in vacuo. The residue was purified by pre-TLC (petroleum ether/ethyl acetate=3:1) to provide 5-(4-(2-(4- bromophenyl)-6-hydroxybenzo[b]thiophen-3-yloxy)phenoxy)pentanal (62 mg, 61.1%) as a white solid.

Step 6: Preparation of 5-{4-[5-(4-{[2-(4-bromophenyl)-6-hydroxy-1-benzothiophen-3-yl]oxy}phenoxy)pentyl]piperazin-1-yl}-2-(2,6-dioxopiperidin-3-yl)-2,3-dihydro-1H-isoindole-1,3-dione To a solution of 5-(4-(2-(4-bromophenyl)-6-hydroxybenzo[b]thiophen-3-yloxy)phenoxy)pentanal (62 mg, 0.125 mmol) in dry DCM/MeOH/HOAc (2 mL/2 mL/0.1 mL) was added 2-(2,6-dioxopiperidin-3-yl)-5-(piperazin-1-yl)isoindoline-1,3-dione (43 mg, 0.125 mmol). The mixture was left to stir for 30 min under $N_2$ gas. Then sodium triacetoxyborohydride (79.5 mg, 0.375 mmol) was added and the reaction mixture was left to stir overnight. The solvent was removed and the residue was partitioned between dichloromethane and water. The organic layer was washed with brine, dried over anhydrous sodium sulfate, filtered, and concentrated in vacuo to give a crude product. The residue was purified by pre-HPLC to afford 5-{4-[5-(4-{[2-(4-bromophenyl)-6-hydroxy-1-benzothiophen-3-yl]oxy}phenoxy)pentyl]piperazin-1-yl}-2-(2,6-dioxopiperidin-3-yl)-2,3-dihydro-1H-isoindole-1,3-dione (35 mg, 33.5%) as a yellow solid.

LC-MS: MS (ESI) m/z 823.2, 825.1 [M+H]+; $^1$H NMR (400 MHz, DMSO-$d_6$) δ 1.40-1.54 (4H, m), 1.66-1.73 (2H, m), 1.99-2.02 (1H, m), 2.31 (2H, t, J=7.4 Hz), 2.47-2.51 (5H, m), 2.53-2.60 (1H, m), 2.83-2.93 (1H, m), 3.36-3.41 (4H, m), 3.88 (2H, t, J=6.2 Hz), 5.07 (1H, dd, J=5.2, 12.8 Hz), 6.82 (1H, dd, J=2.0, 8.4 Hz), 6.86 (4H, s), 7.15 (1H, d, J=8.8 Hz), 7.24 (1H, dd, J=2.0, 8.4 Hz), 7.32 (2H, dd, J=1.6, 9.6 Hz), 7.62 (4H, s), 7.67 (1H, d, J=8.8 Hz), 9.92 (1H, s), 11.08 (1H, s).

PREPARATION OF INTERMEDIATES

Intermediate 1: (2S,4R)-1-[(2S)-2-amino-3,3-dimethylbutanoyl]-4-hydroxy-N-[(1S)-1-[4-(4-methyl-1,3-thiazol-5-yl)phenyl]ethyl]pyrrolidine-2-carboxamide hydrochloride

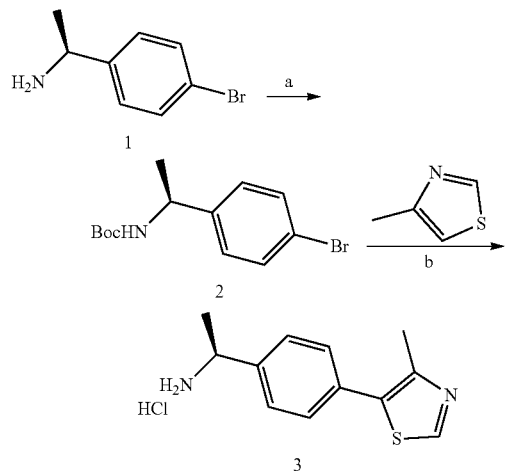

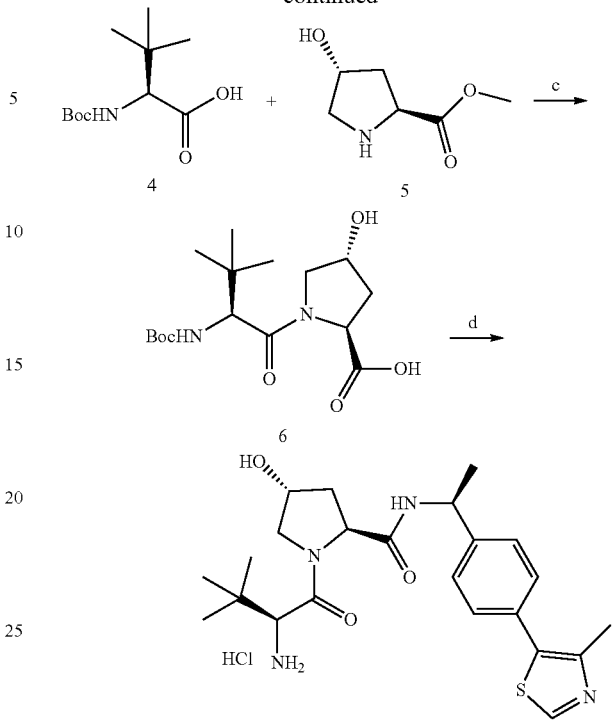

Reagents and Conditions: (a) (Boc)$_2$O, NaHCO$_3$, EtOAc/H$_2$O; (b) (1) Pd(OAc)$_2$, KOAc, 90° C.; (2) 4N HCl in MeOH; (c) (1) HATU, DIPEA, DMF; (2) LiOH, THF, H$_2$O; (d) (1) intermediate compound 3, HATU, DIPEA, THF; (2) 4N HCl in MeOH Step 1: Preparation of (S)-tert-butyl-1-(4-bromophenyl)-ethyl carbamate (2)

To a mixture of (S)-1-(4-bromophenyl)ethanamine (3.98 g, 19.9 mmol) and NaHCO$_3$ (1.24 g, 14.8 mmol) in H$_2$O (10 mL) and ethyl acetate (10 mL) was added (Boc)$_2$O (5.20 g, 23.8 mmol) at 5° C. The reaction was continued to react for 2 hours. TLC showed the reaction was complete. The reaction mixture was filtered. The solid was collected and suspended in a mixture of hexane (10 mL) and H$_2$O (10 mL) for 0.5 h. The mixture was filtered and the solid was collected and dried in oven at 50° C. to afford the title compound as white solid (5.9 g, 98.7%). $^1$HNMR (400 MHz, DMSO-$d_6$): δ 1.28 (d, J=7.2 Hz, 3H), 1.36 (s, 9H), 4.55-4.60 (m, 1H), 7.25 (d, J=8.4 Hz, 2H), 7.39 (br, 1H), 7.49 (d, J=8.4 Hz, 2H).

Step 2: Preparation of (S)-1-(4-(4-methylthiazol-5-yl)phenyl)ethanamine hydrochloride (3)

A mixture of intermediate compound 2 (4.0 g, 13.3 mmol), 4-methylthiazole (2.64 g, 26.6 mmol), palladium (II) acetate (29.6 mg, 0.13 mmol) and potassium acetate (2.61 g, 26.6 mmol) in N,N-dimethylacetamide (10 mL) was stirred at 90° C. under N$_2$ for 18 h. After cooling to ambient temperature, the reaction mixture was filtered. To the filtrate was added H$_2$O (50 mL) and the resulting mixture was stirred at ambient temperature for 4 h. The reaction mixture was filtered. The solid was collected by filtration and dried in oven at 50° C. to afford (S)-tert-butyl 1-(4-(4-methylthiazol-5-yl)phenyl)ethylcarbamate (3.48 g, 82.3%) as gray solid. $^1$HNMR (400 MHz, DMSO-d$_6$): δ 1.33 (d, J=7.2 Hz, 3H), 1.38 (s, 9H), 2.46 (s, 3H), 4.64-4.68 (m, 1H), 7.23 (br d, 0.5H), 7.39 (d, J=8 Hz, 2H), 7.44 (d, J=8.4 Hz, 2H), 7.50 (br d, 0.5H), 8.99 (s, 1H); LC-MS [M+1]$^+$: 319.5

This solid material (1.9 g, 6.0 mmol) was dissolved in 4N hydrochloride in methanol (5 mL, 20 mmol, prepared from acetyl chloride and methanol) and the mixture was stirred at ambient temperature for 3 h. the mixture was filtered and the solid was collected and dried in oven at 60° C. to afford (S)-1-(4-(4-methylthiazol-5-yl)phenyl)ethanamine hydrochloride (1.3 g, 85%) as a light green solid. $^1$HNMR (400 MHz, DMSO-d6): δ 1.56 (d, J=6.8 Hz, 3H), 2.48 (s, 3H), 4.41-4.47 (m, 1H), 7.57 (d, J=8.4 Hz, 2H), 7.67 (d, J=8.4 Hz), 8.75 (s, 3H), 9.17 (s, 1H); LC-MS [M+1]$^+$: 219.2

Step 3: Preparation of (2S, 4R)-1-{(S)-2-[(tert-butoxycarbonyl)amino]-3,3-dimethylbutanoyl}-4-hydroxypyrrolidine-2-carboxylic acid (6)

HATU (2.15 g, 5.7 mmol) was added to a solution of (S)-2-(tert-butoxycarbonyl)amino-3,3-dimethylbutanoic acid (1.25 g, 5.4 mol), (2S,4R)-methyl 4-hydroxypyrrolidine-2-carboxylate hydrochloride (0.98 g, 5.4 mmol) and DIPEA (2.43 g, 18.9 mmol) in DMF (10 mL) at 0° C. under nitrogen. The mixture was stirred at ambient temperature for 18 hours. TLC showed the reaction complete. The reaction mixture was quenched with water (30 mL) and extracted with ethyl acetate (15 mL×4). The combined organic layer was washed with the 5% citric acid (10 mL×2), saturated NaHCO$_3$ solution (10 mL×2), brine (10 mL×2) and dried over Na$_2$SO$_4$. The organic solution was filtered and concentrated to afford (2S, 4R)-methyl 1-{(S)-2-[(tert-butoxycarbonyl)amino]-3,3-dimethylbutanoyl}-4-hydroxypyrrolidine-2-carboxylate as pale yellow oil (1.93 g, 100% yield). This crude product (1.93 g) and lithium hydroxide hydrate (2.2 g, 54 mmol) were taken into THF (20 mL) and H$_2$O (10 mL). The resulting mixture was stirred at ambient temperature for 18 h. THF was removed by concentration. The residue was diluted with ice-water (10 mL) and slowly adjusted to pH 2-3 with 3N HCl. The resulting suspension was filtered, washed with H$_2$O (6 mL×2). The solid was collected by filtration and dried in oven at 50° C. to afford the title compound as a white solid (1.4 g, 75% for two steps). $^1$HNMR (400 MHz, DMSO-d$_6$): δ 6.50 (d, J=9.6 Hz, 1H), 5.19 (br s, 1H), 4.32 (br s, 1H), 4.25 (t, J=8.4 Hz, 1H), 4.16 (d, J=9.2 Hz, 1H), 3.57-3.66 (m, 2H), 2.08-2.13 (m, 1H), 1.85-1.91 (m, 1H), 1.38 (s, 9H), 0.94 (s, 9H).

Step 4: Preparation of (2S,4R)-1-[(2S)-2-amino-3,3-dimethylbutanoyl]-4-hydroxy-N-[(1S)-1-[4-(4-methyl-1,3-thiazol-5-yl)phenyl]ethyl]pyrrolidine-2-carboxamide hydrochloride (7)

HATU (1.6 g, 4.2 mmol) was added to a stirred solution of intermediate compound 6 (1.21 g, 3.5 mmol), intermediate compound 3 (0.9 g, 3.5 mmol), and DIPEA (1.36 g, 10.5 mmol) in anhydrous THF (15 mL) at 0° C. The resulting mixture was allowed to warm up to ambient temperature and continued to stir for 2 hours. TLC showed reaction complete. THF was removed by concentration. To the residue was added water (15 mL) and the resulting mixture was stirred for 4 hours. The resulting mixture was filtered. The solid was collected and dried in oven at 50° C. to give a white solid. This solid was taken into methanol (10 mL) and activated carbon (150 mg) was added. The resulting mixture was heated at 80° C. and stirred for 1 hour. The mixture was filtered while it was hot. Water (5 mL) was added to the filtrate at 80° C. The resulting mixture was cooled to ambient temperature and continued to stir for 18 hours. The suspension was filtered. The solid was collected and dried in oven at 50° C. to afford tert-butyl-{(S)-1-[(2S, 4R)-4-hydroxy]-2-[(S)-1-(4-(4-methylthiazol-5-yl)phenyl)ethylcarbamoyl]pyrrolidin-1-yl}-3,3-dimethyl-1-oxobutan-2-yl-carbamate (1.41 g, 74.2%) as white solid. $^1$H NMR (400 MHz, CDCl$_3$): δ 1.05 (s, 9H), 1.42 (s, 9H), 1.47 (d, J=7.2 Hz, 3H), 2.04-2.10 (m, 1H), 2.53 (s, 3H), 2.58-2.64 (m, 1H), 3.23 (s, 1H), 3.58 (dd, J=11.2 Hz, 3.2 Hz, 1H), 4.11 (d, J=11.6 Hz, 1H), 4.22 (d, J=9.2 Hz, 1H), 4.51 (br, 1H), 4.79 (t, J=8.0 Hz, 1H), 5.04-5.11 (m, 1H), 5.22 (d, J=8.8 Hz, 1H), 7.36-7.42 (m, 4H), 7.61 (d, J=7.6 Hz 1H), 8.68 (s, 1H).

This solid (1.04 g, 1.9 mmol) was dissolved in 4N hydrogen chloride in methanol (3.0 mL) and the mixture was stirred at ambient temperature for 3 hours. TLC showed reaction complete. The reaction mixture was concentrated to remove all volatiles under reduced pressure to give a light yellow solid. The solid was added to TBME (5 mL) and the resulting mixture was stirred at ambient temperature for 4 h. The reaction mixture was filtered and the solid was collected and dried in oven at 50° C. to afford intermediate compound 7 (0.92 g, 100%). $^1$H NMR (400 MHz, DMSO-d6): δ 1.03 (s, 9H), 1.38 (d, J=7.2 Hz, 3H), 1.72-1.79 (m, 1H), 2.09-2.14 (m, 1H), 2.49 (s, 3H), 3.48-3.52 (m, 1H), 3.75-3.79 (m, 1H), 3.88-3.90 (m, 1H), 4.31 (br, 1H), 4.56 (t, J=8.4 Hz, 1H), 4.89-4.95 (m, 1H), 7.41 (d, J=8.4 Hz, 2H), 7.47 (d, J=8.4 Hz, 2H), 8.20 (br, 3H), 8.67 (d, J=7.6 Hz, 1H), 9.22 (s, 1H); $^{13}$C NMR (400 MHz, DMSO-d6): δ 170.7, 167.1, 153.0, 146.5, 145.7, 132.5, 129.4, 129.3, 126.9, 69.4, 59.3, 58.5, 56.9, 48.3, 38.4, 34.8, 26.6, 23.0, 15.7; LC-MS [M+1]$^+$: 445.6

Intermediate 2: (2S,4R)-1-[(2S)-2-amino-3,3-dimethylbutanoyl]-4-hydroxy-N-{[4-(4-methyl-1,3-thiazol-5-yl)phenyl]methyl}pyrrolidine-2-carboxamide hydrochloride

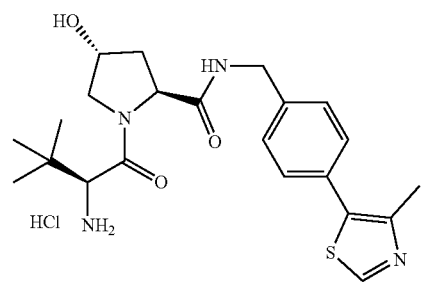 [SMILES: Cc1ncsc1-c1ccc(CNC(=O)[C@@H]2C[C@@H](O)CN2C(=O)[C@@H](N)C(C)(C)C)cc1 ; Cl]

Intermediate 2 was prepared using exactly the same method as described in the preparation of Intermediate 1.

Intermediate 3: (2S,4R)-4-hydroxy-1-(2-(3-hydroxyisoxazol-5-yl)-3-methylbutanoyl)-N-(4-(4-methylthiazol-5-yl)benzyl)pyrrolidine-2-carboxamide

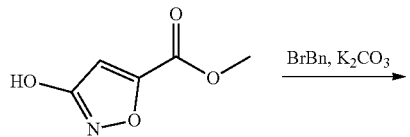

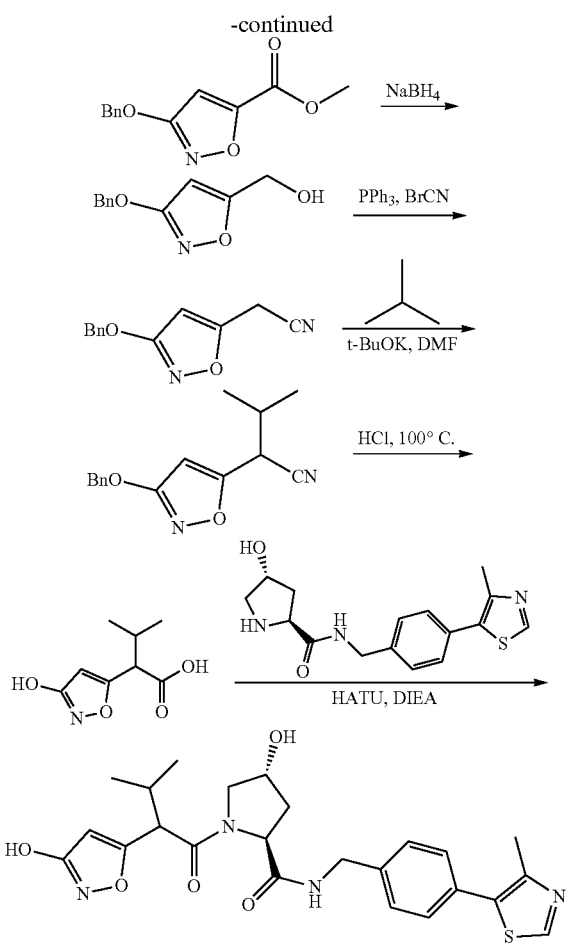

Step 1: Preparation of methyl 3-(benzyloxy) isoxazole-5-carboxylate

To a solution of methyl 3-hydroxyisoxazole-5-carboxylate (7.20 g, 50.31 mmol, 1.00 eq) in acetone (150 mL) was added potassium carbonate (13.91 g, 100.62 mmol, 2.00 eq). The mixture was heated to 80° C. for 1 hr, then (bromomethyl) benzene (10.33 g, 60.37 mmol, 1.20 eq) was added. The resulting mixture was stirred at 80° C. for another 3 hr. LC/MS showed the reaction was completed. The solid was filtered off and the filtrated was concentrated under vacuum. The residue was further purified by silica gel column chromatography (petroleum ether: Ethyl acetate=15:1 to 10:1) to afford methyl 3-benzyloxyisoxazole-5-carboxylate (9.50 g, 40.73 mmol, 81% yield) as a colorless oil. The oil was solidified after standing at 15° C. for 15 hr. LC-MS (ESI) m/z: 256.0 [M+Na$^+$]; $^1$H NMR (400 MHz, CDCl3) δ 7.49-7.41 (m, 5H), 6.60 (s, 1H), 5.34 (s, 2H), 3.97 (s, 3H).

Step 2: Preparation of (3-(benzyloxy)isoxazol-5-yl)methanol

To a solution of methyl 3-benzyloxyisoxazole-5-carboxylate (2.33 g, 9.99 mmol, 1.00 eq) in methanol (50 mL) was added sodium borohydride (756 mg, 19.98 mmol, 2.00 eq) in portions. The resulting mixture was stirred at 15° C. for 3 hr. TLC (petroleum ether:ethyl acetate=5:1) showed the reaction was completed. The mixture was poured into hydrochloric acid (0.2 M, 200 mL), and extracted with ethyl acetate (150 mL×2). The combined organic layers were washed with saturated brine (200 mL×2), dried over anhydrous sodium sulfate, filtered and concentrated in vacuum to afford (3-benzyloxyisoxazol-5-yl)methanol (1.85 g, 9.02 mmol, 90% yield) as colorless oil. LC-MS (ESI) m/z: 206.1 [M+H$^+$].

Step 3: Preparation of 2-(3-(benzyloxy) isoxazol-5-yl)acetonitrile

To a solution of cyanic bromide (334 mg, 3.15 mmol, 1.05 eq) and triphenylphosphine (787 mg, 3.00 mmol, 1.00 eq) in dichloromethane (10 mL) was added a solution of (3-benzyloxyisoxazol-5-yl)methanol (616 mg, 3.00 mmol, 1.00 eq) in dichloromethane (10 mL). The mixture was stirred at 15° C. for 1 hour, then 2,3,4,6,7,8,9,10-octahydropyrimido [1,2-a]azepine (480 mg, 3.15 mmol, 1.05 eq) was added at 0° C. The resulting mixture was stirred at 0° C. for another 14 hr. LC-MS showed the reaction was completed. The solvent was concentrated under vacuum. The residue was further purified by silica gel column chromatography (petroleum ether:ethyl acetate=5:1 to 4:1) to afford 2-(3-benzyloxyisoxazol-5-yl)acetonitrile (320 mg, 1.49 mmol, 50% yield) as a colorless oil. LC-MS (ESI) m/z: 215.0 [M+H$^+$]; $^1$H NMR (400 MHz, CDCl$_3$) δ 7.48-7.41 (m, 5H), 6.06 (s, 1H), 5.30 (s, 2H), 3.82 (s, 2H).

Step 4: Preparation of 2-(3-(benzyloxy)isoxazol-5-yl)-3-methylbutane nitrile To a solution of 2-(3-benzyloxyisoxazol-5-yl)acetonitrile (214 mg, 1.00 mmol, 1.00 eq) in N,N-dimethylformamide (3 mL) was added potassium carbonate (138 mg, 1.00 mmol, 1.00 eq). The mixture was stirred at 15° C. for half an hour, then 2-iodopropane (170 mg, 1.00 mmol, 1.00 eq) was added. The resulting mixture was stirred at 15° C. for another 2.5 hr. LC-MS showed no reaction. Then potassium 2-methylpropan-2-olate (90 mg, 0.8 mmol, 0.80 eq) was added to the mixture, the mixture was stirred at 15° C. for another 12 hr. TLC (petroleum ether: ethyl acetate=3:1) showed the reaction was almost complete. The mixture was poured into hydrochloric acid (0.2M, 30 mL), extracted with ethyl acetate (30 mL×2). The combined organic layers were dried over anhydrous sodium sulfate, filtered and concentrated under vacuum. The residue was purified by silica gel column chromatography (petroleum ether:ethyl acetate=10:1 to 8:1) to afford 2-(3-benzyloxyisoxazol-5-yl)-3-methyl-butanenitrile (150 mg, 0.56 mmol, 59% yield) as a colorless oil. $^1$H NMR (400 MHz, CDCl$_3$) δ 7.48-7.41 (m, 5H), 6.04 (s, 1H), 5.28 (s, 2H), 3.85 (d, J=5.6 Hz, 1H), 2.42-2.37 (m, 1H), 1.18 (d, J=6.8 Hz, 3H), 1.10 (d, J=6.8 Hz, 3H).

Step 5: Preparation of 2-(3-hydroxyisoxazol-5-yl)-3-methylbutanoic acid

To a solution of 2-(3-benzyloxyisoxazol-5-yl)-3-methyl-butanenitrile (3.40 g, 13.27 mmol, 1.00 eq) in dioxane (30 mL) was added hydrochloric acid (11.8M, 120 mL). The mixture was heated to 100° C. and stirred at 100° C. for 15 hr. LC/MS showed the reaction was complete. The mixture was cooled to 15° C., and extracted with ethyl acetate (150 mL×3). The combined organic layers were dried over anhydrous sodium sulfate, filtered and concentrated under vacuum. The crude product was further purified by preparative HPLC (column: Daiso 150×25 mm, 5 micron; mobile phase: [water (0.225% TFA)-ACN] to afford 2-(3-hydroxy-isoxazol-5-yl)-3-methyl-butanoic acid (230 mg, 1.19 mmol, 9% yield) as a yellow solid. LC-MS (ESI) m/z: 186.1 [M+H$^+$].

Step 6: Preparation of (2S,4R)-4-hydroxy-1-(2-(3-hydroxyisoxazol-5-yl)-3-methylbutanoyl)-N-(4-(4-methylthiazol-5-yl)benzyl)pyrrolidine-2-carboxamide To a solution of 2-(3-hydroxyisoxazol-5-yl)-3-methyl-butanoic acid (185 mg, 1.00 mmol, 1.00 eq) and O-(7-azabenzotriazol-1-yl)-N,N,N',N'-tetramethyluronium hexafluorophosphate (570 mg, 1.50 mmol, 1.50 eq) in N,N-dimethylformamide (5 mL) was added diisopropyleth-ylamine (645 mg, 5.0 mmol, 5.00 eq). The mixture was stirred at 15° C. for half an hour, then (2S,4R)-4-hydroxy-N-[[4-(4-methylthiazol-5-yl)phenyl]methyl]pyrrolidine-2-carboxamide (353 mg, 1.0 mmol, 1.00 eq, hydrochloride salt) was added. The resulting mixture was stirred at 15° C. for another 14.5 hr. The mixture was poured into saturated brine (50 mL), and extracted with ethyl acetate (30 mL×2). The combined organic layers were dried over anhydrous sodium sulfate, filtered and concentrated in vacuum. The residue was further purified by preparative HPLC (Phenom-enex Synergi C18 150×25 mm, 10 micron; mobile phase: [water (0.225% FA)-ACN] to afford (2S,4R)-4-hydroxy-1-[2-(3-hydroxyisoxazol-5-yl)-3-methyl-butanoyl]-N-[[4-(4-methylthiazol-5-yl)phenyl]methyl]pyrrolidine-2-carboxamide (220 mg, 0.45 mmol, 46% yield) as an off-white solid. LC-MS (ESI) m/z: 485.1 [M+H$^+$].

Compound 111: (2S,4R)-1-((S)-2-tert-butyl-14-(4-(2-(4-fluorophenyl)-6-hydroxybenzo[b]thiophen-3-yloxy)phenoxy)-4-oxo-6,9,12-trioxa-3-azatetrade-cane)-4-hydroxy-N—((S)-1-(4-(4-methylthiazol-5-yl)phenyl)ethyl)pyrrolidine-2-carboxamide Step 1: Preparation of 3-bromo-2-(4-fluorophenyl)-6-methoxybenzo[b]thiophene-1-oxide A mixture of 3-bromo-2-(4-fluorophenyl)-6-methoxy-benzo[b]thiophene (2 g, 6.23 mmol) and trifluoroacetic acid (20 ml) in dichloromethane (20 mL) was stirred at 0° C. for 5 minutes, followed by addition of aqueous hydrogen per-oxide (30%, 862 mg, 7.47 mmol). After stirring at 0° C. for additional 30 minutes, the resulting mixture was allowed to warm up to room temperature and stirred at room tempera-ture for 3 hours. TLC showed formation of desired product. Solid sodium bisulfite (392 mg, 3.1 mmol) was added cautiously to the dark solution followed by water (3 mL). The resulting mixture was stirred at room temperature for 15 minutes. The volatiles were removed under reduced pres-sure, the residue was partitioned between dichloromethane (150 mL) and water (80 mL), the organic phase was washed with aqueous sodium bicarbonate (1N, 50 mL) and brine (50 mL), dried over anhydrous sodium sulfate, and concentrated under reduced pressure to give a crude residue which was purified by silica gel flash chromatography (eluted with 0-4% ethyl acetate in dichloromethane) to afford 3-bromo-2-(4-fluorophenyl)-6-methoxybenzo[b]thiophene 1-oxide (620 mg, yield 30%) as a yellow solid. $^1$H NMR (400 MHz, CDCl$_3$): δ 3.93 (s, 3H), 7.13-7.16 (m, 1H), 7.19-7.23 (m, 2H), 7.49-7.50 (m, 1H), 7.56-7.58 (m, 1H), 7.79-7.82 (m, 2H).

Step 2: Preparation of 2-(4-fluorophenyl)-6-methoxy-3-(4-((tetrahydro-2H-pyran-2-yl)oxy)phe-noxy)benzo[b]thiophene-1-oxide To a stirred solution of 4-(tetrahydro-2H-pyran-2-yloxy) phenol (303 mg, 1.56 mmol) in anhydrous N,N-dimethyl-formamide (5 mL) was added sodium hydride (60% in mineral oil, 113 mg, 2.83 mmol) in portions at 0° C. After stirring at 0° C. for 10 minutes, 3-bromo-2-(4-fluorophe-nyl)-6-methoxybenzo[b]thiophene-1-oxide(500 mg, 1.42 mmol) was added, the resulting mixture was allowed to warm up to room temperature and stirred at room tempera-ture for 2 hours. TLC showed formation of desired product. The reaction mixture was carefully quenched with water (25 mL) at 0° C. and extracted with ethyl acetate (30 mL×3). The combined organic layer was washed with water (30 mL) and brine (30 mL), dried over anhydrous sodium sulfate, and concentrated under reduced pressure to give a crude residue which was purified by silica gel flash chromatography (eluted with 0-4% ethyl acetate in dichloromethane) to afford 2-(4-fluorophenyl)-6-methoxy-3-(4-((tetrahydro-2H-pyran-2-yl)oxy)phenoxy)benzo[b]thiophene-1-oxide (500 mg, yield 75%) as yellow oil. LC/MS: (ES$^+$): m/z 467.10 [M+H$^+$]; $^1$H NMR (400 MHz, CDCl$_3$): δ 1.59-1.70 (m, 3H), 1.82-1.86 (m, 2H), 1.93-2.04 (m, 1H), 3.57-3.62 (m, 1H), 3.85-3.91 (m, 4H), 5.29-5.31 (m, 1H), 6.90-6.99 (m, 5H), 7.02-7.07 (m, 3H), 7.50 (s, 1H), 7.72-7.75 (m, 2H).

Step 3: Preparation of 4-(2-(4-fluorophenyl)-6-methoxybenzo[b]thiophen-3-yloxy)phenol To a stirred solution of 2-(4-fluorophenyl)-6-methoxy-3-(4-((tetrahydro-2H-pyran-2-yl)oxy)phenoxy)benzo[b]thio-phene-1-oxide (500 mg, 1.0 mmol) and sodium iodide (804 mg, 5.36 mmol) in acetonitrile (5 mL) was added chlorot-rimethylsilane (349 mg, 3.22 mmol) dropwise at room temperature, the resulting mixture was stirred at room tem-perature for 30 minutes. TLC showed formation of desired product. The reaction mixture was partitioned between aqueous sodium sulfite solution (1N, 60 mL) and ethyl acetate (150 mL). The organic layer was collected, washed with water (50 mL) and brine (50 mL), dried over anhydrous sodium sulfate, and concentrated under reduced pressure to give a crude residue which was purified by silica gel flash chromatography (eluted with 0-4% ethyl acetate in dichlo-romethane) to afford 4-(2-(4-fluorophenyl)-6-methoxy-benzo[b]thiophen-3-yloxy)phenol (350 mg, yield 89%) as white solid. LC/MS: (ES$^+$): m/z 366.90 [M+H$^+$]; $^1$H NMR (400 MHz, CDCl$_3$): δ 3.87 (s, 3H), 4.55 (s, 1H), 6.70-6.73 (m, 2H), 6.82-6.89 (m, 3H), 7.02-7.06 (m, 2H), 7.25-7.29 (m, 2H), 7.69-7.72 (m, 2H).

Step 4: Preparation of tert-butyl 2-(2-(2-(2-(4-(2-(4-fluorophenyl)-6-methoxybenzo[b]thiophen-3-yloxy) phenoxy)ethoxy)ethoxy)ethoxy)acetate A mixture of 4-(2-(4-fluorophenyl)-6-methoxybenzo[b] thiophen-3-yloxy)phenol (350 mg, 1.00 mmol), tert-butyl 2-(2-(2-(2-(tosyloxy)ethoxy)ethoxy)ethoxy)acetate (418 mg, 1.00 mmol) and potassium carbonate (414 mg, 3.00 mmol) in acetonitrile (10 mL) was stirred at refluxing temperature overnight. TLC showed formation of desired product. The reaction mixture was cooled to room tempera-ture, partitioned between ethyl acetate (120 mL) and water (50 mL). The organic layer was collected, washed with brine (50 mL), dried over anhydrous sodium sulfate, and concen-trated under reduced pressure to give a crude residue which was purified by silica gel flash chromatography (eluted with 0-5% ethyl acetate in dichloromethane) to afford tert-butyl 2-(2-(2-(2-(4-(2-(4-fluorophenyl)-6-methoxybenzo[b]thiophen-3-yloxy)phenoxy)ethoxy)ethoxy)ethoxy)acetate (500 mg, yield 85%) as lightless oil. LC/MS: (ES+): m/z 635.10 [M+Na+]; 1H NMR (400 MHz, CDCl3): δ1.46 (s, 9H), 3.66-3.73 (m, 8H), 3.81-3.83 (m, 2H), 3.87 (s, 3H), 4.01 (m, 2H), 4.04-4.07 (m, 2H), 6.78-6.82 (m, 2H), 6.85-6.89 (m, 3H), 7.02-7.06 (m, 2H), 7.25-7.27 (m, 2H), 7.68-7.72 (m, 2H).

Step 5: Preparation of 2-(2-(2-(2-(4-(2-(4-fluorophenyl)-6-hydroxybenzo[b]thiophen-3-yloxy)phenoxy)ethoxy)ethoxy)ethoxy)acetic acid A mixture of tert-butyl 2-(2-(2-(2-(4-(2-(4-fluorophenyl)-6-methoxybenzo[b]thiophen-3-yloxy)phenoxy)ethoxy)ethoxy)ethoxy)acetate (440 mg, 0.72 mmol) and lithium chloride (610 mg, 14.38 mmol) in dry 1-methylpyrrolidin-2-one (4 mL) was stirred at 220° C. for 3 hours. LC/MS showed formation of the desired product. The reaction mixture was cooled to room temperature and directly purified by preparative HPLC to afford 2-(2-(2-(2-(4-(2-(4-fluorophenyl)-6-hydroxybenzo[b]thiophen-3-yloxy)phenoxy)ethoxy)ethoxy)ethoxy)acetic acid (200 mg, yield 51%) as brown oil. LC/MS: (ES+): m/z 543.20 [M+H+].

Step 6: Preparation of (2S, 4R)-1-((S)-2-tert-butyl-14-(4-(2-(4-fluorophenyl)-6-hydroxybenzo[b]thiophen-3-yloxy)phenoxy)-4-oxo-6,9,12-trioxa-3-azatetradecane)-4-hydroxy-N—((S)-1-(4-(4-methylthiazol-5-yl)phenyl)ethyl)pyrrolidine-2-carboxamide To a stirred solution of 2-(2-(2-(2-(4-(2-(4-fluorophenyl)-6-hydroxybenzo[b]thiophen-3-yloxy)phenoxy)ethoxy)ethoxy)ethoxy)acetic acid (130 mg, 0.24 mmol), (2S,4R)-1-((S)-2-amino-3,3-dimethylbutanoyl)-4-hydroxy-N—((S)-1-(4-(4-methylthiazol-5-yl)phenyl)ethyl)pyrrolidine-2-carboxamide hydrochloric acid salt (200 mg, crude), and N-ethyl-N-isopropylpropan-2-amine (124 mg, 0.96 mmol) in anhydrous N,N-dimethylformamide (2 mL) was added HATU (2-(7-aza-1H-benzotriazole-1-yl)-1,1,3,3-tetramethyluronium hexafluorophosphate) (230 mg, 0.60 mmol) at 0° C., the resulting mixture was allowed to warm up to room temperature and stirred at room temperature for 30 min. TLC showed formation of desired product. The reaction mixture was partitioned between ethyl acetate (150 mL) and water (50 mL). The organic layer was collected, washed with brine (50 mL), dried over anhydrous sodium sulfate, and concentrated under reduced pressure to give a crude residue which was purified by preparative HPLC to afford (2S,4R)-1-((S)-2-tert-butyl-14-(4-(2-(4-fluorophenyl)-6-hydroxybenzo[b]thiophen-3-yloxy)phenoxy)-4-oxo-6,9,12-trioxa-3-azatetradecane)-4-hydroxy-N—((S)-1-(4-(4-methylthiazol-5-yl)phenyl)ethyl)pyrrolidine-2-carboxamide (25 mg, yield 11%) as white solid. LC/MS: (ES+): m/z 969.30 [M+H+]; 1H NMR (400 MHz, CD3OD): δ 1.03 (s, 9H), 1.49 (d, J=6.8 Hz, 3H), 1.92-1.99 (m, 1H), 2.18-2.23 (m, 1H), 2.48, 2.49 (two singles, 3H), 3.70-3.75 (m, 9H), 3.81-3.86 (m, 3H), 4.03-4.09 (m, 4H), 4.43 (br, 1H), 4.55-4.59 (m, 1H), 4.68 (br, 1H), 4.97-5.02 (m, 1H), 6.78-6.81 (m, 1H), 6.85-6.87 (m, 4H), 7.07-7.12 (m, 2H), 7.18-7.20 (m, 2H), 7.38-7.45 (m, 4H), 7.12-7.76 (m, 2H), 8.88 and 8.89 (two singles, 1H).

Compound 112: (2S,4R)-1-((S)-2-(2-(3-(3-(4-(2-(4-fluorophenyl)-6-hydroxybenzo[b]thiophen-3-yloxy)phenoxy)propoxy)propoxy)acetamido)-3,3-dimethylbutanoyl)-4-hydroxy-N—((S)-1-(4-(4-methylthiazol-5-yl)phenyl)ethyl)pyrrolidine-2-carboxamide Compound 112 was prepared using the same method as described for Compound 111. 1H NMR (400 MHz, CD3OD): δ 1.03, 1.04 (two singles, 9H), 1.48-1.58 (m, 3H), 1.87-2.03 (m, 5H), 2.19-2.24 (m, 1H), 2.47, 2.49 (two singles, 3H), 3.57-3.65 (m, 6H), 3.76-4.02 (m, 6H), 4.45 (br, 1H), 4.55-4.71 (m, 2H), 4.97-5.02 (m, 1H), 6.79-6.87 (m, 5H), 7.08-7.20 (m, 4H), 7.40-7.46 (m, 4H), 7.72-7.76 (m, 2H), 8.87, 8.89 (two singles, 1H). LC/MS: (ES+): m/z 953.30 [M+H+].

Compound 113: (2S,4R)-1-((S)-2-(2-(2-(3-(4-(2-(4-fluorophenyl)-6-hydroxybenzo[b]thiophen-3-yloxy)phenoxy)propoxy)ethoxy)acetamido)-3,3-dimethylbutanoyl)-4-hydroxy-N—((S)-1-(4-(4-methylthiazol-5-yl)phenyl)ethyl)pyrrolidine-2-carboxamide Compound 113 was prepared using the same method as described for Compound 111. 1H NMR (400 MHz, CD3OD): δ 1.02 (s, 9H), 1.46-1.57 (m, 3H), 1.96-2.05 (m, 3H), 2.17-2.23 (m, 1H), 2.47 (s, 3H), 3.66-3.76 (m, 7H), 3.83-3.86 (m, 1H), 3.99-4.08 (m, 4H), 4.44 (br, 1H), 4.55-4.59 (m, 1H), 4.68-4.69 (m, 1H), 4.97-4.99 (m, 1H), 6.78-6.80 (m, 1H), 6.84, 6.86 (two singles, 4H), 7.07-7.11 (m, 2H), 7.18-7.20 (m, 2H), 7.38-7.44 (m, 4H), 7.64-7.76 (m, 3H), 8.88 and 8.89 (two singles, 1H). LC/MS: (ES+): m/z 939.30 [M+H+].

Compound 140: (2S,4R)-1-[(2S)-2-[2-(2-[4-[2-(4-[[2-(4-bromophenyl)-6-hydroxy-1-benzothiophen-3-yl]oxy]phenoxy)ethyl]piperazin-1-yl]ethoxy)acetamido]-3,3-dimethylbutanoyl]-4-hydroxy-N-[[4-(4-methyl-1,3-thiazol-5-yl)phenyl]methyl]pyrrolidine-2-carboxamide Step 1: Preparation of 3-bromo-2-(4-bromophenyl)-1-benzothiophen-6-ol To a 3-necked round-bottom flask purged and maintained with nitrogen, was placed a solution of 3-bromo-2-(4-bromophenyl)-6-methoxy-1-benzothiophene (3.2 g, 7.99 mmol, 1.00 equiv) in dichloromethane (50 mL). Then boron tribromide (IM in dichloromethane) (50 mL, 5.00 equiv) was added dropwise with stirring at room temperature. The resulting solution was stirred for 1 hour at room temperature. The reaction was then quenched by the addition of water. The resulting solution was extracted with dichloromethane (100 mL×2), and the organic layers were combined. The resulting mixture was washed with brine. The mixture was dried over anhydrous sodium sulfate. The solids were filtered out. The resulting mixture was concentrated under vacuum. This resulted in 3.0 g (crude) of 3-bromo-2-(4-bromophenyl)-1-benzothiophen-6-ol as a brown solid. LC/MS (ES+): m/z 383.86/385.86 [M+H+].

Step 2: Preparation of 6-(benzyloxy)-3-bromo-2-(4-bromophenyl) benzo[b]thiophene Into a 100-mL round-bottom flask purged and maintained with nitrogen, was placed a solution of 3-bromo-2-(4-bromophenyl)-1-benzothiophen-6-ol (3.0 g, 7.85 mmol, 1.00 equiv), sodium hydride (471.2 mg, 11.78 mmol, 1.50 equiv) in N,N-dimethylformamide (20 mL). The resulting solution was stirred for 10 minutes at room temperature. Then (bromomethyl)benzene (1.5 g, 8.64 mmol, 1.1 equiv) was added dropwise at room temperature. The resulting solution was stirred for 1 hour at room temperature. The reaction was then quenched by the addition of water (150 mL). The solids were filtered and the crude product was purified by re-crystallization from ethyl acetate. This resulted in 3.5 g (96%) of 6-(benzyloxy)-3-bromo-2-(4-bromophenyl)-benzo[b]thiophene as a white solid. LC-MS (ES+): m/z 473.91/475.91 [M+H+].

Step 3: Preparation of 6-(benzyloxy)-3-bromo-2-(4-bromophenyl)-benzothiophen-1-one Into a 100-mL round-bottom flask, was placed a solution of 6-(benzyloxy)-3-bromo-2-(4-bromophenyl)-1-benzothiophene (2.5 g, 5.27 mmol, 1.0 equiv) in trifluoroacetic acid (10 mL) and dichloromethane (10 mL). Then hydrogen peroxide (0.5 mL, 1.20 equiv, 33% aq) was added dropwise at room temperature. The resulting solution was stirred for 5 hours at room temperature. The resulting solution was extracted with dichloromethane (100 mL×2), and the organic layers were combined. The resulting mixture was washed with brine. The mixture was dried over anhydrous sodium sulfate. The solids were filtered out. The resulting mixture was concentrated under vacuum. The crude product was purified by re-crystallization from ethyl acetate. This resulted in 2.2 g (85%) of 6-(benzyloxy)-3-bromo-2-(4-bromophenyl)-1-benzothiophen-1-one as a yellow solid. LC-MS (ES+): m/z 489.91/491.91 [M+H+].

Step 4: Preparation of 6-(benzyloxy)-2-(4-bromophenyl)-3-[4-(oxan-2-yloxy)phenoxy]-benzothiophen-1-one To a round bottom flask was placed a solution of 6-(benzyloxy)-3-bromo-2-(4-bromophenyl)-benzothiophen-1-one (1.2 g, 2.45 mmol, 1.00 equiv), sodium hydride (147.0 mg, 6.12 mmol, 1.50 equiv) in N, N-dimethylformamide (20 mL). The resulting solution was stirred for 10 minutes at room temperature. Then 4-(oxan-2-yloxy) phenol (570.0 mg, 2.93 mmol, 1.20 equiv) was added. The resulting solution was stirred for 1 hour at room temperature. The reaction was then quenched by the addition of water. The resulting solution was extracted with ethyl acetate (100 mL×2), and the organic layers were combined. The resulting mixture was washed with brine. The mixture was dried over anhydrous sodium sulfate. The solids were filtered out. The resulting mixture was concentrated under vacuum. This resulted in 1.5 g (crude) of 6-(benzyloxy)-2-(4-bromophenyl)-3-[4-(oxan-2-yloxy)phenoxy]benzothiophen-1-one as yellow oil. LC/MS (ES+): m/z 604.95/606.95 [M+H+].

Step 5: Preparation of 4-[[6-(benzyloxy)-2-(4-bromophenyl)-1-benzothiophen-3-yl]oxy] phenol To a solution of 6-(benzyloxy)-2-(4-bromophenyl)-3-[4-(oxan-2-yloxy)phenoxy]-benzothiophen-1-one (1.5 g, 2.49 mmol, 1.00 equiv) in acetonitrile (20 mL) was added trimethylchlorosilane (540 mg, 4.97 mmol, 2.00 equiv) and sodium iodide (1.1 g, 3.00 equiv). The resulting solution was stirred for 5 minutes at room temperature. The reaction was then quenched by the addition of saturated sodium thiosulfate solution. The resulting solution was extracted with ethyl acetate (20 mL×2), and the organic layers were combined. The resulting mixture was washed with brine. The mixture was dried over anhydrous sodium sulfate. The solids were filtered out. The resulting mixture was concentrated under vacuum. The residue was applied onto a silica gel column eluted with ethyl acetate/petroleum ether (v:v=1:2). This resulted in 800.0 mg (64%) of 4-[[6-(benzyloxy)-2-(4-bromophenyl)-1-benzothiophen-3-yl]oxy]phenol as a yellow solid. $^1$H NMR (400 MHz, CD$_3$OD): δ 7.62 (d, J=6.4 Hz, 2H), 7.35 (m, 9H), 6.95 (m, 1H), 6.80 (m, 2H), 6.70 (m, 2H), 5.15 (d, J=14.2 Hz, 2H); LC-MS (ES+): m/z 504.95 [M+H+].

Step 6: Preparation of tert-butyl 2-[2-(benzyloxy)ethoxy]acetate

Into a 1000-mL round-bottom flask, was placed 2-(benzyloxy)ethan-1-ol (10.0 g, 65.71 mmol, 1.00 equiv), tert-butyl 2-bromoacetate (19.2 g, 98.43 mmol, 1.50 equiv), dichloromethane (150 mL), 37% sodium hydroxide (150 mL), and tetrabutylammonium chloride (18.3 g, 65.83 mmol, 1.00 equiv). The resulting solution was stirred for 4 h at room temperature in a water/ice bath. The resulting solution was extracted with dichloromethane (100 mL×3) and the organic layers were combined and concentrated under vacuum. The residue was applied onto a silica gel column eluted with ethyl acetate/petroleum ether (1/15). This resulted in 15.0 g (86%) of tert-butyl 2-[2-(benzyloxy)ethoxy]acetate as yellow oil.

Step 7: Preparation of tert-butyl 2-(2-hydroxyethoxy)acetate

Into a a solution of tert-butyl 2-[2-(benzyloxy)ethoxy]acetate (20.9 g, 78.47 mmol, 1.00 equiv) in methanol (250 mL) was added palladium on carbon (15.0 g, 92.02 mmol, 10.00 equiv). The solution was degassed and stirred under hydrogen for 16 h. The resulting mixture was filtered and the filtrate was concentrated under vacuum. This resulted in 9.9 g (72%) of tert-butyl 2-(2-hydroxyethoxy)acetate as a light yellow solid.

Step 8: Preparation of tert-butyl 2-(2-[[(4-methylbenzene)sulfonyl]oxy]ethoxy)acetate To a solution of tert-butyl 2-(2-hydroxyethoxy)acetate (4.5 g, 25.54 mmol, 1.00 equiv) in dichloromethane (50 mL) was added triethylamine (5.2 g, 51.39 mmol, 2.01 equiv), 4-methylbenzene-1-sulfonyl chloride (5.8 g, 30.42 mmol, 1.20 equiv) and catalytic amount of 4-dimethylaminopyridine. The resulting solution was stirred for 8 h at room temperature. The reaction was then quenched by the addition of water (100 mL). The resulting solution was extracted with dichloromethane (30 mL×3) and the organic layers were combined. The resulting mixture was washed with brine (20 mL×1). The mixture was dried over anhydrous sodium sulfate and concentrated under vacuum. The residue was applied onto a silica gel column eluted with ethyl acetate/petroleum ether (1:3). This resulted in 6.1 g (72%) of tert-butyl 2-(2-[[(4-methylbenzene)sulfonyl]oxy]ethoxy)acetate as colorless oil. LC/MS (ES+): m/z 275.06 [M+H+—Bu$^t$].

Step 9: Preparation of tert-butyl 4-[2-(4-[[6-(benzyloxy)-2-(4-bromophenyl)-1-benzothiophen-3-yl]oxy]phenoxy)ethyl]piperazine-1-carboxylate Into a 250-mL 3-necked round-bottom flask purged with nitrogen, was placed a solution of 4-[[6-(benzyloxy)-2-(4- bromophenyl)-1-benzothiophen-3-yl]oxy]phenol (6.4 g, 12.71 mmol, 1.00 equiv) in methylbenzene (120 mL). To this solution was added tert-butyl 4-(2-hydroxyethyl)piperazine-1-carboxylate (5.9 g, 25.62 mmol, 2.00 equiv), triphenylphosphine (5.0 g, 19.06 mmol, 1.50 equiv), and diethyl azodicarboxylate (3.3 g, 18.95 mmol, 1.50 equiv). The resulting solution was stirred for 4 h at 110° C. in an oil bath. The reaction was then quenched by the addition of water/ice (100 mL). The resulting solution was extracted with ethyl acetate (80 mL×3) and the organic layers were combined. The resulting mixture was washed with brine (50 mL×1). The mixture was dried over anhydrous sodium sulfate and concentrated under vacuum. The residue was applied onto a C18 reverse phase column eluted with methanol/water (3:5). The collected fractions were combined and concentrated under vacuum. This resulted in 4.0 g (44%) of tert-butyl 4-[2-(4-[[6-(benzyloxy)-2-(4-bromophenyl)-1-benzothiophen-3-yl]oxy]phenoxy)ethyl]piperazine-1-carboxylate as a yellow solid. LC/MS (ES$^+$): 716.95/718.95 [M+H$^+$].

Step 10: Preparation of 1-[2-(4-[[6-(benzyloxy)-2-(4-bromophenyl)-1-benzothiophen-3-yl]oxy]phenoxy)ethyl]piperazine hydrochloride To a solution of tert-butyl 4-[2-(4-[[6-(benzyloxy)-2-(4-bromophenyl)-1-benzothiophen-3-yl]oxy]phenoxy)ethyl]piperazine-1-carboxylate (4.0 g, 5.59 mmol, 1.00 equiv) in methanol (30 mL) was added hydrogen chloride in dioxane (4N, 5 mL). The resulting solution was stirred for 16 h at room temperature. The resulting mixture was concentrated under vacuum. This resulted in 3.3 g (91%) of 1-[2-(4-[[6-(benzyloxy)-2-(4-bromophenyl)-1-benzothiophen-3-yl]oxy]phenoxy)ethyl]piperazine hydrochloride as a yellow solid.

Step 11: Preparation of tert-butyl 2-(2-[4-[2-(4-[[2-(4-bromophenyl)-6-benzylkoxy-1-benzothiophen-3-yl]oxy]phenoxy)ethyl]piperazin-1-yl]ethoxy)acetate To a solution of 1-[2-(4-[[6-(benzyloxy)-2-(4-bromophenyl)-1-benzothiophen-3-yl]oxy]phenoxy)ethyl]piperazine hydrochloride (5.6 g, 8.59 mmol, 1.00 equiv) in N,N-dimethylformamide (80 mL) was added potassium carbonate (2.4 g, 17.36 mmol, 2.00 equiv), tert-butyl 2-(2-[(4-methylbenzene)sulfonyl]oxyethoxy)acetate (3.7 g, 11.20 mmol, 1.30 equiv), and sodium iodide (430.0 mg, 4.30 mmol, 0.50 equiv). The resulting mixture was stirred for 12 h at 80° C. in an oil bath. The reaction was then quenched by the addition of water/ice (50 mL×1). The resulting solution was extracted with ethyl acetate (50 mL×3) and the organic layers were combined. The resulting mixture was washed with brine (30 mL×1). The mixture was dried over anhydrous sodium sulfate and concentrated under vacuum. The residue was applied onto a silica gel column eluted with ethyl acetate/petroleum ether (2:1) to provide 5.3 g (90%) of tert-butyl 2-(2-[4-[2-(4-[[2-(4-bromophenyl)-6-benzyloxy-1-benzothiophen-3-yl]oxy]phenoxy)ethyl]piperazin-1-yl]ethoxy)acetate as a yellow solid. LC-MS (ES$^+$): m/z 773.20/775.20 [M+H$^+$].

Step 12: Preparation of 2-(2-[4-[2-(4-[[2-(4-bromophenyl)-6-hydroxy-1-benzothiophen-3-yl]oxy]phenoxy)ethyl]piperazin-1-yl]ethoxy)acetic acid To a stirred solution of tert-butyl 2-(2-[4-[2-(4-[[6-(benzyloxy)-2-(4-bromophenyl)-1-benzothiophen-3-yl]oxy]phenoxy)ethyl]piperazin-1-yl]ethoxy)acetate (5.1 g, 6.59 mmol, 1.00 equiv) in dichloromethane (30 mL) was added boron tribromide in dichloromethane (1N, 30.0 mL) dropwised at −78° C. The resulting solution was stirred for 2 h at −78° C. The reaction was then quenched by the addition of water (50 mL). The resulting mixture was concentrated under vacuum. The residue was applied onto a silica gel column eluted with acetonitrile in water (40%). The collected fractions were combined and concentrated under vacuum. This resulted in 3.7 g (89%) of 2-(2-[4-[2-(4-[[2-(4-bromophenyl)-6-hydroxy-1-benzothiophen-3-yl]oxy]phenoxy)ethyl]piperazin-1-yl]ethoxy)acetic acid as a crude yellow solid. LC-MS (ES$^+$): m/z 626.90/628.90 [M+H$^+$]. This solid was further purified by reverse phase preparative HPLC.

Step 13: Preparation of (2S,4R)-1-[(2S)-2-[2-(2-[4-[2-(4-[[2-(4-bromophenyl)-6-hydroxy-1-benzothiophen-3-yl]oxy]phenoxy)ethyl]piperazin-1-yl]ethoxy)acetamido]-3,3-dimethylbutanoyl]-4-hydroxy-N-[[4-(4-methyl-1,3-thiazol-5-yl)phenyl]methyl]pyrrolidine-2-carboxamide To a solution of 2-(2-[4-[2-(4-[[2-(4-bromophenyl)-6-hydroxy-1-benzothiophen-3-yl]oxy]phenoxy)ethyl]piperazin-1-yl]ethoxy)acetic acid (500.0 mg, 0.80 mmol) in N,N-dimethylformamide (10 mL) was added (2S, 4R)-1-[(2S)-2-amino-3,3-dimethylbutanoyl]-4-hydroxy-N-[[4-(4-methyl-1,3-thiazol-5-yl)phenyl]methyl]pyrrolidine-2-carboxamide (445.0 mg, 1.03 mmol, 1.20 equiv), (benzotriazole-1-yloxy) tris (dimethylamino)phosphonium hexafluorophosphate (353.0 mg, 0.80 mmol, 1.00 equiv), and ethyldiisopropylamine (0.5 mL) at 0° C. The resulting solution was stirred for 1 h at room temperature. The reaction was then quenched by the addition of water (100 mL). The resulting solution was extracted with ethyl acetate (100 mL×3) and the organic layers were combined. The resulting mixture was washed with brine (20 mL×2). The mixture was dried over anhydrous sodium sulfate and concentrated under vacuum. The crude product was purified by preparative HPLC with the following conditions: column, Gemini-NX C18 AXAI Packed, 21.2×150 mm, 5 um; mobile phase, water (10 mmol/L ammonium bicarbonate) and acetonitrile (hold 54.0% acetonitrile in 16 min); Detector, uv 220 nm. This resulted in 207.1 mg (25%) of (2S, 4R)-1-[(2S)-2-[2-(2-[4-[2-(4-[[2-(4-bromophenyl)-6-hydroxy-1-benzothiophen-3-yl]oxy]phenoxy)ethyl]piperazin-1-yl]ethoxy)acetamido]-3,3-dimethylbutanoyl]-4-hydroxy-N-[[4-(4-methyl-1,3-thiazol-5-yl)phenyl]methyl]pyrrolidine-2-carboxamide as a white solid. $^1$H NMR (400 MHz, CD$_3$OD) δ 8.81 (s, 1H), 7.63-7.61 (d, J=8.4 Hz, 2H), 7.48-7.46 (d, J=8.4 Hz, 2H), 7.44-7.41 (m, 2H), 7.39-7.36 (m, 2H), 7.19-7.18 (m, 2H), 6.83-6.76 (m, 5H), 4.68 (s, 1H), 4.53-4.50 (m, 3H), 4.31-4.30 (m, 1H), 4.04-3.98 (m, 4H), 3.97-3.94 (m, 2H), 3.69-3.67 (m, 2H), 2.74-2.65 (m, 12H), 2.67 (s, 3H), 2.36-2.22 (m, 1H), 2.12-2.01 (m, 1H), 1.00 (m, 9H). LC-MS (ES$^+$): m/z 1041.25/1043.25 [MH$^+$].

Compound 118: (2S,4R)-1-((S)-2-(2-(2-(4-(2-(4-((2-(4-fluorophenyl)-6-hydroxybenzo[b]thiophen-3-yl)oxy)phenoxy)ethyl)piperazin-1-yl)ethoxy)acetamido)-3,3-dimethylbutanoyl)-4-hydroxy-N-(4-(4-methylthiazol-5-yl)benzyl)pyrrolidine-2-carboxamide Compound 118 was prepared using the same method as described in Compound 140. $^1$H NMR (400 MHz, CD$_3$OD): δ 1.02, 1.05 (two singles, 9H), 2.07-2.12 (m, 1H), 2.21-2.27 (m, 1H), 2.47, 2.48 (two singles, 3H), 2.94-3.22 (m, 12H), 3.80-3.88 (m, 4H), 4.07-4.18 (m, 4H), 4.34-4.38 (m, 1H), 4.50-4.55 (m, 3H), 4.70 (br, 1H), 6.78-6.86 (m, 5H), 7.07-7.12 (m, 2H), 7.17-7.18 (m, 1H), 7.21 (d, J=2.0 Hz, 1H), 7.39-7.45 (m, 4H), 7.72-7.76 (m, 2H), 8.87, 8.88 (two singles, 1H). LC/MS: (ES$^+$): m/z 979.30 [M+H$^+$].

Compound 151: (2S,4R)-1-[(2S)-2-[2-(2-[4-[2-(4-[[2-(4-chlorophenyl)-6-hydroxy-1-benzothiophen-3-yl]oxy]phenoxy)ethyl]piperazin-1-yl]ethoxy)acetamido]-3,3-dimethylbutanoyl]-4-hydroxy-N-[[4-(4-methyl-1,3-thiazol-5-yl)phenyl]methyl]pyrrolidine-2-carboxamide Compound 151 was prepared using the same method as described for Compound 140. $^1$H NMR (300 MHz, CD$_3$OD): δ 8.818 (s, 1H), 7.69-7.66 (m, 2H), 7.50-7.30 (m, 6H), 7.18-7.14 (m, 1H), 6.83-6.75 (m, 5H), 4.79 (s, 1H), 4.67-4.48 (m, 4H), 4.31-4.26 (m, 1H), 4.08-3.98 (m, 4H), 3.93-3.80 (m, 2H), 3.79-3.75 (m, 2H), 2.90-2.61 (m, 11H), 2.43 (s, 3H), 2.19-2.11 (m, 1H), 2.10-2.06 (m, 1H), 1.01 (s, 9H); LC-MS (ES$^+$): m/z 995.30/997.30 [M+H$^+$].

Compound 153: (2S,4R)-1-[(2S)-2-[2-(2-[4-[2-(4-[[2-(4-bromophenyl)-6-hydroxy-1-benzothiophen-3-yl]oxy]phenoxy)ethyl]piperazin-1-yl]ethoxy)acetamido]-3,3-dimethylbutanoyl]-4-hydroxy-N-[(1S)-1-[4-(4-methyl-1,3-thiazol-5-yl)phenyl]ethyl]pyrrolidine-2-carboxamide Compound 153 was prepared using the same method as described for Compound 140. Briefly, to a solution of 2-(2-[4-[2-(4-[[2-(4-bromophenyl)-6-hydroxy-1-benzothiophen-3-yl]oxy]phenoxy)ethyl]piperazin-1-yl]ethoxy)acetic acid (50.0 mg, 0.08 mmol, step 12 for Compound 140) in N,N-dimethylformamide (10 mL) was added (2S,4R)-1-[(2S)-2-amino-3,3-dimethylbutanoyl]-4-hydroxy-N-[(1S)-1-[4-(4-methyl-1,3-thiazol-5-yl)phenyl]ethyl]pyrrolidine-2-carboxamide hydrochloride (47.0 mg, 0.10 mmol, 1.20 equiv), (benzotriazole-1-yloxy)tris(dimethylamino)phosphonium hexafluorophosphate (43.0 mg, 0.10 mmol, 1.20 equiv), and N,N-diisopropylethylamine (41.0 mg, 0.32 mmol, 4.00 equiv). The resulting solution was stirred for 1 h at room temperature. The reaction was then quenched by the addition of water (10 mL). The resulting solution was extracted with ethyl acetate (15 mL×3) and the organic layers were combined. The resulting mixture was washed with brine (10 mL×1). The mixture was dried over anhydrous sodium sulfate and concentrated under vacuum. The crude material was purified by preparative HPLC to give 26.0 mg (31%) of (2S,4R)-1-[(2S)-2-[2-(2-[4-[2-(4-[[2-(4-bromophenyl)-6-hydroxy-1-benzothiophen-3-yl]oxy]phenoxy)ethyl]piperazin-1-yl]ethoxy)acetamido]-3,3-dimethylbutanoyl]-4-hydroxy-N-[(1S)-1-[4-(4-methyl-1,3-thiazol-5-yl)phenyl]ethyl]pyrrolidine-2-carboxamide as a white solid. $^1$H NMR (400 MHz, CD$_3$OD): δ 8.90-8.80 (s, 1H), 7.64-7.61 (m, 2H), 7.49-7.46 (m 2H), 7.43-7.36 (m, 4H), 7.19-7.17 (m, 2H), 6.86-6.83 (m, 4H), 6.79-6.76 (m, 1H), 4.99-4.97 (m, 1H), 4.67 (s, 1H), 4.60-4.52 (m, 1H), 4.40 (m, 1H), 4.12-4.05 (m, 4H), 3.90-3.75 (m, 4H), 3.10-2.85 (m, 12H), 2.46-2.45 (2s, 3H), 2.25-2.15 (m, 1H), 2.00-1.95 (m, 1H), 1.55 and 1.50 (2d, 3H), 1.01 (s, 9H); LC-MS (ES$^+$): m/z 1055.45/1057.45 [M+H$^+$].

Compound 121: (2S,4R)-1-[(2S)-2-[2-(4-[1-[2-(4-[[2-(4-fluorophenyl)-6-hydroxy-1-benzothiophen-3-yl]oxy]phenoxy)ethyl]-1H-pyrazol-3-yl]phenyl)acetamido]-3,3-dimethylbutanoyl]-4-hydroxy-N-[[4-(4-methyl-1,3-thiazol-5-yl)phenyl]methyl]pyrrolidine-2-carboxamide Into a 25-mL round-bottom flask, was placed a solution of 2-(4-[1-[2-(4-[[2-(4-fluorophenyl)-6-hydroxy-1-benzothiophen-3-yl]oxy]phenoxy)ethyl]-1H-pyrazol-3-yl]phenyl)acetic acid (40.0 mg, 0.07 mmol, 1.00 equiv, prepared according to Scheme 9A) in N,N-dimethylformamide (5.0 mL), and (2S,4R)-1-[(2S)-2-amino-3,3-dimethylbutanoyl]-4-hydroxy-N-[[4-(4-methyl-1,3-thiazol-5-yl)phenyl]methyl]pyrrolidine-2-carboxamide hydrochloride (39.0 mg, 0.08 mmol, 1.20 equiv) was added. This was followed by the addition of (benzotriazole-1-yloxy)tris(dimethylamino)phosphonium hexafluorophosphate (37.0 mg, 0.08 mmol, 1.20 equiv) and N-ethyl-N-isopropylpropan-2-amine (0.3 mL) at 10° C. The resulting solution was stirred for 1 h at room temperature. The reaction was then quenched by the addition of water (20 mL). The resulting solution was extracted with ethyl acetate (20 mL×3) and the organic layers were combined. The resulting mixture was washed with brine (10 mL×1). The mixture was dried over anhydrous sodium sulfate and concentrated under vacuum then purified by preparative HPLC under the following condition: Column, X Bridge C18, 19×250 mm, 5 um; Mobile Phase A: water/110 mmol/L ammonium bicarbonate, Mobile Phase B: acetonitrile; Flow rate: 20 mL/min; Gradient: 10% B to 80% B in 12 min; detected at 254 nm. This resulted in 15.4 mg (23%) of (2S,4R)-1-[(2S)-2-[2-(4-[1-[2-(4-[[2-(4-fluorophenyl)-6-hydroxy-1-benzothiophen-3-yl]oxy]phenoxy)ethyl]-1H-pyrazol-3-yl]phenyl)acetamido]-3,3-dimethylbutanoyl]-4-hydroxy-N-[[4-(4-methyl-1,3-thiazol-5-yl)phenyl]methyl]pyrrolidine-2-carboxamide as a white solid. $^1$H NMR (400 MHz, CD$_3$OD): δ 9.01 (s, 1H), 7.71-7.68 (m, 5H), 7.48-7.42 (m, 4H), 7.40-7.36 (m, 2H), 7.34-7.10 (m, 4H), 6.78-6.76 (m, 5H), 6.58-6.58 (m, 1H), 4.64 (s, 1H), 4.62-4.60 (m, 5H), 4.38-4.30 (m, 3H), 3.87-3.80 (m, 1H), 3.77-3.70 (m, 1H), 3.65-3.63 (m, 2H), 2.47 (s, 3H), 2.19-2.06 (m, 1H), 2.06-1.98 (m, 1H), 0.99 (s, 9H); LC-MS (ES$^+$): m/z 993.05 [MH$^+$].

Compound 142: (2S,4R)-1-[(2S)-2-[2-(2-[2-[4-(4-[[2-(4-fluorophenyl)-6-hydroxy-1-benzothiophen-3-yl]oxy]phenyl)piperidin-1-yl]ethoxy]ethoxy)acetamido]-3,3-dimethylbutanoyl]-4-hydroxy-N-[(1S)-1-[4-(4-methyl-1,3-thiazol-5-yl)phenyl]ethyl]pyrrolidine-2-carboxamide

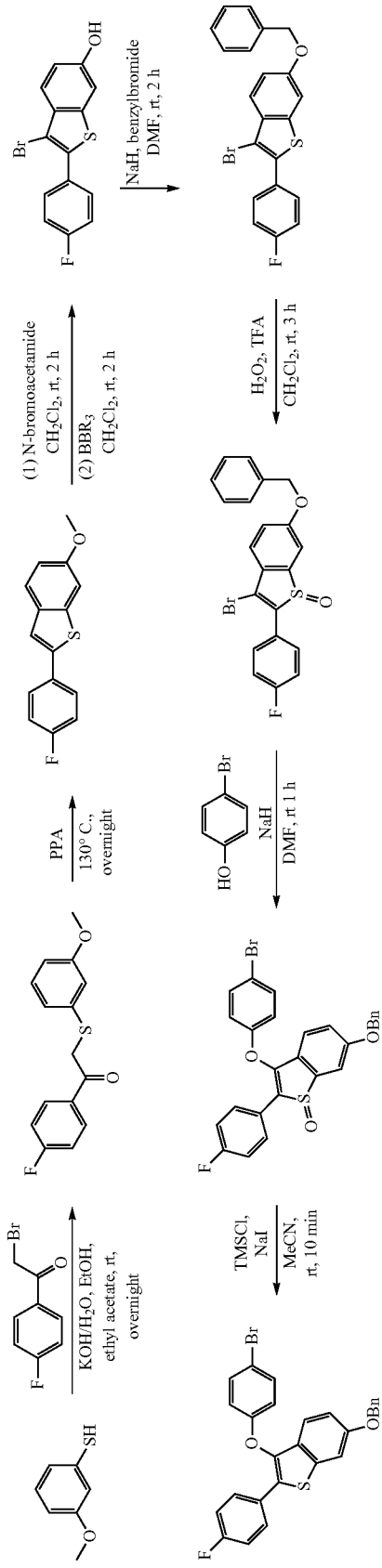
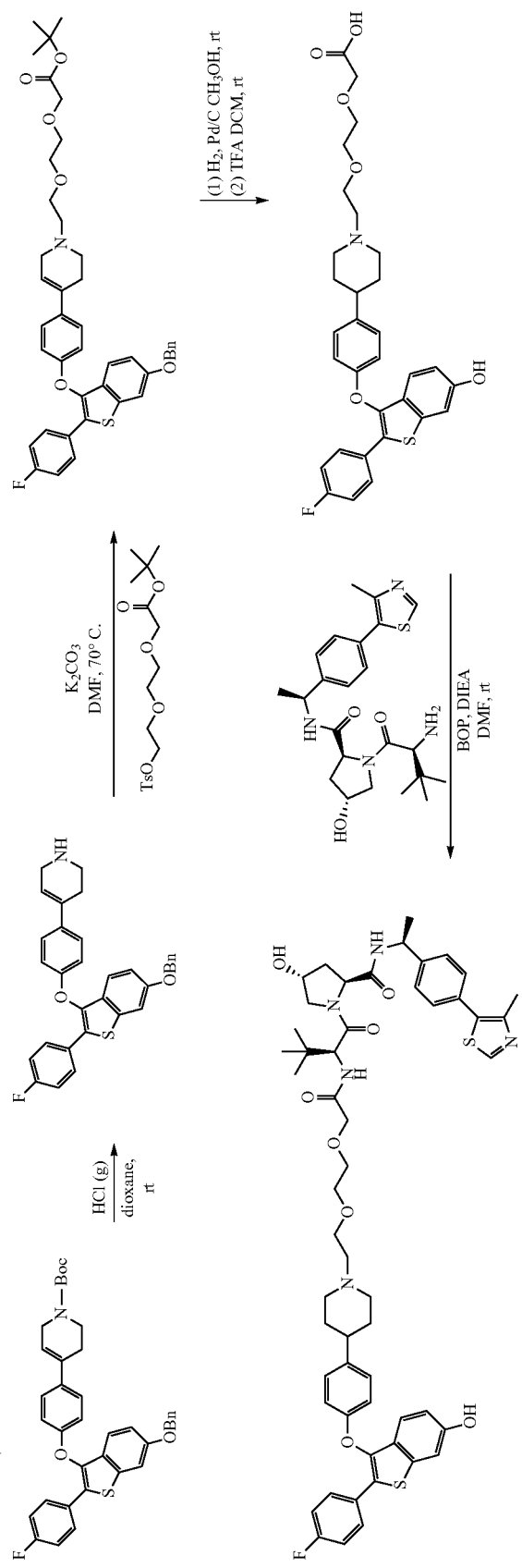

Step 1: Preparation of 1-(4-fluorophenyl)-2-[(3-methoxyphenyl)sulfanyl] ethan-1-one Into a 500-mL round-bottom flask purged and maintained with an inert atmosphere of nitrogen, was placed a solution of potassium hydroxide (15.6 g, 278.03 mmol, 10.00 equiv), 3-methoxybenzene-1-thiol (35.6 g, 253.92 mmol, 1.00 equiv) in water (100 mL), ethanol (250 mL). This was followed by the addition of a solution of 2-bromo-1-(4-fluorophenyl)ethan-1-one (50.0 g, 230.38 mmol, 1.00 equiv) in ethyl acetate (80 mL) dropwise with stirring at 0° C. over 30 minutes. The resulting solution was stirred overnight at room temperature. The resulting mixture was concentrated under vacuum. The solids were filtered out. The mixture was dried over anhydrous sodium sulfate. The residue was applied onto a silica gel column eluted with ethyl acetate/petroleum ether (v:v=1:10). This resulted in 133 g (80%) of 1-(4-fluorophenyl)-2-[(3-methoxyphenyl)sulfanyl]ethan-1-one as yellow oil. LC/MS (ESI) m/z: 276.95 [M+1]$^+$.

Step 2: Preparation of 2-(4-fluorophenyl)-6-methoxy-1-benzothiophene

Into a 500-mL round-bottom flask, was placed a solution of 1-(4-fluorophenyl)-2-[(3-methoxyphenyl)sulfanyl]ethan-1-one (111.7 g, 404.23 mmol, 1.00 equiv) in PPA (950 g). The resulting solution was stirred overnight at 130° C. Then the mixture was cooled, poured into ice/water and adjusted pH to 7 by sodium carbonate. The solids were collected by filtration. The solid was dried in an oven under reduced pressure. This resulted in 37.6 g (36%) of 2-(4-fluorophenyl)-6-methoxy-1-benzothiophene as a brown solid. $^1$H NMR (300 MHz, DMSO) δ 7.77 (m, 4H), 7.56 (s, 1H), 7.33 (t, J=3.0 Hz, 2H), 7.02 (d, J=2.4 Hz, 1H), 3.83 (s, 3H).

Step 3: Preparation of 3-bromo-2-(4-fluorophenyl)-6-methoxy-1-benzothiophene Into a 1000-mL round bottom flask was placed a solution of 2-(4-fluorophenyl)-6-methoxy-1-benzothiophene (17.0 g, 65.81 mmol, 1.00 equiv), N-bromoacetamide (9.1 g, 65.96 mmol, 1.01 equiv) in dichloromethane (420 mL). The resulting solution was stirred for 2 hours at room temperature. The resulting solution was extracted with ethyl acetate (500 mL×2), and the organic layers were combined. The resulting mixture was washed with brine. The mixture was dried over anhydrous sodium sulfate. The solids were filtered out. The resulting mixture was concentrated under vacuum. The residue was applied onto a silica gel column with ethyl acetate/petroleum ether (v:v=1:100). This resulted in 42.2 g (95%) of 3-bromo-2-(4-fluorophenyl)-6-methoxy-1-benzothiophene as a gray solid. LC/MS (ESI) m/z: 336.85 [M+1]$^+$.

Step 4: Preparation of 3-bromo-2-(4-fluorophenyl)-1-benzothiophen-6-ol

Into a 250-mL round-bottom flask, was placed a solution of 3-bromo-2-(4-fluorophenyl)-6-methoxy-1-benzothiophene (5.1 g, 15.12 mmol, 1.00 equiv) in dichloromethane (15 mL, 3.00 equiv). To this was added tribromoborane (2M in dichloromethane, 20 mL) dropwise at room temperature. The resulting solution was stirred for 2 h outs at room temperature. The reaction was then quenched by the addition of water. The resulting solution was extracted with dichloromethane (100 mL×2), and the organic layers were combined. The resulting mixture was washed with brine. The mixture was dried over anhydrous sodium sulfate. The solids were filtered out. The resulting mixture was concentrated under vacuum. This resulted in 4.8 g (98%) of 3-bromo-2-(4-fluorophenyl)-1-benzothiophen-6-ol as a white solid.

Step 5: Preparation of 6-(benzyloxy)-3-bromo-2-(4-fluorophenyl)-1-benzothiophene Into a 250-mL round-bottom flask purged and maintained with an inert atmosphere of nitrogen, was placed a solution of 3-bromo-2-(4-fluorophenyl)-1-benzothiophen-6-ol (4.8 g, 14.85 mmol, 1.00 equiv), sodium hydride (890.0 mg, 37.08 mmol, 1.50 equiv) in N, N-dimethylformamide (100 mL). The resulting solution was stirred for 10 minutes at room temperature. Then (bromomethyl)benzene (3.8 g, 22.22 mmol, 1.50 equiv) was added dropwise with stirring for 2 hours at room temperature. The reaction was then quenched by the addition of water. The solids were collected by filtration. The crude product was purified by re-crystallization from ethyl acetate. This resulted in 5.6 g (91%) of 6-(benzyloxy)-3-bromo-2-(4-fluorophenyl)-1-benzothiophene as a white solid. $^1$H-NMR (400 MHz, CDCl$_3$) δ 7.77 (m, 3H), 7.45 (m, 6H), 7.17 (m, 3H), 5.25 (s, 2H).

Step 6: Preparation of 6-(benzyloxy)-3-bromo-2-(4-fluorophenyl)-benzothiophen-1-one Into a 1000-mL round-bottom flask, was placed a solution of 6-(benzyloxy)-3-bromo-2-(4-fluorophenyl)-1-benzothiophene (20.0 g, 48.39 mmol, 1.00 equiv), trifluoroacetic acid (200 mL), dichloromethane (200 mL). Then H$_2$O$_2$(30%, 11.3 mL, 3.00 equiv) was added dropwise at 0° C. The resulting solution was stirred for 3 hours at room temperature. The reaction was then quenched by the addition of sodium sulfite. The resulting solution was extracted with dichloromethane (500 mL×2) and the organic layers were combined and dried over anhydrous sodium sulfate. The solids were filtered out. The resulting mixture was concentrated under vacuum. The crude product was purified by re-crystallization from ethyl acetate, which resulted in 15.5 g (75%) of 6-(benzyloxy)-3-bromo-2-(4-fluorophenyl)-benzothiophen-1-one as a yellow solid. LC/MS (ESI) m/z: 428.90 [M+1]$^+$.

Step 7: Preparation of 6-(benzyloxy)-3-(4-bromophenoxy)-2-(4-fluorophenyl)-benzothiophen-1-one Into a 100-mL round-bottom flask, was placed 4-bromophenol (725.9 mg, 4.20 mmol, 1.00 equiv), 6-(benzyloxy)-3-bromo-2-(4-fluorophenyl)-benzothiophen-1-one (1.8 g, 4.19 mmol, 1.00 equiv), potassium carbonate (1.7 g, 12.30 mmol, 3.00 equiv), N,N-dimethylformamide (15 mL). The resulting solution was first stirred for 3 hours at 70° C. in an oil bath and then stirred for 10 minutes at room temperature. The reaction was quenched with water (50 mL), extracted with ethyl acetate (50 mL×2), washed with water (50 mL) and brine (50 mL), dried over anhydrous sodium sulfate and concentrated under vacuum. The residue was applied onto a silica gel column eluted with ethyl acetate/petroleum ether (v:v=1:8). This resulted in 1.7 g (78%) of 6-(benzyloxy)-3-(4-bromophenoxy)-2-(4-fluorophenyl)-benzothiophen-1-one as a yellow solid. LC/MS (ESI) m/z: 520.75 [M+1]$^+$.

Step 8: Preparation of tert-butyl 4-(4-[[6-(benzyloxy)-2-(4-fluorophenyl)-1-benzothiophen-3-yl]oxy]phenyl)-1,2,3,6-tetrahydropyridine-1-carboxylate Into a 25-mL round-bottom flask, was placed 6-(benzyloxy)-3-(4-bromophenoxy)-2-(4-fluorophenyl)-1-benzothiophene (50.0 mg, 0.10 mmol, 1.00 equiv), tert-butyl 4-(tetramethyl-1,3,2-dioxaborolan-2-yl)-1,2,3,6-tetrahydropyridine-1-carboxylate (61.2 mg, 0.20 mmol, 2.00 equiv), potassium carbonate (41.0 mg, 0.30 mmol, 3.00 equiv), ethylene glycol dimethyl ether (2 mL), water (0.5 mL), tetrakis(triphenylphosphine)palladium (22.9 mg, 0.02 mmol, 0.05 equiv). The resulting solution was stirred for 2 hours at 100° C. in an oil bath. The mixture was concentrated under vacuum. The residue was applied onto a silica gel column eluted with ethyl acetate/petroleum ether (v:v=1:5). This resulted in 40.0 mg (67%) of tert-butyl 4-(4-[[6-(benzyloxy)-2-(4-fluorophenyl)-1-benzothiophen-3-yl]oxy]phenyl)-1,2,3,6-tetrahydropyridine-1-carboxylate as yellow oil. LC/MS (ESI) m/z: 608.15 [M+1]$^+$.

Step 9: Preparation of 4-(4-[[6-(benzyloxy)-2-(4-fluorophenyl)-1-benzothiophen-3-yl]oxy]phenyl)-1,2,3,6-tetrahydropyridine Into a 25-mL round-bottom flask, was placed tert-butyl 4-(4-[[6-(benzyloxy)-2-(4-fluorophenyl)-1-benzothiophen-3-yl]oxy]phenyl)-1,2,3,6-tetrahydropyridine-1-carboxylate (250.0 mg, 0.41 mmol, 1.00 equiv) and hydrogen chloride/dioxane (5 mL). The resulting solution was stirred for 2 hours at room temperature. The mixture was concentrated under vacuum. This resulted in 230.0 mg (crude) of 4-(4-[[6-(benzyloxy)-2-(4-fluorophenyl)-1-benzothiophen-3-yl]oxy]phenyl)-1,2,3,6-tetrahydropyridine as yellow oil. LC/MS (ESI) m/z: 508.05 [M+1]$^+$.

Step 10a: Preparation of tert-butyl [2-(2-hydroxyethoxy)ethoxy]acetate

To a cold and stirred solution of diethylene glycol (3 eq) in anhydrous N,N-dimethylformamide [amount of di-alcohol (g) ×5 mL] was added sodium hydride (60%, 1.2 eq) in portions at 0° C. under nitrogen atmosphere. The reaction mixture was allowed to warm to room temperature and stirred at room temperature for 1 hour, then re-cooled to 0° C., and tert-butyl 2-bromoacetate (1 eq) was added in portions. The resulting mixture was allowed to warm up to room temperature and stirred at room temperature for 2 hours. The reaction was carefully quenched with water (amount of di-alcohol×10 mL) under ice-water cooling and extracted with methylene dichloride. The combined organic phase was washed with brine, dried over anhydrous magnesium sulfate and evaporated to dryness under reduced pressure. The crude product was purified by silica gel chromatography (eluent 1-6% methanol in methylene dichloride) to afford the desired product as colorless oil (yield 46%). $^1$H-NMR (400 MHz, CDCl$_3$) δ 4.03 (s, 2H), 3.62-3.76 (m, 8H), 2.46 (br, 1H), 1.48 (s, 9H).

Step 10b: Preparation of tert-butyl 2-(2-[2-[4-(4-[[6-(benzyloxy)-2-(4-fluorophenyl)-1-benzothiophen-3-yl]oxy]phenyl)-1,2,3,6-tetrahydropyridin-1-yl]ethoxy]ethoxy)acetate Into a 50-mL round-bottom flask, was placed 4-(4-[[6-(benzyloxy)-2-(4-fluorophenyl)-1-benzothiophen-3-yl]oxy]phenyl)-1,2,3,6-tetrahydropyridine (230.0 mg, 0.45 mmol, 1.00 equiv), tert-butyl 2-[2-(2-[[(4-methylbenzene)sulfonyl]oxy]ethoxy)ethoxy]acetate (169.3 g, 452.13 mmol, 1.00 equiv), potassium carbonate (187.4 g, 1.36 mol, 3.00 equiv), N,N-dimethylformamide (5 mL). The resulting solution was stirred for 3 hours at 70° C. in an oil bath. The mixture was diluted with water (15 mL), extracted with ethyl acetate (20 mL×3), washed with brine (20 mL×2), dried over anhydrous sodium sulfate and concentrated under vacuum. The residue was applied onto a silica gel column eluted with dichloromethane/methanol (v:v=10:1). This resulted in 200.0 mg (62%) of tert-butyl 2-(2-[2-[4-(4-[[6-(benzyloxy)-2-(4-fluorophenyl)-1-benzothiophen-3-yl]oxy]phenyl)-1,2,3,6-tetrahydropyridin-1-yl]ethoxy]ethoxy)acetate as yellow oil. LC/MS (ESI) m/z: 710.15 [M+1]$^+$.

Step 11: Preparation of tert-butyl 2-(2-[2-[4-(4-[[2-(4-fluorophenyl)-6-hydroxy-1-benzothiophen-3-yl]oxy]phenyl)piperidin-1-yl]ethoxy]ethoxy)acetate Into a 50-mL round-bottom flask, was placed tert-butyl 2-(2-[2-[4-(4-[[6-(benzyloxy)-2-(4-fluorophenyl)-1-benzothiophen-3-yl]oxy]phenyl)-1,2,3,6-tetrahydropyridin-1-yl]ethoxy]ethoxy)acetate (200.0 mg, 0.28 mmol, 1.00 equiv), methanol (5 mL), palladium on carbon (150.0 mg). Then hydrogen was introduced in. The resulting solution was stirred for 3 hours at room temperature. The solids were filtered out. The resulting mixture was concentrated under vacuum. This resulted in 150.0 mg (86%) of tert-butyl 2-(2-[2-[4-(4-[[2-(4-fluorophenyl)-6-hydroxy-1-benzothiophen-3-yl]oxy]phenyl)piperidin-1-yl]ethoxy]ethoxy)acetate as yellow oil. LC/MS (ESI) m/z: 622.15 [M+1]$^+$.

Step 12: Preparation of 2-(2-[2-[4-(4-[[2-(4-fluorophenyl)-6-hydroxy-1-benzothiophen-3-yl]oxy]phenyl)piperidin-1-yl]ethoxy]ethoxy)acetic acid Into a 20-mL round-bottom flask, was placed tert-butyl 2-(2-[2-[4-(4-[[2-(4-fluorophenyl)-6-hydroxy-1-benzothiophen-3-yl]oxy]phenyl)piperidin-1-yl]ethoxy]ethoxy)acetate (150.0 mg, 0.24 mmol, 1.00 equiv), dichloromethane (1 mL), trifluoroacetic acid (1 mL). The resulting solution was stirred for 2 hours at room temperature. The resulting mixture was concentrated under vacuum. This resulted in 120.0 mg (88%) of 2-(2-[2-[4-(4-[[2-(4-fluorophenyl)-6-hydroxy-1-benzothiophen-3-yl]oxy]phenyl)piperidin-1-yl]ethoxy]ethoxy)acetic acid as yellow oil. LC/MS (ESI) m/z: 566.25 [M+1]$^+$.

Step 13: Preparation of (2S,4R)-1-[(2S)-2-[2-(2-[2-[4-(4-[[2-(4-fluorophenyl)-6-hydroxy-1-benzothiophen-3-yl]oxy]phenyl)piperidin-1-yl]ethoxy]ethoxy)acetamido]-3,3-dimethylbutanoyl]-4-hydroxy-N-[(1S)-1-[4-(4-methyl-1,3-thiazol-5-yl)phenyl]ethyl]pyrrolidine-2-carboxamide (Compound 142)

Into a 50-mL round-bottom flask, was placed a solution of 2-(2-[2-[4-(4-[[2-(4-fluorophenyl)-6-hydroxy-1-benzothiophen-3-yl]oxy]phenyl)piperidin-1-yl]ethoxy]ethoxy)acetic acid (100.0 mg, 0.18 mmol, 1.00 equiv), (2S,4R)-1-[(2S)-2-amino-3,3-dimethylbutanoyl]-4-hydroxy-N-[(1S)-1-[4-(4-methyl-1,3-thiazol-5-yl)phenyl] ethyl]pyrrolidine-2-carboxamide (78.5 mg, 0.18 mmol, 1.00 equiv), (benzotriazole-1-yloxy)tris(dimethylamino)phosphonium hexafluorophosphate (94.0 mg, 1.20 equiv), N,N-diisopropylethylamine (68.5 mg, 0.53 mmol, 3.00 equiv) in N,N-dimethylformamide (1 mL). The resulting solution was stirred for 10 minutes at 0° C. The reaction was then quenched by the addition of water. The mixture was extracted with ethyl acetate (20 mL×2), and the organic layers were combined. The solution was washed with brine, dried over anhydrous sodium sulfate. The solids were filtered out. The resulting solution was concentrated under vacuum. The crude product was purified by Prep-HPLC with the following conditions: Column, XBridge Shield RP18 OBD Column; 5 um, 19×150 mm; mobile phase, water with 0.05% trifluoroacetic acid and acetonitrile/methanol=1/1; Detector, UV 254 nm. This resulted in 38.0 mg (22%) of (2S,4R)-1-[(2S)-2-[2-(2-[2-[4-(4-[[2-(4-fluorophenyl)-6-hydroxy-1-benzothiophen-3-yl]oxy]phenyl)piperidin-1-yl]ethoxy]ethoxy)acetamido]-3,3-dimethylbutanoyl]-4-hydroxy-N-[(1S)-1-[4-(4-methyl-1,3-thiazol-5-yl)phenyl]ethyl]pyrrolidine-2-carboxamide as a white solid. LC/MS (ESI) m/z: 992.40 [M+1]$^+$; $^1$H-NMR (400 MHz, CD$_3$OD) δ 8.87 (s, 1H), 7.72 (m, 3H), 7.40 (m, 4H), 7.15 (m, 6H), 6.92 (m, 1H), 6.79 (m, 1H), 4.97 (m, 1H), 4.72 (m, 1H), 4.55 (m, 1H), 4.30 (m, 1H), 4.09 (m, 2H), 3.89 (m, 2H), 3.74 (m, 7H), 3.45 (m, 3H), 3.18 (m, 2H), 2.89 (m, 1H), 2.45 (s, 3H), 2.22 (m, 1H), 2.11 (m, 2H), 1.95 (m, 3H), 1.45 (m, 3H), 1.05 (s, 9H).

Compound 147: (2S,4R)—N-[(1S)-1-(4-cyanophenyl)ethyl]-1-[(2S)-2-[2-(2-[2-[4-(4-[[2-(4-fluorophenyl)-6-hydroxy-1-benzothiophen-3-yl]oxy]phenyl)piperidin-1-yl]ethoxy]ethoxy)acetamido]-3,3-dimethylbutanoyl]-4-hydroxypyrrolidine-2-carboxamide Step 1: Preparation of tert-butyl N-[(2S)-1-[(2S,4R)-2-{[(1S)-1-(4-cyanophenyl)ethyl]carbamoyl}-4-hydroxypyrrolidin-1-yl]-3,3-dimethyl-1-oxobutan-2-yl]carbamate To a solution containing (2S,4R)-1-((S)-2-((tert-butoxycarbonyl)amino)-3,3-dimethylbutanoyl)-4-hydroxypyrrolidine-2-carboxylic acid (1.75 g, 5.10 mmol) and (S)-4-(1-aminoethyl)benzonitrile hydrochloride (933.0 mg, 5.10 mmol) in DMF (10.00 ml) at room temperature was added TBTU (2.45 g, 7.64 mmol) and DIPEA (2.70 mL, 15.6 mmol). The mixture was stirred for 2 hours and then quenched with water and extracted with EtOAc. The mixture was washed with water (3×), brine (2×), filtered through a Biotage Universal Phase Separator and then concentrated in vacuum. The crude material was purified by silica gel chromatography on a Teledyne Combiflash ISCO eluting with MeOH/DCM (0:100 to 7:93) to yield tert-butyl ((S)-1-((2S,4R)-2-(((S)-1-(4-cyanophenyl)ethyl)carbamoyl)-4-hydroxypyrrolidin-1-yl)-3,3-dimethyl-1-oxobutan-2-yl)carbamate (2.02 g, 4.27 mmol, 83.8%). LC/MS (ESI) m/z: 473.21 [M+1]$^+$; $^1$H-NMR (400 MHz, CDCl$_3$) δ 7.72 (d, J=4.7 Hz, 1H), 7.64 (dd, J=3.5, 8.2 Hz, 2H), 7.42 (dd, J=3.5, 8.2 Hz, 2H), 5.20 (d, J=8.6 Hz, 1H), 5.05 (dt, J=3.5, 7.0 Hz, 1H), 4.79 (dt, J=3.1, 7.8 Hz, 1H), 4.50 (br. s., 1H), 4.12-4.23 (m, 2H), 3.55 (d, J=11.3 Hz, 1H), 2.52-2.62 (m, 1H), 2.03-2.12 (m, 1H), 1.68 (br. s., 1H), 1.39-1.47 (m, 12H), 1.05 (d, J=3.5 Hz, 9H).

Step 2: Preparation of (2S,4R)-1-[(2S)-2-amino-3,3-dimethylbutanoyl]-N-[(1S)-1-(4-cyanophenyl)ethyl]-4-hydroxypyrrolidine-2-carboxamide hydrochloride A solution of tert-butyl ((S)-1-((2S,4R)-2-(((S)-1-(4-cyanophenyl)ethyl)carbamoyl)-4-hydroxypyrrolidin-1-yl)-3,3-dimethyl-1-oxobutan-2-yl)carbamate (2.03 g, 4.29 mmol) in hydrogen chloride solution (4M) in dioxane (5.93 mL, 171 mmol) was stirred at room temperature for 30 minutes. The reaction mixture was concentrated under reduced pressure to give a white solid. The material was diluted with toluene and concentrated several times and then placed on the high vacuum for 30 minutes to yield an off white solid as (2S,4R)-1-((S)-2-amino-3,3-dimethylbutanoyl)-N-((S)-1-(4-cyanophenyl)ethyl)-4-hydroxypyrrolidine-2-carboxamide hydrochloride (1.60 g, 3.91 mmol, 91.4%). LC/MS (ESI) m/z: 411.24 [M+1]$^+$; $^1$H-NMR (400 MHz, CDCl$_3$) δ 8.68 (d, J=5.9 Hz, 1H), 8.04 (br. s., 3H), 7.54 (d, J=8.6 Hz, 2H), 7.38 (d, J=8.2 Hz, 2H), 4.93-5.04 (m, 2H), 4.56 (br. s., 1H), 4.46 (d, J=4.3 Hz, 1H), 4.09 (d, J=11.7 Hz, 1H), 3.59 (d, J=11.0 Hz, 1H), 2.24 (dd, J=7.6, 13.1 Hz, 1H), 1.93-2.04 (m, 1H), 1.53 (d, J=7.0 Hz, 3H), 1.29 (s, 9H).

Step 3: Preparation of (2S,4R)—N-[(1S)-1-(4-cyanophenyl)ethyl]-1-[(2S)-2-[2-(2-[2-[4-(4-[[2-(4-fluorophenyl)-6-hydroxy-1-benzothiophen-3-yl]oxy]phenyl)piperidin-1-yl]ethoxy]ethoxy)acetamido]-3,3-dimethylbutanoyl]-4-hydroxypyrrolidine-2-carboxamide (147)

Into a 50-mL round-bottom flask, was placed a solution of 2-(2-[2-[4-(4-[[2-(4-fluorophenyl)-6-hydroxy-1-benzothiophen-3-yl]oxy]phenyl)piperidin-1-yl]ethoxy]ethoxy)acetic acid (100.0 mg, 0.18 mmol, 1.00 equiv), (2S,4R)-1-[(2S)-2-amino-3,3-dimethylbutanoyl]-N-[(1S)-1-(4-cyanophenyl)ethyl]-4-hydroxypyrrolidine-2-carboxamide hydrogen chloride (66.0 mg, 0.18 mmol, 1.00 equiv) in N,N-dimethylformamide (5 mL). Then (benzotriazole-1-yloxy)tris (dimethylamino)phosphonium hexafluorophosphate (94.0 mg, 1.20 equiv), N,N-diisopropylethylamine (68.0 mg, 0.53 mmol, 3.00 equiv) were added into at 0° C. The reaction was stirred for 4 hours and then quenched by the addition of water. The resulting solution was extracted with ethyl acetate (20 mL×2), and the organic layers were combined. The solution was washed with brine. The mixture was dried over anhydrous sodium sulfate. The solids were filtered out. The filtrate was concentrated under vacuum. The crude product was purified by preparative HPLC with the following conditions: Column, XBridge Shield RP18 OBD, 5 um, 19×150 mm; mobile phase, water with 0.05% trifluoroacetic acid and acetonitrile/methanol=1/1; Detector, UV 254 nm. This resulted in 35.2 mg (22%) of (2S,4R)—N-[(1S)-1-(4-cyanophenyl)ethyl]-1-[(2S)-2-[2-(2-[2-[4-(4-[[2-(4-fluorophenyl)-6-hydroxy-1-benzothiophen-3-yl]oxy]phenyl)piperidin-1-yl]ethoxy]ethoxy)acetamido]-3,3-dimethylbutanoyl]-4-hydroxypyrrolidine-2-carboxamide as a white solid. LC/MS (ESI) m/z: 920.35 [M+1]$^+$; $^1$H-NMR (400 MHz, CD$_3$OD) δ 7.77 (m, 4H), 7.45 (m, 2H), 7.20 (m, 4H), 7.09 (m, 2H), 6.92 (m, 2H), 6.79 (m, 1H), 4.93 (m, 1H), 4.72 (m, 1H), 4.55 (m, 1H), 4.30 (m, 1H), 4.09 (m, 2H), 3.89 (m, 2H), 3.74 (m, 7H), 3.45 (m, 3H), 3.18 (m, 2H), 2.89 (m, 1H), 2.22 (m, 1H), 2.12 (m, 2H), 1.90 (m, 3H), 1.45 (m, 3H), 1.02 (s, 9H).

Compound 158: (2S,4R)-1-[(2S)-2-[2-(4-[2-[2-(4-[[2-(4-bromophenyl)-6-hydroxy-1-benzothiophen-3-yl]oxy]phenoxy)ethoxy]ethyl]piperazin-1-yl)acetamido]-3,3-dimethylbutanoyl]-4-hydroxy-N-[[4-(4-methyl-1,3-thiazol-5-yl)phenyl]methyl]pyrrolidine-2-carboxamide

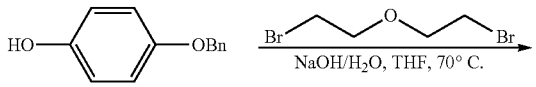

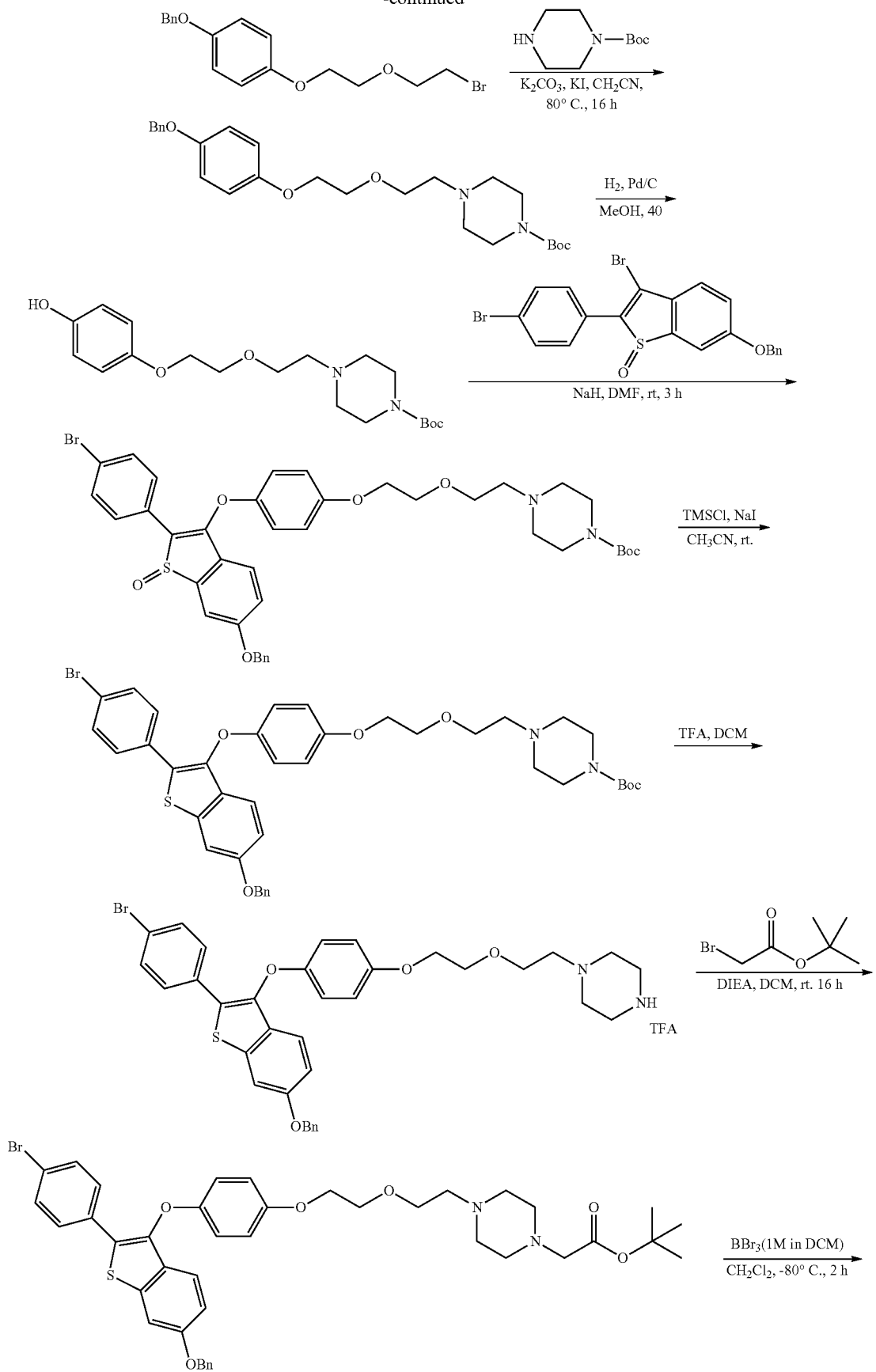

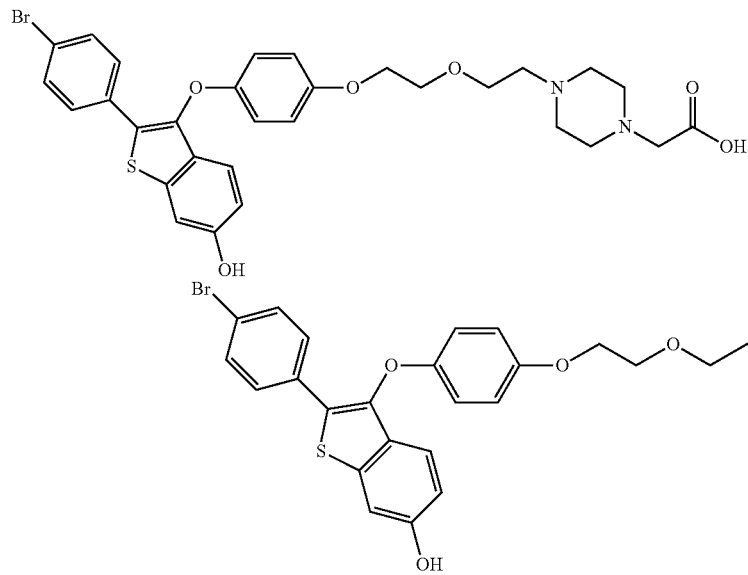
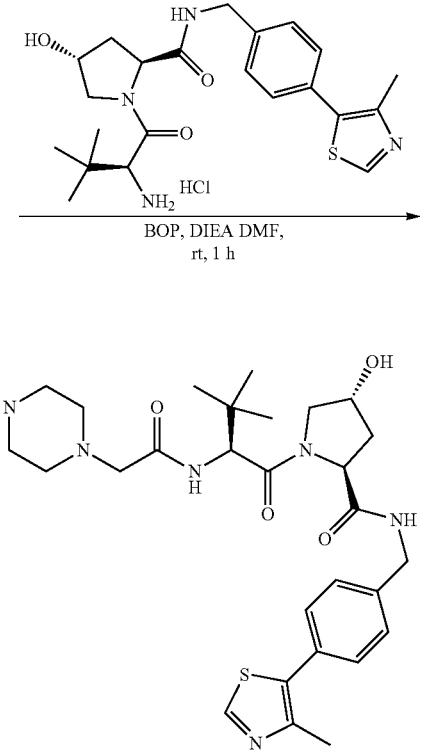

Step 1: Preparation of 1-(benzyloxy)-4-[2-(2-bromoethoxy)ethoxy]benzene

Into a 1000-mL round-bottom flask was placed a solution of 4-(benzyloxy)phenol (5 g, 24.97 mmol, 1.00 equiv) in tetrahydrofuran (200 mL), 37% NaOH (200 mL), and 1-bromo-2-(2-bromoethoxy)ethane (57.5 g, 247.94 mmol, 10.00 equiv). The resulting solution was stirred overnight at 70° C. in an oil bath. The reaction mixture was cooled. The resulting solution was extracted with dichloromethane and the organic layers were combined. The solution was dried over anhydrous sodium sulfate, filtered and concentrated under vacuum. The residue was purified by silica gel column (ethyl acetate/petroleum ether) to afford 1-(benzyloxy)-4-[2-(2-bromoethoxy)ethoxy]benzene (6.67 g, 76%) as a white solid. LC/MS (ESI) m/z: 350.05 [M+1]$^+$.

Step 2: Preparation of tert-butyl 4-(2-[2-[4-(benzyloxy)phenoxy]ethoxy]ethyl)piperazine-1-carboxylate Into a 250-mL round-bottom flask, was placed a solution of 1-(benzyloxy)-4-[2-(2-bromoethoxy)ethoxy]benzene (2 g, 5.69 mmol, 1.00 equiv) in acetonitrile (100 mL), tert-butyl piperazine-1-carboxylate (1.79 g, 9.61 mmol, 1.20 equiv), potassium carbonate (3.31 g, 23.95 mmol, 3.00 equiv), and KI (0.0664 g, 0.05 equiv). The resulting mixture was stirred for 16 hours at 80° C. in an oil bath and then filtered and concentrated under vacuum. The residue was applied onto a silica gel column eluted with dichloromethane/methanol (10:1) to afford tert-butyl 4-(2-[2-[4-(benzyloxy)phenoxy]ethoxy]ethyl)piperazine-1-carboxylate (2.48 g, 95%) as yellow oil. LC/MS (ESI) m/z: 456.26 [M+1]$^+$.

Step 3: Preparation of tert-butyl 4-[2-[2-(4-hydroxyphenoxy)ethoxy]ethyl]piperazine-1-carboxylate To a solution of tert-butyl 4-(2-[2-[4-(benzyloxy)phenoxy]ethoxy]ethyl)piperazine-1-carboxylate (2.48 g, 5.43 mmol, 1.00 equiv) in 50 mL MeOH was added Pd/C (10%, 1.0 g) under nitrogen atmosphere in a 100 ml round bottom flask. The flask was degassed and flushed with hydrogen. The reaction mixture was hydrogenated at 40° C. for 16 hours under hydrogen atmosphere using a hydrogen balloon, then filtered through a Celite pad and concentrated under reduced pressure. The residue was applied onto a silica gel column eluted with dichloromethane/methanol (10:1) to afford tert-butyl 4-[2-[2-(4-hydroxyphenoxy)ethoxy]ethyl]piperazine-1-carboxylate (1.6 g, 80%) as a off-white solid. LC/MS (ESI) m/z: 366.22 [M+1]$^+$.

Step 4: Preparation of tert-butyl 4-[2-[2-(4-[[6-(benzyloxy)-2-(4-bromophenyl)-1-oxo-benzothiophen-3-yl]oxy]phenoxy)ethoxy] ethyl]piperazine-1-carboxylate Into a 100-mL round-bottom flask, was placed a solution of tert-butyl 4-[2-[2-(4-hydroxyphenoxy)ethoxy]ethyl]piperazine-1-carboxylate (500 mg, 1.36 mmol, 1.00 equiv) in N,N-dimethylformamide (30 mL). This was followed by the addition of sodium hydride (56.6 mg, 2.36 mmol, 2.30 equiv) and the mixture was stirred at 0° C. for 30 minutes. To this mixture was added 6-(benzyloxy)-3-bromo-2-(4-bromophenyl)-benzothiophen-1-one (450 mg, 0.92 mmol, 1.20 equiv). The resulting solution was stirred for 16 hours at room temperature and then diluted with ethyl acetate. The mixture was washed with brine, dried over anhydrous sodium sulfate, filtered and concentrated under vacuum. The residue was purified by silica gel column (dichloromethane/methanol=10/1 to 8/1) to afford tert-butyl 4-[2-[2-(4-[[6-(benzyloxy)-2-(4-bromophenyl)-1-oxo-benzothiophen-3-yl]oxy]phenoxy)ethyl]piperazine-1-carboxylate (916 mg, 87%) as yellow crude oil. LC/MS (ESI) m/z: 774.20 $[M+1]^+$.

Step 5: Preparation of tert-butyl 4-[2-(4-[[6-(benzyloxy)-2-(4-bromophenyl)-1-benzothiophen-3-yl]oxy]phenoxy)ethyl]piperazine-1-carboxylate Into a 100-mL round-bottom flask, was placed tert-butyl 4-[2-(4-[[6-(benzyloxy)-2-(4-bromophenyl)-1-oxo-benzothiophen-3-yl]oxy]phenoxy)ethyl]piperazine-1-carboxylate (916 mg, 1.25 mmol, 1.00 equiv), NaI (1882.5 mg, 10.00 equiv), TMSCl (406.6 mg, 3.74 mmol, 3.00 equiv) in 40 mL of acetonitrile. The mixture was stirred for 16 hours at room temperature. The resulting mixture was concentrated under vacuum. The residue was purified by silica gel column (dichloromethane/methanol=(10/1 to 8/1) to afford tert-butyl4-[2-(4-[[6-(benzyloxy)-2-(4-bromophenyl)-1-benzothiophen-3-yl]oxy]phenoxy)ethyl]piperazine-1-carboxylate (147 mg, 16%) as yellow oil. LC/MS (ESI) m/z: 758.20 $[M+1]^+$.

Step 6: Preparation of 1-[2-[2-(4-[[6-(benzyloxy)-2-(4-bromophenyl)-1-benzothiophen-3-yl]oxy]phenoxy)ethoxy] ethyl]piperazine Into a 50-mL round-bottom flask, was placed a solution of tert-butyl 4-[2-[2-(4-[[6-(benzyloxy)-2-(4-bromophenyl)-1-benzothiophen-3-yl]oxy]phenoxy)ethoxy]ethyl]piperazine-1-carboxylate (147 mg, 0.19 mmol, 1.00 equiv) in dichloromethane (10 mL) and trifluoroacetic acid (3 mL). The resulting solution was stirred for 1 hour at room temperature. The resulting mixture was concentrated under vacuum. This resulted in 1-[2-[2-(4-[[6-(benzyloxy)-2-(4-bromophenyl)-1-benzothiophen-3-yl]oxy]phenoxy)ethoxy]ethyl]piperazine; 2,2,2-trifluoroacetaldehyde (920 mg) as yellow crude oil. LC/MS (ESI) m/z: 658.15 $[M+1]^+$.

Step 7: Preparation of tert-butyl 2-(4-[2-[2-(4-[[6-(benzyloxy)-2-(4-bromophenyl)-1-benzothiophen-3-yl]oxy]phenoxy)ethoxy]ethyl]piperazin-1-yl)acetate Into a 100-mL round-bottom flask, was placed a solution of 1-[2-[2-(4-[[6-(benzyloxy)-2-(4-bromophenyl)-1-benzothiophen-3-yl]oxy]phenoxy)ethoxy]ethyl]piperazine in acetonitrile (20 mL), DIEA (2.0 mL), and tert-butyl 2-bromoacetate (619.1 mg, 3.17 mmol, 3.00 equiv). The resulting solution was stirred for 3 h at room temperature and then evaporated. The residue was diluted with dichloromethane and washed with brine. The mixture was dried over anhydrous sodium sulfate, filtered and concentrated under vacuum. The residue was applied onto a silica gel column eluted with ethyl acetate/petroleum ether. This resulted in tert-butyl 2-(4-[2-[2-(4-[[6-(benzyloxy)-2-(4-bromophenyl)-1-benzothiophen-3-yl]oxy]phenoxy)ethoxy]ethyl]piperazin-1-yl)acetate (280 mg, 39%) as yellow oil. LC/MS (ESI) m/z: 772.22 $[M+1]^+$.

Step 8: Preparation of 2-(4-[2-[2-(4-[[2-(4-bromophenyl)-6-hydroxy-1-benzothiophen-3-yl]oxy]phenoxy)ethoxy]ethyl]piperazin-1-yl)acetic acid Into a 100-mL round-bottom flask, was placed a solution of tert-butyl 2-(4-[2-[2-(4-[[6-(benzyloxy)-2-(4-bromophenyl)-1-benzothiophen-3-yl]oxy]phenoxy)ethoxy] ethyl]piperazin-1-yl)acetate (266 mg, 0.34 mmol, 1.00 equiv) in dichloromethane (30 mL). This was followed by the addition of $BBr_3$ (10 mL) dropwise with stirring at −70° C. The resulting solution was stirred for 4 h at −70° C. The reaction was then quenched by the addition of water. The resulting mixture was concentrated under vacuum. The crude product was purified by preparative HPLC and resulted in 2-(4-[2-[2-(4-[[2-(4-bromophenyl)-6-hydroxy-1-benzothiophen-3-yl]oxy]phenoxy)ethoxy]ethyl]piperazin-1-yl)acetic acid (147 mg, 68%) as yellow oil. LC/MS (ESI) m/z: 626.11 $[M+1]^+$.

Step 9: Preparation of (2S,4R)-1-[(2S)-2-[2-(4-[2-[2-(4-[[2-(4-bromophenyl)-6-hydroxy-1-benzothiophen-3-yl]oxy]phenoxy)ethoxy]ethyl]piperazin-1-yl)acetamido]-3,3-dimethylbutanoyl]-4-hydroxy-N-[[4-(4-methyl-1,3-thiazol-5-yl)phenyl]methyl] pyrrolidine-2-carboxamide (Compound 158)

Into a 50-mL round-bottom flask, was placed a solution of 2-(4-[2-[2-(4-[[2-(4-bromophenyl)-6-hydroxy-1-benzothiophen-3-yl]oxy]phenoxy)ethoxy]ethyl]piperazin-1-yl)acetic acid (50 mg, 0.08 mmol, 1.00 equiv) in N,N-dimethylformamide (20 mL). To this solution was added (2S,4R)-1-[(2S)-2-amino-3,3-dimethylbutanoyl]-4-hydroxy-N-[[4-(4-methyl-1,3-thiazol-5-yl)phenyl]methyl]pyrrolidine-2-carboxamide (37.3 mg, 0.09 mmol, 1.00 equiv), BOP (35.3 mg, 1.00 equiv), and DIEA (2 mL). The mixture was stirred for 1 hour at 0° C. in a water/ice bath. The resulting solution was diluted with ethyl acetate and washed with brine. The solution was dried over anhydrous sodium sulfate, filtered and concentrated under vacuum. The crude product was purified by preparative HPLC with the following conditions: Column, XSelect CSH Prep C18 OBD, 5 um, 19×150 mm; mobile phase, water (0.1% formic acid) and acetonitrile (32.0% to 52.0% acetonitrile in 8 min); Detector, UV 254 nm. This resulted in (2S,4R)-1-[(2S)-2-[2-(4-[2-[2-(4-[[2-(4-bromophenyl)-6-hydroxy-1-benzothiophen-3-yl]oxy]phenoxy)ethoxy]ethyl]piperazin-1-yl)acetamido]-3,3-dimethylbutanoyl]-4-hydroxy-N-[[4-(4-methyl-1,3-thiazol-5-yl)phenyl]methyl]pyrrolidine-2-carboxamide (31.3 mg, 38%) as a white solid. LC/MS (ESI) m/z: 1038.30/1040.30 $[M+1]^+$; $^1$H-NMR (300 MHz, $CD_3OD$) δ 8.862 (s, 1H), 8.323 (s, 1H), 7.64-7.60 (m, 2H), 7.49-7.37 (m, 5H), 7.18-7.15 (m, 2H), 6.83-6.75 (m, 5H), 4.63-4.31 (m, 5H), 4.08-4.05 (m, 2H), 3.85-3.78 (m, 5H), 3.18-3.07 (m, 7H), 2.71-2.62 (m, 3H), 2.45-2.40 (m, 3H), 2.29-2.03 (m, 2H), 1.28-1.27 (m, 1H), 1.01-0.99 (m, 9H).

Compound 164: (2S,4R)-1-((S)-2-(3-(2-(4-(2-(4-((2-(4-bromophenyl)-6-hydroxybenzo[b]thiophen-3-yl)oxy)phenoxy)ethyl)piperazin-1-yl)ethoxy)isoxazol-5-yl)-3-methylbutanoyl)-4-hydroxy-N-(4-(4-methylthiazol-5-yl)benzyl)pyrrolidine-2-carboxamide

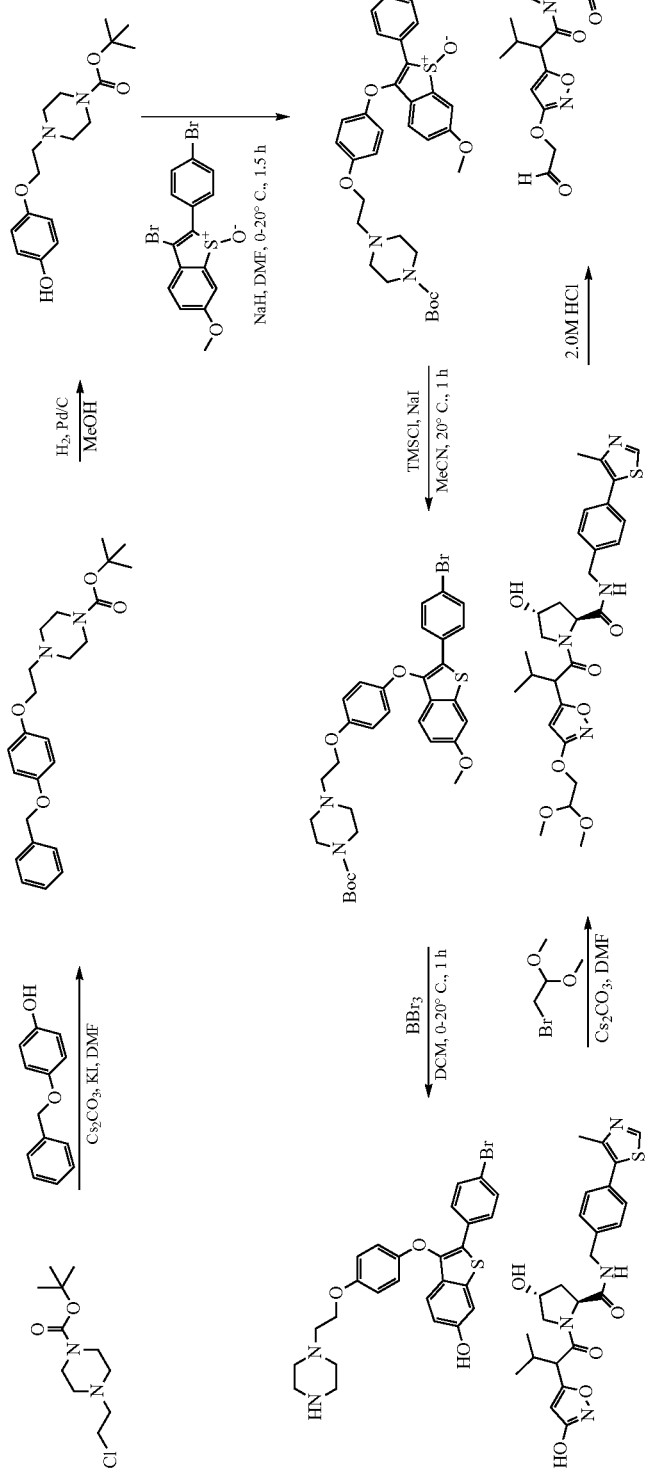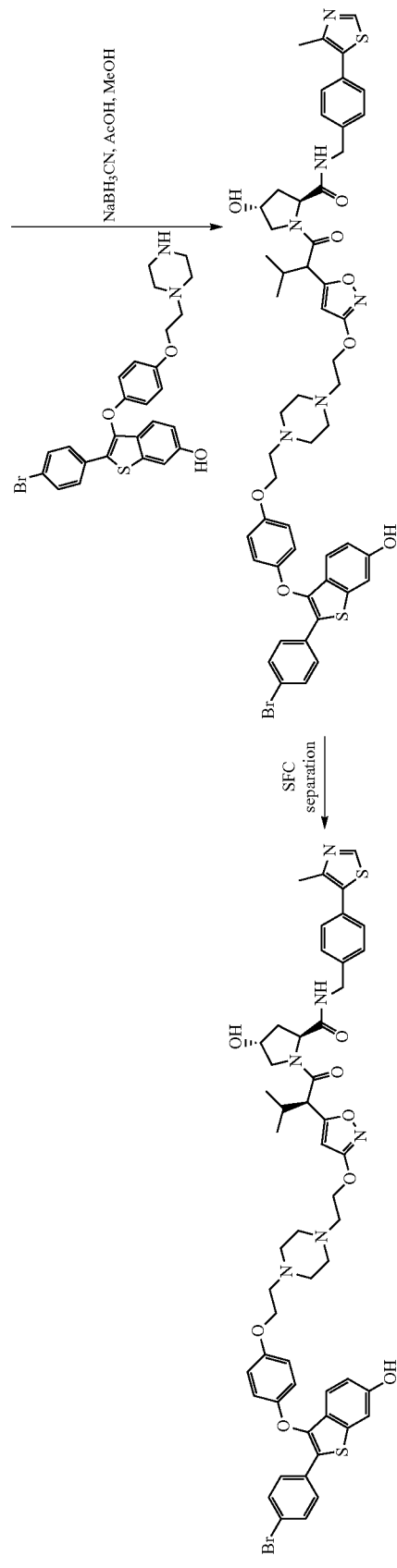

Step 1: Preparation of tert-butyl4-[2-(4-benzyloxy-phenoxy)ethyl]piper azine-1-carboxylate To a solution of tert-butyl 4-(2-chloroethyl)piperazine-1-carboxylate (1.00 g, 4.02 mmol, 1.00 eq), 4-benzyloxyphenol (965 mg, 4.82 mmol, 1.20 eq) in N,N-dimethylformamide (20 mL) was added cesium carbonate (1.57 g, 4.82 mmol, 1.20 eq) and potassium iodide (66 mg, 0.4 mmol, 0.10 eq) under nitrogen. The reaction was stirred at 80° C. for 10 hours. TLC (Petroleum ether/Ethyl acetate=3/1) and LC/MS showed most of the starting material was consumed. Water (100 mL) was added to the mixture, and the resulting mixture was extracted with ethyl acetate (50 mL×3). The combined organic phase was washed with brine (80 mL), dried over sodium sulfate, filtered and concentrated under vacuum. The residue was purified by silica gel column chromatography (petroleum ether/ethyl acetate=50/1 to 3/1) to provide tert-butyl 4-[2-(4-benzyloxyphenoxy)ethyl]piperazine-1-carboxylate (1.4 g, 3.39 mmol, 84% yield) as a colorless oil. $^1$H NMR (400 MHz, CDCl$_3$) δ 7.46-7.29 (m, 5H), 6.95-6.88 (m, 2H), 6.88-6.81 (m, 2H), 5.02 (s, 2H), 4.07 (t, J=5.8 Hz, 2H), 3.51-3.42 (m, 4H), 2.80 (t, J=5.8 Hz, 2H), 2.56-2.48 (m, 4H), 1.47 (s, 9H).

Step 2: Preparation of tert-butyl 4-[2-(4-hydroxyphenoxy)ethyl]piper azine-1-carboxylate To a solution of tert-butyl 4-[2-(4-benzyloxyphenoxy) ethyl]piperazine-1-carboxylate (1.40 g, 3.39 mmol, 1.00 eq) in methanol (20 mL) was added palladium on carbon (200 mg, 10% purity) under nitrogen. The suspension was degassed under vacuum and purged with hydrogen several times. The mixture was stirred under hydrogen (50 psi) at 20° C. for 4 hours. TLC (petroleum ether/ethyl acetate=1/1) showed most of the starting material was consumed. The reaction mixture was filtered and the filtrate was evaporated and dried under vacuum to provide tert-butyl 4-[2-(4-hydroxyphenoxy)ethyl]piperazine-1-carboxylate (1 g, 3.07 mmol, 90% yield, 99% purity as a light yellow solid. $^1$H NMR (400 MHz, CDCl$_3$) δ 6.74 (s, 4H), 4.04 (t, J=5.6 Hz, 2H), 3.54-3.38 (m, 5H), 2.79 (t, J=5.6 Hz, 2H), 2.53 (s, 4H), 1.46 (s, 9H).

Step 3: Preparation of tert-butyl 4-(2-(4-((2-(4-bromophenyl)-6-methoxy-1-oxidobenzo[b]thiophen-3-yl)oxy)phenoxy)ethyl)piperazine-1-carboxylate To a solution of tert-butyl 4-[2-(4-hydroxyphenoxy)ethyl] piperazine-1-carboxylate (234 mg, 0.72 mmol, 1.00 eq) in N,N-dimethylformamide (5 mL) was added NaH (29 mg, 0.72 mmol, 60% mineral oil, 1.00 eq) at 0° C. The mixture was stirred at 20° C. for 0.5 hour. Then 3-bromo-2-(4-bromophenyl)-6-methoxy-1-oxido-benzothiophen-1-ium (300 mg, 0.72 mmol, 1.00 eq) was added, and the mixture was stirred at 20° C. for 1 hour. LC/MS showed the reaction was completed and desired MS can be detected. The reaction mixture was quenched with water (10 mL) and extracted with ethyl acetate (10 mL×3). The combined organic phase was washed with brine (10 mL×2), dried over anhydrous sodium sulfate, filtered and concentrated in vacuum to afford tert-butyl 4-[2-[4-[2-(4-bromophenyl)-6-methoxy-1-oxido-benzothiophen-1-ium-3-yl]oxyphenoxy]ethyl]piperazine-1-carboxylate (430 mg, 0.66 mmol, 90% yield) as a yellow solid, which was directly used for next step without further purification. LC/MS (ESI) m/z: 657.5 [M+1]$^+$; $^1$H NMR (400 MHz, CDCl$_3$) δ 7.65 (d, J=8.4 Hz, 2H), 7.52-7.46 (m, 3H), 7.05-6.89 (m, 4H), 6.81 (d, J=8.4 Hz, 2H), 4.05 (t, J=5.6 Hz, 2H), 3.89 (s, 3H), 3.50-3.42 (m, 4H), 2.81 (t, J=5.6 Hz, 2H), 2.52 (s, 4H), 1.47 (s, 9H).

Step 4: Preparation of tert-butyl 4-(2-(4-((2-(4-bromophenyl)-6-methoxybenzo[b]thiophen-3-yl)oxy) phenoxy)ethyl)piperazine-1-carboxylate To a solution of tert-butyl 4-[2-[4-[2-(4-bromophenyl)-6-methoxy-1-oxido-benzothiophen-1-ium-3-yl]oxyphenoxy] ethyl]piperazine-1-carboxylate (370 mg, 0.56 mmol, 1.00 eq) in acetonitrile (6 mL) was added sodium iodide (254 mg, 1.69 mmol, 3.00 eq) and trimethylchlorosilane (123 mg, 1.13 mmol, 2.00 eq). The mixture was stirred at 20° C. for 1 hour. LC/MS showed the reaction was completed and desired MS was detected. The reaction mixture was quenched with saturated sodium sulfite (2 mL), diluted with water (15 mL) and extracted with ethyl acetate (10 mL×2). The combined organic phase was washed with brine (10 mL×2), dried over anhydrous sodium sulfate, filtered and concentrated in vacuum to give the crude product tert-butyl 4-[2-[4-[2-(4-bromophenyl)-6-methoxy-benzothiophen-3-yl]oxyphenoxy]ethyl] piperazine-1-carboxylate (350 mg, crude) as a yellow oil, which was directly used for next step without further purification. LC/MS (ESI) m/z: 639.0 [M+1]$^+$.

Step 5: Preparation of 2-(4-bromophenyl)-3-(4-(2-(piperazin-1-yl)ethoxy) phenoxy)benzo[b]thiophen-6-ol To a solution of tert-butyl 4-[2-[4-[2-(4-bromophenyl)-6-methoxy-benzothiophen-3-yl] oxyphenoxy]ethyl]piperazine-1-carboxylate (350 mg, 0.55 mmol, 1.00 eq) in dichloromethane (6 mL) was added boron tribromide (410 mg, 1.64 mmol, 0.16 mL, 3.00 eq) at 0° C. The mixture was stirred at 20° C. for 1 hour. The reaction mixture was quenched with saturated sodium bicarbonate (5 mL) at 0° C., diluted with water (10 mL) and extracted with dichloromethane (10 mL×3). The combined organic phase was washed with brine (5 mL×2), dried over anhydrous sodium sulfate, filtered and concentrated in vacuum to give 2-(4-bromophenyl)-3-[4-(2-piperazin-1-ylethoxy)phenoxy]benzothiophen-6-ol (250 mg, crude) as a yellow solid, which was directly used for next step without further purification. LC/MS (ESI) m/z: 527.0 [M+1]$^+$; $^1$H NMR (400 MHz, DMSO) δ 7.65-7.56 (m, 4H), 7.31 (d, J=2.0 Hz, 1H), 7.14 (d, J=8.4 Hz, 1H), 6.86 (s, 4H), 6.83 (dd, J=2.0, 8.4 Hz, 1H), 5.75 (s, 1H), 3.97 (t, J=5.6 Hz, 2H), 2.78-2.66 (m, 4H), 2.61 (t, J=5.6 Hz, 2H), 2.40 (s, 4H), 2.45-2.34 (m, 1H).

Step 6: Preparation of (2S,4R)-1-(2-(3-(2,2-dimethoxyethoxy)isoxazol-5-yl)-3-methylbutanoyl)-4-hydroxy-N-(4-(4-methylthiazol-5-yl)benzyl)pyrrolidine-2-carboxamide To a solution of (2S,4R)-4-hydroxy-1-[2-(3-hydroxy-isoxazol-5-yl)-3-methyl-butanoyl]-N-[[4-(4-methylthiazol-5-yl)phenyl]methyl]pyrrolidine-2-carboxamide (220 mg, 0.45 mmol, 1.00 eq) and 2-bromo-1,1-dimethoxy-ethane (153 mg, 0.91 mmol, 2.00 eq) in N,N-dimethylformamide (5 mL) was added cesium carbonate (296 mg, 0.91 mmol, 2.00 eq). The mixture was stirred at 100° C. for 3 hours. The mixture was poured into brine (50 mL), and then extracted with ethyl acetate (50 mL×2). The combined organic layers were washed with brine (50 mL×3), dried over anhydrous sodium sulfate, filtered and concentrated in vacuum to afford (2S,4R)-1-[2-[3-(2,2-dimethoxyethoxy)isoxazol-5-yl]-3-methyl-butanoyl]-4-hydroxy-N-[[4-(4-methylthiazol-5-yl)phenyl]methyl]pyrrolidine-2-carboxamide (220 mg, crude) as a yellow oil, which was directly used for next step without further purification. LC/MS (ESI) m/z: 573.2 [M+1]⁺.

Step 7: Preparation of (2S,4R)-4-hydroxy-1-(3-methyl-2-(3-(2-oxoethoxy)isoxazol-5-yl)butanoyl)-N-(4-(4-methylthiazol-5-yl)benzyl)pyrrolidine-2-carboxamide To a solution of (2S,4R)-1-[2-[3-(2,2-dimethoxyethoxy)isoxazol-5-yl]-3-methyl-butanoyl]-4-hydroxy-N-[[4-(4-methylthiazol-5-yl)phenyl]methyl]pyrrolidine-2-carboxamide (200 mg, 0.35 mmol, 1.00 eq) in dioxane (2 mL) was added hydrochloric acid (2.0M, 2 mL). The mixture was stirred at 50° C. for 3 hours. The mixture was diluted with brine (30 mL), adjusted the pH to 7.0-8.0 with sodium carbonate solid, and then extracted with ethyl acetate (30 mL×5). The combined organic layers were dried over anhydrous sodium sulfate, filtered and concentrated in vacuum to afford (2S,4R)-4-hydroxy-1-[3-methyl-2-[3-(2-oxoethoxy)isoxazol-5-yl] butanoyl]-N-[[4-(4-methylthiazol-5-yl)phenyl]methyl]pyrrolidine-2-carboxamide (160 mg, crude) as a yellow oil, which was directly used for next step without further purification. LC/MS (ESI) m/z: 527.1 [M+1]⁺.

Step 8: Preparation of (2S,4R)-1-(2-(3-(2-(4-(2-(4-((2-(4-bromophenyl)-6-hydroxybenzo[b]thiophen-3-yl)oxy)phenoxy)ethyl)piperazin-1-yl)ethoxy)isoxazol-5-yl)-3-methylbutanoyl)-4-hydroxy-N-(4-(4-methylthiazol-5-yl)benzyl)pyrrolidine-2-carboxamide To a solution of (2S,4R)-4-hydroxy-1-[3-methyl-2-[3-(2-oxoethoxy)isoxazol-5-yl]butanoyl]-N-[[4-(4-methylthiazol-5-yl)phenyl]methyl]pyrrolidine-2-carboxamide (160 mg, 0.30 mmol, 1.00 eq) and 2-(4-bromophenyl)-3-[4-(2-piperazin-1-ylethoxy)phenoxy]benzothiophen-6-ol (184 mg, 0.30 mmol, 1.00 eq, hydrobromide salt) in methanol (5 mL) was added acetic acid (5 mg, 0.06 mmol, 0.20 eq). The mixture was stirred at 20° C. for 1 hour. Then sodium cyanoborohydride (38 mg, 0.60 mmol, 2.00 eq) was added. The resulting mixture was stirred at 20° C. for another 14 hours. The resulting solution was poured into saturated sodium bicarbonate solution (50 mL), and then extracted with ethyl acetate (50 mL×2). The combined organic layers were dried over anhydrous sodium sulfate, filtered and concentrated in vacuum. The residue was purified by preparative HPLC (Phenomenex Synergi C18 150×25 mm, 10 um; mobile phase: [water (0.05% HCl)-ACN]; B %: 35%-55%, 7.8 min) to afford (2S,4R)-1-(2-(3-(2-(4-(2-(4-((2-(4-bromophenyl)-6-hydroxybenzo[b]thiophen-3-yl)oxy)phenoxy)ethyl)piperazin-1-yl)ethoxy)isoxazol-5-yl)-3-methylbutanoyl)-4-hydroxy-N-(4-(4-methylthiazol-5-yl)benzyl)pyrrolidine-2-carboxamide (85 mg, 0.08 mmol, 27% yield) as an off-white solid. LC/MS (ESI) m/z: 1037.1 [M+1]⁺.

Step 9: Preparation of (2S,4R)-1-((S)-2-(3-(2-(4-(2-(4-((2-(4-bromophenyl)-6-hydroxybenzo[b]thiophen-3-yl)oxy)phenoxy)ethyl)piperazin-1-yl)ethoxy)isoxazol-5-yl)-3-methylbutanoyl)-4-hydroxy-N-(4-(4-methylthiazol-5-yl)benzyl)pyrrolidine-2-carboxamide (Compound 164)

(2S,4R)-1-[2-[3-[2-[4-[2-[4-[2-(4-bromophenyl)-6-hydroxy-benzothiophen-3-yl]oxyphenoxy]ethyl]piperazin-1-yl]ethoxy]isoxazol-5-yl]-3-methyl-butanoyl]-4-hydroxy-N-[[4-(4-methylthiazol-5-yl)phenyl]methyl]pyrrolidine-2-carboxamide (85 mg, 0.08 mmol, 1.00 eq) was separated by SFC (column: OD, 250 mm×50 mm, 10 um); mobile phase: [0.1% NH₃H₂O EtOH]; B %: 60%-60%, 3.3 min each run, 70 min total) to afford (2S,4R)-1-[(2R)-2-[3-[2-[4-[2-[4-[2-(4-bromophenyl)-6-hydroxy-benzothiophen-3-yl]oxyphenoxy]ethyl]piperazin-1-yl]ethoxy]isoxazol-5-yl]-3-methyl-butanoyl]-4-hydroxy-N-[[4-(4-methylthiazol-5-yl)phenyl]methyl]pyrrolidine-2-carboxamide (19 mg, 0.018 mmol, 56% yield, 99% purity) and (2S,4R)-1-[(2S)-2-[3-[2-[4-[2-[4-[2-(4-bromophenyl)-6-hydroxy-benzothiophen-3-yl]oxyphenoxy]ethyl]piperazin-1-yl]ethoxy]isoxazol-5-yl]-3-methyl-butanoyl]-4-hydroxy-N-[[4-(4-methylthiazol-5-yl)phenyl]methyl]pyrrolidine-2-carboxamide (50 mg, 0.46 mmol, 93% yield, 96% purity) as a yellow solid. LC/MS (ESI) m/z: 1037.3 [M+1]⁺; ¹H-NMR for Compound 164 (400 MHz, CD₃OD) δ 8.89 (s, 1H), 7.64 (d, J=8.8 Hz, 2H), 7.51-7.48 (m, 6H), 7.22-7.19 (m, 2H), 6.92-6.79 (m, 5H), 6.05 (s, 1H), 4.60-4.42 (m, 6H), 3.90-3.68 (m, 5H), 3.20-2.74 (m, 12H), 2.49 (s, 3H), 2.48-2.45 (m, 1H), 2.38-2.35 (m, 1H), 2.10-2.08 (m, 1H), 1.05 (d, J=7.2 Hz, 3H), 0.90 (d, J=7.2 Hz, 3H).

Compound 232: 3-[5-[4-[[1-[5-[2-(4-fluorophenyl)-6-hydroxy-benzothiophen-3-yl]oxy-2-pyridyl]-4-piperidyl]methyl]piperazin-1-yl]-1-oxo-isoindolin-2-yl]piperidine-2,6-dione

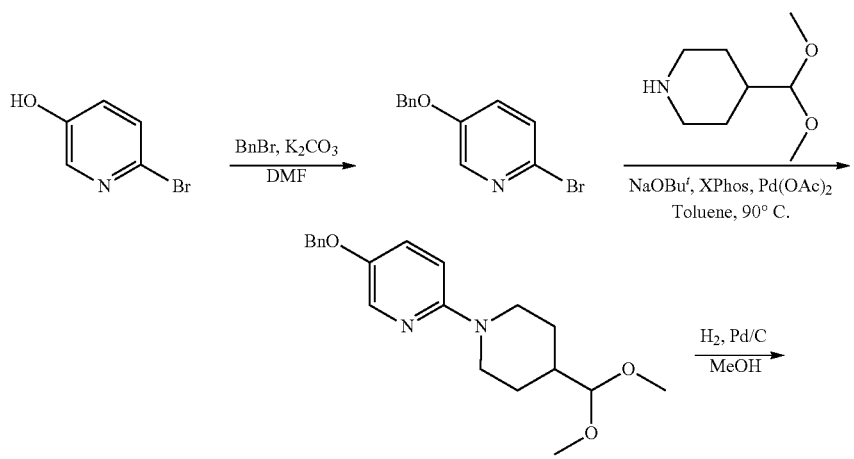

-continued
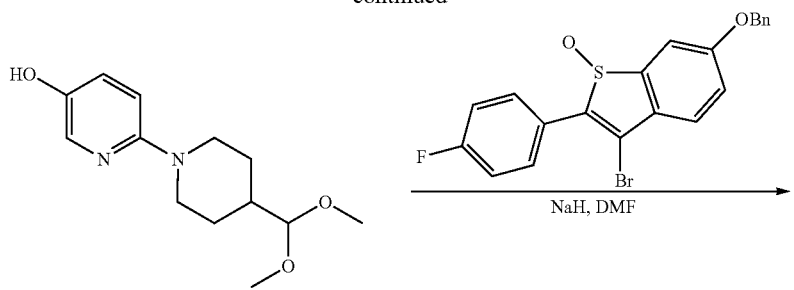
NaH, DMF
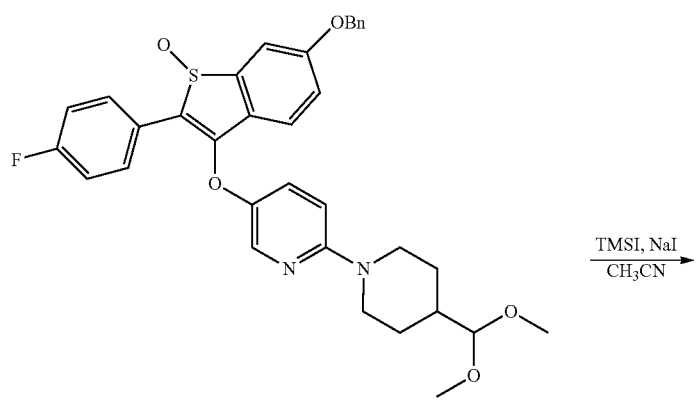
TMSI, NaI
CH₃CN
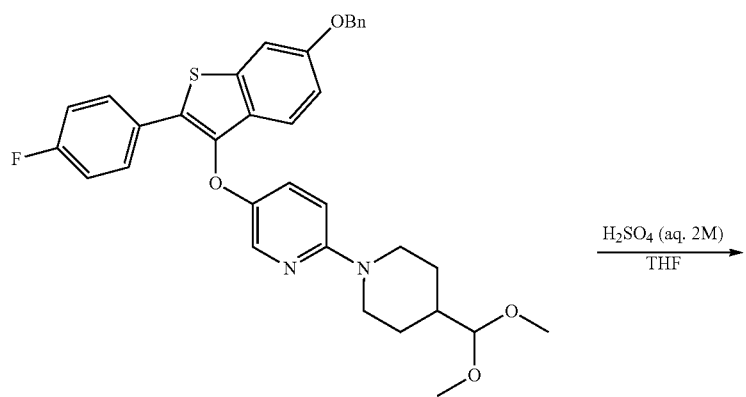
H₂SO₄ (aq. 2M)
THF
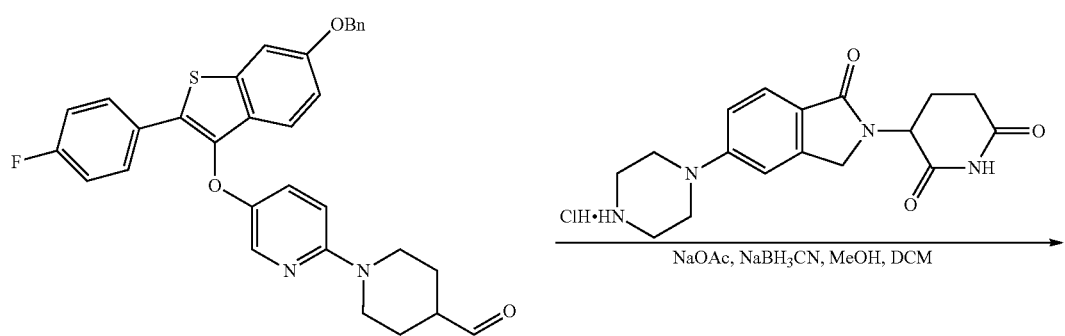
NaOAc, NaBH₃CN, MeOH, DCM -continued

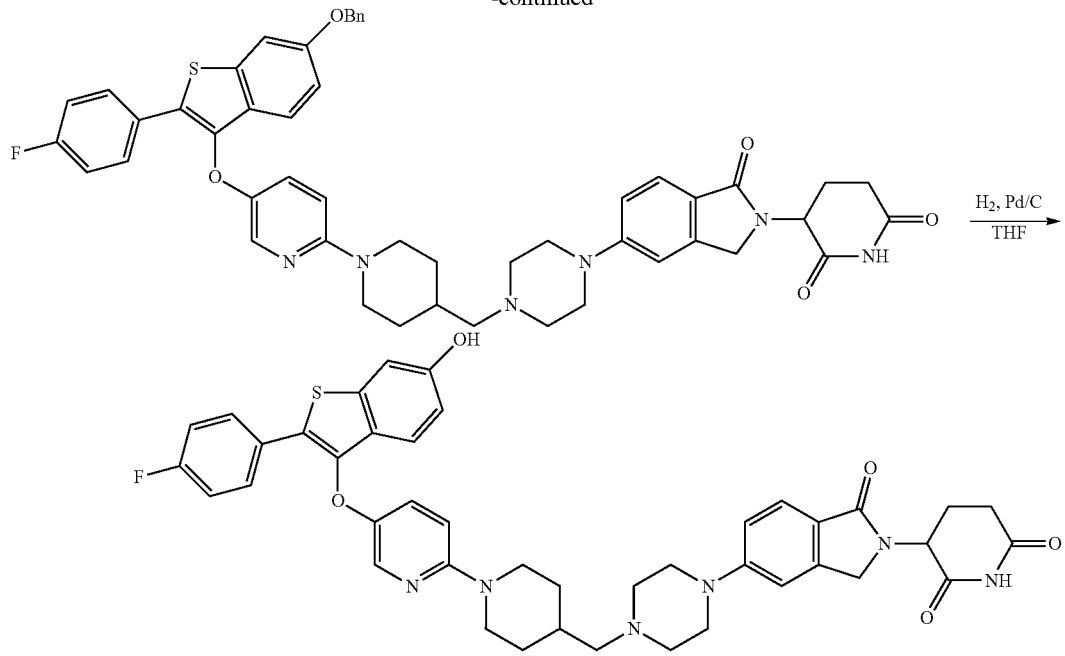

Step 1: Preparation of 5-benzyloxy-2-bromo-pyridine

To a solution of 6-bromopyridin-3-ol (2 g, 11.49 mmol, 1 eq) in N,N-dimethylformamide (20 mL) was added potassium carbonate (3.18 g, 22.99 mmol, 2 eq) and benzyl bromide (2.16 g, 12.64 mmol, 1.5 mL, 1.1 eq). The mixture was stirred at 20° C. for 2 hours. Thin layer chromatography (petroleum ether:ethyl acetate=3:1) indicated the starting material was consumed completely and one new spot formed. The reaction mixture was diluted with water (50 mL) and extracted with ethyl acetate (20 mL×3). The combined organic layers were washed with brine (30 mL), dried over anhydrous sodium sulfate, filtered and concentrated under reduced pressure. The residue was purified by silica gel column chromatography (petroleum ether:ethyl acetate=1:0 to 50:1). Compound 5-benzyloxy-2-bromo-pyridine (2.6 g, 9.84 mmol, 86% yield) was obtained as a white solid. $^1$H NMR (400 MHz, CDCl$_3$-d) δ 8.14 (d, J=3.2 Hz, 1H), 7.46-7.31 (m, 6H), 7.16 (dd, J=3.2, 8.8 Hz, 1H), 5.10 (s, 2H).

Step 2: Preparation of 5-benzyloxy-2-[4-(dimethoxymethyl)-1-piperidyl]pyridine To a solution containing 5-benzyloxy-2-bromo-pyridine (2.4 g, 9.09 mmol, 1 eq), 4-(dimethoxymethyl)piperidine (2.67 g, 13.63 mmol, 1.5 eq, HCl) in toluene (20 mL) was added sodium tert-butoxide (2.62 g, 27.26 mmol, 3 eq), XPhos (866 mg, 1.82 mmol, 0.2 eq) and palladium acetate (306 mg, 1.36 mmol, 0.15 eq) under nitrogen. The reaction mixture was stirred at 90° C. for 16 hours. Thin layer chromatography (petroleum ether:ethyl acetate=3:1) indicated the starting material was consumed completely and one new spot was formed. The reaction mixture was filtered and the filtrate was concentrated. Water (50 mL) was poured into the mixture and stirred for 1 minute. The aqueous phase was extracted with ethyl acetate (30 mL×3). The combined organic phase was washed with brine (50 mL×2), dried over anhydrous sodium sulfate, filtered and concentrated in vacuum. The crude product was triturated with dichloromethane and methanol (10/1, 50 mL x 2). Compound 5-benzyloxy-2-[4-(dimethoxymethyl)-1-piperidyl]pyridine (2.95 g, 8.61 mmol, 95% yield) was confirmed by $^1$H NMR as a yellow solid. $^1$H NMR (400 MHz, CDCl$_3$-d) δ: 7.98 (d, J=2.8 Hz, 1H), 7.49-7.29 (m, 5H), 7.18 (dd, J=3.2, 9.2 Hz, 1H), 6.64 (d, J=9.2 Hz, 1H), 5.02 (s, 2H), 4.06 (d, J=6.8 Hz, 1H), 3.67 (s, 6H), 2.79-2.66 (m, 2H), 1.95-1.64 (m, 5H), 1.45-1.33 (m, 2H).

Step 3: Preparation of 6-[4-(dimethoxymethyl)-1-piperidyl]pyridin-3-ol

To a solution of 5-benzyloxy-2-[4-(dimethoxymethyl)-1-piperidyl]pyridine (3 g, 8.76 mmol, 1 eq) in methanol (15 mL) was added palladium (10%) on activated carbon catalyst (300 mg). The mixture was stirred at 20° C. for 12 h under hydrogen (15 psi). The reaction mixture was filtered and concentrated under reduced pressure. The residue was purified by silica gel column chromatography (petroleum ether:ethyl acetate=20:1 to 3:1). The desired compound 6-[4-(dimethoxymethyl)-1-piperidyl]pyridin-3-ol (1.54 g, 6.10 mmol, 70% yield) was obtained as a light yellow solid. $^1$H-NMR (400 MHz, CDCl$_3$-d) δ 7.83 (d, J=2.8 Hz, 1H), 7.11 (dd, J=3.2, 9.2 Hz, 1H), 6.64 (d, J=9.2 Hz, 1H), 4.12-4.00 (m, 3H), 3.37 (s, 6H), 2.72 (dt, J=2.0, 12.4 Hz, 2H), 1.91-1.71 (m, 3H), 1.47-1.30 (m, 2H).

Step 4: Preparation of 5-[6-benzyloxy-2-(4-fluorophenyl)-1-oxido-benzothiophen-1-ium-3-yl]oxy-2-[4-(dimethoxymethyl)-1-piperidyl]pyridine To a solution of 6-[4-(dimethoxymethyl)-1-piperidyl]pyridin-3-ol (176 mg, 0.70 mmol, 1 eq) in N,N-dimethylformamide (8 mL) was added sodium hydride (34 mg, 0.84 mmol, 60% in mineral oil, 1.2 eq) at 0° C. The mixture was stirred at 0° C. for 0.5 hour, then to the mixture was added 6-benzyloxy-3-bromo-2-(4-fluorophenyl)-1-oxido-benzothiophen-1-ium (300 mg, 0.70 mmol, 1 eq). The reaction mixture was stirred at 20° C. for 1 hour. The reaction was quenched by addition of saturated ammonium chloride solution (10 mL) at 20° C., and then diluted with water 10 mL and extracted with ethyl acetate (20 mL×3). The combined organic layers were washed with brine (30 mL×2), dried over anhydrous sodium sulfate, filtered and concentrated under reduced pressure. The residue was purified by silica gel chromatography (petroleum ether:ethyl acetate=20/1 to 3/1). The desired compound 5-[6-benzyloxy-2-(4-fluorophenyl)-1-oxido-benzothiophen-1-ium-3-yl]oxy-2-[4-(dimethoxymethyl)-1-piperidyl]pyridine (350 mg, 0.58 mmol, 83% yield) was obtained as a light yellow solid.

Step 5: Preparation of 5-[6-benzyloxy-2-(4-fluorophenyl)benzothiophen-3-yl]oxy-2-[4-(dimethoxymethyl)-1-piperidyl]pyridine To a solution of 5-[6-benzyloxy-2-(4-fluorophenyl)-1-oxido-benzothiophen-1-ium-3-yl]oxy-2-[4-(dimethoxymethyl)-1-piperidyl]pyridine (350 mg, 0.58 mmol, 1 eq) in acetonitrile (4 mL) was added trimethylchlorosilane (190 mg, 1.75 mmol, 3 eq) and sodium iodide (262 mg, 1.75 mmol, 3 eq). The mixture was stirred at 20° C. for 1 hour and quenched with water. The reaction mixture was extracted with ethyl acetate (20 mL×2). The combined organic layers were first washed with anhydrous sodium sulfite (40 mL), then washed with brine (40 mL), dried over anhydrous sodium sulfate, filtered and concentrated under reduced pressure. The product was taken to the next step without further purification. The desired compound 5-[6-benzyloxy-2-(4-fluorophenyl)benzothiophen-3-yl]oxy-2-[4-(dimethoxymethyl)-1-piperidyl]pyridine (320 mg, 0.55 mmol, 94% yield) was obtained as a light yellow oil. LC/MS (ESI) m/z: 585.1 [M+1]$^+$.

Step 6: Preparation of 1-[5-[6-benzyloxy-2-(4-fluorophenyl)benzothiophen-3-yl]oxy-2-pyridyl]piperidine-4-carbaldehyde To a solution of 5-[6-benzyloxy-2-(4-fluorophenyl)benzothiophen-3-yl]oxy-2-[4-(dimethoxymethyl)-1-piperidyl]pyridine (320 mg, 0.55 mmol, 1 eq) in tetrahydrofuran (11 mL) was added sulfuric acid (2M, 11 mL, 40 eq). The reaction mixture was stirred at 70° C. for 0.5 hour. LC-MS showed the starting material was consumed completely and one main peak with desired MS was detected. The reaction mixture was quenched by addition of saturated sodium bicarbonate solution to adjust pH to 7-8, and extracted with ethyl acetate (30 mL×2). The combined organic layers were washed with brine (30 mL), dried over sodium sulfate, filtered and concentrated under reduced pressure. The product was taken to the next step without further purification. The desired compound 1-[5-[6-benzyloxy-2-(4-fluorophenyl)benzothiophen-3-yl]oxy-2-pyridyl]piperidine-4-carbaldehyde (270 mg, 0.5 mmol, 92% yield) was obtained as a light yellow oil. LC/MS (ESI) m/z: 539.1 [M+1]$^+$.

Step 7: Preparation of 3-[5-[4-[[1-[5-[6-benzyloxy-2-(4-fluorophenyl)benzothiophen-3-yl]oxy-2-pyridyl]-4-piperidyl] methyl]piperazin-1-yl]-1-oxo-isoindolin-2-yl]piperidine-2,6-dione To a solution of 3-(1-oxo-5-piperazin-1-yl-isoindolin-2-yl)piperidine-2,6-dione (176 mg, 0.48 mmol, 1 eq, HCl salt) in dichloromethane (2 mL) and methyl alcohol (2 mL) was added sodium acetate (158 mg, 1.93 mmol, 4 eq). The mixture was stirred at 20° C. for 0.5 h. Then to the mixture was added 1-[5-[6-benzyloxy-2-(4-fluorophenyl)benzothiophen-3-yl]oxy-2-pyridyl]piperidine-4-carbaldehyde (260 mg, 0.48 mmol, 1 eq). The mixture was stirred at 20° C. for 0.5 hour followed by the addition of sodium cyanoborohydride (60 mg, 0.97 mmol, 2 eq). The reaction mixture was stirred at 20° C. for 2 hours. LC-MS showed the starting material was consumed completely and one main peak with desired MS was detected. The reaction mixture was concentrated under reduced pressure. The residue was purified by preparative TLC (DCM:MeOH=10:1). The desired compound 3-[5-[4-[[1-[5-[6-benzyloxy-2-(4-fluorophenyl)benzothiophen-3-yl]oxy-2-pyridyl]-4-piperidyl]methyl]piperazin-1-yl]-1-oxo-isoindolin-2-yl]piperidine-2,6-dione (300 mg, 0.32 mmol, 65% yield, 89% purity) was obtained as a white solid. LC/MS (ESI) m/z: 851.1[M+1]$^+$.

Step 8: Preparation of 3-[5-[4-[[1-[5-[2-(4-fluorophenyl)-6-hydroxy-benzothiophen-3-yl]oxy-2-pyridyl]-4-piperidyl] methyl]piperazin-1-yl]-1-oxo-isoindolin-2-yl]piperidine-2,6-dione (Compound 232)

To a solution of 3-[5-[4-[[1-[5-[6-benzyloxy-2-(4-fluorophenyl)benzothiophen-3-yl]oxy-2-pyridyl]-4-piperidyl]methyl]piperazin-1-yl]-1-oxo-isoindolin-2-yl]piperidine-2,6-dione (300 mg, 0.31 mmol, 1 eq) in tetrahydrofuran (10 mL) was added palladium (10%) on activated carbon catalyst (30 mg). The reaction mixture was stirred at 20° C. for 1 hour under hydrogen (15 psi). To the mixture was added ethyl alcohol (5 mL), the reaction mixture was stirred at 20° C. under hydrogen (15 psi) for 18 hours. The resulting mixture was filtered and concentrated under reduced pressure. The residue was purified by preparative HPLC (column: Phenomenex Synergi C18 150×25 mm, 10 um; mobile phase: [water (0.225% formic acid)-ACN]; B %: 18%-38%, 10 min). The desired compound 3-[5-[4-[[1-[5-[2-(4-fluorophenyl)-6-hydroxy-benzothiophen-3-yl]oxy-2-pyridyl]-4-piperidyl]methyl]piperazin-1-yl]-1-oxo-isoindolin-2-yl]piperidine-2,6-dione (126.0 mg, 0.15 mmol, 49% yield, 98% purity, formate) was obtained as a white solid. LC/MS (ESI) m/z: 761.3 [M+1]$^+$; $^1$H NMR (400 MHz, DMSO-d) δ 10.94 (s, 1H), 8.14 (s, 1H), 7.89 (d, J=3.2 Hz, 1H), 7.73-7.67 (m, 2H), 7.51 (d, J=8.4 Hz, 1H), 7.32-7.19 (m, 4H), 7.11 (dd, J=2.8, 9.2 Hz, 1H), 7.08-7.01 (m, 2H), 6.84 (dd, J=2.4, 8.8 Hz, 1H), 6.74 (d, J=9.6 Hz, 1H), 5.04 (dd, J=5.2, 13.2 Hz, 1H), 4.37-4.28 (m, 1H), 4.23-4.15 (m, 1H), 4.14-4.06 (m, 2H), 3.29-3.21 (m, 7H), 2.96-2.84 (m, 1H), 2.76-2.68 (m, 2H), 2.62-2.53 (m, 2H), 2.42-2.29 (m, 1H), 2.22-2.15 (m, 2H), 2.01-1.90 (m, 1H), 1.80-1.68 (m, 3H), 1.16-1.00 (m, 2H).

EXAMPLES

All synthesized compounds were characterized by both $^1$H-NMR and purity was analyzed by LC/MS under the wave length of 214 and 254 nM with UV detection as described below. Purity of each compound in Tables 1-5 was over 90%. The observed molecular weight from LC/MS in Table 1, Table 2, and Table 3 as [M+H]$^+$. The synthetic methods used for preparing individual compound are also listed in Tables 1-3.

All NMR experiments were recorded either on Bruker Mercury Plus 400 NMR Spectrometer equipped with a Bruker 400 BBFO probe at 400 MHz for proton NMR or on Bruker Mercury Plus 300 NMR Spectrometer equipped with a Bruker 300 BBFO probe at 300 MHz for proton NMR. All deuterated solvents contained typically 0.03% to 0.05% v/v tetramethylsilane, which was used as the reference signal (set at δ 0.00 for both $^1$H and $^{13}$C).

LC-MS analyses were performed on a SHIMADZU LC-MS machine consisting of an UFLC 20-AD system and LCMS 2020 MS detector. The column used was a Shimpack XR-ODS, 2.2 am, 3.0×50 mm. A linear gradient was applied, starting at 95% A (A: 0.05% TFA in water) and ending at 100% B (B: 0.05% TFA in acetonitrile) over 2.2 min with a total run time of 3.6 min. The column temperature was at 40° C. with the flow rate at 1.0 mL/min. The Diode Array detector was scanned from 200-400 nm. The mass spectrometer was equipped with an electro spray ion source (ES) operated in a positive or negative mode. The mass spectrometer was scanned between m/z 90-900 with a scan time of 0.6 s.

Chimeric molecules were assessed for target engagement in T47D cells using the commercial kit of ERE luciferase reporter gene assay. In the assay, 10% FBS was included and estrogen level was measured to be 10 pM. Target engagement was expressed as $IC_{50}$ in the suppression of estrogen induced signing and the result was listed in Table 1-3.

Figure 2A:
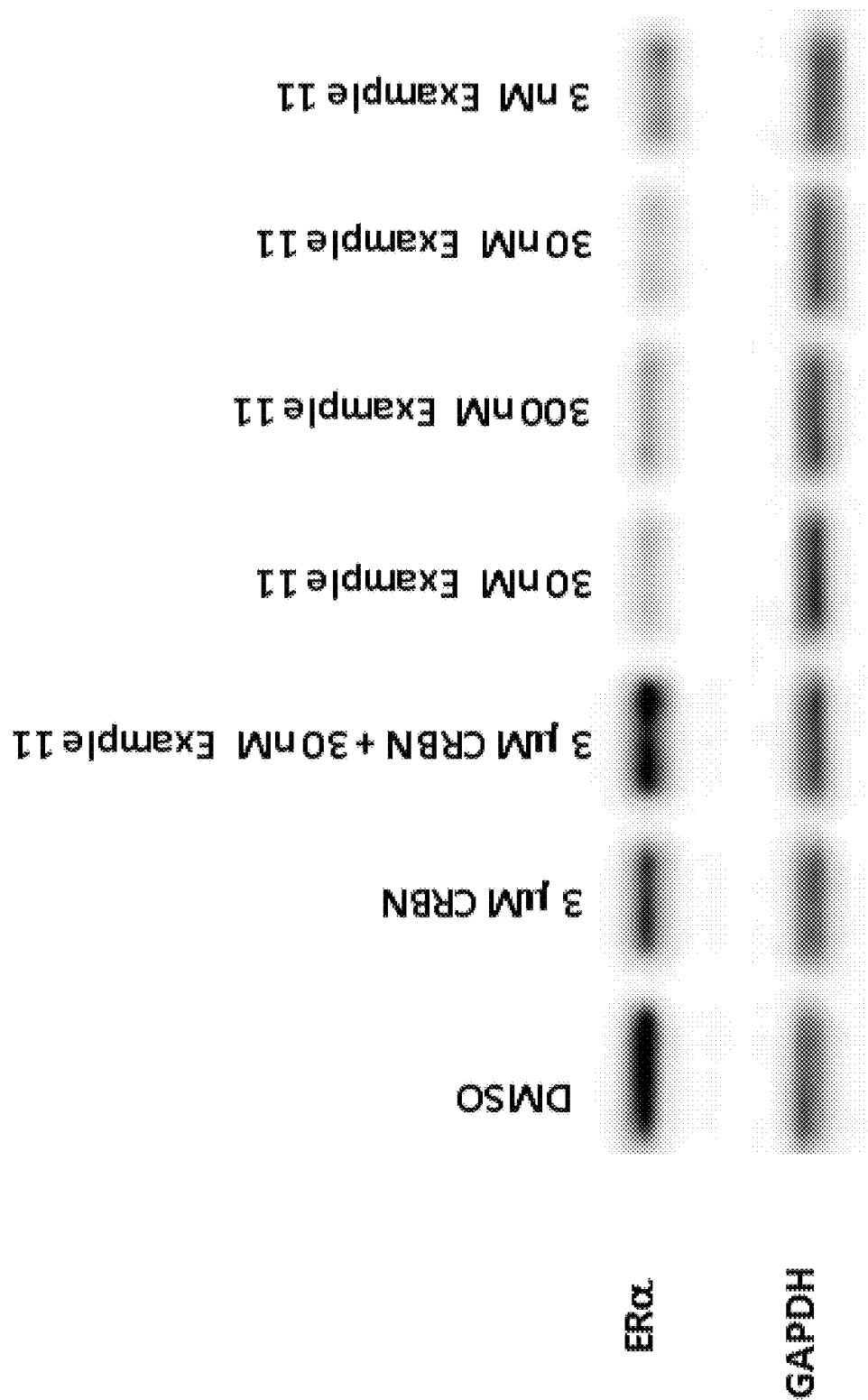
FIG. 2A. Degradation of ERα by Compound 11 in MCF7 cells after a 24 hour incubation: column 1, DMSO control; column 2, 3 μM pomalidomide; column 3, 30 nM Compound 11 plus 3 μM pomalidomide; column 4, 30 nM Compound 11; column 5, 300 nM Compound 11; column 6, 30 nM Compound 11; and column 7, 3 nM Compound 11.
Figure 2B:
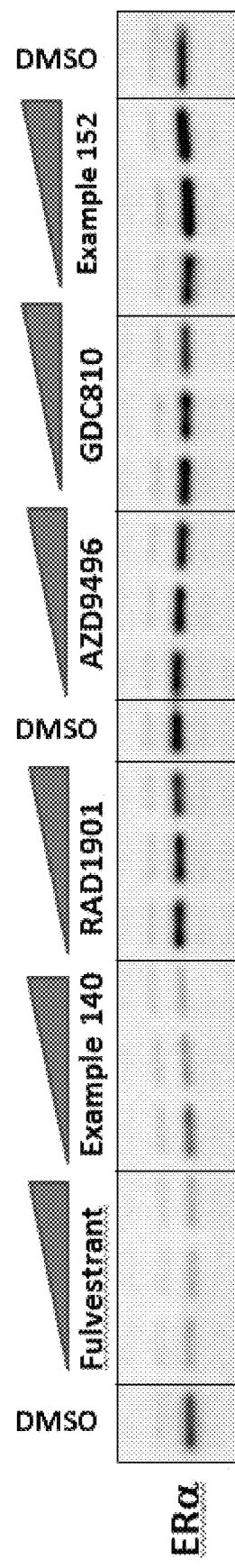
FIG. 2B. Degradation of ERα by Fulvestrant, Compound 140, Compound 152, AZD9496, RAD1901, and GDC810 in T47D cells after a 24 hour incubation. Concentrations for all compounds are 6, 25 and 100 nM.

Compounds prepared in this application were also analyzed for the degradation of ERα in MCF7 and T47D cells. FIG. 2 showed the degradation result with the selected compound and demonstrated the degradation mechanism through cereblon E3 ligase mediated pathway.

ERE Luciferase Assay for Compounds in Table 1-3.

T47D-KBluc cells (ATCC #CRL_2865, T47D human breast cancer cells stably transfected with estrogen responsive element/promoter/luciferase reporter gene) were seeded into 96-well white opaque plates in RPMI growth medium supplemented with 10% fetal bovine serum and allowed to adhere overnight in a 37° C. humidified incubator. The following day, cells were treated with PROTACs in a 12-point concentration curve (top final concentration of 300 nM with subsequent concentrations being 3-fold less with 2 pM being the lowest concentration in the assay). Each PROTAC was tested independently in two experiments on 96-well plates. After 24 hours, media was removed and lysis buffer was added to the wells. Following lysis, Bright-Glo™ Luciferase Assay Substrate (Promega, Madison Wis.) was added and the luciferase activity was measured using a Cytation 3 plate reader (TioTek™, Winooski, Vt.). Each compound was assayed in duplicates and the activity was calculated as IC50 using GraphPad Prism software (San Diego, Calif.).

Estrogen Receptor-Alpha (ERα) Degradation Assay in MCF-7 Cells Using Western Blot Method for Table 4.

The exemplary novel ERα degraders were assessed for their activity in degrading ERα in MCF-7 cells via western blot. The assay was carried out in the presence of 10% fetal bovine serum (FBS) or high percentage of human or mouse serum. Protocols of the western blot assay are described below, which provide comparable results.

MCF7 cells were grown in DMEM/F12 with 10% fetal bovine serum and seeded at 24,000 cells per well in 100 µl into 96-well clear tissue culture plates. The following day, the cells were treated with PROTACs in a 7-point concentration curve with 100 nM being the top concentration and serial dilutions to make the other concentrations (30 nM, 10 nM, 3 nM, 1 nM, and 0.3 nM). At all concentrations, 0.01% DMSO is the final concentration in the well. The following day, the plates are aspirated, washed with 50 µl of cold PBS. The cells are lysed with 50 µl/well 4° C. Cell Lysis Buffer (Catalog #9803; Cell Signaling Technology, Danvers, Mass.) (20 mM Tris-HCL (pH 7.5), 150 mM NaCl, 1 mM Na$_2$DTA, 1 mM EGTA, 1% Triton, 2.5 mM sodium pyrophosphate, 1 mM B-glycerophosphate, 1 mM sodium vanadate, 1 ug/ml leupeptin). Lysates were clarified at 16,000×g for 10 minutes, and 2 µg of protein was subjected to SDS-PAGE analysis and followed by immunoblotting according to standard protocols. The antibodies used were ERα (Cell Signaling Technologies Catalog #8644), and Tubulin (Sigma Catalog #T9026; St. Louis, Mo.). Detection reagents were Clarity Western ECL substrate (Bio-Rad Catalog #170-5060; Hercules, Calif.).

Alternatively, MCF7 cells were grown in DMEM/F12 with 10% fetal bovine serum and seeded at 24,000 cells per well in 500 µl in 24-well clear tissue culture plates. The following day, the cells were treated with PROTACs in a 5-point concentration curve (100 nM, 33 nM, 11 nM, 3.7 nM, and 1.2 nM) in the presence of 0.01% DMSO. After 72 hours, the wells are aspirated and washed with 500 µl of PBS. The cells are lysed with 100 µl/well 4° C. Cell Lysis Buffer (Catalog #9803; Cell Signaling Technology, Danvers, M A) (20 mM Tris-HCL (pH 7.5), 150 mM NaCl, 1 mM Na$_2$EDTA, 1 mM EGTA, 1% Triton, 2.5 mM sodium pyrophosphate, 1 mM B-glycerophosphate, 1 mM sodium vanadate, 1 ug/ml leupeptin). Lysates were clarified at 16,000×g for 10 minutes, and 2 µg of protein was subjected to SDS-PAGE analysis and followed by immunoblotting according to standard protocols. The antibodies used were ER(X (Cell Signaling Technologies Catalog #8644), and Tubulin (Sigma Catalog #T9026; St. Louis, Mo.). Detection reagents were Clarity Western ECL substrate (Bio-Rad Catalog #170-5060; Hercules, Calif.).

Estrogen Receptor-Alpha (ERα) Degradation Assay in T47D Cells Using Western Blot Method.

The same protocol that was described above with MCF7 cells was utilized, except that T47D cells were utilized instead of the MCF7 cells.

Estrogen Receptor-Alpha (ERα) Degradation Assay Using in-Cell Western™ Assay for Table 5.

Degradation of ERα by claimed compounds were determined in MCF7 cells using an In-Cell Western™ assay. Briefly, MCF7 cells were plated in 96-well plates (2000 cells per well in 100 µl media) and incubated at 37° C. under an atmosphere of 5% CO$_2$ in a humidified incubator overnight. One-hundred (100) µl of media containing test compound (at 2x concentration) was added to the appropriate wells to provide 11 serially decreasing concentrations (top final concentration, 1 µM then 3-fold less for the next 10 concentrations); a vehicle control (DMSO) was also added for each compound. For each experiment, all compounds were assayed on duplicate plates. Cells were then incubated for 3 or 5 days in the above-mentioned environment. The assay was terminated by removal of media, a single wash with ice-cold PBS and the addition of 50 µl paraformaldehyde (PFA: 4% in PBS). After 15 minutes in PFA at room temperature, the cells were permeabilized in Tris-phosphate-buffered saline with Tween (0.1%) (TBST) supplemented with Triton X-100 (0.5%) for 15 minutes. Cells were then blocked in BSA (TBST with BSA, 3%) for one hour. Primary antibodies for the detection of ERa (rabbit monoclonal, 1:1000, Cell Signaling Technology Catalog #8644) and tubulin (mouse monoclonal, 1:5000, Sigma Catalog #T6074) in TBST with BSA (3%) were added. The cells were incubated overnight at 4° C. The cells were then washed thrice with TBST at room temperature and then incubated with anti-rabbit and anti-mouse fluorescently-labelled secondary antibodies (IRDye®; LI-COR; Lincoln, Nebr.) in LI-COR blocking buffer (Catalog #927-50000) for one hour at room temperature. Following 3 washes with TBST, the buffer was removed and the plates were read on an Odyssey® infrared imaging system (LI-COR®, Lincoln, Nebr.) at 700 nm and 800 nm. Using commercial software (ImageStudio™; LI-COR, Lincoln, Nebr.), the staining intensity for ERa and tubulin in each well was quantified and exported for analysis. For each data point, ERa intensity was normalized to tubulin intensity and for each compound all normalized intensity values were normalized to the vehicle control. $DC_{50}$ and $D_{max}$ values were determined following a 4-parameter $IC_{50}$ curve fit using ACAS dose response module (McNeil & Co Inc.).

The following PROTACs demonstrated target protein degradation when tested under the conditions described above:

TABLE 1

Activity, characterization and synthetic methods of cereblon centric benzthiophene derived ER PROTACs

| Ex. # | Structure | ER-α Luciferase IC50 (nM) | *Obsd [M + H]+ | Synthetic Method |
|---|---|---|---|---|
| 1 | 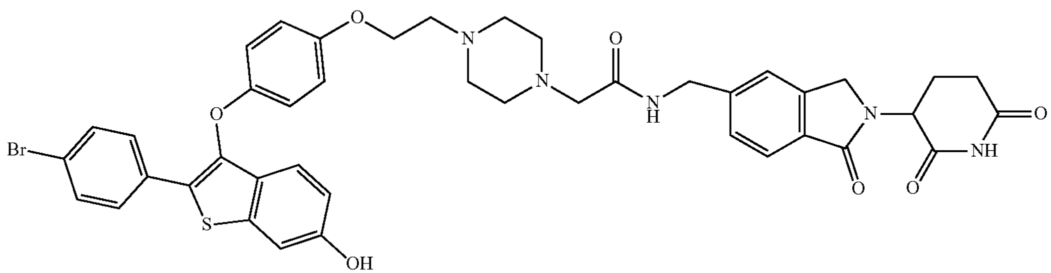 [SMILES: O=C(CN1CCN(CCOc2ccc(Oc3c(-c4ccc(Br)cc4)sc4cc(O)ccc34)cc2)CC1)NCc1ccc2c(c1)CN(C1CCC(=O)NC1=O)C2=O] | 12.7 | 838.1, 840.1 | Scheme 14 |
| 2 | 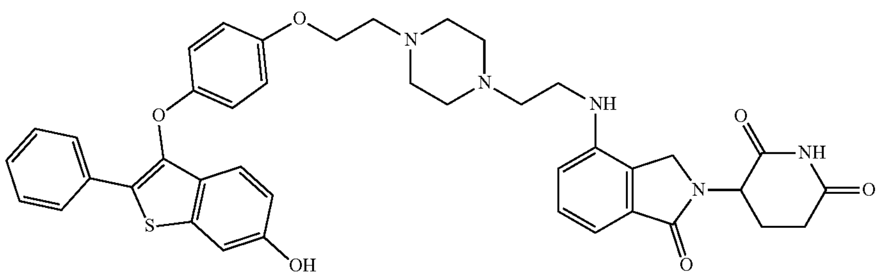 [SMILES: O=C1CCC(N2Cc3c(NCCN4CCN(CCOc5ccc(Oc6c(-c7ccccc7)sc7cc(O)ccc67)cc5)CC4)cccc3C2=O)C(=O)N1] | 0.36 | 732.2 | Scheme 15 |
| 3 | 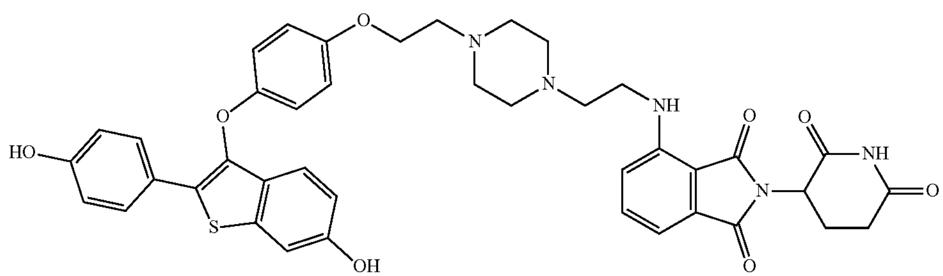 [SMILES: O=C1CCC(N2C(=O)c3cccc(NCCN4CCN(CCOc5ccc(Oc6c(-c7ccc(O)cc7)sc7cc(O)ccc67)cc5)CC4)c3C2=O)C(=O)N1] | 0.14 | 762.2 | Scheme 16 |

TABLE 1-continued

Activity, characterization and synthetic methods of cereblon centric benzthiophene derived ER PROTACs

| Ex. # | Structure | ER-α Luciferase IC50 (nM) | *Obsd [M + H]+ | Synthetic Method |
|---|---|---|---|---|
| 4 | 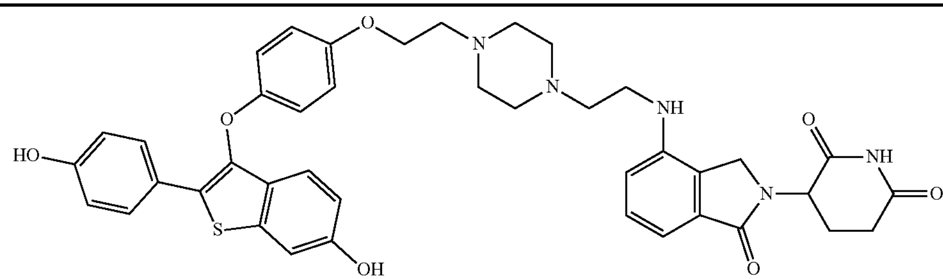 | 0.09 | 748.3 | Scheme 15 |
| 5 | 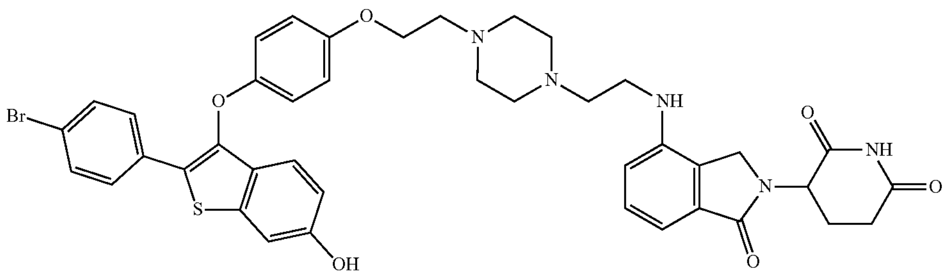 [SMILES: O=C1CCC(N2Cc3c(NCCN4CCN(CCOc5ccc(Oc6c(-c7ccc(Br)cc7)sc7cc(O)ccc67)cc5)CC4)cccc3C2=O)C(=O)N1] | 0.9 | 810.1, 812.2 | Scheme 15 |
| 6 | 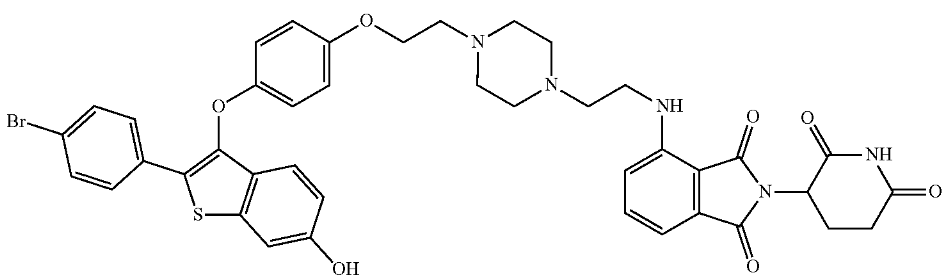 [SMILES: O=C1CCC(N2C(=O)c3cccc(NCCN4CCN(CCOc5ccc(Oc6c(-c7ccc(Br)cc7)sc7cc(O)ccc67)cc5)CC4)c3C2=O)C(=O)N1] | 1.3 | 824.1, 826.1 | Scheme 16 |

TABLE 1-continued

Activity, characterization and synthetic methods of cereblon centric benzthiophene derived ER PROTACs

| Ex. # | Structure | ER-α Luciferase IC50 (nM) | *Obsd [M + H]+ | Synthetic Method |
|---|---|---|---|---|
| 7 | 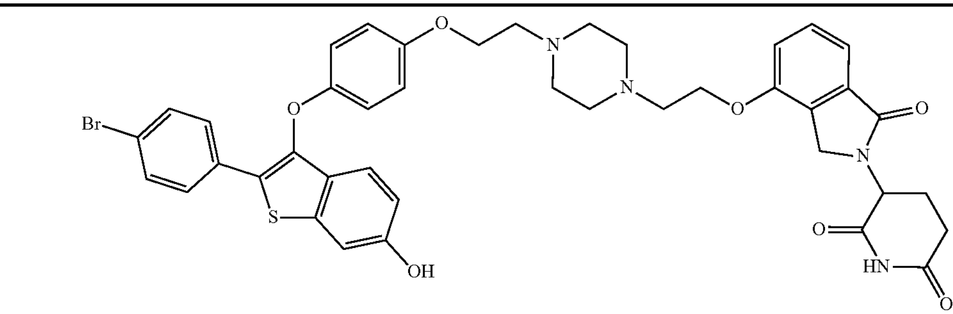 | 1.1 | 811.2, 813.2 | Scheme 17 |
| 8 | 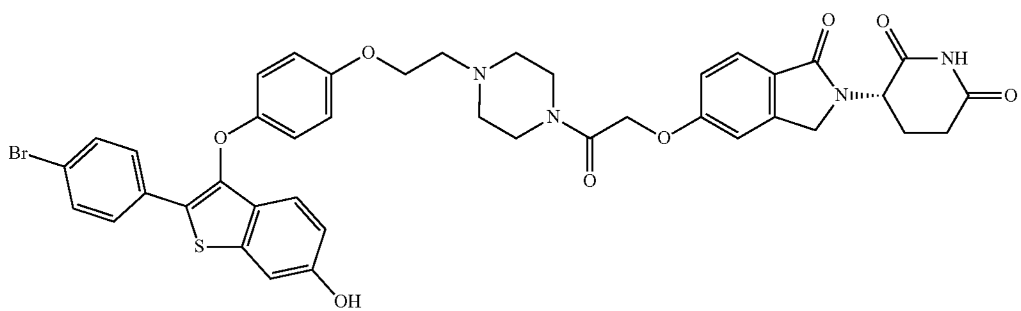 [SMILES: O=C1CC[C@H](N2Cc3cc(OCC(=O)N4CCN(CCOc5ccc(Oc6c(-c7ccc(Br)cc7)sc7cc(O)ccc67)cc5)CC4)ccc3C2=O)C(=O)N1] | 1.9 | 825.2, 827.0 | Scheme 18 |
| 9 | 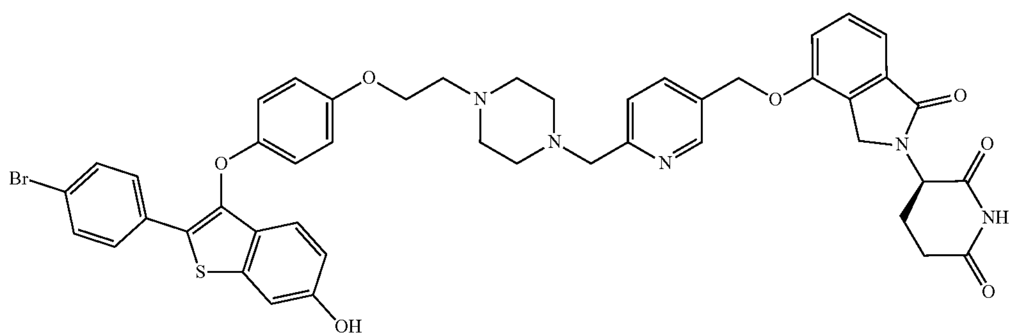 [SMILES: O=C1CC[C@@H](N2Cc3c(OCc4ccc(CN5CCN(CCOc6ccc(Oc7c(-c8ccc(Br)cc8)sc8cc(O)ccc78)cc6)CC5)nc4)cccc3C2=O)C(=O)N1] | 2.9 | 888.2, 890.1 | Scheme 19 |

TABLE 1-continued
Activity, characterization and synthetic methods of cereblon centric benzthiophene derived ER PROTACs
| Ex. # | Structure | ER-α Luciferase IC50 (nM) | *Obsd [M + H]+ | Synthetic Method |
|---|---|---|---|---|
| 10 | 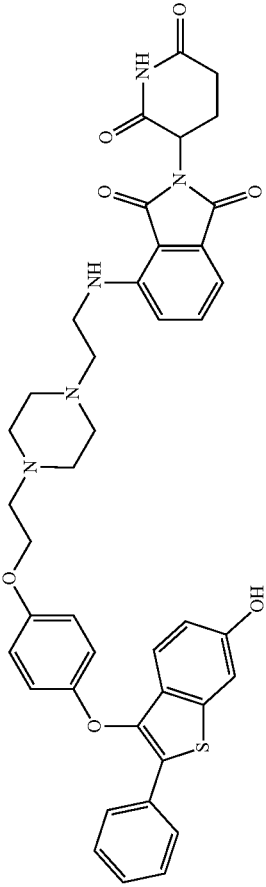 | 0.63 | 746.2 | Scheme 15 |
| 11 | 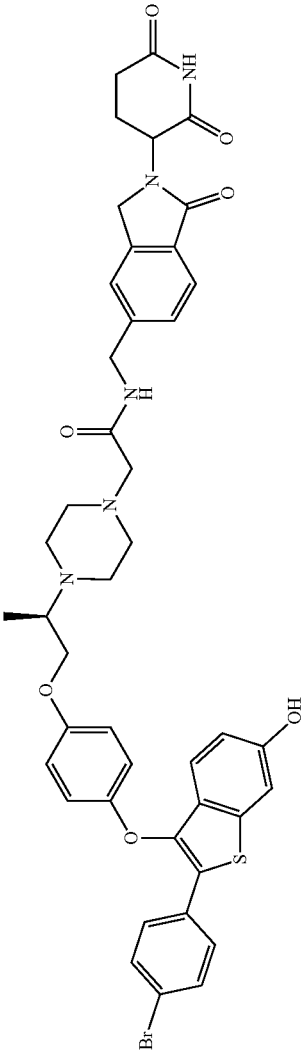 | 2.6 | 852.2, 854.2 | Scheme 14 |
| 12 | 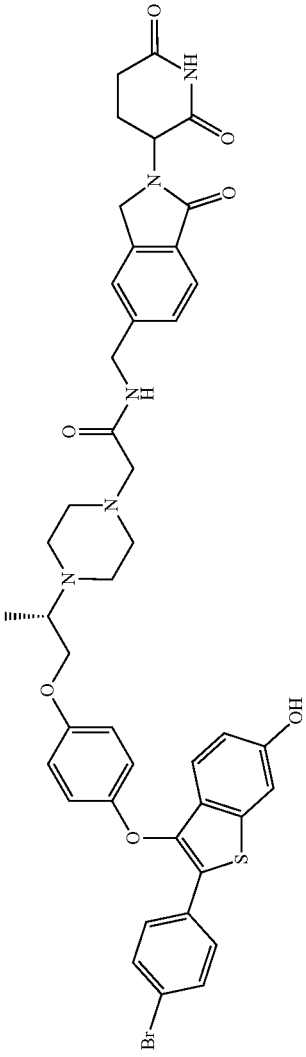 | 2.5 | 852.2, 854.2 | Scheme 14 |

TABLE 1-continued

Activity, characterization and synthetic methods of cereblon centric benzthiophene derived ER PROTACs

| Ex. # | Structure | ER-α Luciferase IC50 (nM) | *Obsd [M + H]+ | Synthetic Method |
|---|---|---|---|---|
| 13 | 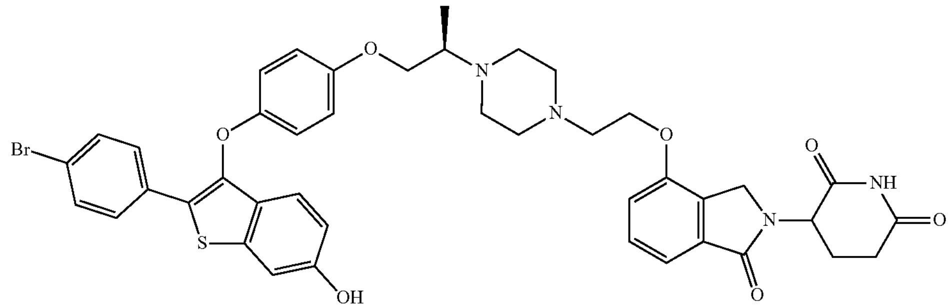 [SMILES: C[C@H](COc1ccc(Oc2c(-c3ccc(Br)cc3)sc3cc(O)ccc23)cc1)N1CCN(CCOc2cccc3c2CN(C2CCC(=O)NC2=O)C3=O)CC1] | 1.3 | 825.2, 827.2 | Scheme 20 |
| 14 | 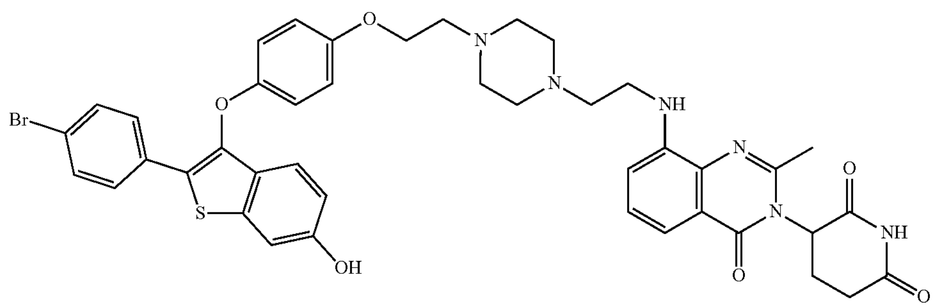 [SMILES: Cc1nc2c(NCCN3CCN(CCOc4ccc(Oc5c(-c6ccc(Br)cc6)sc6cc(O)ccc56)cc4)CC3)cccc2c(=O)n1C1CCC(=O)NC1=O] | 17.7 | 837.2, 839.2 | Scheme 21 |
| 15 | 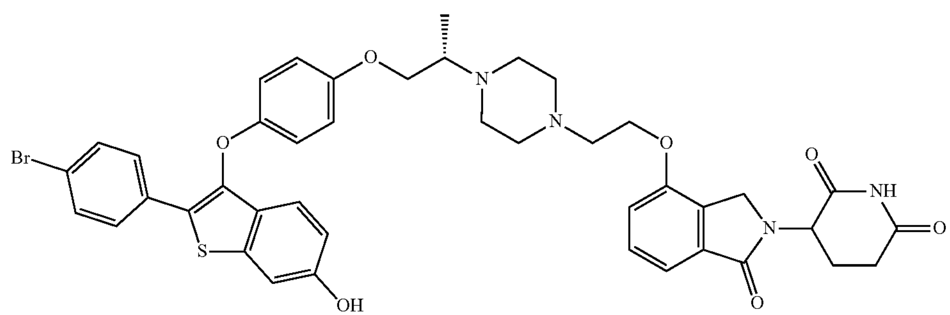 [SMILES: C[C@@H](COc1ccc(Oc2c(-c3ccc(Br)cc3)sc3cc(O)ccc23)cc1)N1CCN(CCOc2cccc3c2CN(C2CCC(=O)NC2=O)C3=O)CC1] | 1.7 | 825.2, 827.2 | Scheme 20 |

TABLE 1-continued
Activity, characterization and synthetic methods of cereblon centric benzthiophene derived ER PROTACs
| Ex. # | Structure | ER-α Luciferase IC50 (nM) | *Obsd [M + H]+ | Synthetic Method |
|---|---|---|---|---|
| 16 | 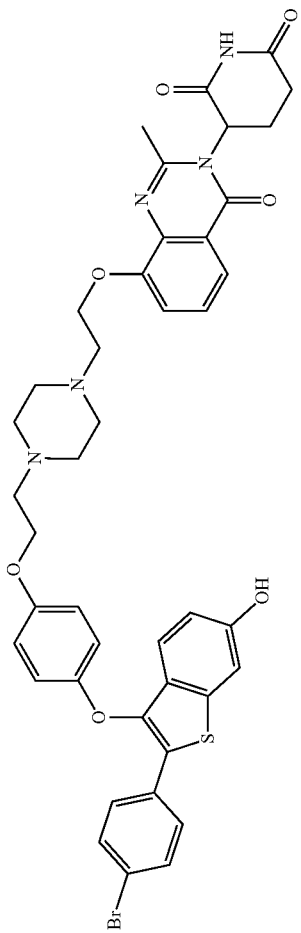 | 8.8 | 838.1, 840.2 | Scheme 22 |
| 17 | 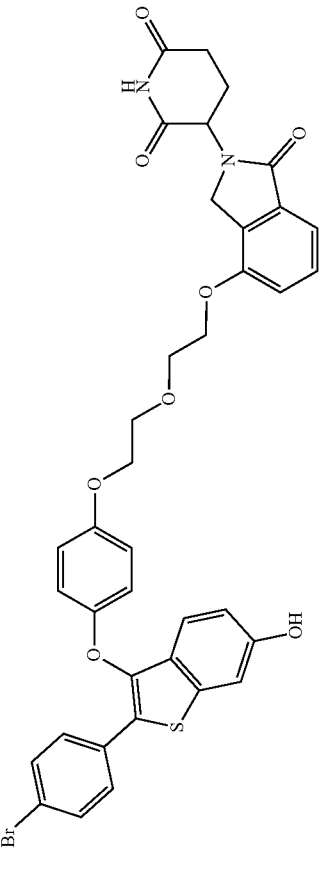 | 2.9 | 743.1, 745.1 | Scheme 23 |

TABLE 1-continued
Activity, characterization and synthetic methods of cereblon centric benzthiophene derived ER PROTACs
| Ex. # | Structure | ER-α Luciferase IC50 (nM) | *Obsd [M + H]+ | Synthetic Method |
|---|---|---|---|---|
| 18 | 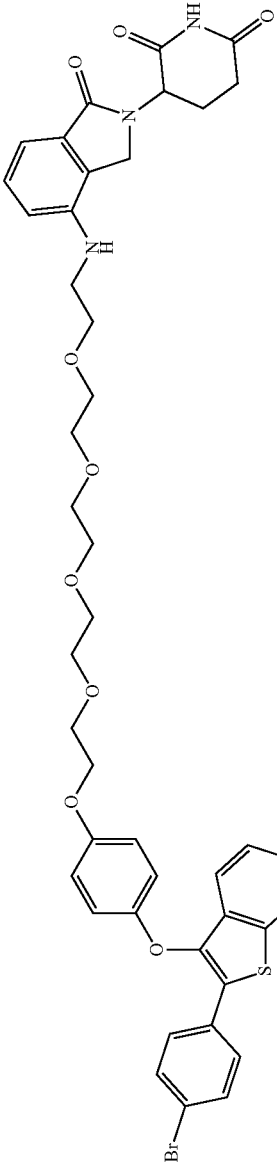 | 81.4 | 874.2, 876.2 | Scheme 23 |
| 19 | 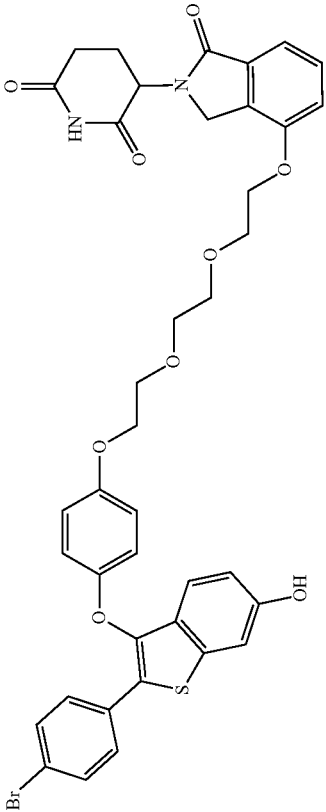 | 8.9 | 787.0, 789.1 | Scheme 25 |

TABLE 1-continued
Activity, characterization and synthetic methods of cereblon centric benzthiophene derived ER PROTACs
| Ex. # | Structure | ER-α Luciferase IC50 (nM) | *Obsd [M + H]+ | Synthetic Method |
|---|---|---|---|---|
| 20 | 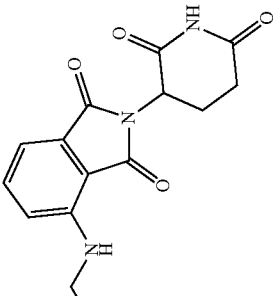 | 39.9 | 888.1, 890.1 | Scheme 24 |
| 21 | 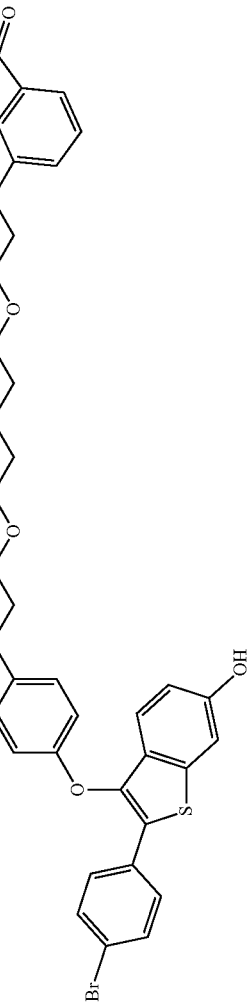 | 17.4 | 831.1, 833.1 | Scheme 25 |

TABLE 1-continued

Activity, characterization and synthetic methods of cereblon centric benzthiophene derived ER PROTACs

| Ex. # | Structure | ER-α Luciferase IC50 (nM) | *Obsd [M + H]+ | Synthetic Method |
|---|---|---|---|---|
| 22 | 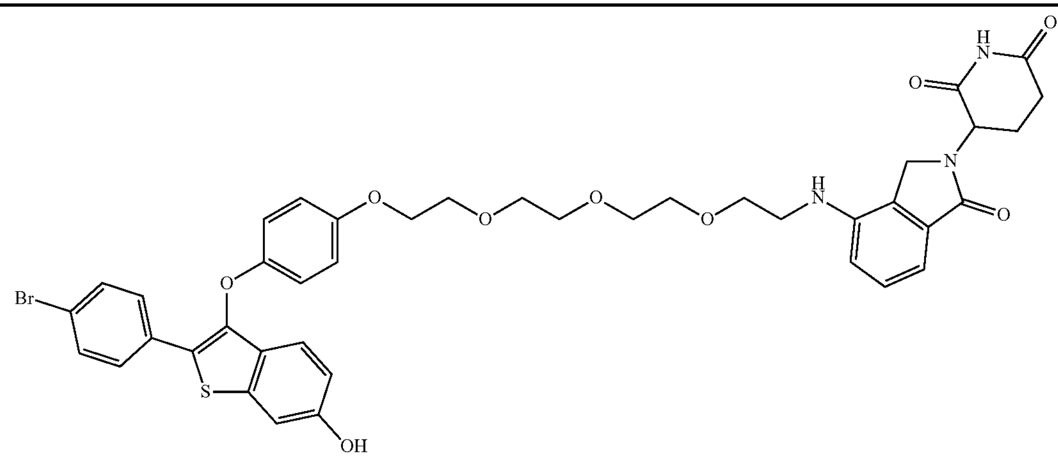 | 41.4 | 830.2, 832.2 | Scheme 26 |
| 23 | 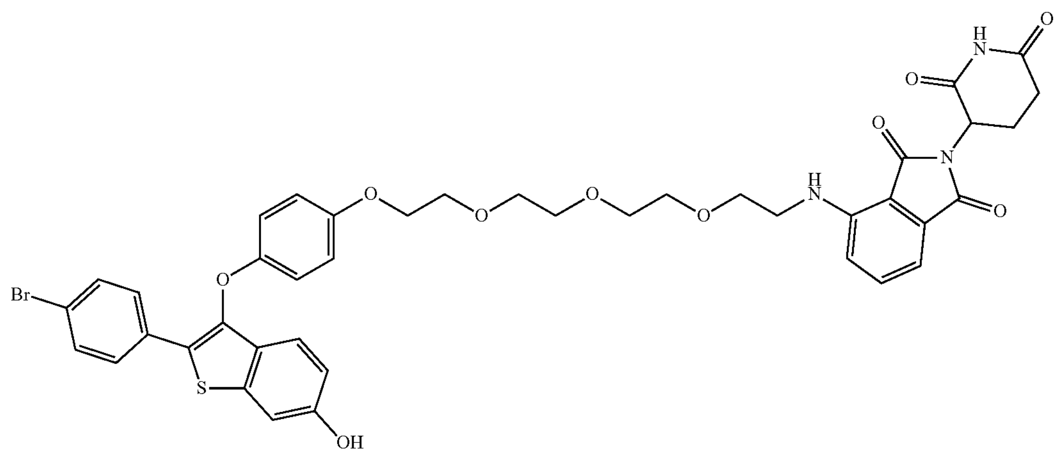 | 22.4 | 844.1, 846.1 | Scheme 24 |

TABLE 1-continued

Activity, characterization and synthetic methods of cereblon centric benzthiophene derived ER PROTACs

| Ex. # | Structure | ER-α Luciferase IC50 (nM) | *Obsd [M + H]+ | Synthetic Method |
|---|---|---|---|---|
| 24 | 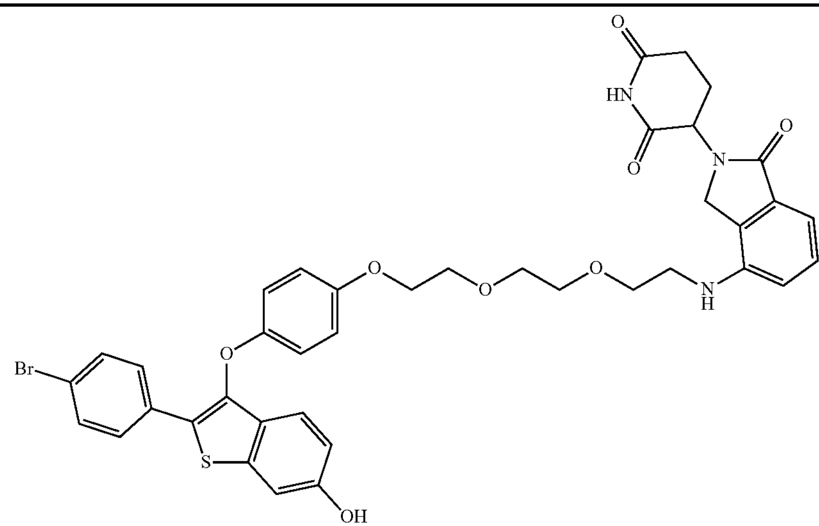 | 16.8 | 786.1, 788.1 | Scheme 26 |
| 25 | 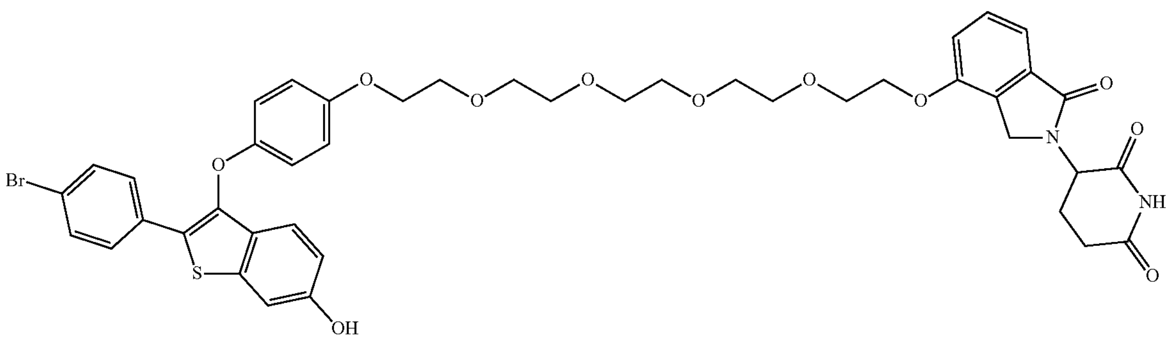 [SMILES: O=C1CCC(N2Cc3c(OCCOCCOCCOCCOCCOc4ccc(Oc5c(-c6ccc(Br)cc6)sc6cc(O)ccc56)cc4)cccc3C2=O)C(=O)N1] | 8.6 | 875.1, 877.2 | Scheme 25 |

TABLE 1-continued

Activity, characterization and synthetic methods of cereblon centric benzthiophene derived ER PROTACs

| Ex. # | Structure | ER-α Luciferase IC50 (nM) | *Obsd [M + H]+ | Synthetic Method |
|---|---|---|---|---|
| 26 | 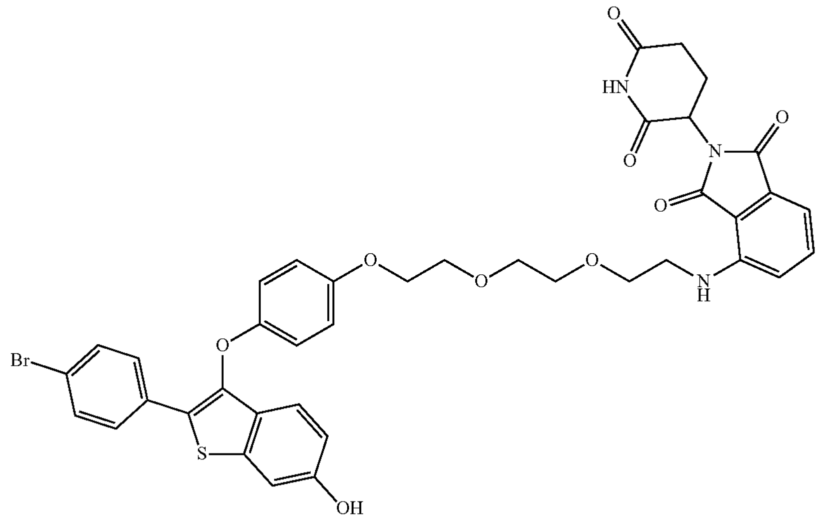 [SMILES: O=C1CCC(N2C(=O)c3cccc(NCCOCCOCCOc4ccc(Oc5c(-c6ccc(Br)cc6)sc6cc(O)ccc56)cc4)c3C2=O)C(=O)N1] | 9.7 | 800.0, 802.1 | Scheme 26 |
| 27 | 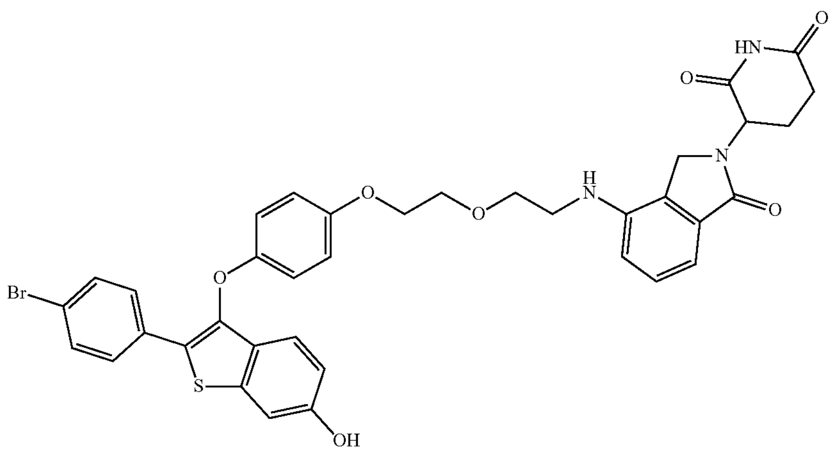 [SMILES: O=C1CCC(N2Cc3c(NCCOCCOc4ccc(Oc5c(-c6ccc(Br)cc6)sc6cc(O)ccc56)cc4)cccc3C2=O)C(=O)N1] | 8.3 | 742.2, 744.1 | Scheme 26 |

TABLE 1-continued

Activity, characterization and synthetic methods of cereblon centric benzthiophene derived ER PROTACs

| Ex. # | Structure | ER-α Luciferase IC50 (nM) | *Obsd [M + H]+ | Synthetic Method |
|---|---|---|---|---|
| 28 | 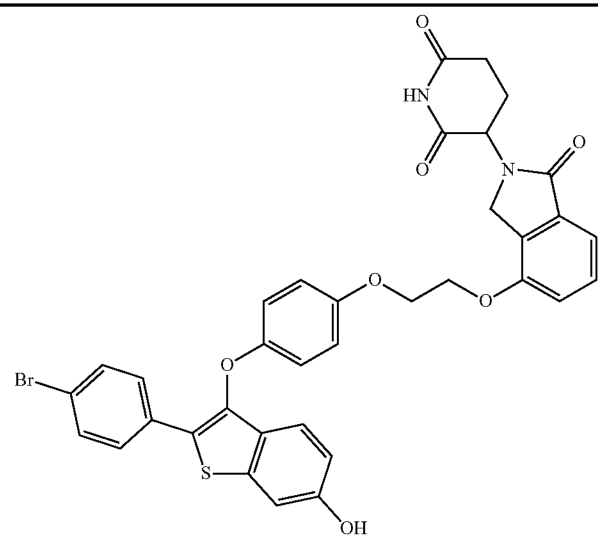 | 2.7 | 699.0, 701.0 | Scheme 25 |
| 29 | 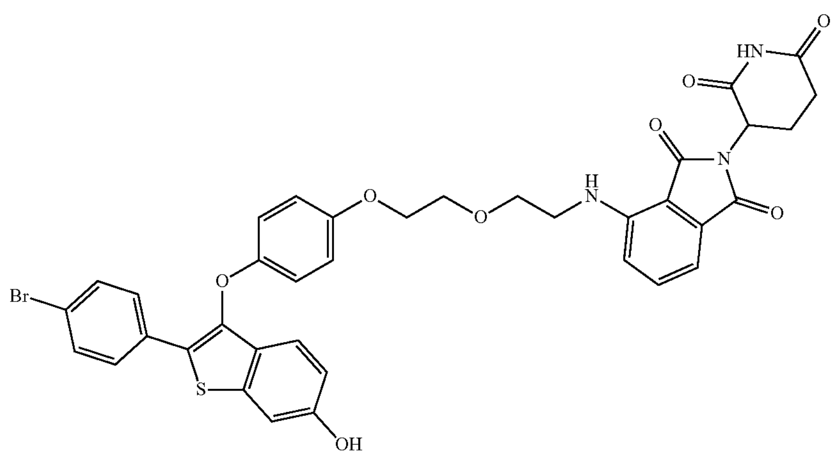 [SMILES: O=C1CCC(N2C(=O)c3cccc(NCCOCCOc4ccc(Oc5c(-c6ccc(Br)cc6)sc6cc(O)ccc56)cc4)c3C2=O)C(=O)N1] | 19.2 | 756.1, 758.1 | Scheme 26 |

TABLE 1-continued

Activity, characterization and synthetic methods of cereblon centric benzthiophene derived ER PROTACs

| Ex. # | Structure | ER-α Luciferase IC50 (nM) | *Obsd [M + H]+ | Synthetic Method |
|---|---|---|---|---|
| 30 | 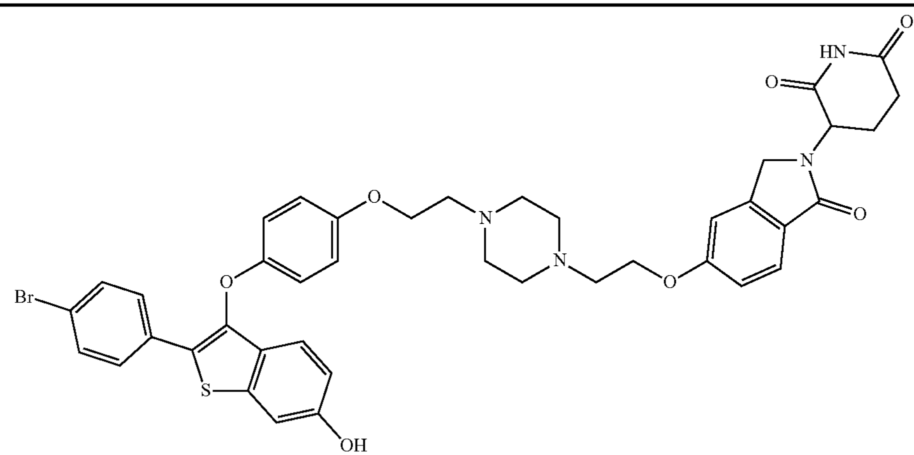 | 1.3 | 811.2, 813.2 | Scheme 17 |
| 31 | 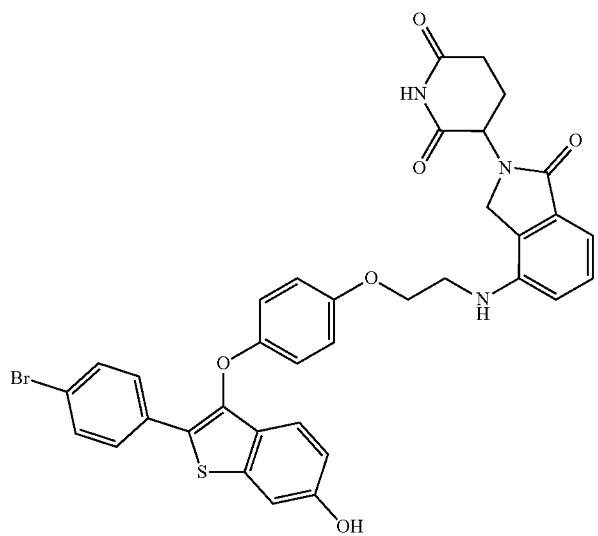 [SMILES: O=C1CCC(N2Cc3c(NCCOc4ccc(Oc5c(-c6ccc(Br)cc6)sc6cc(O)ccc56)cc4)cccc3C2=O)C(=O)N1] | | 698.1, 700.1 | Scheme 26 |

TABLE 1-continued

Activity, characterization and synthetic methods of cereblon centric benzthiophene derived ER PROTACs

| Ex. # | Structure | ER-α Luciferase IC50 (nM) | *Obsd [M + H]+ | Synthetic Method |
|---|---|---|---|---|
| 32 | 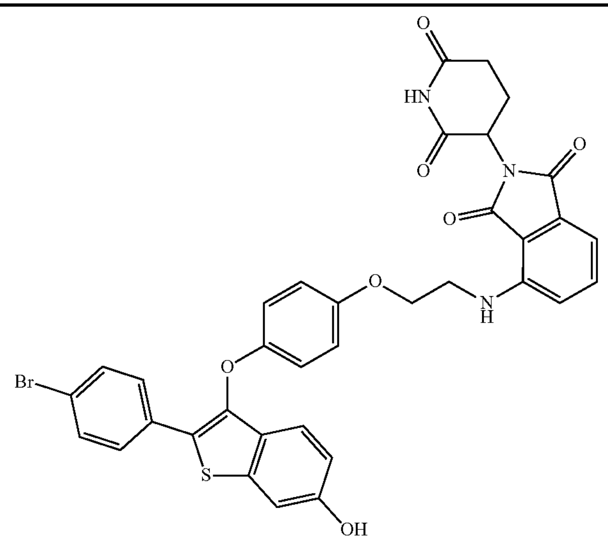 | 8.2 | 712.0, 714.0 | Scheme 24 |
| 33 | 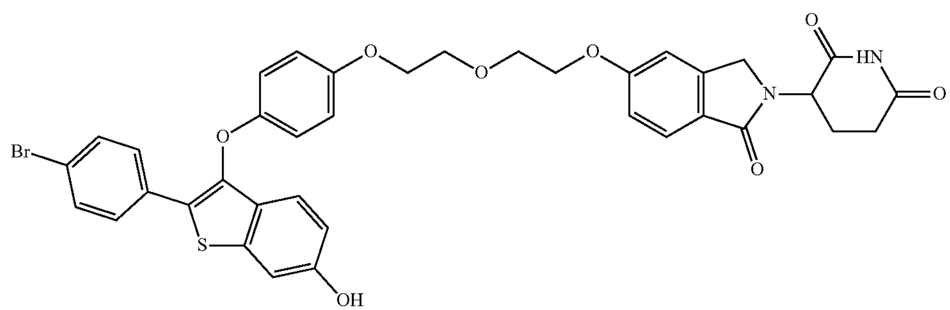 [SMILES: O=C1CCC(N2Cc3cc(OCCOCCOc4ccc(Oc5c(-c6ccc(Br)cc6)sc6cc(O)ccc56)cc4)ccc3C2=O)C(=O)N1] | 2.7 | 743.2, 745.2 | Scheme 25 |

TABLE 1-continued

Activity, characterization and synthetic methods of cereblon centric benzthiophene derived ER PROTACs

| Ex. # | Structure | ER-α Luciferase IC50 (nM) | *Obsd [M + H]⁺ | Synthetic Method |
|---|---|---|---|---|
| 34 | 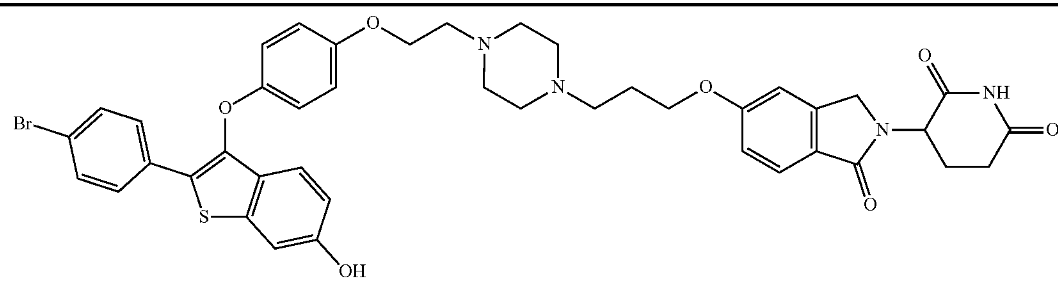 | 1 | 825.1, 827.1 | Scheme 17 |
| 35 | 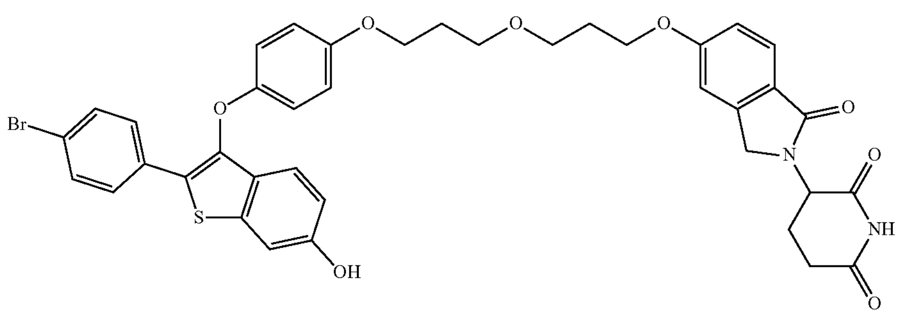 [SMILES: O=C1CCC(N2Cc3cc(OCCCOCCCOc4ccc(Oc5c(-c6ccc(Br)cc6)sc6cc(O)ccc56)cc4)ccc3C2=O)C(=O)N1] | 9.9 | 771.0, 773.2 | Scheme 25 |

TABLE 1-continued

Activity, characterization and synthetic methods of cereblon centric benzthiophene derived ER PROTACs

| Ex. # | Structure | ER-α Luciferase IC50 (nM) | *Obsd [M + H]+ | Synthetic Method |
|---|---|---|---|---|
| 36 | 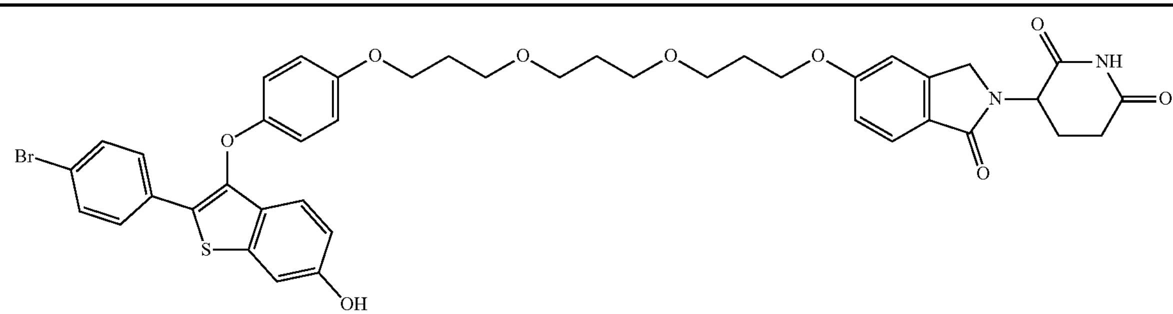 | 4.7 | 829.2, 831.1 | Scheme 25 |
| 37 | 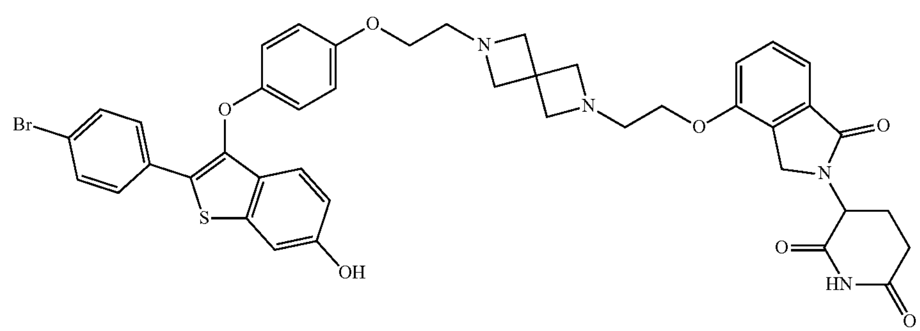 [SMILES: O=C1CCC(N2Cc3c(OCCN4CC5(CN(CCOc6ccc(Oc7c(-c8ccc(Br)cc8)sc8cc(O)ccc78)cc6)C5)C4)cccc3C2=O)C(=O)N1] | 4.2 | 823.2, 825.2 | Scheme 17 |

TABLE 1-continued

Activity, characterization and synthetic methods of cereblon centric benzthiophene derived ER PROTACs

| Ex. # | Structure | ER-α Luciferase IC50 (nM) | *Obsd [M + H]+ | Synthetic Method |
|---|---|---|---|---|
| 38 | 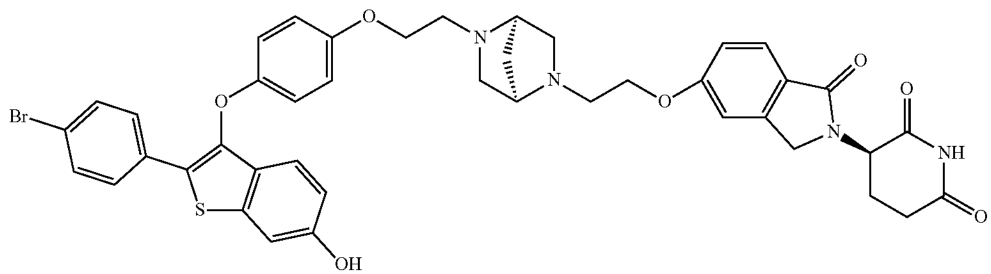 [SMILES: O=C1CC[C@@H](N2Cc3cc(OCCN4C[C@H]5C[C@@H]4CN5CCOc4ccc(Oc5c(-c6ccc(Br)cc6)sc6cc(O)ccc56)cc4)ccc3C2=O)C(=O)N1] | 1.1 | 823.2, 825.2 | Scheme 17 |
| 39 | 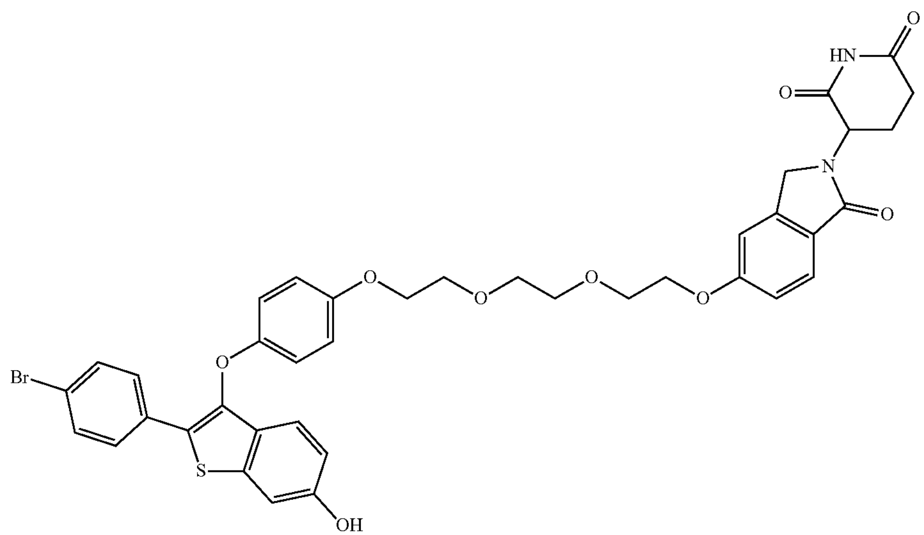 [SMILES: O=C1CCC(N2Cc3cc(OCCOCCOCCOc4ccc(Oc5c(-c6ccc(Br)cc6)sc6cc(O)ccc56)cc4)ccc3C2=O)C(=O)N1] | 3.1 | 787.0, 789.2 | Scheme 25 |

TABLE 1-continued
Activity, characterization and synthetic methods of cereblon centric benzthiophene derived ER PROTACs
| Ex. # | Structure | ER-α Luciferase IC50 (nM) | *Obsd [M + H]+ | Synthetic Method |
|---|---|---|---|---|
| 40 | 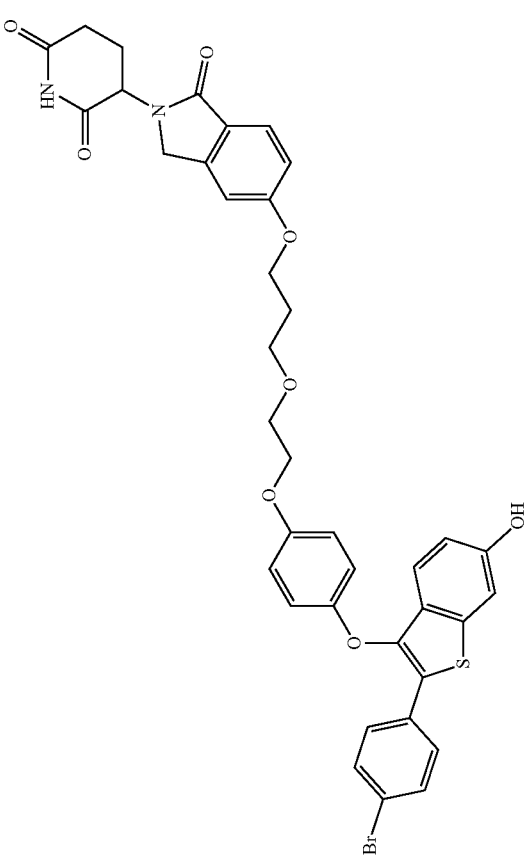 | 3.9 | 757.1, 759.0 | Scheme 25 |
| 41 | 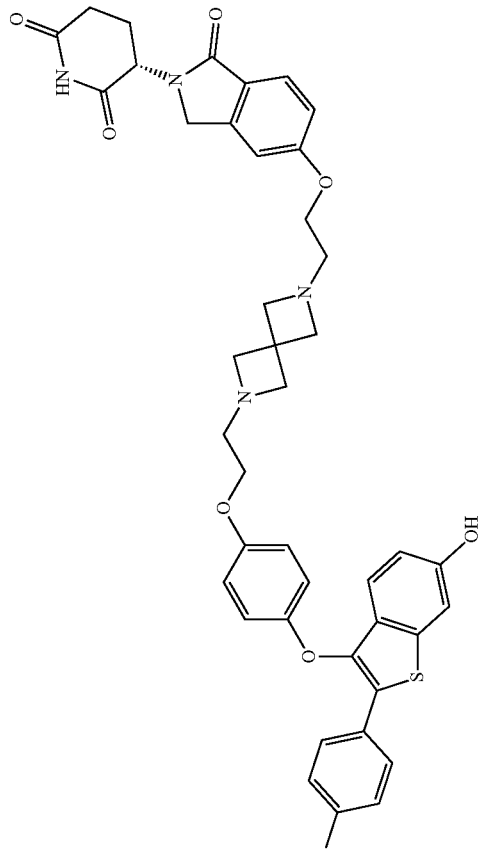 | 2.4 | 823.0, 825.1 | Scheme 17 |

TABLE 1-continued

Activity, characterization and synthetic methods of cereblon centric benzthiophene derived ER PROTACs

| Ex. # | Structure | ER-α Luciferase IC50 (nM) | *Obsd [M + H]+ | Synthetic Method |
|---|---|---|---|---|
| 42 | 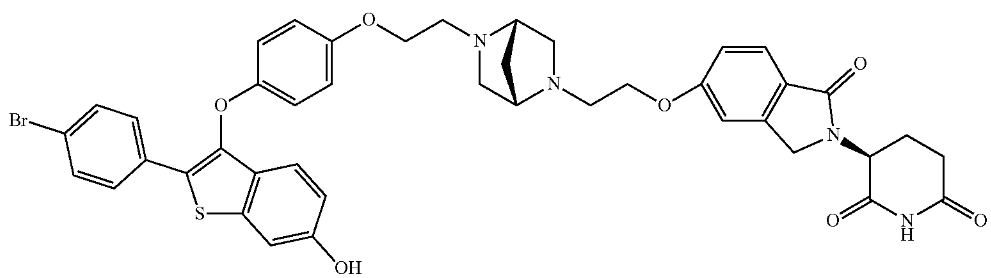 [SMILES: O=C1CC[C@H](N2Cc3cc(OCCN4C[C@@H]5C[C@H]4CN5CCOc4ccc(Oc5c(-c6ccc(Br)cc6)sc6cc(O)ccc56)cc4)ccc3C2=O)C(=O)N1] | 0.53 | 823.1, 825.1 | Scheme 17 |
| 43 | 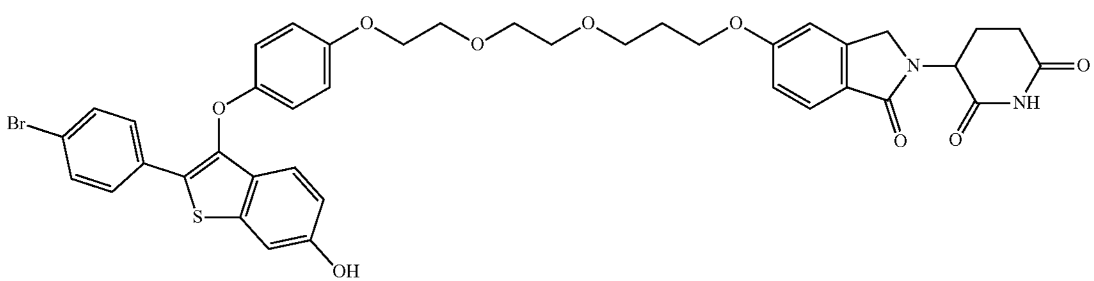 [SMILES: O=C1CCC(N2Cc3cc(OCCCOCCOCCOc4ccc(Oc5c(-c6ccc(Br)cc6)sc6cc(O)ccc56)cc4)ccc3C2=O)C(=O)N1] | 6.1 | 801.1, 803.3 | Scheme 25 |
| 44 | 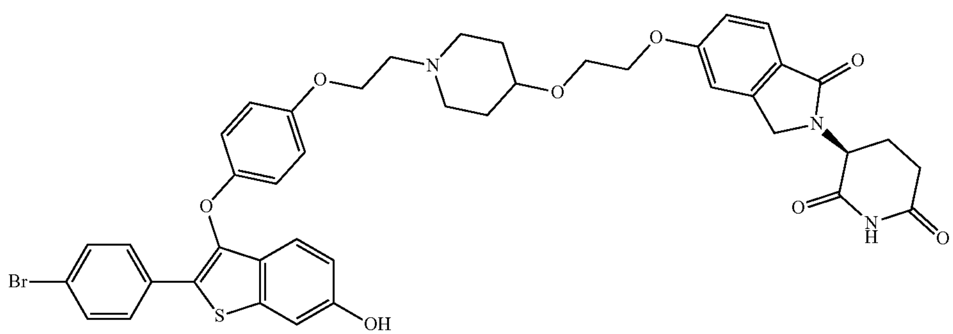 [SMILES: O=C1CC[C@H](N2Cc3cc(OCCOC4CCN(CCOc5ccc(Oc6c(-c7ccc(Br)cc7)sc7cc(O)ccc67)cc5)CC4)ccc3C2=O)C(=O)N1] | 0.54 | 826.2, 828.1 | Scheme 27 |

TABLE 1-continued

Activity, characterization and synthetic methods of cereblon centric benzthiophene derived ER PROTACs

| Ex. # | Structure | ER-α Luciferase IC50 (nM) | *Obsd [M + H]+ | Synthetic Method |
|---|---|---|---|---|
| 45 | 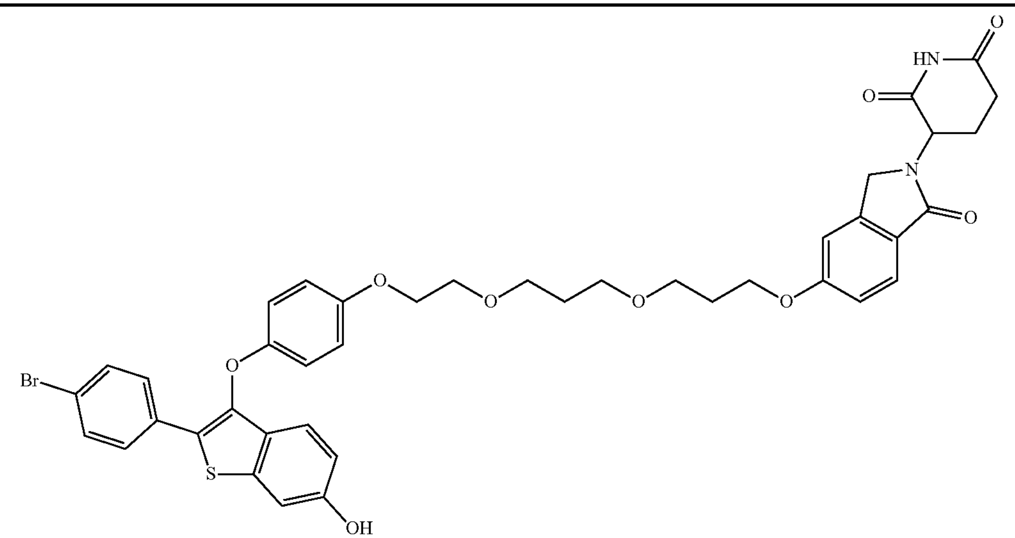 | 6.5 | 815.2, 817.1 | Scheme 25 |
| 46 | 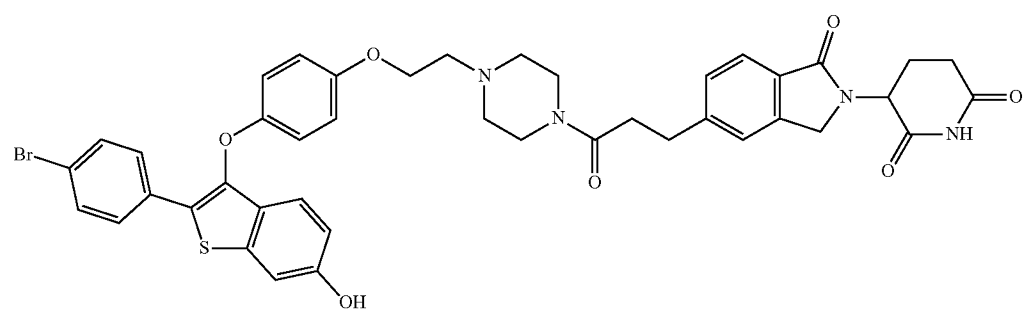 [SMILES: O=C1CCC(N2Cc3cc(CCC(=O)N4CCN(CCOc5ccc(Oc6c(-c7ccc(Br)cc7)sc7cc(O)ccc67)cc5)CC4)ccc3C2=O)C(=O)N1] | 1.9 | 823.2, 825.2 | Scheme 8 |

TABLE 1-continued

Activity, characterization and synthetic methods of cereblon centric benzthiophene derived ER PROTACs

| Ex. # | Structure | ER-α Luciferase IC50 (nM) | *Obsd [M + H]+ | Synthetic Method |
|---|---|---|---|---|
| 47 | 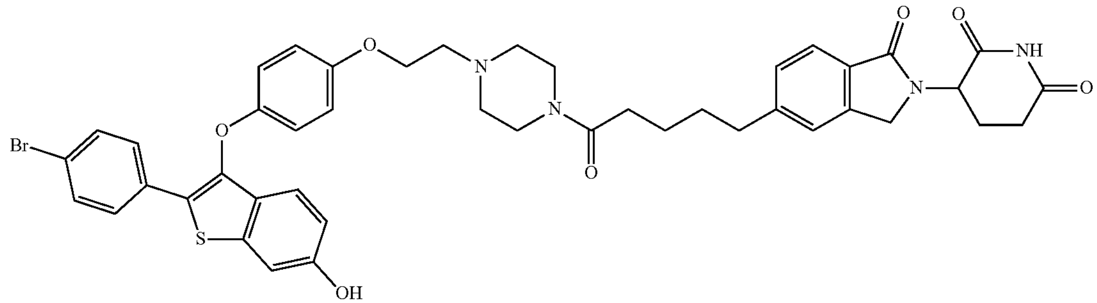 [SMILES: O=C1CCC(N2Cc3cc(CCCCC(=O)N4CCN(CCOc5ccc(Oc6c(-c7ccc(Br)cc7)sc7cc(O)ccc67)cc5)CC4)ccc3C2=O)C(=O)N1] | 0.86 | 851.1, 853.1 | Scheme 8 |
| 48 | 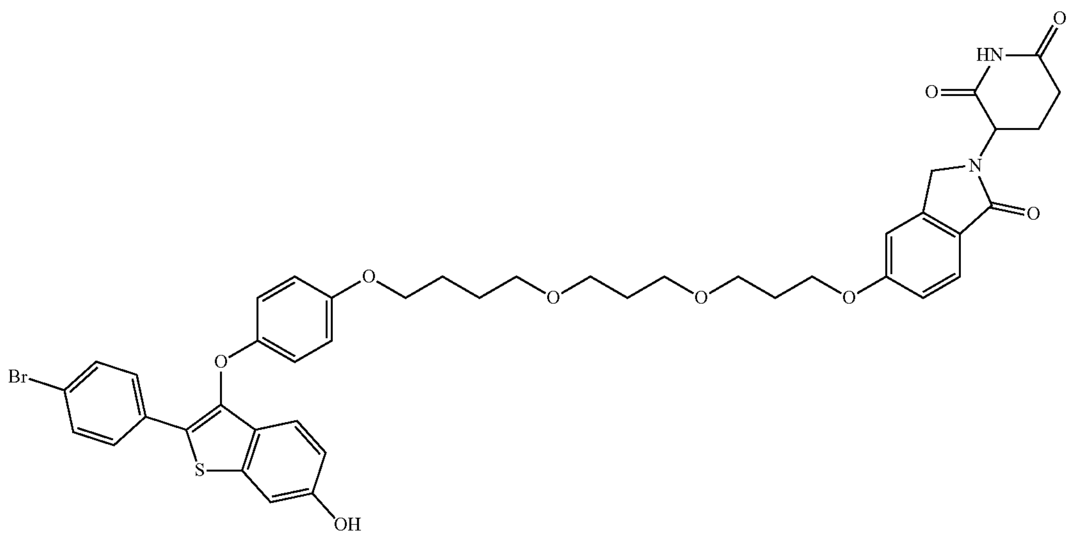 [SMILES: O=C1CCC(N2Cc3cc(OCCCOCCCOCCCCOc4ccc(Oc5c(-c6ccc(Br)cc6)sc6cc(O)ccc56)cc4)ccc3C2=O)C(=O)N1] | 8.3 | 842.8, 844.8 | Scheme 25 |

TABLE 1-continued

Activity, characterization and synthetic methods of cereblon centric benzthiophene derived ER PROTACs

| Ex. # | Structure | ER-α Luciferase IC50 (nM) | *Obsd [M + H]+ | Synthetic Method |
|---|---|---|---|---|
| 49 | 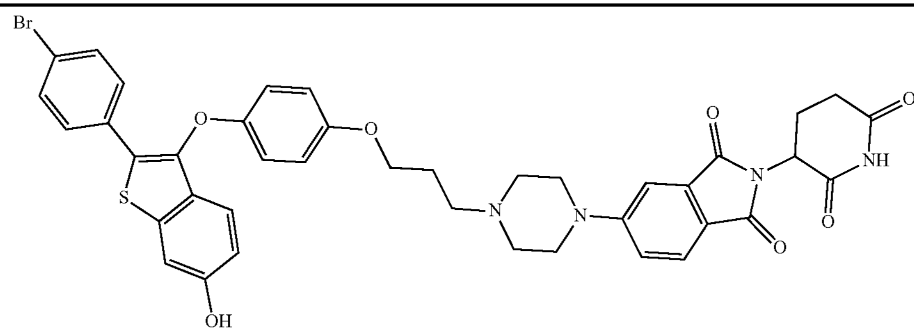 | 17.7 | 795.1, 797.1 | Scheme 29 |
| 50 | 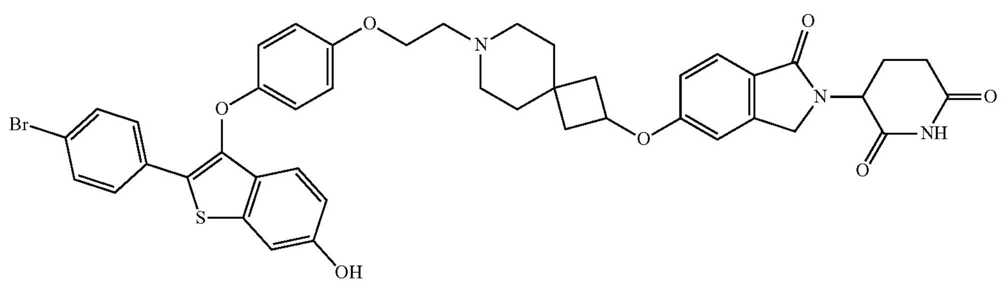 [SMILES: O=C1CCC(N2Cc3cc(OC4CC5(CCN(CCOc6ccc(Oc7c(-c8ccc(Br)cc8)sc8cc(O)ccc78)cc6)CC5)C4)ccc3C2=O)C(=O)N1] | 2.2 | 822.1, 824.0 | Scheme 30 |
| 51 | 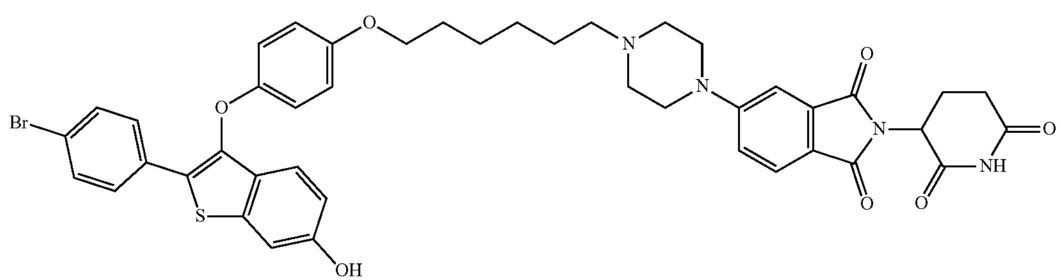 [SMILES: O=C1CCC(N2C(=O)c3ccc(N4CCN(CCCCCCOc5ccc(Oc6c(-c7ccc(Br)cc7)sc7cc(O)ccc67)cc5)CC4)cc3C2=O)C(=O)N1] | 26.2 | 836.8, 838.8 | Scheme 29 |

TABLE 1-continued

Activity, characterization and synthetic methods of cereblon centric benzthiophene derived ER PROTACs

| Ex. # | Structure | ER-α Luciferase IC50 (nM) | *Obsd [M + H]+ | Synthetic Method |
|---|---|---|---|---|
| 52 | 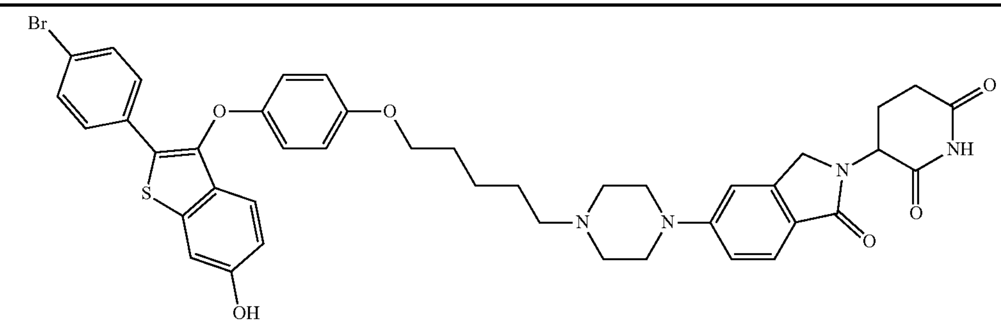 | 7.4 | 809.2, 811.2 | Scheme 28 |
| 53 | 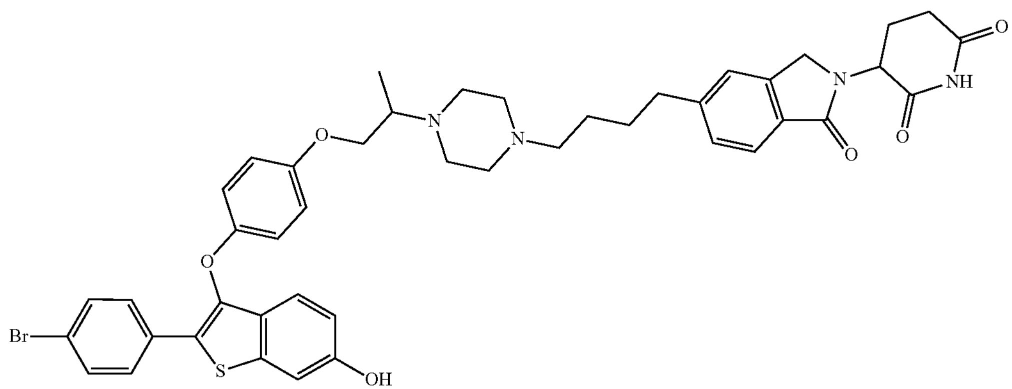 [SMILES: CC(COc1ccc(Oc2c(-c3ccc(Br)cc3)sc3cc(O)ccc23)cc1)N1CCN(CCCCc2ccc3c(c2)CN(C2CCC(=O)NC2=O)C3=O)CC1] | 0.6 | 837.2, 839.2 | Scheme 33 |
| 54 | 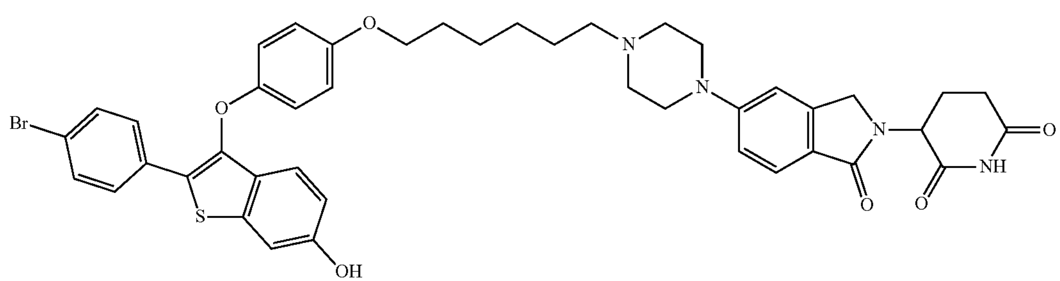 [SMILES: O=C1CCC(N2Cc3cc(N4CCN(CCCCCCOc5ccc(Oc6c(-c7ccc(Br)cc7)sc7cc(O)ccc67)cc5)CC4)ccc3C2=O)C(=O)N1] | 12.1 | 823.2, 825.2 | Scheme 28 |

TABLE 1-continued

Activity, characterization and synthetic methods of cereblon centric benzthiophene derived ER PROTACs

| Ex. # | Structure | ER-α Luciferase IC50 (nM) | *Obsd [M + H]+ | Synthetic Method |
|---|---|---|---|---|
| 55 | 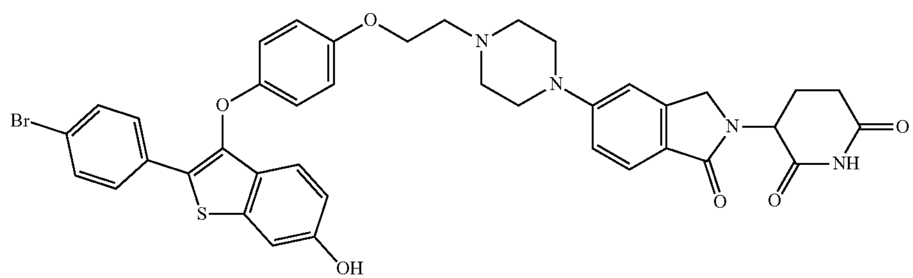 [SMILES: O=C1CCC(N2Cc3cc(N4CCN(CCOc5ccc(Oc6c(-c7ccc(Br)cc7)sc7cc(O)ccc67)cc5)CC4)ccc3C2=O)C(=O)N1] | 1.8 | 767.2, 769.2 | Scheme 28 |
| 56 | 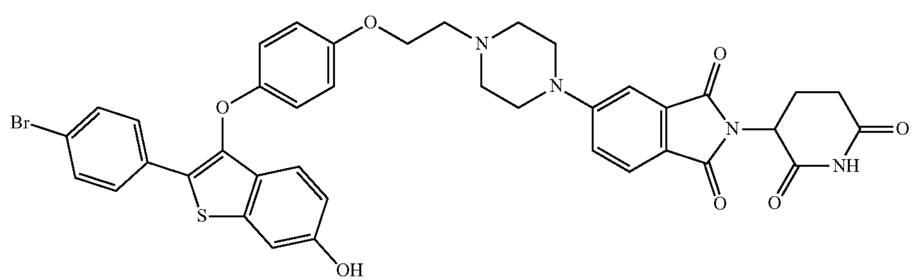 [SMILES: O=C1CCC(N2C(=O)c3ccc(N4CCN(CCOc5ccc(Oc6c(-c7ccc(Br)cc7)sc7cc(O)ccc67)cc5)CC4)cc3C2=O)C(=O)N1] | 10.6 | 781.1, 783.1 | Scheme 29 |
| 57 | 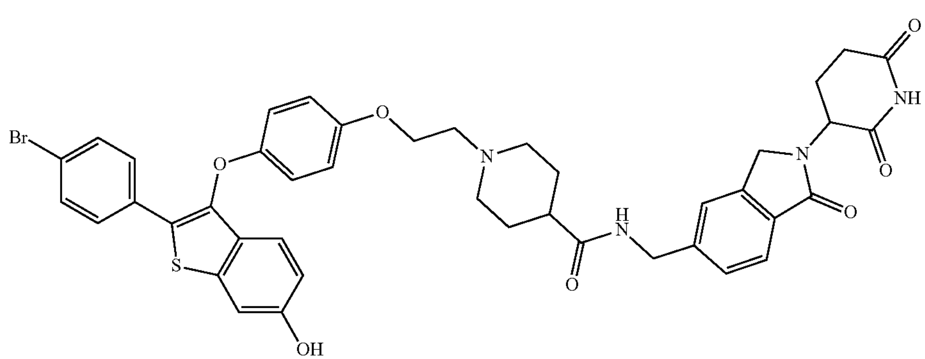 [SMILES: O=C1CCC(N2Cc3cc(CNC(=O)C4CCN(CCOc5ccc(Oc6c(-c7ccc(Br)cc7)sc7cc(O)ccc67)cc5)CC4)ccc3C2=O)C(=O)N1] | 3 | 823.2, 825.2 | Scheme 31 |

TABLE 1-continued
Activity, characterization and synthetic methods of cereblon centric benzthiophene derived ER PROTACs
| Ex. # | Structure | ER-α Luciferase IC50 (nM) | *Obsd [M + H]+ | Synthetic Method |
|---|---|---|---|---|
| 58 | 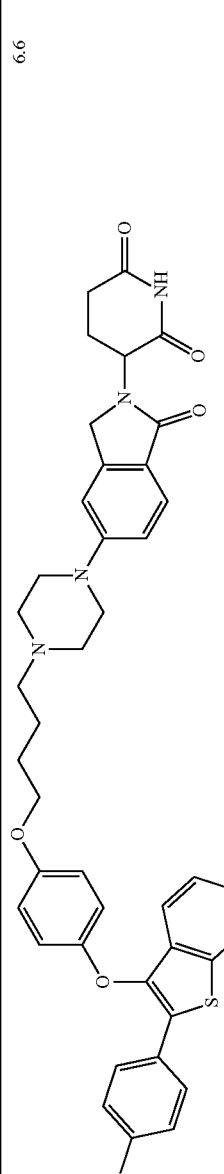 | 6.6 | 795.2, 797.2 | Scheme 28 |
| 59 | 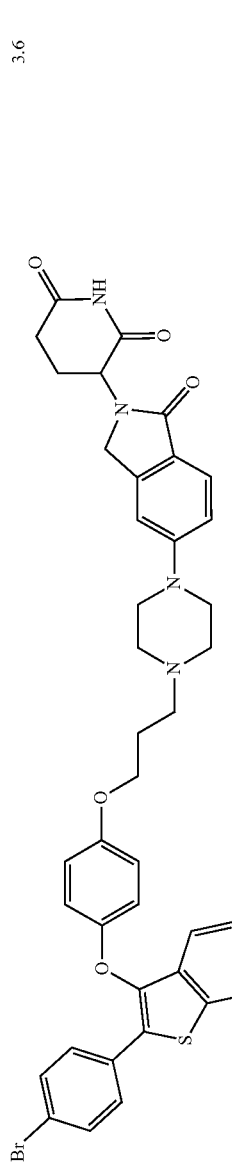 | 3.6 | 781.2, 783.2 | Scheme 28 |
| 60 | 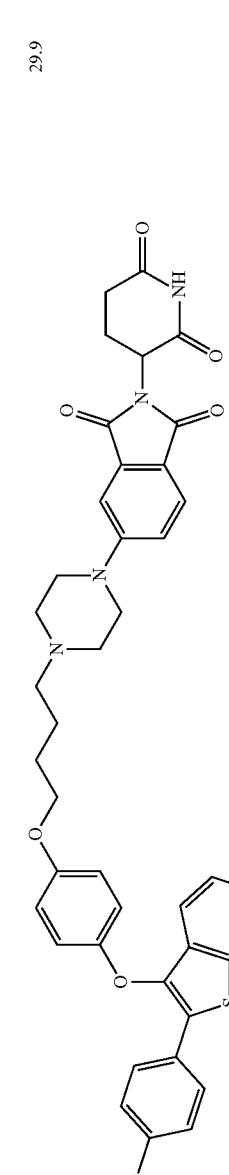 | 29.9 | 809.2, 811.2 | Scheme 29 |

TABLE 1-continued

Activity, characterization and synthetic methods of cereblon centric benzthiophene derived ER PROTACs

| Ex. # | Structure | ER-α Luciferase IC50 (nM) | *Obsd [M + H]+ | Synthetic Method |
|---|---|---|---|---|
| 61 | 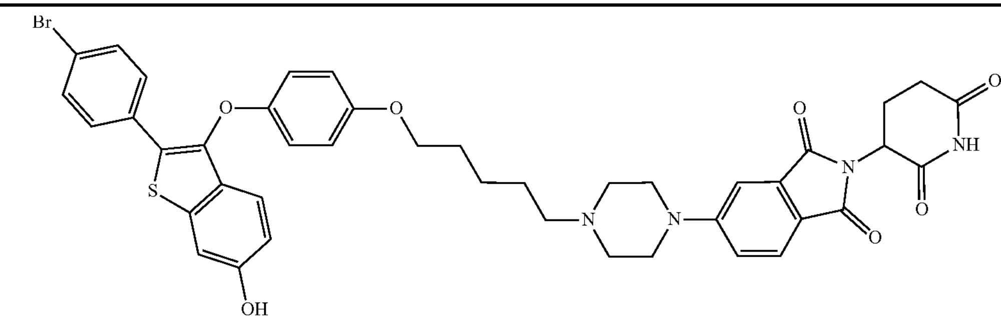 | 18.3 | 823.2, 825.1 | Scheme 29 |
| 62 | 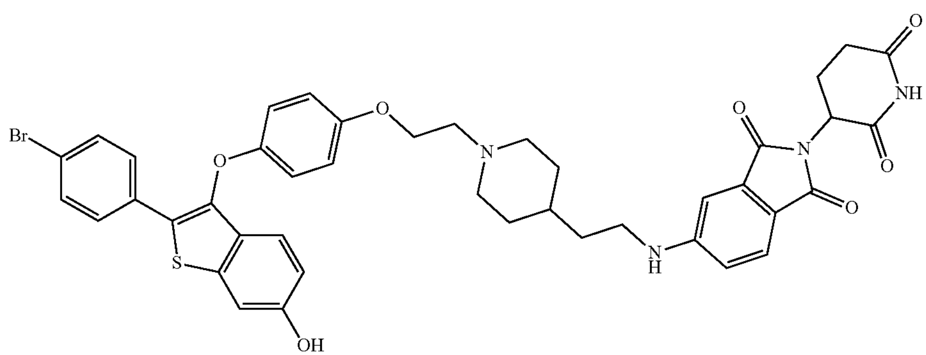 [SMILES: O=C1CCC(N2C(=O)c3ccc(NCCC4CCN(CCOc5ccc(Oc6c(-c7ccc(Br)cc7)sc7cc(O)ccc67)cc5)CC4)cc3C2=O)C(=O)N1] | 8.5 | 823.2, 825.1 | Scheme 29 |
| 63 | 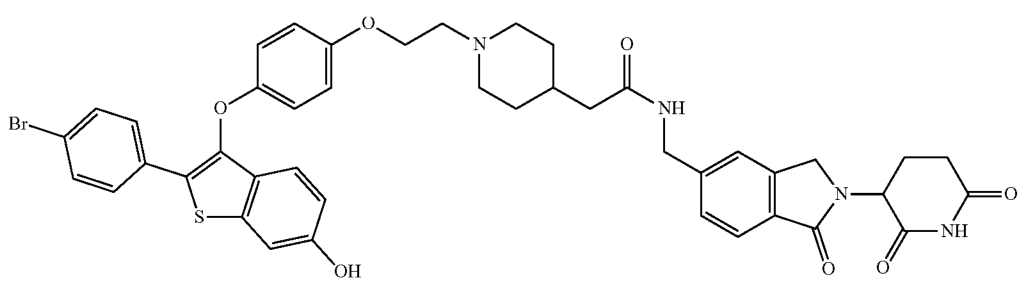 [SMILES: O=C(CC1CCN(CCOc2ccc(Oc3c(-c4ccc(Br)cc4)sc4cc(O)ccc34)cc2)CC1)NCc1ccc2c(c1)CN(C1CCC(=O)NC1=O)C2=O] | 0.82 | 837.2, 839.2 | Scheme 31 |

TABLE 1-continued

Activity, characterization and synthetic methods of cereblon centric benzthiophene derived ER PROTACs

| Ex. # | Structure | ER-α Luciferase IC50 (nM) | *Obsd [M + H]+ | Synthetic Method |
|-------|-----------|---------------------------|----------------|------------------|
| 64 | 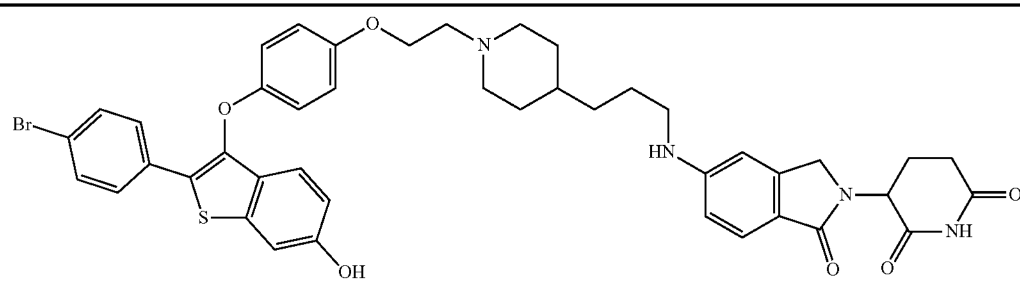 | 2.9 | 823.2, 825.2 | Scheme 32 |
| 65 | 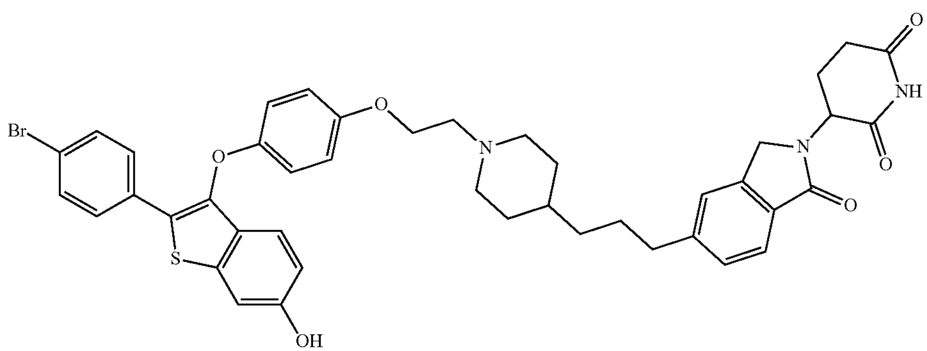 [SMILES: O=C1CCC(N2Cc3cc(CCCC4CCN(CCOc5ccc(Oc6c(-c7ccc(Br)cc7)sc7cc(O)ccc67)cc5)CC4)ccc3C2=O)C(=O)N1] | 2.7 | 809.2, 811.2 | Scheme 32 |

TABLE 1-continued

Activity, characterization and synthetic methods of cereblon centric benzthiophene derived ER PROTACs

| Ex. # | Structure | ER-α Luciferase IC50 (nM) | *Obsd [M + H]+ | Synthetic Method |
|---|---|---|---|---|
| 66 | 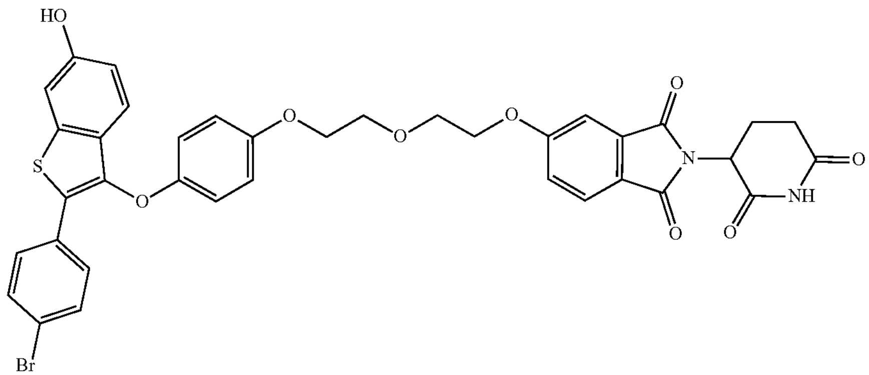 [SMILES: O=C1CCC(N2C(=O)c3ccc(OCCOCCOc4ccc(Oc5c(-c6ccc(Br)cc6)sc6cc(O)ccc56)cc4)cc3C2=O)C(=O)N1] | 5.8 | 757.1, 759.1 | Scheme 25 |
| 67 | 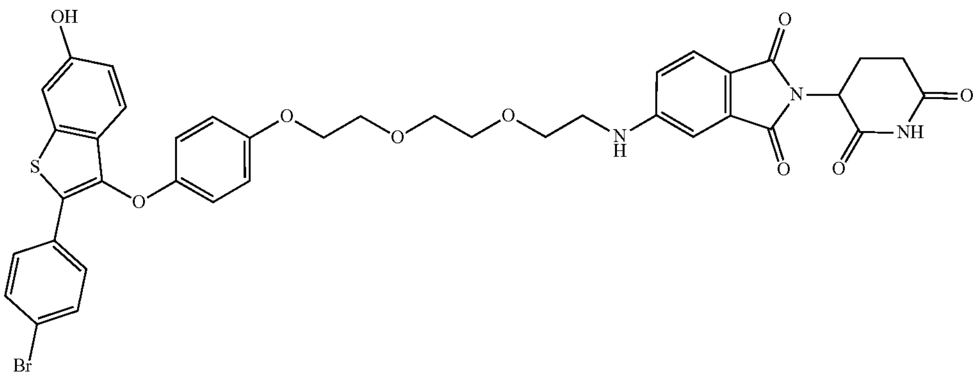 [SMILES: O=C1CCC(N2C(=O)c3ccc(NCCOCCOCCOc4ccc(Oc5c(-c6ccc(Br)cc6)sc6cc(O)ccc56)cc4)cc3C2=O)C(=O)N1] | 11.4 | 799.9, 802.0 | Scheme 24 |

TABLE 1-continued
Activity, characterization and synthetic methods of cereblon centric benzthiophene derived ER PROTACs
| Ex. # | Structure | ER-α Luciferase IC50 (nM) | *Obsd [M + H]+ | Synthetic Method |
|---|---|---|---|---|
| 68 | 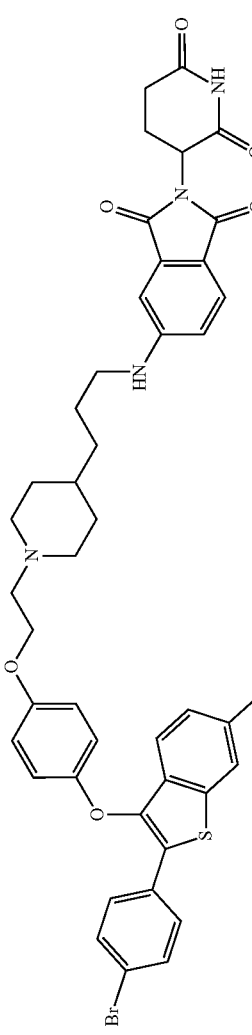 | 5.9 | 837.2, 839.2 | Scheme 32 |
| 69 | 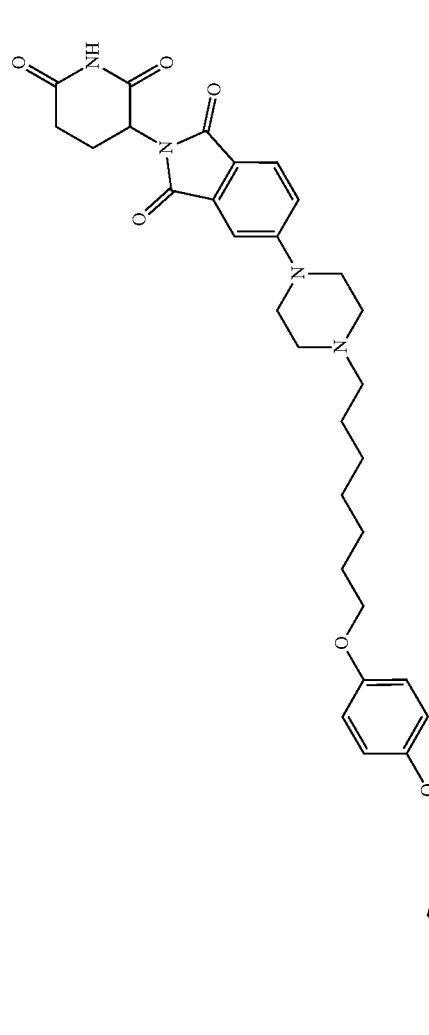 | 103.3 | 851.2, 853.2 | Scheme 29 |

TABLE 1-continued

Activity, characterization and synthetic methods of cereblon centric benzthiophene derived ER PROTACs

| Ex. # | Structure | ER-α Luciferase IC50 (nM) | *Obsd [M + H]+ | Synthetic Method |
|---|---|---|---|---|
| 70 | 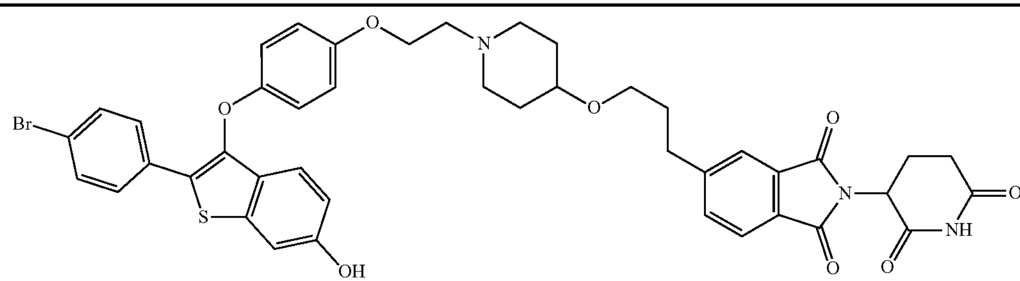 | 1.6 | 838.2, 840.2 | Scheme 33 |
| 71 | 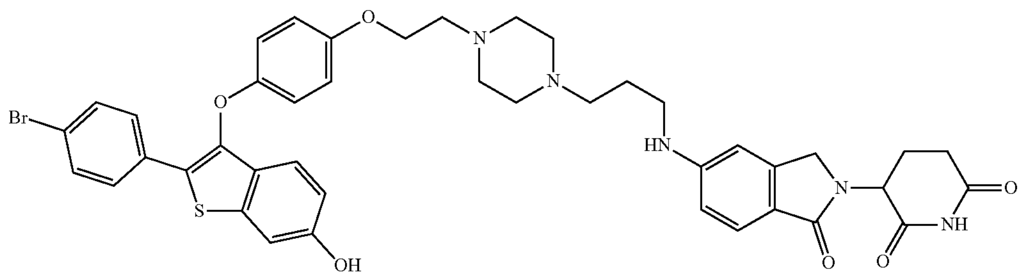 | 0.94 | 824.2, 826.2 | Scheme 15 |
| 72 | 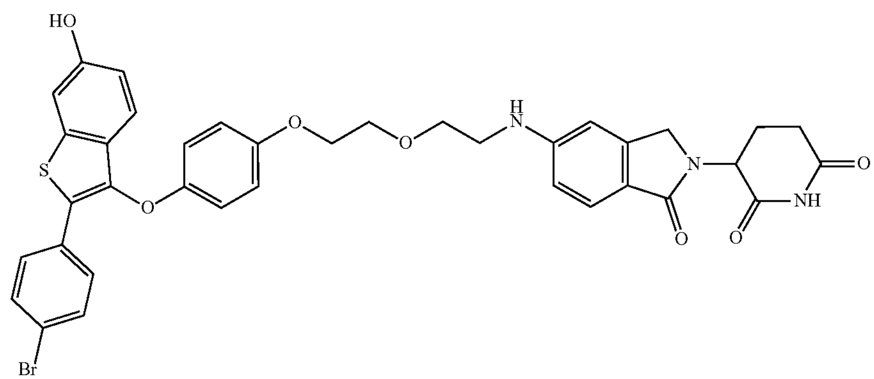 [SMILES: O=C1CCC(N2Cc3cc(NCCOCCOc4ccc(Oc5c(-c6ccc(Br)cc6)sc6cc(O)ccc56)cc4)ccc3C2=O)C(=O)N1] | 3.1 | 742.0, 744.0 | Scheme 26 |

TABLE 1-continued

Activity, characterization and synthetic methods of cereblon centric benzthiophene derived ER PROTACs

| Ex. # | Structure | ER-α Luciferase IC50 (nM) | *Obsd [M + H]+ | Synthetic Method |
|---|---|---|---|---|
| 73 | 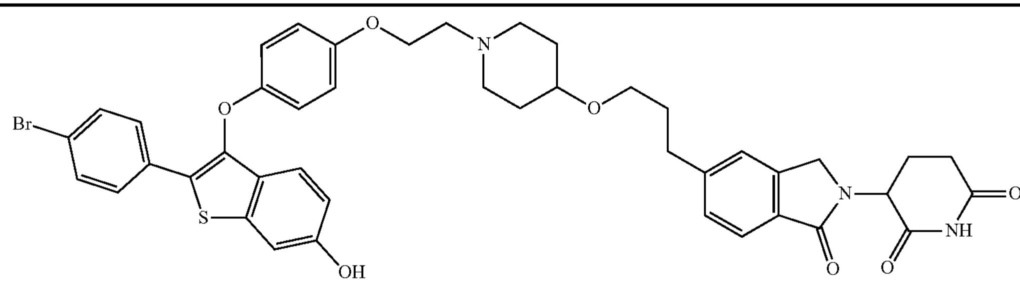 | 1.3 | 824.1, 826.1 | Scheme 33 |
| 74 | 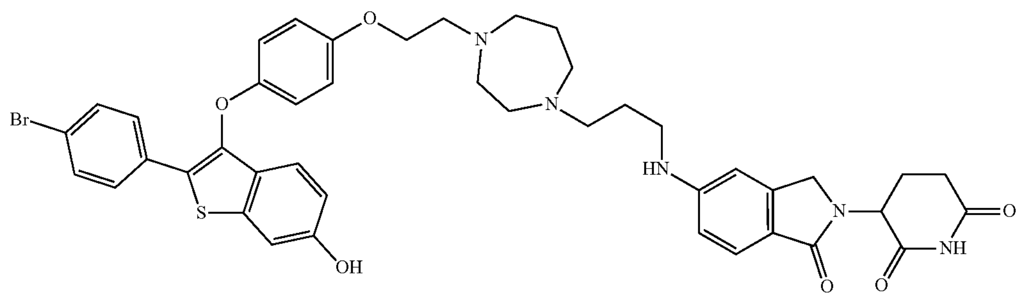 [SMILES: O=C1CCC(N2Cc3cc(NCCCN4CCCN(CCOc5ccc(Oc6c(-c7ccc(Br)cc7)sc7cc(O)ccc67)cc5)CC4)ccc3C2=O)C(=O)N1] | 11 | 838.0, 840.0 | Scheme 15 |
| 75 | 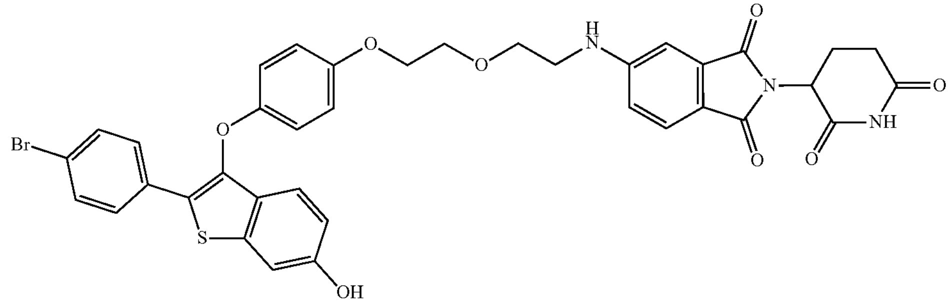 [SMILES: O=C1CCC(N2C(=O)c3ccc(NCCOCCOc4ccc(Oc5c(-c6ccc(Br)cc6)sc6cc(O)ccc56)cc4)cc3C2=O)C(=O)N1] | 6.6 | 756.0, 758.1 | Scheme 24 |

TABLE 1-continued

Activity, characterization and synthetic methods of cereblon centric benzthiophene derived ER PROTACs

| Ex. # | Structure | ER-α Luciferase IC50 (nM) | *Obsd [M + H]+ | Synthetic Method |
|---|---|---|---|---|
| 76 | 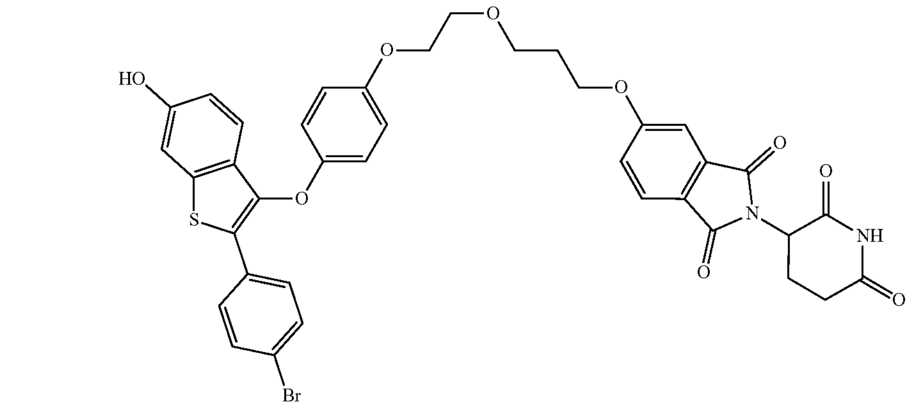 [SMILES: O=C1CCC(N2C(=O)c3ccc(OCCCOCCOc4ccc(Oc5c(-c6ccc(Br)cc6)sc6cc(O)ccc56)cc4)cc3C2=O)C(=O)N1] | 17 | 770.9, 773.0 | Scheme 25 |
| 77 | 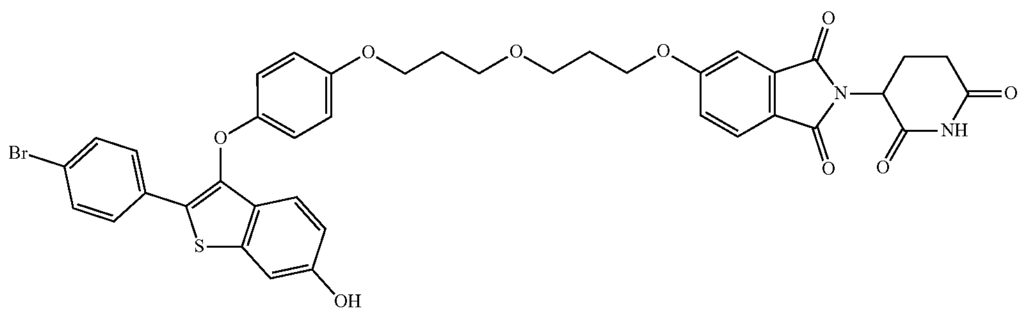 [SMILES: O=C1CCC(N2C(=O)c3ccc(OCCCOCCCOc4ccc(Oc5c(-c6ccc(Br)cc6)sc6cc(O)ccc56)cc4)cc3C2=O)C(=O)N1] | 34.1 | 807.0, 809.0* | Scheme 25 |

TABLE 1-continued
Activity, characterization and synthetic methods of cereblon centric benzthiophene derived ER PROTACs
| Ex. # | Structure | ER-α Luciferase IC50 (nM) | *Obsd [M + H]+ | Synthetic Method |
|---|---|---|---|---|
| 78 | 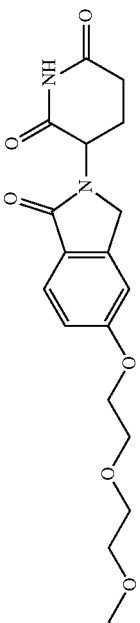 | 28.8 | 822.8, 824.8* | Scheme 25 |
| 79 | 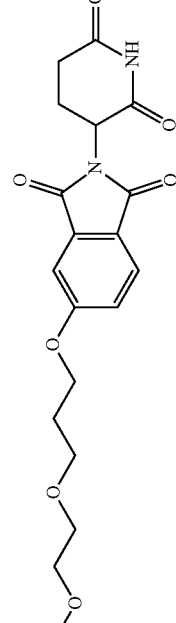 | 27.8 | 837.0, 839.0* | Scheme 25 |
| 80 | 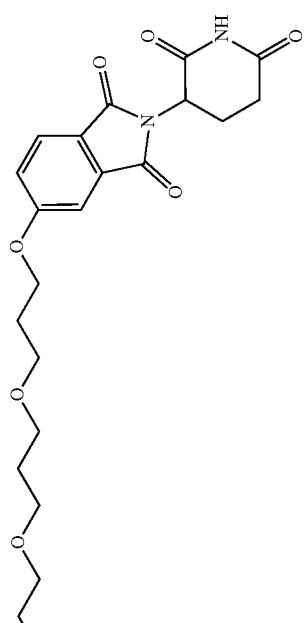 | 37.4 | 843.3, 845.1 | Scheme 25 |

TABLE 1-continued

Activity, characterization and synthetic methods of cereblon centric benzthiophene derived ER PROTACs

| Ex. # | Structure | ER-α Luciferase IC50 (nM) | *Obsd [M + H]+ | Synthetic Method |
|---|---|---|---|---|
| 81 | 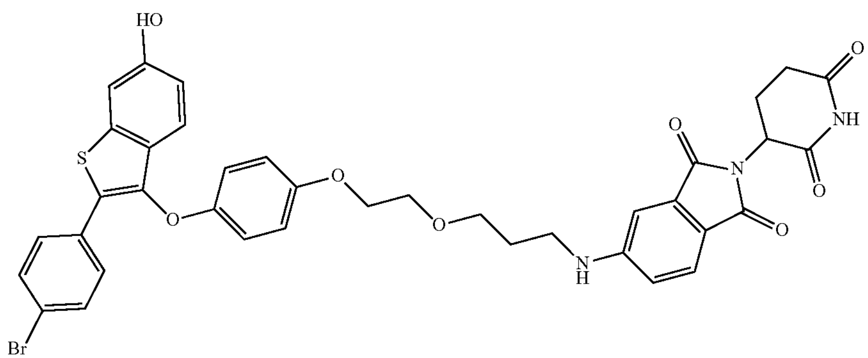 [SMILES: O=C1CCC(N2C(=O)c3ccc(NCCCOCCOc4ccc(Oc5c(-c6ccc(Br)cc6)sc6cc(O)ccc56)cc4)cc3C2=O)C(=O)N1] | 8.4 | 770.0, 772.0 | Scheme 24 |
| 82 | 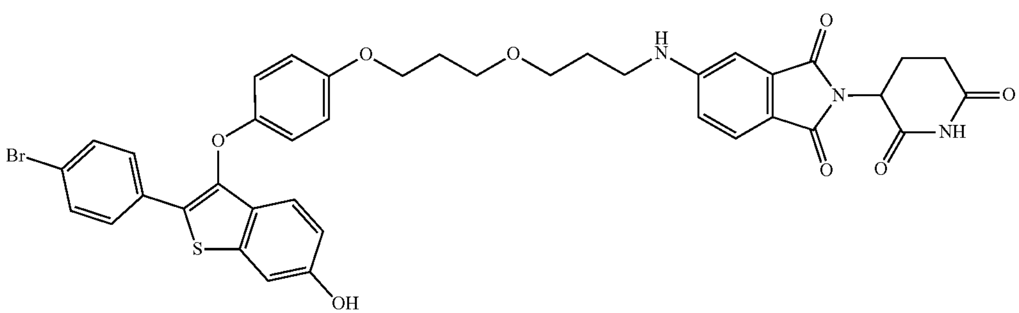 [SMILES: O=C1CCC(N2C(=O)c3ccc(NCCCOCCCOc4ccc(Oc5c(-c6ccc(Br)cc6)sc6cc(O)ccc56)cc4)cc3C2=O)C(=O)N1] | 32.2 | 784.0, 786.0 | Scheme 24 |

TABLE 1-continued

Activity, characterization and synthetic methods of cereblon centric benzthiophene derived ER PROTACs

| Ex. # | Structure | ER-α Luciferase IC50 (nM) | *Obsd [M + H]+ | Synthetic Method |
|---|---|---|---|---|
| 83 | 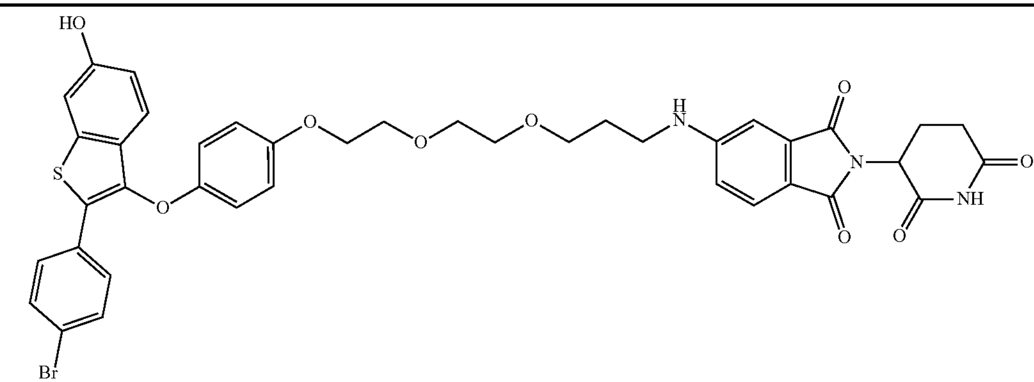 | 44.9 | 814.2, 816.1 | Scheme 24 |
| 84 | 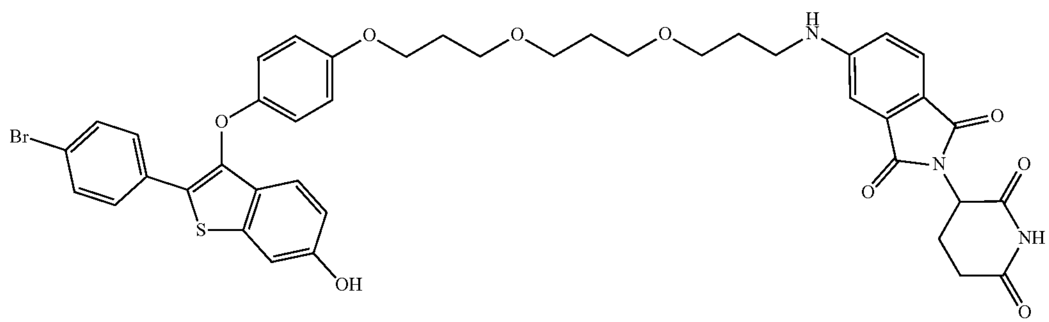 [SMILES: O=C1CCC(N2C(=O)c3ccc(NCCCOCCCOCCCOc4ccc(Oc5c(-c6ccc(Br)cc6)sc6cc(O)ccc56)cc4)cc3C2=O)C(=O)N1] | 30.9 | 842.0, 844.0 | Scheme 24 |

TABLE 1-continued

Activity, characterization and synthetic methods of cereblon centric benzthiophene derived ER PROTACs

| Ex. # | Structure | ER-α Luciferase IC50 (nM) | *Obsd [M + H]+ | Synthetic Method |
|---|---|---|---|---|
| 85 | 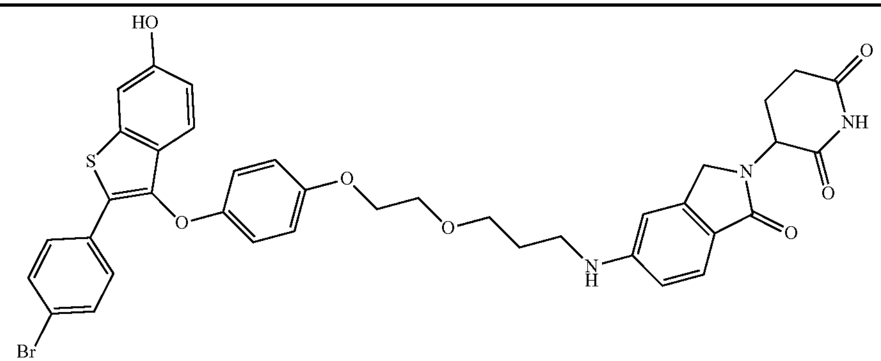 | 6 | 756.0, 758.0 | Scheme 26 |
| 86 | 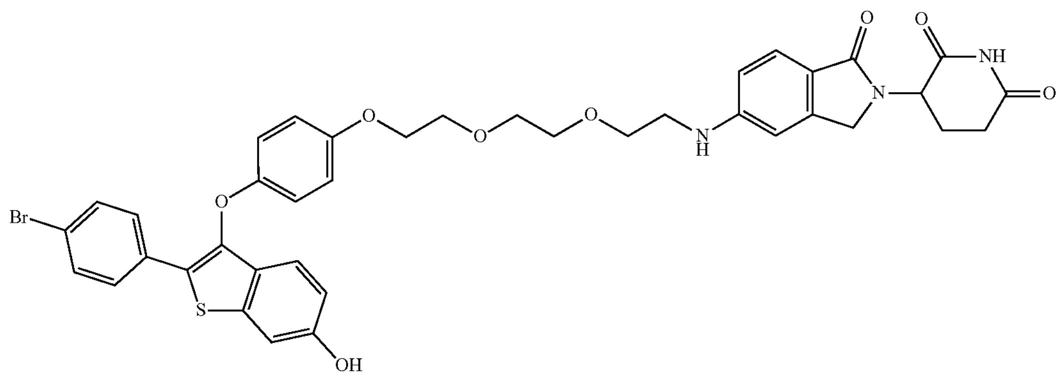 [SMILES: O=C1CCC(N2Cc3cc(NCCOCCOCCOc4ccc(Oc5c(-c6ccc(Br)cc6)sc6cc(O)ccc56)cc4)ccc3C2=O)C(=O)N1] | 11 | 786.1, 788.0 | Scheme 26 |

TABLE 1-continued

Activity, characterization and synthetic methods of cereblon centric benzthiophene derived ER PROTACs

| Ex. # | Structure | ER-α Luciferase IC50 (nM) | *Obsd [M + H]+ | Synthetic Method |
|---|---|---|---|---|
| 87 | 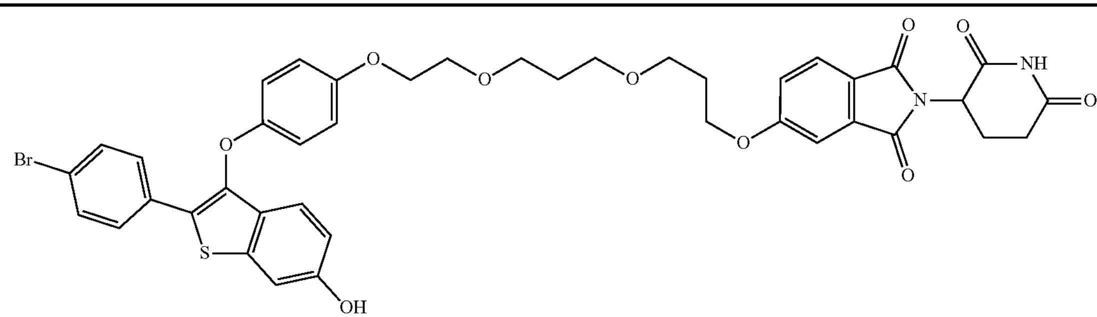 | 21.5 | 829.1, 831.0 | Scheme 25 |
| 88 | 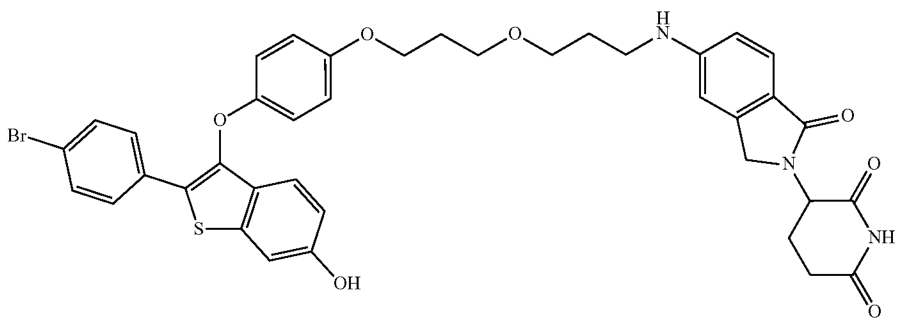 [SMILES: O=C1CCC(N2Cc3cc(NCCCOCCCOc4ccc(Oc5c(-c6ccc(Br)cc6)sc6cc(O)ccc56)cc4)ccc3C2=O)C(=O)N1] | | 770.2, 772.3 | Scheme 26 |
| 89 | 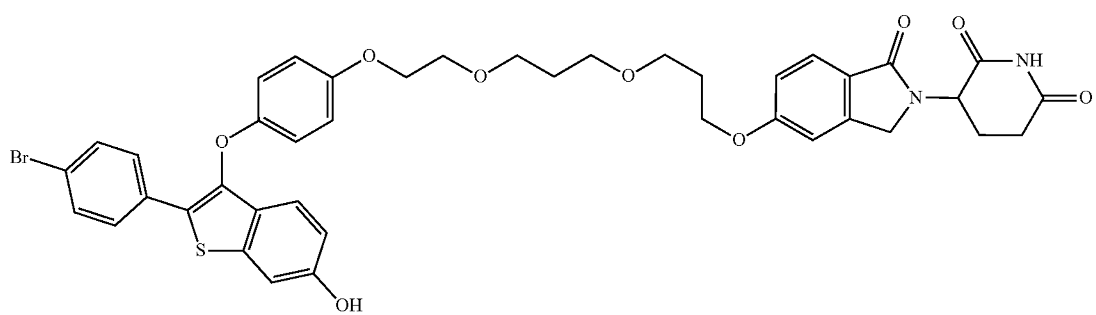 [SMILES: O=C1CCC(N2Cc3cc(OCCCOCCCOCCOc4ccc(Oc5c(-c6ccc(Br)cc6)sc6cc(O)ccc56)cc4)ccc3C2=O)C(=O)N1] | 4.8 | 814.0, 816.0 | Scheme 26 |

TABLE 1-continued

Activity, characterization and synthetic methods of cereblon centric benzthiophene derived ER PROTACs

| Ex. # | Structure | ER-α Luciferase IC50 (nM) | *Obsd [M + H]+ | Synthetic Method |
|---|---|---|---|---|
| 90 | 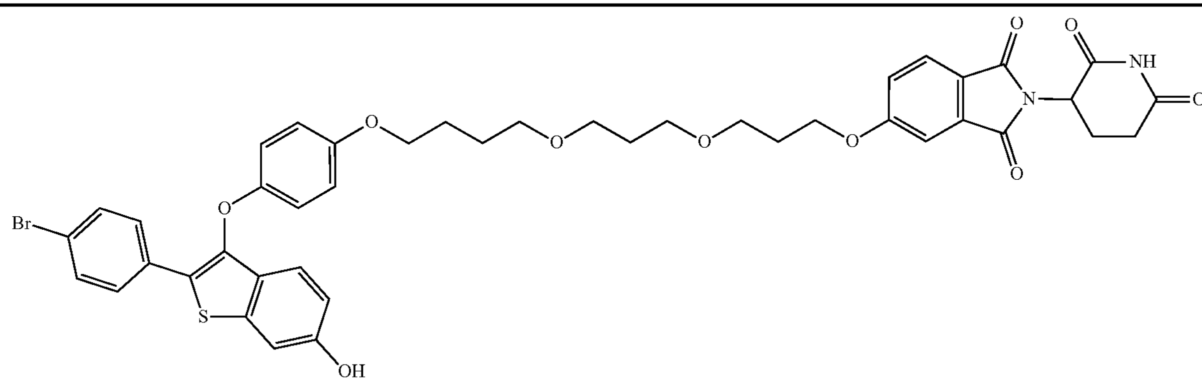 | | | Scheme 25 |
| 91 | 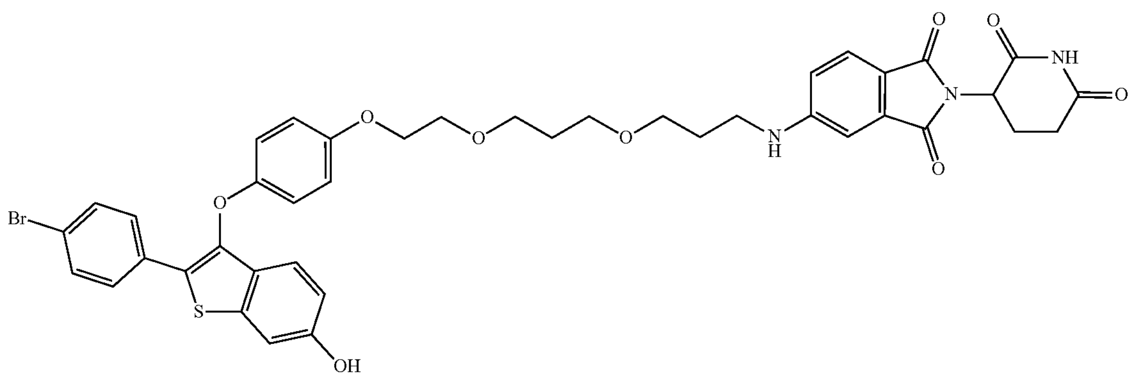 [SMILES: O=C1CCC(N2C(=O)c3ccc(NCCCOCCCOCCOc4ccc(Oc5c(-c6ccc(Br)cc6)sc6cc(O)ccc56)cc4)cc3C2=O)C(=O)N1] | | | Scheme 24 |

TABLE 1-continued

Activity, characterization and synthetic methods of cereblon centric benzthiophene derived ER PROTACs

| Ex. # | Structure | ER-α Luciferase IC50 (nM) | *Obsd [M + H]+ | Synthetic Method |
|---|---|---|---|---|
| 92 | 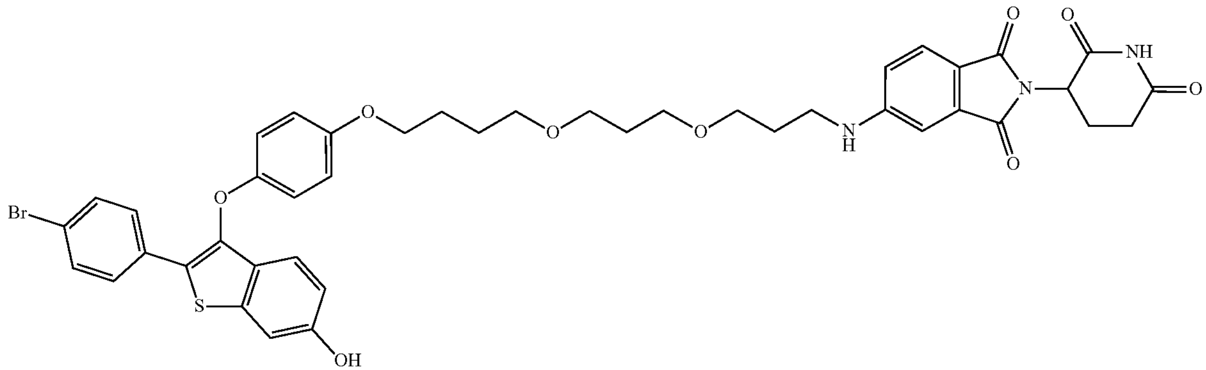 [SMILES: O=C1CCC(N2C(=O)c3ccc(NCCCOCCCOCCCCOc4ccc(Oc5c(-c6ccc(Br)cc6)sc6cc(O)ccc56)cc4)cc3C2=O)C(=O)N1] | | | Scheme 24 |
| 93 | 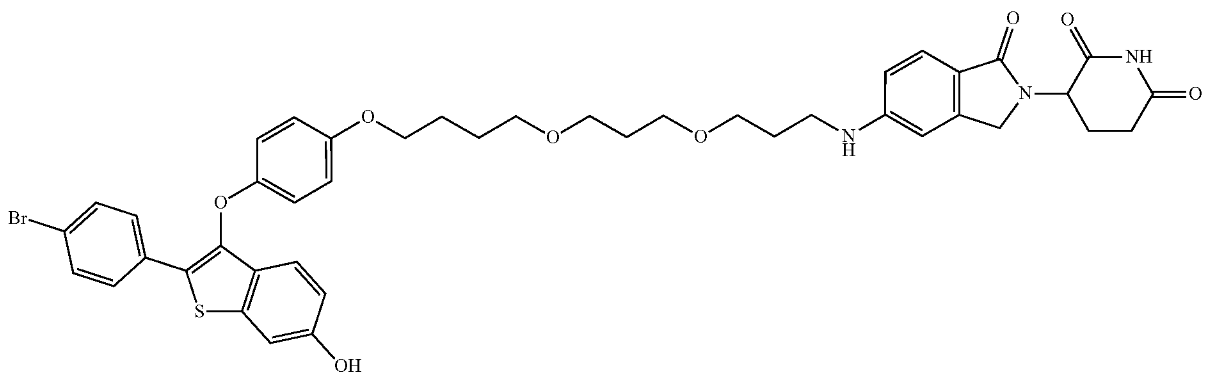 [SMILES: O=C1CCC(N2Cc3cc(NCCCOCCCOCCCCOc4ccc(Oc5c(-c6ccc(Br)cc6)sc6cc(O)ccc56)cc4)ccc3C2=O)C(=O)N1] | | | Scheme 26 |

TABLE 1-continued

Activity, characterization and synthetic methods of cereblon centric benzthiophene derived ER PROTACs

| Ex. # | Structure | ER-α Luciferase IC50 (nM) | *Obsd [M + H]+ | Synthetic Method |
|---|---|---|---|---|
| 94 | 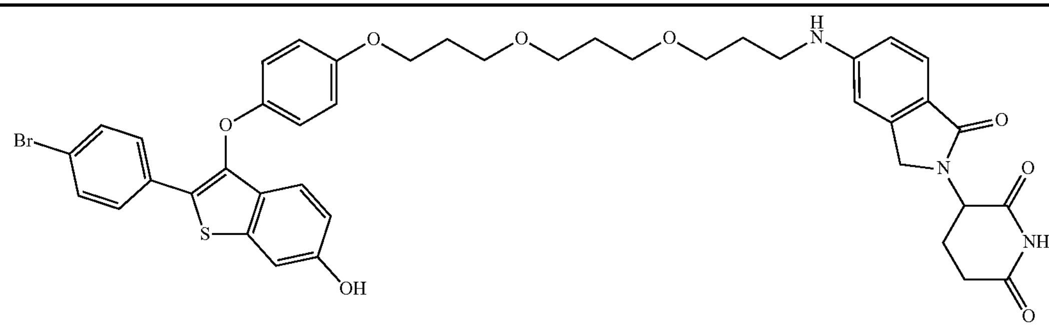 | | | Scheme 26 |
| 95 | 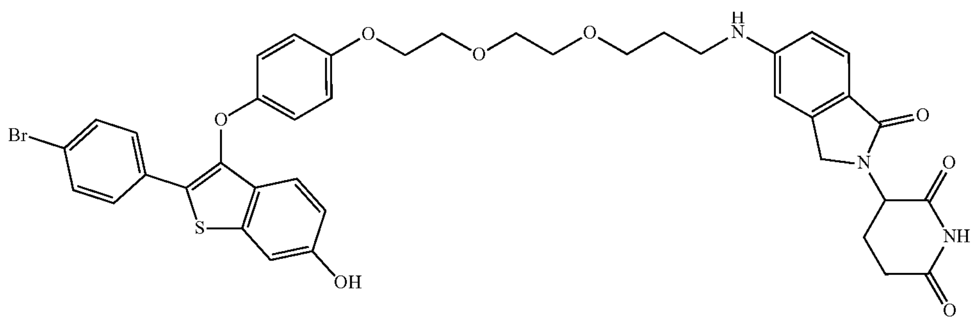 [SMILES: O=C1CCC(N2Cc3cc(NCCCOCCOCCOc4ccc(Oc5c(-c6ccc(Br)cc6)sc6cc(O)ccc56)cc4)ccc3C2=O)C(=O)N1] | | | Scheme 26 |
| 96 | 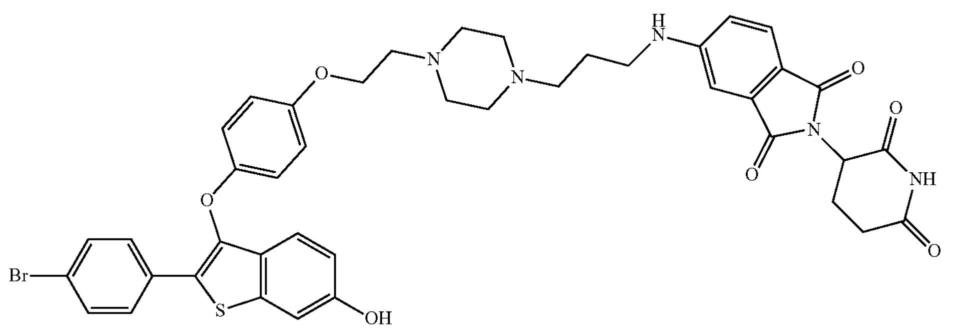 [SMILES: O=C1CCC(N2C(=O)c3ccc(NCCCN4CCN(CCOc5ccc(Oc6c(-c7ccc(Br)cc7)sc7cc(O)ccc67)cc5)CC4)cc3C2=O)C(=O)N1] | | | Scheme 16 |

TABLE 1-continued
Activity, characterization and synthetic methods of cereblon centric benzthiophene derived ER PROTACs
| Ex. # | Structure | ER-α Luciferase IC50 (nM) | *Obsd [M + H]+ | Synthetic Method |
|---|---|---|---|---|
| 97 | 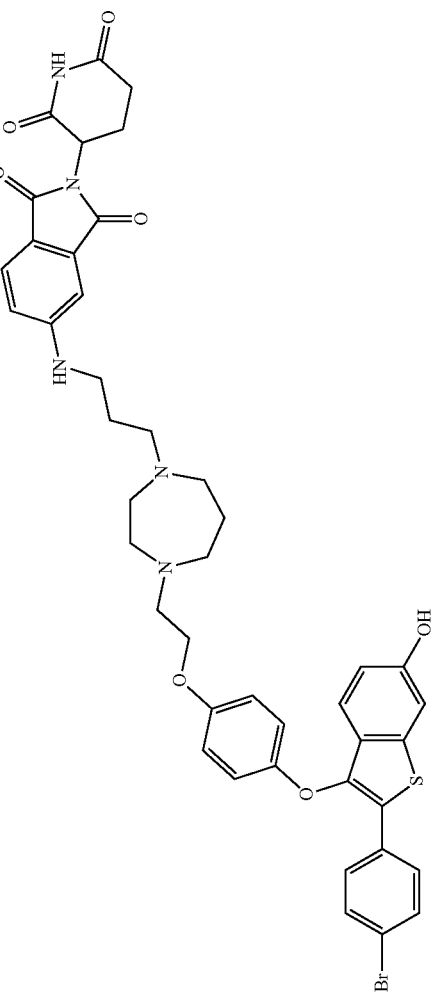 | | | Scheme 16 |
| 98 | 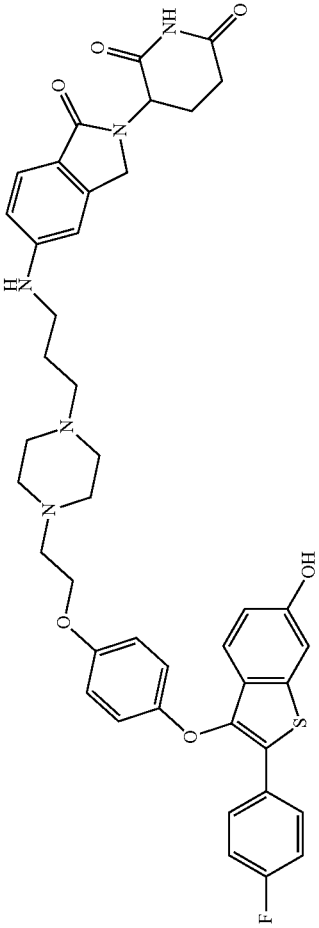 | | | Scheme 15 |

TABLE 1-continued

Activity, characterization and synthetic methods of cereblon centric benzthiophene derived ER PROTACs

| Ex. # | Structure | ER-α Luciferase IC50 (nM) | *Obsd [M + H]+ | Synthetic Method |
|---|---|---|---|---|
| 99 | 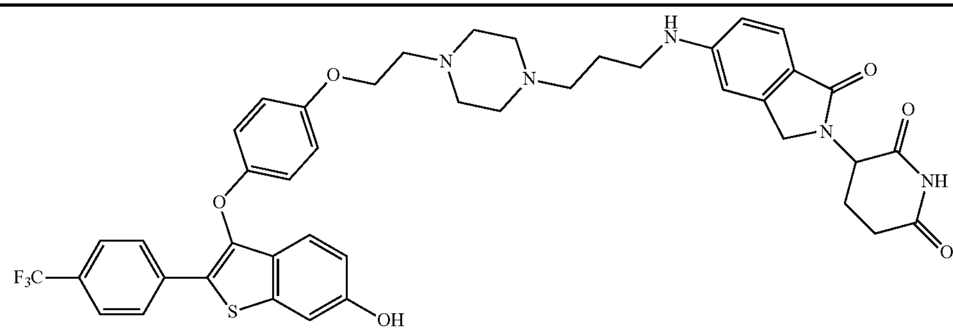 | | | Scheme 15 |
| 100 | 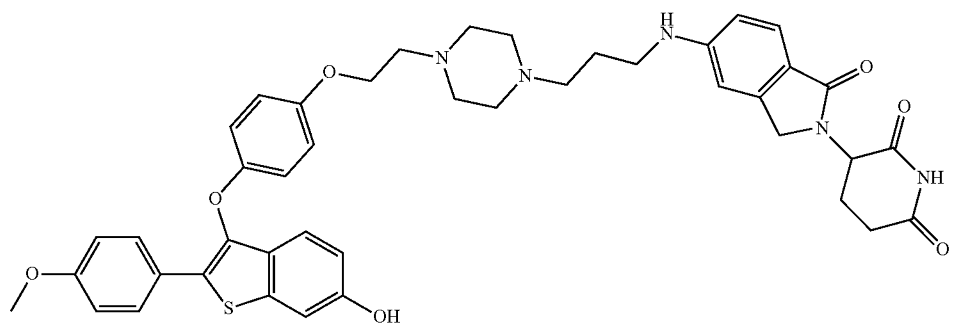 [SMILES: COc1ccc(-c2sc3cc(O)ccc3c2Oc2ccc(OCCN3CCN(CCCNc4ccc5c(c4)CN(C4CCC(=O)NC4=O)C5=O)CC3)cc2)cc1] | | | Scheme 15 |

TABLE 1-continued

Activity, characterization and synthetic methods of cereblon centric benzthiophene derived ER PROTACs

| Ex. # | Structure | ER-α Luciferase IC50 (nM) | *Obsd [M + H]+ | Synthetic Method |
|---|---|---|---|---|
| 101 | 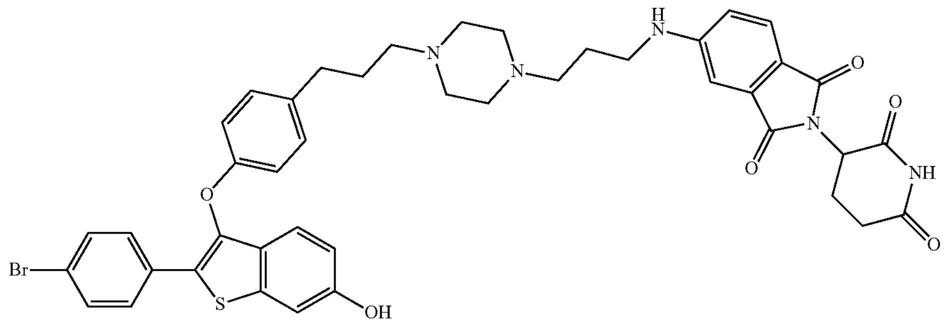 | | | Scheme 16 |
| 102 | 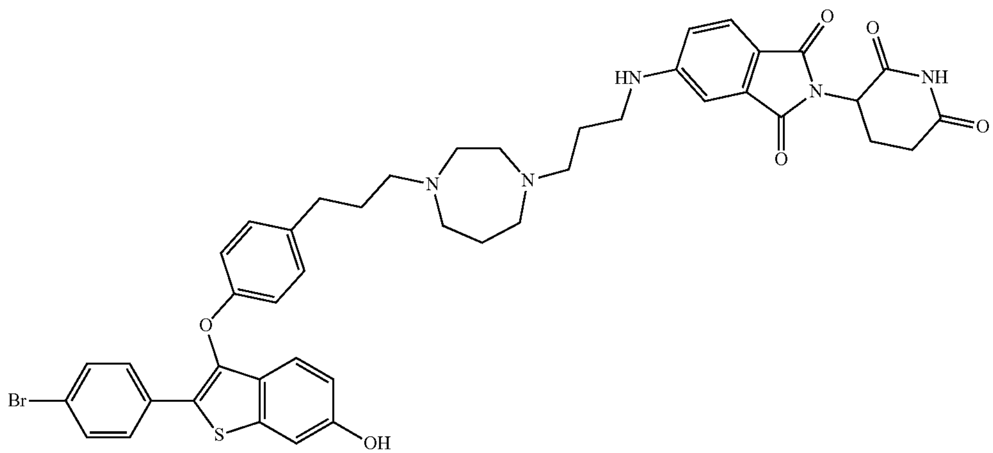 [SMILES: O=C1CCC(N2C(=O)c3ccc(NCCCN4CCCN(CCCc5ccc(Oc6c(-c7ccc(Br)cc7)sc7cc(O)ccc67)cc5)CC4)cc3C2=O)C(=O)N1] | | | Scheme 16 |

TABLE 1-continued

Activity, characterization and synthetic methods of cereblon centric benzthiophene derived ER PROTACs

| Ex. # | Structure | ER-α Luciferase IC50 (nM) | *Obsd [M + H]+ | Synthetic Method |
|-------|-----------|---------------------------|----------------|------------------|
| 103 | 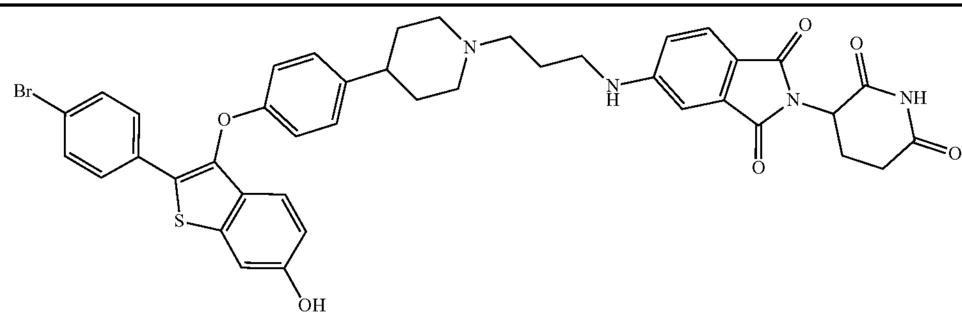 | | | |
| 104 | 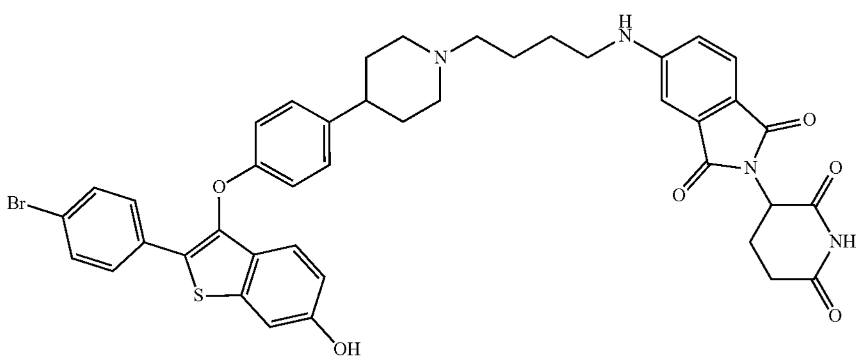 [SMILES: O=C1CCC(N2C(=O)c3ccc(NCCCCN4CCC(c5ccc(Oc6c(-c7ccc(Br)cc7)sc7cc(O)ccc67)cc5)CC4)cc3C2=O)C(=O)N1] | | | |

TABLE 1-continued

Activity, characterization and synthetic methods of cereblon centric benzthiophene derived ER PROTACs

| Ex. # | Structure | ER-α Luciferase IC50 (nM) | *Obsd [M + H]+ | Synthetic Method |
|---|---|---|---|---|
| 105 | 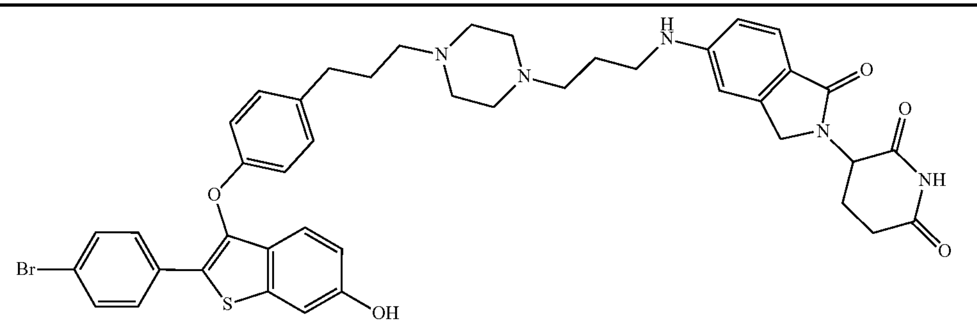 | | | |
| 106 | 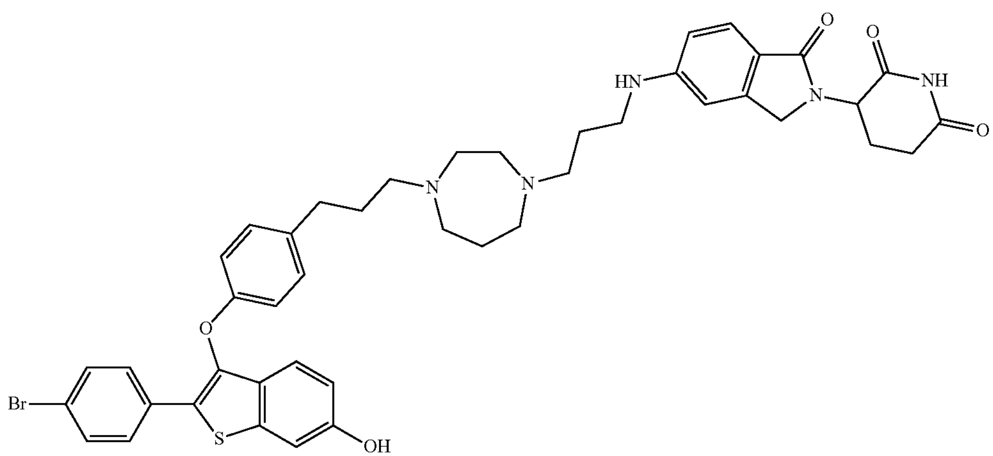 [SMILES: O=C1CCC(N2Cc3cc(NCCCN4CCCN(CCCc5ccc(Oc6c(-c7ccc(Br)cc7)sc7cc(O)ccc67)cc5)CC4)ccc3C2=O)C(=O)N1] | | | |

TABLE 1-continued

Activity, characterization and synthetic methods of cereblon centric benzthiophene derived ER PROTACs

| Ex. # | Structure | ER-α Luciferase IC50 (nM) | *Obsd [M + H]+ | Synthetic Method |
|---|---|---|---|---|
| 107 | 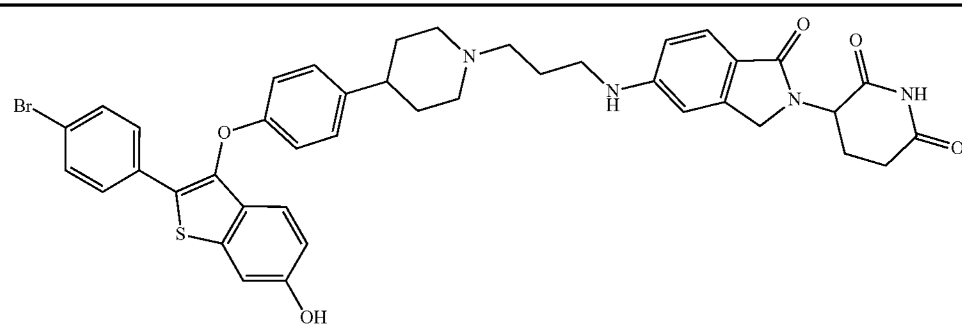 | | | |
| 108 | 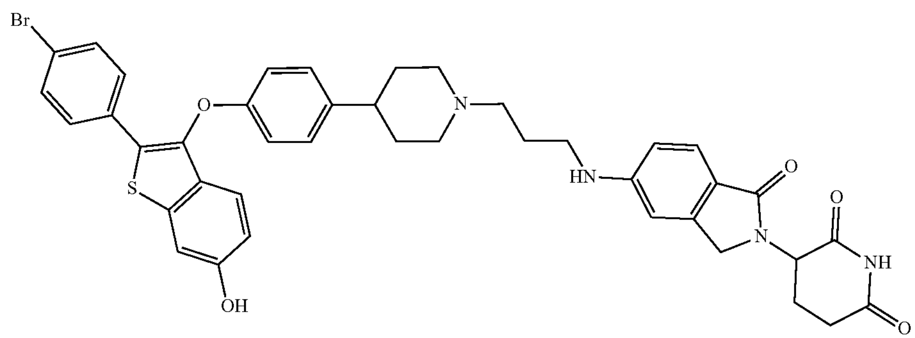 [SMILES: O=C1CCC(N2Cc3cc(NCCCN4CCC(c5ccc(Oc6c(-c7ccc(Br)cc7)sc7cc(O)ccc67)cc5)CC4)ccc3C2=O)C(=O)N1] | | | |

TABLE 1-continued
Activity, characterization and synthetic methods of cereblon centric benzthiophene derived ER PROTACs
| Ex. # | Structure | ER-α Luciferase IC50 (nM) | *Obsd [M + H]+ | Synthetic Method |
|---|---|---|---|---|
| 109 | 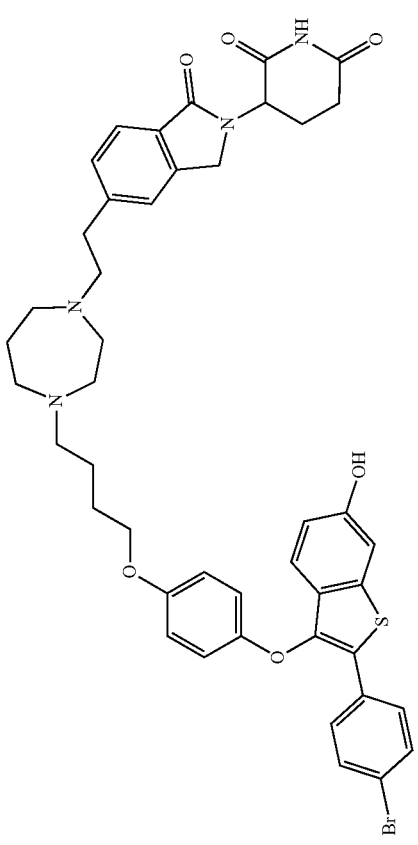 | | | |
| 110 | 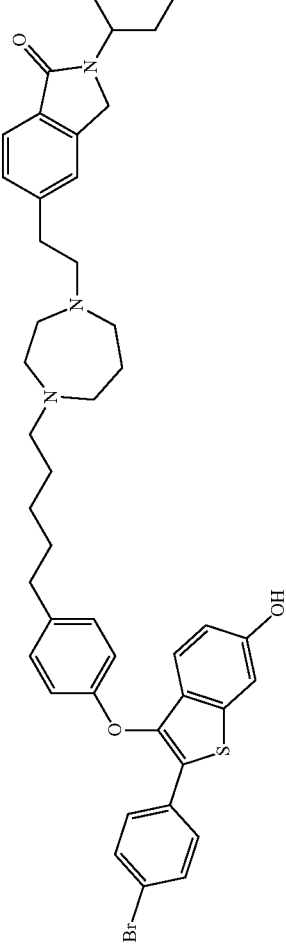 | | | |
*Observed [M + Na]+ from LC/MS

TABLE 2

Activity, characterization and synthetic methods of VHL centric benzthiophene derived ER PROTACs

| Ex. # | Chemical Structure | IC$_{50}$ (nM) | Obsd [M + H]$^+$ | Synthetic Methods |
|---|---|---|---|---|
| 111 | 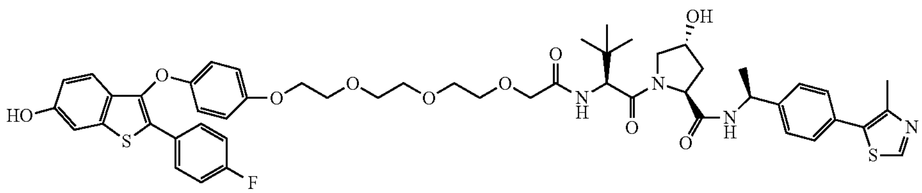 [SMILES: Cc1ncsc1-c1ccc([C@H](C)NC(=O)[C@@H]2C[C@@H](O)CN2C(=O)[C@@H](NC(=O)COCCOCCOCCOc2ccc(Oc3c(-c4ccc(F)cc4)sc4cc(O)ccc34)cc2)C(C)(C)C)cc1] | 0.6 | 969.3 | Scheme 2A, 18A |
| 112 | 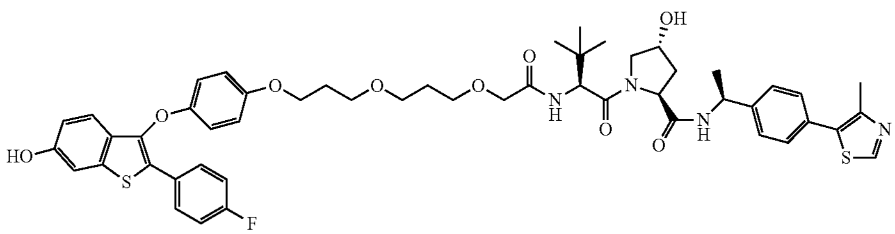 [SMILES: Cc1ncsc1-c1ccc([C@H](C)NC(=O)[C@@H]2C[C@@H](O)CN2C(=O)[C@@H](NC(=O)COCCCOCCCOc2ccc(Oc3c(-c4ccc(F)cc4)sc4cc(O)ccc34)cc2)C(C)(C)C)cc1] | 15.8 | 953.3 | Scheme 18A |
| 113 | 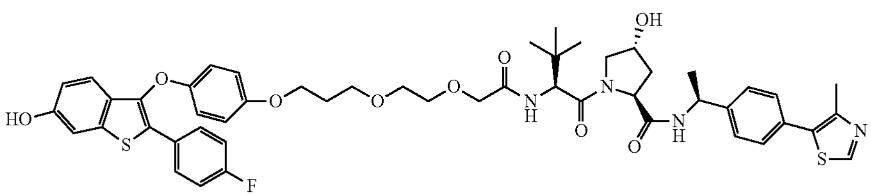 [SMILES: Cc1ncsc1-c1ccc([C@H](C)NC(=O)[C@@H]2C[C@@H](O)CN2C(=O)[C@@H](NC(=O)COCCOCCCOc2ccc(Oc3c(-c4ccc(F)cc4)sc4cc(O)ccc34)cc2)C(C)(C)C)cc1] | 23.7 | 939.3 | Scheme 18A |
| 114 | 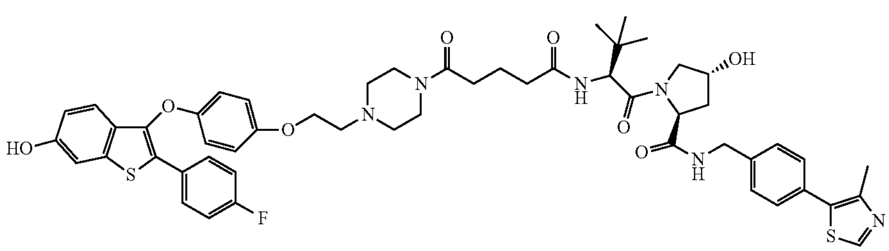 [SMILES: Cc1ncsc1-c1ccc(CNC(=O)[C@@H]2C[C@@H](O)CN2C(=O)[C@@H](NC(=O)CCCC(=O)N2CCN(CCOc3ccc(Oc4c(-c5ccc(F)cc5)sc5cc(O)ccc45)cc3)CC2)C(C)(C)C)cc1] | 22 | 991.4 | Scheme 5A |
| 115 | 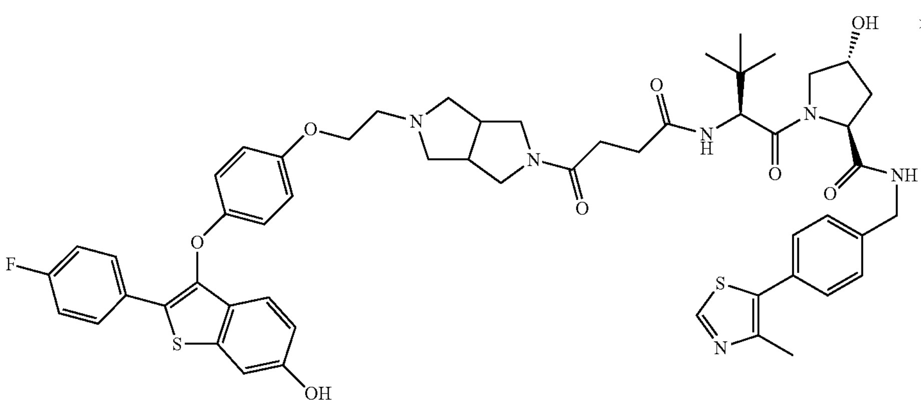 [SMILES: Cc1ncsc1-c1ccc(CNC(=O)[C@@H]2C[C@@H](O)CN2C(=O)[C@@H](NC(=O)CCC(=O)N2CC3CN(CCOc4ccc(Oc5c(-c6ccc(F)cc6)sc6cc(O)ccc56)cc4)CC3C2)C(C)(C)C)cc1] | >100 | 1003.2 | Scheme 3A, 5A, 6A |

TABLE 2-continued

Activity, characterization and synthetic methods of VHL centric benzthiophene derived ER PROTACs

| Ex. # | Chemical Structure | IC$_{50}$ (nM) | Obsd [M + H]$^+$ | Synthetic Methods |
|---|---|---|---|---|
| 116 | 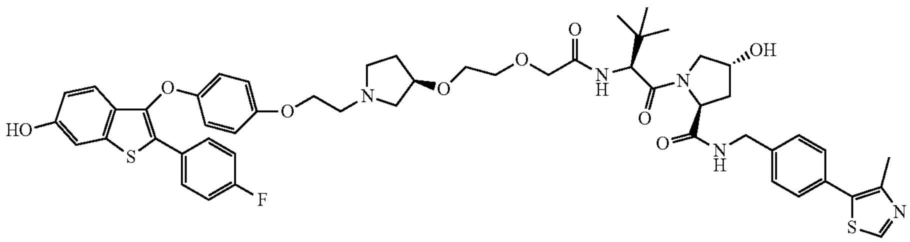 [SMILES: Cc1ncsc1-c1ccc(CNC(=O)[C@@H]2C[C@@H](O)CN2C(=O)[C@@H](NC(=O)COCCO[C@@H]2CCN(CCOc3ccc(Oc4c(-c5ccc(F)cc5)sc5cc(O)ccc45)cc3)C2)C(C)(C)C)cc1] | 3 | 980.3 | Scheme 7A |
| 117 | 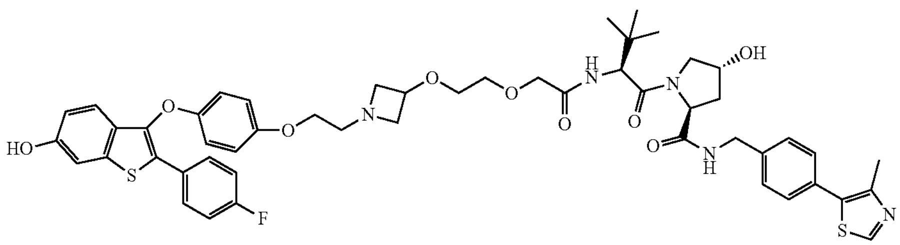 [SMILES: Cc1ncsc1-c1ccc(CNC(=O)[C@@H]2C[C@@H](O)CN2C(=O)[C@@H](NC(=O)COCCOC2CN(CCOc3ccc(Oc4c(-c5ccc(F)cc5)sc5cc(O)ccc45)cc3)C2)C(C)(C)C)cc1] | 3.3 | 966.2 | Scheme 8A |
| 118 | 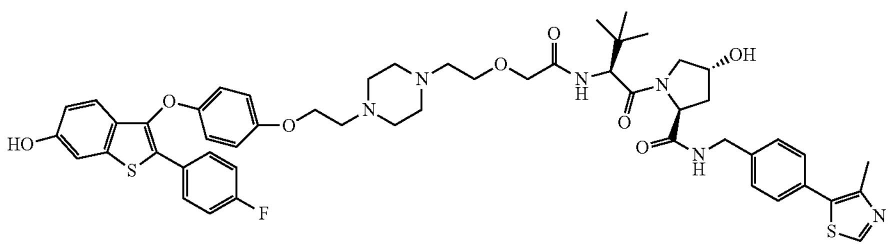 [SMILES: Cc1ncsc1-c1ccc(CNC(=O)[C@@H]2C[C@@H](O)CN2C(=O)[C@@H](NC(=O)COCCN2CCN(CCOc3ccc(Oc4c(-c5ccc(F)cc5)sc5cc(O)ccc45)cc3)CC2)C(C)(C)C)cc1] | 0.4 | 979.3 | Scheme 19A |
| 119 | 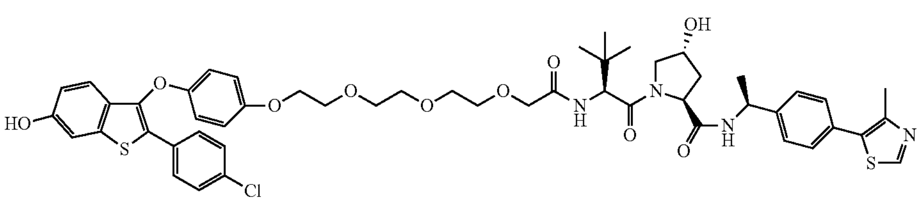 [SMILES: Cc1ncsc1-c1ccc([C@H](C)NC(=O)[C@@H]2C[C@@H](O)CN2C(=O)[C@@H](NC(=O)COCCOCCOCCOc2ccc(Oc3c(-c4ccc(Cl)cc4)sc4cc(O)ccc34)cc2)C(C)(C)C)cc1] | 1.1 | 985.3 | Scheme 18A |
| 120 | 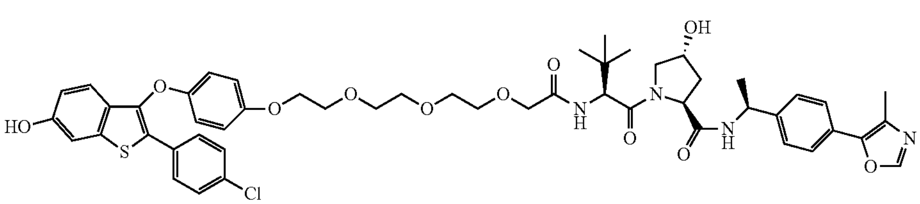 | 4.1 | 969.3 | Scheme 18A |

TABLE 2-continued

Activity, characterization and synthetic methods of VHL centric benzthiophene derived ER PROTACs

| Ex. # | Chemical Structure | IC$_{50}$ (nM) | Obsd [M + H]$^+$ | Synthetic Methods |
|---|---|---|---|---|
| 121 | 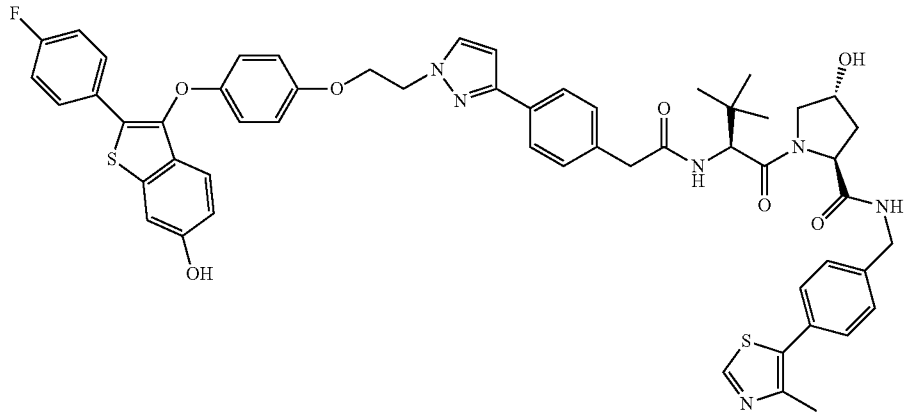 [SMILES: Cc1ncsc1-c1ccc(CNC(=O)[C@@H]2C[C@@H](O)CN2C(=O)[C@@H](NC(=O)Cc2ccc(-c3ccn(CCOc4ccc(Oc5c(-c6ccc(F)cc6)sc6cc(O)ccc56)cc4)n3)cc2)C(C)(C)C)cc1] | 1 | 993.1 | Scheme 9A |
| 122 | 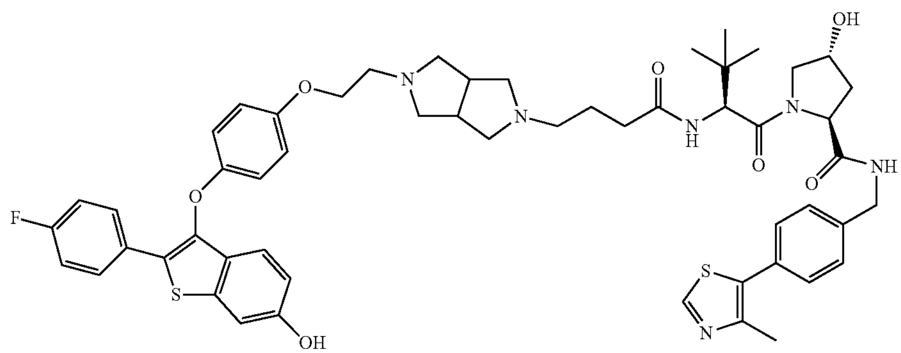 [SMILES: Cc1ncsc1-c1ccc(CNC(=O)[C@@H]2C[C@@H](O)CN2C(=O)[C@@H](NC(=O)CCCN2CC3CN(CCOc4ccc(Oc5c(-c6ccc(F)cc6)sc6cc(O)ccc56)cc4)CC3C2)C(C)(C)C)cc1] | >100 | 989.5 | Scheme 6A |
| 123 | 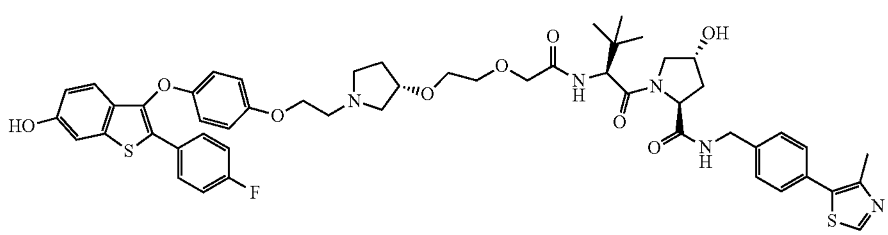 [SMILES: Cc1ncsc1-c1ccc(CNC(=O)[C@@H]2C[C@@H](O)CN2C(=O)[C@@H](NC(=O)COCCO[C@H]2CCN(CCOc3ccc(Oc4c(-c5ccc(F)cc5)sc5cc(O)ccc45)cc3)C2)C(C)(C)C)cc1] | 5.5 | 980.2 | Scheme 7A |
| 124 | 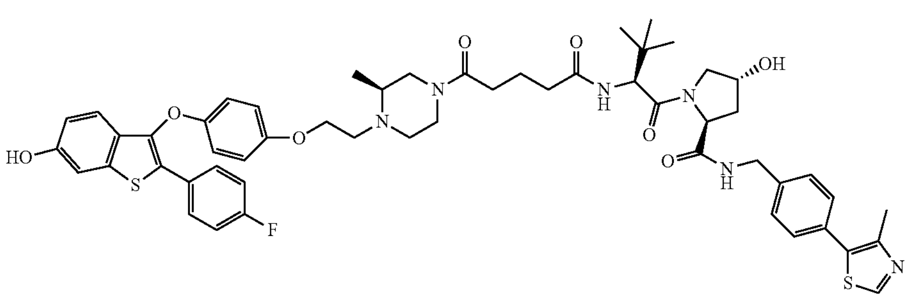 [SMILES: Cc1ncsc1-c1ccc(CNC(=O)[C@@H]2C[C@@H](O)CN2C(=O)[C@@H](NC(=O)CCCC(=O)N2CCN(CCOc3ccc(Oc4c(-c5ccc(F)cc5)sc5cc(O)ccc45)cc3)[C@@H](C)C2)C(C)(C)C)cc1] | 2.2 | 1005.2 | Scheme 6A |

TABLE 2-continued

Activity, characterization and synthetic methods of VHL centric benzthiophene derived ER PROTACs

| Ex. # | Chemical Structure | IC$_{50}$ (nM) | Obsd [M + H]$^+$ | Synthetic Methods |
|---|---|---|---|---|
| 125 | 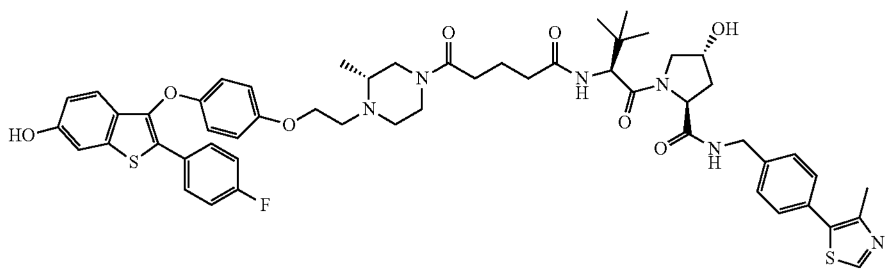 [SMILES: Cc1ncsc1-c1ccc(CNC(=O)[C@@H]2C[C@@H](O)CN2C(=O)[C@@H](NC(=O)CCCC(=O)N2CCN(CCOc3ccc(Oc4c(-c5ccc(F)cc5)sc5cc(O)ccc45)cc3)[C@H](C)C2)C(C)(C)C)cc1] | 1.6 | 1005.2 | Scheme 6A |
| 126 | 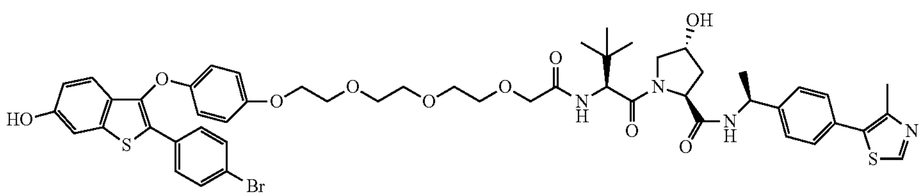 | 0.2 | 1031.2 | Scheme 18A |
| 127 | 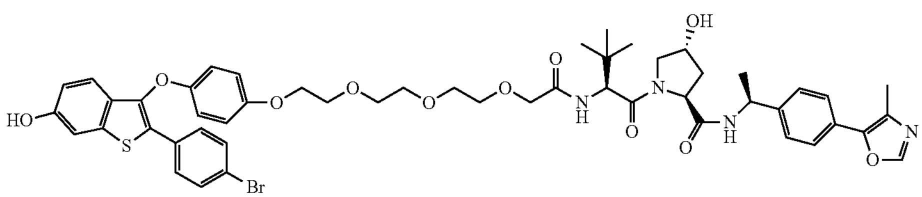 | 0.2 | 1015.3 | Scheme 18A |
| 128 | 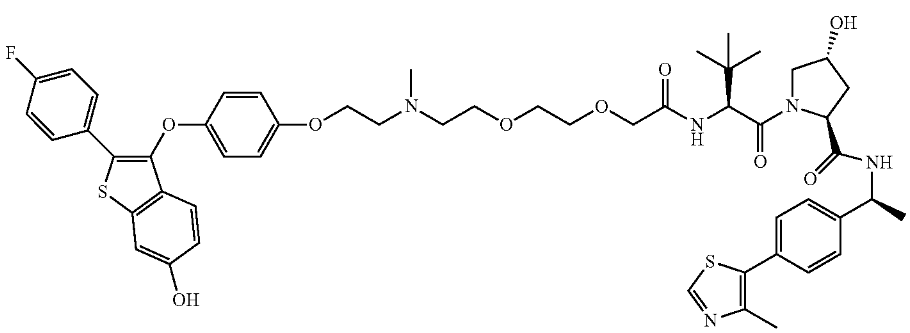 [SMILES: Cc1ncsc1-c1ccc([C@H](C)NC(=O)[C@@H]2C[C@@H](O)CN2C(=O)[C@@H](NC(=O)COCCOCCN(C)CCOc2ccc(Oc3c(-c4ccc(F)cc4)sc4cc(O)ccc34)cc2)C(C)(C)C)cc1] | 0.3 | 982.2 | Scheme 10A |
| 129 | 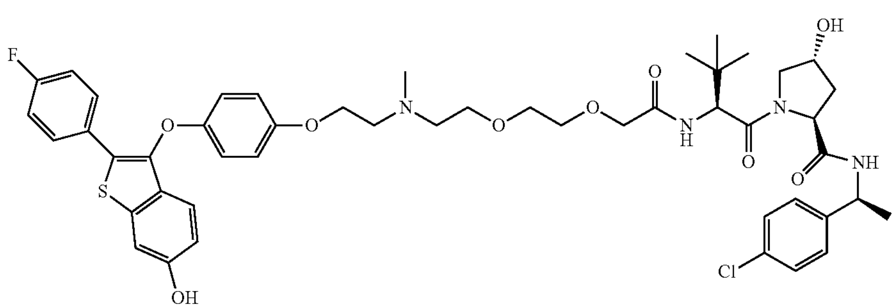 [SMILES: C[C@H](NC(=O)[C@@H]1C[C@@H](O)CN1C(=O)[C@@H](NC(=O)COCCOCCN(C)CCOc1ccc(Oc2c(-c3ccc(F)cc3)sc3cc(O)ccc23)cc1)C(C)(C)C)c1ccc(Cl)cc1] | 1.4 | 919.3 | Scheme 10A |

TABLE 2-continued

Activity, characterization and synthetic methods of VHL centric benzthiophene derived ER PROTACs

| Ex. # | Chemical Structure | IC$_{50}$ (nM) | Obsd [M + H]$^+$ | Synthetic Methods |
|---|---|---|---|---|
| 130 | 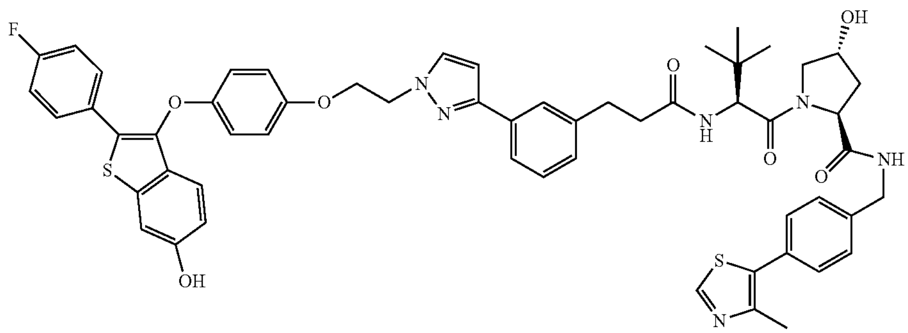 [SMILES: Cc1ncsc1-c1ccc(CNC(=O)[C@@H]2C[C@@H](O)CN2C(=O)[C@@H](NC(=O)CCc2cccc(-c3ccn(CCOc4ccc(Oc5c(-c6ccc(F)cc6)sc6cc(O)ccc56)cc4)n3)c2)C(C)(C)C)cc1] | 3.5 | 504.1 (M + 2H)/2 | Scheme 9A |
| 131 | 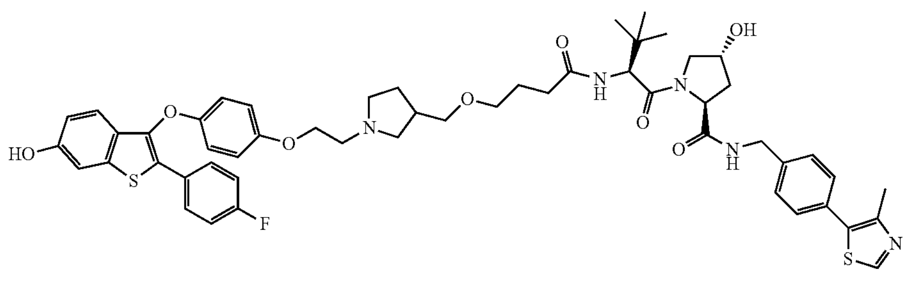 [SMILES: Cc1ncsc1-c1ccc(CNC(=O)[C@@H]2C[C@@H](O)CN2C(=O)[C@@H](NC(=O)CCCOCC2CCN(CCOc3ccc(Oc4c(-c5ccc(F)cc5)sc5cc(O)ccc45)cc3)C2)C(C)(C)C)cc1] | 0.4 | 978.3 | Scheme 7A |
| 132 | 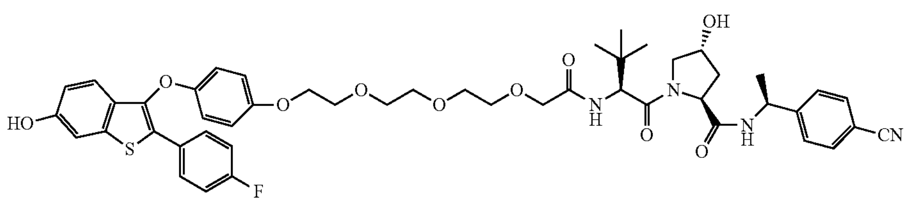 [SMILES: C[C@H](NC(=O)[C@@H]1C[C@@H](O)CN1C(=O)[C@@H](NC(=O)COCCOCCOCCOc1ccc(Oc2c(-c3ccc(F)cc3)sc3cc(O)ccc23)cc1)C(C)(C)C)c1ccc(C#N)cc1] | 1.3 | 897.2 | Scheme 11A, 18A |
| 133 | 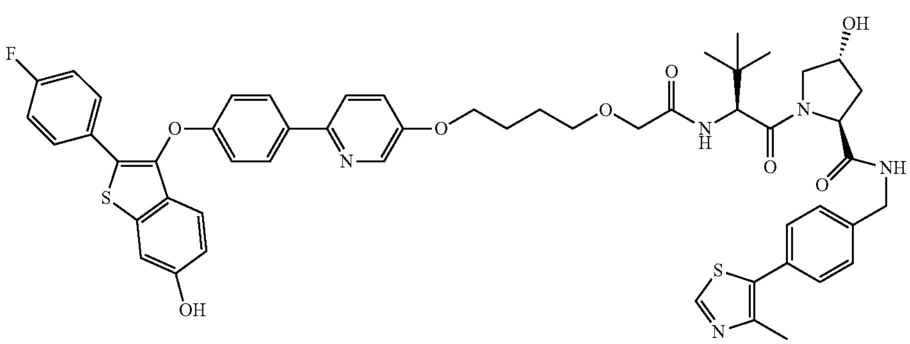 [SMILES: Cc1ncsc1-c1ccc(CNC(=O)[C@@H]2C[C@@H](O)CN2C(=O)[C@@H](NC(=O)COCCCCOc2ccc(-c3ccc(Oc4c(-c5ccc(F)cc5)sc5cc(O)ccc45)cc3)nc2)C(C)(C)C)cc1] | 3.7 | 972.3 | Scheme 12A |
| 134 | 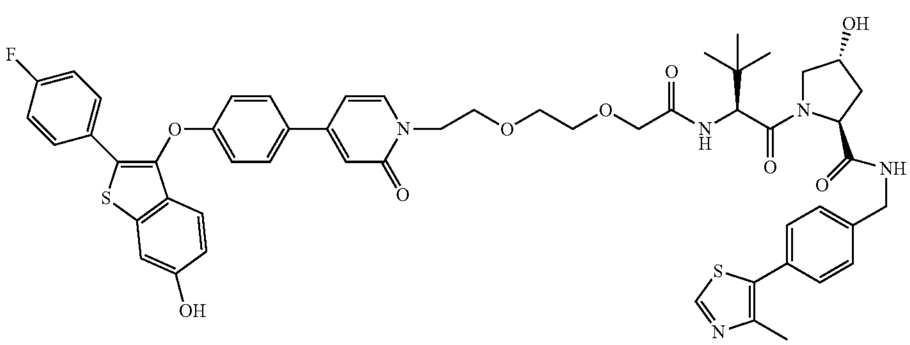 [SMILES: Cc1ncsc1-c1ccc(CNC(=O)[C@@H]2C[C@@H](O)CN2C(=O)[C@@H](NC(=O)COCCOCCn2ccc(-c3ccc(Oc4c(-c5ccc(F)cc5)sc5cc(O)ccc45)cc3)cc2=O)C(C)(C)C)cc1] | 2.6 | 988.1 | Scheme 13A |

TABLE 2-continued

Activity, characterization and synthetic methods of VHL centric benzthiophene derived ER PROTACs

| Ex. # | Chemical Structure | IC$_{50}$ (nM) | Obsd [M + H]$^+$ | Synthetic Methods |
|---|---|---|---|---|
| 135 | 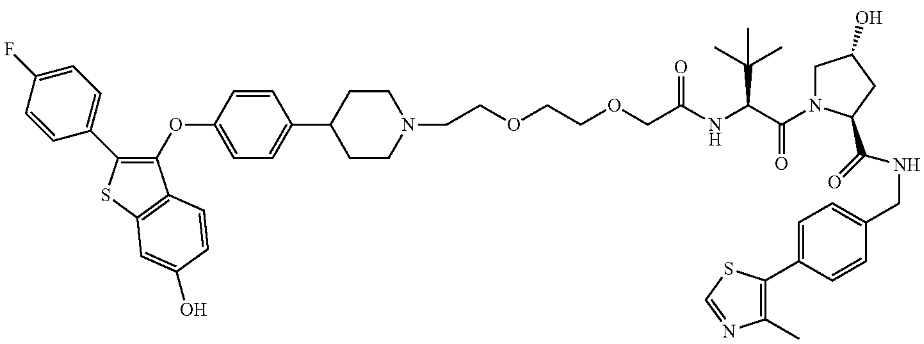 [SMILES: Cc1ncsc1-c1ccc(CNC(=O)[C@@H]2C[C@@H](O)CN2C(=O)[C@@H](NC(=O)COCCOCCN2CCC(c3ccc(Oc4c(-c5ccc(F)cc5)sc5cc(O)ccc45)cc3)CC2)C(C)(C)C)cc1] | 0.8 | 978.5 | Scheme 14A |
| 136 | 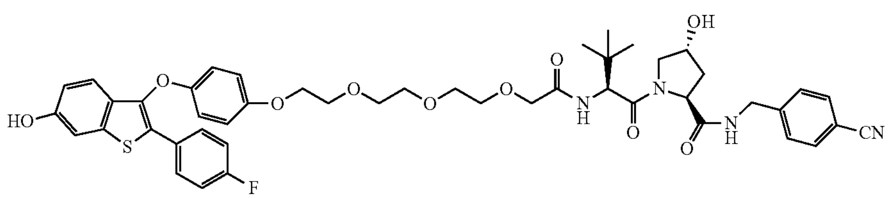 [SMILES: CC(C)(C)[C@H](NC(=O)COCCOCCOCCOc1ccc(Oc2c(-c3ccc(F)cc3)sc3cc(O)ccc23)cc1)C(=O)N1C[C@H](O)C[C@H]1C(=O)NCc1ccc(C#N)cc1] | 1.5 | 905.3 (M + Na) | Scheme 11A |
| 137 | 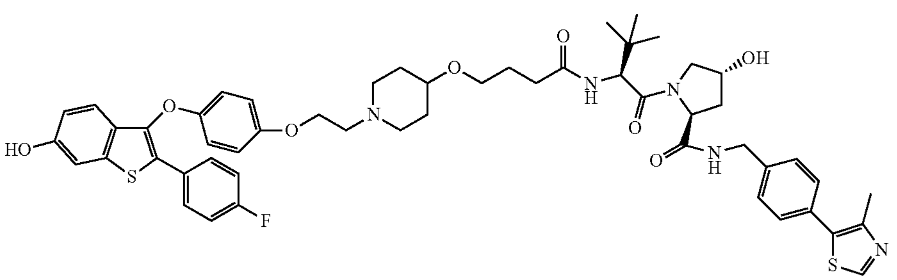 [SMILES: Cc1ncsc1-c1ccc(CNC(=O)[C@@H]2C[C@@H](O)CN2C(=O)[C@@H](NC(=O)CCCOC2CCN(CCOc3ccc(Oc4c(-c5ccc(F)cc5)sc5cc(O)ccc45)cc3)CC2)C(C)(C)C)cc1] | 87 | 978.6 | Scheme 7A |
| 138 | 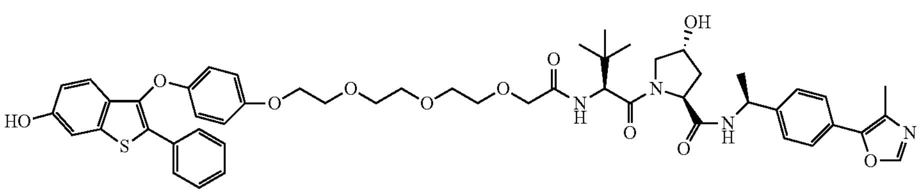 [SMILES: Cc1ncoc1-c1ccc([C@H](C)NC(=O)[C@@H]2C[C@@H](O)CN2C(=O)[C@@H](NC(=O)COCCOCCOCCOc2ccc(Oc3c(-c4ccccc4)sc4cc(O)ccc34)cc2)C(C)(C)C)cc1] | 0.1 | 935.3 | Scheme 18A |
| 139 | 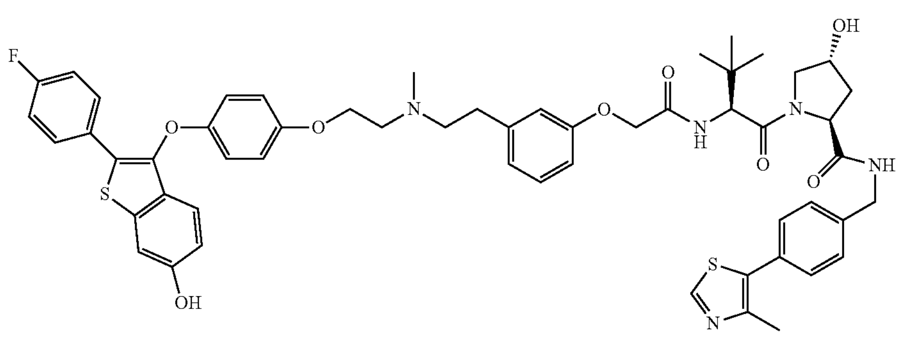 [SMILES: Cc1ncsc1-c1ccc(CNC(=O)[C@@H]2C[C@@H](O)CN2C(=O)[C@@H](NC(=O)COc2cccc(CCN(C)CCOc3ccc(Oc4c(-c5ccc(F)cc5)sc5cc(O)ccc45)cc3)c2)C(C)(C)C)cc1] | 0.6 | 1000.1 | Scheme 10A |

TABLE 2-continued

Activity, characterization and synthetic methods of VHL centric benzthiophene derived ER PROTACs

| Ex. # | Chemical Structure | IC$_{50}$ (nM) | Obsd [M + H]$^+$ | Synthetic Methods |
|---|---|---|---|---|
| 140 | 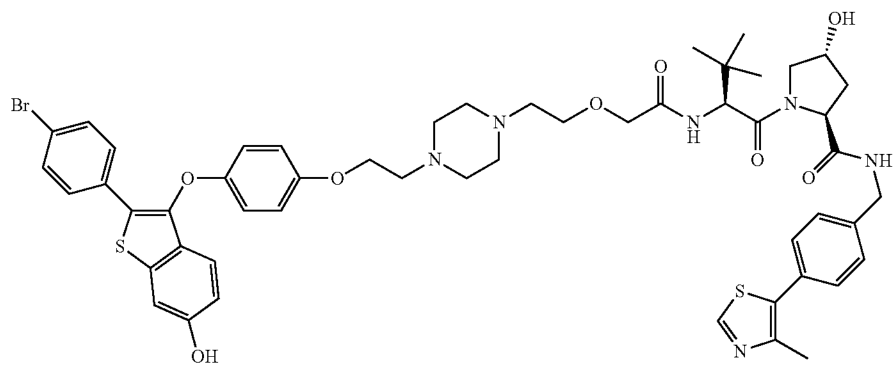 | 11 | 1039.6 | Scheme 19A |
| 141 | 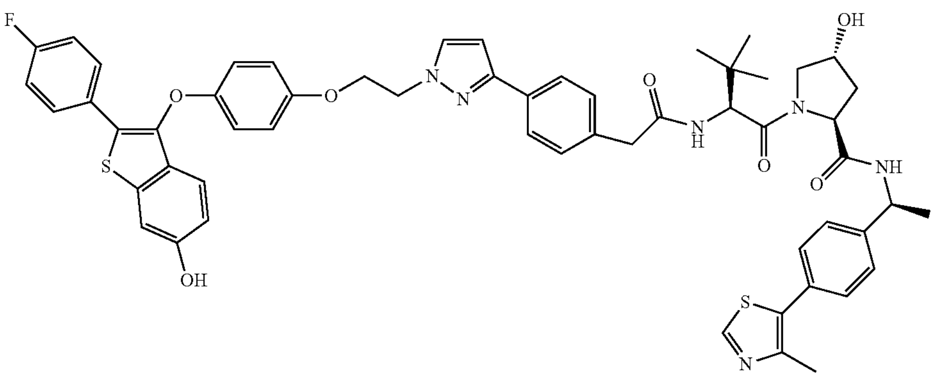 [SMILES: Cc1ncsc1-c1ccc([C@H](C)NC(=O)[C@@H]2C[C@@H](O)CN2C(=O)[C@@H](NC(=O)Cc2ccc(-c3ccn(CCOc4ccc(Oc5c(-c6ccc(F)cc6)sc6cc(O)ccc56)cc4)n3)cc2)C(C)(C)C)cc1] | 1.5 | 1007.5 | Scheme 9A |
| 142 | 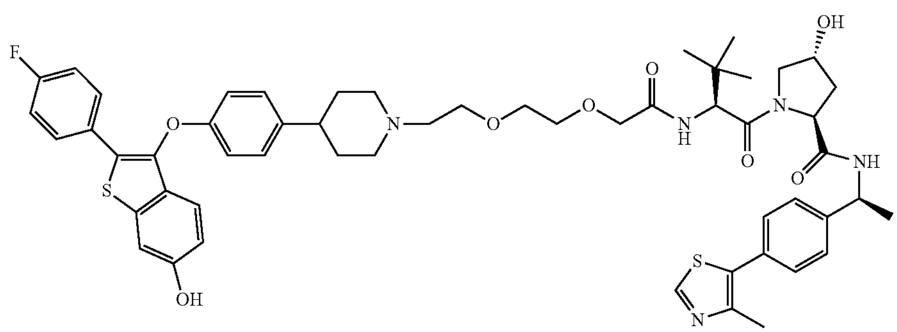 [SMILES: Cc1ncsc1-c1ccc([C@H](C)NC(=O)[C@@H]2C[C@@H](O)CN2C(=O)[C@@H](NC(=O)COCCOCCN2CCC(c3ccc(Oc4c(-c5ccc(F)cc5)sc5cc(O)ccc45)cc3)CC2)C(C)(C)C)cc1] | 0.5 | 992.5 | Scheme 14A |
| 143 | 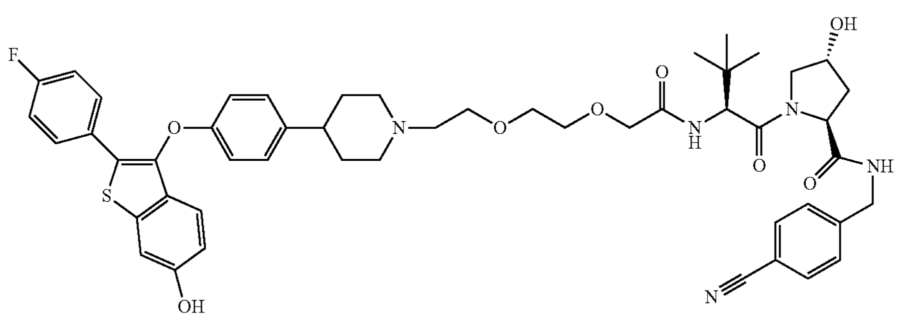 [SMILES: CC(C)(C)[C@H](NC(=O)COCCOCCN1CCC(c2ccc(Oc3c(-c4ccc(F)cc4)sc4cc(O)ccc34)cc2)CC1)C(=O)N1C[C@H](O)C[C@H]1C(=O)NCc1ccc(C#N)cc1] | 32 | 906.5 | Scheme 14A |

TABLE 2-continued

Activity, characterization and synthetic methods of VHL centric benzthiophene derived ER PROTACs

| Ex. # | Chemical Structure | IC$_{50}$ (nM) | Obsd [M + H]$^+$ | Synthetic Methods |
|---|---|---|---|---|
| 144 | 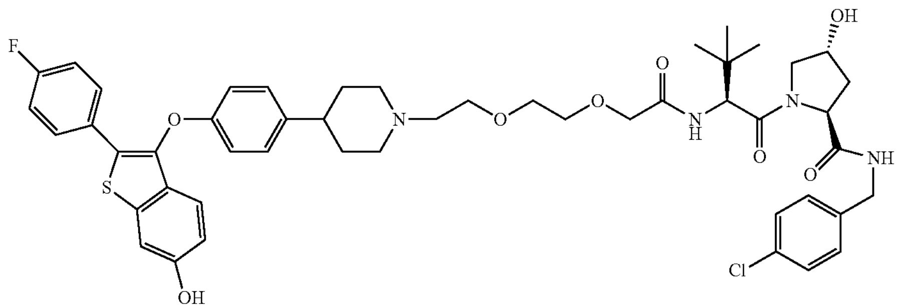 [SMILES: CC(C)(C)[C@H](NC(=O)COCCOCCN1CCC(c2ccc(Oc3c(-c4ccc(F)cc4)sc4cc(O)ccc34)cc2)CC1)C(=O)N1C[C@H](O)C[C@H]1C(=O)NCc1ccc(Cl)cc1] | >100 | 915.4 | Scheme 14A |
| 145 | 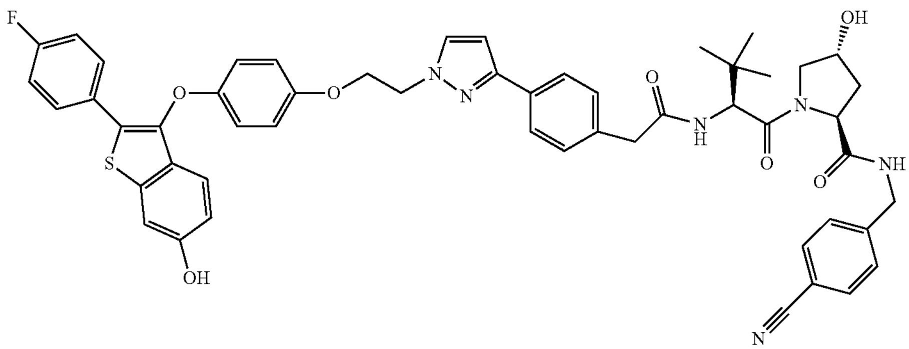 [SMILES: CC(C)(C)[C@H](NC(=O)Cc1ccc(-c2ccn(CCOc3ccc(Oc4c(-c5ccc(F)cc5)sc5cc(O)ccc45)cc3)n2)cc1)C(=O)N1C[C@H](O)C[C@H]1C(=O)NCc1ccc(C#N)cc1] | 97 | 921.4 | Scheme 9A |
| 146 | 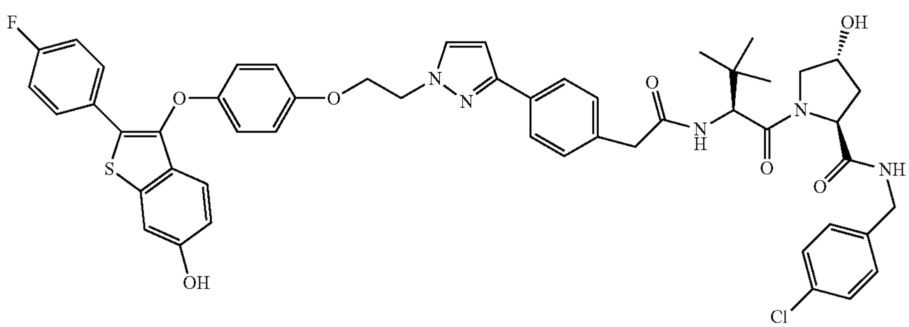 [SMILES: CC(C)(C)[C@H](NC(=O)Cc1ccc(-c2ccn(CCOc3ccc(Oc4c(-c5ccc(F)cc5)sc5cc(O)ccc45)cc3)n2)cc1)C(=O)N1C[C@H](O)C[C@H]1C(=O)NCc1ccc(Cl)cc1] | >100 | 930.2 | Scheme 9A |
| 147 | 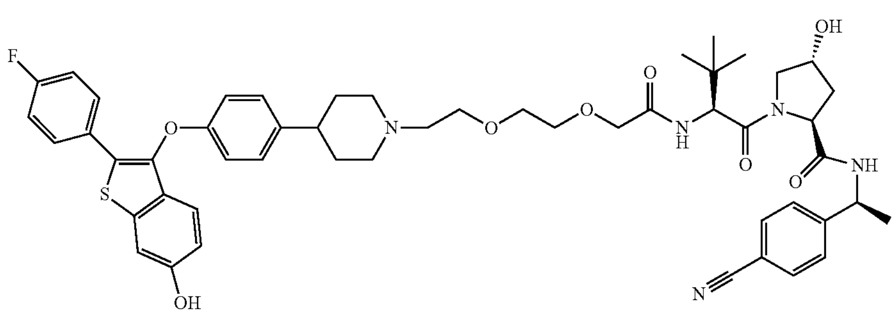 [SMILES: C[C@H](NC(=O)[C@@H]1C[C@@H](O)CN1C(=O)[C@@H](NC(=O)COCCOCCN1CCC(c2ccc(Oc3c(-c4ccc(F)cc4)sc4cc(O)ccc34)cc2)CC1)C(C)(C)C)c1ccc(C#N)cc1] | 1 | 920.4 | Scheme 14A |

TABLE 2-continued

Activity, characterization and synthetic methods of VHL centric benzthiophene derived ER PROTACs

| Ex. # | Chemical Structure | IC$_{50}$ (nM) | Obsd [M + H]$^+$ | Synthetic Methods |
|---|---|---|---|---|
| 148 | 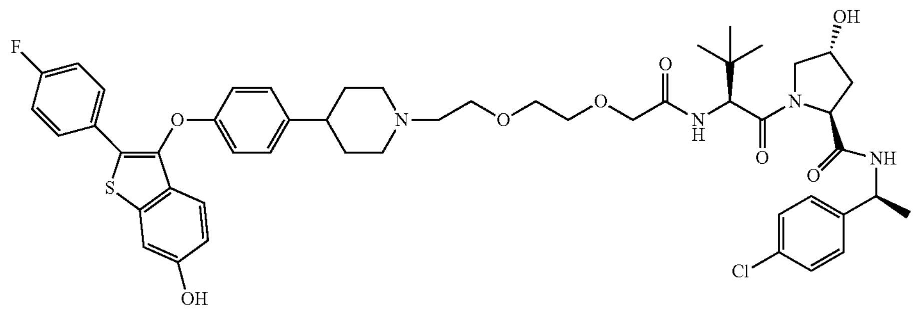 [SMILES: C[C@H](NC(=O)[C@@H]1C[C@@H](O)CN1C(=O)[C@@H](NC(=O)COCCOCCN1CCC(c2ccc(Oc3c(-c4ccc(F)cc4)sc4cc(O)ccc34)cc2)CC1)C(C)(C)C)c1ccc(Cl)cc1] | >100 | 929.3 | Scheme 14A |
| 149 | 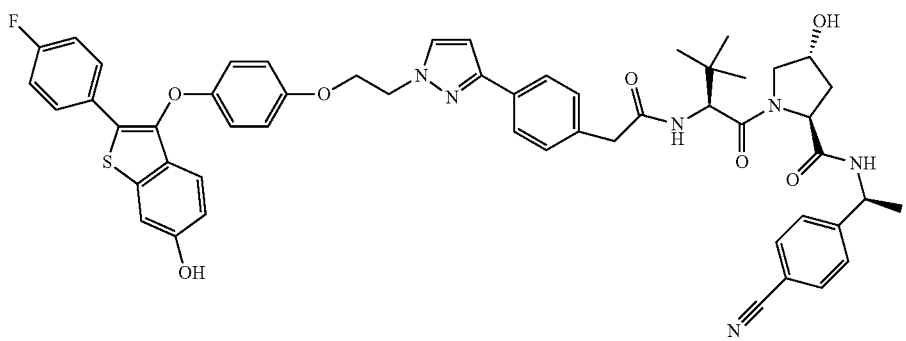 [SMILES: C[C@H](NC(=O)[C@@H]1C[C@@H](O)CN1C(=O)[C@@H](NC(=O)Cc1ccc(-c2ccn(CCOc3ccc(Oc4c(-c5ccc(F)cc5)sc5cc(O)ccc45)cc3)n2)cc1)C(C)(C)C)c1ccc(C#N)cc1] | 1.4 | 935.4 | Scheme 9A |
| 150 | 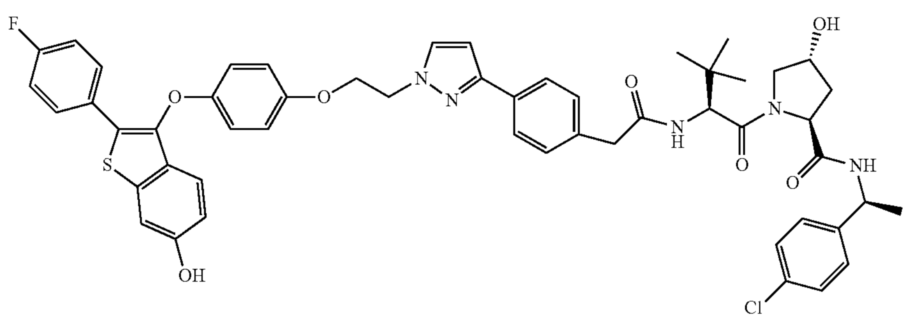 [SMILES: C[C@H](NC(=O)[C@@H]1C[C@@H](O)CN1C(=O)[C@@H](NC(=O)Cc1ccc(-c2ccn(CCOc3ccc(Oc4c(-c5ccc(F)cc5)sc5cc(O)ccc45)cc3)n2)cc1)C(C)(C)C)c1ccc(Cl)cc1] | 17 | 944.4 | Scheme 9A |
| 151 | 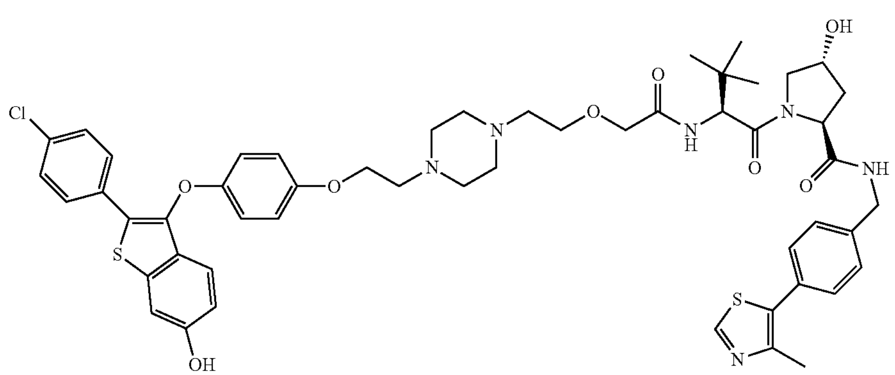 [SMILES: Cc1ncsc1-c1ccc(CNC(=O)[C@@H]2C[C@@H](O)CN2C(=O)[C@@H](NC(=O)COCCN2CCN(CCOc3ccc(Oc4c(-c5ccc(Cl)cc5)sc5cc(O)ccc45)cc3)CC2)C(C)(C)C)cc1] | 0.4 | 995.3 | Scheme 19A |

TABLE 2-continued

Activity, characterization and synthetic methods of VHL centric benzthiophene derived ER PROTACs

| Ex. # | Chemical Structure | IC$_{50}$ (nM) | Obsd [M + H]$^+$ | Synthetic Methods |
|---|---|---|---|---|
| 152 | 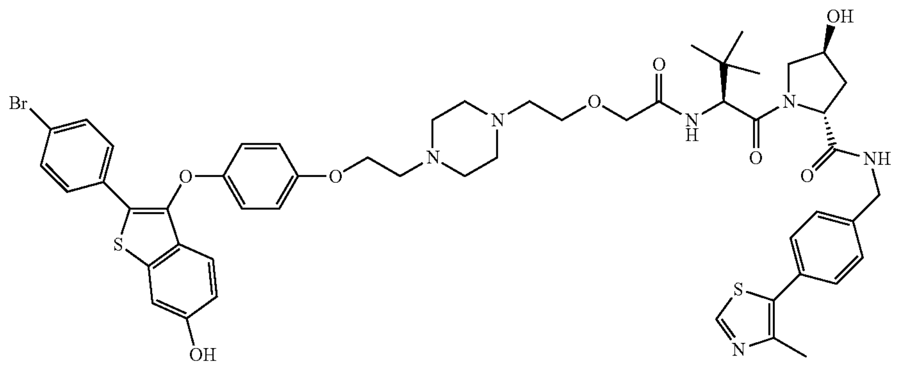 [SMILES: Cc1ncsc1-c1ccc(CNC(=O)[C@H]2C[C@H](O)CN2C(=O)[C@@H](NC(=O)COCCN2CCN(CCOc3ccc(Oc4c(-c5ccc(Br)cc5)sc5cc(O)ccc45)cc3)CC2)C(C)(C)C)cc1] | >100 | 1039.4 | Scheme 19A |
| 153 | 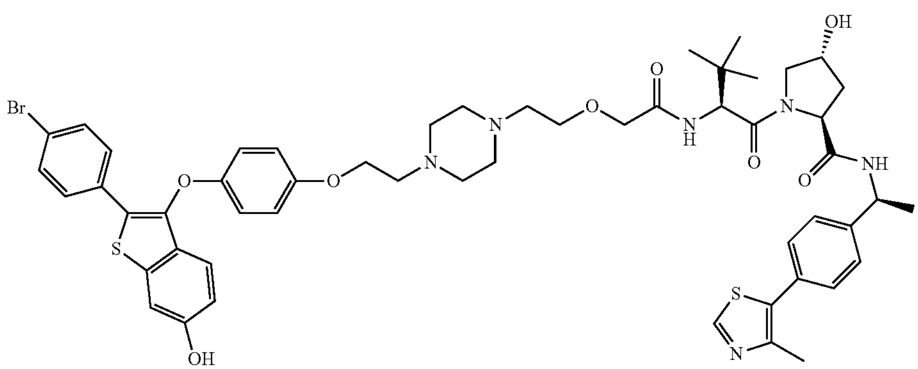 [SMILES: Cc1ncsc1-c1ccc([C@H](C)NC(=O)[C@@H]2C[C@@H](O)CN2C(=O)[C@@H](NC(=O)COCCN2CCN(CCOc3ccc(Oc4c(-c5ccc(Br)cc5)sc5cc(O)ccc45)cc3)CC2)C(C)(C)C)cc1] | 3.2 | 1053.5 | Scheme 19A |
| 154 | 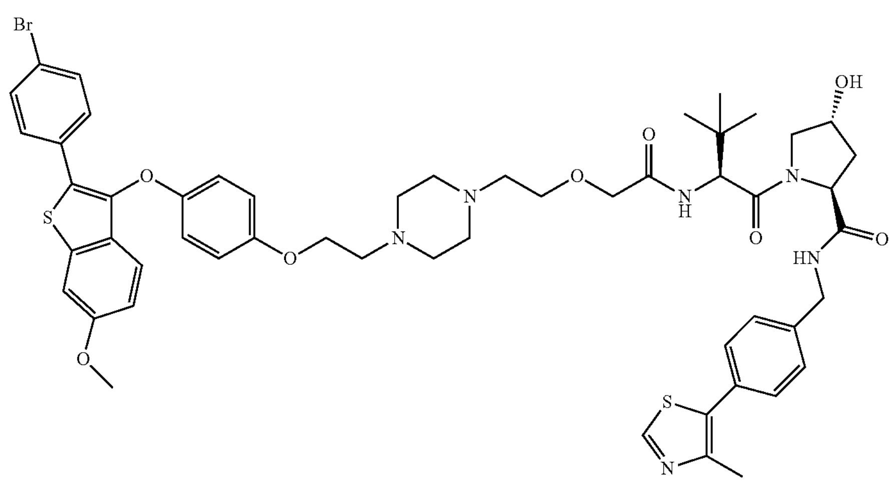 [SMILES: COc1ccc2c(Oc3ccc(OCCN4CCN(CCOCC(=O)N[C@H](C(=O)N5C[C@H](O)C[C@H]5C(=O)NCc5ccc(-c6scnc6C)cc5)C(C)(C)C)CC4)cc3)c(-c3ccc(Br)cc3)sc2c1] | >100 | 1053.4 | Scheme 1A, 4A, 19A |

TABLE 2-continued

Activity, characterization and synthetic methods of VHL centric benzthiophene derived ER PROTACs

| Ex. # | Chemical Structure | IC$_{50}$ (nM) | Obsd [M + H]$^+$ | Synthetic Methods |
|---|---|---|---|---|
| 155 | 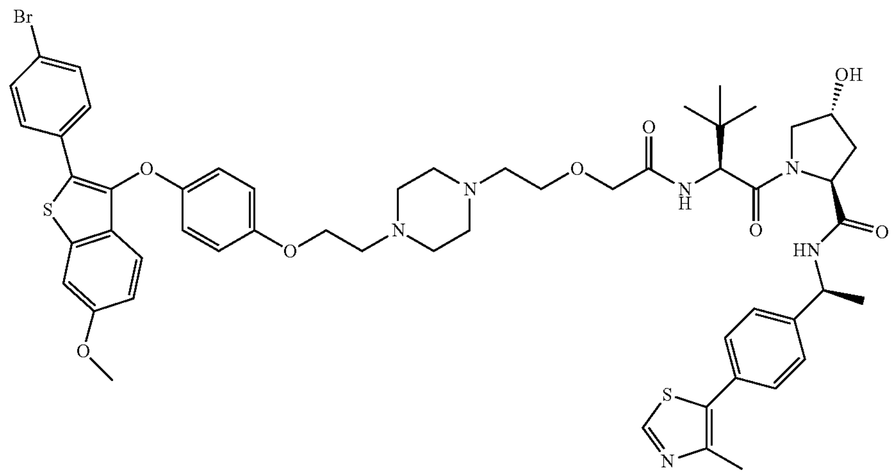 [SMILES: COc1ccc2c(Oc3ccc(OCCN4CCN(CCOCC(=O)N[C@H](C(=O)N5C[C@H](O)C[C@H]5C(=O)N[C@@H](C)c5ccc(-c6scnc6C)cc5)C(C)(C)C)CC4)cc3)c(-c3ccc(Br)cc3)sc2c1] | >100 | 1067.3 | Scheme 1A, 4A, 19A |
| 156 | 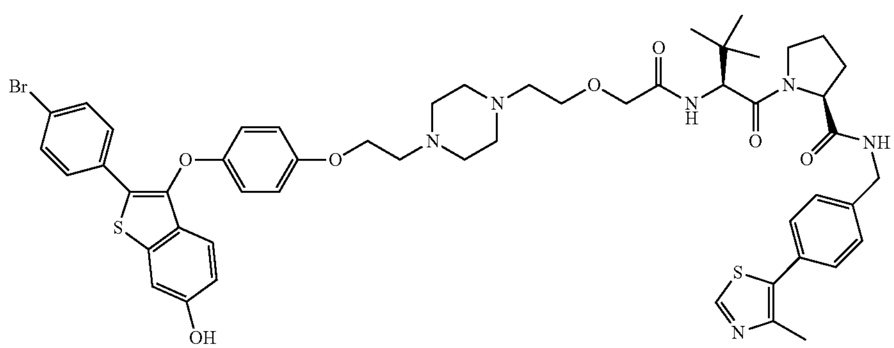 [SMILES: Cc1ncsc1-c1ccc(CNC(=O)[C@@H]2CCCN2C(=O)[C@@H](NC(=O)COCCN2CCN(CCOc3ccc(Oc4c(-c5ccc(Br)cc5)sc5cc(O)ccc45)cc3)CC2)C(C)(C)C)cc1] | >100 | 1023.3 | Scheme 19A |
| 157 | 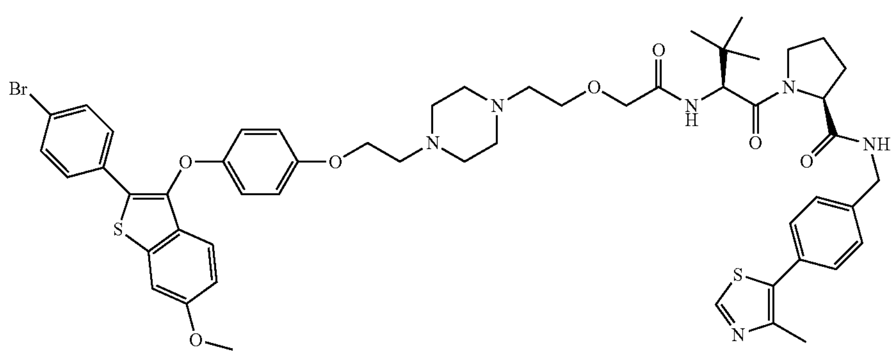 [SMILES: COc1ccc2c(Oc3ccc(OCCN4CCN(CCOCC(=O)N[C@H](C(=O)N5CCC[C@H]5C(=O)NCc5ccc(-c6scnc6C)cc5)C(C)(C)C)CC4)cc3)c(-c3ccc(Br)cc3)sc2c1] | >100 | 1037.4 | Scheme 1A, 4A, 19A |

TABLE 2-continued

Activity, characterization and synthetic methods of VHL centric benzthiophene derived ER PROTACs

| Ex. # | Chemical Structure | IC$_{50}$ (nM) | Obsd [M + H]$^+$ | Synthetic Methods |
|---|---|---|---|---|
| 158 | 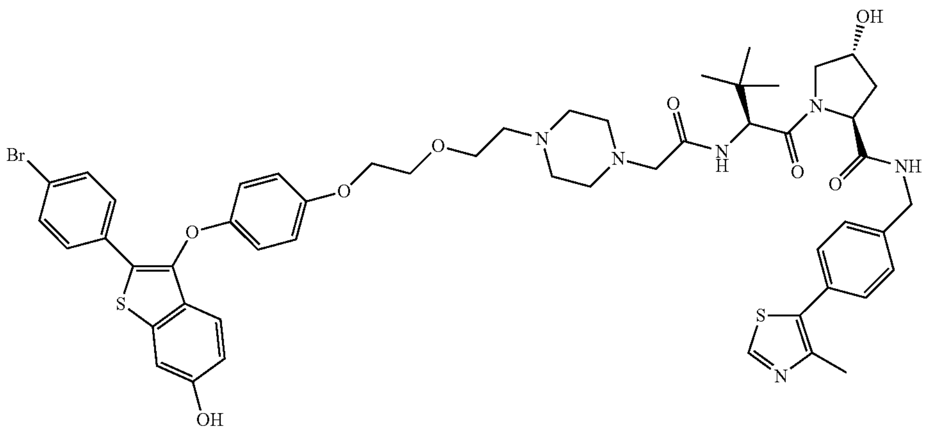 [SMILES: Cc1ncsc1-c1ccc(CNC(=O)[C@@H]2C[C@@H](O)CN2C(=O)[C@@H](NC(=O)CN2CCN(CCOCCOc3ccc(Oc4c(-c5ccc(Br)cc5)sc5cc(O)ccc45)cc3)CC2)C(C)(C)C)cc1] | 13.7 | 1039.4 | Scheme 15A |
| 159 | 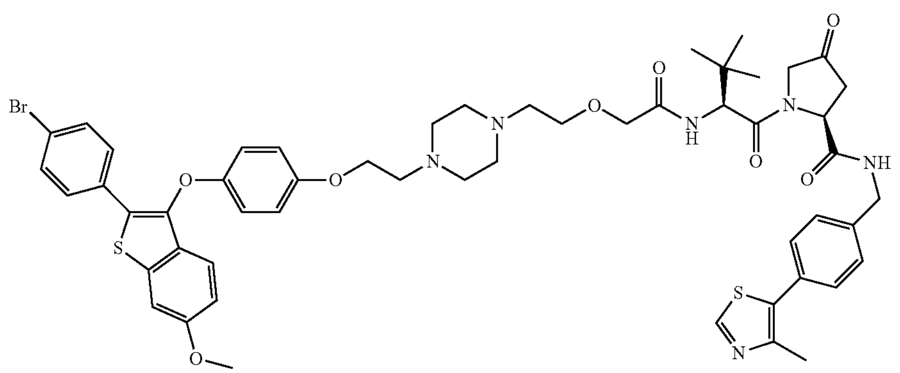 [SMILES: COc1ccc2c(Oc3ccc(OCCN4CCN(CCOCC(=O)N[C@H](C(=O)N5CC(=O)C[C@H]5C(=O)NCc5ccc(-c6scnc6C)cc5)C(C)(C)C)CC4)cc3)c(-c3ccc(Br)cc3)sc2c1] | >100 | 1051.4 | Scheme 1A, 4A, 19A |
| 160 | 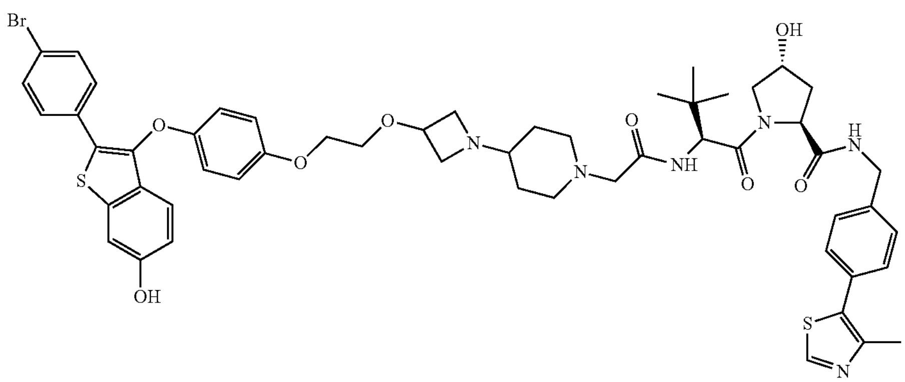 [SMILES: Cc1ncsc1-c1ccc(CNC(=O)[C@@H]2C[C@@H](O)CN2C(=O)[C@@H](NC(=O)CN2CCC(N3CC(OCCOc4ccc(Oc5c(-c6ccc(Br)cc6)sc6cc(O)ccc56)cc4)C3)CC2)C(C)(C)C)cc1] | 6.3 | 1065.4 | Scheme 16A |
| 161 | 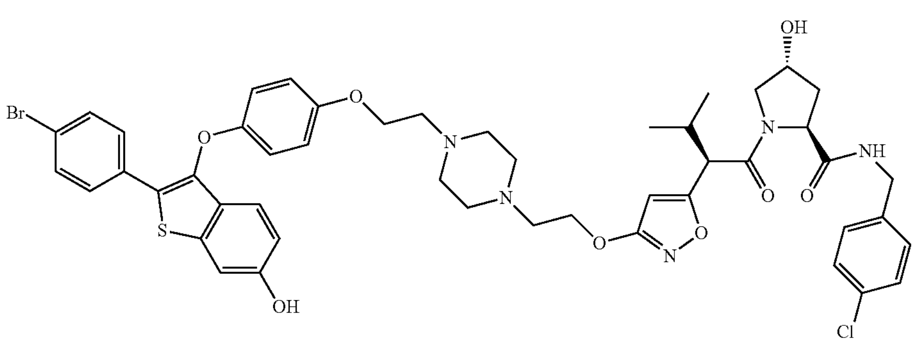 [SMILES: CC(C)[C@@H](C(=O)N1C[C@H](O)C[C@H]1C(=O)NCc1ccc(Cl)cc1)c1cc(OCCN2CCN(CCOc3ccc(Oc4c(-c5ccc(Br)cc5)sc5cc(O)ccc45)cc3)CC2)no1] | | 972.2 | Scheme 20A |

TABLE 2-continued

Activity, characterization and synthetic methods of VHL centric benzthiophene derived ER PROTACs

| Ex. # | Chemical Structure | IC$_{50}$ (nM) | Obsd [M + H]$^+$ | Synthetic Methods |
|---|---|---|---|---|
| 162 | 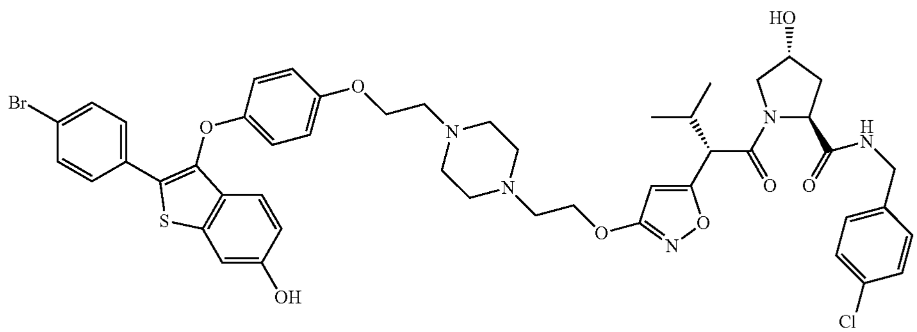 [SMILES: CC(C)[C@H](C(=O)N1C[C@H](O)C[C@H]1C(=O)NCc1ccc(Cl)cc1)c1cc(OCCN2CCN(CCOc3ccc(Oc4c(-c5ccc(Br)cc5)sc5cc(O)ccc45)cc3)CC2)no1] | | 972.2 | Scheme 20A |
| 163 | 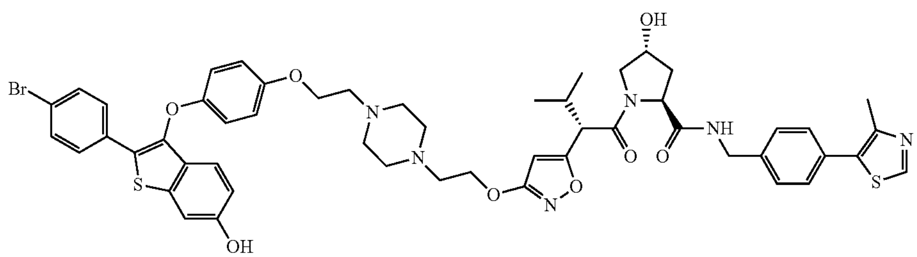 [SMILES: Cc1ncsc1-c1ccc(CNC(=O)[C@@H]2C[C@@H](O)CN2C(=O)[C@H](c2cc(OCCN3CCN(CCOc4ccc(Oc5c(-c6ccc(Br)cc6)sc6cc(O)ccc56)cc4)CC3)no2)C(C)C)cc1] | >100 | 518.2 (M + 2H)/2 | Scheme 20A |
| 164 | 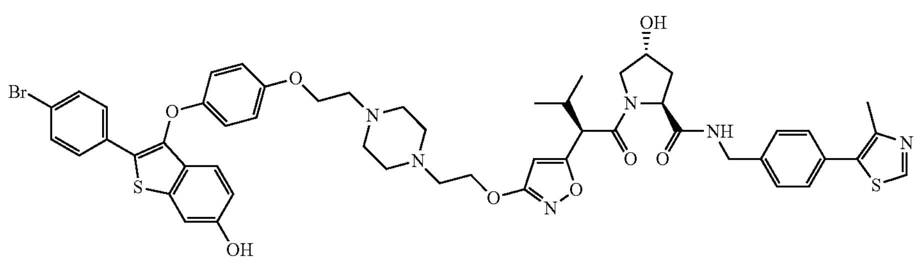 [SMILES: Cc1ncsc1-c1ccc(CNC(=O)[C@@H]2C[C@@H](O)CN2C(=O)[C@@H](c2cc(OCCN3CCN(CCOc4ccc(Oc5c(-c6ccc(Br)cc6)sc6cc(O)ccc56)cc4)CC3)no2)C(C)C)cc1] | 2.7 | 518.3 (M + 2H)/2 | Scheme 20A |
| 165 | 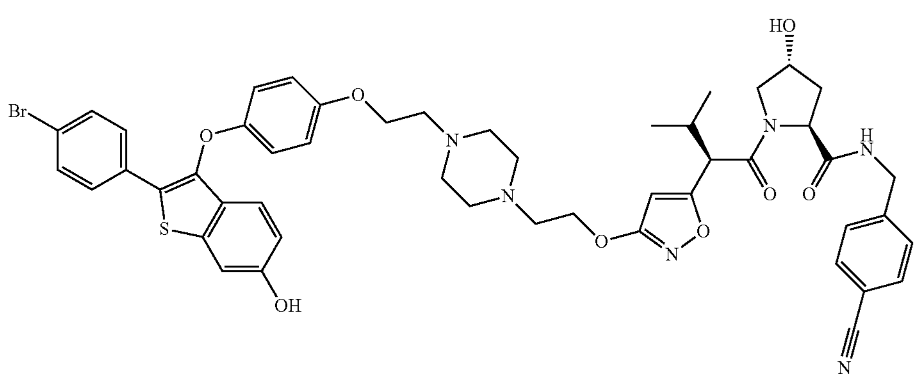 [SMILES: CC(C)[C@@H](C(=O)N1C[C@H](O)C[C@H]1C(=O)NCc1ccc(C#N)cc1)c1cc(OCCN2CCN(CCOc3ccc(Oc4c(-c5ccc(Br)cc5)sc5cc(O)ccc45)cc3)CC2)no1] | | 963.2 | Scheme 20A |

TABLE 2-continued

Activity, characterization and synthetic methods of VHL centric benzthiophene derived ER PROTACs

| Ex. # | Chemical Structure | IC$_{50}$ (nM) | Obsd [M + H]$^+$ | Synthetic Methods |
|---|---|---|---|---|
| 166 | 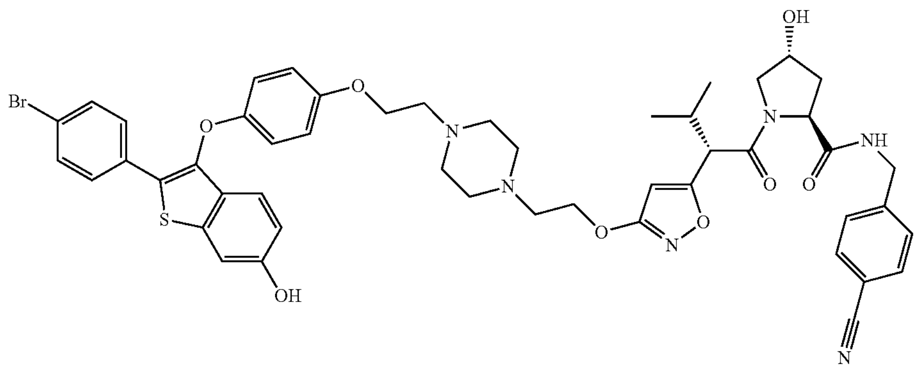 [SMILES: CC(C)[C@H](C(=O)N1C[C@H](O)C[C@H]1C(=O)NCc1ccc(C#N)cc1)c1cc(OCCN2CCN(CCOc3ccc(Oc4c(-c5ccc(Br)cc5)sc5cc(O)ccc45)cc3)CC2)no1] | | 963.2 | Scheme 20A |
| 167 | 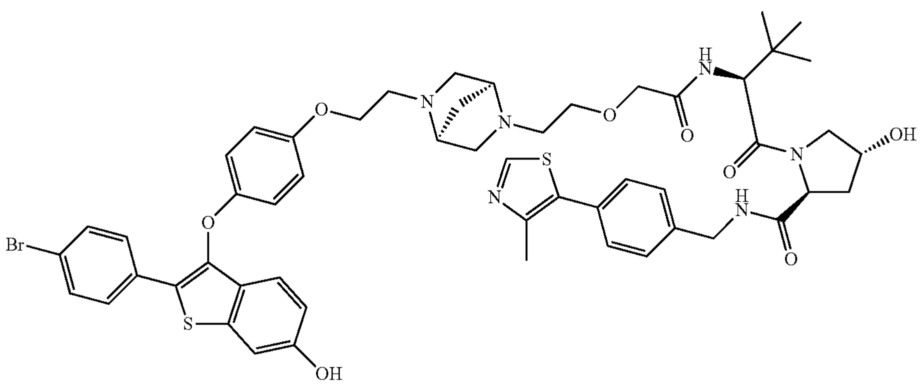 [SMILES: Cc1ncsc1-c1ccc(CNC(=O)[C@@H]2C[C@@H](O)CN2C(=O)[C@@H](NC(=O)COCCN2C[C@@H]3C[C@H]2CN3CCOc2ccc(Oc3c(-c4ccc(Br)cc4)sc4cc(O)ccc34)cc2)C(C)(C)C)cc1] | | 1053.3 | Scheme 19A |
| 168 | 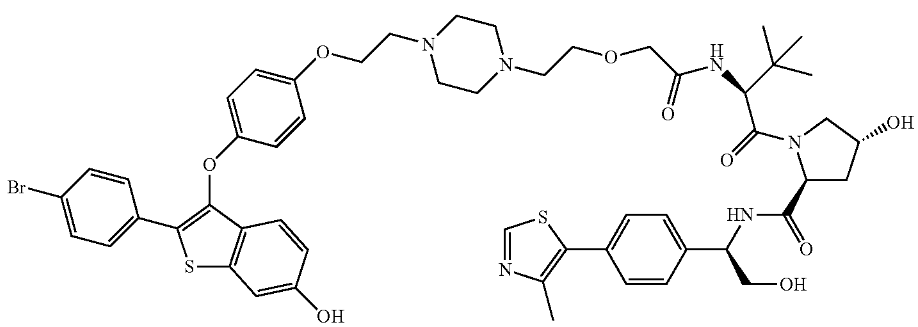 [SMILES: Cc1ncsc1-c1ccc([C@H](CO)NC(=O)[C@@H]2C[C@@H](O)CN2C(=O)[C@@H](NC(=O)COCCN2CCN(CCOc3ccc(Oc4c(-c5ccc(Br)cc5)sc5cc(O)ccc45)cc3)CC2)C(C)(C)C)cc1] | | 536.2 (M + 2H)/2 | Scheme 17A, 11A, 19A |
| 169 | 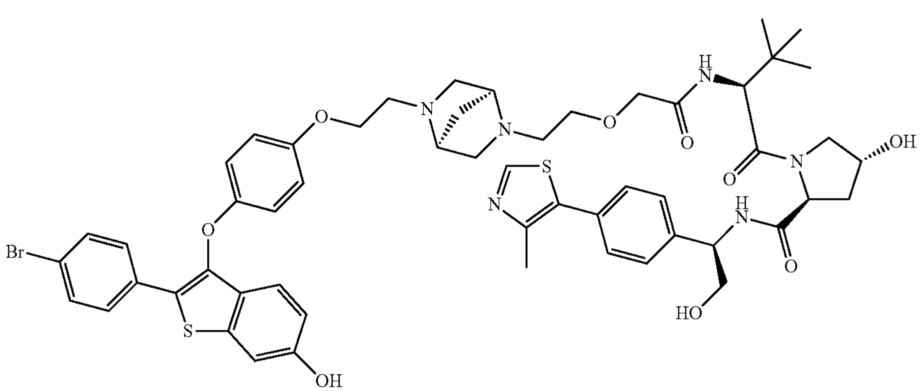 [SMILES: Cc1ncsc1-c1ccc([C@H](CO)NC(=O)[C@@H]2C[C@@H](O)CN2C(=O)[C@@H](NC(=O)COCCN2C[C@@H]3C[C@H]2CN3CCOc2ccc(Oc3c(-c4ccc(Br)cc4)sc4cc(O)ccc34)cc2)C(C)(C)C)cc1] | | 1083.2 | Scheme 17A, 11A, 19A |

TABLE 3

Activity, characterization and synthetic methods of cereblon centric benzthiophene derived ER PROTACs

| Ex. # | Structure | ER-α Luciferase IC50 (nM) | *Obsd [M + H]+ | Synthetic Method |
|---|---|---|---|---|
| 170 | 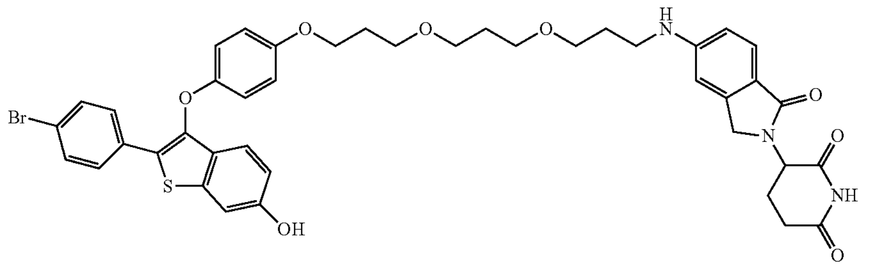 [SMILES: O=C1CCC(N2Cc3cc(NCCCOCCCOCCCOc4ccc(Oc5c(-c6ccc(Br)cc6)sc6cc(O)ccc56)cc4)ccc3C2=O)C(=O)N1] | 5.6 | 830.2 | Scheme 1B |
| 171 | 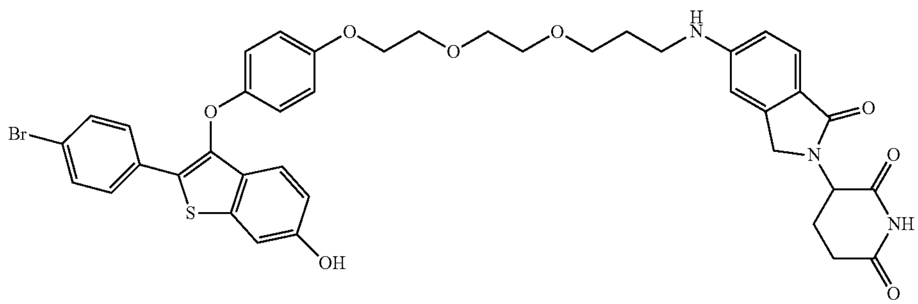 [SMILES: O=C1CCC(N2Cc3cc(NCCCOCCOCCOc4ccc(Oc5c(-c6ccc(Br)cc6)sc6cc(O)ccc56)cc4)ccc3C2=O)C(=O)N1] | 8.7 | 802.1 | Scheme 1B |
| 172 | 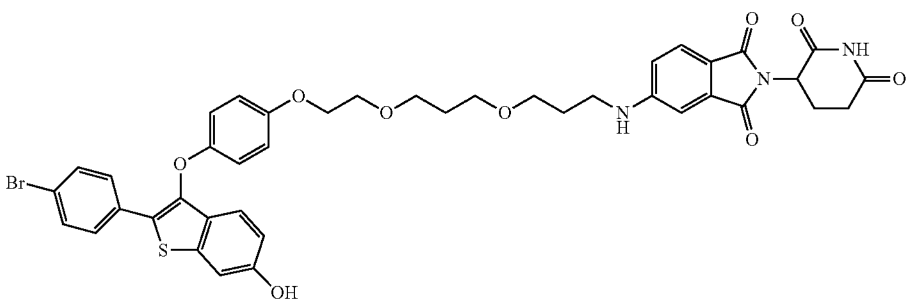 [SMILES: O=C1CCC(N2C(=O)c3ccc(NCCCOCCCOCCOc4ccc(Oc5c(-c6ccc(Br)cc6)sc6cc(O)ccc56)cc4)cc3C2=O)C(=O)N1] | 15.7 | 828.1 | Scheme 1B |
| 173 | 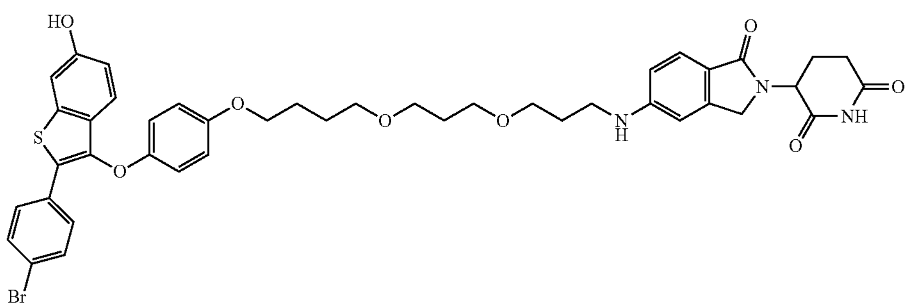 [SMILES: O=C1CCC(N2Cc3cc(NCCCOCCCOCCCCOc4ccc(Oc5c(-c6ccc(Br)cc6)sc6cc(O)ccc56)cc4)ccc3C2=O)C(=O)N1] | 8 | 844.2 | Scheme 1B |
| 174 | 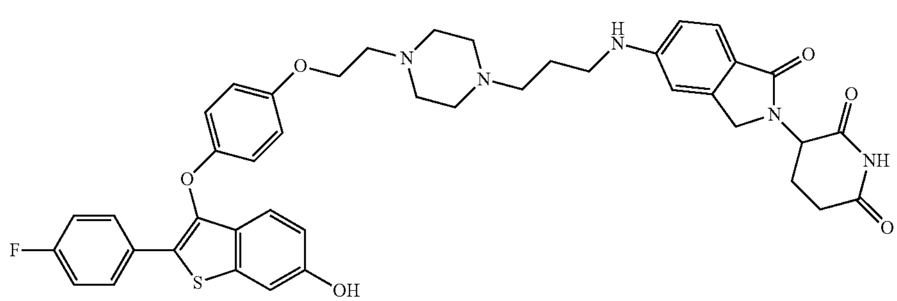 [SMILES: O=C1CCC(N2Cc3cc(NCCCN4CCN(CCOc5ccc(Oc6c(-c7ccc(F)cc7)sc7cc(O)ccc67)cc5)CC4)ccc3C2=O)C(=O)N1] | 0.54 | 764.2 | Scheme 2B |

TABLE 3-continued

Activity, characterization and synthetic methods of cereblon centric benzthiophene derived ER PROTACs

| Ex. # | Structure | ER-α Luciferase IC50 (nM) | *Obsd [M + H]+ | Synthetic Method |
|---|---|---|---|---|
| 175 | 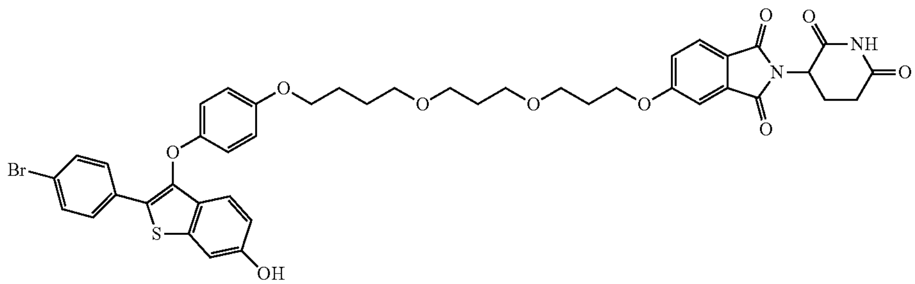 [SMILES: O=C1CCC(N2C(=O)c3ccc(OCCCOCCCOCCCCOc4ccc(Oc5c(-c6ccc(Br)cc6)sc6cc(O)ccc56)cc4)cc3C2=O)C(=O)N1] | 66.7 | 859.1 | Scheme 3B |
| 176 | 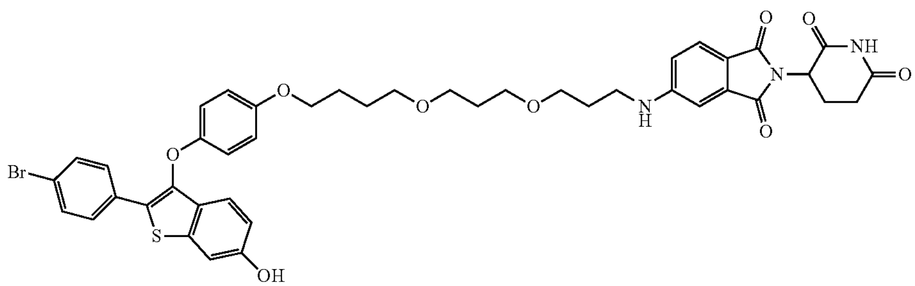 [SMILES: O=C1CCC(N2C(=O)c3ccc(NCCCOCCCOCCCCOc4ccc(Oc5c(-c6ccc(Br)cc6)sc6cc(O)ccc56)cc4)cc3C2=O)C(=O)N1] | 28.7 | 858.1 | Scheme 1B |
| 177 | 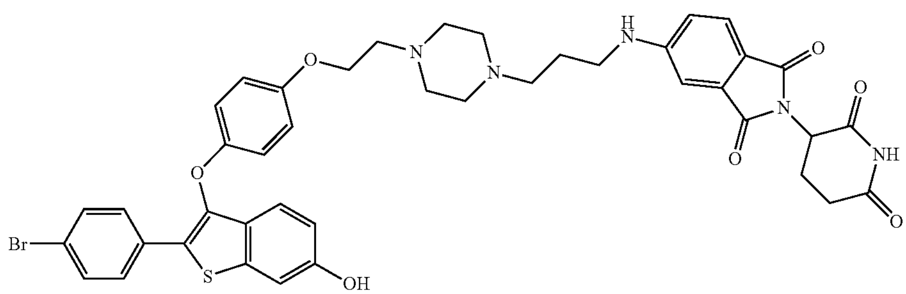 [SMILES: O=C1CCC(N2C(=O)c3ccc(NCCCN4CCN(CCOc5ccc(Oc6c(-c7ccc(Br)cc7)sc7cc(O)ccc67)cc5)CC4)cc3C2=O)C(=O)N1] | 2.3 | 840.1 | Scheme 4B |
| 178 | 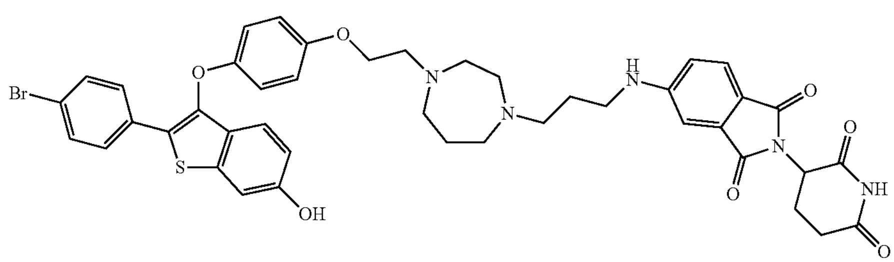 [SMILES: O=C1CCC(N2C(=O)c3ccc(NCCCN4CCCN(CCOc5ccc(Oc6c(-c7ccc(Br)cc7)sc7cc(O)ccc67)cc5)CC4)cc3C2=O)C(=O)N1] | 2.4 | 854.2 | Scheme 5B |
| 179 | 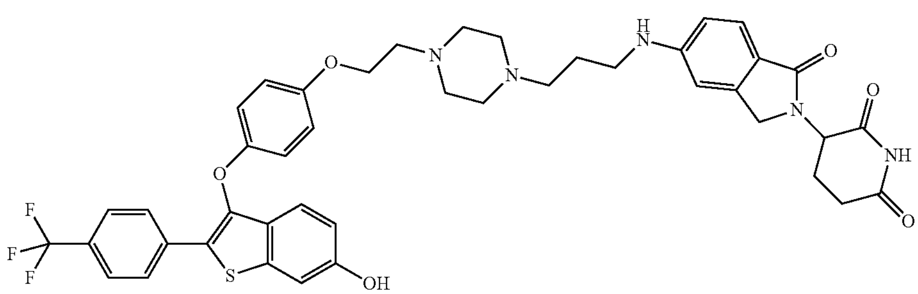 [SMILES: O=C1CCC(N2Cc3cc(NCCCN4CCN(CCOc5ccc(Oc6c(-c7ccc(C(F)(F)F)cc7)sc7cc(O)ccc67)cc5)CC4)ccc3C2=O)C(=O)N1] | 1 | 814.2 | Scheme 2B |

TABLE 3-continued

Activity, characterization and synthetic methods of cereblon centric benzthiophene derived ER PROTACs

| Ex. # | Structure | ER-α Luciferase IC50 (nM) | *Obsd [M + H]+ | Synthetic Method |
|---|---|---|---|---|
| 180 | 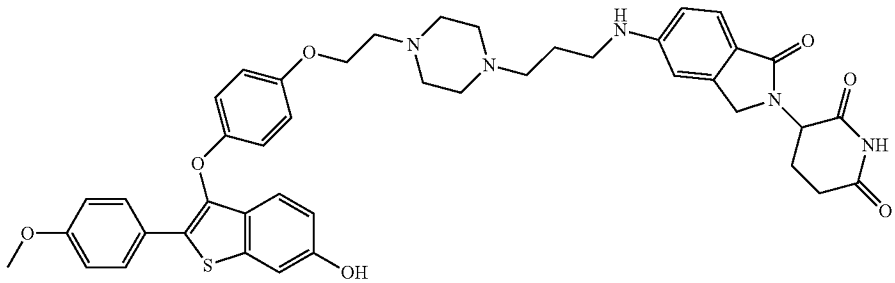 [SMILES: COc1ccc(-c2sc3cc(O)ccc3c2Oc2ccc(OCCN3CCN(CCCNc4ccc5c(c4)CN(C4CCC(=O)NC4=O)C5=O)CC3)cc2)cc1] | 0.22 | 776.2 | Scheme 6B |
| 181 | 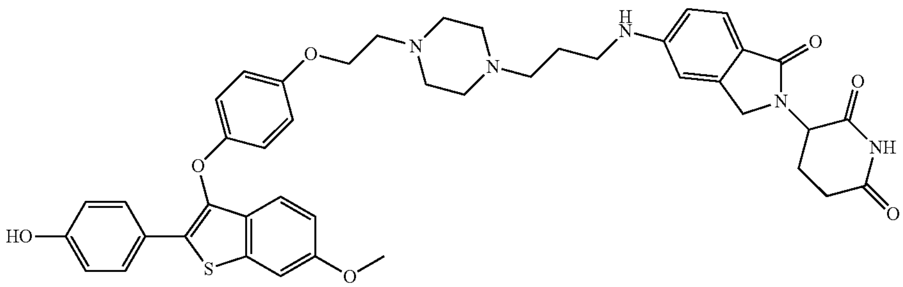 [SMILES: COc1ccc2c(Oc3ccc(OCCN4CCN(CCCNc5ccc6c(c5)CN(C5CCC(=O)NC5=O)C6=O)CC4)cc3)c(-c3ccc(O)cc3)sc2c1] | 2.2 | 776.2 | Scheme 6B |
| 182 | 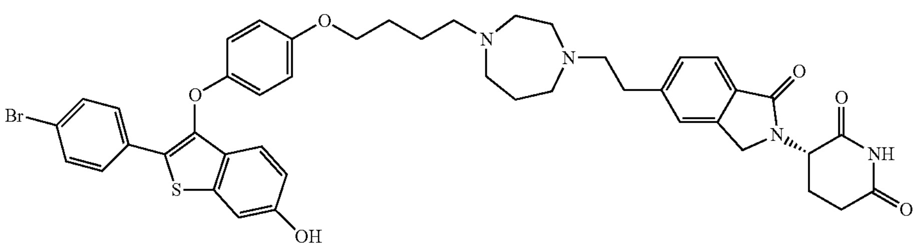 [SMILES: O=C1CC[C@H](N2Cc3cc(CCN4CCCN(CCCCOc5ccc(Oc6c(-c7ccc(Br)cc7)sc7cc(O)ccc67)cc5)CC4)ccc3C2=O)C(=O)N1] | 1.9 | 839.1 | Scheme 7B |
| 183 | 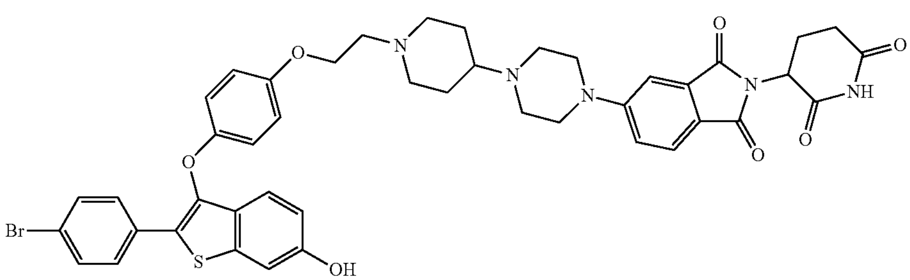 [SMILES: O=C1CCC(N2C(=O)c3ccc(N4CCN(C5CCN(CCOc6ccc(Oc7c(-c8ccc(Br)cc8)sc8cc(O)ccc78)cc6)CC5)CC4)cc3C2=O)C(=O)N1] | 2.5 | 866.4 | Scheme 8B |
| 184 | 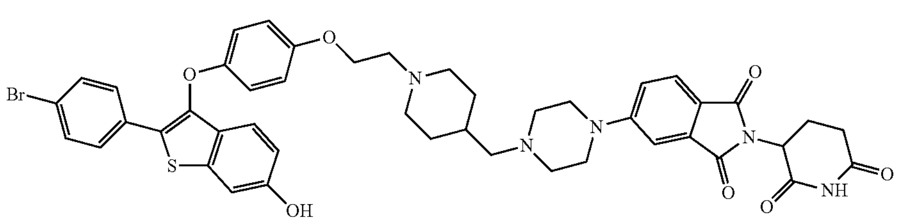 [SMILES: O=C1CCC(N2C(=O)c3ccc(N4CCN(CC5CCN(CCOc6ccc(Oc7c(-c8ccc(Br)cc8)sc8cc(O)ccc78)cc6)CC5)CC4)cc3C2=O)C(=O)N1] | 13.3 | 880.5 | Scheme 9B |

TABLE 3-continued

Activity, characterization and synthetic methods of cereblon centric benzthiophene derived ER PROTACs

| Ex. # | Structure | ER-α Luciferase IC50 (nM) | *Obsd [M + H]+ | Synthetic Method |
|---|---|---|---|---|
| 185 | 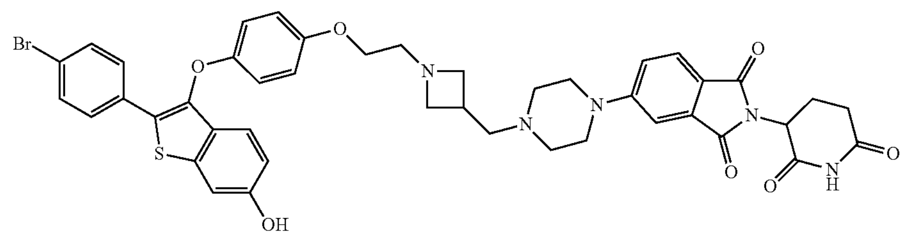 [SMILES: O=C1CCC(N2C(=O)c3ccc(N4CCN(CC5CN(CCOc6ccc(Oc7c(-c8ccc(Br)cc8)sc8cc(O)ccc78)cc6)C5)CC4)cc3C2=O)C(=O)N1] | 4.5 | 852.4 | Scheme 10B |
| 186 | 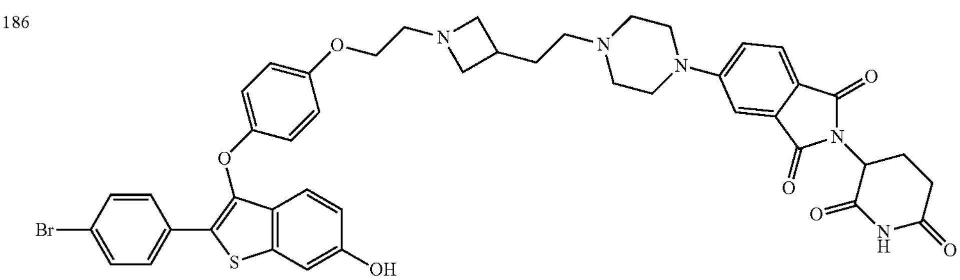 | >300 | 866.4 | Scheme 11B |
| 187 | 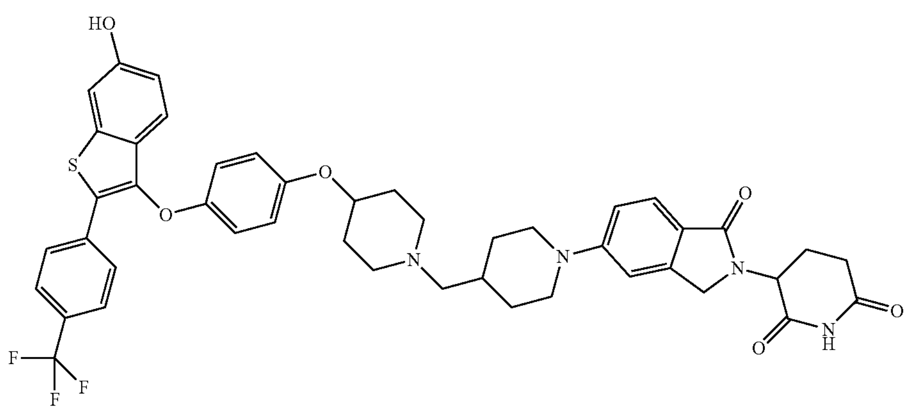 [SMILES: O=C1CCC(N2Cc3cc(N4CCC(CN5CCC(Oc6ccc(Oc7c(-c8ccc(C(F)(F)F)cc8)sc8cc(O)ccc78)cc6)CC5)CC4)ccc3C2=O)C(=O)N1] | 5.1 | 825.5 | Scheme 12B |
| 188 | 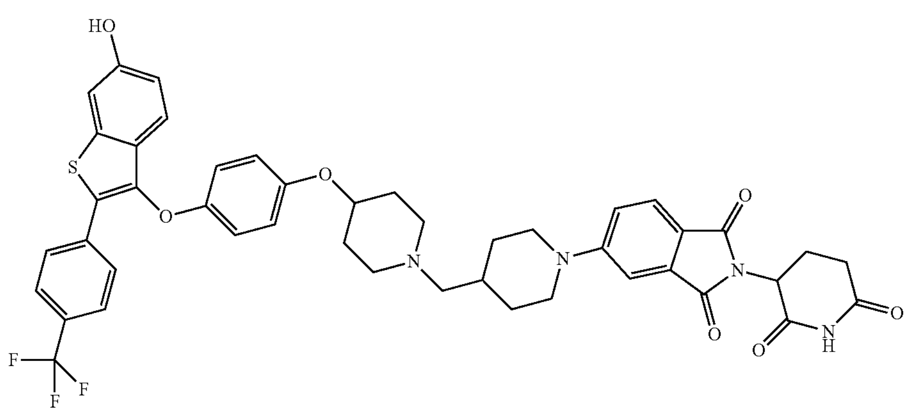 [SMILES: O=C1CCC(N2C(=O)c3ccc(N4CCC(CN5CCC(Oc6ccc(Oc7c(-c8ccc(C(F)(F)F)cc8)sc8cc(O)ccc78)cc6)CC5)CC4)cc3C2=O)C(=O)N1] | 8.7 | 839.5 | Scheme 12B, 13B |

TABLE 3-continued

Activity, characterization and synthetic methods of cereblon centric benzthiophene derived ER PROTACs

| Ex. # | Structure | ER-α Luciferase IC50 (nM) | *Obsd [M + H]+ | Synthetic Method |
|---|---|---|---|---|
| 189 | 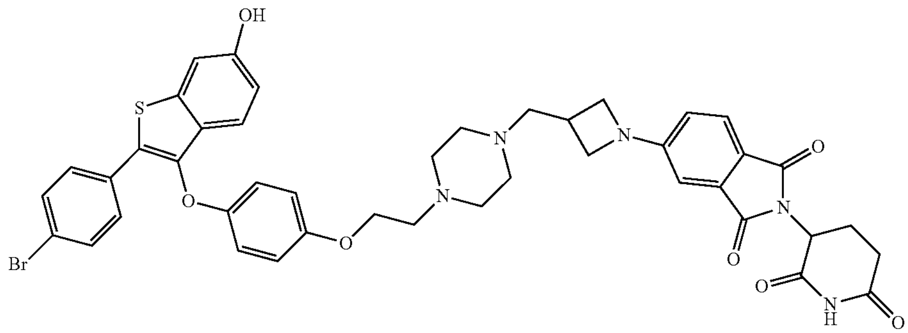 [SMILES: O=C1CCC(N2C(=O)c3ccc(N4CC(CN5CCN(CCOc6ccc(Oc7c(-c8ccc(Br)cc8)sc8cc(O)ccc78)cc6)CC5)C4)cc3C2=O)C(=O)N1] | 3 | 852.4 | Scheme 14B |
| 190 | 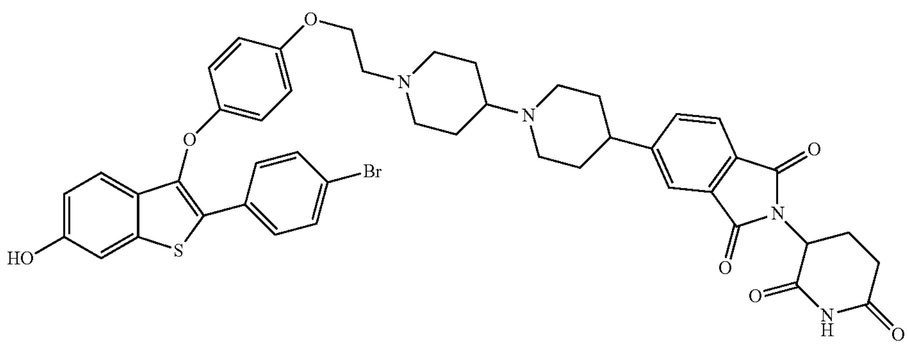 [SMILES: O=C1CCC(N2C(=O)c3ccc(C4CCN(C5CCN(CCOc6ccc(Oc7c(-c8ccc(Br)cc8)sc8cc(O)ccc78)cc6)CC5)CC4)cc3C2=O)C(=O)N1] | 11.6 | 865.4 | Scheme 15B |
| 191 | 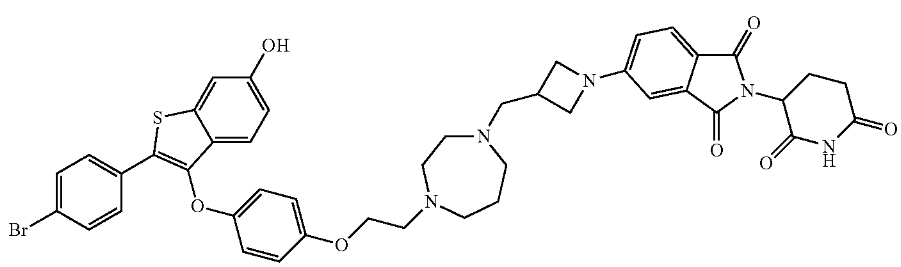 [SMILES: O=C1CCC(N2C(=O)c3ccc(N4CC(CN5CCCN(CCOc6ccc(Oc7c(-c8ccc(Br)cc8)sc8cc(O)ccc78)cc6)CC5)C4)cc3C2=O)C(=O)N1] | 1.8 | 866.4 | Scheme 14B |
| 192 | 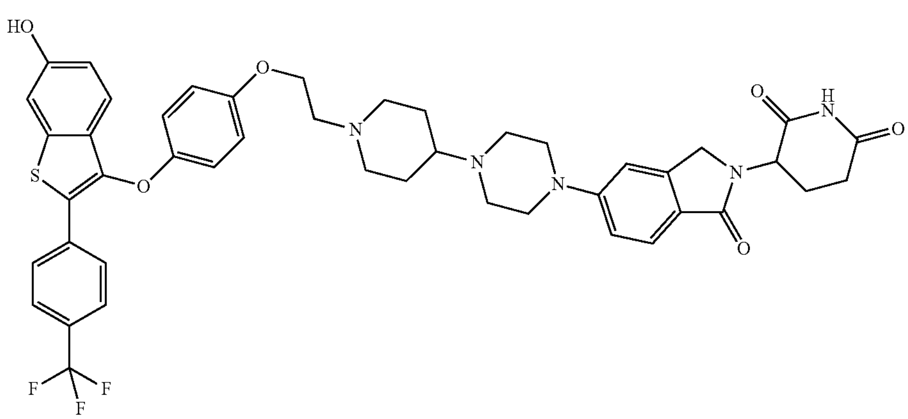 [SMILES: O=C1CCC(N2Cc3cc(N4CCN(C5CCN(CCOc6ccc(Oc7c(-c8ccc(C(F)(F)F)cc8)sc8cc(O)ccc78)cc6)CC5)CC4)ccc3C2=O)C(=O)N1] | 2.9 | 840.5 | Scheme 16B |

TABLE 3-continued

Activity, characterization and synthetic methods of cereblon centric benzthiophene derived ER PROTACs

| Ex. # | Structure | ER-α Luciferase IC50 (nM) | *Obsd [M + H]+ | Synthetic Method |
|---|---|---|---|---|
| 193 | 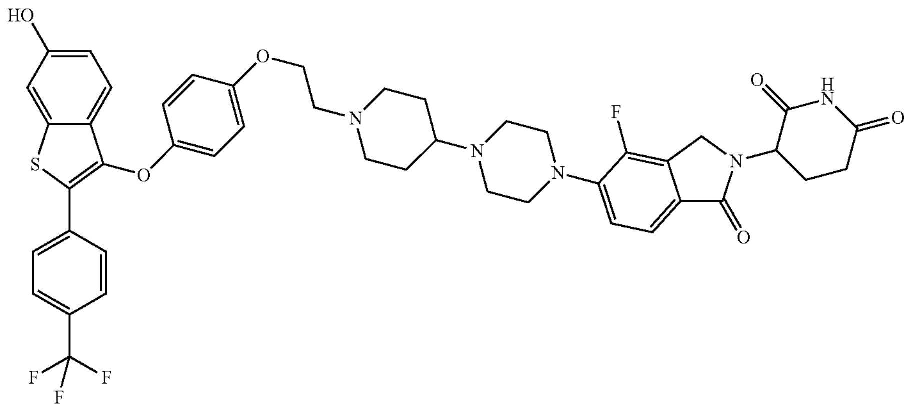 [SMILES: O=C1CCC(N2Cc3c(ccc(N4CCN(C5CCN(CCOc6ccc(Oc7c(-c8ccc(C(F)(F)F)cc8)sc8cc(O)ccc78)cc6)CC5)CC4)c3F)C2=O)C(=O)N1] | 9.8 | 858.5 | Scheme 16B, 17B |
| 194 | 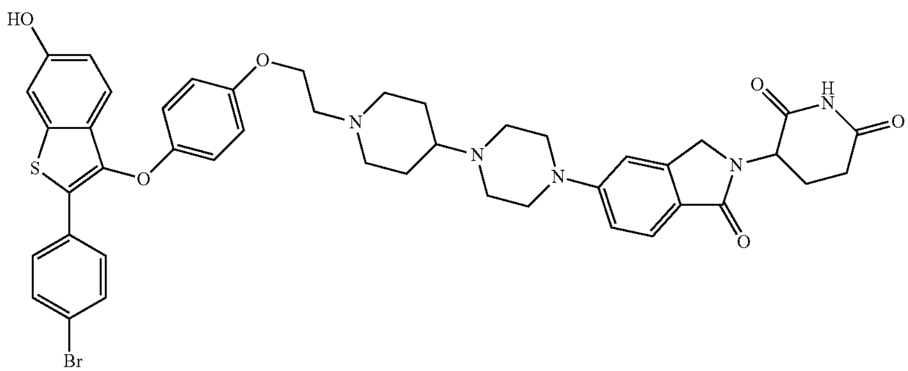 [SMILES: O=C1CCC(N2Cc3cc(N4CCN(C5CCN(CCOc6ccc(Oc7c(-c8ccc(Br)cc8)sc8cc(O)ccc78)cc6)CC5)CC4)ccc3C2=O)C(=O)N1] | 3.9 | 852.5 | Scheme 16B |
| 195 | 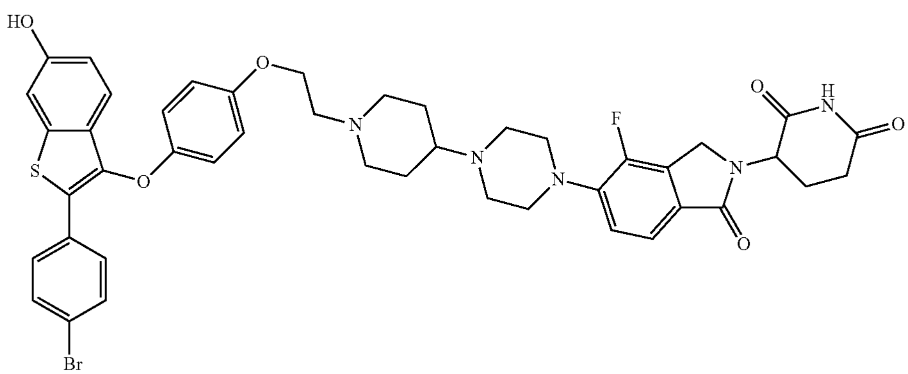 [SMILES: O=C1CCC(N2Cc3c(ccc(N4CCN(C5CCN(CCOc6ccc(Oc7c(-c8ccc(Br)cc8)sc8cc(O)ccc78)cc6)CC5)CC4)c3F)C2=O)C(=O)N1] | 2.9 | 870.5 | Scheme 16B, 17B |
| 196 | 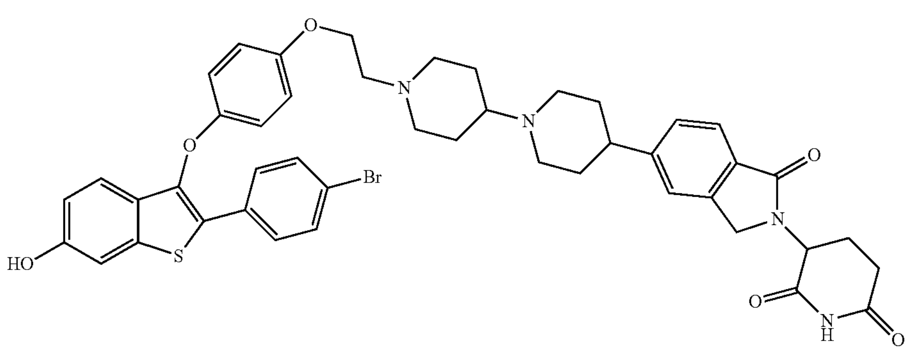 [SMILES: O=C1CCC(N2Cc3cc(C4CCN(C5CCN(CCOc6ccc(Oc7c(-c8ccc(Br)cc8)sc8cc(O)ccc78)cc6)CC5)CC4)ccc3C2=O)C(=O)N1] | 8.6 | 851.5 | Scheme 15B |

TABLE 3-continued

Activity, characterization and synthetic methods of cereblon centric benzthiophene derived ER PROTACs

| Ex. # | Structure | ER-α Luciferase IC50 (nM) | *Obsd [M + H]+ | Synthetic Method |
|---|---|---|---|---|
| 197 | 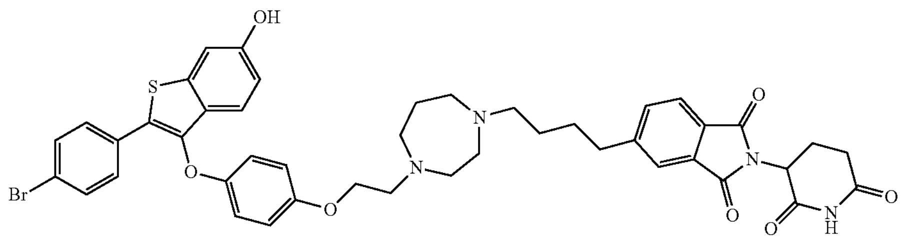 [SMILES: O=C1CCC(N2C(=O)c3ccc(CCCCN4CCCN(CCOc5ccc(Oc6c(-c7ccc(Br)cc7)sc7cc(O)ccc67)cc5)CC4)cc3C2=O)C(=O)N1] | 2.8 | 853.4 | Scheme 18B |
| 198 | 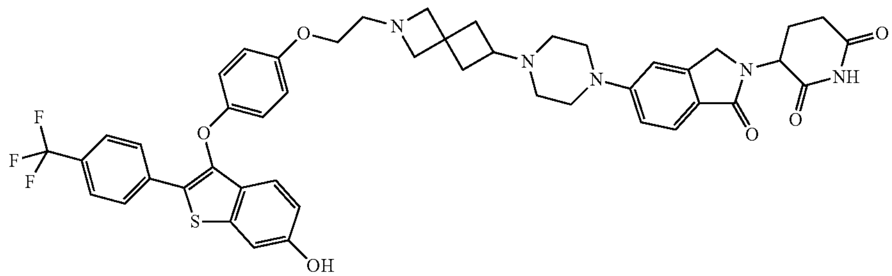 [SMILES: O=C1CCC(N2Cc3cc(N4CCN(C5CC6(C5)CN(CCOc5ccc(Oc7c(-c8ccc(C(F)(F)F)cc8)sc8cc(O)ccc78)cc5)C6)CC4)ccc3C2=O)C(=O)N1] | 10.2 | 852.5 | Scheme 19B |
| 199 | 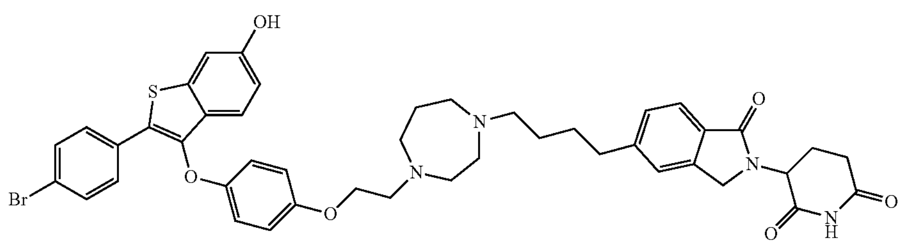 [SMILES: O=C1CCC(N2Cc3cc(CCCCN4CCCN(CCOc5ccc(Oc6c(-c7ccc(Br)cc7)sc7cc(O)ccc67)cc5)CC4)ccc3C2=O)C(=O)N1] | 0.82 | 839.5 | Scheme 18B |
| 200 | 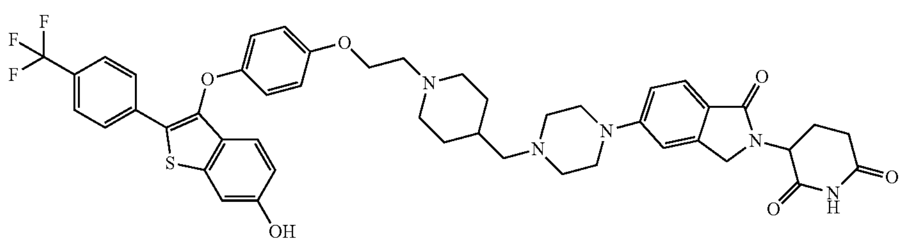 [SMILES: O=C1CCC(N2Cc3cc(N4CCN(CC5CCN(CCOc6ccc(Oc7c(-c8ccc(C(F)(F)F)cc8)sc8cc(O)ccc78)cc6)CC5)CC4)ccc3C2=O)C(=O)N1] | 8.4 | 854.5 | Scheme 16B |
| 201 | 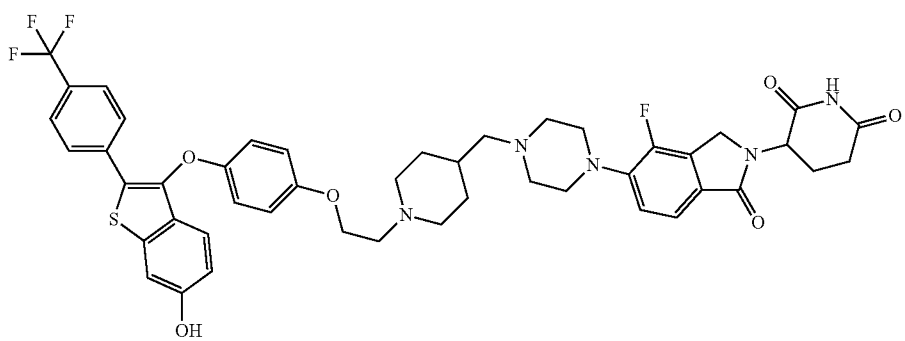 [SMILES: O=C1CCC(N2Cc3c(ccc(N4CCN(CC5CCN(CCOc6ccc(Oc7c(-c8ccc(C(F)(F)F)cc8)sc8cc(O)ccc78)cc6)CC5)CC4)c3F)C2=O)C(=O)N1] | 8.4 | 872.5 | Scheme 17B |

TABLE 3-continued

Activity, characterization and synthetic methods of cereblon centric benzthiophene derived ER PROTACs

| Ex. # | Structure | ER-α Luciferase IC50 (nM) | *Obsd [M + H]+ | Synthetic Method |
|---|---|---|---|---|
| 202 | 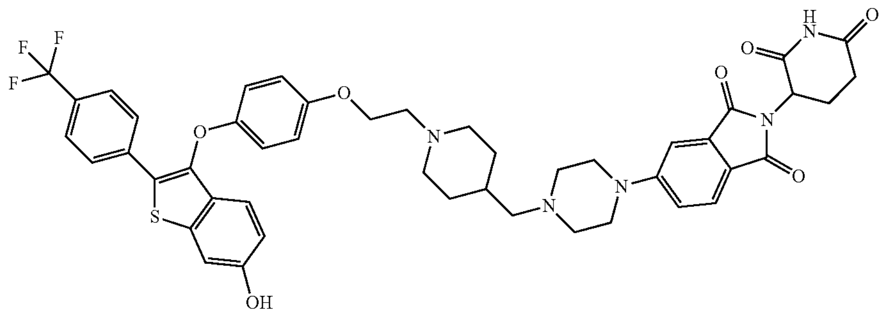 [SMILES: O=C1CCC(N2C(=O)c3ccc(N4CCN(CC5CCN(CCOc6ccc(Oc7c(-c8ccc(C(F)(F)F)cc8)sc8cc(O)ccc78)cc6)CC5)CC4)cc3C2=O)C(=O)N1] | 14.8 | 868.5 | Scheme 9B |
| 203 | 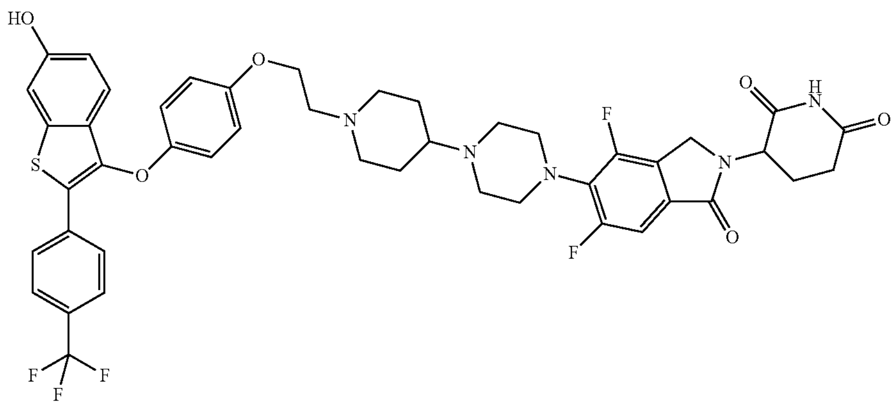 | 4.7 | 876.5 | Scheme 20B |
| 204 | 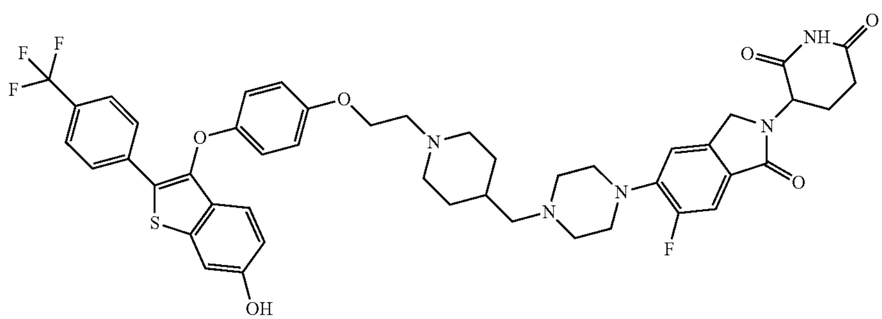 [SMILES: O=C1CCC(N2Cc3cc(N4CCN(CC5CCN(CCOc6ccc(Oc7c(-c8ccc(C(F)(F)F)cc8)sc8cc(O)ccc78)cc6)CC5)CC4)c(F)cc3C2=O)C(=O)N1] | 16.4 | 872.3 | Scheme 21B |
| 205 | 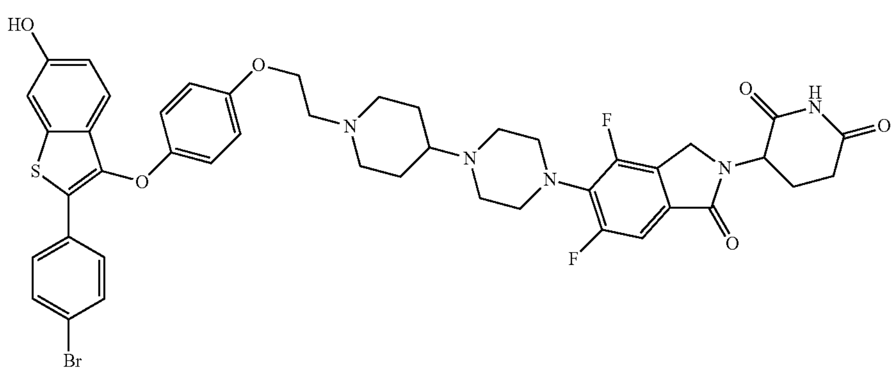 [SMILES: O=C1CCC(N2Cc3c(cc(F)c(N4CCN(C5CCN(CCOc6ccc(Oc7c(-c8ccc(Br)cc8)sc8cc(O)ccc78)cc6)CC5)CC4)c3F)C2=O)C(=O)N1] | 3.5 | 888.4 | Scheme 20B |

TABLE 3-continued

Activity, characterization and synthetic methods of cereblon centric benzthiophene derived ER PROTACs

| Ex. # | Structure | ER-α Luciferase IC50 (nM) | *Obsd [M + H]+ | Synthetic Method |
|---|---|---|---|---|
| 206 | 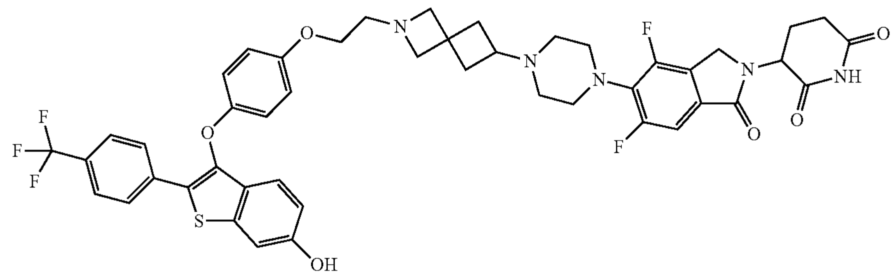 [SMILES: O=C1CCC(N2Cc3c(cc(F)c(N4CCN(C5CC6(C5)CN(CCOc5ccc(Oc7c(-c8ccc(C(F)(F)F)cc8)sc8cc(O)ccc78)cc5)C6)CC4)c3F)C2=O)C(=O)N1] | 13.3 | 888.5 | Scheme 20B |
| 207 | 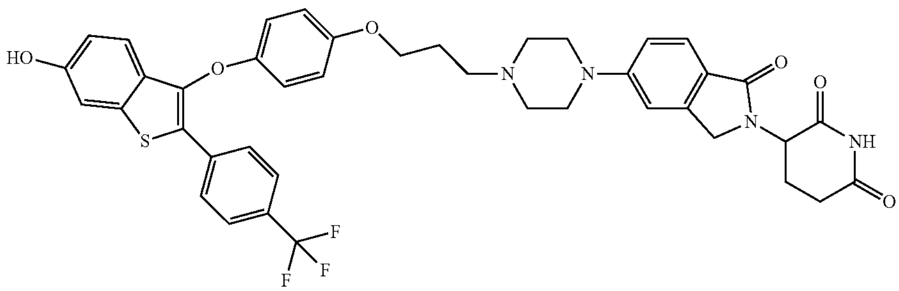 [SMILES: O=C1CCC(N2Cc3cc(N4CCN(CCCOc5ccc(Oc6c(-c7ccc(C(F)(F)F)cc7)sc7cc(O)ccc67)cc5)CC4)ccc3C2=O)C(=O)N1] | 11.4 | 771.5 | Scheme 22B |
| 208 | 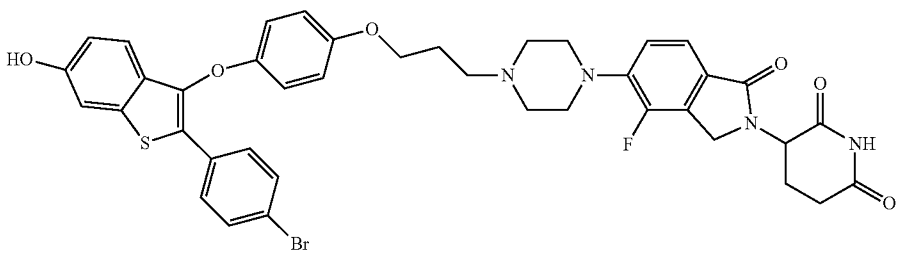 [SMILES: O=C1CCC(N2Cc3c(ccc(N4CCN(CCCOc5ccc(Oc6c(-c7ccc(Br)cc7)sc7cc(O)ccc67)cc5)CC4)c3F)C2=O)C(=O)N1] | 8.4 | 801.4 | Scheme 17B, 22B |
| 209 | 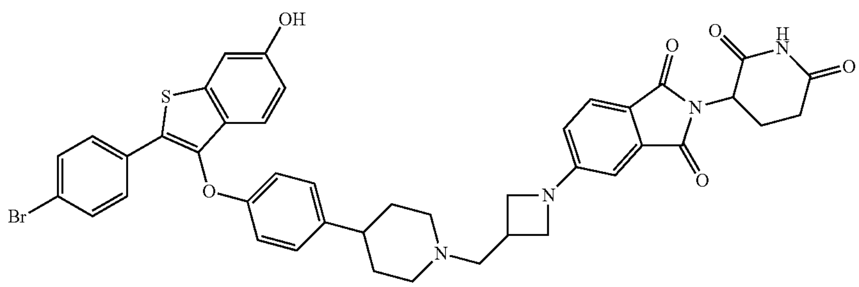 [SMILES: O=C1CCC(N2C(=O)c3ccc(N4CC(CN5CCC(c6ccc(Oc7c(-c8ccc(Br)cc8)sc8cc(O)ccc78)cc6)CC5)C4)cc3C2=O)C(=O)N1] | 2.8 | 807.4 | Scheme 23B |
| 210 | 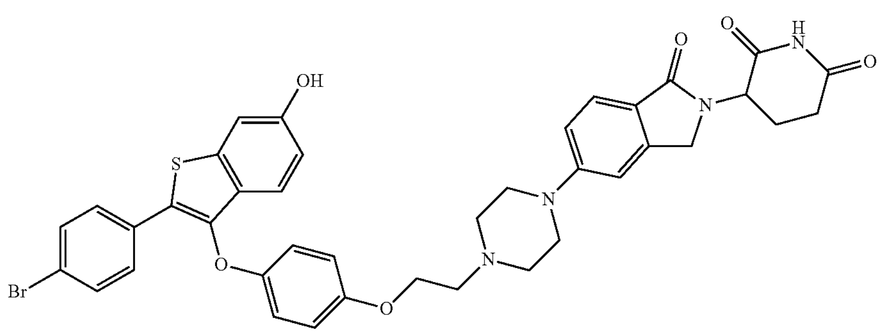 [SMILES: O=C1CCC(N2Cc3cc(N4CCN(CCOc5ccc(Oc6c(-c7ccc(Br)cc7)sc7cc(O)ccc67)cc5)CC4)ccc3C2=O)C(=O)N1] | 2.3 | 769.1 | Scheme 22B |

TABLE 3-continued

Activity, characterization and synthetic methods of cereblon centric benzthiophene derived ER PROTACs

| Ex. # | Structure | ER-α Luciferase IC50 (nM) | *Obsd [M + H]+ | Synthetic Method |
|---|---|---|---|---|
| 211 | 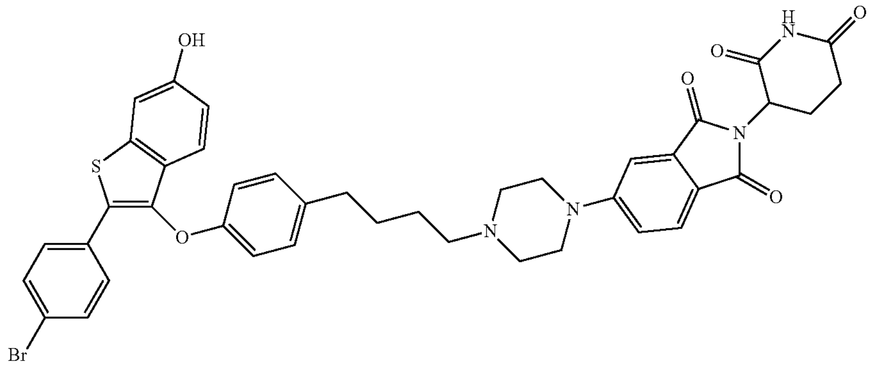 [SMILES: O=C1CCC(N2C(=O)c3ccc(N4CCN(CCCCc5ccc(Oc6c(-c7ccc(Br)cc7)sc7cc(O)ccc67)cc5)CC4)cc3C2=O)C(=O)N1] | 31.6 | 795.4 | Scheme 24B |
| 212 | 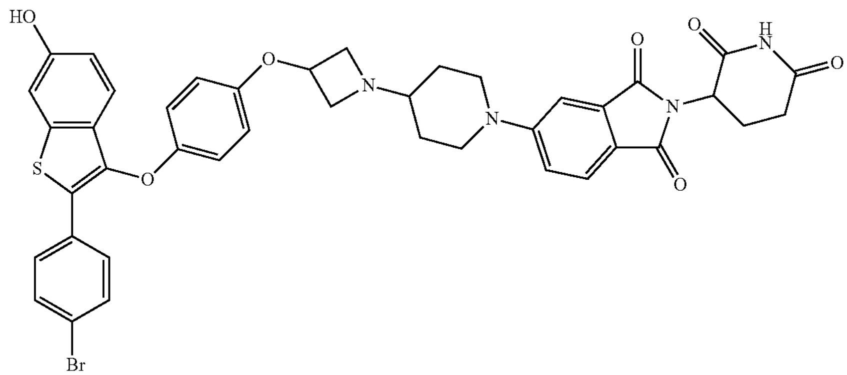 [SMILES: O=C1CCC(N2C(=O)c3ccc(N4CCC(N5CC(Oc6ccc(Oc7c(-c8ccc(Br)cc8)sc8cc(O)ccc78)cc6)C5)CC4)cc3C2=O)C(=O)N1] | 15 | 809.4 | Scheme 25B |
| 213 | 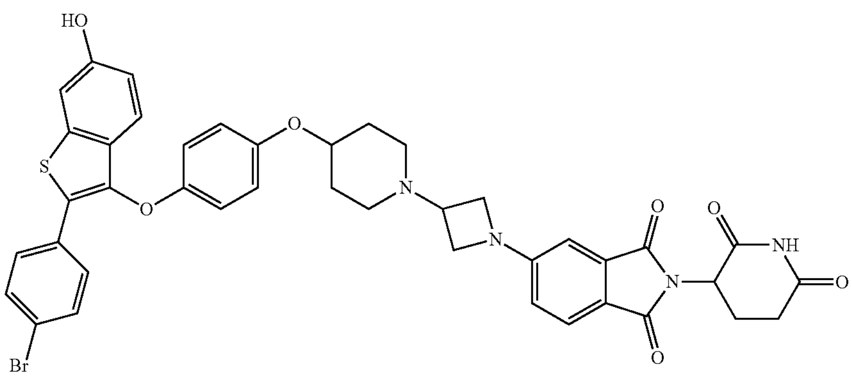 [SMILES: O=C1CCC(N2C(=O)c3ccc(N4CC(N5CCC(Oc6ccc(Oc7c(-c8ccc(Br)cc8)sc8cc(O)ccc78)cc6)CC5)C4)cc3C2=O)C(=O)N1] | 11.2 | 809.4 | Scheme 26B |
| 214 | 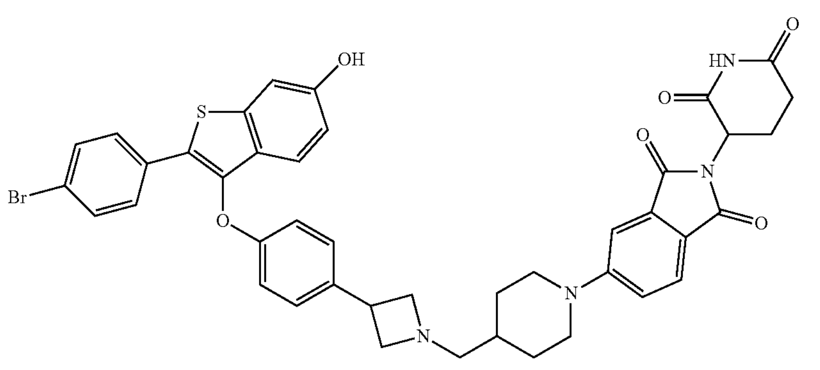 [SMILES: O=C1CCC(N2C(=O)c3ccc(N4CCC(CN5CC(c6ccc(Oc7c(-c8ccc(Br)cc8)sc8cc(O)ccc78)cc6)C5)CC4)cc3C2=O)C(=O)N1] | 10.4 | 807.4 | Scheme 27B |

TABLE 3-continued

Activity, characterization and synthetic methods of cereblon centric benzthiophene derived ER PROTACs

| Ex. # | Structure | ER-α Luciferase IC50 (nM) | *Obsd [M + H]+ | Synthetic Method |
|---|---|---|---|---|
| 215 | 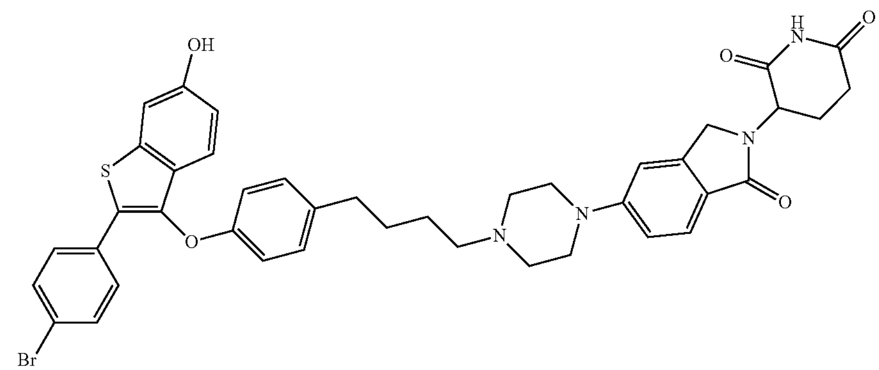 [SMILES: O=C1CCC(N2Cc3cc(N4CCN(CCCCc5ccc(Oc6c(-c7ccc(Br)cc7)sc7cc(O)ccc67)cc5)CC4)ccc3C2=O)C(=O)N1] | 5.3 | 781.4 | Scheme 24B |
| 216 | 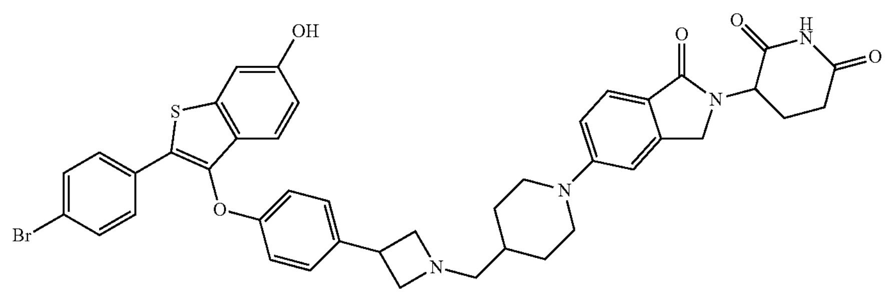 [SMILES: O=C1CCC(N2Cc3cc(N4CCC(CN5CC(c6ccc(Oc7c(-c8ccc(Br)cc8)sc8cc(O)ccc78)cc6)C5)CC4)ccc3C2=O)C(=O)N1] | 2.7 | 793.4 | Scheme 27B |
| 217 | 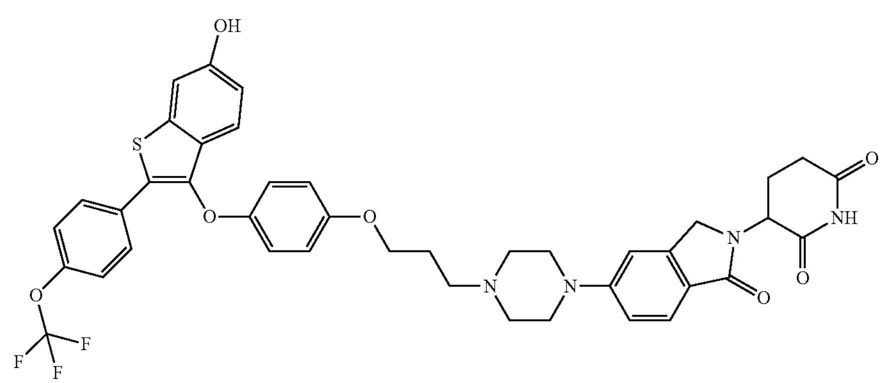 [SMILES: O=C1CCC(N2Cc3cc(N4CCN(CCCOc5ccc(Oc6c(-c7ccc(OC(F)(F)F)cc7)sc7cc(O)ccc67)cc5)CC4)ccc3C2=O)C(=O)N1] | 7.5 | 787.5 | Scheme 22B |
| 218 | 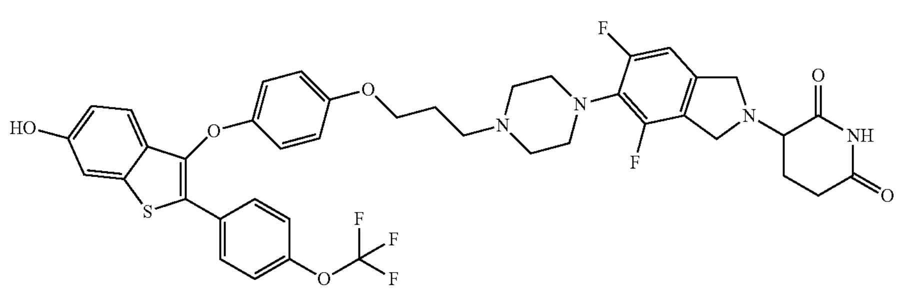 [SMILES: O=C1CCC(N2Cc3cc(F)c(N4CCN(CCCOc5ccc(Oc6c(-c7ccc(OC(F)(F)F)cc7)sc7cc(O)ccc67)cc5)CC4)c(F)c3C2)C(=O)N1] | 58.2 | 823.4 | Scheme 20B, 28B |

TABLE 3-continued

Activity, characterization and synthetic methods of cereblon centric benzthiophene derived ER PROTACs

| Ex. # | Structure | ER-α Luciferase IC50 (nM) | *Obsd [M + H]+ | Synthetic Method |
|---|---|---|---|---|
| 219 | 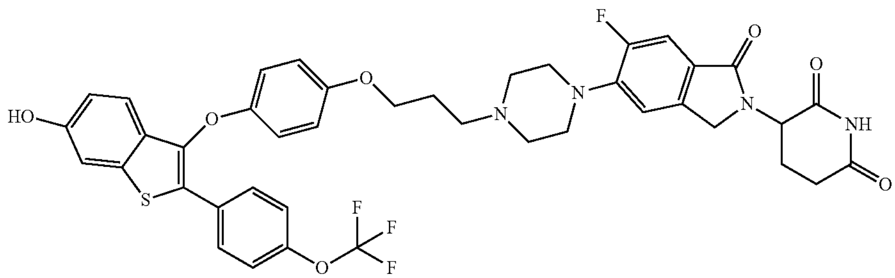 [SMILES: O=C1CCC(N2Cc3cc(N4CCN(CCCOc5ccc(Oc6c(-c7ccc(OC(F)(F)F)cc7)sc7cc(O)ccc67)cc5)CC4)c(F)cc3C2=O)C(=O)N1] | 19.1 | 805.4 | Scheme 21B, 28B |
| 220 | 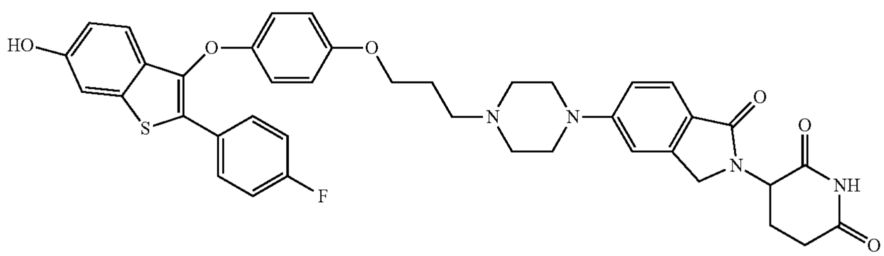 [SMILES: O=C1CCC(N2Cc3cc(N4CCN(CCCOc5ccc(Oc6c(-c7ccc(F)cc7)sc7cc(O)ccc67)cc5)CC4)ccc3C2=O)C(=O)N1] | 1.5 | 721.4 | Scheme 22B |
| 221 | 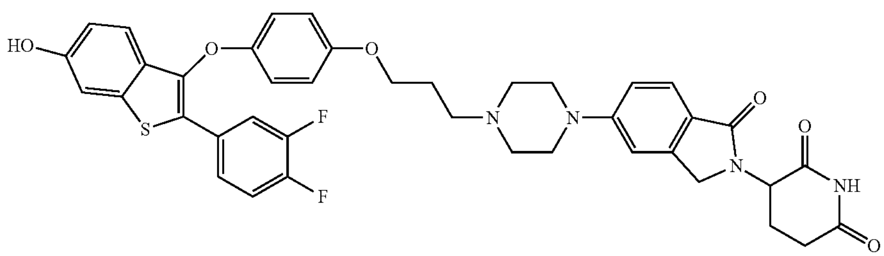 [SMILES: O=C1CCC(N2Cc3cc(N4CCN(CCCOc5ccc(Oc6c(-c7ccc(F)c(F)c7)sc7cc(O)ccc67)cc5)CC4)ccc3C2=O)C(=O)N1] | 2.4 | 739.4 | Scheme 22B |
| 222 | 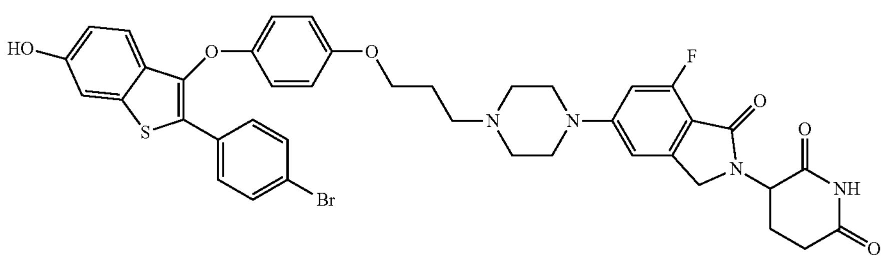 [SMILES: O=C1CCC(N2Cc3cc(N4CCN(CCCOc5ccc(Oc6c(-c7ccc(Br)cc7)sc7cc(O)ccc67)cc5)CC4)cc(F)c3C2=O)C(=O)N1] | 8.9 | 801.4 | Scheme 29B |
| 223 | 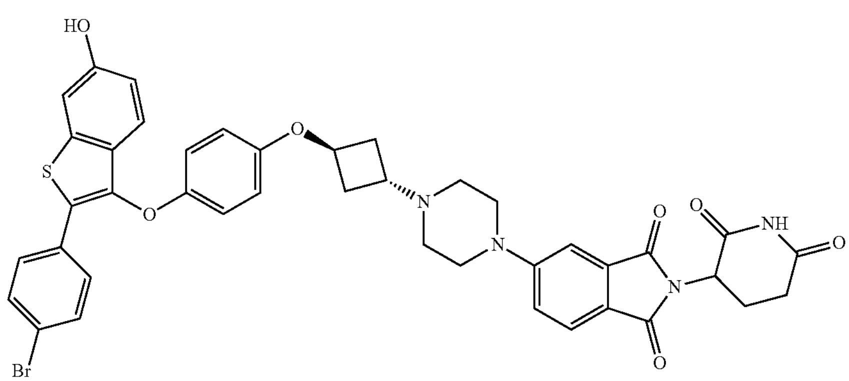 [SMILES: O=C1CCC(N2C(=O)c3ccc(N4CCN([C@H]5C[C@H](Oc6ccc(Oc7c(-c8ccc(Br)cc8)sc8cc(O)ccc78)cc6)C5)CC4)cc3C2=O)C(=O)N1] | 41.1 | 809.4 | Scheme 30B |

TABLE 3-continued

Activity, characterization and synthetic methods of cereblon centric benzthiophene derived ER PROTACs

| Ex. # | Structure | ER-α Luciferase IC50 (nM) | *Obsd [M + H]+ | Synthetic Method |
|---|---|---|---|---|
| 224 | 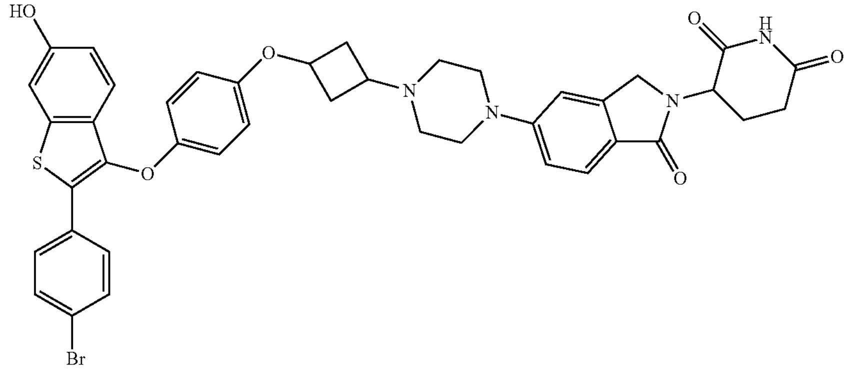 | 7.7 | 793.1 | Scheme 31B |
| 225 | 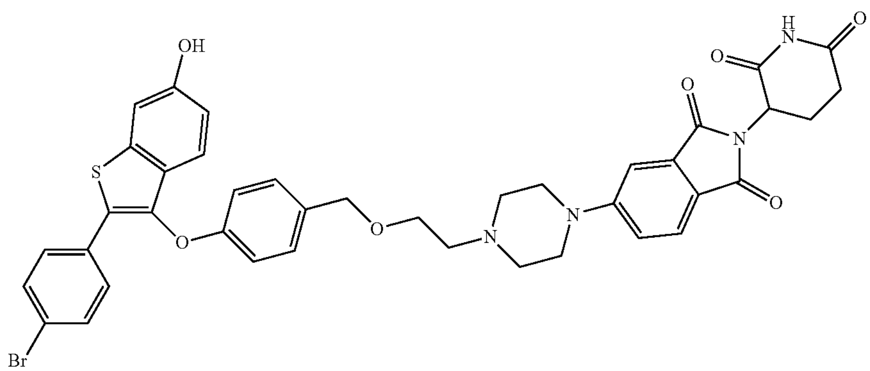 | 4.8 | 797.4 | Scheme 32B |
| 226 | 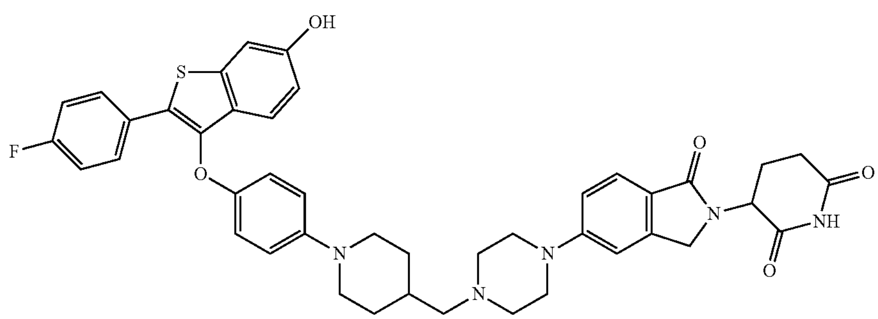 [SMILES: O=C1CCC(N2Cc3cc(N4CCN(CC5CCN(c6ccc(Oc7c(-c8ccc(F)cc8)sc8cc(O)ccc78)cc6)CC5)CC4)ccc3C2=O)C(=O)N1] | 1.2 | 760.5 | Scheme 33B |
| 227 | 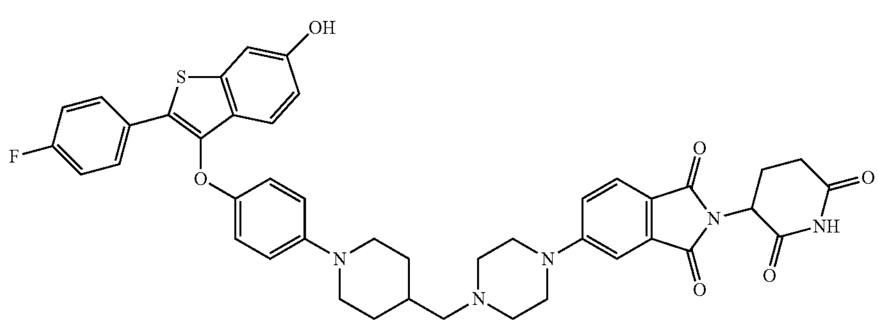 [SMILES: O=C1CCC(N2C(=O)c3ccc(N4CCN(CC5CCN(c6ccc(Oc7c(-c8ccc(F)cc8)sc8cc(O)ccc78)cc6)CC5)CC4)cc3C2=O)C(=O)N1] | 7 | 774.5 | Scheme 33B |

TABLE 3-continued

Activity, characterization and synthetic methods of cereblon centric benzthiophene derived ER PROTACs

| Ex. # | Structure | ER-α Luciferase IC50 (nM) | *Obsd [M + H]+ | Synthetic Method |
|---|---|---|---|---|
| 228 | 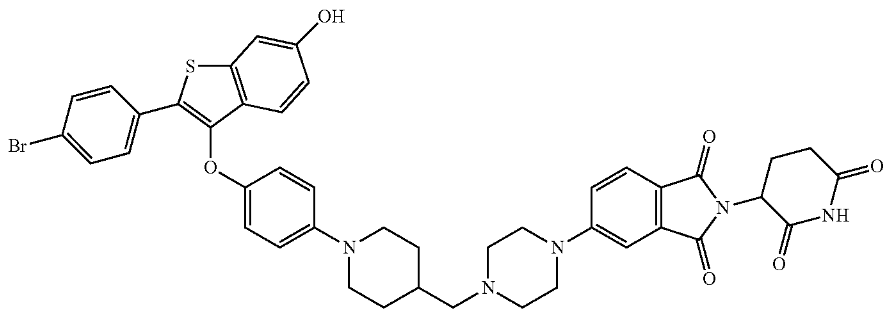 [SMILES: O=C1CCC(N2C(=O)c3ccc(N4CCN(CC5CCN(c6ccc(Oc7c(-c8ccc(Br)cc8)sc8cc(O)ccc78)cc6)CC5)CC4)cc3C2=O)C(=O)N1] | 24.9 | 836.4 | Scheme 33B |
| 229 | 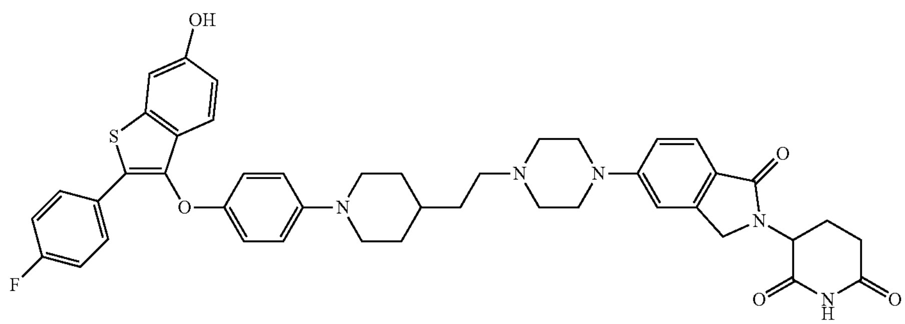 [SMILES: O=C1CCC(N2Cc3cc(N4CCN(CCC5CCN(c6ccc(Oc7c(-c8ccc(F)cc8)sc8cc(O)ccc78)cc6)CC5)CC4)ccc3C2=O)C(=O)N1] | 1 | 774.5 | Scheme 33B |
| 230 | 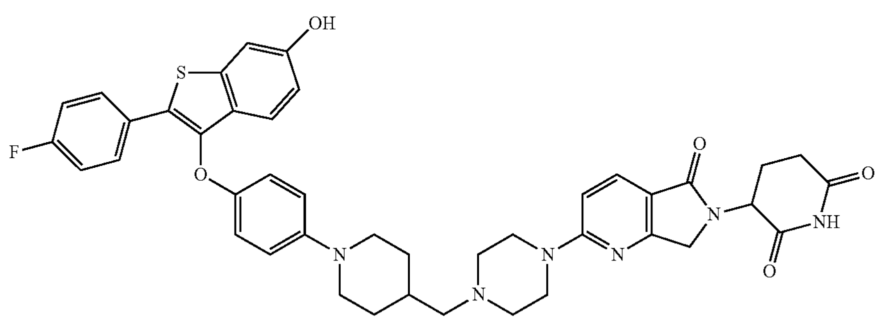 [SMILES: O=C1CCC(N2Cc3nc(N4CCN(CC5CCN(c6ccc(Oc7c(-c8ccc(F)cc8)sc8cc(O)ccc78)cc6)CC5)CC4)ccc3C2=O)C(=O)N1] | 1.1 | 761.5 | Scheme 33B, 34B |
| 231 | 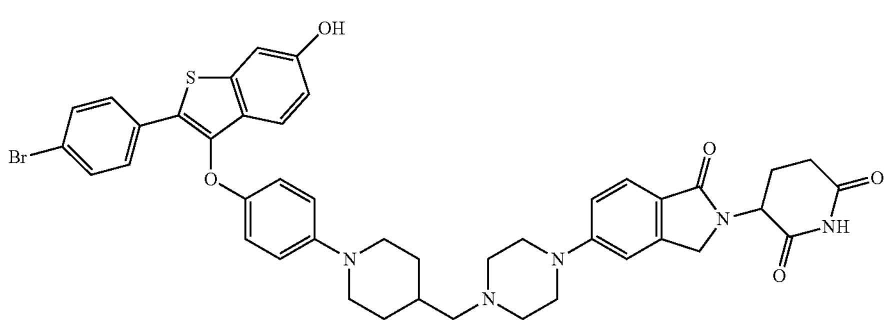 [SMILES: O=C1CCC(N2Cc3cc(N4CCN(CC5CCN(c6ccc(Oc7c(-c8ccc(Br)cc8)sc8cc(O)ccc78)cc6)CC5)CC4)ccc3C2=O)C(=O)N1] | 7.1 | 822.4 | Scheme 35B |

TABLE 3-continued

Activity, characterization and synthetic methods of cereblon centric benzthiophene derived ER PROTACs

| Ex. # | Structure | ER-α Luciferase IC50 (nM) | *Obsd [M + H]+ | Synthetic Method |
|---|---|---|---|---|
| 232 | 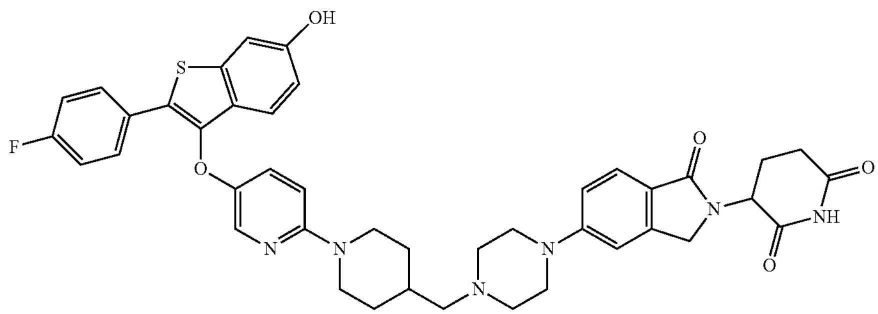 [SMILES: O=C1CCC(N2Cc3cc(N4CCN(CC5CCN(c6ccc(Oc7c(-c8ccc(F)cc8)sc8cc(O)ccc78)cn6)CC5)CC4)ccc3C2=O)C(=O)N1] | 1.6 | 761.5 | Scheme 36B |
| 233 | 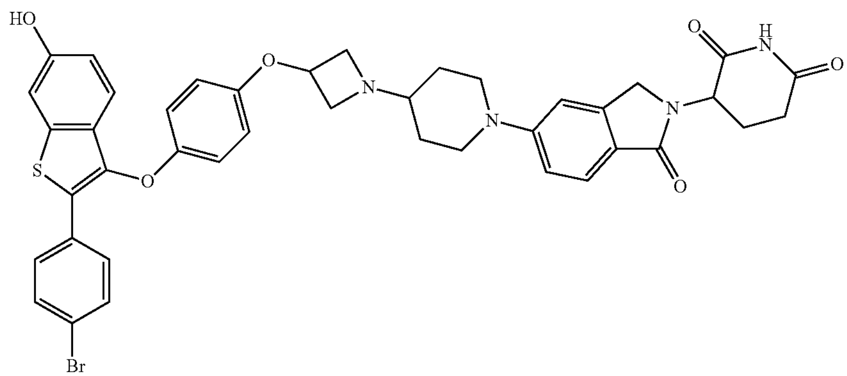 [SMILES: O=C1CCC(N2Cc3cc(N4CCC(N5CC(Oc6ccc(Oc7c(-c8ccc(Br)cc8)sc8cc(O)ccc78)cc6)C5)CC4)ccc3C2=O)C(=O)N1] | 2.1 | 795.4 | Scheme 25B, 38B |
| 234 | 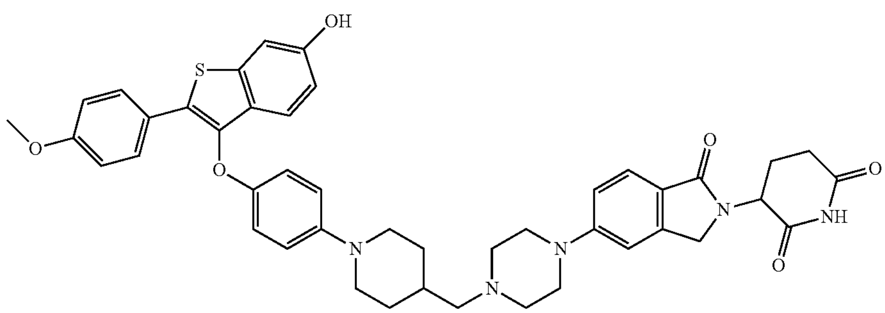 [SMILES: COc1ccc(-c2sc3cc(O)ccc3c2Oc2ccc(N3CCC(CN4CCN(c5ccc6c(c5)CN(C5CCC(=O)NC5=O)C6=O)CC4)CC3)cc2)cc1] | 0.65 | 772.5 | Scheme 6B, 33B |
| 235 | 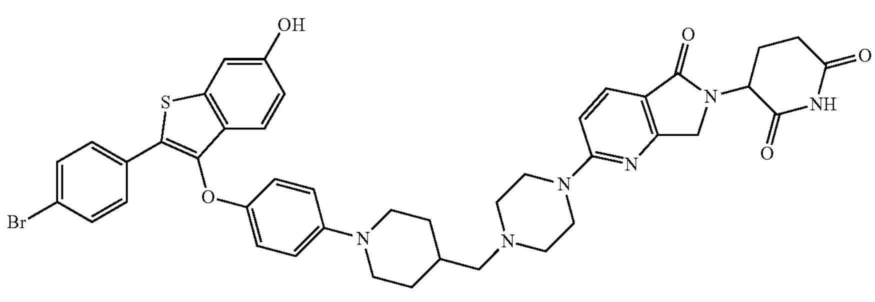 [SMILES: O=C1CCC(N2Cc3nc(N4CCN(CC5CCN(c6ccc(Oc7c(-c8ccc(Br)cc8)sc8cc(O)ccc78)cc6)CC5)CC4)ccc3C2=O)C(=O)N1] | 6.9 | 823.4 | Scheme 34B, 35B |

TABLE 3-continued

Activity, characterization and synthetic methods of cereblon centric benzthiophene derived ER PROTACs

| Ex. # | Structure | ER-α Luciferase IC50 (nM) | *Obsd [M + H]+ | Synthetic Method |
|---|---|---|---|---|
| 236 | 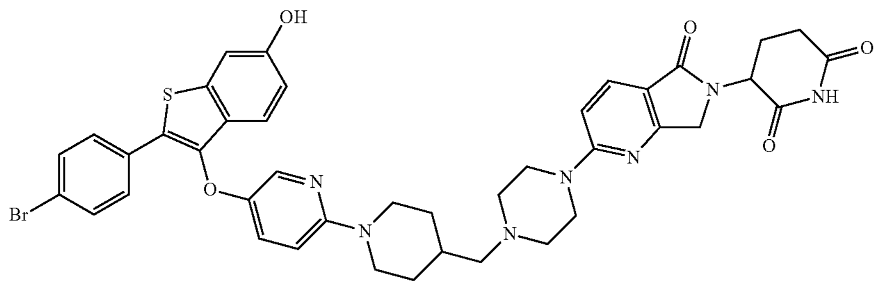 [SMILES: O=C1CCC(N2Cc3nc(N4CCN(CC5CCN(c6ccc(Oc7c(-c8ccc(Br)cc8)sc8cc(O)ccc78)cn6)CC5)CC4)ccc3C2=O)C(=O)N1] | 4.9 | 823.4 | Scheme 36B |
| 237 | 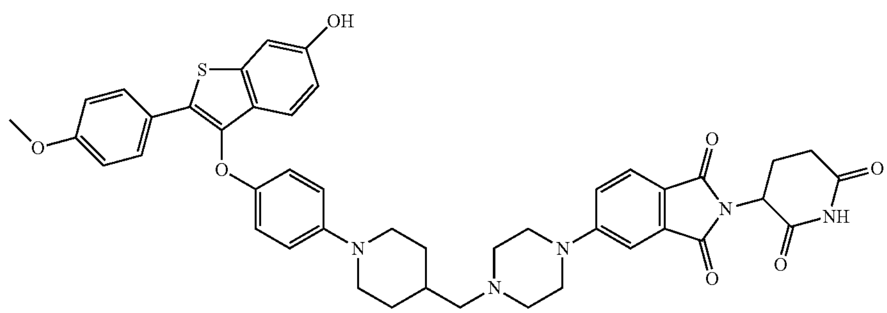 [SMILES: COc1ccc(-c2sc3cc(O)ccc3c2Oc2ccc(N3CCC(CN4CCN(c5ccc6c(c5)C(=O)N(C5CCC(=O)NC5=O)C6=O)CC4)CC3)cc2)cc1] | 4.9 | 786.5 | Scheme 6B, 33B |
| 238 | 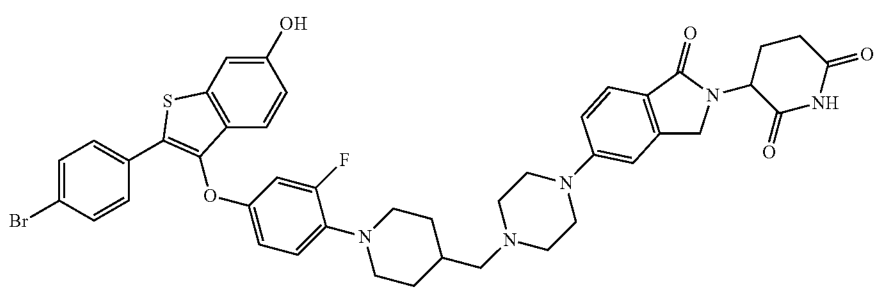 [SMILES: O=C1CCC(N2Cc3cc(N4CCN(CC5CCN(c6ccc(Oc7c(-c8ccc(Br)cc8)sc8cc(O)ccc78)cc6F)CC5)CC4)ccc3C2=O)C(=O)N1] | 10.9 | 840.4 | Scheme 35B, 37B |
| 239 | 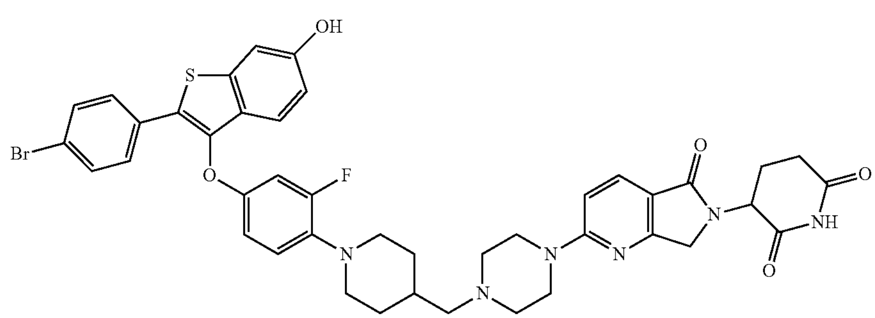 [SMILES: O=C1CCC(N2Cc3nc(N4CCN(CC5CCN(c6ccc(Oc7c(-c8ccc(Br)cc8)sc8cc(O)ccc78)cc6F)CC5)CC4)ccc3C2=O)C(=O)N1] | 13.5 | 841.4 | Scheme 34B, 37B |

TABLE 3-continued

Activity, characterization and synthetic methods of cereblon centric benzthiophene derived ER PROTACs

| Ex. # | Structure | ER-α Luciferase IC50 (nM) | *Obsd [M + H]+ | Synthetic Method |
|---|---|---|---|---|
| 240 | 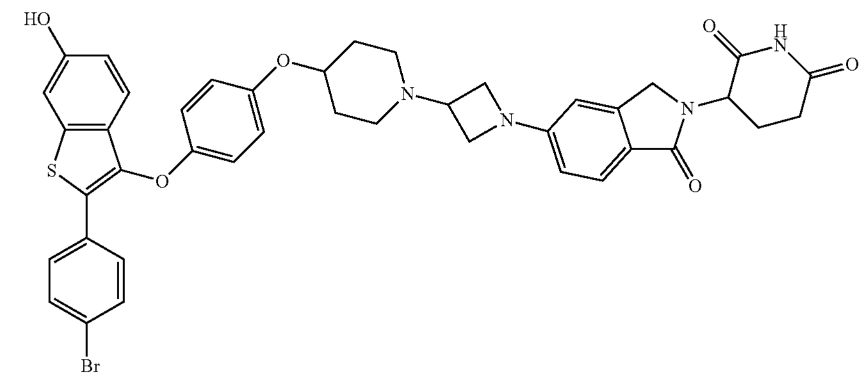 [SMILES: O=C1CCC(N2Cc3cc(N4CC(N5CCC(Oc6ccc(Oc7c(-c8ccc(Br)cc8)sc8cc(O)ccc78)cc6)CC5)C4)ccc3C2=O)C(=O)N1] | 1.2 | 795.4 | Scheme 38B |
| 241 | 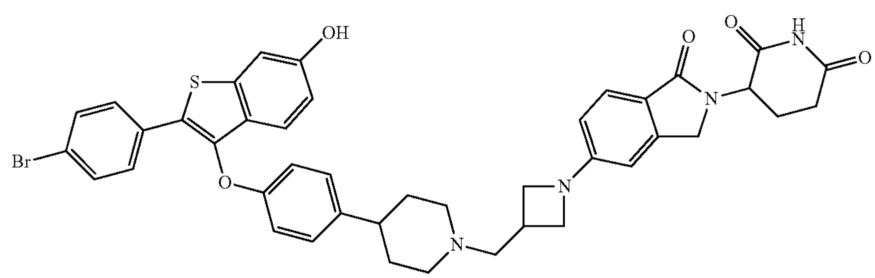 [SMILES: O=C1CCC(N2Cc3cc(N4CC(CN5CCC(c6ccc(Oc7c(-c8ccc(Br)cc8)sc8cc(O)ccc78)cc6)CC5)C4)ccc3C2=O)C(=O)N1] | 6.7 | 793.4 | Scheme 38B, 39B |
| 242 | 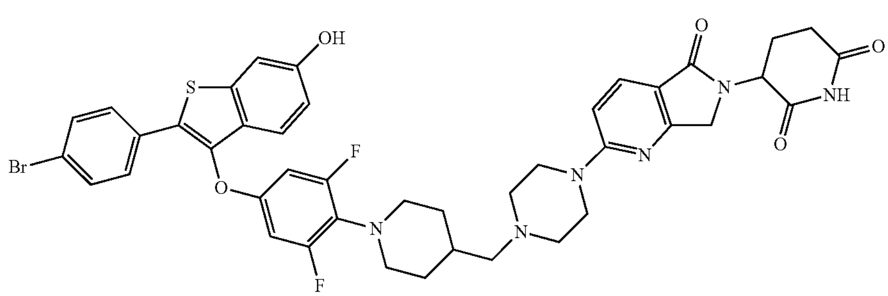 [SMILES: O=C1CCC(N2Cc3nc(N4CCN(CC5CCN(c6c(F)cc(Oc7c(-c8ccc(Br)cc8)sc8cc(O)ccc78)cc6F)CC5)CC4)ccc3C2=O)C(=O)N1] | 18.7 | 859.4 | Scheme 40B |
| 243 | 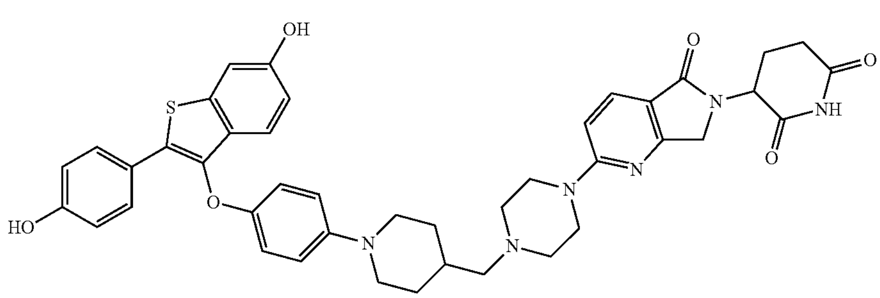 [SMILES: O=C1CCC(N2Cc3nc(N4CCN(CC5CCN(c6ccc(Oc7c(-c8ccc(O)cc8)sc8cc(O)ccc78)cc6)CC5)CC4)ccc3C2=O)C(=O)N1] | 0.18 | 759.5 | Scheme 41B |

TABLE 3-continued

Activity, characterization and synthetic methods of cereblon centric benzthiophene derived ER PROTACs

| Ex. # | Structure | ER-α Luciferase IC50 (nM) | *Obsd [M + H]+ | Synthetic Method |
|---|---|---|---|---|
| 244 | 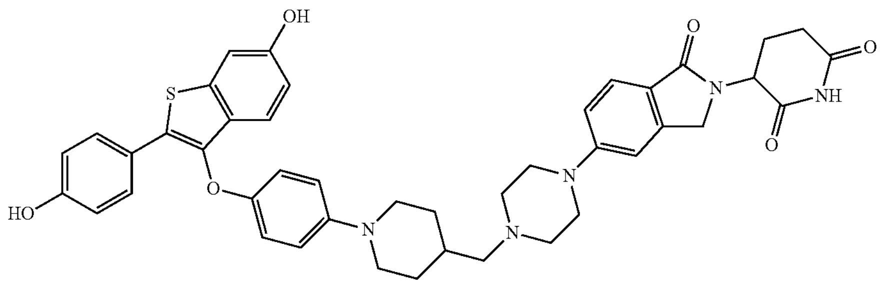 [SMILES: O=C1CCC(N2Cc3cc(N4CCN(CC5CCN(c6ccc(Oc7c(-c8ccc(O)cc8)sc8cc(O)ccc78)cc6)CC5)CC4)ccc3C2=O)C(=O)N1] | 0.18 | 758.5 | Scheme 41B |
| 245 | 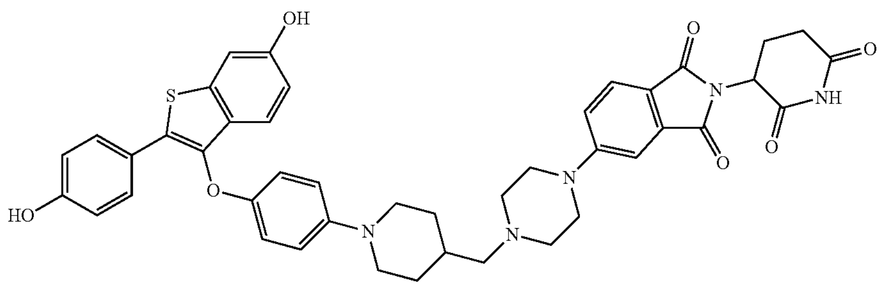 [SMILES: O=C1CCC(N2C(=O)c3ccc(N4CCN(CC5CCN(c6ccc(Oc7c(-c8ccc(O)cc8)sc8cc(O)ccc78)cc6)CC5)CC4)cc3C2=O)C(=O)N1] | 0.53 | 772.5 | Scheme 41B |

*Observed [M + Na]+ from LC/MS

TABLE 4

Data for VHL centric benzthiophene derived ER PROTACs

| Ex. # | IUPAC | $^1$H-NMR | $DC_{50}$* | $D_{max}$ (%)** |
|---|---|---|---|---|
| 111 | (2S,4R)-1-((S)-2-tert-butyl-14-(4-(2-(4-fluorophenyl)-6-hydroxybenzo[b]thiophen-3-yloxy)phenoxy)-4-oxo-6,9,12-trioxa-3-azatetradecane)-4-hydroxy-N-((S)-1-(4-(4-methylthiazol-5-yl)phenyl)ethyl)pyrrolidine-2-carboxamide | δ 1.03 (s, 9H), 1.49 (d, J = 6.8Hz, 3H), 1.92-1.99 (m, 1H), 2.18-2.23 (m, 1H), 2.48, 2.49 (two singles, 3H), 3.70-3.75 (m, 9H), 3.81-3.86 (m, 3H), 4.03-4.09 (m, 4H), 4.43 (br, 1H), 4.55-4.59 (m, 1H), 4.68 (br, 1H), 4.97-5.02 (m, 1H), 6.78-6.81 (m, 1H), 6.85-6.87 (m,4H), 7.07-7.12 (m, 2H), 7.18-7.20 (m, 2H), 7.38-7.45 (m, 4H), 7.12-7.76 (m, 2H), 8.88, 8.89 (two singles, 1H). (CD$_3$OD, 400 MHz) | A | A |
| 117 | (2S,4R)-1-((S)-2-(2-(2-(1-(2-(4-(2-(4-fluorophenyl)-6-hydroxybenzo[b]thiophen-3-yloxy)phenoxy)ethyl)azetidin-3-yloxy)ethoxy)acetamido)-3,3-dimethylbutanoyl)-4-hydroxy-N-(4-(4-methylthiazol-5-yl)benzyl)pyrrolidine-2-carboxamide | δ 1.02, 1.04 (two singles, 9H), 2.06-2.11 (m, 1H), 2.24-2.27 (m, 1H), 2.45, 2.47 (two singles, 3H), 3.54-3.87 (m, 8H), 4.06-4.58 (m, 13H), 4.76-4.80 (m, 1H), 6.76-6.89 (m, 5H), 7.06-7.10 (m, 2H), 7.15-7.21 (m, 2H), 7.38-7.44 (m, 4H), 7.67-7.75 (m, 2H), 8.41 (br, 1H), 8.86, 8.89 (two singles, 1H). (CD$_3$OD, 400 MHz) | B | B |
| 118 | [(2S,4R)-1-((S)-2-(2-(2-(4-(2-(4-((2-(4-fluorophenyl)-6-hydroxybenzo[b]thiophen-3-yl)oxy)phenoxy)ethyl)piperazin-1-yl)ethoxy)acetamido)-3,3-dimethylbutanoyl)-4-hydroxy-N-(4-(4-methylthiazol-5-yl)benzyl)pyrrolidine-2-carboxamide | δ 1.02, 1.05 (two singles, 9H), 2.07-2.12 (m, 1H), 2.21-2.27 (m, 1H), 2.47, 2.48 (two singles, 3H), 2.94-3.22 (m, 12H), 3.80-3.88 (m, 4H), 4.07-4.18 (m, 4H), 4.34-4.38 (m, 1H), 4.50-4.55 (m, 3H), 4.70 (br, 1H), 6.78-6.86 (m, 5H), 7.07-7.12 (m, 2H), 7.17-7.18 (m, 1H), 7.21 (d, J = 2.0 Hz, 1H), 7.39-7.45 (m, 4H), 7.72-7.76 (m, 2H), 8.87, 8.88 (two singles, 1H). (CD$_3$OD, 400 MHz) | A | A |

TABLE 4-continued

Data for VHL centric benzthiophene derived ER PROTACs

| Ex. # | IUPAC | ¹H-NMR | DC$_{50}$* | D$_{max}$ (%)** |
|---|---|---|---|---|
| 119 | (2S,4R)-1-((S)-2-tert-butyl-14-(4-(2-(4-chlorophenyl)-6-hydroxybenzo[b]thiophen-3-yloxy)phenoxy)-4-oxo-6,9,12-trioxa-3-azatetradecane)-4-hydroxy-N-((S)-1-(4-(4-methylthiazol-5-yl)phenyl) ethyl)pyrrolidine-2-carboxamide | δ 1.03 (s, 9H), 1.47-1.57 (m, 3H), 1.93-1.99 (m, 1H), 2.18-2.23 (m, 1H), 2.47, 2.48 (two singles, 3H), 3.67-3.76 (m, 9H), 3.81-3.86 (m, 3H), 4.03-4.09 (m, 4H), 4.38 (br,1H), 4.55-4.59 (m, 1H), 4.68(s, 1H), 4.96-5.01 (m, 1H), 6.78-6.81 (m, 5H), 7.18-7.21 (m,2H), 7.33-7.45(m, 6H), 7.70-7.72 (m, 2H), 8.87,8.89 (two singles, 1H). (CD$_3$OD, 400 MHz) | B | A |
| 121 | (2S,4R)-1-[(2S)-2-[2-(4-[1-[2-(4-[[2-(4-fluorophenyl)-6-hydroxy-1-benzothiophen-3-yl]oxy]phenoxy) ethyl]-1H-pyrazol-3-yl) phenyl]acetamido]-3,3-dimethylbutanoyl]-4-hydroxy-N-[[4-(4-methyl-1,3-thiazol-5-yl)phenyl]methyl] pyrrolidine-2-carboxamide | δ 9.01 (s, 1H) 7.74-7.69 (m, 5H), 7.49-7.43 (m , 4H), 7.36-7.34 (m, 2H), 7.34-7.10 (m, 4H), 6.82-6.79 (m, 3H), 6.78-6.76 (m, 1H), 6.60-6.59 (m, J =2.4 Hz, 1H), 4.64-4.50 (m, 6H), 4.38-4.30 (m, 3H), 3.89-3.81 (m, 2H), 3.65-3.63 (m, 2H), 2.45 (s, 3H), 2.25-2.20 (m, 1H), 2.08-2.02 (m, 1H), 1.00 (s, 9H). (CD$_3$OD, 400 MHz) | B | A |
| 126 | (2S,4R)-1-((S)-14-(4-(2-(4-bromophenyl)-6-hydroxybenzo[b]thiophen-3-yloxy) phenoxy)-2-tert-butyl-4-oxo-6,9,12-trioxa-3-azatetradecane)-4-hydroxy-N-((S)-1-(4-(4-methylthiazol-5-yl)phenyl)ethyl) pyrrolidine-2-carboxamide | δ 1.03 (s, 9H), 1.47-1.57 (m, 3H), 1.93-1.99 (m, 1H), 2.17-2.23 (m, 1H), 2.47, 2.48 (two singles, 3H), 3.66-3.76 (m,9H), 3.80-3.87 (m, 3H), 4.03-4.08 (m, 4H), 4.44 (br, 1H), 4.55-4.59 (m,1H), 4.68 (d, J = 9.2 Hz, 1H), 4.96-5.03 (m, 1H), 6.79 (dd, J = 8.8Hz, 2.4 Hz, 1H), 6.85, 6.86 (two singles, 4H), 7.17-7.20 (m, 2H), 7.37-7.44 (m, 4H), 7.48-7.50 (m,2H), 7.62-7.66 (m, 3H), 8.57 (d, J = 9.2 Hz, 1H), 8.87,8.88 (two singles, 1H). (CD$_3$OD, 400 MHz) | A | A |
| 127 | (2S,4R)-1-((S)-14-(4-(2-(4-bromophenyl)-6-hydroxybenzo[b]thiophen-3-yloxy)phenoxy)-2-tert-butyl-4-oxo-6,9,12-trioxa-3-azatetradecane)-4-hydroxy-N-((S)-1-(4-(4-methyloxazol-5-yl)phenyl)ethyl)pyrrolidine-2-carboxamide | δ 1.03 (s, 9H), 1.47-1.56 (m,3H), 1.92-1.98 (m, 1H), 2.17-2.22 (m, 1H), 2.39, 2.41 (two singles, 3H), 3.67-3.76 (m,9H), 3.81-3.86 (m, 3H), 4.03-4.09 (m, 4H), 4.44 (br, 1H), 4.55-4.59 (m,1H), 4.67-4.70 (m, 1H), 4.96-5.01 (m, 1H), 6.79 (dd, J = 8.4 Hz, 2.0 Hz, 1H), 6.85-6.87 (m, 4H), 7.18-7.21 (m, 2H), 7.39-7.42 (m, 2H), 7.48-7.50 (m,2H), 7.60-7.66(m, 4H), 8.14,8.16 (two singles, 1H). (CD$_3$OD, 400 MHz) | A | A |
| 128 | (2S,4R)-1-[(2S)-2-[1-(4[[2-(4-fluorophenyl)-6-hydroxy-1-benzothiophen-3-yl]oxy]phenyl)-4-methyl-1,7,10-trioxa-4-azadodecan-12-amido]-3,3-dimethylbutanoyl]-4-hydroxy-N-[(1S)-1-[4-(4-methyl-1,3-thiazol-5-yl)phenyl]ethyl]pyrrolidine-2-carboxamide | δ 8.94 (s, 1H), 7.76 (m, 2H), 7.43 (m, 4H), 7.20 (m, 2H), 7.10 (m, 2H), 6.95 (m, 5H), 5.01 (m, 1H), 4.75 (m, 1H), 4.55 (m, 1H), 4.30 (m, 3H), 4.05 (m, 4H), 3.70 (m, 10H), 3.04 (s, 3H), 2.49 (s, 3H), 2.29 (m, 1H), 1.95 (m, 1H), 1.45 (m, 3H), 1.02 (s, 9H). (CD$_3$OD, 400 MHz) | A | A |
| 129 | (2S,4R)-N4(1S)-1-(4-chlorophenyl)ethyl]-1-[(2S)-2-[1-(4-[[2-(4-fluorophenyl)-6-hydroxy-1-benzothiophen-3-yl]oxy]phenyl)-4-methyl-1,7,10-trioxa-4-azadodecan-12-amido]-3,3-dimethylbutanoyl]-4-hydroxypyrrolidine-2-carboxamide | δ 7.76 (m, 2H), 7.30 (m, 6H), 7.13 (m, 2H), 6.92 (m, 4H), 6.81 (m, 1H), 4.91 (m, 1H), 4.72 (m, 1H), 4.57 (m, 1H), 4.35 (m, 3H), 3.92 (m, 5H), 4.75 (m, 5H), 3.65 (m, 3H), 3.45 (m, 1H), 3.05 (s, 3H), 2.22 (m, 1H), 1.88 (m, 1H), 1.44 (m, 3H), 1.01 (s, 9H). (CD$_3$OD, 400 MHz) | B | A |
| 130 | (2S,4R)-1-[(2S)-2-[3-(3-[1-[2-(4-[[2-(4-fluorophenyl)-6-hydroxy-1-benzothiophen-3-yl]oxy]phenoxy) ethyl]-1H-pyrazol-3-yl]phenyl) propanamido]-3,3-dimethylbutanoyl]-4-hydroxy-N-[[4-(4-methyl-1,3-thiazol-5-yl)phenyl]methyl] pyrrolidine-2-carboxamide | δ 9.30 (s, 1H), 7.69-7.68 (m, 3H), 7.67-7.64 (d, J = 8.8 Hz, 1H), 7.56-7.54 (d, J = 7.6 Hz, 1H), 7.42-7.41 (m, 4H), 7.29-7.27 (d, J = 7.6 Hz, 1H), 7.15-7.04 (m, 5H), 6.80 (s, 4H), 6.77-6.76 (m, 1H), 6.56 (s, 1H), 4.56-4.49 (m, 6H), 4.35-4.29 (m, 3H), 3.90-3.85 (m, 1H), 3.75-3.70 (m, 1H), 3.00-2.95 (m, 2H), 2.70-2.59 (m, 2H), 2.49 (s, 3H), 2.21-2.11 (m, 1H), 2.06-2.03 (m, 1H), 0.88 (s, 9H). (CD$_3$OD, 400 MHz) | B | A |

TABLE 4-continued

Data for VHL centric benzthiophene derived ER PROTACs

| Ex. # | IUPAC | ¹H-NMR | DC$_{50}$* | D$_{max}$ (%)** |
|---|---|---|---|---|
| 133 | (2S,4R)-1-[(2S)-2-[2-(4-[[6-(4-[[2-(4-fluorophenyl)-6-hydroxy-1-benzothiophen-3-yl]oxy]phenyl)pyridin-3-yl]oxy]butoxy)acetamido]-3,3-dimethylbutanoyl]-4-hydroxy-N-[[4-(4-methyl-1,3-thiazol-5-yl)phenyl]methyl]pyrrolidine-2-carboxamide | δ 8.89 (s, 1H), 8.39 (s, 1H), 8.00 (m, 2H), 7.72-7.78 (m, 4H), 7.36-7.45 (m, 4H), 7.24-7.27 (m, 2H), 7.09-7.14 (m, 4H), 6.83-6.86 (m, 1H), 4.71-7.42 (m, 1H), 4.50-4.59 (m, 3H), 4.26-4.38 (m, 3H), 3.97-4.04 (m, 2H), 3.88 (m, 1H), 3.83 (m, 1H), 3.65-3.68 (m, 2H), 2.44 (s, 3H), 2.28-2.21 (m, 1H), 2.00-2.09 (m, 3H), 1.86-1.90 (m, 2H), 1.04 (s, 9H). (CD$_3$OD, 400 MHz) | B | A |
| 134 | (2S,4R)-1-[(2S)-2-[2-(2-[2-[4-(4-[[2-(4-fluorophenyl)-6-hydroxy-1-benzothiophen-3-yl]oxy]phenyl)-2-oxo-1,2-dihydropyridin-1-yl[ethoxy]ethoxy)acetamido]-3,3-dimethylbutanoyl]-4-hydroxy-N-[[4-(4-methyl-1,3-thiazol-5-yl)phenyl]methyl]pyrrolidine-2-carboxamide | δ 8.81 (s, 1H), 7.76-7.71 (m, 3H), 7.57 (d, J = 8.8 Hz, 2H), 7.42-7.31 (m, 4H), 7.25-7.20 (m, 2H), 7.12-7.08 (m, 2H), 7.02 (d, J = 8.8 Hz, 2H), 6.84-6.81 (m, 1H), 6.67 (m, 1H), 6.62-6.59 (m, 1H), 4.71 (s, 1H) 4.61-4.48 (m, 3H), 4.31-4.16 (m, 3H), 4.07-3.95 (m, 2H), 3.90-3.77 (m, 4H), 3.72-3.58 (m, 4H), 2.42 (s, 3H), 2.28-2.20 (m, 1H), 2.12-2.06 (m, 1H), 1.03 (s, 9H). (CD$_3$OD, 300 MHz) | B | A |
| 135 | (2S,4R)-1-[(2S)-2-[2-(2-[2-[4-(4-[[2-(4-fluorophenyl)-6-hydroxy-1-benzothiophen-3-yl]oxy]phenyl)piperidin-1-yl]ethoxy]ethoxy)acetamido]-3,3-dimethylbutanoyl]-4-hydroxy-N-[[4-(4-methyl-1,3-thiazol-5-yl)phenyl]methyl]pyrrolidine-2-carboxamide | δ 9.88 (s, 1H), 8.96 (s, 1H), 8.59 (m, 1H), 7.68-7.72 (m, 2H), 7.39-7.42 (m, 5H), 7.24-7.31 (m, 3H), 7.12-7.14 (m, 3H), 6.81-6.85 (m, 3H), 5.15-5.16 (m, 1H), 4.55-4.57 (m, 1H), 4.35-4.44 (m, 3H), 4.19-4.27 (m, 1H), 3.97 (s, 2H), 3.65-3.69 (m, 1H), 3.59-3.61 (m, 3H), 3.52-3.56 (m, 4H), 2.92 (d, J = 10.8 Hz, 2H), 2.49 (m, 2H), 2.42 (s, 3H), 2.30-2.38 (m, 1H), 1.86-2.08 (m, 4H), 1.50-1.64 (m, 4H), 0.94 (s, 9H). (DMSO-d6, 400 MHz) | A | A |
| 138 | (2S,4R)-1-((S)-2-tert-butyl-14-(4-(6-hydroxy-2-phenylbenzo[b]thiophen-3-yloxy)phenoxy)-4-oxo-6,9,12-trioxa-3-azatetradecane)-4-hydroxy-N-((S)-1-(4-(4-methyloxazol-5-yl)phenyl)ethyl)pyrrolidine-2-carboxamide | δ 1.02, 1.03 (two singles, 9H), 1.47-1.56 (m, 3H), 1.93-1.99 (m, 1H), 2.16-2.22 (m, 1H), 2.39, 2.40 (two singles, 3H), 3.69-3.76 (m, 9H), 3.80-3.86 (m, 3H), 4.02-4.08 (m, 4H), 4.43 (br,1H), 4.55-4.59 (m, 1H), 4.67-4.69 (m, 1H), 4.96-5.01 (m, 1H), 6.79 (dd, J = 8.4 Hz, 2.0 Hz, 1H), 6.85, 6.86 (two singles, 4H), 7.18-7.26 (m,3H), 7.31-7.35 (m, 2H), 7.40-7.42 (m, 2H),7.59-7.65 (m, 3H), 7.71-7.73 (m, 2H), 8.12, 8.14 (two singles, 1H). (CD$_3$OD, 400 MHz) | A | A |
| 139 | (2S,4R)-1-[(2S)-2-[2-[3-(2-[[2-(4-[[2-(4-fluorophenyl)-6-hydroxy-1-benzothiophen-3-yl]oxy]phenoxy)ethyl](methyl)amino]ethyl)phenoxy]acetamido]-3,3-dimethylbutanoyl]-4-hydroxy-N-[[4-(4-methyl-1,3-thiazol-5-yl)phenyl]methyl]pyrrolidine-2-carboxamide | δ 8.91 (s, 1H) 7.71-7.70 (m, 2H), 7.45-7.41 (m , 4H), 7.30-7.28 (m, 1H), 7.26-7.16 (m , 2H), 7.09-7.05 (m, 2H), 7.00-6.96 (m , 7H), 6.78-6.76 (m, 1H), 4.79-4.76 (m, 1H), 4.64-4.56 (m, 4H), 4.36-429 (m, 3H), 3.92-3.70 (m, 3H), 3.62-3.53 (m, 4H), 3.19-3.01 (m, 5H), 2.45 (s, 3H), 2.26-2.20 (m, 1H), 2.09-2.00 (m, 1H), 10.98 (s, 9H). (CD$_3$OD, 400 MHz) | A | A |
| 140 | (2S,4R)-1-[(2S)-2-[2-(2-[4-[2-(4-[[2-(4-bromophenyl)-6-hydroxy-1-benzothiophen-3-yl]oxy]phenoxy)ethyl]piperazin-1-yl]ethoxy)acetamido]-3,3-dimethylbutanoyl]-4-hydroxy-N-[[4-(4-methyl-1,3-thiazol-5-yl)phenyl]methyl]pyrrolidine-2-carboxamide | δ 8.81 (s, 1H), 7.63-7.61 (d, J = 8.4Hz, 2H) 7.48-7.46 (d, J = 8.4Hz, 2H), 7.44-7.41 (m, 2H), 7.39-7.36 (m, 2H), 7.19-7.18 (m, 2H), 6.83-6.76 (m, 5H), 4.68 (s, 1H), 4.53-4.50 (m, 3H), 4.31-4.30 (m, 1H), 4.04-3.98 (m, 4H), 3.97-3.94 (m, 2H), 3.69-3.67 (m, 2H), 2.74-2.65 (m, 12H), 2.67 (s, 3H), 2.36-2.22 (m, 1H), 2.12-2.01 (m, 1H), 1.00 (m, 9H). (CD$_3$OD, 400 MHz) | B | A |
| 141 | (2S,4R)-1-[(2S)-2-[2-(4-[1-[2-(4-[[2-(4-fluorophenyl)-6-hydroxy-1-benzothiophen-3-yl]oxy]phenoxy)ethyl]-1H-pyrazol-3-yl]phenyl)acetamido]-3,3-dimethylbutanoyl]-4-hydroxy-N-[(1S)-1-[4-(4-methyl-1,3-thiazol-5-yl)phenyl]ethyl]pyrrolidine-2-carboxamide | δ 8.91 (s, 1H), 7.85-7.71 (m, 5H), 7.51-7.39 (m, 4H), 7.34-7.31 (m, 2H), 7.25-7.05 (m, 4H), 6.94-6.78 (m, 5H), 6.65 (s, 1H), 5.28-5.25 (m, 1H), 4.70-50 (m, 4H), 4.50-4.40 (m, 1H), 4.40-4.38 (m, 2H), 3.92-3.82 (m, 1H), 3.80-3.70 (m, 1H), 3.70-3.55 (m, 2H), 2.55 (s, 3H), 2.23-2.21 (m, 1H), 1.95-1.91 (m, 1H), 1.47-1.43 (m, 3H), 1.00 (s, 9H). (CD$_3$OD, 300 MHz) | B | A |

TABLE 4-continued

Data for VHL centric benzthiophene derived ER PROTACs

| Ex. # | IUPAC | ¹H-NMR | DC$_{50}$* | D$_{max}$ (%)** |
|---|---|---|---|---|
| 142 | (2S,4R)-1-(2S)-2-[2-(2-[2-[4-[4-[[2-(4-fluorophenyl)-6-hydroxy-1-benzothiophen-3-yl]oxy]phenyl)piperidin-1-yl]ethoxl]ethoxy)acetamido]-3,3-dimethylbutanoyl]-4-hydroxy-N-[(1S)-1-[4-[4-methyl-1,3-thiazol-5-yl]phenyl]ethyl]pyrrohdine-2-carboxamide | δ 8.87 (s, 1H), 7.72 (m, 3H), 7.40 (m, 4H), 7.15 (m, 6H), 6.92 (m, 1H), 6.79 (m, 1H), 4.97 (m, 1H), 4.72 (m, 1H), 4.55 (m, 1H), 4.30 (m, 1H), 4.09 (m, 2H), 3.89 (m, 2H), 3.74 (m, 7H), 3.45 (m, 3H), 3.18 (m, 2H), 2.89 (m, 1H), 2.45 (s, 3H), 2.22 (m, 1H), 2.11 (m, 2H), 1.95 (m, 3H), 1.45 (m, 3H), 1.05 (s, 9H). (CD$_3$OD, 400 MHz) | A | A |
| 147 | (2S,4R)-N4(1S)-1-(4-cyanophenyl)ethyl]-1-[(2S)-2-[2-(2-[2-[4-(4-[[2-(4-fluorophenyl)-6-hydroxy-1-benzothiophen-3-yl]oxy]phenyl)ppenduci-1-yl]ethoxy]ethoxy)acetamido]-3,3-dimethylbutanoyl]-4-hydroxypyrrolidine-2-carboxamide | δ 7.77 (m, 4H), 7.45 (m, 2H), 7.20 (m, 4H), 7.09 (m, 2H), 6.92 (m, 2H), 6.79 (m, 1H), 4.93 (m, 1H), 4.72 (m, 1H), 4.55 (m, 1H), 4.30 (m, 1H), 4.09 (m, 2H), 3.89 (m, 2H), 3.74 (m, 7H), 3.45 (m, 3H), 3.18 (m, 2H), 2.89 (m, 1H), 2.22 (m, 1H), 2.12 (m, 2H), 1.90 (m, 3H), 1.45 (m, 3H), 1.02 (s, 9H). (CD$_3$OD, 400 MHz) | B | A |
| 149 | (2S,4R)-N-(1S)-1-(4-cyanophenyl)ethyl]-1-[(2S)-2-[2-(4-[-1-[2-(4-[[2-(4-fluorophenyl)-6-hydroxy-1-benzothiophen-3-yl]oxy]phenoxy)ethyl]-1H-pyrazol-3-yl]phenyl)acetamido]-3,3-dimethylbutanoyl]-4-hydroxypyrrolidine-2-carboxamide | δ 7.77-7.70 (m, 7H), 7.70-7.47 (m, 2H), 7.36-7.34 (m, 2H), 7.20-7.06 (m, 4H), 6.83-6.77 (m, 5H), 6.60 (s, 1H), 5.00-4.98 (m, 1H), 4.62-5.52 (m, 4H), 4.50-4.31 (m, 3H), 3.89-3.86 (m, 1H), 3.75-3.32 (m, 3H), 2.18-2.15 (m, 1H), 1.95-1.90 (m, 1H), 1.49-1.47 (m, 3H), 1.00 (s, 9H). (CD$_3$OD, 300 MHz) | B | A |
| 150 | (2S,4R)-N-[(1S)-1-(4-chlorophenyl)ethyl]-1-[(2S)-2-[2-(4-[1-[2-[4-[[2(4-fluorophenyl)-6-hydroxy-1-benzothiophen-3-yl]oxy]phenoxy)ethyl]-1H-pyrazol-3-yl]phenyl)acetamido]-3,3-dimethylbutanoyl]-4-hydroxypyrrolidine-2-carboxamide | δ 7.74-7.71 (m, 5H), 7.38-7.30 (m, 5H), 7.27-7.06 (m, 5H), 6.83-6.80 (m, 5H), 6.60 (s, 1H), 4.95-4.93 (m, 1H), 4.87 (m, 1H), 4.63 (s, 1H), 4.57-4.54 (m, 3H), 4.50-4.42 (m, 1H), 4.35-4.31 (m, 2H), 3.89-3.85 (m, 1H), 3.76-3.75 (m, 1H), 3.65-3.56 (m, 2H), 2.21-2.11 (m, 1H), 1.94-1.91 (m, 1H), 1.47-1.43 (m, 3H), 0.99 (s, 9H). (CD$_3$OD, 300 MHz) | C | A |
| 151 | (2S,4R)-1-[(2S)-2-[2-(2-[4-[2-(4-[[2-(4-chlorophenyl)-6-hydroxy-1-benzothiophen-3-yl]oxy]phenoxy)ethyl]piperazin-1-yl]ethoxy)acetamido]-3,3-dimethylbutanoyl]-4-hydroxy-N-[[4-(4-methyl-1,3-thiazol-5-yl)phenyl]methyl]pyrrolidine-2-carboxamide | δ 8.818 (s, 1H) 7.69-7.66 (m, 2H), 7.50-7.30 (m, 6H), 7.18-7.14 (m, 2H), 6.83-6.75 (m, 5H), 4.79 (s, 1H), 4.67-4.48 (m, 4H), 4.31-4.26 (m, 1H), 4.08-3.98 (m, 4H), 3.93-3.80 (m, 2H), 3.79-3.75 (m, 2H), 2.90-2.61 (m, 11H), 2.43 (s, 3H), 2.19-2.11 (m, 1H), 2.10-2.06 (m, 1H), 1.01 (s, 9H). (CD$_3$OD, 300 MHz) | A | A |
| 153 | (2S,4R)-1-[(2S)-2-[2-(2-[4-[2-(4[[2-(4-bromophenyl)-6-hydroxy-1-benzothiophen-3-yl]oxy]phenoxy)ethyl]piperazin-1-yl]ethoxy)acetamido]-3,3-dimethylbutanoyl]-4-hydroxy-N-[(1S)-1-[4-(4-methyl-1,3-thiazol-5-yl)phenyl]ethyl]pyrrolidine-2-carboxamide | δ 8.90-8.80 (s, 1H), 7.64-7.61 (m, 2H), 7.49-7.46 (m 2H), 7.43-7.36 (m, 4H), 7.19-7.17 (m, 2H), 6.86-6.83 (m, 4H), 6.79-6.76 (m, 1H), 4.99-4.97 (m, 1H), 4.67 (s, 1H), 4.60-4.52 (m, 1H), 4.40 (m, 1H), 4.12-4.05 (m, 4H), 3.90-3.75 (m, 4H), 3.10-2.85 (m, 11H), 2.46-2.45 (s, 3H), 2.25-2.15 (m, 1H), 2.00-1.95 (m, 1H), 1.75-1.65 (m, 1H), 1.50 (s, 3H), 1.39-1.26 (m, 3H), 1.01 (s, 9H). (CD$_3$OD, 400 MHz) | B | A |
| 158 | (2S,4R)-1-[(2S)-2-[2-(4-[2-[2-(4-[[2-(4-bromophenyl)-6-hydroxy-1-benzothiophen-3-yl]oxy]phenoxy)ethoxy]ethyl]piperazin-1-yl)acetamido]-3,3-dimethylbutanoyl]-4-hydroxy-N-[[4-(4-methyl-1,3-thiazol-5-yl)phenyl]methyl]pyrrolidine-2-carboxamide | δ 8.862 (s, 1H), 8.323 (s, 1H), 7.64-7.60 (m, 2H), 7.49-7.37 (m, 5H), 7.18-7.15 (m, 2H), 6.83-6.75 (m, 5H), 4.63-4.31 (m, 5H), 4.08-4.05 (m, 2H), 3.85-3.78 (m, 5H), 3.18-3.07 (m, 7H), 2.71-2.62 (m, 3H), 2.45-2.40 (m, 3H), 2.29-2.03 (m, 2H), 1.28-1.27 (m, 1H), 1.01-0.99 (m, 9H). (CD$_3$OD, 300 MHz) | C | A |
| 160 | (2S,4R)-1-[(2S)-2-[2-(4-[3-[2-(4-[[2-(4-bromophenyl)-6-hydroxy-1-benzothiophen-3-yl]oxy]phenoxy)ethoxy]azetidin-1-yl]piperidin-1-yl]acetamido]-3,3-dimethylbutanoyl]-4-hydroxy-N-[[4-(4-methyl-1,3-thiazol-5-yl)phenyl]methyl] pyrrolidine-2-carboxamide | δ 8.87 (d, J = 8.3 Hz, 1H), 7.69-7.59 (m, 2H), 7.54-7.37 (m, 6H), 7.24-7.14 (m, 2H), 6.90-6.74 (m, 5H), 4.65-4.46 (m, 4H), 4.36 (d, J = 15.3 Hz, 1H), 4.25 (s, 1H), 4.03 (d, J = 4.7 Hz, 2H), 3.95-3.70 (m, 6H), 3.65-3.54 (m, 1H), 3.06 (s, 3H), 2.89 (m, 2H), 2.47 (m, 3H), 2.23 (t, J = 11.1 Hz, 2H), 2.20-2.08 (m,1H), 1.83 (m, 2H), 1.30 (m, 4H), 1.02 (d, J = 8.9 Hz, 9H), 0.10 (m, 2H). (CD$_3$OD, 300 MHz) | B | A |

TABLE 4-continued

Data for VHL centric benzthiophene derived ER PROTACs

| Ex. # | IUPAC | $^1$H-NMR | DC$_{50}$* | D$_{max}$ (%)** |
|---|---|---|---|---|
| 164 | (2S,4R)-1-[(2S)-2-[3-[2-[4-[2-[4-[2-(4-bromophenyl)-6-hydroxy-benzothiophen-3-yl]oxyphenoxy]ethyl]piperazin-1-yl]ethoxy]isoxazol-5-yl]-3-methyl-butanoyl]-4-hydroxy-N-[[4-(4-methylthiazol-5-yl)phenyl]methyl]pyrrolidine-2-carboxamide | δ 8.89 (s, 1H), 7.64 (d, J = 8.8 Hz, 2H), 7.51-7.48 (m, 6H), 7.22-7.19 (m, 2H), 6.92-6.79 (m, 5H), 6.05 (s, 1H), 4.60-4.42 (m, 6H), 3.90-3.68 (m, 5H), 3.20-2.74 (m, 12H), 2.49 (s, 3H), 2.48-2.45 (m, 1H), 2.38 2.35 (m, 1H), 2.10-2.08 (m, 1H), 1.05 (d, J = 7.2 Hz, 3H), 0.90 (d, J = 7.2 Hz, 3H). (CD$_3$OD, 400 MHz) | B | B |

\* and ** ER-alpha degradation measured in MCF7 cells western blot assay following 3 days of incubation \* DC50: A <1 nM; B 1 to 10 nM; C 10-100 nM

**Dmax: A >75%; B 50% to 75%; C <50%

TABLE 5

Data for cereblon centric benzthiophene derived ER PROTACs

| Ex. | IUPAC Name | H-NMR | DC$_{50}$ (nM)* | D$_{max}$ (%)** |
|---|---|---|---|---|
| 33 | 3-[5-[2-[2-[4-[2-(4-bromophenyl)-6-hydroxy-benzothiophen-3-yl]oxyphenoxy]ethoxy]ethoxy]-1-oxo-isoindolin-2-yl]piperidine-2,6-dione | δ 10.95 (s, 1H), 9.92 (s, 1H), 7.65 - 7.60 (m, 5H), 7.31 (d, J = 2.0 Hz, 1H), 7.17-7.14 (m, 2H), 7.07 (dd, J = 8.8, 2.0 Hz, 1H), 6.88 (s, 4H), 6.83 (dd, J = 8.8, 2.0 Hz, 1H), 5.07 (dd, J = 13.2, 5.2 Hz, 1H), 4.41-4.36 (m, 1H), 4.29-4.24 (m, 1H), 4.21-4.19 (m, 2H), 4.05-4.03 (m, 2H), 3.81 (m, 4H), 2.95-2.86 (m, 1H), 2.56-2.53 (m, 1H), 2.37-2.36 (m, 1H), 1.97-1.94 (m, 1H). (400 MHz, DMSO-d6) | B | B |
| 52 | 3-(6-(4-(5-(4-(2-(4-bromophenyl)-6-hydroxybenzo[b]thiophen-3-yloxy)phenoxy)pentyl)piperazin-1-yl)-1-oxoisoindolin-2-yl)piperidine-2,6-dione | δ 1.39-1.44 (2H, m), 1.46-1.52 (2H, m), 1.66-1.71 (2H, m), 1.93-1.99 (1H, m), 2.28-2.33 (4H, m), 2.54-2.56 (2H, m), 2.61-2.67 (1H, m), 2.87-2.93 (1H, m), 3.22-3.32 (5H, m), 3.88 (2H, t, J = 6.4 Hz), 4.18-4.34 (2H, m), 5.04 (1H, dd, J = 4.8, 13.2 Hz), 6.82 (1H, dd, J =2.0, 8.4 Hz), 6.86 (4H, s), 7.03-7.06 (2H, m), 7.14 (1H, d, J = 8.8 Hz), 7.30 (1H, d, J = 2.0 Hz), 7.51 (1H, d, J = 8.8 Hz), 7.62 (4H, s), 9.92 (1H, s), 10.94 (1H, s). (400 MHz, DMSO-d6) | C | B |
| 57 | 1-(2-(4-(2-(4-bromophenyl)-6-hydroxybenzo[b]thiophen-3-yloxy)phenoxy)ethyl)-N-((2-(2,6-dioxopiperidin-3-yl)-1-oxoisoindolin-5-yl)methyl)piperidine-4-carboxamide | δ 1.57-1.69 (4H, m), 1.97-2.02 (3H, m), 2.12-2.16 (1H, m), 2.36-2.04 (1H, m), 2.57-2.64 (3H, m), 2.88-2.94 (3H, m), 3.97 (2H, t, J = 5.6 Hz), 4.27-4.45 (4H, m), 5.10 (1H, dd, J = 13.2, 5.2 Hz), 6.81-6.84 (1H, m), 6.87 (4H, s), 7.15 (1H, d, B J = 8.8 Hz), 7.30 (1H, d, J = 2.0 Hz), 7.36 (1H, d, J = 7.6 Hz), 7.43 (1H, s), 7.62 (4H, s), 7.67 (1H, d, J = 8.0 Hz), 8.38 (1H, t, J = 6.0 Hz), 9.93 (1H, s), 10.97 (1H, s). (400 MHz, DMSO-d6) | B | B |
| 61 | 5-(4-(5-(4-(2-(4-bromophenyl)-6-hydroxybenzo[b]thiophen-3-yloxy)phenoxy)pentyl)piperazin-1-yl)-2-(2,6-dioxopiperidin-3-yl)isoindoline-1,3-dione | δ 1.40-1.54 (4H, m), 1.66-1.73 (2H, m), 1.99-2.02 (1H, m), 2.31 (2H, t, J = 7.4 Hz), 2.47-2.51 (5H, m), 2.53-2.60 (1H, m), 2.83-2.93 (1H, m), 3.36-3.41 (4H, m), 3.88 (2H, t, J = 6.2 Hz), 5.07 (1H, dd, J = 5.2, 12.8 Hz), 6.82 (1H, dd, J = 2.0, 8.4 Hz), 6.86 (4 H, s), 7.15 (1H, d, J = 8.8 Hz), 7.24 (1H, dd, J = 2.0, 8.4 Hz), 7.32 (2H, dd, J = 1.6, 9.6 Hz), 7.62 (4H, s), 7.67 (1H, d, J = 8.8 Hz), 9.92 (1H, s), 11.08 (1H, s). (400 MHz, DMSO-d6) | C | B |
| 74 | 3-(5-(3-(4-(2-(4-(2-(4-bromophenyl)-6-hydroxybenzo[b]thiophen-3-yloxy)phenoxy)ethyl)-1,4-diazepan-1-yl)propylamino)-1-oxoisoindolin-2-yl)piperidine-2,6-dione | δ 1.40-1.50 (2H, m), 1.65-1.78 (2H, m), 1.90-2.03 (1H, m), 2.59-2.94 (12H, m), 3.07-3.12 (2H, m), 3.30-3.33 (2H, m), 3.90-4.02 (2H, m), 4.09-4.28 (2H, m), 4.99-5.03 (1H, m), 5.32 (1H, t, J = 4.6 Hz), 6.41 (1H, t, J = 5.4 Hz), 6.62-6.66 (2H, m), 6.81-6.87 (5H, m), 7.15 (1H, d, J = 8.8 Hz), 7.30 (1H, d, J = 2.0 Hz), 7.38 (1H, d, J = 8.4 Hz), 7.60-7.464 (4H, m), 9.93 (1H, s), 10.92 (1H, s). (400 MHz, DMSO-d6) | B | A |

TABLE 5-continued

Data for cereblon centric benzthiophene derived ER PROTACs

| Ex. | IUPAC Name | H-NMR | $DC_{50}$ (nM)* | $D_{max}$ (%)** |
|---|---|---|---|---|
| 89 | 3-[5-[3-[3-[2-[4-[2-(4-bromophenyl)-6-hydroxy-benzothiophen-3-yl]oxyphenoxy]ethoxy]propoxy]propylamino]-1-oxo-isoindolin-2-yl]piperidine-2,6-dione | δ 10.93 (s, 1H), 9.93 (s, 1H), 7.64-7.59 (m, 4H), 7.37 (d, J = 8.4 Hz, 1H), 7.30 (d, J = 2.0 Hz, 1H), 7.14 (d, J = 8.8 Hz, 1H), 6.86 (s, 4H), 6.82 (dd, J = 2.0, 8.4 Hz, 1H), 6.66-6.59 (m, 2H), 6.35 (t, J = 5.2 Hz, 1H), 5.01 (dd, J = 5.2, 13.2 Hz, 1H), 4.29-4.22 (m, 1H), 4.16-4.09 (m, 1H), 4.01-3.95 (m, 2H), 3.68-3.61 (m, 2H), 3.48 (t, J = 6.4 Hz, 2H), 3.43-3.38 (m, 4H), 3.16-3.06 (m, 2H), 2.95-2.82 (m, 1H), 2.52 (s, 1H), 2.34-2.23 (m, 1H), 1.96-1.88 (m, 1H), 1.81-1.68 (m, 4H). (400 MHz, DMSO-d6) | B | B |
| 94 | 3-[5-[3-[3-[3-[4-[2-(4-bromophenyl)-6-hydroxy-benzothiophen-3-yl]oxyphenoxy]propoxy]propoxy]propylamino]-1-oxo-isoindolin-2-yl]piperidine-2,6-dione | δ 10.94 (s, 1H), 10.01 (s, 1H), 7.68-7.57 (m, 4H), 7.38 (d, J = 8.4, 1H), 7.31 (d, J = 2.0 Hz, 1H), 7.15 (d, J = 8.8 Hz, 1H), 6.91-6.79 (m, 5H), 6.68-6.58 (m, 2H), 6.35 (t, J = 5.6 Hz, 1H), 5.02 (m, 1H), 4.31-4.07 (m, 2H), 3.92 (t, J = 6.0 Hz, 2H), 3.47 (t, J = 6.0 Hz, 2H), 3.44-3.39 (m, 6H), 3.11 (m, 2H), 2.97-2.81 (m, 1H), 2.59 (m, 2H), 2.37-2.29 (m, 1H), 1.91-1.86 (m, 2H), 1.74 (m, 4H). (400 MHz, DMSO-d6) | B | B |
| 95 | 3-[5-[3-[2-[2-[4[2-(4-bromophenyl)-6-hydroxy-benzothiophen-3-yl]oxyphenoxy]ethoxy]ethoxy]propylamino]-1-oxo-isoindolin-2-yl]piperidine-2,6-dione | δ 10.91 (s, 1H), 9.99 (s, 1H), 7.59 (s, 4H), 7.35 (d, J = 8.4 Hz, 1H), 7.28 (d, 2.0 Hz, 1H), 7.12 (d, 8.8 Hz, 1H), 6.64-6.58 (m, 2H), 6.33 (t, J = 5.2 Hz, 1H), 4.99 (dd, J = 5.2, 13.2 Hz, 1H), 4.26-4.20 (m, 1H), 4.14-4.08 (m, 1H), 4.00-3.95 (m, 2H), 3.71-3.66 (m, 2H), 3.58-3.53 (m, 2H), 3.50-3.44 (m, 4H), 2.92-2.81 (m, 1H), 1.93-1.86 (m, 1H), 1.79-1.71 (m, 2H). (400 MHz, CDCl3) | | C |
| 174 | 3-[5-[3-[4-[2-[4-[2-(4-fluorophenyl)-6-hydroxy-benzothiophen-3-yl]oxyphenoxy]ethyl]piperazin-1-yl]propylamino]-1-oxo-isoindolin-2-yl]piperidine-2,6-dione | δ 10.93 (s, 1H), 8.20 (s, 1H), 7.72-7.68 (m, 2H), 7.37 (d, J = 8.4 Hz, 1H), 7.30-7.24 (m, 3H), 7.13 (d, J = 8.8 Hz, 1H), 6.86 (s, 4H), 6.82 (dd, J = 2.0, 8.8 Hz, 1H), 6.65-6.13 (m, 2H), 6.40 (hr s, 1H), 5.01 (dd, J = 5.2, 13.2 Hz, 1H), 4.28-4.24 (m, 1H), 4.15-4.11 (m, 1H), 3.97 (t, J = 5.6 Hz, 4H), 3.09 (t, J = 6.0 Hz, 2H), 2.94-2.84 (m, 2H), 2.67-2.63 (m, 3H), 2.52-2.50 (m, 5H), 2.37-2.29 (m, 5H), 1.94-1.92 (m, 1H), 1.72-1.67 (m, 1H). (400 MHz, DMSO-d6) | A | A |
| 177 | 5-[3-[4-[2-[4-[2-(4-bromophenyl)-6-hydroxy-benzothiophen-3-yl]oxyphenoxy]ethyl]piperazin-1-yl]propylamino]-2-(2,6-dioxo-3-piperidyl)isoindoline-1,3-dione | δ 11.07 (s, 1H), 8.29 (s, 2H), 7.62 (s, 4H), 7.55 (d, J 1H), 7.17-7.12 (m, 2H), 6.95 (d, J 1H), 6.88-6.81 (m, 6H), 5.03 (dd, J = 5.6, 12.8 Hz, 1H), 3.98 (t, J = 5.6 Hz, 2H), 3.23-3.14 (m, 2H), 2.92-2.82 (m, 1H), 2.59 (d, J 5H), 2.41-2.30 (m, 4H), 2.03-1.95 (m, 1H), 1.70 (t, J = 6.8 Hz, 2H) (400 MHz, DMSO-d6) | B | A |
| 178 | 5-[3-[4-[2-[4-[2-(4-bromophenyl)-6-hydroxy-benzothiophen-3-yl]oxyphenoxy]ethyl]-1,4-diazepan-1-yl]propylamino]-2-(2,6-dioxo-3-piperidyl)isoindoline-1,3-dione | δ 11.07 (s, 1H), 8.31 (s, 2H), 7.66-7.58 (m, 4H), 7.55 (d, J = 8.4 Hz, 1H), 7.30 (d, J = 2.0 Hz, 1H), 7.20-7.12 (m, 2H), 6.94 (d, J = 1.6 Hz, 1H), 6.88-6.80 (m, 6H), 5.02 (dd, J = 5.2, 12.8 Hz, 1H), 3.95 (t, J = 5.6 Hz, 2H), 3.22-3.14 (m, 2 Hz), 2.93-2.77 (m, 4H), 2.75-2.69 (m, 4H), 2.65-2.57 (m, 5H), 2.52 (s, 2H), 1.99 (td, J = 4.4, 6.8 Hz, 1H), 1.73-1.63 (m, 4H). (400 MHz, DMSO-d6) | B | A |
| 179 | 3-[5-[3-[4-[2-[4-[6-hydroxy-2-[4-(trifluoromethyl)phenyl]benzothiophen-3-yl]oxyphenoxy]ethyl]piperazin-1-yl]propylamino]-1-oxo-isoindolin-2-yl]piperidine-2,6-dione | δ 10.94 (s, 1H), 10.01 (s, 1H), 7.89 (d, J = 8.4 Hz, 2H), 7.80 (d, J = 8.4 Hz, 2H), 7.38-7.34 (m, 2H), 7.17 (d, J = 8.4 Hz, 1H), 6.88 (m, 4H), 6.84 (dd, J = 2.0, 8.8 Hz, 1H), 6.65-6.61 (m, 2H), 6.41 (t, J = 4.8 Hz, 1H), 5.01 (dd, J = 5.1, 13.4 Hz, 1H), 4.28-4.24 (m, 1H), 4.15-4.11 (m, 1H), 3.98 (t, J = 5.6 Hz, 2H), 3.33-3.32 (m, 2H), 3.11-3.08 (m, 2H), 2.94-2.85 (m, 1H), 2.67-2.57 (m, 4H), 2.54-2.52 (m, 4H), 2.42-2.23 (m, 4H), 1.94-1.91 (m, 1H), 1.75-1.61 (m, 2H). (400 MHz, DMSO-d6) | B | B |

TABLE 5-continued

Data for cereblon centric benzthiophene derived ER PROTACs

| Ex. | IUPAC Name | H-NMR | $DC_{50}$ (nM)* | $D_{max}$ (%)** |
|---|---|---|---|---|
| 180 | 3-[5-[3-[4-[2-[4-[6-hydroxy-2-(4-methoxyphenyl)benzothiophen-3-yl]oxyphenoxy]ethyl]piperazin-1-yl]propylamino]-1-oxo-isoindolin-2-yl]piperidine-2,6-dione | δ 10.94 (s, 1H), 8.17 (s, 1H), 7.65-7.57 (m, 2H), 7.38 (d, J = 8.4 Hz, 1H), 7.28 (d, J = 2.0 Hz, 1H), 7.11 (d, J = 8.8 Hz, 1H), 7.02-6.95 (m, 2H), 6.89-6.83 (m, 4H), 6.81 (dd, J = 2.1, 8.8 Hz, 1H), 6.69-6.59 (m, 2H), 6.54-6.32 (m, 1H), 5.02 (dd, J = 5.0, 13.2 Hz, 1H), 4.32-4.11 (m, 2H), 4.04-3.92 (m, 3H), 3.75 (s, 3H), 3.10 (t, J = 6.0 Hz, 2H), 2.97-2.83 (m, 1H), 2.70-2.56 (m, 4H), 2.47-2.24 (m, 9H), 1.97-1.91 (m, 1H), 1.70 (t, J = 6.8 Hz, 2H). (400 MHz, DMSO-d6) | A | A |
| 181 | 3-[5-[3-[4-[2-[4-2-(4-hydroxyphenyl)-6-methoxy-benzothiophen-3-yl]oxyphenoxy]ethyl]piperazin-1-yl]propylamino]-1-oxo-isoindolin-2-yl]piperidine-2,6-dione | δ 10.94 (s, 1H), 8.28 (s, 2H), 7.58-7.49 (m, 3H), 7.38 (d, J = 8.4 Hz, 1H), 7.16 (d, J = 8.8 Hz, 1H), 6.93 (dd, J = 2.3, 8.8 Hz, 1H), 6.89-6.83 (m, 4H), 6.80 (d, J = 8.8 Hz, 2H), 6.67-6.60 (m, 2H), 6.41 (s, 1H), 5.01 (dd, J = 5.0, 13.2 Hz, 1H), 4.32-4.07 (m, 2H), 4.02-3.92 (m, 3H), 3.82 (s, 3H), 3.10 (s, 2H), 2.95-2.83 (m, 1H), 2.71-2.53 (m, 4H), 2.45-2.24 (m, 9H), 1.97-1.90 (m, 1H), 1.75-1.60 (m, 2H). (400 MHz, DMSO-d6) | B | B |
| 182 | (3S)-3-[5-[2-[4-[4-[2-(4-bromophenyl)-6-hydroxy-benzothiophen-3-yl]oxyphenoxy]butyl]-1,4-diazepan-1-yl]ethyl]-1-oxo-isoindolin-2-yl]piperidine-2,6-dione | δ 11.57-11.19 (m, 1H), 11.18-10.87 (m, 2H), 9.97 (s, 1H), 7.71 (d, J = 7.6 Hz, 1H), 7.64-7.62 (m, 4H), 7.54 (s, 1H), 7.45 (d, J = 8.0 Hz, 1H), 7.32 (d, J = 2.0 Hz, 1H), 7.15 (d, J = 8.8 Hz, 1H), 6.92-6.79 (m, 5H), 5.12 (dd, J = 4.8, 12.8 Hz, 1H), 4.48-4.40 (m, 1H), 4.36-4.27 (m, 1H), 3.92 (t, J = 5.6 Hz, 2H), 3.49 (m, 2H), 3.49-3.40 (m, 3H), 3.18 (s, 4H), 2.98-2.84 (m, 1H), 2.65-2.56 (m, 1H), 2.56-2.53 (m, 1H), 2.41-2.34 (m, 1H), 2.30-2.16 (m, 2H), 2.04-1.93 (m, 1H), 1.83 (s, 2H), 1.76-1.67 (m, 2H). (400 MHz, DMSO-d6) | B | A |
| 183 | 5-[4-[1-[2-[4-[2-(4-bromophenyl)-6-hydroxy-benzothiophen-3-yl]oxyphenoxy]ethyl]-4-piperidyl]piperazin-1-yl]-2-(2,6-dioxo-3-piperidyl)isoindoline-1,3-dione | δ 11.69 (s, 1H), 11.10 (s, 1H), 10.79 (s, 1H), 10.02 (s, 1H), 7.76 (d, J = 7.6 Hz, 1H), 7.62 (s, 4H), 7.48 (s, 1H), 7.33 (s, 2H), 7.15 (d, J = 8.8 Hz, 1H), 7.01 6.78 (m, 5H), 5.09 (d, J = 7.6 Hz, 1H), 4.43-4.07 (m, 4H), 3.79-3.44 (m, 3H), 3.33-3.30 (m, 7H), 3.20-2.99 (m, 4H), 2.89 (s, 2H), 2.67 (s, 1H), 2.35 (d, J = 16.4 Hz, 2H), 2.25-1.92 (m, 2H). (400 MHz, DMSO-d6) | C | B |
| 184 | 5-[4-[1-[2-[4-[2-(4-bromophenyl)-6-hydroxy-benzothiophen-3-yl]oxyphenoxy]ethyl]-4-piperidylmethyl]piperazin-1-yl]-2-(2,6-dioxo-3-piperidyl)isoindoline-1,3-dione | δ 11.10 (s, 1H), 11.06-10.80 (m, 1H), 10.7-10.3 (m, 1H), 9.99 (s, 1H), 7.76 (d, J 1H), 7.62 (s, 4H), 7.49 (s, 1H), 7.39-7.30 (m, 2H), 7.15 (d, J = 8.8 Hz, 1H), 6.99-6.88 (m, 4H), 6.84 (dd, J = 2.0, 8.8 Hz, 1H), 5.09 (dd, J = 5.2, 12.8 Hz, 1H), 4.33 (s, 2H), 4.19 (d, J = 14.0 Hz, 2H), 3.68-3.49 (m, 6H), 3.44 (s, 2H), 3.27-2.97 (m, 6H), 2.95-2.81 (m, 1H), 2.63-2.52 (m, 2H), 2.22-1.94 (m, 4H), 1.70-1.47 (m, 2H). (400 MHz, DMSO-d6) | C | A |
| 185 | 5-[4-[[1-[2-[4-[2-(4-bromophenyl)-6-hydroxy-benzothiophen-3-yl]oxyphenoxy]ethyl]azetidin-3-yl]methyl]piperazin-1-yl]-2-(2,6-dioxo-3-piperidyl)isoindoline-1,3-dione | δ 11.08 (s, 1H), 8.21 (s, 1H), 7.67 (d, J 1H), 7.62 (s, 4H), 7.35-7.29 (m, 2H), 7.24 (dd, J = 2.4, 8.8 Hz, 1H), 7.14 (d, J = 8.8 Hz, 1H), 6.90-6.79 (m, 5H), 5.07 (dd, J = 5.6, 12.8 Hz, 1H), 3.83 (t, J = 5.2 Hz, 2H), 3.44-3.38 (m, 7H), 2.94-2.82 (m, 3H), 2.75-2.69 (m, 2H), 2.65-2.55 (m, 4H), 2.46-2.41 (m, 4H), 2.07-1.96 (m, 1H). (400 MHz, DMSO-d6) | B | B |
| 190 | 5-(1'-(2-(4-((2-(4-bromophenyl)-6-hydroxybenzo[b]thiophen-3-yl)oxy)phenoxy)ethyl)-[1,4'-bipiperidin]-4-yl)-2-(2,6-dioxopiperidin-3-yl)isoindoline-1,3-dione Hydrochloride | δ 11.32-11.15 (m, 1H), 11.14 (s, 1H), 10.70 (br s, 1H), 9.99 (hr s, 1H), 7.97-7.91 (m, 1H), 7.81-7.72 (m, 2H), 7.70-7.61 (m, 4H), 7.36-7.33 (m, 1H), 7.20-7.13 (m, 1H), 7.02-6.91 (m, 4H), 6.88-6.82 (m, 1H), 5.22-5.10 (m, 1H), 4.42-4.26 (m, 2H), 3.81-3.42 (m, 9H), 3.21-3.04 (m, 4H), 2.99-2.84 (m, 1H), 2.70-2.56 (m, 2H), 2.43-1.99 (m, 8H). (400 MHz, DMSO-d6) | B | B |

TABLE 5-continued

Data for cereblon centric benzthiophene derived ER PROTACs

| Ex. | IUPAC Name | H-NMR | DC$_{50}$ (nM)* | D$_{max}$ (%)** |
|---|---|---|---|---|
| 191 | 5-(3-((4-(2-(4-((2-(4-bromophenyl)-6-hydroxybenzo[b]thiophen-3-yl)oxy)phenoxy)ethyl)-1,4-diazepan-1-yl)methyl)azetidin-1-yl)-2-(2,6-dioxopiperidin-3-yl)isoindoline-1,3-dione | δ 11.09 (s, 3H), 10.13-9.79 (m, 1H), 7.72-7.66 (m, 1H), 7.63 (s, 3H), 7.48 (d, J = 8.1 Hz, 1H), 7.33 (d, J = 2.1 Hz, 1H), 7.18-7.14 (m, 1H), 7.13-7.09 (m, 1H), 6.98-6.92 (m, 3H), 6.87-6.82 (m, 1H), 6.81-6.77 (m, 1H), 6.68-6.63 (m, 1H), 5.08 (hr d, J = 12.8 Hz, 1H), 4.41-4.26 (m, 2H), 4.26-4.14 (m, 2H), 3.86 (hr s, 3H), 3.67-3.48 (m, 6H), 3.33-3.09 (m, 1H), 3.33-3.09 (m, 2H), 2.97-2.81 (m, 1H), 2.63-2.53 (m, 5H), 2.29 (s, 3H), 2.06-1.95 (m, 1H). (400 MHz, DMSO-d6) | B | B |
| 192 | 3-[5-[4-[1-[2-[4-[6-hydroxy-2-[4-(trifluoromethyl)phenyl]benzothiophen-3-yl]oxyphenoxy]ethyl]-4-piperidyl]piperazin-1-yl]-1-oxo-isoindolin-2-yl]piperidine-2,6-dione | δ 10.95 (s, 1H), 10.02 (s, 1H), 8.15 (s, 1H), 7.90 (d, J = 8.4 Hz, 2H), 7.78 (d, J = 8.4 Hz, 2H), 7.51 (d, J = 8.8 Hz, 1H), 7.34 (d, J = 2.0 Hz, 1H), 7.18 (d, J = Hz, 1H), 7.10-7.01 (m, 2H), 6.95-6.81 (m, 5H), 5.04 (dd, J = 5.2, 13.2 Hz, 1H), 4.39-4.13 (m, 2H), 4.00 (t, J = 5.6 Hz, 2H), 3.26 (s, 5H) 3.05-2.84 (m, 3H), 2.72 (s, 2H), 2.62 (s, 4H), 2.43-2.35 (m, 1H), 2.24 (s, 1H), 2.17-2.03 (m, 2H), 2.00-190 (m, 1H), 1.77 (d, J = 11.6 Hz, 2H), 1.52-1.37 (m-2H). (400 MHz, DMSO-d6) | C | A |
| 193 | 3-[4-fluoro-5-[4-[1-[2-[4-[6-hydroxy-2-[4-(trifluoromethyl)phenyl]benzothiophen-3-yl]oxyphenoxy]ethyl]-4-piperidyl]piperazin-1-yl]-1-oxo-isoindolin-2-yl]piperidine-2,6-dione | δ 10.99 (s, 1H), 8.19 (s, 1H), 7.90 (d, J = 8.4 Hz, 2H), 7.78 (d, J = 8.4 Hz, 2H), 7.47 (d, J = 8.4 Hz, 1H), 7.34 (d, J = 2.0 Hz, 1H), 7.19-7.12 (m, 2H), 6.89 (s, 4H), 6.85 (dd, J = 2.0, 8.8 Hz, 1H), 5.07 (dd, J = 5.1, 13.4 Hz, 1H), 5.50-4.46 (m, 1H), 4.33-4.28 (m, 2H), 3.98 (t, J = 5.6 Hz, 2H), 3.18-3.11 (m, 4H), 2.97-2.87 (m, 3H), 2.67-2.60 (m, 6H), 2.4-2.39 (m, 2H), 2.23- 2.18 (m, 1H), 2.04-1.95 (m, 3H), 1.76-1.73 (m, 2H), 1.46-1.38 (m, 2H). (400 MHz, DMSO-d6) | B | A |
| 194 | 3-[5-[4-[1-[2-[4-[2-(4-bromophenyl)-6-hydroxybenzothiophen-3-yl]oxyphenoxy]ethyl]-4-piperidyl]piperazin-1-yl]-1-oxo-isoindolin-2-yl]piperidine-2,6-dione | δ 10.95 (s, 1H), 8.18 (s, 2H), 7.62 (s, 4H), 7.51 (d, J = 8.8 Hz, 1H), 7.31 (d, J = 2.0 Hz, 1H), 7.15 (d, J = 8.8 Hz, 1H), 7.11-7.00 (m, 2H), 6.92-6.79 (m, 5H), 5.04 (dd, J = 5.2, 13.6 Hz, 1H), 4.37-4.14 (m, 2H), 3.97 (t, J = 5.6 Hz, 2H), 3.26 (s, 5H), 3.00-2.85 (m, 3H), 2.65-2.57 (m, 6H), 2.43-2.34 (m, 1H), 2.20 (s, 1H), 2.08-1.91 (m, 3H), 1.75 (d, J = 10.8 Hz, 2H), 1.41 (q, J = 10.8 Hz, 2H). (400 MHz, DMSO-d6) | B | A |
| 199 | 3-[5-[4-[4-[2-[4-[2-(4-bromophenyl)-6-hydroxybenzothiophen-3-yl]oxyphenoxy]ethyl]-1,4-diazepan-1-yl]butyl]-1-oxo-isoindolin-2-yl]piperidine-2,6-dione | δ 10.98 (s, 1H), 8.20 (s, 1H), 7.72-7.57 (m, 5H), 7.42 (s, 1H), 7.37-7.30 (m, 2H), 7.15 (d, J = 8.8 Hz, 1H), 6.87 (s, 4H), 6.83 (dd, J = 2.1, 8.8 Hz, 1H), 5.10 (dd, J = 5.0, 13.2 Hz, 1H), 4.46-4.38 (m, 1H), 4.33-4.24 (m, 1H), 3.96 (m, 2H), 2.97-2.80 (m, 4H), 2.75-2.67 (m, 9H), 2.58 (s, 2H), 2.45-2.33 (m, 2H), 2.03-1.96 (m, 1H), 1.78-1.69 (m, 2H), 1.64-1.55 (m, 2H), 1.51-1.41 (m, 2H). (400 MHz, DMSO) | B | B |
| 201 | 3-[4-fluoro-5-[4-[[1-[2-[4-[6-hydroxy-2-[4-(trifluoromethyl)phenyl]benzothiophen-3-yl]oxyphenoxy]ethyl]-4-piperidyl]methyl]piperazin-1-yl]-1-oxo-isoindolin-2-yl]piperidine-2,6-dione | δ 10.99 (s, 1H), 10.05-10.00 (m, 1H), 8.14 (s, 2H), 7.90 (d, J = 8.0 Hz, 2H), 7.78 (d, J = 8.4 Hz, 2H), 7.48 (d, J = 8.0 Hz, 1H), 7.34 (d, J = 2.0 Hz, 1H), 7.19-7.13 (m , 2H), 6.91 (s, 4H), 6.85 (dd, J = 2.0, 8.8 Hz, 1H), 6.58-6.54 (m, 1H), 5.07 (dd, J = 5.2, 13.4 Hz, 1H), 5.50-4.46 (m, 1H), 4.33-4.29 (m, 1H), 4.07-4.02 (m, 2H), 3.21-3.13 (m, 8H), 2.98-2.81 (m, 4H), 2.63-2.52 (m ,2H), 2.46-2.34 (m, 3H), 2.25-2.16 (m, 2H), 1.98-1.94 (m, 1H), 1.76-1.57 (m, 3H), 1.2-1.14 (m, 2H). (400 MHz, DMSO-d6) | C | A |
| 205 | 3-[5-[4-[1-[2-[4-[2-(4-bromophenyl)-6-hydroxybenzothiophen-3-yl]oxyphenoxy]ethyl]-4-piperidyl]piperazin-1-yl]-4,6-difluoro-1-oxo-isoindolin-2-yl]piperidine-2,6-dione | δ 11.00 (s, 1H), 8.19 (s, 1H), 7.64-7.60 (m, 4H), 7.39 (d, J = 10 Hz, 1H), 7.30 (d, J = 2.0Hz, 1H), 7.15 (d, J = 8.4 Hz, 1H), 6.87-6.81 (m, 5H), 5.08 (dd, J = 5.2, 13.4 Hz, 1H), 4.49-4.45 (m, 1H), 4.33-4.28 (m, 1H), 3.98 (t, J = 6.0 Hz, 2H), 3.20-3.18 (m, 4H), 2.98-2.87 (m, 4H), 2.65-2.55 (m, 6H), 2.43-2.39 (m, 1H), 2.25-2.19 (m, 1H), 2.05-1.96 (m, 3H), 1.75-1.71 (m, 2H), 1.48-1.39 (m, 2H). (400 MHz, DMSO-d6) | C | A |

TABLE 5-continued

Data for cereblon centric benzthiophene derived ER PROTACs

| Ex. | IUPAC Name | H-NMR | $DC_{50}$ (nM)* | $D_{max}$ (%)** |
|---|---|---|---|---|
| 213 | 5-[3-[4-[4-[2-(4-bromophenyl)-6-hydroxybenzothiophen-3-yl]oxyphenoxy]-1-pipendyl]azetidin-1-yl]2-(2,6-dioxo-3-piperidyl)isoindoline-1,3-dione | δ 11.07 (s, 1H), 8.32 (s, 1H), 7.67-7.59 (m, 5H), 7.30 (d, J = 2.0 Hz, 1H), 7.16 (d J = 8.8 Hz, 1H), 6.91-6.81 (m, 5H), 6.78 (d, J = 2.0 Hz, 1H), 6.65 (dd, J = 2.0, 8.4 Hz, 1H), 5.05 (dd, J = 5.6, 13.0 Hz, 1H), 4.34-4.24 (m, 1H), 4.10 (t, J = 7.6 Hz, 2H), 3.83 (dd, J = 5.2, 8.8 Hz, 2H), 2.94-2.80 (m, 1H), 2.65-2.54 (m, 2H), 2.56-2.52 (hr s, 3H), 2.23-2.14 (m, 2H), 2.06-1.94 (m, 1H), 1.96-1.94 (m, 1H), 1.64-1.58 (m, 2H). (400 MHz, DMSO-d6) | | C |
| 214 | 5-[4-[[3-[2-[4-bromophenyl)-6-hydroxybenzothiophen-3-yl]oxyphenyl]azetidin-1-yl]methyl]-1-piperidyl]-2-(2,6-dioxo-3-piperidyl)isoindoline-1,3-dione | δ 9.61 (s, 1H), 7.11-7.03 (m, 3H), 6.78-6.69 (m, 3H), 6.62 (d, 1H), 6.53-6.43 (m, 3H), 6.22 (d, 2H), 4.96-4.73 (m, 1H), 4.13 (d, 1H), 3.41 (d, 2H), 3.37-3.23 (m, 1H), 3.04-2.86 (m, 2H), 2.73-2.62 (m, 2H), 2.33-2.21 (m, 1H), 2.17-2.01 (m, 1H), 1.95-1.86 (m, 2H), 1.77-1.62 (m, 3H). (400 MHz, CDCl₃) | B | B |
| 215 | 3-[5-[4-[4-[2-(4-bromophenyl)-6-hydroxybenzothiophen-3-yl]oxyphenyl]butyl]piperazin-1-yl]-1-oxo-isoindolin-2-yl]piperidine-2,6-dione | δ 10.94 (s, 1H), 9.98 (s, 1H), 8.22 (s, 1H), 7.61 (s, 4H), 7.51 (d, J = 9.2 Hz, 1H), 7.31, (d, J = 2.0 Hz, 1H), 7.14 (dd, J = 5.6, 8.8 Hz, 3H), 7.06-7.01 (m, 2H), 6.88-6.80 (m, 3H), 5.04 (dd, J = 4.8, 13.2 Hz,1H), 4.36-4.28 (m, 1H), 4.23-4.15 (m, 1H), 3.24 (s, 3H), 2.95-2.85 (m, 1H), 2.63-2.54 (m, 2H), 2.47-2.36 (m, 6H), 2.33-2.25 (m, 3H), 1.96 (d, J = 5.0 Hz, 1H), 1.59 - 1.40 (m, 4H). (400 MHz, DMSO-d6) | B | B |
| 216 | 3-[5-[4-[[3-[4-[2-[4-bromophenyl)-6-hydroxy-benzothiophen-3-yl]oxyphenyl]azetidin-1-yl]methyl]-1-piperidyl]-1-oxo-isoindolin-2-yl]piperidine-2,6-dione | δ 10.97-10.91 (m, 1H), 8.33 (s, 2H), 7.62 (s, 4H), 7.47 (d, = 9.2 Hz, 1H), 7.32 (d, J = 2.1 Hz, 1H), 7.28 (d, J = 8.8 Hz, 2H), 7.15 (d, J = 8.8 Hz, 1H) 6.89 (d, J = 8.8 Hz, 2H), 6.86-6.81 (m, 1H), 6.62-6.58 (m, 2H), 5.03 (dd, J = 5.2, 13.2 Hz, 1H), 4.32-4.15 (m, 2H), 3.61-3.45 (m, 2H), 3.03-2.87 (m, 5H), 2.64-2.53 (m, 5H), 2.30-2.26 (m, 1H), 2.18-1.89 (m, 3H), 1.69-1.57 (m, 1H), 1.49-1.40 (m, 2H), 1.26-1.22 (m, 1H). (400 MHz, DMSO-d6) | B | B |
| 217 | 3-[5-[4-[3-[4-[6-hydroxy-2-[4-(trifluoromethoxy)phenyl]benzothiophen-3-yl]oxyphenoxy]propyl]piperazin-1-yl]-1-oxo-isoindolin-2-yl]piperidine-2,6-dione | δ 10.95 (s, 1H), 10.10-9.78 (m, 1H), 8.24-8.12 (m, 1H), 7.84-7.77 (m, 2H), 7.55-7.49 (m, 1H), 7.47-7.41 (m, 2H), 7.35-7.31 (m, 1H), 7.19-7.13 (m, 1H), 7.10-7.03 (m, 2H), 6.89 (s, 4H), 6.86-6.80 (m, 1H), 5.10-5.00 (m, 1H), 4.38-4.16 (m, 2H), 4.00-3.91 (m, 2H), 3.28-3.26 (m, 4H), 2.97-2.83 (m, 1H), 2.53 (s, 4H), 2.47-2.39 (m, 4H), 2.00-1.85 (m, 3H). (400 MHz, DMSO-d6) | B | B |
| 220 | 3-[5-[4-[3-[4-[2-(4-fluorophenyl)-6-hydroxybenzothiophen-3-yl]oxyphenoxy]propyl]piperazin-1-yl]-1-oxo-isoindolin-2-yl]piperidine-2,6-dione | δ 10.95 (s, 1H), 9.91 (s, 1H), 7.74-7.68 (m, 2H), 7.59 (d, J = 8.4 Hz, 1H), 7.33-7.23 (m, 3H), 7.19-7.11 (m, 3H), 6.89 (s, 4H), 6.83 (dd, J = 2.1, 8.7 Hz, 1H), 5.06 (dd, J = 5.0, 13.3 Hz, 1H), 4.42-4.18 (m, 2H), 4.08-3.96 (m, 4H), 3.62 (d, J = 10.4 Hz, 2H), 3.29 (s, 2H), 3.25-3.12 (m, 4H), 2.98-2.83 (m, 1H), 2.59 (d, J = 17.4 Hz, 1H), 2.38 (dd, J = 4.5, 13.1 Hz, 1H), 2.17 (s, 2H), 2.00-1.93 (m, 1H). (400 MHz, DMSO-d6) | B | B |
| 221 | 3-[5-[4-[3-[4-[2-(3,4-difluorophenyl)-6-hydroxy-benzothiophen-3-yl]oxyphenoxy]propyl]piperazin-1-yl]-1-oxo-isoindolin-2-yl]piperidine-2,6-dione | δ 10.95 (s, 1H), 9.51 (s, 1H), 8.14 (s, 1H), 7.70-7.64 (m, 1H), 7.55-7.47 (m, 3H), 7.31 (d, J = 2.0 Hz, 1H), 7.16 (d, J = 8.8 Hz, 1H), 7.06-7.04 (m, 2H), 6.88 (s, 4H), 6.84 (dd, J = 2.4, 8.8 Hz, 1H), 5.04 (dd, J = 5.2, 13.2 Hz, 1H), 4.34-4.30 (m, 1H), 4.22-4.17 (m, 1H), 3.95 (d, J = 6.4 Hz, 2H), 3.28-3.30 (m, 8H), 2.94-2.85 (m, 1H), 2.60-2.56 (m, 1H), 2.46-2.34 (m, 2H), 2.38-2.33 (m, 1H), 1.99-1.84 (m, 3H). (400 MHz, DMSO-d6) | B | B |
| 223 | trans-5-[4-[3-[4-[2-(4-bromophenyl)-6-hydroxy-benzothiophen-3-yl]oxyphenoxy]cyclobutyl]piperazin-1-yl]-2-(2,6-dioxo-3-piperidyl)isoindoline-1,3-dione | δ 11.09 (s, 1H), 9.93 (s, 1H), 8.25 (s, 1H), 7.67 (d, J = 8.4 Hz, 1H), 7.65-7.58 (m, 4H), 7.34 (d, J = 1.6 Hz, 1H), 7.30 (d, J = 2.0 HZ, 1H), 7.28-7.23 (m, 1H), 7.15 (d, J = 8.8 Hz, 1H), 6.89-6.81 (m, 3H), 6.79-6.73 (m, 2H), 5.07 (dd, J = 5.2, 12.8 Hz, 1H), 4.72-4.62 (m, 1H), 3.45-3.43 (m, 4H), 2.94-2.83 (m, 2H), 2.62-2.53 (m, 2H), 2.44-2.39 (m, 4H), 2.39-2.34 (m, 2H), 2.16-2.09 (m, 2H), 2.05-1.97 (m, 1H). (400 MHz, DMSO-d6) | C | A |

TABLE 5-continued

Data for cereblon centric benzthiophene derived ER PROTACs

| Ex. | IUPAC Name | H-NMR | DC$_{50}$ (nM)* | D$_{max}$ (%)** |
|---|---|---|---|---|
| 224 | 3-[5-[4-[3-[4-[2-(4-bromophenyl)-6-hydroxy-benzothiophen-3-yl]oxyphenoxy]cyclobutyl]piperazin-1-yl]-1-oxo-isoindolin-2-yl]piperidine-2,6-dione | δ 10.94 (s, 1H), 9.97-9.87 (m, 1H), 7.62 (s, 4H), 7.51-7.49 (d, J = 0.8 Hz, 1H), 7.30-7.29 (d, J = 4 Hz, 1H), 7.16-7.14 (d, J = 8 Hz, 1H), 7.06 (s, 2H), 6.92-6.75 (m, 5H), 5.10-4.98 (m, 1H), 4.43-4.28 (m, 2H), 4.24-4.14 (m, 1H), 3.28 ( s, 4H), 2.96-2.83 (m, 1H), 2.65-2.58 (m, 2H), 2.41 ( s, 5H), 2.36-2.10 (m, 2H), 2.18-2.06 (m, 1H), 2.01-1.91 (m, 1H), 1.89-1.78 (m, 2H). (400 MHz, DMSO-d6) | B | B |
| 225 | 5-[4-[2-[[4-[2-(4-bromophenyl)-6-hydroxy-benzothiophen-3-yl]oxyphenyl]methoxy]ethyl]piperazin-1-yl]-2-(2,6-dioxo-3-piperidyl)isoindoline-1,3-dione | δ 11.09 (s, 1H), 9.95 (s, 1H), 7.68 (d, J = 8.4 Hz, 1H), 7.62 (s, 4H), 7.33 (d, J = 2.0 Hz, 2H), 7.28 (d, J = 8.8 Hz, 2H), 7.24 (d, J = 8.4 Hz, 1H), 7.16 (d, J = 8.8 Hz, 1H), 6.93 (d, J = 8.8 Hz, 2H), 6.84 (dd, J = 2.0, 8.8 Hz, 1H), 5.11-5.04 (m, 1H), 4.41 (s, 2H), 3.56 (t, J = 5.6 Hz, 2H), 3.40 (s, 4H), 3.31 (s, 2H), 2.90 (d, J = 13.6 Hz, 1H), 2.61 (s, 2H), 2.56-2.54 (m, 4H), 2.06-1.99 (m, 1H). (400 MHz, DMSO-d6) | | C |
| 226 | 3-[5-[4-[[1-[4-[2-(4-fluorophenyl)-6-hydroxy-benzothiophen-3-yl]oxyphenyl]-4-piperidyl]methyl]piperazin-1-yl]-1-oxo-isoindolin-2-yl]piperidine-2,6-dione | δ 10.95 (s, 1H), 8.19 (s, 1H), 7.71 (dd, J = 5.4, 8.8 Hz, 2H), 7.52 (d, J = 8.8 Hz, 1H), 7.33-7.24 (m, 3H), 7.14 (d, J = 8.7 Hz, 1H), 7.08-7.03 (m, 2H), 6.89-6.79 (m, 5H), 5.04 (dd, J = 5.1, 13.4 Hz, 1H), 4.36-4.29 (m, 1H), 4.23-4.17 (m, 1H), 3.49-3.47 (m, 4H), 3.33-3.30 (m, 6H), 2.95-2.85 (m, 1H), 2.52 (d, J 3H), 2.35-2.32 (m, 1H), 2.21 (d, J = 7.2 Hz, 2H), 2.00-1.92 (m, 1H), 1.79 (d, J = 10.9 Hz, 2H), 1.84-1.75 (m, 1H), 1.65 (s, 1H), 1.27-1.14 (m, 2H). (400 MHz, DMSO-d6) | B | A |
| 227 | 2-(2,6-dioxo-3-piperidyl)-5-[4-[[1-[4-[2-(4-fluorophenyl)-6-hydroxy-benzothiophen-3-yl]oxyphenyl]-4-piperidyl]methyl]piperazin-1-yl]isoindoline-1,3-dione | δ 11.08 (s, 1H), 8.21 (s, 1H), 7.76-7.61 (m, 3H), 7.33-7.20 (m, 5H), 7.13 (d, J = 8.7 Hz, 1H), 6.89-6.74 (m, 5H), 5.06 (dd, J = 5.3, 12.9 Hz, 1H), 3.50 (d, J = 12.4 Hz, 8H), 2.93-2.81 (m, 1H), 2.69-2.52 (m, 6H), 2.20 (d, J = 7.2 Hz, 2H), 2.04-1.97 (m, 1H), 1.83-1.59 (m, 3H), 1.25-1.14 (m, 2H). (400 MHz, DMSO-d6) | B | A |
| 228 | 5-[4-[[1-[4-[2-(4-bromophenyl)-6-hydroxy-benzothiophen-3-yl]oxyphenyl]-4-pipendyl]methyl]piperazin-1-yl]-2-(2,6-dioxo-3-piperidyl)isoindoline-1,3-dione | δ 11.08 (s, 1H), 9.91 (s, 1H), 7.69-7.60 (m, 5H), 7.34-7.24 (m, 3H), 7.15 (d, J = 8.4 Hz, 1H), 6.88-6.79 (m, 5H), 5.07 (dd, J = 4.4, 12.4 Hz, 1H), 3.53-3.37 (m, 6H), 3.31-3.17 (m, 2H), 2.91-2.83 (m, 1H), 2.60-2.56 (m, 4H), 2.45-2.35 (m, 2H), 2.21 (d, J = 6.8 Hz, 2H), 2.02-1.99 (m, 1H), 1.81-1.77 (m, 2H), 1.66-1.62 (m, 1H), 1.24-1.16 (m, 2H). (400 MHz, DMSO-d6) | B | A |
| 229 | 3-[5-[4-[2-[1-[4-[2-(4-fluorophenyl)-6-hydroxy-benzothiophen-3-yl]oxyphenyl]-4-piperidyl]ethyl]piperazin-1-yl]-1-oxo-isoindolin-2-yl]piperidine-2,6-dione | δ 10.94 (s, 1H), 8.22 (s, 1H), 7.71 (dd, J = 5.4, 8.8 Hz, 2H), 7.51 (d, J = 8.9 Hz, 1H), 7.30-7.23 (m, 3H), 7.14 (d, J = 8.7 Hz, 1H), 7.08 - 7.02 (m, 2H), 6.90 - 6.78 (m, 5H), 5.04 (dd, J = 5.1, 13.3 Hz, 1H), 4.36-4.17 (m, 2H), 3.50 (s, 8H), 3.27 (s, 3H), 2.94-2.84 (m, 1H), 2.63-2.54 (m, 2H), 2.35 (dd, J = 7.0, 14.4 Hz, 3H), 1.98-1.92 (m, 1H), 1.75 (d, J = 11.5 Hz, 2H), 1.47-1.20 (m, 5H). (400 MHz, DMSO-d6) | B | A |
| 230 | 3-[2-[4-[[1-[4-[2-(4-fluorophenyl)-6-hydroxy-benzothiophen-3-yl]oxyphenyl]-4-pipendyl]methyl]piperazin-1-yl]-5-oxo-7H-pyrrolo[3,4-b]pyridin-6-yl]piperidine-2,6-dione | δ 10.93 (s, 1H), 9.87 (s, 1H), 7.77-7.66 (m, 3H), 7.28-7.22 (m, 3H), 7.12 (d, J = 8.7 Hz, 1H), 6.89-6.77 (m, 6H), 5.04 (dd, J = 5.1, 13.4 Hz, 1H), 4.25 (d, J 3.62 (s, 3H), 4.07 (d, J = 17.4 Hz, 1H) 3.62 (s, 3H), 3.54-3.44 (m, 2H), 2.94-2.82 (m, 1H), 2.53 (s, 3H), 2.41 (s, 6H), 2.17 (d, J = 6.9 Hz, 2H), 1.99-1.90 (m, 1H), 1.77 (d, J = 12.8 Hz, 2H) 1.62 (s, 1H), 1.23-1.13 (m, 2H). (400 MHz, DMSO-d6) | B | A |
| 231 | 3-[5-[4-[[1-[4-[2-(4-bromophenyl)-6-hydroxy-benzothiophen-3-yl]oxyphenyl]-4-piperidyl]methyl]piperazin-1-yl]-1-oxo-isoindolin-2-yl]piperidine-2,6-dione | δ 10.96 (s, 1H), 8.20 (s, 1H), 7.63 (d, J 4H), 7.53 (d, J = 8.8 Hz, 1H), 7.31 (d, J = 2.0 Hz, 1H), 7.16 (d, J = 8.8 Hz, 1H), 7.09-7.04 (m, 2H), 6.91-6.79 (m, 5H), 5.05 (dd, J = 5.2, 13.2 Hz, 1H), 4.36-4.30 (m, 1H), 4.24-4.17 (m, 1H), 3.53 (d, J = 10.8 Hz, 1H), 3.29 (br s, 7H), 2.98-2.83 (m, 2H), 2.63-2.54 (m, 4H), 2.40-2.35 (m, 1H), 2.22 (d, J = 6.8 Hz, 2H), 2.01-1.92 (m, 1H), 1.80 (d, J = 11.2 Hz, 2H), 1.65 (br s, 1H), 1.27-1.15 (m, 2H). (400 MHz, DMSO-d6) | B | B |

TABLE 5-continued

Data for cereblon centric benzthiophene derived ER PROTACs

| Ex. | IUPAC Name | H-NMR | DC$_{50}$ (nM)* | D$_{max}$ (%)** |
|---|---|---|---|---|
| 232 | 3-[5-[4-[[1-[5-[2-(4-fluorophenyl)-6-hydroxy-benzothiophen-3-yl]oxy-2-pyridyl]-4-piperidyl]methyl]piperazin-1-yl]-1-oxo-isoindolin-2-yl]piperidine-2,6-dione | δ 10.94 (s, 1H), 8.14 (s, 1H), 7.89 (d, J = 3.2 Hz, 1H), 7.73-7.67 (m, 2H), 7.51 (d, J = 8.4 Hz, 1H), 7.32-7.19 (m, 4H), 7.11 (dd, J = 2.8, 9.2 Hz, 1H), 7.08-7.01 (m, 2H), 6.84 (dd, J = 2.4, 8.8 Hz, 1H), 6.74 (d, J = 9.6 Hz, 1H), 5.04 (dd, J = 5.2, 13.2 Hz, 1H), 4.37-4.28 (m, 1H), 4.23-4.15 (m, 1H), 4.14-4.06 (m, 2H), 3.29-3.21 (m, 7H), 2.96-2.84 (m, 1H), 2.76-2.68 (m, 2H), 2.62-2.53 (m, 2H), 2.42-2.29 (m, 1H), 2.22-2.15 (m, 2H), 2.01-1.90 (m, 1H), 1.80-1.68 (m, 3H), 1.16-1.00 (m, 2H). (400 MHz, DMSO-d) | A | A |
| 234 | 3-[5-[4-[[1-[4-[6-hydroxy-2-(4-methoxyphenyl)benzothiophen-3-yl]-oxyphenyl]-4-piperidyl]methyl]piperazin-1-yl]-1-oxo-isoindolin-2-yl]piperidine-2,6-dione | δ 10.94 (s, 1H), 9.78 (s, 1H), 7.61 (d, J = 8.9 Hz, 2H), 7.51 (d, J = 8.7 Hz, 1H), 7.26 (d, J = 2.0 Hz, 1H), 7.13-6.97 (m, 5H), 6.89-6.78 (m, 5H), 5.04 (dd, J = 5.0, 13.2 Hz, 1H), 4.35-4.16 (m, 2H), 3.75 (s, 3H), 3.51 (d, J = 11.3 Hz, 2H), 3.29 (d, J = 9.5Hz, 5H), 2.96-2.83 (m, 1H), 2.66-2.52 (m, 7H), 2.21 (d, J = 6.1Hz, 2H), 1.98-1.92 (m, 1H), 1.79 (d, J = 11.9 Hz, 2H), 1.64 (s, 1H), 1.21 (d, J = 16.3 2H). (400 MHz, DMSO-d) | A | B |
| 235 | 3-[2-[4-[[1-[4-[2-(4-bromophenyl)-6-hydroxy-benzothiophen-3-yl]oxyphenyl]-4-piperidyl]methyl]piperazin-1-yl]-5-oxo-7H-pyrrolo[3,4-b]pyridin-6-yl]piperidine-2,6-dione | δ 10.95 (s, 1H), 8.22 (s, 1H), 7.76 (d, J = 8.8 Hz, 1H), 7.62 (d, J = 1.9 Hz, 4H), 7.29 (d, J = 2.0 Hz, 1H), 7.15 (d, J = 8.7 Hz, 1H), 6.92-6.80 (m, 6H), 5.06 (dd, J = 5.1, 13.1 Hz, 1H), 4.30-4.23 (m, 1H), 4.09 (d, J = 17.4 Hz, 1H), 3.64 (s, 4H), 2.94-2.82 (m, 1H), 2.57 (d, J = 14.2 Hz, 2H), 2.48-2.36 (m, 8H), 2.19 (d, J = 7.0 Hz, 2H), 2.01-1.91 (m, 1H), 1.83-1.76 (m, 2H), 1.64 (s, 1H), 1.24-1.16 (m, 2H). (400 MHz, DMSO-d6) | B | A |
| 236 | 3-[5-[4-[[1-[5-[2-(4-bromophenyl)-6-hydroxy-benzothiophen-3-yl]oxy-2-pyridyl]-4-piperidyl]methyl]piperazin-1-yl]-1-oxo-isoindolin--2-yl]piperidine-2,6-dione | δ 10.93 (s, 1H), 8.18 (s, 1H), 7.89 (d, J = 3.3 Hz, 1H), 7.62 (s, 4H), 7.51 (d, J = 8.7 Hz, 1H), 7.30 (d, J = 2.0 Hz, 1H), 7.22 (d, J = 8.7 Hz, 1H), 7.11 (dd, J = 3.1, 9.2 Hz, 1H), 7.08-7.02 (m, 2H), 6.85 (dd, J = 2.1, 8.7 Hz, 1H), 6.74 (d, J = 9.4 Hz, 1H), 5.04 (dd, J = 5.0, 13.4 Hz, 1H), 4.35-4.16 (m, 2H), 4.11 (d, J = 13.3 Hz, 2H), 3.16 (s, 1H), 2.88 (d, J = 12.4 Hz, 1H), 2.76-2.56 (m, 6H), 2.44-2.29 (m, 6H), 2.18 (d, J = 6.3 Hz, 2H), 2.00-1.90 (m, 1H), 1.76 (d, J 3H), 1.11-1.04 (m, 2H). (400 MHz, DMSO-d6) | B | A |
| 237 | 2-(2,6-dioxo-3-piperidyl)-5-[4-[[1-[4-[6-hydroxy-2-(4-methoxyphenyl)benzothiophen-3-yl]oxyphenyl]-4-piperidyl]methyl]piperazin-1-yl]isoindoline-1,3-dione | δ 11.07 (s, 1H), 9.78 (s, 1H), 7.70-7.58 (m, 3H), 7.35-7.21 (m, 3H), 7.13-7.08 (m, 1H), 7.13-7.08 (m, 1H), 6.97 (d, J = 8.9 Hz, 2H), 6.90-6.83 (m, 2H), 6.82-6.76 (m, 3H), 5.06 (dd, J = 5.4, 12.9 Hz, 1H), 3.75 (s, 3H), 3.53-3.40 (m, 5H), 2.95-2.81 (m, 1H), 2.67-2.53 (m, 6H), 2.32 (d, J = 1.8 Hz, 1H), 2.20 (d, J = 7.0 Hz, 2H), 2.10-1.96 (m, 2H), 1.78 (d, J = 11.2 Hz, 2H), 1.63 (s, 1H), 1.26-1.13 (m, 2H). (400 MHz, DMSO-d6) | C | A |
| 238 | 3-[5-[4-[[1-[4-[2-(4-bromophenyl)-6-hydroxy-benzothiophen-3-yl]oxy-2-fluoro-phenyl]-4-piperidyl]methyl]piperazin-1-yl]-1-oxo-isoindolin-2-yl]piperidine-2,6-dione | δ 10.95 (s, 1H), 9.95 (br, s, 1H), 8.18 (s, 1H), 7.64-7.60 (m, 4H), 7.52 (d, J = 8.8 Hz, 1H), 7.33 (d, J = 2.0 Hz, 1H), 7.19 (d, J = 8.8 Hz, 1H), 7.09-7.03 (m, 2H), 6.96 (t, J = 9.6 Hz, 1H), 6.90-6.83 (m, 2H), 6.61 (dd, J = 2.4, 8.4 Hz, 1H), 5.05 (dd, J = 5.2, 13.2 Hz, 1H), 4.36-4.29 (m, 1H), 4.25-4.16 (m, 1H), 3.30-3.19 (m, 9H), 2.96-2.85 (m, 1H), 2.64-2.53 (m, 4H), 2.42-2.35 (m, 1H), 2.23 (d, J = 7.2 Hz, 2H), 2.00-1.93 (m, 1H), 1.79 (d, J = 12.8 Hz, 2H), 1.65 (br s, 1H), 1.32-1.20 (m, 2H). (400 MHz, DMSO-d6) | C | A |
| 239 | 3-[5-[4-[[1-[4-[2-(4-bromophenyl)-6-hydroxy-benzothiophen-3-yl]oxyphenyl]-4-piperidyl]methyl]piperazin-1-yl]-5-oxo-7H-pyrrolo[3,4-b]pyridin-6-yl]piperidine-2,6-dione | | C | A |

TABLE 5-continued

Data for cereblon centric benzthiophene derived ER PROTACs

| Ex. | IUPAC Name | H-NMR | $DC_{50}$ (nM)* | $D_{max}$ (%)** |
|---|---|---|---|---|
| 243 | 3-[2-[4-[[1-[4-[6-hydroxy-2-(4-hydroxyphenyl)benzothiophen-3-yl]oxyphenyl]-4-piperidyl]methyl]piperazin-1-yl]-5-oxo-7H-pyrrolo[3,4-b]pyridin-6-yl]piperidine-2,6-dione | δ 8.33(s, 1H), 7.84 (d, J = 8.8 Hz, 1H), 7.53 (d, J = 8.8 Hz, 2H), 7.16-7.13 (m, 1H), 6.95 (d, J = 8.8 Hz, 2H), 6.90 (d, J = 6.8 Hz, 1H), 6.83 (d, J = 9.2 Hz, 2H), 6.77-6.73 (m, 3H), 5.11 (dd, J = 4.8, 13.6 Hz, 1H), 4.35-4.24 (m, 2H), 3.8 (s, 4H), 3.52 (d, J = 12.0 Hz, 2H), 2.93-2.84 (m, 1H), 2.78-2.75 (m, 5H), 2.69-2.63(m, 2H), 2.52-2.47 (m, 2H), 2.44-2.41 (m, 1H), 2.16-2.13 (m, 1H), 1.92-1.89 (m, 2H), 1.44-1.36 (m, 2H). (400 MHz, MeOD) | B | B |
| 244 | 3-[5-[4-[[1-[4-(6-hydroxy-2-(4-hydroxyphenyl)benzothiophen-3-yl]oxyphenyl]-4-piperidyl]methyl]piperazin-1-yl]-1-oxo-isoindolin-2-yl]piperidine-2,6-dione | δ 8.29(s, 2H), 7.66 (d, J = 8.4 Hz, 1H), 7.53 (d, J = 8.4 Hz, 2H), 7.16-7.10 (m, 4H), 6.95 (d, J = 8.8 Hz, 2H), 6.84 (d, J = 9.2 Hz, 2H), 6.74 (d, J = 8.8 Hz, 3H), 5.01 (dd, J = 4.2, 13.8 Hz, 1H), 4.45-4.35 (m, 2H), 3.54-3.48 (m, 6H), 3.33-2.97 (m, 4H), 2.96-2.86 (m, 1H), 2.79-2.75 (m, 1H), 2.70-2.67 (m, 4H), 2.51-2.40 (m, 1H), 2.16-2.12 (m, 1H), 1.94-1.84 (m, 3H), 1.46-1.41 (m, 2H). (400 MHz, MeOD) | B | B |
| 245 | 2-(2,6-dioxo-3-piperidyl)-5-[4-[[1-[4-[6-hydroxy-2-(4-hydroxyphenyl)benzothiophen-3-yl]oxyphenyl]-4-piperidyl]methyl]piperazin-1-yl]isoindoline-1,3-dione | δ 8.31 (s, 1H), 7.69 (d, J = 8.8 Hz, 1H), 7.53 (d, J = 8.8 Hz, 2H), 7.37 (d, J = 2.4 Hz, 1H), 7.24 (dd, J = 1.2, 8.4 Hz, 1H), 7.16-7.13 (m, 2H), 8.95 (d, J = 9.2 Hz, 2H), 6.83 (d, J = 9.2 Hz, 2H), 9.77-6.73 (m, 3H), 6.83 (d, J = 9.2 Hz, 2H), 5.07 (d, J = 5.2, 12.8 Hz, 1H), 3.53-3.51 (m, 6H), 2.81-2.77 (m, 1H), 2.76-2.72 (m, 5H), 2.68-2.65 (m, 3H), 2.49-2.47 (m, 2H), 2.13-2.09 (m, 1H), 1.94-1.88 (m, 2H), 1.78 (s, 1H), 1.44-1.35 (m, 2H). (400 MHz, MeOD) | C | B |

* and ** ER-alpha degradation measured in MCF7 cells by in cell western assay method following 5 days of incubation
*$DC_{50}$: A <1 nM; B 1 to 10 nM; C 10-100 nM
**$D_{max}$: A >75%; B 50% to 75%; C <50%

Specific Embodiments of the Present Disclosure

As described above, in any aspect or embodiment described herein, the present disclosure provides bifunctional PROTAC compounds comprising: at least one of benzothiophene derivative, a ER binding moiety, or a combination thereof; a linker; and at least one of a cereblon binding ligand, VHL binding ligand, IAP binding moiety, MDM2 binding moiety, or a combination thereof. The present disclosure encompasses the following specific embodiments. These following embodiments may include all of the features recited in a proceeding embodiment, as specified. Where applicable, the following embodiments may also include the features recited in any proceeding embodiment inclusively or in the alternative (e.g., an eighth embodiment may include the features recited in a first embodiment, as recited, and/or the features of any of the second through seventh embodiments).

In any aspect or embodiment described herein, wherein the compound is selected from the compounds of Table 1, 2, 3, 4, or 5 (e.g., selected from Compounds 1-245).

A further aspect of the present disclosure provides a composition comprising an effective amount of the bifunctional compound of the present disclosure, and a pharmaceutically acceptable carrier.

In any aspect or embodiment described herein, the composition further comprises at least one of additional bioactive agent or another bifunctional compound of the present disclosure.

In any aspect or embodiment described herein, the additional bioactive agent is an anti-cancer agent.

Another aspect of the present disclosure provides a composition comprising a pharmaceutically acceptable carrier and an effective amount of at least one compound of the present disclosure for treating a disease or disorder in a subject, the method comprising administering the composition to a subject in need thereof, wherein the compound is effective in treating or ameliorating at least one symptom of the disease or disorder.

In any aspect or embodiment described herein, the disease or disorder is associated with estrogen receptor accumulation and aggregation.

In any aspect or embodiment described herein, the disease or disorder is a cancer associated with estrogen receptor accumulation and aggregation.

In any aspect or embodiment described herein, the disease or disorder is at least one of breast cancer, uterine cancer, ovarian cancer, prostate cancer, endometrial cancer, endometriosis, or a combination thereof.

In any aspect or embodiment described herein, the disease or disorder is breast cancer.

In certain embodiments, the description provides the following exemplary ER PROTAC molecules (compounds 1-245 of Table 1, Table 2, Table 3, Table 4, and Table 5), including salts, prodrugs, polymorphs, analogs, derivatives, and deuterated forms thereof. In any aspect or embodiment described herein the compound of the present disclosure is selected from Tables 1, 2, 3, 4, and 5. For example, the compound may be selected from compounds 1-245 in any aspect or embodiment described herein.

A novel bifunctional molecule, which contains a ER recruiting moiety and an E3 Ligase Cereblon recruiting moiety, through PROTAC technology is described. The bifunctional molecules of the present disclosure actively degrades ER. PROTAC mediated protein degradation provides a promising strategy in targeting the "undruggable" pathological proteins by traditional approaches.

The contents of all references, patents, pending patent applications and published patents, cited throughout this application are hereby expressly incorporated by reference.

Those skilled in the art will recognize, or be able to ascertain using no more than routine experimentation, many equivalents to the specific embodiments of the disclosure described herein. Such equivalents are intended to be encompassed by the following claims. It is understood that the detailed examples and embodiments described herein are given by way of example for illustrative purposes only, and are in no way considered to be limiting to the disclosure. Various modifications or changes in light thereof will be suggested to persons skilled in the art and are included within the spirit and purview of this application and are considered within the scope of the appended claims. For example, the relative quantities of the ingredients may be varied to optimize the desired effects, additional ingredients may be added, and/or similar ingredients may be substituted for one or more of the ingredients described. Additional advantageous features and functionalities associated with the systems, methods, and processes of the present disclosure will be apparent from the appended claims. Moreover, those skilled in the art will recognize, or be able to ascertain using no more than routine experimentation, many equivalents to the specific embodiments of the disclosure described herein. Such equivalents are intended to be encompassed by the following claims.

What is claimed is:

1. A bifunctional compound selected from the group consisting of:

(118)

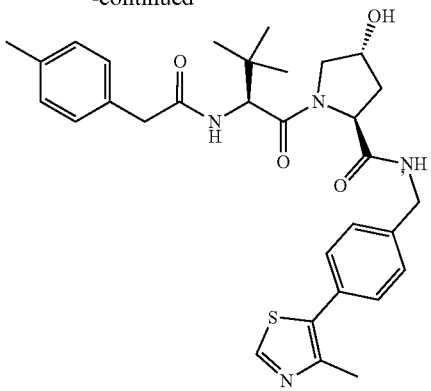

(130)

(21)

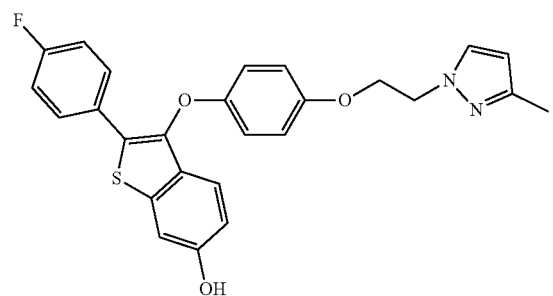

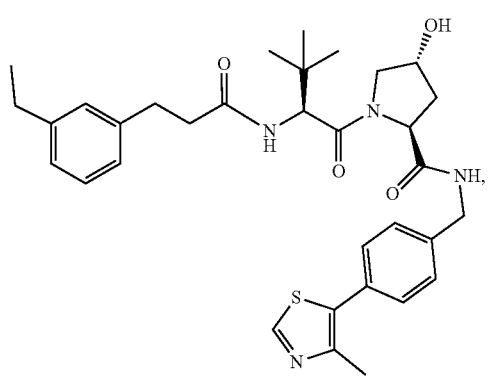

(133)

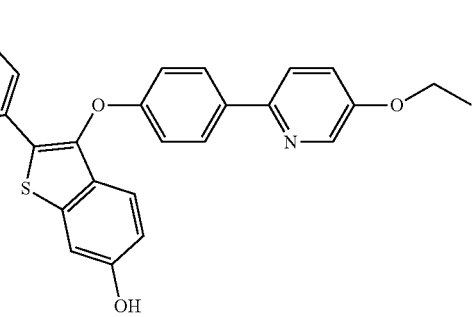

767
-continued
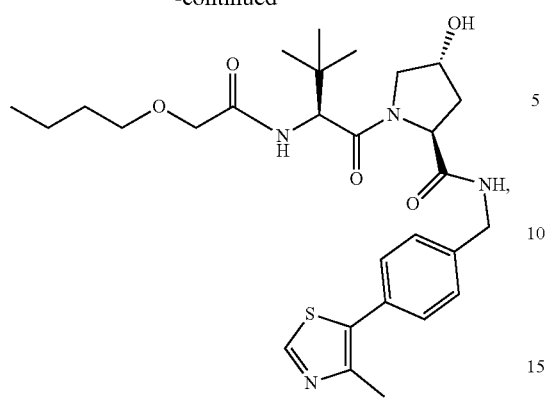
768
-continued
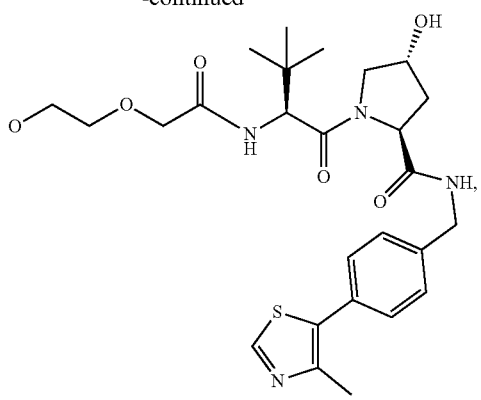
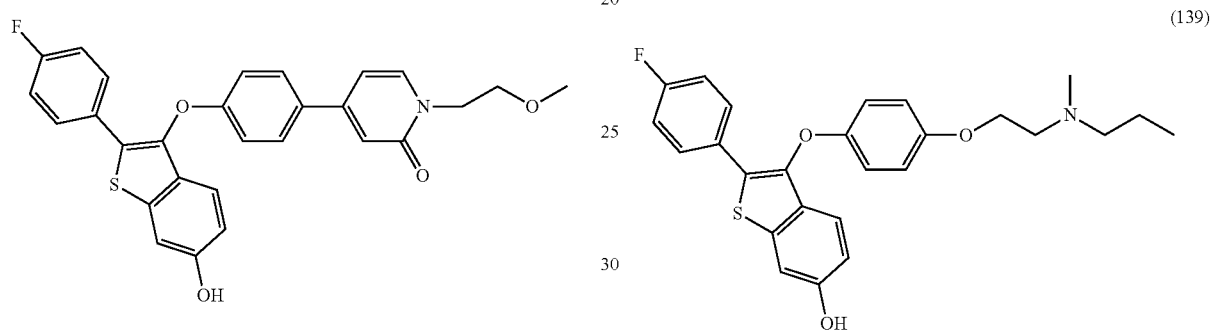
(134)
(139)
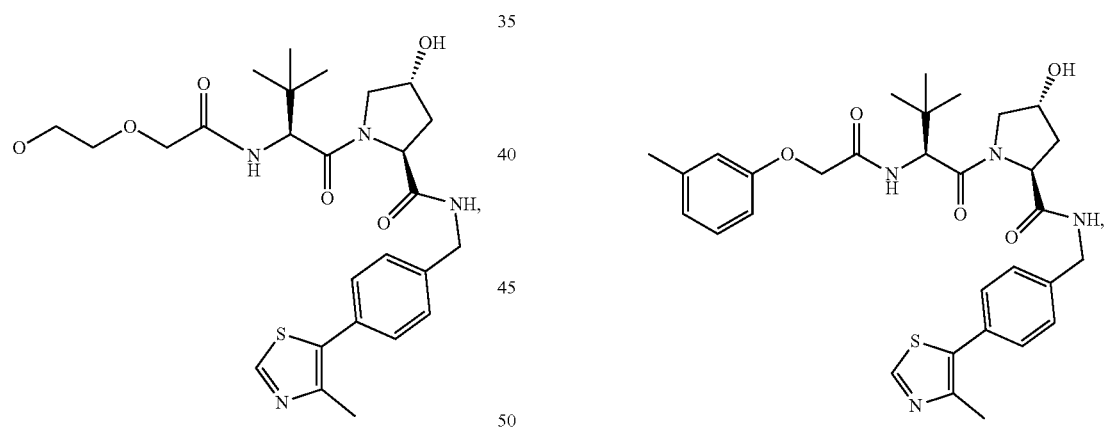
(135)
(140)
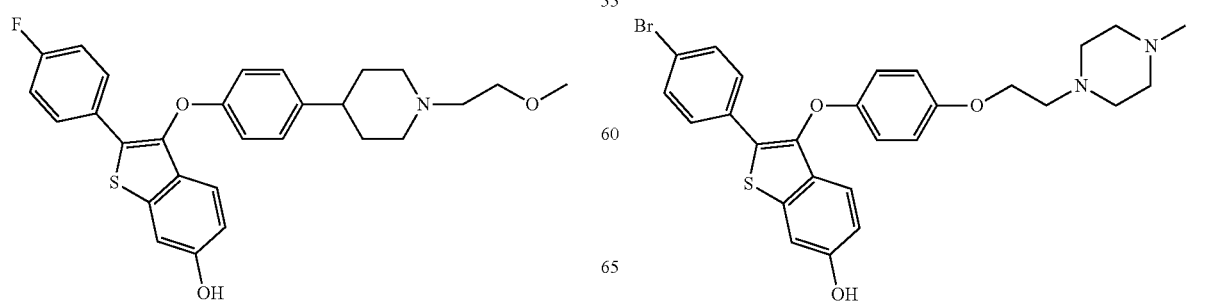

769
-continued
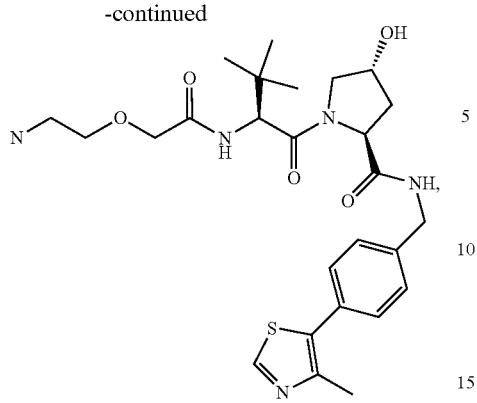
770
-continued
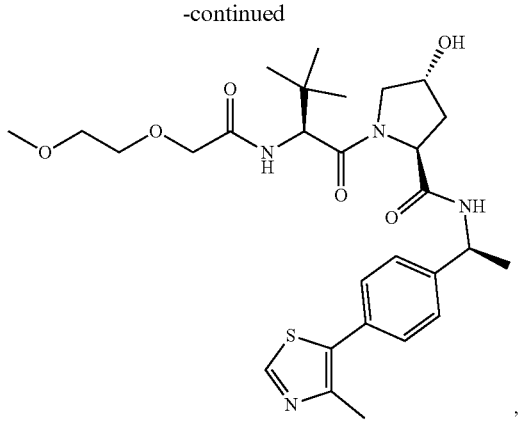
(141)
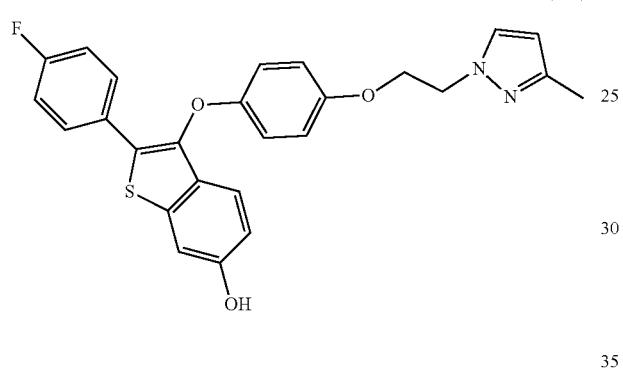
(147)
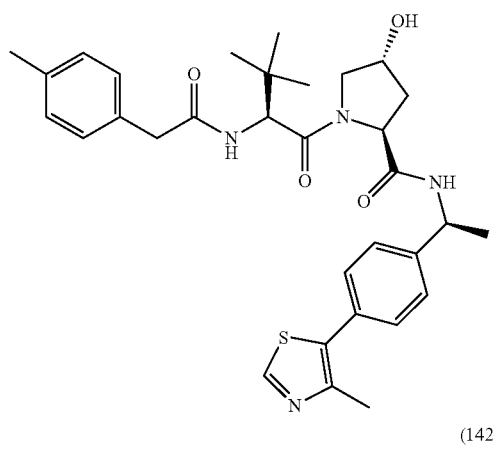
(142)
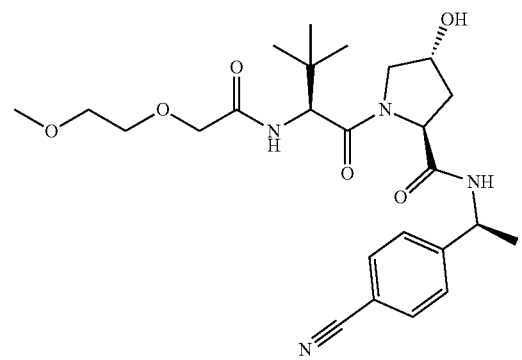
(149)
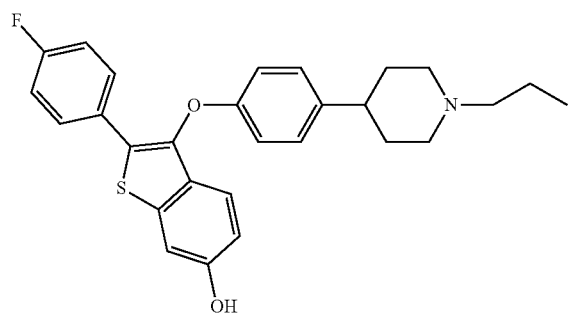

771
-continued
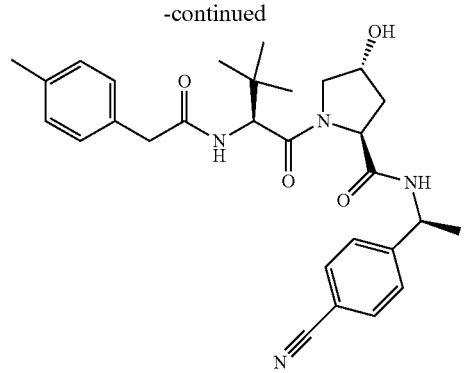
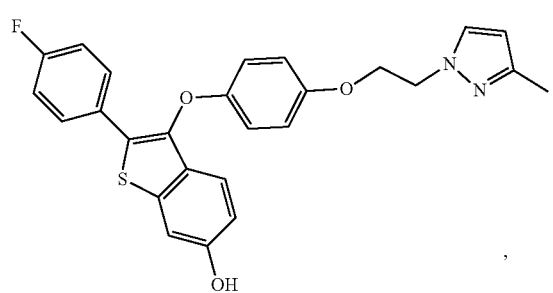
(151)
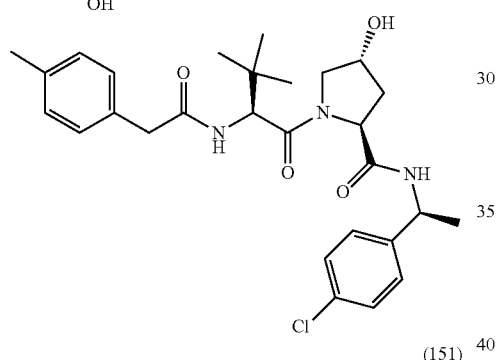
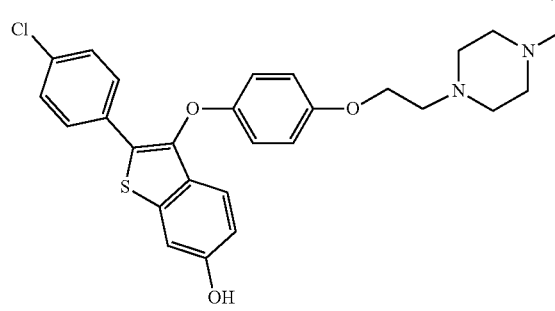
772
-continued
(153)
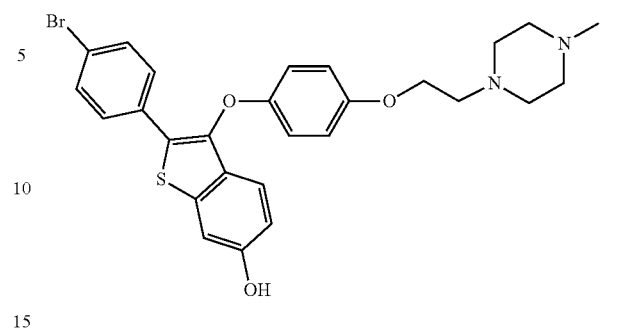
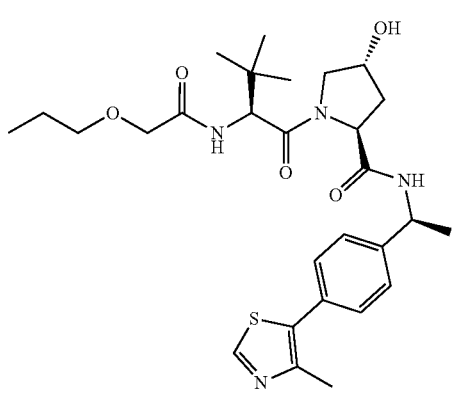
(158)
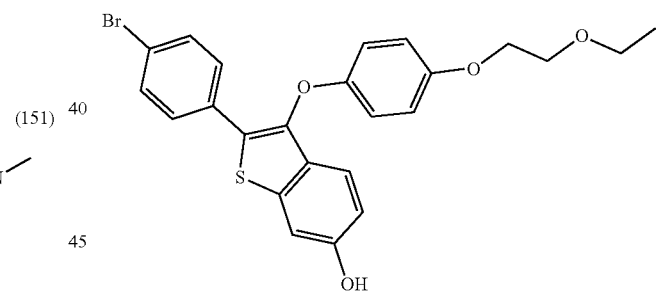
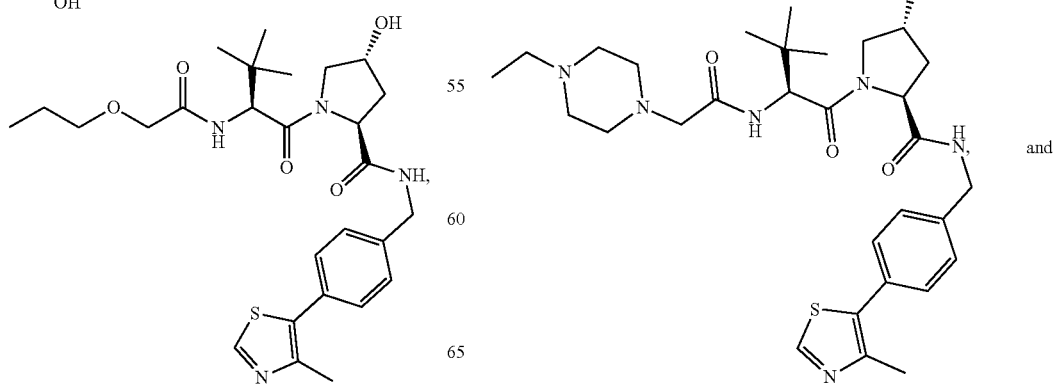
and -continued (160)

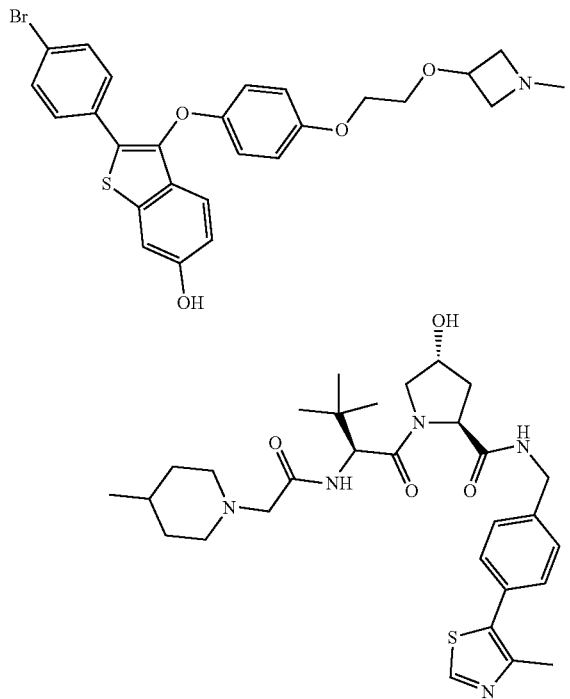

2. A composition comprising an effective amount of a bifunctional compound of claim 1, and a pharmaceutically acceptable carrier.

3. The composition of claim 2, wherein the composition further comprises an additional bioactive agent.

4. The composition of claim 3, wherein the additional bioactive agent is an anti-cancer agent.

5. A method of treating a disease or disorder selected from endometriosis or a cancer associated with estrogen receptor accumulation and aggregation in a subject, the method comprising administering a composition comprising a pharmaceutically acceptable carrier and an effective amount of at least one bifunctional compound of claim 1 to a subject in need thereof, wherein the composition is effective in treating or ameliorating at least one symptom of the disease or disorder.

6. The method of claim 5, wherein the disease or disorder is cancer associated with estrogen receptor accumulation and aggregation is selected from at least one of breast cancer, uterine cancer, ovarian cancer, prostate cancer, endometrial cancer, endometriosis, or a combination thereof.

7. The method of claim 6, wherein the disease or disorder is breast cancer.

8. The method of claim 6, wherein the disease or disorder is endometriosis.

\* \* \* \* \*